(12) United States Patent
Ladziata et al.

(10) Patent No.: US 9,902,702 B2
(45) Date of Patent: Feb. 27, 2018

(54) SPIROCYCLOHEPTANES AS INHIBITORS OF ROCK

(71) Applicant: BRISTOL-MYERS SQUIBB COMPANY, Princeton, NJ (US)

(72) Inventors: Vladimir Ladziata, Ewing, NJ (US); Peter W. Glunz, Yardley, PA (US); Zilun Hu, Jamison, PA (US); Yufeng Wang, North Brunswick, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/797,414

(22) Filed: Jul. 13, 2015

(65) Prior Publication Data

US 2016/0016914 A1 Jan. 21, 2016

Related U.S. Application Data

(60) Provisional application No. 62/024,555, filed on Jul. 15, 2014.

(51) Int. Cl.

| | |
|---|---|
| *A01N 43/58* | (2006.01) |
| *A01N 43/60* | (2006.01) |
| *A61K 31/50* | (2006.01) |
| *A61K 31/495* | (2006.01) |
| *C07D 237/26* | (2006.01) |
| *C07D 487/00* | (2006.01) |
| *C07D 237/32* | (2006.01) |
| *C07D 403/12* | (2006.01) |
| *C07D 417/12* | (2006.01) |
| *C07D 417/14* | (2006.01) |
| *C07D 413/12* | (2006.01) |
| *C07D 471/04* | (2006.01) |
| *C07D 513/04* | (2006.01) |
| *C07D 487/04* | (2006.01) |
| *C07D 405/14* | (2006.01) |
| *C07D 471/10* | (2006.01) |
| *C07D 413/14* | (2006.01) |
| *C07D 403/08* | (2006.01) |
| *C07D 519/00* | (2006.01) |

(52) U.S. Cl.
CPC ......... *C07D 237/32* (2013.01); *C07D 403/08* (2013.01); *C07D 403/12* (2013.01); *C07D 405/14* (2013.01); *C07D 413/12* (2013.01); *C07D 413/14* (2013.01); *C07D 417/12* (2013.01); *C07D 417/14* (2013.01); *C07D 471/04* (2013.01); *C07D 471/10* (2013.01); *C07D 487/04* (2013.01); *C07D 513/04* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 8,742,116 B2 | 6/2014 | Plettenburg et al. | |
| 9,221,767 B2 | 12/2015 | Glunz et al. | |
| 2012/0122842 A1 | 5/2012 | Curtin et al. | |

FOREIGN PATENT DOCUMENTS

| | | | |
|---|---|---|---|
| CN | 102180909 A | 9/2011 | |
| CN | 103242647 A | 8/2013 | |
| DE | 25 31 776 A1 | 2/1977 | |
| DE | 198 04 085 A1 | 8/1999 | |
| EP | 0 475 527 A2 | 3/1992 | |
| EP | 0 481 383 A1 | 4/1992 | |
| EP | 0 634 402 A1 | 1/1995 | |
| EP | 2 025 676 A1 | 2/2009 | |
| JP | 2000-72675 A | 3/2000 | |
| WO | WO 98/38168 A1 | 9/1998 | |
| WO | WO 99/40072 A1 | 8/1999 | |
| WO | WO 00/44726 A1 | 8/2000 | |
| WO | WO 00/50419 A1 | 8/2000 | |
| WO | WO 02/36576 A1 | 5/2002 | |
| WO | WO 03/068750 A1 | 8/2003 | |
| WO | WO 2004/024694 A1 | 3/2004 | |

(Continued)

OTHER PUBLICATIONS

CAS Registry No. 401646-88-6, Entered STN: Mar. 18, 2002.

(Continued)

*Primary Examiner* — Jeffrey H Murray

(74) *Attorney, Agent, or Firm* — Hong Liu

(57) ABSTRACT

The present invention provides compounds of Formula (I):

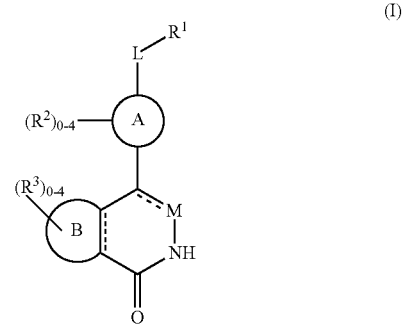

or stereoisomers, tautomers, or pharmaceutically-acceptable salts thereof, wherein all the variables are as defined herein. These compounds are selective ROCK inhibitors. This invention also relates to pharmaceutical compositions comprising these compounds and methods of treating cardiovascular, smooth muscle, oncologic, neuropathologic, autoimmune, fibrotic, and/or inflammatory disorders using the same.

15 Claims, No Drawings

(56) References Cited

FOREIGN PATENT DOCUMENTS

| WO | WO 2005/097750 A1 | 10/2005 |
|---|---|---|
| WO | WO 2006/036981 A2 | 4/2006 |
| WO | WO 2006/124874 A2 | 11/2006 |
| WO | WO 2008/086014 A2 | 7/2008 |
| WO | WO 2009/064422 A2 | 5/2009 |
| WO | WO 2011/019400 A2 | 2/2011 |
| WO | WO 2012/072033 A1 | 6/2012 |
| WO | WO 2014/079850 A1 | 5/2014 |
| WO | WO 2014/113620 A2 | 7/2014 |
| WO | WO 2014/134388 A1 | 9/2014 |
| WO | WO 2014/134391 A1 | 9/2014 |
| WO | WO 2015/002915 A1 | 1/2015 |
| WO | WO 2015/002926 A1 | 1/2015 |
| WO | WO 2015/107053 A1 | 7/2015 |

OTHER PUBLICATIONS

CAS Registry No. 674337-79-2, Entered STN: Apr. 12, 2004.
CAS Registry No. 692279-56-4, Entered STN: Jun. 13, 2004.
CAS Registry No. 700349-58-2, Entered STN: Jun. 28, 2004.
CAS Registry No. 939750-00-2, Entered STN: Jun. 28, 2007.
CAS Registry No. 1180660-61-0, Entered STN: Sep. 4, 2009.
Kiselyov, A.S. et al., "1-(Azolyl)-4-(aryl)-phthalazines: Novel Potent Inhibitors of VEGF Receptors I and II", Chem. Biol. Drug. Des., vol. 68, pp. 250-255 (2006).
Mei, Q. et al., "Highly efficient red iridium(III) complexes based on phthalazine derivatives for organic light-emitting diodes", Dyes and Pigments, vol. 97, pp. 43-51 (2013).
REAXYS® PubChem Report generated Dec. 23, 2013.

SPIROCYCLOHEPTANES AS INHIBITORS OF ROCK

CROSS REFERENCE TO RELATED APPLICATIONS

This application is entitled to priority pursuant to 35 U.S.C. § 119(e) to U.S. provisional patent application No. 62/024,555, filed on Jul. 15, 2014, which is incorporated herein in its entirety.

FIELD OF THE INVENTION

The present invention relates generally to novel spirocycloheptanes and their analogues thereof, which are inhibitors of Rho kinases, compositions containing them, and methods of using them, for example, for the treatment or prophylaxis of disorders associated with aberrant Rho kinase activity.

BACKGROUND OF THE INVENTION

Rho-Kinase (ROCK) is a member of the serine-threonine protein kinase family. ROCK exists in two isoforms, ROCK1 and ROCK2 (Ishizaki, T. et al., *EMBO J.*, 15:1885-1893 (1996)). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as ACTIN® organization, cell adhesion, cell migration, and cytokinesis (Riento, K. et al., *Nat. Rev. Mol. Cell Biol.*, 4:446-456 (2003)). It is also directly involved in regulating smooth muscle contraction (Somlyo, A. P., *Nature*, 389:908-911 (1997)). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the Rho A/ROCK signaling pathway plays an important role in signal transduction initiated by several vasoactive factors, for example angiotensin II (Yamakawa, T. et al., *Hypertension*, 35:313-318 (2000)), urotension II (Sauzeau, V. et al., *Circ. Res.*, 88:1102-1104 (2001)), endothelin-1 (Tangkijvanich, P. et al., *Hepatology*, 33:74-80 (2001)), serotonin (Shimokawa, H., *Jpn. Circ. J.*, 64:1-12 (2000)), norepinephrine (Martinez, M. C. et al., *Am. J. Physiol.*, 279:H1228-H1238 (2000)) and platelet-derived growth factor (PDGF) (Kishi, H. et al., *J. Biochem.*, 128:719-722 (2000)). Many of these factors are implicated in the pathogenesis of cardiovascular disease.

Additional studies in the literature, some using the known ROCK inhibitors fasudil (Asano, T. et al., *J. Pharmacol. Exp. Ther.*, 241:1033-1040 (1987)) or Y-27632 (Uehata, M. et al., *Nature*, 389:990-994 (1997)) further illustrate the link between ROCK and cardiovascular disease. For example, ROCK expression and activity have been shown to be elevated in spontaneously hypertensive rats, suggesting a link to the development of hypertension in these animals (Mukai, Y. et al., *FASEB J.*, 15:1062-1064 (2001)). The ROCK inhibitor Y-27632 (Uehata, M. et al., *Nature, ibid.*) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Eto, Y. et al., *Am. J. Physiol. Heart Circ. Physiol.*, 278:H1744-H1750 (2000)). In a similar model, ROCK inhibitor Y-27632 also inhibited neointimal formation in rats (Sawada, N. et al., *Circulation*, 101:2030-2033 (2000)). In a porcine model of IL-1 beta-induced coronary stenosis, long term treatment with the ROCK inhibitor fasudil was shown to progressively reduce coronary stenosis, as well as promote a regression of coronary constrictive remodeling (Shimokawa, H. et al., *Cardiovasc. Res.*, 51:169-177 (2001)).

Additional investigations suggest that a ROCK inhibitor would be useful in treating other cardiovascular diseases. For example, in a rat stroke model, fasudil was shown to reduce both the infarct size and neurologic deficit (Toshima, Y., *Stroke*, 31:2245-2250 (2000)). The ROCK inhibitor Y-27632 was shown to improve ventricular hypertrophy, fibrosis and function in a model of congestive heart failure in Dahl salt-sensitive rats (Kobayashi, N. et al., *Cardiovasc. Res.*, 55:757-767 (2002)).

Other animal or clinical studies have implicated ROCK in additional diseases including coronary vasospasm (Shimokawa, H. et al., *Cardiovasc. Res.*, 43:1029-1039 (1999)), cerebral vasospasm (Sato, M. et al., *Circ. Res.*, 87:195-200 (2000)), ischemia/reperfusion injury (Yada, T. et al., *J. Am. Coll. Cardiol.*, 45:599-607 (2005)), pulmonary hypertension (Fukumoto, Y. et al., *Heart*, 91:391-392 (2005)), angina (Shimokawa, H. et al., *J. Cardiovasc. Pharmacol.*, 39:319-327 (2002)), renal disease (Satoh, S. et al., *Eur. J. Pharmacol.*, 455:169-174 (2002)) and erectile dysfunction (Gonzalez-Cadavid, N. F. et al., *Endocrine*, 23:167-176 (2004)).

In another study, it has been demonstrated that inhibition of the RhoA/ROCK signaling pathway allows formation of multiple competing lamellipodia that disrupt the productive migration of monocytes (Worthylake, R. A. et al., *J. Biol. Chem.*, 278:13578-13584 (2003)). It has also been reported that small molecule inhibitors of Rho Kinase are capable of inhibiting MCP-1 mediated chemotaxis in vitro (Iijima, H., *Bioorg. Med. Chem.*, 15:1022-1033 (2007)). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (Shimokawa, H. et al., *Arterioscler. Thromb. Vasc. Biol.*, 25:1767-1775 (2005)). Furthermore, Rho-kinase has been indicated as a drug target for the treatment of various other diseases, including airway inflammation and hyperresponsiveness (Henry, P. J. et al., *Pulm. Pharmacol Ther.*, 18:67-74 (2005)), cancer (Rattan, R. et al., *J. Neurosci. Res.*, 83:243-255 (2006); Lepley, D. et al., *Cancer Res.*, 65:3788-3795 (2005)), fibrotic diseases (Jiang, C. et al., *Int. J. Mol. Sci.*, 13:8293-8307 (2012); Zhou, L. et al., *Am. J. Nephrol.*, 34:468-475 (2011)), as well as neurological disorders, such as spinal-cord injury, Alzheimer's disease, multiple sclerosis, stroke and neuropathic pain (Mueller, B. K. et al., *Nat. Rev. Drug Disc.*, 4:387-398 (2005); Sun, X. et al., *J. Neuroimmunol.*, 180:126-134 (2006)).

There remains an unmet medical need for new drugs to treat cardiovascular disease. In the 2012 update of Heart Disease and Stroke Statistics from the American Heart Association (*Circulation*, 125:e2-e220 (2012)), it was reported that cardiovascular disease accounted for 32.8% of all deaths in the U.S., with coronary heart disease accounting for ~1 in 6 deaths overall in the U.S. Contributing to these numbers, it was found that ~33.5% of the adult U.S. population was hypertensive, and it was estimated that in 2010 ~6.6 million U.S. adults would have heart failure. Therefore, despite the number of medications available to treat cardiovascular diseases (CVD), including diuretics, beta blockers, angiotensin converting enzyme inhibitors, angiotensin blockers and calcium channel blockers, CVD remains poorly controlled or resistant to current medication for many patients.

Although there are many reports of ROCK inhibitors under investigation (see, for example, US 2012/0122842 A1, US 2010/0041645 A1, US 2008/0161297 A1, and Hu, E. et al., *Exp. Opin. Ther. Targets*, 9:715-736 (2005)), fasudil is the only marketed ROCK inhibitor at this time. An i.v. formulation was approved in Japan for treatment of cerebral vasospasm. There remains a need for new therapeutics, including ROCK inhibitors, for the treatment of cardiovascular diseases, cancer, neurological diseases, renal diseases, fibrotic diseases, bronchial asthma, erectile dysfunction, and glaucoma.

SUMMARY OF THE INVENTION

The present invention provides novel spirocycloheptanes, their analogues, including stereoisomers, tautomers, pharmaceutically-acceptable salts, or solvates thereof, which are useful as selective inhibitors of Rho kinases.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically-acceptable salts, or solvates thereof.

The compounds of the invention may be used in the treatment and/or prophylaxis of conditions associated with aberrant ROCK activity.

The compounds of the present invention may be used in therapy.

The compounds of the present invention may be used for the manufacture of a medicament for the treatment and/or prophylaxis of a condition associated with aberrant ROCK activity.

In another aspect, the present invention is directed to a method of treating a cardiovascular or related disease which method comprises administering to a patient in need of such treatment a compound of the present invention as described above. Examples of such diseases that may be treated include, for example, hypertension, atherosclerosis, restenosis, stroke, heart failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma, erectile dysfunction and glaucoma, which method comprises administering to a patient in need of such treatment a compound of the present invention as described above.

In another aspect, the present invention is directed to a method of treating diseases mediated at least partially by Rho kinase including fibrotic diseases, oncology, spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

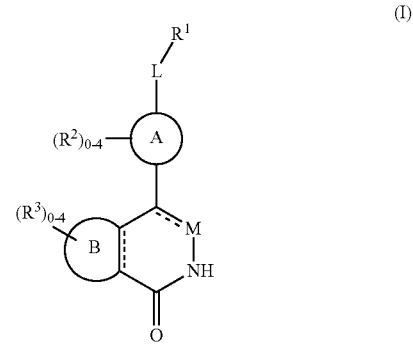

or stereoisomers, tautomers, pharmaceutically-acceptable salts, solvates, or prodrugs thereof, wherein:

Ring A is a 5- to 9-membered bicyclic spiro carbocycle;
Ring B is selected from a $C_{5-6}$ carbocycle and a 5- to 6-membered heterocycle;
- - - - is an optional bond;
M is absent or selected from N and $CR^{10}$;
L is selected from $—(CR^4R^4)_{0-1}—$, $—(CR^4R^4)_{0-1}C(O)—$, $—OC(O)—$, $—NR^6C(O)—$, and $—NR^6—$;
$R^1$ is selected from $NR^5R^5$, $OR^5$, $—(CR^4R^4)_nC_{3-10}$ carbocycle and $—(CR^4R^4)_n$-4- to 15-membered heterocycle comprising carbon atoms and 1-4 heteroatoms selected from N, $NR^8$, O, and $S(O)_p$; wherein said alkyl, carbocycle, and heterocycle are substituted with 1-4 $R^7$;
$R^2$, at each occurrence, is independently selected from halogen, $C_{1-6}$ alkyl, $C_{1-4}$ alkoxy, $C_{1-4}$ alkylthio, $C_{1-4}$ haloalkyl, $—OH$, $—CH_2OH$, $—OCH_2F$, $—OCHF_2$, —OCF$_3$, CN, —NH$_2$, —NH(C$_{1-4}$ alkyl), —N(C$_{1-4}$ alkyl)$_2$, —CO$_2$H, —CH$_2$CO$_2$H, —CO$_2$(C$_{1-4}$alkyl), —CO(C$_{1-4}$ alkyl), —CH$_2$NH$_2$, —CONH$_2$, —CONH(C$_{1-4}$ alkyl), —CON(C$_{1-4}$ alkyl)$_2$, —OCH$_2$CO$_2$H, —NHCO(C$_{1-4}$ alkyl), —NHCO$_2$(C$_{1-4}$ alkyl), —NHSO$_2$(C$_{1-4}$ alkyl), —SO$_2$NH$_2$, —C(=NH)NH$_2$, a carbocycle, and a heterocycle, wherein said alkyl, alkoxy, alkylthio, haloalkyl, carbocycle, and heterocycle are substituted with 0-4 R$^9$;

R$^3$, at each occurrence, is independently selected from halogen, C$_{1-6}$ alkyl, C$_{1-4}$ alkoxy, C$_{1-4}$ alkylthio, C$_{1-4}$ haloalkyl, —CH$_2$OH, —OCH$_2$F, —OCHF$_2$, —OCF$_3$, CN, —NH$_2$, —NH(C$_{1-4}$ alkyl), —N(C$_{1-4}$ alkyl)$_2$, —CO$_2$H, —CH$_2$CO$_2$H, —CO$_2$(C$_{1-4}$ alkyl), —CO(C$_{1-4}$ alkyl), —CH$_2$NH$_2$, —CONH$_2$, —CONH(C$_{1-4}$ alkyl), —CON(C$_{1-4}$ alkyl)$_2$, —OCH$_2$CO$_2$H, —NHCO(C$_{1-4}$ alkyl), —NHCO$_2$(C$_{1-4}$ alkyl), —NHSO$_2$(C$_{1-4}$ alkyl), —SO$_2$NH$_2$, —C(=NH)NH$_2$, a carbocycle, and a heterocycle, wherein said alkyl, alkoxy, alkylthio, haloalkyl, carbocycle, and heterocycle are substituted with 0-4 R$^9$;

R$^4$, at each occurrence, is independently selected from H, OH, NH$_2$, CH$_2$NH$_2$, C$_{1-4}$ haloalkyl, OCH$_2$F, OCHF$_2$, OCF$_3$, —NH(C$_{1-4}$ alkyl), —N(C$_{1-4}$ alkyl)$_2$, C$_{1-4}$ alkoxy, CH$_2$OH, CH$_2$O(C$_{1-4}$ alkyl), CH$_2$CO$_2$H, CH$_2$CO$_2$(C$_{1-4}$ alkyl), C$_{1-4}$ alkyl, a carbocycle, and a heterocycle, wherein said alkyl, alkoxy, haloalkyl, carbocycle, and heterocycle are substituted with 0-4 R$^9$;

R$^5$, at each occurrence, is independently selected from H, C$_{1-4}$ alkyl, —(CR$^6$R$^6$)$_n$—C$_{3-10}$ carbocycle and —(CR$^6$R$^6$)$_n$-4- to 10-membered heterocycle comprising carbon atoms and 1-4 heteroatoms selected from N, NR$^8$, O, and S(O)$_p$, wherein said alkyl, carbocycle and heterocycle are substituted with 1-4 R$^7$;

alternatively, R$^5$ and R$^5$ are taken together with the nitrogen atom to which they are attached to form a 4- to 15-membered heterocycle substituted with 1-4 R$^7$;

R$^6$, at each occurrence, is independently selected from H, C$_{1-4}$ alkyl, CH$_2$NH$_2$, C$_{1-4}$ haloalkyl, C$_{1-4}$ alkoxy, CH$_2$OH, CH$_2$O(C$_{1-4}$ alkyl), CH$_2$CO$_2$H, CH$_2$CO$_2$(C$_{1-4}$ alkyl), a carbocycle, and a heterocycle, wherein said alkyl, alkoxy, haloalkyl, carbocycle, and heterocycle are substituted with 0-4 R$^9$;

alternatively, R$^1$ and R$^6$ are taken together with the nitrogen atom to which they are attached to form a heterocycle comprising carbon atoms and 1-4 heteroatoms selected from N, NR$^8$, O, and S(O)$_p$ and substituted with 1-4 R$^7$;

R$^7$, at each occurrence, is independently selected from H, =O, NO$_2$, halogen, C$_{1-7}$ alkyl, C$_{1-4}$ alkyl, C$_{2-4}$ alkenyl, C$_{2-4}$ alkynyl, C$_{1-4}$ alkoxy, CN, OH, CHF$_2$, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCOH, —NHCO(C$_{1-4}$alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NR$^8$R$^8$, —NHSO$_2$(C$_{1-4}$ alkyl), —S(O)$_p$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —(CH$_2$)$_n$—CONR$^8$R$^8$, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxyl, carbocycle, and heterocycle are substituted with 0-4 R$^9$;

R$^8$, at each occurrence, is independently selected from H, C$_{1-6}$ alkyl, C$_{1-4}$ alkyl, C$_{2-4}$ alkenyl, C$_{2-4}$ alkynyl, —(CH$_2$)$_n$—C(O)C$_{1-4}$alkyl, —(CH$_2$)$_n$—C(O)carbocycle, —(CH$_2$)$_n$—C(O)heterocycle, —(CH$_2$)$_n$—C(O)NR$^a$R$^a$, —(CH$_2$)$_n$—NR$^a$C(O) C$_{1-4}$alkyl, —(CH$_2$)$_n$—C(O)O-alkyl, —(CH$_2$)$_n$—C(O)OC$_{1-4}$-alkyl, —(CH$_2$)$_n$—C(O)C$_{1-4}$ alkyl, —(CH$_2$)$_n$—C(O)O-carbocycle, —(CH$_2$)$_n$—C(O)O-heterocycle, —(CH$_2$)$_n$—SO$_2$alkyl, —(CH$_2$)$_n$SO$_2$carbocycle, —(CH$_2$)$_n$—SO$_2$heterocycle, —(CH$_2$)$_n$—SO$_2$NR$^a$R$^a$, —(CH$_2$)$_n$-carbocycle, and —(CH$_2$)$_n$-heterocycle, wherein said alkyl, carbocycle, and heterocycle are substituted with 0-4 R$^9$;

alternatively, R$^8$ and R$^8$ are taken together with the nitrogen atom to which they are attached to form a 4- to 10-membered heterocycle substituted with 0-4 R$^9$;

R$^9$, at each occurrence, is independently selected from halogen, OH, =O, CN, NO$_2$, CHF$_2$, CF$_3$, C$_{1-4}$ alkyl, C$_{1-4}$ alkoxy, CH$_2$OH, CO(C$_{1-4}$ alkyl), CO$_2$H, CO$_2$(C$_{1-4}$ alkyl), —(CHR$^{10}$)$_n$NR$^a$R$^a$, —(CHR$^{10}$)$_n$CONR$^a$R$^a$, —(CHR$^{10}$)$_n$NR$^a$CO(C$_{1-4}$ alkyl), —O(CHR$^{10}$)$_n$carbocycle, —O(CHR$^{10}$)$_n$heterocycle, —O(CHR$^{10}$)$_n$NR$^a$R$^a$, and —(CR$^{10}$R$^{10}$)$_n$-4- to 10-membered heterocycle, wherein said alkyl, alkoxy, carbocycle, and heterocycle are substituted with 0-4 R$^b$;

R$^{10}$ is selected from H and C$_{1-4}$ alkyl;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^2$; alternatively, R$^a$ and R$^a$ are taken together with the nitrogen atom to which they are attached to form a 4- to 10-membered heterocycle, wherein said alkyl, alkylene, and heterocycle are substituted with 0-4 R$^b$;

R$^b$, at each occurrence, is independently selected from =O, OH, halogen, C$_{1-4}$ alkyl, C$_{1-4}$ alkoxy, OCF$_3$, OC(O)C$_{1-4}$ alkyl, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —CONH—C$_{1-4}$ alkylene-N(C$_{1-4}$ alkyl)$_2$, —C$_{1-4}$ alkylene-O—P(O)(OH)$_2$, —NHCO$_2$(C$_{1-4}$ alkyl), —R$^c$, COR$^c$, CO$_2$R$^c$, and CONHR$^c$, wherein said alkyl and alkoxy are substituted with R$^d$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and a heterocycle containing carbon atoms and 1-4 heteroatoms selected from the group consisting of: N, NH, N(C$_{1-4}$ alkyl), O, and S(O)$_p$;

n, at each occurrence, is independently selected from 0, 1, 2, 3, and 4; and p, at each occurrence, is independently selected from 0, 1, and 2.

According to one particular embodiment of the present invention, the ring A corresponds to a 7-membered bicyclic spiro carbocycle, i.e., a spiro[3.3]heptan-2yl.

According to another particular embodiment of the present invention, the ring B corresponds to a 6-membered carbocycle or heterocycle; optionally unsubstituted 6 membered carbocycle or heterocycle. Typically, the ring B is selected in such way that the following structure

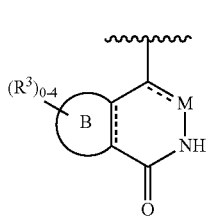

is selected from:

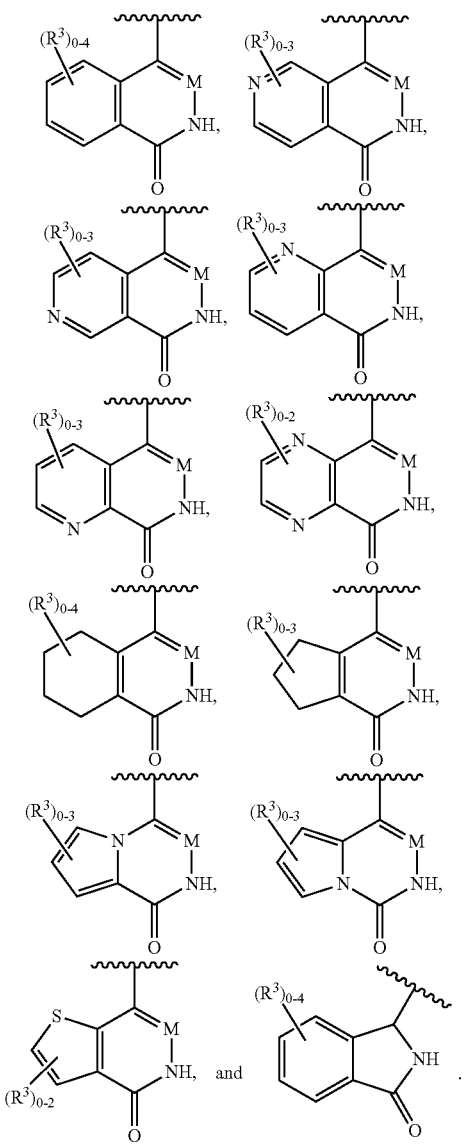

According to another particular embodiment of the present invention, M is an N moiety.

According to another particular embodiment of the present invention, L is selected from —OC(O)—, —NR⁶C(O)— and —NR⁶— and typically from —NR⁶C(O)— and —NR⁶—.

According to another particular embodiment of the present invention, R¹ is selected from NR⁵R⁵, OR⁵, —(CH₂)$_n$— C$_{3-10}$ carbocycle, and —(CH₂)$_n$-5- to 10-membered heterocycle, wherein said carbocycle and heterocycle are substituted with 1-4 R⁷. Typically, R¹ is selected from NR⁵R⁵ or heteroaryl substituted with 1-4 R⁷ particularly 5- to 10-membered heterocycle substituted with 1-4 R⁷. For example, R¹ may be selected from

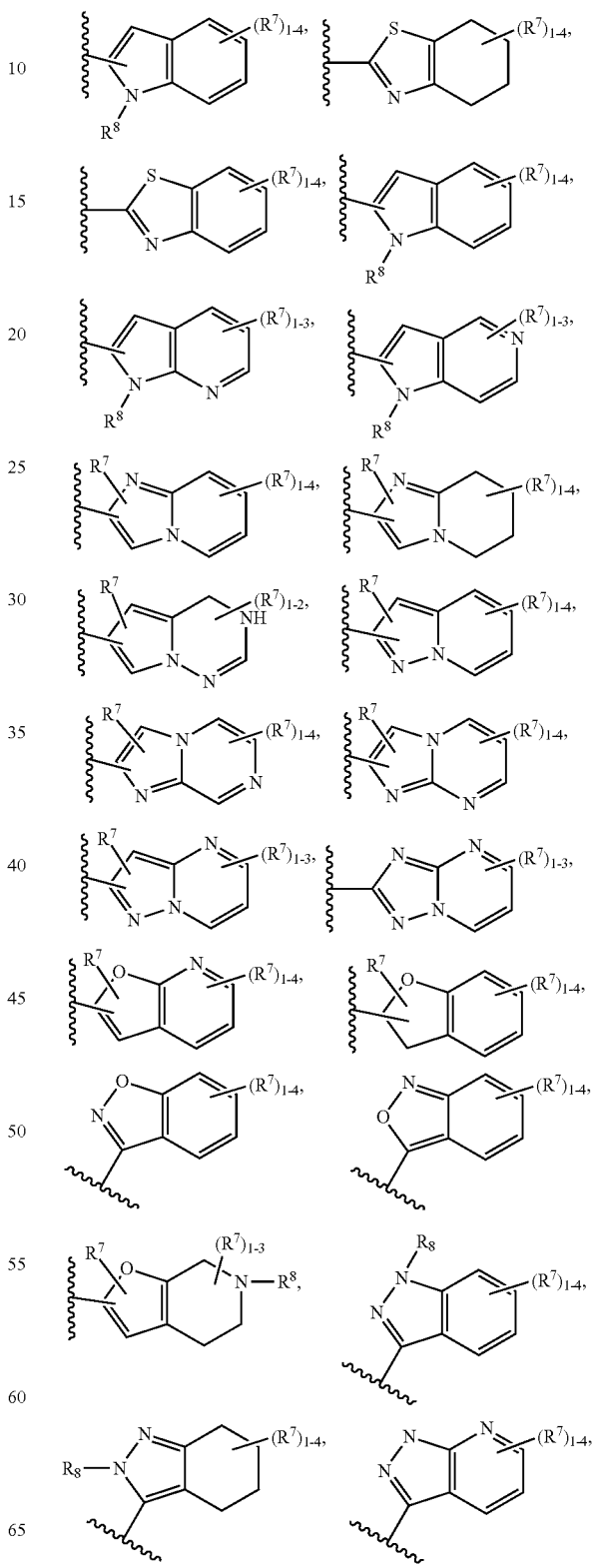

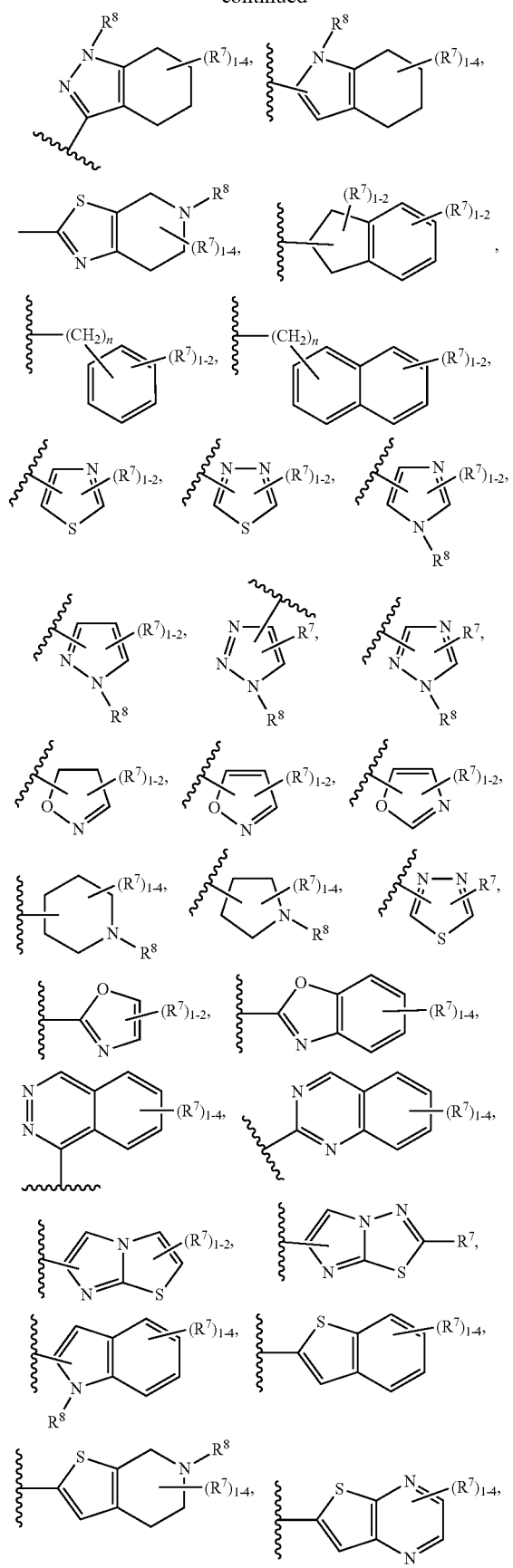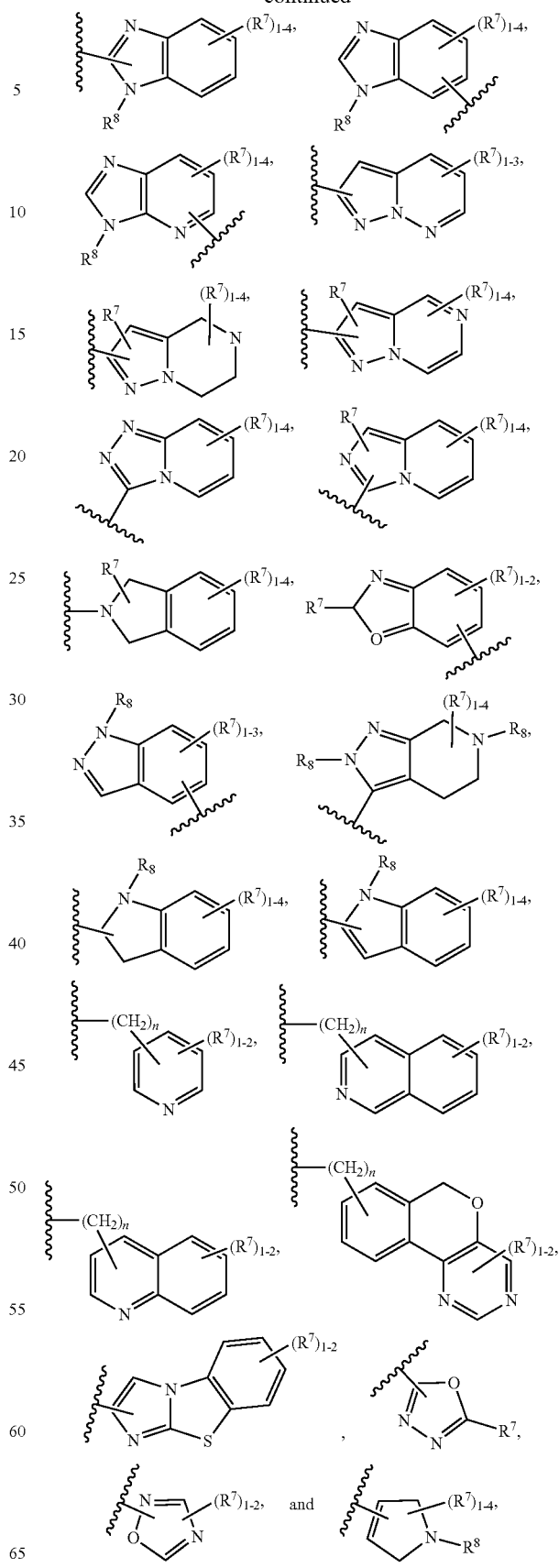

typically, from:

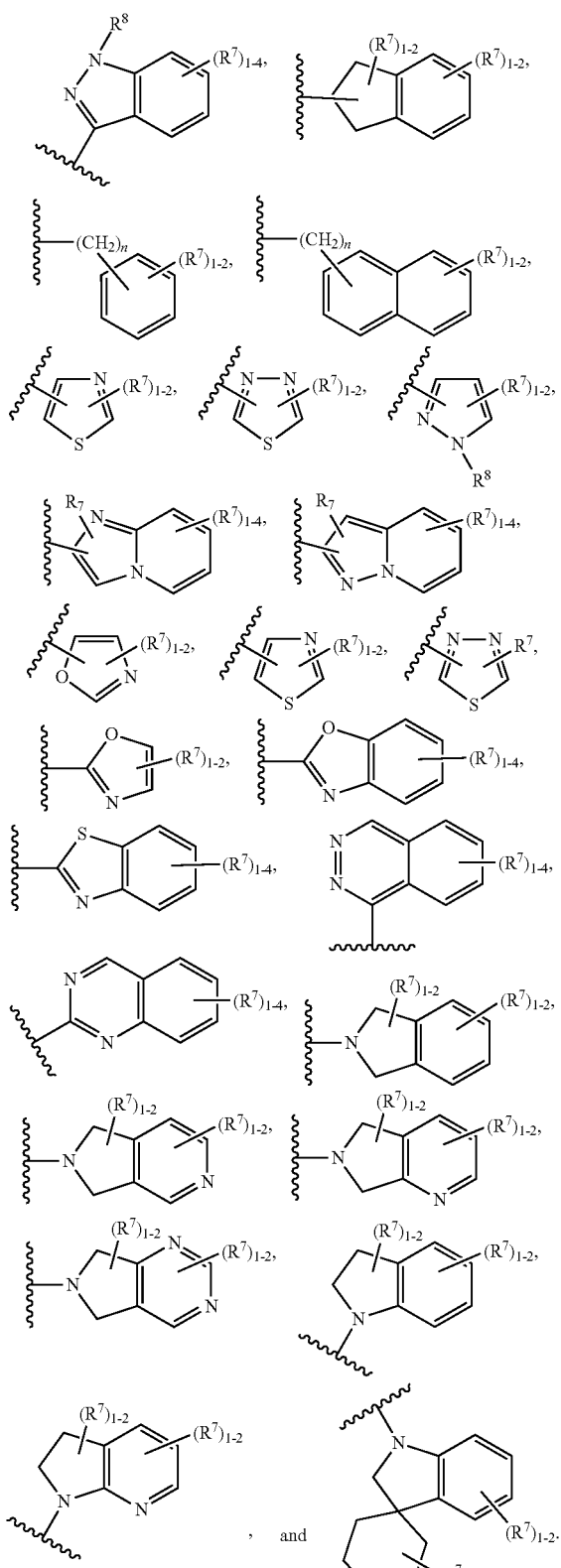

According to another particular embodiment of the present invention, R¹ is selected from

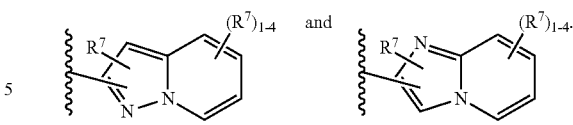

According to another embodiment of the present invention, $R^6$ is selected from H and $C_{1-4}$ alkyl and is typically H.

According to one further embodiment of the present invention, $R^7$ is selected from H, =O, halogen, F, Cl, Br, CN; OH, $CF_3$, $C_{1-4}$ alkyl, $C_{1-4}$ alkoxy, $-NR^8R^8$, $-(CH_2)_n-NR^8R^8$, $-(CH_2)_n-NR^8R^8$, $-NHSO_2(C_{1-4}$ alkyl), $-SO_2NH_2$, $-SO_2NH(C_{1-4}$ alkyl), $-SO_2N(C_{1-4}$ alkyl)$_2$, $-(CH_2)_n-CONR^8R^8$, $-(CH_2)_n$-phenyl and $-(CH_2)_n$-heterocycle or from

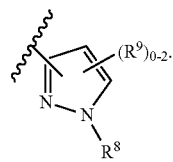

Typically, $R^7$ is selected from H, halogen, $C_{1-4}$ alkyl, $C_{1-4}$ alkoxy, CN, OH, $CF_3$, and $-NR^8R^8$.

According to another embodiment of the present invention, $R^8$ is independently selected from H, $CF_3$, $CD_3$, $CH_3$, $C(CH_3)_3$,

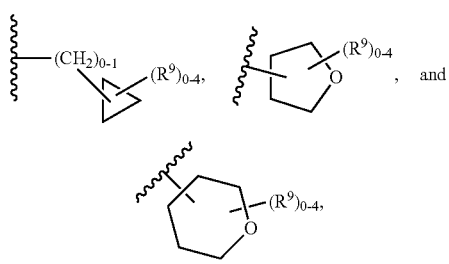

or alternatively $R^8$ and $R^8$ are taken together to form

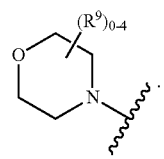

According to one further embodiment of the present invention, $R^9$ is independently selected from F, Cl, OH, $NO_2$, $CHF_2$, $(CH_2)_{0-2}CF_3$, $CD_3$, $CH_3$, $OC_{1-4}$ alkyl, $SO_2NH_2$ and phenyl substituted with $C_{1-4}$ alkyl. Alternatively, $R^9$ can be selected from $CF_3$, $C_{1-4}$ alkyl, $C_{1-4}$ alkoxy, $CH_2OH$, $CO_2H$, $CO_2(C_{1-4}$ alkyl), $CONH_2$, $-NH_2$, and a 4- to 10-membered heterocycle.

In another aspect, the present invention provides compounds of Formula (II):

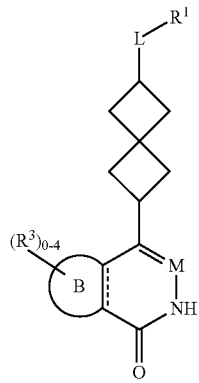

or stereoisomers, tautomers, pharmaceutically-acceptable salts, solvates, or prodrugs thereof, wherein:

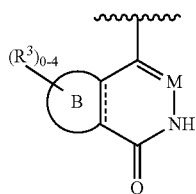

is selected from:

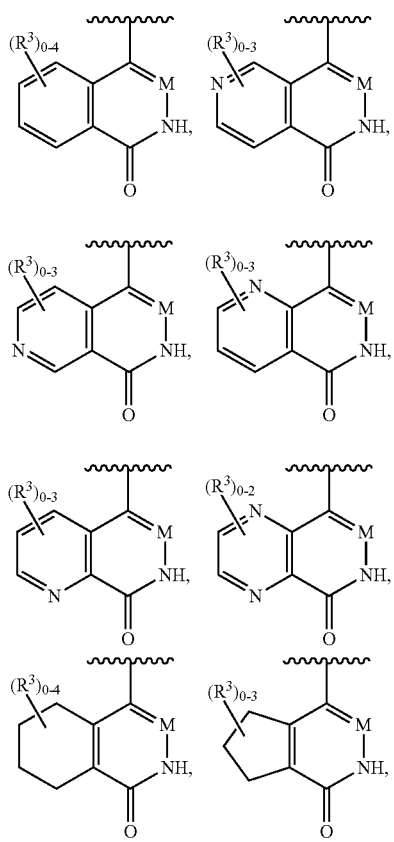

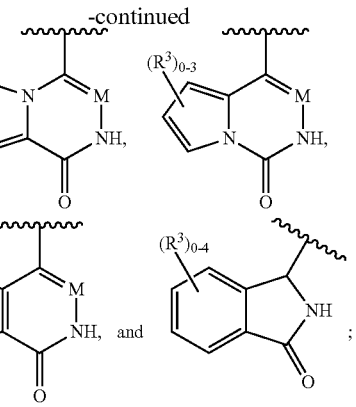

M is selected from N and $CR^{10}$;

L is selected from $-(CR^4R^4)_{0-1}-$, $-(CR^4R^4)_{0-1}C(O)-$, $-OC(O)-$, $-NR^6C(O)-$, and $-NR^6-$;

$R^1$ is selected from $NR^5R^5$, $OR^5$, $-(CR^4R^4)_n$ $C_{3-10}$ carbocycle and $-(CR^4R^4)_n$-4- to 15-membered heterocycle comprising carbon atoms and 1-4 heteroatoms selected from N, $NR^8$, O, and $S(O)_p$; wherein said alkyl, carbocycle, and heterocycle are substituted with 1-4 $R^7$;

$R^2$, at each occurrence, is independently selected from halogen, $C_{1-6}$ alkyl, $C_{1-4}$ alkoxy, $C_{1-4}$ alkylthio, $C_{1-4}$ haloalkyl, $-OH$, $-CH_2OH$, $-OCH_2F$, $-OCHF_2$, $-OCF_3$, CN, $-NH_2$, $-NH(C_{1-4}$ alkyl), $-N(C_{1-4}$ alkyl)$_2$, $-CO_2H$, $-CH_2CO_2H$, $-CO_2(C_{1-4}$ alkyl), $-CO(C_{1-4}$ alkyl), $-CH_2NH_2$, $-CONH_2$, $-CONH(C_{1-4}$ alkyl), $-CON(C_{1-4}$ alkyl)$_2$, $-OCH_2CO_2H$, $-NHCO(C_{1-4}$ alkyl), $-NHCO_2(C_{1-4}$ alkyl), $-NHSO_2(C_{1-4}$ alkyl), $-SO_2NH_2$, $-C(=NH)NH_2$, a carbocycle, and a heterocycle, wherein said alkyl, alkoxy, alkylthio, haloalkyl, carbocycle, and heterocycle are substituted with 0-4 $R^9$;

$R^3$, at each occurrence, is independently selected from halogen, $C_{1-6}$ alkyl, $C_{1-4}$ alkoxy, $C_{1-4}$ alkylthio, $C_{1-4}$ haloalkyl, $-CH_2OH$, $-OCH_2F$, $-OCHF_2$, $-OCF_3$, CN, $-NH_2$, $-NH(C_{1-4}$ alkyl), $-N(C_{1-4}$ alkyl)$_2$, $-CO_2H$, $-CH_2CO_2H$, $-CO_2(C_{1-4}$ alkyl), $-CO(C_{1-4}$ alkyl), $-CH_2NH_2$, $-CONH_2$, $-CONH(C_{1-4}$ alkyl), $-CON(C_{1-4}$ alkyl)$_2$, $-OCH_2CO_2H$, $-NHCO(C_{1-4}$ alkyl), $-NHCO_2$ $(C_{1-4}$ alkyl), $-NHSO_2(C_{1-4}$ alkyl), $-SO_2NH_2$, $-C(=NH)NH_2$, a carbocycle, and a heterocycle, wherein said alkyl, alkoxy, alkylthio, haloalkyl, carbocycle, and heterocycle are substituted with 0-4 $R^9$;

$R^4$, at each occurrence, is independently selected from H, OH, $NH_2$, $CH_2NH_2$, $C_{1-4}$ haloalkyl, $OCH_2F$, $OCHF_2$, $OCF_3$, $-NH(C_{1-4}$ alkyl), $-N(C_{1-4}$ alkyl)$_2$, $C_{1-4}$ alkoxy, $CH_2OH$, $CH_2O(C_{1-4}$ alkyl), $CH_2CO_2H$, $CH_2CO_2(C_{1-4}$ alkyl), $C_{1-4}$ alkyl, a carbocycle, and a heterocycle, wherein said alkyl, alkoxy, haloalkyl, carbocycle, and heterocycle are substituted with 0-4 $R^9$;

$R^5$, at each occurrence, is independently selected from H, $C_{1-4}$ alkyl, $-(CR^6R^6)_n-C_{3-10}$ carbocycle and $-(CR^6R^6)_n$-4- to 10-membered heterocycle comprising carbon atoms and 1-4 heteroatoms selected from N, $NR^8$, O, and $S(O)_p$, wherein said alkyl, carbocycle and heterocycle are substituted with 1-4 $R^7$;

alternatively, $R^5$ and $R^5$ are taken together with the nitrogen atom to which they are attached to form a 4- to 15-membered substituted with 1-4 $R^7$;

$R^6$, at each occurrence, is independently selected from H, $C_{1-4}$ alkyl, $CH_2NH_2$, $C_{1-4}$ haloalkyl, $C_{1-4}$ alkoxy, $CH_2OH$, $CH_2O(C_{1-4}$ alkyl), $CH_2CO_2H$, $CH_2CO_2(C_{1-4}$ alkyl), a carbocycle, and a heterocycle, wherein said alkyl, alkoxy, haloalkyl, carbocycle, and heterocycle are substituted with 0-4 $R^9$;

alternatively, $R^1$ and $R^6$ are taken together with the nitrogen atom to which they are attached to form a heterocycle comprising carbon atoms and 1-4 heteroatoms selected from N, $NR^8$, O, and $S(O)_p$ and substituted with 1-4 $R^7$;

$R^7$, at each occurrence, is independently selected from H, =O, $NO_2$, halogen, $C_{1-6}$ alkyl, $C_{1-4}$ alkyl, $C_{2-4}$ alkenyl, $C_{1-4}$ alkoxy, CN, OH, $CF_3$, —$(CH_2)_n$—$CO_2H$, —$(CH_2)_n$—$CO_2$ ($C_{1-4}$ alkyl), —$(CH_2)_n$—$NR^8R^8$, —NHCOH, —NHCO($C_{1-4}$ alkyl), —$NHCOCF_3$, —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl)$_2$, —$NHCO_2CH_2CO_2H$, —$CH_2NHCO_2(C_{1-4}$ alkyl), —NHC(O)$NR^8R^8$, —$NHSO_2(C_{1-4}$ alkyl), —$S(O)_p(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkoxyl, carbocycle, and heterocycle are substituted with 0-4 $R^9$;

$R^8$, at each occurrence, is independently selected from H, $C_{1-4}$ alkyl, $C_{2-4}$ alkenyl, $C_{2-4}$ alkynyl, —$(CH_2)_n$—$C(O)C_{1-4}$alkyl, —$(CH_2)_n$—C(O)carbocycle, —$(CH_2)_n$—C(O)heterocycle, —$(CH_2)_n$—$C(O)NR^aR^a$, —$(CH_2)_n$—$NR^aC(O)C_{1-4}$alkyl, —$(CH_2)_n$—C(O)O $C_{1-4}$alkyl, —$(CH_2)_n$—C(O) $C_{1-4}$alkyl, —$(CH_2)_n$—C(O)O-carbocycle, —$(CH_2)_n$—C(O)O-heterocycle, —$(CH_2)_n$—$SO_2$alkyl, —$(CH_2)_n$—$SO_2$carbocycle, —$(CH_2)_n$—$SO_2$heterocycle, —$(CH_2)_n$—$SO_2NR^aR^a$, —$(CH_2)_n$-carbocycle, and —$(CH_2)_n$-heterocycle, wherein said alkyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, =O, CN, $NO_2$, $CHF_2$, $CF_3$, $C_{1-4}$ alkyl, $C_{1-4}$ alkoxy, $CH_2OH$, $CO(C_{1-4}$ alkyl), $CO_2H$, $CO_2(C_{1-4}$ alkyl), —$(CHR^{10})_n NR^aR^a$, —$(CHR^{10})_n CONR^aR^a$, —$(CHR^{10})_n NR^aCO(C_{1-4}$ alkyl), —$O(CHR^{10})_n$carbocycle, —$O(CHR^{10})_n$heterocycle, —$O(CHR^{10})_n NR^aR^a$, and —$(CR^{10}R^{10})_n$-4- to 10-membered heterocycle, wherein said alkyl, alkoxy, carbocycle, and heterocycle are substituted with 0-4 $R^b$;

$R^{10}$ is selected from H and $C_{1-4}$ alkyl;

$R^a$, at each occurrence, is independently selected from H, $C_{1-4}$ alkyl, —$(CH_2)_nOH$, $CO(C_{1-4}$ alkyl), $COCF_3$, $CO_2(C_{1-4}$ alkyl), —$CONH_2$, —CONH—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, OH, halogen, $C_{1-4}$ alkyl, $C_{1-4}$ alkoxy, $OCF_3$, OC(O) $C_{1-4}$ alkyl, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —CONH ($C_{1-4}$ alkyl), —CON($C_{1-4}$ alkyl)$_2$, —CONH—$C_{1-4}$ alkylene-O($C_{1-4}$ alkyl), —CONH—$C_{1-4}$ alkylene-N($C_{1-4}$ alkyl)$_2$, —CONH—$C_{1-4}$ alkylene-N($C_{1-4}$ alkyl)$_2$, —$C_{1-4}$ alkylene-O—P(O)(OH)$_2$, —$NHCO_2(C_{1-4}$ alkyl), —$R^c$, $COR^c$, $CO_2R^c$, and $CONHR^c$, wherein said alkyl and alkoxy are substituted with $R^d$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, N($C_{1-4}$ alkyl), O, and $S(O)_p$; wherein each ring moiety is substituted with 0-2 $R^d$;

$R^d$, at each occurrence, is independently selected from =O, halogen, —OH, $C_{1-4}$ alkyl, $NH_2$, $NH(C_{1-4}$ alkyl), $N(C_{1-4}$ alkyl)$_2$, $C_{1-4}$ alkoxy, and —$NHCO(C_{1-4}$ alkyl), and a heterocycle containing carbon atoms and 1-4 heteroatoms selected from the group consisting of: N, NH, $N(C_{1-4}$ alkyl), O, and $S(O)_p$;

n, at each occurrence, is independently selected from 0, 1, 2, 3, and 4; and p, at each occurrence, is independently selected from 0, 1, and 2.

In another aspect, the present invention provides compounds of Formula (III):

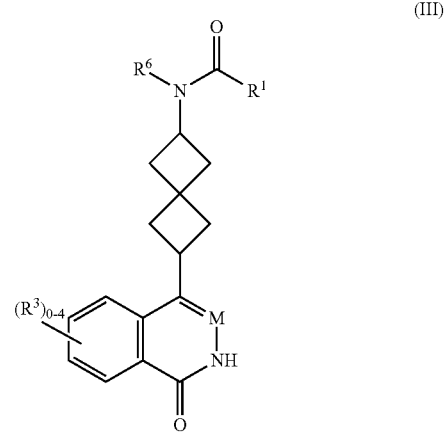

(III)

or stereoisomers, tautomers, pharmaceutically-acceptable salts, solvates, or prodrugs thereof, wherein:

M is selected from N and $CR^{19}$;

$R^1$ is selected from $NR^5R^5$, $OR^5$, —$(CH_2)_n$—$C_{3-10}$ carbocycle, and —$(CH_2)_n$-5- to 10-membered heterocycle, wherein said carbocycle and heterocycle are substituted with 1-4 $R^7$;

$R^5$, at each occurrence, is independently selected from H, $C_{1-4}$ alkyl, —$(CR^6R^6)_n$—$C_{3-10}$ carbocycle, and —$(CR^6R^6)_n$-4- to 10-membered heterocycle comprising carbon atoms and 1-4 heteroatoms selected from N, $NR^8$, O, and $S(O)_p$, wherein said alkyl, carbocycle, and heterocycle are substituted with 1-4 $R^7$;

alternatively, $R^5$ and $R^5$ are taken together with the nitrogen atom to which they are attached to form a 4- to 10-membered heterocycle substituted with 1-4 $R^7$;

$R^6$, at each occurrence, is independently selected from H and $C_{1-4}$ alkyl;

$R^7$, at each occurrence, is independently selected from H, =O, $NO_2$, halogen, $C_{1-6}$ alkyl, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —NHCOH, —NHCO($C_{1-4}$ alkyl), —$NHCOCF_3$, —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl)$_2$, —$NHCO_2CH_2CO_2H$, —$CH_2NHCO_2(C_{1-4}$ alkyl), —NHC(O)$NR^8R^8$, —$NHSO_2(C_{1-4}$ alkyl), —$S(O)_p(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —(CH₂)ₙ—CONR⁸R⁸, —O(CH₂)ₙ-carbocycle, —O(CH₂)ₙ-heterocycle, —NHCO-carbocycle, —NHCO-heterocycle, —(CH₂)ₙ-carbocycle, and —(CH₂)ₙ-heterocycle comprising carbon atoms and 1-4 heteroatoms selected from N, NR⁸, O, and S(O)ₚ, wherein said alkyl, alkenyl, alkynyl, alkoxyl, carbocycle, and heterocycle are substituted with 0-4 R⁹;

R⁸, at each occurrence, is independently selected from H, C₁₋₄ alkyl, C₂₋₄ alkenyl, C(O)C₁₋₄alkyl, C(O)carbocycle, C(O)heterocycle, —(CH₂)ₙ—C(O)NRᵃRᵃ, —(CH₂)ₙ—NHC(O)C₁₋₄alkyl, C(O)OC₁₋₄alkyl, C(O)O-carbocycle, C(O)O-heterocycle, SO₂alkyl, SO₂carbocycle, SO₂heterocycle, SO₂NRᵃRᵃ, —(CH₂)ₙ-carbocycle, and —(CH₂)ₙ-heterocycle, wherein said alkyl, alkenyl, carbocycle, and heterocycle are substituted with 0-4 R⁹;

R⁹, at each occurrence, is independently selected from halogen, OH, CN, NO₂, CHF₂, CF₃, C₁₋₄ alkyl, C₁₋₄ alkoxy, CH₂OH, CO(C₁₋₄ alkyl), CO₂H, CO₂(C₁₋₄ alkyl), —(CHR¹⁰)ₙNRᵃRᵃ, —(CHR¹⁰)ₙCONRᵃRᵃ, —(CHR¹⁰)ₙNRᵃCO(C₁₋₄ alkyl), —O(CHR¹⁰)ₙcarbocycle, —O(CHR¹⁰)ₙheterocycle, —O(CHR¹⁰)ₙNRᵃRᵃ, and —(CR¹⁰R¹⁰)ₙ-4- to 10-membered heterocycle, wherein said alkyl, alkoxy, carbocycle, and heterocycle are substituted with 0-4 Rᵇ;

R¹⁰ is selected from H and C₁₋₄ alkyl;

Rᵃ, at each occurrence, is independently selected from H, C₁₋₄ alkyl, —(CH₂)ₙOH, CO(C₁₋₄ alkyl), COCF₃, CO₂(C₁₋₄ alkyl), —CONH₂, —CONH—C₁₋₄ alkylene-CO₂(C₁₋₄ alkyl), C₁₋₄ alkylene-CO₂(C₁₋₄ alkyl), Rᶜ, CO₂Rᶜ, and CONHRᶜ; alternatively, Rᵃ and Rᵃ are taken together with the nitrogen atom to which they are attached to form a 4- to 10-membered heterocycle, wherein said alkyl, alkylene, and heterocycle are substituted with 0-4 Rᵇ;

Rᵇ, at each occurrence, is independently selected from =O, halogen, C₁₋₄ alkyl, C₁₋₄ alkoxy, OCF₃, OC(O)C₁₋₄ alkyl, NH₂, NO₂, N(C₁₋₄ alkyl)₂, CO(C₁₋₄ alkyl), CO(C₁₋₄ haloalkyl), CO₂(C₁₋₄ alkyl), CONH₂, —CONH(C₁₋₄ alkyl), —CON(C₁₋₄ alkyl)₂, —CONH—C₁₋₄ alkylene-O(C₁₋₄ alkyl), —CONH—C₁₋₄ alkylene-N(C₁₋₄ alkyl)₂, —CONH—C₁₋₄ alkylene-N(C₁₋₄ alkyl)₂, —C₁₋₄ alkylene-O—P(O)(OH)₂, —NHCO₂(C₁₋₄ alkyl), —Rᶜ, CORᶜ, CO₂Rᶜ, and CONHRᶜ, wherein said alkyl and alkoxy are substituted with Rᵈ;

Rᶜ, at each occurrence, is independently selected from —(CH₂)ₙ—C₃₋₆ cycloalkyl, —(CH₂)ₙ-phenyl, and —(CH₂)ₙ-5- to 6-membered heterocycle containing carbon atoms and 1-4 heteroatoms selected from the group consisting of: N, NH, N(C₁₋₄ alkyl), O, and S(O)ₚ; wherein each ring moiety is substituted with 0-2 Rᵈ;

Rᵈ, at each occurrence, is independently selected from =O, halogen, —OH, C₁₋₄ alkyl, NH₂, NH(C₁₋₄ alkyl), N(C₁₋₄ alkyl)₂, C₁₋₄ alkoxy, and —NHCO(C₁₋₄ alkyl), and a heterocycle containing carbon atoms and 1-4 heteroatoms selected from the group consisting of: N, NH, N(C₁₋₄ alkyl), O, and S(O)ₚ;

n, at each occurrence, is independently selected from 0, 1, 2, 3, and 4;

p, at each occurrence, is independently selected from 0, 1, and 2; and other variables are as defined in Formula (II) above.

In another aspect, the present invention provides compounds of Formula (IV):

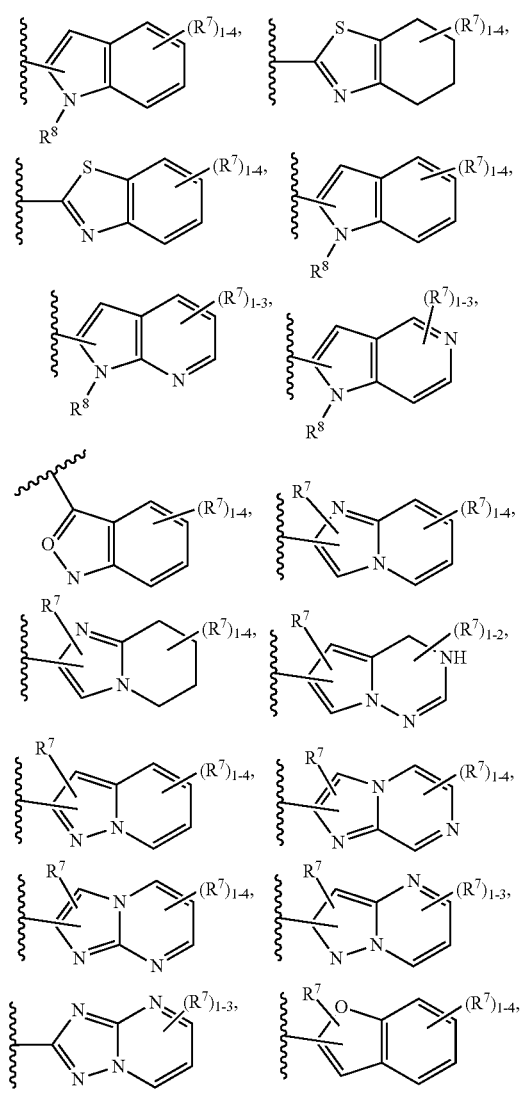

(IV)

or stereoisomers, tautomers, pharmaceutically-acceptable salts, solvates, or prodrugs thereof, wherein:

R¹ is selected from

-continued

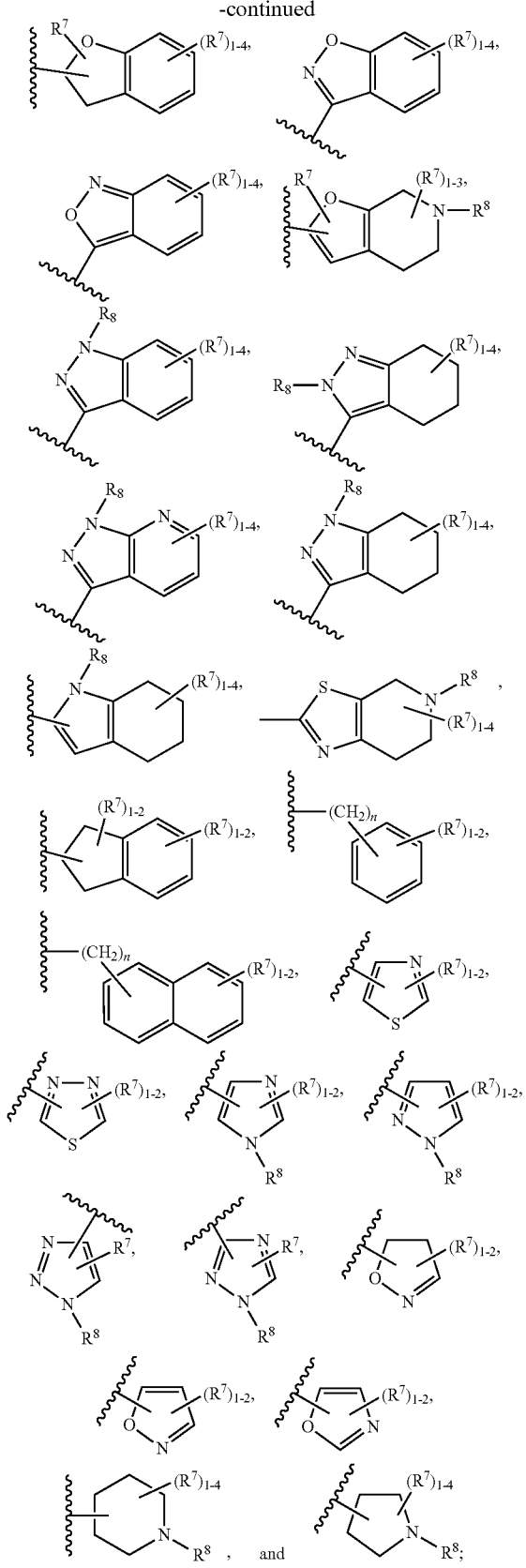

$R^7$, at each occurrence, is independently selected from H, =O, $NO_2$, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$NHCO(C_{1-4}$ alkyl), —$NHCOCF_3$, —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl)$_2$, —$NHCO_2CH_2CO_2H$, —$CH_2NHCO_2(C_{1-4}$ alkyl), —$NHC(O)NR^8R^8$, —$NHSO_2(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxyl, carbocycle, and heterocycle are substituted with 0-4 $R^9$;

$R^8$, at each occurrence, is independently selected from H, $C_{1-4}$ alkyl, $C(O)C_{1-4}$alkyl, $C(O)$carbocycle, $C(O)$heterocycle, —$(CH_2)_n$—$C(O)NR^aR^a$, $C(O)OC_{1-4}$alkyl, $C(O)O$-carbocycle, $C(O)O$-heterocycle, $SO_2$alkyl, $SO_2$carbocycle, $SO_2$heterocycle, $SO_2NR^aR^a$, —$(CH_2)_n$-carbocycle, and —$(CH_2)_n$-heterocycle, wherein said alkyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, CN, $NO_2$, $CHF_2$, $CF_3$, $C_{1-4}$ alkyl, $C_{1-4}$ alkoxy, $CH_2OH$, $CO_2H$, $CO_2(C_{1-4}$ alkyl), $CONH_2$, —$(CH_2)_nNR^aR^a$, —$(CH_2)_nCONR^aR^a$, —$(CH_2)_nNHCO(C_{1-4}$ alkyl), —$O(CH_2)_n$heterocycle, —$O(CH_2)_{2-4}NR^aR^a$, and —$(CR^{10}R^{10})_n$-4- to 10-membered heterocycle, wherein said alkyl, alkoxyl, carbocycle, and heterocycle are substituted with 0-4 $R^b$;

$R^a$, at each occurrence, is independently selected from H and $C_{1-4}$ alkyl; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, halogen, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl)$_2$, —CONH—$C_{1-4}$ alkylene-$O(C_{1-4}$ alkyl), —CONH—$C_{1-4}$ alkylene-$N(C_{1-4}$ alkyl)$_2$, —CONH—$C_{1-4}$ alkylene-$N(C_{1-4}$ alkyl)$_2$, and —$NHCO_2(C_{1-4}$ alkyl): and other variables are as defined in Formula (II) above.

In another aspect, the present invention provides compounds of Formula (IV) or stereoisomers, tautomers, pharmaceutically-acceptable salts, solvates, or prodrugs thereof, wherein:

$R^1$ is selected from

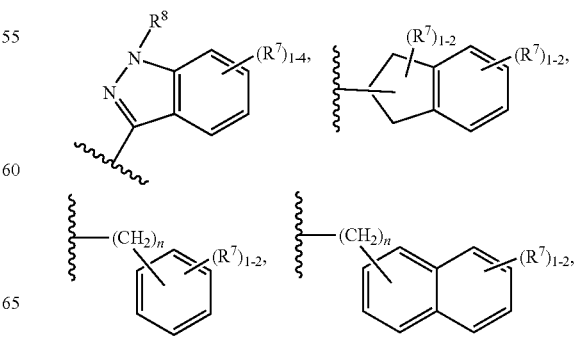

-continued

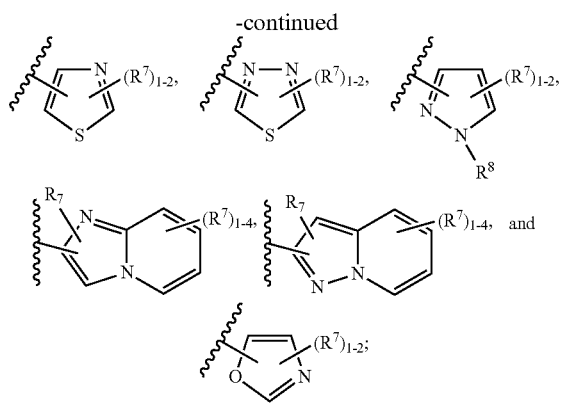

R[7], at each occurrence, is independently selected from H, halogen, $C_{1-4}$ alkyl, $C_{1-4}$ alkoxy, —NR[8]R[8], $C_{3-6}$ cycloalkyl, phenyl, and —(CH$_2$)$_n$-heterocycle comprising carbon atoms and 1-4 heteroatoms selected from N, NR[8], O, and S(O)$_p$, wherein said alkyl, alkenyl, alkynyl, alkoxyl, carbocycle, and heterocycle are substituted with 0-4 R[9];

R[8], at each occurrence, is independently selected from H, $C_{1-4}$ alkyl, —(CH$_2$)$_n$—$C_{3-6}$ cycloalkyl, —(CH$_2$)$_n$-phenyl, and —(CH$_2$)$_n$-heterocycle, wherein said alkyl, cycloalkyl, phenyl, and heterocycle are substituted with 0-4 R[9];

alternatively, R[8] and R[8] are taken together with the nitrogen atom to which they are attached to form a heterocycle selected from

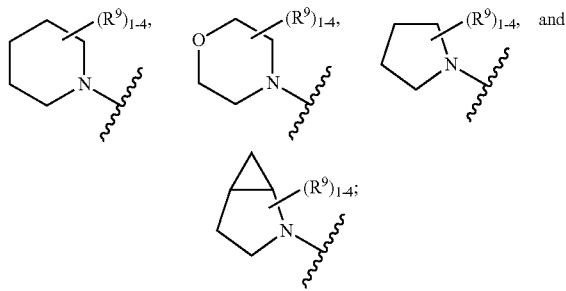

R[9], at each occurrence, is independently selected from F, Cl, OH, CN, $C_{1-4}$ alkyl, $C_{1-4}$ alkoxy, —(CH$_2$)$_n$NR$^a$R$^a$, and a 4- to 10-membered heterocycle, wherein said alkyl, alkoxyl, and heterocycle are substituted with 0-4 R$^b$;

R$^a$, at each occurrence, is independently selected from H, $C_{1-4}$ alkyl, —(CH$_2$)$_n$OH, CO($C_{1-4}$ alkyl), COCF$_3$, CO$_2$($C_{1-4}$ alkyl), —CONH$_2$, —CONH—$C_{1-4}$ alkylene-CO$_2$($C_{1-4}$ alkyl), and $C_{1-4}$ alkylene-CO$_2$($C_{1-4}$ alkyl);

R$^b$, at each occurrence, is independently selected from halogen, $C_{1-4}$ alkyl, $C_{1-4}$ alkoxy, OCF$_3$, NH$_2$, NO$_2$, N($C_{1-4}$ alkyl)$_2$, CO($C_{1-4}$ alkyl), CO($C_{1-4}$ haloalkyl), CO$_2$($C_{1-4}$ alkyl), CONH$_2$, —CONH($C_{1-4}$ alkyl), —CON($C_{1-4}$ alkyl)$_2$, —CONH—$C_{1-4}$ alkylene-O($C_{1-4}$ alkyl), —CONH—$C_{1-4}$ alkylene-N($C_{1-4}$ alkyl)$_2$, —CONH—$C_{1-4}$ alkylene-N($C_{1-4}$ alkyl)$_2$, —$C_{1-4}$ alkylene-O—P(O)(OH)$_2$, and —NHCO$_2$($C_{1-4}$ alkyl); and other variables are as defined in Formula (IV) above.

In another aspect, the present invention provides compounds of Formula (III) or stereoisomers, tautomers, pharmaceutically-acceptable salts, solvates, or prodrugs thereof, wherein:

R[1] is NR[5]R[5];

R[5] and R[5] are taken together with the nitrogen atom to which they are attached to form a 4- to 10-membered heterocycle substituted with 1-4 R[7];

R[7], at each occurrence, is independently selected from H, halogen, $C_{1-4}$ alkyl, $C_{1-4}$ alkoxy, CN, OH, CF$_3$, and —NR[8]R[8];

R[8], at each occurrence, is independently selected from H and $C_{1-4}$ alkyl; and other variables are as defined in Formula (III) above.

In still another aspect, the present invention provides compounds of Formula (V):

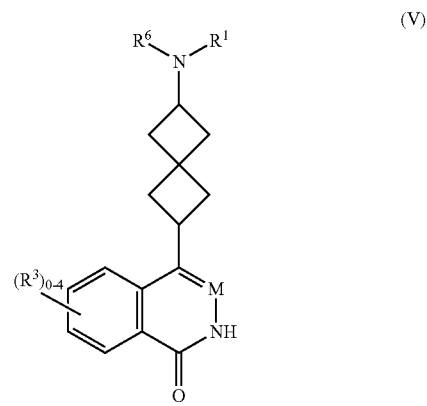

(V)

or stereoisomers, tautomers, pharmaceutically-acceptable salts, solvates, or prodrugs thereof, wherein:

M is selected from N and CR[10];

R[1] is heteroaryl substituted with 1-4 R[7];

R[6], at each occurrence, is independently selected from H and $C_{1-4}$ alkyl;

R[7], at each occurrence, is independently selected from H, =O, NO$_2$, halogen, $C_{1-4}$ alkyl, $C_{1-4}$ alkoxy, CN, OH, CF$_3$, —(CH$_2$)$_n$—CO$_2$H, —(CH$_2$)$_n$—CO$_2$($C_{1-4}$ alkyl), —(CH$_2$)$_n$—NR[8]R[8], —NHCO($C_{1-4}$ alkyl), —NHCOCF$_3$, —NHCO$_2$($C_{1-4}$ alkyl), —NHCO$_2$(CH$_2$)$_2$O($C_{1-4}$ alkyl), —NHCO$_2$(CH$_2$)$_3$O($C_{1-4}$ alkyl), —NHCO$_2$(CH$_2$)$_2$OH, —NHCO$_2$(CH$_2$)$_2$NH$_2$, —NHCO$_2$(CH$_2$)$_2$N($C_{1-4}$ alkyl)$_2$, —NHCO$_2$CH$_2$CO$_2$H, —CH$_2$NHCO$_2$($C_{1-4}$ alkyl), —NHC(O)NR[8]R[8], —NHSO$_2$($C_{1-4}$ alkyl), —SO$_2$NH$_2$, —SO$_2$NH($C_{1-4}$ alkyl), —SO$_2$N($C_{1-4}$ alkyl)$_2$, —SO$_2$NH(CH$_2$)$_2$OH, —SO$_2$NH(CH$_2$)$_2$O($C_{1-4}$ alkyl), —(CH$_2$)$_n$—CONR[8]R[8], —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR[8], O, and S(O)$_p$, wherein said alkyl, alkenyl, alkynyl, alkoxyl, carbocycle, and heterocycle are substituted with 0-4 R[9];

R[8], at each occurrence, is independently selected from H, $C_{1-4}$ alkyl, —(CH$_2$)$_n$-carbocycle, and —(CH$_2$)$_n$-heterocycle, wherein said alkyl, carbocycle, and heterocycle are substituted with 0-4 R[9];

R[9], at each occurrence, is independently selected from halogen, OH, CN, NO$_2$, CHF$_2$, CF$_3$, $C_{1-4}$ alkyl, $C_{1-4}$ alkoxy, CH$_2$OH, CO($C_{1-4}$ alkyl), CO$_2$H, CO$_2$($C_{1-4}$ alkyl), —(CHR[10])$_n$NR$^a$R$^a$, —(CHR[10])$_n$CONR$^a$R$^a$, —(CHR[10])$_n$NR$^a$CO($C_{1-4}$ alkyl), —O(CHR[10])$_n$carbocycle, —O(CHR[10])$_n$heterocycle, —O(CHR[10])$_n$NR$^a$R$^a$, and —(CR[10]R[10])$_n$-4- to 10-membered heterocycle, wherein said alkyl, alkoxy, carbocycle, and heterocycle are substituted with 0-4 R$^b$;

R[10] is selected from H and $C_{1-4}$ alkyl;

$R^a$, at each occurrence, is independently selected from H, $C_{1-4}$ alkyl, —$(CH_2)_nOH$, $CO(C_{1-4}$ alkyl), $COCF_3$, $CO_2(C_{1-4}$ alkyl), —$CONH_2$, —$CONH$—$C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, halogen, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl)$_2$, —$CONH$—$C_{1-4}$ alkylene-$O(C_{1-4}$ alkyl), —$CONH$—$C_{1-4}$ alkylene-$N(C_{1-4}$ alkyl)$_2$, —$CONH$—$C_{1-4}$ alkylene-$N(C_{1-4}$ alkyl)$_2$, —$C_{1-4}$ alkylene-$O$—$P(O)(OH)_2$, —$NHCO_2(C_{1-4}$ alkyl), —$R^c$, $COR^c$, $CO_2R^c$, and $CONHR^c$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, $N(C_{1-4}$ alkyl), O, and $S(O)_p$; wherein each ring moiety is substituted with 0-2 $R^d$;

$R^d$, at each occurrence, is independently selected from =O, halogen, —OH, $C_{1-4}$ alkyl, $NH_2$, $NH(C_{1-4}$ alkyl), $N(C_{1-4}$ alkyl)$_2$, $C_{1-4}$ alkoxy, and —$NHCO(C_{1-4}$ alkyl), and a heterocycle containing carbon atoms and 1-4 heteroatoms selected from the group consisting of: N, NH, $N(C_{1-4}$ alkyl), O, and $S(O)_p$;

n, at each occurrence, is independently selected from 0, 1, 2, 3, and 4;

p, at each occurrence, is independently selected from 0, 1, and 2; and other variables are as defined in Formula (II) above.

In still another aspect, the present invention provides compounds of Formula (VI):

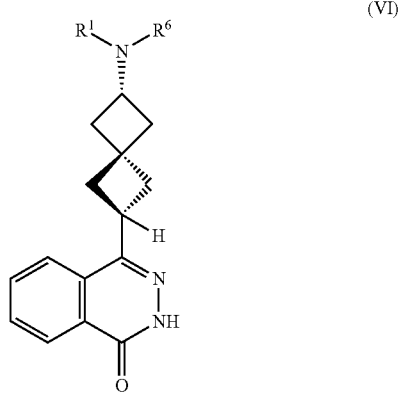

(VI)

or stereoisomers, tautomers, pharmaceutically-acceptable salts, solvates, or prodrugs thereof, wherein:

$R^1$ is selected from

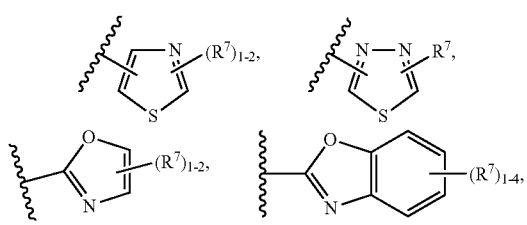

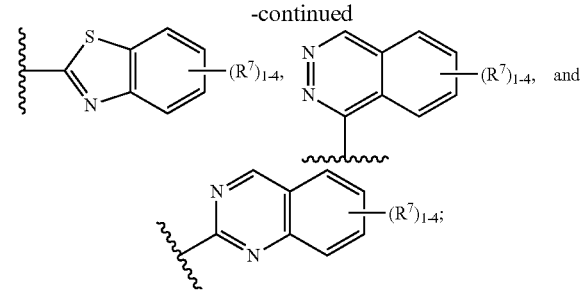

$R^6$ is H; and $R^7$, at each occurrence, is independently selected from H, halogen, $C_{1-4}$ alkyl, $C_{1-4}$ alkoxy, CN, OH, —$(CH_2)_n$-carbocycle, and —$(CH_2)_n$-heterocycle, wherein said alkyl, alkoxyl, carbocycle, and heterocycle are substituted with 0-4 $R^9$.

In still another aspect, the present invention provides compounds of Formula (VII):

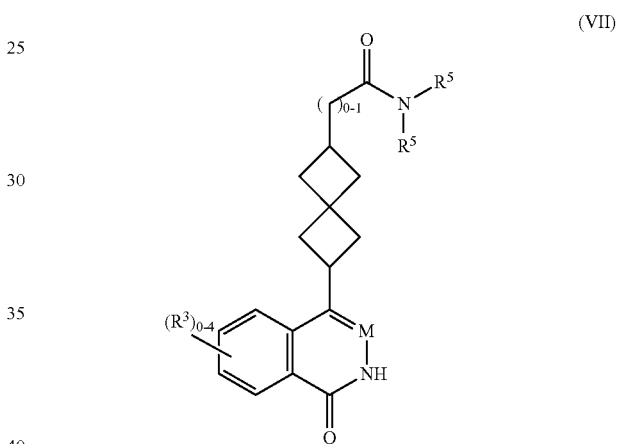

(VII)

or stereoisomers, tautomers, pharmaceutically-acceptable salts, solvates, or prodrugs thereof, wherein:

M is selected from N and $CR^{19}$;

$R^5$, at each occurrence, is independently selected from H, $C_{1-4}$ alkyl, —$(CR^6R^6)_n$—$C_{3-10}$ carbocycle, and —$(CR^6R^6)_n$-4 to 10-membered heterocycle comprising carbon atoms and 1-4 heteroatoms selected from N, $NR^8$, O, and $S(O)_p$, wherein said alkyl, carbocycle, and heterocycle are substituted with 1-4 $R^7$;

alternatively, $R^5$ and $R^5$ are taken together with the nitrogen atom to which they are attached to form a 4- to 10-membered heterocycle substituted with 1-4 $R^7$;

$R^7$, at each occurrence, is independently selected from H, =O, $NO_2$, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$NHCO(C_{1-4}$ alkyl), —$NHCOCF_3$, —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl)$_2$, —$NHCO_2CH_2CO_2H$, —$CH_2NHCO_2(C_{1-4}$ alkyl), —$NHC(O)NR^8R^8$, —$NHSO_2(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxyl, carbocycle, and heterocycle are substituted with 0-4 $R^9$;

$R^8$, at each occurrence, is independently selected from H, $C_{1-4}$ alkyl, $C(O)C_{1-4}$alkyl, C(O)carbocycle, C(O)heterocycle, —$(CH_2)$—$C(O)NR^aR^a$, $C(O)OC_{1-4}$ alkyl, C(O)O-carbocycle, C(O)O-heterocycle, $SO_2$alkyl, $SO_2$carbocycle, $SO_2$heterocycle, $SO_2NR^aR^a$, —$(CH_2)_n$-carbocycle, and —$(CH_2)_n$-heterocycle, wherein said alkyl, carbocycle, and heterocycle are substituted with 0-4 $R^9$;

$R^9$, at each occurrence, is independently selected from halogen, OH, CN, $NO_2$, $CHF_2$, $CF_3$, $C_{1-4}$ alkyl, $C_{1-4}$ alkoxy, $CH_2OH$, $CO(C_{1-4}$ alkyl), $CO_2H$, $CO_2(C_{1-4}$ alkyl), —$(CHR^{10})_n NR^a R^a$, —$(CHR^{10})_n$—$CONR^a R^a$, —$(CHR^{10})_n NR^a CO(C_{1-4}$ alkyl), —$O(CHR^{10})_n$carbocycle, —$O(CHR^{10})_n$heterocycle, —$O(CHR^{10})_n NR^a R^a$, and —$(CR^{10}R^{10})_n$-4- to 10-membered heterocycle, wherein said alkyl, alkoxy, carbocycle, and heterocycle are substituted with 0-4 $R^b$;

$R^{10}$ is selected from H and $C_{1-4}$ alkyl;

$R^a$, at each occurrence, is independently selected from H, $C_{1-4}$ alkyl, —$(CH_2)_n OH$, $CO(C_{1-4}$ alkyl), $COCF_3$, $CO_2(C_{1-4}$ alkyl), —$CONH_2$, —$CONH$—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form 4- to 10-membered heterocycle, wherein said alkyl, alkylene, and heterocycle are substituted with 0-4 $R^b$;

$R^b$, at each occurrence, is independently selected from =O, halogen, $C_{1-4}$ alkyl, $C_{1-4}$ alkoxy, $OCF_3$, $NH_2$, $NO_2$, $N(C_{1-4}$ alkyl$)_2$, $CO(C_{1-4}$ alkyl), $CO(C_{1-4}$ haloalkyl), $CO_2$ $(C_{1-4}$ alkyl), $CONH_2$, —$CONH(C_{1-4}$ alkyl), —$CON(C_{1-4}$ alkyl$)_2$, —$CONH$—$C_{1-4}$ alkylene-$O(C_{1-4}$ alkyl), —$CONH$—$C_{1-4}$ alkylene-$N(C_{1-4}$ alkyl$)_2$, —$CONH$—$C_{1-4}$ alkylene-$N(C_{1-4}$ alkyl$)_2$, —$C_{1-4}$ alkylene-O—$P(O)(OH)_2$, —$NHCO_2(C_{1-4}$ alkyl), —$R^c$, $COR^c$, $CO_2R^c$, and $CONHR^c$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, $N(C_{1-4}$ alkyl), O, and $S(O)_p$; wherein each ring moiety is substituted with 0-2 $R^d$;

$R^d$, at each occurrence, is independently selected from =O, halogen, —OH, $C_{1-4}$ alkyl, $NH_2$, $NH(C_{1-4}$ alkyl), $N(C_{1-4}$ alkyl$)_2$, $C_{1-4}$ alkoxy, and —$NHCO(C_{1-4}$ alkyl), and a heterocycle containing carbon atoms and 1-4 heteroatoms selected from the group consisting of: N, NH, $N(C_{1-4}$ alkyl), O, and $S(O)_p$;

n, at each occurrence, is independently selected from 0, 1, 2, 3, and 4;

p, at each occurrence, is independently selected from 0, 1, and 2; and other variables are as defined in Formula (II) above.

In another aspect, the present invention provides compounds of Formula (VII) or stereoisomers, tautomers, pharmaceutically-acceptable salts, solvates, or prodrugs thereof, wherein:

M is N;

$R^5$ is selected from H, $C_{1-4}$ alkyl, —$(CH_2)_n$—$C_{3-10}$ carbocycle, —$(CH_2)_n$-aryl, —$(CH_2)_n$-4- to 10-membered heterocycle selected from

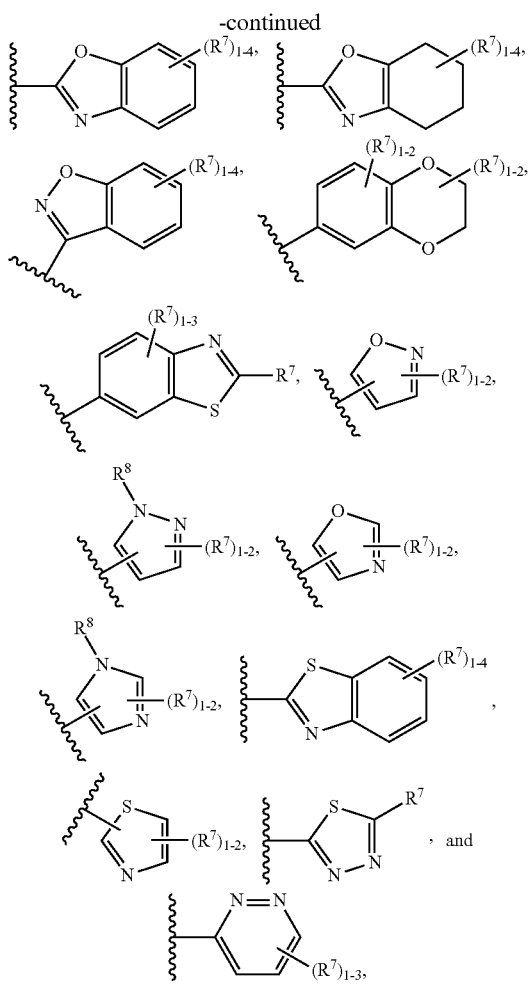

wherein said alkyl, cycloalkyl, aryl are substituted with 1-4 $R^7$;

$R^7$, at each occurrence, is independently selected from H, halogen, $C_{1-4}$ alkyl, $C_{1-4}$ alkoxy, CN, OH, —$(CH_2)_n$-carbocycle, and —$(CH_2)_n$-heterocycle, wherein said alkyl, alkoxyl, carbocycle, and heterocycle are substituted with 0-4 $R^9$; and other variables are as defined in Formula (V) above.

In another aspect, the present invention provides compounds of Formula (VII) or stereoisomers, tautomers, pharmaceutically-acceptable salts, solvates, or prodrugs thereof, wherein:

M is N;

$R^5$ and $R^5$ are taken together with the nitrogen atom to which they are attached to form a heterocycle selected from

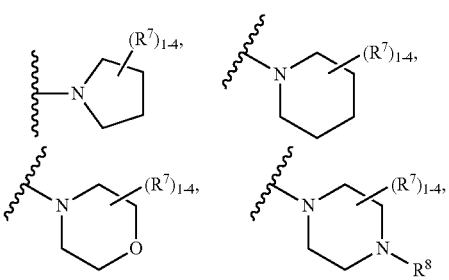

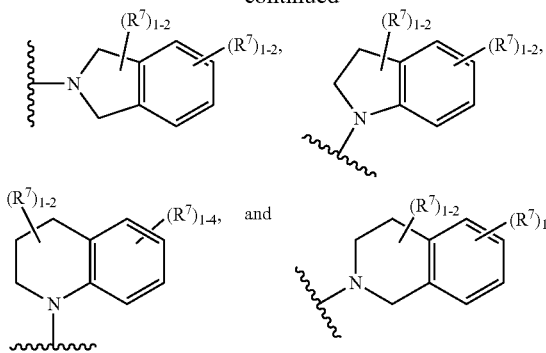

R[7], at each occurrence, is independently selected from H, =O, halogen, $C_{1-4}$ alkyl, $C_{1-4}$ alkoxy, CN, OH, $CF_3$, $-(CH_2)_n-CO_2H$, $-(CH_2)_n-CO_2(C_{1-4}$ alkyl), $-(CH_2)_n-NR^8R^8$, $-CH_2NH_2$, $-NHCO(C_{1-4}$ alkyl), $-NHCOCF_3$, $-NHCO_2(C_{1-4}$ alkyl), $-NHC(O)NH_2$, $-NHC(O)NH(C_{1-4}$ alkyl), $-NHC(O)N(C_{1-4}$ alkyl)$_2$, $-NHSO_2(C_{1-4}$ alkyl), $-SO_2NH_2$, $-SO_2NH(C_{1-4}$ alkyl), $-SO_2N(C_{1-4}$ alkyl)$_2$, $-SO_2NH(CH_2)_2OH$, $-SO_2NH(CH_2)_2O(C_{1-4}$ alkyl), $-(CH_2)_n-CONR^8R^8$, $-O(CH_2)_n$-carbocycle, $-O(CH_2)_n$-heterocycle, $-NHCO$-carbocycle, $-NHCO$-heterocycle, $-(CH_2)_n$-carbocycle, and $-(CH_2)_n$-heterocycle comprising carbon atoms and 1-4 heteroatoms selected from N, $NR^8$, O, and $S(O)_p$, wherein said alkyl, alkoxyl, carbocycle, and heterocycle are substituted with 0-4 $R^9$;

$R^8$, at each occurrence, is independently selected from H, $C_{1-4}$ alkyl, $-(CH_2)_n$-carbocycle, and $-(CH_2)_n$-heterocycle, wherein said alkyl, carbocycle, and heterocycle are substituted with 0-4 $R^9$;

$R^9$, at each occurrence, is independently selected from halogen, OH, $NO_2$, $CHF_2$, $CF_3$, $C_{1-4}$ alkyl, $C_{1-4}$ alkoxy, $CH_2OH$, $CO_2H$, $CO_2(C_{1-4}$ alkyl), $CONH_2$, $-NH_2$, and a 4- to 10-membered heterocycle; and other variables are as defined in Formula (VII) above.

In another aspect, the present invention provides compounds of Formula (VIII):

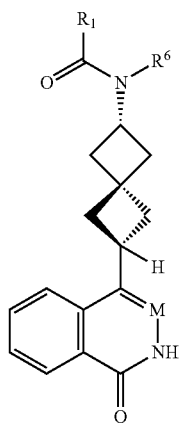

(VIII)

or stereoisomers, tautomers, pharmaceutically-acceptable salts, solvates, or prodrugs thereof, wherein:

M is selected from N and CH;

$R^1$ is selected from

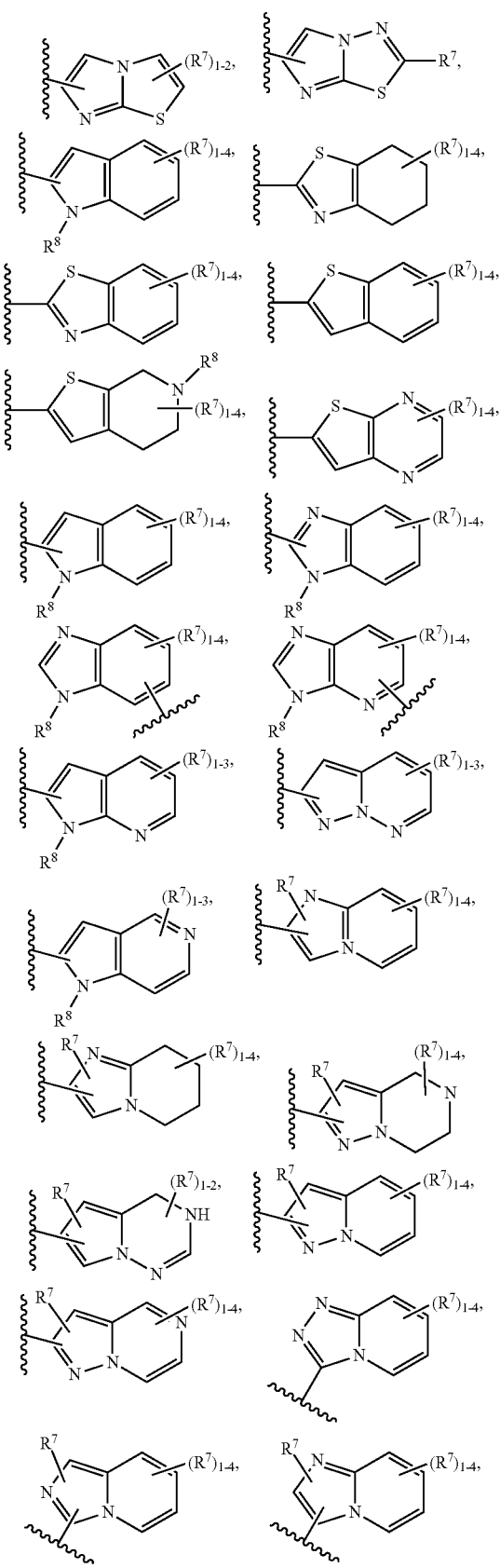

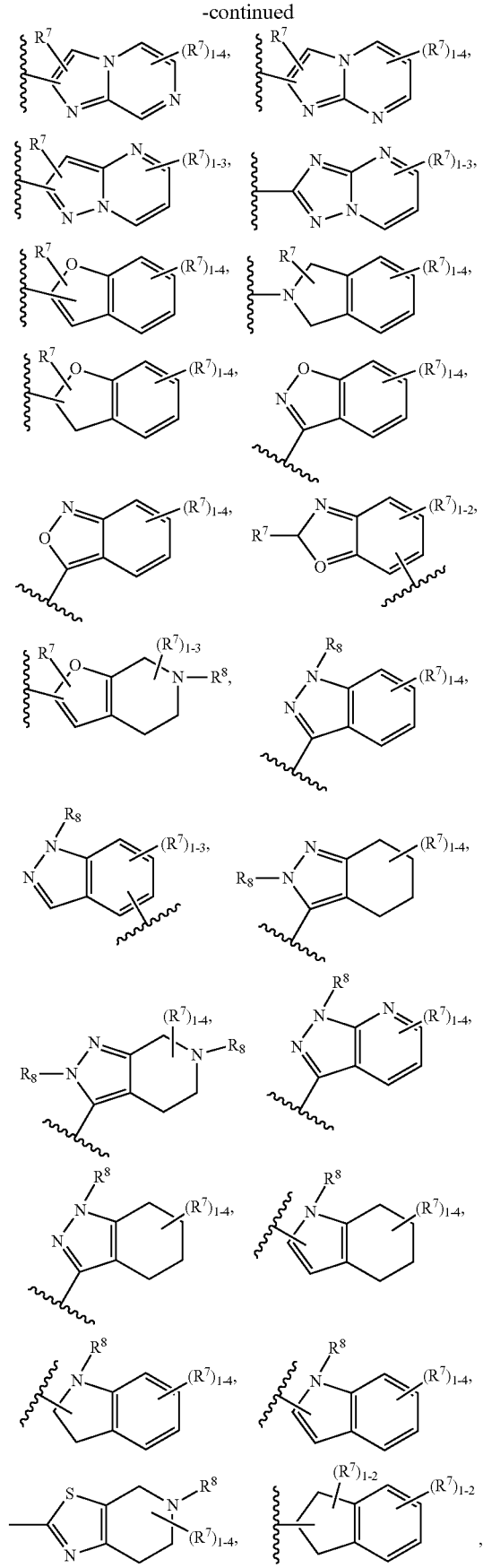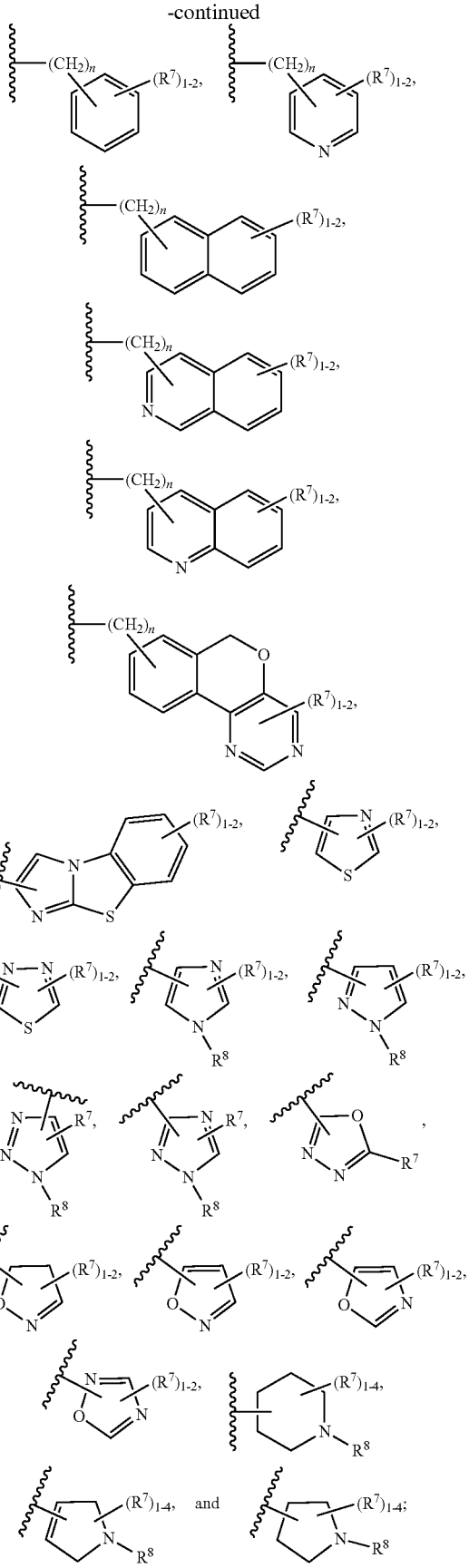

$R^7$, at each occurrence, is independently selected from H, =O, $NO_2$, F, Cl, Br, $C_{1-6}$ alkyl, $C_{2-4}$ alkenyl, $C_{2-4}$ alkynyl, $C_{1-4}$ alkoxy, CN, OH, $CF_3$, $-(CH_2)_n-CO_2H$, $-(CH_2)_n-CO_2(C_{1-4}$ alkyl), $-(CH_2)_n-NR^8R^8$, $-NHCOH$, $-NHCO(C_{1-4}$ alkyl), $-NHCOCF_3$, $-NHCO_2(C_{1-4}$ alkyl), $-NHCO_2(CH_2)_2O(C_{1-4}$ alkyl), $-NHCO_2(CH_2)_3O(C_{1-4}$ alkyl), $-NHCO_2(CH_2)_2OH$, $-NHCO_2(CH_2)_2NH_2$, $-NHCO_2(CH_2)_2N(C_{1-4}$ alkyl)$_2$, $-NHCO_2CH_2CO_2H$, $-(CH_2)_{1-2}NHCO_2(C_{1-4}$ alkyl), $-NHC(O)NR^8R^8$, $S(C_{1-4}$ alkyl), $-NHSO_2(C_{1-4}$ alkyl), $-SO_2NH_2$, $-SO_2NH(C_{1-4}$ alkyl), $-SO_2N(C_{1-4}$ alkyl)$_2$, $-SO_2NH(CH_2)_2OH$, $-SO_2NH(CH_2)_2O(C_{1-4}$ alkyl), $-(CH_2)_n-CONR^8R^8$, $-O(CH_2)_n$-carbocycle, $-O(CH_2)_n$-heterocycle, $-NHCO$-carbocycle, $-NHCO$-heterocycle, $-(CH_2)_n$-carbocycle, and $-(CH_2)_n$-heterocycle comprising carbon atoms and 1-4 heteroatoms selected from N, $NR^8$, O, and $S(O)_p$, wherein said alkyl, alkenyl, alkynyl, alkoxyl, carbocycle, and heterocycle are substituted with 0-4 $R^9$ and wherein said carbocycle is selected from

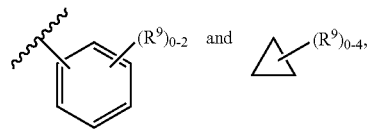

and wherein said heterocycle is selected from

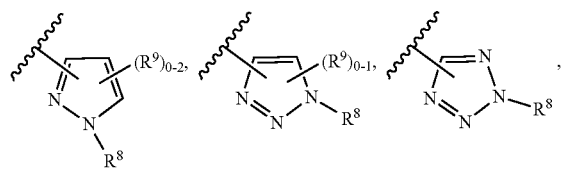

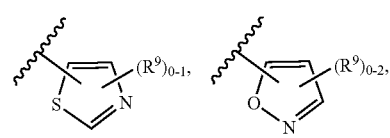

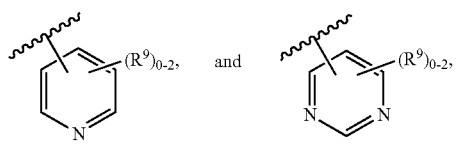

$R^8$, at each occurrence, is independently selected from H, $C_{1-4}$ alkyl, $C(O)C_{1-4}$alkyl, $C(O)$carbocycle, $C(O)$heterocycle, $-(CH_2)_n-C(O)NR^aR^a$, $C(O)OC_{1-4}$alkyl, $C(O)O$-carbocycle, $C(O)O$-heterocycle, $SO_2$alkyl, $SO_2$carbocycle, $SO_2$heterocycle, $-(CH_2)_n-NHC(O)$ $C_{1-4}$alkyl, $SO_2NR^aR^a$, $-(CH_2)_n-C_{3-6}$cycloalkyl, $-(CH_2)_n$-aryl, and $-(CH_2)_n$-heterocycle, wherein said alkyl, cycloalkyl, aryl, and heterocycle are substituted with 0-4 $R^9$;

alternatively, $R^8$ and $R^8$ are taken together with the nitrogen atom to which they are attached to form a heterocycle selected from

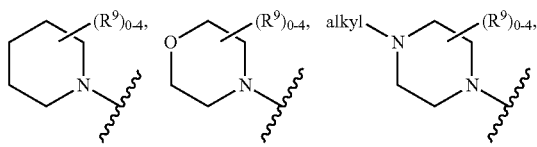

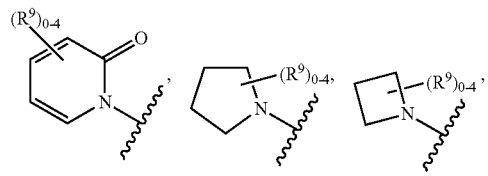

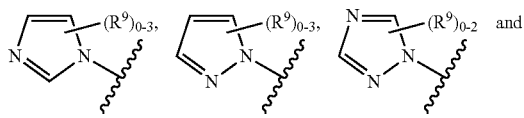

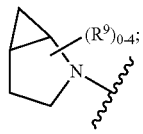

$R^9$, at each occurrence, is independently selected from F, Cl, Br, I, OH, =O, CN, $NO_2$, $CHF_2$, $CF_3$, $C_{1-4}$ alkyl, $C_{1-4}$ alkoxy, $CH_2OH$, $CO_2H$, $CO_2(C_{1-4}$ alkyl), $CONH_2$, $-(CH_2)_nNR^aR^a$, $-(CH_2)_nCONR^aR^a$, $-(CH_2)_nNHCO(C_{1-4}$ alkyl), $-O(CH_2)_n$heterocycle, $-O(CH_2)_{2-4}NR^aR^a$, $-(CH_2)_n$-carbocycle, and $-(CH_2)_n$-4- to 10-membered heterocycle, wherein said alkyl, alkoxyl, carbocycle, and heterocycle are substituted with 0-4 $R^b$;

$R^a$, at each occurrence, is independently selected from H and $C_{1-4}$ alkyl; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, halogen, $C_{1-4}$ alkyl, $C_{1-4}$ alkoxy, $OCF_3$, $OC(O)C_{1-4}$ alkyl, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, $-CONH(C_{1-4}$ alkyl), $-CON(C_{1-4}$ alkyl)$_2$, $-CONH-C_{1-4}$ alkylene-$O(C_{1-4}$ alkyl), $-CONH-C_{1-4}$ alkylene-$N(C_{1-4}$ alkyl)$_2$, $-CONH-C_{1-4}$ alkylene-N $(C_{1-4}$ alkyl)$_2$, and $-NHCO_2$ $(C_{1-4}$ alkyl), wherein said alkyl and alkoxy are substituted with $R^d$;

$R^d$, at each occurrence, is independently selected from =O, halogen, $-OH$, $C_{1-4}$ alkyl, $NH_2$, $NH(C_{1-4}$ alkyl), $N(C_{1-4}$ alkyl)$_2$, $C_{1-4}$ alkoxy, and $-NHCO(C_{1-4}$ alkyl), and a heterocycle containing carbon atoms and 1-4 heteroatoms selected from the group consisting of: N, NH, $N(C_{1-4}$ alkyl), O, and $S(O)_p$;

n, at each occurrence, is independently selected from 0, 1, 2, 3, and 4;

p, at each occurrence, is independently selected from 0, 1, and 2; and other variables are as defined in Formula (III) above.

In another aspect, the present invention provides compounds of Formula (VIII):

(VIII)

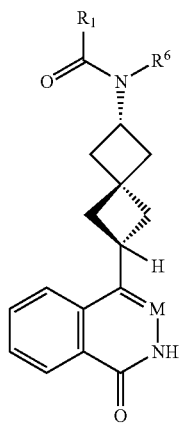

or stereoisomers, tautomers, pharmaceutically-acceptable salts, solvates, or prodrugs thereof, wherein:

M is selected from N and CH;

$R^1$ is $NR^5R^5$;

$R^5$ and $R^5$ are taken together with the nitrogen atom to which they are attached to form a heterocycle selected from

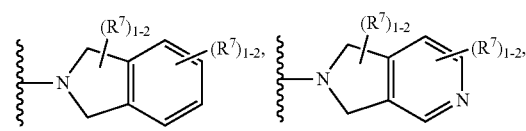

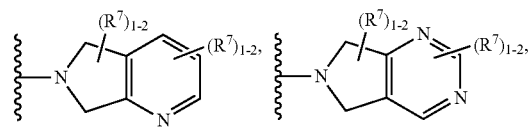

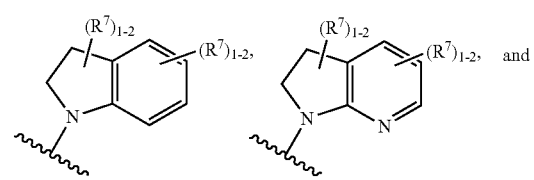

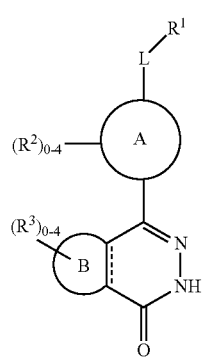

$R^7$, at each occurrence, is independently selected from H, =O, F, Cl, Br, $C_{1-4}$ alkyl, $C_{1-4}$ alkoxy, CN, OH, $CF_3$, $-(CH_2)_n-NR^8R^8$, $-NHSO_2(C_{1-4}$ alkyl), $-SO_2NH_2$, $-SO_2NH(C_{1-4}$ alkyl), $-SO_2N(C_{1-4}$ alkyl)$_2$, $-(CH_2)_n-$ $CONR^8R^8$, $-(CH_2)_n$-phenyl, and $-(CH_2)_n$-heterocycle selected from

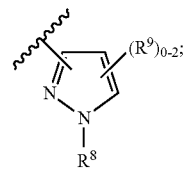

$R^8$, at each occurrence, is independently selected from H, $CF_3$, $CD_3$, $CH_3$, $C(CH_3)_3$,

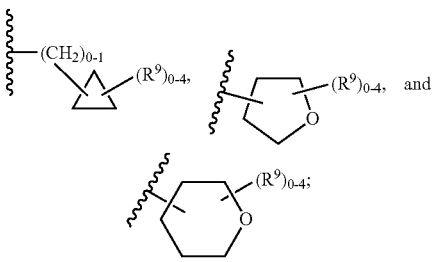

alternatively, $R^8$ and $R^8$ are taken together to form

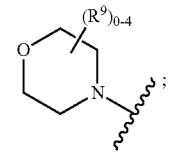

and $R^9$, at each occurrence, is independently selected from F, Cl, OH, $NO_2$, $CHF_2$, $(CH_2)_{0-2}CF_3$, $CD_3$, $CH_3$, $OC_{1-4}$ alkyl, $SO_2NH_2$, and phenyl substituted with $C_{1-4}$ alkyl.

In another aspect, the present invention provides compounds of Formula (Ia):

(Ia)

or stereoisomers, tautomers, pharmaceutically-acceptable salts, solvates, or prodrugs thereof, wherein:

Ring A is a 5- to 9-membered bicyclic spiro carbocycle;

Ring B is selected from a $C_{5-6}$ carbocycle and a 5- to 6-membered heterocycle;

- - - - is an optional bond;

L is selected from $-(CR^4R^4)_{0-1}-$, $-(CR^4R^4)_{0-1}C(O)-$, $-OC(O)-$, $-NR^6C(O)-$, and $-NR^6-$;

$R^1$ is selected from $NR^5R^5$, $OR^5$, $-(CR^4R^4)_nC_{3-10}$ carbocycle and $-(CR^4R^4)_n$-4- to 15-membered heterocycle comprising carbon atoms and 1-4 heteroatoms selected from N, $NR^8$, O, and $S(O)_p$; wherein said alkyl, carbocycle, and heterocycle are substituted with 1-4 $R^7$;

$R^2$, at each occurrence, is independently selected from halogen, $C_{1-6}$ alkyl, $C_{1-4}$ alkoxy, $C_{1-4}$ alkylthio, $C_{1-4}$ haloalkyl, —OH, —$CH_2OH$, —$OCH_2F$, —$OCHF_2$, —$OCF_3$, CN, —$NH_2$, —$NH(C_{1-4}$ alkyl), —$N(C_{1-4}$ alkyl$)_2$, —$CO_2H$, —$CH_2CO_2H$, —$CO_2(C_{1-4}$ alkyl), —$CO(C_{1-4}$ alkyl), —$CH_2NH_2$, —$CONH_2$, —$CONH(C_{1-4}$ alkyl), —$CON(C_{1-4}$ alkyl$)_2$, —$OCH_2CO_2H$, —$NHCO(C_{1-4}$ alkyl), —$NHCO_2(C_{1-4}$ alkyl), —$NHSO_2(C_{1-4}$ alkyl), —$SO_2NH_2$, —$C(=NH)NH_2$, a carbocycle, and a heterocycle, wherein said alkyl, alkoxy, alkylthio, haloalkyl, carbocycle, and heterocycle are substituted with 0-4 $R^9$; $R^3$, at each occurrence, is independently selected from halogen, $C_{1-6}$ alkyl, $C_{1-4}$ alkoxy, $C_{1-4}$ alkylthio, $C_{1-4}$ haloalkyl, —$CH_2OH$, —$OCH_2F$, —$OCHF_2$, —$OCF_3$, CN, —$NH_2$, —$NH(C_{1-4}$ alkyl), —$N(C_{1-4}$ alkyl$)_2$, —$CO_2H$, —$CH_2CO_2H$, —$CO_2(C_{1-4}$ alkyl), —$CO(C_{1-4}$ alkyl), —$CH_2NH_2$, —$CONH_2$, —$CONH(C_{1-4}$ alkyl), —$CON(C_{1-4}$ alkyl$)_2$, —$OCH_2CO_2H$, —$NHCO(C_{1-4}$ alkyl), —$NHCO_2(C_{1-4}$ alkyl), —$NHSO_2(C_{1-4}$ alkyl), —$SO_2NH_2$, —$C(=NH)NH_2$, a carbocycle, and a heterocycle, wherein said alkyl, alkoxy, alkylthio, haloalkyl, carbocycle, and heterocycle are substituted with 0-4 $R^9$;

$R^4$, at each occurrence, is independently selected from H, OH, $NH_2$, $CH_2NH_2$, $C_{1-4}$ haloalkyl, $OCH_2F$, $OCHF_2$, $OCF_3$, —$NH(C_{1-4}$ alkyl), —$N(C_{1-4}$ alkyl$)_2$, $C_{1-4}$ alkoxy, $CH_2OH$, $CH_2O(C_{1-4}$ alkyl), $CH_2CO_2H$, $CH_2CO_2(C_{1-4}$ alkyl), $C_{1-4}$ alkyl, a carbocycle, and a heterocycle, wherein said alkyl, alkoxy, haloalkyl, carbocycle, and heterocycle are substituted with 0-4 $R^9$;

$R^5$, at each occurrence, is independently selected from H, $C_{1-4}$ alkyl, —$(CR^6R^6)_n$—$C_{3-10}$ carbocycle and —$(CR^6R^6)_n$-4- to 10-membered heterocycle comprising carbon atoms and 1-4 heteroatoms selected from N, $NR^8$, O, and $S(O)_p$, wherein said alkyl, carbocycle and heterocycle are substituted with 1-4 $R^7$;

alternatively, $R^5$ and $R^5$ are taken together with the nitrogen atom to which they are attached to form a 4- to 15-membered heterocycle substituted with 1-4 $R^7$;

$R^6$, at each occurrence, is independently selected from H, $C_{1-4}$ alkyl, $CH_2NH_2$, $C_{1-4}$ haloalkyl, $C_{1-4}$ alkoxy, $CH_2OH$, $CH_2O(C_{1-4}$ alkyl), $CH_2CO_2H$, $CH_2CO_2(C_{1-4}$ alkyl), a carbocycle, and a heterocycle, wherein said alkyl, alkoxy, haloalkyl, carbocycle, and heterocycle are substituted with 0-4 $R^9$;

alternatively, $R^1$ and $R^6$ are taken together with the nitrogen atom to which they are attached to form a heterocycle comprising carbon atoms and 1-4 heteroatoms selected from N, $NR^8$, O, and $S(O)_p$ and substituted with 1-4 $R^7$;

$R^7$, at each occurrence, is independently selected from H, =O, $NO_2$, halogen, $C_{1-7}$ alkyl, $C_{2-4}$ alkenyl, $C_{2-4}$ alkynyl, $C_{1-4}$ alkoxy, CN, OH, $CHF_2$, $CF_3$, —$(CH_2)_n$—$CO_2H$, —$(CH_2)_n$—$CO_2(C_{1-4}$ alkyl), —$(CH_2)_n$—$NR^8R^8$, —NHCO($C_{1-4}$ alkyl), —$NHCOCF_3$, —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl$)_2$, —$NHCO_2CH_2CO_2H$, —$CH_2NHCO_2(C_{1-4}$ alkyl), —$NHC(O)NR^8R^8$, —$NHSO_2(C_{1-4}$ alkyl), —$S(O)_p(C_{1-4}$ alkyl), —$SO_2NH_2$, —$SO_2NH(C_{1-4}$ alkyl), —$SO_2N(C_{1-4}$ alkyl$)_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxyl, carbocycle, and heterocycle are substituted with 0-4 $R^9$;

$R^8$, at each occurrence, is independently selected from H, $C_{1-4}$ alkyl, $C_{2-4}$ alkenyl, $C_{2-4}$ alkynyl, —$(CH_2)_n$—$C(O)$$C_{1-4}$alkyl, —$(CH_2)_n$—$C(O)$carbocycle, —$(CH_2)_n$—$C(O)$ heterocycle, —$(CH_2)_n$—$C(O)NR^aR^a$, —$(CH_2)_n$—$NR^aC(O)$ $C_{1-4}$ alkyl, —$(CH_2)_n$—$C(O)OC_{1-4}$ alkyl, —$(CH_2)_n$—$C(O)$$C_{1-4}$alkyl, —$(CH_2)_n$—$C(O)O$-carbocycle, —$(CH_2)_n$—$C(O)$O-heterocycle, —$(CH_2)_n$—$SO_2$alkyl, —$(CH_2)_n$—$SO_2$carbocycle, —$(CH_2)_n$—$SO_2$heterocycle, —$(CH_2)_n$—$SO_2NR^aR^a$, —$(CH_2)_n$-carbocycle, and —$(CH_2)_n$-heterocycle, wherein said alkyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, =O, CN, $NO_2$, $CHF_2$, $CF_3$, $C_{1-4}$ alkyl, $C_{1-4}$ alkoxy, $CH_2OH$, $CO(C_{1-4}$ alkyl), $CO_2H$, $CO_2(C_{1-4}$ alkyl), —$(CHR^{10})_n NR^aR^a$, —$(CHR^{10})_n CONR^aR^a$, —$(CHR^{10})_n NR^aCO(C_{1-4}$ alkyl), —$O(CHR^{10})_n$carbocycle, —$O(CHR^{10})_n$heterocycle, —$O(CHR^{10})_n NR^aR^a$, and —$(CR^{10}R^{10})_n$-4- to 10-membered heterocycle, wherein said alkyl, alkoxy, carbocycle, and heterocycle are substituted with 0-4 $R^b$;

$R^a$, at each occurrence, is independently selected from H, $C_{1-4}$ alkyl, —$(CH_2)_n OH$, $CO(C_{1-4}$ alkyl), $COCF_3$, $CO_2(C_{1-4}$ alkyl), —$CONH_2$, —CONH—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, OH, halogen, $C_{1-4}$ alkyl, $C_{1-4}$ alkoxy, $OCF_3$, $OC(O)$ $C_{1-4}$ alkyl, $NH_2$, $NO_2$, $N(C_{1-4}$ alkyl$)_2$, $CO(C_{1-4}$ alkyl), $CO(C_{1-4}$ haloalkyl), $CO_2(C_{1-4}$ alkyl), $CONH_2$, —CONH ($C_{1-4}$ alkyl), —$CON(C_{1-4}$ alkyl$)_2$, —CONH—$C_{1-4}$ alkylene-$O(C_{1-4}$ alkyl), —CONH—$C_{1-4}$ alkylene-$N(C_{1-4}$ alkyl$)_2$, —CONH—$C_{1-4}$ alkylene-$N(C_{1-4}$ alkyl$)_2$, —$C_{1-4}$ alkylene-O—$P(O)(OH)_2$, —$NHCO_2(C_{1-4}$ alkyl), —$R^c$, $COR^c$, $CO_2R^c$, and $CONHR^c$, wherein said alkyl and alkoxy are substituted with $R^d$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, $N(C_{1-4}$ alkyl), O, and $S(O)_p$; wherein each ring moiety is substituted with 0-2 $R^d$;

$R^d$, at each occurrence, is independently selected from =O, halogen, —OH, $C_{1-4}$ alkyl, $NH_2$, $NH(C_{1-4}$ alkyl), $N(C_{1-4}$ alkyl$)_2$, $C_{1-4}$ alkoxy, and —$NHCO(C_{1-4}$ alkyl), and a heterocycle containing carbon atoms and 1-4 heteroatoms selected from the group consisting of: N, NH, $N(C_{1-4}$ alkyl), O, and $S(O)_p$;

n, at each occurrence, is independently selected from 0, 1, 2, 3, and 4; and p, at each occurrence, is independently selected from 0, 1, and 2.

In another aspect, the present invention provides compounds of Formula (IIa):

(IIa)

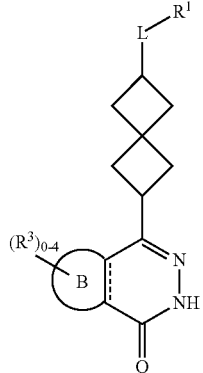

or stereoisomers, tautomers, pharmaceutically-acceptable salts, solvates, or prodrugs thereof, wherein:

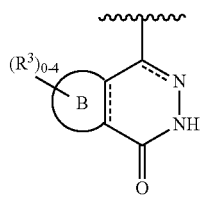

is selected from:

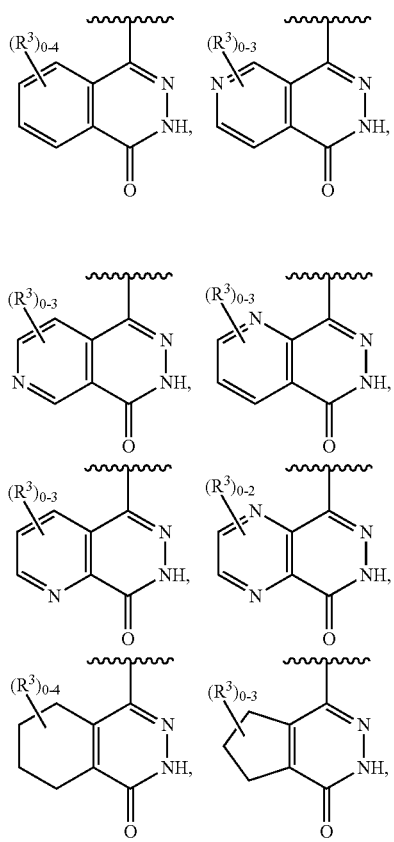

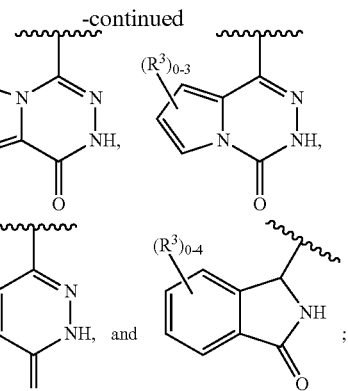

L is selected from —(CR$^4$R$^4$)$_{0-1}$—, —(CR$^4$R$^4$)$_{0-1}$C(O)—, —OC(O)—, —NR$^6$C(O)—, and —NR$^6$—;

R$^1$ is selected from NR$^5$R$^5$, OR$^5$, —(CR$^4$R$^4$)$_n$C$_{3-10}$ carbocycle and —(CR$^4$R$^4$)$_n$-4- to 15-membered heterocycle comprising carbon atoms and 1-4 heteroatoms selected from N, NR$^8$, O, and S(O)$_p$; wherein said alkyl, carbocycle, and heterocycle are substituted with 1-4 R$^7$;

R$^2$, at each occurrence, is independently selected from halogen, C$_{1-6}$ alkyl, C$_{1-4}$ alkoxy, C$_{1-4}$ alkylthio, C$_{1-4}$ haloalkyl, —OH, —CH$_2$OH, —OCH$_2$F, —OCHF$_2$, —OCF$_3$, CN, —NH$_2$, —NH(C$_{1-4}$ alkyl), —N(C$_{1-4}$ alkyl)$_2$, —CO$_2$H, —CH$_2$CO$_2$H, —CO$_2$(C$_{1-4}$ alkyl), —CO(C$_{1-4}$ alkyl), —CH$_2$NH$_2$, —CONH$_2$, —CONH(C$_{1-4}$ alkyl), —CON(C$_{1-4}$ alkyl)$_2$, —OCH$_2$CO$_2$H, —NHCO(C$_{1-4}$ alkyl), —NHCO$_2$(C$_{1-4}$ alkyl), —NHSO$_2$(C$_{1-4}$ alkyl), —SO$_2$NH$_2$, —C(=NH)NH$_2$, a carbocycle, and a heterocycle, wherein said alkyl, alkoxy, alkylthio, haloalkyl, carbocycle, and heterocycle are substituted with 0-4 R$^9$;

R$^3$, at each occurrence, is independently selected from halogen, C$_{1-6}$ alkyl, C$_{1-4}$ alkoxy, C$_{1-4}$ alkylthio, C$_{1-4}$ haloalkyl, —CH$_2$OH, —OCH$_2$F, —OCHF$_2$, —OCF$_3$, CN, —NH$_2$, —NH(C$_{1-4}$ alkyl), —N(C$_{1-4}$ alkyl)$_2$, —CO$_2$H, —CH$_2$CO$_2$H, —CO$_2$(C$_{1-4}$ alkyl), —CO(C$_{1-4}$ alkyl), —CH$_2$NH$_2$, —CONH$_2$, —CONH(C$_{1-4}$ alkyl), —CON(C$_{1-4}$ alkyl)$_2$, —OCH$_2$CO$_2$H, —NHCO(C$_{1-4}$ alkyl), —NHCO$_2$(C$_{1-4}$ alkyl), —NHSO$_2$(C$_{1-4}$ alkyl), —SO$_2$NH$_2$, —C(=NH)NH$_2$, a carbocycle, and a heterocycle, wherein said alkyl, alkoxy, alkylthio, haloalkyl, carbocycle, and heterocycle are substituted with 0-4 R$^9$;

R$^4$, at each occurrence, is independently selected from H, OH, NH$_2$, CH$_2$NH$_2$, C$_{1-4}$ haloalkyl, OCH$_2$F, OCHF$_2$, OCF$_3$, —NH(C$_{1-4}$ alkyl), —N(C$_{1-4}$ alkyl)$_2$, C$_{1-4}$ alkoxy, CH$_2$OH, CH$_2$O(C$_{1-4}$ alkyl), CH$_2$CO$_2$H, CH$_2$CO$_2$(C$_{1-4}$ alkyl), C$_{1-4}$ alkyl, a carbocycle, and a heterocycle, wherein said alkyl, alkoxy, haloalkyl, carbocycle, and heterocycle are substituted with 0-4 R$^9$;

R$^5$, at each occurrence, is independently selected from H, C$_{1-4}$ alkyl, —(CR$^6$R$^6$)$_n$—C$_{3-10}$ carbocycle and —(CR$^6$R$^6$)$_n$-4- to 10-membered heterocycle comprising carbon atoms and 1-4 heteroatoms selected from N, NR$^8$, O, and S(O)$_p$, wherein said alkyl, carbocycle and heterocycle are substituted with 1-4 R$^7$;

alternatively, R$^5$ and R$^5$ are taken together with the nitrogen atom to which they are attached to form a 4- to 15-membered heterocycle substituted with 1-4 R$^7$;

R$^6$, at each occurrence, is independently selected from H, C$_{1-4}$ alkyl, CH$_2$NH$_2$, C$_{1-4}$ haloalkyl, C$_{1-4}$ alkoxy, CH$_2$OH, CH$_2$O(C$_{1-4}$ alkyl), CH$_2$CO$_2$H, CH$_2$CO$_2$(C$_{1-4}$ alkyl), a carbocycle, and a heterocycle, wherein said alkyl, alkoxy, haloalkyl, carbocycle, and heterocycle are substituted with 0-4 $R^9$;

alternatively, $R^1$ and $R^6$ are taken together with the nitrogen atom to which they are attached to form a heterocycle comprising carbon atoms and 1-4 heteroatoms selected from N, $NR^8$, O, and $S(O)_p$ and substituted with 1-4 $R^7$;

$R^7$, at each occurrence, is independently selected from H, =O, $NO_2$, halogen, $C_{1-6}$ alkyl, $C_{1-4}$ alkyl, $C_{2-4}$ alkenyl, $C_{1-4}$ alkoxy, CN, OH, $CF_3$, —$(CH_2)_n$—$CO_2H$, —$(CH_2)_n$—$CO_2$($C_{1-4}$ alkyl), —$(CH_2)_n$—$NR^8R^8$, —$NHCO(C_{1-4}$ alkyl), —$NHCOCF_3$, —$NHCO_2(C_{1-4}$ alkyl), —$NHCO_2(CH_2)_2O$($C_{1-4}$ alkyl), —$NHCO_2(CH_2)_3O(C_{1-4}$ alkyl), —$NHCO_2$($CH_2)_2OH$, —$NHCO_2(CH_2)_2NH_2$, —$NHCO_2(CH_2)_2N(C_{1-4}$ alkyl)$_2$, —$NHCO_2CH_2CO_2H$, —$CH_2NHCO_2(C_{1-4}$ alkyl), —$NHC(O)NR^8R^8$, —$NHSO_2(C_{1-4}$ alkyl), —$S(O)_p(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkoxyl, carbocycle, and heterocycle are substituted with 0-4 $R^9$;

$R^8$, at each occurrence, is independently selected from H, $C_{1-4}$ alkyl, $C_{2-4}$ alkenyl, $C_{2-4}$ alkynyl, —$(CH_2)_n$—$C(O)$$C_{1-4}$alkyl, —$(CH_2)_n$—$C(O)$carbocycle, —$(CH_2)_n$—$C(O)$heterocycle, —$(CH_2)_n$—$C(O)NR^aR^a$, —$(CH_2)_n$—$NR^aC(O)$$C_{1-4}$alkyl, —$(CH_2)_n$—$C(O)OC_{1-4}$alkyl, —$(CH_2)_n$—$C(O)$$C_{1-4}$alkyl, —$(CH_2)_n$—$C(O)O$-carbocycle, —$(CH_2)_n$—$C(O)$O-heterocycle, —$(CH_2)_n$—$SO_2$alkyl, —$(CH_2)_n$—$SO_2$carbocycle, —$(CH_2)_n$—$SO_2$heterocycle, —$(CH_2)_n$—$SO_2NR^aR^a$, —$(CH_2)_n$-carbocycle, and —$(CH_2)_n$-heterocycle, wherein said alkyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, =O, CN, $NO_2$, $CHF_2$, $CF_3$, $C_{1-4}$ alkyl, $C_{1-4}$ alkoxy, $CH_2OH$, $CO(C_{1-4}$ alkyl), $CO_2H$, $CO_2(C_{1-4}$ alkyl), —$(CHR^{10})_n NR^aR^a$, —$(CHR^{10})_n CONR^aR^a$, —$(CHR^{10})_n NR^aCO(C_{1-4}$ alkyl), —$O(CHR^{10})_n$carbocycle, —$O(CHR^{10})_n$heterocycle, —$O(CHR^{10})_n NR^aR^a$, and —$(CR^{10}R^{10})_n$-4- to 10-membered heterocycle, wherein said alkyl, alkoxy, carbocycle, and heterocycle are substituted with 0-4 $R^b$;

$R^a$, at each occurrence, is independently selected from H, $C_{1-4}$ alkyl, —$(CH_2)_nOH$, $CO(C_{1-4}$ alkyl), $COCF_3$, $CO_2(C_{1-4}$ alkyl), —$CONH_2$, —$CONH$—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, OH, halogen, $C_{1-4}$ alkyl, $C_{1-4}$ alkoxy, $OCF_3$, $OC(O)$$C_{1-4}$ alkyl, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl)$_2$, —$CONH$—$C_{1-4}$ alkylene-$O(C_{1-4}$ alkyl), —$CONH$—$C_{1-4}$ alkylene-$N(C_{1-4}$ alkyl)$_2$, —$CONH$—$C_{1-4}$ alkylene-$N(C_{1-4}$ alkyl)$_2$, —$C_{1-4}$ alkylene-O—$P(O)(OH)_2$, —$NHCO_2(C_{1-4}$ alkyl), —$R^c$, $COR^c$, $CO_2R^c$, and $CONHR^c$, wherein said alkyl and alkoxy are substituted with $R^d$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, N($C_{1-4}$ alkyl), O, and $S(O)_p$; wherein each ring moiety is substituted with 0-2 $R^d$;

$R^d$, at each occurrence, is independently selected from =O, halogen, —OH, $C_{1-4}$ alkyl, $NH_2$, $NH(C_{1-4}$ alkyl), $N(C_{1-4}$ alkyl)$_2$, $C_{1-4}$ alkoxy, and —$NHCO(C_{1-4}$ alkyl), and a heterocycle containing carbon atoms and 1-4 heteroatoms selected from the group consisting of: N, NH, N($C_{1-4}$ alkyl), O, and $S(O)_p$;

n, at each occurrence, is independently selected from 0, 1, 2, 3, and 4; and p, at each occurrence, is independently selected from 0, 1, and 2.

In another aspect, the present invention provides compounds of Formula (IIIa):

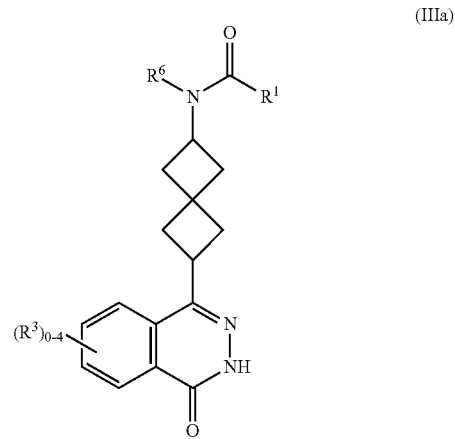

(IIIa)

or stereoisomers, tautomers, pharmaceutically-acceptable salts, solvates, or prodrugs thereof, wherein:

$R^1$ is selected from $NR^5R^5$, $OR^5$, —$(CH_2)_n$—$C_{3-10}$ carbocycle, and —$(CH_2)_n$-5- to 10-membered heterocycle, wherein said carbocycle and heterocycle are substituted with 1-4 $R^7$;

$R^5$, at each occurrence, is independently selected from H, $C_{1-4}$ alkyl, —$(CR^6R^6)_n$—$C_{3-10}$ carbocycle, and —$(CR^6R^6)_n$-4- to 10-membered heterocycle comprising carbon atoms and 1-4 heteroatoms selected from N, $NR^8$, O, and $S(O)_p$, wherein said alkyl, carbocycle, and heterocycle are substituted with 1-4 $R^7$;

alternatively, $R^5$ and $R^5$ are taken together with the nitrogen atom to which they are attached to form a 4- to 10-membered heterocycle substituted with 1-4 $R^7$;

$R^6$, at each occurrence, is independently selected from H and $C_{1-4}$ alkyl;

$R^7$, at each occurrence, is independently selected from H, =O, $NO_2$, halogen, $C_{1-6}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$NHCO(C_{1-4}$ alkyl), —$NHCOCF_3$, —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl)$_2$, —$NHCO_2CH_2CO_2H$, —$CH_2NHCO_2(C_{1-4}$ alkyl), —$NHC(O)NR^8R^8$, —$NHSO_2(C_{1-4}$ alkyl), —$S(O)_p(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —(CH₂)ₙ-carbocycle, and —(CH₂)ₙ-heterocycle comprising carbon atoms and 1-4 heteroatoms selected from N, NR⁸, O, and S(O)ₚ, wherein said alkyl, alkenyl, alkynyl, alkoxyl, carbocycle, and heterocycle are substituted with 0-4 R⁹;

R⁸, at each occurrence, is independently selected from H, C₁₋₄ alkyl, C₂₋₄ alkenyl, C(O)C₁₋₄alkyl, C(O)carbocycle, C(O)heterocycle, —(CH₂)ₙ—C(O)NRᵃRᵃ, C(O)OC₁₋₄ alkyl, C(O)O-carbocycle, C(O)O-heterocycle, SO₂alkyl, SO₂carbocycle, SO₂heterocycle, SO₂NRᵃRᵃ, —(CH₂)ₙ-carbocycle, and —(CH₂)ₙ-heterocycle, wherein said alkyl, alkenyl, carbocycle, and heterocycle are substituted with 0-4 R⁹;

R⁹, at each occurrence, is independently selected from halogen, OH, CN, NO₂, CHF₂, CF₃, C₁₋₄ alkyl, C₁₋₄ alkoxy, CH₂OH, CO(C₁₋₄ alkyl), CO₂H, CO₂(C₁₋₄ alkyl), —(CHR¹⁰)ₙNRᵃRᵃ, —(CHR¹⁰)ₙCONRᵃRᵃ, —(CHR¹⁰)ₙNRᵃCO(C₁₋₄ alkyl), —O(CHR¹⁰)ₙcarbocycle, —O(CHR¹⁰)ₙheterocycle, —O(CHR¹⁰)ₙNRᵃRᵃ, and —(CR¹⁰R¹⁰)ₙ-4- to 10-membered heterocycle, wherein said alkyl, alkoxy, carbocycle, and heterocycle are substituted with 0-4 Rᵇ;

Rᵃ, at each occurrence, is independently selected from H, C₁₋₄ alkyl, —(CH₂)ₙOH, CO(C₁₋₄ alkyl), COCF₃, CO₂(C₁₋₄ alkyl), —CONH₂, —CONH—C₁₋₄ alkylene-CO₂(C₁₋₄ alkyl), C₁₋₄ alkylene-CO₂(C₁₋₄ alkyl), Rᶜ, CO₂Rᶜ, and CONHRᶜ; alternatively, Rᵃ and Rᵃ are taken together with the nitrogen atom to which they are attached to form 4- to 10-membered heterocycle, wherein said alkyl, alkylene, and heterocycle are substituted with 0-4 Rᵇ;

Rᵇ, at each occurrence, is independently selected from =O, halogen, C₁₋₄ alkyl, C₁₋₄ alkoxy, OCF₃, OC(O)C₁₋₄ alkyl, NH₂, NO₂, N(C₁₋₄ alkyl)₂, CO(C₁₋₄ alkyl), CO(C₁₋₄ haloalkyl), CO₂(C₁₋₄ alkyl), CONH₂, —CONH(C₁₋₄ alkyl), —CON(C₁₋₄ alkyl)₂, —CONH—C₁₋₄ alkylene-O(C₁₋₄ alkyl), —CONH—C₁₋₄ alkylene-N(C₁₋₄ alkyl)₂, —CONH—C₁₋₄ alkylene-N(C₁₋₄ alkyl)₂, —C₁₋₄ alkylene-O—P(O)(OH)₂, —NHCO₂(C₁₋₄ alkyl), —Rᶜ, CORᶜ, CO₂Rᶜ, and CONHRᶜ, wherein said alkyl and alkoxy are substituted with Rᵈ;

Rᶜ, at each occurrence, is independently selected from —(CH₂)ₙ—C₃₋₆ cycloalkyl, —(CH₂)ₙ-phenyl, and —(CH₂)ₙ-5- to 6-membered heterocycle containing carbon atoms and 1-4 heteroatoms selected from the group consisting of: N, NH, N(C₁₋₄ alkyl), O, and S(O)ₚ; wherein each ring moiety is substituted with 0-2 Rᵈ;

Rᵈ, at each occurrence, is independently selected from =O, halogen, —OH, C₁₋₄ alkyl, NH₂, NH(C₁₋₄ alkyl), N(C₁₋₄ alkyl)₂, C₁₋₄ alkoxy, and —NHCO(C₁₋₄ alkyl), and a heterocycle containing carbon atoms and 1-4 heteroatoms selected from the group consisting of: N, NH, N(C₁₋₄ alkyl), O, and S(O)ₚ;

n, at each occurrence, is independently selected from 0, 1, 2, 3, and 4;

p, at each occurrence, is independently selected from 0, 1, and 2; and other variables are as defined in Formula (II) above.

In another aspect, the present invention provides compounds of Formula (IIIa) or stereoisomers, tautomers, pharmaceutically-acceptable salts, solvates, or prodrugs thereof, wherein:

R¹ is NR⁵R⁵;

R⁵ and R⁵ are taken together with the nitrogen atom to which they are attached to form a 4- to 10-membered heterocycle substituted with 1-4 R⁷;

R⁷, at each occurrence, is independently selected from H, halogen, C₁₋₄ alkyl, C₁₋₄ alkoxy, CN, OH, CF₃, and —NR⁸R⁸;

R⁸, at each occurrence, is independently selected from H and C₁₋₄ alkyl; and other variables are as defined in Formula (IIIa) above.

In still another aspect, the present invention provides compounds of Formula (Va):

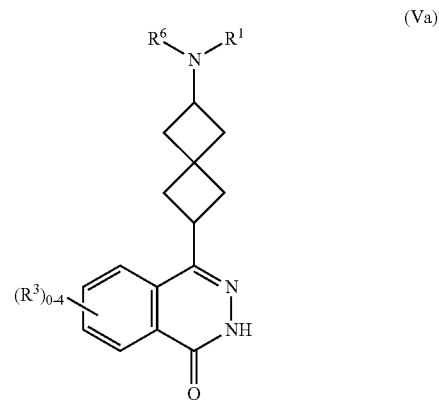

(Va)

or stereoisomers, tautomers, pharmaceutically-acceptable salts, solvates, or prodrugs thereof, wherein:

R¹ is heteroaryl substituted with 1-4 R⁷;

R⁶, at each occurrence, is independently selected from H and C₁₋₄ alkyl;

R⁷, at each occurrence, is independently selected from H, =O, NO₂, halogen, C₁₋₄ alkyl, C₁₋₄ alkoxy, CN, OH, CF₃, —(CH₂)ₙ—CO₂H, —(CH₂)ₙ—CO₂(C₁₋₄ alkyl), —(CH₂)ₙ—NR⁸R⁸, —NHCO(C₁₋₄ alkyl), —NHCOCF₃, —NHCO₂(C₁₋₄ alkyl), —NHCO₂(CH₂)₂O(C₁₋₄ alkyl), —NHCO₂(CH₂)₃O(C₁₋₄ alkyl), —NHCO₂(CH₂)₂OH, —NHCO₂(CH₂)₂NH₂, —NHCO₂(CH₂)₂N(C₁₋₄ alkyl)₂, —NHCO₂CH₂CO₂H, —CH₂NHCO₂(C₁₋₄ alkyl), —NHC(O)NR⁸R⁸, —NHSO₂(C₁₋₄ alkyl), —SO₂NH₂, —SO₂NH(C₁₋₄ alkyl), —SO₂N(C₁₋₄ alkyl)₂, —SO₂NH(CH₂)₂OH, —SO₂NH(CH₂)₂O(C₁₋₄ alkyl), —(CH₂)ₙ—CONR⁸R⁸, —O(CH₂)ₙ-carbocycle, —O(CH₂)ₙ-heterocycle, —NHCO-carbocycle, —NHCO-heterocycle, —(CH₂)ₙ-carbocycle, and —(CH₂)ₙ-heterocycle comprising carbon atoms and 1-4 heteroatoms selected from N, NR⁸, O, and S(O)ₚ, wherein said alkyl, alkenyl, alkynyl, alkoxyl, carbocycle, and heterocycle are substituted with 0-4 R⁹;

R⁸, at each occurrence, is independently selected from H, C₁₋₄ alkyl, —(CH₂)ₙ-carbocycle, and —(CH₂)ₙ-heterocycle, wherein said alkyl, carbocycle, and heterocycle are substituted with 0-4 R⁹;

R⁹, at each occurrence, is independently selected from halogen, OH, CN, NO₂, CHF₂, CF₃, C₁₋₄ alkyl, C₁₋₄ alkoxy, CH₂OH, CO(C₁₋₄ alkyl), CO₂H, CO₂(C₁₋₄ alkyl), —(CHR¹⁰)ₙNRᵃRᵃ, —(CHR¹⁰)ₙCONRᵃRᵃ, —(CHR¹⁰)ₙNRᵃCO(C₁₋₄ alkyl), —O(CHR¹⁰)ₙcarbocycle, —O(CHR¹⁰)ₙheterocycle, —O(CHR¹⁰)ₙNRᵃRᵃ, and —(CR¹⁰R¹⁰)ₙ-4- to 10-membered heterocycle, wherein said alkyl, alkoxy, carbocycle, and heterocycle are substituted with 0-4 Rᵇ;

Rᵃ, at each occurrence, is independently selected from H, C₁₋₄ alkyl, —(CH₂)ₙOH, CO(C₁₋₄ alkyl), COCF₃, CO₂(C₁₋₄ alkyl), —CONH₂, —CONH—C₁₋₄ alkylene-CO₂(C₁₋₄ alkyl), C₁₋₄ alkylene-CO₂(C₁₋₄ alkyl), Rᶜ, CO₂Rᶜ, and CONHRᶜ; alternatively, Rᵃ and Rᵃ are taken together with the nitrogen atom to which they are attached to form a 4- to 10-membered heterocycle, wherein said alkyl, alkylene, and heterocycle are substituted with 0-4 Rᵇ;

$R^b$, at each occurrence, is independently selected from =O, halogen, $C_{1-4}$ alkyl, $C_{1-4}$ alkoxy, $OCF_3$, $NH_2$, $NO_2$, $N(C_{1-4}$ alkyl$)_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl$)_2$, —CONH—$C_{1-4}$ alkylene-O($C_{1-4}$ alkyl), —CONH—$C_{1-4}$ alkylene-N($C_{1-4}$ alkyl$)_2$, —CONH—$C_{1-4}$ alkylene-N($C_{1-4}$ alkyl$)_2$, —$C_{1-4}$ alkylene-O—P(O)(OH)$_2$, —$NHCO_2(C_{1-4}$ alkyl), —$R^c$, $COR^c$, $CO_2R^c$, and $CONHR^c$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, N($C_{1-4}$ alkyl), O, and $S(O)_p$; wherein each ring moiety is substituted with 0-2 $R^d$;

$R^d$, at each occurrence, is independently selected from =O, halogen, —OH, $C_{1-4}$ alkyl, $NH_2$, $NH(C_{1-4}$ alkyl), $N(C_{1-4}$ alkyl$)_2$, $C_{1-4}$ alkoxy, and —$NHCO(C_{1-4}$ alkyl), and a heterocycle containing carbon atoms and 1-4 heteroatoms selected from the group consisting of: N, NH, N($C_{1-4}$ alkyl), O, and $S(O)_p$;

n, at each occurrence, is independently selected from 0, 1, 2, 3, and 4;

p, at each occurrence, is independently selected from 0, 1, and 2; and other variables are as defined in Formula (II) above.

In still another aspect, the present invention provides compounds of Formula (VIIa):

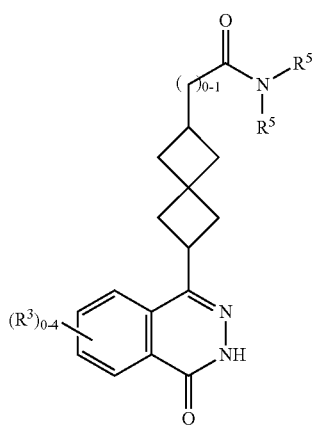

(VIIa)

or stereoisomers, tautomers, pharmaceutically-acceptable salts, solvates, or prodrugs thereof, wherein:

$R^5$, at each occurrence, is independently selected from H, $C_{1-4}$ alkyl, —$(CR^6R^6)_n$—$C_{3-10}$ carbocycle, and —$(CR^6R^6)_n$-4 to 10-membered heterocycle comprising carbon atoms and 1-4 heteroatoms selected from N, $NR^8$, O, and $S(O)_p$, wherein said alkyl, carbocycle, and heterocycle are substituted with 1-4 $R^7$;

alternatively, $R^5$ and $R^5$ are taken together with the nitrogen atom to which they are attached to form a 4- to 10-membered heterocycle substituted with 1-4 $R^7$;

$R^7$, at each occurrence, is independently selected from H, =O, $NO_2$, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$NHCO(C_{1-4}$ alkyl), —$NHCOCF_3$, —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl$)_2$, —$NHCO_2CH_2CO_2H$, —$CH_2NHCO_2(C_{1-4}$ alkyl), —NHC(O)$NR^8R^8$, —$NHSO_2(C_{1-4}$ alkyl), —$SO_2NH_2$, —$SO_2NH(C_{1-4}$ alkyl), —$SO_2N(C_{1-4}$ alkyl$)_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxyl, carbocycle, and heterocycle are substituted with 0-4 $R^9$;

$R^8$, at each occurrence, is independently selected from H, $C_{1-4}$ alkyl, $C(O)C_{1-4}$alkyl, C(O)carbocycle, C(O)heterocycle, —$(CH_2)$—$C(O)NR^aR^a$, $C(O)OC_{1-4}$alkyl, C(O)O-carbocycle, C(O)O-heterocycle, $SO_2$alkyl, $SO_2$carbocycle, $SO_2$heterocycle, $SO_2NR^aR^a$, —$(CH_2)_n$-carbocycle, and —$(CH_2)_n$-heterocycle, wherein said alkyl, carbocycle, and heterocycle are substituted with 0-4 $R^9$;

$R^9$, at each occurrence, is independently selected from halogen, OH, CN, $NO_2$, $CHF_2$, $CF_3$, $C_{1-4}$ alkyl, $C_{1-4}$ alkoxy, $CH_2OH$, $CO(C_{1-4}$ alkyl), $CO_2H$, $CO_2(C_{1-4}$ alkyl), —$(CHR^{10})_n NR^aR^a$, —$(CHR^{10})_n CONR^aR^a$, —$(CHR^{10})_n NR^a CO(C_{1-4}$ alkyl), —$O(CHR^{10})_n$carbocycle, —$O(CHR^{10})_n$heterocycle, —$O(CHR^{10})_n NR^aR^a$, and —$(CR^{10}R^{10})_n$-4- to 10-membered heterocycle, wherein said alkyl, alkoxy, carbocycle, and heterocycle are substituted with 0-4 $R^b$;

$R^a$, at each occurrence, is independently selected from H, $C_{1-4}$ alkyl, —$(CH_2)_n OH$, $CO(C_{1-4}$ alkyl), $COCF_3$, $CO_2(C_{1-4}$ alkyl), —$CONH_2$, —CONH—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, halogen, $C_{1-4}$ alkyl, $C_{1-4}$ alkoxy, $OCF_3$, $NH_2$, $NO_2$, $N(C_{1-4}$ alkyl$)_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl$)_2$, —CONH—$C_{1-4}$ alkylene-O($C_{1-4}$ alkyl), —CONH—$C_{1-4}$ alkylene-N($C_{1-4}$ alkyl$)_2$, —CONH—$C_{1-4}$ alkylene-N($C_{1-4}$ alkyl$)_2$, —$C_{1-4}$ alkylene-O—P(O)(OH)$_2$, —$NHCO_2(C_{1-4}$ alkyl), —$R^c$, $COR^c$, $CO_2R^c$, and $CONHR^c$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, N($C_{1-4}$ alkyl), O, and $S(O)_p$; wherein each ring moiety is substituted with 0-2 $R^d$;

$R^d$, at each occurrence, is independently selected from =O, halogen, —OH, $C_{1-4}$ alkyl, $NH_2$, $NH(C_{1-4}$ alkyl), $N(C_{1-4}$ alkyl$)_2$, $C_{1-4}$ alkoxy, and —$NHCO(C_{1-4}$ alkyl), and a heterocycle containing carbon atoms and 1-4 heteroatoms selected from the group consisting of: N, NH, N($C_{1-4}$ alkyl), O, and $S(O)_p$;

n, at each occurrence, is independently selected from 0, 1, 2, 3, and 4;

p, at each occurrence, is independently selected from 0, 1, and 2; and other variables are as defined in Formula (IIa) above.

In another aspect, the present invention provides compounds of Formula (VIII) or stereoisomers, tautomers, pharmaceutically-acceptable salts, solvates, or prodrugs thereof, wherein:

M is N;

$R^1$ is selected from

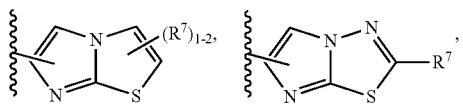

-continued
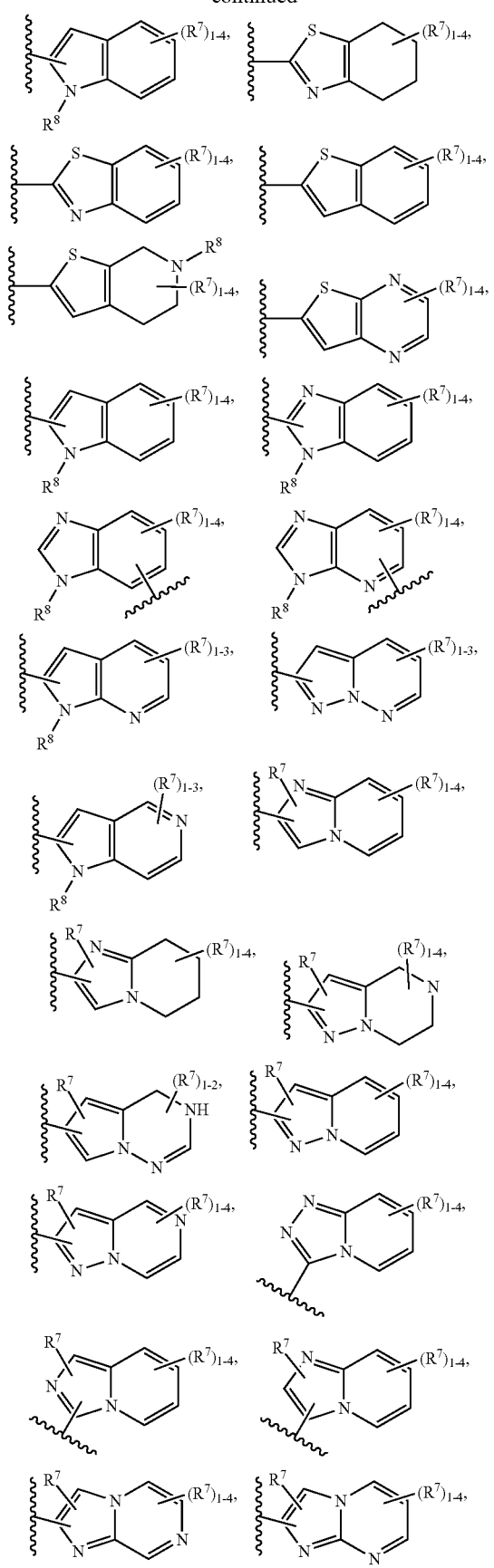
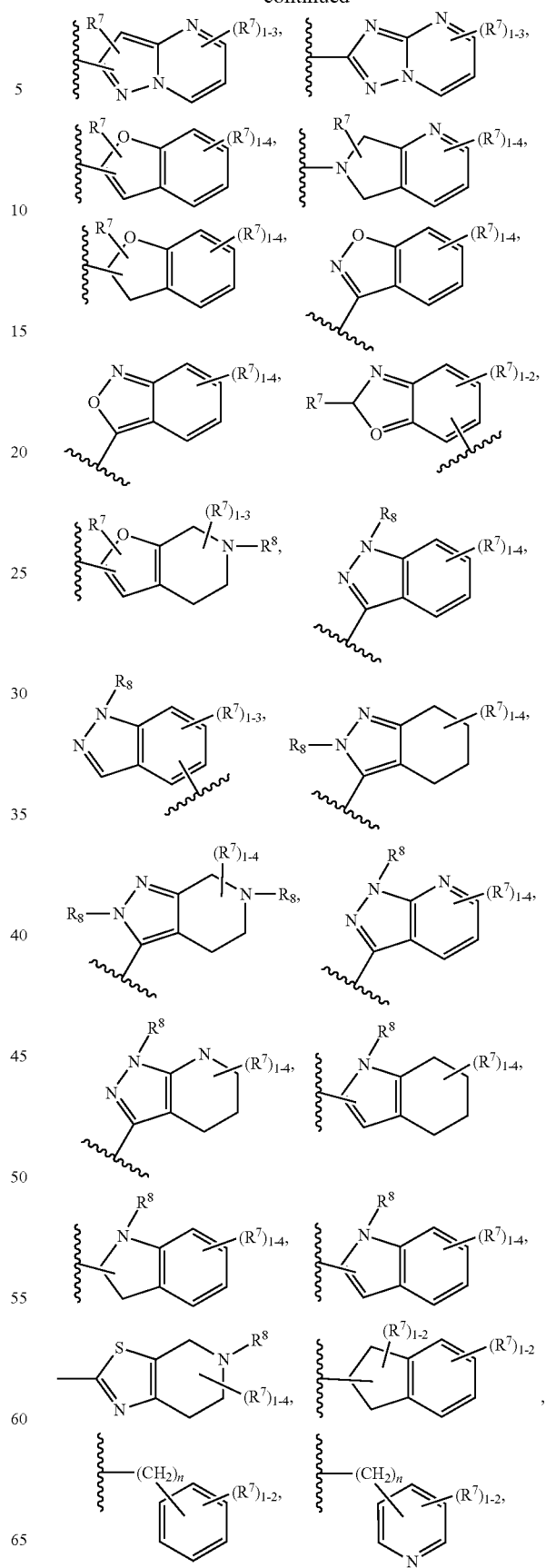

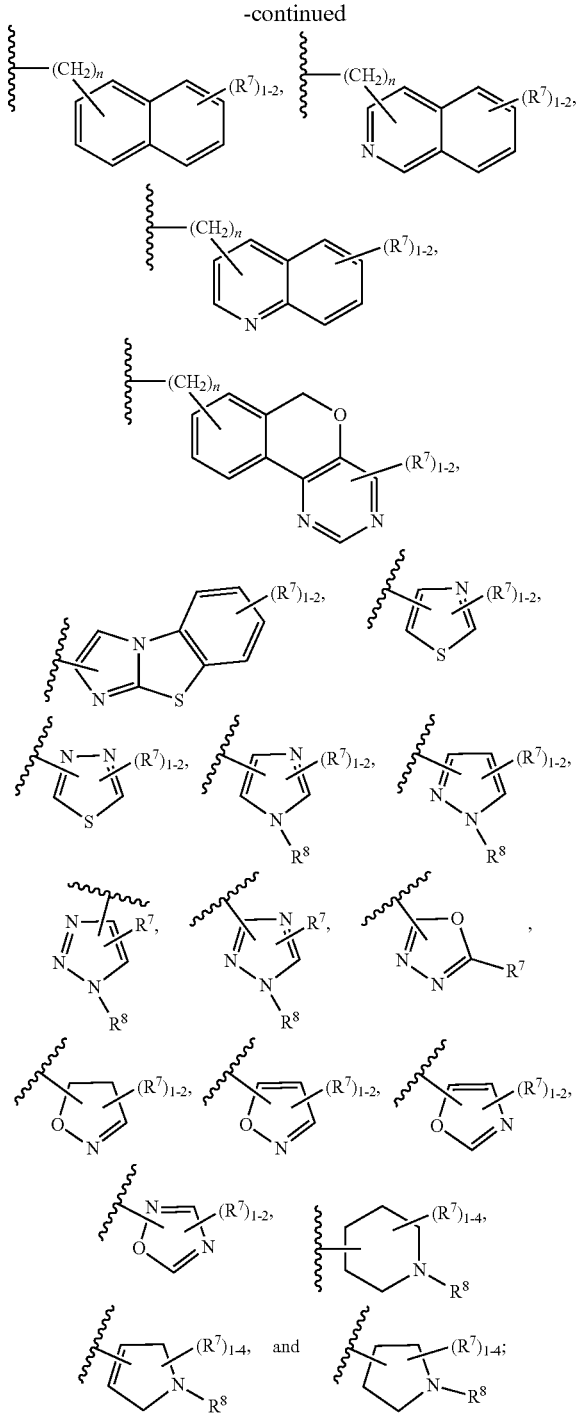

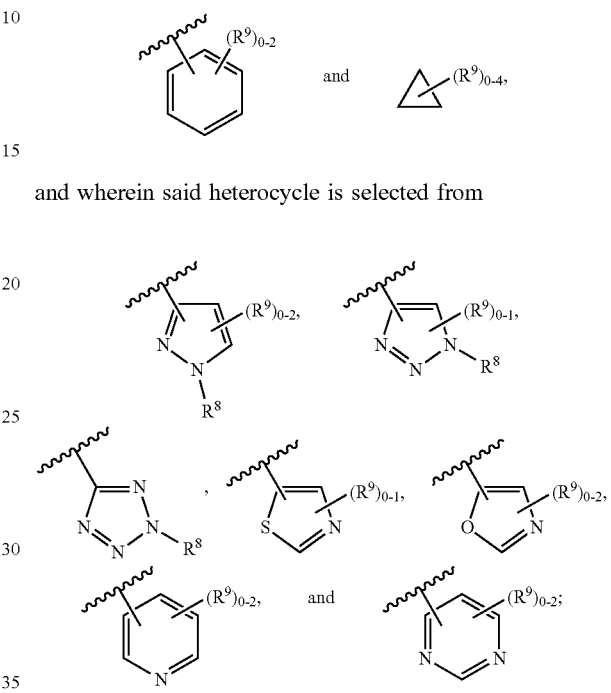

—O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxyl, carbocycle, and heterocycle are substituted with 0-4 R$^9$ and wherein said carbocycle is selected from and wherein said heterocycle is selected from R$^8$, at each occurrence, is independently selected from H, C$_{1-4}$ alkyl, C(O)C$_{1-4}$alkyl, C(O)carbocycle, C(O)heterocycle, —(CH$_2$)$_n$—C(O)NR$^a$R$^a$, C(O)OC$_{1-4}$alkyl, C(O)O-carbocycle, C(O)O-heterocycle, SO$_2$alkyl, SO$_2$carbocycle, SO$_2$heterocycle, —(CH$_2$)$_n$—NHC(O) C$_{1-4}$ alkyl, SO$_2$NR$^a$R$^a$, —(CH$_2$)$_n$—C$_{3-6}$cycloalkyl, —(CH$_2$)$_n$-aryl, and —(CH$_2$)$_n$-heterocycle, wherein said alkyl, cycloalkyl, aryl, and heterocycle are substituted with 0-4 R$^9$;

alternatively, R$^8$ and R$^8$ are taken together with the nitrogen atom to which they are attached to form a heterocycle selected from

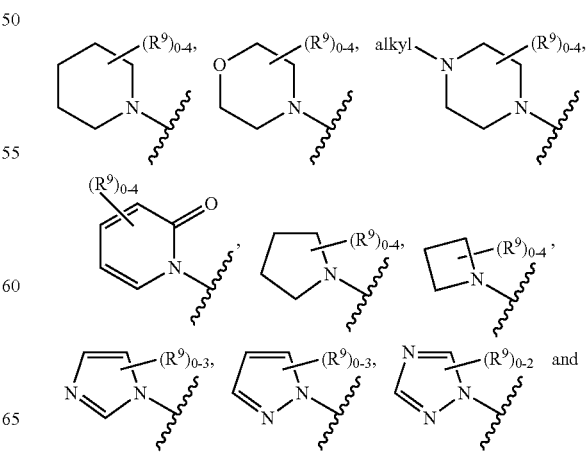

R$^7$, at each occurrence, is independently selected from H, =O, NO$_2$, F, Cl, Br, C$_{1-6}$ alkyl, C$_{2-4}$ alkenyl, C$_{2-4}$ alkynyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCOH, —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —(CH$_2$)$_{1-2}$NHCO$_2$(C$_{1-4}$ alkyl), —NHC(O)NR$^8$R$^8$, S(C$_{1-4}$ alkyl), —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —(CH$_2$)$_n$—CONR$^8$R$^8$, -continued

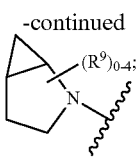

R⁹, at each occurrence, is independently selected from F, Cl, Br, I, OH, =O, CN, NO₂, CHF₂, CF₃, $C_{1-4}$ alkyl, $C_{1-4}$ alkoxy, CH₂OH, CO₂H, CO₂($C_{1-4}$ alkyl), CONH₂, —(CH₂)ₙNRᵃRᵃ, —(CH₂)ₙCONRᵃRᵃ, —(CH₂)ₙNHCO ($C_{1-4}$ alkyl), —O(CH₂)ₙheterocycle, —O(CH₂)₂₋₄NRᵃRᵃ, —(CH₂)ₙ-carbocycle, and —(CH₂)ₙ-4- to 10-membered heterocycle, wherein said alkyl, alkoxyl, carbocycle, and heterocycle are substituted with 0-4 Rᵇ;

Rᵃ, at each occurrence, is independently selected from H and $C_{1-4}$ alkyl; alternatively, Rᵃ and Rᵃ are taken together with the nitrogen atom to which they are attached to form a 4- to 10-membered heterocycle, wherein said alkyl, alkylene, and heterocycle are substituted with 0-4 Rᵇ;

Rᵇ, at each occurrence, is independently selected from =O, halogen, $C_{1-4}$ alkyl, $C_{1-4}$ alkoxy, OCF₃, OC(O)$C_{1-4}$ alkyl, NH₂, NO₂, N($C_{1-4}$ alkyl)₂, CO($C_{1-4}$ alkyl), CO($C_{1-4}$ haloalkyl), CO₂($C_{1-4}$ alkyl), CONH₂, —CONH($C_{1-4}$ alkyl), —CON($C_{1-4}$ alkyl)₂, —CONH—$C_{1-4}$ alkylene-O($C_{1-4}$ alkyl), —CONH—$C_{1-4}$ alkylene-N($C_{1-4}$ alkyl)₂, —CONH—$C_{1-4}$ alkylene-N($C_{1-4}$ alkyl)₂, and —NHCO₂ ($C_{1-4}$ alkyl), wherein said alkyl and alkoxy are substituted with Rᵈ;

Rᵈ, at each occurrence, is independently selected from =O, halogen, —OH, $C_{1-4}$ alkyl, NH₂, NH($C_{1-4}$ alkyl), N($C_{1-4}$ alkyl)₂, $C_{1-4}$ alkoxy, and —NHCO($C_{1-4}$ alkyl), and a heterocycle containing carbon atoms and 1-4 heteroatoms selected from the group consisting of: N, NH, N($C_{1-4}$ alkyl), O, and S(O)ₚ;

n, at each occurrence, is independently selected from 0, 1, 2, 3, and 4;

p, at each occurrence, is independently selected from 0, 1, and 2; and other variables are as defined in Formula (VIII) above.

In another aspect, the present invention provides compounds of Formula (VIII) or stereoisomers, tautomers, pharmaceutically-acceptable salts, solvates, or prodrugs thereof, wherein:

M is N;

R¹ is NR⁵R⁵;

R⁵ and R⁵ are taken together with the nitrogen atom to which they are attached to form a heterocycle selected from

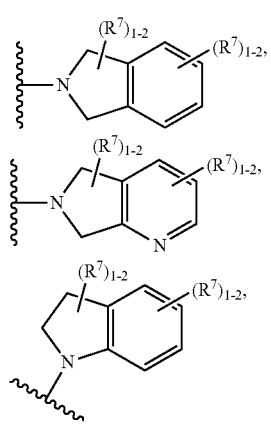

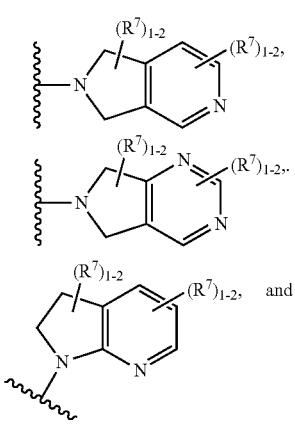

-continued

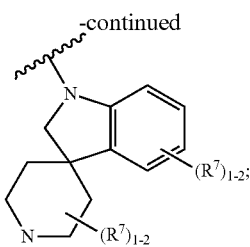

R⁷, at each occurrence, is independently selected from H, =O, F, Cl, Br, $C_{1-4}$ alkyl, $C_{1-4}$ alkoxy, CN, OH, CF₃, —(CH₂)ₙ—NR⁸R⁸, —NHSO₂($C_{1-4}$ alkyl), —SO₂NH₂, —SO₂NH($C_{1-4}$ alkyl), —SO₂N($C_{1-4}$ alkyl)₂, —(CH₂)ₙ— CONR⁸R⁸, —(CH₂)ₙ-phenyl, and —(CH₂)ₙ-heterocycle selected from

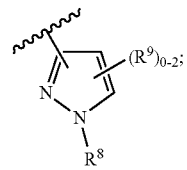

R⁸, at each occurrence, is independently selected from H, CF₃, CD₃, CH₃, C(CH₃)₃,

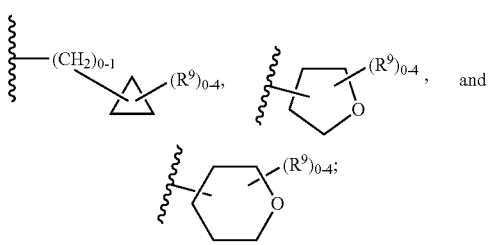

alternatively, R⁸ and R⁸ are taken together to form

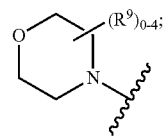

R⁹, at each occurrence, is independently selected from F, Cl, OH, NO₂, CHF₂, (CH₂)₀₋₂CF₃, CD₃, CH₃, OC₁₋₄ alkyl, SO₂NH₂, and phenyl substituted with $C_{1-4}$ alkyl; and other variables are as defined in Formula (VIII) above.

In another aspect, the present invention provides compounds of Formula (Va) or stereoisomers, tautomers, pharmaceutically-acceptable salts, solvates, or prodrugs thereof, wherein:

R¹ and R⁶ are taken together with the nitrogen atom to which they are attached to form a heterocycle selected from

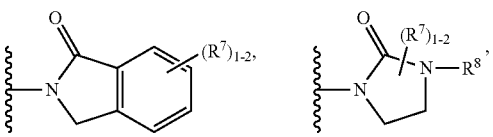

-continued

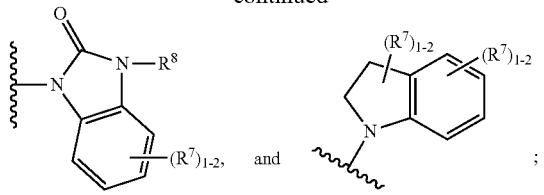

R⁷, at each occurrence, is independently selected from H, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$NHCO(C_{1-4}$ alkyl), —$NHC(O)NR^8R^8$, —$NHSO_2(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$(CH_2)_n$—$CONR^8R^8$, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxyl, carbocycle, and heterocycle are substituted with 0-4 $R^9$;

$R^8$, at each occurrence, is independently selected from H and $C_{1-4}$ alkyl:

$R^9$, at each occurrence, is independently selected from halogen, OH, CN, $NO_2$, $CHF_2$, $CF_3$, $C_{1-4}$ alkyl, $C_{1-4}$ alkoxy, $CH_2OH$, $CO(C_{1-4}$ alkyl), and $CO_2H$, $CO_2(C_{1-4}$ alkyl);

n, at each occurrence, is independently selected from 0, 1, 2, 3, and 4;

p, at each occurrence, is independently selected from 0, 1, and 2; and other variables are as defined in Formula (IIa) above.

In another aspect, the present invention provides compounds of Formula (IX) or stereoisomers, tautomers, pharmaceutically-acceptable salts, solvates, or prodrugs thereof, wherein:

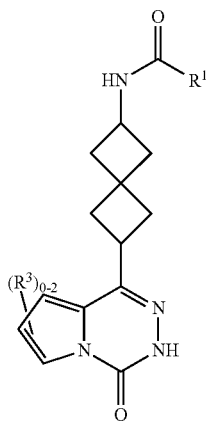

(IX)

or a stereoisomer, a tautomer, a pharmaceutically-acceptable salt thereof, wherein:

$R^1$ is selected from $NR^5R^5$, and a 5- to 10-membered heterocycle substituted with 1-4 $R^7$;

$R^3$, at each occurrence, is independently selected from halogen and $C_{1-6}$ alkyl; $R^5$ and $R^5$ are taken together with the nitrogen atom to which they are attached to form a 4- to 10-membered heterocycle substituted with 1-4 $R^7$;

$R^7$, at each occurrence, is independently selected from H, =O, $NO_2$, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —$NHCO(C_{1-4}$ alkyl), —$NHCOCF_3$, —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl)$_2$, —$NHCO_2CH_2CO_2H$, —$CH_2NHCO_2(C_{1-4}$ alkyl), —$NHC(O)NR^8R^8$, —$NHSO_2(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxyl, carbocycle, and heterocycle are substituted with 0-4 $R^9$;

$R^8$, at each occurrence, is independently selected from H, $C_{1-4}$ alkyl, $C_{2-4}$ alkenyl, $C(O)C_{1-4}$alkyl, $C(O)$carbocycle, $C(O)$heterocycle, —$(CH_2)_n$—$C(O)NR^aR^a$, $C(O)OC_{1-4}$ alkyl, $C(O)O$-carbocycle, $C(O)O$-heterocycle, $SO_2$alkyl, $SO_2$carbocycle, $SO_2$heterocycle, $SO_2NR^aR^a$, —$(CH_2)_n$-carbocycle, and —$(CH_2)_n$-heterocycle, wherein said alkyl, alkenyl, carbocycle, and heterocycle are substituted with 0-4 $R^9$;

$R^9$, at each occurrence, is independently selected from halogen, OH, CN, $NO_2$, $CHF_2$, $CF_3$, $C_{1-4}$ alkyl, $C_{1-4}$ alkoxy, $CH_2OH$, $CO(C_{1-4}$ alkyl), $CO_2H$, $CO_2(C_{1-4}$ alkyl), —$(CHR^{10})_n NR^aR^a$, —$(CHR^{10})_n CONR^aR^a$, —$(CHR^{10})_n NR^a CO(C_{1-4}$ alkyl), —$O(CHR^{10})_n$carbocycle, —$O(CHR^{10})_n$heterocycle, —$O(CHR^{10})_n NR^aR^a$, and —$(CR^{10}R^{10})_n$-4- to 10-membered heterocycle, wherein said alkyl, alkoxy, carbocycle, and heterocycle are substituted with 0-4 $R^b$;

$R^{10}$ is selected from H and $C_{1-4}$ alkyl;

$R^a$, at each occurrence, is independently selected from H, $C_{1-4}$ alkyl, —$(CH_2)_n OH$, $CO(C_{1-4}$ alkyl), $COCF_3$, $CO_2(C_{1-4}$ alkyl), —$CONH_2$, —$CONH$—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, halogen, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —$CONH(C_{1-4}$ alkyl), —$CON(C_{1-4}$ alkyl)$_2$, —$CONH$—$C_{1-4}$ alkylene-$O(C_{1-4}$ alkyl), —$CONH$—$C_{1-4}$ alkylene-$N(C_{1-4}$ alkyl)$_2$, —$CONH$—$C_{1-4}$ alkylene-$N(C_{1-4}$ alkyl)$_2$, —$C_{1-4}$ alkylene-O—$P(O)(OH)_2$, —$NHCO_2(C_{1-4}$ alkyl), —$R^c$, $COR^c$, $CO_2R^c$, and $CONHR^c$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, $N(C_{1-4}$ alkyl), O, and $S(O)_p$; wherein each ring moiety is substituted with 0-2 $R^d$;

$R^d$, at each occurrence, is independently selected from =O, halogen, —OH, $C_{1-4}$ alkyl, $NH_2$, $NH(C_{1-4}$ alkyl), $N(C_{1-4}$ alkyl)$_2$, $C_{1-4}$ alkoxy, and —$NHCO(C_{1-4}$ alkyl), and a heterocycle containing carbon atoms and 1-4 heteroatoms selected from the group consisting of: N, NH, $N(C_{1-4}$ alkyl), O, and $S(O)_p$;

n, at each occurrence, is independently selected from 0, 1, 2, 3, and 4; and p, at each occurrence, is independently selected from 0, 1, and 2.

In another aspect, the present invention provides a compound selected from any subset list of compounds exemplified in the present application.

In another aspect, the present invention provides a compound selected from the group consisting of:

N-[6-(4-oxo-3,4-dihydrophthalazin-1-yl)spiro[3.3]heptan-2-yl]-2,3-dihydro-1H-indene-2-carboxamide;
4-(dimethylamino)-N-[6-(4-oxo-3,4-dihydrophthalazin-1-yl)spiro[3.3]heptan-2-yl]benzamide;
2-(naphthalen-1-yl)-N-[6-(4-oxo-3,4-dihydrophthalazin-1-yl)spiro[3.3]heptan-2-yl]acetamide;
2-(naphthalen-2-yl)-N-[6-(4-oxo-3,4-dihydrophthalazin-1-yl)spiro[3.3]heptan-2-yl]acetamide;
1-methyl-N-[6-(4-oxo-3,4-dihydrophthalazin-1-yl)spiro[3.3]heptan-2-yl]-1H-indazole-3-carboxamide;
N-[6-(4-oxo-3,4-dihydrophthalazin-1-yl)spiro[3.3]heptan-2-yl]-3-phenylpropanamide;
N-[6-(4-oxo-3,4-dihydrophthalazin-1-yl)spiro[3.3]heptan-2-yl]-1-(2,2,2-trifluoroethyl)-1H-pyrazole-3-carboxamide;
3-methyl-N-[6-(4-oxo-3,4-dihydrophthalazin-1-yl)spiro[3.3]heptan-2-yl]-1-phenyl-1H-pyrazole-4-carboxamide;
1-tert-butyl-N-[6-(4-oxo-3,4-dihydrophthalazin-1-yl)spiro[3.3]heptan-2-yl]-1H-pyrazole-4-carboxamide;
N-[6-(4-oxo-3,4-dihydrophthalazin-1-yl)spiro[3.3]heptan-2-yl]-1-phenyl-1H-pyrazole-3-carboxamide;
1-(2-hydroxy-2-methylpropyl)-N-[6-(4-oxo-3,4-dihydrophthalazin-1-yl)spiro[3.3]heptan-2-yl]-1H-indazole-3-carboxamide;
N-[6-(4-oxo-3,4-dihydrophthalazin-1-yl)spiro[3.3]heptan-2-yl]-1-phenyl-1H-pyrazole-4-carboxamide;
5-methyl-N-[6-(4-oxo-3,4-dihydrophthalazin-1-yl)spiro[3.3]heptan-2-yl]-1-phenyl-1H-pyrazole-4-carboxamide;
1-methyl-N-[(aR)-6-(4-oxo-3,4-dihydrophthalazin-1-yl)spiro[3.3]heptan-2-yl]-1H-indazole-3-carboxamide;
N-[(aR)-6-(4-oxo-3,4-dihydrophthalazin-1-yl)spiro[3.3]heptan-2-yl]-1-(2,2,2-trifluoroethyl)-1H-pyrazole-3-carboxamide;
1-(2,2-difluoroethyl)-N-[(aR)-6-(4-oxo-3,4-dihydrophthalazin-1-yl)spiro[3.3]heptan-2-yl]-1H-pyrazole-3-carboxamide;
1-methyl-N-[(aS)-6-(4-oxo-3,4-dihydrophthalazin-1-yl)spiro[3.3]heptan-2-yl]-1H-indazole-3-carboxamide;
N-[(aS)-6-(4-oxo-3,4-dihydrophthalazin-1-yl)spiro[3.3]heptan-2-yl]-1-(2,2,2-trifluoroethyl)-1H-pyrazole-3-carboxamide;
1-(2,2-difluoroethyl)-N-[(aS)-6-(4-oxo-3,4-dihydrophthalazin-1-yl)spiro[3.3]heptan-2-yl]-1H-pyrazole-3-carboxamide;
5-methyl-N-[(aR)-6-(4-oxo-3,4-dihydrophthalazin-1-yl)spiro[3.3]heptan-2-yl]-1-phenyl-1H-pyrazole-4-carboxamide;
1-(2-hydroxy-2-methylpropyl)-N-[(aR)-6-(4-oxo-3,4-dihydrophthalazin-1-yl)spiro[3.3]heptan-2-yl]-1H-indazole-3-carboxamide;
N-[(aR)-6-(4-oxo-3,4-dihydrophthalazin-1-yl)spiro[3.3]heptan-2-yl]-1-(3,3,3-trifluoropropyl)-1H-pyrazole-3-carboxamide;
1-(cyclopropylmethyl)-N-[(aR)-6-(4-oxo-3,4-dihydrophthalazin-1-yl)spiro[3.3]heptan-2-yl]-1H-pyrazole-3-carboxamide;
3-cyclopropyl-1-methyl-N-[(aR)-6-(4-oxo-3,4-dihydrophthalazin-1-yl)spiro[3.3]heptan-2-yl]-1H-pyrazole-5-carboxamide;
1-methyl-N-[(aR)-6-(4-oxo-3,4-dihydrophthalazin-1-yl)spiro[3.3]heptan-2-yl]-3-(trifluoromethyl)-1H-pyrazole-5-carboxamide;
5-cyclopropyl-1-methyl-N-[(aR)-6-(4-oxo-3,4-dihydrophthalazin-1-yl)spiro[3.3]heptan-2-yl]-1H-pyrazole-3-carboxamide;
1-cyclopropyl-N-[(aR)-6-(4-oxo-3,4-dihydrophthalazin-1-yl)spiro[3.3]heptan-2-yl]-1H-pyrazole-4-carboxamide;
5-(difluoromethoxy)-1-methyl-N-[(aR)-6-(4-oxo-3,4-dihydrophthalazin-1-yl)spiro[3.3]heptan-2-yl]-1H-pyrazole-3-carboxamide;
1-cyclopropyl-N-[(aR)-6-(4-oxo-3,4-dihydrophthalazin-1-yl)spiro[3.3]heptan-2-yl]-1H-pyrazole-3-carboxamide;
1-(2-hydroxy-2-methylpropyl)-N-[(aR)-6-(4-oxo-3,4-dihydrophthalazin-1-yl)spiro[3.3]heptan-2-yl]-1H-pyrazole-3-carboxamide;
6-fluoro-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide;
1-(2,2-difluoroethyl)-3-methyl-N-[(aR)-6-(4-oxo-3,4-dihydrophthalazin-1-yl)spiro[3.3]heptan-2-yl]-1H-pyrazole-4-carboxamide;
4-methyl-N-[(aR)-6-(4-oxo-3,4-dihydrophthalazin-1-yl)spiro[3.3]heptan-2-yl]-2-(piperidin-1-yl)-1,3-thiazole-5-carboxamide;
4-methyl-2-(morpholin-4-yl)-N-[(aR)-6-(4-oxo-3,4-dihydrophthalazin-1-yl)spiro[3.3]heptan-2-yl]-1,3-thiazole-5-carboxamide;
4-methyl-N-[(aR)-6-(4-oxo-3,4-dihydrophthalazin-1-yl)spiro[3.3]heptan-2-yl]-2-(pyrrolidin-1-yl)-1,3-thiazole-5-carboxamide;
2-[(3S)-3-fluoropyrrolidin-1-yl]-4-methyl-N-[(aR)-6-(4-oxo-3,4-dihydrophthalazin-1-yl)spiro[3.3]heptan-2-yl]-1,3-thiazole-5-carboxamide;
2-[(3R)-3-fluoropyrrolidin-1-yl]-4-methyl-N-[(aR)-6-(4-oxo-3,4-dihydrophthalazin-1-yl)spiro[3.3]heptan-2-yl]-1,3-thiazole-5-carboxamide;
2-[(3S)-3-cyanopyrrolidin-1-yl]-4-methyl-N-[(aR)-6-(4-oxo-3,4-dihydrophthalazin-1-yl)spiro[3.3]heptan-2-yl]-1,3-thiazole-5-carboxamide;
2-[(3R)-3-cyanopyrrolidin-1-yl]-4-methyl-N-[(aR)-6-(4-oxo-3,4-dihydrophthalazin-1-yl)spiro[3.3]heptan-2-yl]-1,3-thiazole-5-carboxamide;
rel-2-[(1S,5R)-2-azabicyclo[3.1.0]hexan-2-yl]-4-methyl-N-[(aR)-6-(4-oxo-3,4-dihydrophthalazin-1-yl)spiro[3.3]heptan-2-yl]-1,3-thiazole-5-carboxamide;
2-(3,3-difluoropyrrolidin-1-yl)-4-methyl-N-[(aR)-6-(4-oxo-3,4-dihydrophthalazin-1-yl)spiro[3.3]heptan-2-yl]-1,3-thiazole-5-carboxamide;
2-(cyclopropylamino)-4-methyl-N-[(aR)-6-(4-oxo-3,4-dihydrophthalazin-1-yl)spiro[3.3]heptan-2-yl]-1,3-thiazole-5-carboxamide;
4-(aR)-{6-[(5-phenyl-1,3,4-thiadiazol-2-yl)amino]spiro[3.3]heptan-2-yl}-1,2-dihydrophthalazin-1-one;
4-(aR)-{6-[(5-phenyl-1,3-oxazol-2-yl)amino]spiro[3.3]heptan-2-yl}-1,2-dihydrophthalazin-1-one;
4-(aR)-{6-[(phthalazin-1-yl)amino]spiro[3.3]heptan-2-yl}-1,2-dihydrophthalazin-1-one;
4-[6-(2,3-dihydro-1H-indole-1-carbonyl)spiro[3.3]heptan-2-yl]-1,2-dihydrophthalazin-1-one;
4-[6-(2,3-dihydro-1H-isoindole-2-carbonyl)spiro[3.3]heptan-2-yl]-1,2-dihydrophthalazin-1-one;
N-(5-methyl-1,3,4-thiadiazol-2-yl)-6-(4-oxo-3,4-dihydrophthalazin-1-yl)spiro[3.3]heptane-2-carboxamide;
N-(5-methyl-1,2-oxazol-3-yl)-6-(4-oxo-3,4-dihydrophthalazin-1-yl)spiro[3.3]heptane-2-carboxamide;
N-[(aR)-6-(4-oxo-3,4-dihydrophthalazin-1-yl)spiro[3.3]heptan-2-yl]-2,3-dihydro-1H-indole-1-carboxamide;
N-[(aR)-6-(4-oxo-3,4-dihydrophthalazin-1-yl)spiro[3.3]heptan-2-yl]-2,3-dihydro-1H-isoindole-2-carboxamide;
4-{6-[2-(2,3-dihydro-1H-indol-1-yl)-2-oxoethyl]spiro[3.3]heptan-2-yl}-1,2-dihydrophthalazin-1-one;

2-[(3R)-3-fluoropyrrolidin-1-yl]-5-methyl-N-[(aR)-6-(4-oxo-3,4-dihydrophthalazin-1-yl)spiro[3.3]heptan-2-yl]-1,3-thiazole-4-carboxamide;

2-(3,3-difluoropyrrolidin-1-yl)-5-methyl-N-[(aR)-6-(4-oxo-3,4-dihydrophthalazin-1-yl)spiro[3.3]heptan-2-yl]-1,3-thiazole-4-carboxamide;

2-[(3S)-3-cyanopyrrolidin-1-yl]-5-methyl-N-[(aR)-6-(4-oxo-3,4-dihydrophthalazin-1-yl)spiro[3.3]heptan-2-yl]-1,3-thiazole-4-carboxamide;

2-[(3R)-3-cyanopyrrolidin-1-yl]-5-methyl-N-[(aR)-6-(4-oxo-3,4-dihydrophthalazin-1-yl)spiro[3.3]heptan-2-yl]-1,3-thiazole-4-carboxamide;

2-[(3,3-difluorocyclobutyl)amino]-5-methyl-N-[(aR)-6-(4-oxo-3,4-dihydrophthalazin-1-yl)spiro[3.3]heptan-2-yl]-1,3-thiazole-4-carboxamide;

2-[(3S)-3-fluoropyrrolidin-1-yl]-5-methyl-N-[(aR)-6-(4-oxo-3,4-dihydrophthalazin-1-yl)spiro[3.3]heptan-2-yl]-1,3-thiazole-4-carboxamide;

5-methyl-N-[(aR)-6-(4-oxo-3,4-dihydrophthalazin-1-yl)spiro[3.3]heptan-2-yl]-2-[(2S)-2-(trifluoromethyl)pyrrolidin-1-yl]-1,3-thiazole-4-carboxamide;

5-methyl-N-[(aR)-6-(4-oxo-3,4-dihydrophthalazin-1-yl)spiro[3.3]heptan-2-yl]-2-[(2R)-2-(trifluoromethyl)pyrrolidin-1-yl]-1,3-thiazole-4-carboxamide;

1-(2-hydroxy-2-methylpropyl)-5-methoxy-N-[(aR)-6-(4-oxo-3,4-dihydrophthalazin-1-yl)spiro[3.3]heptan-2-yl]-1H-indazole-3-carboxamide;

1-(2-hydroxy-2-methylpropyl)-6-methoxy-N-[(aR)-6-(4-oxo-3,4-dihydrophthalazin-1-yl)spiro[3.3]heptan-2-yl]-1H-indazole-3-carboxamide;

6-methoxy-N-[(aR)-6-(4-oxo-3,4-dihydrophthalazin-1-yl)spiro[3.3]heptan-2-yl]pyrazolo[1,5-a]pyridine-3-carboxamide;

5-methoxy-N-[(aR)-6-(4-oxo-3,4-dihydrophthalazin-1-yl)spiro[3.3]heptan-2-yl]pyrazolo[1,5-a]pyridine-3-carboxamide;

5-fluoro-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide;

1-(2-hydroxy-2-methylpropyl)-N-[(aR)-6-(4-oxo-3,4-dihydrophthalazin-1-yl)spiro[3.3]heptan-2-yl]-1H-pyrrolo[2,3-b]pyridine-3-carboxamide;

6-(2-hydroxy-2-methylpropoxy)-N-[(aR)-6-(4-oxo-3,4-dihydrophthalazin-1-yl)spiro[3.3]heptan-2-yl]pyrazolo[1,5-a]pyridine-3-carboxamide;

6-[2-(morpholin-4-yl)ethoxy]-N-[(aR)-6-(4-oxo-3,4-dihydrophthalazin-1-yl)spiro[3.3]heptan-2-yl]pyrazolo[1,5-a]pyridine-3-carboxamide;

2-(morpholin-4-yl)-N-[(aR)-6-(4-oxo-3,4-dihydrophthalazin-1-yl)spiro[3.3]heptan-2-yl]-1,3-thiazole-5-carboxamide;

N-[(aR)-6-(4-oxo-3,4-dihydrophthalazin-1-yl)spiro[3.3]heptan-2-yl]-2-(pyrrolidin-1-yl)-1,3-thiazole-5-carboxamide;

N-[(aR)-6-(4-oxo-3,4-dihydrophthalazin-1-yl)spiro[3.3]heptan-2-yl]-1,2-benzoxazole-3-carboxamide;

1-(2-hydroxy-2-methylpropyl)-N-[(aR)-6-(4-oxo-3,4-dihydrophthalazin-1-yl)spiro[3.3]heptan-2-yl]-1H-indole-3-carboxamide;

5-[2-(morpholin-4-yl)ethoxy]-N-[(aR)-6-(4-oxo-3,4-dihydrophthalazin-1-yl)spiro[3.3]heptan-2-yl]pyrazolo[1,5-a]pyridine-3-carboxamide;

N-[(aR)-6-(4-oxo-3,4-dihydrophthalazin-1-yl)spiro[3.3]heptan-2-yl]pyrazolo[1,5-a]pyridine-3-carboxamide;

5-(2-hydroxy-3-methoxypropoxy)-N-[(aR)-6-(4-oxo-3,4-dihydrophthalazin-1-yl)spiro[3.3]heptan-2-yl]pyrazolo[1,5-a]pyridine-3-carboxamide;

6-(morpholin-4-yl)-N-[(aR)-6-(4-oxo-3,4-dihydrophthalazin-1-yl)spiro[3.3]heptan-2-yl]pyrazolo[1,5-a]pyridine-3-carboxamide;

5-(2-hydroxyethoxy)-N-[(aR)-6-(4-oxo-3,4-dihydrophthalazin-1-yl)spiro[3.3]heptan-2-yl]pyrazolo[1,5-a]pyridine-3-carboxamide;

N-[(aR)-6-(4-oxo-3,4-dihydrophthalazin-1-yl)spiro[3.3]heptan-2-yl]-2,1-benzoxazole-3-carboxamide;

6-(difluoromethoxy)-N-[(aR)-6-(4-oxo-3,4-dihydrophthalazin-1-yl)spiro[3.3]heptan-2-yl]pyrazolo[1,5-a]pyridine-3-carboxamide;

6-(2,2-difluoroethoxy)-N-[(aR)-6-(4-oxo-3,4-dihydrophthalazin-1-yl)spiro[3.3]heptan-2-yl]pyrazolo[1,5-a]pyridine-3-carboxamide;

N-[(aR)-6-(4-oxo-3,4-dihydrophthalazin-1-yl)spiro[3.3]heptan-2-yl]-6-[2-(1H-pyrazol-1-yl)ethoxy]pyrazolo[1,5-a]pyridine-3-carboxamide;

6-(4,4-difluoropiperidin-1-yl)-N-[(aR)-6-(4-oxo-3,4-dihydrophthalazin-1-yl)spiro[3.3]heptan-2-yl]pyrazolo[1,5-a]pyridine-3-carboxamide;

N-[(aR)-6-(4-oxo-3,4-dihydrophthalazin-1-yl)spiro[3.3]heptan-2-yl]-6-[2-(pyrrolidin-1-yl)ethoxy]pyrazolo[1,5-a]pyridine-3-carboxamide;

5-(morpholin-4-yl)-N-[(aR)-6-(4-oxo-3,4-dihydrophthalazin-1-yl)spiro[3.3]heptan-2-yl]pyrazolo[1,5-a]pyridine-3-carboxamide;

5-(1-methyl-1H-pyrazol-4-yl)-N-[(aR)-6-(4-oxo-3,4-dihydrophthalazin-1-yl)spiro[3.3]heptan-2-yl]pyrazolo[1,5-a]pyridine-3-carboxamide;

6-(4-methylpiperazin-1-yl)-N-[(aR)-6-(4-oxo-3,4-dihydrophthalazin-1-yl)spiro[3.3]heptan-2-yl]pyrazolo[1,5-a]pyridine-3-carboxamide;

N-[(aR)-6-(4-oxo-3,4-dihydrophthalazin-1-yl)spiro[3.3]heptan-2-yl]-6-(pyrrolidin-1-yl)pyrazolo[1,5-a]pyridine-3-carboxamide;

6-[(3R)-3-fluoropyrrolidin-1-yl]-N-[(aR)-6-(4-oxo-3,4-dihydrophthalazin-1-yl)spiro[3.3]heptan-2-yl]pyrazolo[1,5-a]pyridine-3-carboxamide;

6-[(3S)-3-fluoropyrrolidin-1-yl]-N-[(aR)-6-(4-oxo-3,4-dihydrophthalazin-1-yl)spiro[3.3]heptan-2-yl]pyrazolo[1,5-a]pyridine-3-carboxamide;

6-(3,3-difluoropyrrolidin-1-yl)-N-[(aR)-6-(4-oxo-3,4-dihydrophthalazin-1-yl)spiro[3.3]heptan-2-yl]pyrazolo[1,5-a]pyridine-3-carboxamide;

6-(3-fluoroazetidin-1-yl)-N-[(aR)-6-(4-oxo-3,4-dihydrophthalazin-1-yl)spiro[3.3]heptan-2-yl]pyrazolo[1,5-a]pyridine-3-carboxamide;

6-(3,3-difluoroazetidin-1-yl)-N-[(aR)-6-(4-oxo-3,4-dihydrophthalazin-1-yl)spiro[3.3]heptan-2-yl]pyrazolo[1,5-a]pyridine-3-carboxamide;

N-[(aR)-6-(4-oxo-3,4-dihydrophthalazin-1-yl)spiro[3.3]heptan-2-yl]-7-thia-2,5-diazatricyclo[6.4.0.0$^{2,6}$]dodeca-1(8),3,5,9,11-pentaene-4-carboxamide;

N-[(aR)-6-(4-oxo-3,4-dihydrophthalazin-1-yl)spiro[3.3]heptan-2-yl]imidazo[2,1-b][1,3]thiazole-6-carboxamide;

2-ethyl-N-[(aR)-6-(4-oxo-3,4-dihydrophthalazin-1-yl)spiro[3.3]heptan-2-yl]imidazo[2,1-b][1,3,4]thiadiazole-6-carboxamide;

N-[(aR)-6-(4-oxo-3,4-dihydrophthalazin-1-yl)spiro[3.3]heptan-2-yl]pyrazolo[1,5-b]pyridazine-3-carboxamide;

7-cyclopropyl-6-(2-hydroxy-2-methylpropoxy)-N-[(aR)-6-(4-oxo-3,4-dihydrophthalazin-1-yl)spiro[3.3]heptan-2-yl]pyrazolo[1,5-a]pyridine-3-carboxamide;

N-[(aR)-6-(4-oxo-3,4-dihydrophthalazin-1-yl)spiro[3.3]heptan-2-yl]-6-[3,3,3-trifluoro-2-hydroxy-2-(trifluoromethyl)propoxy]pyrazolo[1,5-a]pyridine-3-carboxamide;

6-(benzyloxy)-N-[(aR)-6-(4-oxo-3,4-dihydrophthalazin-1-yl)spiro[3.3]heptan-2-yl]pyrazolo[1,5-a]pyridine-3-carboxamide;

1-(2,2-difluoroethyl)-N-[(aR)-6-(4-oxo-3,4-dihydrophthalazin-1-yl)spiro[3.3]heptan-2-yl]-1H-pyrazole-5-carboxamide;

N-[(aR)-6-(4-oxo-3,4-dihydrophthalazin-1-yl)spiro[3.3]heptan-2-yl]-1-(3,3,3-trifluoropropyl)-1H-pyrazole-5-carboxamide;

1-[(4-methoxyphenyl)methyl]-N-[(aR)-6-(4-oxo-3,4-dihydrophthalazin-1-yl)spiro[3.3]heptan-2-yl]-1H-pyrazole-4-carboxamide;

1-(cyclopropylmethyl)-N-[(aR)-6-(4-oxo-3,4-dihydrophthalazin-1-yl)spiro[3.3]heptan-2-yl]-1H-pyrazole-5-carboxamide;

1-(oxan-4-yl)-N-[(aR)-6-(4-oxo-3,4-dihydrophthalazin-1-yl)spiro[3.3]heptan-2-yl]-1H-pyrazole-5-carboxamide;

N-[(aR)-6-(4-oxo-3,4-dihydrophthalazin-1-yl)spiro[3.3]heptan-2-yl]-6-(oxolan-3-yloxy)pyrazolo[1,5-a]pyridine-3-carboxamide;

tert-butyl N-[2-(4-{[(aR)-6-(4-oxo-3,4-dihydrophthalazin-1-yl)spiro[3.3]heptan-2-yl]carbamoyl}-1H-pyrazol-1-yl)ethyl]carbamate;

N-[(aR)-6-(4-oxo-3,4-dihydrophthalazin-1-yl)spiro[3.3]heptan-2-yl]-6-(3,3,3-trifluoro-2-hydroxypropoxy)pyrazolo[1,5-a]pyridine-3-carboxamide;

1-(3-methoxyphenyl)-N-[(aR)-6-(4-oxo-3,4-dihydrophthalazin-1-yl)spiro[3.3]heptan-2-yl]-1H-pyrazole-4-carboxamide;

1-benzyl-N-[(aR)-6-(4-oxo-3,4-dihydrophthalazin-1-yl)spiro[3.3]heptan-2-yl]-1H-pyrazole-4-carboxamide;

6-(2-hydroxy-2-methylpropoxy)-3-N-[(aR)-6-(4-oxo-3,4-dihydrophthalazin-1-yl)spiro[3.3]heptan-2-yl]pyrazolo[1,5-a]pyridine-3,7-dicarboxamide;

7-cyano-6-hydroxy-N-[(aR)-6-(4-oxo-3,4-dihydrophthalazin-1-yl)spiro[3.3]heptan-2-yl]pyrazolo[1,5-a]pyridine-3-carboxamide;

6-(2-hydroxy-2-methylpropoxy)-7-methyl-N-[(aR)-6-(4-oxo-3,4-dihydrophthalazin-1-yl)spiro[3.3]heptan-2-yl]pyrazolo[1,5-a]pyridine-3-carboxamide;

6-(2-hydroxy-2-methylpropoxy)-7-(methoxymethyl)-N-[(aR)-6-(4-oxo-3,4-dihydrophthalazin-1-yl)spiro[3.3]heptan-2-yl]pyrazolo[1,5-a]pyridine-3-carboxamide;

5-methyl-N-[(aR)-6-(4-oxo-3,4-dihydrophthalazin-1-yl)spiro[3.3]heptan-2-yl]-1-phenyl-1H-1,2,3-triazole-4-carboxamide;

1-(4-methoxyphenyl)-5-methyl-N-[(aR)-6-(4-oxo-3,4-dihydrophthalazin-1-yl)spiro[3.3]heptan-2-yl]-1H-1,2,3-triazole-4-carboxamide;

1-(3-methoxyphenyl)-N-[(aR)-6-(4-oxo-3,4-dihydrophthalazin-1-yl)spiro[3.3]heptan-2-yl]-1H-1,2,3-triazole-4-carboxamide;

1-(2-methoxyphenyl)-5-methyl-N-[(aR)-6-(4-oxo-3,4-dihydrophthalazin-1-yl)spiro[3.3]heptan-2-yl]-1H-1,2,3-triazole-4-carboxamide;

5-(4-fluorophenyl)-N-[(aR)-6-(4-oxo-3,4-dihydrophthalazin-1-yl)spiro[3.3]heptan-2-yl]-1,2,4-oxadiazole-3-carboxamide;

N-[(aR)-6-(4-oxo-3,4-dihydrophthalazin-1-yl)spiro[3.3]heptan-2-yl]-6-(3,3,3-trifluoro-2-hydroxypropoxy)pyrazolo[1,5-a]pyridine-3-carboxamide;

N-[(aR)-6-(4-oxo-3,4-dihydrophthalazin-1-yl)spiro[3.3]heptan-2-yl]-6-(3,3,3-trifluoro-2-hydroxypropoxy)pyrazolo[1,5-a]pyridine-3-carboxamide;

N-[(aR)-6-(4-oxo-3,4-dihydrophthalazin-1-yl)spiro[3.3]heptan-2-yl]-6-(oxolan-3-yloxy)pyrazolo[1,5-a]pyridine-3-carboxamide;

N-[(aR)-6-(4-oxo-3,4-dihydrophthalazin-1-yl)spiro[3.3]heptan-2-yl]-6-(oxolan-3-yloxy)pyrazolo[1,5-a]pyridine-3-carboxamide;

7-methyl-N-[(aR)-6-(4-oxo-3,4-dihydrophthalazin-1-yl)spiro[3.3]heptan-2-yl]pyrazolo[1,5-a]pyridine-3-carboxamide;

3-methoxy-N-[(aR)-6-(4-oxo-3,4-dihydrophthalazin-1-yl)spiro[3.3]heptan-2-yl]imidazo[1,2-a]pyridine-2-carboxamide;

6-(benzyloxy)-7-cyclopropyl-N-[(aR)-6-(4-oxo-3,4-dihydrophthalazin-1-yl)spiro[3.3]heptan-2-yl]pyrazolo[1,5-a]pyridine-3-carboxamide;

6-(benzyloxy)-7-methyl-N-[(aR)-6-(4-oxo-3,4-dihydrophthalazin-1-yl)spiro[3.3]heptan-2-yl]pyrazolo[1,5-a]pyridine-3-carboxamide;

6-(benzyloxy)-7-cyano-N-[(aR)-6-(4-oxo-3,4-dihydrophthalazin-1-yl)spiro[3.3]heptan-2-yl]pyrazolo[1,5-a]pyridine-3-carboxamide;

7-cyclopropyl-6-hydroxy-N-[(aR)-6-(4-oxo-3,4-dihydrophthalazin-1-yl)spiro[3.3]heptan-2-yl]pyrazolo[1,5-a]pyridine-3-carboxamide;

1-(2-methoxyphenyl)-N-[(aR)-6-(4-oxo-3,4-dihydrophthalazin-1-yl)spiro[3.3]heptan-2-yl]-1H-1,2,3-triazole-4-carboxamide;

6-(benzyloxy)-7-[(dimethylamino)methyl]-N-[(aR)-6-(4-oxo-3,4-dihydrophthalazin-1-yl)spiro[3.3]heptan-2-yl]pyrazolo[1,5-a]pyridine-3-carboxamide;

6-[(1,3-difluoropropan-2-yl)oxy]-N-[(aR)-6-(4-oxo-3,4-dihydrophthalazin-1-yl)spiro[3.3]heptan-2-yl]pyrazolo[1,5-a]pyridine-3-carboxamide;

6-[(1,1-dioxo-1$\lambda^6$-thian-4-yl)oxy]-N-[(aR)-6-(4-oxo-3,4-dihydrophthalazin-1-yl)spiro[3.3]heptan-2-yl]pyrazolo[1,5-a]pyridine-3-carboxamide;

N-[(aR)-6-(4-oxo-3,4-dihydrophthalazin-1-yl)spiro[3.3]heptan-2-yl]-6-(3,3,3-trifluoropropoxy)pyrazolo[1,5-a]pyridine-3-carboxamide;

6-[(4,4-difluorocyclohexyl)oxy]-N-[(aR)-6-(4-oxo-3,4-dihydrophthalazin-1-yl)spiro[3.3]heptan-2-yl]pyrazolo[1,5-a]pyridine-3-carboxamide;

6-(oxan-4-yloxy)-N-[(aR)-6-(4-oxo-3,4-dihydrophthalazin-1-yl)spiro[3.3]heptan-2-yl]pyrazolo[1,5-a]pyridine-3-carboxamide;

methyl 3-[(3-{[(aR)-6-(4-oxo-3,4-dihydrophthalazin-1-yl)spiro[3.3]heptan-2-yl]carbamoyl}pyrazolo[1,5-a]pyridin-6-yl)oxy]azetidine-1-carboxylate;

6-hydroxy-N-[(aR)-6-(4-oxo-3,4-dihydrophthalazin-1-yl)spiro[3.3]heptan-2-yl]pyrazolo[1,5-a]pyridine-3-carboxamide;

6-(3,3-difluorocyclobutoxy)-N-[(aR)-6-(4-oxo-3,4-dihydrophthalazin-1-yl)spiro[3.3]heptan-2-yl]pyrazolo[1,5-a]pyridine-3-carboxamide;

N-[(aR)-6-(4-oxo-3,4-dihydrophthalazin-1-yl)spiro[3.3]heptan-2-yl]-6-[2-(2,2,2-trifluoroethoxy)ethoxy]pyrazolo[1,5-a]pyridine-3-carboxamide;

6-[(5-cyclopropyl-1,3,4-thiadiazol-2-yl)methoxy]-N-[(aR)-6-(4-oxo-3,4-dihydrophthalazin-1-yl)spiro[3.3]heptan-2-yl]pyrazolo[1,5-a]pyridine-3-carboxamide;

6-(benzyloxy)-N-[(aR)-6-(4-oxo-3,4-dihydrophthalazin-1-yl)spiro[3.3]heptan-2-yl]-7-(trifluoromethyl)pyrazolo[1,5-a]pyridine-3-carboxamide;

6-cyclopropyl-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide;

1-(2-hydroxy-2-methylpropyl)-N-[(aR)-6-(4-oxo-3,4-dihydrophthalazin-1-yl)spiro[3.3]heptan-2-yl]-6-phenyl-1H-indazole-3-carboxamide;

6-(4-chlorophenyl)-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide;

1-(2-hydroxy-2-methylpropyl)-6-(1-methyl-1H-pyrazol-3-yl)-N-[(aR)-6-(4-oxo-3,4-dihydrophthalazin-1-yl)spiro[3.3]heptan-2-yl]-1H-indazole-3-carboxamide;

1-(2-hydroxy-2-methylpropyl)-6-(1-methyl-1H-pyrazol-5-yl)-N-[(aR)-6-(4-oxo-3,4-dihydrophthalazin-1-yl)spiro[3.3]heptan-2-yl]-1H-indazole-3-carboxamide;

1-(2-hydroxy-2-methylpropyl)-6-(1-methyl-1H-pyrazol-4-yl)-N-[(aR)-6-(4-oxo-3,4-dihydrophthalazin-1-yl)spiro[3.3]heptan-2-yl]-1H-indazole-3-carboxamide;

1-(2-hydroxy-2-methylpropyl)-N-[(aR)-6-(4-oxo-3,4-dihydrophthalazin-1-yl)spiro[3.3]heptan-2-yl]-6-[(E)-2-phenylethenyl]-1H-indazole-3-carboxamide;

6-[(E)-2-cyclopropylethenyl]-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide;

1-(2-hydroxy-2-methylpropyl)-6-(6-methoxypyridin-2-yl)-N-[(aR)-6-(4-oxo-3,4-dihydrophthalazin-1-yl)spiro[3.3]heptan-2-yl]-1H-indazole-3-carboxamide;

6-[(Z)-2-cyclopropylethenyl]-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide;

6-bromo-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide;

1-(2-hydroxy-2-methylpropyl)-6-(4-methoxyphenyl)-N-[(aR)-6-(4-oxo-3,4-dihydrophthalazin-1-yl)spiro[3.3]heptan-2-yl]-1H-indazole-3-carboxamide;

1-(2-hydroxy-2-methylpropyl)-6-(1-methyl-1H-1,2,3-triazol-4-yl)-N-[(aR)-6-(4-oxo-3,4-dihydrophthalazin-1-yl)spiro[3.3]heptan-2-yl]-1H-indazole-3-carboxamide;

6-(dimethyl-1,2-oxazol-4-yl)-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide;

6-(3-chlorophenyl)-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide;

1-(2-hydroxy-2-methylpropyl)-6-(2-methoxyphenyl)-N-[(aR)-6-(4-oxo-3,4-dihydrophthalazin-1-yl)spiro[3.3]heptan-2-yl]-1H-indazole-3-carboxamide;

1-(2-hydroxy-2-methylpropyl)-6-(3-methoxyphenyl)-N-[(aR)-6-(4-oxo-3,4-dihydrophthalazin-1-yl)spiro[3.3]heptan-2-yl]-1H-indazole-3-carboxamide;

6-(2,6-difluorophenyl)-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide;

6-(2-cyanophenyl)-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide;

1-(2-hydroxy-2-methylpropyl)-6-(1,2-oxazol-4-yl)-N-[(aR)-6-(4-oxo-3,4-dihydrophthalazin-1-yl)spiro[3.3]heptan-2-yl]-1H-indazole-3-carboxamide;

N-[6-fluoro-6-(4-oxo-3,4-dihydrophthalazin-1-yl)spiro[3.3]heptan-2-yl]-1-(2-hydroxy-2-methylpropyl)-1H-indazole-3-carboxamide;

6-fluoro-N-[6-fluoro-6-(4-oxo-3,4-dihydrophthalazin-1-yl)spiro[3.3]heptan-2-yl]-1-(2-hydroxy-2-methylpropyl)-1H-indazole-3-carboxamide;

N-[6-fluoro-6-(4-oxo-3,4-dihydrophthalazin-1-yl)spiro[3.3]heptan-2-yl]pyrazolo[1,5-a]pyridine-3-carboxamide;

N-[(aR)-6-(4-oxo-3,4-dihydrophthalazin-1-yl)spiro[3.3]heptan-2-yl]-6-(2-oxopyrrolidin-1-yl)pyrazolo[1,5-a]pyridine-3-carboxamide;

6-cyclopropyl-N-[(aR)-6-(4-oxo-3,4-dihydrophthalazin-1-yl)spiro[3.3]heptan-2-yl]pyrazolo[1,5-a]pyridine-3-carboxamide;

6-[1-(difluoromethyl)-1H-pyrazol-4-yl]-N-[(aR)-6-(4-oxo-3,4-dihydrophthalazin-1-yl)spiro[3.3]heptan-2-yl]pyrazolo[1,5-a]pyridine-3-carboxamide;

6-cyano-N-[(aR)-6-(4-oxo-3,4-dihydrophthalazin-1-yl)spiro[3.3]heptan-2-yl]pyrazolo[1,5-a]pyridine-3-carboxamide;

6-(2-oxo-1,2-dihydropyridin-1-yl)-N-[(aR)-6-(4-oxo-3,4-dihydrophthalazin-1-yl)spiro[3.3]heptan-2-yl]pyrazolo[1,5-a]pyridine-3-carboxamide;

6-(1-methyl-1H-pyrazol-4-yl)-N-[(aR)-6-(4-oxo-3,4-dihydrophthalazin-1-yl)spiro[3.3]heptan-2-yl]pyrazolo[1,5-a]pyridine-3-carboxamide;

N-[(aR)-6-(4-oxo-3,4-dihydrophthalazin-1-yl)spiro[3.3]heptan-2-yl]-6-{1-[(2S)-3,3,3-trifluoro-2-hydroxypropyl]-1H-pyrazol-4-yl}pyrazolo[1,5-a]pyridine-3-carboxamide;

N-[(aR)-6-(4-oxo-3,4-dihydrophthalazin-1-yl)spiro[3.3]heptan-2-yl]-6-[3-(trifluoromethyl)-1H-pyrazol-4-yl]pyrazolo[1,5-a]pyridine-3-carboxamide;

N-[(aR)-6-(4-oxo-3,4-dihydrophthalazin-1-yl)spiro[3.3]heptan-2-yl]-6-(1,3-thiazol-2-yl)pyrazolo[1,5-a]pyridine-3-carboxamide;

N-[(aR)-6-(4-oxo-3,4-dihydrophthalazin-1-yl)spiro[3.3]heptan-2-yl]-6-(1H-pyrazol-4-yl)pyrazolo[1,5-a]pyridine-3-carboxamide;

6-(dimethyl-1H-1,2,3-triazol-5-yl)-N-[(aR)-6-(4-oxo-3,4-dihydrophthalazin-1-yl)spiro[3.3]heptan-2-yl]pyrazolo[1,5-a]pyridine-3-carboxamide;

6-(1H-imidazol-1-yl)-N-[(aR)-6-(4-oxo-3,4-dihydrophthalazin-1-yl)spiro[3.3]heptan-2-yl]pyrazolo[1,5-a]pyridine-3-carboxamide;

N-[(aR)-6-(4-oxo-3,4-dihydrophthalazin-1-yl)spiro[3.3]heptan-2-yl]-6-(1H-pyrazol-1-yl)pyrazolo[1,5-a]pyridine-3-carboxamide;

N-[(aR)-6-(4-oxo-3,4-dihydrophthalazin-1-yl)spiro[3.3]heptan-2-yl]-6-(1H-1,2,4-triazol-1-yl)pyrazolo[1,5-a]pyridine-3-carboxamide;

6-(2-methoxyethoxy)-N-[(aR)-6-(4-oxo-3,4-dihydrophthalazin-1-yl)spiro[3.3]heptan-2-yl]pyrazolo[1,5-a]pyridine-3-carboxamide;

6-(4-oxo-1,4-dihydropyridin-1-yl)-N-[(aR)-6-(4-oxo-3,4-dihydrophthalazin-1-yl)spiro[3.3]heptan-2-yl]pyrazolo[1,5-a]pyridine-3-carboxamide;

6-(2-hydroxyethoxy)-N-[(aR)-6-(4-oxo-3,4-dihydrophthalazin-1-yl)spiro[3.3]heptan-2-yl]pyrazolo[1,5-a]pyridine-3-carboxamide;

6-[2-(3-fluoroazetidin-1-yl)ethoxy]-N-[(aR)-6-(4-oxo-3,4-dihydrophthalazin-1-yl)spiro[3.3]heptan-2-yl]pyrazolo[1,5-a]pyridine-3-carboxamide;

6-[2-(dimethylamino)ethoxy]-N-[(aR)-6-(4-oxo-3,4-dihydrophthalazin-1-yl)spiro[3.3]heptan-2-yl]pyrazolo[1,5-a]pyridine-3-carboxamide;

6-[2-(4-hydroxy-3,3-dimethylpiperidin-1-yl)ethoxy]-N-[(aR)-6-(4-oxo-3,4-dihydrophthalazin-1-yl)spiro[3.3]heptan-2-yl]pyrazolo[1,5-a]pyridine-3-carboxamide;

6-[2-(3,3-difluoropyrrolidin-1-yl)ethoxy]-N-[(aR)-6-(4-oxo-3,4-dihydrophthalazin-1-yl)spiro[3.3]heptan-2-yl]pyrazolo[1,5-a]pyridine-3-carboxamide;

6-[2-(azetidin-1-yl)ethoxy]-N-[(aR)-6-(4-oxo-3,4-dihydrophthalazin-1-yl)spiro[3.3]heptan-2-yl]pyrazolo[1,5-a]pyridine-3-carboxamide;

6-[2-(2,2-dimethylmorpholin-4-yl)ethoxy]-N-[(aR)-6-(4-oxo-3,4-dihydrophthalazin-1-yl)spiro[3.3]heptan-2-yl]pyrazolo[1,5-a]pyridine-3-carboxamide;

6-[2-(4-methylpiperazin-1-yl)ethoxy]-N-[(aR)-6-(4-oxo-3,4-dihydrophthalazin-1-yl)spiro[3.3]heptan-2-yl]pyrazolo[1,5-a]pyridine-3-carboxamide;

6-{2-[(3R)-3-fluoropyrrolidin-1-yl]ethoxy}-N-[(aR)-6-(4-oxo-3,4-dihydrophthalazin-1-yl)spiro[3.3]heptan-2-yl]pyrazolo[1,5-a]pyridine-3-carboxamide;

6-{2-[(3S)-3-fluoropyrrolidin-1-yl]ethoxy}-N-[(aR)-6-(4-oxo-3,4-dihydrophthalazin-1-yl)spiro[3.3]heptan-2-yl]pyrazolo[1,5-a]pyridine-3-carboxamide;

6-[3-(morpholin-4-yl)propyl]-N-[(aR)-6-(4-oxo-3,4-dihydrophthalazin-1-yl)spiro[3.3]heptan-2-yl]pyrazolo[1,5-a]pyridine-3-carboxamide;

N-[(aR)-6-(4-oxo-3,4-dihydrophthalazin-1-yl)spiro[3.3]heptan-2-yl]-6-[3-(pyrrolidin-1-yl)propyl]pyrazolo[1,5-a]pyridine-3-carboxamide;

6-[3-(dimethylamino)propyl]-N-[(aR)-6-(4-oxo-3,4-dihydrophthalazin-1-yl)spiro[3.3]heptan-2-yl]pyrazolo[1,5-a]pyridine-3-carboxamide;

6-[3-(cyclopropylamino)propyl]-N-[(aR)-6-(4-oxo-3,4-dihydrophthalazin-1-yl)spiro[3.3]heptan-2-yl]pyrazolo[1,5-a]pyridine-3-carboxamide;

6-(3-hydroxypropyl)-N-[(aR)-6-(4-oxo-3,4-dihydrophthalazin-1-yl)spiro[3.3]heptan-2-yl]pyrazolo[1,5-a]pyridine-3-carboxamide;

6-[3-(4,4-difluoropiperidin-1-yl)propyl]-N-[(aR)-6-(4-oxo-3,4-dihydrophthalazin-1-yl)spiro[3.3]heptan-2-yl]pyrazolo[1,5-a]pyridine-3-carboxamide;

6-[3-(3,3-difluoropyrrolidin-1-yl)propyl]-N-[(aR)-6-(4-oxo-3,4-dihydrophthalazin-1-yl)spiro[3.3]heptan-2-yl]pyrazolo[1,5-a]pyridine-3-carboxamide;

6-(3-hydroxy-3-methylbutyl)-N-[(aR)-6-(4-oxo-3,4-dihydrophthalazin-1-yl)spiro[3.3]heptan-2-yl]pyrazolo[1,5-a]pyridine-3-carboxamide;

N-[(aR)-6-(4-oxo-3,4-dihydrophthalazin-1-yl)spiro[3.3]heptan-2-yl]-6-[4,4,4-trifluoro-3-hydroxy-3-(trifluoromethyl)butyl]pyrazolo[1,5-a]pyridine-3-carboxamide;

6-(morpholin-4-ylmethyl)-N-[(aR)-6-(4-oxo-3,4-dihydrophthalazin-1-yl)spiro[3.3]heptan-2-yl]pyrazolo[1,5-a]pyridine-3-carboxamide;

6-[(4-methylpiperazin-1-yl)methyl]-N-[(aR)-6-(4-oxo-3,4-dihydrophthalazin-1-yl)spiro[3.3]heptan-2-yl]pyrazolo[1,5-a]pyridine-3-carboxamide;

N-[(aR)-6-(4-oxo-3,4-dihydrophthalazin-1-yl)spiro[3.3]heptan-2-yl]-6-(piperidin-1-ylmethyl)pyrazolo[1,5-a]pyridine-3-carboxamide;

6-[(dimethylamino)methyl]-N-[(aR)-6-(4-oxo-3,4-dihydrophthalazin-1-yl)spiro[3.3]heptan-2-yl]pyrazolo[1,5-a]pyridine-3-carboxamide;

6-benzyl-N-[(aR)-6-(4-oxo-3,4-dihydrophthalazin-1-yl)spiro[3.3]heptan-2-yl]pyrazolo[1,5-a]pyridine-3-carboxamide;

6-[3-(morpholin-4-yl)-3-oxopropyl]-N-[(aR)-6-(4-oxo-3,4-dihydrophthalazin-1-yl)spiro[3.3]heptan-2-yl]pyrazolo[1,5-a]pyridine-3-carboxamide;

N-[(aR)-6-(4-oxo-3,4-dihydrophthalazin-1-yl)spiro[3.3]heptan-2-yl]-6-(3,3,3-trifluoropropyl)pyrazolo[1,5-a]pyridine-3-carboxamide;

6-(2-cyanoethyl)-N-[(aR)-6-(4-oxo-3,4-dihydrophthalazin-1-yl)spiro[3.3]heptan-2-yl]pyrazolo[1,5-a]pyridine-3-carboxamide;

6-{[2-(morpholin-4-yl)ethoxy]methyl}-N-[(aR)-6-(4-oxo-3,4-dihydrophthalazin-1-yl)spiro[3.3]heptan-2-yl]pyrazolo[1,5-a]pyridine-3-carboxamide;

6-(methoxymethyl)-N-[(aR)-6-(4-oxo-3,4-dihydrophthalazin-1-yl)spiro[3.3]heptan-2-yl]pyrazolo[1,5-a]pyridine-3-carboxamide;

6-(2-methoxypyrimidin-5-yl)-N-[(aR)-6-(4-oxo-3,4-dihydrophthalazin-1-yl)spiro[3.3]heptan-2-yl]pyrazolo[1,5-a]pyridine-3-carboxamide;

6-[(oxan-4-ylmethoxy)methyl]-N-[(aR)-6-(4-oxo-3,4-dihydrophthalazin-1-yl)spiro[3.3]heptan-2-yl]pyrazolo[1,5-a]pyridine-3-carboxamide;

N-[(aR)-6-(4-oxo-3,4-dihydrophthalazin-1-yl)spiro[3.3]heptan-2-yl]-6-[(prop-2-en-1-yloxy)methyl]pyrazolo[1,5-a]pyridine-3-carboxamide;

6-(hydroxymethyl)-N-[(aR)-6-(4-oxo-3,4-dihydrophthalazin-1-yl)spiro[3.3]heptan-2-yl]pyrazolo[1,5-a]pyridine-3-carboxamide;

6-acetyl-N-[(aR)-6-(4-oxo-3,4-dihydrophthalazin-1-yl)spiro[3.3]heptan-2-yl]pyrazolo[1,5-a]pyridine-3-carboxamide;

6-(2-hydroxypropan-2-yl)-N-[(aR)-6-(4-oxo-3,4-dihydrophthalazin-1-yl)spiro[3.3]heptan-2-yl]pyrazolo[1,5-a]pyridine-3-carboxamide;

6-(1,5-dimethyl-1H-pyrazol-4-yl)-N-[(aR)-6-(4-oxo-3,4-dihydrophthalazin-1-yl)spiro[3.3]heptan-2-yl]pyrazolo[1,5-a]pyridine-3-carboxamide;

6-(1-cyclopropyl-1H-pyrazol-4-yl)-N-[(aR)-6-(4-oxo-3,4-dihydrophthalazin-1-yl)spiro[3.3]heptan-2-yl]pyrazolo[1,5-a]pyridine-3-carboxamide;

6-[1-(cyclopropylmethyl)-1H-pyrazol-4-yl]-N-[(aR)-6-(4-oxo-3,4-dihydrophthalazin-1-yl)spiro[3.3]heptan-2-yl]pyrazolo[1,5-a]pyridine-3-carboxamide;

6-[1-($^2$H$_3$)methyl-1H-pyrazol-4-yl]-N-[(aR)-6-(4-oxo-3,4-dihydrophthalazin-1-yl)spiro[3.3]heptan-2-yl]pyrazolo[1,5-a]pyridine-3-carboxamide;

N-[(aR)-6-(4-oxo-3,4-dihydrophthalazin-1-yl)spiro[3.3]heptan-2-yl]-6-[1-(propan-2-yl)-1H-pyrazol-4-yl]pyrazolo[1,5-a]pyridine-3-carboxamide;

N-[(aR)-6-(4-oxo-3,4-dihydrophthalazin-1-yl)spiro[3.3]heptan-2-yl]-6-(trimethyl-1H-pyrazol-4-yl)pyrazolo[1,5-a]pyridine-3-carboxamide;

6-[1-(oxan-4-yl)-1H-pyrazol-4-yl]-N-[(aR)-6-(4-oxo-3,4-dihydrophthalazin-1-yl)spiro[3.3]heptan-2-yl]pyrazolo[1,5-a]pyridine-3-carboxamide;

6-[1-methyl-3-(trifluoromethyl)-1H-pyrazol-4-yl]-N-[(aR)-6-(4-oxo-3,4-dihydrophthalazin-1-yl)spiro[3.3]heptan-2-yl]pyrazolo[1,5-a]pyridine-3-carboxamide;

N-[(aR)-6-(4-oxo-3,4-dihydrophthalazin-1-yl)spiro[3.3]heptan-2-yl]-6-[1-(propan-2-yl)-3-(trifluoromethyl)-1H-pyrazol-4-yl]pyrazolo[1,5-a]pyridine-3-carboxamide;

6-(1-tert-butyl-1H-pyrazol-4-yl)-N-[(aR)-6-(4-oxo-3,4-dihydrophthalazin-1-yl)spiro[3.3]heptan-2-yl]pyrazolo[1,5-a]pyridine-3-carboxamide;

N-[(aR)-6-(4-oxo-3,4-dihydrophthalazin-1-yl)spiro[3.3]heptan-2-yl]-6-[1-(oxolan-3-yl)-1H-pyrazol-4-yl]pyrazolo[1,5-a]pyridine-3-carboxamide;

1-(4-bromophenyl)-3-[(aR)-6-(4-oxo-3,4-dihydrophthalazin-1-yl)spiro[3.3]heptan-2-yl]urea;

1-[4-(1-methyl-1H-pyrazol-4-yl)phenyl]-3-[(aR)-6-(4-oxo-3,4-dihydrophthalazin-1-yl)spiro[3.3]heptan-2-yl]urea;

1-{4-[1-($^2$H$_3$)methyl-1H-pyrazol-4-yl]phenyl}-3-[(aR)-6-(4-oxo-3,4-dihydrophthalazin-1-yl)spiro[3.3]heptan-2-yl]urea;

1-[4-(1-cyclopropyl-1H-pyrazol-4-yl)phenyl]-3-[(aR)-6-(4-oxo-3,4-dihydrophthalazin-1-yl)spiro[3.3]heptan-2-yl]urea;

1-{4-[1-(oxan-4-yl)-1H-pyrazol-4-yl]phenyl}-3-[(aR)-6-(4-oxo-3,4-dihydrophthalazin-1-yl)spiro[3.3]heptan-2-yl]urea;

1-{4-[1-methyl-3-(trifluoromethyl)-1H-pyrazol-4-yl]phenyl}-3-[(aR)-6-(4-oxo-3,4-dihydrophthalazin-1-yl)spiro[3.3]heptan-2-yl]urea;

3-[(aR)-6-(4-oxo-3,4-dihydrophthalazin-1-yl)spiro[3.3]heptan-2-yl]-1-[4-(trimethyl-1H-pyrazol-4-yl)phenyl]urea;

5-bromo-N-[(aR)-6-(4-oxo-3,4-dihydrophthalazin-1-yl)spiro[3.3]heptan-2-yl]-2,3-dihydro-1H-indole-1-carboxamide;

5-(1-methyl-1H-pyrazol-4-yl)-N-[(aR)-6-(4-oxo-3,4-dihydrophthalazin-1-yl)spiro[3.3]heptan-2-yl]-2,3-dihydro-1H-indole-1-carboxamide;

5-(1-cyclopropyl-1H-pyrazol-4-yl)-N-[(aR)-6-(4-oxo-3,4-dihydrophthalazin-1-yl)spiro[3.3]heptan-2-yl]-2,3-dihydro-1H-indole-1-carboxamide;

N-[(aR)-6-(4-oxo-3,4-dihydrophthalazin-1-yl)spiro[3.3]heptan-2-yl]-5-(trimethyl-1H-pyrazol-4-yl)-2,3-dihydro-1H-indole-1-carboxamide;

5-[1-methyl-3-(trifluoromethyl)-1H-pyrazol-4-yl]-N-[(aR)-6-(4-oxo-3,4-dihydrophthalazin-1-yl)spiro[3.3]heptan-2-yl]-2,3-dihydro-1H-indole-1-carboxamide;

5-[1-($^2$H$_3$)methyl-1H-pyrazol-4-yl]-N-[(aR)-6-(4-oxo-3,4-dihydrophthalazin-1-yl)spiro[3.3]heptan-2-yl]-2,3-dihydro-1H-indole-1-carboxamide;

5-[1-(oxan-4-yl)-1H-pyrazol-4-yl]-N-[(aR)-6-(4-oxo-3,4-dihydrophthalazin-1-yl)spiro[3.3]heptan-2-yl]-2,3-dihydro-1H-indole-1-carboxamide;

5-[1-(cyclopropylmethyl)-1H-pyrazol-4-yl]-N-[(aR)-6-(4-oxo-3,4-dihydrophthalazin-1-yl)spiro[3.3]heptan-2-yl]-2,3-dihydro-1H-indole-1-carboxamide;

5-(1-tert-butyl-1H-pyrazol-4-yl)-N-[(aR)-6-(4-oxo-3,4-dihydrophthalazin-1-yl)spiro[3.3]heptan-2-yl]-2,3-dihydro-1H-indole-1-carboxamide;

N-[(aR)-6-(4-oxo-3,4-dihydrophthalazin-1-yl)spiro[3.3]heptan-2-yl]-5-[1-(oxolan-3-yl)-1H-pyrazol-4-yl]-2,3-dihydro-1H-indole-1-carboxamide;

N-[(aR)-6-(4-oxo-3,4-dihydrophthalazin-1-yl)spiro[3.3]heptan-2-yl]-5-[1-(propan-2-yl)-3-(trifluoromethyl)-1H-pyrazol-4-yl]-2,3-dihydro-1H-indole-1-carboxamide;

N-[(aR)-6-(4-oxo-3,4-dihydrophthalazin-1-yl)spiro[3.3]heptan-2-yl]-5-(3,3,3-trifluoropropyl)-2,3-dihydro-1H-indole-1-carboxamide;

N-[(aR)-6-(4-oxo-3,4-dihydrophthalazin-1-yl)spiro[3.3]heptan-2-yl]-5-(trimethyl-1H-pyrazol-4-yl)-2,3-dihydro-1H-isoindole-2-carboxamide;

5-(1-cyclopropyl-1H-pyrazol-4-yl)-N-[(aR)-6-(4-oxo-3,4-dihydrophthalazin-1-yl)spiro[3.3]heptan-2-yl]-2,3-dihydro-1H-isoindole-2-carboxamide;

5-[1-methyl-3-(trifluoromethyl)-1H-pyrazol-4-yl]-N-[(aR)-6-(4-oxo-3,4-dihydrophthalazin-1-yl)spiro[3.3]heptan-2-yl]-2,3-dihydro-1H-isoindole-2-carboxamide;

N-[(aR)-6-(4-oxo-3,4-dihydrophthalazin-1-yl)spiro[3.3]heptan-2-yl]-5-[1-(propan-2-yl)-3-(trifluoromethyl)-1H-pyrazol-4-yl]-2,3-dihydro-1H-isoindole-2-carboxamide;

5-(1-methyl-1H-pyrazol-4-yl)-N-[(aR)-6-(4-oxo-3,4-dihydrophthalazin-1-yl)spiro[3.3]heptan-2-yl]-2,3-dihydro-1H-isoindole-2-carboxamide;

5-[1-(oxan-4-yl)-1H-pyrazol-4-yl]-N-[(aR)-6-(4-oxo-3,4-dihydrophthalazin-1-yl)spiro[3.3]heptan-2-yl]-2,3-dihydro-1H-isoindole-2-carboxamide;

5-(1-tert-butyl-1H-pyrazol-4-yl)-N-[(aR)-6-(4-oxo-3,4-dihydrophthalazin-1-yl)spiro[3.3]heptan-2-yl]-2,3-dihydro-1H-isoindole-2-carboxamide;

5-[1-($^2$H$_3$)methyl-1H-pyrazol-4-yl]-N-[(aR)-6-(4-oxo-3,4-dihydrophthalazin-1-yl)spiro[3.3]heptan-2-yl]-2,3-dihydro-1H-isoindole-2-carboxamide;

3,3-dimethyl-N-[(aR)-6-(4-oxo-3,4-dihydrophthalazin-1-yl)spiro[3.3]heptan-2-yl]-2,3-dihydro-1H-indole-1-carboxamide;

N-[(aR)-6-(4-oxo-3,4-dihydrophthalazin-1-yl)spiro[3.3]heptan-2-yl]-1H,2H,3H-pyrrolo[2,3-b]pyridine-1-carboxamide;

N-[(aR)-6-(4-oxo-3,4-dihydrophthalazin-1-yl)spiro[3.3]heptan-2-yl]-5H,6H,7H-pyrrolo[3,4-b]pyridine-6-carboxamide;

5-methoxy-N-[(aR)-6-(4-oxo-3,4-dihydrophthalazin-1-yl)spiro[3.3]heptan-2-yl]-2,3-dihydro-1H-indole-1-carboxamide;

N-[(aR)-6-(4-oxo-3,4-dihydrophthalazin-1-yl)spiro[3.3]heptan-2-yl]-6-(trifluoromethyl)-2,3-dihydro-1H-indole-1-carboxamide;

5-(dimethylsulfamoyl)-N-[(aR)-6-(4-oxo-3,4-dihydrophthalazin-1-yl)spiro[3.3]heptan-2-yl]-2,3-dihydro-1H-indole-1-carboxamide;

3-(morpholin-4-ylmethyl)-N-[(aR)-6-(4-oxo-3,4-dihydrophthalazin-1-yl)spiro[3.3]heptan-2-yl]-2,3-dihydro-1H-indole-1-carboxamide;

2-(4-methylphenyl)-N-[(aR)-6-(4-oxo-3,4-dihydrophthalazin-1-yl)spiro[3.3]heptan-2-yl]-5H,6H,7H-pyrrolo[3,4-d]pyrimidine-6-carboxamide;

5-methoxy-N-[(aR)-6-(4-oxo-3,4-dihydrophthalazin-1-yl)spiro[3.3]heptan-2-yl]-2,3-dihydro-1H-isoindole-2-carboxamide;

N-[(aR)-6-(4-oxo-3,4-dihydrophthalazin-1-yl)spiro[3.3]heptan-2-yl]-1H,2H,3H-pyrrolo[3,4-c]pyridine-2-carboxamide;

N-[(aR)-6-(4-oxo-3,4-dihydrophthalazin-1-yl)spiro[3.3]heptan-2-yl]-1,2-dihydrospiro[indole-3,4'-piperidine]-1-carboxamide;

N,1-dimethyl-N-[(aR)-6-(4-oxo-3,4-dihydrophthalazin-1-yl)spiro[3.3]heptan-2-yl]-1H-indazole-3-carboxamide;

N-ethyl-1-methyl-N-[(aR)-6-(4-oxo-3,4-dihydrophthalazin-1-yl)spiro[3.3]heptan-2-yl]-1H-indazole-3-carboxamide;

2-methyl-1-[(3-{[(aR)-6-(4-oxo-3,4-dihydrophthalazin-1-yl)spiro[3.3]heptan-2-yl]carbamoyl}pyrazolo[1,5-a]pyridin-6-yl)oxy]propan-2-yl-2-aminoacetate;

2-methyl-1-[(3-{[(aR)-6-(4-oxo-3,4-dihydrophthalazin-1-yl)spiro[3.3]heptan-2-yl]carbamoyl}pyrazolo[1,5-a]pyridin-6-yl)oxy]propan-2-yl(2S)-2-amino-3-methylbutanoate;

2-methyl-1-[(3-{[(aR)-6-(4-oxo-3,4-dihydrophthalazin-1-yl)spiro[3.3]heptan-2-yl]carbamoyl}pyrazolo[1,5-a]pyridin-6-yl)oxy]propan-2-yl(2S)-2-aminopropanoate;

6-(2-hydroxy-2-methylpropoxy)-N-[6-(1-oxo-1,2-dihydroisoquinolin-4-yl)spiro[3.3]heptan-2-yl]pyrazolo[1,5-a]pyridine-3-carboxamide;

tert-butyl 3-{[(aR)-6-(4-oxo-3,4-dihydrophthalazin-1-yl)spiro[3.3]heptan-2-yl]carbamoyl}-4H,5H,6H,7H-thieno[2,3-c]pyridine-6-carboxylate;

N-[(aR)-6-(4-oxo-3,4-dihydrophthalazin-1-yl)spiro[3.3]heptan-2-yl]-4H,5H,6H,7H-thieno[2,3-c]pyridine-3-carboxamide;

6-acetyl-N-[(aR)-6-(4-oxo-3,4-dihydrophthalazin-1-yl)spiro[3.3]heptan-2-yl]-4H,5H,6H,7H-thieno[2,3-c]pyridine-3-carboxamide;

methyl 3-{[(aR)-6-(4-oxo-3,4-dihydrophthalazin-1-yl)spiro[3.3]heptan-2-yl]carbamoyl}-4H,5H,6H,7H-thieno[2,3-c]pyridine-6-carboxylate;

6-methanesulfonyl-N-[(aR)-6-(4-oxo-3,4-dihydrophthalazin-1-yl)spiro[3.3]heptan-2-yl]-4H,5H,6H,7H-thieno[2,3-c]pyridine-3-carboxamide;

6-(1-methyl-1H-pyrazol-4-yl)-N-[(aR)-6-(4-oxo-3,4-dihydrophthalazin-1-yl)spiro[3.3]heptan-2-yl]-2,1-benzoxazole-3-carboxamide;

1-(2-hydroxy-2-methylpropyl)-N-(6-{4-oxo-3H,4H-pyrrolo[1,2-d][1,2,4]triazin-1-yl}spiro[3.3]heptan-2-yl)-1H-indazole-3-carboxamide;

6-(2-hydroxy-2-methylpropoxy)-N-(6-{4-oxo-3H,4H-pyrrolo[1,2-d][1,2,4]triazin-1-yl}spiro[3.3]heptan-2-yl)pyrazolo[1,5-a]pyridine-3-carboxamide;

1-methyl-N-(6-{4-oxo-3H,4H-pyrrolo[1,2-d][1,2,4]triazin-1-yl}spiro[3.3]heptan-2-yl)-1H-indazole-3-carboxamide;

6-(2-hydroxy-2-methylpropoxy)-N-(6-{8-methyl-4-oxo-3H,4H-pyrrolo[1,2-d][1,2,4]triazin-1-yl}spiro[3.3]heptan-2-yl)pyrazolo[1,5-a]pyridine-3-carboxamide;

N-[(aR)-6-(4-oxo-3,4-dihydrophthalazin-1-yl)spiro[3.3]heptan-2-yl]pyrazolo[1,5-a]pyrimidine-3-carboxamide;

6-[(3,5-dimethylphenyl)amino]-N-[(aR)-6-(4-oxo-3,4-dihydrophthalazin-1-yl)spiro[3.3]heptan-2-yl]imidazo[1,2-b]pyridazine-3-carboxamide;

6-bromo-N-[(aR)-6-(4-oxo-3,4-dihydrophthalazin-1-yl)spiro[3.3]heptan-2-yl]-2,1-benzoxazole-3-carboxamide;

1-ethyl-N-[(aR)-6-(4-oxo-3,4-dihydrophthalazin-1-yl)spiro[3.3]heptan-2-yl]-1H-pyrazole-5-carboxamide;

1-(difluoromethyl)-N-[(aR)-6-(4-oxo-3,4-dihydrophthalazin-1-yl)spiro[3.3]heptan-2-yl]-1H-pyrazole-5-carboxamide;

6-(2-hydroxy-2-methylpropoxy)-N-[(aR)-6-(4-oxo-3,4-dihydrophthalazin-1-yl)spiro[3.3]heptan-2-yl]-2,1-benzoxazole-3-carboxamide;

1-(3-chlorophenyl)-7-oxo-N-[(aR)-6-(4-oxo-3,4-dihydrophthalazin-1-yl)spiro[3.3]heptan-2-yl]-1H,4H,5H,6H,7H-pyrazolo[3,4-c]pyridine-3-carboxamide;

1-(4-methoxyphenyl)-7-oxo-N-[(aR)-6-(4-oxo-3,4-dihydrophthalazin-1-yl)spiro[3.3]heptan-2-yl]-1H,4H,5H,6H,7H-pyrazolo[3,4-c]pyridine-3-carboxamide;

5-chloro-N-[(aR)-6-(4-oxo-3,4-dihydrophthalazin-1-yl)spiro[3.3]heptan-2-yl]-1,2-benzoxazole-3-carboxamide;

6-acetamido-N-[(aR)-6-(4-oxo-3,4-dihydrophthalazin-1-yl)spiro[3.3]heptan-2-yl]-1,2-benzoxazole-3-carboxamide;

N-[(aR)-6-(4-oxo-3,4-dihydrophthalazin-1-yl)spiro[3.3]heptan-2-yl]imidazo[1,5-a]pyridine-1-carboxamide;

5-methoxy-1-methyl-N-[(aR)-6-(4-oxo-3,4-dihydrophthalazin-1-yl)spiro[3.3]heptan-2-yl]-1H-indole-2-carboxamide;

1-methyl-N-[(aR)-6-(4-oxo-3,4-dihydrophthalazin-1-yl)spiro[3.3]heptan-2-yl]-1H-indole-2-carboxamide;

7-methoxy-N-[(aR)-6-(4-oxo-3,4-dihydrophthalazin-1-yl)spiro[3.3]heptan-2-yl]-1H-indole-2-carboxamide;

5-methyl-N-[(aR)-6-(4-oxo-3,4-dihydrophthalazin-1-yl)spiro[3.3]heptan-2-yl]-4H,5H,6H,7H-[1,3]thiazolo[5,4-c]pyridine-2-carboxamide;

4-chloro-1-methyl-N-[(aR)-6-(4-oxo-3,4-dihydrophthalazin-1-yl)spiro[3.3]heptan-2-yl]-1H-indole-2-carboxamide;

N-[(aR)-6-(4-oxo-3,4-dihydrophthalazin-1-yl)spiro[3.3]heptan-2-yl]-1H-indole-2-carboxamide;

2-methyl-N-[(aR)-6-(4-oxo-3,4-dihydrophthalazin-1-yl)spiro[3.3]heptan-2-yl]imidazo[1,2-a]pyridine-3-carboxamide;

N-[(aR)-6-(4-oxo-3,4-dihydrophthalazin-1-yl)spiro[3.3]heptan-2-yl]-1H-indole-3-carboxamide;

7-chloro-1-methyl-N-[(aR)-6-(4-oxo-3,4-dihydrophthalazin-1-yl)spiro[3.3]heptan-2-yl]-1H-indole-2-carboxamide;

4-chloro-7-methyl-N-[(aR)-6-(4-oxo-3,4-dihydrophthalazin-1-yl)spiro[3.3]heptan-2-yl]-1H-indole-2-carboxamide;

N-[(aR)-6-(4-oxo-3,4-dihydrophthalazin-1-yl)spiro[3.3]heptan-2-yl]thieno[2,3-b]pyrazine-6-carboxamide;

4-bromo-N-[(aR)-6-(4-oxo-3,4-dihydrophthalazin-1-yl)spiro[3.3]heptan-2-yl]pyrazolo[1,5-a]pyridine-3-carboxamide;

6-chloro-N-[(aR)-6-(4-oxo-3,4-dihydrophthalazin-1-yl)spiro[3.3]heptan-2-yl]-1H-1,3-benzodiazole-2-carboxamide;

5-chloro-1-methyl-N-[(aR)-6-(4-oxo-3,4-dihydrophthalazin-1-yl)spiro[3.3]heptan-2-yl]-1H-indole-2-carboxamide;

N-[(aR)-6-(4-oxo-3,4-dihydrophthalazin-1-yl)spiro[3.3]heptan-2-yl]-1-(propan-2-yl)-1H-1,3-benzodiazole-5-carboxamide;

N-[(aR)-6-(4-oxo-3,4-dihydrophthalazin-1-yl)spiro[3.3]heptan-2-yl]-1H-1,3-benzodiazole-5-carboxamide;

2-methyl-N-[(aR)-6-(4-oxo-3,4-dihydrophthalazin-1-yl)spiro[3.3]heptan-2-yl]-1H-1,3-benzodiazole-5-carboxamide;

N-[(aR)-6-(4-oxo-3,4-dihydrophthalazin-1-yl)spiro[3.3]heptan-2-yl]-3H-imidazo[4,5-b]pyridine-6-carboxamide;

4-formamido-3-hydroxy-N-[(aR)-6-(4-oxo-3,4-dihydrophthalazin-1-yl)spiro[3.3]heptan-2-yl]benzamide;

N-[(aR)-6-(4-oxo-3,4-dihydrophthalazin-1-yl)spiro[3.3]heptan-2-yl]-1H-pyrrolo[2,3-b]pyridine-2-carboxamide;

6-chloro-N-[(aR)-6-(4-oxo-3,4-dihydrophthalazin-1-yl)spiro[3.3]heptan-2-yl]-1-benzothiophene-2-carboxamide;

6-methoxy-1-methyl-N-[(aR)-6-(4-oxo-3,4-dihydrophthalazin-1-yl)spiro[3.3]heptan-2-yl]-1H-indole-2-carboxamide;

2-methyl-N-[(aR)-6-(4-oxo-3,4-dihydrophthalazin-1-yl)spiro[3.3]heptan-2-yl]-1,3-benzoxazole-6-carboxamide;

N-[(aR)-6-(4-oxo-3,4-dihydrophthalazin-1-yl)spiro[3.3]heptan-2-yl]-1H-indazole-6-carboxamide;

1-methyl-N-[(aR)-6-(4-oxo-3,4-dihydrophthalazin-1-yl)spiro[3.3]heptan-2-yl]-1H-1,3-benzodiazole-5-carboxamide;

N-[(aR)-6-(4-oxo-3,4-dihydrophthalazin-1-yl)spiro[3.3]heptan-2-yl]imidazo[1,2-a]pyridine-3-carboxamide;

5-(benzyloxy)-N-[(aR)-6-(4-oxo-3,4-dihydrophthalazin-1-yl)spiro[3.3]heptan-2-yl]-1H-indole-2-carboxamide;

6-fluoro-N-[(aR)-6-(4-oxo-3,4-dihydrophthalazin-1-yl)spiro[3.3]heptan-2-yl]-1H-indole-2-carboxamide;

N-[(aR)-6-(4-oxo-3,4-dihydrophthalazin-1-yl)spiro[3.3]heptan-2-yl]-2,3-dihydro-1H-indene-1-carboxamide;

7-methyl-N-[(aR)-6-(4-oxo-3,4-dihydrophthalazin-1-yl)spiro[3.3]heptan-2-yl]-1H-indole-2-carboxamide;

N-[(aR)-6-(4-oxo-3,4-dihydrophthalazin-1-yl)spiro[3.3]heptan-2-yl]-2,3-dihydro-1H-isoindole-1-carboxamide;

N-[(aR)-6-(4-oxo-3,4-dihydrophthalazin-1-yl)spiro[3.3]heptan-2-yl]pyrazolo[1,5-a]pyridine-2-carboxamide;

N-[(aR)-6-(4-oxo-3,4-dihydrophthalazin-1-yl)spiro[3.3]heptan-2-yl]isoquinoline-3-carboxamide;

7-hydroxy-N-[(aR)-6-(4-oxo-3,4-dihydrophthalazin-1-yl)spiro[3.3]heptan-2-yl]-1H-indole-2-carboxamide;

7-chloro-N-[(aR)-6-(4-oxo-3,4-dihydrophthalazin-1-yl)spiro[3.3]heptan-2-yl]-1H-indole-2-carboxamide;

6-fluoro-7-methyl-N-[(aR)-6-(4-oxo-3,4-dihydrophthalazin-1-yl)spiro[3.3]heptan-2-yl]-1H-indole-2-carboxamide;

N-[(aR)-6-(4-oxo-3,4-dihydrophthalazin-1-yl)spiro[3.3]heptan-2-yl]quinoline-2-carboxamide;

4-bromo-N-[(aR)-6-(4-oxo-3,4-dihydrophthalazin-1-yl)spiro[3.3]heptan-2-yl]benzamide;

N-[(aR)-6-(4-oxo-3,4-dihydrophthalazin-1-yl)spiro[3.3]heptan-2-yl]-7-(trifluoromethyl)-1H-indole-2-carboxamide;

7-fluoro-N-[(aR)-6-(4-oxo-3,4-dihydrophthalazin-1-yl)spiro[3.3]heptan-2-yl]-1H-indole-2-carboxamide;

4,7-dimethoxy-N-[(aR)-6-(4-oxo-3,4-dihydrophthalazin-1-yl)spiro[3.3]heptan-2-yl]-1H-indole-2-carboxamide;
5-fluoro-7-methanesulfonyl-N-[(aR)-6-(4-oxo-3,4-dihydrophthalazin-1-yl)spiro[3.3]heptan-2-yl]-1H-indole-2-carboxamide;
N-[(aR)-6-(4-oxo-3,4-dihydrophthalazin-1-yl)spiro[3.3]heptan-2-yl]-3-(1H-pyrazol-1-yl)benzamide;
N-[(aR)-6-(4-oxo-3,4-dihydrophthalazin-1-yl)spiro[3.3]heptan-2-yl]-4-(1H-pyrazol-4-yl)benzamide;
3-[2-(morpholin-4-yl)ethoxy]-N-[(aR)-6-(4-oxo-3,4-dihydrophthalazin-1-yl)spiro[3.3]heptan-2-yl]benzamide;
N-[(aR)-6-(4-oxo-3,4-dihydrophthalazin-1-yl)spiro[3.3]heptan-2-yl]-3-(1H-pyrazol-4-yl)benzamide;
3-(4-methyl-1,3-thiazol-2-yl)-N-[(aR)-6-(4-oxo-3,4-dihydrophthalazin-1-yl)spiro[3.3]heptan-2-yl]benzamide;
6-methoxy-N-[(aR)-6-(4-oxo-3,4-dihydrophthalazin-1-yl)spiro[3.3]heptan-2-yl]pyridine-3-carboxamide;
N-[(aR)-6-(4-oxo-3,4-dihydrophthalazin-1-yl)spiro[3.3]heptan-2-yl]-6-(trifluoromethyl)pyridine-3-carboxamide;
2-hydroxy-6-methyl-N-[(aR)-6-(4-oxo-3,4-dihydrophthalazin-1-yl)spiro[3.3]heptan-2-yl]pyridine-3-carboxamide;
N-[(aR)-6-(4-oxo-3,4-dihydrophthalazin-1-yl)spiro[3.3]heptan-2-yl]-6-[2-(pyrrolidin-1-yl)ethyl]pyridine-3-carboxamide;
N-[(aR)-6-(4-oxo-3,4-dihydrophthalazin-1-yl)spiro[3.3]heptan-2-yl]-4-(2H-1,2,3,4-tetrazol-5-yl)benzamide;
N-[(aR)-6-(4-oxo-3,4-dihydrophthalazin-1-yl)spiro[3.3]heptan-2-yl]-6-(1H-pyrazol-1-yl)pyridine-3-carboxamide;
5-chloro-6-hydroxy-N-[(aR)-6-(4-oxo-3,4-dihydrophthalazin-1-yl)spiro[3.3]heptan-2-yl]pyridine-3-carboxamide;
N-[(aR)-6-(4-oxo-3,4-dihydrophthalazin-1-yl)spiro[3.3]heptan-2-yl]-4-(1H-1,2,4-triazol-1-yl)benzamide;
3-methoxy-4-(4-methyl-1H-imidazol-1-yl)-N-[(aR)-6-(4-oxo-3,4-dihydrophthalazin-1-yl)spiro[3.3]heptan-2-yl]benzamide;
3-methoxy-4-(2-methyl-1,3-thiazol-5-yl)-N-[(aR)-6-(4-oxo-3,4-dihydrophthalazin-1-yl)spiro[3.3]heptan-2-yl]benzamide;
5-methoxy-N-[(aR)-6-(4-oxo-3,4-dihydrophthalazin-1-yl)spiro[3.3]heptan-2-yl]pyridine-2-carboxamide;
3-(1H-imidazol-1-yl)-N-[(aR)-6-(4-oxo-3,4-dihydrophthalazin-1-yl)spiro[3.3]heptan-2-yl]benzamide;
3-cyano-N-[(aR)-6-(4-oxo-3,4-dihydrophthalazin-1-yl)spiro[3.3]heptan-2-yl]-4-(propan-2-yloxy)benzamide;
3-(difluoromethoxy)-N-[(aR)-6-(4-oxo-3,4-dihydrophthalazin-1-yl)spiro[3.3]heptan-2-yl]benzamide;
4-ethoxy-5-oxo-N-[(aR)-6-(4-oxo-3,4-dihydrophthalazin-1-yl)spiro[3.3]heptan-2-yl]-1-(2,2,2-trifluoroethyl)-2,5-dihydro-1H-pyrrole-3-carboxamide;
6-(dimethylamino)-N-[(aR)-6-(4-oxo-3,4-dihydrophthalazin-1-yl)spiro[3.3]heptan-2-yl]pyridine-3-carboxamide;
N-[(aR)-6-(4-oxo-3,4-dihydrophthalazin-1-yl)spiro[3.3]heptan-2-yl]-4-(1H-pyrazol-3-yl)benzamide;
4-(1,3-oxazol-5-yl)-N-[(aR)-6-(4-oxo-3,4-dihydrophthalazin-1-yl)spiro[3.3]heptan-2-yl]benzamide;
4-(1H-imidazol-1-yl)-N-[(aR)-6-(4-oxo-3,4-dihydrophthalazin-1-yl)spiro[3.3]heptan-2-yl]benzamide;
4-(5-methyl-1,2,4-oxadiazol-3-yl)-N-[(aR)-6-(4-oxo-3,4-dihydrophthalazin-1-yl)spiro[3.3]heptan-2-yl]benzamide;
N-[(aR)-6-(4-oxo-3,4-dihydrophthalazin-1-yl)spiro[3.3]heptan-2-yl]-3-(1H-pyrazol-3-yl)benzamide;
8-methyl-N-[(aR)-6-(4-oxo-3,4-dihydrophthalazin-1-yl)spiro[3.3]heptan-2-yl]imidazo[1,2-a]pyridine-2-carboxamide;
6-bromo-N-[(aR)-6-(4-oxo-3,4-dihydrophthalazin-1-yl)spiro[3.3]heptan-2-yl]imidazo[1,2-a]pyridine-2-carboxamide;
1-methyl-N-[(aR)-6-(4-oxo-3,4-dihydrophthalazin-1-yl)spiro[3.3]heptan-2-yl]-1H-indole-3-carboxamide;
5-methyl-N-[(aR)-6-(4-oxo-3,4-dihydrophthalazin-1-yl)spiro[3.3]heptan-2-yl]-2-(pyridin-4-yl)-1,3-thiazole-4-carboxamide;
1-methyl-N-[(aR)-6-(4-oxo-3,4-dihydrophthalazin-1-yl)spiro[3.3]heptan-2-yl]-1H-indazole-6-carboxamide;
1-methyl-N-[(aR)-6-(4-oxo-3,4-dihydrophthalazin-1-yl)spiro[3.3]heptan-2-yl]-1H-indole-6-carboxamide;
1-methyl-N-[(aR)-6-(4-oxo-3,4-dihydrophthalazin-1-yl)spiro[3.3]heptan-2-yl]-1H-indole-5-carboxamide;
N-[(aR)-6-(4-oxo-3,4-dihydrophthalazin-1-yl)spiro[3.3]heptan-2-yl]-5-(pyrrolidin-1-yl)pyridine-2-carboxamide;
N-[(aR)-6-(4-oxo-3,4-dihydrophthalazin-1-yl)spiro[3.3]heptan-2-yl]-5-(trifluoromethyl)pyridine-2-carboxamide;
5-cyano-6-methyl-N-[(aR)-6-(4-oxo-3,4-dihydrophthalazin-1-yl)spiro[3.3]heptan-2-yl]pyridine-2-carboxamide;
7-methoxy-3-methyl-N-[(aR)-6-(4-oxo-3,4-dihydrophthalazin-1-yl)spiro[3.3]heptan-2-yl]-1H-indole-2-carboxamide;
1-methyl-N-[(aR)-6-(4-oxo-3,4-dihydrophthalazin-1-yl)spiro[3.3]heptan-2-yl]-1H-indazole-5-carboxamide;
7-bromo-N-[(aR)-6-(4-oxo-3,4-dihydrophthalazin-1-yl)spiro[3.3]heptan-2-yl]imidazo[1,2-a]pyridine-2-carboxamide;
5-bromo-N-[(aR)-6-(4-oxo-3,4-dihydrophthalazin-1-yl)spiro[3.3]heptan-2-yl]pyridine-2-carboxamide;
N-[(aR)-6-(4-oxo-3,4-dihydrophthalazin-1-yl)spiro[3.3]heptan-2-yl]imidazo[1,2-a]pyridine-2-carboxamide;
7-(4-methylpiperazin-1-yl)-N-[(aR)-6-(4-oxo-3,4-dihydrophthalazin-1-yl)spiro[3.3]heptan-2-yl]imidazo[1,2-a]pyridine-3-carboxamide;
7-cyano-N-[(aR)-6-(4-oxo-3,4-dihydrophthalazin-1-yl)spiro[3.3]heptan-2-yl]imidazo[1,2-a]pyridine-3-carboxamide;
8-cyano-N-[(aR)-6-(4-oxo-3,4-dihydrophthalazin-1-yl)spiro[3.3]heptan-2-yl]imidazo[1,2-a]pyridine-3-carboxamide;
N-[(aR)-6-(4-oxo-3,4-dihydrophthalazin-1-yl)spiro[3.3]heptan-2-yl]-8-(trifluoromethyl)imidazo[1,2-a]pyridine-3-carboxamide;
8-chloro-N-[(aR)-6-(4-oxo-3,4-dihydrophthalazin-1-yl)spiro[3.3]heptan-2-yl]imidazo[1,2-a]pyridine-3-carboxamide;
N-[(aR)-6-(4-oxo-3,4-dihydrophthalazin-1-yl)spiro[3.3]heptan-2-yl]-7-phenylimidazo[1,2-a]pyridine-3-carboxamide;
7-(benzyloxy)-N-[(aR)-6-(4-oxo-3,4-dihydrophthalazin-1-yl)spiro[3.3]heptan-2-yl]imidazo[1,2-a]pyridine-3-carboxamide;
7-methoxy-N-[(aR)-6-(4-oxo-3,4-dihydrophthalazin-1-yl)spiro[3.3]heptan-2-yl]imidazo[1,2-a]pyridine-3-carboxamide;
8-chloro-7-methyl-N-[(aR)-6-(4-oxo-3,4-dihydrophthalazin-1-yl)spiro[3.3]heptan-2-yl]imidazo[1,2-a]pyridine-3-carboxamide;
7-fluoro-N-[(aR)-6-(4-oxo-3,4-dihydrophthalazin-1-yl)spiro[3.3]heptan-2-yl]imidazo[1,2-a]pyridine-3-carboxamide;

N-[(aR)-6-(4-oxo-3,4-dihydrophthalazin-1-yl)spiro[3.3]
heptan-2-yl]-3-(propan-2-yl)-5H,6H,7H,8H-imidazo[1,5-
a]pyridine-1-carboxamide;
N-[(aR)-6-(4-oxo-3,4-dihydrophthalazin-1-yl)spiro[3.3]
heptan-2-yl]-[1,2,4]triazolo[4,3-a]pyridine-3-carboxam-
ide;
N-[(aR)-6-(4-oxo-3,4-dihydrophthalazin-1-yl)spiro[3.3]
heptan-2-yl]-6-(trifluoromethyl)imidazo[1,2-a]pyridine-
3-carboxamide;
7-(4,4-difluoropiperidin-1-yl)-N-[(aR)-6-(4-oxo-3,4-dihy-
drophthalazin-1-yl)spiro[3.3]heptan-2-yl]imidazo[1,2-a]
pyridine-3-carboxamide;
7-(3,3-difluoropyrrolidin-1-yl)-N-[(aR)-6-(4-oxo-3,4-dihy-
drophthalazin-1-yl)spiro[3.3]heptan-2-yl]imidazo[1,2-a]
pyridine-3-carboxamide;
7-[(3R)-3-fluoropyrrolidin-1-yl]-N-[(aR)-6-(4-oxo-3,4-di-
hydrophthalazin-1-yl)spiro[3.3]heptan-2-yl]imidazo[1,2-
a]pyridine-3-carboxamide;
7-[(3S)-3-fluoropyrrolidin-1-yl]-N-[(aR)-6-(4-oxo-3,4-di-
hydrophthalazin-1-yl)spiro[3.3]heptan-2-yl]imidazo[1,2-
a]pyridine-3-carboxamide;
7-[(3R)-3-hydroxypyrrolidin-1-yl]-N-[(aR)-6-(4-oxo-3,4-
dihydrophthalazin-1-yl)spiro[3.3]heptan-2-yl]imidazo[1,
2-a]pyridine-3-carboxamide;
7-[(2-hydroxyethyl)(methyl)amino]-N-[(aR)-6-(4-oxo-3,4-
dihydrophthalazin-1-yl)spiro[3.3]heptan-2-yl]imidazo[1,
2-a]pyridine-3-carboxamide;
7-[(2-methoxyethyl)(methyl)amino]-N-[(aR)-6-(4-oxo-3,4-
dihydrophthalazin-1-yl)spiro[3.3]heptan-2-yl]imidazo[1,
2-a]pyridine-3-carboxamide;
7-[2-(morpholin-4-yl)ethoxy]-N-[(aR)-6-(4-oxo-3,4-dihy-
drophthalazin-1-yl)spiro[3.3]heptan-2-yl]imidazo[1,2-a]
pyridine-3-carboxamide;
7-[(2-hydroxy-2-methylpropyl)(methyl)amino]-N-[(aR)-6-
(4-oxo-3,4-dihydrophthalazin-1-yl)spiro[3.3]heptan-2-yl]
imidazo[1,2-a]pyridine-3-carboxamide;
7-(2-hydroxy-2-methylpropoxy)-N-[(aR)-6-(4-oxo-3,4-di-
hydrophthalazin-1-yl)spiro[3.3]heptan-2-yl]imidazo[1,2-
a]pyridine-3-carboxamide;
N-[(aR)-6-(4-oxo-3,4-dihydrophthalazin-1-yl)spiro[3.3]
heptan-2-yl]-7-[2-(pyrrolidin-1-yl)ethoxy]imidazo[1,2-a]
pyridine-3-carboxamide;
1-(2-hydroxy-2-methylpropyl)-7-oxo-N-[(aR)-6-(4-oxo-3,
4-dihydrophthalazin-1-yl)spiro[3.3]heptan-2-yl]-1H,7H-
imidazo[1,2-a]pyridine-3-carboxamide;
N-[(aR)-6-(4-oxo-3,4-dihydrophthalazin-1-yl)spiro[3.3]
heptan-2-yl]-7-(trifluoromethyl)imidazo[1,2-a]pyridine-
3-carboxamide;
8-fluoro-N-[(aR)-6-(4-oxo-3,4-dihydrophthalazin-1-yl)
spiro[3.3]heptan-2-yl]-6-(trifluoromethyl)imidazo[1,2-a]
pyridine-3-carboxamide;
6-fluoro-8-methyl-N-[(aR)-6-(4-oxo-3,4-dihy-
drophthalazin-1-yl)spiro[3.3]heptan-2-yl]imidazo[1,2-a]
pyridine-3-carboxamide;
7-(difluoromethoxy)-N-[(aR)-6-(4-oxo-3,4-dihy-
drophthalazin-1-yl)spiro[3.3]heptan-2-yl]imidazo[1,2-a]
pyridine-3-carboxamide;
6-fluoro-5-methyl-N-[(aR)-6-(4-oxo-3,4-dihy-
drophthalazin-1-yl)spiro[3.3]heptan-2-yl]imidazo[1,2-a]
pyridine-3-carboxamide;
6-fluoro-N-[(aR)-6-(4-oxo-3,4-dihydrophthalazin-1-yl)
spiro[3.3]heptan-2-yl]imidazo[1,2-a]pyridine-3-carbox-
amide;
7-[(2-hydroxy-2-methylpropyl)amino]-N-[(aR)-6-(4-oxo-3,
4-dihydrophthalazin-1-yl)spiro[3.3]heptan-2-yl]imidazo
[1,2-a]pyridine-3-carboxamide;
6-fluoro-7-methyl-N-[(aR)-6-(4-oxo-3,4-dihy-
drophthalazin-1-yl)spiro[3.3]heptan-2-yl]imidazo[1,2-a]
pyridine-3-carboxamide;
6,8-difluoro-N-[(aR)-6-(4-oxo-3,4-dihydrophthalazin-1-yl)
spiro[3.3]heptan-2-yl]imidazo[1,2-a]pyridine-3-carbox-
amide;
7-methyl-N-[(aR)-6-(4-oxo-3,4-dihydrophthalazin-1-yl)
spiro[3.3]heptan-2-yl]imidazo[1,2-a]pyridine-3-carbox-
amide;
8-(benzyloxy)-N-[(aR)-6-(4-oxo-3,4-dihydrophthalazin-1-
yl)spiro[3.3]heptan-2-yl]imidazo[1,2-a]pyridine-3-car-
boxamide;
7-(methylsulfanyl)-N-[(aR)-6-(4-oxo-3,4-dihy-
drophthalazin-1-yl)spiro[3.3]heptan-2-yl]imidazo[1,2-a]
pyridine-3-carboxamide;
4-oxo-N-[(aR)-6-(4-oxo-3,4-dihydrophthalazin-1-yl)spiro
[3.3]heptan-2-yl]-4H,5H,6H,7H-pyrazolo[1,5-a]pyra-
zine-2-carboxamide;
3-methoxy-N-[(aR)-6-(4-oxo-3,4-dihydrophthalazin-1-yl)
spiro[3.3]heptan-2-yl]-4-(1H-pyrazol-4-yl)benzamide;
3-cyano-N-[(aR)-6-(4-oxo-3,4-dihydrophthalazin-1-yl)
spiro[3.3]heptan-2-yl]-4-(1H-pyrazol-4-yl)benzamide;
3-methyl-N-[(aR)-6-(4-oxo-3,4-dihydrophthalazin-1-yl)
spiro[3.3]heptan-2-yl]-4-(1H-pyrazol-4-yl)benzamide;
2-methoxy-N-[(aR)-6-(4-oxo-3,4-dihydrophthalazin-1-yl)
spiro[3.3]heptan-2-yl]-4-(1H-pyrazol-4-yl)benzamide;
7-(1-methyl-1H-pyrazol-4-yl)-N-[(aR)-6-(4-oxo-3,4-dihy-
drophthalazin-1-yl)spiro[3.3]heptan-2-yl]-1H-indole-2-
carboxamide;
N-[(aR)-6-(4-oxo-3,4-dihydrophthalazin-1-yl)spiro[3.3]
heptan-2-yl]-6H-isochromeno[4,3-d]pyrimidine-8-car-
boxamide;
3-methoxy-4-(1-methyl-1H-pyrazol-4-yl)-N-[(aR)-6-(4-
oxo-3,4-dihydrophthalazin-1-yl)spiro[3.3]heptan-2-yl]
benzamide;
3-fluoro-4-(1-methyl-1H-pyrazol-4-yl)-N-[(aR)-6-(4-oxo-3,
4-dihydrophthalazin-1-yl)spiro[3.3]heptan-2-yl]benz-
amide;
6-(1-methyl-1H-pyrazol-4-yl)-N-[(aR)-6-(4-oxo-3,4-dihy-
drophthalazin-1-yl)spiro[3.3]heptan-2-yl]pyridine-3-car-
boxamide;
7-acetyl-N-[(aR)-6-(4-oxo-3,4-dihydrophthalazin-1-yl)
spiro[3.3]heptan-2-yl]imidazo[1,2-a]pyridine-3-carbox-
amide;
3-fluoro-4-[1-($^{2}H_3$)methyl-1H-pyrazol-4-yl]-N-[(aR)-6-(4-
oxo-3,4-dihydrophthalazin-1-yl)spiro[3.3]heptan-2-yl]
benzamide;
4-[1-(difluoromethyl)-1H-pyrazol-4-yl]-3-fluoro-N-[(aR)-
6-(4-oxo-3,4-dihydrophthalazin-1-yl)spiro[3.3]heptan-2-
yl]benzamide;
7-(2-hydroxypropan-2-yl)-N-[(aR)-6-(4-oxo-3,4-dihy-
drophthalazin-1-yl)spiro[3.3]heptan-2-yl]imidazo[1,2-a]
pyridine-3-carboxamide;
7-(1-hydroxyethyl)-N-[(aR)-6-(4-oxo-3,4-dihy-
drophthalazin-1-yl)spiro[3.3]heptan-2-yl]imidazo[1,2-a]
pyridine-3-carboxamide;
7-[(1,1-dioxo-1$\lambda^{6}$-thian-4-yl)oxy]-N-[(aR)-6-(4-oxo-3,4-di-
hydrophthalazin-1-yl)spiro[3.3]heptan-2-yl]imidazo[1,2-
a]pyridine-3-carboxamide;
N-[(aR)-6-(4-oxo-3,4-dihydrophthalazin-1-yl)spiro[3.3]
heptan-2-yl]-7-(3,3,3-trifluoropropoxy)imidazo[1,2-a]
pyridine-3-carboxamide;
7-[(1,3-difluoropropan-2-yl)oxy]-N-[(aR)-6-(4-oxo-3,4-di-
hydrophthalazin-1-yl)spiro[3.3]heptan-2-yl]imidazo[1,2-
a]pyridine-3-carboxamide;

N-[(aR)-6-(4-oxo-3,4-dihydrophthalazin-1-yl)spiro[3.3]
heptan-2-yl]-7-(pyridin-2-yloxy)imidazo[1,2-a]pyridine-
3-carboxamide;
N-[(aR)-6-(4-oxo-3,4-dihydrophthalazin-1-yl)spiro[3.3]
heptan-2-yl]-3-(propan-2-yl)imidazo[1,5-a]pyridine-1-
carboxamide;
7-(2,2-difluoroethoxy)-N-[(aR)-6-(4-oxo-3,4-dihy-
drophthalazin-1-yl)spiro[3.3]heptan-2-yl]imidazo[1,2-a]
pyridine-3-carboxamide;
N-[(aR)-6-(4-oxo-3,4-dihydrophthalazin-1-yl)spiro[3.3]
heptan-2-yl]-7-(propan-2-yloxy)imidazo[1,2-a]pyridine-
3-carboxamide;
4-(morpholin-4-yl)-N-[(aR)-6-(4-oxo-3,4-dihy-
drophthalazin-1-yl)spiro[3.3]heptan-2-yl]pyrazolo[1,5-a]
pyridine-3-carboxamide;
7-(1-ethyl-1H-pyrazol-4-yl)-N-[(aR)-6-(4-oxo-3,4-dihy-
drophthalazin-1-yl)spiro[3.3]heptan-2-yl]imidazo[1,2-a]
pyridine-3-carboxamide;
7-(1-methyl-1H-pyrazol-4-yl)-N-[(aR)-6-(4-oxo-3,4-dihy-
drophthalazin-1-yl)spiro[3.3]heptan-2-yl]imidazo[1,2-a]
pyridine-3-carboxamide;
N-[(aR)-6-(4-oxo-3,4-dihydrophthalazin-1-yl)spiro[3.3]
heptan-2-yl]-7-[1-(propan-2-yl)-1H-pyrazol-4-yl]imi-
dazo[1,2-a]pyridine-3-carboxamide;
7-[1-($^2$H$_3$)methyl-1H-pyrazol-4-yl]-N-[(aR)-6-(4-oxo-3,4-
dihydrophthalazin-1-yl)spiro[3.3]heptan-2-yl]imidazo[1,
2-a]pyridine-3-carboxamide;
7-[1-(oxan-4-yl)-1H-pyrazol-4-yl]-N-[(aR)-6-(4-oxo-3,4-
dihydrophthalazin-1-yl)spiro[3.3]heptan-2-yl]imidazo[1,
2-a]pyridine-3-carboxamide;
N-[(aR)-6-(4-oxo-3,4-dihydrophthalazin-1-yl)spiro[3.3]
heptan-2-yl]-7-[1-(propan-2-yl)-3-(trifluoromethyl)-1H-
pyrazol-4-yl]imidazo[1,2-a]pyridine-3-carboxamide;
4-(1-ethyl-1H-pyrazol-4-yl)-3-fluoro-N-[(aR)-6-(4-oxo-3,
4-dihydrophthalazin-1-yl)spiro[3.3]heptan-2-yl]benz-
amide;
3-fluoro-N-[(aR)-6-(4-oxo-3,4-dihydrophthalazin-1-yl)
spiro[3.3]heptan-2-yl]-4-[1-(propan-2-yl)-1H-pyrazol-4-
yl]benzamide;
3-fluoro-4-[1-methyl-5-(trifluoromethyl)-1H-pyrazol-4-yl]-
N-[(aR)-6-(4-oxo-3,4-dihydrophthalazin-1-yl)spiro[3.3]
heptan-2-yl]benzamide;
4-(1-cyclopropyl-1H-pyrazol-4-yl)-3-fluoro-N-[(aR)-6-(4-
oxo-3,4-dihydrophthalazin-1-yl)spiro[3.3]heptan-2-yl]
benzamide;
3-fluoro-4-[1-(oxan-4-yl)-1H-pyrazol-4-yl]-N-[(aR)-6-(4-
oxo-3,4-dihydrophthalazin-1-yl)spiro[3.3]heptan-2-yl]
benzamide;
5-(1-methyl-1H-pyrazol-4-yl)-N-[(aR)-6-(4-oxo-3,4-dihy-
drophthalazin-1-yl)spiro[3.3]heptan-2-yl]pyridine-2-car-
boxamide;
4-(1-methyl-1H-pyrazol-4-yl)-N-[(aR)-6-(4-oxo-3,4-dihy-
drophthalazin-1-yl)spiro[3.3]heptan-2-yl]benzamide;
N-[(aR)-6-(4-oxo-3,4-dihydrophthalazin-1-yl)spiro[3.3]
heptan-2-yl]-7-(pyridin-3-yl)imidazo[1,2-a]pyridine-3-
carboxamide;
N-[(aR)-6-(4-oxo-3,4-dihydrophthalazin-1-yl)spiro[3.3]
heptan-2-yl]-7-(pyridin-3-yl)imidazo[1,2-a]pyridine-2-
carboxamide;
7-(2-methyl-1,3-thiazol-5-yl)-N-[(aR)-6-(4-oxo-3,4-dihy-
drophthalazin-1-yl)spiro[3.3]heptan-2-yl]imidazo[1,2-a]
pyridine-2-carboxamide;
7-(2-methyl-1,3-thiazol-5-yl)-N-[(aR)-6-(4-oxo-3,4-dihy-
drophthalazin-1-yl)spiro[3.3]heptan-2-yl]imidazo[1,2-a]
pyridine-3-carboxamide;
4-[6-(1-oxo-2,3-dihydro-1H-isoindol-2-yl)spiro[3.3]heptan-
2-yl]-1,2-dihydrophthalazin-1-one;
4-{6-[(4S)-4-benzyl-2-oxoimidazolidin-1-yl]spiro[3.3]hep-
tan-2-yl}-1,2-dihydrophthalazin-1-one;
4-{6-[(4R)-4-benzyl-2-oxoimidazolidin-1-yl]spiro[3.3]hep-
tan-2-yl}-1,2-dihydrophthalazin-1-one;
4-{6-[(2-nitrophenyl)amino]spiro[3.3]heptan-2-yl}-1,2-di-
hydrophthalazin-1-one;
4-[6-(2-oxo-2,3-dihydro-1H-1,3-benzodiazol-1-yl)spiro
[3.3]heptan-2-yl]-1,2-dihydrophthalazin-1-one;
4-cyclopropyl-N-[(aR)-6-(4-oxo-3,4-dihydrophthalazin-1-
yl)spiro[3.3]heptan-2-yl]pyrazolo[1,5-a]pyridine-3-car-
boxamide;
3-fluoro-5-(1-methyl-1H-pyrazol-4-yl)-N-[(aR)-6-(4-oxo-3,
4-dihydrophthalazin-1-yl)spiro[3.3]heptan-2-yl]pyridine-
2-carboxamide;
6-(4-oxo-3,4-dihydrophthalazin-1-yl)spiro[3.3]heptan-2-
yl2,3-dihydro-1H-isoindole-2-carboxylate;
7-methanesulfonyl-N-[(aR)-6-(4-oxo-3,4-dihy-
drophthalazin-1-yl)spiro[3.3]heptan-2-yl]imidazo[1,2-a]
pyridine-3-carboxamide;
N-[(aR)-6-(4-oxo-3,4-dihydrophthalazin-1-yl)spiro[3.3]
heptan-2-yl]pyrazolo[1,5-a]pyrazine-3-carboxamide;
5-bromo-N-[(aR)-6-(4-oxo-3,4-dihydrophthalazin-1-yl)
spiro[3.3]heptan-2-yl]-2,3-dihydro-1H-indole-2-carbox-
amide;
2-methyl-2-[(3-{[(aR)-6-(4-oxo-3,4-dihydrophthalazin-1-
yl)spiro[3.3]heptan-2-yl]carbamoyl}pyrazolo[1,5-a]pyri-
din-6-yl)oxy]propanoic acid;
7-(morpholin-4-yl)-N-[(aR)-6-(4-oxo-3,4-dihy-
drophthalazin-1-yl)spiro[3.3]heptan-2-yl]imidazo[1,2-a]
pyridine-3-carboxamide; and
7-[(4,4-difluorocyclohexyl)oxy]-N-[(aR)-6-(4-oxo-3,4-di-
hydrophthalazin-1-yl)spiro[3.3]heptan-2-yl]imidazo[1,2-
a]pyridine-3-carboxamide.

Typically, the present invention is directed to the following compounds:
1-methyl-N-[6-(4-oxo-3,4-dihydrophthalazin-1-yl)spiro
[3.3]heptan-2-yl]-1H-indazole-3-carboxamide;
5-methyl-N-[6-(4-oxo-3,4-dihydrophthalazin-1-yl)spiro
[3.3]heptan-2-yl]-1-phenyl-1H-pyrazole-4-carboxamide;
1-methyl-N-[(aR)-6-(4-oxo-3,4-dihydrophthalazin-1-yl)
spiro[3.3]heptan-2-yl]-1H-indazole-3-carboxamide;
1-(2,2-difluoroethyl)-N-[(aR)-6-(4-oxo-3,4-dihy-
drophthalazin-1-yl)spiro[3.3]heptan-2-yl]-1H-pyrazole-
3-carboxamide;
1-(2-hydroxy-2-methylpropyl)-N-[(aR)-6-(4-oxo-3,4-dihy-
drophthalazin-1-yl)spiro[3.3]heptan-2-yl]-1H-indazole-
3-carboxamide;
3-cyclopropyl-1-methyl-N-[(aR)-6-(4-oxo-3,4-dihy-
drophthalazin-1-yl)spiro[3.3]heptan-2-yl]-1H-pyrazole-
5-carboxamide;
5-cyclopropyl-1-methyl-N-[(aR)-6-(4-oxo-3,4-dihy-
drophthalazin-1-yl)spiro[3.3]heptan-2-yl]-1H-pyrazole-
3-carboxamide;
1-(2-hydroxy-2-methylpropyl)-N-[(aR)-6-(4-oxo-3,4-dihy-
drophthalazin-1-yl)spiro[3.3]heptan-2-yl]-1H-pyrazole-
3-carboxamide;
4-methyl-N-((aR)-6-(4-oxo-3,4-dihydrophthalazin-1-yl)
spiro[3.3]heptan-2-yl)-2-(piperidin-1-yl)thiazole-5-car-
boxamide;
2-[(3S)-3-fluoropyrrolidin-1-yl]-4-methyl-N-[(aR)-6-(4-
oxo-3,4-dihydrophthalazin-1-yl)spiro[3.3]heptan-2-yl]-1,
3-thiazole-5-carboxamide;
2-(3,3-difluoropyrrolidin-1-yl)-5-methyl-N-((aR)-6-(4-oxo-
3,4-dihydrophthalazin-1-yl)spiro[3.3]heptan-2-yl)thiaz-
ole-4-carboxamide;

1-(2-hydroxy-2-methylpropyl)-6-methoxy-N-((aR)-6-(4-oxo-3,4-dihydrophthalazin-1-yl)spiro[3.3]heptan-2-yl)-1H-indazole-3-carboxamide;

6-methoxy-N-((aR)-6-(4-oxo-3,4-dihydrophthalazin-1-yl)spiro[3.3]heptan-2-yl)pyrazolo[1,5-a]pyridine-3-carboxamide;

1-(2-hydroxy-2-methylpropyl)-N-((aR)-6-(4-oxo-3,4-dihydrophthalazin-1-yl)spiro[3.3]heptan-2-yl)-1H-indole-3-carboxamide;

6-(2,2-difluoroethoxy)-N-((aR)-6-(4-oxo-3,4-dihydrophthalazin-1-yl)spiro[3.3]heptan-2-yl)pyrazolo[1,5-a]pyridine-3-carboxamide;

6-(2-(1H-pyrazol-1-yl)ethoxy)-N-((aR)-6-(4-oxo-3,4-dihydrophthalazin-1-yl)spiro[3.3]heptan-2-yl)pyrazolo[1,5-a]pyridine-3-carboxamide;

6-(4-methylpiperazin-1-yl)-N-((aR)-6-(4-oxo-3,4-dihydrophthalazin-1-yl)spiro[3.3]heptan-2-yl)pyrazolo[1,5-a]pyridine-3-carboxamide;

N-((aR)-6-(4-oxo-3,4-dihydrophthalazin-1-yl)spiro[3.3]heptan-2-yl)-6-(pyrrolidin-1-yl)pyrazolo[1,5-a]pyridine-3-carboxamide;

6-((R)-3-fluoropyrrolidin-1-yl)-N-((aR)-6-(4-oxo-3,4-dihydrophthalazin-1-yl)spiro[3.3]heptan-2-yl)pyrazolo[1,5-a]pyridine-3-carboxamide;

6-((S)-3-fluoropyrrolidin-1-yl)-N-((aR)-6-(4-oxo-3,4-dihydrophthalazin-1-yl)spiro[3.3]heptan-2-yl)pyrazolo[1,5-a]pyridine-3-carboxamide;

6-(3,3-difluoropyrrolidin-1-yl)-N-((aR)-6-(4-oxo-3,4-dihydrophthalazin-1-yl)spiro[3.3]heptan-2-yl)pyrazolo[1,5-a]pyridine-3-carboxamide;

6-(3-fluoroazetidin-1-yl)-N-((aR)-6-(4-oxo-3,4-dihydrophthalazin-1-yl)spiro[3.3]heptan-2-yl)pyrazolo[1,5-a]pyridine-3-carboxamide;

6-(3,3-difluoroazetidin-1-yl)-N-((aR)-6-(4-oxo-3,4-dihydrophthalazin-1-yl)spiro[3.3]heptan-2-yl)pyrazolo[1,5-a]pyridine-3-carboxamide;

7-cyclopropyl-6-(2-hydroxy-2-methylpropoxy)-N-((aR)-6-(4-oxo-3,4-dihydrophthalazin-1-yl)spiro[3.3]heptan-2-yl)pyrazolo[1,5-a]pyridine-3-carboxamide;

6-(benzyloxy)-N-((aR)-6-(4-oxo-3,4-dihydrophthalazin-1-yl)spiro[3.3]heptan-2-yl)pyrazolo[1,5-a]pyridine-3-carboxamide;

N-((aR)-6-(4-oxo-3,4-dihydrophthalazin-1-yl)spiro[3.3]heptan-2-yl)-6-((tetrahydrofuran-3-yl)oxy)pyrazolo[1,5-a]pyridine-3-carboxamide;

N-((aR)-6-(4-oxo-3,4-dihydrophthalazin-1-yl)spiro[3.3]heptan-2-yl)-6-(3,3,3-trifluoro-2-hydroxypropoxy)pyrazolo[1,5-a]pyridine-3-carboxamide;

N-((aR)-6-(4-oxo-3,4-dihydrophthalazin-1-yl)spiro[3.3]heptan-2-yl)-6-(3,3,3-trifluoro-2-hydroxypropoxy)pyrazolo[1,5-a]pyridine-3-carboxamide;

N-((aR)-6-(4-oxo-3,4-dihydrophthalazin-1-yl)spiro[3.3]heptan-2-yl)-6-((tetrahydrofuran-3-yl)oxy)pyrazolo[1,5-a]pyridine-3-carboxamide;

N-((aR)-6-(4-oxo-3,4-dihydrophthalazin-1-yl)spiro[3.3]heptan-2-yl)-6-((tetrahydrofuran-3-yl)oxy)pyrazolo[1,5-a]pyridine-3-carboxamide;

6-(benzyloxy)-7-methyl-N-((aR)-6-(4-oxo-3,4-dihydrophthalazin-1-yl)spiro[3.3]heptan-2-yl)pyrazolo[1,5-a]pyridine-3-carboxamide;

6-(benzyloxy)-7-cyano-N-((aR)-6-(4-oxo-3,4-dihydrophthalazin-1-yl)spiro[3.3]heptan-2-yl)pyrazolo[1,5-a]pyridine-3-carboxamide;

6-((1,3-difluoropropan-2-yl)oxy)-N-((aR)-6-(4-oxo-3,4-dihydrophthalazin-1-yl)spiro[3.3]heptan-2-yl)pyrazolo[1,5-a]pyridine-3-carboxamide;

6-((1,1-dioxidotetrahydro-2H-thiopyran-4-yl)oxy)-N-((aR)-6-(4-oxo-3,4-dihydrophthalazin-1-yl)spiro[3.3]heptan-2-yl)pyrazolo[1,5-a]pyridine-3-carboxamide;

N-((aR)-6-(4-oxo-3,4-dihydrophthalazin-1-yl)spiro[3.3]heptan-2-yl)-6-(3,3,3-trifluoropropoxy)pyrazolo[1,5-a]pyridine-3-carboxamide;

6-((4,4-difluorocyclohexyl)oxy)-N-((aR)-6-(4-oxo-3,4-dihydrophthalazin-1-yl)spiro[3.3]heptan-2-yl)pyrazolo[1,5-a]pyridine-3-carboxamide;

N-((aR)-6-(4-oxo-3,4-dihydrophthalazin-1-yl)spiro[3.3]heptan-2-yl)-6-((tetrahydro-2H-pyran-4-yl)oxy)pyrazolo[1,5-a]pyridine-3-carboxamide;

6-(3,3-difluorocyclobutoxy)-N-((aR)-6-(4-oxo-3,4-dihydrophthalazin-1-yl)spiro[3.3]heptan-2-yl)pyrazolo[1,5-a]pyridine-3-carboxamide;

N-((aR)-6-(4-oxo-3,4-dihydrophthalazin-1-yl)spiro[3.3]heptan-2-yl)-6-(2-(2,2,2-trifluoroethoxy)ethoxy)pyrazolo[1,5-a]pyridine-3-carboxamide;

6-((5-cyclopropyl-1,3,4-thiadiazol-2-yl)methoxy)-N-((aR)-6-(4-oxo-3,4-dihydrophthalazin-1-yl)spiro[3.3]heptan-2-yl)pyrazolo[1,5-a]pyridine-3-carboxamide;

1-(2-hydroxy-2-methylpropyl)-6-(2-methoxyphenyl)-N-((aR)-6-(4-oxo-3,4-dihydrophthalazin-1-yl)spiro[3.3]heptan-2-yl)-1H-indazole-3-carboxamide;

6-(2-cyanophenyl)-1-(2-hydroxy-2-methylpropyl)-N-((aR)-6-(4-oxo-3,4-dihydrophthalazin-1-yl)spiro[3.3]heptan-2-yl)-1H-indazole-3-carboxamide;

6-cyclopropyl-N-((aR)-6-(4-oxo-3,4-dihydrophthalazin-1-yl)spiro[3.3]heptan-2-yl)pyrazolo[1,5-a]pyridine-3-carboxamide;

6-(1-(difluoromethyl)-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide;

6-(1-methyl-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide;

N-((aR)-6-(4-oxo-3,4-dihydrophthalazin-1-yl)spiro[3.3]heptan-2-yl)-6-(thiazol-2-yl)pyrazolo[1,5-a]pyridine-3-carboxamide;

N-((aR)-6-(4-oxo-3,4-dihydrophthalazin-1-yl)spiro[3.3]heptan-2-yl)-6-(1H-pyrazol-4-yl)pyrazolo[1,5-a]pyridine-3-carboxamide;

N-((aR)-6-(4-oxo-3,4-dihydrophthalazin-1-yl)spiro[3.3]heptan-2-yl)-6-(1H-pyrazol-1-yl)pyrazolo[1,5-a]pyridine-3-carboxamide;

6-(2-methoxyethoxy)-N-((aR)-6-(4-oxo-3,4-dihydrophthalazin-1-yl)spiro[3.3]heptan-2-yl)pyrazolo[1,5-a]pyridine-3-carboxamide;

6-(2-(4-hydroxy-3,3-dimethylpiperidin-1-yl)ethoxy)-N-((aR)-6-(4-oxo-3,4-dihydrophthalazin-1-yl)spiro[3.3]heptan-2-yl)pyrazolo[1,5-a]pyridine-3-carboxamide;

6-(2-(3,3-difluoropyrrolidin-1-yl)ethoxy)-N-((aR)-6-(4-oxo-3,4-dihydrophthalazin-1-yl)spiro[3.3]heptan-2-yl)pyrazolo[1,5-a]pyridine-3-carboxamide;

6-(2-(2,2-dimethylmorpholino)ethoxy)-N-((aR)-6-(4-oxo-3,4-dihydrophthalazin-1-yl)spiro[3.3]heptan-2-yl)pyrazolo[1,5-a]pyridine-3-carboxamide;

6-(2-(4-methylpiperazin-1-yl)ethoxy)-N-((aR)-6-(4-oxo-3,4-dihydrophthalazin-1-yl)spiro[3.3]heptan-2-yl)pyrazolo[1,5-a]pyridine-3-carboxamide;

6-(2-((R)-3-fluoropyrrolidin-1-yl)ethoxy)-N-((aR)-6-(4-oxo-3,4-dihydrophthalazin-1-yl)spiro[3.3]heptan-2-yl)pyrazolo[1,5-a]pyridine-3-carboxamide;

6-(2-((S)-3-fluoropyrrolidin-1-yl)ethoxy)-N-((aR)-6-(4-oxo-3,4-dihydrophthalazin-1-yl)spiro[3.3]heptan-2-yl)pyrazolo[1,5-a]pyridine-3-carboxamide;

6-(3-(3,3-difluoropyrrolidin-1-yl)propyl)-N-((aR)-6-(4-oxo-3,4-dihydrophthalazin-1-yl)spiro[3.3]heptan-2-yl)pyrazolo[1,5-a]pyridine-3-carboxamide;

6-(3-hydroxy-3-methylbutyl)-N-((aR)-6-(4-oxo-3,4-dihydrophthalazin-1-yl)spiro[3.3]heptan-2-yl)pyrazolo[1,5-a]pyridine-3-carboxamide;

6-benzyl-N-((aR)-6-(4-oxo-3,4-dihydrophthalazin-1-yl)spiro[3.3]heptan-2-yl)pyrazolo[1,5-a]pyridine-3-carboxamide;

N-((aR)-6-(4-oxo-3,4-dihydrophthalazin-1-yl)spiro[3.3]heptan-2-yl)-6-(3,3,3-trifluoropropyl)pyrazolo[1,5-a]pyridine-3-carboxamide;

6-((allyloxy)methyl)-N-((aR)-6-(4-oxo-3,4-dihydrophthalazin-1-yl)spiro[3.3]heptan-2-yl)pyrazolo[1,5-a]pyridine-3-carboxamide;

6-(1,5-dimethyl-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide;

6-(1-cyclopropyl-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide;

6-(1-(cyclopropylmethyl)-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide;

6-(1-(($^2$H$_3$)methyl-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide;

6-(1-isopropyl-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide;

N-((aR)-6-(4-oxo-3,4-dihydrophthalazin-1-yl)spiro[3.3]heptan-2-yl)-6-(1,3,5-trimethyl-1H-pyrazol-4-yl)pyrazolo[1,5-a]pyridine-3-carboxamide;

N-((aR)-6-(4-oxo-3,4-dihydrophthalazin-1-yl)spiro[3.3]heptan-2-yl)-6-(1-(tetrahydro-2H-pyran-4-yl)-1H-pyrazol-4-yl)pyrazolo[1,5-a]pyridine-3-carboxamide;

6-(1-methyl-3-(trifluoromethyl)-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide;

6-(1-isopropyl-3-(trifluoromethyl)-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide;

6-(1-(tert-butyl)-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide;

N-((aR)-6-(4-oxo-3,4-dihydrophthalazin-1-yl)spiro[3.3]heptan-2-yl)-6-(1-(tetrahydrofuran-3-yl)-1H-pyrazol-4-yl)pyrazolo[1,5-a]pyridine-3-carboxamide;

5-(1-methyl-1H-pyrazol-4-yl)-N-((aR)-6-(4-oxo-3,4-dihydrophthalazin-1-yl)spiro[3.3]heptan-2-yl)indoline-1-carboxamide;

5-(1-cyclopropyl-1H-pyrazol-4-yl)-N-((aR)-6-(4-oxo-3,4-dihydrophthalazin-1-yl)spiro[3.3]heptan-2-yl)indoline-1-carboxamide;

5-(1-($^2$H$_3$)methyl-1H-pyrazol-4-yl)-N-((aR)-6-(4-oxo-3,4-dihydrophthalazin-1-yl)spiro[3.3]heptan-2-yl)indoline-1-carboxamide;

2-methyl-1-((3-(((aR)-6-(4-oxo-3,4-dihydrophthalazin-1-yl)spiro[3.3]heptan-2-yl)carbamoyl)pyrazolo[1,5-a]pyridin-6-yl)oxy)propan-2-yl2-aminoacetate;

(S)-2-methyl-1-((3-(((aR)-6-(4-oxo-3,4-dihydrophthalazin-1-yl)spiro[3.3]heptan-2-yl)carbamoyl)pyrazolo[1,5-a]pyridin-6-yl)oxy)propan-2-yl2-amino-3-methylbutanoate;

(S)-2-methyl-1-((3-(((aR)-6-(4-oxo-3,4-dihydrophthalazin-1-yl)spiro[3.3]heptan-2-yl)carbamoyl)pyrazolo[1,5-a]pyridin-6-yl)oxy)propan-2-yl2-aminopropanoate;

6-(1-methyl-1H-pyrazol-4-yl)-N-((aR)-6-(4-oxo-3,4-dihydrophthalazin-1-yl)spiro[3.3]heptan-2-yl)benzo[c]isoxazole-3-carboxamide;

6-(2-hydroxy-2-methylpropoxy)-N-((aR)-6-(4-oxo-3,4-dihydrophthalazin-1-yl)spiro[3.3]heptan-2-yl)benzo[c]isoxazole-3-carboxamide;

6-fluoro-7-methyl-N-((aR)-6-(4-oxo-3,4-dihydrophthalazin-1-yl)spiro[3.3]heptan-2-yl)-1H-indole-2-carboxamide;

N-((aR)-6-(4-oxo-3,4-dihydrophthalazin-1-yl)spiro[3.3]heptan-2-yl)-7-(trifluoromethyl)-1H-indole-2-carboxamide;

7-(4-methylpiperazin-1-yl)-N-((aR)-6-(4-oxo-3,4-dihydrophthalazin-1-yl)spiro[3.3]heptan-2-yl)imidazo[1,2-a]pyridine-3-carboxamide);

N-((aR)-6-(4-oxo-3,4-dihydrophthalazin-1-yl)spiro[3.3]heptan-2-yl)-7-phenylimidazo[1,2-a]pyridine-3-carboxamide;

7-(benzyloxy)-N-((aR)-6-(4-oxo-3,4-dihydrophthalazin-1-yl)spiro[3.3]heptan-2-yl)imidazo[1,2-a]pyridine-3-carboxamide;

7-methoxy-N-((aR)-6-(4-oxo-3,4-dihydrophthalazin-1-yl)spiro[3.3]heptan-2-yl)imidazo[1,2-a]pyridine-3-carboxamide;

7-(4,4-difluoropiperidin-1-yl)-N-((aR)-6-(4-oxo-3,4-dihydrophthalazin-1-yl)spiro[3.3]heptan-2-yl)imidazo[1,2-a]pyridine-3-carboxamide;

7-(3,3-difluoropyrrolidin-1-yl)-N-((aR)-6-(4-oxo-3,4-dihydrophthalazin-1-yl)spiro[3.3]heptan-2-yl)imidazo[1,2-a]pyridine-3-carboxamide;

7-((R)-3-fluoropyrrolidin-1-yl)-N-((aR)-6-(4-oxo-3,4-dihydrophthalazin-1-yl)spiro[3.3]heptan-2-yl)imidazo[1,2-a]pyridine-3-carboxamide;

7-((S)-3-fluoropyrrolidin-1-yl)-N-((aR)-6-(4-oxo-3,4-dihydrophthalazin-1-yl)spiro[3.3]heptan-2-yl)imidazo[1,2-a]pyridine-3-carboxamide;

7-((2-methoxyethyl)(methyl)amino)-N-((aR)-6-(4-oxo-3,4-dihydrophthalazin-1-yl)spiro[3.3]heptan-2-yl)imidazo[1,2-a]pyridine-3-carboxamide;

7-(2-morpholinoethoxy)-N-((aR)-6-(4-oxo-3,4-dihydrophthalazin-1-yl)spiro[3.3]heptan-2-yl)imidazo[1,2-a]pyridine-3-carboxamide;

7-(2-hydroxy-2-methylpropoxy)-N-((aR)-6-(4-oxo-3,4-dihydrophthalazin-1-yl)spiro[3.3]heptan-2-yl)imidazo[1,2-a]pyridine-3-carboxamide;

6-fluoro-8-methyl-N-((aR)-6-(4-oxo-3,4-dihydrophthalazin-1-yl)spiro[3.3]heptan-2-yl)imidazo[1,2-a]pyridine-3-carboxamide;

7-(difluoromethoxy)-N-((aR)-6-(4-oxo-3,4-dihydrophthalazin-1-yl)spiro[3.3]heptan-2-yl)imidazo[1,2-a]pyridine-3-carboxamide;

8-(benzyloxy)-N-((aR)-6-(4-oxo-3,4-dihydrophthalazin-1-yl)spiro[3.3]heptan-2-yl)imidazo[1,2-a]pyridine-3-carboxamide;

7-(methylthio)-N-((aR)-6-(4-oxo-3,4-dihydrophthalazin-1-yl)spiro[3.3]heptan-2-yl)imidazo[1,2-a]pyridine-3-carboxamide;

3-methoxy-N-((aR)-6-(4-oxo-3,4-dihydrophthalazin-1-yl)spiro[3.3]heptan-2-yl)-4-(1H-pyrazol-4-yl)benzamide;

3-cyano-N-((aR)-6-(4-oxo-3,4-dihydrophthalazin-1-yl)spiro[3.3]heptan-2-yl)-4-(1H-pyrazol-4-yl)benzamide;

3-methyl-N-((aR)-6-(4-oxo-3,4-dihydrophthalazin-1-yl)spiro[3.3]heptan-2-yl)-4-(1H-pyrazol-4-yl)benzamide;

7-((1,1-dioxidotetrahydro-2H-thiopyran-4-yl)oxy)-N-((aR)-6-(4-oxo-3,4-dihydrophthalazin-1-yl)spiro[3.3]heptan-2-yl)imidazo[1,2-a]pyridine-3-carboxamide;

N-((aR)-6-(4-oxo-3,4-dihydrophthalazin-1-yl)spiro[3.3]
heptan-2-yl)-7-(pyridin-2-yloxy)imidazo[1,2-a]pyridine-3-carboxamide;
7-(2,2-difluoroethoxy)-N-((aR)-6-(4-oxo-3,4-dihydrophthalazin-1-yl)spiro[3.3]heptan-2-yl)imidazo[1,2-a]pyridine-3-carboxamide;
7-(1-ethyl-1H-pyrazol-4-yl)-N-((aR)-6-(4-oxo-3,4-dihydrophthalazin-1-yl)spiro[3.3]heptan-2-yl)imidazo[1,2-a]pyridine-3-carboxamide;
7-(1-methyl-1H-pyrazol-4-yl)-N-((aR)-6-(4-oxo-3,4-dihydrophthalazin-1-yl)spiro[3.3]heptan-2-yl)imidazo[1,2-a]pyridine-3-carboxamide;
7-(1-isopropyl-1H-pyrazol-4-yl)-N-((aR)-6-(4-oxo-3,4-dihydrophthalazin-1-yl)spiro[3.3]heptan-2-yl)imidazo[1,2-a]pyridine-3-carboxamide;
7-(1-(methyl-d3)-1H-pyrazol-4-yl)-N-((aR)-6-(4-oxo-3,4-dihydrophthalazin-1-yl)spiro[3.3]heptan-2-yl)imidazo[1,2-a]pyridine-3-carboxamide;
N-((aR)-6-(4-oxo-3,4-dihydrophthalazin-1-yl)spiro[3.3]
heptan-2-yl)-7-(1-(tetrahydro-2H-pyran-4-yl)-1H-pyrazol-4-yl)imidazo[1,2-a]pyridine-3-carboxamide;
N-((aR)-6-(4-oxo-3,4-dihydrophthalazin-1-yl)spiro[3.3]
heptan-2-yl)-7-(pyridin-3-yl)imidazo[1,2-a]pyridine-3-carboxamide;
N-((aR)-6-(4-oxo-3,4-dihydrophthalazin-1-yl)spiro[3.3]
heptan-2-yl)-7-(pyridin-3-yl)imidazo[1,2-a]pyridine-2-carboxamide;
7-(2-methylthiazol-5-yl)-N-((aR)-6-(4-oxo-3,4-dihydrophthalazin-1-yl)spiro[3.3]heptan-2-yl)imidazo[1,2-a]pyridine-2-carboxamide;
7-(2-methylthiazol-5-yl)-N-((aR)-6-(4-oxo-3,4-dihydrophthalazin-1-yl)spiro[3.3]heptan-2-yl)imidazo[1,2-a]pyridine-3-carboxamide;
4-((aR)-6-(1-oxoisoindolin-2-yl)spiro[3.3]heptan-2-yl)
phthalazin-1(2H)-one;
4-((aR)-6-((S)-4-benzyl-2-oxoimidazolidin-1-yl)spiro[3.3]
heptan-2-yl)phthalazin-1(2H)-one;
4-((aR)-6-((R)-4-benzyl-2-oxoimidazolidin-1-yl)spiro[3.3]
heptan-2-yl)phthalazin-1(2H)-one;
4-((aR)-6-((2-nitrophenyl)amino)spiro[3.3]heptan-2-yl)
phthalazin-1(2H)-one;
4-((aR)-6-(2-oxo-2,3-dihydro-1H-benzo[d]imidazol-1-yl)
spiro[3.3]heptan-2-yl)phthalazin-1(2H)one;
4-cyclopropyl-N-((aR)-6-(4-oxo-3,4-dihydrophthalazin-1-yl)spiro[3.3]heptan-2-yl)pyrazolo[1,5-a]pyridine-3-carboxamide;
3-fluoro-5-(1-methyl-1H-pyrazol-4-yl)-N-((aR)-6-(4-oxo-3,4-dihydrophthalazin-1-yl)spiro[3.3]heptan-2-yl)picolinamide;
6-(4-oxo-3,4-dihydrophthalazin-1-yl)spiro[3.3]heptan-2-ylisoindoline-2-carboxylate;
7-(methylsulfonyl)-N-((aR)-6-(4-oxo-3,4-dihydrophthalazin-1-yl)spiro[3.3]heptan-2-yl)imidazo[1,2-a]pyridine-3-carboxamide; and
2-methyl-2-((3-(((aR)-6-(4-oxo-3,4-dihydrophthalazin-1-yl)spiro[3.3]heptan-2-yl)carbamoyl)pyrazolo[1,5-a]pyridin-6-yl)oxy)propanoic acid.

In another embodiment, the compounds of the present invention have ROCK $IC_{50}$ values ≤10 μM.

In another embodiment, the compounds of the present invention have ROCK $IC_{50}$ values ≤1 μM.

In another embodiment, the compounds of the present invention have ROCK $IC_{50}$ values ≤0.1 μM.

In another embodiment, the compounds of the present invention have ROCK $IC_{50}$ values ≤0.05 μM.

In another embodiment, the compounds of the present invention have ROCK $IC_{50}$ values ≤0.01 μM.

II. Other Embodiments of the Invention

In another embodiment, the present invention provides a composition comprising at least one of the compounds of the present invention or a stereoisomer, a tautomer, a pharmaceutically-acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically-acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically-acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment and/or prophylaxis of a condition associated with aberrant ROCK activity comprising administering to a patient in need of such treatment and/or prophylaxis a therapeutically effective amount of at least one of the compounds of the present invention or a stereoisomer, a tautomer, a pharmaceutically-acceptable salt, or a solvate thereof. As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a or a stereoisomer, a tautomer, a pharmaceutically-acceptable salt, or a solvate thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

As used herein, "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population.

In another embodiment, the present invention provides a combined preparation of a compound of the present invention and additional therapeutic agent(s) for simultaneous, separate or sequential use in therapy.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

II. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluoroethoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

As used herein, the term "bicyclic spiro carbocycle" refers to 5- to 20-membered polycyclic hydrocarbon group with rings connected through one common carbon atom (called as spiro atom), wherein one or more rings may contain one or more double bonds, but none of the rings has a completely conjugated pi-electron system. Preferably a bicyclic spiro carbocycle is 6 to 14 membered, more preferably is 7 to 10 membered. Bicyclic spiro carbocycle may be 4-membered/4-membered, 4-membered/5-membered, 4-membered/6-membered, 5-membered/5-membered, or 5-membered/6-membered spiro ring.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., Hawley's Condensed Chemical Dictionary, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically-acceptable salts" refer to derivatives of the disclosed compounds wherein the parent compound is modified by making acid or base salts thereof. Examples of pharmaceutically-acceptable salts include, but are not limited to, mineral or organic acid salts of basic groups such as amines; and alkali or organic salts of acidic groups such as carboxylic acids. The pharmaceutically-acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically-acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs,* Elsevier (1985), and Widder, K. et al., eds., *Methods in Enzymology,* 112:309-396, Academic Press (1985);
b) Bundgaard, H., Chapter 5, "Design and Application of Prodrugs", *A Textbook of Drug Design and Development,* pp. 113-191, Krosgaard-Larsen, P. et al., eds., Harwood Academic Publishers (1991);
c) Bundgaard, H., *Adv. Drug Deliv. Rev.,* 8:1-38 (1992);
d) Bundgaard, H. et al., *J. Pharm. Sci.,* 77:285 (1988); and
e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice,* The Royal Society of Chemistry, Cambridge, UK (1994); Testa, B. et al., *Hydrolysis in Drug and Prodrug Metabolism. Chemistry, Biochemistry and Enzymology,* VCHA and Wiley-VCH, Zurich, Switzerland (2003); Wermuth, C. G., ed., *The Practice of Medicinal Chemistry,* Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain an N-halo, S(O)$_2$H, or S(O)H group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "saturated" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.
Me Methyl
Et Ethyl
Pr Propyl
i-Pr Isopropyl
Bu Butyl
i-Bu Isobutyl
t-Bu tert-butyl
Ph Phenyl
Bn Benzyl
Boc tert-butyloxycarbonyl
AcOH or HOAc acetic acid
$AlCl_3$ aluminum chloride
AIBN Azobisisobutyronitrile
$BBr_3$ boron tribromide
$BCl_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonylmethanimidate
CBz Carbobenzyloxy
$CH_2Cl_2$ Dichloromethane
$CH_3CN$ or ACN Acetonitrile
$CDCl_3$ deutero-chloroform
$CHCl_3$ Chloroform
mCPBA or m-CPBA meta-chloroperbenzoic acid
$Cs_2CO_3$ cesium carbonate
$Cu(OAc)_2$ copper (II) acetate
$Cy_2NMe$ N-cyclohexyl-N-methylcyclohexanamine
DBU 1,8-diazabicyclo[5.4.0]undec-7-ene
DCE 1,2 dichloroethane
DCM dichloromethane
DEA diethylamine
Dess-Martin 1,1,1-tris(acetyloxy)-1,1-dihydro-1,2-beniziodoxol-3-(1H)-one
DIC or DIPCDI diisopropylcarbodiimide
DIEA, DIPEA or diisopropylethylamine Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylphospholano)benzene EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
$Et_3N$ or TEA triethylamine
EtOAc ethyl acetate
$Et_2O$ diethyl ether
EtOH Ethanol
GMF glass microfiber filter
Grubbs (II) (1,3-bis(2,4,6-trimethylphenyl)-2-imidazolidinylidene)dichloro(phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex Hexane
HOBt or HOBT 1-hydroxybenzotriazole
$H_2SO_4$ sulfuric acid
$K_2CO_3$ potassium carbonate
KOAc potassium acetate
$K_3PO_4$ potassium phosphate
LAH lithium aluminum hydride
LG leaving group
LiOH lithium hydroxide
MeOH Methanol
$MgSO_4$ magnesium sulfate
MsOH or MSA methylsulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
NBS N-bromosuccinimide
NCS N-chlorosuccinimide
$NH_3$ Ammonia
$NH_4Cl$ ammonium chloride
$NH_4OH$ ammonium hydroxide
OTf triflate or trifluoromethanesulfonate
$Pd_2(dba)_3$ tris(dibenzylideneacetone)dipalladium(0)
$Pd(OAc)_2$ palladium(II) acetate
Pd/C palladium on carbon
$Pd(dppf)Cl_2$ [1,1'-bis(diphenylphosphino)-ferrocene]dichloropalladium(II) $Ph_3PCl_2$ triphenylphosphine dichloride
PG protecting group
$POCl_3$ phosphorus oxychloride
i-PrOH or IPA isopropanol
PS polystyrene
SEM-Cl 2-(trimethysilyl)ethoxymethyl chloride
$SiO_2$ silica oxide
$SnCl_2$ tin(II) chloride
TBAI tetra-n-butylammonium iodide
TEA triethylamine
TFA trifluoroacetic acid
THF tetrahydrofuran
$TMSCHN_2$ trimethylsilyldiazomethane
T3P® propane phosphonic acid anhydride TRIS tris (hydroxymethyl) aminomethane The compounds of the present invention can be prepared in a number of ways known to one skilled in the art of organic synthesis.

IV. Biology

In Vitro Assays

The effectiveness of compounds of the present invention as ROCK inhibitors can be determined in a 30 μL assay containing 20 mM HEPES, pH 7.5, 20 mM $MgCl_2$, 0.015% Brij-35, 4 mM DTT, 5 μM ATP and 1.5 μM peptide substrate (FITC-AHA-AKRRRLSSLRA-OH). Compounds were dissolved in DMSO so that the final concentration of DMSO was <2%, and the reaction was initiated with Rho kinase variants. After incubation, the reaction was terminated by the addition of EDTA and the phosphorylated and non-phosphorylated peptides separated using a LABCHIP® 3000 Reader (Caliper Life Sciences). Controls consisted of assays that did not contain compound, and backgrounds consisted of assays that contained enzyme and substrate but had EDTA from the beginning of the reaction to inhibit kinase activity. Compounds were tested in dose-response format, and the inhibition of kinase activity was calculated at each concentration of compound. The inhibition data were fit using a curve-fitting program to determine the $IC_{50}$; i.e., the concentration of compound required to inhibit 50% of kinase activity.

Representative Examples were tested in the ROCK assay described above and found having ROCK inhibitory activity. Their ROCK inhibitory activity ($IC_{50}$ values) of ≤3 μM (3000 nM) was observed and shown in Table A below. The ranges of the ROCK $IC_{50}$ values are as follows: +(100.1-2100 nM)++(15.1-100 nM)+++(5.1-15 nM)++++(2.01-5 nM)+++++(0.2-2 nM)

TABLE A

| Example No. | ROCK2 Activity |
|---|---|
| 1 | + |
| 2 | + |
| 3 | + |
| 4 | + |
| 5 | ++++ |
| 6 | + |
| 7 | +++ |
| 8 | ++ |
| 9 | ++ |
| 10 | + |
| 11 | ++ |
| 12 | ++ |
| 13 | ++++ |
| 14 | ++++ |
| 15 | +++ |
| 16 | ++++ |
| 17 | + |
| 18 | + |
| 19 | + |
| 20 | +++++ |
| 21 | ++++ |
| 22 | +++ |
| 23 | +++ |
| 24 | ++++ |
| 25 | +++ |
| 26 | ++++ |
| 27 | +++ |
| 28 | ++ |
| 29 | +++ |
| 30 | ++ |
| 31 | ++++ |
| 32 | ++++ |
| 33 | +++++ |
| 34 | ++ |
| 35 | +++ |
| 36 | ++++ |
| 37 | +++ |
| 38 | +++ |
| 39 | +++ |
| 40 | ++++ |
| 41 | ++++ |
| 42 | ++ |
| 43 | +++ |
| 44 | + |
| 45 | +++ |
| 46 | + |
| 47 | + |
| 48 | + |
| 49 | + |
| 50 | +++ |
| 51 | +++ |
| 52 | ++ |
| 53 | ++++ |
| 54 | +++++ |
| 55 | +++ |
| 56 | +++ |
| 57 | +++ |
| 58 | ++++ |
| 59 | +++ |
| 60 | ++ |
| 61 | ++++ |
| 62 | +++++ |
| 63 | +++++ |
| 64 | +++ |
| 65 | ++++ |
| 66 | +++ |
| 67 | ++++ |
| 68 | ++++ |
| 69 | ++++ |
| 70 | ++++ |
| 71 | +++ |
| 72 | +++++ |
| 73 | ++++ |
| 74 | ++++ |
| 75 | ++ |
| 76 | ++++ |
| 77 | ++ |
| 78 | +++ |
| 79 | ++++ |
| 80 | +++++ |
| 81 | +++++ |
| 82 | ++++ |
| 83 | +++++ |
| 84 | +++ |
| 85 | ++++ |
| 86 | +++++ |
| 87 | +++++ |
| 88 | +++++ |
| 89 | +++++ |
| 90 | +++++ |
| 91 | +++++ |
| 92 | +++++ |
| 93 | ++++ |
| 94 | +++ |
| 95 | +++ |
| 96 | ++ |
| 97 | +++++ |
| 98 | ++++ |
| 99 | +++++ |
| 100 | + |
| 101 | ++ |
| 102 | +++ |
| 103 | ++ |
| 104 | + |
| 105 | +++++ |
| 106 | + |
| 107 | +++++ |
| 108 | ++++ |
| 109 | ++++ |
| 110 | ++ |
| 111 | ++ |
| 112 | ++++ |
| 113 | ++++ |
| 114 | ++++ |
| 115 | ++++ |
| 116 | ++++ |

TABLE A-continued

| Example No. | ROCK2 Activity |
|---|---|
| 117 | ++ |
| 118 | ++ |
| 119 | +++++ |
| 120 | +++++ |
| 121 | +++++ |
| 122 | +++++ |
| 123 | ++++ |
| 124 | ++ |
| 125 | ++++ |
| 126 | +++++ |
| 127 | +++++ |
| 128 | ++++ |
| 129 | +++ |
| 130 | +++ |
| 131 | +++++ |
| 132 | +++++ |
| 133 | +++++ |
| 134 | +++++ |
| 135 | +++++ |
| 136 | ++++ |
| 137 | ++++ |
| 138 | +++++ |
| 139 | +++++ |
| 140 | +++++ |
| 141 | +++ |
| 142 | ++++ |
| 143 | ++++ |
| 144 | +++ |
| 145 | ++++ |
| 146 | ++++ |
| 147 | ++++ |
| 148 | +++ |
| 149 | +++ |
| 150 | ++++ |
| 151 | +++ |
| 152 | ++++ |
| 153 | ++++ |
| 154 | ++++ |
| 155 | ++++ |
| 156 | +++ |
| 157 | +++++ |
| 158 | ++++ |
| 159 | ++++ |
| 160 | +++++ |
| 161 | +++ |
| 162 | ++ |
| 163 | ++ |
| 164 | ++ |
| 165 | +++ |
| 166 | +++++ |
| 167 | +++++ |
| 168 | ++ |
| 169 | +++ |
| 170 | +++++ |
| 171 | ++++ |
| 172 | ++++ |
| 173 | +++++ |
| 174 | +++++ |
| 175 | ++ |
| 176 | +++ |
| 177 | +++++ |
| 178 | ++++ |
| 179 | +++++ |
| 180 | ++ |
| 181 | +++++ |
| 182 | ++++ |
| 183 | ++++ |
| 184 | +++++ |
| 185 | +++++ |
| 186 | ++++ |
| 187 | +++++ |
| 188 | +++++ |
| 189 | +++++ |
| 190 | +++++ |
| 191 | ++++ |
| 192 | ++++ |
| 193 | +++ |
| 194 | +++ |

TABLE A-continued

| Example No. | ROCK2 Activity |
|---|---|
| 195 | +++ |
| 196 | ++++ |
| 197 | +++++ |
| 198 | +++++ |
| 199 | ++++ |
| 200 | +++ |
| 201 | ++++ |
| 202 | +++ |
| 203 | +++ |
| 204 | +++++ |
| 205 | ++++ |
| 206 | +++++ |
| 207 | ++++ |
| 208 | ++++ |
| 209 | +++ |
| 210 | ++++ |
| 211 | ++++ |
| 212 | +++++ |
| 213 | +++ |
| 214 | ++++ |
| 215 | +++ |
| 216 | +++++ |
| 217 | +++++ |
| 218 | +++++ |
| 219 | +++++ |
| 220 | +++++ |
| 221 | +++++ |
| 222 | +++++ |
| 223 | +++++ |
| 224 | +++++ |
| 225 | +++++ |
| 226 | +++++ |
| 227 | ++ |
| 228 | +++ |
| 229 | +++ |
| 230 | ++ |
| 231 | ++ |
| 232 | +++ |
| 233 | +++ |
| 234 | ++++ |
| 235 | +++++ |
| 236 | +++++ |
| 237 | ++++ |
| 238 | ++++ |
| 239 | +++++ |
| 240 | ++++ |
| 241 | ++++ |
| 242 | ++++ |
| 243 | ++++ |
| 244 | +++ |
| 245 | +++ |
| 246 | ++++ |
| 247 | ++++ |
| 248 | +++ |
| 249 | +++ |
| 250 | +++ |
| 251 | +++ |
| 252 | +++ |
| 253 | +++ |
| 255 | +++ |
| 256 | ++ |
| 257 | ++ |
| 258 | +++ |
| 259 | +++ |
| 260 | +++ |
| 261 | ++ |
| 262 | + |
| 263 | +++ |
| 264 | ++ |
| 265 | + |
| 266 | + |
| 267 | + |
| 268 | +++++ |
| 269 | +++++ |
| 270 | +++++ |
| 271 | ++++ |
| 272 | +++ |
| 273 | |

TABLE A-continued

| Example No. | ROCK2 Activity |
|---|---|
| 274 | +++ |
| 275 | +++ |
| 276 | ++ |
| 277 | +++++ |
| 278 | +++ |
| 279 | ++++ |
| 280 | +++ |
| 281 | +++ |
| 282 | + |
| 283 | + |
| 284 | ++++ |
| 285 | ++ |
| 286 | ++ |
| 287 | +++++ |
| 288 | ++ |
| 289 | ++ |
| 290 | ++++ |
| 291 | +++ |
| 292 | ++ |
| 293 | ++ |
| 294 | +++ |
| 295 | +++ |
| 296 | + |
| 297 | ++++ |
| 298 | +++ |
| 299 | ++ |
| 300 | +++ |
| 301 | ++++ |
| 302 | +++++ |
| 303 | +++ |
| 304 | ++ |
| 305 | ++ |
| 306 | +++ |
| 307 | +++ |
| 308 | +++ |
| 309 | ++ |
| 310 | ++ |
| 311 | +++ |
| 312 | +++ |
| 313 | +++ |
| 314 | +++ |
| 315 | ++ |
| 316 | +++ |
| 317 | +++ |
| 318 | +++ |
| 319 | ++ |
| 320 | +++ |
| 321 | + |
| 322 | ++++ |
| 323 | + |
| 325 | +++ |
| 326 | ++++ |
| 327 | ++++ |
| 328 | ++++ |
| 329 | +++++ |
| 330 | ++ |
| 331 | +++ |
| 332 | +++++ |
| 333 | +++ |
| 334 | +++ |
| 335 | ++++ |
| 336 | ++ |
| 337 | +++ |
| 338 | ++ |
| 339 | ++ |
| 340 | +++ |
| 341 | ++ |
| 342 | + |
| 343 | ++ |
| 344 | + |
| 345 | + |
| 346 | ++ |
| 347 | + |
| 348 | ++ |
| 349 | +++ |
| 350 | ++++ |
| 351 | + |
| 352 | ++ |
| 353 | +++ |
| 354 | +++ |
| 355 | ++ |
| 356 | ++ |
| 357 | ++ |
| 358 | ++ |
| 359 | + |
| 360 | ++ |
| 361 | +++ |
| 362 | ++ |
| 363 | ++ |
| 364 | +++ |
| 365 | ++ |
| 366 | +++ |
| 367 | +++ |
| 368 | +++ |
| 369 | ++ |
| 370 | +++ |
| 371 | ++ |
| 372 | ++ |
| 373 | ++ |
| 374 | ++ |
| 375 | ++ |
| 377 | ++ |
| 378 | +++++ |
| 379 | +++ |
| 380 | +++ |
| 381 | ++++ |
| 382 | ++++ |
| 383 | +++++ |
| 384 | +++++ |
| 385 | +++++ |
| 386 | ++++ |
| 387 | ++++ |
| 388 | ++++ |
| 389 | +++ |
| 390 | +++ |
| 391 | +++++ |
| 392 | +++++ |
| 393 | +++++ |
| 394 | +++++ |
| 395 | ++++ |
| 396 | ++++ |
| 397 | +++++ |
| 398 | +++++ |
| 399 | ++++ |
| 400 | +++++ |
| 401 | ++++ |
| 402 | + |
| 403 | ++++ |
| 404 | ++ |
| 405 | +++++ |
| 406 | +++++ |
| 407 | ++ |
| 408 | ++++ |
| 409 | ++++ |
| 410 | ++++ |
| 411 | +++ |
| 412 | ++++ |
| 413 | +++++ |
| 414 | +++++ |
| 415 | + |
| 416 | +++++ |
| 417 | +++++ |
| 418 | +++++ |
| 419 | ++++ |
| 420 | +++ |
| 421 | ++ |
| 422 | ++++ |
| 423 | ++++ |
| 425 | +++ |
| 426 | +++++ |
| 427 | +++ |
| 428 | +++ |
| 429 | ++ |
| 430 | +++ |
| 431 | +++++ |
| 432 | ++++ |

TABLE A-continued

| Example No. | ROCK2 Activity |
|---|---|
| 433 | ++++ |
| 434 | +++++ |
| 435 | +++ |
| 436 | +++++ |
| 437 | ++++ |
| 438 | + |
| 439 | +++++ |
| 440 | +++++ |
| 441 | +++++ |
| 442 | +++++ |
| 443 | +++++ |
| 444 | ++++ |
| 445 | ++ |
| 446 | ++++ |
| 447 | ++++ |
| 448 | ++++ |
| 449 | +++ |
| 450 | ++ |
| 451 | +++ |
| 452 | +++++ |
| 453 | ++ |
| 454 | ++ |
| 455 | ++++ |
| 457 | ++ |
| 458 | + |
| 459 | + |
| 460 | ++ |
| 461 | + |
| 462 | ++ |
| 463 | ++ |
| 464 | + |
| 465 | +++ |
| 467 | ++ |
| 468 | + |
| 469 | ++ |
| 470 | +++++ |
| 471 | ++++ |

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the patient to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the inhibition of ROCK. Such compounds may be provided in a commercial kit, for example, for use in pharmaceutical research involving ROCK. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically-acceptable salt form thereof; and, (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al., (*Protective Groups in Organic Synthesis*, 4th Edition, Wiley-Interscience (2006)).

Scheme 1

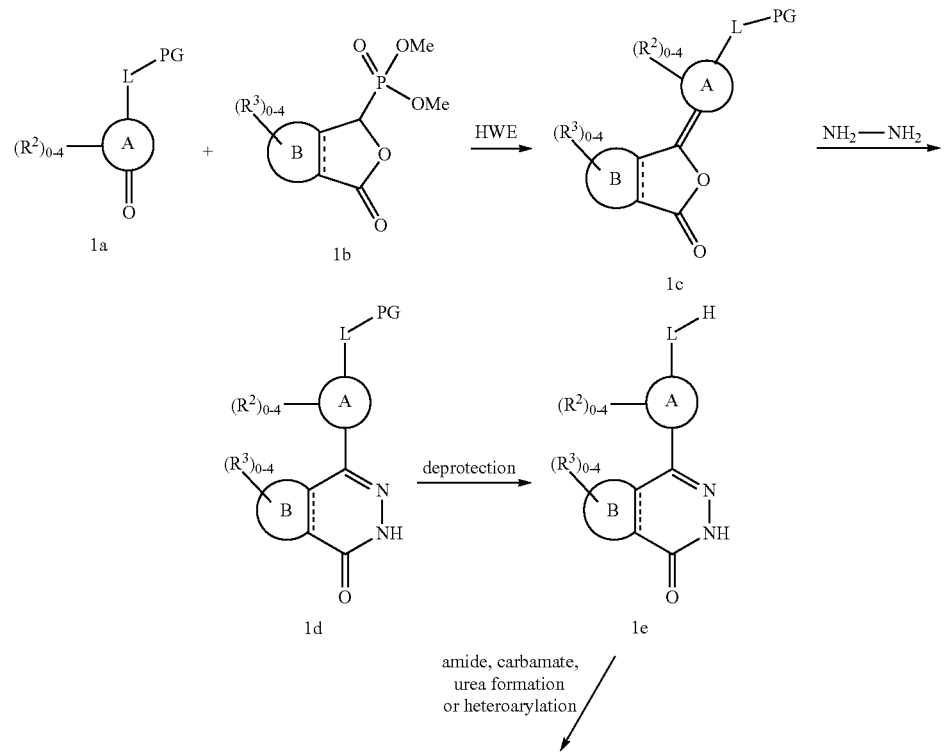

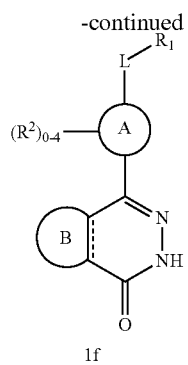

1f

Scheme 1 shows the synthesis of the generic compound if from the common intermediate 1e via functionalization of the top linker portion L-H. The functionalization of intermediate 1e includes, but is not limited to amide, carbamate and urea formations. Horner-Wadsworth-Emmons reaction between commercially available (or prepared via known literature procedures) bicyclic ketone 1a and commercially available (or prepared via known literature procedures) phosphonate 1b under treatment with bases such as, but not limited to, $Cs_2CO_3$, KOtBu and LiHMDS, and in solvents such as iPrOH, tBuOH and THF gives rise to the alkene 1c. The alkene 1c is treated with hydrazine or hydrazine hydrate in solvents, such as dioxane and THF, to afford the protected intermediate 1d. Cleavage of the protecting group, such as using TFA or HCl in dioxane when PG=Boc, affords the free linker intermediate 1e. Intermediate 1e is converted to the target if by treatment with a functionalizing reagents including, but not limited to an acid chloride, an isocyanate or a carbamic chloride, in the presence of a base such as pyridine or DIEA. In addition, intermediate 1e is derivatized with heteroaryl halide in the presence of a base such as pyridine or DIEA and an optional catalysts such as Cu(I), Cu(II), Pd(0) and Pd(II) compounds, and an appropriate ligand such as L-proline, XantPhos and SPhos. Alternatively, target if is prepared by coupling of intermediate 1e with a carboxylic acid in the presence of a coupling reagent, such as HATU or BOP, and a base such as DIEA. Alternatively, when L-PG is an alkyl ester, removal of the protecting group via saponification, such as using LiOH in aqueous MeOH, affords a free carboxylic acid intermediate 1e. Intermediate 1e can then be converted to the target if by coupling with an appropriate amine using a coupling agent such as HATU or BOP or via heterocycle formation.

Scheme 2

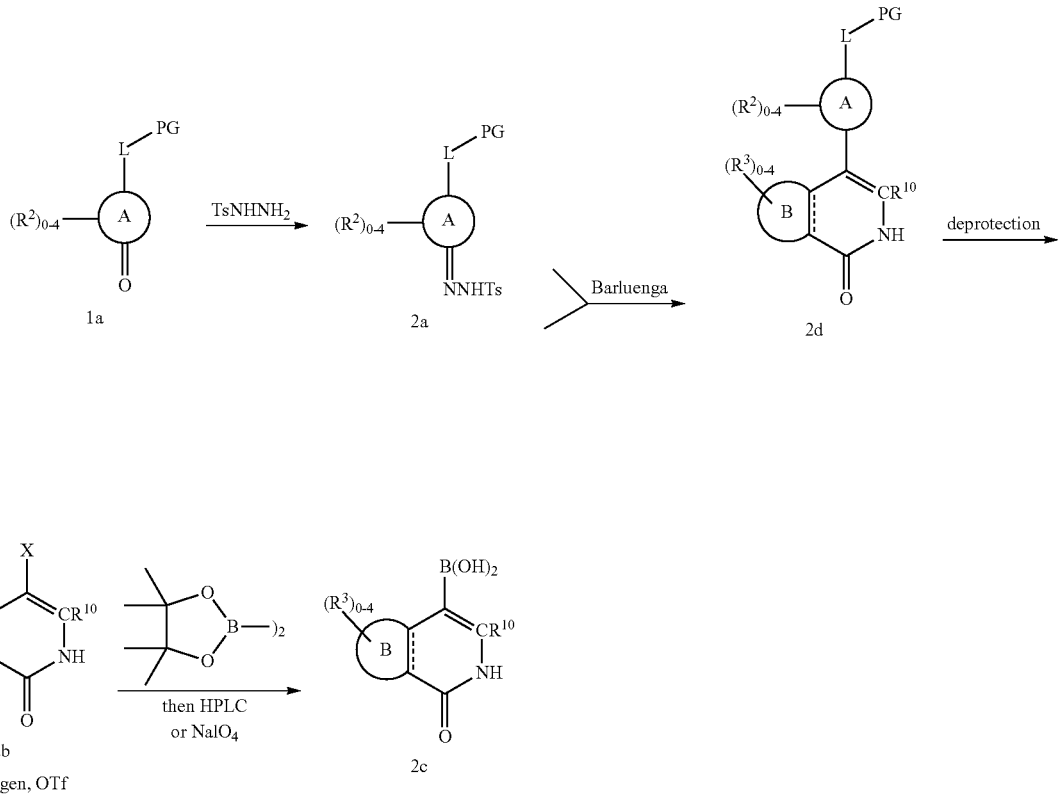

-continued

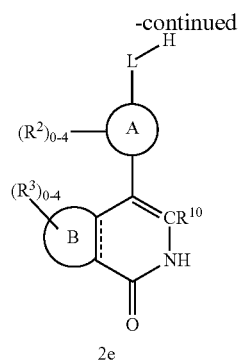

2e amide, carbamate,
urea formation
or heteroarylation

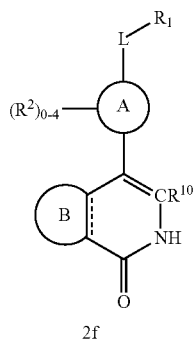

2f

Scheme 2 depicts the synthesis of the generic compound 2f, beginning from bicyclic ketone 1a (either commercially available or prepared by literature methods). The conversion of the ketone 1a to the respective tosylhydrazone 2a is achieved by treatment with tosylhydrazine. Intermediate 2a is then coupled via Barluenga reaction (*Nature Chem.* 2009, 1, 494) with boronic acid 2c, prepared via Suzuki-Miyaura borylation of commercially available (or prepared by literature methods) heterocyclic scaffold 2b. Removal of the protecting group, such as using LiOH in aqueous MeOH when L-PG is an alkyl ester or by treatment with TFA or HCl when L-PG=N-Boc, affords the free linker intermediate 2e. Intermediate 2e is then converted to the target 2f by means described in Scheme 1.

Scheme 3

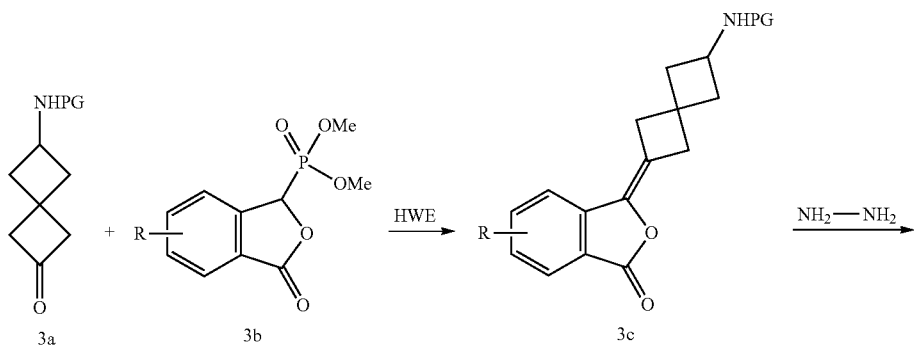

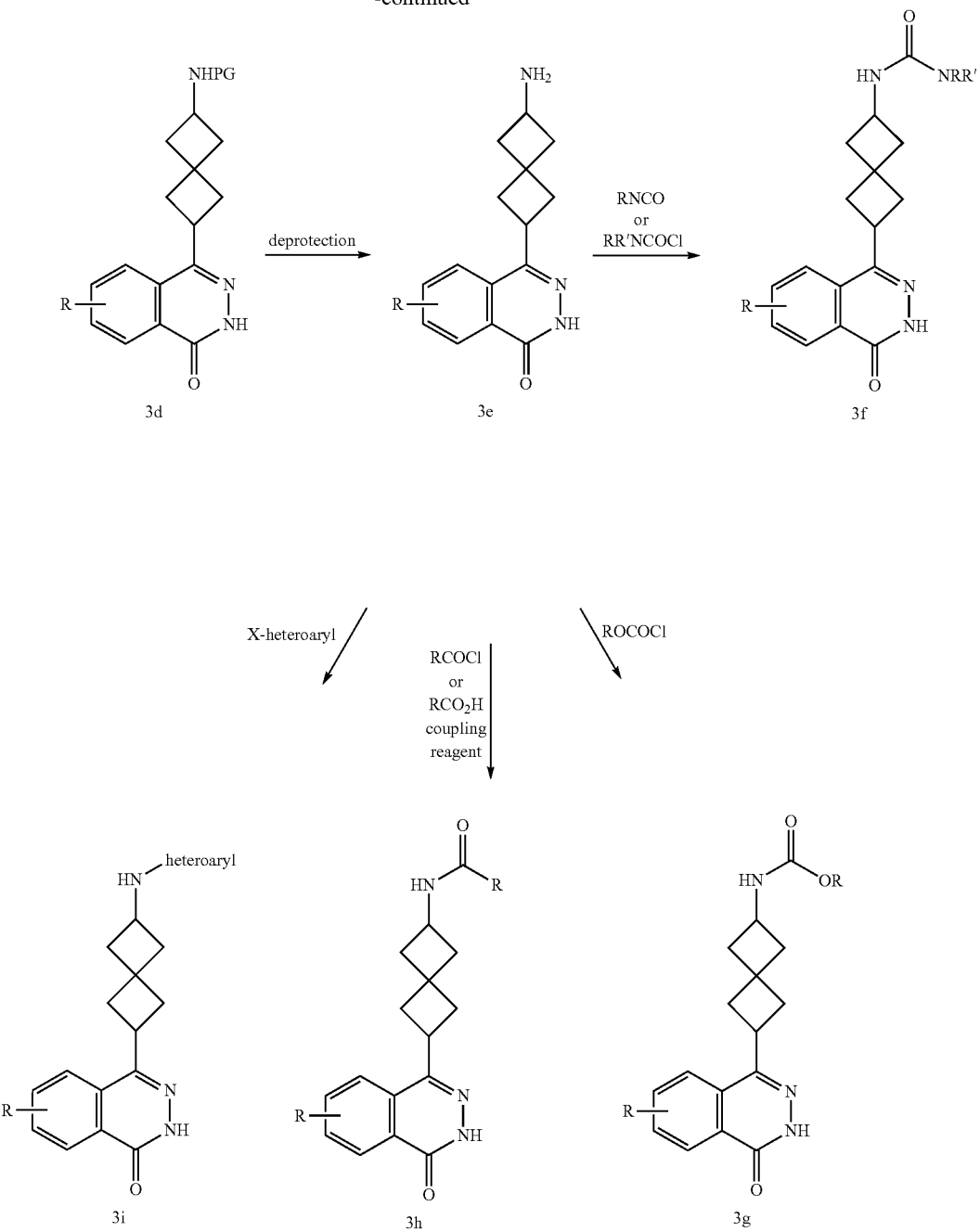

Scheme 3 shows a synthesis of phthalazinone targets 3f-i, beginning from spiro[3,3]heptane intermediate 3a, which is either commercially available or can be prepared by literature methods. As outlined in Scheme 1, Horner-Wadsworth-Emmons reaction with commercially available (or prepared according to known literature procedure) phosphonate 3b, and subsequent treatment of the respective alkene 3c with hydrazine or hydrazine hydrate affords protected intermediate 3d. An appropriate deprotection method yields common intermediate 3e. Intermediate 3e is converted to the urea target 3f by treatment with an isocyanate, carbamic chloride or 4-nitrophenyl carbamate. Intermediate 3e is converted to the carbamate target 3g by treatment with a chloroformate in the presence of a base such as DIEA or TEA. Intermediate 3e is converted to the amide target 3h by treatment with an acid chloride in the presence of a base such as pyridine or DIEA. Alternatively, target 3h is prepared by coupling of intermediate 3e with a carboxylic acid in the presence of a coupling reagent, such as HATU or BOP, and a base such as DIEA. Intermediate 3e is coupled with heteroaryl halide under thermal $S_NAr$ conditions in the presence of a base such as DIEA in a solvent such as DMF or NMP to afford 3i. Alternatively, 3e and heteroaryl halide may be coupled under Buchwald-Hartwig N-arylation conditions using a base such as $Cs_2CO_3$, a catalyst such as $Pd_2(dba)_3$ and an appropriate ligand to afford 3i.

Scheme 4

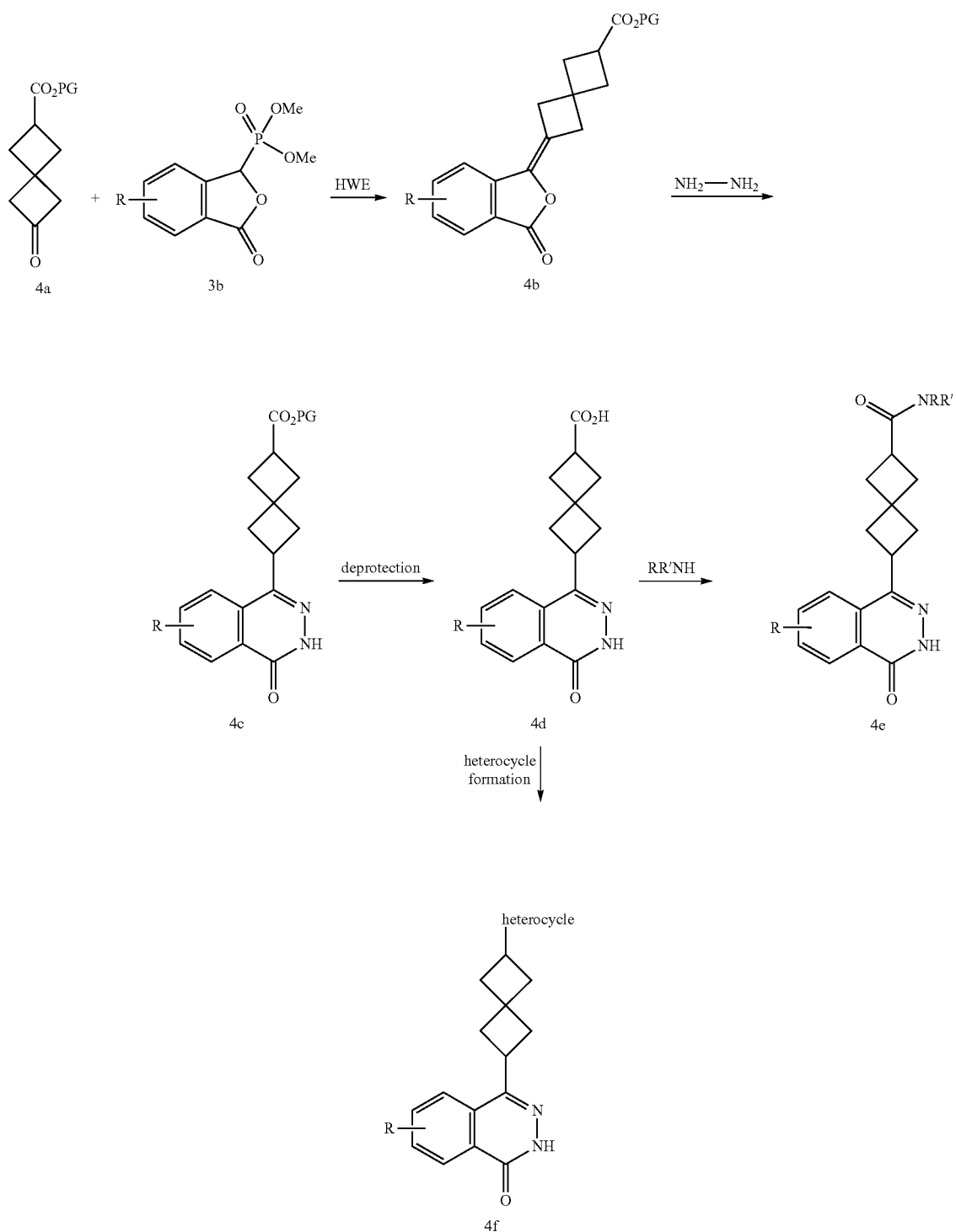

Scheme 4 shows a synthesis of phthalazinone targets 4e-f, beginning from spiro[3,3]heptane intermediate 4a, which is either commercially available or can be prepared by literature methods. Analogously to the previously described sequence in Scheme 3, common intermediate 4d is obtained. After activation with an appropriate reagent such as HATU, BOP or oxalyl chloride, the subsequent coupling with an amine gives rise to amides 4e. Alternatively, intermediate 4d may be converted to heterocyclic analog 4f, which include, but not limited to oxazoles, isoxazoles, imidazoles, triazoles, tetrazoles and oxadiazoles. For instance, conversion of acid 4d to the respective hydrazide, and subsequent treatment with an acid chloride, and T3P® to affect ring closure may lead to the oxadiazole 4f derivatives.

Scheme 5
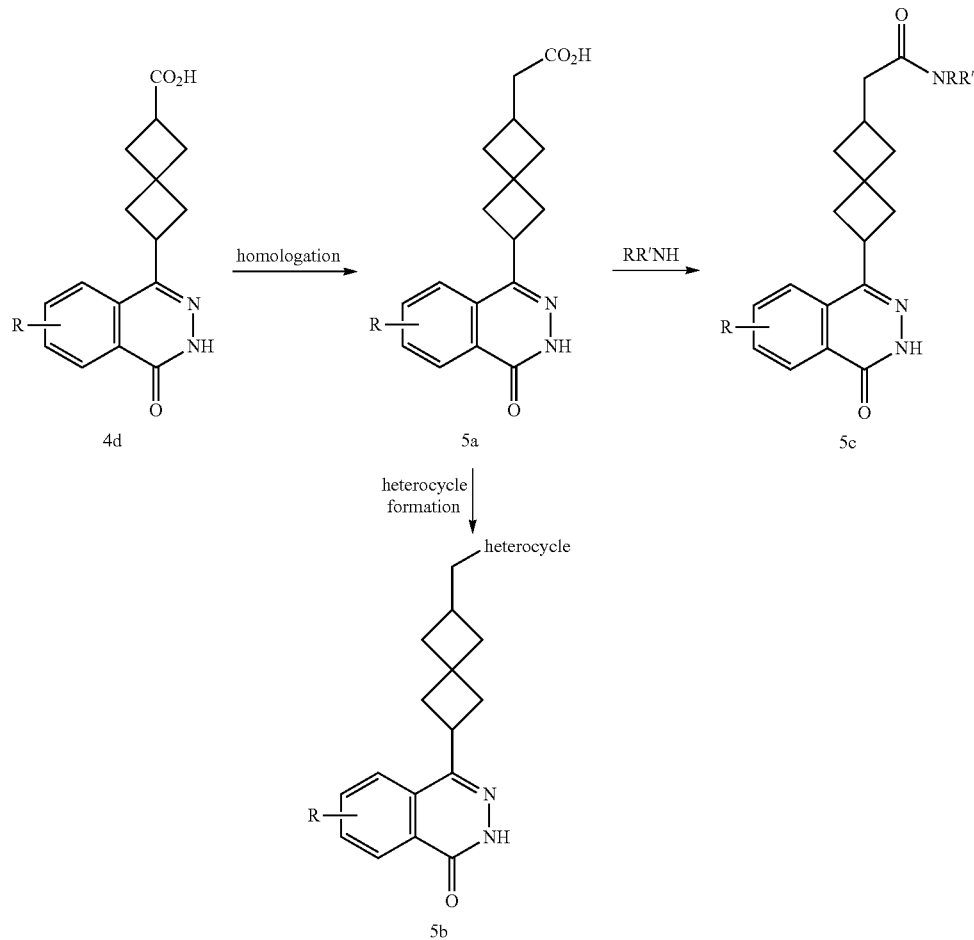
Scheme 5 starts with an acid intermediate 4d, which is subjected to a homologation protocol, which may include, but not limited to Arndt-Eistert homologation or the reduction/trichloromethylation/NaBH$_4$ sequence as described in *Org. Lett.* 2008, 10, 3853. The homologated precursor 5a is then converted to the target amides 5c or heterocycles 5b as described in Scheme 4.

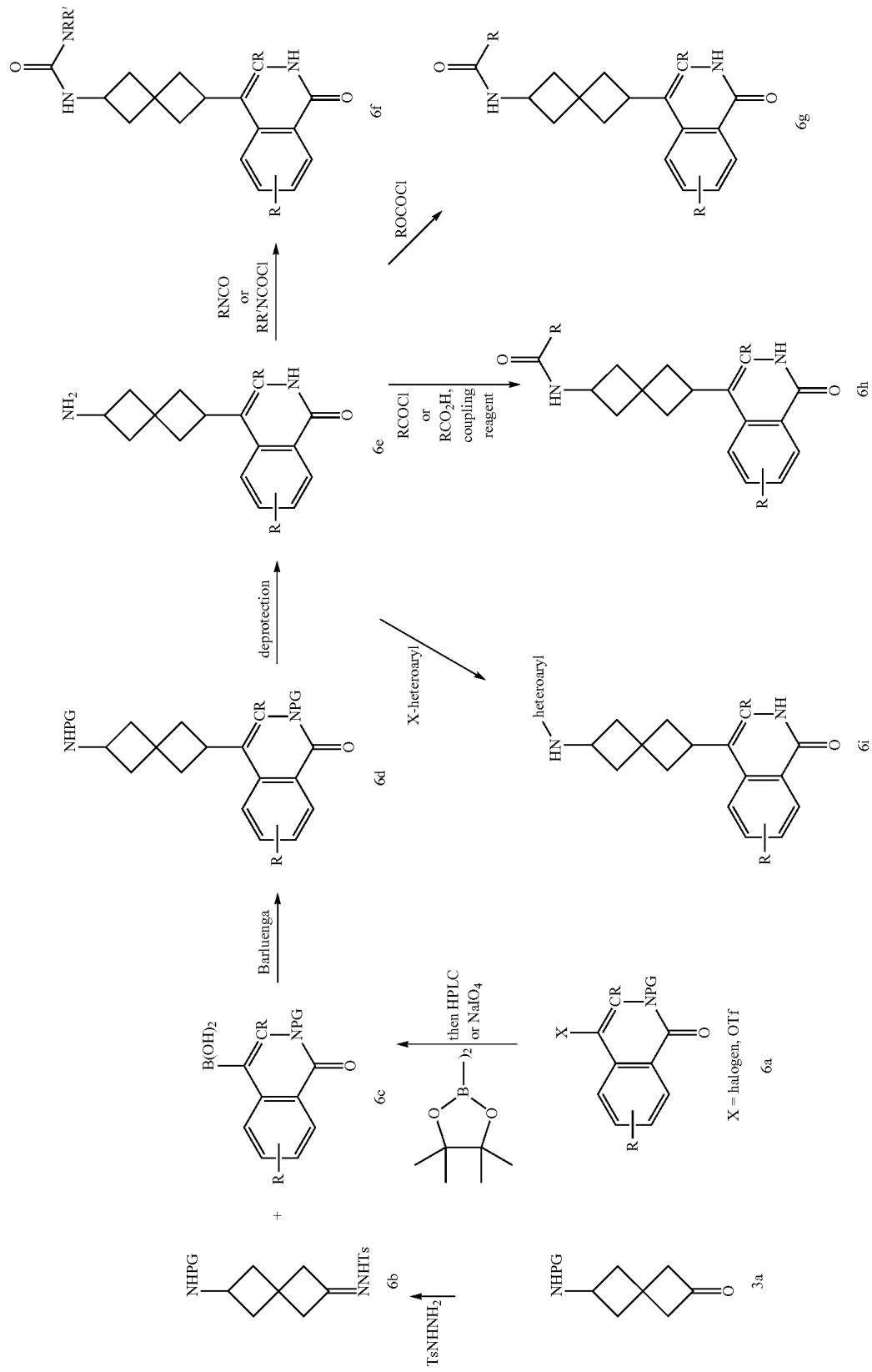

Scheme 6 reveals the preparation of isoquinolinone targets 6f-i, beginning from spiro[3,3]heptane intermediate 3a, which is either commercially available or can be prepared by literature methods. As outlined in Scheme 2, after preparation of the respective tosylhydrazone 6b and boronic acid 6c according to known procedures, and subsequent Barluenga coupling (*Nature Chem.* 2009, 1, 494) allows for the preparation of protected intermediate 6d. An appropriate deprotection method, which may include but not limited to treatment with TFA or HCl in dioxane when PG=Boc, gives rise to the common intermediate 6e. Intermediate 6e is then converted to the targets 6f-i using the approaches outlined in Scheme 3.

Scheme 7 shows a synthesis of isoquinolinone targets 4e-f, beginning from spiro[3,3]heptane intermediate 4a, which is either commercially available or can be prepared by literature methods. Analogously to the previously described sequence in Scheme 6, common intermediate 7c is obtained. After activation with an appropriate reagent such as HATU, BOP or oxalyl chloride, the subsequent coupling with an amine provides access to amides 7d. Alternatively, intermediate 7c may be converted to the heterocyclic analog 4e as described in Scheme 4.

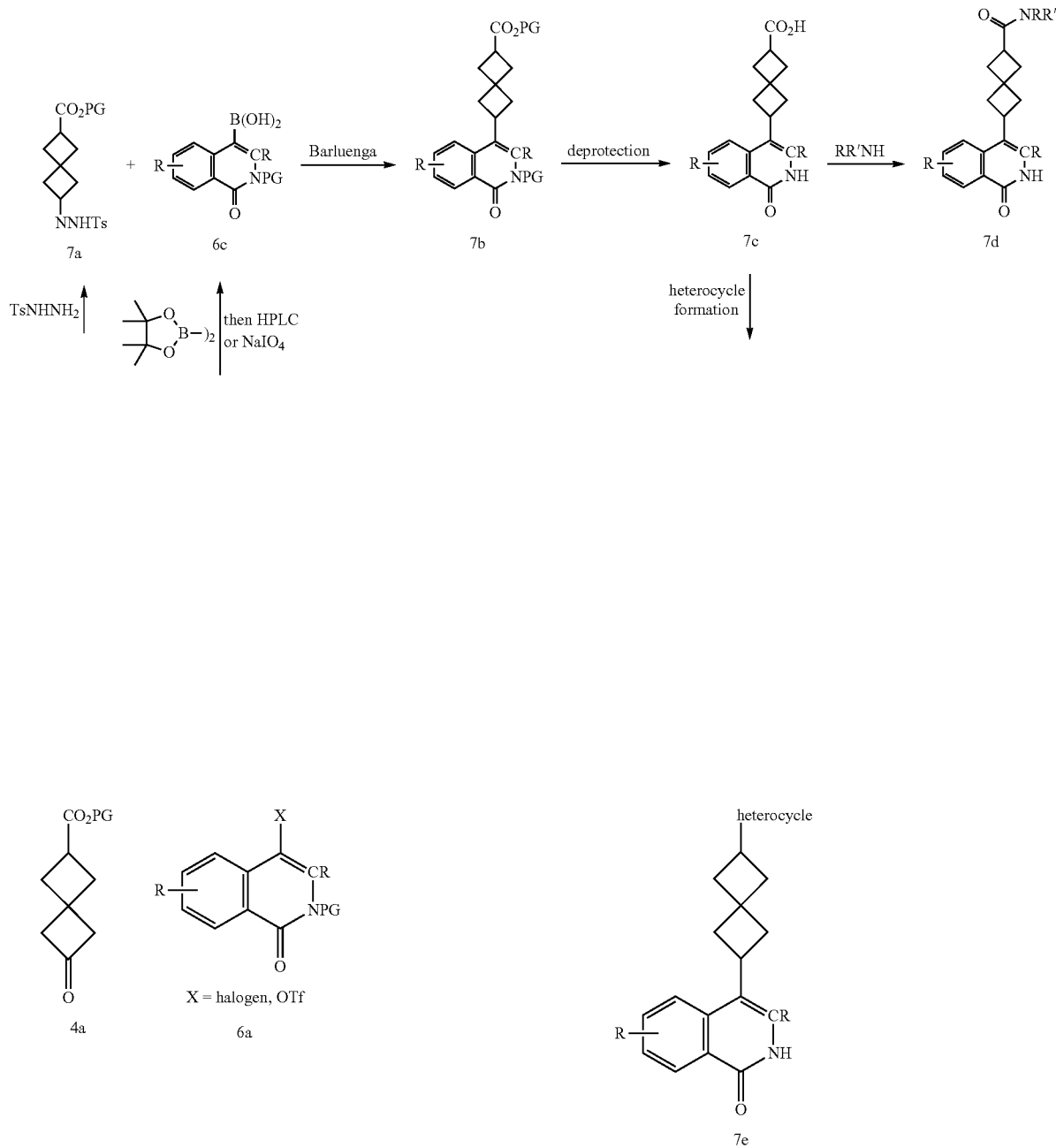

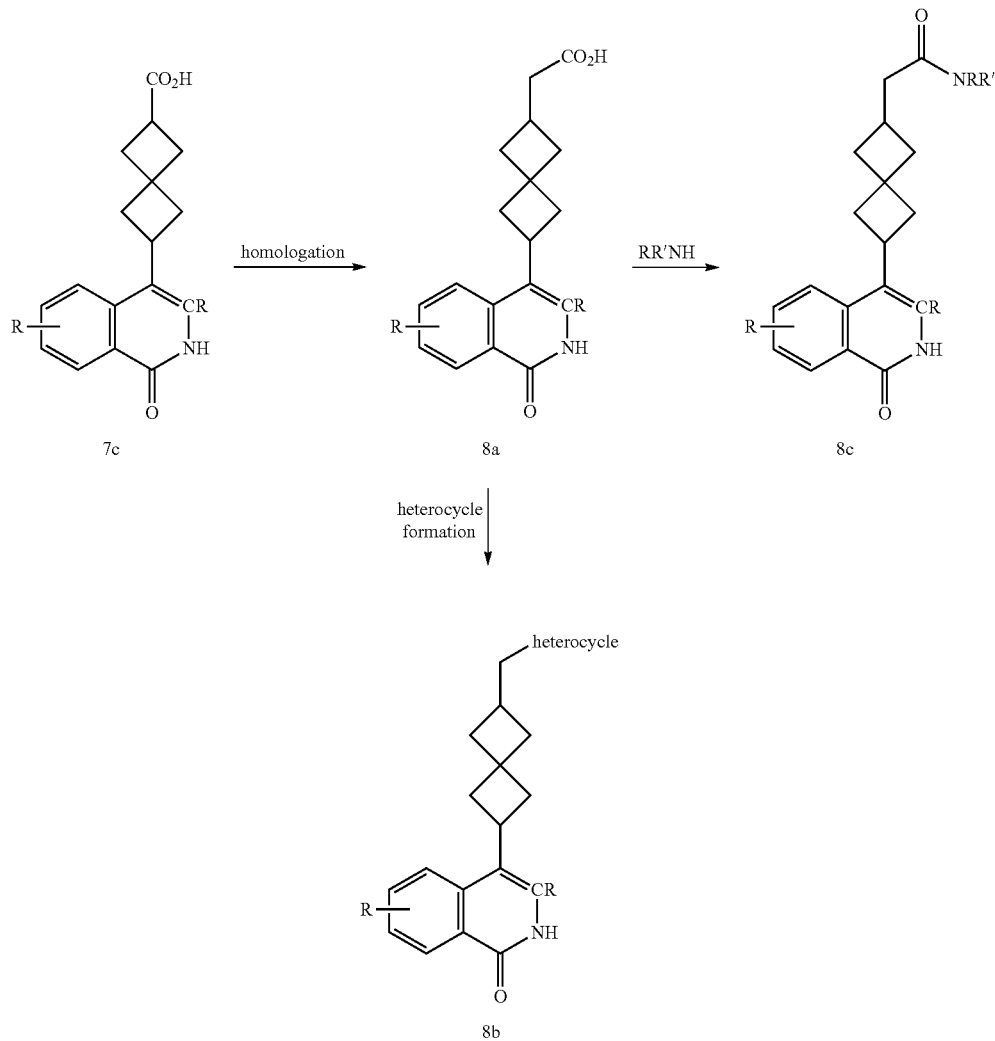
Scheme 8 begins with an acid intermediate 7c, which is subjected to a homologation protocol as described in Scheme 5. The homologated precursor 8a is then converted to the target amides 8c or heterocycles 8b as described in Scheme 4.
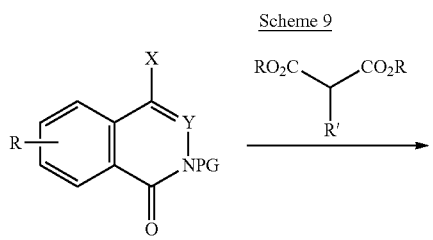
Scheme 9
X = halogen, OTf
Y = N, CR
9a
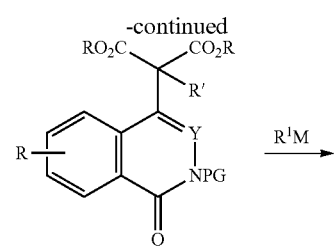
9b
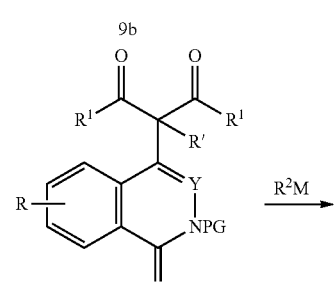
9c

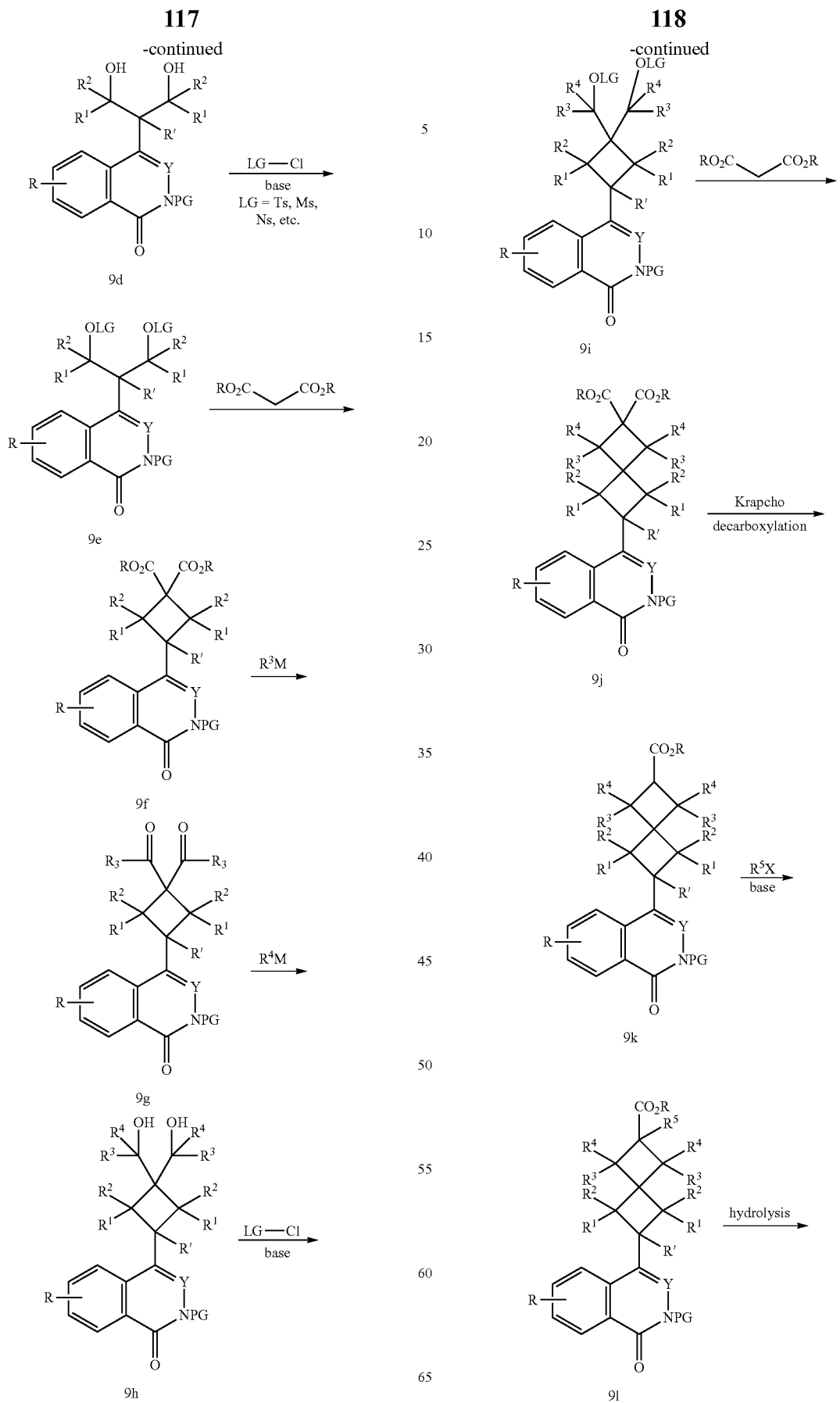

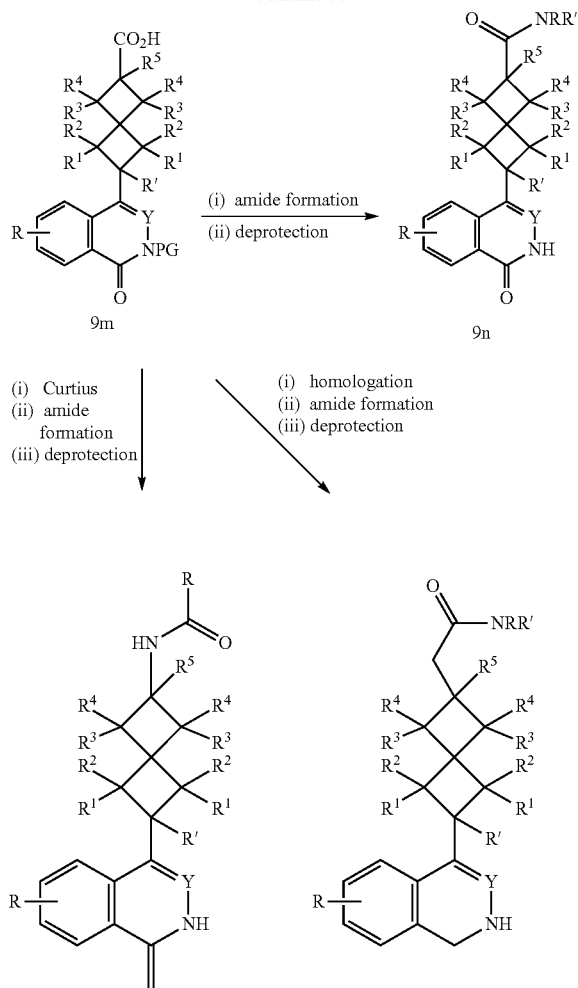

Scheme 9 outlines the general pathway to access substituted spiro[3,3]heptanes 9n-p, and constitutes a series of malonate additions, functionalizations and repeated malonate additions to build diversely derivatized spiroheptane systems. The sequence begins with a coupling of the activated heterocycle 9a (either commercially available or prepared by a known procedure) and malonate under $S_NAr$ reaction conditions in the presence of bases such as NaH, NaOtBu, LiHMDS and such, or optionally under copper-catalyzed conditions involving, but not limited to, CuI and a ligand such as L-proline, to afford the malonate 9b. Subsequent treatment of 9b with an organometallic reagent such as organolithium, organomagnesium, organozinc or organoaluminum species where $R^1$=H, alkyl, aryl or heteroaryl can afford derivatives 9c. Repeated addition of the aforementioned organometallic species affords diol 9d. Organometallic species may be represented by hydride sources like LAH, $NaBH_4$ and similar reducing agents giving rise analogs where $R^1$, $R^2$, etc. =H. Diol 9d is then is activated with TsCl, MsCl, NsCl or similar reagents in the present of bases such as pyridine, TEA or DIEA to afford derivative 9e, which is further condensed with a malonate to yield the cyclobutane 9f. Repeating of the above sequence then gives rise to spiro[3,3]heptane malonate analog 9j. Subsequent Krapcho decarboxylation in solvents such as wet DMSO and optionally in the presence of salts like LiCl, and subsequent hydrolysis provides analog 9m. Compound 9m is then converted directly, or after the respective Curtius rearrangement, to the target derivatives 9n-p using the methods described in Schemes 1 to 8.

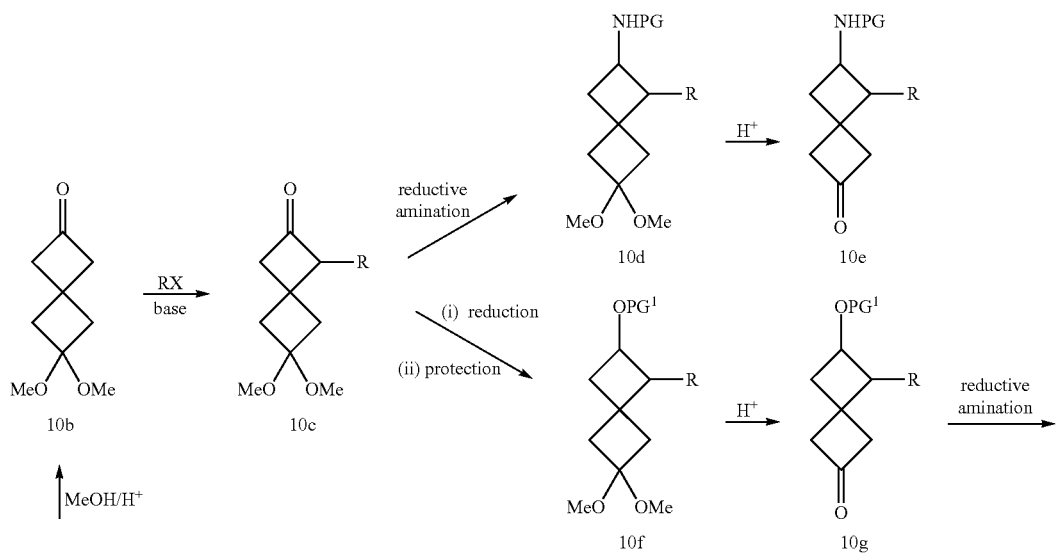

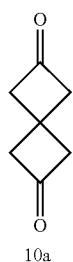

10a

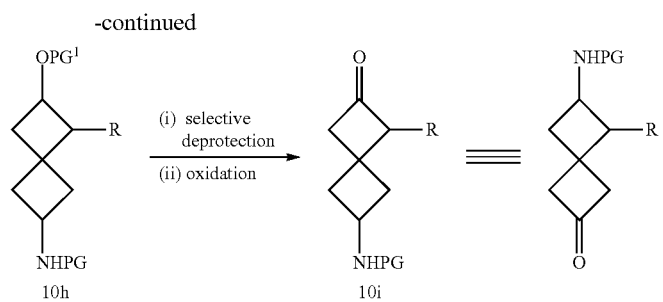

Scheme 10 shows routes to the substituted spiroheptanes, where derivatization occurs either on the top cyclobutane ring in compound 10e, or the bottom ring in 10i. Commercially available (or prepared via known procedure) diketone 10a is converted to the monoketal 10b, and subsequently is functionalized using RX such as alkyl halides under the presence of a base such as LiHMDS, LDA, etc. to provide substituted analog 10c. Reductive amination under appropriate conditions (such as amine/NaBH$_4$/methanol) affords analog 10d. Ensuing cleavage of the ketal group under acidic conditions such as TsOH or HCl unmasks ketone 10e. Alternatively, intermediate 10c may be reduced and protected at the alcohol portion of the molecule to give the compound 10f. After ketal cleavage and reductive amination described above compound 10h may be obtained. Finally, selective deprotection and oxidation of the acquired alcohol provides target 10i. Both ketones 10e and 10i may be used in Schemes 3 and 6 as a starting materials to provide the respective substituted spiro[3,3]heptane targets.

Purification of intermediates and final products was carried out via either normal or reverse phase chromatography. Normal phase chromatography was carried out using prepacked SiO$_2$ cartridges eluting with either gradients of hexanes and EtOAc or DCM and MeOH unless otherwise indicated. Reverse phase preparative HPLC was carried out using C18 columns eluting with gradients of Solvent A (90% H$_2$O, 10% MeOH, 0.1% TFA) and Solvent B (10% H$_2$O, 90% MeOH, 0.1% TFA, UV 220 nm) or with gradients of Solvent A (90% H$_2$O, 10% ACN, 0.1% TFA) and Solvent B (10% H$_2$O, 90% ACN, 0.1% TFA, UV 220 nm) or with gradients of Solvent A (98% H$_2$O, 2% ACN, 0.05% TFA) and Solvent B (98% ACN, 2% H$_2$O, 0.05% TFA, UV 220 nm) (or) SunFire Prep C18 OBD 5μ 30×100 mm, 25 min gradient from 0-100% B. A=H$_2$O/ACN/TFA 90:10:0.1. B=ACN/H$_2$O/TFA 90:10:0.1 (or) Waters XBridge C18, 19×200 mm, 5-μm particles; Guard Column: Waters XBridge C18, 19×10 mm, 5-μm particles; Solvent A: water with 20-mM ammonium acetate; Solvent B: 95:5 acetonitrile:water with 20-mM ammonium acetate; Gradient: 25-65% B over 20 minutes, then a 5-minute hold at 100% B; Flow: 20 mL/min.

Unless otherwise stated, analysis of final products was carried out by reverse phase analytical HPLC.

Method A: SunFire C18 column (3.5 μm C18, 3.0×150 mm). Gradient elution (1.0 mL/min) from 10-100% Solvent B over 10 min and then 100% Solvent B for 5 min was used. Solvent A is (95% water, 5% acetonitrile, 0.05% TFA) and Solvent B is (5% water, 95% acetonitrile, 0.05% TFA, UV 254 nm).

Method B: XBridge Phenyl column (3.5 μm C18, 3.0×150 mm). Gradient elution (1.0 mL/min) from 10-100% Solvent B over 10 min and then 100% Solvent B for 5 min was used. Solvent A is (95% water, 5% acetonitrile, 0.05% TFA) and Solvent B is (5% water, 95% acetonitrile, 0.05% TFA, UV 254 nm).

Method C: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min.

Method D: Waters BEH C18, 2.1×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

Method E: Waters BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes; Flow: 1.11 mL/min.

Method F: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes; Flow: 1.11 mL/min.

Intermediate 1: 4-(6-Aminospiro[3.3]heptan-2-yl)phthalazin-1(2H)-one, 2 TFA

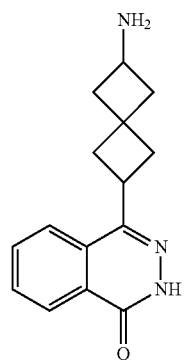 [SMILES: NC1CC2(C1)CC(c1n[nH]c(=O)c3ccccc13)C2]

Intermediate 1A: tert-butyl(6-(3-oxoisobenzofuran-1(3H)-ylidene)spiro[3.3]heptan-2-yl)carbamate

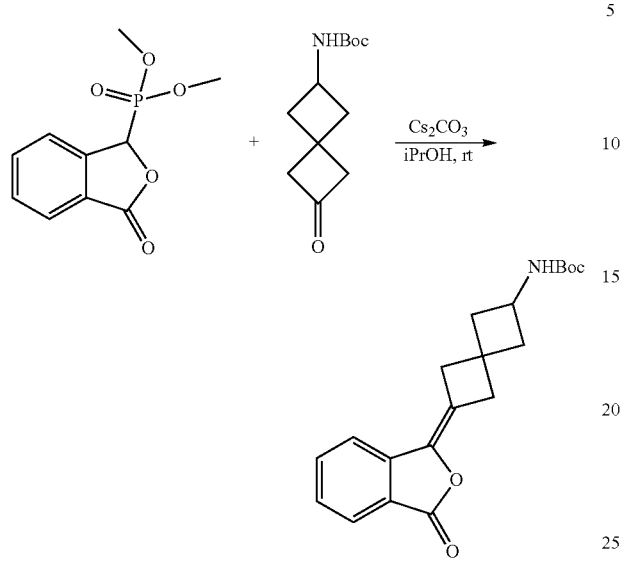

Dimethyl (3-oxo-1,3-dihydroisobenzofuran-1-yl)phosphonate (0.591 g, 2.44 mmol) (*J. Med. Chem.* 2008, 51, 6581) and tert-butyl (6-oxospiro[3.3]heptan-2-yl)carbamate (0.500 g, 2.22 mmol) were dissolved in anhydrous iPrOH (14.80 mL). Then, cesium carbonate (0.868 g, 2.66 mmol) was added, and the reaction mixture was stirred at rt for 16 h. A thick white suspension formed. The reaction mixture was diluted with DCM, CELITE® was added, and solvent was removed under reduced pressure and purified via flash chromatography (gradient from 0 to 50% ethyl acetate/hexanes) to give 0.740 g (98% yield) of Intermediate 1A as a white solid. MS(ESI) m/z: 342.0 (M+H)$^+$; $^1$H NMR (500 MHz, DMSO-d$_6$) δ 7.89 (d, J=7.7 Hz, 1H), 7.86-7.76 (m, 1H), 7.67-7.54 (m, 2H), 7.12 (d, J=7.9 Hz, 1H), 3.96-3.81 (m, 1H), 3.25-3.18 (m, 1H), 3.09 (d, J=5.7 Hz, 2H), 2.97 (d, J=1.3 Hz, 1H), 2.44-2.33 (m, 2H), 2.11-1.99 (m, 2H), 1.37 (s, 9H).

Intermediate 1B: tert-butyl (6-(4-oxo-3,4-dihydrophthalazin-1-yl)spiro[3.3]heptan-2-yl)carbamate

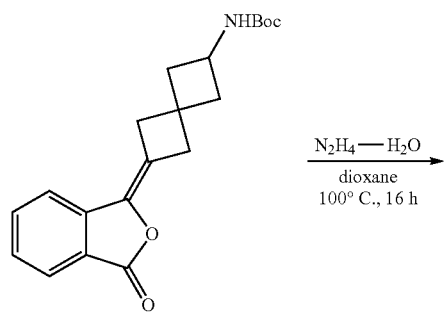

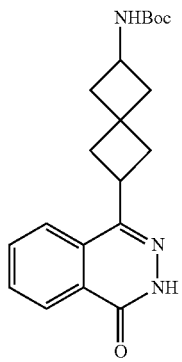

Intermediate 1A (0.740 g, 2.17 mmol) was placed in a pressure vial, thereafter dioxane (10 mL) and hydrazine hydrate (1.58 mL, 32.5 mmol) were added sequentially. The reaction mixture was stirred at rt for 15 min, and then at 100° C. for 16 h. The reaction mixture was cooled to rt, diluted with EtOAc (100 mL), washed with water (2×50 mL), brine (1×50 mL), dried (Na$_2$SO$_4$) and concentrated. The residue was purified via flash chromatography (gradient from 20 to 100% ethyl acetate/hexanes) to afford 0.703 g (91% yield) of Intermediate 1B as a white solid. MS(ESI) m/z: 356.1 (M+H)$^+$; $^1$H NMR (400 MHz, DMSO-d$_6$) δ 12.43 (s, 1H), 8.28-8.20 (m, 1H), 7.93-7.86 (m, 1H), 7.85-7.76 (m, 2H), 7.04 (d, J=7.9 Hz, 1H), 3.84 (quin, J=8.5 Hz, 2H), 2.47-2.40 (m, 1H), 2.33 (d, J=9.0 Hz, 1H), 2.28 (d, J=8.6 Hz, 2H), 2.16-2.05 (m, 1H), 2.05-1.98 (m, 1H), 1.88-1.78 (m, 1H), 1.36 (s, 9H).

Intermediate 1

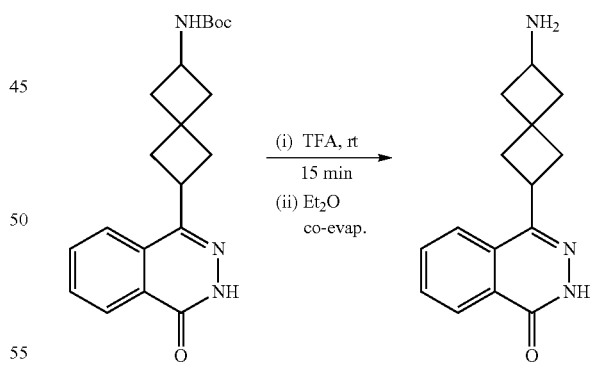

Intermediate 1B (0.105 g, 0.295 mmol) was dissolved in neat TFA (3 mL), and the reaction mixture was stirred at rt for 15 min. TFA was removed under reduced pressure, then the residue was co-evaporated with Et$_2$O (3×5 mL) and dried under vacuum to give 0.140 g (98% yield) of Intermediate 1 as an off-white solid. MS(ESI) m/z: 256.1 (M+H)$^+$; $^1$H NMR (400 MHz, DMSO-d$_6$) δ 12.46 (s, 1H), 8.25 (d, J=7.7 Hz, 1H), 7.98-7.88 (m, 3H), 7.87-7.78 (m, 3H), 3.68-3.51 (m, 1H), 2.62-2.51 (m, 3H), 2.42-2.29 (m, 3H), 2.28-2.14 (m, 2H), 2.06 (dd, J=11.7, 8.6 Hz, 1H).

Intermediate 2: 4-((aR)-6-Aminospiro[3.3]heptan-2-yl)phthalazin-1(2H)-one, TFA

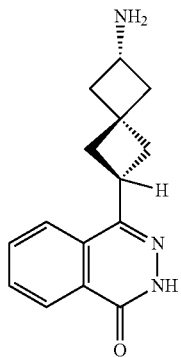

Intermediate 3: 4-((aS)-6-Aminospiro[3.3]heptan-2-yl)phthalazin-1(2H)-one, TFA

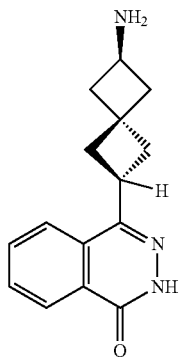

Intermediate 2A: tert-butyl ((aR)-6-(4-oxo-3,4-dihydrophthalazin-1-yl)spiro[3.3]heptan-2-yl)carbamate Intermediate 3A: tert-butyl ((aS)-6-(4-oxo-3,4-dihydrophthalazin-1-yl)spiro[3.3]heptan-2-yl)carbamate

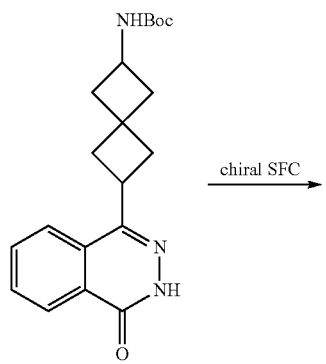

chiral SFC

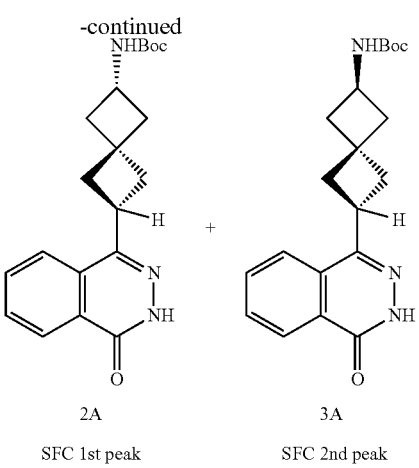

2A
SFC 1st peak

3A
SFC 2nd peak

Intermediate 1B (0.100 g, 0.281 mmol) was separated on chiral SFC (Instrument: Berger Multigram II SFC; Column: CHIRALCEL® OJ, 21×250 mm, 5 g; Mobile Phase: 15% Methanol/85% $CO_2$; Flow Conditions: 45 mL/min, 120 Bar, 40° C.; Detector Wavelength: 220 nm). Collected 1st peak at 5.12 min, concentrated to afford Intermediate 2A (0.046 g, 46% yield) as an off-white solid. MS(ESI) m/z: 356.1 $(M+H)^+$; ee>99%; $^1$H NMR (400 MHz, DMSO-$d_6$) δ 12.40 (s, 1H), 8.29-8.20 (m, 1H), 7.93-7.86 (m, 1H), 7.85-7.76 (m, 2H), 7.04 (d, J=7.9 Hz, 1H), 3.85 (quin, J=8.5 Hz, 2H), 2.47-2.40 (m, 1H), 2.33 (d, J=9.0 Hz, 1H), 2.28 (d, J=8.6 Hz, 2H), 2.15-2.05 (m, 1H), 2.05-1.98 (m, 1H), 1.88-1.78 (m, 1H), 1.36 (s, 9H).

Collected 2nd peak at 6.36 min, concentrated to afford Intermediate 3A (0.049 g, 49% yield) as an off-white solid. MS(ESI) m/z: 356.1 $(M+H)^+$; ee=99%; $^1$H NMR (400 MHz, DMSO-$d_6$) δ 12.43 (s, 1H), 8.28-8.20 (m, 1H), 7.92-7.87 (m, 1H), 7.85-7.76 (m, 2H), 7.04 (d, J=7.9 Hz, 1H), 3.83 (quin, J=8.5 Hz, 2H), 2.47-2.40 (m, 1H), 2.33 (d, J=9.0 Hz, 1H), 2.28 (d, J=8.6 Hz, 2H), 2.16-2.05 (m, 1H), 2.05-1.98 (m, 1H), 1.88-1.78 (m, 1H), 1.35 (s, 9H).

Intermediate 2

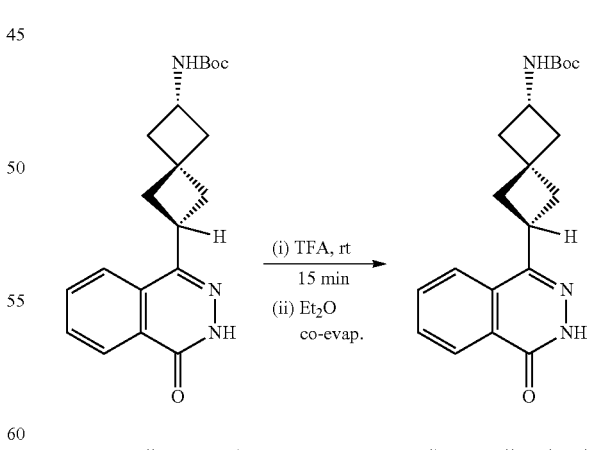

(i) TFA, rt
15 min
(ii) Et₂O
co-evap.

Intermediate 2A (40 mg, 0.113 mmol) was dissolved in neat TFA (1.5 mL), and the reaction mixture was stirred at rt for 15 min. TFA was removed under reduced pressure, then the residue was co-evaporated with Et₂O (5×10 mL) and dried under vacuum to give Intermediate 2 (41 mg, 99% yield) as an off-white solid. MS(ESI) m/z: 256.1 $(M+H)^+$; $^1$H NMR (400 MHz, DMSO-$d_6$) δ 12.39 (s, 1H), 8.25 (d, J=7.7 Hz, 1H), 7.99-7.88 (m, 3H), 7.87-7.78 (m, 2H), 3.68-3.51 (m, 1H), 2.62-2.50 (m, 3H), 2.42-2.29 (m, 3H), 2.28-2.14 (m, 2H), 2.06 (dd, J=11.7, 8.6 Hz, 1H).

Intermediate 3

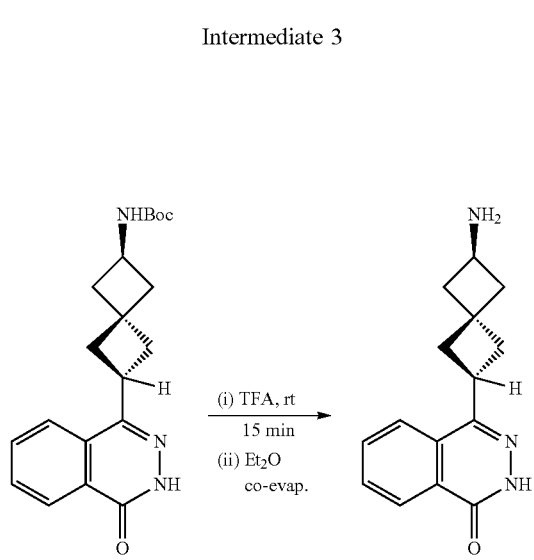

Intermediate 3A (40 mg, 0.113 mmol) was dissolved in neat TFA (1.5 mL), and the reaction mixture was stirred at rt for 15 min. TFA was removed under reduced pressure, then the residue was co-evaporated with Et$_2$O (5×10 mL) and dried under vacuum to give Intermediate 3 (41 mg, 99% yield) as an off-white solid. MS(ESI) m/z: 256.1 (M+H)$^+$; $^1$H NMR (400 MHz, DMSO-d$_6$) δ 12.39 (s, 1H), 8.25 (d, J=7.7 Hz, 1H), 7.99-7.88 (m, 3H), 7.87-7.78 (m, 2H), 3.68-3.51 (m, 1H), 2.62-2.50 (m, 3H), 2.42-2.29 (m, 3H), 2.28-2.14 (m, 2H), 2.06 (dd, J=11.7, 8.6 Hz, 1H).

Intermediate 4: 6-(4-Oxo-3,4-dihydrophthalazin-1-yl)spiro[3.3]heptane-2-carboxylic acid

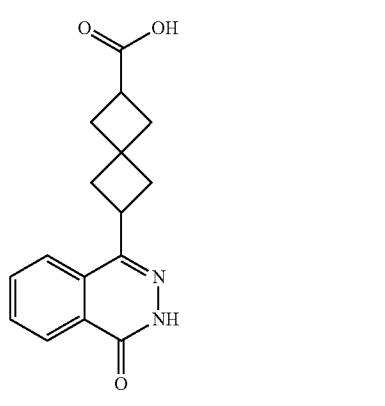 [SMILES: O=C(O)C1CC2(C1)CC(c1n[nH]c(=O)c3ccccc13)C2]

Intermediate 4A: Methyl 6-(3-oxoisobenzofuran-1(3H)-ylidene)spiro[3.3]heptane-2-carboxylate

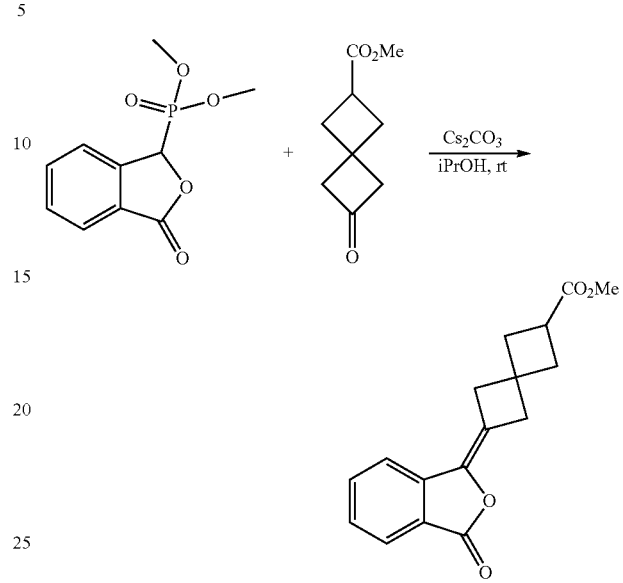

Dimethyl (3-oxo-1,3-dihydroisobenzofuran-1-yl)phosphonate (1.584 g, 6.54 mmol) (*J. Med. Chem.* 2008, 51, 6581) and methyl 6-oxospiro[3.3]heptane-2-carboxylate (1.00 g, 5.95 mmol) were dissolved in anhydrous iPrOH (39.6 mL). Then, cesium carbonate (2.13 g, 6.54 mmol) was added, and the reaction mixture was stirred at rt for 16 h. A thick white suspension formed. The reaction mixture was diluted with DCM, CELITE® was added, and solvent was removed under reduced pressure. The residue was purified via flash chromatography (gradient from 10 to 100% ethyl acetate/hexanes) to afford Intermediate 4A (1.61 g, 95% yield) as an amber syrup. MS(ESI) m/z: 285.0 (M+H)$^+$; $^1$H NMR (500 MHz, DMSO-d$_6$) δ 7.95-7.84 (m, 1H), 7.66 (t, J=7.6 Hz, 1H), 7.52-7.40 (m, 2H), 3.70 (s, 3H), 3.24-3.07 (m, 4H), 2.52-2.36 (m, 5H).

Intermediate 4B: Methyl 6-(4-oxo-3,4-dihydrophthalazin-1-yl)spiro[3.3]heptane-2-carboxylate

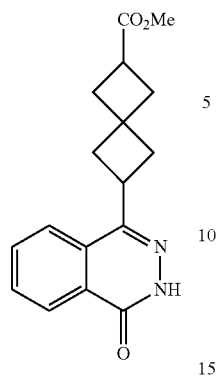

Intermediate 4A (1.61 g, 5.66 mmol) was placed in a pressure vial, and dioxane (15 mL) and hydrazine hydrate (0.824 mL, 17.0 mmol) were added sequentially. The reaction mixture was stirred at rt for 15 min, and then at 100° C. for 16 h. The reaction mixture was cooled to rt, diluted with EtOAc (250 mL), washed with water (2×100 mL), brine (1×50 mL), dried ($Na_2SO_4$) and concentrated. The residue was purified via flash chromatography (gradient from 1 to 15% MeOH/DCM) to afford Intermediate 4B (1.185 g, 70% yield) as a white solid. MS(ESI) m/z: 299.1 $(M+H)^+$; $^1H$ NMR (500 MHz, DMSO-$d_6$) δ 12.44 (s, 1H), 8.31-8.18 (m, 1H), 7.95-7.86 (m, 1H), 7.86-7.77 (m, 2H), 3.83 (quin, J=8.4 Hz, 1H), 3.59 (s, 3H), 3.05 (quin, J=8.4 Hz, 1H), 2.48-2.41 (m, 2H), 2.40-2.22 (m, 4H), 2.11 (d, J=8.6 Hz, 2H).

Intermediate 4

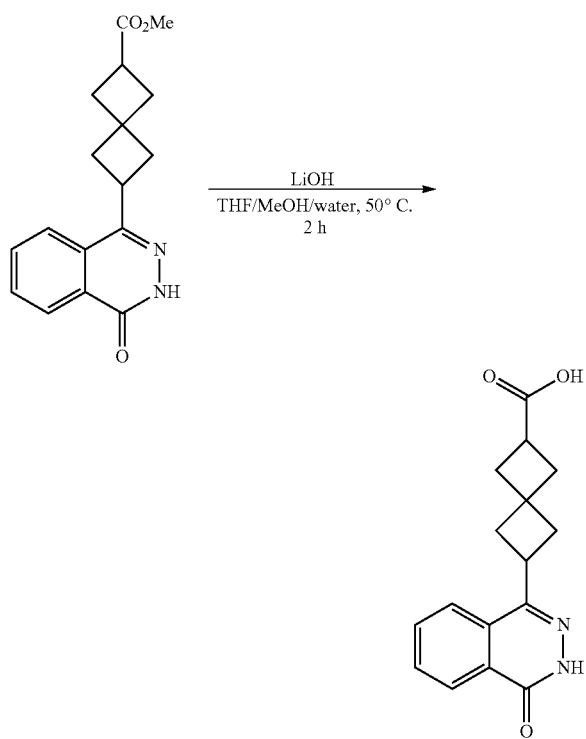

Intermediate 4B (0.500 g, 1.68 mmol) was dissolved in THF (7.0 mL) and MeOH (1.397 mL), then LiOH (1 M in water) (5.03 mL, 5.03 mmol) was added. The reaction was heated to 50° C. for 2 h. The reaction mixture was quenched with TFA (0.387 mL, 5.03 mmol) and concentrated under reduced pressure. The residue was purified by preparative HPLC to give Intermediate 4 (0.261 g, 55% yield) as a white solid. MS(ESI) m/z: 285.0 $(M+H)^+$; $^1H$ NMR (500 MHz, DMSO-$d_6$) δ 12.44 (s, 1H), 8.24 (d, J=8.1 Hz, 1H), 7.94-7.87 (m, 1H), 7.86-7.78 (m, 2H), 3.83 (quin, J=8.5 Hz, 1H), 2.95 (quin, J=8.4 Hz, 1H), 2.47-2.36 (m, 2H), 2.36-2.32 (m, 2H), 2.30-2.21 (m, 2H), 2.08 (d, J=8.4 Hz, 2H).

Intermediate 5: 2-(6-(4-oxo-3,4-dihydrophthalazin-1-yl)spiro[3.3]heptan-2-yl)acetic acid

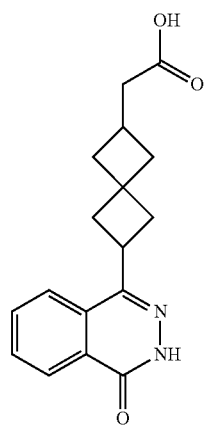 [SMILES: O=C(O)CC1CC2(C1)CC(c1n[nH]c(=O)c3ccccc13)C2]

Intermediate 5A: 4-(6-(hydroxymethyl)spiro[3.3]heptan-2-yl)phthalazin-1(2H)-one

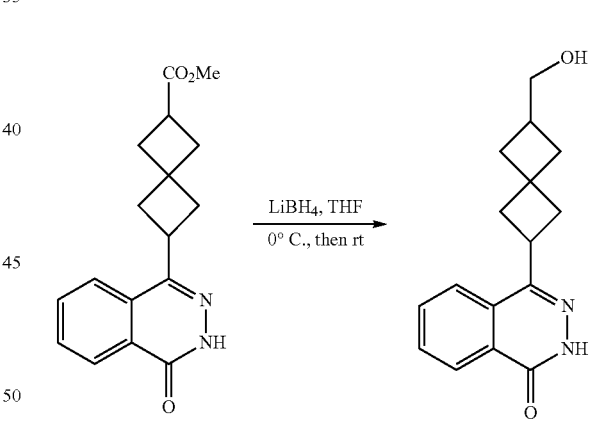

Intermediate 4B (0.150 g, 0.503 mmol) was dissolved in anhydrous THF (7.5 mL), and the reaction mixture was stirred at 0° C. for 5 min. Then, $LiBH_4$ (0.027 g, 1.257 mmol) was added, and the reaction mixture was stirred at 0° C. for additional 15 min. Then ice bath was removed, the reaction was allowed to reach rt and stir at this temperature for 1 h. Additional $LiBH_4$ (0.027 g, 1.257 mmol) was added, and the reaction mixture was stirred at rt for 16 h. The reaction mixture was carefully quenched with $NH_4Cl$ (aq.; ~5 mL; CAUTION: hydrogen gas evolution), and diluted with EtOAc (100 mL). The organic phase was washed with aq. $NH_4Cl$ (25 mL) and brine (50 mL), dried ($Na_2SO_4$) and concentrated. The residue was purified via flash chromatography (gradient from 1 to 15% MeOH/DCM) to afford Intermediate 5A (0.108 g, 79% yield) as a white solid.

MS(ESI) m/z: 271.0 (M+H)⁺; ¹H NMR (400 MHz, DMSO-d₆) δ 12.43 (s, 1H), 8.27-8.21 (m, 1H), 7.94-7.87 (m, 1H), 7.86-7.78 (m, 2H), 4.40 (t, J=5.3 Hz, 1H), 3.83 (quin, J=8.5 Hz, 1H), 3.34 (t, J=5.6 Hz, 2H), 2.48-2.41 (m, 1H), 2.38-2.16 (m, 5H), 1.95-1.84 (m, 2H), 1.66 (dd, J=11.3, 6.9 Hz, 1H).

Intermediate 5B: 4-(6-(2,2,2-trichloro-1-hydroxyethyl)spiro[3.3]heptan-2-yl)phthalazin-1(2H)-one

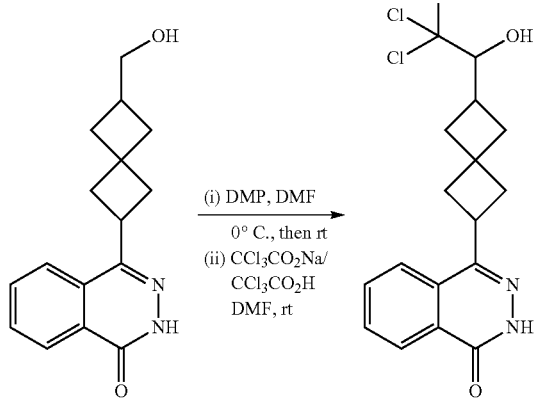

To a solution of Intermediate 5A in anhydrous DMF (4.0 mL) was added DMP (0.203 g, 0.479 mmol) at 0° C. under Ar atmosphere. The cooling bath was removed, and the reaction mixture was stirred at rt for 12 h. The reaction mixture was cooled to 0° C., then sodium trichloroacetate (0.244 g, 1.318 mmol) and trichloroacetic acid (0.215 g, 1.318 mmol) were added quickly. The reaction mixture was allowed to warm to rt and was stirred at this temperature for 16 h. Additional sodium trichloroacetate (0.488 g, 2.636 mmol) and trichloroacetic acid (0.430 g, 2.636 mmol) were added, and the reaction mixture was stirred at rt for additional 3 h. The reaction mixture was quenched with aq. NaHCO₃ (~5 mL; CAUTION: carbon dioxide evolution), and the reaction mixture was diluted with EtOAc (100 mL) and water (50 mL). The organic phase was separated, washed with water (2×50 mL), dried (Na₂SO₄), and concentrated. The residue was purified via flash chromatography (gradient from 1 to 10% MeOH/DCM) to afford Intermediate 5B (0.085 g, 55% yield) as an off-white solid. MS(ESI) m/z: 386.9 (M+H)⁺; ¹H NMR (400 MHz, DMSO-d₆) δ 12.45 (s, 1H), 8.25 (d, J=7.9 Hz, 1H), 8.00-7.77 (m, 3H), 6.57 (dd, J=15.4, 6.8 Hz, 1H), 3.95-3.75 (m, 2H), 2.81-2.66 (m, 1H), 2.60-2.53 (m, 1H), 2.41-2.24 (m, 4H), 2.24-2.05 (m, 1H), 2.00-1.78 (m, 2H).

Intermediate 5

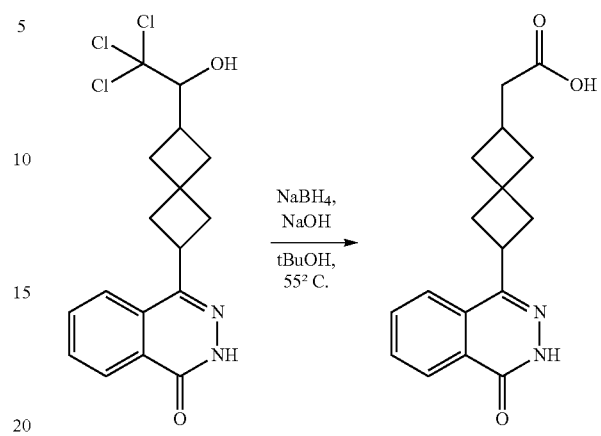

To a solution/suspension of Intermediate 5B (0.050 g, 0.129 mmol) in tBuOH (3.0 mL), was added freshly powdered sodium hydroxide (0.017 g, 0.426 mmol) at rt under Ar atmosphere. The reaction mixture was stirred rapidly at rt for 10 min, then sodium borohydride (7.32 mg, 0.193 mmol) was added. The heterogeneous reaction mixture was warmed to 55° C. and stirred at this temperature for 16 h. Solvent was removed under reduced pressure, then the residue was dissolved in MeOH/DMF/TFA and purified by preparative HPLC to afford Intermediate 5 (5.1 mg, 13% yield). MS(ESI) m/z: 299.1 (M+H)⁺; ¹H NMR (400 MHz, THF-d₈) δ 11.35 (br. s., 1H), 8.21 (d, J=7.7 Hz, 1H), 7.72-7.62 (m, 2H), 7.62-7.54 (m, 1H), 3.68 (quin, J=8.4 Hz, 1H), 2.50-2.23 (m, 6H), 2.21 (d, J=7.7 Hz, 2H), 1.99 (ddd, J=11.5, 7.6, 4.2 Hz, 1H), 1.79 (dd, J=10.8, 8.1 Hz, 1H), 1.59-1.52 (m, 1H).

Intermediate 6: 1-(2-Hydroxy-2-methylpropyl)-1H-indazole-3-carboxylic acid

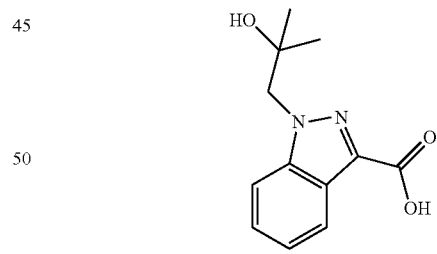

Intermediate 6A: Ethyl 1-(2-hydroxy-2-methylpropyl)-1H-indazole-3-carboxylate

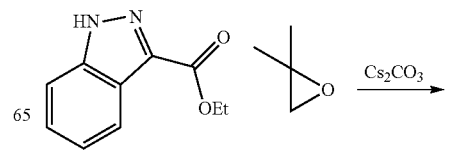

-continued

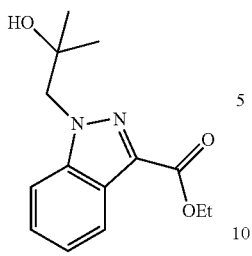

To a vial containing ethyl 1H-indazole-3-carboxylate (75 mg, 0.39 mmol) and 2,2-dimethyloxirane (0.088 mL, 0.99 mmol), was added acetonitrile (1.5 mL). To this mixture was added $Cs_2CO_3$ (193 mg, 0.591 mmol). The vial was sealed and the mixture was stirred at 90° C. for 2.5 h. The reaction mixture was partitioned between EtOAc and $H_2O$. The aqueous phase was extracted with EtOAc. The combined organic phase was washed with brine, dried ($Na_2SO_4$) and concentrated. The crude product was purified by flash chromatography (gradient from 0 to 100% ethyl acetate/hexanes) to afford Intermediate 6A (45 mg, 43.5% yield) as a colorless oil. MS(ESI) m/z: 263.1 $(M+H)^+$; $^1$H NMR (400 MHz, chloroform-d) δ 8.24 (dt, J=8.3, 0.9 Hz, 1H), 7.58-7.52 (m, 1H), 7.50-7.43 (m, 1H), 7.32 (ddd, J=8.0, 6.9, 0.9 Hz, 1H), 4.52 (q, J=7.2 Hz, 2H), 4.45 (s, 2H), 2.73 (s, 1H), 1.48 (t, J=7.2 Hz, 3H), 1.26 (s, 6H).

Intermediate 6

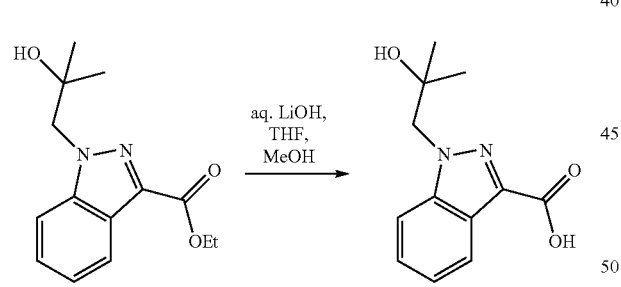

To a solution of Intermediate 6A (45 mg, 0.17 mmol) in THF (1 mL), was added 1M aq. LiOH (0.20 mL, 0.20 mmol), followed by MeOH (0.3 mL). The homogeneous mixture was stirred at rt for 1.5 h. Additional 1M aq. LiOH (0.1 mL, 0.1 mmol) was added and the mixture was stirred at rt for 14 h. The reaction mixture was partially evaporated to remove volatile solvents. The solution was diluted with $H_2O$, then was acidified with 1 N HCl (~0.3 mL). The aqueous phase was extracted with EtOAc (3×). The combined organic phase was washed with brine, dried ($Na_2SO_4$) and concentrated to afford Intermediate 6 (40 mg, 100% yield) as an off-white solid. MS(ESI) m/z: 235.1 $(M+H)^+$; $^1$H NMR (400 MHz, chloroform-d) δ 8.27 (d, J=8.1 Hz, 1H), 7.59 (d, J=8.4 Hz, 1H), 7.48 (t, J=7.6 Hz, 1H), 7.41-7.31 (m, 1H), 4.48 (s, 2H), 1.30 (s, 6H).

Intermediate 7:
1-(2,2-Difluoroethyl)-1H-pyrazole-5-carboxylic acid

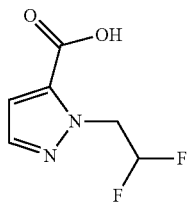 [SMILES: O=C(O)c1ccnn1CC(F)F]

Intermediate 8:
1-(2,2-Difluoroethyl)-1H-pyrazole-3-carboxylic acid

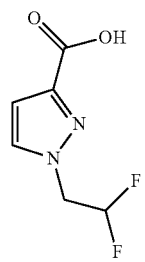

Intermediate 7A: Methyl 1-(2,2-difluoroethyl)-1H-pyrazole-5-carboxylate

Intermediate 8A: Methyl 1-(2,2-difluoroethyl)-1H-pyrazole-3-carboxylate

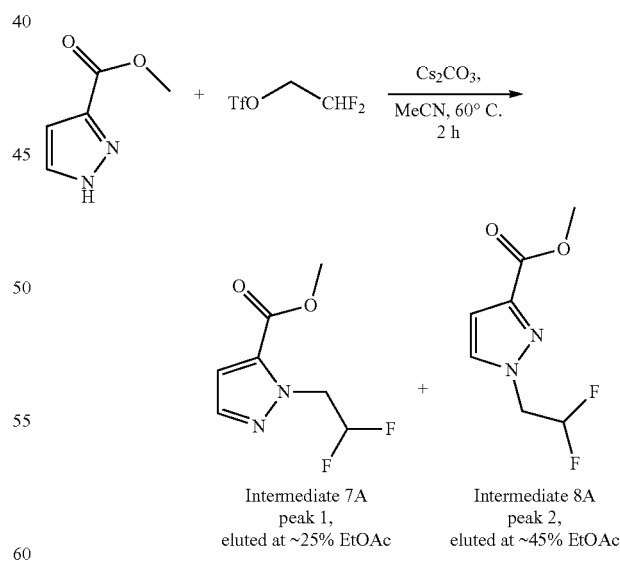

Intermediate 7A
peak 1,
eluted at ~25% EtOAc

Intermediate 8A
peak 2,
eluted at ~45% EtOAc

Methyl 1H-pyrazole-3-carboxylate (0.500 g, 3.96 mmol) was dissolved in dry MeCN (30 mL), then 2,2-difluoroethyl trifluoromethanesulfonate (0.633 mL, 4.76 mmol) was added, followed by cesium carbonate (1.94 g, 5.95 mmol), and the reaction mixture was stirred at 60° C. for 2 h. The reaction mixture was cooled to rt, diluted with EtOAc. Then CELITE® was added, and solvent was removed under reduced pressure. The residue was purified by flash chromatography (solid loading on CELITE®): 0-60% EtOAc/Hex affording two products.

Intermediate 7A (0.271 g, 36% yield) as a colorless syrup: peak 1 eluted at ~25% EtOAc. MS(ESI) m/z: 190.9 (M+H)+; $^1$H NMR: (400 MHz, CDCl$_3$) δ ppm 7.57 (d, J=2.0 Hz, 1H), 6.89 (d, J=2.0 Hz, 1H), 6.31-5.95 (m, 1H), 4.98 (td, J=13.1, 4.4 Hz, 2H), 3.91 (s, 3H); $^{19}$F-NMR: (376 MHz, CDCl$_3$) δ ppm −122.87 (s, 2F).

Intermediate 8A: (0.398 g, 53% yield) as a colorless syrup: peak 2 eluted at ~45% EtOAc. MS(ESI) m/z: 190.9 (M+H)+; $^1$H NMR: (400 MHz, CDCl$_3$) δ ppm 7.51 (d, J=2.4 Hz, 1H), 6.87 (d, J=2.4 Hz, 1H), 6.29-5.94 (m, 1H), 4.55 (td, J=13.4, 4.3 Hz, 2H), 3.94 (s, 3H); $^{19}$F-NMR: (376 MHz, CDCl$_3$) δ ppm −122.42 (s, 2F).

Intermediate 7

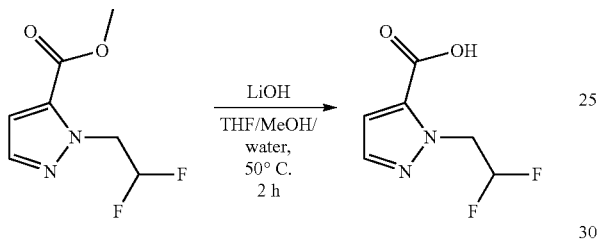

Intermediate 7A (0.398 g, 2.093 mmol) was dissolved in THF (8.7 mL) and MeOH (1.7 mL), then LiOH (1 M in water) (6.28 mL, 6.28 mmol) were added. The reaction was heated to 50° C. for 2 h. The reaction mixture was quenched with TFA (0.484 mL, 6.28 mmol), then concentrated under reduced pressure. The residue was diluted with DMSO/MeOH/water and was purified by preparative to afford Intermediate 7 (0.173 g, 46.9% yield) as a white solid. MS(ESI) m/z: 176.9 (M+H)+; $^1$H NMR (400 MHz, DMSO-d$_6$) δ 13.59 (br. s., 1H), 7.64 (d, J=2.0 Hz, 1H), 6.90 (d, J=2.0 Hz, 1H), 6.60-6.12 (m, 1H), 4.98 (td, J=14.5, 4.0 Hz, 2H).

Intermediate 8

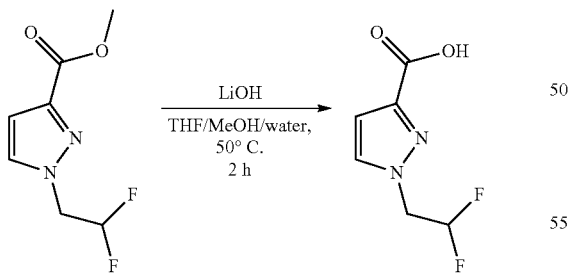

Intermediate 8A (0.271 g, 1.43 mmol) was dissolved in THF (5.9 mL) and MeOH (1.2 mL), then LiOH (1 M in water) (4.28 mL, 4.28 mmol) was added. The reaction was heated to 50° C. for 2 h. The reaction mixture was quenched with TFA (0.329 mL, 4.28 mmol) and concentrated under reduced pressure. The residue was diluted with DMSO/MeOH/water and was purified by preparative HPLC to afford Intermediate 8 (0.177 g, 71% yield) as a white solid. MS(ESI) m/z: 176.9 (M+H)+; $^1$H NMR (400 MHz, DMSO-d$_6$) δ 12.76 (s, 1H), 7.88 (d, J=2.4 Hz, 1H), 6.75 (d, J=2.4 Hz, 1H), 6.59-6.19 (m, 1H), 4.72 (td, J=15.2, 3.7 Hz, 2H).

Intermediate 9:
1-(3,3,3-trifluoropropyl)-1H-pyrazole-5-carboxylic acid

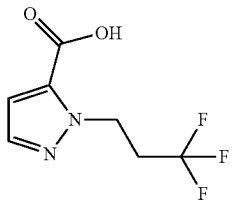 [SMILES: O=C(O)c1ccnn1CCC(F)(F)F]

Intermediate 10:
1-(3,3,3-trifluoropropyl)-1H-pyrazole-3-carboxylic acid

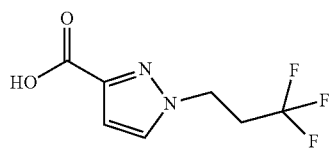 [SMILES: O=C(O)c1ccn(CCC(F)(F)F)n1]

Intermediate 9A: Methyl 1-(3,3,3-trifluoropropyl)-1H-pyrazole-5-carboxylate

Intermediate 10A: Methyl 1-(3,3,3-trifluoropropyl)-1H-pyrazole-3-carboxylate

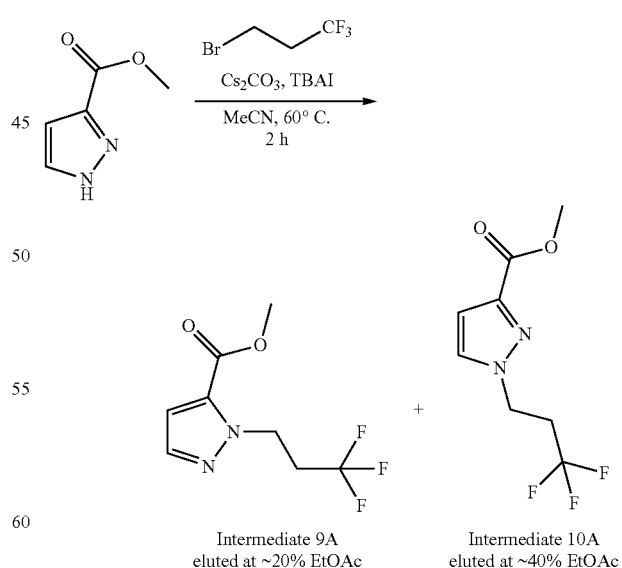

Intermediate 9A
eluted at ~20% EtOAc

Intermediate 10A
eluted at ~40% EtOAc

Methyl 1H-pyrazole-3-carboxylate (0.500 g, 3.96 mmol) was dissolved in dry MeCN (30 mL), then 3-bromo-1,1,1-trifluoropropane (0.507 mL, 4.76 mmol) was added, followed by cesium carbonate (1.938 g, 5.95 mmol). The reaction mixture was stirred at 60° C. for 2 h. Additional 3-bromo-1,1,1-trifluoropropane (0.507 mL, 4.76 mmol) was added, followed by TBAI (0.146 g, 0.396 mmol), and the reaction mixture was stirred at 60° C. for 14 h. Additional cesium carbonate (1.938 g, 5.95 mmol), TBAI (0.146 g, 0.396 mmol) and 3-bromo-1,1,1-trifluoropropane (0.507 mL, 4.76 mmol) were added, and the reaction mixture was stirred at 60° C. for 6 h. The reaction mixture was cooled to rt, diluted with EtOAc. Then CELITE® was added, and solvent was removed under reduced pressure. The residue was purified by flash chromatography (solid loading on CELITE®, 0-55% EtOAc/Hex) affording two products.

Intermediate 9A (0.228 g, 26% yield) as a colorless syrup eluted at ~20% EtOAc. MS(ESI) m/z: 222.9 (M+H)$^+$; $^1$H NMR: (500 MHz, CDCl$_3$) δ ppm 7.52 (d, J=1.9 Hz, 1H), 6.86 (d, J=1.9 Hz, 1H), 4.87-4.80 (m, 2H), 3.90 (s, 3H), 2.78-2.66 (m, 2H); $^{19}$F-NMR: (471 MHz, CDCl$_3$) δ ppm −65.71 (s, 3F).

Intermediate 10A (0.257 g, 29% yield) as a colorless syrup eluted at ~40% EtOAc. MS(ESI) m/z: 222.9 (M+H)$^+$; $^1$H NMR: (500 MHz, CDCl$_3$) δ ppm 7.45 (d, J=2.2 Hz, 1H), 6.82 (d, J=2.5 Hz, 1H), 4.44 (t, J=7.3 Hz, 2H), 3.94 (s, 3H), 2.79 (qt, J=10.3, 7.2 Hz, 2H); $^{19}$F-NMR: (471 MHz, CDCl$_3$) δ ppm −65.66 (s, 3F).

Intermediate 9

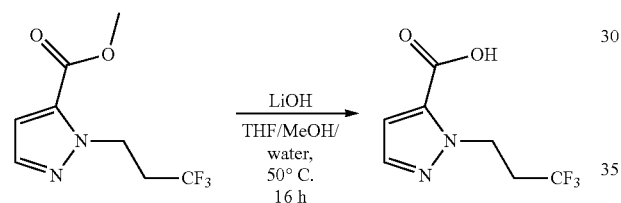

Intermediate 9A (0.228 g, 1.026 mmol) was dissolved in THF (4.3 mL) and MeOH (0.9 mL), then LiOH (1 M in water) (3.08 mL, 3.08 mmol) was added. The reaction was heated to 50° C. for 16 h. The reaction mixture was quenched with TFA (0.237 mL, 3.08 mmol) and concentrated under reduced pressure. The residue was diluted with DMSO/MeOH/water and was purified by preparative HPLC to afford Intermediate 9 (0.115 g, 54% yield) as a white solid. MS(ESI) m/z: 208.9 (M+H)$^+$; $^1$H NMR: (400 MHz, CDCl$_3$) δ ppm 13.47 (br. s., 1H), 7.58 (d, J=2.0 Hz, 1H), 6.84 (d, J=2.0 Hz, 1H), 4.77 (t, J=6.8 Hz, 2H), 2.83 (qt, J=11.3, 6.8 Hz, 2H); $^{19}$F-NMR: (376 MHz, CDCl$_3$) δ ppm −64.15 (s, 3F).

Intermediate 10

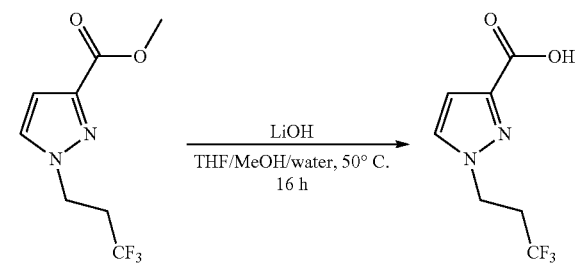

Intermediate 10A (0.257 g, 1.157 mmol) was dissolved in THF (4.8 mL) and MeOH (1.0 mL), then LiOH (1 M in water) (3.47 mL, 3.47 mmol) was added. The reaction was heated to 50° C. for 16 h. The reaction mixture was quenched with TFA (0.267 mL, 3.47 mmol) and concentrated under reduced pressure. The residue was diluted with DMSO/MeOH/water and was purified by preparative HPLC to give Intermediate 10 (0.173 g, 72% yield) as a white solid. MS(ESI) m/z: 208.9 (M+H)$^+$; $^1$H NMR: (400 MHz, CDCl$_3$) δ ppm 12.67 (br. s., 1H), 7.90 (d, J=2.4 Hz, 1H), 6.69 (d, J=2.2 Hz, 1H), 4.46 (t, J=6.9 Hz, 2H), 2.91 (qt, J=11.2, 6.9 Hz, 2H); $^{19}$F-NMR: (376 MHz, CDCl$_3$) δ ppm −64.10 (s, 3F).

Intermediate 11:
1-(Cyclopropylmethyl)-1H-pyrazole-5-carboxylic acid

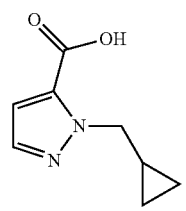 [SMILES: O=C(O)c1ccnn1CC1CC1]

Intermediate 12:
1-(Cyclopropylmethyl)-1H-pyrazole-3-carboxylic acid

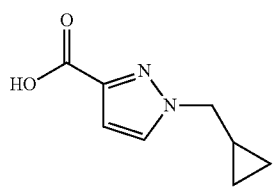 [SMILES: O=C(O)c1ccn(CC2CC2)n1]

Intermediate 11A: Methyl 1-(cyclopropylmethyl)-1H-pyrazole-5-carboxylate

Intermediate 12A: Methyl 1-(cyclopropylmethyl)-1H-pyrazole-3-carboxylate

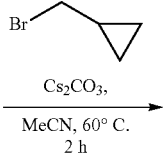

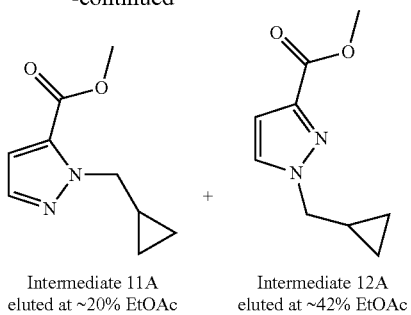

Intermediate 11A
eluted at ~20% EtOAc

Intermediate 12A
eluted at ~42% EtOAc

Methyl 1H-pyrazole-3-carboxylate (0.500 g, 3.96 mmol) was dissolved in dry MeCN (30 mL), then (bromomethyl)cyclopropane (0.461 mL, 4.76 mmol) was added, followed by cesium carbonate (1.94 g, 5.95 mmol). The reaction mixture was stirred at 60° C. for 2 h. The reaction mixture was cooled to rt and diluted with EtOAc. Then CELITE® was added, and the solvent was removed under reduced pressure. The residue was purified by flash chromatography (solid loading on CELITE®, 0-55% EtOAc/Hex) affording two products.

Intermediate 11A (0.197 g, 28% yield) as a colorless syrup eluted at ~20% EtOAc. MS(ESI) m/z: 180.9 (M+H)$^+$; $^1$H NMR: (500 MHz, CDCl$_3$) δ ppm 7.49 (d, J=1.9 Hz, 1H), 6.84 (d, J=1.9 Hz, 1H), 4.44 (d, J=7.2 Hz, 2H), 3.88 (s, 3H), 1.44-1.31 (m, 1H), 0.57-0.48 (m, 2H), 0.45-0.37 (m, 2H).

Intermediate 12A (0.415 g, 58% yield) as a colorless syrup eluted at ~42% EtOAc. MS(ESI) m/z: 180.9 (M+H)$^+$; $^1$H NMR: (500 MHz, CDCl$_3$) δ ppm 7.54 (d, J=2.5 Hz, 1H), 6.84 (d, J=2.5 Hz, 1H), 4.07 (d, J=7.2 Hz, 2H), 3.93 (s, 3H), 1.32 (quint, J=7.6, 4.9 Hz, 1H), 0.71-0.64 (m, 2H), 0.45-0.36 (m, 2H).

Intermediate 11

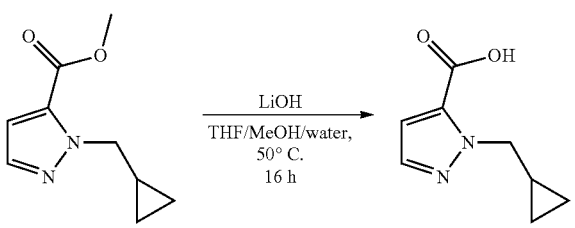

Intermediate 11A (0.197 g, 1.093 mmol) was dissolved in THF (4.6 mL) and MeOH (0.9 mL), then LiOH (1 M in water) (3.28 mL, 3.28 mmol) was added. The reaction was heated to 50° C. for 16 h. The reaction mixture was quenched with TFA (0.25 mL, 3.3 mmol) and concentrated under reduced pressure. The residue was diluted with DMSO/MeOH/water and was purified by preparative HPLC to afford Intermediate 11 (118 mg, 65% yield) as a white solid. MS(ESI) m/z: 167.0 (M+H)$^+$; $^1$H NMR: (500 MHz, CDCl$_3$) δ ppm 13.30 (s, 1H), 7.52 (d, J=2.0 Hz, 1H), 6.82 (d, J=2.0 Hz, 1H), 4.36 (d, J=7.0 Hz, 2H), 1.32-1.19 (m, 1H), 0.50-0.41 (m, 2H), 0.37-0.30 (m, 2H).

Intermediate 12

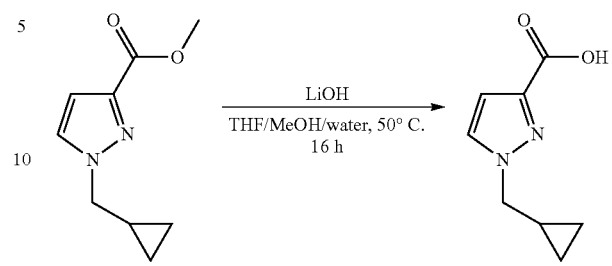

Intermediate 12A (0.415 g, 2.30 mmol) was dissolved in THF (9.6 mL) and MeOH (1.92 mL), then LiOH (1 M in water) (6.91 mL, 6.91 mmol) was added. The reaction was heated to 50° C. for 16 h. The reaction mixture was quenched with TFA (0.532 mL, 6.91 mmol) and concentrated under reduced pressure. The residue was diluted with DMSO/MeOH/water and was purified by preparative HPLC to afford Intermediate 12 (270 mg, 71% yield) as a white solid. MS(ESI) m/z: 167.0 (M+H)$^+$; $^1$H NMR: (500 MHz, CDCl$_3$) δ ppm 12.55 (br. s., 1H), 7.85 (d, J=2.2 Hz, 1H), 6.68 (d, J=2.2 Hz, 1H), 4.03 (d, J=7.3 Hz, 2H), 1.38-1.15 (m, 1H), 0.62-0.47 (m, 2H), 0.44-0.30 (m, 2H).

Intermediate 13:
1-cyclopropyl-1H-pyrazole-4-carboxylic acid

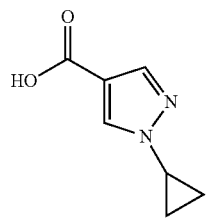

Intermediate 13A: Ethyl
1-cyclopropyl-1H-pyrazole-4-carboxylate

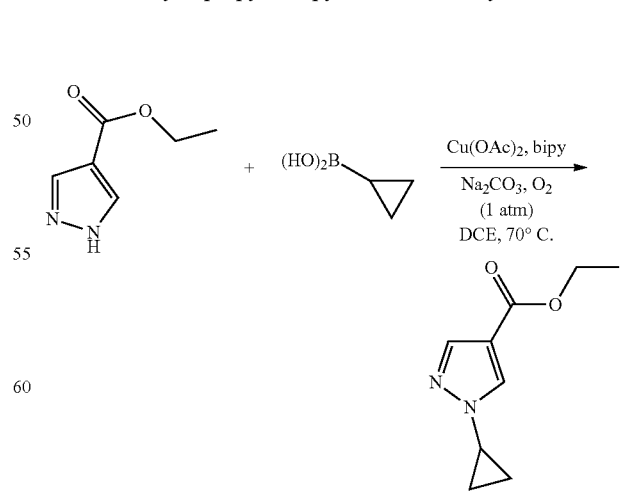

Ethyl 1H-pyrazole-4-carboxylate (0.500 g, 3.57 mmol) was dissolved in DCE (25 mL), then cyclopropylboronic acid (0.613 g, 7.14 mmol) and sodium carbonate (0.756 g, 7.14 mmol) were added. The reaction mixture was heated to 70° C., and then a mixture of 2,2'-bipyridine (0.557 g, 3.57 mmol) and copper(II) acetate (0.648 g, 3.57 mmol) were added to the reaction mixture in one batch. The reaction mixture was stirred at 70° C. under oxygen atmosphere (1 atm) for 24 h. Saturated aq. NaHCO₃ solution was added to the reaction mixture, and it was extracted with EtOAc (3×). The organic phase was combined, and the solvent was removed under reduced pressure. The residue was purified via flash chromatography (gradient from 0 to 65% ethyl acetate/hexanes) to afford Intermediate 13A (0.460 g, 72% yield) as a colorless syrup. MS(ESI) m/z: 181.0 (M+H)⁺; ¹H NMR: (500 MHz, CDCl₃) δ ppm 7.93 (s, 1H), 7.87 (s, 1H), 4.28 (q, J=7.0 Hz, 2H), 3.62 (tt, J=7.4, 3.9 Hz, 1H), 1.34 (t, J=7.2 Hz, 3H), 1.18-1.11 (m, 2H), 1.10-1.00 (m, 2H).

Intermediate 13

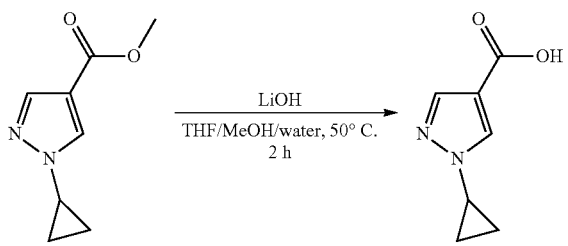

Intermediate 13A (0.460 g, 2.77 mmol) was dissolved in THF (11.5 mL) and MeOH (2.3 mL), then LiOH (1 M in water) (8.30 mL, 8.30 mmol) was added. The reaction was heated to 50° C. for 2 h. The reaction mixture was quenched with TFA (0.64 mL, 8.3 mmol), and concentrated under reduced pressure. The residue was diluted with DMSO/MeOH/water and was purified by preparative HPLC to give Intermediate 13 (0.307 g, 73% yield) as a white solid. MS(ESI) m/z: 152.9 (M+H)⁺; ¹H NMR: (500 MHz, CDCl₃) δ ppm 12.28 (br. s., 1H), 8.27 (s, 1H), 7.76 (s, 1H), 3.79 (tt, J=7.4, 3.8 Hz, 1H), 1.13-1.05 (m, 2H), 1.02-0.88 (m, 2H).

Intermediate 14: 5-(Difluoromethoxy)-1-methyl-1H-pyrazole-3-carboxylic acid

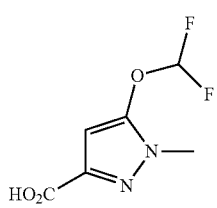

Intermediate 14A: Methyl 5-(difluoromethoxy)-1-methyl-1H-pyrazole-3-carboxylate

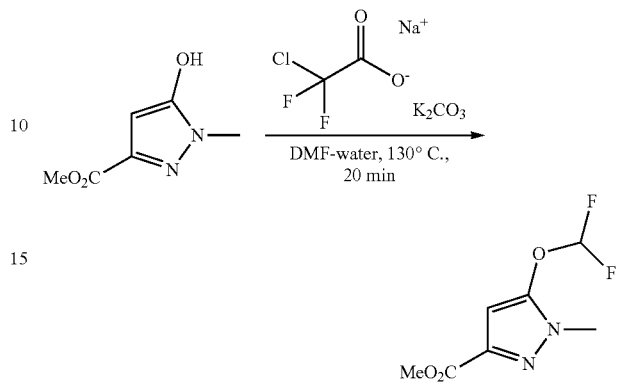

Methyl 5-hydroxy-1-methyl-1H-pyrazole-3-carboxylate (J. Med. Chem., 54:8174 (2011)) (0.35 g, 2.24 mmol), K₂CO₃ (0.62 g, 4.48 mmol), and sodium chlorodifluoroacetate (0.684 g, 4.48 mmol) were dissolved in DMF (10 mL) and water (1 mL). The reaction was heated to 130° C. for 20 min. The reaction was diluted with water (100 mL) and EtOAc (200 mL). The organic phase was separated, washed with water (5×) and brine, dried (Na₂SO₄) and concentrated. The residue was purified by flash chromatography (0-80% EtOAc/Hex gradient) to give Intermediate 14A (0.373 g, 81% yield) as a colorless syrup. MS(ESI) m/z: 207.0 (M+H)⁺; ¹H NMR: (400 MHz, CDCl₃) δ ppm 6.44 (t, J=1.0 Hz, 1H), 6.46 (t, J=72.2 Hz, 1H), 3.92 (s, 3H), 3.82 (s, 3H); ¹⁹F-NMR: (376 MHz, CDCl₃) δ ppm −84.02 (s, 2F).

Intermediate 14: 5-(Difluoromethoxy)-1-methyl-1H-pyrazole-3-carboxylic acid

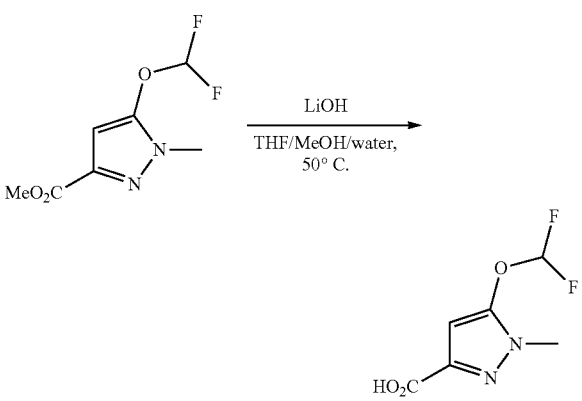

Intermediate 14A (0.373 g, 1.81 mmol) was dissolved in THF (7.5 mL) and MeOH (1.5 mL), then LiOH (1 M in water) (5.43 mL, 5.43 mmol) was added. The reaction was heated to 50° C. for 2 h. The reaction mixture was quenched with TFA (0.42 mL, 5.4 mmol), and concentrated under reduced pressure. The residue was diluted with DMSO/MeOH/water and was purified by preparative HPLC to afford Intermediate 14 (0.230 g, 66% yield) as a white solid. MS(ESI) m/z: 192.9 (M+H)⁺; ¹H NMR: (500 MHz, DMSO- $d_6$) δ ppm 7.30 (t, J=70.4 Hz, 1H), 6.42 (s, 1H), 3.74 (s, 3H); $^{19}$F-NMR: (376 MHz, DMSO-$d_6$) δ ppm −84.72 (s, 2F).

Intermediate 15:
1-(Cyclopropyl)-1H-pyrazole-5-carboxylic acid

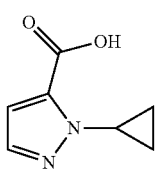 [SMILES: O=C(O)c1ccnn1C1CC1]

Intermediate 16:
1-(Cyclopropyl)-1H-pyrazole-3-carboxylic acid

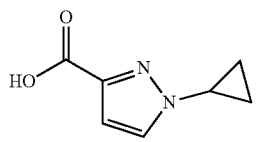 [SMILES: O=C(O)c1ccn(C2CC2)n1]

Intermediate 15A: Methyl 1-(cyclopropyl)-1H-pyrazole-5-carboxylate

Intermediate 16A: Methyl 1-(cyclopropyl)-1H-pyrazole-3-carboxylate

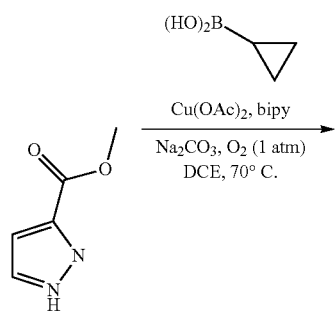

Methyl 1H-pyrazole-3-carboxylate (0.500 g, 3.96 mmol), was dissolved in DCE (25 mL), then cyclopropylboronic acid (0.681 g, 7.93 mmol) and sodium carbonate (0.840 g, 7.93 mmol) were added. The reaction mixture was heated to 70° C., and then a mixture of 2,2′-bipyridine (0.619 g, 3.96 mmol) and copper(II) acetate (0.720 g, 3.96 mmol) were added in one batch. The reaction mixture was stirred at 70° C. under oxygen atmosphere (1 atm) for 2 d. Saturated aq. NaHCO$_3$ solution was added to the reaction mixture, and it was extracted with EtOAc (3×). The combined organic phase was concentrated. The residue was purified by flash chromatography (solid loading on CELITE®, 0-65% EtOAc/Hex) affording two products.

Intermediate 15A (0.119 g, 18% yield) as a colorless syrup eluted at ~20% EtOAc. MS(ESI) m/z: 167.0 (M+H)$^+$; $^1$H NMR: (400 MHz, DMSO-$d_6$) δ ppm 7.40 (d, J=2.0 Hz, 1H), 6.82 (d, J=2.0 Hz, 1H), 4.31-4.24 (m, 1H), 2.11 (s, 3H), 1.29-1.22 (m, 2H), 1.10-1.00 (m, 2H).

Intermediate 16A (0.371 g, 56% yield) as a colorless syrup eluted at ~45% EtOAc. MS(ESI) m/z: 167.0 (M+H)$^+$; $^1$H NMR: (400 MHz, DMSO-$d_6$) δ ppm 77.46 (d, J=2.4 Hz, 1H), 6.78 (d, J=2.2 Hz, 1H), 3.92 (s, 3H), 3.67 (tt, J=7.4, 3.9 Hz, 1H), 1.23-1.15 (m, 2H), 1.09-1.01 (m, 2H).

Intermediate 15

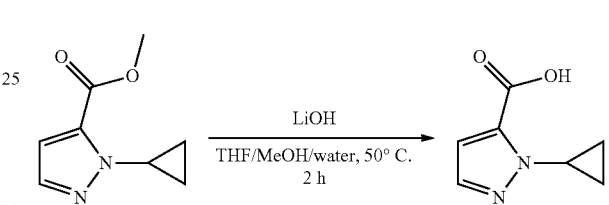

Intermediate 15A (0.119 g, 0.716 mmol) was dissolved in THF (3 mL) and MeOH (0.6 mL), then LiOH (1 M in water) (2.15 mL, 2.15 mmol) was added. The reaction was heated to 50° C. for 2 h. The reaction mixture was quenched with TFA (0.166 mL, 2.15 mmol) and concentrated under reduced pressure. The residue was diluted with DMSO/MeOH/water and was purified by preparative HPLC to give Intermediate 15 (0.064 g, 59% yield) as a white solid. MS(ESI) m/z: 152.9 (M+H)$^+$; $^1$H NMR: (400 MHz, DMSO-$d_6$) δ ppm 13.31 (br. s., 1H), 7.45 (d, J=2.0 Hz, 1H), 6.81 (d, J=2.0 Hz, 1H), 4.40 (tt, J=7.5, 3.9 Hz, 1H), 1.16-1.08 (m, 2H), 1.03-0.93 (m, 2H).

Intermediate 16

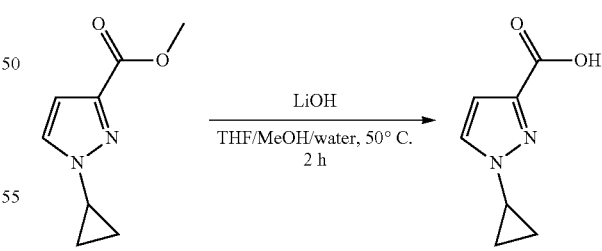

Intermediate 16A (0.371 g, 2.23 mmol) was dissolved in THF (9.3 mL) and MeOH (1.9 mL), then LiOH (1 M in water) (6.7 mL, 6.7 mmol) was added. The reaction was heated to 50° C. for 2 h. The reaction mixture was quenched with TFA (0.516 mL, 6.70 mmol) and concentrated under reduced pressure. The residue was diluted with DMSO/MeOH/water and was purified by preparative HPLC to afford Intermediate 16 (0.215 g, 63% yield) as a white solid. MS(ESI) m/z: 152.9 (M+H)$^+$; $^1$H NMR: (400 MHz, DMSOd$_6$) δ ppm 12.59 (br. s., 1H), 7.87 (d, J=2.2 Hz, 1H), 6.65 (d, J=2.2 Hz, 1H), 3.82 (tt, J=7.5, 3.8 Hz, 1H), 1.11-1.05 (m, 2H), 1.03-0.94 (m, 2H).

Intermediate 17: 1-(2-Hydroxy-2-methylpropyl)-1H-pyrazole-3-carboxylic acid

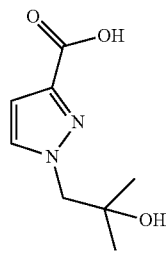

Intermediate 17A: Ethyl 1-(2-hydroxy-2-methylpropyl)-1H-pyrazole-3-carboxylate

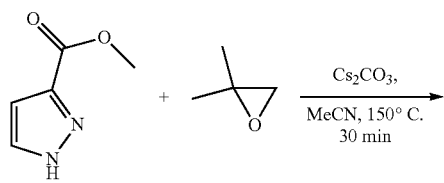

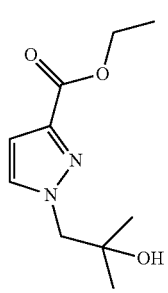

Methyl 1H-pyrazole-3-carboxylate (0.500 g, 3.96 mmol) was dissolved in dry MeCN (12 mL), then 2,2-dimethyloxirane (0.531 mL, 5.95 mmol) was added, followed by cesium carbonate (1.94 g, 5.95 mmol). The reaction mixture was stirred at 150° C. under microwave irradiation for 30 min. The reaction mixture was cooled to rt, diluted with EtOAc (transesterification occurred upon EtOAc addition). The residue was purified by flash chromatography (solid loading on CELITE®, 20-100% EtOAc/Hex) affording Intermediate 17A (0.305 g, 36% yield) as a colorless syrup. MS(ESI) m/z: 213.0 (M+H)$^+$; $^1$H NMR: (400 MHz, DMSO-d$_6$) δ ppm 7.50 (d, J=2.4 Hz, 1H), 6.83 (d, J=2.4 Hz, 1H), 4.40 (q, J=7.0 Hz, 2H), 4.17 (s, 2H), 2.77 (s, 1H), 1.39 (t, J=7.2 Hz, 3H), 1.20 (s, 6H).

Intermediate 17

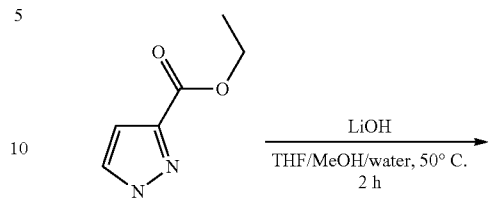

Intermediate 17A (0.305 g, 1.44 mmol) was dissolved in THF (6 mL) and MeOH (1.2 mL), then LiOH (1 M in water) (4.31 mL, 4.31 mmol) was added. The reaction was heated to 50° C. for 2 h. The reaction mixture was quenched with TFA (0.332 mL, 4.31 mmol), and concentrated under reduced pressure. The residue was diluted with DMSO/MeOH/water and was purified by preparative HPLC to give Intermediate 17 (0.239 g, 90% yield) as a colorless syrup, which solidified upon standing. MS(ESI) m/z: 184.9 (M+H)$^+$; $^1$H NMR: (400 MHz, DMSO-d$_6$) δ ppm 7.73 (d, J=2.2 Hz, 1H), 6.67 (d, J=2.4 Hz, 1H), 4.08 (s, 2H), 1.06 (s, 6H).

Intermediate 18: 6-Fluoro-1-(2-methylprop-1-en-1-yl)-1H-indazole-3-carboxylic acid

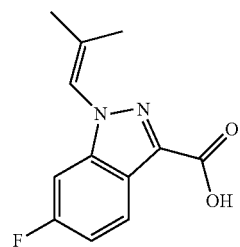 [SMILES: CC(C)=Cn1nc(C(=O)O)c2ccc(F)cc21]

Intermediate 19: 6-Fluoro-1-(2-hydroxy-2-methyl-propyl)-1H-indazole-3-carboxylic acid

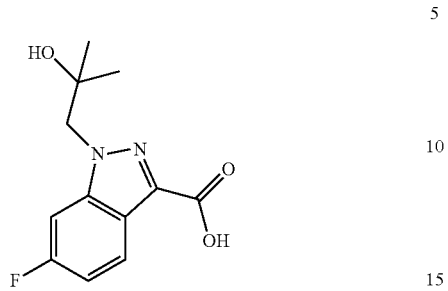

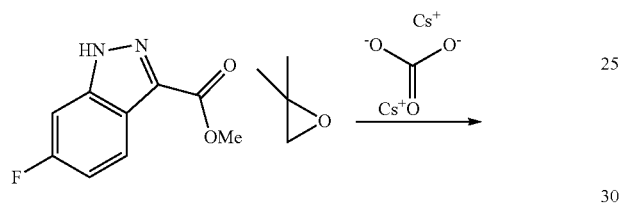

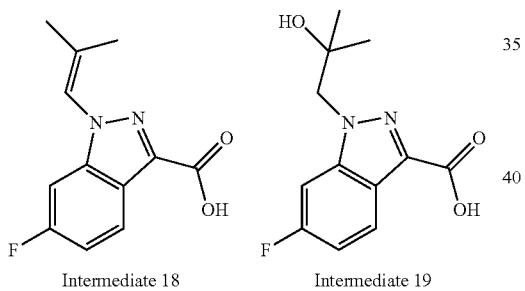

Intermediate 18      Intermediate 19

To a vial containing methyl 6-fluoro-1H-indazole-3-carboxylate (200 mg, 1.03 mmol) in DMF (3 mL), were added 2,2-dimethyloxirane (0.458 mL, 5.15 mmol) and $Cs_2CO_3$ (403 mg, 1.236 mmol). The vial was sealed and the mixture was stirred at 80° C. for 3 h. The mixture was quenched with water, acidified with 1 N HCl and extracted with EtOAc. The organic layer was concentrated and purified by flash chromatography (eluted with MeOH/DCM). Collected two fractions: 1st fraction: 5% MeOH; 2nd fraction: 8% MeOH.

1st fraction afforded Intermediate 18 (26 mg, 11%). MS(ESI) 235.1 (M+H)$^+$; $^1$H NMR (500 MHz, DMSO-$d_6$) δ 13.78 (br. s., 1H), 8.05 (dd, J=9.1, 5.5 Hz, 1H), 7.55 (dt, J=9.9, 1.1 Hz, 1H), 7.44-7.32 (m, 1H), 7.21 (td, J=9.3, 2.3 Hz, 1H), 1.93 (d, J=1.1 Hz, 3H), 1.79 (d, J=1.4 Hz, 3H).

2nd fraction afforded Intermediate 19 (90 mg, 36%). MS(ESI) 253.1 (M+H)$^+$; $^1$H NMR (400 MHz, methanol-$d_4$) d 8.10 (dd, J=9.0, 5.3 Hz, 1H), 7.44 (dd, J=9.5, 2.0 Hz, 1H), 7.08 (td, J=9.1, 2.1 Hz, 1H), 4.39 (s, 2H), 1.24 (s, 6H).

Intermediate 20: 1-(2,2-Difluoroethyl)-3-methyl-1H-pyrazole-4-carboxylic acid

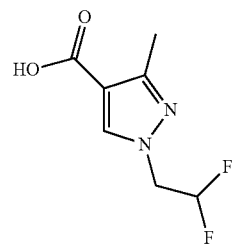

Intermediate 21: 1-(2,2-Difluoroethyl)-5-methyl-1H-pyrazole-4-carboxylic acid

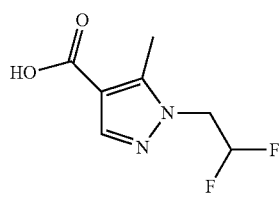

Intermediate 20A: Ethyl 1-(2,2-difluoroethyl)-3-methyl-1H-pyrazole-4-carboxylate Intermediate 21A: Ethyl 1-(2,2-difluoroethyl)-5-methyl-1H-pyrazole-4-carboxylate

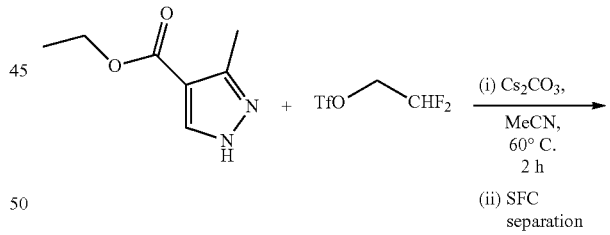

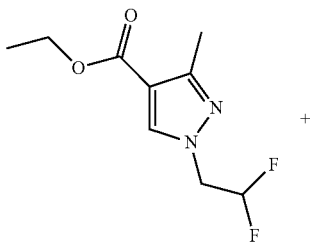

Intermediate 20A
SPC peak 1

-continued

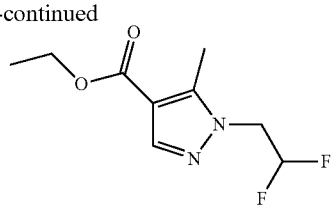

Intermediate 21A
SPC peak 2

Ethyl 3-methyl-1H-pyrazole-4-carboxylate (0.300 g, 1.95 mmol) was dissolved in dry MeCN (15 mL), then 2,2-difluoroethyl trifluoromethanesulfonate (0.311 mL, 2.34 mmol) was added, followed by cesium carbonate (0.951 g, 2.92 mmol) and the reaction mixture was stirred at 60° C. for 2 h. The reaction mixture was cooled to rt and diluted with EtOAc. Then CELITE® was added, and the solvent was removed under reduced pressure. The residue was purified by flash chromatography and was further purified by chiral SFC to afford two products.

Intermediate 20A (0.056 g, 13% yield) as a colorless oil, which solidified upon standing. MS(ESI) 219.0 (M+H)$^+$; $^1$H NMR (400 MHz, DMSO-d$_6$) δ ppm 7.89 (s, 1H), 6.29-5.90 (m, 1H), 4.38 (td, J=13.4, 4.4 Hz, 2H), 4.28 (q, J=7.0 Hz, 2H), 2.46 (s, 3H), 1.34 (t, J=7.2 Hz, 3H); $^{19}$F-NMR: (376 MHz, CDCl$_3$) δ ppm −122.64 (s, 2F).

Intermediate 21A (0.032 g, 7% yield) as a colorless oil. MS(ESI) 219.0 (M+H)$^+$; $^1$H NMR (400 MHz, DMSO-d$_6$) δ ppm 7.90 (s, 1H), 6.29-5.91 (m, 1H), 4.41 (td, J=13.2, 4.4 Hz, 2H), 4.30 (q, J=7.1 Hz, 2H), 2.58 (s, 3H), 1.35 (t, J=7.2 Hz, 3H); $^{19}$F-NMR: (376 MHz, CDCl$_3$) δ ppm −122.36 (s, 2F).

Intermediate 20

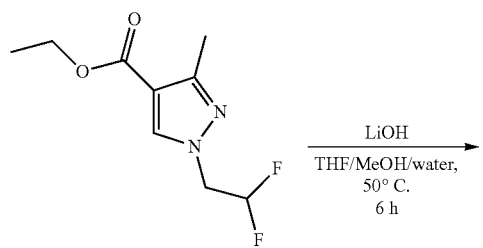

Intermediate 20A (0.056 g, 0.257 mmol) was dissolved in THF (2.6 mL) and MeOH (2.6 mL), then LiOH (1 M in water) (0.77 mL, 0.77 mmol) was added. The reaction was heated to 50° C. for 2 h. The reaction mixture was quenched with TFA (0.059 mL, 0.77 mmol) and concentrated under reduced pressure. The residue was diluted with DMSO/MeOH/water and was purified by preparative HPLC to afford Intermediate 20 (31.5 mg, 64% yield) as a white solid. MS(ESI) 190.9 (M+H)$^+$; $^1$H NMR (400 MHz, DMSO-d$_6$) δ ppm 12.25 (s, 1H), 8.19 (s, 1H), 6.56-6.12 (m, 1H), 4.57 (td, J=15.0, 3.7 Hz, 2H), 2.32 (s, 3H); $^{19}$F-NMR: (376 MHz, DMSO-d$_6$) δ ppm −122.94 (s, 2F).

Intermediate 21

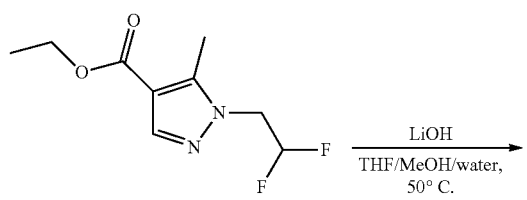

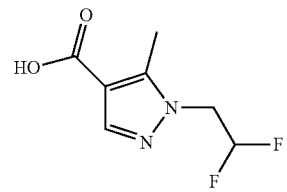

Intermediate 21A (0.032 g, 0.147 mmol) was dissolved in THF (1.5 mL) and MeOH (1.5 mL), then LiOH (1 M in water) (0.44 mL, 0.44 mmol) was added. The reaction was heated to 50° C. for 2 h. The reaction mixture was quenched with TFA (0.034 mL, 0.440 mmol) and concentrated under reduced pressure. The residue was diluted with DMSO/MeOH/water and was purified by preparative HPLC to afford Intermediate 21 (19.2 mg, 69% yield) as a white solid. MS(ESI) 190.9 (M+H)$^+$; $^1$H NMR (400 MHz, DMSO-d$_6$) δ ppm 12.32 (br. s., 1H), 7.80 (s, 1H), 6.58-6.19 (m, 1H), 4.62 (td, J=15.2, 3.7 Hz, 2H), 2.51 (br. s., 3H); $^{19}$F-NMR: (376 MHz, DMSO-d$_6$) δ ppm −122.32 (s, 2F).

Intermediate 22: 2-bromo-4-methyl-N-((aR)-6-(4-oxo-3,4-dihydrophthalazin-1-yl)spiro[3.3]heptan-2-yl)thiazole-5-carboxamide

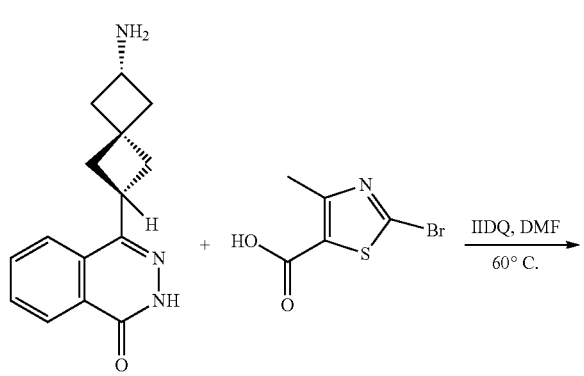

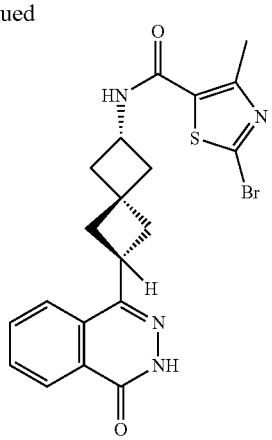

Intermediate 22, TFA (128 mg, 0.347 mmol) and 2-bromo-4-methylthiazole-5-carboxylic acid (77 mg, 0.347 mmol) were dissolved in anhydrous DMF (5 mL). Then, isobutyl 1,2-dihydro-2-isobutoxy-1-quinoline-carboxylate (0.103 mL, 0.347 mmol) was added, and the reaction mixture was stirred at 60° C. for 2 h. Additional 2-bromo-4-methylthiazole-5-carboxylic acid (77 mg, 0.35 mmol) and isobutyl 1,2-dihydro-2-isobutoxy-1-quinoline-carboxylate (0.103 mL, 0.347 mmol) were added, and the reaction mixture was stirred at 60° C. for 16 h. The reaction mixture was cooled to rt and quenched with MeOH (1 mL). The reaction mixture was diluted with DMSO/MeOH/TFA and purified by preparative HPLC to afford Intermediate 22 (30 mg, 19% yield) as a white solid. MS(ESI) 458.9 (M+H)+; 1H NMR (400 MHz, DMSO-d6) δ ppm 12.45 (s, 1H), 8.47 (d, J=7.3 Hz, 1H), 8.25 (d, J=7.9 Hz, 1H), 7.96-7.79 (m, 3H), 4.31-4.17 (m, 1H), 3.97-3.83 (m, 1H), 2.66-2.55 (m, 1H), 2.52 (s, 3H), 2.43-2.30 (m, 4H), 2.27-2.14 (m, 2H), 2.09-1.97 (m, 1H).

Intermediate 23: (R)-2-(3-fluoropyrrolidin-1-yl)-5-methylthiazole-4-carboxylic acid, TFA

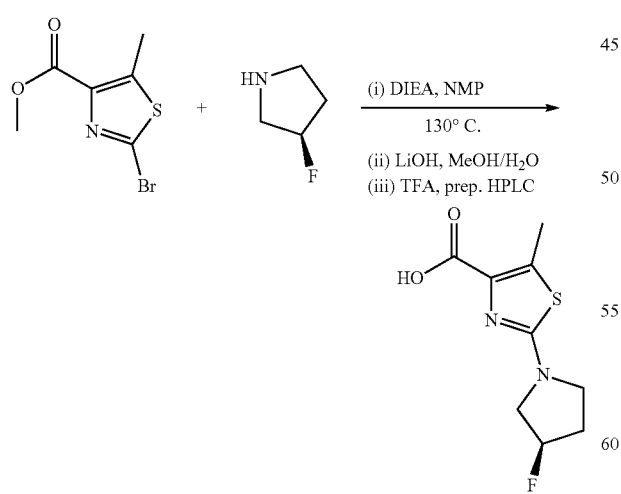

Methyl-2-bromo-5-methylthiazole-4-carboxylate (188 mg, 0.796 mmol) and (R)-3-fluoropyrrolidine, HCl (250 mg, 1.99 mmol) were placed in a pressure vial. Then NMP (3.0 mL) and DIEA (0.695 mL, 3.98 mmol) were added. The pressure vial was capped, and the reaction mixture was stirred at 130° C. for 4 h. The reaction mixture was stirred at 130° C. for additional 14 h. The reaction mixture was diluted with EtOAc (100 mL), washed with water (3×50 mL), brine (1×50 mL), and dried (Na2SO4). Solvent was removed under reduced pressure, the residue was dissolved in MeOH (7.5 mL), and LiOH (1 M aq.) (2.39 mL, 2.39 mmol) was added. The reaction mixture was stirred at 50° C. for 1 h. The reaction mixture was acidified with TFA (0.184 mL, 2.39 mmol), the solvent was removed under reduced pressure, and the residue was purified by preparative HPLC to afford Intermediate 23 (80 mg, 29% yield) as white hydroscopic solid. MS(ESI) m/z: 231.0 (M+H)+; 1H NMR: (400 MHz, DMSO-d6) δ ppm 5.54-5.35 (m, 1H), 3.69 (s, 1H), 3.64-3.59 (m, 1H), 3.59-3.52 (m, 1H), 3.50-3.39 (m, 1H), 2.53 (s, 3H), 2.34-2.11 (m, 2H).

Intermediate 24: 2-bromo-5-methyl-N-((aR)-6-(4-oxo-3,4-dihydrophthalazin-1-yl)spiro[3.3]heptan-2-yl)thiazole-4-carboxamide

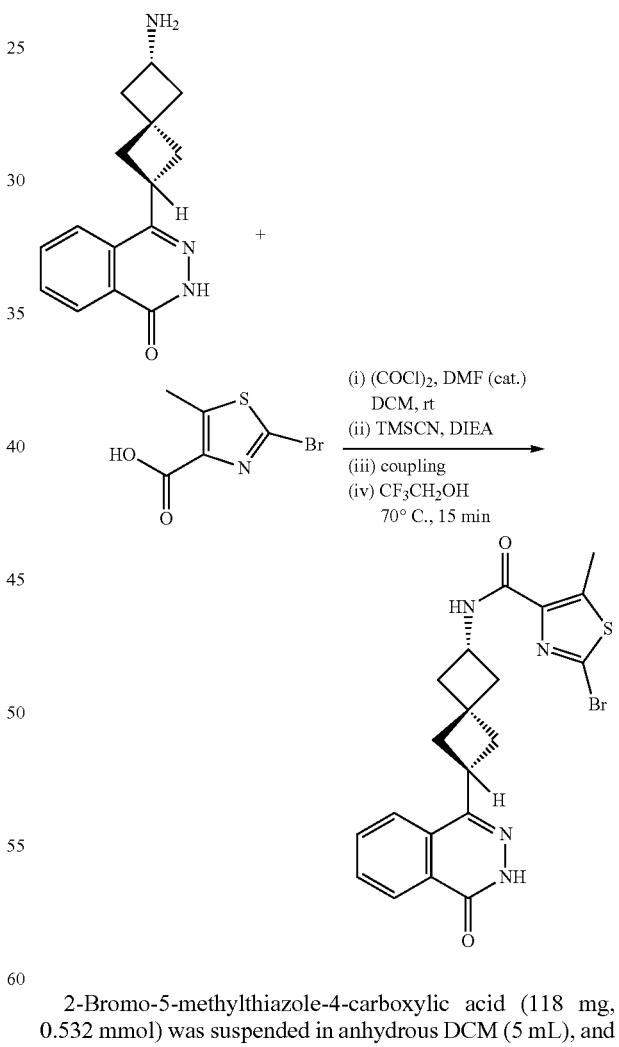

2-Bromo-5-methylthiazole-4-carboxylic acid (118 mg, 0.532 mmol) was suspended in anhydrous DCM (5 mL), and a drop a DMF was added. Then, oxalyl chloride (2 M in DCM) (0.725 mL, 1.45 mmol) was added dropwise, and the reaction mixture was stirred for 1 h at rt (bubbling observed; the mixture became homogeneous). Then, DCM was removed under reduced pressure, and the obtained acid chloride (brown syrup) was used in the subsequent step. In a separate flask, to a suspension of Intermediate 2, HCl (141 mg, 0.483 mmol) in THF (5 mL), was added DIEA (0.084 mL, 0.483 mmol) and trimethylsilyl cyanide (0.644 mL, 4.83 mmol). The resultant solution was stirred at rt for 10 min, and then was treated with a solution of acid chloride obtained as described above in THF (5 mL). The mixture was stirred at 50° C. for 1.5 h. The reaction mixture was concentrated, then trifluoroethanol (10 mL) was added. The residue was purified by flash chromatography (solid loading on CELITE®, 0-100% EtOAc/Hex) affording Intermediate 24 (86 mg, 39% yield) as a off-white solid. MS(ESI) m/z: 459.0 (M+H)$^+$; $^1$H NMR: (400 MHz, CDCl$_3$) δ ppm 9.91 (s, 1H), 8.46 (dd, J=7.8, 1.0 Hz, 1H), 7.86-7.80 (m, 1H), 7.80-7.74 (m, 1H), 7.70 (d, J=8.1 Hz, 1H), 7.37 (br d, J=7.9 Hz, 1H), 4.47 (sxt, J=8.2 Hz, 1H), 3.83 (quin, J=8.5 Hz, 1H), 2.77-2.69 (m, 1H), 2.63-2.34 (m, 5H), 2.17 (dd, J=10.8, 8.8 Hz, 1H), 2.04-1.97 (m, 1H), 1.60 (s, 3H).

Intermediates 25-28 was prepared in a manner similar to Intermediate 17 preparation, starting from the respective heterocyclic derivatives (indazole, indole, azaindazole, etc.).

Intermediate 25: 1-(2-hydroxy-2-methylpropyl)-5-methoxy-1H-indazole-3-carboxylic acid

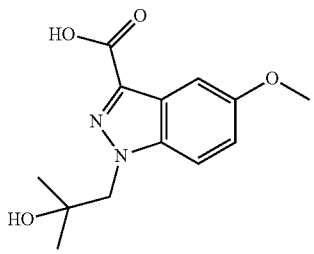 [SMILES: COc1ccc2c(c1)c(C(=O)O)nn2CC(C)(C)O]

MS(ESI) m/z: 265.1 (M+H)$^+$; $^1$H NMR (400 MHz, methanol-d$_4$) δ ppm 7.64 (d, J=9.2 Hz, 1H), 7.53 (d, J=2.4 Hz, 1H), 7.11 (dd, J=9.2, 2.4 Hz, 1H), 4.43 (s, 2H), 3.88 (s, 3H), 1.25 (s, 6H).

Intermediate 26: 1-(2-hydroxy-2-methylpropyl)-6-methoxy-1H-indazole-3-carboxylic acid

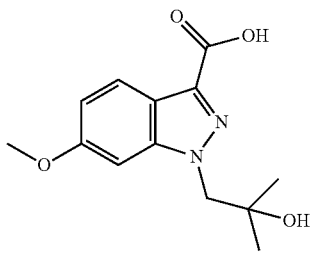 [SMILES: COc1ccc2c(C(=O)O)nn(CC(C)(C)O)c2c1]

MS(ESI) m/z: 265 (M+H)$^+$; $^1$H NMR (400 MHz, methanol-d$_4$) δ ppm 7.93 (d, J=9.0 Hz, 1H), 7.10 (d, J=2.0 Hz, 1H), 6.89 (dd, J=8.9, 2.1 Hz, 1H), 4.36 (s, 2H), 3.86 (s, 3H), 1.22 (s, 6H)

Intermediate 27: 5-fluoro-1-(2-hydroxy-2-methylpropyl)-1H-indazole-3-carboxylic acid

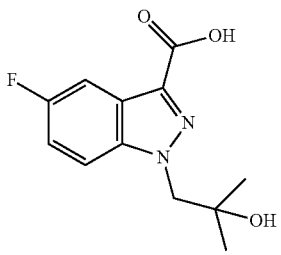 [SMILES: CC(C)(O)Cn1nc(C(=O)O)c2cc(F)ccc21]

MS(ESI) m/z: 253.1 (M+H)$^+$; $^1$H NMR (500 MHz, methanol-d$_4$) δ ppm 7.77-7.68 (m, 2H), 7.32-7.20 (m, 1H), 4.43 (s, 2H), 1.30-1.21 (m, 6H)

Intermediate 28: 1-(2-hydroxy-2-methylpropyl)-1H-pyrrolo[2,3-b]pyridine-3-carboxylic acid

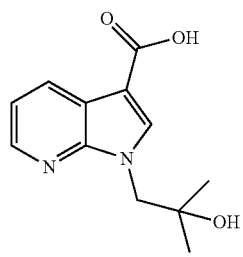 [SMILES: CC(C)(O)Cn1cc(C(=O)O)c2cccnc21]

MS(ESI) m/z: 235.2 (M+H)$^+$; $^1$H NMR (400 MHz, methanol-d$_4$) δ ppm 8.47 (dd, J=7.9, 1.5 Hz, 1H), 8.29 (d, J=4.0 Hz, 1H), 8.14 (s, 1H), 7.23 (dd, J=7.9, 4.8 Hz, 1H), 4.33 (s, 2H), 1.17 (s, 6H)

Intermediate 29: 6-(2-hydroxy-2-methylpropoxy)pyrazolo[1,5-a]pyridine-3-carboxylic acid

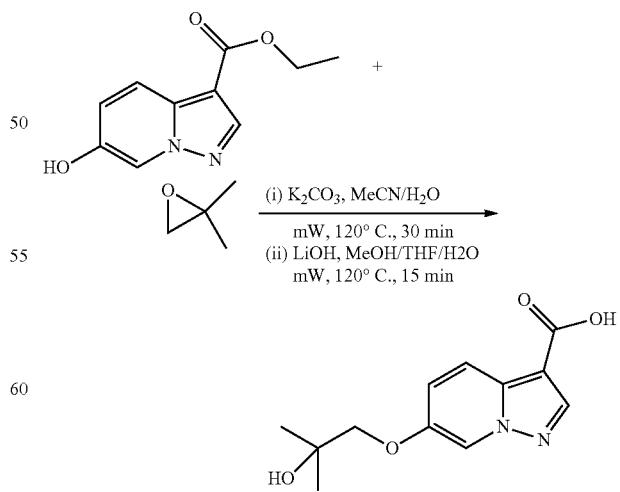

Ethyl 6-hydroxypyrazolo[1,5-a]pyridine-3-carboxylate (0.250 g, 1.21 mmol) was suspended in MeCN (10 mL), then 2,2-dimethyloxirane (1.62 mL, 18.2 mmol), K$_2$CO$_3$ (0.67 g, 4.85 mmol) and water (0.667 mL) were added. The reaction mixture was stirred under microwave irradiation at 120° C. for 30 min. The reaction mixture was concentrated under reduced pressure, the residue was dissolved in MeOH (4.5 mL)/THF (4.5 mL), and LiOH (1 M aq.) (3.64 mL, 3.64 mmol) was added. The reaction mixture was stirred under microwave irradiation at 120° C. for 15 min. Solvent was removed under reduced pressure, and the residue was purified by preparative HPLC to afford Intermediate 29 (0.185 g, 61% yield) as a white solid. MS(ESI) m/z: 251.0. (M+H)$^+$; $^1$H NMR (500 MHz, DMSO-d$_6$) δ ppm 8.55 (d, J=1.7 Hz, 1H), 8.28 (s, 1H), 7.96 (d, J=9.4 Hz, 1H), 7.38 (dd, J=9.6, 2.2 Hz, 1H), 3.82 (s, 2H), 1.22 (s, 6H).

Intermediates outlined below and pertaining to Table 6 (Intermediate 30-31, and so on) were described in PCT Int. Appl. (2014), WO 2014113620 A2 20140724.

Intermediate 30: 6-(2-morpholinoethoxy)pyrazolo[1,5-a]pyridine-3-carboxylic acid

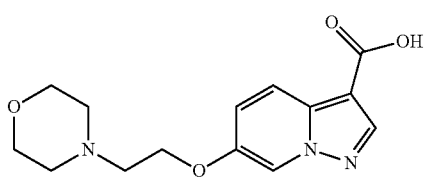 [SMILES: O=C(O)c1cnn2cc(OCCN3CCOCC3)ccc12]

MS(ESI) m/z: 292.3. (M+H)$^+$; $^1$H NMR (400 MHz, methanol-d$_4$) δ ppm 8.38 (dd, J=2.2, 0.7 Hz, 1H), 8.32 (s, 1H), 8.09 (dd, J=9.7, 0.7 Hz, 1H), 7.36 (dd, J=9.7, 2.2 Hz, 1H), 4.51-4.43 (m, 2H), 3.97 (br. s., 4H), 3.72-3.64 (m, 2H), 3.61-3.35 (m, 4H).

Intermediate 31: 2-morpholinothiazole-5-carboxylic acid

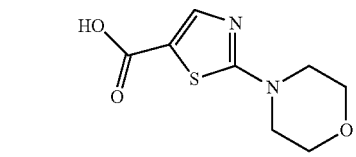

MS(ESI) m/z: 215.0. (M+H)$^+$; $^1$H NMR (400 MHz, methanol-d$_4$) δ ppm 7.82 (s, 1H), 3.82-3.74 (m, 4H), 3.56-3.49 (m, 4H).

Intermediate 32: 6-morpholinopyrazolo[1,5-a]pyridine-3-carboxylic acid

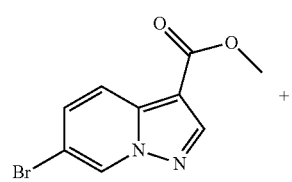

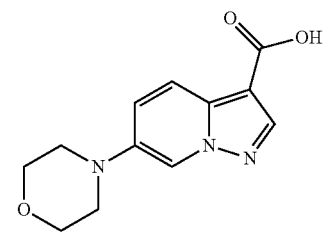

Methyl 6-bromopyrazolo[1,5-a]pyridine-3-carboxylate (0.100 g, 0.392 mmol), palladium(II) acetate (5.3 mg, 0.024 mmol), BINAP (0.022 g, 0.035 mmol) and cesium carbonate (0.192 g, 0.588 mmol) were placed in a pressure vial. The reaction mixture was degassed (3× vacuum/Ar), then Toluene (2 mL) and morpholine (0.044 mL, 0.510 mmol) were added. The reaction mixture was degassed again, and stirred at 160° C. under microwave irradiation for 30 min. Additional amount of palladium(II) acetate (5.3 mg, 0.024 mmol). BINAP (0.022 g, 0.035 mmol) and morpholine (0.044 mL, 0.51 mmol) was added, and the reaction mixture was stirred for additional 30 min at 160° C. Solvent was removed under reduced pressure. The obtained residue was dissolved in MeOH (2.0 mL)/THF (2.0 mL), and LiOH (1 M aq.) (1.18 mL, 1.18 mmol) was added. The reaction mixture was stirred under microwave irradiation at 120° C. for 15 min. The mixture was acidified with TFA, the solvent was removed under reduced pressure, the residue was purified by preparative HPLC to give Intermediate 32 (0.023 g, 24% yield) as an off-white solid. MS(ESI) m/z: 248.0. (M+H)$^+$; $^1$H NMR (500 MHz, DMSO-d$_6$) δ ppm 12.29 (br s, 1H), 8.27-8.20 (m, 2H), 7.92 (d, J=9.4 Hz, 1H), 7.58 (dd, J=9.6, 2.2 Hz, 1H), 3.81-3.73 (m, 4H), 3.17-3.07 (m, 4H).

Intermediate 33: 6-(difluoromethoxy)pyrazolo[1,5-a]pyridine-3-carboxylic acid

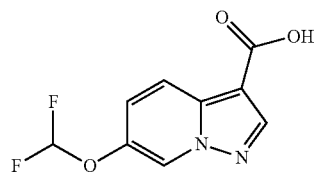 [SMILES: O=C(O)c1cnn2cc(OC(F)F)ccc12]

Intermediate 33A: ethyl 6-(difluoromethoxy)pyrazolo[1,5-a]pyridine-3-carboxylate

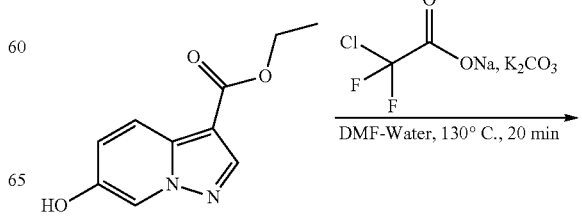

-continued

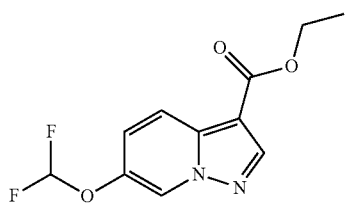

Ethyl 6-hydroxypyrazolo[1,5-a]pyridine-3-carboxylate (0.100 g, 0.485 mmol), K$_2$CO$_3$ (0.134 g, 0.970 mmol), and sodium chlorodifluoroacetate (0.148 g, 0.97 mmol) were dissolved in DMF (2.2 mL) and water (0.22 mL). The reaction was heated to 130° C. for 20 min (CAUTION: gas evolution observed; use open system). Reaction diluted with water (50 mL) and EtOAc (100 mL). Organic phase was separated, washed with water (3×25 mL), brine (1×25 mL) and dried (Na$_2$SO$_4$). EtOAc was removed under reduced pressure and the residue was purified by flash chromatography (solid loading on CELITE®, 0-40% EtOAc/Hex) affording Intermediate 33A (74 mg, 60% yield) as a white solid. MS(ESI) m/z: 257.0. (M+H)$^+$; $^1$H NMR (500 MHz, DMSO-d$_6$) δ ppm 9.03 (d, J=1.7 Hz, 1H), 8.49 (s, 1H), 8.11 (dd, J=9.6, 0.8 Hz, 1H), 7.61 (dd, J=9.6, 1.9 Hz, 1H), 7.30 (t, J=73.3 Hz, 1H), 4.31 (q, J=7.1 Hz, 2H), 1.34 (t, J=7.2 Hz, 3H); $^{19}$F-NMR: (471 MHz, DMSO-d$_6$) δ ppm −82.68 (s, 2F).

Intermediate 33

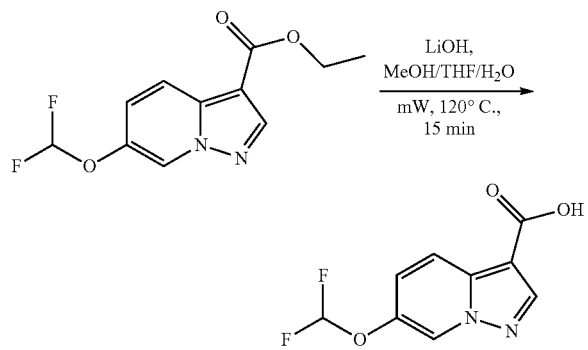

Intermediate 33A (0.050 g, 0.195 mmol) was dissolved in MeOH (1.5 mL)/THF (1.5 mL), and LiOH (1 M aq.) (0.585 mL, 0.585 mmol) was added. The reaction mixture was stirred under microwave irradiation at 150° C. for 15 min. Solvent was removed under reduced pressure, the residue was purified by preparative HPLC to afford Intermediate 33 (0.035 g, 79% yield) as a white solid. MS(ESI) m/z: 257.0 (M+H)$^+$; $^1$H NMR (500 MHz, DMSO-d$_6$) δ ppm 8.99 (s, 1H), 8.43 (s, 1H), 8.11 (d, J=9.6 Hz, 1H), 7.56 (dd, J=9.5, 2.1 Hz, 1H), 7.28 (t, J=73.2 Hz, 1H); $^{19}$F-NMR: (471 MHz, DMSO-d$_6$) δ ppm −82.58 (s, 2F).

Intermediate 34: 6-(2,2-difluoroethoxy)pyrazolo[1,5-a]pyridine-3-carboxylic acid

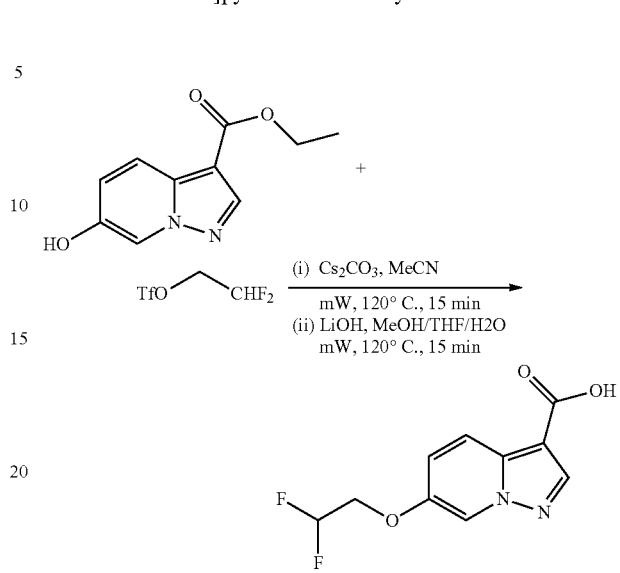

Ethyl 6-hydroxypyrazolo[1,5-a]pyridine-3-carboxylate (0.080 g, 0.388 mmol) was suspended in MeCN (3.0 mL), then 2,2-difluoroethyl trifluoromethanesulfonate (0.062 mL, 0.466 mmol) and cesium carbonate (0.379 g, 1.16 mmol) were added. The reaction mixture was stirred under microwave irradiation at 120° C. for 15 min. The reaction mixture was concentrated under reduced pressure, the residue was dissolved in MeOH (1.5 mL)/THF (1.5 mL), and LiOH (1 M aq.) (1.94 mL, 1.94 mmol) was added. The reaction mixture was stirred under microwave irradiation at 120° C. for 15 min. The reaction mixture was acidified with TFA, DMF was added, and the obtained solution was purified by preparative HPLC to afford Intermediate 34 (0.064 g, 68% yield) as a white solid. MS(ESI) m/z: 243.0 (M+H)$^+$; $^1$H NMR (500 MHz, DMSO-d$_6$) δ ppm 12.41 (s, 1H), 8.72 (d, J=1.7 Hz, 1H), 8.32 (s, 1H), 7.99 (d, J=10.2 Hz, 1H), 7.43 (dd, J=9.6, 2.5 Hz, 1H), 6.45 (tt, J=54.3, 3.5 Hz, 1H), 4.44 (td, J=14.6, 3.4 Hz, 2H); $^{19}$F-NMR: (471 MHz, DMSO-d$_6$) δ ppm −125.92 (s, 2F).

Intermediate 35: 6-(2-(1H-pyrazol-1-yl)ethoxy)pyrazolo[1,5-a]pyridine-3-carboxylic acid

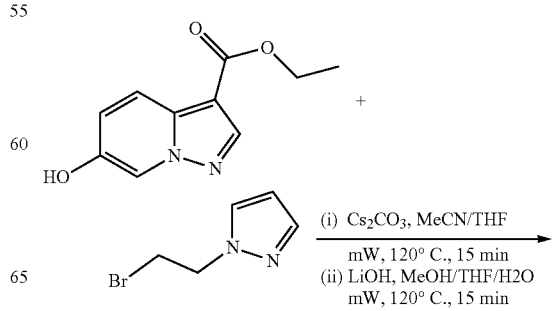

-continued

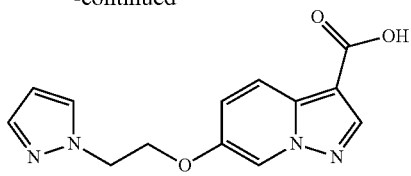

Ethyl 6-hydroxypyrazolo[1,5-a]pyridine-3-carboxylate (0.025 g, 0.121 mmol) was dissolved in MeCN (1.00 mL)/THF (1.000 mL), then 1-(2-bromoethyl)-1H-pyrazole (0.023 g, 0.133 mmol) and cesium carbonate (0.079 g, 0.242 mmol) were added. The reaction mixture was stirred under microwave irradiation at 120° C. for 15 min. The reaction mixture was concentrated under reduced pressure, the residue was dissolved in MeOH (1 mL)/THF (1 mL), and LiOH (1 M aq.) (0.364 mL, 0.364 mmol) was added. The reaction mixture was stirred under microwave irradiation at 120° C. for 15 min. The reaction mixture was acidified with TFA, DMF was added, and the obtained solution was purified by preparative HPLC to afford Intermediate 35 (0.018 g, 55% yield) as a light-brown solid. MS(ESI) m/z: 272.9 (M+H)$^+$; $^1$H NMR (500 MHz, DMSO-d$_6$) δ ppm 8.59 (d, J=1.7 Hz, 1H), 8.29 (s, 1H), 7.94 (d, J=9.6 Hz, 1H), 7.80 (d, J=1.7 Hz, 1H), 7.47 (d, J=1.4 Hz, 1H), 7.29 (dd, J=9.6, 2.2 Hz, 1H), 6.25 (t, J=2.1 Hz, 1H), 4.55-4.49 (m, 2H), 4.46-4.41 (m, 2H).

Intermediate 36: 6-(4,4-difluoropiperidin-1-yl)pyrazolo[1,5-a]pyridine-3-carboxylic acid

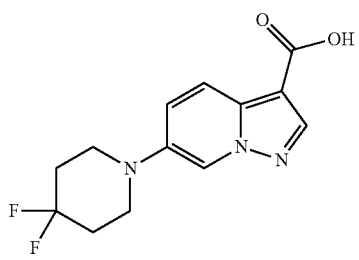 [SMILES: O=C(O)c1cnn2cc(N3CCC(F)(F)CC3)ccc12]

Intermediate 36 was prepared by following a similar procedure to that described for Intermediate 32 employing the appropriate amine. MS(ESI) m/z: 282.0 (M+H)$^+$; $^1$H NMR (500 MHz, DMSO-d$_6$) δ ppm 12.30 (s, 1H), 8.35 (d, J=1.7 Hz, 1H), 8.26 (s, 1H), 7.93 (d, J=9.6 Hz, 1H), 7.61 (dd, J=9.8, 2.1 Hz, 1H), 3.33 (br s, 4H), 2.18-2.06 (m, 4H); $^{19}$F-NMR: (471 MHz, DMSO-d$_6$) δ ppm −95.96 (br s, 2F).

Intermediate 37: 6-(2-(pyrrolidin-1-yl)ethoxy)pyrazolo[1,5-a]pyridine-3-carboxylic acid

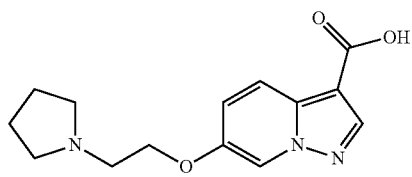 [SMILES: O=C(O)c1cnn2cc(OCCN3CCCC3)ccc12]

Intermediate 37 was prepared by following a similar procedure to that described for Intermediate 35 employing the appropriate alkyl halide/triflate. MS(ESI) m/z: 276.0 (M+H)$^+$; $^1$H NMR (500 MHz, DMSO-d$_6$) δ ppm 9.96 (br s, 1H), 8.78 (d, J=1.7 Hz, 1H), 8.40 (s, 1H), 8.08 (d, J=9.6 Hz, 1H), 7.48 (dd, J=9.6, 2.2 Hz, 1H), 4.50-4.45 (m, 2H), 3.71 (br d, J=4.1 Hz, 2H), 2.16-2.03 (m, 4H), 2.00-1.88 (m, 4H).

Intermediate 38: 5-morpholinopyrazolo[1,5-a]pyridine-3-carboxylic acid

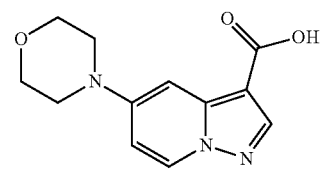 [SMILES: O=C(O)c1cnn2ccc(N3CCOCC3)cc12]

Intermediate 38 was prepared by following a similar procedure to that described for Intermediate 32 employing the appropriate amine. MS(ESI) m/z: 248.0 (M+H)$^+$.

Intermediate 39: 5-(1-methyl-1H-pyrazol-4-yl)pyrazolo[1,5-a]pyridine-3-carboxylic acid

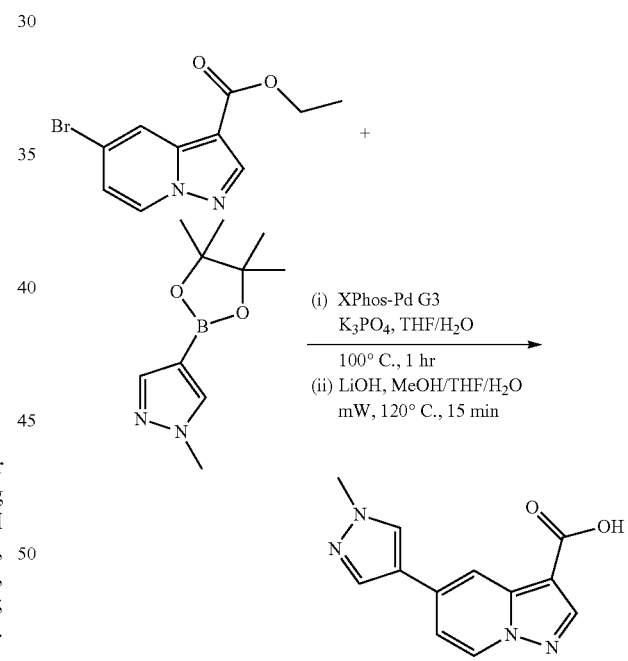

Ethyl 5-bromopyrazolo[1,5-a]pyridine-3-carboxylate (0.100 g, 0.372 mmol), 1-methyl-4-(4,4,5,5-tetramethyl-1,3,2-dioxaborolan-2-yl)-1H-pyrazole (0.101 g, 0.483 mmol) and XPhos-Pd G3 (7.9 mg, 9.3 μmol) were placed in a pressure vial. The reaction mixture was degassed (3× vacuum/Ar), then THF (2 mL) and potassium phosphate tribasic (0.5 M aq.) (1.12 mL, 0.557 mmol) were added. The reaction mixture was degassed again, and stirred at 100° C. for 1 h. Solvent was removed under reduced pressure. The obtained residue was dissolved in MeOH (1.0 mL)/THF (1.0 mL), and LiOH (1 M aq.) (1.12 mL, 1.12 mmol) was added. The reaction mixture was stirred under microwave irradiation at 120° C. for 15 min. The mixture was acidified with TFA, the solvent was removed under reduced pressure, the residue was purified by preparative HPLC to afford Intermediate 39 (0.055 g, 61% yield) as an off-white solid. MS(ESI) m/z: 243.0 (M+H)$^+$; $^1$H NMR (500 MHz, DMSO-d$_6$) δ ppm 8.81 (dd, J=7.2, 0.8 Hz, 1H), 8.43 (s, 1H), 8.33 (s, 1H), 8.10 (dd, J=1.9, 0.8 Hz, 1H), 8.05 (s, 1H), 7.36 (dd, J=7.3, 2.1 Hz, 1H), 3.90 (s, 3H).

Intermediate 40: 6-(4-methylpiperazin-1-yl)pyrazolo[1,5-a]pyridine-3-carboxylic acid

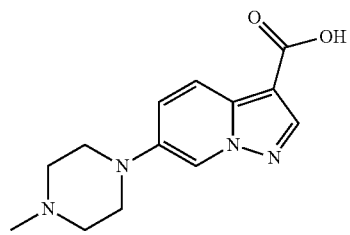 [SMILES: CN1CCN(c2ccc3c(C(=O)O)cnn3c2)CC1]

Intermediate 40 was prepared by following a similar procedure to that described for Intermediate 32 employing the appropriate amine. MS(ESI) m/z: 261.0 (M+H)$^+$; $^1$H NMR (500 MHz, DMSO-d$_6$) δ ppm 9.81 (br s, 1H), 8.41 (d, J=1.4 Hz, 1H), 8.28 (s, 1H), 7.96 (d, J=9.6 Hz, 1H), 7.59 (dd, J=9.8, 2.1 Hz, 1H), 3.84 (br d, J=12.9 Hz, 2H), 3.54 (br d, J=11.8 Hz, 2H), 3.21 (br d, J=9.4 Hz, 2H), 3.03 (br t, J=12.2 Hz, 2H), 2.87 (s, 3H).

Intermediate 41: 6-(pyrrolidin-1-yl)pyrazolo[1,5-a]pyridine-3-carboxylic acid

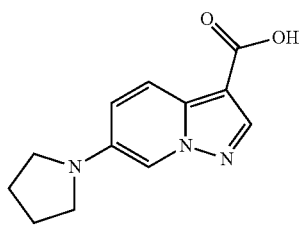 [SMILES: O=C(O)c1cnn2cc(N3CCCC3)ccc12]

Intermediate 41 was prepared by following a similar procedure to that described for Intermediate 32 employing the appropriate amine. MS(ESI) m/z: 232.0 (M+H)$^+$; $^1$H NMR (500 MHz, DMSO-d$_6$) δ ppm 12.15 (br s, 1H), 8.17 (s, 1H), 7.92 (d, J=1.9 Hz, 1H), 7.90 (d, J=9.4 Hz, 1H), 7.29 (dd, J=9.6, 2.2 Hz, 1H), 3.30-3.25 (m, 4H), 1.98 (dt, J=6.6, 3.3 Hz, 4H).

Intermediate 42: (R)-6-(3-fluoropyrrolidin-1-yl)pyrazolo[1,5-a]pyridine-3-carboxylic acid

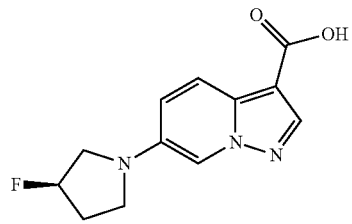 [SMILES: O=C(O)c1cnn2cc(N3CC[C@@H](F)C3)ccc12]

Intermediate 42 was prepared by following a similar procedure to that described for Intermediate 32 employing the appropriate amine. MS(ESI) m/z: 250.0 (M+H)$^+$; $^1$H NMR (500 MHz, DMSO-d$_6$) δ ppm 12.18 (br s, 1H), 8.19 (s, 1H), 8.02 (d, J=1.7 Hz, 1H), 7.92 (d, J=9.6 Hz, 1H), 7.32 (dd, J=9.5, 2.1 Hz, 1H), 5.57-5.40 (m, 1H), 3.64-3.51 (m, 2H), 3.46-3.37 (m, 2H), 2.33-2.17 (m, 2H); $^{19}$F-NMR: (471 MHz, DMSO-d$_6$) δ ppm −172.81 (s, 1F).

Intermediate 43: (S)-6-(3-fluoropyrrolidin-1-yl)pyrazolo[1,5-a]pyridine-3-carboxylic acid

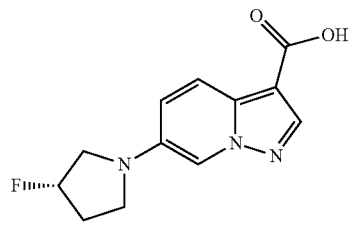 [SMILES: O=C(O)c1cnn2cc(N3CC[C@H](F)C3)ccc12]

Intermediate 43 was prepared by following a similar procedure to that described for Intermediate 32 employing the appropriate amine. MS(ESI) m/z: 250.0 (M+H)$^+$; $^1$H NMR (500 MHz, DMSO-d$_6$) δ ppm 8.19 (s, 1H), 8.02 (d, J=1.9 Hz, 1H), 7.92 (d, J=9.6 Hz, 1H), 7.32 (dd, J=9.5, 2.1 Hz, 1H), 5.57-5.39 (m, 1H), 3.65-3.50 (m, 2H), 3.46-3.38 (m, 2H), 2.33-2.14 (m, 2H). $^{19}$F-NMR: (471 MHz, DMSO-d$_6$) δ ppm −173.02 (s, 1F).

Intermediate 44: 6-(3,3-difluoropyrrolidin-1-yl)pyrazolo[1,5-a]pyridine-3-carboxylic acid

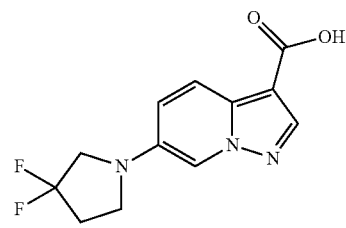 [SMILES: O=C(O)c1cnn2cc(N3CCC(F)(F)C3)ccc12]

Intermediate 44 was prepared by following a similar procedure to that described for Intermediate 32 employing the appropriate amine. MS(ESI) m/z: 268.0 (M+H)$^+$; $^1$H NMR (500 MHz, DMSO-d$_6$) δ ppm 12.24 (br s, 1H), 8.22 (s, 1H), 8.10 (d, J=1.7 Hz, 1H), 7.93 (d, J=9.6 Hz, 1H), 7.34

(dd, J=9.5, 2.1 Hz, 1H), 3.75 (t, J=13.3 Hz, 2H), 3.53 (t, J=7.2 Hz, 2H), 2.63-2.51 (m, 2H); ¹⁹F-NMR: (471 MHz, DMSO-d₆) δ ppm −96.75 (s, 2F).

Intermediate 45: 6-(3-fluoroazetidin-1-yl)pyrazolo[1,5-a]pyridine-3-carboxylic acid

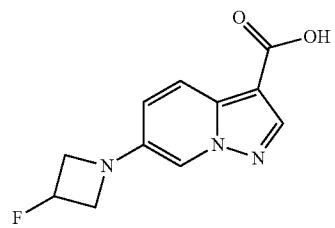 [SMILES: O=C(O)c1cnn2cc(N3CC(F)C3)ccc12]

Intermediate 45 was prepared by following a similar procedure to that described for Intermediate 32 employing the appropriate amine. MS(ESI) m/z: 235.9 (M+H)⁺; ¹H NMR (500 MHz, DMSO-d₆) δ ppm 12.25 (br s, 1H), 8.22 (s, 1H), 8.04 (d, J=1.9 Hz, 1H), 7.96-7.90 (m, 1H), 7.10 (dd, J=9.4, 2.2 Hz, 1H), 5.60-5.40 (m, 1H), 4.21 (dddd, J=20.5, 9.4, 5.6, 1.1 Hz, 2H), 3.95 (dddd, J=24.0, 9.3, 3.3, 1.1 Hz, 2H); ¹⁹F-NMR: (471 MHz, DMSO-d₆) δ ppm −179.34 (s, 1F).

Intermediate 46: 6-(3,3-difluoroazetidin-1-yl)pyrazolo[1,5-a]pyridine-3-carboxylic acid

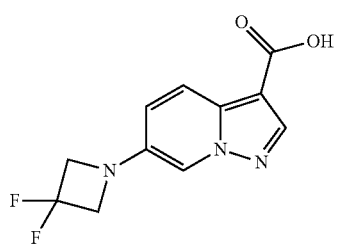 [SMILES: O=C(O)c1cnn2cc(N3CC(F)(F)C3)ccc12]

Intermediate 46 was prepared by following a similar procedure to that described for Intermediate 32 employing the appropriate amine. MS(ESI) m/z: 253.9 (M+H)⁺; ¹H NMR: (500 MHz, DMSO-d₆) δ ppm 12.30 (s, 1H), 8.25 (s, 1H), 8.18 (d, J=1.9 Hz, 1H), 7.96 (d, J=9.6 Hz, 1H), 7.16 (dd, J=9.5, 2.1 Hz, 1H), 4.35 (t, J=12.2 Hz, 4H); ¹⁹F-NMR: (471 MHz, DMSO-d₆) δ ppm −98.56 (s, 2F).

Intermediate 47: methyl 6-(benzyloxy)-7-bromopyrazolo[1,5-a]pyridine-3-carboxylate

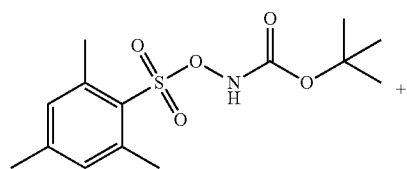

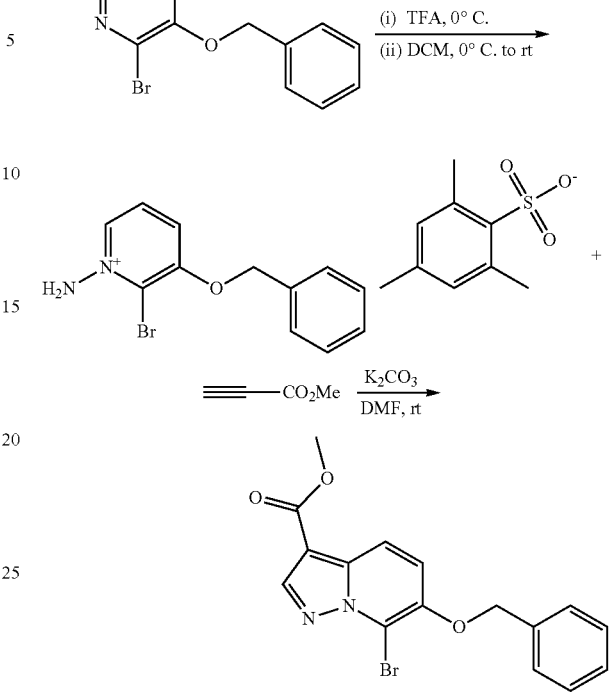

TFA (30 mL) was placed in the round-bottom flask equipped with a magnetic stirred, and the reaction mixture was cooled to 0° C. under Ar. Then, tert-butyl (mesitylsulfonyl)oxycarbamate (6.34 g, 20.00 mmol) was added portionwise over 5 min, and the reaction mixture was stirred at 0° C. for 1 h under Ar. Afterwards, the reaction mixture was quenched with ice water (100 mL), producing white solid. The reaction mixture was diluted with cold water (150 mL), the solid was filtered off, and was washed with cold water until pH~7.0. The obtained solid was dissolved in DCM (75.0 mL), and was stirred with Na₂SO₄ at 0° C. for 15 min to remove water. Afterwards, Na₂SO₄ was removed by filtration, and the DCM solution was added to a cooled (ice bath) solution of 3-(benzyloxy)-2-bromopyridine (4.41 g, 16.1 mmol) in DCM (25 mL). The reaction mixture was stirred at 0° C. for 2 h. Then, ice bath was removed, and the reaction mixture was allowed to reach rt and was stirred at this temperature for 1 h. Solvent was removed under reduced pressure, the residue was dissolved in DMF (100 mL), then methyl propiolate (2.86 mL, 32.1 mmol) and K₂CO₃ (6.66 g, 48.2 mmol) were added sequentially. The obtained suspension was stirred at rt for 16 h. The reaction mixture was diluted with EtOAc (500 mL), washed with water (3×250 mL), brine (1×250 mL), dried (Na₂SO₄) and filtered. The residue was purified by flash chromatography to give Intermediate 47 (0.88 g, 15% yield) as an off-white solid. MS(ESI) m/z: 260.8 (M+H)⁺; ¹H NMR (300 MHz, CDCl₃) δ ppm 8.45 (s, 1H), 8.15 (d, J=9.6 Hz, 1H), 7.48-7.16 (m, 6H), 5.24 (s, 2H), 3.91 (s, 3H).

Intermediate 48: 7-cyclopropyl-6-(2-hydroxy-2-methylpropoxy)pyrazolo[1,5-a]pyridine-3-carboxylic acid

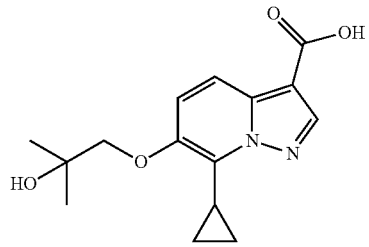 [SMILES: CC(C)(O)COc1ccc2c(C(=O)O)cnn2c1C1CC1]

Intermediate 48A: methyl 6-(benzyloxy)-7-cyclopropylpyrazolo[1,5-a]pyridine-3-carboxylate

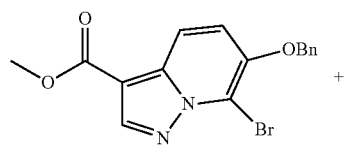

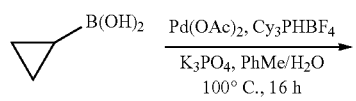

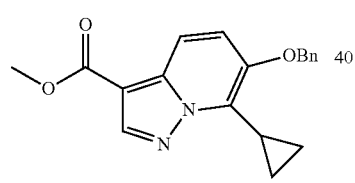

Intermediate 47 (350 mg, 0.969 mmol), cyclopropylboronic acid (333 mg, 3.88 mmol), palladium(II) acetate (10.98 mg, 0.048 mmol), tricyclohexylphosphonium tetrafluoroborate (35.7 mg, 0.097 mmol) and phosphoric acid, potassium salt (617 mg, 2.91 mmol) were placed in a pressure vial, and the mixture was degassed (3×Ar/vacuum). Then, PhMe (10.0 mL) and water (0.2 mL) were added, and the reaction mixture was degassed again. Afterwards, the vial was capped, the reaction mixture was heated to 100° C. for 16 h. Solvent was removed under reduced pressure, and the residue was purified by flash chromatography to give Intermediate 48A (279 mg, 89% yield) as a white solid. MS(ESI) m/z: 323.0 (M+H)$^+$; $^1$H NMR (500 MHz, DMSO-d$_6$) δ ppm 8.38 (s, 1H), 7.98 (d, J=9.4 Hz, 1H), 7.46-7.38 (m, 4H), 7.37-7.33 (m, 1H), 7.30 (d, J=9.6 Hz, 1H), 5.11 (s, 2H), 3.89 (s, 3H), 2.49 (tt, J=8.7, 5.6 Hz, 1H), 1.46-1.41 (m, 2H), 1.17-1.11 (m, 2H).

Intermediate 48B: methyl 7-cyclopropyl-6-hydroxypyrazolo[1,5-a]pyridine-3-carboxylate

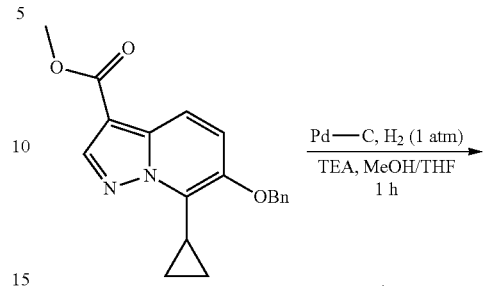

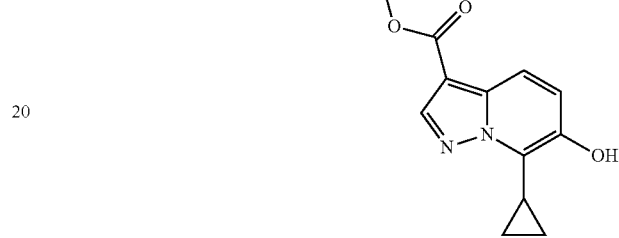

Intermediate 48A (150 mg, 0.465 mmol) was dissolved in THF (4 mL) and MeOH (4 mL), and TEA (0.324 mL, 2.33 mmol) was added. The reaction mixture was degassed (3× vacuum/Ar), then palladium on carbon (10 wt %) (49.5 mg, 0.047 mmol) was added. The reaction mixture was degassed again, and it was stirred under dihydrogen atmosphere (1 atm; balloon) for 1 h. Pd—C was filtered off using membrane filter, and the filtrate was concentrated to afford Intermediate 48B (103 mg, 95% yield) as a white solid. MS(ESI) m/z: 233.1 (M+H)$^+$; $^1$H NMR (500 MHz, DMSO-d$_6$) δ ppm 9.74 (br s, 1H), 8.32 (s, 1H), 7.81 (d, J=9.4 Hz, 1H), 7.30 (d, J=9.4 Hz, 1H), 3.79 (s, 3H), 2.48-2.44 (m, 1H), 1.44-1.37 (m, 2H), 1.06-0.98 (m, 2H).

Intermediate 48

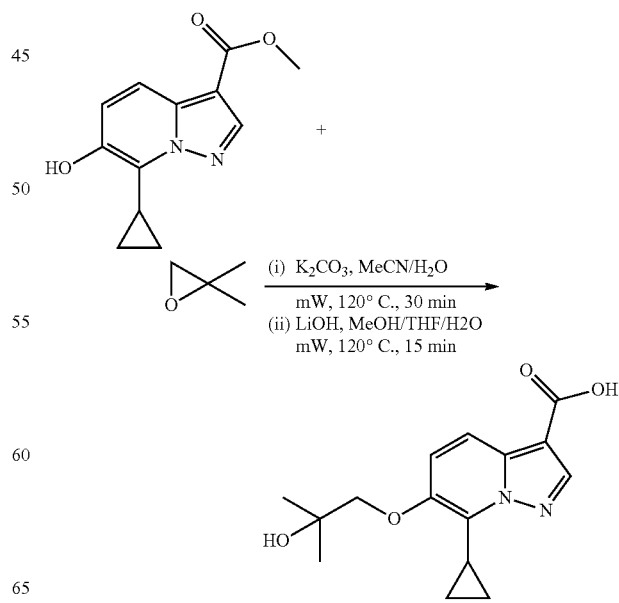

Intermediate 48B (0.050 g, 0.215 mmol) was suspended in MeCN (2.0 mL), then 2,2-dimethyloxirane (0.288 mL, 3.23 mmol), $K_2CO_3$ (0.119 g, 0.861 mmol) and water (0.133 mL) were added. The reaction mixture was stirred under microwave irradiation at 120° C. for 30 min. The reaction mixture was concentrated under reduced pressure, the residue was dissolved in MeOH (1 mL)/THF (1 mL), and LiOH (1 M aq.) (0.646 mL, 0.646 mmol) was added. The reaction mixture was stirred under microwave irradiation at 120° C. for 15 min. Solvent was removed under reduced pressure, the residue was purified by preparative HPLC to afford Intermediate 48 (0.037 g, 59% yield) as a white solid. MS(ESI) m/z: 291.0 (M+H)$^+$; $^1$H NMR (500 MHz, DMSO-$d_6$) δ ppm 8.34 (s, 1H), 7.90 (d, J=9.6 Hz, 1H), 7.57 (d, J=9.6 Hz, 1H), 3.81 (s, 2H), 2.63 (tt, J=8.8, 5.6 Hz, 1H), 1.55-1.49 (m, 2H), 1.25 (s, 6H), 1.11-1.02 (m, 2H).

Intermediate 49: 6-(3,3,3-trifluoro-2-hydroxy-2-(trifluoromethyl)propoxy)pyrazolo[1,5-a]pyridine-3-carboxylic acid

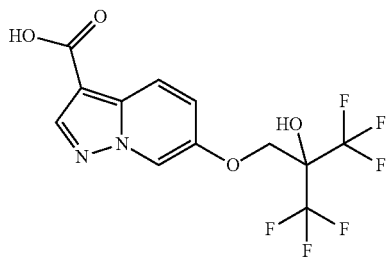 [SMILES: O=C(O)c1cnn2cc(OCC(O)(C(F)(F)F)C(F)(F)F)ccc12]

Intermediate 49 was prepared by following a similar procedure to that described for Intermediate 29 employing the appropriate oxirane. MS(ESI) m/z: 359.0 (M+H)$^+$; $^1$H NMR (500 MHz, DMSO-$d_6$) δ ppm 12.43 (br s, 1H), 8.81 (d, J=1.7 Hz, 1H), 8.51 (s, 1H), 8.33 (s, 1H), 8.00 (d, J=9.6 Hz, 1H), 7.38 (dd, J=9.6, 2.2 Hz, 1H), 4.54 (s, 2H); $^{19}$F-NMR: (471 MHz, DMSO-$d_6$) δ ppm −74.51 (s, 3F).

Intermediate 50: 6-(benzyloxy)pyrazolo[1,5-a]pyridine-3-carboxylic acid

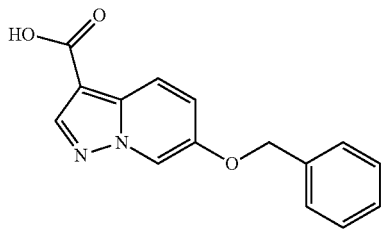 [SMILES: O=C(O)c1cnn2cc(OCc3ccccc3)ccc12]

Intermediate 50 was prepared by following a similar procedure to that described for Intermediate 35 employing the appropriate alkyl/benzyl halide/triflate/methanesulfonate. MS(ESI) m/z: 269.0 (M+H)$^+$; $^1$H NMR (500 MHz, DMSO-$d_6$) δ ppm 12.38 (s, 1H), 8.66 (d, J=1.7 Hz, 1H), 8.30 (s, 1H), 7.98 (d, J=9.6 Hz, 1H), 7.50 (d, J=7.2 Hz, 2H), 7.45-7.39 (m, 3H), 7.39-7.32 (m, 1H), 5.20 (s, 2H).

Intermediate 51: 6-((tetrahydrofuran-3-yl)oxy)pyrazolo[1,5-a]pyridine-3-carboxylic acid

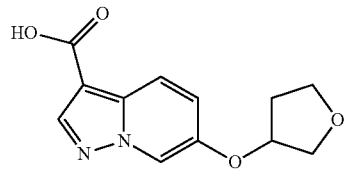 [SMILES: O=C(O)c1cnn2cc(OC3CCOC3)ccc12]

Intermediate 51 was prepared by following a similar procedure to that described for Intermediate 35 employing the appropriate alkyl/benzyl halide/triflate/methanesulfonate. MS(ESI) m/z: 249.0 (M+H)$^+$; $^1$H NMR (500 MHz, DMSO-$d_6$) δ ppm 12.36 (br s, 1H), 8.58 (d, J=1.7 Hz, 1H), 8.30 (s, 1H), 7.96 (d, J=9.6 Hz, 1H), 7.34 (dd, J=9.6, 2.2 Hz, 1H), 5.12 (ddt, J=6.1, 4.0, 1.7 Hz, 1H), 3.93-3.83 (m, 3H), 3.77 (td, J=8.4, 4.4 Hz, 1H), 2.32-2.20 (m, 1H), 2.09-1.98 (m, 1H).

Intermediate 52: 6-(3,3,3-trifluoro-2-hydroxypropoxy)pyrazolo[1,5-a]pyridine-3-carboxylic acid

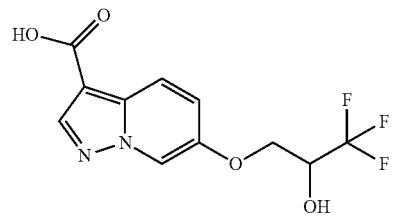 [SMILES: O=C(O)c1cnn2cc(OCC(O)C(F)(F)F)ccc12]

Intermediate 52 was prepared by following a similar procedure to that described for Intermediate 35 employing the appropriate alkyl/benzyl halide/triflate/methanesulfonate. MS(ESI) m/z: 291.0 (M+H)$^+$; $^1$H NMR (500 MHz, DMSO-$d_6$) δ ppm 12.39 (br s, 1H), 8.69 (d, J=1.9 Hz, 1H), 8.31 (s, 1H), 7.98 (d, J=9.4 Hz, 1H), 7.38 (dd, J=9.6, 2.2 Hz, 1H), 6.72 (br d, J=6.1 Hz, 1H), 4.45 (br s, 1H), 4.30 (dd, J=10.7, 3.9 Hz, 1H), 4.18 (dd, J=10.6, 6.5 Hz, 1H); $^{19}$F-NMR: (471 MHz, DMSO-$d_6$) δ ppm −75.93 (s, 3F).

Intermediate 53: 7-carbamoyl-6-(2-hydroxy-2-methylpropoxy)pyrazolo[1,5-a]pyridine-3-carboxylic acid

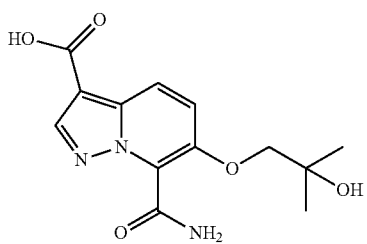 [SMILES: CC(C)(O)COc1ccc2c(C(=O)O)cnn2c1C(N)=O]

Intermediate 54: 7-cyano-6-hydroxypyrazolo[1,5-a]pyridine-3-carboxylic acid

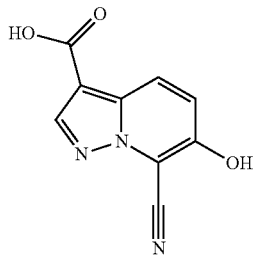 [SMILES: N#Cc1c(O)ccc2c(C(=O)O)cnn12]

Intermediate 54A: methyl 6-(benzyloxy)-7-cyano-pyrazolo[1,5-a]pyridine-3-carboxylate

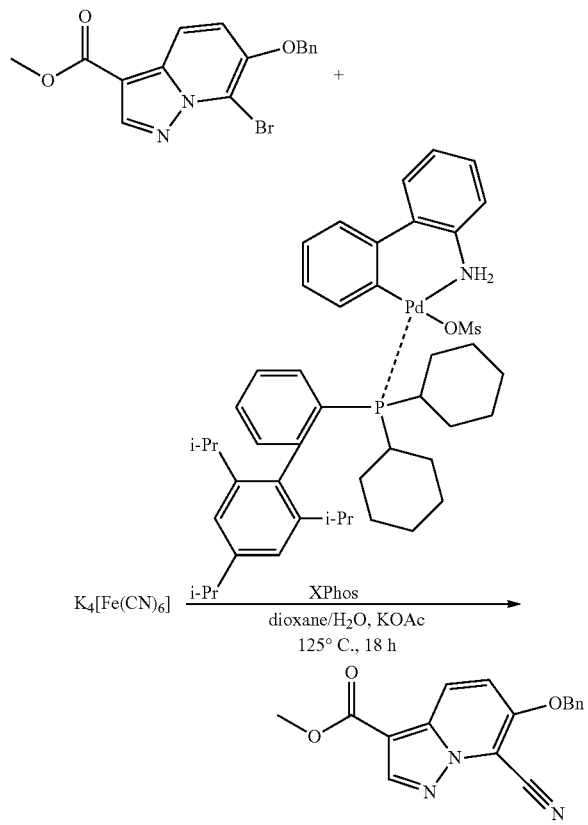

Intermediate 47 (350 mg, 0.969 mmol), potassium ferrocyanide, 3H$_2$O (205 mg, 0.485 mmol), XPhos (11.6 mg, 0.024 mmol), Pd-XPhos G3 (20.5 mg, 0.024 mmol) were placed in a pressure vial. Then dioxane (10.0 mL) and Potassium acetate (0.1 M aq) (1.21 mL, 0.121 mmol) were added, and the reaction mixture was degassed (3×, vacuum/Ar). The pressure vial was capped, and the reaction mixture was stirred at 100° C. for 16 h. Additional amounts of XPhos (11.6 mg, 0.024 mmol) and Pd-XPhos G3 (20.5 mg, 0.024 mmol) were added, the reaction mixture was degassed, and was stirred at 125° C. for 18 h. The reaction mixture was diluted with EtOAc, and CELITE® was added. Solvent was removed under reduced pressure, and the residue was purified by flash chromatography (solid loading on CELITE®) to give Intermediate 54A (163 mg, 55% yield) as an off-white solid. MS(ESI) m/z: 308.0 (M+H)$^+$; $^1$H NMR (500 MHz, DMSO-d$_6$) δ ppm 8.54 (s, 1H), 8.34 (d, J=9.9 Hz, 1H), 7.93 (d, J=9.9 Hz, 1H), 7.54-7.49 (m, 2H), 7.48-7.42 (m, 2H), 7.40-7.33 (m, 1H), 5.50 (s, 2H), 3.85 (s, 3H).

Intermediate 54B: methyl 7-cyano-6-hydroxypyrazolo[1,5-a]pyridine-3-carboxylate

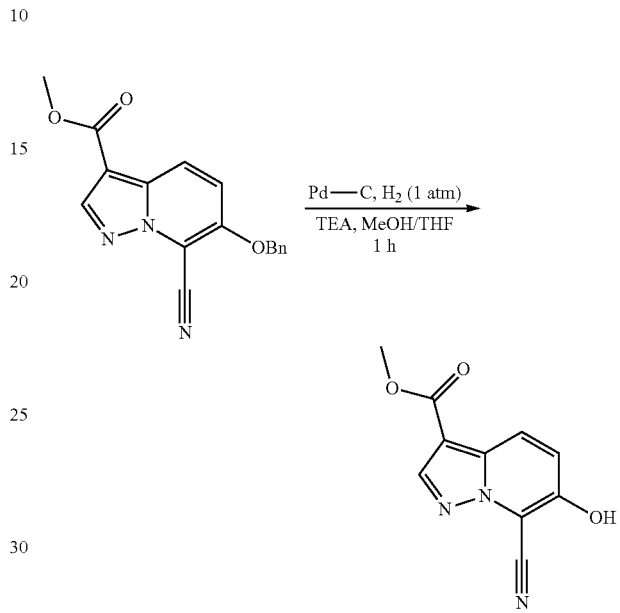

Intermediate 54A (150 mg, 0.488 mmol) was dissolved in THF (4 mL) and MeOH (4 mL), and TEA (0.34 mL, 2.44 mmol) was added. The reaction mixture was degassed (3× vacuum/Ar), then palladium on carbon (10 wt %) (51.9 mg, 0.049 mmol) was added. The reaction mixture was degassed again, and it was stirred under dihydrogen atmosphere (1 atm; balloon) for 1 h. Pd—C was filtered off using membrane filter, and the filtrate was concentrated to afford crude material, which was further purified by flash chromatography to give Intermediate 54B (50 mg, 47% yield) as a yellow solid. MS(ESI) m/z: 218.0 (M+H)$^+$; $^1$H NMR (500 MHz, DMSO-d$_6$) δ ppm 8.43 (s, 1H), 8.21 (d, J=9.6 Hz, 1H), 7.43 (d, J=9.6 Hz, 1H), 3.83 (s, 3H).

Intermediate 53: 7-carbamoyl-6-(2-hydroxy-2-methylpropoxy)pyrazolo[1,5-a]pyridine-3-carboxylic acid

Intermediate 54: 7-cyano-6-hydroxypyrazolo[1,5-a]pyridine-3-carboxylic acid

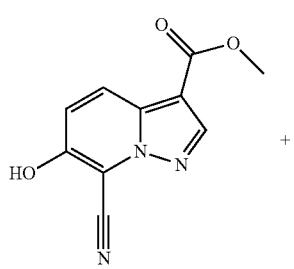

172

Intermediate 55A: methyl 6-(benzyloxy)-7-methyl-pyrazolo[1,5-a]pyridine-3-carboxylate

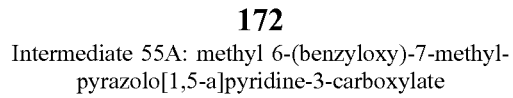

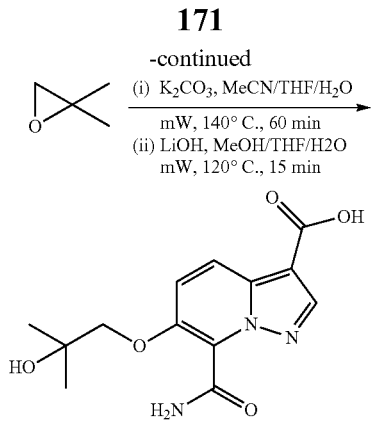

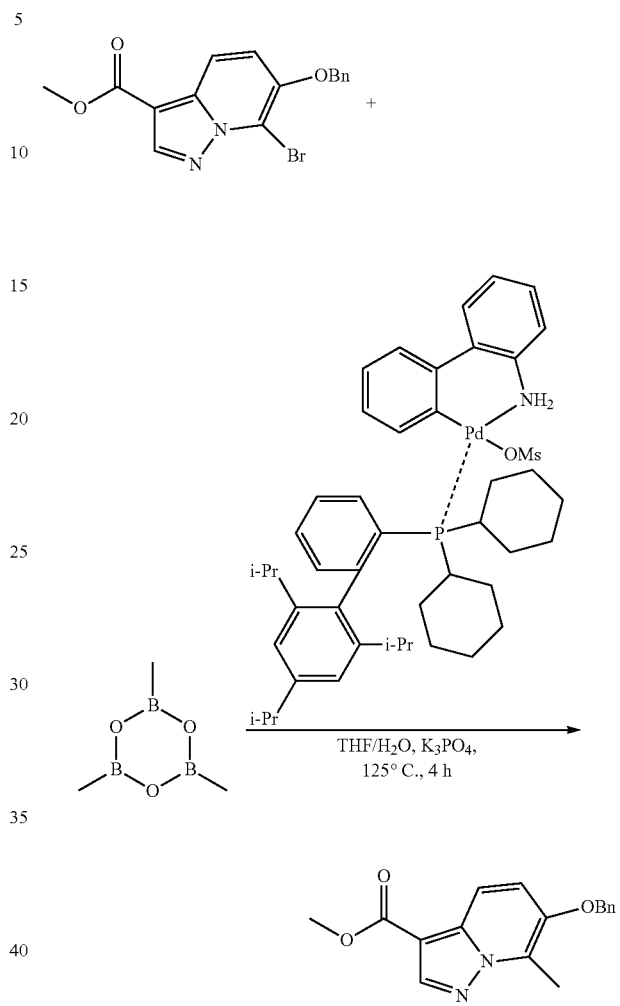

Intermediate 54B (0.050 g, 0.230 mmol) was suspended in MeCN (2.0 mL), then 2,2-dimethyloxirane (0.308 mL, 3.45 mmol), K₂CO₃ (0.127 g, 0.921 mmol) and water (0.133 mL) were added. The reaction mixture was stirred under microwave irradiation at 120° C. for 30 min. Additional amount of 2,2-dimethyloxirane (0.308 mL, 3.45 mmol) was added along with THF (1 mL), and the reaction mixture was stirred under microwave irradiation at 140° C. for 60 min. The reaction mixture was concentrated under reduced pressure, the residue was dissolved in MeOH (1 mL)/THF (1 mL), and LiOH (1 M aq.) (0.276 mL, 0.276 mmol) was added. The reaction mixture was stirred under microwave irradiation at 120° C. for 15 min. Solvent was removed under reduced pressure, the residue was purified by preparative HPLC to afford Intermediate 53 and Intermediate 54.

Intermediate 53 (5 mg, 7% yield) as an off-white solid. MS(ESI) m/z: 294.0 (M+H)⁺; ¹H NMR (500 MHz, THF-d₈) δ ppm 8.27 (s, 1H), 8.17 (d, J=9.6 Hz, 1H), 7.51 (d, J=9.6 Hz, 1H), 3.96 (s, 2H), 1.23 (s, 6H).

Intermediate 54 (5 mg, 11% yield) as an off-white solid. MS(ESI) m/z: 204.0 (M+H)⁺; ¹H NMR (500 MHz, DMSO-d₆) δ ppm 12.66 (br s, 1H), 12.22 (br s, 1H), 8.36 (s, 1H), 8.21 (d, J=9.6 Hz, 1H), 7.40 (d, J=9.6 Hz, 1H).

Intermediate 55: 6-(2-hydroxy-2-methylpropoxy)-7-methylpyrazolo[1,5-a]pyridine-3-carboxylic acid

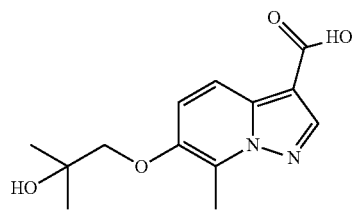 [SMILES: Cc1c(OCC(C)(C)O)ccc2c(C(=O)O)cnn12]

Intermediate 47 (350 mg, 0.969 mmol), 2,4,6-trimethyl-1,3,5,2,4,6-trioxatriborinane (0.203 mL, 1.45 mmol) and Pd-XPhos G3 (20.5 mg, 0.024 mmol) were placed in a pressure vial. Then THF (10 mL) and phosphoric acid, potassium salt (0.5 M aq.) (3.88 mL, 1.94 mmol) were added, and the reaction mixture was degassed (3×, vacuum/Ar). The pressure vial was capped, and the reaction mixture was stirred at 100° C. for 16 h. Additional amounts of Pd-XPhos G3 (20.5 mg, 0.024 mmol) and 2,4,6-trimethyl-1,3,5,2,4,6-trioxatriborinane (0.203 mL, 1.45 mmol) were added, the reaction mixture was degassed, and was stirred at 125° C. for 4 h. The reaction mixture was diluted with EtOAc, and CELITE® was added. Solvent was removed under reduced pressure, and the residue was purified by flash chromatography (solid loading on CELITE®) to give Intermediate 55A (166 mg, 58% yield) as a white solid. MS(ESI) m/z: 297.0 (M+H)⁺; ¹H NMR (500 MHz, DMSO-d₆) δ ppm 8.39 (s, 1H), 8.01 (d, J=9.6 Hz, 1H), 7.44-7.36 (m, 5H), 7.26 (s, 1H), 5.13 (s, 2H), 3.90 (s, 3H), 2.72 (s, 3H).

Intermediate 55B: methyl 6-hydroxy-7-methylpyrazolo[1,5-a]pyridine-3-carboxylate

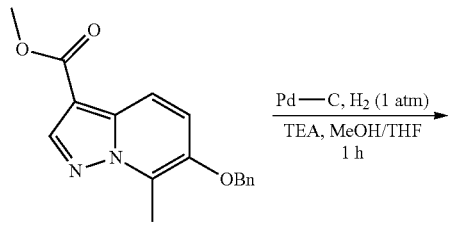

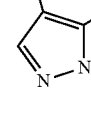

Intermediate 55A (150 mg, 0.506 mmol) was dissolved in THF (4 mL) and MeOH (4 mL), and TEA (0.353 mL, 2.53 mmol) was added. The reaction mixture was degassed (3× vacuum/Ar), then palladium on carbon (10 wt %) (53.9 mg, 0.051 mmol) was added. The reaction mixture was degassed again, and it was stirred under dihydrogen atmosphere (1 atm; balloon) for 1 h. Pd—C was filtered off using membrane filter, and the filtrate was concentrated to afford Intermediate 55B (90 mg, 86% yield) as a white solid. MS(ESI) m/z: 207.0 (M+H)$^+$; $^1$H NMR (500 MHz, DMSO-$d_6$) δ ppm 9.88 (br s, 1H), 8.34 (s, 1H), 7.85 (d, J=8.8 Hz, 1H), 7.37 (d, J=9.4 Hz, 1H), 3.80 (s, 3H), 2.60 (s, 3H).

Intermediate 55: 6-(2-hydroxy-2-methylpropoxy)-7-methylpyrazolo[1,5-a]pyridine-3-carboxylic acid

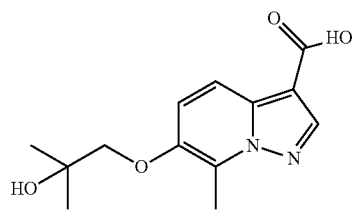 [SMILES: Cc1c(OCC(C)(C)O)ccc2c(C(=O)O)cnn12]

Intermediate 55 was prepared from Intermediate 55B by following a similar procedure to that described for Intermediate 29 employing the appropriate oxirane. MS(ESI) m/z: 265.0 (M+H)$^+$; $^1$H NMR (500 MHz, DMSO-$d_6$) δ ppm 8.36 (s, 1H), 7.94 (d, J=9.5 Hz, 1H), 7.61 (d, J=9.7 Hz, 1H), 3.82 (s, 2H), 2.67 (s, 3H), 1.24 (s, 6H).

Intermediate 56: 6-(2-hydroxy-2-methylpropoxy)-7-(methoxymethyl)pyrazolo[1,5-a]pyridine-3-carboxylic acid

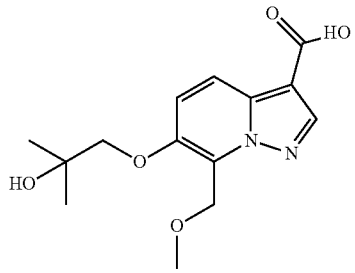 [SMILES: COCc1c(OCC(C)(C)O)ccc2c(C(=O)O)cnn12]

Intermediate 56A: methyl 6-(benzyloxy)-7-(methoxymethyl)pyrazolo[1,5-a]pyridine-3-carboxylate

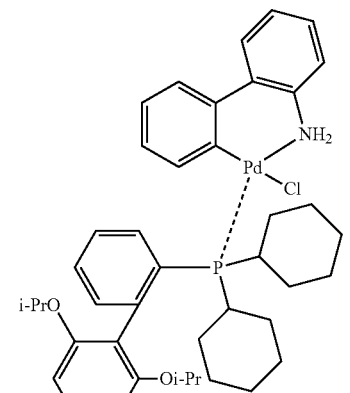

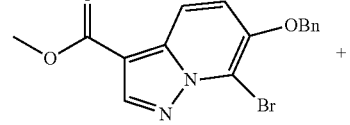

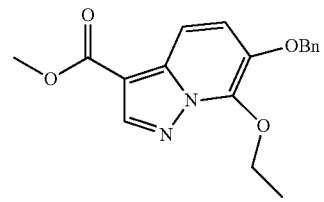

A pressure vial was charged with Intermediate 47 (350 mg, 0.969 mmol), potassium (methoxymethyl)trifluoroborate (295 mg, 1.94 mmol), RuPhos-Pd G2 (37.6 mg, 0.048 mmol) and cesium carbonate (947 mg, 2.91 mmol). The mixture was degassed (3×, vacuum/Ar). Then dioxane (10 mL) and water (1.000 mL) were added, and the reaction mixture was degassed again. The pressure vial was capped, and the reaction mixture was stirred at 100° C. for 18 h. Additional amounts of potassium (methoxymethyl)trifluoroborate (295 mg, 1.938 mmol), SPhos-Pd G2 (34.7 mg, 0.048 mmol), and cesium carbonate (947 mg, 2.91 mmol) were added. The reaction mixture was degassed (3× vacuum/Ar), the pressure vial was capped, and the reaction mixture was stirred at 100° C. for 18 h. Additional amount of SPhos-Pd G2 (34.7 mg, 0.048 mmol) was added, the reaction mixture was degassed, and was stirred at 125° C. for 18 h. The reaction mixture was diluted with EtOAc, and CELITE® was added. Solvent was removed under reduced pressure, and the residue was purified by flash chromatography (solid loading on CELITE®) to give Intermediate 56A (61 mg, 19% yield) as an off-white solid. MS(ESI) m/z: 327.0 (M+H)+; 1H NMR (500 MHz, DMSO-d6) δ ppm 8.44 (s, 1H), 8.09 (d, J=9.6 Hz, 1H), 7.81 (d, J=9.6 Hz, 1H), 7.51-7.46 (m, 2H), 7.44-7.38 (m, 2H), 7.37-7.31 (m, 1H), 5.28 (s, 2H), 4.94 (s, 2H), 3.83 (s, 3H), 3.32 (s, 3H).

Intermediate 56B: methyl 6-hydroxy-7-(methoxymethyl)pyrazolo[1,5-a]pyridine-3-carboxylate

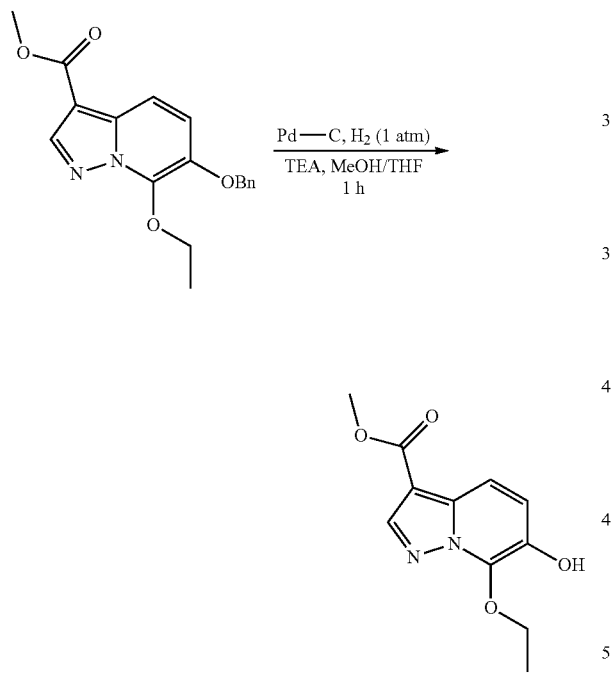

Intermediate 56A (50 mg, 0.153 mmol) was dissolved in THF (4 mL) and MeOH (4 mL), and TEA (0.107 mL, 0.766 mmol) was added. The reaction mixture was degassed (3× vacuum/Ar), then palladium on carbon (10 wt %) (16.3 mg, 0.015 mmol) was added. The reaction mixture was degassed again, and it was stirred under dihydrogen atmosphere (1 atm; balloon) for 1 h. Pd—C was filtered off using membrane filter, and the filtrate was concentrated to afford Intermediate 56B (36 mg, 99% yield) as a colorless film. MS(ESI) m/z: 237.0 (M+H)+; 1H NMR (500 MHz, DMSO-d6) δ ppm 8.33 (s, 1H), 7.96 (d, J=9.6 Hz, 1H), 7.39 (d, J=9.4 Hz, 1H), 4.90 (s, 2H), 3.81 (s, 3H), 3.32 (s, 3H).

Intermediate 56: 6-(2-hydroxy-2-methylpropoxy)-7-(methoxymethyl)pyrazolo[1,5-a]pyridine-3-carboxylic acid

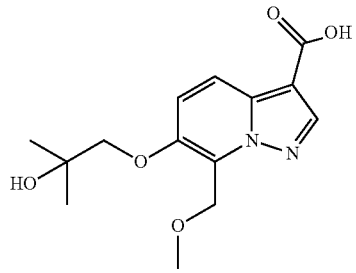

Intermediate 56 was prepared from Intermediate 56B by following a similar procedure to that described for Intermediate 29 employing the appropriate oxirane. MS(ESI) m/z: 295.0 (M+H)+; 1H NMR (500 MHz, DMSO-d6) δ ppm 8.25 (s, 1H), 8.12 (d, J=9.7 Hz, 1H), 7.50 (d, J=9.5 Hz, 1H), 5.09 (s, 2H), 3.90 (s, 2H), 3.39 (s, 3H), 1.30 (s, 6H).

Intermediate 57: methyl 6-(benzyloxy)-7-((dimethylamino)methyl)pyrazolo[1,5-a]pyridine-3-carboxylate

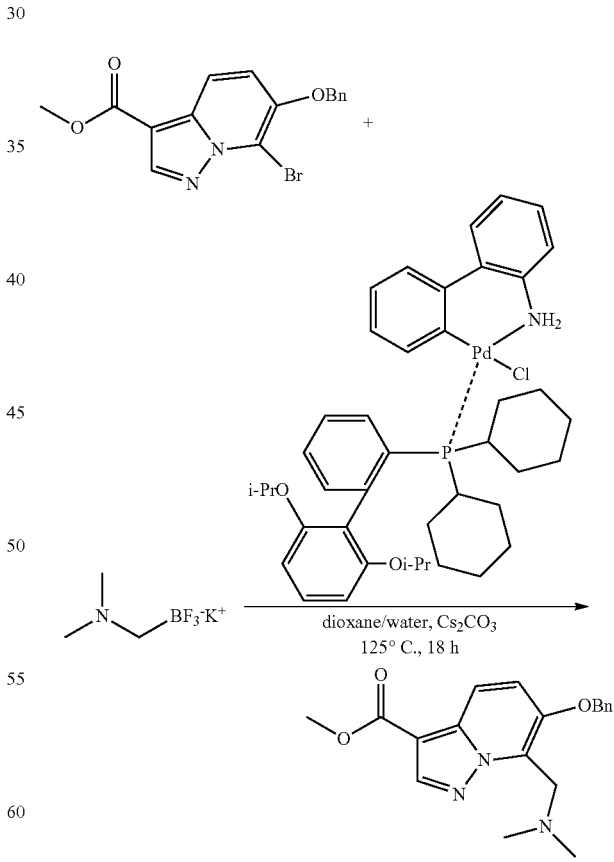

A pressure vial was charged with Intermediate 47 (350 mg, 0.969 mmol), potassium ((dimethylamino)methyl)trifluoroborate (320 mg, 1.938 mmol), RuPhos-Pd G2 (37.6 mg, 0.048 mmol) and cesium carbonate (947 mg, 2.91 mmol). The mixture was degassed (3×, vacuum/Ar). Then dioxane (10 mL) and water (1.000 mL) were added, and the reaction mixture was degassed again. The pressure vial was capped, and the reaction mixture was stirred at 125° C. for 18 h. Additional amount of RuPhos-Pd G2 (37.6 mg, 0.048 mmol) was added, the reaction mixture was degassed (3× Ar/vacuum), and was stirred at 125° C. for 18 h. The reaction mixture was diluted with EtOAc, and CELITE® was added. Solvent was removed under reduced pressure, and the residue was purified by flash chromatography (solid loading on CELITE®) to give Intermediate 57 (60 mg, 18% yield) as an off-white solid. MS(ESI) m/z: 340.1 (M+H)+; 1H NMR (500 MHz, DMSO-d6) δ ppm 8.43 (s, 1H), 8.05 (d, J=9.6 Hz, 1H), 7.81 (d, J=9.6 Hz, 1H), 7.50 (d, J=7.2 Hz, 2H), 7.42 (t, J=7.4 Hz, 2H), 7.38-7.31 (m, 1H), 5.25 (s, 2H), 4.00 (s, 2H), 3.83 (s, 3H), 2.22 (s, 6H).

Intermediate 58: methyl 6-((1,3-difluoropropan-2-yl)oxy)pyrazolo[1,5-a]pyridine-3-carboxylate

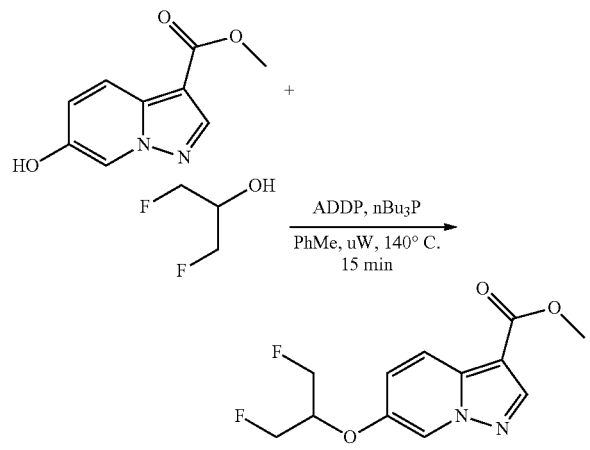

Methyl 6-hydroxypyrazolo[1,5-a]pyridine-3-carboxylate (0.100 g, 0.520 mmol), 1,3-difluoropropan-2-ol (0.090 mL, 1.04 mmol), and 1,1'-(azodicarbonyl)dipiperidine (0.394 g, 1.56 mmol) were placed in a pressure vial. Then, anhydrous PhMe (5 mL) and tri-N-butylphosphine (0.390 mL, 1.56 mmol) were added, and the reaction mixture was stirred at 140° C. under microwave irradiation for 15 min. The reaction mixture was quenched with MeOH (1 mL), diluted with EtOAc (50 mL), CELITE® was added, and solvent was removed under reduced pressure. The residue was purified by flash chromatography (solid loading on CELITE®) to give Intermediate 58 (0.124 g, 88% yield) as a white solid. MS(ESI) m/z: 271.0 (M+H)+; 1H NMR (500 MHz, DMSO-d6) δ ppm 8.83 (d, J=1.7 Hz, 1H), 8.39 (s, 1H), 8.01 (d, J=9.6 Hz, 1H), 7.49 (dd, J=9.5, 2.3 Hz, 1H), 5.11-4.96 (m, 1H), 4.90-4.84 (m, 1H), 4.80-4.72 (m, 2H), 4.67 (dd, J=10.6, 5.1 Hz, 1H), 3.82 (s, 3H); 19F-NMR: (471 MHz, DMSO-d6) δ ppm −231.76 (s, 2F).

Intermediate 59: methyl 6-((1,1-dioxidotetrahydro-2H-thiopyran-4-yl)oxy)pyrazolo[1,5-a]pyridine-3-carboxylate

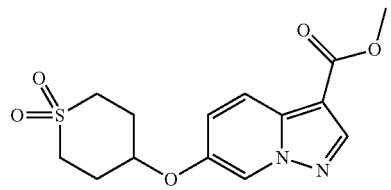 [SMILES: COC(=O)c1cnn2cc(OC3CCS(=O)(=O)CC3)ccc12]

Intermediate 59 was prepared by following a similar procedure to that described for Intermediate 58 employing the appropriate alcohol. MS(ESI) m/z: 325.0 (M+H)+; 1H NMR (500 MHz, DMSO-d6) δ ppm 8.84 (d, J=2.2 Hz, 1H), 8.39 (s, 1H), 8.00 (d, J=9.4 Hz, 1H), 7.53 (dd, J=9.6, 1.9 Hz, 1H), 4.78 (quin, J=4.6 Hz, 1H), 3.82 (s, 3H), 3.30-3.23 (m, 2H), 3.19-3.12 (m, 2H), 2.26 (q, J=5.4 Hz, 4H).

Intermediate 60: methyl 6-(3,3,3-trifluoropropoxy)pyrazolo[1,5-a]pyridine-3-carboxylate

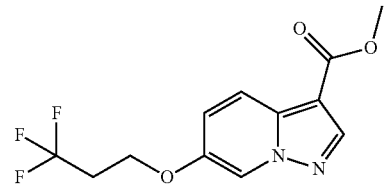 [SMILES: COC(=O)c1cnn2cc(OCCC(F)(F)F)ccc12]

Intermediate 60 was prepared by following a similar procedure to that described for Intermediate 58 employing the appropriate alcohol. MS(ESI) m/z: 289.0 (M+H)+; 1H NMR (500 MHz, DMSO-d6) δ ppm 8.70 (d, J=1.9 Hz, 1H), 8.38 (s, 1H), 7.98 (d, J=9.6 Hz, 1H), 7.40 (dd, J=9.6, 2.2 Hz, 1H), 4.33 (t, J=5.9 Hz, 2H), 3.82 (s, 3H), 2.85 (qt, J=11.3, 5.8 Hz, 2H); 19F-NMR: (471 MHz, DMSO-d6) δ ppm −63.03 (s, 3F).

Intermediate 61: methyl 6-((4,4-difluorocyclohexyl)oxy)pyrazolo[1,5-a]pyridine-3-carboxylate

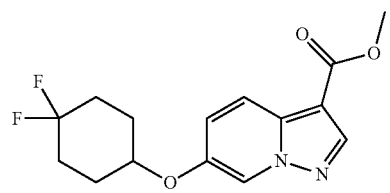 [SMILES: COC(=O)c1cnn2cc(OC3CCC(F)(F)CC3)ccc12]

Intermediate 61 was prepared by following a similar procedure to that described for Intermediate 58 employing the appropriate alcohol. MS(ESI) m/z: 311.0 (M+H)+; 1H NMR (500 MHz, DMSO-d6) δ ppm 8.78 (d, J=1.7 Hz, 1H), 8.38 (s, 1H), 8.03-7.96 (m, 1H), 7.47 (dd, J=9.6, 2.2 Hz, 1H), 4.69 (br dd, J=6.3, 3.3 Hz, 1H), 3.82 (s, 3H), 2.17-2.04 (m, 2H), 2.04-1.92 (m, 4H), 1.91-1.80 (m, 2H).

Intermediate 62: methyl 6-((tetrahydro-2H-pyran-4-yl)oxy)pyrazolo[1,5-a]pyridine-3-carboxylate

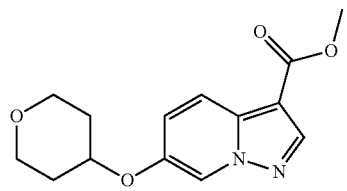 [SMILES: COC(=O)c1cnn2cc(OC3CCOCC3)ccc12]

Intermediate 62 was prepared by following a similar procedure to that described for Intermediate 58 employing the appropriate alcohol. MS(ESI) m/z: 277.0 (M+H)$^+$; $^1$H NMR (500 MHz, DMSO-d$_6$) δ ppm 8.75 (s, 1H), 8.37 (s, 1H), 7.98 (d, J=9.6 Hz, 1H), 7.44 (dd, J=9.6, 2.2 Hz, 1H), 4.67 (tt, J=8.7, 4.1 Hz, 1H), 3.87 (dt, J=11.7, 4.3 Hz, 2H), 3.82 (s, 3H), 3.49 (ddd, J=11.8, 9.4, 2.8 Hz, 2H), 2.07-1.99 (m, 2H), 1.68-1.56 (m, 2H).

Intermediate 63: methyl 6-((1-(methoxycarbonyl)azetidin-3-yl)oxy)pyrazolo[1,5-a]pyridine-3-carboxylate

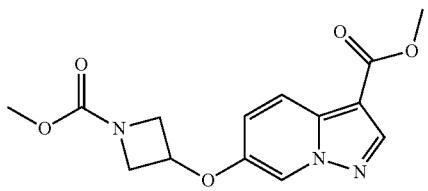

Intermediate 63 was prepared by following a similar procedure to that described for Intermediate 58 employing the appropriate alcohol. MS(ESI) m/z: 306.0 (M+H)$^+$; $^1$H NMR (500 MHz, DMSO-d$_6$) δ ppm 8.47 (d, J=1.7 Hz, 1H), 8.38 (s, 1H), 8.01 (d, J=9.6 Hz, 1H), 7.42 (dd, J=9.6, 2.2 Hz, 1H), 5.15-5.09 (m, 1H), 4.46-4.39 (m, 2H), 3.97-3.89 (m, 2H), 3.82 (s, 3H), 3.58 (s, 3H).

Intermediate 64: methyl 6-(3,3-difluorocyclobutoxy)pyrazolo[1,5-a]pyridine-3-carboxylate

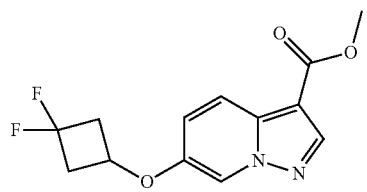 [SMILES: COC(=O)c1cnn2cc(OC3CC(F)(F)C3)ccc12]

Intermediate 64 was prepared by following a similar procedure to that described for Intermediate 58 employing the appropriate alcohol. MS(ESI) m/z: 283.0 (M+H)$^+$; $^1$H NMR (500 MHz, DMSO-d$_6$) δ ppm 8.56 (d, J=1.7 Hz, 1H), 8.38 (s, 1H), 8.00 (d, J=9.6 Hz, 1H), 7.41 (dd, J=9.6, 2.2 Hz, 1H), 4.92-4.84 (m, 1H), 3.82 (s, 3H), 3.29-3.24 (m, 2H), 2.83-2.71 (m, 2H); $^{19}$F-NMR: (471 MHz, DMSO-d$_6$) δ ppm -83.24 (s, 1F), -92.94 (s, 1F).

Intermediate 65: methyl 6-(2-(2,2,2-trifluoroethoxy)ethoxy)pyrazolo[1,5-a]pyridine-3-carboxylate

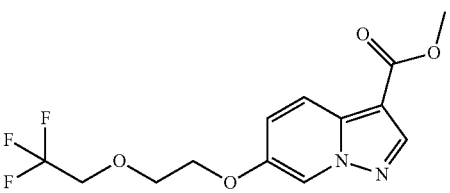 [SMILES: COC(=O)c1cnn2cc(OCCOCC(F)(F)F)ccc12]

Intermediate 65 was prepared by following a similar procedure to that described for Intermediate 58 employing the appropriate alcohol. MS(ESI) m/z: 319.0 (M+H)$^+$; $^1$H NMR (500 MHz, DMSO-d$_6$) δ ppm 8.63 (d, J=1.7 Hz, 1H), 8.36 (s, 1H), 7.97 (d, J=9.6 Hz, 1H), 7.43 (dd, J=9.5, 2.3 Hz, 1H), 4.28-4.23 (m, 2H), 4.17 (q, J=9.4 Hz, 2H), 4.00-3.93 (m, 2H), 3.82 (s, 3H); $^{19}$F-NMR: (471 MHz, DMSO-d$_6$) δ ppm -72.89 (s, 3F).

Intermediate 66: methyl 6-((5-cyclopropyl-1,3,4-thiadiazol-2-yl)methoxy)pyrazolo[1,5-a]pyridine-3-carboxylate

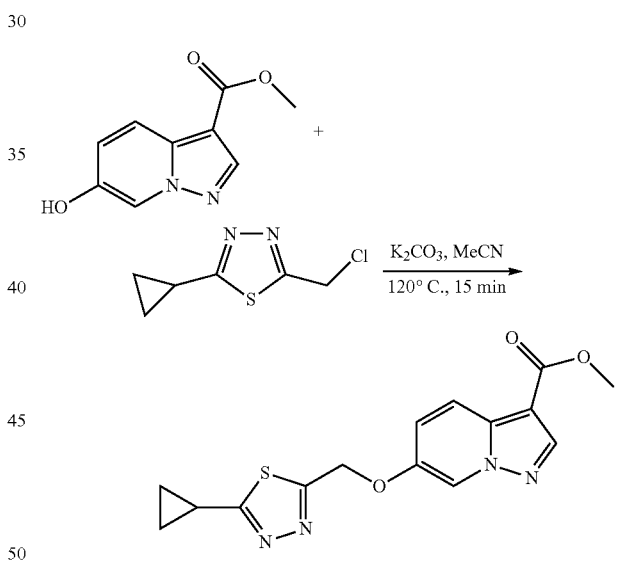

Methyl 6-hydroxypyrazolo[1,5-a]pyridine-3-carboxylate (0.100 g, 0.520 mmol), 2-(chloromethyl)-5-cyclopropyl-1,3,4-thiadiazole (0.136 g, 0.781 mmol), and K$_2$CO$_3$ (0.144 g, 1.04 mmol) were placed in a pressure vial. Then, anhydrous MeCN (5 mL) was added, and the reaction mixture was stirred at 120° C. under microwave irradiation for 15 min. The reaction mixture was diluted with EtOAc (25 mL), filtered, and the solvent was removed under reduced pressure. The residue was purified by flash chromatography to give Intermediate 66 (40 mg, 23% yield) as a off-white solid. MS(ESI) m/z: 331.0 (M+H)$^+$; $^1$H NMR (500 MHz, DMSO-d$_6$) δ ppm 8.82 (d, J=1.8 Hz, 1H), 8.40 (s, 1H), 8.01 (d, J=9.7 Hz, 1H), 7.48 (dd, J=9.5, 2.2 Hz, 1H), 5.63 (s, 2H), 3.82 (s, 3H), 2.59-2.52 (m, 1H), 1.25-1.18 (m, 2H), 1.06-1.01 (m, 2H).

Intermediate 67: methyl 6-(benzyloxy)-7-(trifluoromethyl)pyrazolo[1,5-a]pyridine-3-carboxylate

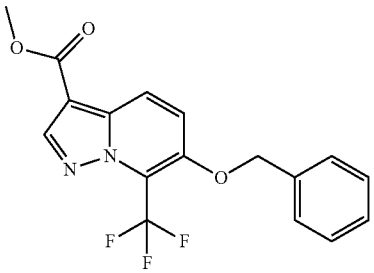 [SMILES: COC(=O)c1cnn2c(C(F)(F)F)c(OCc3ccccc3)ccc12]

Intermediate 67A:
3-(benzyloxy)-2-(trifluoromethyl)pyridine

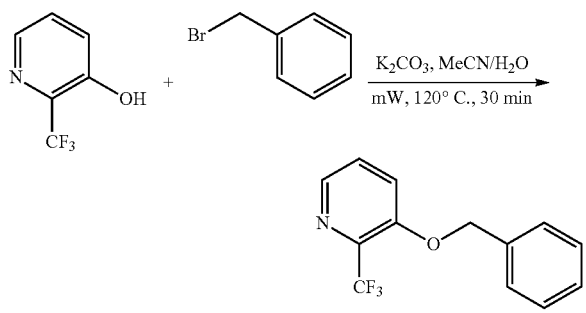

2-(trifluoromethyl)pyridin-3-ol (0.500 g, 3.07 mmol) was suspended in MeCN (10 mL), then (bromomethyl)benzene (0.419 mL, 3.53 mmol), K$_2$CO$_3$ (1.06 g, 7.66 mmol) and water (0.67 mL) were added. The reaction mixture was stirred under microwave irradiation at 120° C. for 30 min. The reaction mixture was diluted with EtOAc (50 mL), CELITE® was added, and the solvent was removed under reduced pressure. The residue was purified by flash chromatography (solid loading on CELITE®) to give Intermediate 67A (0.724 g, 93% yield) as a colorless oil. MS(ESI) m/z: 254.0 (M+H)$^+$; $^1$H NMR (500 MHz, DMSO-d$_6$) δ ppm 8.26 (dd, J=4.0, 1.5 Hz, 1H), 7.45-7.37 (m, 6H), 7.36-7.31 (m, 1H), 5.22 (s, 2H); $^{19}$F-NMR: (471 MHz, CDCl$_3$) δ ppm −66.35 (s, 3F).

Intermediate 67

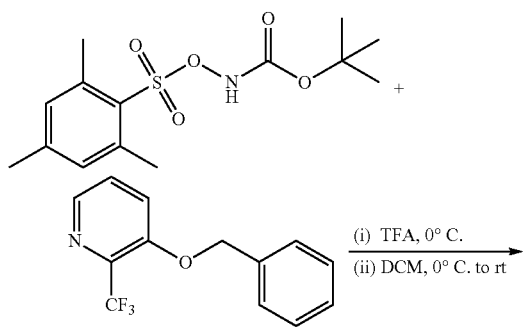

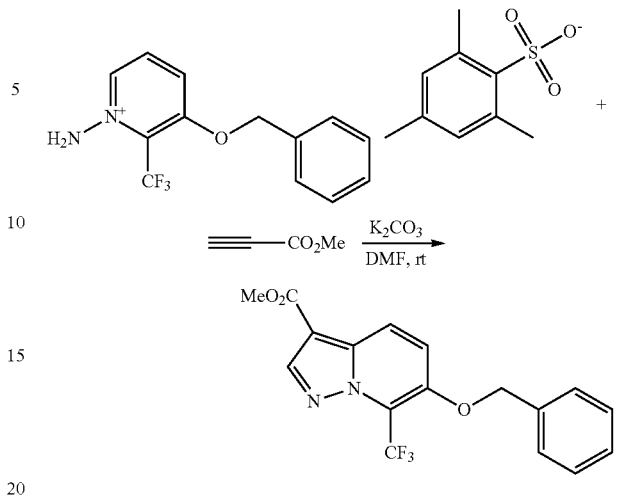

TFA (3 mL) was placed in the round-bottom flask equipped with a magnetic stirred, and the reaction mixture was cooled to 0° C. under Ar. Then, tert-butyl (mesitylsulfonyl)oxycarbamate (0.778 g, 2.47 mmol) was added portionwise over 5 min, and the reaction mixture was stirred at 0° C. for 1 h under Ar. Afterwards, the reaction mixture was quenched with ice water (10 mL), producing white solid. The reaction mixture was diluted with cold water (15 mL), the solid was filtered off, and was washed with cold water until pH-7.0. The obtained solid was dissolved in DCM (7.50 mL), and was stirred with MS 4A (beads) at 0° C. for 15 min to remove water. Afterwards, DCM solution cannulated from the beads, to a cooled (ice bath) solution of Intermediate 67A (0.500 g, 1.98 mmol) in DCM (2.5 mL). The reaction mixture was stirred at 0° C. for 2 h. Then, ice bath was removed, and the reaction mixture was allowed to reach rt and was stirred at this temperature for 16 h. Additional batch of MSH was prepared as described above, and was added to the reaction mixture at 0° C. The reaction mixture was allowed to reach rt and stirred for additional 16 h. Solvent was removed under reduced pressure, the residue was dissolved in DMF (10 mL), then methyl propiolate (0.351 mL, 3.95 mmol) and K$_2$CO$_3$ (0.819 g, 5.92 mmol) were added sequentially. The obtained suspension was stirred at rt for 16 h. The reaction mixture was filtered, and the solution was purified by preparative HPLC to afford Intermediate 67 (24 mg, 3% yield) was obtained as an off-white solid. MS(ESI) m/z: 351.1 (M+H)$^+$; $^1$H NMR (500 MHz, DMSO-d$_6$) δ ppm 8.53 (s, 1H), 8.34 (d, J=9.9 Hz, 1H), 7.97 (d, J=9.9 Hz, 1H), 7.50-7.44 (m, 2H), 7.44-7.39 (m, 2H), 7.38-7.32 (m, 1H), 5.40 (s, 2H), 3.86 (s, 3H); $^{19}$F-NMR: (471 MHz, DMSO-d$_6$) δ ppm −59.24 (s, 3F).

Intermediate 68: 6-bromo-1-(2-hydroxy-2-methyl-propyl)-N-((aR)-6-(4-oxo-3,4-dihydrophthalazin-1-yl)spiro[3.3]heptan-2-yl)-1H-indazole-3-carboxamide

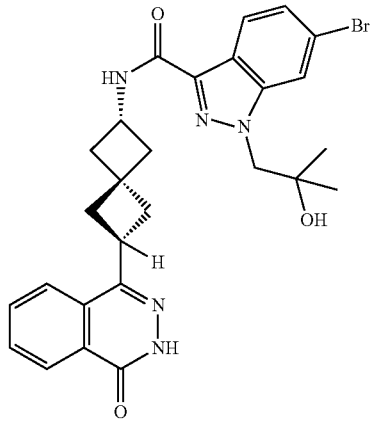

Intermediate 68A: 6-bromo-1-(2-hydroxy-2-methyl-propyl)-1H-indazole-3-carboxylic acid

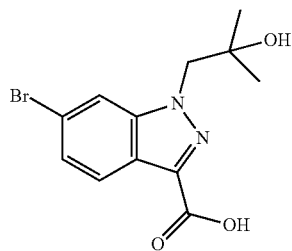 [SMILES: CC(C)(O)Cn1nc(C(=O)O)c2ccc(Br)cc21]

Intermediate 68A was prepared by following a similar procedure to that described for Intermediate 29 employing the appropriate oxirane. MS(ESI) m/z: 312.9 (M+H)+; 1H NMR (400 MHz, methanol-d4) δ ppm 8.06 (dd, J=8.7, 0.6 Hz, 1H), 8.03-8.01 (m, 1H), 7.42 (dd, J=8.6, 1.5 Hz, 1H), 4.43 (s, 2H), 1.25 (s, 6H).

Intermediate 68

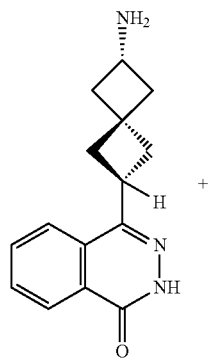

+

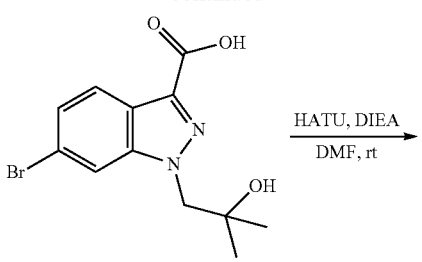

Intermediate 68A (269 mg, 0.859 mmol) was dissolved in anhydrous DMF (5 mL), then DIEA (0.300 mL, 1.72 mmol) and HATU (283 mg, 0.744 mmol) were added. After stirring for 30 min at rt, the obtained solution was added to a solution of Intermediate 2, HCl (167 mg, 0.572 mmol) and DIEA (0.300 mL, 1.717 mmol) in anhydrous DMF (5 mL), and the reaction mixture was stirred at rt for 1 h. The reaction mixture was quenched with MeOH (0.5 mL), diluted with EtOAc (100 mL), washed with water (2×50 mL), brine (1×50 mL), and dried (Na2SO4). EtOAc was removed under reduced pressure and the residue was purified by flash chromatography to give Intermediate 68 (295 mg, 94% yield) as a colorless glass, which solidified upon standing. MS(ESI) m/z: 550.1 (M+H)+; 1H NMR (500 MHz, DMSO-d6) δ ppm 12.46 (s, 1H), 8.46 (d, J=8.0 Hz, 1H), 8.26 (dd, J=8.0, 0.8 Hz, 1H), 8.10 (d, J=1.1 Hz, 1H), 8.06 (d, J=8.8 Hz, 1H), 7.98-7.85 (m, 2H), 7.86-7.80 (m, 1H), 7.36 (dd, J=8.7, 1.5 Hz, 1H), 4.70 (s, 1H), 4.37 (s, 2H), 4.03 (q, J=7.2 Hz, 1H), 3.90 (quin, J=8.5 Hz, 1H), 2.65-2.54 (m, 2H), 2.45-2.31 (m, 4H), 2.26-2.12 (m, 2H), 1.15 (s, 6H).

Intermediate 69: 4-(6-amino-2-fluorospiro[3.3]heptan-2-yl)phthalazin-1(2H)one

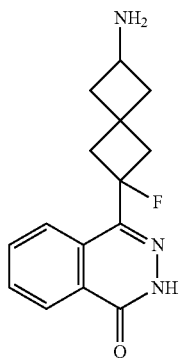 [SMILES: NC1CC2(C1)CC(F)(c1n[nH]c(=O)c3ccccc13)C2]

Intermediate 69A: tert-butyl (6-hydroxy-6-(4-oxo-3,4-dihydrophthalazin-1-yl)spiro[3.3]heptan-2-yl)carbamate

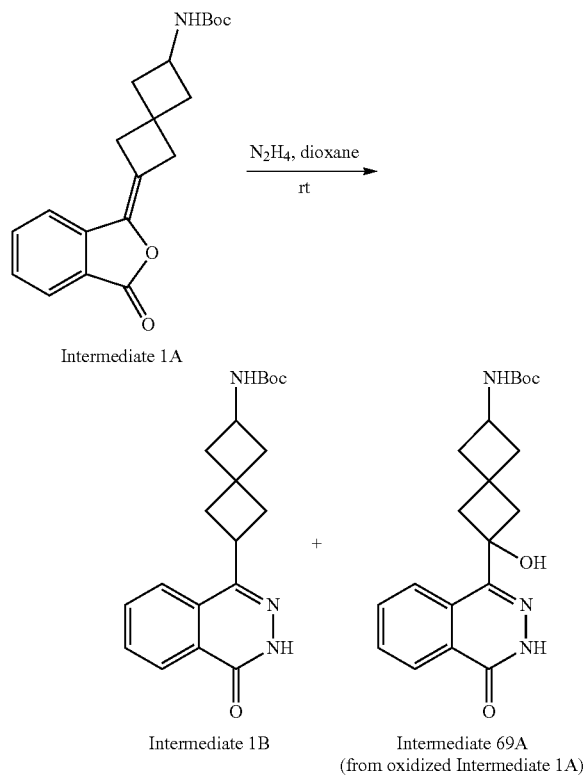

Intermediate 1A (2.46 g, 7.20 mmol) was placed in a round-bottom flask, then dioxane (36.0 mL) was added, and the mixture was stilled until complete dissolution (~5 min). Afterwards, hydrazine (2.26 mL, 72.0 mmol) was added, and the reaction mixture was stirred under Ar at rt for 2 h. The reaction mixture was heated to 65° C., and was stirred at this temperature for 5 h (at this point the reaction mixture became heterogeneous). The reaction mixture was cooled to rt, and the solvent was removed under reduced pressure, and the residue was co-evaporated with THF (2×50 mL). The residue was dissolved THF/MeOH, CELITE® was added, the solvent was removed under reduced pressure, and the residue was purified by flash chromatography (solid loading on CELITE®) to afford Intermediate 1B (1.43 g, 56% yield) as a white solid (eluted at 70% EtOAc) and Intermediate 69A (0.235 g, 9% yield) was obtained as a colorless foam (eluted at ~85% EtOAc).

Intermediate 69A: MS(ESI) m/z: 372.1 (M+H)$^+$; $^1$H NMR (500 MHz, DMSO-d$_6$) δ ppm 12.47 (s, 1H), 8.26 (dd, J=7.8, 1.0 Hz, 1H), 8.11 (d, J=7.7 Hz, 1H), 7.88 (ddd, J=8.3, 7.1, 1.4 Hz, 1H), 7.84-7.78 (m, 1H), 6.99 (br d, J=7.7 Hz, 1H), 5.87 (s, 1H), 3.83-3.70 (m, 1H), 2.90 (br dd, J=11.7, 3.2 Hz, 1H), 2.76 (br dd, J=11.8, 3.3 Hz, 1H), 2.40 (br d, J=11.3 Hz, 1H), 2.31 (br d, J=11.8 Hz, 2H), 2.02-1.95 (m, 1H), 1.74 (t, J=9.8 Hz, 1H), 1.34 (s, 9H).

Intermediate 69B: tert-butyl (6-fluoro-6-(4-oxo-3,4-dihydrophthalazin-1-yl)spiro[3.3]heptan-2-yl)carbamate

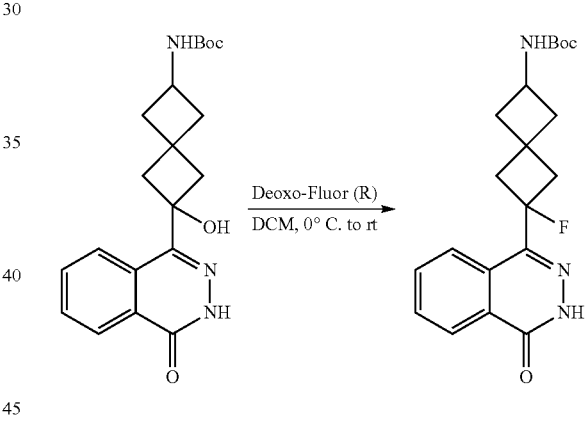

Intermediate 69A (50 mg, 0.135 mmol) was dissolved in anhydrous DCM (2 mL), and the reaction mixture was cooled to 0° C. (ice bath). bis(2-methoxyethyl)aminosulfur trifluoride (0.074 mL, 0.404 mmol) was added dropwise, the reaction mixture was stirred at 0° C. for 1 h, and then was allowed to reach rt in the course of 14 h. Reaction mixture was quenched with MeOH (1 mL). The solvent was removed under reduced pressure and the residue was purified by flash chromatography to Intermediate 69B (50 mg, 99% yield) as a white solid. MS(ESI) m/z: 374.1 (M+H)$^+$; $^1$H NMR (500 MHz, DMSO-d$_6$) δ ppm 12.78 (s, 1H), 8.31 (dd, J=8.1, 1.2 Hz, 1H), 7.98-7.93 (m, 1H), 7.91-7.85 (m, 2H), 7.06 (br d, J=7.4 Hz, 1H), 3.87-3.77 (m, 1H), 3.06-2.97 (m, 1H), 2.89 (td, J=13.7, 4.0 Hz, 1H), 2.78-2.71 (m, 1H), 2.71-2.64 (m, 1H), 2.64-2.58 (m, 1H), 2.43-2.34 (m, 1H), 2.12-2.04 (m, 1H), 1.87-1.78 (m, 1H), 1.35 (s, 9H).

Intermediate 69: 4-(6-amino-2-fluorospiro[3.3]hep-tan-2-yl)phthalazin-1(2H)-one(2H)-one

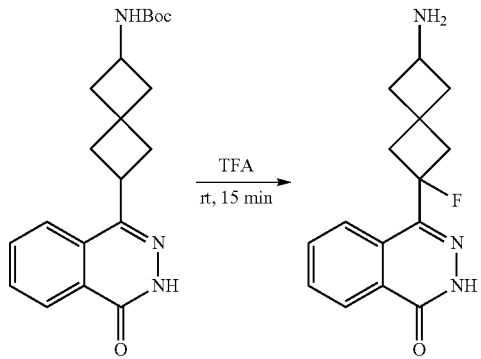 [SMILES: CC(C)(C)OC(=O)NC1CC2(C1)CC(c1n[nH]c(=O)c3ccccc13)C2 ; NC1CC2(C1)CC(F)(c1n[nH]c(=O)c3ccccc13)C2]

Intermediate 69B was dissolved in TFA (3 mL), and the reaction mixture was stirred at rt for 15 min. Solvent was removed under reduced pressure, and co-evaporated with Et$_2$O (3×3 mL) to give Intermediate 69, TFA (52 mg, 0.134 mmol, 100% yield) as an off-white solid. MS(ESI) m/z: 274.0 (M+H)$^+$; $^1$H NMR (500 MHz, DMSO-d$_6$) δ ppm 6 ppm 12.80 (s, 1H), 8.54 (br s, 1H), 8.36-8.26 (m, 1H), 8.00-7.93 (m, 1H), 7.92-7.87 (m, 4H), 3.05 (td, J=13.5, 4.4 Hz, 1H), 2.97 (td, J=13.7, 4.3 Hz, 1H), 2.75 (ddd, J=33.5, 20.8, 12.8 Hz, 2H), 2.47-2.43 (m, 1H), 2.30 (dd, J=12.0, 8.4 Hz, 1H), 2.16 (ddd, J=11.8, 7.3, 4.8 Hz, 1H), 2.05 (dd, J=11.8, 8.5 Hz, 1H); $^{19}$F-NMR: (471 MHz, DMSO-d$_6$) δ ppm −129.78 (s, 1F).

Intermediate 70: 6-bromo-N-((aR)-6-(4-oxo-3,4-dihydrophthalazin-1-yl)spiro[3.3]heptan-2-yl)pyrazolo[1,5-a]pyridine-3-carboxamide

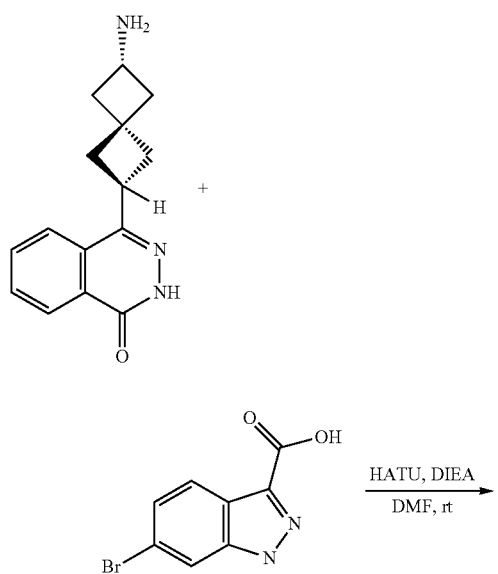

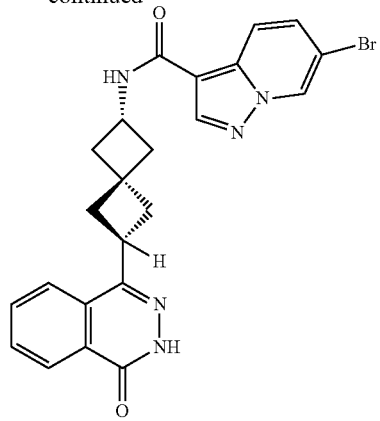

6-Bromopyrazolo[1,5-a]pyridine-3-carboxylic acid (180 mg, 0.749 mmol) was dissolved in anhydrous DMF (5 mL), then DIEA (0.302 mL, 1.73 mmol) and HATU (252 mg, 0.662 mmol) were added. After stirring for 30 min at rt, the obtained solution was added to a solution of Intermediate 2, HCl (168 mg, 0.576 mmol) and DIEA (0.302 mL, 1.73 mmol) in anhydrous DMF (5 mL), and the reaction mixture was stirred at rt for 1 h. The reaction progress was checked by LC-MS: complete conversion to the target product. The reaction mixture was quenched with MeOH (0.5 mL), diluted with EtOAc (100 mL), washed with water (2×50 mL), brine (1×50 mL), and dried (Na$_2$SO$_4$). EtOAc was removed under reduced pressure and the residue was purified by flash chromatography to give Intermediate 70 (274 mg, 99% yield) as a colorless glass, which solidified upon standing. MS(ESI) m/z: 478.0 (M+H)$^+$; $^1$H NMR (500 MHz, DMSO-d$_6$) δ ppm 12.47 (s, 1H), 9.17 (dd, J=1.7, 0.8 Hz, 1H), 8.57 (s, 1H), 8.37 (d, J=7.4 Hz, 1H), 8.26 (dd, J=7.7, 0.8 Hz, 1H), 8.14 (d, J=9.4 Hz, 1H), 7.94-7.90 (m, 1H), 7.90-7.87 (m, 1H), 7.86-7.81 (m, 1H), 7.58 (dd, J=9.5, 1.8 Hz, 1H), 4.38 (sxt, J=8.1 Hz, 1H), 3.91 (quin, J=8.5 Hz, 1H), 2.64 (ddd, J=10.7, 7.3, 5.4 Hz, 1H), 2.58 (ddd, J=11.0, 8.1, 3.2 Hz, 1H), 2.45-2.34 (m, 3H), 2.29-2.19 (m, 2H), 2.05 (dd, J=11.0, 9.1 Hz, 1H).

Intermediate 71: 6-(2-hydroxyethoxy)-N-((aR)-6-(4-oxo-3,4-dihydrophthalazin-1-yl)spiro[3.3]heptan-2-yl)pyrazolo[1,5-a]pyridine-3-carboxamide

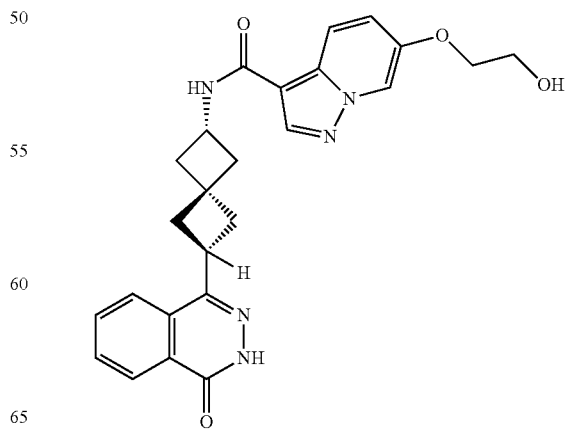

Intermediate 71A: 6-(2-hydroxyethoxy)pyrazolo[1,5-a]pyridine-3-carboxylic acid

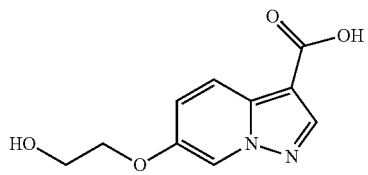 [SMILES: O=C(O)c1cnn2cc(OCCO)ccc12]

Intermediate 71A was prepared by following a similar procedure to that described for Intermediate 29 employing the appropriate oxirane. MS(ESI) m/z: 223.0 (M+H)+; $^1$H NMR (500 MHz, DMSO-d$_6$) δ ppm 12.21 (br s, 1H), 8.57 (d, J=1.7 Hz, 1H), 8.29 (s, 1H), 7.96 (d, J=9.6 Hz, 1H), 7.36 (dd, J=9.5, 2.1 Hz, 1H), 4.94 (br s, 1H), 4.13-4.03 (m, 2H), 3.74 (br s, 2H).

Intermediate 71

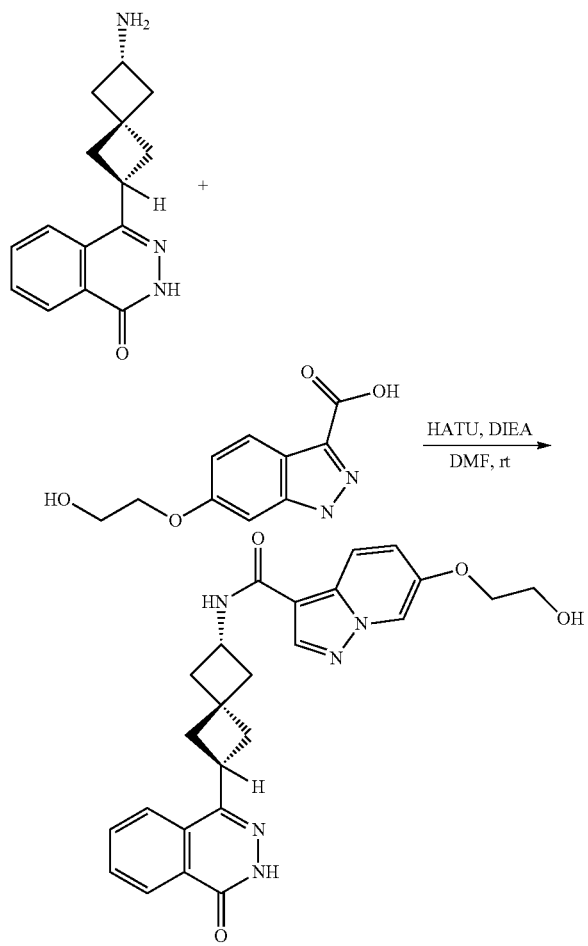

Intermediate 2, HCl (382 mg, 1.31 mmol) and Intermediate 71A (320 mg, 1.440 mmol) were suspended in anhydrous DMF (12 mL). Then DIEA (0.915 mL, 5.24 mmol) and HATU (548 mg, 1.44 mmol) were added and the reaction mixture was stirred at rt for 1 h. The reaction mixture was quenched with MeOH (0.75 mL), diluted with EtOAc (450 mL), washed with water (2×100 mL), brine (1×50 mL), and dried (Na$_2$SO$_4$). EtOAc was removed under reduced pressure and the residue was purified by flash chromatography to give Intermediate 71 (132 mg, 22% yield) as a colorless glass, which solidified upon standing. MS(ESI) m/z: 460.0 (M+H)+; $^1$H NMR (500 MHz, DMSO-d$_6$) δ ppm 12.46 (s, 1H), 8.50-8.41 (m, 2H), 8.29-8.19 (m, 2H), 8.08 (d, J=9.6 Hz, 1H), 7.95-7.90 (m, 1H), 7.90-7.86 (m, 1H), 7.86-7.81 (m, 1H), 7.26 (dd, J=9.6, 2.2 Hz, 1H), 4.98-4.89 (m, 1H), 4.42-4.33 (m, 1H), 4.06 (br t, J=4.7 Hz, 2H), 3.91 (quin, J=8.5 Hz, 1H), 3.79-3.70 (m, 2H), 2.67-2.60 (m, 1H), 2.60-2.54 (m, 1H), 2.43-2.34 (m, 3H), 2.28-2.18 (m, 2H), 2.08-2.01 (m, 1H).

Intermediate 72: 6-(2-iodoethoxy)-N-((aR)-6-(4-oxo-3,4-dihydrophthalazin-1-yl)spiro[3.3]heptan-2-yl)pyrazolo[1,5-a]pyridine-3-carboxamide

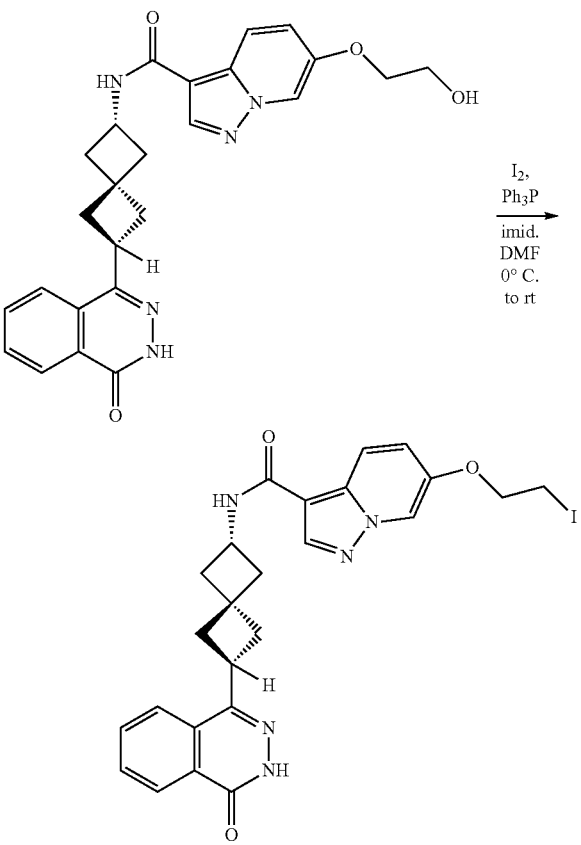

To a solution/suspension of Intermediate 71 (132 mg, 0.287 mmol) in MeCN (6 mL) and THF (9 mL) was sequentially added triphenylphosphine (98 mg, 0.373 mmol), iodine (102 mg, 0.402 mmol) and imidazole (29.3 mg, 0.431 mmol) at 0° C., and the reaction mixture was stirred at the same temperature for 30 min. The cooling bath was removed, and the reaction mixture was stirred at rt for 1 h. Solvent was removed under reduced pressure, and the residue was redissolved in anhydrous DMF (4 mL). The solution was cooled to 0° C., and triphenylphosphine (98 mg, 0.37 mmol), iodine (102 mg, 0.402 mmol) and imidazole (29.3 mg, 0.431 mmol) were added sequentially. The reaction mixture was stirred at 0° C. for 30 min. The cooling bath was removed, and the reaction mixture was stirred at rt for 1 h. The reaction mixture was quenched with MeOH/ H₂O/TFA, acidified with TFA and purified by preparative HPLC to afford Intermediate 72 (100 mg, 61% yield) as an off-white solid. MS(ESI) m/z: 569.9 (M+H)⁺; ¹H NMR (500 MHz, DMSO-d₆) δ ppm 12.46 (s, 1H), 8.28-8.22 (m, 2H), 8.09 (d, J=9.6 Hz, 1H), 7.95-7.90 (m, 1H), 7.90-7.86 (m, 1H), 7.86-7.81 (m, 1H), 7.28 (dd, J=9.6, 2.2 Hz, 1H), 4.37 (br d, J=7.7 Hz, 1H), 4.34 (t, J=6.1 Hz, 2H), 3.91 (quin, J=8.5 Hz, 1H), 3.56 (t, J=5.9 Hz, 2H), 2.67-2.61 (m, 1H), 2.60-2.54 (m, 1H), 2.45-2.35 (m, 3H), 2.27-2.17 (m, 2H), 2.08-2.01 (m, 1H).

Intermediate 73: N-((aR)-6-(4-oxo-3,4-dihydrophthalazin-1-yl)spiro[3.3]heptan-2-yl)-6-(3-oxopropyl)pyrazolo[1,5-a]pyridine-3-carboxamide

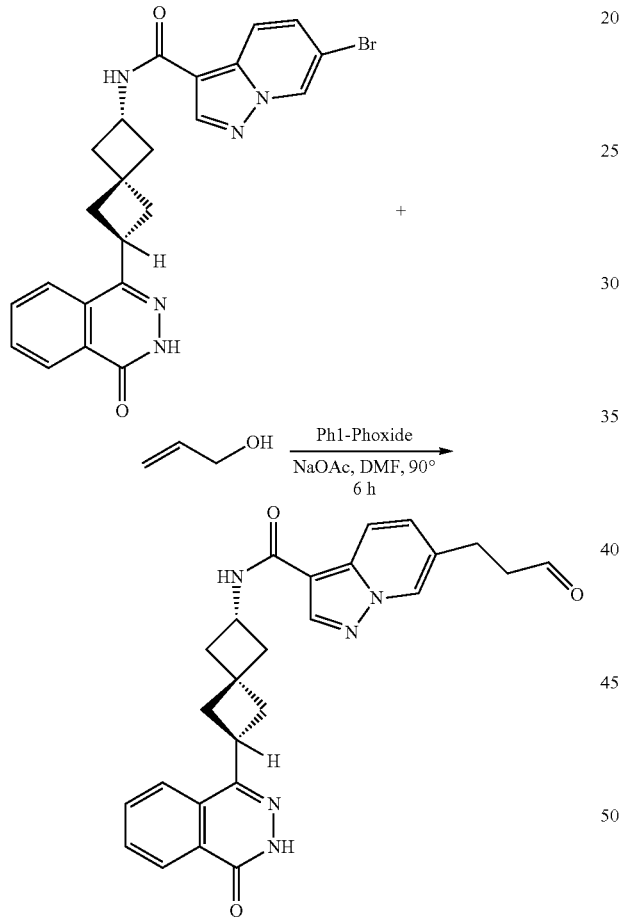

A solution of Intermediate 70 (50 mg, 0.105 mmol), prop-2-en-1-ol (8.53 μl, 0.125 mmol), dihydrogen di-mu-chlorotetrakis(diphenylphosphinito-kp)dipalladate(2-) (5.7 mg, 5.23 μmol) and sodium acetate (11.2 mg, 0.136 mmol) in anhydrous DMF (1 mL) was degassed (3× vacuum/Ar) at rt, and then was stirred at 90° C. for 6 h under Ar atmosphere. The reaction mixture was diluted with EtOAc (50 mL), washed with water (2×15 mL), brine (1×20 mL), and dried (Na₂SO₄). EtOAc was removed under reduced pressure and the residue was purified by flash chromatography to give Intermediate 73 (20 mg, 42% yield). MS(ESI) m/z: 456.1 (M+H)⁺; ¹H NMR (500 MHz, DMSO-d₆) δ ppm 12.46 (s, 1H), 9.74 (t, J=1.0 Hz, 1H), 8.50 (d, J=3.9 Hz, 1H), 8.28-8.25 (m, 1H), 8.25-8.22 (m, 1H), 8.12-8.08 (m, 1H), 7.95-7.90 (m, 1H), 7.90-7.86 (m, 1H), 7.86-7.82 (m, 1H), 7.37 (ddd, J=14.2, 9.2, 1.4 Hz, 1H), 4.46-4.34 (m, 2H), 3.91 (quin, J=8.5 Hz, 1H), 2.94-2.84 (m, 2H), 2.71-2.61 (m, 2H), 2.58 (ddd, J=10.8, 8.0, 3.2 Hz, 1H), 2.46-2.33 (m, 2H), 2.28-2.18 (m, 2H), 2.05 (dd, J=11.1, 9.2 Hz, 1H), 1.88-1.76 (m, 1H).

Intermediate 74: 5-bromo-N-((aR)-6-(4-oxo-3,4-dihydrophthalazin-1-yl)spiro[3.3]heptan-2-yl)isoindoline-2-carboxamide

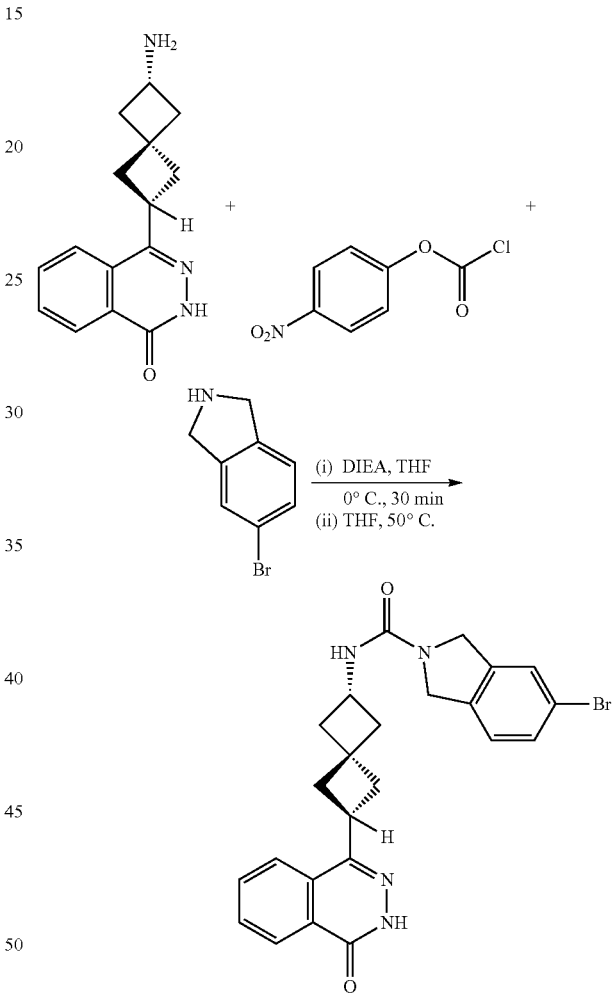

Intermediate 2, HCl (300 mg, 1.028 mmol) was suspended in THF (15 mL), and DIEA (0.449 mL, 2.57 mmol) was added. The reaction mixture was cooled to 0° C., and 4-nitrophenyl carbonochloridate (249 mg, 1.23 mmol) was added. The reaction mixture was stirred at 0° C. for 30 min, then 5-bromoisoindoline (407 mg, 2.06 mmol) and DIEA (0.449 mL, 2.57 mmol) were added. The cooling bath was removed, and the reaction mixture was stirred at 50° C. for 16 h. The reaction mixture was cooled to rt, quenched with MeOH (3 mL) and concentrated. The residue was purified by flash chromatography (30-100% EtOAc/DCM gradient) to afford Intermediate 74 (400 mg, 81% yield) as a light yellow solid. MS(ESI) m/z: 481.2 (M+H)⁺; ¹H NMR: (500 MHz, DMSO-d₆) δ ppm 12.45 (s, 1H), 8.25 (dd, J=7.8, 1.0

Hz, 1H), 7.94-7.89 (m, 1H), 7.88-7.85 (m, 1H), 7.85-7.80 (m, 1H), 7.54 (s, 1H), 7.46 (dd, J=8.1, 1.8 Hz, 1H), 7.28 (d, J=8.0 Hz, 1H), 6.47 (d, J=7.7 Hz, 1H), 4.55 (br d, J=20.9 Hz, 4H), 4.15-4.05 (m, 1H), 3.88 (quin, J=8.5 Hz, 1H), 2.58-2.53 (m, 2H), 2.40-2.28 (m, 3H), 2.19-2.12 (m, 2H), 1.98-1.93 (m, 1H).

Intermediate 75: tert-butyl ((aR)-6-(3-(dicyclopropylmethyl)-4-oxo-3,4-dihydrophthalazin-1-yl)spiro[3.3]heptan-2-yl)carbamate

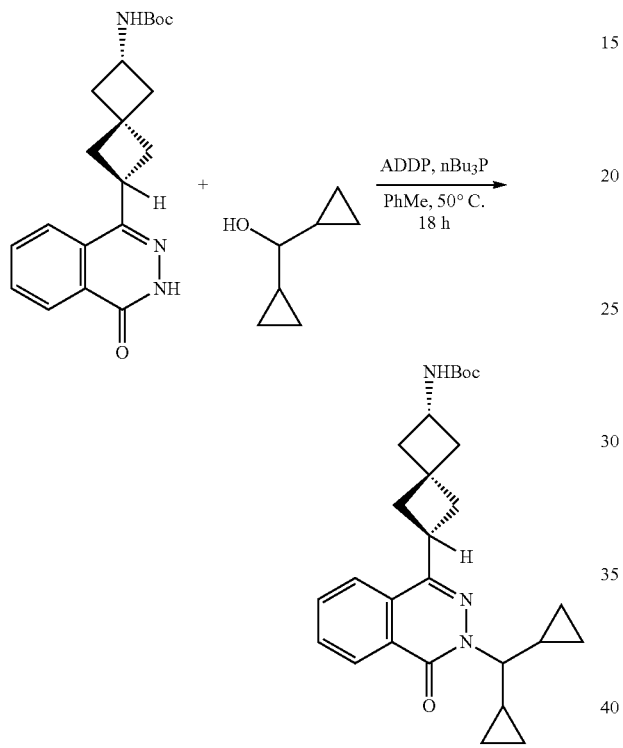

Intermediate 2A (2.00 g, 5.63 mmol) and 1,1'-(azodicarbonyl)dipiperidine (3.55 g, 14.1 mmol) were placed in a pressure vial. Then, PhMe (50 mL), dicyclopropylmethanol (1.33 mL, 11.3 mmol) and tri-N-butylphosphine (3.51 mL, 14.17 mmol) were added, and the reaction mixture was stirred at 50° C. under Ar atmosphere for 2 d. Additional dicyclopropylmethanol (1.32 mL, 11.2 mmol) was added, followed by 1,1'-(azodicarbonyl)dipiperidine (3.55 g, 14.1 mmol) and tri-N-butylphosphine (3.51 mL, 14.1 mmol), and the reaction mixture was stirred at 50° C. for 3 h. The reaction mixture was quenched with MeOH (15 mL), diluted with EtOAc, and the solvent was removed under reduced pressure. The residue was purified by flash chromatography (0-20% EtOAc/DCM gradient) to give Intermediate 75 (1.299 g, 2.89 mmol, 51% yield) as a colorless foam. MS(ESI) m/z: 450.4 (M+H)+; 1H NMR: (500 MHz, DMSO-d6) δ ppm 8.27 (dd, J=8.3, 1.1 Hz, 1H), 7.90 (dd, J=7.3, 1.8 Hz, 1H), 7.86-7.80 (m, 2H), 3.91 (quin, J=8.0 Hz, 1H), 3.86-3.77 (m, 1H), 3.67 (br t, J=9.2 Hz, 1H), 2.58-2.52 (m, 1H), 2.48-2.42 (m, 1H), 2.41-2.32 (m, 3H), 2.16-2.09 (m, 1H), 2.03-1.97 (m, 1H), 1.87 (br t, J=9.9 Hz, 1H), 1.54-1.45 (m, 2H), 1.26-1.19 (m, 2H), 1.18-1.12 (m, 2H), 0.69-0.61 (m, 2H), 0.54 (dq, J=9.6, 4.8 Hz, 2H), 0.35-0.27 (m, 2H), 0.20-0.11 (m, 2H).

Intermediate 76: 4-((aR)-6-aminospiro[3.3]heptan-2-yl)-2-(dicyclopropylmethyl)phthalazin-1(2H)-one (2H)-one

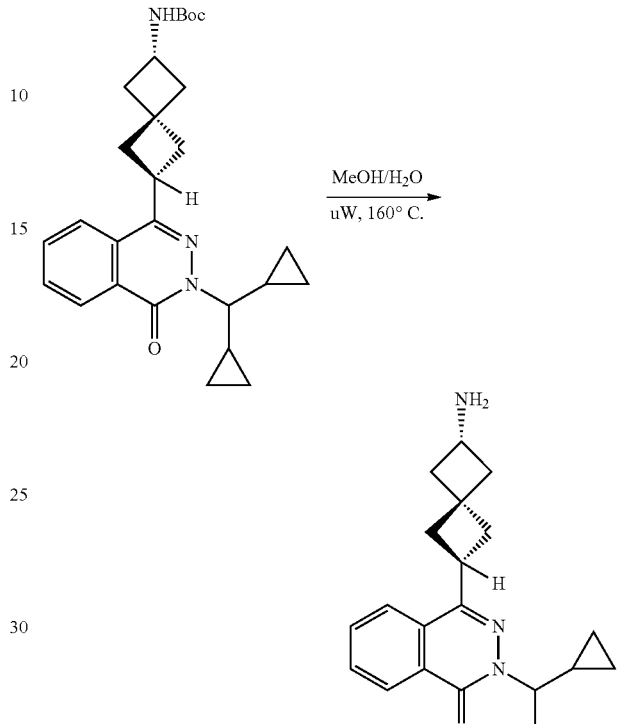

Intermediate 75 (1.30 g, 2.89 mmol) was dissolved in MeOH (5 mL), and water (15 mL) was added to the reaction mixture. The reaction mixture was stirred under microwave irradiation at 160° C. for 90 min. The reaction mixture was diluted with MeCN, and solvent was removed under reduced pressure. The residue was co-evaporated with MeCN (3×), then was purified by flash chromatography (1-15% MeOH/DCM gradient) to afford Intermediate 76 (0.205 g, 20% yield) as a colorless foam. MS(ESI) m/z: 350.3 (M+H)+; 1H NMR: (500 MHz, DMSO-d6) δ ppm 8.30-8.26 (m, 1H), 7.95-7.89 (m, 1H), 7.87-7.81 (m, 2H), 3.93 (quin, J=7.8 Hz, 1H), 3.68 (br t, J=9.2 Hz, 1H), 3.54 (quin, J=8.0 Hz, 1H), 3.17 (s, 1H), 2.62-2.55 (m, 1H), 2.47-2.37 (m, 3H), 2.26-2.14 (m, 2H), 2.04 (dd, J=11.7, 8.7 Hz, 1H), 1.54-1.44 (m, 2H), 0.69-0.61 (m, 2H), 0.56 (dq, J=9.7, 4.8 Hz, 2H), 0.36-0.27 (m, 2H), 0.21-0.12 (m, 2H).

Intermediate 77: 6-((1-(tert-butoxy)-2-methyl-1-oxopropan-2-yl)oxy)pyrazolo[1,5-a]pyridine-3-carboxylic acid

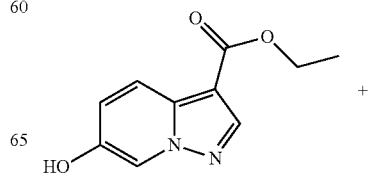

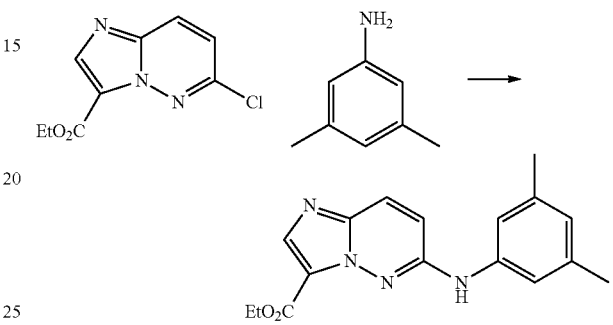

To a suspension of ethyl 6-hydroxypyrazolo[1,5-a]pyridine-3-carboxylate (70 mg, 0.34 mmol) in MeCN (2 mL), were added tert-butyl-2-bromoisobutyrate (0.076 mL, 0.41 mmol) and cesium carbonate (166 mg, 0.509 mmol). The reaction mixture was stirred at rt for 1 h, then at 120° C. for 15 min. The mixture was concentrated. The residue was suspended in THF (3 mL), then was treated with 1M aq. LiOH (0.679 mL, 0.679 mmol) and a MeOH (0.5 mL). The mixture was stirred was heated in a microwave reactor at 120° C. for 15 min. The mixture was partially evaporated, then was cooled to 0° C. and treated with TFA (0.13 mL, 1.7 mmol). The mixture was purified by preparative HPLC to afford Intermediate 77 (59 mg, 54% yield) as a white solid. MS(ESI) m/z: 321.1 (M+H)+; 1H NMR (400 MHz, DMSO-$d_6$) δ 12.41 (br s, 1H), 8.39 (dd, J=2.2, 0.7 Hz, 1H), 8.34 (s, 1H), 8.00 (dd, J=9.6, 0.6 Hz, 1H), 7.36 (dd, J=9.6, 2.1 Hz, 1H), 1.53 (s, 6H), 1.42 (s, 9H).

Intermediate 78. 2-((3-(ethoxycarbonyl)pyrazolo[1,5-a]pyridin-6-yl)oxy)acetic acid

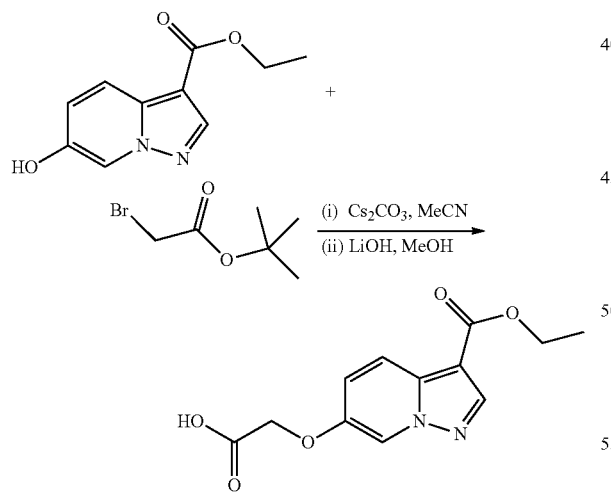

To a suspension of ethyl 6-hydroxypyrazolo[1,5-a]pyridine-3-carboxylate (50 mg, 0.24 mmol) in MeCN (2 mL), were added tert-butyl-2-bromoacetate (0.043 mL, 0.29 mmol) and cesium carbonate (87 mg, 0.27 mmol). The reaction mixture was stirred at rt for 2 h. The mixture was concentrated. The residue was suspended in THF (2 mL), then was treated with 1M aq. LiOH (0.485 mL, 0.485 mmol) and MeOH (0.5 mL). The mixture was stirred at rt for 2 h. The mixture was acidified with 1N HCl (~0.5 mL) and the volatiles were evaporated. The precipitate was collected by filtration and was dried overnight in a vacuum oven at 50° C. to afford Intermediate 78 (53.7 mg, 84% yield) as a white solid. MS(ESI) m/z: 265.0 (M+H)+; 1H NMR (400 MHz, DMSO-$d_6$) δ 13.18 (s, 1H), 8.60 (d, J=2.0 Hz, 1H), 8.36 (s, 1H), 7.98 (d, J=9.5 Hz, 1H), 7.45 (dd, J=9.7, 2.2 Hz, 1H), 4.80 (s, 2H), 4.29 (q, J=7.1 Hz, 2H), 1.33 (t, J=7.2 Hz, 3H).

Intermediate 79. ethyl 6-((3,5-dimethylphenyl)amino)imidazo[1,2-b]pyridazine-3-carboxylate

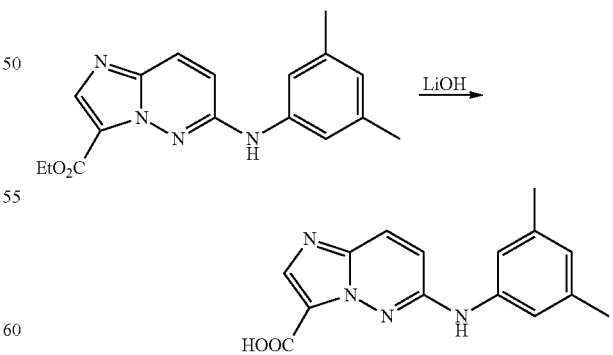

A solution of ethyl 6-chloroimidazo[1,2-b]pyridazine-3-carboxylate (500 mg, 2.22 mmol) in DMA (15 mL) was purged with N$_2$ for 15 min. To this mixture were added 3,5-dimethylaniline (537 mg, 4.43 mmol), Pd$_2$(dba)$_3$ (406 mg, 0.443 mmol), XANTPHOS (513 mg, 0.886 mmol) and cesium carbonate (2.89 g, 8.86 mmol). The reaction vessel was sealed and heated at 125° C. for 1.5 h. The reaction was cooled to r.t. and filtered through CELITE®. EtOAc (100 mL) was added to dilute the filtrate. The solution was washed with water (3×). The organic layer was dried (Na$_2$SO$_4$), filtered and concentrated to provide a crude product. The product was purified using silica gel chromatography (0 to 100% EtOAc/hexanes gradient) to afford Intermediate 79 (340 mg, 49%) as a brown solid. MS(ESI) m/z: 311.3 (M+H)+.

Intermediate 80. 6-((3,5-dimethylphenyl)amino)imidazo[1,2-b]pyridazine-3-carboxylic acid To a solution of Intermediate 79 (340 mg, 1.10 mmol) in THF (22 mL) and MeOH (11 mL) at 0° C., was carefully add 3M aq. LiOH (11.5 mL, 34.5 mmol). The mixture was warmed to room temperature and stirred for 2 hours. The mixture was poured into 100 mL 0.01 M NaOH (aq). The aqueous was washed with hexanes and 1:1 hexanes:EtOAc. The aqueous phase was acidified and extracted with EtOAc (4x). The organic phase was concentrated to provide Intermediate 80 (250 mg, 81%), which was used without further purification. MS(ESI) m/z: 283.1 (M+H)+.

Intermediate 81. methyl 6-aminobenzo[d]isoxazole-3-carboxylate

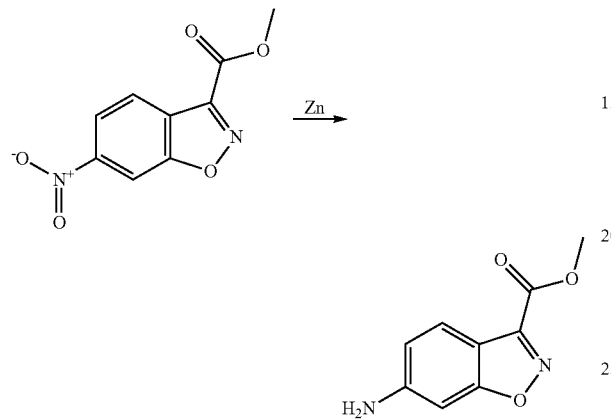

To a solution of methyl 6-nitro-1,2-benzisoxazole-3-carboxylate (98 mg, 0.44 mmol) in Methanol (5 mL) and water (2.5 mL), was added ammonium chloride (118 mg, 2.21 mmol) and zinc (144 mg, 2.21 mmol). The resulting suspension was heated at 70° with vigorous stirring for 2 h. The reaction mixture was filtered through CELITE®, diluted with brine (200 mL), and the resulting solution was extracted with ethyl acetate (200 mL). The organic layer was washed with of brine (3x), dried (MgSO$_4$) and concentrated. The residue was purified by flash chromatography (0-10% MeOH/CH$_2$Cl$_2$ gradient) to afford Intermediate 81 (8 mg, 9% yield). MS(ESI) m/z: 193.1 (M+H)+; $^1$H NMR (400 MHz, chloroform-d) δ 7.83 (dd, J=8.5, 0.6 Hz, 1H), 6.80-6.77 (m, 1H), 6.75 (dd, J=8.6, 2.0 Hz, 1H), 4.27-4.09 (m, 2H), 4.05 (s, 3H).

Intermediate 82. methyl 6-acetamidobenzo[d]isoxazole-3-carboxylate

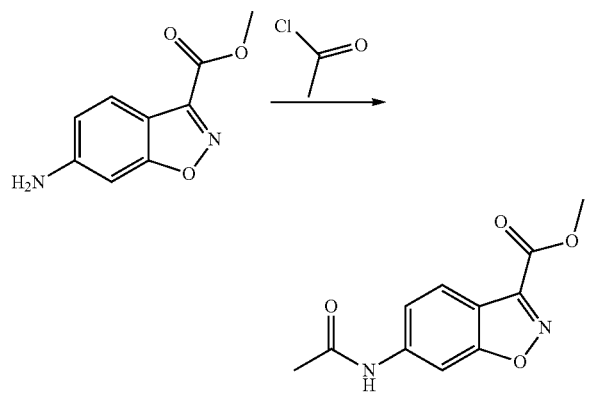

To a mixture of Intermediate 81 (8 mg, 0.042 mmol) and DIEA (10 μL, 0.057 mmol) in DCM (1 mL) at 0° C., was added acetyl chloride (4 μL, 0.06 mmol). The mixture was stirred at rt for 30 min, then was quenched with water and extracted with EtOAc. The organic layer was concentrated and the product was purified by flash chromatography (0-100% EtOAc/hexanes gradient) to afford Intermediate 82 (7 mg, 72% yield) as a white solid. MS(ESI) m/z: 235.1 (M+H)+; $^1$H NMR (400 MHz, methanol-d$_4$) δ 8.31 (d, J=1.1 Hz, 1H), 7.98 (dd, J=8.6, 0.7 Hz, 1H), 7.42 (dd, J=8.7, 1.7 Hz, 1H), 4.05 (s, 3H), 2.18 (s, 3H).

Intermediate 83. 6-bromobenzo[c]isoxazole-3-carboxylic acid

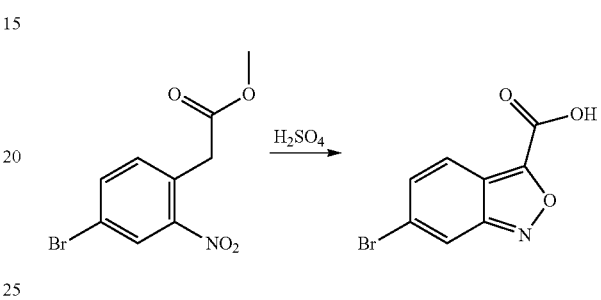

Methyl-2-(4-bromo-2-nitrophenyl)acetate (1.64 g, 5.98 mmol) in H$_2$SO$_4$ (10 mL, 188 mmol) was heated at 110° C. for 2 h. The dark brown solution was poured onto ice, then was extracted with EtOAc (2x). The combine organic layer was concentrated and the residue was purified by flash chromatography (0-100% EtOAc/hexanes gradient) to afford Intermediate 83 (468 mg, 32% yield) as an orange solid. MS(ESI) m/z: 243.9 (M+H)+; $^1$H NMR (400 MHz, methanol-d$_4$) δ 8.01 (t, J=1.2 Hz, 1H), 7.89 (dd, J=9.2, 0.9 Hz, 1H), 7.37 (dd, J=9.1, 1.4 Hz, 1H).

Intermediate 84. methyl 6-bromobenzo[c]isoxazole-3-carboxylate

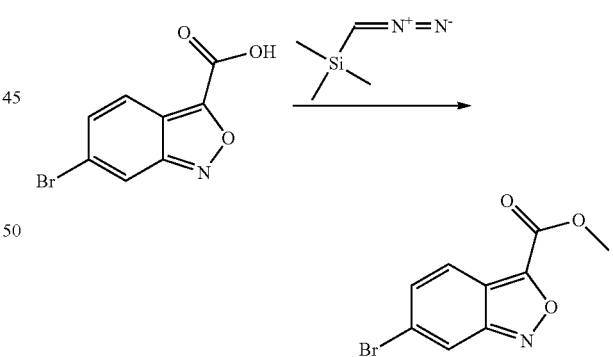

To a solution of Intermediate 83 (200 mg, 0.826 mmol) in CH$_2$Cl$_2$ (10 mL) and MeOH (1 mL) at 0° C., was added 2M TMS-diazomethane (0.537 mL, 1.074 mmol), dropwise. The mixture was allowed to slowly warm to rt and was stirred for 1 h. The mixture was concentrated and the residue was purified by flash chromatography (0-100% EtOAc/hexanes gradient) to afford Intermediate 84 (185 mg, 0.723 mmol, 87% yield) as pale yellow solid. MS(ESI) m/z: 255.9 (M+H)+; $^1$H NMR (400 MHz, chloroform-d) δ 7.95 (t, J=1.2 Hz, 1H), 7.83 (dd, J=9.2, 0.9 Hz, 1H), 7.30 (dd, J=9.1, 1.4 Hz, 1H), 4.09 (s, 3H)

Intermediate 85. methyl 6-(5,5-dimethyl-1,3,2-dioxaborinan-2-yl)benzo[c]isoxazole-3-carboxylate

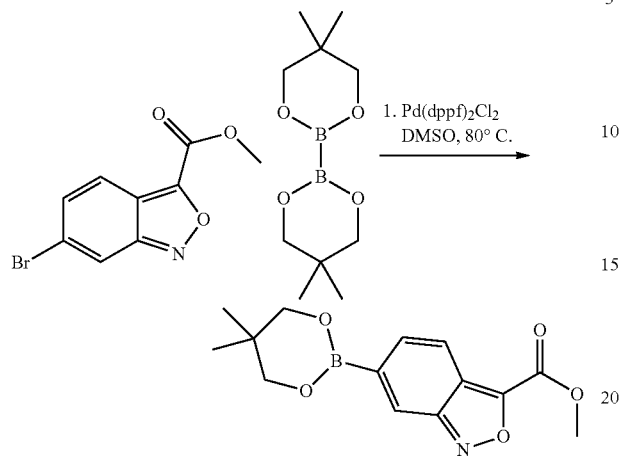

To a sealable vial containing a suspension of potassium acetate (138 mg, 1.406 mmol), Intermediate 84 (120 mg, 0.469 mmol), and 5,5,5',5'-tetramethyl-2,2'-bi(1,3,2-dioxaborinane) (138 mg, 0.609 mmol) in DMSO (1 mL), purged with Ar for 10 min, was added 1,1'-bis(diphenylphosphino) ferrocenedichloro palladium(II) dichloromethane complex (34.3 mg, 0.047 mmol). The vial was capped and the reaction was heated and stirred at 80° C. for 1 h. The mixture was diluted with water and extracted with EtOAc (2×). The organic phase was concentrated and the residue was purified by flash chromatography (0-100% EtOAc/hexanes gradient) to afford Intermediate 85 (65 mg, 48% yield) as a white solid. MS(ESI) m/z: 222.0 (M(boronic acid)+H)$^+$; $^1$H NMR (400 MHz, THF) δ 10.81 (s, 1H), 8.15 (s, 1H), 7.84 (dd, J=8.8, 1.1 Hz, 1H), 7.57 (dd, J=8.8, 0.4 Hz, 1H), 4.02 (s, 3H), 3.82 (s, 4H), 1.03 (s, 6H).

Intermediate 86. methyl 6-hydroxybenzo[c]isoxazole-3-carboxylate

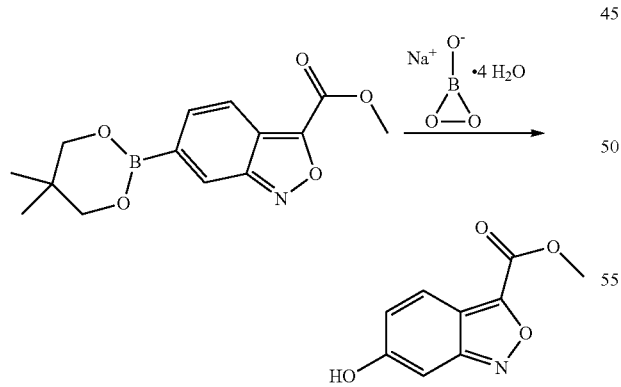

A homogeneous mixture of Intermediate 85 (65 mg, 0.225 mmol) in THF (2 mL) at rt was treated with a mixture of sodium perborate tetrahydrate (41.5 mg, 0.270 mmol) in water (2 mL) for 2.5 h. The reaction was quenched with satd. aq. NH$_4$Cl, then was extracted with EtOAc (2×). The combined organic phase was dried (MgSO$_4$) and concentrated. The residue was purified by flash chromatography (0-100% EtOAc/hexanes gradient) to afford Intermediate 86 (40 mg, 92% yield) as a yellow solid. MS(ESI) m/z: 194.1 (M+H)$^+$; $^1$H NMR (400 MHz, chloroform-d) δ 7.79 (dd, J=9.4, 0.8 Hz, 1H), 6.94 (dd, J=9.4, 1.9 Hz, 1H), 6.77 (dd, J=1.9, 0.8 Hz, 1H), 4.06 (s, 3H).

Intermediate 87. 6-(2-hydroxy-2-methylpropoxy)benzo[c]isoxazole-3-carboxylic acid

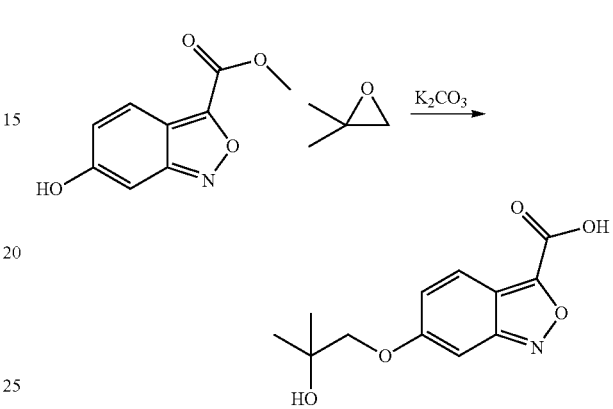

To a solution of Intermediate 86 (40 mg, 0.207 mmol) in acetonitrile (2 mL) and water (0.13 mL), were added K$_2$CO$_3$ (114 mg, 0.828 mmol) and 2,2-dimethyloxirane (0.280 mL, 3.11 mmol) at rt. The reaction was heated with microwave at 120° C. for 30 min. The reaction mixture was diluted with EtOAc, acidified with 1.0 N HCl, washed with H$_2$O and brine. The organic phase was dried (MgSO$_4$) and concentrated. The product was purified by preparative HPLC to afford Intermediate 87 (13 mg, 25% yield) as a yellow foam. MS(ESI) m/z: 252.1 (M+H)$^+$; $^1$H NMR (400 MHz, THF) δ 7.80 (dd, J=9.4, 0.8 Hz, 1H), 7.06-6.82 (m, 2H), 3.86 (s, 2H), 1.29 (s, 6H).

Intermediate 88. 1-tert-butyl-2-methyl 5-bromoindoline-1,2-dicarboxylate

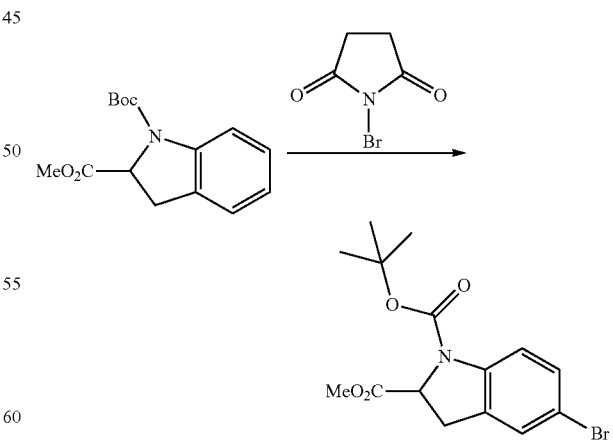

NBS (128 mg, 0.721 mmol) was added to a solution of 1-tert-butyl-2-methyl indoline-1,2-dicarboxylate (200 mg, 0.721 mmol) in DMF (1 mL) at 0° C. The mixture was stirred at rt for 3 d, then was diluted with water and extracted with EtOAc. The organic phase was concentrated and the residue was purified by flash chromatography (0-100% EtOAc/hexanes gradient) to afford Intermediate 88 (175 mg, 68% yield) as a colorless oil. MS(ESI) m/z: 300.0 (M-t-Bu+2H)$^+$; $^1$H NMR (400 MHz, chloroform-d) δ 7.81-7.70 (m, 1H), 7.30 (d, J=7.9 Hz, 1H), 7.22 (s, 1H), 4.86 (d, J=7.9 Hz, 1H), 3.75 (s, 3H), 3.48 (dd, J=16.7, 11.4 Hz, 1H), 3.09 (dd, J=16.7, 4.4 Hz, 1H), 1.65-1.41 (m, 9H).

Intermediate 89: ethyl 7-hydroxyimidazo[1,2-a]pyridine-3-carboxylate

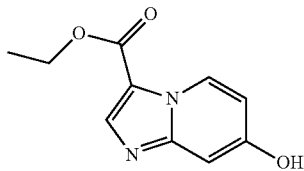

Intermediate 89A: ethyl-2-chloro-3-hydroxyacrylate

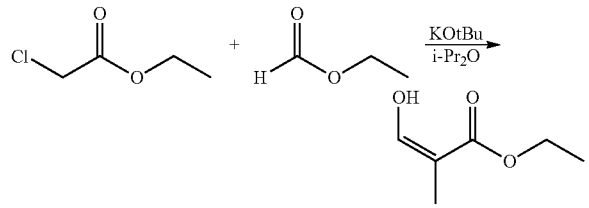

To a cooled (ice-water) suspension of KO$^t$Bu (10.5 g, 94 mmol) in diisopropylether (150 mL) were added ethyl-2-chloroacetate (10.0 mL, 94 mmol) and ethyl formate (7.55 mL, 94 mmol). The reaction was stirred under N$_2$ at rt overnight. The solid formed was collected by filtration, and then was washed with diethyl ether. The solid was redissolved in H$_2$O (100 mL), and the aqueous solution was washed with diethyl ether (50 mL). The aqueous solution was then cooled to 0° C., and it was acidified to pH ~5 with 1.0 N HCl. It was extracted with ether (2×60 mL). The combined organic phase was dried over MgSO$_4$, filtered and the solvent was removed to give a beige liquid (7.03 g, 50%) as the product.

Intermediate 89

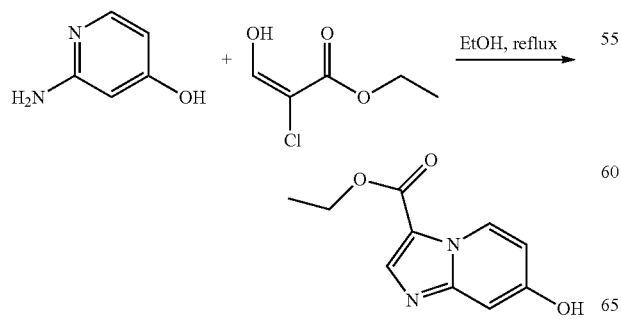

A solution of 2-aminopyridin-4-ol (0.50 g, 4.54 mmol) and Intermediate 89A (1.03 g, 6.81 mmol) in EtOH (10 mL) was stirred under N$_2$ at reflux for 4 h. The solvent was removed. The crude product was purified by normal phase chromatography to provide Intermediate 89 (0.55 g, 60%) as a light tan solid. $^1$H NMR (500 MHz, CD$_3$OD) δ 9.35 (d, J=7.4 Hz, 1H), 8.49 (s, 1H), 7.21-7.11 (m, 2H), 4.47 (q, J=7.2 Hz, 2H), 1.43 (t, J=7.2 Hz, 3H). LC-MS(ESI) m/z: 207.1 [M+H]$^+$.

The following intermediates were prepared by following a similar procedure to that described in Intermediate 89 by reacting Intermediate 89A with the appropriate aminopyridine derivatives.

Intermediate 90: ethyl 7-cyanoimidazo[1,2-a]pyridine-3-carboxylate

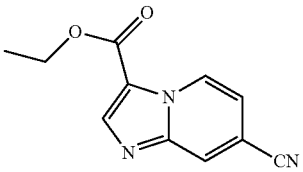 [SMILES: CCOC(=O)c1cnc2cc(C#N)ccn12]

$^1$H NMR (400 MHz, CDCl$_3$) δ 9.42 (dd, J=7.3, 0.9 Hz, 1H), 8.43 (s, 1H), 8.16-8.08 (m, 1H), 7.18 (dd, J=7.0, 1.5 Hz, 1H), 4.45 (q, J=7.0 Hz, 2H), 1.44 (t, J=7.2 Hz, 3H). LC-MS(ESI) m/z: 216.0 [M+H]$^+$.

Intermediate 91: ethyl 8-cyanoimidazo[1,2-a]pyridine-3-carboxylate

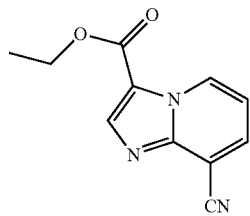 [SMILES: CCOC(=O)c1cnc2c(C#N)cccn12]

$^1$H NMR (400 MHz, CDCl$_3$) δ 9.54 (dd, J=7.0, 1.1 Hz, 1H), 8.39 (s, 1H), 7.85 (dd, J=7.2, 1.2 Hz, 1H), 7.14 (t, J=7.0 Hz, 1H), 4.45 (q, J=7.3 Hz, 2H), 1.44 (t, J=7.0 Hz, 3H). LC-MS(ESI) m/z: 216.0 [M+H]$^+$.

Intermediate 92: ethyl 8-(trifluoromethyl)imidazo[1,2-a]pyridine-3-carboxylate

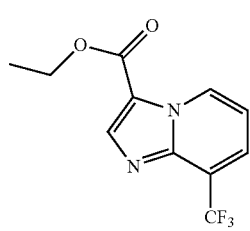 [SMILES: CCOC(=O)c1cnc2c(C(F)(F)F)cccn12]

203

$^1$H NMR (400 MHz, CDCl$_3$) δ 9.50 (d, J=6.8 Hz, 1H), 8.38 (s, 1H), 7.76 (d, J=7.3 Hz, 1H), 7.12 (t, J=7.0 Hz, 1H), 4.44 (q, J=7.2 Hz, 2H), 1.43 (t, J=7.2 Hz, 3H). LC-MS(ESI) m/z: 259.0 [M+H]$^+$.

Intermediate 93: ethyl 8-chloroimidazo[1,2-a]pyridine-3-carboxylate

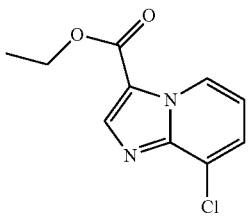

$^1$H NMR (400 MHz, CDCl$_3$) δ 9.26 (dd, J=7.0, 0.9 Hz, 1H), 8.32 (s, 1H), 7.49 (dd, J=7.5, 0.9 Hz, 1H), 6.99 (t, J=7.2 Hz, 1H), 4.43 (q, J=7.2 Hz, 2H), 1.43 (t, J=7.2 Hz, 3H). LC-MS(ESI) m/z: 225.0/227.0 [M+H]$^+$.

Intermediate 94: ethyl 7-phenylimidazo[1,2-a]pyridine-3-carboxylate

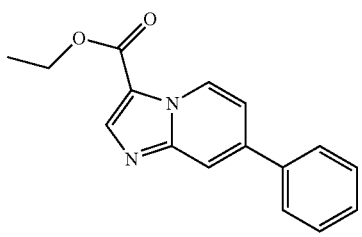 [SMILES: CCOC(=O)c1cnc2cc(-c3ccccc3)ccn12]

$^1$H NMR (400 MHz, CDCl$_3$) δ 9.33 (dd, J=7.2, 0.8 Hz, 1H), 8.32 (s, 1H), 7.93 (d, J=0.9 Hz, 1H), 7.72-7.66 (m, 2H), 7.54-7.48 (m, 2H), 7.47-7.41 (m, 1H), 7.33 (dd, J=7.2, 1.9 Hz, 1H), 4.44 (q, J=7.0 Hz, 2H), 1.44 (t, J=7.2 Hz, 3H). LC-MS(ESI) m/z: 267.0 [M+H]$^+$.

Intermediate 95: ethyl 7-methoxyimidazo[1,2-a]pyridine-3-carboxylate

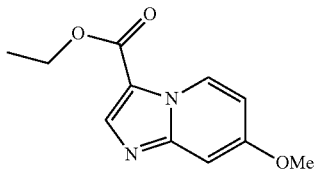 [SMILES: CCOC(=O)c1cnc2cc(OC)ccn12]

$^1$H NMR (400 MHz, CDCl$_3$) δ 9.09 (d, J=7.5 Hz, 1H), 8.17 (s, 1H), 6.99 (d, J=2.4 Hz, 1H), 6.72 (dd, J=7.7, 2.6 Hz, 1H), 4.39 (q, J=7.0 Hz, 2H), 3.90 (s, 3H), 1.40 (t, J=7.2 Hz, 3H). LC-MS(ESI) m/z: 221.0 [M+H]$^+$.

204

Intermediate 96: ethyl 8-chloro-7-methylimidazo[1,2-a]pyridine-3-carboxylate

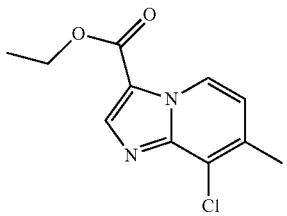 [SMILES: CCOC(=O)c1cnc2c(Cl)c(C)ccn12]

$^1$H NMR (400 MHz, CDCl$_3$) δ 9.36 (s, 1H), 8.23 (s, 1H), 7.57 (s, 1H), 4.41 (q, J=7.2 Hz, 2H), 2.49 (s, 3H), 1.42 (t, J=7.2 Hz, 3H). LC-MS(ESI) m/z: 239.0 [M+H]$^+$.

Intermediate 97: ethyl 8-(benzyloxy)imidazo[1,2-a]pyridine-3-carboxylate

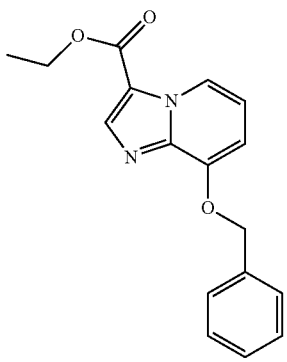 [SMILES: CCOC(=O)c1cnc2c(OCc3ccccc3)cccn12]

$^1$H NMR (400 MHz, CDCl$_3$) δ 8.92 (d, J=6.8 Hz, 1H), 8.25 (s, 1H), 7.49 (d, J=7.0 Hz, 2H), 7.42-7.28 (m, 3H), 6.87 (t, J=7.4 Hz, 1H), 6.73 (d, J=7.7 Hz, 1H), 5.36 (s, 2H), 4.41 (q, J=7.0 Hz, 2H), 1.42 (t, J=7.2 Hz, 3H). LC-MS(ESI) m/z: 297.0 [M+H]$^+$.

Intermediate 98: ethyl 7-fluoroimidazo[1,2-a]pyridine-3-carboxylate

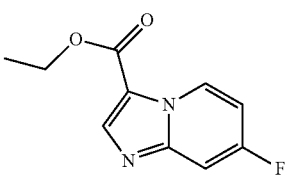

$^1$H NMR (400 MHz, CDCl$_3$) δ 9.36-9.23 (m, 1H), 8.26 (s, 1H), 7.43-7.30 (m, 1H), 6.91 (td, J=7.3, 2.5 Hz, 1H), 4.41 (q, J=7.0 Hz, 2H), 1.42 (t, J=7.0 Hz, 3H). LC-MS(ESI) m/z: 209.0 [M+H]$^+$.

Intermediate 99: ethyl 7-(methylthio)imidazo[1,2-a]pyridine-3-carboxylate

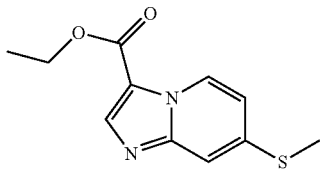 [SMILES: CCOC(=O)c1cnc2cc(SC)ccn12]

¹H NMR (400 MHz, CDCl₃) δ 9.09 (dd, J=7.3, 0.7 Hz, 1H), 8.21 (s, 1H), 7.37 (d, J=1.3 Hz, 1H), 6.88 (dd, J=7.3, 2.0 Hz, 1H), 4.40 (q, J=7.1 Hz, 2H), 2.56 (s, 3H), 1.41 (t, J=7.2 Hz, 3H). LC-MS(ESI) m/z: 237.1 [M+H]⁺.

Intermediate 100: ethyl 7-(benzyloxy)imidazo[1,2-a]pyridine-3-carboxylate

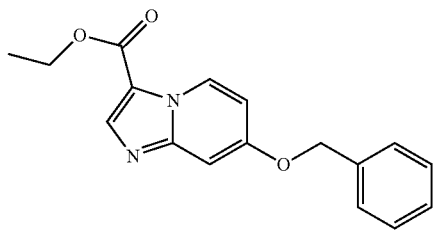 [SMILES: CCOC(=O)c1cnc2cc(OCc3ccccc3)ccn12]

¹H NMR (400 MHz, CDCl₃) δ 9.12 (d, J=7.7 Hz, 1H), 8.17 (s, 1H), 7.49-7.34 (m, 5H), 7.06 (d, J=2.4 Hz, 1H), 6.79 (dd, J=7.6, 2.5 Hz, 1H), 5.14 (s, 2H), 4.39 (q, J=7.2 Hz, 2H), 1.41 (t, J=7.2 Hz, 3H). LC-MS(ESI) m/z: 297.0 [M+H]⁺.

Intermediate 101: 7-(trifluoromethyl)imidazo[1,2-a]pyridine-3-carboxylic acid

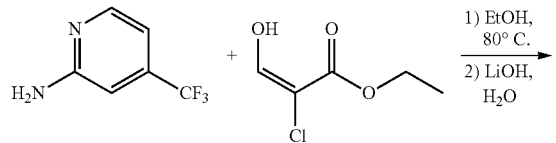

A solution of 4-(trifluoromethyl)pyridin-2-amine (100 mg, 0.62 mmol) and ethyl-2-chloro-3-hydroxyacrylate (139 mg, 0.93 mmol) in EtOH (3 mL) in a sealed vial was stirred under N₂ at 80° C. overnight. The reaction was cooled to rt. To the reaction were added water (0.5 mL) and LiOH (57.0 mg, 2.34 mmol). It was stirred at 60° C. for 3 h. The solvent was removed. The crude product was purified by reverse phase chromatography to provide Intermediate 101 (132 mg, 93% yield) as a white solid. ¹H NMR (400 MHz, DMSO-d₆) δ 9.43 (d, J=7.3 Hz, 1H), 8.42 (s, 1H), 8.32-8.22 (m, 1H), 7.49 (dd, J=7.4, 1.9 Hz, 1H). LC-MS(ESI) m/z: 230.9 [M+H]⁺.

The following intermediates were prepared by following a similar procedure to that described in Intermediate 101 by reacting Intermediate 88A with the appropriate aminopyridine derivatives.

Intermediate 102: 8-fluoro-6-(trifluoromethyl)imidazo[1,2-a]pyridine-3-carboxylic acid

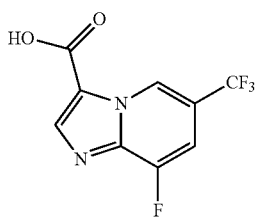 [SMILES: O=C(O)c1cnc2c(F)cc(C(F)(F)F)cn12]

¹H NMR (400 MHz, DMSO-d₆) δ 9.47 (s, 1H), 8.39 (s, 1H), 7.94 (dd, J=10.6, 1.3 Hz, 1H). LC-MS(ESI) m/z: 248.9 [M+H]⁺.

Intermediate 103: 6-fluoro-8-methylimidazo[1,2-a]pyridine-3-carboxylic acid

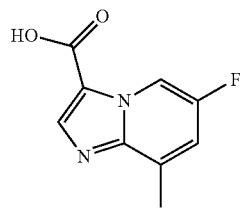

¹H NMR (400 MHz, DMSO-d₆) δ 9.14 (ddd, J=4.6, 2.4, 0.7 Hz, 1H), 8.32 (s, 1H), 7.64-7.55 (m, 1H), 2.59 (s, 3H). LC-MS(ESI) m/z: 195.0 [M+H]⁺.

Intermediate 104: 6,8-difluoroimidazo[1,2-a]pyridine-3-carboxylic acid

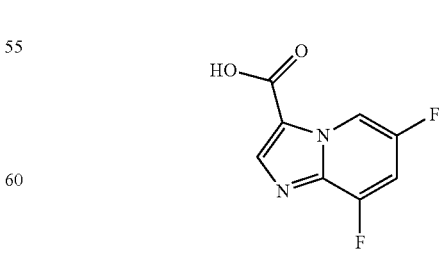

¹H NMR (400 MHz, DMSO-d₆) δ 13.50 (br s, 1H), 9.15 (ddd, J=4.4, 2.0, 0.9 Hz, 1H), 8.29 (s, 1H), 7.87 (ddd, J=11.1, 9.1, 2.2 Hz, 1H). LC-MS(ESI) m/z: 199.0 [M+H]⁺.

Intermediate 105: 6-fluoro-5-methylimidazo[1,2-a]pyridine-3-carboxylic acid

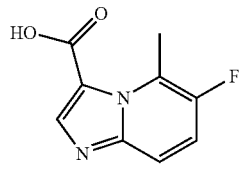

LC-MS(ESI) m/z: 195.0 [M+H]$^+$.

Intermediate 106: 6-fluoroimidazo[1,2-a]pyridine-3-carboxylic acid

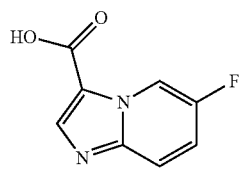 [SMILES: O=C(O)c1cnc2ccc(F)cn12]

$^1$H NMR (400 MHz, DMSO-d$_6$) δ 9.27 (ddd, J=4.8, 2.5, 0.7 Hz, 1H), 8.34 (s, 1H), 7.90 (ddd, J=9.9, 5.3, 0.7 Hz, 1H), 7.71 (ddd, J=9.9, 8.1, 2.6 Hz, 1H). LC-MS(ESI) m/z: 180.9 [M+H]$^+$.

Intermediate 107: 6-fluoro-7-methylimidazo[1,2-a]pyridine-3-carboxylic acid

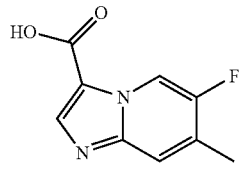

$^1$H NMR (400 MHz, DMSO-d$_6$) δ 9.23 (d, J=5.3 Hz, 1H), 8.34 (s, 1H), 7.81 (d, J=7.0 Hz, 1H), 2.42 (s, 3H). LC-MS (ESI) m/z: 195.0 [M+H]$^+$.

Intermediate 108: 7-methylimidazo[1,2-a]pyridine-3-carboxylic acid

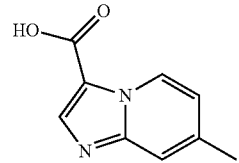

$^1$H NMR (400 MHz, DMSO-d$_6$) δ 9.22 (d, J=7.0 Hz, 1H), 8.41 (s, 1H), 7.68 (s, 1H), 7.24 (dd, J=7.0, 1.5 Hz, 1H), 2.48 (s, 3H). LC-MS(ESI) m/z: 177.0 [M+H]$^+$.

Intermediate 109: methyl 4-morpholinopyrazolo[1,5-a]pyridine-3-carboxylate

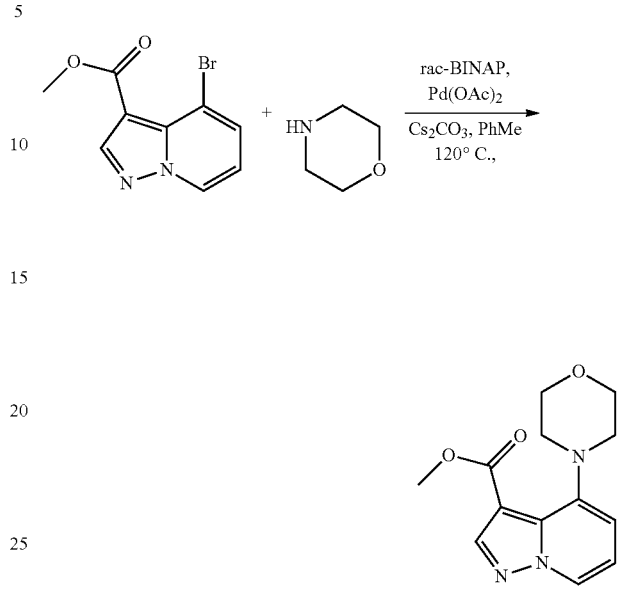

Methyl 4-bromopyrazolo[1,5-a]pyridine-3-carboxylate (100 mg, 0.39 mmol), Pd(OAc)$_2$ (5.3 mg, 0.024 mmol), BINAP (22 mg, 0.035 mmol) and Cs$_2$CO$_3$ (192 mg, 0.59 mmol) were placed in a pressure vial. The reaction mixture was degassed (3× vacuum and argon), then toluene (2 mL) and morpholine (0.044 mL, 0.51 mmol) were added. The reaction mixture was degassed again, and then was stirred at 120° C. for 3 h. After cooled to rt, the reaction was filtered through a pad of CELITE®, and the solvent was removed. The crude product was purified by reverse phase chromatography to provide Intermediate 109 (74 mg, 72%) as a light tan solid. $^1$H NMR (400 MHz, CDCl$_3$) δ 8.46 (s, 1H), 8.43 (d, J=6.6 Hz, 1H), 7.31 (d, J=7.7 Hz, 1H), 7.05 (t, J=7.2 Hz, 1H), 4.11-4.04 (m, 4H), 3.94 (s, 3H), 3.40-3.27 (m, 4H). LC-MS(ESI) m/z: 262.0 [M+H]$^+$.

Intermediate 110: 4-morpholinopyrazolo[1,5-a]pyridine-3-carboxylic acid

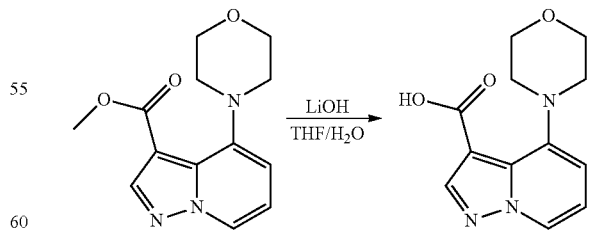

To a solution of Intermediate 109 (63 mg, 0.24 mmol) in THF (2 mL) and H$_2$O (1 mL) was added LiOH (29 mg, 1.21 mmol) at rt. The reaction was stirred under N$_2$ at rt for 2 days. The solvent was removed to give a white solid a crude product (85 mg). LC-MS(ESI) m/z: 248.0 [M+H]$^+$.

Intermediate 111: ethyl 7-(difluoromethoxy)imidazo[1,2-a]pyridine-3-carboxylate

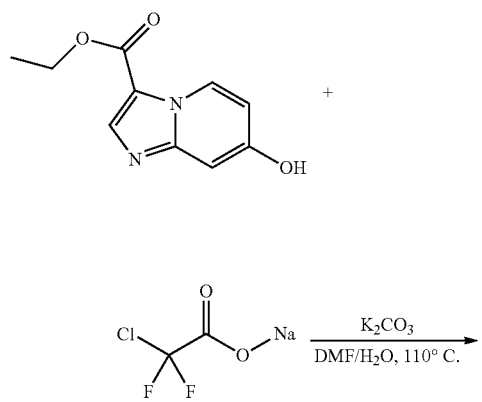

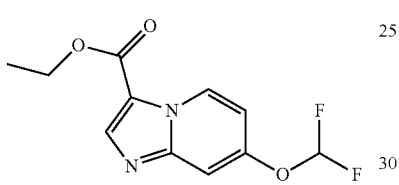

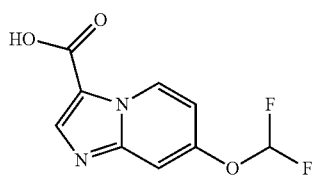 [SMILES: O=C(O)c1cnc2cc(OC(F)F)ccn12]

To a solution of ethyl 7-hydroxyimidazo[1,2-a]pyridine-3-carboxylate (55 mg, 0.27 mmol) in DMF (2 mL) were added sodium 2-chloro-2,2-difluoroacetate (81 mg, 0.53 mmol), $K_2CO_3$ (74 mg, 0.53 mmol) and $H_2O$ (0.4 mL) at rt. The reaction was stirred under $N_2$ at 110° C. for 2 h. The solvent was removed. The crude product was purified by normal phase chromatography to provide Intermediate 111 (21 mg, 31%) as a white solid. $^1$H NMR (400 MHz, CDCl$_3$) δ 9.27 (d, J=7.5 Hz, 1H), 8.26 (s, 1H), 7.37 (d, J=2.4 Hz, 1H), 6.88 (dd, J=7.5, 2.4 Hz, 1H), 6.65 (t, J=72.6 Hz, 1H), 4.41 (q, J=7.1 Hz, 2H), 1.41 (t, J=7.2 Hz, 3H). LC-MS(ESI) m/z: 257.0 [M+H]$^+$.

The following compounds were prepared by following similar procedure to those described in the synthesis of Intermediate 109 and Intermediate 110.

Intermediate 112: 7-(difluoromethoxy)imidazo[1,2-a]pyridine-3-carboxylic acid $^1$H NMR (400 MHz, DMSO-d$_6$) δ 9.28 (dd, J=7.5, 0.7 Hz, 1H), 8.31 (s, 1H), 7.56 (d, J=2.0 Hz, 1H), 7.43 (t, J=73.1 Hz, 1H), 7.18 (dd, J=7.7, 2.6 Hz, 1H). LC-MS(ESI) m/z: 229.0 [M+H]$^+$.

Intermediate 113: 8-(benzyloxy)imidazo[1,2-a]pyridine-3-carboxylic acid

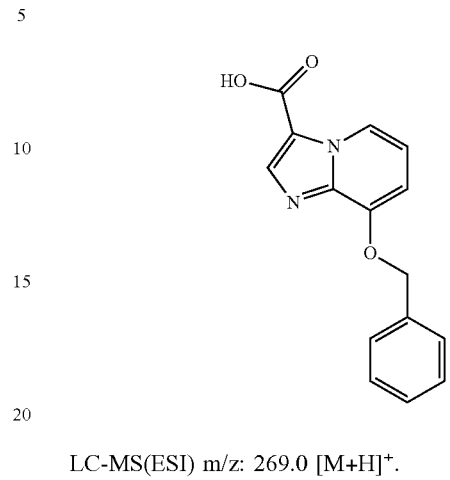

LC-MS(ESI) m/z: 269.0 [M+H]$^+$.

Intermediate 114: ethyl 7-morpholinoimidazo[1,2-a]pyridine-3-carboxylate

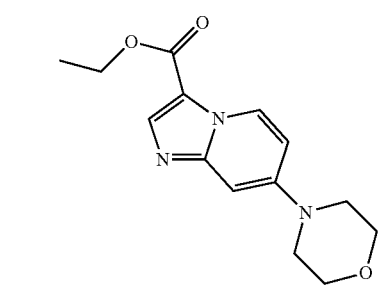 [SMILES: CCOC(=O)c1cnc2cc(N3CCOCC3)ccn12]

$^1$H NMR (400 MHz, CDCl$_3$) δ 9.04 (d, J=7.7 Hz, 1H), 8.14 (s, 1H), 6.86 (d, J=2.4 Hz, 1H), 6.74 (dd, J=7.7, 2.6 Hz, 1H), 4.36 (q, J=7.0 Hz, 2H), 3.93-3.75 (m, 4H), 3.33-3.16 (m, 4H), 1.39 (t, J=7.2 Hz, 3H). LC-MS(ESI) m/z: 276.1 [M+H]$^+$.

Intermediate 115: ethyl 7-(4,4-difluoropiperidin-1-yl)imidazo[1,2-a]pyridine-3-carboxylate

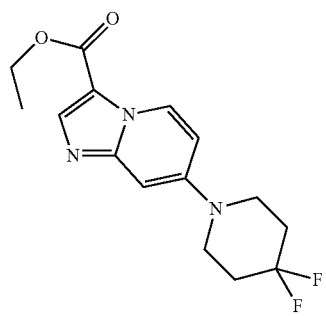 [SMILES: CCOC(=O)c1cnc2cc(N3CCC(F)(F)CC3)ccn12]

$^1$H NMR (400 MHz, CDCl$_3$) δ 9.05 (d, J=7.7 Hz, 1H), 8.14 (s, 1H), 6.90 (d, J=2.6 Hz, 1H), 6.75 (dd, J=7.7, 2.6 Hz,

1H), 4.37 (q, J=7.3 Hz, 2H), 3.56-3.44 (m, 4H), 2.21-2.04 (m, 4H), 1.39 (t, J=7.2 Hz, 3H). LC-MS(ESI) m/z: 310.0 [M+H]⁺.

Intermediate 116: ethyl 7-(3,3-difluoropyrrolidin-1-yl)imidazo[1,2-a]pyridine-3-carboxylate

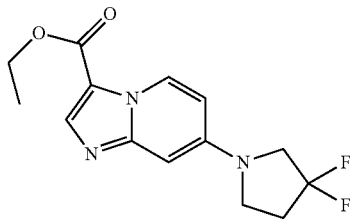 [SMILES: CCOC(=O)c1cnc2cc(N3CCC(F)(F)C3)ccn12]

¹H NMR (400 MHz, CDCl₃) δ 9.07 (d, J=7.7 Hz, 1H), 8.14 (s, 1H), 6.55 (d, J=2.4 Hz, 1H), 6.46 (dd, J=7.6, 2.5 Hz, 1H), 4.37 (q, J=7.0 Hz, 2H), 3.76 (t, J=12.9 Hz, 2H), 3.64 (t, J=7.3 Hz, 2H), 2.67-2.45 (m, 2H), 1.39 (t, J=7.0 Hz, 3H). LC-MS(ESI) m/z: 296.0 [M+H]⁺.

Intermediate 117: (R)-ethyl 7-(3-fluoropyrrolidin-1-yl)imidazo[1,2-a]pyridine-3-carboxylate

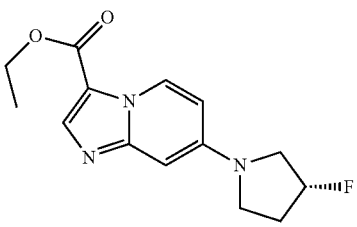 [SMILES: CCOC(=O)c1cnc2cc(N3CC[C@@H](F)C3)ccn12]

¹H NMR (400 MHz, CDCl₃) δ 9.03 (d, J=7.5 Hz, 1H), 8.12 (s, 1H), 6.55 (d, J=2.4 Hz, 1H), 6.50 (dd, J=7.7, 2.4 Hz, 1H), 5.53-5.31 (m, 1H), 4.36 (q, J=7.1 Hz, 2H), 3.69 (d, J=1.8 Hz, 1H), 3.64-3.53 (m, 3H), 2.53-2.37 (m, 1H), 2.33-2.08 (m, 1H), 1.39 (t, J=7.2 Hz, 3H). LC-MS(ESI) m/z: 278.0 [M+H]⁺.

Intermediate 118: (S)-ethyl 7-(3-fluoropyrrolidin-1-yl)imidazo[1,2-a]pyridine-3-carboxylate

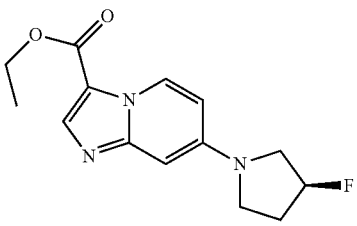 [SMILES: CCOC(=O)c1cnc2cc(N3CC[C@H](F)C3)ccn12]

¹H NMR (400 MHz, CDCl₃) δ 9.03 (d, J=7.5 Hz, 1H), 8.12 (s, 1H), 6.55 (d, J=2.4 Hz, 1H), 6.50 (dd, J=7.6, 2.5 Hz, 1H), 5.52-5.32 (m, 1H), 4.36 (q, J=7.0 Hz, 2H), 3.69 (d, J=2.0 Hz, 1H), 3.63-3.54 (m, 3H), 2.52-2.36 (m, 1H), 2.33-2.08 (m, 1H), 1.39 (t, J=7.0 Hz, 3H). LC-MS(ESI) m/z: 278.0 [M+H]⁺.

Intermediate 119: methyl 7-(4-methylpiperazin-1-yl)imidazo[1,2-a]pyridine-3-carboxylate

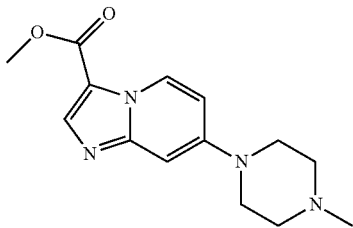

¹H NMR (400 MHz, CDCl₃) δ 9.01 (d, J=7.7 Hz, 1H), 8.13 (s, 1H), 6.87 (d, J=2.4 Hz, 1H), 6.76 (dd, J=7.8, 2.3 Hz, 1H), 3.89 (s, 3H), 3.42-3.27 (m, 4H), 2.63-2.52 (m, 4H), 2.36 (s, 3H). LC-MS(ESI) m/z: 275.0 [M+H]⁺.

Intermediate 120: (R)-ethyl 7-(3-hydroxypyrrolidin-1-yl)imidazo[1,2-a]pyridine-3-carboxylate

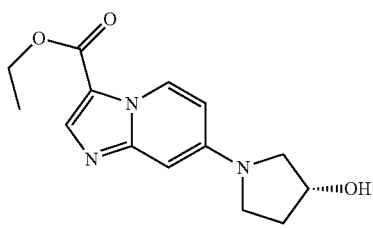 [SMILES: CCOC(=O)c1cnc2cc(N3CC[C@@H](O)C3)ccn12]

¹H NMR (400 MHz, CDCl₃) δ 8.92 (d, J=7.5 Hz, 1H), 8.07 (s, 1H), 6.43 (d, J=2.2 Hz, 1H), 6.40 (dd, J=7.6, 2.5 Hz, 1H), 4.68-4.60 (m, 1H), 4.36 (q, J=7.1 Hz, 2H), 3.62-3.50 (m, 2H), 3.47-3.35 (m, 2H), 2.25-2.09 (m, 2H), 1.39 (t, J=7.2 Hz, 3H). LC-MS(ESI) m/z: 276.1 [M+H]⁺.

Intermediate 121: 7-(4,4-difluoropiperidin-1-yl)imidazo[1,2-a]pyridine-3-carboxylic acid

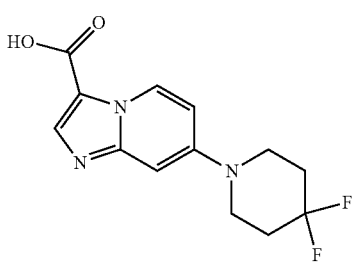 [SMILES: O=C(O)c1cnc2cc(N3CCC(F)(F)CC3)ccn12]

¹H NMR (400 MHz, DMSO-d₆) δ 9.04 (d, J=7.9 Hz, 1H), 8.45 (s, 1H), 7.40 (dd, J=7.9, 2.6 Hz, 1H), 7.03 (d, J=2.4 Hz, 1H), 3.76-3.57 (m, 4H), 2.22-1.93 (m, 4H). LC-MS(ESI) m/z: 282.0 [M+H]⁺.

Intermediate 122: 7-(3,3-difluoropyrrolidin-1-yl)imidazo[1,2-a]pyridine-3-carboxylic acid

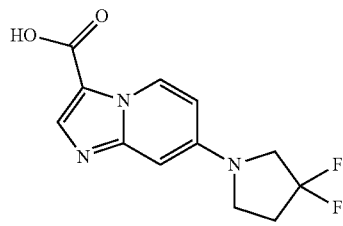 [SMILES: O=C(O)c1cnc2cc(N3CCC(F)(F)C3)ccn12]

$^1$H NMR (400 MHz, DMSO-$d_6$) δ 9.09 (d, J=7.7 Hz, 1H), 8.45 (s, 1H), 7.05 (dd, J=7.8, 2.5 Hz, 1H), 6.62 (d, J=2.4 Hz, 1H), 3.97 (t, J=13.0 Hz, 2H), 3.72 (t, J=7.3 Hz, 2H), 2.63 (tt, J=14.3, 7.4 Hz, 2H). LC-MS(ESI) m/z: 268.0 [M+H]$^+$.

Intermediate 123: (R)-7-(3-fluoropyrrolidin-1-yl)imidazo[1,2-a]pyridine-3-carboxylic acid

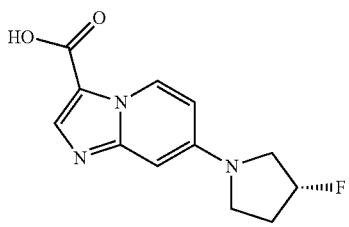 [SMILES: O=C(O)c1cnc2cc(N3CC[C@@H](F)C3)ccn12]

$^1$H NMR (400 MHz, DMSO-$d_6$) δ 9.06 (d, J=7.7 Hz, 1H), 8.45 (s, 1H), 7.05 (dd, J=7.7, 2.4 Hz, 1H), 6.57 (d, J=2.2 Hz, 1H), 5.71-5.38 (m, 1H), 3.78 (s, 1H), 3.68 (t, J=10.2 Hz, 1H), 3.58-3.51 (m, 2H), 2.42-2.12 (m, 2H). LC-MS(ESI) m/z: 250.0 [M+H]$^+$.

Intermediate 124: (S)-7-(3-fluoropyrrolidin-1-yl)imidazo[1,2-a]pyridine-3-carboxylic acid

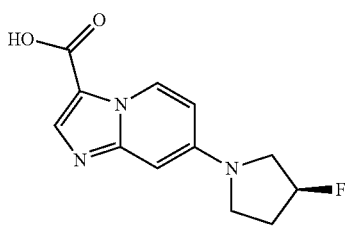 [SMILES: O=C(O)c1cnc2cc(N3CC[C@H](F)C3)ccn12]

$^1$H NMR (400 MHz, DMSO-$d_6$) δ 9.06 (d, J=7.7 Hz, 1H), 8.45 (s, 1H), 7.05 (dd, J=7.7, 2.4 Hz, 1H), 6.57 (d, J=2.2 Hz, 1H), 5.65-5.39 (m, 1H), 3.83-3.73 (m, 1H), 3.72-3.54 (m, 3H), 2.42-2.11 (m, 2H). LC-MS(ESI) m/z: 250.0 [M+H]$^+$.

Intermediate 125: (R)-7-(3-hydroxypyrrolidin-1-yl)imidazo[1,2-a]pyridine-3-carboxylic acid

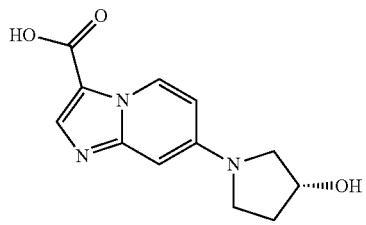 [SMILES: O=C(O)c1cnc2cc(N3CC[C@@H](O)C3)ccn12]

$^1$H NMR (400 MHz, DMSO-$d_6$) δ 9.03 (d, J=7.7 Hz, 1H), 8.48 (s, 1H), 7.05 (dd, J=7.8, 2.3 Hz, 1H), 6.50 (d, J=2.2 Hz, 1H), 4.47 (br. s., 1H), 3.65-3.50 (m, 4H), 2.17-2.03 (m, 1H), 2.03-1.93 (m, 1H). LC-MS(ESI) m/z: 248.1 [M+H]$^+$.

Intermediate 126: 7-(methylthio)imidazo[1,2-a]pyridine-3-carboxylic acid

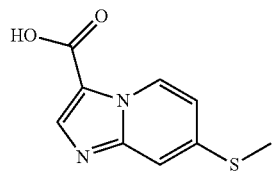

$^1$H NMR (400 MHz, CD$_3$OD) δ 9.36 (dd, J=7.4, 0.6 Hz, 1H), 8.43 (s, 1H), 7.55 (d, J=1.5 Hz, 1H), 7.40 (dd, J=7.3, 2.0 Hz, 1H), 2.68 (s, 3H). LC-MS(ESI) m/z: 209.0 [M+H]$^+$.

Intermediate 127: 7-((2-hydroxyethyl)(methyl)amino)imidazo[1,2-a]pyridine-3-carboxylic acid

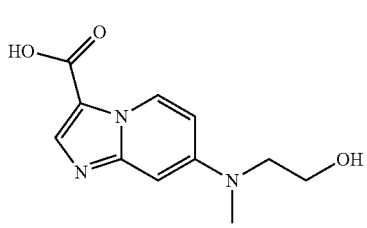 [SMILES: CN(CCO)c1ccn2c(C(=O)O)cnc2c1]

$^1$H NMR (400 MHz, DMSO-$d_6$) δ 8.98 (d, J=7.9 Hz, 1H), 8.44 (s, 1H), 7.21 (dd, J=7.9, 2.6 Hz, 1H), 6.66 (d, J=2.4 Hz, 1H), 3.62 (t, J=3.6 Hz, 4H), 3.12 (s, 3H). LC-MS(ESI) m/z: 236.0 [M+H]$^+$.

Intermediate 128: 7-((2-methoxyethyl)(methyl)amino)imidazo[1,2-a]pyridine-3-carboxylic acid

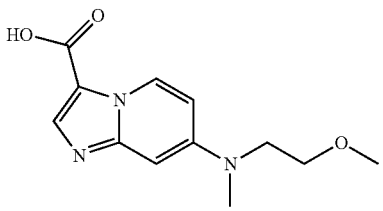 [SMILES: COCCN(C)c1ccn2c(C(=O)O)cnc2c1]

$^1$H NMR (400 MHz, DMSO-d$_6$) δ 8.99 (d, J=7.9 Hz, 1H), 8.42 (s, 1H), 7.21 (dd, J=8.0, 2.5 Hz, 1H), 6.66 (d, J=2.2 Hz, 1H), 3.77-3.69 (m, 2H), 3.56 (t, J=5.3 Hz, 2H), 3.25 (s, 3H), 3.11 (s, 3H). LC-MS(ESI) m/z: 250.0 [M+H]$^+$.

Intermediate 129: 7-((2-hydroxy-2-methylpropyl)(methyl)amino)imidazo[1,2-a]pyridine-3-carboxylic acid

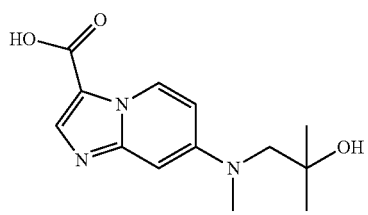 [SMILES: CN(CC(C)(C)O)c1ccn2c(C(=O)O)cnc2c1]

$^1$H NMR (400 MHz, DMSO-d$_6$) δ 8.95 (d, J=8.1 Hz, 1H), 8.44 (s, 1H), 7.32 (d, J=7.9 Hz, 1H), 6.71 (br. s., 1H), 4.66 (br. s., 1H), 3.52 (s, 2H), 3.16 (s, 3H), 1.15 (s, 6H). LC-MS(ESI) m/z: 264.1 [M+H]$^+$.

Intermediate 130: ethyl 7-(2-morpholinoethoxy)imidazo[1,2-a]pyridine-3-carboxylate

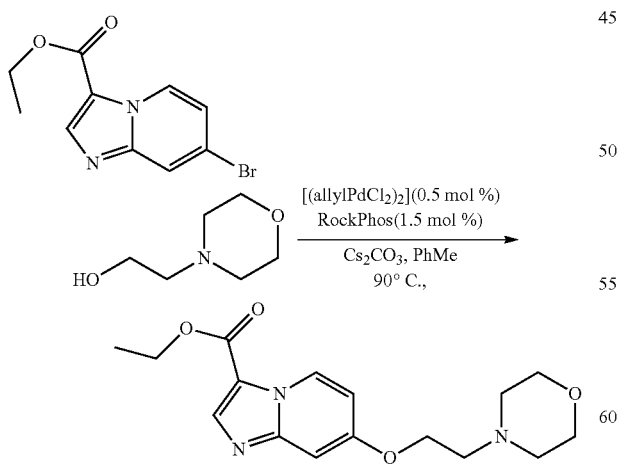

Ethyl 7-bromoimidazo[1,2-a]pyridine-3-carboxylate (100 mg, 0.37 mmol), allylpalladium chloride dimer (2.0 mg, 5.6 µmol), RockPhos (5.2 mg, 0.011 mmol) and Cs$_2$CO$_3$ (182 mg, 0.56 mmol) were placed in a pressure vial. The reaction mixture was degassed (3× vacuum and argon), then toluene (2 mL) and 2-morpholinoethanol (73 mg, 0.56 mmol) were added. The reaction mixture was degassed again, and was stirred at 90° C. for 5 h. After cooled to rt, the solvent was removed. The crude product was purified by reverse phase chromatography to provide Intermediate 130 (96 mg, 81%) as a light tan solid. LC-MS(ESI) m/z: 320.0 [M+H]$^+$.

The following compounds were prepared by following similar procedures to those described in the synthesis of Intermediate 110, Intermediate 111 and Intermediate 130.

Intermediate 131: 7-(2-morpholinoethoxy)imidazo[1,2-a]pyridine-3-carboxylic acid

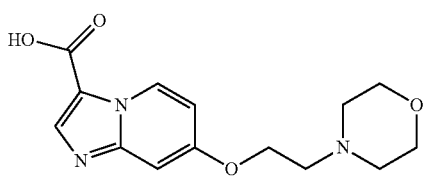 [SMILES: O=C(O)c1cnc2cc(OCCN3CCOCC3)ccn12]

$^1$H NMR (400 MHz, DMSO-d$_6$) δ 9.23 (d, J=7.7 Hz, 1H), 8.42 (s, 1H), 7.40 (d, J=2.4 Hz, 1H), 7.12 (dd, J=7.6, 2.5 Hz, 1H), 4.60-4.54 (m, 2H), 3.68-3.64 (m, 2H), 3.59-3.17 (br. m, 8H). LC-MS(ESI) m/z: 292.0 [M+H]$^+$.

Intermediate 132: 7-(2-(pyrrolidin-1-yl)ethoxy)imidazo[1,2-a]pyridine-3-carboxylic acid

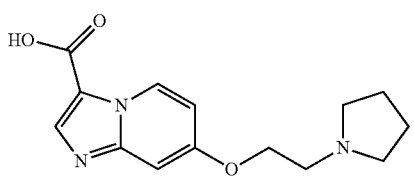 [SMILES: O=C(O)c1cnc2cc(OCCN3CCCC3)ccn12]

$^1$H NMR (400 MHz, DMSO-d$_6$) δ 9.17 (d, J=7.5 Hz, 1H), 7.33 (d, J=2.4 Hz, 1H), 7.07 (d, J=1.8 Hz, 1H), 7.02 (dd, J=7.6, 2.5 Hz, 1H), 4.54-4.36 (m, 2H), 3.86-2.93 (m, 6H), 2.06 (d, J=9.0 Hz, 2H), 1.95-1.75 (m, 2H). LC-MS(ESI) m/z: 276.0 [M+H]$^+$.

Intermediate 133: 7-((2-hydroxy-2-methylpropyl)amino)imidazo[1,2-a]pyridine-3-carboxylic acid

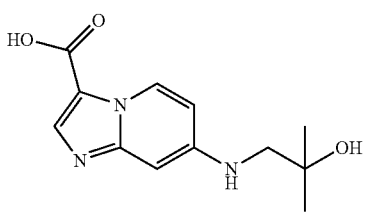 [SMILES: CC(C)(O)CNc1ccn2c(C(=O)O)cnc2c1]

$^1$H NMR (400 MHz, DMSO-d$_6$) δ 8.93 (d, J=7.7 Hz, 1H), 8.41 (s, 1H), 7.68 (br. s., 1H), 7.11 (dd, J=7.7, 2.4 Hz, 1H), 6.66 (br. s., 1H), 3.12 (d, J=5.7 Hz, 2H), 1.18 (s, 6H). LC-MS(ESI) m/z: 250.0 [M+H]$^+$.

Intermediate 134: 7-(2-hydroxy-2-methylpropoxy) imidazo[1,2-a]pyridine-3-carboxylic acid, and Intermediate 135: 1-(2-hydroxy-2-methylpropyl)-7-oxo-1,7-dihydroimidazo[1,2-a]pyridine-3-carboxylic acid

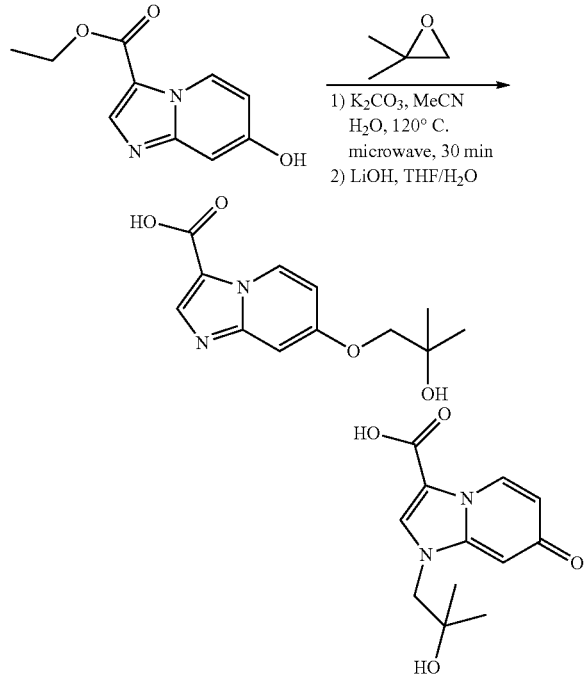

To a solution of ethyl 7-hydroxyimidazo[1,2-a]pyridine-2-carboxylate (100 mg, 0.46 mmol) in acetonitrile (3 mL) and H₂O (0.2 mL) were added K₂CO₃ (268 mg, 1.94 mmol) and 2,2-dimethyloxirane (0.66 mL, 7.27 mmol) at rt. The reaction was heated with microwave at 120° C. for 30 min. The solvent was removed. The residue were added THF (2 mL), H₂O (0.5 mL) and LiOH (20 mg). After stirring at 50° C. for 5 h, the solvent was removed. Purification by reverse phase chromatography gave Intermediate 134 (55 mg, 45%) and Intermediate 135 (23 mg, 13%). Intermediate 134: $^1$H NMR (500 MHz, DMSO-d₆) δ 9.20 (d, J=7.7 Hz, 1H), 8.44 (s, 1H), 7.28 (d, J=2.5 Hz, 1H), 7.15 (dd, J=7.7, 2.5 Hz, 1H), 3.94 (s, 2H), 1.24 (s, 6H). LC-MS(ESI) m/z: 251.0 [M+H]⁺. Intermediate 135: $^1$H NMR (500 MHz, DMSO-d₆) δ 9.30 (d, J=7.7 Hz, 1H), 8.56 (s, 1H), 7.49 (d, J=2.2 Hz, 1H), 7.24 (dd, J=7.7, 2.5 Hz, 1H), 4.24 (s, 2H), 1.16 (s, 6H). LC-MS(ESI) m/z: 251.0 [M+H]⁺.

Intermediate 136: ethyl 7-(1-methyl-1H-pyrazol-4-yl)-1H-indole-2-carboxylate

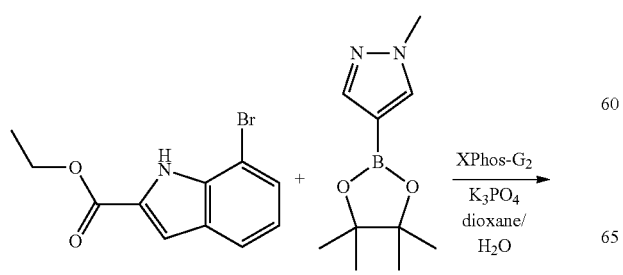

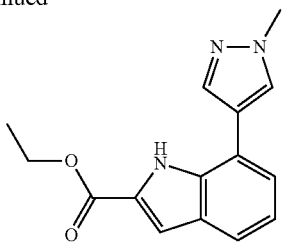

To a solution of ethyl 7-bromo-1H-indole-2-carboxylate (100 mg, 0.37 mmol) in dioxane (3 mL) and H₂O (0.5 mL) were added 1-methyl-4-(4,4,5,5-tetramethyl-1,3,2-dioxaborolan-2-yl)-1H-pyrazole (93 mg, 0.45 mmol), K₃PO₄ (198 mg, 0.93 mmol) and XPhos-G2-Pd-preCat (14.7 mg, 0.019 mmol) at rt. The reaction was stirred under N₂ at 100° C. for 1 h. The reaction was cooled to rt. The solvent was removed. Purification by normal phase chromatography provided Intermediate 136 (94 mg, 94%) as a white solid. $^1$H NMR (400 MHz, CDCl₃) δ 8.92 (br. s., 1H), 7.82 (s, 1H), 7.69 (s, 1H), 7.61 (d, J=7.9 Hz, 1H), 7.31 (dd, J=7.3, 1.1 Hz, 1H), 7.27 (d, J=2.2 Hz, 1H), 7.18 (dd, J=7.9, 7.3 Hz, 1H), 4.41 (q, J=7.2 Hz, 2H), 4.03 (s, 3H), 1.42 (t, J=7.2 Hz, 3H). LC-MS (ESI) m/z: 270.1 [M+H]⁺.

Intermediate 137: 7-(1-methyl-1H-pyrazol-4-yl)-1H-indole-2-carboxylic acid

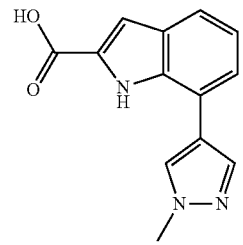 [SMILES: Cn1cc(-c2cccc3cc(C(=O)O)[nH]c23)cn1]

LC-MS(ESI) m/z: 242.1 [M+H]⁺.

Intermediate 138: ethyl 4-oxo-4,5,6,7-tetrahydropyrazolo[1,5-a]pyrazine-2-carboxylate

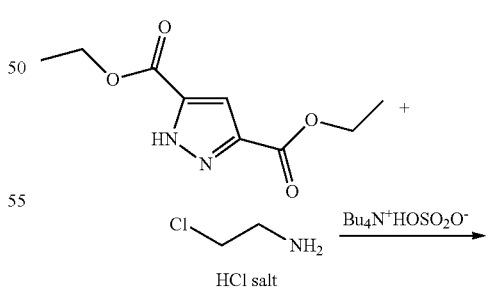

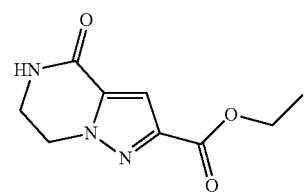

NaOH (3.53 g, 88 mmol) was added to a solution of diethyl 1H-pyrazole-3,5-dicarboxylate (5.35 g, 25.2 mmol) in acetonitrile (40 mL). After 30 min, 2-chloroethanamine hydrochloride (3.22 g, 27.7 mmol) and tetrabutylammonium hydrogen sulfate (0.43 g, 1.26 mmol) were added. The mixture was refluxed for 20 h. After cooled, conc. HCl (5 mL) was added. The mixture was extracted with $CH_2Cl_2$, washed with brine. The combined organic layers were dried over $Na_2SO_4$, filtered and concentrated. Normal phase chromatography afforded Intermediate 138 (2.72 g, 52%) as a white solid. $^1$H NMR (500 MHz, DMSO-$d_6$) δ 8.39 (br s, 1H), 7.07 (s, 1H), 4.40 (dd, J=6.7, 5.5 Hz, 2H), 4.27 (q, J=7.2 Hz, 2H), 3.68-3.61 (m, 2H), 1.28 (t, J=7.0 Hz, 3H). LC-MS(ESI) m/z: 210.1 [M+H]$^+$.

Intermediate 139: 4-oxo-4,5,6,7-tetrahydropyrazolo[1,5-a]pyrazine-2-carboxylic acid

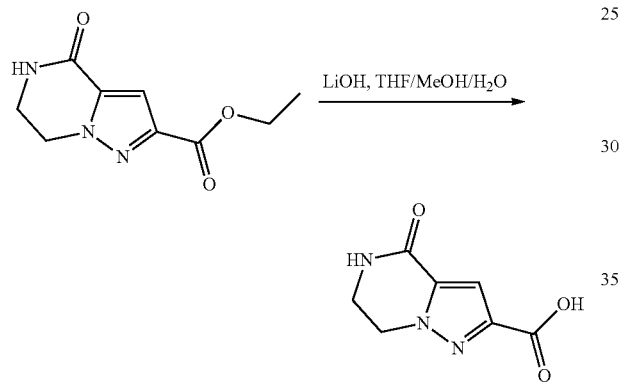

A solution of lithium hydroxide monohydrate (2.73 g, 65.0 mmol) in $H_2O$ (30.0 mL) was added to a suspension of ethyl 4-oxo-4,5,6,7-tetrahydropyrazolo[1,5-a]pyrazine-2-carboxylate (2.72 g, 13.0 mmol) in THF (30 mL) and MeOH (30 mL) at 0° C. Then, the suspension was stirred at rt overnight. The solvents were removed. $H_2O$ (20 mL) was added. The clear solution was cooled to 0° C., conc. HCl (5.42 mL, 65.0 mmol) was added to bring pH to ~3. The suspension was stirred at 0° C. for 2 h, filtered, and dried to give a white solid (2.2 g, 93%). LC-MS(ESI) m/z: 182.1 [M+H]$^+$.

Intermediate 140: ethyl 3-(prop-1-en-2-yl)imidazo[1,5-a]pyridine-1-carboxylate

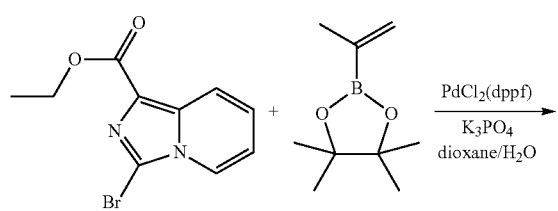

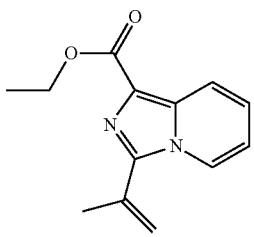

To a solution of ethyl 3-bromoimidazo[1,5-a]pyridine-1-carboxylate (30 mg, 0.11 mmol) in dioxane (2 mL) and $H_2O$ (0.5 mL) were added 4,4,5,5-tetramethyl-2-(prop-1-en-2-yl)-1,3,2-dioxaborolane (28 mg, 0.17 mmol), $K_3PO_4$ (59 mg, 0.28 mmol) and $PdCl_2$(dppf) (8.2 mg, 0.011 mmol) at rt. The reaction was heated with microwave at 120° C. for 15 min. The organic phase was separated, and the solvent was removed. The crude product was purified by normal phase chromatography to provide ethyl 3-(prop-1-en-2-yl)imidazo[1,5-a]pyridine-1-carboxylate (21 mg, 82%) as a white solid. $^1$H NMR (400 MHz, CDCl$_3$) δ 8.38 (dd, J=7.3, 1.1 Hz, 1H), 8.24 (dt, J=9.1, 1.3 Hz, 1H), 7.12 (ddd, J=9.1, 6.5, 0.9 Hz, 1H), 6.84-6.75 (m, 1H), 5.70-5.60 (m, 1H), 5.53 (s, 1H), 4.50 (q, J=7.2 Hz, 2H), 2.41-2.34 (m, 3H), 1.48 (t, J=7.2 Hz, 3H). LC-MS(ESI) m/z: 231.0 [M+H]$^+$.

Intermediate 141: ethyl 3-isopropyl-5,6,7,8-tetrahydroimidazo[1,5-a]pyridine-1-carboxylate

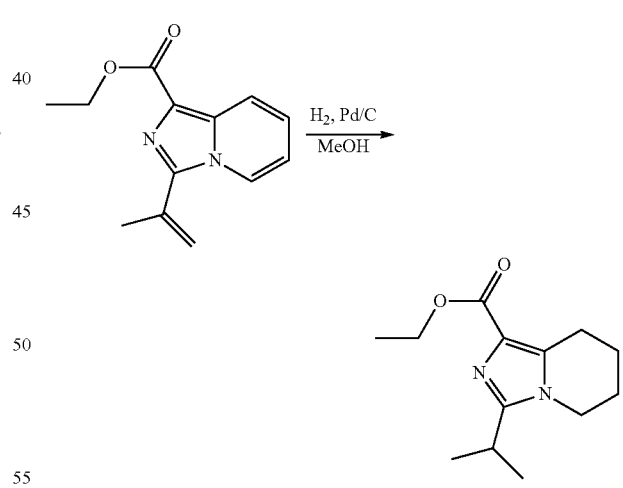

To a solution of ethyl 3-(prop-1-en-2-yl)imidazo[1,5-a]pyridine-1-carboxylate (21 mg, 0.091 mmol) in MeOH (3 mL) was added catalytic amount of 10% Pd/C. The reaction was stirred under a hydrogen balloon at rt for 1 h. The reaction was filtered through a pad of CELITE®, and the solvent was removed to give a white solid. (20 mg, 93%) as a white solid. $^1$H NMR (400 MHz, CDCl$_3$) δ 4.35 (q, J=7.1 Hz, 2H), 3.88 (t, J=6.1 Hz, 2H), 3.08 (t, J=6.5 Hz, 2H), 2.97 (spt, J=6.9 Hz, 1H), 2.02-1.92 (m, 2H), 1.88-1.78 (m, 2H), 1.40-1.31 (m, 9H). LC-MS(ESI) m/z: 237.1 [M+H]$^+$.

Intermediate 142:
ethyl[1,2,4]triazolo[4,3-a]pyridine-3-carboxylate

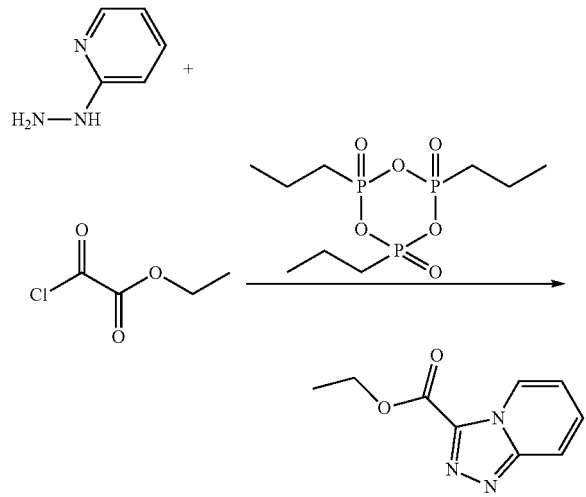

To a solution of 2-hydrazinylpyridine (1.3 g, 11.9 mmol) in toluene (10 mL) were added DIEA (6.2 mL, 35.7 mmol) and ethyl-2-chloro-2-oxoacetate (1.63 g, 11.9 mmol) at 0° C. The reaction was stirred under $N_2$ at 0° C. for 10 min. To the reaction was then added T3P® (50% in EtOAc, 8.5 mL, 14.3 mmol) and the reaction was heated at 110° C. for 5 h. After cooled to rt, the reaction mixture was diluted with EtOAc, washed with 1M HCl, saturated $NaHCO_3$ and brine. The organic phase was dried over $Na_2SO_4$, filtered and concentrated. Purification by normal phase chromatography provided Intermediate 142 (0.36 g, 16%) as a light brown solid. $^1$H NMR (400 MHz, $CDCl_3$) δ 9.13 (d, J=7.0 Hz, 1H), 7.92 (d, J=9.2 Hz, 1H), 7.46 (ddd, J=9.2, 6.8, 1.0 Hz, 1H), 7.15-7.05 (m, 1H), 4.54 (q, J=7.3 Hz, 2H), 1.47 (t, J=7.2 Hz, 3H). LC-MS(ESI) m/z: 191.9 [M+H]$^+$.

Intermediate 143:
3-methoxy-4-(1H-pyrazol-4-yl)benzoic acid

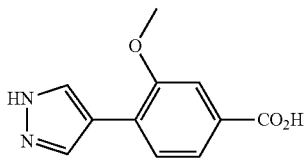 [SMILES: COc1cc(C(=O)O)ccc1-c1cn[nH]c1]

Intermediate 143A: methyl 3-methoxy-4-(1H-pyrazol-4-yl)benzoate

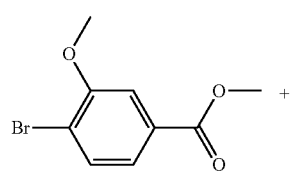

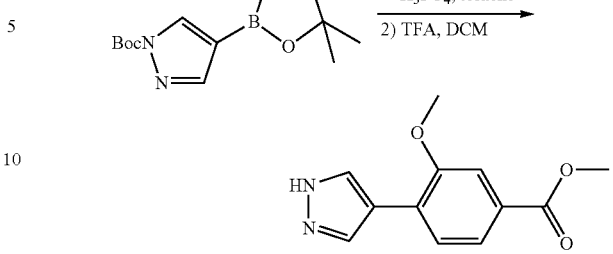

To a solution of methyl 4-bromo-3-methoxybenzoate (1.32 g, 5.39 mmol) in dioxane (30 mL) and water (5 mL) were added tert-butyl 4-(4,4,5,5-tetramethyl-1,3,2-dioxaborolan-2-yl)-1H-pyrazole-1-carboxylate (1.901 g, 6.46 mmol), potassium phosphate (2.86 g, 13.47 mmol) and $PdCl_2$(dppf) (0.197 g, 0.269 mmol) at rt. The reaction was stirred under argon at 100° C. for 3 hrs. The reaction mixture was diluted with EtOAc, washed with $H_2O$. The organic phase was dried over sodium sulfate, filtered and concentrated. The residue was dissolved in DCM (10 mL) and TFA (5 mL) was added. The reaction was stirred at rt for 1.5 hrs. Solvent was removed. The residue was taken into EtOAc, which was washed with $NaHCO_3$ (3×) and brine, dried over $Na_2SO_4$, filtered and concentrated. The crude product was purified by normal phase chromatography. Desired product was isolated as white solid (0.86 g, 69% yield). LCMS(ESI) m/z: 233.0 (M+H)$^+$; $^1$H NMR (400 MHz, $CDCl_3$) δ 8.13 (s, 2H), 7.73-7.66 (m, 1H), 7.66-7.56 (m, 2H), 3.98 (s, 3H), 3.94 (s, 3H).

Intermediate 143

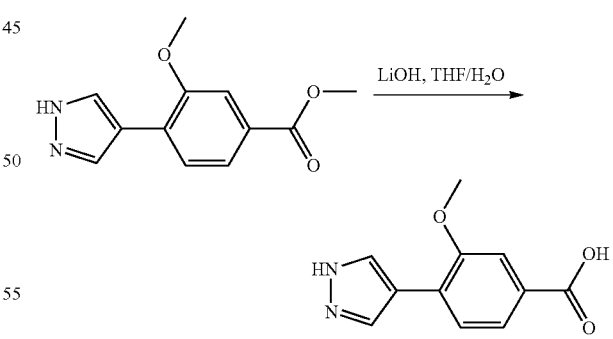

To a solution of Intermediate 143A (860 mg, 3.70 mmol) in THF (10 mL) and water (5 mL) was added LiOH (133 mg, 5.55 mmol) at RT. The reaction was stirred under argon at RT for 5 hrs. The reaction was neutralized with 1 N HCl solution. Solvent was removed to give pale solid of Intermediate 143 (810 mg, 100% yield), which was used without further purification. LCMS(ESI) m/z: 219.0 (M+H)$^+$; $^1$H NMR (400 MHz, DMSO-$d_6$) δ 7.91 (br. s, 2H), 7.54 (br. s, 1H), 7.43 (br. s, 2H), 3.84 (s, 3H).

Intermediate 144: 3-cyano-4-(1H-pyrazol-4-yl)benzoic acid

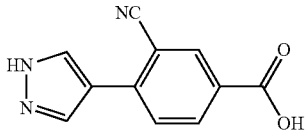

Intermediate 144A: methyl 4-bromo-3-cyanobenzoate

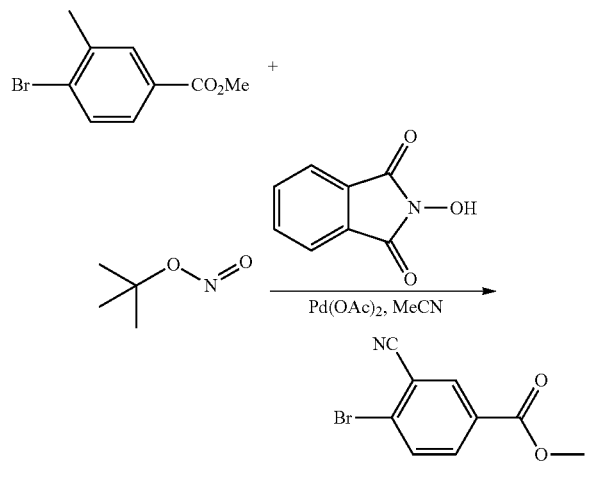

To a solution of methyl 4-bromo-3-methylbenzoate (1.2 g, 5.0 mmol) in acetonitrile (5 mL) were added 2-hydroxyisoindoline-1,3-dione (0.82 g, 5.0 mmol), Pd(OAc)$_2$ (56 mg, 0.25 mmol) and tert-butyl nitrite (1.8 mL, 15 mmol) at rt. The reaction was stirred under argon at 80° C. for 24 h, and then was cooled to rt. The reaction mixture was diluted with EtOAc, washed with H$_2$O and brine. The organic phase was dried over sodium sulfate, filtered and concentrated. The crude product was purified by normal phase chromatography to give Intermediate 144A (0.65 g, 54%) as white solid. LC-MS(ESI) m/z: 249.9/241.9 [M+H]$^+$; $^1$H NMR (400 MHz, CDCl$_3$) δ 8.31 (d, J=1.8 Hz, 1H), 8.09 (dd, J=8.5, 2.1 Hz, 1H), 7.79 (d, J=8.4 Hz, 1H), 3.96 (s, 3H).

Intermediate 144B: methyl 3-cyano-4-(1H-pyrazol-4-yl)benzoate

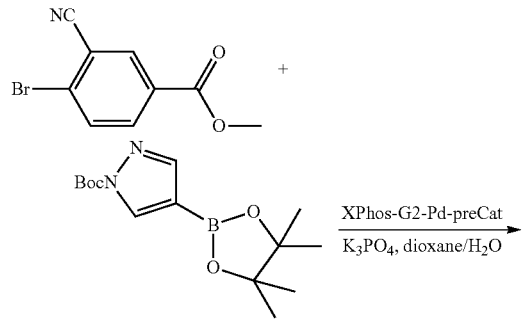

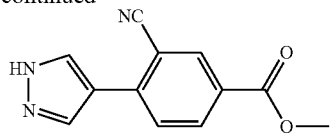

To a solution of Intermediate 144A (0.25 g, 1.0 mmol) in dioxane (10 mL) were added tert-butyl 4-(4,4,5,5-tetramethyl-1,3,2-dioxaborolan-2-yl)-1H-pyrazole-1-carboxylate (0.37 g, 1.3 mmol), K$_3$PO$_4$ (1 M, 3.1 mL, 3.1 mmol) and XPhos-G2-Pd-PreCat (16 mg, 0.021 mmol) at rt. The reaction was stirred under argon at 90° C. for 2 h. The reaction was cooled to rt. The reaction mixture was diluted with EtOAc, washed with H$_2$O and brine. The organic phase was dried over sodium sulfate, filtered and concentrated. The crude product was purified by normal phase chromatography to give Intermediate 144B (0.22 g, 93%) as white solid. LC-MS(ESI) m/z: 228.1 [M+H]$^+$; $^1$H NMR (400 MHz, CDCl$_3$) δ 11.27 (br s, 1H), 8.37 (d, J=1.8 Hz, 1H), 8.27-8.17 (m, 3H), 7.70 (d, J=8.1 Hz, 1H), 3.97 (s, 3H).

Intermediate 144

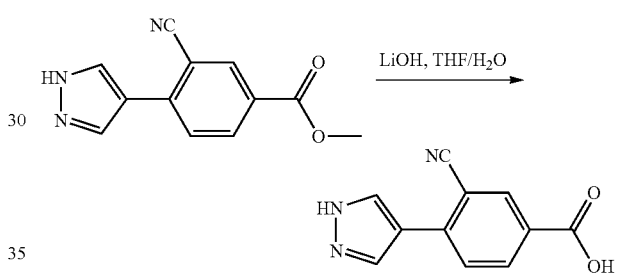

To a solution of Intermediate 144B (0.22 g, 0.97 mmol) in THF (7 mL) and water (3 mL) was added LiOH (70 mg, 2.9 mmol) at rt. The reaction was stirred under argon at rt for 5 h. The reaction was neutralized with 1.0 N HCl. The solvent was removed to give Intermediate 144 (0.21 g, 100%) as white solid. LC-MS(ESI) m/z: 214.1 [M+H]$^+$; $^1$H NMR (400 MHz, DMSO-d$_6$) δ 8.02 (d, J=1.5 Hz, 1H), 7.95-7.87 (m, 3H), 7.47 (d, J=8.1 Hz, 1H).

Intermediate 145: 3-methyl-4-(1H-pyrazol-4-yl)benzoic acid

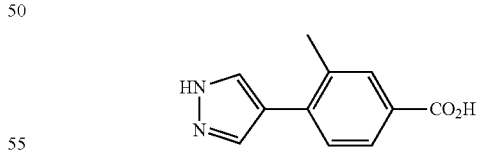

Intermediate 145A: tert-butyl 4-(4-(methoxycarbonyl)-2-methylphenyl)-1H-pyrazole-1-carboxylate, and Intermediate 145B: methyl 3-methyl-4-(1H-pyrazol-4-yl)benzoate

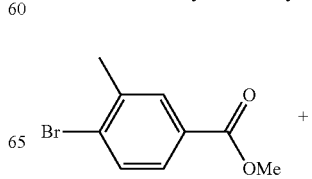

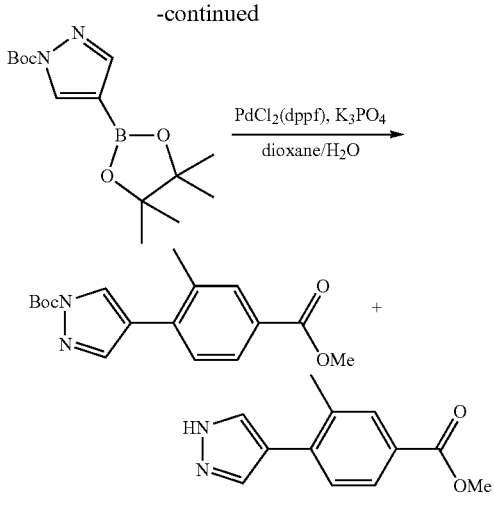

To a solution of methyl 4-bromo-3-methylbenzoate (1.1 g, 4.8 mmol) in dioxane (20 mL) and water (5 mL) were added tert-butyl 4-(4,4,5,5-tetramethyl-1,3,2-dioxaborolan-2-yl)-1H-pyrazole-1-carboxylate (1.6 g, 5.3 mmol), potassium phosphate (2.6 g, 12 mmol) and PdCl$_2$(dppf) (0.18 g, 0.24 mmol) at rt. The reaction was stirred under argon at 90° C. for 3 h. The reaction mixture was diluted with EtOAc, washed with H$_2$O and brine. The organic phase was dried over sodium sulfate, filtered and concentrated. The crude product was purified by normal phase chromatography to give Intermediate 145A (1.1 g, 70%) and Intermediate 145B (0.28 g, 27%) as white solids. Intermediate 145A: LCMS (ESI) m/z: 317.1 [M+H]$^+$; $^1$H NMR (400 MHz, CDCl$_3$) δ 8.23 (s, 1H), 7.95 (d, J=0.4 Hz, 1H), 7.92-7.85 (m, 2H), 7.41 (d, J=8.1 Hz, 1H), 3.93 (s, 3H), 2.45 (s, 3H), 1.69 (s, 9H). Intermediate 145B: LCMS(ESI) m/z: 217.1, (M+H)$^+$; $^1$H NMR (400 MHz, CDCl$_3$) δ 11.03 (br s, 1H), 7.97-7.92 (m, 1H), 7.90-7.85 (m, 1H), 7.80 (s, 2H), 7.43 (d, J=7.9 Hz, 1H), 3.93 (s, 3H), 2.47 (s, 3H).

Intermediate 145

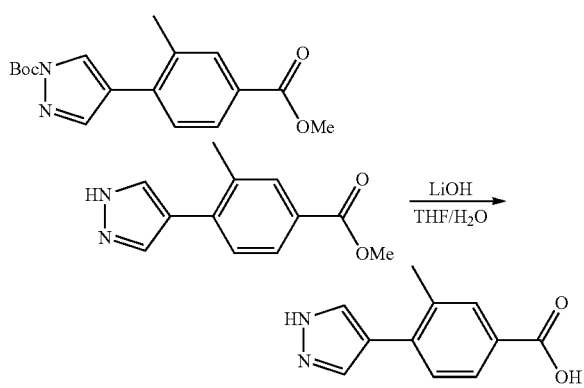

To a solution of a mixture of Intermediate 145A and Intermediate 145B (4.7 mmol) in THF (15 mL) and water (5 mL) was added LiOH (0.34 g, 14 mmol) at rt. The reaction was stirred under argon at rt overnight. The solvent was removed under reduced pressure and the crude product was dried to give Intermediate 145 (0.95 g, 100%) as a light tan solid. LCMS(ESI) m/z: 203.0 [M+H]$^1$; $^1$H NMR (400 MHz, DMSO-d$_6$) δ 7.68 (s, 1H), 7.60 (br s, 3H), 7.26 (d, J=7.9 Hz, 1H), 2.37 (s, 3H).

Intermediate 146:
2-methoxy-4-(1H-pyrazol-4-yl)benzoic acid

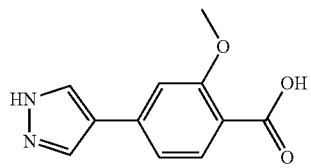 [SMILES: COc1cc(-c2cn[nH]c2)ccc1C(=O)O]

Intermediate 146 was synthesized by following a similar route to Intermediate 143 using methyl 4-bromo-2-methoxybenzoate in step Intermediate 143A. LCMS(ESI) m/z: 219.1 (M+H)$^+$.

Intermediate 147:
6H-isochromeno[3,4-a]pyridine-8-carboxylic acid

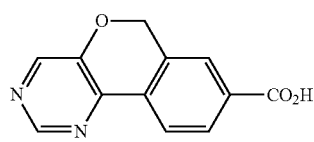 [SMILES: O=C(O)c1ccc2c(c1)COc1cncnc1-2]

Intermediate 147A: methyl 4-bromo-3-(hydroxymethyl)benzoate

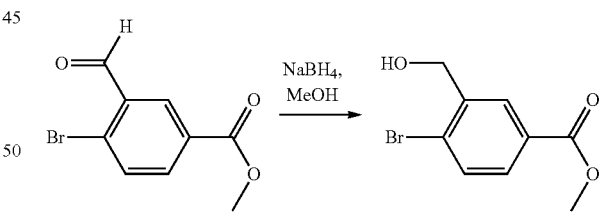

To a solution of methyl 4-bromo-3-formylbenzoate (1.53 g, 6.29 mmol) in MeOH (20 mL) was added NaBH$_4$ (0.238 g, 6.29 mmol) at 0° C. The reaction was stirred under argon at 0° C. for 30 min. LCMS showed the reaction was completed. The reaction mixture was diluted with EtOAc, washed with H$_2$O and brine. The organic phase was dried over sodium sulfate, filtered and concentrated to give Intermediate 147A as a clear colorless oil (1.50 g, 97%). LCMS (ESI) m/z: 244.9/246.9 [M+H]$^+$; $^1$H NMR (400 MHz, CDCl$_3$) δ 8.17 (d, J=2.0 Hz, 1H), 7.82 (dd, J=8.4, 2.2 Hz, 1H), 7.62 (d, J=8.4 Hz, 1H), 4.79 (s, 2H), 3.93 (s, 3H).

Intermediate 147B: methyl 4-bromo-3-(((tert-butyldimethylsilyl)oxy)methyl)benzoate

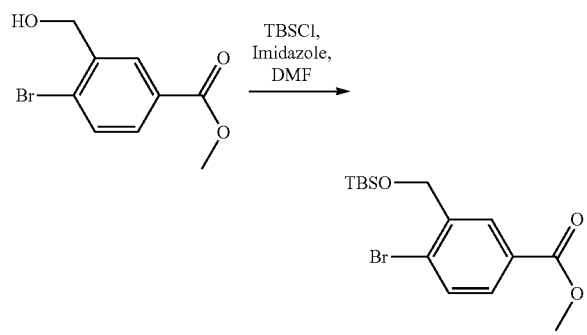

To a solution of Intermediate 147A (1.49 g, 6.08 mmol) in DMF (10 mL) were added imidazole (0.621 g, 9.12 mmol) and TBS-Cl (1.10 g, 7.30 mmol) at 0° C. The reaction was stirred under argon at rt overnight. The reaction mixture was diluted with EtOAc, washed with $H_2O$ and brine. The organic phase was dried over sodium sulfate, filtered and concentrated. The crude product was purified by normal phase chromatography to give Intermediate 147B (1.89 g, 87%). LCMS(ESI) m/z: 359.0/360.9 [M+H]$^+$; $^1$H NMR (400 MHz, CDCl$_3$) δ 8.26-8.21 (m, 1H), 7.79 (dd, J=8.4, 2.2 Hz, 1H), 7.58 (d, J=8.1 Hz, 1H), 4.76 (s, 2H), 3.93 (s, 3H), 1.00 (s, 9H), 0.16 (s, 6H).

Intermediate 147C: methyl 3-4(tert-butyldimethylsilyl)oxy)methyl)-4-(4,4,5,5-tetramethyl-1,3,2-dioxaborolan-2-yl)benzoate

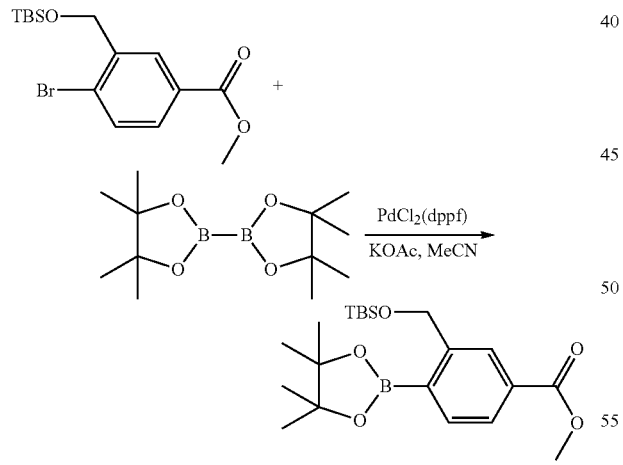

To a solution of Intermediate 147B (1.41 g, 3.92 mmol) in acetonitrile (15 mL) were added 4,4,4',4',5,5,5',5'-octamethyl-2,2'-bi(1,3,2-dioxaborolane) (1.20 g, 4.71 mmol), KOAc (0.77 g, 7.85 mmol), and PdCl$_2$(dppf) (0.14 g, 0.20 mmol) at rt. The reaction was stirred under argon at 90° C. for 5 h. The solvent was removed. The crude product was purified by normal phase chromatography to afford Intermediate 147C as a clear colorless oil (1.18 g, 74%). LCMS (ESI) m/z: 407.1 [M+H]$^+$; $^1$H NMR (400 MHz, CDCl$_3$) δ 8.14 (d, J=0.9 Hz, 1H), 7.79-7.74 (m, 1H), 7.74-7.68 (m, 1H), 4.91 (s, 2H), 3.81 (s, 3H), 1.24 (s, 12H), 0.86 (s, 9H), 0.00 (s, 6H).

Intermediate 147D: methyl 3-(((tert-butyldimethylsilyl)oxy)methyl)-4-(5-fluoropyrimidin-4-yl)benzoate

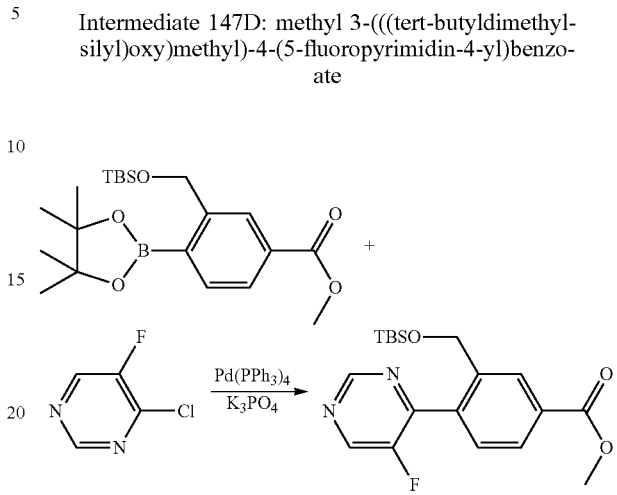

To a solution of Intermediate 147C (285 mg, 0.701 mmol) in dioxane (2 mL) were added 4-chloro-5-fluoropyrimidine (93 mg, 0.701 mmol), K$_3$PO$_4$ (447 mg, 2.10 mmol) and Pd(Ph$_3$P)$_4$ (81 mg, 0.070 mmol) at rt. The reaction was stirred under argon at 90° C. for 3 h. The reaction mixture was diluted with EtOAc, washed with $H_2O$ and brine. The organic phase was dried over sodium sulfate, filtered and concentrated. The crude product was purified by normal phase chromatography to give Intermediate 147D as a clear colorless oil (225 mg, 85%). LCMS(ESI) m/z: 377.1 [M+H]$^+$; $^1$H NMR (400 MHz, CDCl$_3$) δ 9.14 (d, J=2.9 Hz, 1H), 8.71 (d, J=2.0 Hz, 1H), 8.33 (d, J=1.1 Hz, 1H), 8.09 (dd, J=7.9, 1.8 Hz, 1H), 7.55 (dd, J=8.0, 1.4 Hz, 1H), 4.87 (s, 2H), 3.99 (s, 3H), 0.85 (s, 9H), 0.00 (s, 6H).

Intermediate 147E: methyl 6H-isochromeno[4,3-d]pyrimidine-8-carboxylate

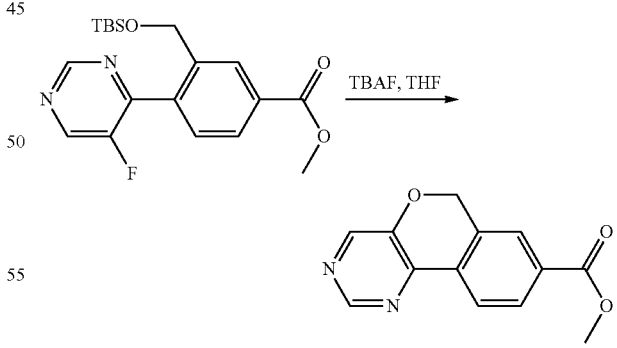

To a solution of Intermediate 147D (225 mg, 0.598 mmol) in THF (3 mL) was added TBAF (1 M in THF, 3.0 mL, 3.0 mmol) at rt. The reaction was stirred under argon at rt for 30 min. LCMS showed the reaction was completed. The solvent was removed. The crude product was purified by normal phase chromatography to afford Intermediate 147E as a white solid (142 mg, 98%). LCMS(ESI) m/z: 243.1 [M+H]$^+$; $^1$H NMR (400 MHz, CDCl$_3$) δ 8.91 (s, 1H), 8.44

(s, 1H), 8.33 (d, J=8.1 Hz, 1H), 8.14 (dd, J=8.0, 1.7 Hz, 1H), 7.87 (d, J=0.9 Hz, 1H), 5.37 (s, 2H), 3.97 (s, 3H).

Intermediate 147

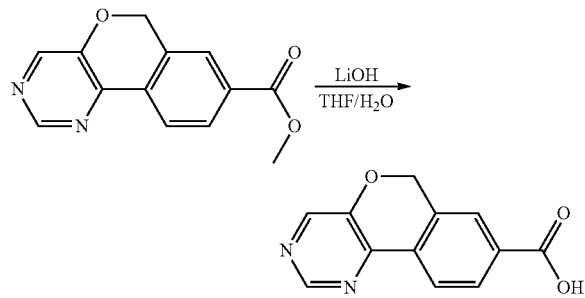

To a solution of Intermediate 147E (142 mg, 0.586 mmol) in THF (6 mL) and H₂O (2 mL) was added LiOH (70.2 mg, 2.93 mmol) at RT. The reaction was stirred under argon at rt for 2 h. The solvent was removed to give Intermediate 147 as a white solid (134 mg, 100%). LCMS(ESI) m/z: 229.1 [M+H]⁺; ¹H NMR (400 MHz, DMSO-d₆) δ 8.82 (s, 1H), 8.46 (s, 1H), 8.04 (d, J=8.1 Hz, 1H), 7.95 (d, J=8.1 Hz, 1H), 7.77 (d, J=1.0 Hz, 1H), 5.39 (s, 2H)

Intermediate 148:
3-methoxy-4-(1-methyl-1H-pyrazol-4-yl)benzoic acid

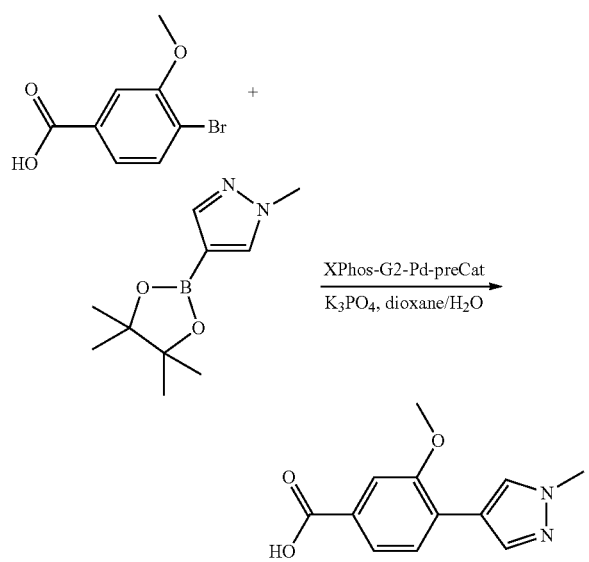

To a solution of 4-bromo-3-methoxybenzoic acid (150 mg, 0.65 mmol) in dioxane (3 mL) were added 1-methyl-4-(4,4,5,5-tetramethyl-1,3,2-dioxaborolan-2-yl)-1H-pyrazole (162 mg, 0.78 mmol), K₃PO₄ (413 mg, 1.95 mmol) and XPhos-G2 (26 mg, 0.032 mmol) at rt. The reaction was stirred in a sealed vial at 100° C. for 1 h. The solvent was removed. Purification by normal phase chromatography provided Intermediate 148 (88 mg, 58%) as an off-white solid. ¹H NMR (400 MHz, DMSO-d₆) δ 12.89 (br s, 1H), 8.22 (s, 1H), 7.98 (s, 1H), 7.72 (d, J=8.6 Hz, 1H), 7.58-7.51 (m, 2H), 3.93 (s, 3H), 3.88 (s, 3H). LC-MS(ESI) m/z: 233.0 [M+H]⁺.

Intermediate 149:
3-fluoro-4-(1-methyl-1H-pyrazol-4-yl)benzoic acid

Intermediate 149A: methyl 3-fluoro-4-(1-methyl-1H-pyrazol-4-yl)benzoate

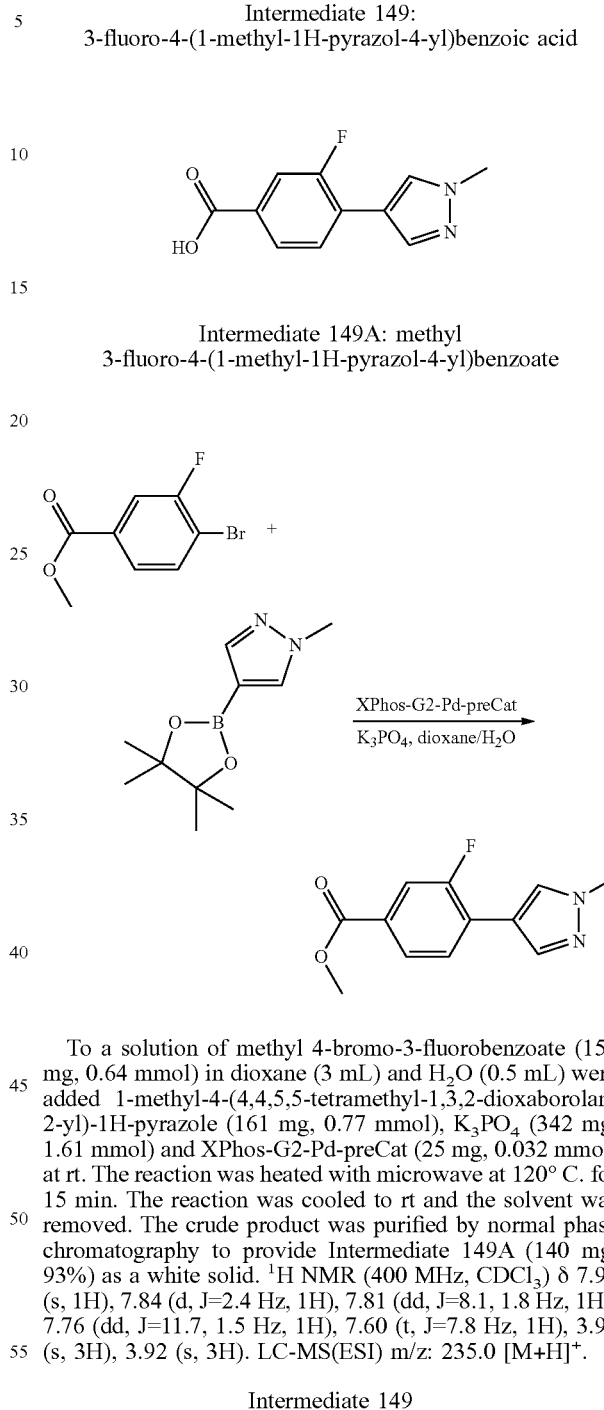

To a solution of methyl 4-bromo-3-fluorobenzoate (150 mg, 0.64 mmol) in dioxane (3 mL) and H₂O (0.5 mL) were added 1-methyl-4-(4,4,5,5-tetramethyl-1,3,2-dioxaborolan-2-yl)-1H-pyrazole (161 mg, 0.77 mmol), K₃PO₄ (342 mg, 1.61 mmol) and XPhos-G2-Pd-preCat (25 mg, 0.032 mmol) at rt. The reaction was heated with microwave at 120° C. for 15 min. The reaction was cooled to rt and the solvent was removed. The crude product was purified by normal phase chromatography to provide Intermediate 149A (140 mg, 93%) as a white solid. ¹H NMR (400 MHz, CDCl₃) δ 7.90 (s, 1H), 7.84 (d, J=2.4 Hz, 1H), 7.81 (dd, J=8.1, 1.8 Hz, 1H), 7.76 (dd, J=11.7, 1.5 Hz, 1H), 7.60 (t, J=7.8 Hz, 1H), 3.96 (s, 3H), 3.92 (s, 3H). LC-MS(ESI) m/z: 235.0 [M+H]⁺.

Intermediate 149

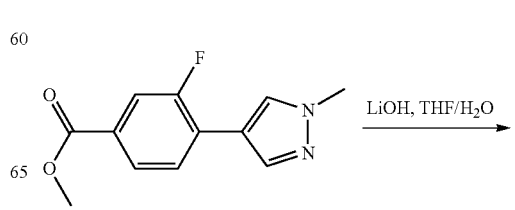

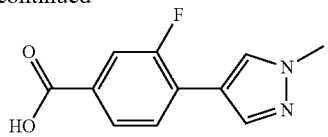

To a solution of Intermediate 149A (130 mg, 0.56 mmol) in THF (2 mL) and H$_2$O (0.5 mL) was added LiOH (53.2 mg, 2.22 mmol) at rt. The reaction was stirred under N$_2$ at rt for overnight. The reaction was acidified with TFA, and the solvent was removed. The crude product was purified by reverse phase chromatography to provide Intermediate 149 (115 mg, 94%) as a white solid. $^1$H NMR (400 MHz, DMSO-d$_6$) δ 13.12 (s, 1H), 8.25 (d, J=2.2 Hz, 1H), 7.99 (s, 1H), 7.90-7.80 (m, 1H), 7.76 (dd, J=8.0, 1.7 Hz, 1H), 7.70 (dd, J=11.9, 1.5 Hz, 1H), 3.91 (s, 3H). LC-MS(ESI) m/z: 221.0 [M+H]$^+$.

Intermediate 150:
7-acetylimidazo[1,2-a]pyridine-3-carboxylic acid

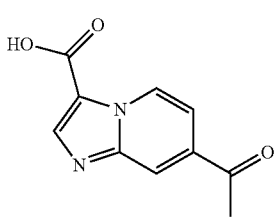

Intermediate 150A, ethyl
7-acetylimidazo[1,2-a]pyridine-3-carboxylate

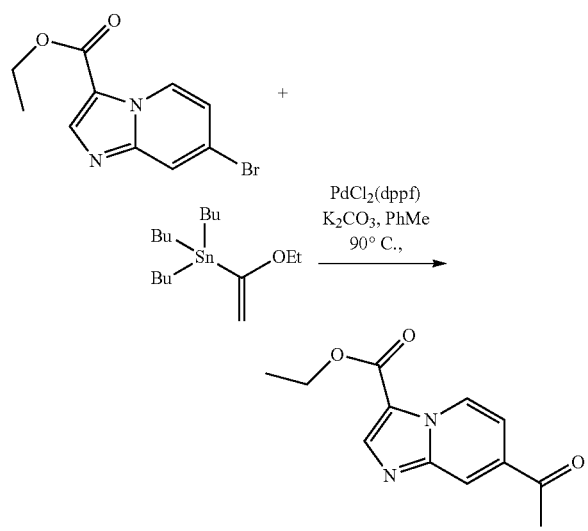

Ethyl 7-bromoimidazo[1,2-a]pyridine-3-carboxylate (0.100 g, 0.372 mmol), tributyl(1-ethoxyvinyl)stannane (0.20 g, 0.56 mmol), K$_2$CO$_3$ (0.103 g, 0.74 mmol) and PdCl$_2$(dppf) (0.027 g, 0.037 mmol) were placed in a pressure vial. The reaction mixture was degassed, and toluene (2 mL) was added. The reaction mixture was stirred at 120° C. for 5 h. After cooled to rt, it was added HCl to adjust pH to ~2. The reaction was heated for another 2 h at 60° C. It was cooled and the solvent was removed. The crude product was purified by normal phase chromatography to Intermediate 150A (27 mg, 31%) as a light brown solid. $^1$H NMR (400 MHz, CDCl$_3$) δ 9.34 (d, J=7.3 Hz, 1H), 8.42 (br. s., 1H), 8.32 (s, 1H), 7.61 (d, J=7.0 Hz, 1H), 4.45 (q, J=7.2 Hz, 2H), 2.69 (s, 3H), 1.47-1.42 (m, 3H). LC-MS(ESI) m/z: 233.0 [M+H]$^+$.

Intermediate 150

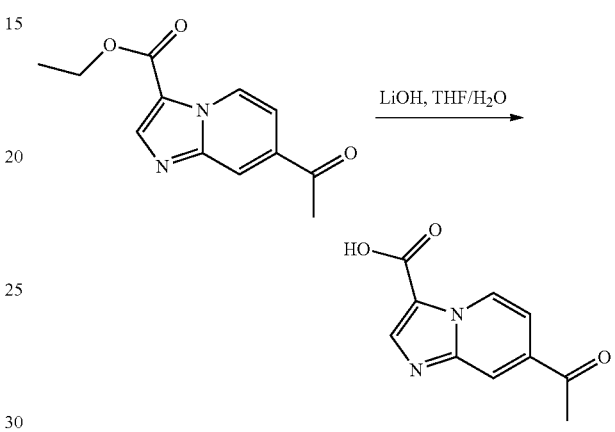

To a solution of Intermediate 150A (27 mg, 0.12 mmol) in THF (2 mL) were added LiOH (14 mg, 0.58 mmol) and H$_2$O (0.5 mL) at rt. The reaction was stirred under N$_2$ at rt for 3 h. The reaction was acidified with TFA, and the solvent was removed. Purification by reverse phase chromatography provided Intermediate 150 (12 mg, 51%) as a white solid. LC-MS(ESI) m/z: 204.9 [M+H]$^+$.

Intermediate 151: 3-fluoro-4-(1-(methyl-d$_3$)-1H-pyrazol-4-yl)benzoic acid

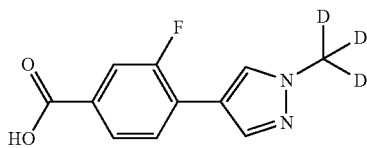 [SMILES: [2H]C([2H])([2H])n1cc(-c2ccc(C(=O)O)cc2F)cn1]

Intermediate 151A: tert-butyl 4-(2-fluoro-4-(methoxycarbonyl)phenyl)-1H-pyrazole-1-carboxylate, and Intermediate 151B: methyl 3-fluoro-4-(1H-pyrazol-4-yl)benzoate

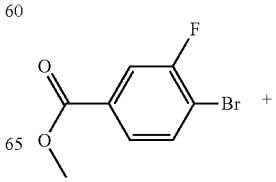

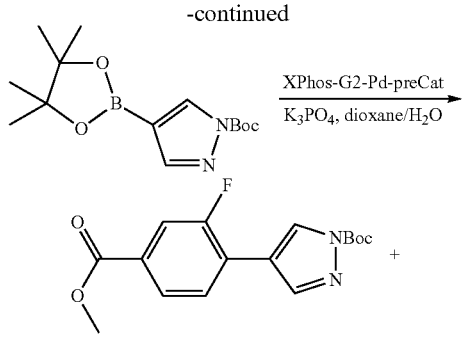

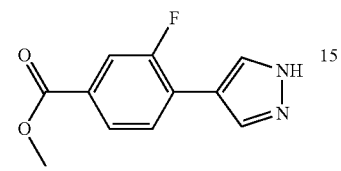

To a solution of methyl 4-bromo-3-fluorobenzoate (526 mg, 2.26 mmol) in dioxane (10 mL) and H₂O (2 mL) were added tert-butyl 4-(4,4,5,5-tetramethyl-1,3,2-dioxaborolan-2-yl)-1H-pyrazole-1-carboxylate (797 mg, 2.71 mmol), K₃PO₄ (958 mg, 4.51 mmol) and XPhos-G2-Pd-preCat (35.5 mg, 0.045 mmol) at rt. The reaction was stirred under N₂ at 60° C. overnight. The reaction mixture was diluted with EtOAc, washed with H₂O and brine. The organic phase was dried over Na₂SO₄, filtered and concentrated. The crude product was purified by normal phase chromatography to give two products as white solids. Intermediate 151A (463 mg, 64%): ¹H NMR (400 MHz, CDCl₃) δ 8.51 (d, J=1.5 Hz, 1H), 8.10 (s, 1H), 7.84 (dd, J=8.1, 1.5 Hz, 1H), 7.79 (dd, J=11.4, 1.5 Hz, 1H), 7.63 (t, J=7.8 Hz, 1H), 3.92 (s, 3H), 1.68 (s, 9H). LC-MS(ESI) m/z: 321.0 [M+H]⁺. Intermediate 151B (175 mg, 35%): ¹H NMR (400 MHz, CDCl₃) δ 8.06 (d, J=1.8 Hz, 2H), 7.85 (dd, J=8.1, 1.8 Hz, 1H), 7.80 (dd, J=11.7, 1.5 Hz, 1H), 7.66 (t, J=7.7 Hz, 1H), 3.94 (s, 3H). LC-MS(ESI) m/z: 221.0 [M+H]⁺.

Alternatively, Intermediate 151B was obtained from Intermediate 151A. To a solution of Intermediate 151A (463 mg, 1.45 mmol) in DCM (5 mL) was added TFA (2 mL, 26.0 mmol) at rt. The reaction was stirred under N₂ at rt for 2 h. The solvent was removed and the product was dried in vacuo to give a beige solid (480 mg, 99%) as TFA salt. ¹H NMR (400 MHz, DMSO-d₆) δ 8.18 (d, J=2.0 Hz, 2H), 7.92 (t, J=7.9 Hz, 1H), 7.82-7.76 (m, 1H), 7.74 (dd, J=11.8, 1.7 Hz, 1H), 3.86 (s, 3H). LC-MS(ESI) m/z: 221.0 [M+H]⁺.

Intermediate 151C: methyl 3-fluoro-4-(1-(methyl-d₃)-1H-pyrazol-4-yl)benzoate

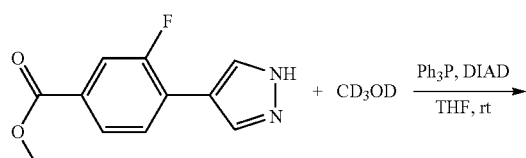

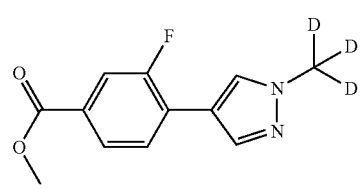

To a solution of Intermediate 151B (160 mg, 0.73 mmol) in THF (5 mL) were added CD₃OD (26.2 mg, 0.73 mmol), Ph₃P (229 mg, 0.872 mmol) and DIAD (0.18 mL, 0.95 mmol) at rt. The reaction was stirred under N₂ at rt overnight. The solvent was removed. The crude product was purified by normal phase chromatography to give Intermediate 151C (92 mg, 53%) as a white solid. ¹H NMR (400 MHz, CDCl₃) δ 7.91 (s, 1H), 7.85 (dd, J=2.6, 0.7 Hz, 1H), 7.82 (dd, J=8.1, 1.8 Hz, 1H), 7.77 (dd, J=11.7, 1.8 Hz, 1H), 7.61 (t, J=7.8 Hz, 1H), 3.92 (s, 3H). LC-MS(ESI) m/z: 238.0 [M+H]⁺.

Intermediate 151

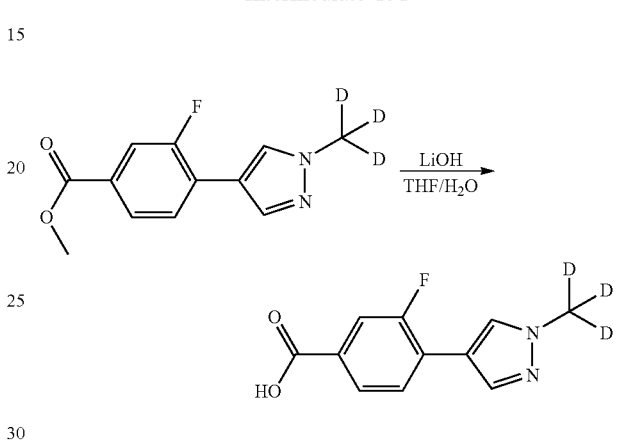

To a solution of Intermediate 151C (92 mg, 0.39 mmol) in THF (2 mL) were added LiOH (27.9 mg, 1.16 mmol) and water (0.5 mL) at rt. The reaction was stirred under N₂ at rt overnight. The reaction was acidified with TFA, and the solvent was removed. The crude product was purified by reverse phase chromatography to afford Intermediate 151 (42 mg, 49%) as a white solid. ¹H NMR (400 MHz, DMSO-d₆) δ 13.14 (br s, 1H), 8.27-8.19 (m, 1H), 7.99 (s, 1H), 7.88-7.80 (m, 1H), 7.78-7.73 (m, 1H), 7.70 (dd, J=11.9, 1.5 Hz, 1H). LC-MS(ESI) m/z: 224.0 [M+H]⁺.

Intermediate 152: 4-(1-(difluoromethyl)-1H-pyrazol-4-yl)-3-fluorobenzoic acid

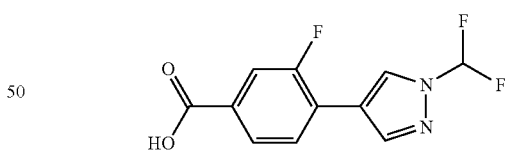

Intermediate 152A: methyl 4-(1-(difluoromethyl)-1H-pyrazol-4-yl)-3-fluorobenzoate

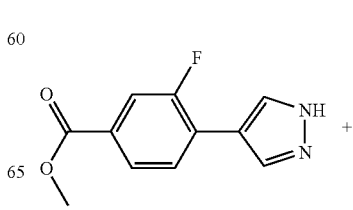

-continued

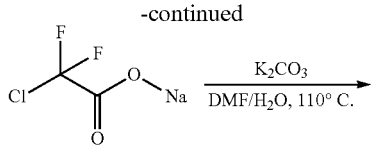

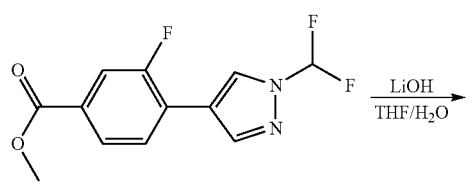

To a solution of Intermediate 151B, TFA salt (150 mg, 0.45 mmol) in DMF (5 mL) and H$_2$O (0.5 mL) were added sodium 2-chloro-2,2-difluoroacetate (137 mg, 0.90 mmol) and K$_2$CO$_3$ (155 mg, 1.12 mmol) at rt. The reaction was stirred under N$_2$ at 110° C. for 5 h. After cooled to rt, The reaction mixture was diluted with EtOAc, washed with H$_2$O and brine. The organic phase was dried over Na$_2$SO$_4$, filtered and concentrated. The crude product was purified by normal phase chromatography to afford Intermediate 152A (76 mg, 63%) as a white solid. $^1$H NMR (400 MHz, CDCl$_3$) δ 8.26 (d, J=1.8 Hz, 1H), 8.06 (s, 1H), 7.85 (dd, J=8.0, 1.7 Hz, 1H), 7.80 (dd, J=11.4, 1.5 Hz, 1H), 7.62 (t, J=7.7 Hz, 1H), 7.24 (t, J=60.3 Hz, 1H), 3.93 (s, 3H). LC-MS(ESI) m/z: 271.0 [M+H]$^+$.

Intermediate 152

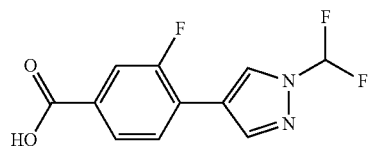 [SMILES: O=C(O)c1ccc(-c2cnn(C(F)F)c2)c(F)c1]

Intermediate 152 was prepared from Intermediate 152A following the same hydrolysis procedure as in Intermediate 149. $^1$H NMR (400 MHz, DMSO-d$_6$) δ 8.61 (d, J=1.5 Hz, 1H), 8.27 (s, 1H), 7.87 (t, J=59.2 Hz, 1H), 7.71-7.66 (m, 2H), 7.62 (d, J=12.5 Hz, 1H). LC-MS(ESI) m/z: 257.0 [M+H]$^+$.

Intermediate 153: 7-(2-hydroxypropan-2-yl)imidazo[1,2-a]pyridine-3-carboxylic acid

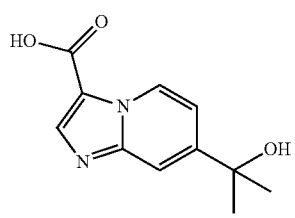 [SMILES: CC(C)(O)c1ccn2c(C(=O)O)cnc2c1]

Intermediate 153A: ethyl 7-(2-hydroxypropan-2-yl)imidazo[1,2-a]pyridine-3-carboxylate

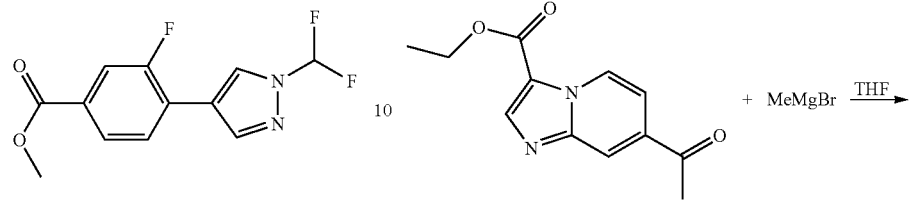

To a suspension of Intermediate 150A (80 mg, 0.298 mmol) in THF (5 mL) was added methylmagnesium bromide (3 M in ether, 0.218 mL, 0.655 mmol) at −78° C. The reaction was stirred under N$_2$ at −78° C. for 1 h and then was warmed up to 0° C. After stirring for another 30 min, MeOH (0.5 mL) was added to quench the reaction. The solvent was removed. The crude product was purified by normal phase chromatography to provide Intermediate 153A (16 mg, 22%) as a white solid. $^1$H NMR (400 MHz, CDCl$_3$) δ 9.17 (dd, J=7.3, 0.7 Hz, 1H), 8.22 (s, 1H), 7.89 (d, J=0.9 Hz, 1H), 7.15 (dd, J=7.3, 1.8 Hz, 1H), 4.39 (q, J=7.1 Hz, 2H), 1.62 (s, 6H), 1.40 (t, J=7.2 Hz, 3H). LC-MS(ESI) m/z: 249.0 [M+H]$^+$.

Intermediate 153

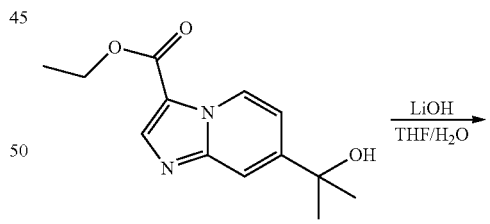

Intermediate 153 was obtained by following the same hydrolysis procedure as in Intermediate 149. $^1$H NMR (400 MHz, DMSO-d$_6$) δ 9.60 (d, J=7.3 Hz, 1H), 7.64 (s, 1H), 7.46 (s, 1H), 6.98 (dd, J=7.3, 1.5 Hz, 1H), 5.16 (br. s., 1H), 1.45 (s, 6H). LC-MS(ESI) m/z: 221.0 [M+H]$^+$;

Intermediate 154: 7-(1-hydroxyethyl)imidazo[1,2-a]pyridine-3-carboxylic acid

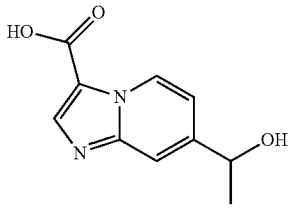

Intermediate 154A: ethyl 7-(1-hydroxyethyl)imidazo[1,2-a]pyridine-3-carboxylate

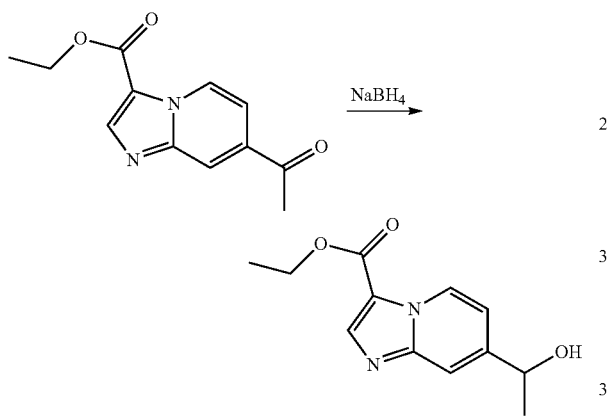

To a solution of Intermediate 150A (80 mg, 0.30 mmol) in MeOH (3 mL) was added NaBH$_4$ (11.3 mg, 0.30 mmol) at 0° C. The reaction was stirred under N$_2$ at 0° C. for 2 h. It was quench with 1.0 N HCl, and the solvent was removed to leave the product as a white solid (70 mg, 100%). LC-MS(ESI) m/z: 235.0 [M+H]$^+$.

Intermediate 154

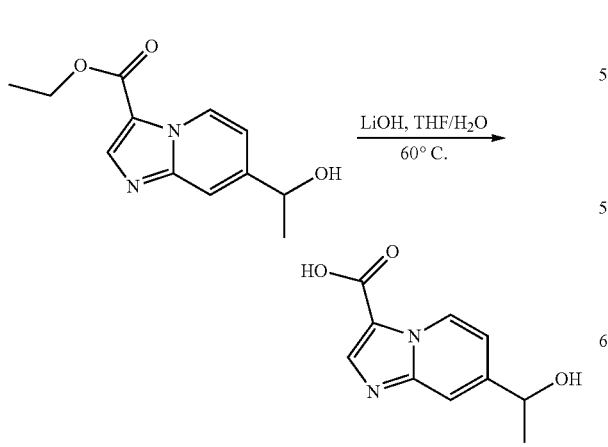

Intermediate 154 was obtained by following the same hydrolysis procedure as in Intermediate 149. $^1$H NMR (400 MHz, CD$_3$OD) δ 9.54 (d, J=7.3 Hz, 1H), 8.55 (s, 1H), 7.93 (d, J=0.7 Hz, 1H), 7.56 (dd, J=7.2, 1.4 Hz, 1H), 5.05 (q, J=6.5 Hz, 1H), 1.53 (d, J=6.6 Hz, 3H). LC-MS(ESI) m/z: 207.1 [M+H]$^+$.

Intermediate 155: 7-((1,1-dioxidotetrahydro-2H-thiopyran-4-yl)oxy)imidazo[1,2-a]pyridine-3-carboxylic acid

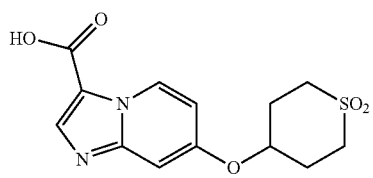 [SMILES: O=C(O)c1cnc2cc(OC3CCS(=O)(=O)CC3)ccn12]

Intermediate 155A: ethyl 7-((1,1-dioxidotetrahydro-2H-thiopyran-4-yl)oxy)imidazo[1,2-a]pyridine-3-carboxylate

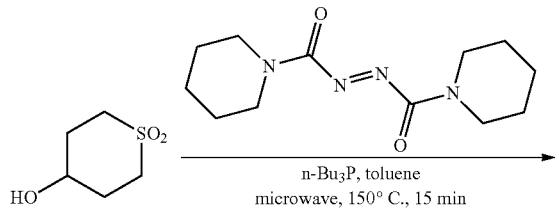

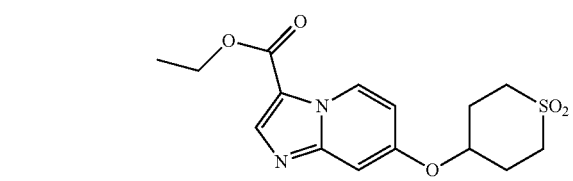

To a microwave vial containing ethyl 7-hydroxyimidazo[1,2-a]pyridine-3-carboxylate (50 mg, 0.24 mmol), 4-hydroxytetrahydro-2H-thiopyran 1,1-dioxide (73 mg, 0.49 mmol), 1,1'-(azodicarbonyl)dipiperidine (184 mg, 0.73 mmol) were added toluene (3 mL) and tri-N-butylphosphine (0.18 mL, 0.73 mmol) at rt. The reaction was heated with microwave at 150° C. for 15 min. The solvent was removed. The crude product was purified by normal phase chromatography to provide Intermediate 155A (62 mg, 76%) as a white solid. LC-MS(ESI) m/z: 339.0 [M+H]$^+$.

Intermediate 155

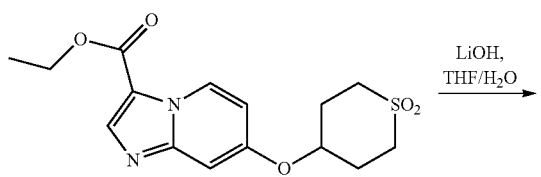

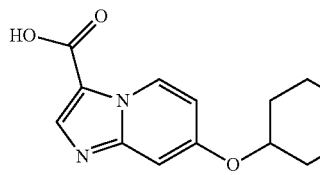

Intermediate 155 was obtained by following the same hydrolysis procedure as in Intermediate 149. $^1$H NMR (400 MHz, CD$_3$OD) δ 9.43 (d, J=7.7 Hz, 1H), 8.59 (s, 1H), 7.50 (d, J=2.2 Hz, 1H), 7.38 (dd, J=7.7, 2.4 Hz, 1H), 5.13 (t, J=4.3 Hz, 1H), 3.47-3.37 (m, 2H), 3.30-3.21 (m, 2H), 2.54-2.43 (m, 4H). LC-MS(ESI) m/z: 311.1 [M+H]$^+$.

Intermediate 156: 7-(3,3,3-trifluoropropoxy)imidazo[1,2-a]pyridine-3-carboxylic acid

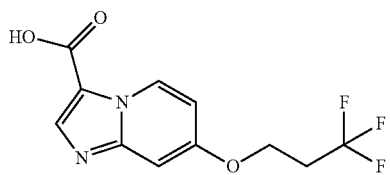 [SMILES: O=C(O)c1cnc2cc(OCCC(F)(F)F)ccn12]

Intermediate 156 was obtained by following a similar procedure to that described in Intermediate 155. LC-MS (ESI) m/z: 275.1 [M+H]$^+$.

Intermediate 157: 7-((1,3-difluoropropan-2-yl)oxy)imidazo[1,2-a]pyridine-3-carboxylic acid

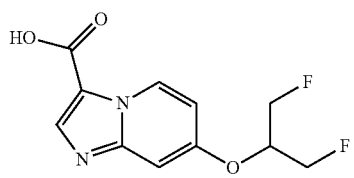 [SMILES: O=C(O)c1cnc2cc(OC(CF)CF)ccn12]

Intermediate 157 was obtained by following a similar procedure to that described in Intermediate 155. LC-MS (ESI) m/z: 257.1 [M+H]$^+$.

Intermediate 158: 7-(pyridin-2-yloxy)imidazo[1,2-a]pyridine-3-carboxylic acid

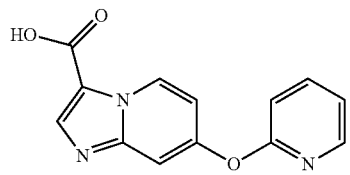 [SMILES: O=C(O)c1cnc2cc(Oc3ccccn3)ccn12]

Intermediate 158A: ethyl 7-(pyridin-2-yloxy)imidazo[1,2-a]pyridine-3-carboxylate

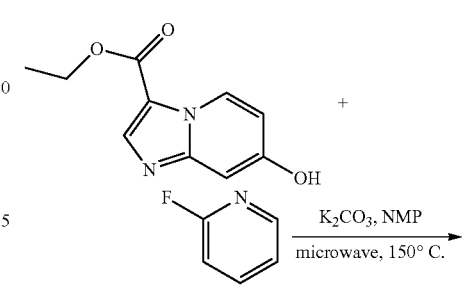

To a solution of Intermediate 89 (30 mg, 0.15 mmol) in NMP (3 mL) were added 2-fluoropyridine (42 mg, 0.44 mmol) and K$_2$CO$_3$ (60 mg, 0.44 mmol) at rt. The reaction was heated with microwave at 160° C. for 60 min. The reaction was filtered. The crude product was purified by reverse phase to provide Intermediate 158A (40 mg, 69%) as a light brown solid. $^1$H NMR (400 MHz, DMSO-d$_6$) δ 9.25 (d, J=7.7 Hz, 1H), 8.40 (s, 1H), 8.30-8.22 (m, 1H), 7.98 (ddd, J=8.2, 7.4, 2.0 Hz, 1H), 7.58 (d, J=2.2 Hz, 1H), 7.29 (ddd, J=7.2, 4.9, 0.7 Hz, 1H), 7.26-7.20 (m, 2H), 4.38 (q, J=7.0 Hz, 2H), 1.36 (t, J=7.0 Hz, 3H). LC-MS(ESI) m/z: 284.1 [M+H]$^+$.

Intermediate 158

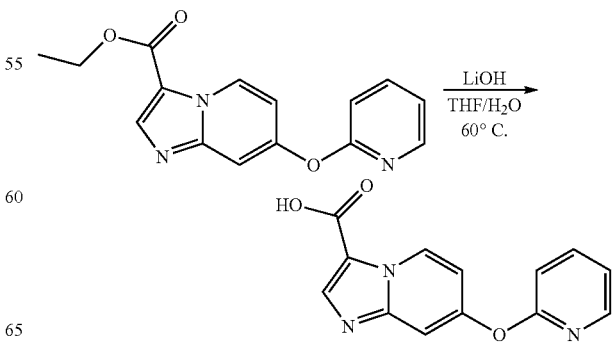

Intermediate 158 was obtained by following a similar hydrolysis procedure to that described in Intermediate 155. ¹H NMR (400 MHz, methanol-d₄) δ 9.55 (dd, J=7.7, 0.7 Hz, 1H), 8.48 (s, 1H), 8.30 (ddd, J=4.9, 1.9, 0.7 Hz, 1H), 8.00 (ddd, J=8.1, 7.3, 2.0 Hz, 1H), 7.65 (dd, J=2.4, 0.7 Hz, 1H), 7.40 (dd, J=7.5, 2.4 Hz, 1H), 7.34 (ddd, J=7.3, 5.0, 0.9 Hz, 1H), 7.28-7.24 (m, 1H). LC-MS(ESI) m/z: 256.0 [M+H]⁺.

Intermediate 159:
3-isopropylimidazo[1,5-a]pyridine-1-carboxylic acid

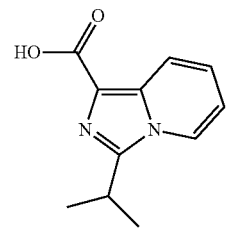

Intermediate 159A: methyl 3-(prop-1-en-2-yl)imidazo[1,5-a]pyridine-1-carboxylate

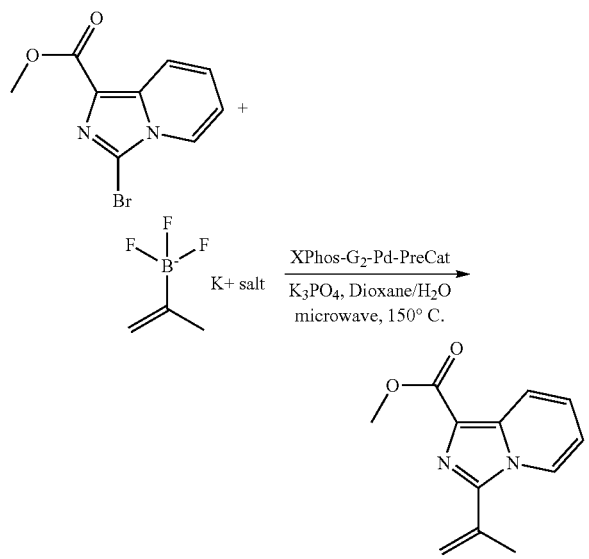

A microwave tube containing methyl 3-bromoimidazo[1,5-a]pyridine-1-carboxylate (50 mg, 0.20 mmol), potassium trifluoro(prop-1-en-2-yl)borate (44 mg, 0.29 mmol), and K₃PO₄ (125 mg, 0.59 mmol) was purged with nitrogen, and then were added dioxane (3 mL), H₂O (0.5 mL) and XPhos-G2-Pd-preCat (15.4 mg, 0.020 mmol). The reaction was heated with microwave at 150° C. for 15 min. The organic layer was separated, and the solvent was removed. The crude product was purified by normal phase chromatography to afford Intermediate 159A (34 mg, 80%) as a white solid. LC-MS(ESI) m/z: 217.1 [M+H]⁺.

Intermediate 159B: methyl 3-isopropylimidazo[1,5-a]pyridine-1-carboxylate

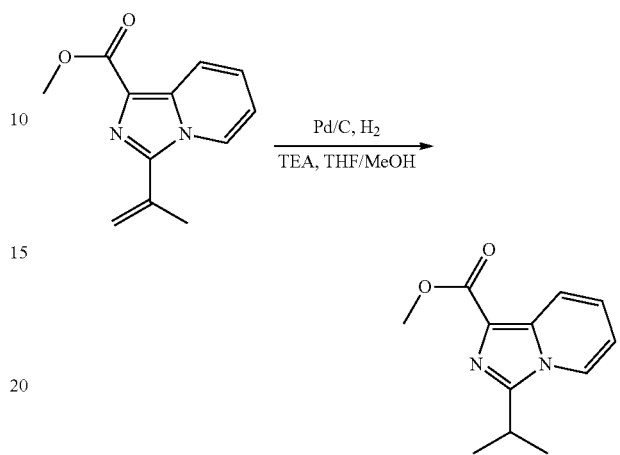

To a solution of Intermediate 159A (34 mg, 0.157 mmol) in THF (3 mL) and MeOH (1 mL) were added TEA (0.11 mL, 0.79 mmol) and 10% Pd—C (16.7 mg, 0.016 mmol) at rt. The reaction was stirred under a H₂ balloon at rt for 1 h. The catalyst was filtered off, and the solvent was removed to give the product (34 mg, 100%). LC-MS(ESI) m/z: 219.1 [M+H]⁺.

Intermediate 159

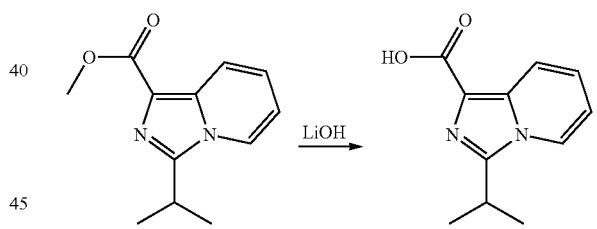

Intermediate 159 was obtained by following a similar hydrolysis procedure to that described in Intermediate 155. LC-MS(ESI) m/z: 205.2 [M+H]⁺.

Intermediate 160: 7-(2,2-difluoroethoxy)imidazo[1,2-a]pyridine-3-carboxylic acid

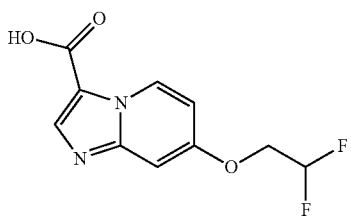 [SMILES: O=C(O)c1cnc2cc(OCC(F)F)ccn12]

Intermediate 160A: ethyl 7-(2,2-difluoroethoxy) imidazo[1,2-a]pyridine-3-carboxylate

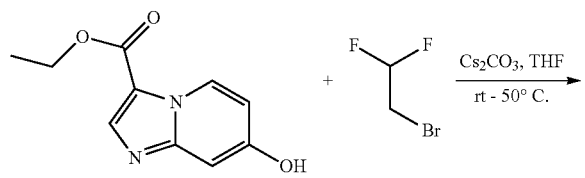

Intermediate 160

To a solution of Intermediate 89 (50 mg, 0.24 mmol) in THF (2 mL) were added 2-bromo-1,1-difluoroethane (70 mg, 0.49 mmol) and $Cs_2CO_3$ (158 mg, 0.49 mmol) at rt. The reaction was heated at 50° C. for 24 h. The solvent was removed. The crude product was purified by normal phase chromatography to afford Intermediate 160A (42 mg, 64%) as a white solid. $^1$H NMR (400 MHz, $CDCl_3$) δ 9.16 (d, J=7.5 Hz, 1H), 8.20 (s, 1H), 6.99 (d, J=2.4 Hz, 1H), 6.78 (dd, J=7.5, 2.6 Hz, 1H), 6.15 (tt, J=54.8, 4.4 Hz, 1H), 4.40 (q, J=7.1 Hz, 2H), 4.27 (td, J=12.9, 4.0 Hz, 2H), 1.41 (t, J=7.2 Hz, 3H). LC-MS(ESI) m/z: 271.0 [M+H]$^+$.

Intermediate 160 was obtained by following a similar hydrolysis procedure to that described in Intermediate 155. $^1$H NMR (400 MHz, DMSO-$d_6$) δ 9.24-9.13 (m, 1H), 8.35 (s, 1H), 7.38 (d, J=2.4 Hz, 1H), 7.13 (dd, J=7.5, 2.6 Hz, 1H), 6.48 (tt, J=54.4, 3.3 Hz, 1H), 4.56 (td, J=14.7, 3.3 Hz, 2H). LC-MS(ESI) m/z: 243.0 [M+H]$^+$.

Intermediate 161: 7-isopropoxyimidazo[1,2-a]pyridine-3-carboxylic acid

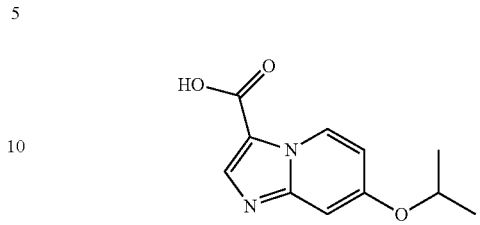

Intermediate 161 was obtained by following a similar procedure as described in Intermediate 160. $^1$H NMR (400 MHz, $CD_3OD$) δ 9.42 (dd, J=7.7, 0.4 Hz, 1H), 8.41 (s, 1H), 7.24 (d, J=2.6 Hz, 1H), 7.20-7.14 (m, 1H), 4.90 (spt, J=6.1 Hz, 1H), 1.45 (d, J=6.2 Hz, 6H). LC-MS(ESI) m/z: 221.1 [M+H]$^+$.

Example 1: N-[6-(4-oxo-3,4-dihydrophthalazin-1-yl)spiro[3.3]heptan-2-yl]-2,3-dihydro-1H-indene-2-carboxamide

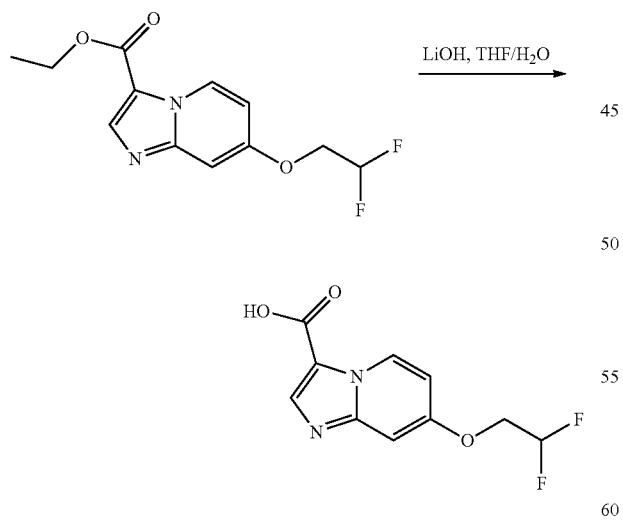

Intermediate 1 (29 mg, 0.060 mmol) was dissolved in dry DMF (1 mL), then 2,3-dihydro-1H-indene-2-carboxylic acid (19.5 mg, 0.120 mmol) and DIEA (0.063 mL, 0.360 mmol) were added. After stirring for 5 min at rt, HATU (22.8 mg, 0.060 mmol) was added, and the reaction mixture was stirred at rt for 2 h. The reaction mixture was quenched with MeOH (0.1 mL), diluted with DMF, filtered and was purified by preparative HPLC to afford Example 1 (15.3 mg, 63% yield). MS(ESI) m/z: 400.3 (M+H)+; 1H NMR (500 MHz, DMSO-d6) δ ppm 12.47 (s, 1H), 8.25 (d, J=7.4 Hz, 1H), 8.17 (d, J=7.4 Hz, 1H), 7.96-7.89 (m, 1H), 7.88-7.75 (m, 2H), 7.17 (d, J=4.4 Hz, 2H), 7.14-7.05 (m, 2H), 4.14 (sxt, J=7.9 Hz, 1H), 3.93-3.82 (m, 1H), 3.17-3.06 (m, 1H), 3.06-2.97 (m, 4H), 2.62-2.51 (m, 2H), 2.41-2.28 (m, 3H), 2.24-2.13 (m, 1H), 2.06 (t, J=9.6 Hz, 1H), 1.88 (t, J=9.8 Hz, 1H). HPLC RT=1.52 min (Method E), 1.61 min (Method F).

The following Examples in Table 1 were made by using the same procedure as shown in Example 1. Intermediate 1 was coupled with the appropriate acid. Various coupling reagents could be used other than the one described in Example 1 such as BOP, PyBop, EDC/HOBt or HATU.

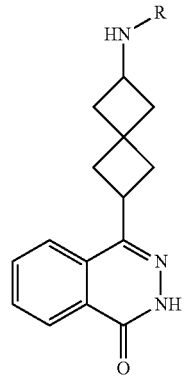

TABLE 1

| Ex. | R | Name | LCMS (M + H)+ | HPLC Method, RT (min.) | 1H NMR |
|---|---|---|---|---|---|
| 2 | 4-(dimethylamino)benzoyl | 4-(dimethylamino)-N-[6-(4-oxo-3,4-dihydrophthalazin-1-yl)spiro[3.3]heptan-2-yl]benzamide | 403.2 | E: 1.31 F: 1.40 | 1H NMR: (500 MHz, DMSO-d6) δ ppm 12.48 (s, 1H), 8.25 (d, J = 1.1 Hz, 1H), 8.21 (d, J = 7.4 Hz, 1H), 7.94-7.89 (m, 1H), 7.89-7.80 (m, 2H), 7.72 (d, J = 8.8 Hz, 2H), 6.68 (d, J = 8.8 Hz, 2H), 4.33 (sxt, J = 8.1 Hz, 1H), 3.95-3.81 (m, 1H), 2.95 (s, 6H), 2.64-2.51 (m, 2H), 2.44-2.30 (m, 3H), 2.27-2.14 (m, 2H), 2.04 (t, J = 9.9 Hz, 1H) |
| 3 | naphthalen-1-yl-acetyl | 2-(naphthalen-1-yl)-N-[6-(4-oxo-3,4-dihydrophthalazin-1-yl)spiro[3.3]heptan-2-yl]acetamide | 424.3 | E: 1.58 F: 1.67 | 1H NMR: (500 MHz, DMSO-d6) δ ppm 12.47 (s, 1H), 8.43 (d, J = 7.4 Hz, 1H), 8.24 (d, J = 7.7 Hz, 1H), 8.07 (d, J = 8.1 Hz, 1H), 7.94-7.87 (m, 2H), 7.86-7.76 (m, 3H), 7.56-7.47 (m, 2H), 7.47-7.42 (m, 1H), 7.42-7.37 (m, 1H), 4.09 (sxt, J = 7.9 Hz, 1H), 3.88 (d, J = 12.1 Hz, 1H), 3.85 (s, 2H), 2.60-2.52 (m, 1H), 2.40-2.27 (m, 3H), 2.22-2.11 (m, 1H), 2.11-2.02 (m, 1H), 2.07 (t, J = 9.8 Hz, 1H), 1.93-1.82 (m, 1H) |
| 4 | naphthalen-2-yl-acetyl | 2-(naphthalen-2-yl)-N-[6-(4-oxo-3,4-dihydrophthalazin-1-yl)spiro[3.3]heptan-2-yl]acetamide | 424.1 | E: 1.68 F: 1.59 | 1H NMR: (500 MHz, DMSO-d6) δ ppm 12.47 (s, 1H), 8.37 (d, J = 7.4 Hz, 1H), 8.24 (d, J = 7.7 Hz, 1H), 7.93-7.79 (m, 6H), 7.73 (s, 1H), 7.53-7.43 (m, 2H), 7.41 (d, J = 8.1 Hz, 1H), 4.10 (sxt, J = 7.9 Hz, 1H), 3.92-3.79 (m, 1H), 3.53 (s, 2H), 2.63-2.52 (m, 1H), 2.40-2.26 (m, 3H), 2.22-2.12 (m, 1H), 2.05 (t, J = 9.6 Hz, 1H), 1.87 (t, J = 9.8 Hz, 1H) |
| 5 | 1-methyl-1H-indazol-3-carbonyl | 1-methyl-N-[6-(4-oxo-3,4-dihydrophthalazin-1-yl)spiro[3.3]heptan-2-yl]-1H-indazole-3-carboxamide | 414.2 | E: 1.61 F: 1.51 | 1H NMR: (500 MHz, DMSO-d6) δ ppm 12.48 (s, 1H), 8.52 (d, J = 7.7 Hz, 1H), 8.25 (d, J = 7.7 Hz, 1H), 8.14 (d, J = 8.4 Hz, 1H), 7.95-7.89 (m, 1H), 7.90-7.80 (m, 2H), 7.71 (d, J = 8.4 Hz, 1H), 7.45 (t, J = 7.6 Hz, 1H), 7.26 (t, J = 7.4 Hz, 1H), 4.48-4.33 (m, 1H), 4.12 (s, 3H), 3.89 (t, J = 8.4 Hz, 1H), 2.64-2.53 (m, 2H), 2.46-2.28 (m, 4H), 2.24-2.07 (m, 2H) |
| 6 | 3-phenylpropanoyl | N-[6-(4-oxo-3,4-dihydrophthalazin-1-yl)spiro[3.3]heptan-2-yl]-3-phenylpropanamide | 388.3 | E: 1.42 F: 1.51 | 1H NMR: (500 MHz, DMSO-d6) δ ppm 12.47 (s, 1H), 8.24 (d, J = 7.7 Hz, 1H), 8.03 (d, J = 7.1 Hz, 1H), 7.95-7.87 (m, 1H), 7.87-7.79 (m, 2H), 7.31-7.22 (m, 2H), 7.21-7.10 (m, 3H), 4.15-4.02 (m, 1H), 3.85 (quin, J = 8.3 Hz, 1H), 2.78 (t, J = 7.6 Hz, 2H), 2.57-2.52 (m, 1H), 2.37-2.25 (m, 5H), 2.18-2.09 (m, 1H), 1.97 (t, J = 9.8 Hz, 1H), 1.80 (t, J = 9.9 Hz, 1H) |
| 7 | 1-(2,2,2-trifluoroethyl)-1H-pyrazol-3-carbonyl | N-[6-(4-oxo-3,4-dihydrophthalazin-1-yl)spiro[3.3]heptan-2-yl]-1-(2,2,2-trifluoroethyl)-1H-pyrazole-3-carboxamide | 432.2 | E: 1.47 F: 1.47 | 1H NMR: (500 MHz, DMSO-d6) δ ppm 12.46 (s, 1H), 8.29 (d, J = 7.6 Hz, 1H), 8.25 (d, J = 7.9 Hz, 1H), 7.97-7.76 (m, 4H), 6.73 (s, 1H), 5.18 (q, J = 8.7 Hz, 2H), 4.40-4.23 (m, 1H), 3.88 (quin, J = 8.3 Hz, 1H), 2.62-2.52 (m, 2H), 2.42-2.30 (m, 3H), 2.31-2.24 (m, 1H), 2.17 (d, J = 5.8 Hz, 1H), 2.13-2.04 (m, 1H) |

TABLE 1-continued

| Ex. | R | Name | LCMS (M + H)+ | HPLC Method, RT (min.) | $^1$H NMR |
|---|---|---|---|---|---|
| 8 | (pyrazole with 3-methyl, N-phenyl, C(=O) linker) | 3-methyl-N-[6-(4-oxo-3,4-dihydrophthalazin-1-yl)spiro[3.3]heptan-2-yl]-1-phenyl-1H-pyrazole-4-carboxamide | 440.25 | E: 1.67 F: 1.67 | $^1$H NMR: (500 MHz, DMSO-$d_6$) δ ppm 12.47 (s, 1H), 8.84 (s, 1H), 8.25 (d, J = 7.6 Hz, 1H), 8.11 (d, J = 6.7 Hz, 1H), 7.98-7.80 (m, 3H), 7.74 (d, J = 7.6 Hz, 2H), 7.52 (t, J = 7.6 Hz, 2H), 7.33 (t, J = 7.2 Hz, 1H), 4.35-4.24 (m, 1H), 3.90 (t, J = 8.2 Hz, 1H), 2.63 (br. s., 1H), 2.59-2.52 (m, 1H), 2.41 (s, 3H), 2.37 (d, J = 8.2 Hz, 3H), 2.24 (br. s., 1H), 2.17 (t, J = 9.8 Hz, 1H), 1.99 (t, J = 9.6 Hz, 1H) |
| 9 | (pyrazole with N-tert-butyl, C(=O) linker) | 1-tert-butyl-N-[6-(4-oxo-3,4-dihydrophthalazin-1-yl)spiro[3.3]heptan-2-yl]-1H-pyrazole-4-carboxamide | 406.2 | E: 1.44 F: 1.44 | $^1$H NMR: (500 MHz, DMSO-$d_6$) δ ppm 12.46 (s, 1H), 8.29-8.20 (m, 2H), 8.11 (d, J = 7.3 Hz, 1H), 7.95-7.88 (m, 1H), 7.86 (d, J = 9.5 Hz, 1H), 7.83 (s, 2H), 4.34-4.22 (m, 1H), 3.95-3.83 (m, 1H), 2.65-2.52 (m, 2H), 2.43-2.32 (m, 3H), 2.20 (br. s., 1H), 2.14 (t, J = 9.6 Hz, 1H), 1.97 (t, J = 10.1 Hz, 1H), 1.51 (s, 9H) |
| 10 | (pyrazole-3-carboxamide with N-phenyl, C(=O) linker) | N-[6-(4-oxo-3,4-dihydrophthalazin-1-yl)spiro[3.3]heptan-2-yl]-1-phenyl-1H-pyrazole-3-carboxamide | 426.2 | E: 1.71 F: 1.71 | $^1$H NMR: (500 MHz, DMSO-$d_6$) δ ppm 12.47 (s, 1H), 8.53 (s, 1H), 8.47 (d, J = 7.9 Hz, 1H), 8.25 (d, J = 7.9 Hz, 1H), 7.98-7.80 (m, 5H), 7.53 (t, J = 7.6 Hz, 2H), 7.37 (t, J = 7.2 Hz, 1H), 6.87 (s, 1H), 4.42-4.32 (m, 1H), 3.90 (quin, J = 8.4 Hz, 1H), 2.65-2.54 (m, 2H), 2.43-2.27 (m, 4H), 2.25-2.18 (m, 1H), 2.17-2.09 (m, 1H) |
| 11 | (indazole with N-(2-hydroxy-2-methylpropyl), C(=O) linker) | 1-(2-hydroxy-2-methylpropyl)-N-[6-(4-oxo-3,4-dihydrophthalazin-1-yl)spiro[3.3]heptan-2-yl]-1H-indazole-3-carboxamide | 472.3 | E: 1.59 F: 1.59 | $^1$H NMR: (500 MHz, DMSO-$d_6$) δ ppm 12.47 (s, 1H), 8.40 (d, J = 8.2 Hz, 1H), 8.25 (d, J = 7.9 Hz, 1H), 8.12 (d, J = 7.9 Hz, 1H), 7.96-7.81 (m, 3H), 7.76 (d, J = 8.5 Hz, 1H), 7.40 (t, J = 7.6 Hz, 1H), 7.22 (t, J = 7.5 Hz, 1H), 4.48-4.39 (m, 1H), 4.37 (s, 2H), 3.90 (quin, J = 8.5 Hz, 1H), 2.67-2.53 (m, 2H), 2.46-2.28 (m, 4H), 2.27-2.19 (m, 1H), 2.19-2.10 (m, 1H), 1.14 (s, 6H) |
| 12 | (pyrazole-4-carboxamide, N-phenyl, C(=O) linker) | N-[6-(4-oxo-3,4-dihydrophthalazin-1-yl)spiro[3.3]heptan-2-yl]-1-phenyl-1H-pyrazole-4-carboxamide | 436.2 | E: 1.57 F: 1.57 | $^1$H NMR: (500 MHz, DMSO-$d_6$) δ ppm 12.47 (s, 1H), 8.87 (s, 1H), 8.35 (d, J = 7.3 Hz, 1H), 8.25 (d, J = 7.6 Hz, 1H), 8.13 (s, 1H), 7.96-7.78 (m, 4H), 7.52 (t, J = 7.5 Hz, 2H), 7.40-7.32 (m, 1H), 4.38-4.27 (m, 1H), 3.90 (t, J = 8.2 Hz, 1H), 2.63 (br. s., 1H), 2.59-2.52 (m, 2H), 2.44-2.31 (m, 3H), 2.24 (br. s., 1H), 2.19 (t, J = 10.1 Hz, 1H), 2.02 (t, J = 9.9 Hz, 1H) |
| 13 | (5-methylpyrazole, N-phenyl, C(=O) linker) | 5-methyl-N-[6-(4-oxo-3,4-dihydrophthalazin-1-yl)spiro[3.3]heptan-2-yl]-1-phenyl-1H-pyrazole-4-carboxamide | 440.2 | E: 1.54 F: 1.55 | $^1$H NMR: (500 MHz, DMSO-$d_6$) δ ppm 12.47 (s, 1H), 8.25 (d, J = 7.6 Hz, 1H), 8.18 (d, J = 7.0 Hz, 1H), 8.11 (s, 1H), 7.97-7.80 (m, 3H), 7.54 (d, J = 7.0 Hz, 2H), 7.49 (d, J = 6.7 Hz, 3H), 4.39-4.25 (m, 1H), 3.96-3.84 (m, 1H), 3.36 (d, J = 5.2 Hz, 1H), 2.70-2.52 (m, 3H), 2.44-2.31 (m, 3H), 2.27-2.14 (m, 2H), 2.03 (t, J = 10.1 Hz, 1H) |

249

Example 14: 1-Methyl-N-[(aR)-6-(4-oxo-3,4-dihydrophthalazin-1-yl)spiro[3.3]heptan-2-yl]-1H-indazole-3-carboxamide

250

Example 15: N-[(aR)-6-(4-Oxo-3,4-dihydrophthalazin-1-yl)spiro[3.3]heptan-2-yl]-1-(2,2,2-trifluoroethyl)-1H-pyrazole-3-carboxamide

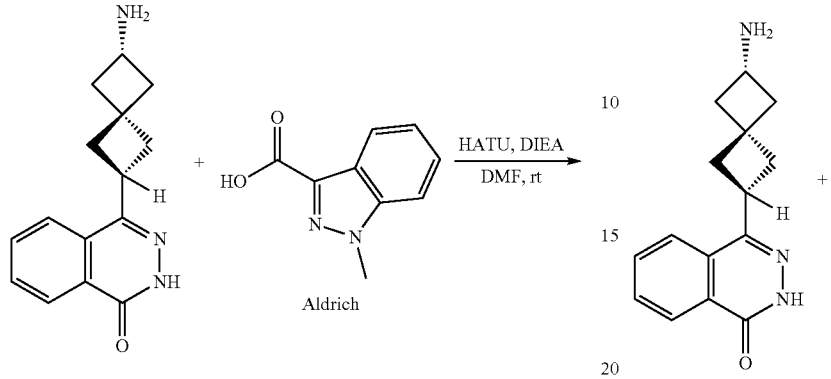

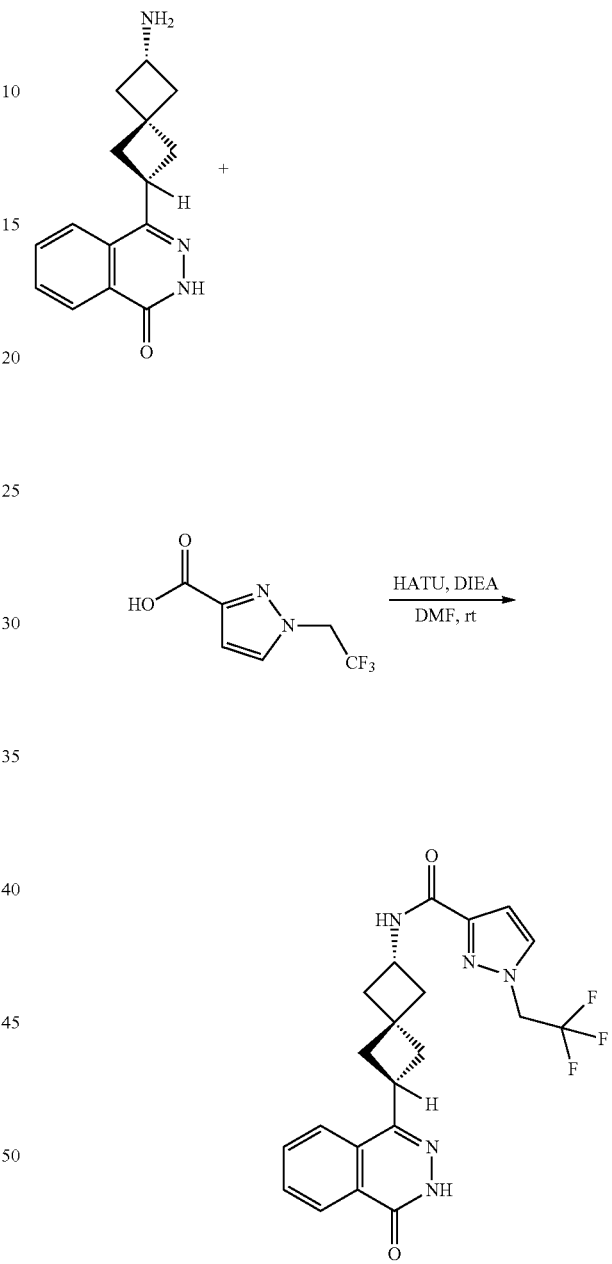

Intermediate 2 (13 mg, 0.035 mmol) was dissolved in dry DMF (1 mL), then 1-methyl-1H-indazole-3-carboxylic acid (12.4 mg, 0.070 mmol) and DIEA (0.037 mL, 0.211 mmol) were added. After stirring for 5 min at rt, HATU (20 mg, 0.053 mmol) was added, and the reaction mixture was stirred at rt for 2 h. The reaction mixture was quenched with MeOH (0.1 mL), diluted with DMF, filtered and purified by preparative HPLC to afford Example 14 (11.2 mg, 75% yield). MS(ESI) m/z: 414.2 (M+H)$^+$; $^1$H NMR (500 MHz, DMSO-d$_6$) δ ppm 12.49 (s, 1H), 8.53 (d, J=8.1 Hz, 1H), 8.26 (d, J=7.7 Hz, 1H), 8.16 (d, J=8.1 Hz, 1H), 7.98-7.81 (m, 3H), 7.72 (d, J=8.4 Hz, 1H), 7.46 (t, J=7.6 Hz, 1H), 7.30-7.23 (m, 1H), 4.48-4.37 (m, 1H), 4.13 (s, 3H), 3.95-3.85 (m, 1H), 2.65-2.55 (m, 2H), 2.46-2.29 (m, 4H), 2.24-2.09 (m, 2H). HPLC RT=1.57 min (Method E), 1.52 min (Method F).

According to the procedure for the preparation of Example 14, coupling of Intermediate 2 (13 mg, 0.035 mmol) and 1-(2,2,2-trifluoroethyl)-1H-pyrazole-3-carboxylic acid (13.7 mg, 0.070 mmol) afforded Example 15 (11.7 mg, 77% yield). MS(ESI) m/z: 432.2 (M+H)$^+$; $^1$H NMR (500 MHz, DMSO-d$_6$) δ ppm 12.49 (s, 1H), 8.32 (d, J=8.1 Hz, 1H), 8.26 (d, J=7.7 Hz, 1H), 7.98-7.90 (m, 2H), 7.89-7.79 (m, 2H), 6.75 (d, J=2.0 Hz, 1H), 5.20 (q, J=9.0 Hz, 2H), 4.33 (sxt, J=8.0 Hz, 1H), 3.95-3.82 (m, 1H), 2.63-2.53 (m, 2H), 2.43-2.26 (m, 4H), 2.22-2.14 (m, 1H), 2.14-2.04 (m, 1H). HPLC RT=1.34 min (Method E), 1.39 min (Method F).

Example 16: 1-(2,2-Difluoroethyl)-N-[(aR)-6-(4-oxo-3,4-dihydrophthalazin-1-yl)spiro[3.3]heptan-2-yl]-1H-pyrazole-3-carboxamide

Example 17: 1-Methyl-N-[(aS)-6-(4-oxo-3,4-dihydrophthalazin-1-yl)spiro[3.3]heptan-2-yl]-1H-indazole-3-carboxamide

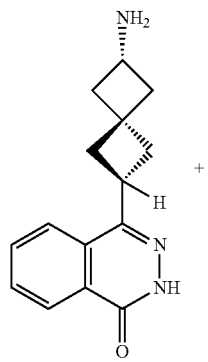

+

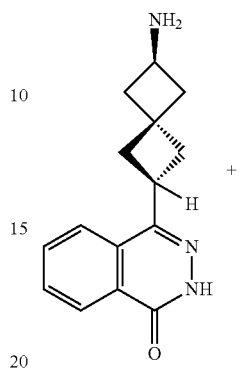

+

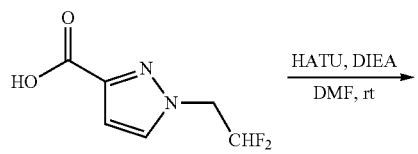

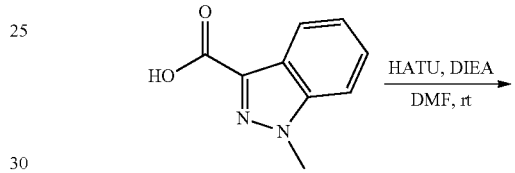

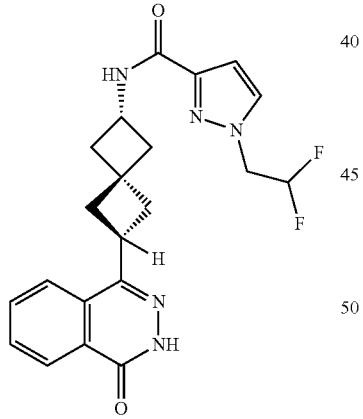

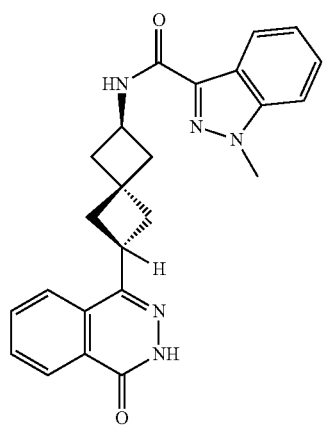

According to the procedure for the preparation of Example 14, coupling of Intermediate 2 (13 mg, 0.035 mmol) and 1-(2,2-difluoroethyl)-1H-pyrazole-3-carboxylic acid (12.4 mg, 0.070 mmol) afforded Example 16 (11.4 mg, 78% yield). MS(ESI) m/z: 414.2 (M+H)$^+$; $^1$H NMR (500 MHz, DMSO-d$_6$) δ ppm 12.49 (s, 1H), 8.27 (dd, J=14.8, 8.1 Hz, 2H), 7.98-7.90 (m, 1H), 7.89-7.80 (m, 3H), 6.70 (s, 1H), 6.56-6.25 (m, 1H), 4.75-4.64 (m, 2H), 4.39-4.27 (m, 1H), 3.89 (quin, J=8.2 Hz, 1H), 2.62-2.53 (m, 2H), 2.44-2.32 (m, 3H), 2.32-2.23 (m, 1H), 2.22-2.14 (m, 1H), 2.13-2.03 (m, 1H). HPLC RT=1.23 min (Method E), 1.27 min (Method F).

Intermediate 3 (13 mg, 0.035 mmol) was dissolved in dry DMF (1 mL), then 1-methyl-1H-indazole-3-carboxylic acid (12.40 mg, 0.070 mmol) and DIEA (0.037 mL, 0.211 mmol) were added. After stirring for 5 min at rt, HATU (20.1 mg, 0.053 mmol) was added, and the reaction mixture was stirred at rt for 2 h. The reaction mixture was quenched with MeOH (0.1 mL), diluted with DMF, filtered and purified by preparative HPLC to afford Example 17 (9.7 mg, 67% yield). MS(ESI) m/z: 414.2 (M+H)$^+$; $^1$H NMR (500 MHz, DMSO-d$_6$) δ ppm 12.50 (s, 1H), 8.53 (d, J=8.1 Hz, 1H), 8.26 (d, J=7.7 Hz, 1H), 8.16 (d, J=8.1 Hz, 1H), 7.95-7.81 (m, 3H), 7.71 (d, J=8.4 Hz, 1H), 7.46 (t, J=7.6 Hz, 1H), 7.30-7.23 (m, 1H), 4.48-4.37 (m, 1H), 4.12 (s, 3H), 3.95-3.85 (m, 1H), 2.65-2.55 (m, 2H), 2.46-2.29 (m, 4H), 2.22-2.09 (m, 2H). HPLC RT=1.57 min (Method E), 1.57 min (Method F).

Example 18: N-[(aS)-6-(4-Oxo-3,4-dihydrophthalazin-1-yl)spiro[3.3]heptan-2-yl]-1-(2,2,2-trifluoroethyl)-1H-pyrazole-3-carboxamide

Example 19: 1-(2,2-Difluoroethyl)-N-[(aR)-6-(4-oxo-3,4-dihydrophthalazin-1-yl)spiro[3.3]heptan-2-yl]-1H-pyrazole-3-carboxamide

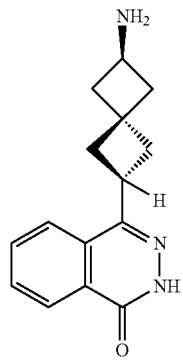

+

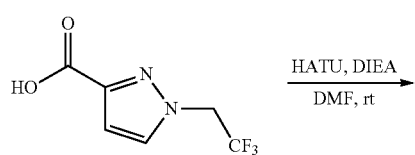

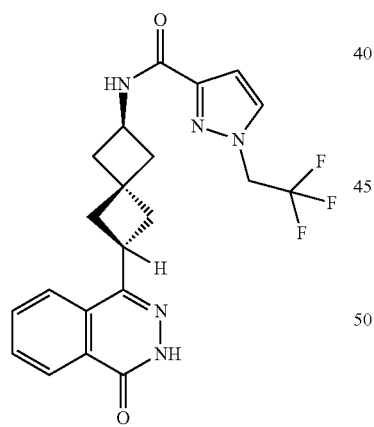

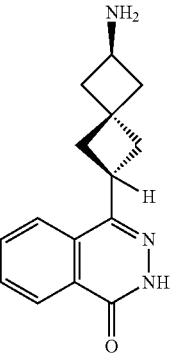

+

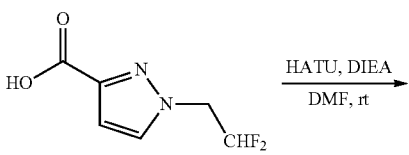

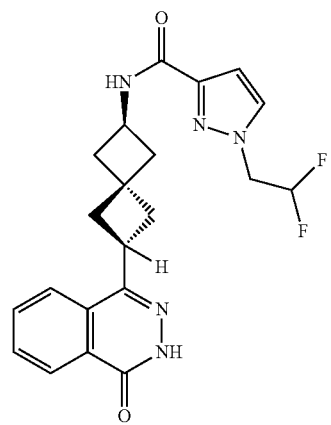

According to the procedure for the preparation of Example 17, coupling of Intermediate 3 (13 mg, 0.035 mmol) and 1-(2,2,2-trifluoroethyl)-1H-pyrazole-3-carboxylic acid (13.7 mg, 0.070 mmol) afforded Example 18 (10.7 mg, 71% yield). MS(ESI) m/z: 432.2 (M+H)$^+$; $^1$H NMR (500 MHz, DMSO-$d_6$) δ ppm 12.49 (s, 1H), 8.32 (d, J=8.1 Hz, 1H), 8.26 (d, J=7.7 Hz, 1H), 7.98-7.90 (m, 2H), 7.88-7.79 (m, 2H), 6.73 (d, J=2.0 Hz, 1H), 5.21 (q, J=9.0 Hz, 2H), 4.33 (sxt, J=8.0 Hz, 1H), 3.95-3.82 (m, 1H), 2.63-2.53 (m, 2H), 2.42-2.26 (m, 4H), 2.22-2.14 (m, 1H), 2.14-2.01 (m, 1H). HPLC RT=1.39 min (Method E), 1.39 min (Method F).

According to the procedure for the preparation of Example 17, coupling of Intermediate 3 (13 mg, 0.035 mmol) and 1-(2,2-difluoroethyl)-1H-pyrazole-3-carboxylic acid (12.4 mg, 0.070 mmol) afforded Example 19 (9.9 mg, 67% yield). MS(ESI) m/z: 414.2 (M+H)$^+$; $^1$H NMR (500 MHz, DMSO-d$_6$) δ ppm 12.50 (s, 1H), 8.27 (dd, J=14.8, 8.1 Hz, 2H), 7.99-7.90 (m, 1H), 7.89-7.80 (m, 3H), 6.70 (s, 1H), 6.56-6.25 (m, 1H), 4.78-4.64 (m, 2H), 4.39-4.27 (m, 1H), 3.89 (quin, J=8.2 Hz, 1H), 2.62-2.53 (m, 2H), 2.44-2.32 (m, 3H), 2.32-2.23 (m, 1H), 2.25-2.14 (m, 1H), 2.13-2.03 (m, 1H). HPLC RT=1.27 min (Method E), 1.27 min (Method F).

The following Examples in Table 2 were made by using the same procedure as shown in Example 14. Intermediate 2 was coupled with the appropriate acid. Various coupling reagents could be used other than the one described in Example 14 such as BOP, PyBop, EDC/HOBt or HATU.

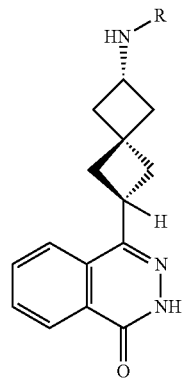

TABLE 2

| Ex. | R | Name | LCMS (M + H)$^+$ | HPLC Method, RT (min.) | $^1$H NMR |
|---|---|---|---|---|---|
| 20 | (5-methyl-1-phenyl-1H-pyrazol-4-yl)carbonyl | 5-methyl-N-[(aR)-6-(4-oxo-3,4-dihydrophthalazin-1-yl)spiro[3.3]heptan-2-yl]-1-phenyl-1H-pyrazole-4-carboxamide | 440.4 | E: 1.56 F: 1.56 | $^1$H NMR: (500 MHz, DMSO-d$_6$) δ ppm 12.48 (s, 1H), 8.25 (d, J = 7.9 Hz, 1H), 8.21 (d, J = 7.3 Hz, 1H), 8.11 (s, 1H), 7.97-7.89 (m, 1H), 7.89-7.77 (m, 2H), 7.60-7.41 (m, 5H), 4.38-4.25 (m, 1H), 3.95-3.84 (m, 1H), 2.66-2.53 (m, 2H), 2.48 (s, 3H), 2.43-2.30 (m, 3H), 2.26-2.13 (m, 2H), 2.07-1.96 (m, 1H) |
| 21 | 1-(2-hydroxy-2-methylpropyl)-1H-indazol-3-yl carbonyl | 1-(2-hydroxy-2-methylpropyl)-N-[(aR)-6-(4-oxo-3,4-dihydrophthalazin-1-yl)spiro[3.3]heptan-2-yl]-1H-indazole-3-carboxamide | 472.5 | E: 1.57 F: 1.57 | $^1$H NMR: (500 MHz, DMSO-d$_6$) δ ppm 12.48 (s, 1H), 8.42 (d, J = 7.9 Hz, 1H), 8.25 (d, J = 7.9 Hz, 1H), 8.12 (d, J = 8.2 Hz, 1H), 7.96-7.80 (m, 3H), 7.76 (d, J = 8.5 Hz, 1H), 7.40 (t, J = 7.6 Hz, 1H), 7.22 (t, J = 7.5 Hz, 1H), 4.76 (s, 1H), 4.47-4.39 (m, 1H), 2.66-2.55 (m, 2H), 2.54 (s, 2H), 2.45-2.30 (m, 4H), 2.26-2.12 (m, 2H), 1.14 (s, 6H) |
| 22 | 1-(3,3,3-trifluoropropyl)-1H-pyrazol-3-yl carbonyl | N-[(aR)-6-(4-oxo-3,4-dihydrophthalazin-1-yl)spiro[3.3]heptan-2-yl]-1-(3,3,3-trifluoropropyl)-1H-pyrazole-3-carboxamide | 446.3 | E: 1.53 F: 1.53 | $^1$H NMR: (500 MHz, DMSO-d$_6$) δ ppm 12.47 (s, 1H), 8.32-8.16 (m, 2H), 7.99-7.71 (m, 5H), 6.61 (s, 1H), 4.42 (t, J = 6.9 Hz, 2H), 4.34-4.20 (m, 1H), 3.93-3.78 (m, 2H), 3.05-2.89 (m, 3H), 2.42-2.30 (m, 4H), 2.11-1.98 (m, 1H) |
| 23 | 1-(cyclopropylmethyl)-1H-pyrazol-3-yl carbonyl | 1-(cyclopropylmethyl)-N-[(aR)-6-(4-oxo-3,4-dihydrophthalazin-1-yl)spiro[3.3]heptan-2-yl]-1H-pyrazole-3-carboxamide | 404.4 | E: 1.51 F: 1.51 | $^1$H NMR: (500 MHz, DMSO-d$_6$) δ ppm 12.47 (s, 1H), 8.25 (d, J = 7.6 Hz, 1H), 8.19 (d, J = 8.2 Hz, 1H), 7.95-7.77 (m, 4H), 6.61 (d, J = 2.1 Hz, 1H), 4.31 (sxt, J = 8.2 Hz, 1H), 4.00 (d, J = 7.3 Hz, 2H), 3.92-3.79 (m, 1H), 2.61-2.52 (m, 2H), 2.41-2.30 (m, 3H), 2.27 (t, J = 9.9 Hz, 1H), 2.21-2.14 (m, 1H), 2.11- 2.02 (m, 1H), 1.31-1.20 (m, 1H), 0.57-0.48 (m, 2H), 0.37 (q, J = 4.9 Hz, 2H) |
| 24 | 3-cyclopropyl-1-methyl-1H-pyrazol-5-yl carbonyl | 3-cyclopropyl-1-methyl-N-[(aR)-6-(4-oxo-3,4-dihydrophthalazin-1-yl)spiro[3.3]heptan-2-yl]-1H-pyrazole-5-carboxamide | 404.6 | E: 1.51 F: 1.52 | $^1$H NMR: (500 MHz, DMSO-d$_6$) δ ppm 12.48 (s, 1H), 8.46 (d, J = 7.6 Hz, 1H), 8.24 (d, J = 7.6 Hz, 1H), 7.95-7.89 (m, 1H), 7.89-7.77 (m, 2H), 6.51 (s, 1H), 4.33-4.18 (m, 1H), 3.91 (s, 3H), 3.87 (d, J = 8.5 Hz, 1H), 2.64-2.52 (m, 2H), 2.42-2.29 (m, 3H), 2.24-2.13 (m, 2H), 2.01 (t, J = 9.9 Hz, 1H), 1.88-1.77 (m, 1H), 0.86 (d, J = 7.3 Hz, 2H), 0.59 (d, J = 4.9 Hz, 2H) |

TABLE 2-continued

| Ex. | R | Name | LCMS (M + H)+ | HPLC Method, RT (min.) | 1H NMR |
|---|---|---|---|---|---|
| 25 | | 1-methyl-N-[(aR)-6-(4-oxo-3,4-dihydrophthalazin-1-yl)spiro[3.3]heptan-2-yl]-3-(trifluoromethyl)-1H-pyrazole-5-carboxamide | 432.2 | E: 1.72 F: 1.72 | 1H NMR: (500 MHz, DMSO-d$_6$) δ ppm 12.48 (s, 1H), 8.80 (d, J = 7.3 Hz, 1H), 8.25 (d, J = 7.6 Hz, 1H), 7.96-7.89 (m, 1H), 7.88-7.76 (m, 2H), 7.31 (s, 1H), 4.36-4.22 (m, 1H), 4.10 (s, 3H), 3.89 (quin, J = 8.5 Hz, 1H), 2.68-2.58 (m, 1H), 2.43-2.30 (m, 3H), 2.28-2.15 (m, 2H), 2.09-1.96 (m, 1H) |
| 26 | | 5-cyclopropyl-1-methyl-N-[(aR)-6-(4-oxo-3,4-dihydrophthalazin-1-yl)spiro[3.3]heptan-2-yl]-1H-pyrazole-3-carboxamide | 404.2 | E: 1.51 F: 1.52 | 1H NMR: (500 MHz, DMSO-d$_6$) δ ppm 12.48 (s, 1H), 8.46 (d, J = 7.6 Hz, 1H), 8.24 (d, J = 7.6 Hz, 1H), 7.95-7.88 (m, 1H), 7.87-7.78 (m, 2H), 6.52 (s, 1H), 4.32-4.20 (m, 1H), 3.91 (s, 3H), 3.89-3.81 (m, 1H), 2.66-2.53 (m, 2H), 2.42-2.28 (m, 3H), 2.21-2.12 (m, 2H), 2.01 (t, J = 9.9 Hz, 1H), 1.86-1.76 (m, 1H), 0.91-0.80 (m, 2H), 0.59 (d, J = 3.1 Hz, 2H) |
| 27 | | 1-cyclopropyl-N-[(aR)-6-(4-oxo-3,4-dihydrophthalazin-1-yl)spiro[3.3]heptan-2-yl]-1H-pyrazole-4-carboxamide | 390.2 | E: 1.22 F: 1.14 | 1H NMR: (500 MHz, DMSO-d$_6$) δ ppm 12.48 (s, 1H), 8.24 (d, J = 7.7 Hz, 1H), 8.20-8.13 (m, 2H), 7.95-7.88 (m, 1H), 7.88-7.76 (m, 3H), 4.31-4.20 (m, 1H), 3.87 (quin, J = 8.4 Hz, 1H), 3.76-3.68 (m, 1H), 2.62-2.55 (m, 1H), 2.41-2.27 (m, 3H), 2.23-2.08 (m, 2H), 1.96 (t, J = 9.9 Hz, 1H), 1.05-0.98 (m, 2H), 0.99-0.92 (m, 2H) |
| 28 | | 5-(difluoromethoxy)-1-methyl-N-[(aR)-6-(4-oxo-3,4-dihydrophthalazin-1-yl)spiro[3.3]heptan-2-yl]-1H-pyrazole-3-carboxamide | 430.1 | E: 1.46 F: 1.47 | 1H NMR: (500 MHz, DMSO-d$_6$) δ ppm 12.49 (s, 1H), 8.37 (d, J = 8.1 Hz, 1H), 8.26 (d, J = 8.1 Hz, 1H), 7.99-7.81 (m, 4H), 7.24 (t, J = 72.7 Hz, 1H), 6.38 (s, 1H), 4.31 (sxt, J = 8.1 Hz, 1H), 3.94-3.84 (m, 1H), 3.73 (s, 3H), 2.43-2.31 (m, 3H), 2.31-2.22 (m, 1H), 2.21-2.14 (m, 1H), 2.12-2.03 (m, 1H) |
| 29 | | 1-cyclopropyl-N-[(aR)-6-(4-oxo-3,4-dihydrophthalazin-1-yl)spiro[3.3]heptan-2-yl]-1H-pyrazole-3-carboxamide | 390.2 | E: 1.4 F: 1.41 | 1H NMR: (500 MHz, DMSO-d$_6$) δ ppm 12.48 (s, 1H), 8.25 (d, J = 7.7 Hz, 1H), 8.21 (d, J = 8.1 Hz, 1H), 7.98-7.79 (m, 5H), 6.57 (d, J = 2.0 Hz, 1H), 4.31 (sxt, J = 8.1 Hz, 1H), 3.93-3.82 (m, 1H), 3.77 (tt, J = 7.3, 3.7 Hz, 1H), 2.42-2.30 (m, 3H), 2.30-2.23 (m, 1H), 2.20-2.03 (m, 2H), 1.13-1.06 (m, 2H), 1.03-0.93 (m, 2H) |
| 30 | | 1-(2-hydroxy-2-methylpropyl)-N-[(aR)-6-(4-oxo-3,4-dihydrophthalazin-1-yl)spiro[3.3]heptan-2-yl]-1H-pyrazole-3-carboxamide | 422.2 | E: 1.22 F: 1.22 | 1H NMR: (500 MHz, DMSO-d$_6$) δ ppm 12.48 (s, 1H), 8.25 (d, J = 7.7 Hz, 1H), 8.17 (d, J = 8.1 Hz, 1H), 7.97-7.88 (m, 2H), 7.88-7.79 (m, 2H), 7.71 (d, J = 2.0 Hz, 1H), 6.61 (d, J = 2.0 Hz, 1H), 4.32 (sxt, J = 8.1 Hz, 1H), 4.05 (s, 2H), 3.88 (quin, J = 8.5 Hz, 1H), 2.62-2.55 (m, 1H), 2.42-2.31 (m, 3H), 2.26 (t, J = 9.8 Hz, 1H), 2.21-2.13 (m, 1H), 2.12-2.04 (m, 1H), 1.06 (s, 6H) |

TABLE 2-continued

| Ex. | R | Name | LCMS (M + H)+ | HPLC Method, RT (min.) | 1H NMR |
|---|---|---|---|---|---|
| 31 | (6-fluoroindazole carbonyl with N-(2-hydroxy-2-methylpropyl) substituent) | 6-fluoro-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide | 490.2 | E: 1.56 F: 1.54 | 1H NMR: (500 MHz, DMSO-$d_6$) δ ppm 12.45 (s, 1H), 8.44 (d, J = 8.1 Hz, 1H), 8.21 (d, J = 7.7 Hz, 1H), 8.08 (dd, J = 8.9, 5.6 Hz, 1H), 7.91-7.75 (m, 3H), 7.58 (d, J = 8.8 Hz, 1H), 7.08 (t, J = 8.2 Hz, 1H), 4.37 (sxt, J = 8.2 Hz, 1H), 4.30 (s, 2H), 3.86 (quin, J = 8.5 Hz, 1H), 2.61-2.52 (m, 2H), 2.40-2.25 (m, 4H), 2.22-2.07 (m, 2H), 1.10 (s, 6H) |
| 32 | (1-(2,2-difluoroethyl)-3-methylpyrazole-4-carbonyl) | 1-(2,2-difluoroethyl)-3-methyl-N-[(aR)-6-(4-oxo-3,4-dihydrophthalazin-1-yl)spiro[3.3]heptan-2-yl]-1H-pyrazole-4-carboxamide | 428.2 | E: 1.20 F: 1.18 | 1H NMR: (500 MHz, DMSO-$d_6$) δ ppm 12.48 (s, 1H), 8.25 (d, J = 7.7 Hz, 1H), 8.16 (s, 1H), 8.09 (d, J = 7.4 Hz, 1H), 7.97-7.81 (m, 3H), 6.34 (tt, J = 54.5, 3.4 Hz, 1H), 4.56 (td, J = 15.4, 3.2 Hz, 2H), 4.31-4.21 (m, 1H), 3.88 (quin, J = 8.5 Hz, 1H), 2.63-2.56 (m, 1H), 2.41-2.32 (m, 3H), 2.30 (s, 3H), 2.23-2.10 (m, 2H), 1.97 (t, J = 10.1 Hz, 1H) |

Example 33: 4-Methyl-N-((aR)-6-(4-oxo-3,4-dihydrophthalazin-1-yl)spiro[3.3]heptan-2-yl)-2-(piperidin-1-yl)thiazole-5-carboxamide

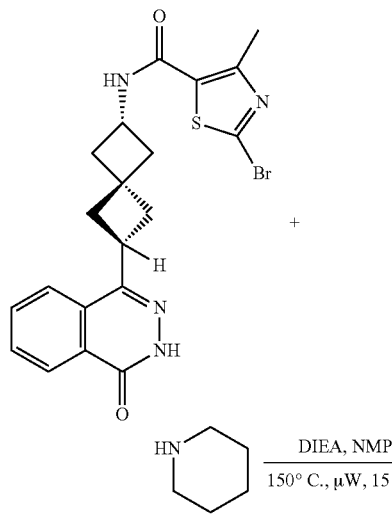

Intermediate 22 (10 mg, 0.022 mmol), piperidine (0.016 mL, 0.16 mmol) and DIEA (0.038 mL, 0.22 mmol) were dissolved in anhydrous NMP (1.5 mL). Then the reaction vial was capped, and the mixture was stirred at 150° C. for 15 min under microwave irradiation. The reaction mixture was cooled to rt, quenched with TFA (few drops), filtered, and purified by preparative HPLC to afford Example 33 (7.6 mg, 69% yield). MS(ESI) m/z: 464.2 (M+H)+; 1H NMR (500 MHz, DMSO-$d_6$) δ ppm 12.62 (s, 1H), 8.39 (d, J=7.7 Hz, 1H), 8.11-7.94 (m, 3H), 7.88 (d, J=7.4 Hz, 1H), 4.37 (sxt, J=8.0 Hz, 1H), 4.02 (quin, J=8.5 Hz, 1H), 2.76-2.59 (m, 5H), 2.50-2.42 (m, 3H), 2.37-2.26 (m, 2H), 2.15 (t, J=9.9 Hz, 1H), 1.72 (br. s., 6H). HPLC RT=1.21 min (Method E), 1.40 min (Method F).

The following Examples in Table 3 were made by using the same procedure as shown in Example 33. Intermediate 22 was coupled with the amine. Various solvents could be used other than the one described in Example 33 such as TEA, DBU, DABCO. Various solvents could be used other than the one described in Example 33 such as DMF, n-butanol, DMPU, THF.

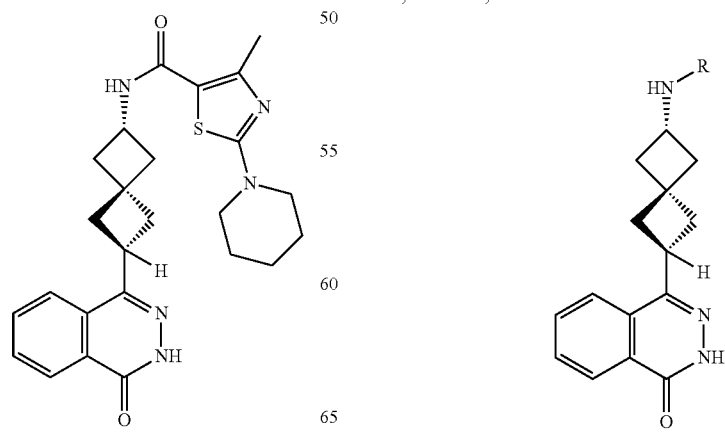

TABLE 3

| Ex. | R | Name | LCMS (M + H)+ | HPLC Method, RT (min.) | 1H NMR |
|---|---|---|---|---|---|
| 34 | (4-methyl-2-morpholinyl-thiazol-5-yl carbonyl) | 4-methyl-2-(morpholin-4-yl)-N-[(aR)-6-(4-oxo-3,4-dihydrophthalazin-1-yl)spiro[3.3]heptan-2-yl]-1,3-thiazole-5-carboxamide | 466.1 | E: 1.14 F: 1.34 | 1H NMR: (500 MHz, DMSO-$d_6$) δ ppm 12.47 (s, 1H), 8.24 (d, J = 7.7 Hz, 1H), 7.98-7.75 (m, 4H), 4.23 (sxt, J = 8.1 Hz, 1H), 3.87 (quin, J = 8.5 Hz, 1H), 3.68 (t, J = 4.7 Hz, 4H), 3.43-3.31 (m, 1H), 2.60-2.51 (m, 2H), 2.42-2.30 (m, 6H), 2.25-2.12 (m, 2H), 2.01 (t, J = 9.9 Hz, 1H) |
| 35 | (4-methyl-2-pyrrolidinyl-thiazol-5-yl carbonyl) | 4-methyl-N-[(aR)-6-(4-oxo-3,4-dihydrophthalazin-1-yl)spiro[3.3]heptan-2-yl]-2-(pyrrolidin-1-yl)-1,3-thiazole-5-carboxamide | 450.2 | E: 1.39 F: 1.53 | 1H NMR: (500 MHz, DMSO-$d_6$) δ ppm 12.59 (s, 1H), 8.36 (d, J = 7.7 Hz, 1H), 8.08-7.92 (m, 3H), 7.85 (d, J = 7.4 Hz, 1H), 4.40-4.29 (m, 1H), 4.05-3.93 (m, 1H), 2.68-2.58 (m, 6H), 2.49-2.41 (m, 3H), 2.37-2.23 (m, 2H), 2.18-2.00 (m, 5H) |
| 36 | (2-[(3S)-3-fluoropyrrolidin-1-yl]-4-methyl-thiazol-5-yl carbonyl) | 2-[(3S)-3-fluoropyrrolidin-1-yl]-4-methyl-N-[(aR)-6-(4-oxo-3,4-dihydrophthalazin-1-yl)spiro[3.3]heptan-2-yl]-1,3-thiazole-5-carboxamide | 468.3 | E: 1.20 F: 1.43 | 1H NMR: (500 MHz, DMSO-$d_6$) δ ppm 12.48 (s, 1H), 8.24 (d, J = 7.7 Hz, 1H), 7.95-7.88 (m, 1H), 7.87-7.75 (m, 3H), 5.43 (d, J = 52.8 Hz, 1H), 4.29-4.15 (m, 1H), 3.87 (quin, J = 8.4 Hz, 1H), 2.57-2.52 (m, 4H), 2.38 (s, 3H), 2.36-2.26 (m, 4H), 2.25-2.09 (m, 3H), 2.01 (t, J = 9.9 Hz, 1H) |
| 37 | (2-[(3R)-3-fluoropyrrolidin-1-yl]-4-methyl-thiazol-5-yl carbonyl) | 2-[(3R)-3-fluoropyrrolidin-1-yl]-4-methyl-N-[(aR)-6-(4-oxo-3,4-dihydrophthalazin-1-yl)spiro[3.3]heptan-2-yl]-1,3-thiazole-5-carboxamide | 468.3 | E: 1.20 F: 1.43 | 1H NMR: (500 MHz, DMSO-$d_6$) δ ppm 12.44 (s, 1H), 8.20 (d, J = 7.7 Hz, 1H), 7.91-7.85 (m, 1H), 7.84-7.71 (m, 3H), 5.39 (d, J = 53.9 Hz, 1H), 4.24-4.12 (m, 1H), 3.83 (quin, J = 8.5 Hz, 1H), 3.43-3.32 (m, 1H), 2.46 (br. s., 6H), 2.34 (s, 3H), 2.31-2.19 (m, 4H), 2.18-2.07 (m, 2H), 2.01-1.91 (m, 1H) |
| 38 | (2-[(3S)-3-cyanopyrrolidin-1-yl]-4-methyl-thiazol-5-yl carbonyl) | 2-[(3S)-3-cyanopyrrolidin-1-yl]-4-methyl-N-[(aR)-6-(4-oxo-3,4-dihydrophthalazin-1-yl)spiro[3.3]heptan-2-yl]-1,3-thiazole-5-carboxamide | 475.2 | E: 1.19 F: 1.36 | 1H NMR: (500 MHz, DMSO-$d_6$) δ ppm 12.44 (s, 1H), 8.20 (d, J = 7.7 Hz, 1H), 7.90-7.84 (m, 1H), 7.80 (dd, J = 12.1, 6.4 Hz, 3H), 4.24-4.12 (m, 1H), 3.83 (quin, J = 8.5 Hz, 1H), 3.72-3.64 (m, 1H), 3.45-3.30 (m, 1H), 2.46 (br. s., 4H), 2.40-2.35 (m, 1H), 2.34 (s, 3H), 2.33-2.19 (m, 4H), 2.17-2.06 (m, 2H), 2.01-1.91 (m, 1H) |

TABLE 3-continued

| Ex. | R | Name | LCMS (M + H)+ | HPLC Method, RT (min.) | 1H NMR |
|---|---|---|---|---|---|
| 39 | (structure) | 2-[(3R)-3-cyanopyrrolidin-1-yl]-4-methyl-N-[(aR)-6-(4-oxo-3,4-dihydrophthalazin-1-yl)spiro[3.3]heptan-2-yl]-1,3-thiazole-5-carboxamide | 475.2 | E: 1.18 F: 1.36 | 1H NMR: (500 MHz, DMSO-$d_6$) δ ppm 12.44 (s, 1H), 8.20 (d, J = 7.7 Hz, 1H), 7.91-7.84 (m, 1H), 7.84-7.72 (m, 3H), 4.17 (sxt, J = 8.0 Hz, 1H), 3.83 (quin, J = 8.4 Hz, 1H), 3.72-3.63 (m, 1H), 3.48-3.31 (m, 2H), 2.46 (br. s., 4H), 2.41-2.35 (m, 1H), 2.33 (s, 3H), 2.32-2.20 (m, 4H), 2.17-2.06 (m, 2H), 1.96 (t, J = 9.9 Hz, 1H) |
| 40 | (structure) | rel-2-[(1S,5R)-2-azabicyclo[3.1.0]hexan-2-yl]-4-methyl-N-[(aR)-6-(4-oxo-3,4-dihydrophthalazin-1-yl)spiro[3.3]heptan-2-yl]-1,3-thiazole-5-carboxamide | 462.3 | E: 1.24 F: 1.54 | 1H NMR: (500 MHz, DMSO-$d_6$) δ ppm 12.44 (s, 1H), 8.20 (d, J = 7.7 Hz, 1H), 7.91-7.84 (m, 1H), 7.83-7.72 (m, 3H), 4.22-4.12 (m, 1H), 3.82 (quin, J = 8.4 Hz, 1H), 3.29 (br. s., 1H), 3.04-2.92 (m, 1H), 2.46 (br. s., 4H), 2.32 (s, 3H), 2.31-2.23 (m, 2H), 2.21-2.05 (m, 3H), 1.97 (q, J = 10.2 Hz, 2H), 1.71-1.62 (m, 1H), 0.80-0.71 (m, 1H), 0.54 (br. s., 1H) |
| 41 | (structure) | 2-(3,3-difluoropyrrolidin-1-yl)-4-methyl-N-[(aR)-6-(4-oxo-3,4-dihydrophthalazin-1-yl)spiro[3.3]heptan-2-yl]-1,3-thiazole-5-carboxamide | 486.2 | E: 1.38 F: 1.55 | 1H NMR: (500 MHz, DMSO-$d_6$) δ ppm 12.48 (s, 1H), 8.24 (d, J = 7.7 Hz, 1H), 7.96-7.77 (m, 4H), 4.29-4.13 (m, 1H), 3.93-3.76 (m, 3H), 2.69-2.53 (m, 4H), 2.38 (s, 3H), 2.36-2.27 (m, 3H), 2.23-2.10 (m, 2H), 2.01 (t, J = 10.1 Hz, 1H) |
| 42 | (structure) | 2-(cyclopropylamino)-4-methyl-N-[(aR)-6-(4-oxo-3,4-dihydrophthalazin-1-yl)spiro[3.3]heptan-2-yl]-1,3-thiazole-5-carboxamide | 436.2 | E: 1.07 F: 1.30 | 1H NMR: (500 MHz, DMSO-$d_6$) δ ppm 12.47 (s, 1H), 8.29 (s, 1H), 8.25 (d, J = 7.7 Hz, 1H), 7.98-7.80 (m, 4H), 7.73 (d, J = 7.7 Hz, 1H), 4.29-4.18 (m, 1H), 3.95-3.81 (m, 1H), 2.35 (m, 6H), 2.24-1.96 (m, 4H), 0.72 (d, J = 5.0 Hz, 2H), 0.52 (br. s., 2H) |

Example 43: 4-((aR)-6-((5-Phenyl-1,3,4-thiadiazol-2-yl)amino)spiro[3.3]heptan-2-yl)phthalazin-1(2H)-one(2H)-one

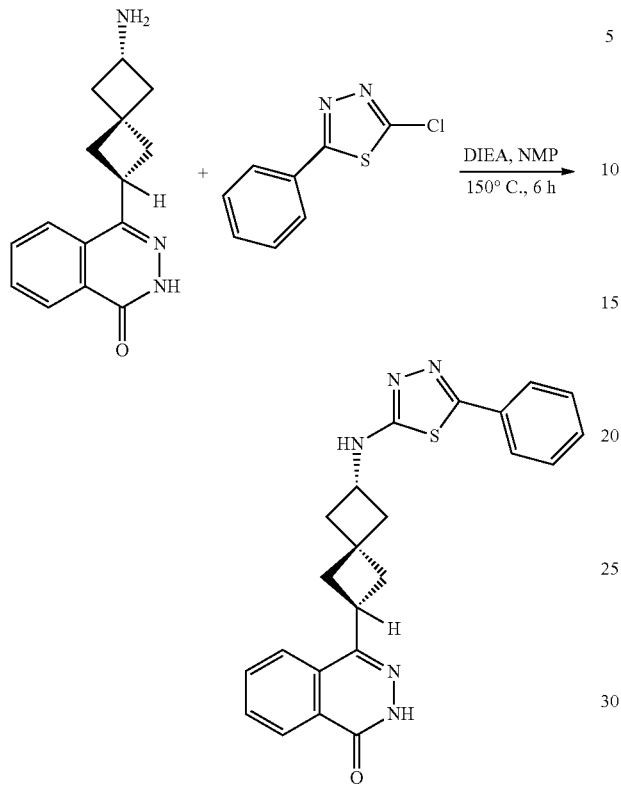

Intermediate 2, HCl (16 mg, 0.055 mmol) and DIEA (0.096 mL, 0.55 mmol) were dissolved in NMP (1.5 mL), and 2-chloro-5-phenyl-1,3,4-thiadiazole (27.0 mg, 0.137 mmol) was added. The reaction mixture was stirred at 150° C. for 6 h. The reaction mixture was cooled to rt, diluted with DMF, filtered, and purified by preparative HPLC to afford Example 43 (11.4 mg, 0.027 mmol, 50% yield). MS(ESI) m/z: 416.2 (M+H)+; $^1$H NMR (500 MHz, DMSO-$d_6$) δ ppm 12.47 (s, 1H), 8.24 (dd, J=12.8, 7.3 Hz, 2H), 7.96-7.89 (m, 1H), 7.89-7.79 (m, 2H), 7.74 (d, J=7.0 Hz, 2H), 7.51-7.37 (m, 3H), 4.11-3.99 (m, 1H), 3.90 (quin, J=8.4 Hz, 1H), 2.78-2.68 (m, 1H), 2.61-2.53 (m, 1H), 2.44-2.29 (m, 4H), 2.17-2.09 (m, 1H), 1.94 (dd, J=11.1, 8.4 Hz, 1H). HPLC RT=1.51 min (Method E), 1.68 min (Method F).

Example 44: 4-((aR)-6-((5-phenyloxazol-2-yl)amino)spiro[3.3]heptan-2-yl)phthalazin-1(2H)-one(2H)-one

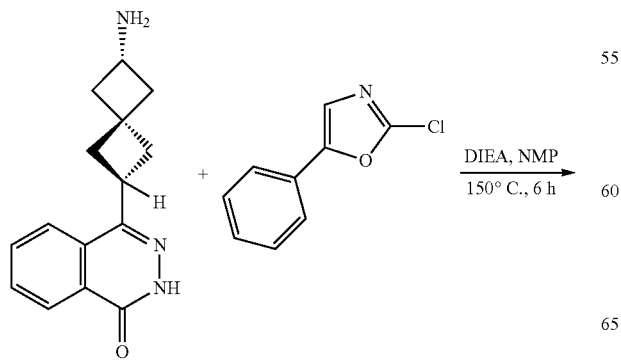

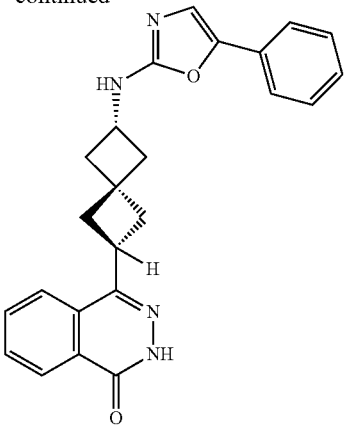

According to the procedure for the preparation of Example 43, coupling of Intermediate 2, HCl (16 mg, 0.055 mmol) and 2-chloro-5-phenyloxazole (24.6 mg, 0.137 mmol) afforded Example 44 (6.4 mg, 0.016 mmol, 29% yield). MS(ESI) m/z: 399.4 (M+H)+; $^1$H NMR (500 MHz, DMSO-$d_6$) δ ppm 12.43 (s, 1H), 10.15 (br. s., 1H), 8.23 (d, J=7.6 Hz, 1H), 7.92-7.86 (m, 1H), 7.84-7.78 (m, 2H), 7.46-7.40 (m, 2H), 7.38-7.32 (m, 1H), 7.30 (d, J=7.0 Hz, 2H), 6.41 (d, J=2.1 Hz, 1H), 4.24 (quin, J=8.7 Hz, 1H), 3.84 (quin, J=8.3 Hz, 1H), 2.99 (t, J=9.9 Hz, 1H), 2.84 (t, J=10.2 Hz, 1H), 2.45 (d, J=8.2 Hz, 3H), 2.36-2.23 (m, 2H), 2.10-2.01 (m, 1H). HPLC RT=1.55 min (Method E), 1.54 min (Method F).

Example 45: 4-((aR)-6-(Phthalazin-1-ylamino)spiro[3.3]heptan-2-yl)phthalazin-1(2H)-one(2H)-one

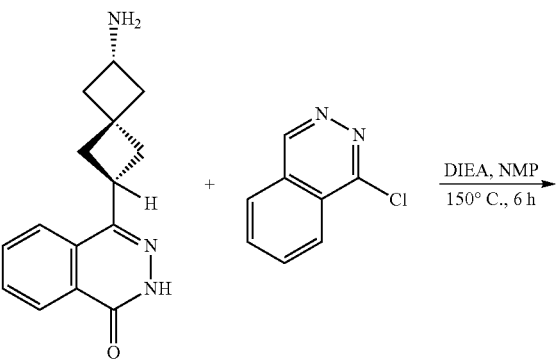

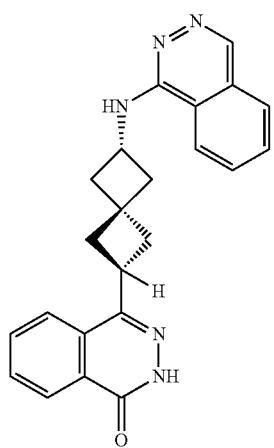

According to the procedure for the preparation of Example 43, coupling of Intermediate 2, HCl (16 mg, 0.055 mmol) and 1-chlorophthalazine (22.56 mg, 0.137 mmol) afforded Example 45 (2.4 mg, 11% yield). MS(ESI) m/z: 384.4 (M+H)$^+$; $^1$H NMR (500 MHz, DMSO-d$_6$) δ ppm 12.49 (s, 1H), 9.00 (s, 1H), 8.71 (d, J=7.6 Hz, 1H), 8.26 (d, J=7.6 Hz, 1H), 8.20-8.08 (m, 3H), 7.98-7.91 (m, 1H), 7.89-7.79 (m, 2H), 4.50-4.39 (m, 1H), 4.00-3.90 (m, 1H), 2.92-2.82 (m, 1H), 2.61 (t, J=7.6 Hz, 1H), 2.48-2.34 (m, 4H), 2.31-2.20 (m, 1H). HPLC RT=1.14 min (Method E), 1.40 min (Method F).

Example 46: 4-(6-(Indoline-1-carbonyl)spiro[3.3]heptan-2-yl)phthalazin-1(2H)-one(2H)-one

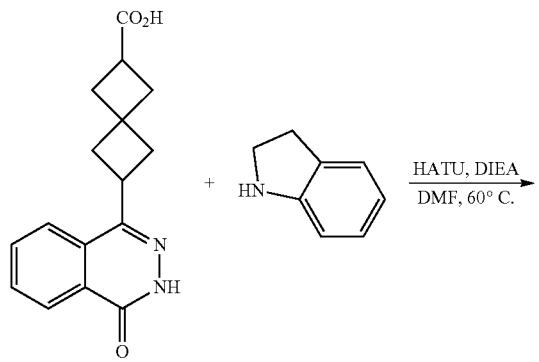

Intermediate 4 (20 mg, 0.070 mmol) was dissolved in dry DMF (1 mL), then indoline (0.014 mL, 0.13 mmol) and DIEA (0.067 mL, 0.38 mmol) were added. After stirring for 5 min at rt, HATU (24.3 mg, 0.064 mmol) was added, and the reaction mixture was stirred at 60° C. for 2 h. The reaction mixture was quenched with MeOH (0.1 mL), diluted with DMF, filtered and purified by HPLC to afford Example 46 (20.0 mg, 0.049 mmol, 77% yield). MS(ESI) m/z: 386.2 (M+H)$^+$; $^1$H NMR (500 MHz, DMSO-d$_6$) δ ppm 12.46 (s, 1H), 8.25 (d, J=7.9 Hz, 1H), 8.07 (d, J=7.9 Hz, 1H), 7.95-7.88 (m, 1H), 7.88-7.77 (m, 2H), 7.21 (d, J=7.3 Hz, 1H), 7.13 (t, J=7.5 Hz, 1H), 6.97 (t, J=7.2 Hz, 1H), 4.04-3.94 (m, 2H), 3.86 (quin, J=8.4 Hz, 1H), 3.11 (t, J=8.4 Hz, 2H), 2.57 (d, J=7.3 Hz, 1H), 2.48-2.33 (m, 4H), 2.32-2.17 (m, 2H), 2.15 (d, J=8.5 Hz, 1H). HPLC RT=1.78 min (Method E), 1.78 min (Method F).

The following Examples in Table 4 were made by using the same procedure as shown in Example 46. Intermediate 4 was coupled with the appropriate amine. Various coupling reagents could be used other than the one described in Example 46 such as BOP, PyBop, EDC/HOBt or HATU.

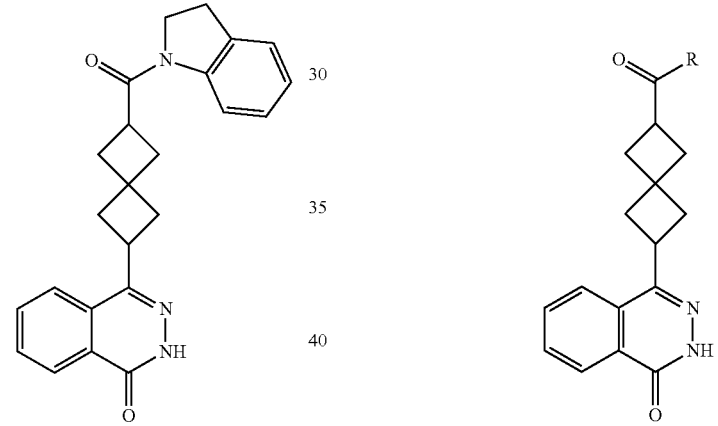

TABLE 4

| Ex. | R | Name | LCMS (M + H)$^+$ | HPLC Method, RT (min.) | $^1$H NMR |
|---|---|---|---|---|---|
| 47 | ![isoindoline] | 4-[6-(2,3-dihydro-1H-isoindole-2-carbonyl)spiro[3.3]heptan-2-yl]-1,2-dihydrophthalazin-1-one | 386.2 | E: 1.64 F: 1.64 | $^1$H NMR: (500 MHz, DMSO-d$_6$) δ ppm 12.46 (s, 1H), 8.25 (d, J = 7.6 Hz, 1H), 7.95-7.89 (m, 1H), 7.87-7.79 (m, 2H), 7.39- 7.25 (m, 4H), 4.74 (br. s., 2H), 4.62 (s, 2H), 3.86 (quin, J = 8.3 Hz, 1H), 3.28 (quin, J = 8.4 Hz, 1H), 2.62-2.55 (m, 1H), 2.43-2.32 (m, 3H), 2.30-2.23 (m, 1H), 2.21-2.10 (m, 2H) |
| 48 | ![thiadiazole] | N-(5-methyl-1,3,4-thiadiazol-2-yl)-6-(4-oxo-3,4-dihydrophthalazin-1-yl)spiro[3.3]heptane-2-carboxamide | 382.4 | E: 1.31 F: 1.31 | $^1$H NMR: (500 MHz, DMSO-d$_6$) δ ppm 12.46 (s, 1H), 8.24 (d, J = 7.6 Hz, 1H), 7.94-7.89 (m, 1H), 7.87-7.79 (m, 2H), 3.85 (quin, J = 8.5 Hz, 1H), 3.28 (quin, J = 8.4 Hz, 1H), 2.59 (s, 3H), 2.49-2.44 (m, 2H), 2.43-2.32 (m, 3H), 2.31-2.23 (m, 1H), 2.21-2.08 (m, 2H) |

TABLE 4-continued

| Ex. | R | Name | LCMS (M + H)+ | HPLC Method, RT (min.) | 1H NMR |
|---|---|---|---|---|---|
| 49 | (structure) | N-(5-methyl-1,2-oxazol-3-yl)-6-(4-oxo-3,4-dihydrophthalazin-1-yl)spiro[3.3]heptane-2-carboxamide | 365.2 | E: 1.38<br>F: 1.38 | 1H NMR: (500 MHz, DMSO-d6) δ ppm 12.45 (s, 1H), 10.69 (s, 1H), 8.24 (d, J = 7.9 Hz, 1H), 7.95-7.88 (m, 1H), 7.87-7.79 (m, 2H), 6.62 (s, 1H), 3.85 (quin, J = 8.4 Hz, 1H), 3.16 (t, J = 8.2 Hz, 1H), 2.58-2.52 (m, 1H), 2.43-2.32 (m, 7H), 2.30-2.23 (m, 1H), 2.18-2.11 (m, 1H), 2.10-2.01 (m, 1H) |

Example 50: N-((aR)-6-(4-Oxo-3,4-dihydrophthalazin-1-yl)spiro[3.3]heptan-2-yl)indoline-1-carboxamide

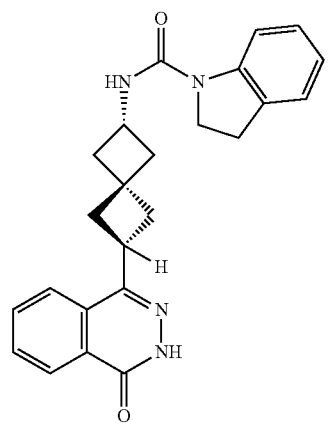

Example 50A

4-Nitrophenyl ((aR)-6-(4-oxo-3,4-dihydrophthalazin-1-yl)spiro[3.3]heptan-2-yl)carbamate

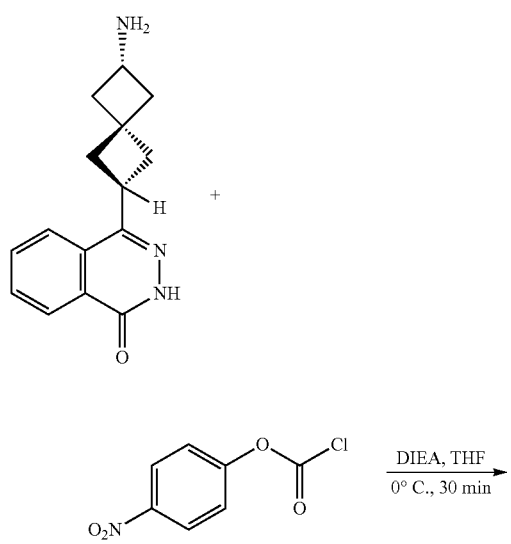

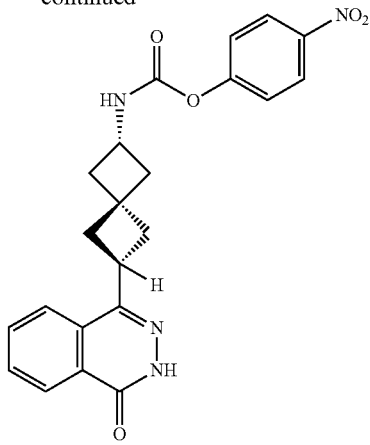

Intermediate 2, HCl was suspended in anhydrous THF (3 mL), and DIEA (0.049 mL, 0.28 mmol) was added. The reaction mixture was cooled to 0° C., and 4-nitrophenyl carbonochloridate (27.4 mg, 0.136 mmol) was added in one portion. The reaction mixture was stirred at 0° C. for 30 min. The reaction mixture was filtered through a membrane filter, and Example 50A was used as is in the subsequent urea formation step. MS(ESI) m/z: 421.0 (M+H)+.

Example 50

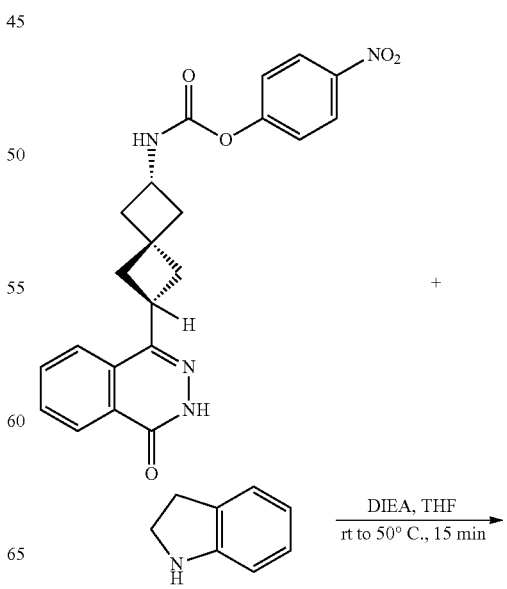

-continued

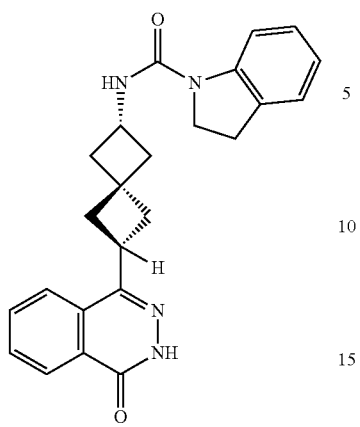

Indoline (0.016 mL, 0.14 mmol) and DIEA (0.029 mL, 0.17 mmol) was dissolved in anhydrous THF (0.5 mL), and Example 50A (0.056 mmol) was added. The reaction mixture was stirred at rt for 5 min and then at 50° C. for 15 min. The reaction mixture was concentrated, diluted with DMF, filtered and purified by preparative HPLC to afford Example 50 (13.1 mg, 58% yield). MS(ESI) m/z: 401.2 (M+H)$^+$; $^1$H NMR (500 MHz, DMSO-d$_6$) δ ppm 12.46 (s, 1H), 8.25 (d, J=7.6 Hz, 1H), 7.96-7.89 (m, 1H), 7.88-7.75 (m, 3H), 7.12 (d, J=7.3 Hz, 1H), 7.05 (t, J=7.6 Hz, 1H), 6.81 (t, J=7.3 Hz, 1H), 6.67 (d, J=7.3 Hz, 1H), 4.13 (sxt, J=8.1 Hz, 1H), 3.90-3.82 (m, 2H), 3.08 (t, J=8.7 Hz, 2H), 2.62-2.54 (m, 2H), 2.43-2.30 (m, 3H), 2.22-2.12 (m, 2H), 2.02 (t, J=10.1 Hz, 1H). HPLC RT=1.64 min (Method E), 1.64 min (Method F).

Example 51: N-((aR)-6-(4-Oxo-3,4-dihydrophthalazin-1-yl)spiro[3.3]heptan-2-yl)isoindoline-2-carboxamide

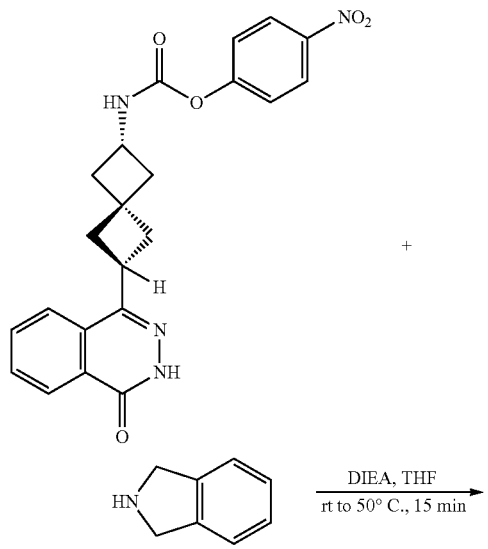

-continued

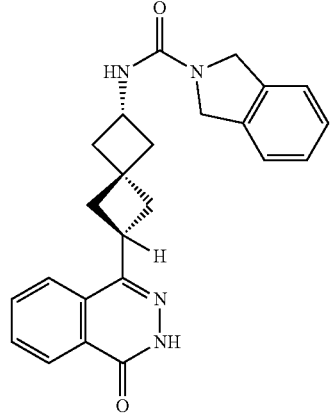

According to the procedure for the preparation of Example 50, reaction of Example 50A (0.056 mmol) and isoindoline (0.016 mL, 0.140 mmol) afforded Example 51 (16.4 mg, 73% yield). MS(ESI) m/z: 401.2 (M+H)$^+$; $^1$H NMR (500 MHz, DMSO-d$_6$) δ ppm 12.41 (s, 1H), 8.21 (d, J=7.6 Hz, 1H), 7.90-7.76 (m, 3H), 7.30-7.20 (m, 4H), 6.40 (d, J=7.6 Hz, 1H), 4.53 (s, 4H), 4.11-4.00 (m, 1H), 3.84 (quin, J=8.5 Hz, 1H), 2.53 (br. s., 1H), 2.37-2.25 (m, 3H), 2.16-2.06 (m, 2H), 1.94 (t, J=9.9 Hz, 1H). HPLC RT=1.53 min (Method E), 1.53 min (Method F).

Example 52: 4-(6-(2-(Indolin-1-yl)-2-oxoethyl)spiro[3.3]heptan-2-yl)phthalazin-1(2H)-one

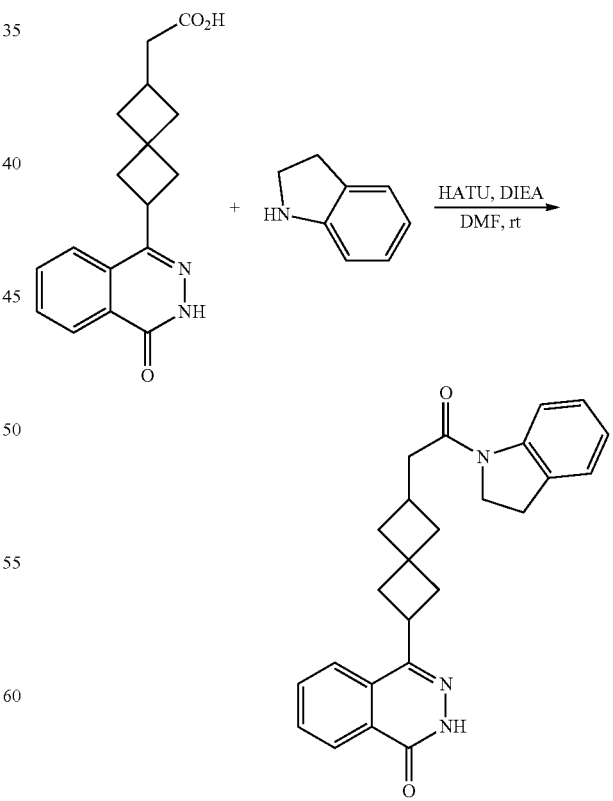

Intermediate 5 (5.1 mg, 0.017 mmol) was dissolved in dry DMF (1 mL), then indoline (3.5 µl, 0.031 mmol) and DIEA (0.016 mL, 0.093 mmol) were added. After stirring for 5 min at rt, HATU (5.9 mg, 0.016 mmol) was added, and the reaction mixture was stirred at rt for 2 h. The reaction mixture was quenched with MeOH (0.1 mL), diluted with DMF, filtered and purified by preparative HPLC to afford Example 52 (2.0 mg, 32% yield). MS(ESI) m/z: 400.2 (M+H)$^+$; $^1$H NMR (500 MHz, DMSO-d$_6$) δ ppm 12.45 (s, 1H), 8.24 (d, J=7.9 Hz, 1H), 8.02 (d, J=7.9 Hz, 1H), 7.94-7.88 (m, 1H), 7.86-7.78 (m, 2H), 7.20 (d, J=7.3 Hz, 1H), 7.11 (t, J=7.5 Hz, 1H), 6.96 (t, J=7.3 Hz, 1H), 4.04 (t, J=8.4 Hz, 2H), 3.83 (quin, J=8.4 Hz, 1H), 3.59 (br. s., 2H), 3.11 (t, J=8.4 Hz, 2H), 2.42 (br. s., 1H), 2.34 (d, J=9.2 Hz, 3H), 2.29-2.21 (m, 1H), 2.12-2.01 (m, 1H), 1.87 (d, J=7.3 Hz, 1H), 1.70-1.60 (m, 1H). HPLC RT=1.88 min (Method E), 1.88 min (Method F).

Example 53: 2-((R)-3-fluoropyrrolidin-1-yl)-5-methyl-N-((aR)-6-(4-oxo-3,4-dihydrophthalazin-1-yl)spiro[3.3]heptan-2-yl)thiazole-4-carboxamide

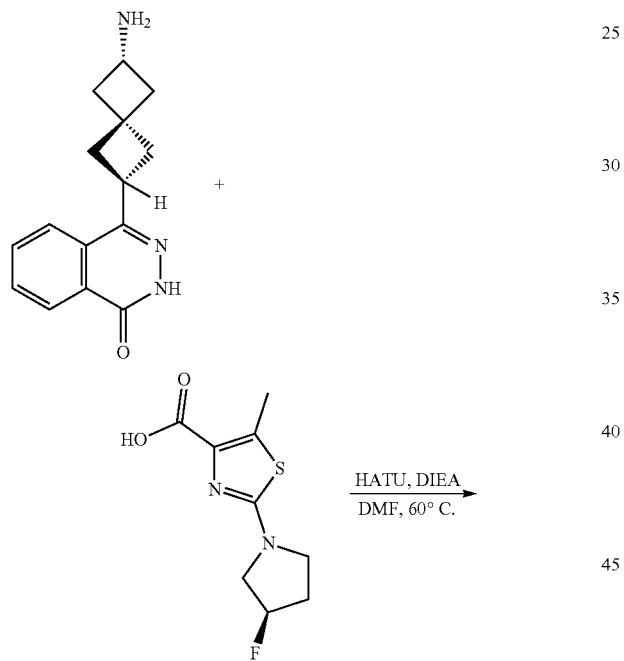

Intermediate 2, HCl and Intermediate 23 were coupled in a manner described in Example 14 to afford Example 53 (36.8 mg, 86% yield). MS(ESI) m/z: 468.2. $^1$H NMR (500 MHz, DMSO-d$_6$) δ ppm 12.48 (s, 1H), 8.25 (d, J=7.7 Hz, 1H), 7.97 (br d, J=8.1 Hz, 1H), 7.94-7.88 (m, 1H), 7.88-7.79 (m, 2H), 5.38 (d, J=52.8 Hz, 1H), 4.32-4.20 (m, 1H), 3.88 (quin, J=8.4 Hz, 1H), 3.77-3.63 (m, 1H), 2.61-2.55 (m, 1H), 2.54 (s, 3H), 2.42-2.32 (m, 3H), 2.30-2.12 (m, 4H), 2.09-2.01 (m, 1H). HPLC RT=E: 1.56; F: 1.73.

The following Examples in Table 5 were prepared by using a similar procedure as shown in Example 33. Intermediate 24 was coupled with the amine. Various bases could be used other than the one described in Example 33 such as TEA, DBU, DABCO. Various solvents could be used other than the one described in Example 33 such as DMF, n-butanol, DMPU, THF.

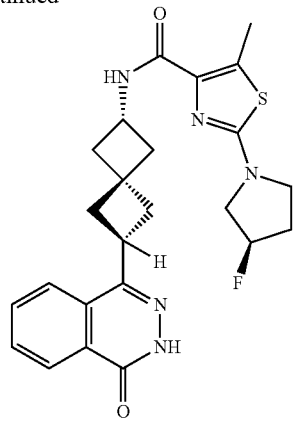

TABLE 5

| Ex. | R | Name | LCMS (M + H)$^+$ | HPLC Method, RT (min.) | $^1$H NMR |
|---|---|---|---|---|---|
| 54 | 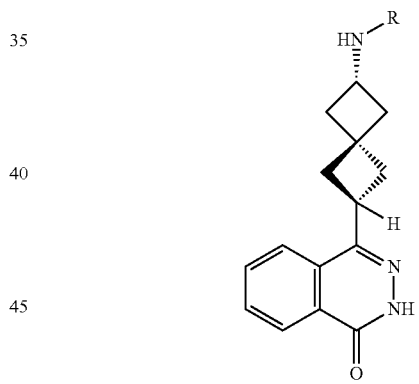 | 2-(3,3-difluoropyrrolidin-1-yl)-5-methyl-N-((aR)-6-(4-oxo-3,4-dihydrophthalazin-1-yl)spiro[3.3]heptan-2-yl)thiazole-4-carboxamide | 486.2 | E: 1.80 F: 1.84 | $^1$H NMR: (500 MHz, DMSO-d$_6$) δ ppm 12.48 (s, 1H), 8.24 (d, J = 7.7 Hz, 1H), 8.03 (br d, J = 8.4 Hz, 1H), 7.95-7.88 (m, 1H), 7.88-7.79 (m, 2H), 4.31-4.20 (m, 1H), 3.87 (br t, J = 12.6 Hz, 3H), 2.62-2.55 (m, 2H), 2.54 (s, 3H), 2.40-2.28 (m, 3H), 2.25-2.12 (m, 2H), 2.08-2.00 (m, 1H) |

TABLE 5-continued

| Ex. | R | Name | LCMS (M + H)+ | HPLC Method, RT (min.) | 1H NMR |
|---|---|---|---|---|---|
| 55 | | 2-((S)-3-cyanopyrrolidin-1-yl)-5-methyl-N-((aR)-6-(4-oxo-3,4-dihydrophthalazin-1-yl)spiro[3.3]heptan-2-yl)thiazole-4-carboxamide | 475.3 | E: 1.52<br>F: 1.59 | 1H NMR: (500 MHz, DMSO-d6) δ ppm 12.48 (s, 1H), 8.24 (d, J = 7.7 Hz, 1H), 7.99 (br d, J = 8.1 Hz, 1H), 7.94-7.89 (m, 1H), 7.88-7.79 (m, 2H), 4.33-4.20 (m, 1H), 3.88 (quin, J = 8.4 Hz, 1H), 3.78-3.70 (m, 1H), 3.70-3.62 (m, 1H), 2.56 (br s, 2H), 2.54 (s, 3H), 2.44-2.32 (m, 4H), 2.31-2.12 (m, 3H), 2.09-1.98 (m, 1H) |
| 56 | | 2-((R)-3-cyanopyrrolidin-1-yl)-5-methyl-N-((aR)-6-(4-oxo-3,4-dihydrophthalazin-1-yl)spiro[3.3]heptan-2-yl)thiazole-4-carboxamide | 475.2 | E: 1.53<br>F: 1.59 | 1H NMR: (500 MHz, DMSO-d6) δ ppm 12.48 (s, 1H), 8.25 (d, J = 7.7 Hz, 1H), 7.99 (br d, J = 8.1 Hz, 1H), 7.95-7.89 (m, 1H), 7.89-7.80 (m, 2H), 4.33-4.20 (m, 1H), 3.89 (quin, J = 8.4 Hz, 1H), 3.79-3.72 (m, 1H), 3.71-3.62 (m, 1H), 3.62-3.53 (m, 1H), 2.61-2.55 (m, 2H), 2.54 (s, 3H), 2.44-2.32 (m, 4H), 2.31-2.13 (m, 3H), 2.10-2.01 (m, 1H) |
| 57 | | 2-((3,3-difluorocyclobutyl)amino)-5-methyl-N-((aR)-6-(4-oxo-3,4-dihydrophthalazin-1-yl)spiro[3.3]heptan-2-yl)thiazole-4-carboxamide | 486.3 | E: 1.68<br>F: 1.72 | 1H NMR: (500 MHz, DMSO-d6) δ ppm 12.48 (s, 1H), 8.24 (d, J = 7.7 Hz, 1H), 7.90 (br d, J = 7.1 Hz, 1H), 7.88-7.79 (m, 3H), 4.29-4.19 (m, 1H), 4.09 (br s, 1H), 3.92-3.81 (m, 1H), 3.09-2.96 (m, 2H), 2.64-2.56 (m, 2H), 2.54 (s, 3H), 2.41-2.27 (m, 3H), 2.24-2.12 (m, 2H), 2.03 (br t, J = 9.9 Hz, 1H) |
| 58 | | 2-((S)-3-fluoropyrrolidin-1-yl)-5-methyl-N-((aR)-6-(4-oxo-3,4-dihydrophthalazin-1-yl)spiro[3.3]heptan-2-yl)thiazole-4-carboxamide | 468.2 | E: 1.55<br>F: 1.72 | 1H NMR: (500 MHz, DMSO-d6) δ ppm 12.47 (s, 1H), 8.25 (br d, J = 7.7 Hz, 1H), 7.96 (br d, J = 8.4 Hz, 1H), 7.94-7.88 (m, 1H), 7.88-7.80 (m, 2H), 5.53-5.34 (m, 1H), 4.32-4.21 (m, 1H), 3.95-3.83 (m, 1H), 3.78-3.63 (m, 1H), 2.63 (br s, 2H), 2.57-2.54 (m, 3H), 2.43-2.33 (m, 3H), 2.31-2.13 (m, 4H), 2.10-2.01 (m, 1H) |
| 59 | | 5-methyl-N-((aR)-6-(4-oxo-3,4-dihydrophthalazin-1-yl)spiro[3.3]heptan-2-yl)-2-((S)-2-(trifluoromethyl)pyrrolidin-1-yl)thiazole-4-carboxamide | 518.2 | E: 2.01<br>F: 2.02 | 1H NMR: (500 MHz, DMSO-d6) δ ppm 12.48 (s, 1H), 8.24 (br d, J = 8.1 Hz, 1H), 7.96 (br d, J = 8.1 Hz, 1H), 7.93-7.88 (m, 1H), 7.87-7.80 (m, 2H), 4.75 (br t, J = 7.7 Hz, 1H), 4.30-4.21 (m, 1H), 3.88 (br t, J = 8.2 Hz, 1H), 2.98 (s, 3H), 2.41-2.31 (m, 3H), 2.19 (br d, J = 8.4 Hz, 3H), 2.11-1.96 (m, 4H) |

TABLE 5-continued

| Ex. | R | Name | LCMS (M + H)+ | HPLC Method, RT (min.) | 1H NMR |
|---|---|---|---|---|---|
| 60 | (structure) | 5-methyl-N-((aR)-6-(4-oxo-3,4-dihydrophthalazin-1-yl)spiro[3.3]heptan-2-yl)-2-((R)-2-(trifluoromethyl)pyrrolidin-1-yl)thiazole-4-carboxamide | 518.2 | E: 2.00 F: 2.02 | 1H NMR: (500 MHz, DMSO-$d_6$) δ ppm 12.48 (s, 1H), 8.25 (d, J = 7.7 Hz, 1H), 7.96 (br d, J = 8.1 Hz, 1H), 7.94-7.88 (m, 1H), 7.88-7.79 (m, 2H), 4.77 (br t, J = 7.6 Hz, 1H), 4.31-4.21 (m, 1H), 3.94-3.83 (m, 1H), 3.57 (br s, 1H), 2.56 (s, 3H), 2.42-2.32 (m, 3H), 2.19 (br d, J = 6.7 Hz, 3H), 2.12-1.97 (m, 4H) |

The following Examples in Table 6 were made by using the same procedure as shown in Example 14. Intermediate 2 was coupled with the appropriate acid. Various coupling reagents could be used other than the one described in Example 14 such as BOP, PyBop, EDC/HOBt or HATU.

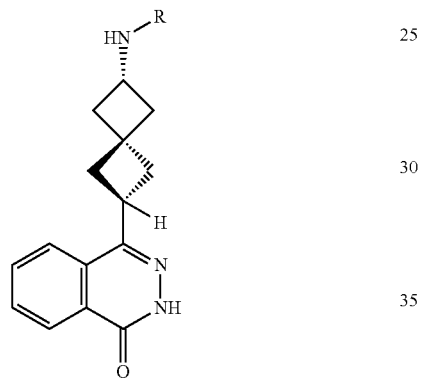

TABLE 6

| Ex. | R | Name | LCMS (M + H)+ | HPLC Method, RT (min.) | 1H NMR |
|---|---|---|---|---|---|
| 61 | (structure) | 1-(2-hydroxy-2-methylpropyl)-5-methoxy-N-((aR)-6-(4-oxo-3,4-dihydrophthalazin-1-yl)spiro[3.3]heptan-2-yl)-1H-indazole-3-carboxamide | 502.3 | E: 1.60 F: 1.61 | 1H NMR: (500 MHz, DMSO-$d_6$) δ ppm 12.47 (s, 1H), 8.32 (br d, J = 7.3 Hz, 1H), 8.25 (d, J = 7.9 Hz, 1H), 7.97-7.89 (m, 1H), 7.89-7.80 (m, 2H), 7.67 (br d, J = 9.2 Hz, 1H), 7.51 (s, 1H), 7.05 (br d, J = 9.2 Hz, 1H), 4.47-4.35 (m, 1H), 4.32 (s, 2H), 3.94-3.85 (m, 2H), 3.79 (s, 3H), 2.67-2.53 (m, 2H), 2.45-2.29 (m, 4H), 2.26-2.10 (m, 2H), 1.12 (s, 6H) |
| 62 | (structure) | 1-(2-hydroxy-2-methylpropyl)-6-methoxy-N-((aR)-6-(4-oxo-3,4-dihydrophthalazin-1-yl)spiro[3.3]heptan-2-yl)-1H-indazole-3-carboxamide | 502.4 | E: 1.62 F: 1.60 | 1H NMR: (500 MHz, DMSO-$d_6$) δ ppm 12.46 (s, 1H), 8.32 (br d, J = 7.9 Hz, 1H), 8.25 (d, J = 7.9 Hz, 1H), 8.01-7.93 (m, 1H), 7.91 (d, J = 7.3 Hz, 1H), 7.89-7.85 (m, 1H), 7.86-7.80 (m, 1H), 7.21 (d, J = 1.2 Hz, 1H), 6.85 (dd, J = 8.9, 1.8 Hz, 1H), 4.40 (sxt, J = 8.3 Hz, 1H), 4.32 (s, 2H), 3.95-3.85 (m, 1H), 3.83 (s, 3H), 2.68-2.53 (m, 2H), 2.44-2.29 (m, 4H), 2.25-2.09 (m, 2H), 1.15 (s, 6H) |

TABLE 6-continued

| Ex. | R | Name | LCMS (M + H)+ | HPLC Method, RT (min.) | 1H NMR |
|---|---|---|---|---|---|
| 63 | (structure) | 6-methoxy-N-((aR)-6-(4-oxo-3,4-dihydrophthalazin-1-yl)spiro[3.3]heptan-2-yl)pyrazolo[1,5-a]pyridine-3-carboxamide | 430.5 | E: 1.44<br>F: 1.41 | 1H NMR: (500 MHz, DMSO-d6) δ ppm 12.46 (s, 1H), 8.44 (br d, J = 5.5 Hz, 2H), 8.25 (br t, J = 8.4 Hz, 2H), 8.07 (br d, J = 9.5 Hz, 1H), 7.95-7.90 (m, 1H), 7.89-7.86 (m, 1H), 7.86-7.79 (m, 1H), 7.24 (br d, J = 9.8 Hz, 1H), 4.42-4.29 (m, 1H), 3.84 (s, 3H), 2.67-2.53 (m, 3H), 2.44-2.30 (m, 3H), 2.27-2.13 (m, 2H), 2.04 (br t, J = 10.1 Hz, 1H) |
| 64 | (structure) | 5-methoxy-N-((aR)-6-(4-oxo-3,4-dihydrophthalazin-1-yl)spiro[3.3]heptan-2-yl)pyrazolo[1,5-a]pyridine-3-carboxamide | 430.4 | E: 1.40<br>F: 1.45 | 1H NMR: (500 MHz, DMSO-d6) δ ppm 12.46 (s, 1H), 8.64-8.53 (m, 1H), 8.50-8.38 (m, 1H), 8.30-8.13 (m, 2H), 7.96-7.85 (m, 1H), 7.86-7.80 (m, 1H), 7.53-7.47 (m, 1H), 6.70 (dd, J = 7.5, 2.6 Hz, 1H), 4.40-4.29 (m, 1H), 3.96-3.89 (m, 1H), 3.88-3.83 (m, 3H), 2.69-2.53 (m, 2H), 2.44-2.32 (m, 2H), 2.28-2.16 (m, 2H), 2.09-1.97 (m, 1H) |
| 65 | (structure) | 5-fluoro-1-(2-hydroxy-2-methylpropyl)-N-((aR)-6-(4-oxo-3,4-dihydrophthalazin-1-yl)spiro[3.3]heptan-2-yl)-1H-indazole-3-carboxamide | 490.4 | E: 1.65<br>F: 1.64 | 1H NMR: (500 MHz, DMSO-d6) δ ppm 12.46 (s, 1H), 8.42 (br d, J = 7.9 Hz, 1H), 8.26 (d, J = 7.6 Hz, 1H), 7.97-7.90 (m, 1H), 7.89-7.86 (m, 1H), 7.86-7.81 (m, 2H), 7.76 (dd, J = 8.9, 2.1 Hz, 1H), 7.33 (td, J = 9.1, 2.3 Hz, 1H), 4.46-4.39 (m, 1H), 4.38 (s, 2H), 3.90 (quin, J = 8.5 Hz, 1H), 2.66-2.56 (m, 2H), 2.46-2.30 (m, 4H), 2.26-2.11 (m, 2H), 1.14 (s, 6H) |
| 66 | (structure) | 1-(2-hydroxy-2-methylpropyl)-N-((aR)-6-(4-oxo-3,4-dihydrophthalazin-1-yl)spiro[3.3]heptan-2-yl)-1H-pyrrolo[2,3-b]pyridine-3-carboxamide | 472.4 | E: 1.33<br>F: 1.40 | 1H NMR: (500 MHz, DMSO-d6) δ ppm 8.45 (d, J = 7.9 Hz, 1H), 8.31-8.17 (m, 4H), 7.95-7.90 (m, 1H), 7.90-7.86 (m, 1H), 7.86-7.80 (m, 1H), 7.23-7.17 (m, 1H), 4.46-4.33 (m, 1H), 4.22 (s, 2H), 3.91 (quin, J = 8.5 Hz, 1H), 2.69-2.55 (m, 2H), 2.44-2.32 (m, 3H), 2.28-2.18 (m, 2H), 2.06 (br t, J = 9.9 Hz, 1H), 1.07 (s, 6H) |
| 67 | (structure) | 6-(2-hydroxy-2-methylpropoxy)-N-((aR)-6-(4-oxo-3,4-dihydrophthalazin-1-yl)spiro[3.3]heptan-2-yl)pyrazolo[1,5-a]pyridine-3-carboxamide | 488.4 | E: 1.41<br>F: 1.38 | 1H NMR: (500 MHz, DMSO-d6) δ ppm 12.46 (s, 1H), 8.48-8.40 (m, 2H), 8.24 (dd, J = 11.1, 8.1 Hz, 2H), 8.08 (d, J = 9.5 Hz, 1H), 7.95-7.90 (m, 1H), 7.90-7.86 (m, 1H), 7.85-7.79 (m, 1H), 7.31-7.21 (m, 1H), 4.69 (s, 1H), 4.43-4.31 (m, 1H), 3.91 (quin, J = 8.5 Hz, 1H), 3.79 (s, 2H), 2.68-2.56 (m, 2H), 2.45-2.34 (m, 3H), 2.29-2.16 (m, 2H), 2.04 (br t, J = 10.1 Hz, 1H), 1.22 (s, 6H) |
| 68 | (structure) | 6-(2-morpholinoethoxy)-N-((aR)-6-(4-oxo-3,4-dihydrophthalazin-1-yl)spiro[3.3]heptan-2-yl)pyrazolo[1,5-a]pyridine-3-carboxamide | 529.5 | E: 1.16<br>F: 1.34 | 1H NMR: (500 MHz, DMSO-d6) δ ppm 12.47 (s, 1H), 8.54 (br s, 1H), 8.47 (s, 1H), 8.26 (br d, J = 7.6 Hz, 2H), 8.10 (br d, J = 9.5 Hz, 1H), 7.96-7.90 (m, 1H), 7.89-7.86 (m, 1H), 7.86-7.79 (m, 1H), 7.28 (br d, J = 9.8 Hz, 1H), 4.42-4.33 (m, 1H), 4.35-4.20 (m, 1H), 3.91 (quin, J = 8.5 Hz, 1H), 2.68-2.59 (m, 1H), 2.54 (s, 4H), 2.45-2.32 (m, 3H), 2.28-2.16 (m, 2H), 2.04 (br t, J = 10.1 Hz, 1H) |

TABLE 6-continued

| Ex. | R | Name | LCMS (M + H)+ | HPLC Method, RT (min.) | 1H NMR |
|---|---|---|---|---|---|
| 69 | (2-morpholino-thiazol-5-yl carbonyl structure) | 2-morpholino-N-((aR)-6-(4-oxo-3,4-dihydrophthalazin-1-yl)spiro[3.3]heptan-2-yl)thiazole-5-carboxamide | 452.4 | E: 1.26 F: 1.33 | 1H NMR: (500 MHz, DMSO-$d_6$) δ ppm 12.46 (s, 1H), 8.35 (br d, J = 7.6 Hz, 1H), 8.26 (d, J = 7.9 Hz, 1H), 7.96-7.90 (m, 1H), 7.89-7.79 (m, 3H), 4.26 (sxt, J = 8.1 Hz, 1H), 3.89 (quin, J = 8.4 Hz, 1H), 3.70 (t, J = 4.9 Hz, 4H), 3.43 (t, J = 4.7 Hz, 2H), 2.65-2.55 (m, 2H), 2.43-2.30 (m, 3H), 2.26-2.12 (m, 2H), 2.01 (t, J = 9.9 Hz, 1H) |
| 70 | (2-pyrrolidin-1-yl-thiazol-5-yl carbonyl structure) | N-((aR)-6-(4-oxo-3,4-dihydrophthalazin-1-yl)spiro[3.3]heptan-2-yl)-2-(pyrrolidin-1-yl)thiazole-5-carboxamide | 436.4 | E: 1.21 F: 1.44 | 1H NMR: (500 MHz, DMSO-$d_6$) δ ppm 12.45 (s, 1H), 8.28-8.21 (m, 2H), 7.94-7.89 (m, 1H), 7.88-7.81 (m, 2H), 7.80 (s, 1H), 4.25 (sxt, J = 8.1 Hz, 1H), 3.89 (quin, J = 8.5 Hz, 1H), 2.65-2.54 (m, 2H), 2.42-2.30 (m, 3H), 2.23-2.11 (m, 2H), 2.06-1.91 (m, 5H) |
| 71 | (benzo[d]isoxazol-3-yl carbonyl structure) | N-((aR)-6-(4-oxo-3,4-dihydrophthalazin-1-yl)spiro[3.3]heptan-2-yl)benzo[d]isoxazole-3-carboxamide | 401.4 | E: 1.73 F: 1.75 | 1H NMR: (500 MHz, DMSO-$d_6$) δ ppm 12.43 (s, 1H), 9.25 (br d, J = 7.6 Hz, 1H), 8.22 (br d, J = 7.6 Hz, 1H), 8.04 (br d, J = 7.9 Hz, 1H), 7.92-7.85 (m, 1H), 7.85-7.76 (m, 3H), 7.69 (br t, J = 7.8 Hz, 1H), 7.46 (t, J = 7.5 Hz, 1H), 4.43-4.31 (m, 1H), 3.92-3.80 (m, 1H), 2.65-2.57 (m, 1H), 2.41-2.29 (m, 4H), 2.25-2.17 (m, 1H), 2.16-2.07 (m, 1H) |
| 72 | (1-(2-hydroxy-2-methylpropyl)-1H-indol-3-yl carbonyl structure) | 1-(2-hydroxy-2-methylpropyl)-N-((aR)-6-(4-oxo-3,4-dihydrophthalazin-1-yl)spiro[3.3]heptan-2-yl)-1H-indole-3-carboxamide | 471.3 | E: 1.52 F: 1.53 | 1H NMR: (500 MHz, DMSO-$d_6$) δ ppm 12.43 (s, 1H), 8.22 (d, J = 7.9 Hz, 1H), 8.09 (d, J = 7.9 Hz, 1H), 8.05-7.97 (m, 2H), 7.91-7.82 (m, 2H), 7.82-7.76 (m, 1H), 7.52 (d, J = 8.2 Hz, 1H), 7.14-7.08 (m, 1H), 7.07-7.00 (m, 1H), 4.40-4.29 (m, 1H), 4.04 (s, 2H), 3.91-3.81 (m, 1H), 2.57 (br d, J = 11.6 Hz, 1H), 2.41-2.27 (m, 3H), 2.23-2.12 (m, 2H), 2.01 (br t, J = 9.9 Hz, 1H), 1.06 (s, 6H) |
| 73 | (5-(2-morpholinoethoxy)pyrazolo[1,5-a]pyridin-3-yl carbonyl structure) | 5-(2-morpholinoethoxy)-N-((aR)-6-(4-oxo-3,4-dihydrophthalazin-1-yl)spiro[3.3]heptan-2-yl)pyrazolo[1,5-a]pyridine-3-carboxamide | 529.3 | E: 1.12 F: 1.35 | 1H NMR: (500 MHz, DMSO-$d_6$) δ ppm 12.47 (s, 1H), 8.58 (d, J = 7.6 Hz, 1H), 8.45 (s, 1H), 8.25 (br d, J = 7.6 Hz, 1H), 8.17 (br d, J = 7.3 Hz, 1H), 7.96-7.78 (m, 3H), 7.52 (d, J = 2.1 Hz, 1H), 6.71 (dd, J = 7.3, 2.4 Hz, 1H), 4.40-4.28 (m, 1H), 4.17 (br t, J = 5.3 Hz, 2H), 3.96-3.84 (m, 1H), 3.61-3.52 (m, 4H), 2.74 (br t, J = 5.5 Hz, 2H), 2.66-2.57 (m, 1H), 2.43-2.31 (m, 3H), 2.29-2.14 (m, 2H), 2.04 (br t, J = 9.9 Hz, 1H) |
| 74 | (pyrazolo[1,5-a]pyridin-3-yl carbonyl structure) | N-((aR)-6-(4-oxo-3,4-dihydrophthalazin-1-yl)spiro[3.3]heptan-2-yl)pyrazolo[1,5-a]pyridine-3-carboxamide | 400.2 | E: 1.33 F: 1.34 | 1H NMR: (500 MHz, DMSO-$d_6$) δ ppm 12.49 (s, 1H), 8.76 (d, J = 7.0 Hz, 1H), 8.58 (s, 1H), 8.31 (br d, J = 7.6 Hz, 1H), 8.27 (d, J = 7.9 Hz, 1H), 8.20 (s, 1H), 7.98-7.88 (m, 2H), 7.87-7.80 (m, 1H), 7.51-7.40 (m, 1H), 7.06 (t, J = 6.9 Hz, 1H), 4.45-4.35 (m, 1H), 3.93 (quin, J = 8.3 Hz, 1H), 2.70-2.57 (m, 2H), |

TABLE 6-continued

| Ex. | R | Name | LCMS (M + H)+ | HPLC Method, RT (min.) | 1H NMR |
|---|---|---|---|---|---|
| | | | | | 2.47-2.34 (m, 3H), 2.31-2.18 (m, 2H), 2.11-2.02 (m, 1H) |
| 75 | | 5-(2-hydroxy-3-methoxypropoxy)-N-((aR)-6-(4-oxo-3,4-dihydrophthalazin-1-yl)spiro[3.3]heptan-2-yl)pyrazolo[1,5-a]pyridine-3-carboxamide | 504.4 | E: 1.28 F: 1.30 | 1H NMR: (500 MHz, DMSO-$d_6$) δ ppm 8.58 (d, J = 7.3 Hz, 1H), 8.45 (s, 1H), 8.25 (d, J = 7.9 Hz, 1H), 8.20 (br d, J = 7.3 Hz, 1H), 7.95-7.89 (m, 1H), 7.89-7.79 (m, 2H), 7.49 (d, J = 2.7 Hz, 1H), 6.71 (dd, J = 7.5, 2.6 Hz, 1H), 5.25 (d, J = 5.2 Hz, 1H), 4.38-4.27 (m, 1H), 4.08-4.03 (m, 1H), 4.03-3.84 (m, 3H), 3.29 (s, 3H), 2.67-2.55 (m, 2H), 2.44-2.33 (m, 3H), 2.27-2.16 (m, 2H), 2.08-1.98 (m, 1H) |
| 76 | | 6-morpholino-N-((aR)-6-(4-oxo-3,4-dihydrophthalazin-1-yl)spiro[3.3]heptan-2-yl)pyrazolo[1,5-a]pyridine-3-carboxamide | 485.2 | E: 1.28 F: 1.28 | 1H NMR: (500 MHz, DMSO-$d_6$) δ ppm 12.49 (s, 1H), 8.41 (s, 1H), 8.25 (br d, J = 7.7 Hz, 2H), 8.11 (s, 1H), 8.04 (d, J = 9.8 Hz, 1H), 7.96-7.90 (m, 1H), 7.89-7.80 (m, 2H), 7.47 (br d, J = 9.4 Hz, 1H), 4.43-4.29 (m, 1H), 3.96-3.85 (m, 1H), 3.75 (br s, 4H), 3.09 (br s, 4H), 2.62 (br s, 1H), 2.43-2.31 (m, 3H), 2.26-2.15 (m, 2H), 2.03 (br t, J = 10.0 Hz, 1H) |
| 77 | | 5-(2-hydroxyethoxy)-N-((aR)-6-(4-oxo-3,4-dihydrophthalazin-1-yl)spiro[3.3]heptan-2-yl)pyrazolo[1,5-a]pyridine-3-carboxamide | 460.1 | E: 1.26 F: 1.24 | 1H NMR: (500 MHz, DMSO-$d_6$) δ ppm 12.44 (s, 1H), 8.52 (d, J = 7.3 Hz, 1H), 8.40 (s, 1H), 8.20 (br dd, J = 11.3, 7.6 Hz, 2H), 7.92-7.85 (m, 1H), 7.85-7.75 (m, 2H), 7.45 (d, J = 2.4 Hz, 1H), 6.68 (dd, J = 7.6, 2.4 Hz, 1H), 4.35-4.24 (m, 1H), 4.03 (br t, J = 4.6 Hz, 2H), 3.86 (br t, J = 8.2 Hz, 1H), 3.72 (br s, 2H), 2.57 (br s, 2H), 2.40-2.26 (m, 3H), 2.23-2.10 (m, 2H), 2.03-1.94 (m, 1H) |
| 78 | | N-((aR)-6-(4-oxo-3,4-dihydrophthalazin-1-yl)spiro[3.3]heptan-2-yl)benzo[c]isoxazole-3-carboxamide | 401.2 | E: 1.52 F: 1.52 | 1H NMR: (500 MHz, DMSO-$d_6$) δ ppm 12.49 (s, 1H), 9.48 (br d, J = 7.5 Hz, 1H), 8.25 (br d, J = 7.7 Hz, 1H), 7.93 (br d, J = 10.3 Hz, 2H), 7.91-7.86 (m, 2H), 7.86-7.81 (m, 1H), 7.75 (d, J = 9.1 Hz, 1H), 7.53-7.43 (m, 1H), 7.32-7.22 (m, 1H), 4.43-4.34 (m, 1H), 3.94-3.85 (m, 1H), 2.63 (br s, 1H), 2.44-2.31 (m, 4H), 2.25 (br s, 1H), 2.21-2.13 (m, 1H) |
| 79 | | 6-(difluoromethoxy)-N-((aR)-6-(4-oxo-3,4-dihydrophthalazin-1-yl)spiro[3.3]heptan-2-yl)pyrazolo[1,5-a]pyridine-3-carboxamide | 466.2 | E: 1.44 F: 1.44 | 1H NMR: (500 MHz, DMSO-$d_6$) δ ppm 12.49 (s, 1H), 8.89 (s, 1H), 8.59 (s, 1H), 8.40 (br d, J = 7.4 Hz, 1H), 8.25 (br d, J = 7.8 Hz, 1H), 8.21 (d, J = 9.7 Hz, 1H), 7.96-7.90 (m, 1H), 7.89-7.80 (m, 2H), 7.45 (br d, J = 9.6 Hz, 1H), 7.26 (t, J = 73.4 Hz, 1H), 4.42-4.32 (m, 1H), 3.90 (quin, J = 8.5 Hz, 1H), 2.68-2.60 (m, 1H), 2.60-2.54 (m, 1H), 2.44-2.31 (m, 3H), 2.28-2.17 (m, 2H), 2.04 (br t, J = 10.0 Hz, 1H) |
| 80 | | 6-(2,2-difluoroethoxy)-N-((aR)-6-(4-oxo-3,4-dihydrophthalazin-1-yl)spiro[3.3]heptan-2-yl)pyrazolo[1,5-a]pyridine-3-carboxamide | 480.1 | E: 1.53 F: 1.53 | 1H NMR: (500 MHz, DMSO-$d_6$) δ ppm 12.47 (s, 1H), 8.59 (s, 1H), 8.48 (s, 1H), 8.29 (br d, J = 7.3 Hz, 1H), 8.25 (br d, J = 7.9 Hz, 1H), 8.10 (br d, J = 9.8 Hz, 1H), 7.96-7.89 (m, 1H), 7.89-7.79 (m, 2H), 7.32 (br d, J = 9.8 Hz, 1H), 6.42 (br t, J = 54.3 Hz, 1H), 4.49-4.30 (m, 3H), 3.95-3.83 (m, 1H), 2.61 (br d, J = 12.2 Hz, 1H), 2.44-2.30 (m, 3H), 2.28-2.16 (m, 2H), 2.08-1.99 (m, 1H) |

TABLE 6-continued

| Ex. | R | Name | LCMS (M + H)+ | HPLC Method, RT (min.) | 1H NMR |
|---|---|---|---|---|---|
| 81 | | 6-(2-(1H-pyrazol-1-yl)ethoxy)-N-((aR)-6-(4-oxo-3,4-dihydrophthalazin-1-yl)spiro[3.3]heptan-2-yl)pyrazolo[1,5-a]pyridine-3-carboxamide | 510.3 | E: 1.11 F: 1.39 | 1H NMR: (500 MHz, DMSO-d6) δ ppm 12.49 (s, 1H), 8.46 (br d, J = 11.0 Hz, 2H), 8.26 (br t, J = 7.2 Hz, 2H), 8.05 (br d, J = 9.6 Hz, 1H), 7.95-7.89 (m, 1H), 7.89-7.86 (m, 1H), 7.86-7.81 (m, 1H), 7.80 (s, 1H), 7.46 (s, 1H), 7.18 (br d, J = 9.7 Hz, 1H), 6.25 (s, 1H), 4.52 (br d, J = 4.8 Hz, 2H), 4.41 (br t, J = 4.7 Hz, 2H), 4.38-4.31 (m, 1H), 3.90 (br t, J = 8.4 Hz, 1H), 2.62 (br s, 1H), 2.44-2.32 (m, 3H), 2.27-2.16 (m, 2H), 2.03 (br t, J = 10.0 Hz, 1H) |
| 82 | | 6-(4,4-difluoropiperidin-1-yl)-N-((aR)-6-(4-oxo-3,4-dihydrophthalazin-1-yl)spiro[3.3]heptan-2-yl)pyrazolo[1,5-a]pyridine-3-carboxamide | 519.1 | E: 1.62 F: 1.63 | 1H NMR: (500 MHz, DMSO-d6) δ ppm 12.49 (s, 1H), 8.42 (s, 1H), 8.28-8.20 (m, 3H), 8.04 (d, J = 9.7 Hz, 1H), 7.94-7.90 (m, 1H), 7.90-7.86 (m, 1H), 7.86-7.81 (m, 1H), 7.49 (br d, J = 9.8 Hz, 1H), 4.42-4.32 (m, 1H), 3.90 (br t, J = 8.5 Hz, 1H), 2.62 (br s, 1H), 2.55 (br d, J = 13.8 Hz, 1H), 2.44-2.33 (m, 3H), 2.28-2.18 (m, 2H), 2.11 (br t, J = 13.6 Hz, 4H), 2.06-1.99 (m, 1H) |
| 83 | | N-((aR)-6-(4-oxo-3,4-dihydrophthalazin-1-yl)spiro[3.3]heptan-2-yl)-6-(2-(pyrrolidin-1-yl)ethoxy)pyrazolo[1,5-a]pyridine-3-carboxamide | 513.1 | E: 1.01 F: 1.05 | 1H NMR: (500 MHz, DMSO-d6) δ ppm 12.49 (s, 1H), 8.45 (br d, J = 6.2 Hz, 2H), 8.26 (br t, J = 7.0 Hz, 2H), 8.07 (d, J = 9.6 Hz, 1H), 7.95-7.90 (m, 1H), 7.89-7.86 (m, 1H), 7.86-7.81 (m, 1H), 7.25 (br d, J = 9.7 Hz, 1H), 4.42-4.31 (m, 1H), 4.12 (br t, J = 5.5 Hz, 2H), 3.90 (quin, J = 8.4 Hz, 1H), 2.81 (br t, J = 5.5 Hz, 2H), 2.61 (br d, J = 11.1 Hz, 1H), 2.59-2.55 (m, 1H), 2.53 (br s, 4H), 2.44-2.31 (m, 3H), 2.27-2.17 (m, 2H), 2.04 (br t, J = 10.0 Hz, 1H), 1.68 (br s, 4H) |
| 84 | | 5-morpholino-N-((aR)-6-(4-oxo-3,4-dihydrophthalazin-1-yl)spiro[3.3]heptan-2-yl)pyrazolo[1,5-a]pyridine-3-carboxamide | 485.2 | E: 1.26 F: 1.29 | 1H NMR: (500 MHz, DMSO-d6) δ ppm 12.49 (s, 1H), 8.50 (d, J = 7.7 Hz, 1H), 8.38 (s, 1H), 8.25 (br d, J = 7.7 Hz, 1H), 8.08 (br d, J = 7.5 Hz, 1H), 7.96-7.90 (m, 1H), 7.89-7.86 (m, 1H), 7.86-7.81 (m, 1H), 7.33 (s, 1H), 6.95-6.89 (m, 1H), 4.39-4.28 (m, 1H), 3.90 (quin, J = 8.4 Hz, 1H), 3.76 (br s, 4H), 3.23 (br s, 4H), 2.65-2.57 (m, 1H), 2.43-2.33 (m, 3H), 2.26-2.16 (m, 2H), 2.07-1.98 (m, 1H), 2.02 (br t, J = 10.0 Hz, 1H) |
| 85 | | 5-(1-methyl-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide | 480.1 | E: 1.26 F: 1.27 | 1H NMR: (500 MHz, DMSO-d6) δ ppm 12.49 (s, 1H), 8.72 (d, J = 7.2 Hz, 1H), 8.51 (s, 1H), 8.36 (s, 1H), 8.30-8.21 (m, 3H), 7.99 (s, 1H), 7.95-7.90 (m, 1H), 7.90-7.86 (m, 1H), 7.86-7.81 (m, 1H), 7.27 (br d, J = 7.2 Hz, 1H), 4.43-4.32 (m, 1H), 3.96-3.90 (m, 1H), 3.89 (s, 3H), 2.64 (br s, 1H), 2.61-2.56 (m, 1H), 2.45-2.32 (m, 3H), 2.29-2.18 (m, 2H), 2.06 (br t, J = 10.1 Hz, 1H) |

TABLE 6-continued

| Ex. | R | Name | LCMS (M + H)+ | HPLC Method, RT (min.) | 1H NMR |
|---|---|---|---|---|---|
| 86 | | 6-(4-methylpiperazin-1-yl)-N-((aR)-6-(4-oxo-3,4-dihydrophthalazin-1-yl)spiro[3.3]heptan-2-yl)pyrazolo[1,5-a]pyridine-3-carboxamide | 498.3 | E: 0.97 F: 1.08 | 1H NMR: (500 MHz, DMSO-d6) δ ppm 12.50 (s, 1H), 8.44 (s, 1H), 8.26 (br t, J = 8.0 Hz, 2H), 8.21 (br s, 1H), 8.06 (br d, J = 9.7 Hz, 1H), 7.96-7.91 (m, 1H), 7.90-7.87 (m, 1H), 7.87-7.82 (m, 1H), 7.48 (br d, J = 9.3 Hz, 1H), 4.43-4.32 (m, 1H), 3.91 (q, J = 8.4 Hz, 1H), 3.37 (br s, 8H), 3.26 (br s, 3H), 2.93 (br s, 2H), 2.63 (br s, 1H), 2.44-2.32 (m, 1H), 2.29-2.16 (m, 2H), 2.05 (br t, J = 10.0 Hz, 1H) |
| 87 | | N-((aR)-6-(4-oxo-3,4-dihydrophthalazin-1-yl)spiro[3.3]heptan-2-yl)-6-(pyrrolidin-1-yl)pyrazolo[1,5-a]pyridine-3-carboxamide | 469.3 | E: 1.52 F: 1.60 | 1H NMR: (500 MHz, DMSO-d6) δ ppm 12.49 (s, 1H), 8.32 (s, 1H), 8.25 (br d, J = 7.7 Hz, 1H), 8.15 (br d, J = 7.6 Hz, 1H), 8.01 (d, J = 9.5 Hz, 1H), 7.95-7.90 (m, 1H), 7.90-7.86 (m, 1H), 7.86-7.82 (m, 1H), 7.80 (s, 1H), 7.18 (br d, J = 9.6 Hz, 1H), 4.41-4.32 (m, 1H), 3.90 (quin, J = 8.4 Hz, 1H), 2.62 (br s, 1H), 2.59-2.52 (m, 1H), 2.44-2.31 (m, 3H), 2.27-2.15 (m, 2H), 2.03 (br t, J = 10.0 Hz, 1H), 1.96 (br s, 4H) |
| 88 | | 6-((R)-3-fluoropyrrolidin-1-yl)-N-((aR)-6-(4-oxo-3,4-dihydrophthalazin-1-yl)spiro[3.3]heptan-2-yl)pyrazolo[1,5-a]pyridine-3-carboxamide | 487 | E: 1.43 F: 1.45 | 1H NMR: (500 MHz, DMSO-d6) δ ppm 12.49 (s, 1H), 8.35 (s, 1H), 8.25 (br d, J = 7.7 Hz, 1H), 8.17 (br d, J = 7.5 Hz, 1H), 8.04 (br d, J = 9.6 Hz, 1H), 7.97-7.86 (m, 3H), 7.86-7.80 (m, 1H), 7.22 (br d, J = 9.6 Hz, 1H), 5.47 (br d, J = 54.9 Hz, 1H), 4.42-4.30 (m, 1H), 3.96-3.85 (m, 1H), 3.63-3.51 (m, 1H), 2.61 (br d, J = 11.5 Hz, 1H), 2.45-2.32 (m, 3H), 2.30-2.14 (m, 4H), 2.04 (br t, J = 10.0 Hz, 1H) |
| 89 | | 6-((S)-3-fluoropyrrolidin-1-yl)-N-((aR)-6-(4-oxo-3,4-dihydrophthalazin-1-yl)spiro[3.3]heptan-2-yl)pyrazolo[1,5-a]pyridine-3-carboxamide | 487.2 | E: 1.43 F: 1.46 | 1H NMR: (500 MHz, DMSO-d6) δ ppm 12.49 (s, 1H), 8.35 (s, 1H), 8.25 (br d, J = 7.8 Hz, 1H), 8.17 (br d, J = 7.6 Hz, 1H), 8.04 (d, J = 9.6 Hz, 1H), 7.97-7.86 (m, 3H), 7.86-7.81 (m, 1H), 7.22 (br d, J = 9.6 Hz, 1H), 5.46 (br d, J = 53.0 Hz, 1H), 4.42-4.31 (m, 1H), 3.95-3.85 (m, 1H), 3.61-3.51 (m, 1H), 2.61 (br d, J = 11.8 Hz, 1H), 2.45-2.32 (m, 3H), 2.30-2.14 (m, 4H), 2.03 (br t, J = 10.0 Hz, 1H) |
| 90 | | 6-(3,3-difluoropyrrolidin-1-yl)-N-((aR)-6-(4-oxo-3,4-dihydrophthalazin-1-yl)spiro[3.3]heptan-2-yl)pyrazolo[1,5-a]pyridine-3-carboxamide | 505.3 | E: 1.53 F: 1.56 | 1H NMR: (500 MHz, DMSO-d6) δ ppm 12.49 (s, 1H), 8.38 (s, 1H), 8.25 (br d, J = 7.7 Hz, 1H), 8.20 (br d, J = 7.6 Hz, 1H), 8.05 (d, J = 9.6 Hz, 1H), 8.00 (s, 1H), 7.95-7.90 (m, 1H), 7.90-7.86 (m, 1H), 7.86-7.81 (m, 1H), 7.25 (br d, J = 9.5 Hz, 1H), 4.42-4.31 (m, 1H), 3.90 (quin, J = 8.4 Hz, 1H), 3.73 (br t, J = 13.2 Hz, 2H), 3.51 (br t, J = 7.1 Hz, 1H), 2.62 (br s, 1H), 2.59-2.52 (m, 3H), 2.44-2.32 (m, 3H), 2.27-2.16 (m, 2H), 2.04 (br t, J = 10.0 Hz, 1H) |
| 91 | | 6-(3-fluoroazetidin-1-yl)-N-((aR)-6-(4-oxo-3,4-dihydrophthalazin-1-yl)spiro[3.3]heptan-2-yl)pyrazolo[1,5-a]pyridine-3-carboxamide | 473.2 | E: 1.36 F: 1.39 | 1H NMR: (500 MHz, DMSO-d6) δ ppm 12.49 (s, 1H), 8.38 (s, 1H), 8.25 (br d, J = 7.7 Hz, 1H), 8.20 (br d, J = 7.5 Hz, 1H), 8.05 (d, J = 9.4 Hz, 1H), 7.95-7.89 (m, 2H), 7.89-7.86 (m, 1H), 7.85-7.80 (m, 1H), 7.00 (br d, J = 9.4 Hz, 1H), 5.49 (br d, J = 57.4 Hz, 1H), 4.42-4.30 (m, 1H), 4.24-4.12 (m, 2H), 3.95 (br d, J = 9.3 Hz, 1H), 3.89 (br d, |

TABLE 6-continued

| Ex. | R | Name | LCMS (M + H)+ | HPLC Method, RT (min.) | 1H NMR |
|---|---|---|---|---|---|
| | | carboxamide | | | J = 8.1 Hz, 2H), 2.61 (br d, J = 11.6 Hz, 1H), 2.44-2.30 (m, 3H), 2.27-2.16 (m, 2H), 2.03 (br t, J = 10.0 Hz, 1H) |
| 92 | | 6-(3,3-difluoroazetidin-1-yl)-N-((aR)-6-(4-oxo-3,4-dihydrophthalazin-1-yl)spiro[3.3]heptan-2-yl)pyrazolo[1,5-a]pyridine-3-carboxamide | 491.3 | E: 1.46 F: 1.49 | $^1$H NMR: (500 MHz, DMSO-$d_6$) δ ppm 12.49 (s, 1H), 8.41 (s, 1H), 8.24 (br t, J = 8.7 Hz, 2H), 8.11-8.03 (m, 2H), 7.95-7.90 (m, 1H), 7.90-7.86 (m, 1H), 7.86-7.80 (m, 1H), 7.06 (br d, J = 9.5 Hz, 1H), 4.33 (br t, J = 12.2 Hz, 4H), 3.94-3.86 (m, 1H), 2.61 (br d, J = 11.3 Hz, 1H), 2.57 (br s, 1H), 2.45-2.32 (m, 3H), 2.27-2.16 (m, 2H), 2.04 (br t, J = 10.1 Hz, 1H) |
| 93 | | N-((aR)-6-(4-oxo-3,4-dihydrophthalazin-1-yl)spiro[3.3]heptan-2-yl)benzo[d]imidazo[2,1-b]thiazole-2-carboxamide | 455.9 | E: 1.73 F: 1.74 | $^1$H NMR: (500 MHz, DMSO-$d_6$) δ ppm 12.47 (s, 1H), 8.39 (br d, J = 7.9 Hz, 1H), 8.25 (br d, J = 7.9 Hz, 1H), 8.13 (d, J = 7.9 Hz, 1H), 8.04 (d, J = 7.9 Hz, 1H), 7.95-7.90 (m, 1H), 7.89-7.86 (m, 1H), 7.85-7.79 (m, 1H), 7.60-7.54 (m, 1H), 7.46 (t, J = 7.6 Hz, 1H), 4.42-4.30 (m, 1H), 3.89 (br t, J = 8.4 Hz, 1H), 2.63-2.52 (m, 3H), 2.44-2.35 (m, 2H), 2.35-2.26 (m, 2H), 2.19 (br d, J = 6.4 Hz, 1H), 2.15-2.08 (m, 1H) |
| 94 | | N-((aR)-6-(4-oxo-3,4-dihydrophthalazin-1-yl)spiro[3.3]heptan-2-yl)benzo[d]imidazo[2,1-b]thiazole-2-carboxamide | 455.9 | E: 1.73 F: 1.74 | $^1$H NMR: (500 MHz, DMSO-$d_6$) δ ppm 12.47 (s, 1H), 8.39 (br d, J = 7.9 Hz, 1H), 8.25 (br d, J = 7.9 Hz, 1H), 8.13 (d, J = 7.9 Hz, 1H), 8.04 (d, J = 7.9 Hz, 1H), 7.95-7.90 (m, 1H), 7.89-7.86 (m, 1H), 7.85-7.79 (m, 1H), 7.60-7.54 (m, 1H), 7.46 (t, J = 7.6 Hz, 1H), 4.42-4.30 (m, 1H), 3.89 (br t, J = 8.4 Hz, 1H), 2.63-2.52 (m, 3H), 2.44-2.35 (m, 2H), 2.35-2.26 (m, 2H), 2.19 (br d, J = 6.4 Hz, 1H), 2.15-2.08 (m, 1H) |
| 95 | | 2-ethyl-N-((aR)-6-(4-oxo-3,4-dihydrophthalazin-1-yl)spiro[3.3]heptan-2-yl)imidazo[2,1-b][1,3,4]thiadiazole-6-carboxamide | 435 | E: 1.57 F: 1.57 | $^1$H NMR: (500 MHz, DMSO-$d_6$) δ ppm 12.46 (s, 1H), 8.49 (s, 1H), 8.32 (br d, J = 7.9 Hz, 1H), 8.25 (br d, J = 7.9 Hz, 1H), 7.96-7.89 (m, 1H), 7.86 (d, J = 8.5 Hz, 1H), 7.85-7.78 (m, 1H), 4.39-4.28 (m, 1H), 3.88 (br t, J = 8.2 Hz, 1H), 3.09 (q, J = 7.5 Hz, 2H), 2.54 (br s, 2H), 2.42-2.23 (m, 4H), 2.18 (br s, 1H), 2.13-2.05 (m, 1H), 1.33 (br t, J = 7.3 Hz, 3H) |
| 96 | | N-((aR)-6-(4-oxo-3,4-dihydrophthalazin-1-yl)spiro[3.3]heptan-2-yl)pyrazolo[1,5-b]pyridazine-3-carboxamide | 401.1 | E: 1.12 F: 1.12 | $^1$H NMR: (500 MHz, DMSO-$d_6$) δ ppm 12.49 (s, 1H), 8.68-8.60 (m, 2H), 8.58 (br s, 1H), 8.53 (br d, J = 7.4 Hz, 1H), 8.25 (br d, J = 7.8 Hz, 1H), 7.96-7.90 (m, 1H), 7.90-7.86 (m, 1H), 7.86-7.80 (m, 1H), 7.41 (dd, J = 8.9, 4.3 Hz, 1H), 4.43-4.31 (m, 1H), 3.91 (br t, J = 8.5 Hz, 1H), 2.64 (br s, 1H), 2.60-2.56 (m, 1H), 2.45-2.32 (m, 3H), 2.30-2.18 (m, 2H) |

TABLE 6-continued

| Ex. | R | Name | LCMS (M + H)+ | HPLC Method, RT (min.) | $^1$H NMR |
|---|---|---|---|---|---|
| 97 | (structure) | 7-cyclopropyl-6-(2-hydroxy-2-methylpropoxy)-N-((aR)-6-(4-oxo-3,4-dihydrophthalazin-1-yl)spiro[3.3]heptan-2-yl)pyrazolo[1,5-a]pyridine-3-carboxamide | 528.3 | E: 1.61 F: 1.55 | $^1$H NMR: (500 MHz, DMSO-$d_6$) δ ppm 12.49 (s, 1H), 8.51 (s, 1H), 8.32-8.20 (m, 2H), 8.03 (d, J = 9.6 Hz, 1H), 7.96-7.90 (m, 1H), 7.90-7.86 (m, 1H), 7.86-7.80 (m, 1H), 7.46 (d, J = 9.8 Hz, 1H), 4.71 (br s, 1H), 4.44-4.28 (m, 1H), 3.90 (quin, J = 8.3 Hz, 1H), 3.78 (s, 2H), 2.69-2.55 (m, 3H), 2.44-2.30 (m, 3H), 2.27-2.16 (m, 2H), 2.04 (br t, J = 10.1 Hz, 1H), 1.48 (br d, J = 3.8 Hz, 2H), 1.23 (s, 6H), 1.05 (br dd, J = 8.6, 2.1 Hz, 2H) |
| 98 | (structure) | N-((aR)-6-(4-oxo-3,4-dihydrophthalazin-1-yl)spiro[3.3]heptan-2-yl)-6-(3,3,3-trifluoro-2-hydroxy-2-(trifluoromethyl)propoxy)pyrazolo[1,5-a]pyridine-3-carboxamide | 596.3 | E: 1.78 F: 1.82 | $^1$H NMR: (500 MHz, DMSO-$d_6$) δ ppm 12.47 (s, 1H), 8.69 (s, 1H), 8.49 (s, 1H), 8.27 (br t, J = 9.2 Hz, 2H), 8.12 (br d, J = 9.8 Hz, 1H), 7.96-7.90 (m, 1H), 7.90-7.86 (m, 1H), 7.86-7.79 (m, 1H), 7.27 (br d, J = 9.5 Hz, 1H), 4.51 (s, 2H), 4.42-4.32 (m, 1H), 2.63 (br s, 1H), 2.46-2.32 (m, 3H), 2.29-2.16 (m, 2H), 2.05 (br t, J = 10.1 Hz, 1H) |
| 99 | (structure) | 6-(benzyloxy)-N-((aR)-6-(4-oxo-3,4-dihydrophthalazin-1-yl)spiro[3.3]heptan-2-yl)pyrazolo[1,5-a]pyridine-3-carboxamide | 506.1 | E: 1.79 F: 1.79 | $^1$H NMR: (500 MHz, DMSO-$d_6$) δ ppm 12.49 (s, 1H), 8.54 (s, 1H), 8.45 (s, 1H), 8.28 (br d, J = 7.5 Hz, 1H), 8.25 (br d, J = 7.9 Hz, 1H), 8.09 (d, J = 9.6 Hz, 1H), 7.96-7.90 (m, 1H), 7.90-7.86 (m, 1H), 7.86-7.78 (m, 1H), 7.49 (br d, J = 7.4 Hz, 2H), 7.41 (br t, J = 7.4 Hz, 2H), 7.38-7.34 (m, 1H), 7.32 (br d, J = 9.6 Hz, 1H), 5.16 (s, 2H), 4.43-4.30 (m, 1H), 3.90 (quin, J = 8.4 Hz, 1H), 2.62 (br t, J = 11.7 Hz, 1H), 2.44-2.31 (m, 3H), 2.27-2.15 (m, 2H), 2.04 (br t, J = 10.0 Hz, 1H) |
| 100 | (structure) | 1-(2,2-difluoroethyl)-N-((aR)-6-(4-oxo-3,4-dihydrophthalazin-1-yl)spiro[3.3]heptan-2-yl)-1H-pyrazole-5-carboxamide | 414.2 | E: 1.42 F: 1.42 | $^1$H NMR: (500 MHz, DMSO-$d_6$) δ ppm 12.49 (s, 1H), 8.73 (br d, J = 7.5 Hz, 1H), 8.25 (d, J = 7.8 Hz, 1H), 7.95-7.88 (m, 1H), 7.86 (d, J = 9.3 Hz, 2H), 7.84-7.79 (m, 1H), 7.58 (s, 1H), 6.95 (s, 1H), 6.31 (br t, J = 55.5 Hz, 1H), 5.04-4.86 (m, 2H), 4.36-4.21 (m, 1H), 3.89 (quin, J = 8.4 Hz, 1H), 2.60 (br s, 1H), 2.43-2.30 (m, 3H), 2.22 (br t, J = 9.4 Hz, 2H), 2.04 (br t, J = 10.0 Hz, 1H) |
| 101 | (structure) | N-((aR)-6-(4-oxo-3,4-dihydrophthalazin-1-yl)spiro[3.3]heptan-2-yl)-1-(3,3,3-trifluoropropyl)-1H-pyrazole-5-carboxamide | 446.2 | E: 1.60 F: 1.60 | $^1$H NMR: (500 MHz, DMSO-$d_6$) δ ppm 12.49 (s, 1H), 8.66 (br d, J = 7.3 Hz, 1H), 8.25 (d, J = 7.8 Hz, 1H), 7.96-7.90 (m, 1H), 7.89-7.78 (m, 2H), 7.52 (s, 1H), 6.91 (s, 1H), 4.73 (br t, J = 6.9 Hz, 2H), 4.37-4.22 (m, 1H), 3.89 (quin, J = 8.5 Hz, 1H), 2.86-2.73 (m, 2H), 2.66-2.57 (m, 1H), 2.44-2.30 (m, 3H), 2.21 (br t, J = 9.8 Hz, 2H), 2.04 (br t, J = 10.0 Hz, 1H) |

TABLE 6-continued

| Ex. | R | Name | LCMS (M + H)+ | HPLC Method, RT (min.) | 1H NMR |
|---|---|---|---|---|---|
| 102 | | 1-(4-methoxybenzyl)-N-((aR)-6-(4-oxo-3,4-dihydrophthalazin-1-yl)spiro[3.3]heptan-2-yl)-1H-pyrazole-4-carboxamide | 470.1 | E: 1.49 F: 1.49 | 1H NMR: (500 MHz, DMSO-d6) δ ppm 12.48 (s, 1H), 8.24 (br d, J = 7.8 Hz, 1H), 8.19 (br d, J = 7.6 Hz, 1H), 8.15 (s, 1H), 7.95-7.89 (m, 1H), 7.88-7.77 (m, 3H), 7.22 (br d, J = 8.4 Hz, 2H), 6.91 (br d, J = 8.4 Hz, 2H), 5.23 (s, 2H), 4.32-4.20 (m, 1H), 3.87 (quin, J = 8.5 Hz, 1H), 3.72 (s, 3H), 2.59 (br s, 1H), 2.42-2.27 (m, 3H), 2.22-2.07 (m, 2H), 1.96 (br t, J = 10.0 Hz, 1H) |
| 103 | | 1-(cyclopropylmethyl)-N-((aR)-6-(4-oxo-3,4-dihydrophthalazin-1-yl)spiro[3.3]heptan-2-yl)-1H-pyrazole-5-carboxamide | 404.3 | E: 1.51 F: 1.51 | 1H NMR: (500 MHz, DMSO-d6) δ ppm 12.49 (s, 1H), 8.61 (br d, J = 7.3 Hz, 1H), 8.25 (d, J = 7.9 Hz, 1H), 7.95-7.89 (m, 1H), 7.88-7.80 (m, 2H), 7.45 (s, 1H), 6.83 (s, 1H), 4.32 (br d, J = 7.1 Hz, 2H), 4.30-4.20 (m, 1H), 3.89 (quin, J = 8.4 Hz, 1H), 2.68-2.58 (m, 1H), 2.45-2.29 (m, 3H), 2.21 (br t, J = 9.6 Hz, 2H), 2.09-1.99 (m, 1H), 1.21 (br d, J = 7.1 Hz, 1H), 0.40 (br d, J = 7.2 Hz, 2H), 0.30 (br d, J = 4.3 Hz, 2H) |
| 104 | | N-((aR)-6-(4-oxo-3,4-dihydrophthalazin-1-yl)spiro[3.3]heptan-2-yl)-1-(tetrahydro-2H-pyran-4-yl)-1H-pyrazole-5-carboxamide | 434.3 | E: 1.36 F: 1.36 | 1H NMR: (500 MHz, DMSO-d6) δ ppm 12.49 (s, 1H), 8.62 (br d, J = 7.6 Hz, 1H), 8.25 (d, J = 7.8 Hz, 1H), 7.97-7.89 (m, 1H), 7.88-7.78 (m, 2H), 7.50 (s, 1H), 6.82 (s, 1H), 5.29 (br t, J = 11.5 Hz, 1H), 4.36-4.23 (m, 1H), 3.94 (br d, J = 10.9 Hz, 2H), 3.89 (br t, J = 8.4 Hz, 1H), 3.40 (br t, J = 11.9 Hz, 2H), 2.59 (br s, 1H), 2.43-2.28 (m, 3H), 2.21 (br t, J = 9.4 Hz, 2H), 2.08-1.94 (m, 3H), 1.79 (br d, J = 11.3 Hz, 2H) |
| 105 | | N-((aR)-6-(4-oxo-3,4-dihydrophthalazin-1-yl)spiro[3.3]heptan-2-yl)-6-((tetrahydrofuran-3-yl)oxy)pyrazolo[1,5-a]pyridine-3-carboxamide | 486.2 | E: 1.41 F: 1.41 | 1H NMR: (500 MHz, DMSO-d6) δ ppm 12.49 (s, 1H), 8.45 (br s, 2H), 8.28 (br d, J = 7.4 Hz, 1H), 8.25 (br d, J = 7.8 Hz, 1H), 8.08 (d, J = 9.6 Hz, 1H), 7.97-7.90 (m, 1H), 7.89-7.85 (m, 2H), 7.85-7.77 (m, 1H), 7.24 (br d, J = 9.6 Hz, 1H), 5.08 (br s, 1H), 4.43-4.29 (m, 1H), 3.96-3.81 (m, 4H), 3.80-3.70 (m, 1H), 2.67-2.58 (m, 1H), 2.44-2.31 (m, 3H), 2.31-2.15 (m, 3H), 2.09-1.96 (m, 2H) |
| 106 | | tert-butyl (2-(4-(((aR)-6-(4-oxo-3,4-dihydrophthalazin-1-yl)spiro[3.3]heptan-2-yl)carbamoyl)-1H-pyrazol-1-yl)ethyl)carbamate | 493 | E: 1.34 F: 1.33 | 1H NMR: (500 MHz, DMSO-d6) δ ppm 12.48 (s, 1H), 8.25 (d, J = 7.7 Hz, 1H), 8.16 (br d, J = 7.3 Hz, 1H), 8.07 (s, 1H), 7.95-7.89 (m, 1H), 7.88-7.79 (m, 3H), 6.92 (br s, 1H), 4.33-4.23 (m, 1H), 4.12 (br t, J = 5.8 Hz, 2H), 3.89 (quin, J = 8.4 Hz, 1H), 3.28 (br d, J = 5.9 Hz, 1H), 2.64-2.55 (m, 1H), 2.43-2.29 (m, 3H), 2.24-2.17 (m, 1H), 2.18-2.09 (m, 1H), 1.34 (s, 9H) |
| 107 | | N-((aR)-6-(4-oxo-3,4-dihydrophthalazin-1-yl)spiro[3.3]heptan-2-yl)-6-(3,3,3-trifluoro-2-hydroxypropoxy)pyrazolo | 528.1 | E: 1.44 F: 1.39 | 1H NMR: (500 MHz, DMSO-d6) δ ppm 8.52 (s, 1H), 8.42 (s, 1H), 8.27 (br d, J = 7.5 Hz, 1H), 8.21 (br d, J = 7.8 Hz, 1H), 8.05 (d, J = 9.6 Hz, 1H), 7.91-7.84 (m, 1H), 7.84-7.74 (m, 2H), 7.23 (br d, J = 9.7 Hz, 1H), 4.40 (br d, J = 3.5 Hz, 1H), 4.37-4.27 (m, 1H), 4.22 (br dd, J = 10.5, 3.2 Hz, 1H), 4.11 (br |

TABLE 6-continued

| Ex. | R | Name | LCMS (M + H)+ | HPLC Method, RT (min.) | 1H NMR |
|---|---|---|---|---|---|
| | | [1,5-a]pyridine-3-carboxamide | | | dd, J = 10.3, 6.6 Hz, 1H), 3.84 (quin, J = 8.4 Hz, 1H), 3.49 (br s, 2H), 2.62-2.55 (m, 1H), 2.40-2.26 (m, 3H), 2.23-2.12 (m, 2H), 1.99 (br t, J = 10.0 Hz, 1H) |
| 108 | [structure: 1-(3-methoxyphenyl)pyrazole-4-carbonyl] | 1-(3-methoxyphenyl)-N-((aR)-6-(4-oxo-3,4-dihydrophthalazin-1-yl)spiro[3.3]heptan-2-yl)-1H-pyrazole-4-carboxamide | 456.3 | E: 1.62 F: 1.61 | 1H NMR: (500 MHz, DMSO-$d_6$) δ ppm 12.50 (s, 1H), 8.90 (s, 1H), 8.37 (br d, J = 7.4 Hz, 1H), 8.25 (br d, J = 7.7 Hz, 1H), 8.12 (s, 1H), 7.96-7.89 (m, 1H), 7.86 (d, J = 8.3 Hz, 1H), 7.85-7.79 (m, 1H), 7.47-7.34 (m, 3H), 4.39-4.25 (m, 1H), 3.89 (br t, J = 8.3 Hz, 1H), 3.82 (s, 3H), 2.63 (br s, 1H), 2.44-2.29 (m, 3H), 2.23 (br s, 1H), 2.21-2.13 (m, 1H), 2.01 (br t, J = 9.8 Hz, 1H) |
| 109 | [structure: 1-benzylpyrazole-4-carbonyl] | 1-benzyl-N-((aR)-6-(4-oxo-3,4-dihydrophthalazin-1-yl)spiro[3.3]heptan-2-yl)-1H-pyrazole-4-carboxamide | 440.1 | E: 1.54 F: 1.58 | 1H NMR: (500 MHz, DMSO-$d_6$) δ ppm 12.46 (s, 1H), 8.25 (br d, J = 7.6 Hz, 1H), 8.21 (s, 1H), 8.17 (br d, J = 7.0 Hz, 1H), 7.90 (br d, J = 7.3 Hz, 1H), 7.88-7.76 (m, 3H), 7.35 (br d, J = 7.0 Hz, 2H), 7.31 (br d, J = 6.7 Hz, 1H), 7.24 (br d, J = 7.0 Hz, 2H), 5.33 (s, 2H), 4.33-4.21 (m, 1H), 3.88 (br t, J = 8.1 Hz, 1H), 2.56 (br s, 1H), 2.42-2.29 (m, 3H), 2.19 (br s, 1H), 2.17-2.10 (m, 1H), 1.97 (br t, J = 10.1 Hz, 1H) |
| 110 | [structure: 6-(2-hydroxy-2-methylpropoxy)-3-carbamoyl-pyrazolo[1,5-a]pyridine-3-carbonyl] | 6-(2-hydroxy-2-methylpropoxy)-N3-((aR)-6-(4-oxo-3,4-dihydrophthalazin-1-yl)spiro[3.3]heptan-2-yl)pyrazolo[1,5-a]pyridine-3,7-dicarboxamide | 531.3 | E: 1.16 F: 1.15 | 1H NMR: (500 MHz, DMSO-$d_6$) δ ppm 12.49 (s, 1H), 8.52 (s, 1H), 8.33 (br d, J = 7.5 Hz, 1H), 8.29-8.21 (m, 2H), 8.17 (br d, J = 9.8 Hz, 1H), 8.03 (br s, 1H), 7.96-7.90 (m, 1H), 7.90-7.86 (m, 1H), 7.86-7.80 (m, 1H), 7.58 (br d, J = 9.8 Hz, 1H), 4.45-4.31 (m, 1H), 3.97-3.87 (m, 2H), 3.84 (s, 2H), 2.45-2.32 (m, 4H), 2.29-2.18 (m, 2H), 2.04 (br t, J = 10.0 Hz, 1H), 1.19 (s, 6H) |
| 111 | [structure: 7-cyano-6-hydroxy-pyrazolo[1,5-a]pyridine-3-carbonyl] | 7-cyano-6-hydroxy-N-((aR)-6-(4-oxo-3,4-dihydrophthalazin-1-yl)spiro[3.3]heptan-2-yl)pyrazolo[1,5-a]pyridine-3-carboxamide | 441 | E: 1.31 F: 0.97 | 1H NMR: (500 MHz, DMSO-$d_6$) δ ppm 12.49 (br s, 1H), 8.29-8.23 (m, 2H), 8.22 (br d, J = 6.8 Hz, 1H), 7.97 (br d, J = 9.5 Hz, 1H), 7.95-7.87 (m, 2H), 7.84 (br d, J = 7.4 Hz, 1H), 6.88 (br d, J = 9.3 Hz, 1H), 4.34 (br d, J = 7.2 Hz, 1H), 3.90 (br t, J = 8.3 Hz, 1H), 2.44-2.30 (m, 4H), 2.21 (br d, J = 8.8 Hz, 2H), 2.03 (br t, J = 9.7 Hz, 1H) |
| 112 | [structure: 6-(2-hydroxy-2-methylpropoxy)-7-methyl-pyrazolo[1,5-a]pyridine-3-carbonyl] | 6-(2-hydroxy-2-methylpropoxy)-7-methyl-N-((aR)-6-(4-oxo-3,4-dihydrophthalazin-1-yl)spiro[3.3]heptan-2-yl)pyrazolo[1,5-a]pyridine-3-carboxamide | 501.9 | E: 1.52 F: 1.57 | 1H NMR: (500 MHz, DMSO-$d_6$) δ ppm 12.47 (s, 1H), 8.55 (s, 1H), 8.26 (br d, J = 7.6 Hz, 2H), 8.07 (d, J = 9.5 Hz, 1H), 7.95-7.89 (m, 1H), 7.89-7.86 (m, 1H), 7.86-7.80 (m, 1H), 7.51 (d, J = 9.8 Hz, 1H), 4.45-4.32 (m, 1H), 3.91 (quin, J = 8.4 Hz, 1H), 3.80 (s, 2H), 2.65 (s, 3H), 2.63-2.56 (m, 2H), 2.44-2.33 (m, 3H), 2.27-2.17 (m, 2H), 2.09-2.00 (m, 1H), 1.24 (s, 6H) |
| 113 | [structure: 6-(2-hydroxy-2-methylpropoxy)-7-(methoxymethyl)-pyrazolo[1,5-a]pyridine-3-carbonyl] | 6-(2-hydroxy-2-methylpropoxy)-7-(methoxymethyl)-N-((aR)-6-(4-oxo-3,4-dihydrophthalazin-1-yl)spiro[3.3]heptan-2- | 532.1 | E: 1.47 F: 1.52 | 1H NMR: (500 MHz, DMSO-$d_6$) δ ppm 12.47 (s, 1H), 8.53 (s, 1H), 8.30 (br d, J = 7.6 Hz, 1H), 8.25 (d, J = 7.9 Hz, 1H), 8.19 (d, J = 9.8 Hz, 1H), 7.95-7.90 (m, 1H), 7.89-7.86 (m, 1H), 7.86-7.80 (m, 1H), 7.56 (d, J = 9.8 Hz, 1H), 4.96 (s, 2H), 4.43-4.32 (m, 1H), 3.95-3.87 (m, 1H), |

TABLE 6-continued

| Ex. | R | Name | LCMS (M + H)+ | HPLC Method, RT (min.) | 1H NMR |
|---|---|---|---|---|---|
| | | yl)pyrazolo[1,5-a]pyridine-3-carboxamide | | | 3.85 (s, 2H), 2.63 (br t, J = 11.6 Hz, 1H), 2.57 (br s, 1H), 2.54 (s, 3H), 2.45-2.33 (m, 3H), 2.29-2.18 (m, 2H), 2.05 (br t, J = 10.1 Hz, 1H), 1.24 (s, 6H) |
| 114 | | 5-methyl-N-((aR)-6-(4-oxo-3,4-dihydrophthalazin-1-yl)spiro[3.3]heptan-2-yl)-1-phenyl-1H-1,2,3-triazole-4-carboxamide | 404.9 | E: 1.70 F: 1.70 | 1H NMR: (500 MHz, DMSO-d6) δ ppm 12.46 (s, 1H), 8.73 (d, J = 7.9 Hz, 1H), 8.25 (d, J = 7.9 Hz, 1H), 7.94-7.89 (m, 1H), 7.88-7.85 (m, 1H), 7.85-7.79 (m, 1H), 7.68-7.57 (m, 5H), 4.37 (sxt, J = 8.2 Hz, 1H), 3.89 (quin, J = 8.5 Hz, 1H), 2.63-2.52 (m, 2H), 2.49 (br s, 3H), 2.44-2.29 (m, 4H), 2.24-2.10 (m, 2H) |
| 115 | | 1-(4-methoxyphenyl)-5-methyl-N-((aR)-6-(4-oxo-3,4-dihydrophthalazin-1-yl)spiro[3.3]heptan-2-yl)-1H-1,2,3-triazole-4-carboxamide | 471 | E: 1.73 F: 1.72 | 1H NMR: (500 MHz, DMSO-d6) δ ppm 12.46 (s, 1H), 8.70 (br d, J = 7.9 Hz, 1H), 8.25 (br d, J = 7.6 Hz, 1H), 7.97-7.90 (m, 1H), 7.90-7.86 (m, 1H), 7.86-7.77 (m, 1H), 7.52 (br d, J = 8.9 Hz, 2H), 7.15 (br d, J = 8.9 Hz, 2H), 4.43-4.30 (m, 1H), 3.95-3.87 (m, 1H), 3.85 (s, 3H), 2.64-2.55 (m, 2H), 2.44-2.29 (m, 5H), 2.25-2.10 (m, 2H) |
| 116 | | 1-(3-methoxyphenyl)-N-((aR)-6-(4-oxo-3,4-dihydrophthalazin-1-yl)spiro[3.3]heptan-2-yl)-1H-1,2,3-triazole-4-carboxamide | 456.9 | E: 1.71 F: 1.70 | 1H NMR: (500 MHz, DMSO-d6) δ ppm 12.47 (s, 1H), 9.29 (s, 1H), 8.83 (d, J = 7.9 Hz, 1H), 8.25 (d, J = 7.9 Hz, 1H), 7.95-7.90 (m, 1H), 7.89-7.86 (m, 1H), 7.86-7.79 (m, 1H), 7.60-7.44 (m, 3H), 7.08 (br d, J = 7.9 Hz, 1H), 4.46-4.34 (m, 1H), 3.89 (t, J = 8.5 Hz, 1H), 3.86 (s, 3H), 2.65-2.53 (m, 2H), 2.45-2.29 (m, 4H), 2.25-2.19 (m, 1H), 2.18-2.11 (m, 1H) |
| 117 | | 1-(2-methoxyphenyl)-5-methyl-N-((aR)-6-(4-oxo-3,4-dihydrophthalazin-1-yl)spiro[3.3]heptan-2-yl)-1H-1,2,3-triazole-4-carboxamide | 471 | E: 1.71 F: 1.71 | 1H NMR: (500 MHz, DMSO-d6) δ ppm 12.47 (s, 1H), 8.70 (br d, J = 7.9 Hz, 1H), 8.25 (d, J = 7.6 Hz, 1H), 7.96-7.89 (m, 1H), 7.89-7.85 (m, 1H), 7.85-7.79 (m, 1H), 7.63 (br t, J = 7.9 Hz, 1H), 7.45 (d, J = 6.4 Hz, 1H), 7.33 (d, J = 8.5 Hz, 1H), 7.17 (t, J = 7.5 Hz, 1H), 4.44-4.31 (m, 1H), 3.89 (quin, J = 8.4 Hz, 1H), 3.79 (s, 3H), 2.63-2.52 (m, 2H), 2.44-2.32 (m, 4H), 2.30 (s, 3H), 2.25-2.11 (m, 2H) |
| 118 | | 5-(4-fluorophenyl)-N-((aR)-6-(4-oxo-3,4-dihydrophthalazin-1-yl)spiro[3.3]heptan-2-yl)-1,2,4-oxadiazole-3-carboxamide | 445.9 | E: 1.74 F: 1.74 | 1H NMR: (500 MHz, DMSO-d6) δ ppm 12.47 (s, 1H), 9.28 (br d, J = 7.6 Hz, 1H), 8.29-8.20 (m, 3H), 7.96-7.89 (m, 1H), 7.89-7.86 (m, 1H), 7.85-7.80 (m, 1H), 7.52 (br t, J = 8.9 Hz, 2H), 4.40-4.30 (m, 1H), 3.90 (quin, J = 8.4 Hz, 1H), 2.66-2.56 (m, 2H), 2.44-2.30 (m, 4H), 2.27-2.20 (m, 1H), 2.19-2.12 (m, 1H) |
| 119[1] | | N-((aR)-6-(4-oxo-3,4-dihydrophthalazin-1-yl)spiro[3.3]heptan-2-yl)-6-(3,3,3-trifluoro-2-hydroxypropoxy)pyrazolo[1,5-a]pyridine-3-carboxamide | 528.1 | E: 1.54 F: 1.60 | 1H NMR: (500 MHz, DMSO-d6) δ ppm 12.47 (s, 1H), 8.57 (s, 1H), 8.47 (s, 1H), 8.32-8.22 (m, 2H), 8.10 (d, J = 9.5 Hz, 1H), 7.95-7.90 (m, 1H), 7.90-7.86 (m, 1H), 7.86-7.79 (m, 1H), 7.27 (br d, J = 9.5 Hz, 1H), 4.44 (br d, J = 4.0 Hz, 1H), 4.40-4.31 (m, 1H), 4.28 (dd, J = 10.4, 3.7 Hz, 1H), 4.16 (dd, J = 10.7, 6.4 Hz, 1H), 3.91 (br t, J = 8.4 Hz, 1H), 2.68-2.60 (m, 1H), |

TABLE 6-continued

| Ex. | R | Name | LCMS (M + H)+ | HPLC Method, RT (min.) | 1H NMR |
|---|---|---|---|---|---|
| | | | | | 2.60-2.54 (m, 1H), 2.45-2.31 (m, 3H), 2.29-2.17 (m, 2H), 2.11-1.99 (m, 1H) |
| 120[1] | (structure) | N-((aR)-6-(4-oxo-3,4-dihydrophthalazin-1-yl)spiro[3.3]heptan-2-yl)-6-(3,3,3-trifluoro-2-hydroxypropoxy)pyrazolo[1,5-a]pyridine-3-carboxamide | 528.1 | E: 1.56 F: 1.60 | 1H NMR: (500 MHz, DMSO-$d_6$) δ ppm 12.47 (s, 1H), 8.57 (s, 1H), 8.47 (s, 1H), 8.32-8.22 (m, 2H), 8.10 (d, J = 9.5 Hz, 1H), 7.95-7.90 (m, 1H), 7.90-7.86 (m, 1H), 7.86-7.79 (m, 1H), 7.27 (br d, J = 9.5 Hz, 1H), 4.44 (br d, J = 4.0 Hz, 1H), 4.40-4.31 (m, 1H), 4.28 (dd, J = 10.4, 3.7 Hz, 1H), 4.16 (dd, J = 10.7, 6.4 Hz, 1H), 3.91 (br t, J = 8.4 Hz, 1H), 2.68-2.60 (m, 1H), 2.60-2.54 (m, 1H), 2.45-2.31 (m, 3H), 2.29-2.17 (m, 2H), 2.11-1.99 (m, 1H) |
| 121[2] | (structure) | N-((aR)-6-(4-oxo-3,4-dihydrophthalazin-1-yl)spiro[3.3]heptan-2-yl)-6-((tetrahydrofuran-3-yl)oxy)pyrazolo[1,5-a]pyridine-3-carboxamide | 486.1 | E: 1.48 F: 1.52 | 1H NMR: (500 MHz, DMSO-$d_6$) δ ppm 12.47 (s, 1H), 8.46 (s, 2H), 8.25 (br d, J = 7.6 Hz, 2H), 8.08 (br d, J = 9.5 Hz, 1H), 7.96-7.90 (m, 1H), 7.90-7.86 (m, 2H), 7.86-7.79 (m, 1H), 7.24 (br d, J = 9.5 Hz, 1H), 5.09 (br s, 1H), 4.43-4.31 (m, 1H), 3.96-3.81 (m, 4H), 3.80-3.70 (m, 1H), 2.45-2.32 (m, 4H), 2.30-2.16 (m, 4H) |
| 122[2] | (structure) | N-((aR)-6-(4-oxo-3,4-dihydrophthalazin-1-yl)spiro[3.3]heptan-2-yl)-6-((tetrahydrofuran-3-yl)oxy)pyrazolo[1,5-a]pyridine-3-carboxamide | 486.1 | E: 1.48 F: 1.54 | 1H NMR: (500 MHz, DMSO-$d_6$) δ ppm 12.49 (br s, 1H), 8.47 (br s, 2H), 8.27 (br d, J = 7.0 Hz, 2H), 8.10 (br d, J = 9.5 Hz, 1H), 7.99-7.75 (m, 3H), 7.26 (br d, J = 9.8 Hz, 1H), 5.11 (br s, 1H), 4.38 (br d, J = 7.9 Hz, 1H), 3.98-3.82 (m, 4H), 3.78 (br d, J = 4.6 Hz, 1H), 2.46-2.33 (m, 4H), 2.32-2.15 (m, 4H), 2.12-1.97 (m, 2H) |

[1]Example 119 (peak 1; RT 19.06 min) and Example 120 (peak 2; RT 26.17 min) were obtained via chiral separation of Example 107 under the following conditions: column: Chiralpak ID, 21 × 250 mm, 5 μ; Mobile Phase: 45% MeOH/55% CO₂; flow conditions: 45 mL/min, 100 Bar, 40° C.; detector wavelength: 220 nm; injection details: 0.5 mL injections.
[2]Example 121 (peak 1; RT 27.80 min) and Example 122 (peak 2; RT 32.73 min) were obtained via chiral separation of Example 105 under the following conditions: column: Chiralpak IC, 21 × 250 mm, 5 μ; Mobile Phase: 50% MeOH/50% CO₂; flow conditions: 55 mL/min, 150 Bar, 40° C.; detector wavelength: 220 nm; injection details: 0.5 mL injections.

Example 123: 7-methyl-N-((aR)-6-(4-oxo-3,4-dihydrophthalazin-1-yl)spiro[3.3]heptan-2-yl)pyrazolo[1,5-a]pyridine-3-carboxamide

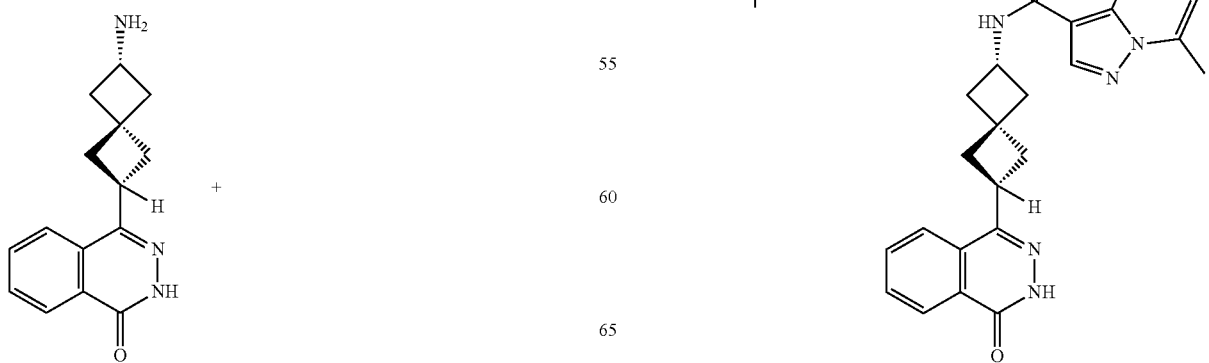

Intermediate 2, HCl (10 mg, 0.034 mmol) was suspended in anhydrous PhMe (1 mL), then trimethylaluminum (2 M in PhMe) (0.051 mL, 0.103 mmol) was added dropwise (CAUTION: methane gas evolution occurs). After stirring for 5 min at rt (clear solution obtained), ethyl 7-methylpyrazolo[1,5-a]pyridine-3-carboxylate (9.10 mg, 0.045 mmol) was added, and the reaction mixture was stirred at 120° C. for 30 min under microwave irradiation. The reaction mixture was cooled to rt, and carefully quenched with TFA (CAUTION: dropwise addition). The reaction mixture was diluted with MeOH, then solvent was removed under reduced pressure, the residue was diluted with DMF, filtered, and purified by preparative HPLC to afford Example 123 (6.8 mg, 48% yield). MS(ESI) m/z: 414.1 (M+H)$^+$; $^1$H NMR (500 MHz, DMSO-d$_6$) δ ppm 12.49 (s, 1H), 8.60 (s, 1H), 8.33 (br d, J=7.5 Hz, 1H), 8.25 (br d, J=7.9 Hz, 1H), 8.10 (br d, J=8.8 Hz, 1H), 7.95-7.89 (m, 1H), 7.89-7.86 (m, 1H), 7.85-7.80 (m, 1H), 7.43-7.35 (m, 1H), 6.96 (br d, J=6.8 Hz, 1H), 4.42-4.32 (m, 1H), 3.90 (br t, J=8.3 Hz, 1H), 2.69 (s, 3H), 2.66-2.59 (m, 1H), 2.44-2.32 (m, 3H), 2.29-2.17 (m, 2H), 2.04 (br t, J=9.9 Hz, 1H). HPLC RT=E: 1.39; F: 1.31.

The following Examples in Table 7 were prepared by using a similar procedure as shown in Example 123 by reacting Intermediate 2 with the appropriate esters.

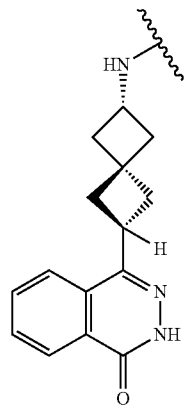

TABLE 7

| Ex. | R | Name | LCMS (M + H)+ | HPLC Method, RT (min.) | 1H NMR |
|---|---|---|---|---|---|
| 124 | 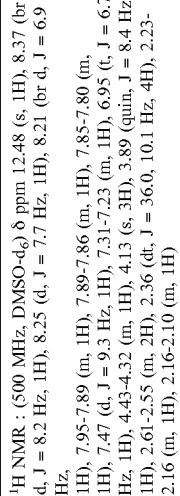 | 3-methoxy-N-((αR)-6-(4-oxo-3,4-dihydrophthalazin-1-yl)spiro[3.3]heptan-2-yl)imidazo[1,2-α]pyridine-2-carboxamide | 430.2 | E: 1.01 F: 1.38 | 1H NMR : (500 MHz, DMSO-d6) δ ppm 12.48 (s, 1H), 8.37 (br d, J = 8.2 Hz, 1H), 8.25 (d, J = 7.7 Hz, 1H), 8.21 (br d, J = 6.9 Hz, 1H), 7.95-7.89 (m, 1H), 7.89-7.86 (m, 1H), 7.85-7.80 (m, 1H), 7.47 (d, J = 9.3 Hz, 1H), 7.31-7.23 (m, 1H), 6.95 (t, J = 6.7 Hz, 1H), 4.43-4.32 (m, 1H), 4.13 (s, 3H), 3.89 (quin, J = 8.4 Hz, 1H), 2.61-2.55 (m, 2H), 2.36 (dt, J = 36.0, 10.1 Hz, 4H), 2.23-2.16 (m, 1H), 2.16-2.10 (m, 1H) |
| 125 | 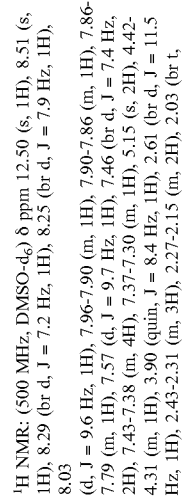 | 6-(benzyloxy)-7-cyclopropyl-N-((αR)-6-(4-oxo-3,4-dihydrophthalazin-1-yl)spiro[3.3]heptan-2-yl)pyrazolo[1,5-α]pyridine-3-carboxamide | 546.4 | E: 2.01 F: 2.07 | 1H NMR: (500 MHz, DMSO-d6) δ ppm 12.50 (s, 1H), 8.51 (s, 1H), 8.29 (br d, J = 7.2 Hz, 1H), 8.25 (br d, J = 7.9 Hz, 1H), 8.03 (d, J = 9.6 Hz, 1H), 7.96-7.90 (m, 1H), 7.90-7.86 (m, 1H), 7.86-7.79 (m, 1H), 7.57 (d, J = 9.7 Hz, 1H), 7.46 (br d, J = 7.4 Hz, 2H), 7.43-7.38 (m, 4H), 7.37-7.30 (m, 1H), 5.15 (s, 2H), 4.42-4.31 (m, 1H), 3.90 (quin, J = 8.4 Hz, 1H), 2.61 (br d, J = 11.5 Hz, 1H), 2.43-2.31 (m, 3H), 2.27-2.15 (m, 2H), 2.03 (br t, J = 10.0 Hz, 1H), 1.37 (br d, J = 3.6 Hz, 2H), 1.02 (br d, J = 6.7 Hz, 2H) |
| 126 | 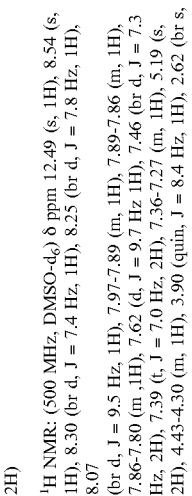 | 6-(benzyloxy)-7-methyl-N-((αR)-6-(4-oxo-3,4-dihydrophthalazin-1-yl)spiro[3.3]heptan-2-yl)pyrazolo[1,5-α]pyridine-3-carboxamide | 520.2 | E: 1.87 F: 1.90 | 1H NMR: (500 MHz, DMSO-d6) δ ppm 12.49 (s, 1H), 8.54 (s, 1H), 8.30 (br d, J = 7.4 Hz, 1H), 8.25 (br d, J = 7.8 Hz, 1H), 8.07 (br d, J = 9.5 Hz, 1H), 7.97-7.89 (m, 1H), 7.89-7.86 (m, 1H), 7.86-7.80 (m, 1H), 7.62 (d, J = 9.7 Hz, 1H), 7.46 (br d, J = 7.3 Hz, 2H), 7.39 (t, J = 7.0 Hz, 2H), 7.36-7.27 (m, 1H), 5.19 (s, 2H), 4.43-4.30 (m, 1H), 3.90 (quin, J = 8.4 Hz, 1H), 2.62 (br s, 1H), 2.58 (s, 3H), 2.43-2.32 (m, 3H), 2.25-2.14 (m, 2H), 2.04 (br t, J = 10.0 Hz, 1H) |
| 127 | 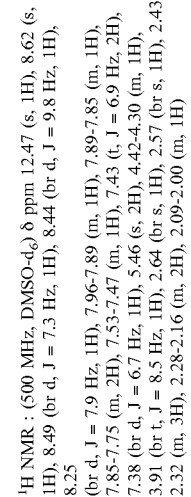 | 6-(benzyloxy)-7-cyano-N-((αR)-6-(4-oxo-3,4-dihydrophthalazin-1-yl)spiro[3.3]heptan-2-yl)pyrazolo[1,5-α]pyridine-3-carboxamide | 531.1 | E: 1.90 F: 1.95 | 1H NMR: (500 MHz, DMSO-d6) δ ppm 12.47 (s, 1H), 8.62 (s, 1H), 8.49 (br d, J = 7.3 Hz, 1H), 8.44 (br d, J = 9.8 Hz, 1H), 8.25 (br d, J = 7.9 Hz, 1H), 7.96-7.89 (m, 1H), 7.89-7.85 (m, 1H), 7.85-7.75 (m, 2H), 7.53-7.47 (m, 1H), 7.43 (t, J = 6.9 Hz, 2H), 7.38 (br d, J = 6.7 Hz, 1H), 5.46 (s, 2H), 4.42-4.30 (m, 1H), 3.91 (br t, J = 8.5 Hz, 1H), 2.64 (s, 1H), 2.57 (br s, 1H), 2.43-2.32 (m, 3H), 2.28-2.16 (m, 2H), 2.09-2.00 (m, 1H) |

TABLE 7-continued

| Ex. | R | Name | LCMS (M + H)+ | HPLC Method, RT (min.) | 1H NMR |
|---|---|---|---|---|---|
| 128 | (structure: 7-cyclopropyl-6-hydroxy pyrazolopyridine with OH) | 7-cyclopropyl-6-hydroxy-N-(((αR)-6-(4-oxo-3,4-dihydrophthalazin-1-yl)spiro[3.3]heptan-2-yl)pyrazolo[1,5-α]pyridine-3-carboxamide | 456.3 | E: 1.40 F: 1.36 | 1H NMR: (500 MHz, DMSO-d6) δ ppm 12.49 (s, 1H), 8.42 (s, 1H), 8.25 (d, J = 7.8 Hz, 1H), 8.20 (br d, J = 7.7 Hz, 1H), 7.94-7.89 (m, 2H), 7.89-7.86 (m, 1H), 7.85-7.79 (m, 1H), 7.16 (d, J = 9.5 Hz, 1H), 4.41-4.30 (m, 1H), 3.95-3.84 (m, 1H), 2.61 (br t, J = 11.6 Hz, 1H), 2.47-2.40 (m, 2H), 2.40-2.32 (m, 3H), 2.27-2.15 (m, 2H), 2.03 (br t, J = 10.0 Hz, 1H), 1.40-1.33 (m, 2H), 1.04-0.96 (m, 2H) |
| 129 | (structure: 2-methoxyphenyl triazole) | 1-(2-methoxyphenyl)-N-(((αR)-6-(4-oxo-3,4-dihydrophthalazin-1-yl)spiro[3.3]heptan-2-yl)-1H-1,2,3-triazole-4-carboxamide | 457.3 | E: 1.62 F: 1.64 | 1H NMR: (500 MHz, DMSO-d6) δ ppm 12.49 (s, 1H), 8.87-8.77 (m, 2H), 8.25 (d, J = 7.8 Hz, 1H), 7.97-7.90 (m, 1H), 7.90-7.86 (m, 1H), 7.86-7.80 (m, 1H), 7.67-7.62 (m, 1H), 7.56 (t, J = 7.9 Hz, 1H), 7.33 (d, J = 8.3 Hz, 1H), 7.16 (t, J = 7.6 Hz, 1H), 4.37 (sxt, J = 8.1 Hz, 1H), 3.89 (t, J = 8.5 Hz, 1H), 3.85 (s, 3H), 2.65-2.55 (m, 2H), 2.43-2.29 (m, 4H), 2.25-2.17 (m, 1H), 2.17-2.08 (m, 1H) |
| 130 | (structure: benzyloxy dimethylaminomethyl pyrazolopyridine) | 6-(benzyloxy)-7-(((dimethylamino)methyl)-N-(((αR)-6-(4-oxo-3,4-dihydrophthalazin-1-yl)spiro[3.3]heptan-2-yl)pyrazolo[1,5-α]pyridine-3-carboxamide | 563.1 | E: 1.38 F: 1.48 | 1H NMR: (500 MHz, DMSO-d6) δ ppm 12.50 (s, 1H), 8.44 (br d, J = 7.6 Hz, 1H), 8.32 (d, J = 9.8 Hz, 1H), 8.25 (d, J = 7.9 Hz, 1H), 7.98-7.91 (m, 1H), 7.90-7.82 (m, 2H), 7.81 (d, J = 9.9 Hz, 1H), 7.53 (d, J = 7.3 Hz, 2H), 7.45-7.39 (m, 2H), 7.38-7.33 (m, 1H), 5.35 (s, 2H), 4.81 (s, 2H), 4.44-4.31 (m, 1H), 3.91 (quin, J = 8.5 Hz, 1H), 2.85 (s, 6H), 2.68-2.62 (m, 1H), 2.44-2.33 (m, 3H), 2.29-2.17 (m, 2H), 2.05 (br t, J = 10.1 Hz, 1H) |
| 131 | (structure: 1,3-difluoropropan-2-yloxy pyrazolopyridine) | 6-((1,3-difluoropropan-2-yl)oxy)-N-(((αR)-6-(4-oxo-3,4-dihydrophthalazin-1-yl)spiro[3.3]heptan-2-yl)pyrazolo[1,5-α]pyridine-3-carboxamide | 494 | E: 1.64 F: 1.65 | 1H NMR: (500 MHz, DMSO-d6) δ ppm 12.47 (s, 1H), 8.67 (s, 1H), 8.48 (s, 1H), 8.26 (br t, J = 8.9 Hz, 2H), 8.11 (d, J = 9.8 Hz, 1H), 7.95-7.89 (m, 1H), 7.89-7.86 (m, 1H), 7.85-7.80 (m, 1H), 7.34 (dd, J = 9.8, 1.5 Hz, 1H), 4.98 (br t, J = 20.9 Hz, 1H), 4.85 (br d, J = 9.8 Hz, 1H), 4.79-4.70 (m, 2H), 4.65 (dd, J = 10.4, 5.2 Hz, 1H), 4.42-4.31 (m, 1H), 3.90 (quin, J = 8.4 Hz, 1H), 2.67-2.58 (m, 1H), 2.45-2.32 (m, 3H), 2.29-2.15 (m, 2H), 2.04 (br t, J = 10.1 Hz, 1H) |
| 132 | (structure: 1,1-dioxidotetrahydro-2H-thiopyran-4-yloxy pyrazolopyridine) | 6-((1,1-dioxidotetrahydro-2H-thiopyran-4-yl)oxy)-N-(((αR)-6-(4-oxo-3,4-dihydrophthalazin-1-yl)spiro[3.3]heptan-2-yl)pyrazolo[1,5-α]pyridine-3-carboxamide | 548.3 | E: 1.47 F: 1.48 | 1H NMR: (500 MHz, DMSO-d6) δ ppm 12.47 (s, 1H), 8.69 (s, 1H), 8.47 (s, 1H), 8.26 (t, J = 8.1 Hz, 2H), 8.11 (d, J = 9.8 Hz, 1H), 7.95-7.89 (m, 1H), 7.88-7.85 (m, 1H), 7.85-7.80 (m, 1H), 7.38 (br d, J = 9.5 Hz, 1H), 4.72 (br t, J = 4.4 Hz, 1H), 4.42-4.30 (m, 1H), 3.95-3.84 (m, 1H), 3.31-3.20 (m, 2H), 3.19-3.09 (m, 2H), 2.67-2.60 (m, 1H), 2.44-2.31 (m, 3H), 2.28-2.15 (m, 6H), 2.04 (br t, J = 10.1 Hz, 1H) |

TABLE 7-continued

| Ex. | Name | R | LCMS (M + H)+ | HPLC Method: RT (min.) | 1H NMR |
|---|---|---|---|---|---|
| 133 | N-((αR)-6-(4-oxo-3,4-dihydrophthalazin-1-yl)spiro[3.3]heptan-2-yl)-6-(3,3,3-trifluoropropoxy)pyrazolo[1,5-a]pyridine-3-carboxamide | | 512.3 | E: 1.18 F: 1.81 | 1H NMR: (500 MHz, DMSO-d6) δ ppm 12.47 (s, 1H), 8.46 (s, 1H), 8.53 (s, 1H), 8.28 (br d, J = 7.6 Hz, 1H), 8.25 (br d, J = 8.2 Hz, 1H), 8.09 (d, J = 9.8 Hz, 1H), 7.94-7.89 (m, 1H), 7.87 (d, J = 8.3 Hz, 1H), 7.85-7.80 (m, 1H), 7.24 (br d, J = 9.5 Hz, 1H), 4.40-4.32 (m, 1H), 4.28 (t, J = 5.8 Hz, 2H), 3.90 (quin, J = 8.4 Hz, 1H), 2.88-2.77 (m, 2H), 2.62 (br t, J = 11.7 Hz, 1H), 2.43-2.32 (m, 3H), 2.27-2.17 (m, 2H), 2.08-2.00 (m, 1H) |
| 134 | 6-((4,4-difluorocyclohexyl)oxy)-N-((αR)-6-(4-oxo-3,4-dihydrophthalazin-1-yl)spiro[3.3]heptan-2-yl)pyrazolo[1,5-a]pyridine-3-carboxamide | | 534.1 | E: 1.88 F: 1.92 | 1H NMR: (500 MHz, DMSO-d6) δ ppm 12.47 (s, 1H), 8.61 (s, 1H), 8.46 (s, 1H), 8.25 (br d, J = 7.3 Hz, 2H), 8.09 (br d, J = 9.8 Hz, 1H), 7.96-7.89 (m, 1H), 7.85-7.80 (m, 1H), 7.31 (br d, J = 9.5 Hz, 1H), 4.62 (br s, 1H), 4.42-4.29 (m, 1H), 3.90 (br t, J = 8.4 Hz, 1H), 2.67-2.59 (m, 1H), 2.44-2.31 (m, 3H), 2.29-2.16 (m, 2H), 2.13-1.99 (m, 4H), 1.99-1.90 (m, 4H), 1.85 (br d, J = 6.4 Hz, 2H) |
| 135 | N-((αR)-6-(4-oxo-3,4-dihydrophthalazin-1-yl)spiro[3.3]heptan-2-yl)-6-((tetrahydro-2H-pyran-4-yl)oxy)pyrazolo[1,5-a]pyridine-3-carboxamide | | 500.1 | E: 1.56 F: 1.62 | 1H NMR: (500 MHz, DMSO-d6) δ ppm 12.47 (s, 1H), 8.57 (s, 1H), 8.45 (s, 1H), 8.25 (br d, J = 7.9 Hz, 2H), 8.08 (d, J = 9.8 Hz, 1H), 7.97-7.89 (m, 1H), 7.89-7.85 (m, 1H), 7.85-7.80 (m, 1H), 7.28 (br d, J = 9.8 Hz, 1H), 4.65-4.56 (m, 1H), 4.41-4.30 (m, 1H), 3.95-3.82 (m ,3H), 2.56 (br s, 1H), 2.43-2.32 (m, 3H), 2.27-2.16 (m, 2H), 2.08-1.95 (m, 3H), 1.67-1.53 (m, 2H) |
| 136 | methyl 3-((3-((αR)-6-(4-oxo-3,4-dihydrophthalazin-1-yl)spiro[3.3]heptan-2-yl)carbamoyl)pyrazolo[1,5-a]pyridin-6-yl)oxy)azetidine-1-carboxylate | | 529.1 | E: 1.54 F: 1.59 | 1H NMR: (500 MHz, DMSOd6) δ ppm 12.47 (s, 1H), 8.47 (s, 1H), 8.32 (s, 1H), 8.26 (br t, J = 7.6 Hz, 2H), 8.11 (d, J = 9.8 Hz, 1H), 7.97-7.89 (m, 1H), 7.89-7.86 (m, 1H), 7.86-7.80 (m, 1H), 7.30-7.23 (m, 1H), 5.09 (br s, 1H), 4.40 (br d, J = 7.9 Hz, 2H), 4.38-4.31 (m, 1H), 3.96-3.84 (m ,3H), 3.58 (s, 3H), 2.66-2.59 (m, 1H), 2.59-2.55 (m, 1H), 2.45-2.32 (m, 3H), 2.29-2.16 (m, 2H), 2.04 (br t, J = 10.1 Hz, 1H) |
| 137 | 6-hydroxy-N-((αR)-6-(4-oxo-3,4-dihydrophthalazin-1-yl)spiro[3.3]heptan-2-yl)pyrazolo[1,5-a]pyridine-3-carboxamide | | 416.2 | E: 1.22 F: 1.24 | 1H NMR: (500 Mhz, DMSO-d6) δ ppm 12.49 (s, 1H), 8.39 (s, 1H), 8.25 (d, J = 7.9 Hz, 1H), 8.21 (br d, J = 9.5 Hz, 1H), 8.14 (d, J = 1.3 Hz, 1H), 8.04 (d, J = 9.5 Hz, 1H), 7.95-7.90 (m, 1H), 7.89-7.86 (m, 1H), 7.86-7.81 (m, 1H), 7.17 (dd, J = 9.6, 1.9 Hz, 1H), 4.40-4.32 (m, 1H), 3.90 (quin, J = 8.4 Hz, 1H), 2.62 (br t, J = 11.6 Hz, 1H), 2.58-2.55 (m, 1H), 2.44-2.32 (m, 3H), 2.26-2.16 (m, 2H), 2.03 (t, J = 10.0 Hz, 1H) |

TABLE 7-continued

| Ex. | R | Name | LCMS (M + H)+ | HPLC Method, RT (min.) | 1H NMR |
|---|---|---|---|---|---|
| 138 | (cyclobutyl difluoro ether pyrazolopyridine structure) | 6-(3,3-difluorocyclobutoxy)-N-((αR)-6-(4-oxo-3,4-dihydrophthalazin-1-yl)spiro[3.3]heptan-2-yl)pyrazolo[1,5-α]pyridine-3-carboxamide | 506 | E: 1.66  F: 1.69 | 1H NMR: (500 MHz, CD3OD) δ ppm 12.49 (s, 1H), 8.47 (s, 1H), 8.40 (s, 1H), 8.29 (br d, J = 7.6 Hz, 1H), 8.25 (d, J = 7.7 Hz, 1H), 8.10 (d, J = 9.6 Hz, 1H), 7.94-7.89 (m, 1H), 7.89-7.86 (m, 1H), 7.86-7.80 (m, 1H), 7.26 (dd, J = 9.6, 1.7 Hz, 1H), 4.83 (br s, 1H), 4.41-4.31 (m, 1H), 3.90 (quin, J = 8.4 Hz, 1H), 3.32-3.19 (m, 1H), 2.81-2.69 (m, 2H), 2.66-2.59 (m, 1H), 2.59-2.55 (m, 1H), 2.42-2.30 (m, 3H), 2.26-2.16 (m, 2H), 2.03 (br t, J = 10.0 Hz, 1H) |
| 139 | (trifluoroethoxyethoxy pyridine structure) | N-((αR)-6-(4-oxo-3,4-dihydrophthalazin-1-yl)spiro[3.3]heptan-2-yl)-6-(2-(2,2,2-trifluoroethoxy)ethoxy)pyrazolo[1,5-α]pyridine-3-carboxamide | 542.1 | E: 1.76  F: 1.75 | 1H NMR: (500 MHz, DMSO-d6) δ ppm 12.47 (s, 1H), 8.46 (br d, J = 9.8 Hz, 2H), 8.29-8.23 (m, 2H), 8.08 (d, J = 9.5 Hz, 1H), 7.95-7.89 (m, 1H), 7.89-7.86 (m, 1H), 7.86-7.79 (m, 1H), 7.27 (br d, J = 9.5 Hz, 1H), 4.42-4.32 (m, 1H), 4.21 (br s, 2H), 4.16 (q, J = 9.5 Hz, 2H), 3.96 (br s, 2H), 3.90 (br t, J = 8.5 Hz, 1H), 2.62 (br s, 1H), 2.44-2.31 (m, 3H), 2.27-2.16 (m, 2H), 2.04 (br t, J = 9.9 Hz, 1H) |
| 140 | (cyclopropyl thiadiazolyl methoxy pyridine structure) | 6-((5-cyclopropyl-1,3,4-thiadiazol-2-yl)methoxy)-N-((αR)-6-(4-oxo-3,4-dihydrophthalazin-1-yl)spiro[3.3]heptan-2-yl)pyrazolo[1,5-α]pyridine-3-carboxamide | 554.1 | E: 1.72  F: 1.76 | 1H NMR: (500 MHz, DMSO-d6) δ ppm 12.47 (s, 1H), 8.64 (s, 1H), 8.47 (s, 1H), 8.30 (br d, J = 7.3 Hz, 1H), 8.24 (s, 1H), 8.10 (br d, J = 9.5 Hz, 1H), 7.96-7.89 (m, 1H), 7.89-7.78 (m, 2H), 7.32 (br d, J = 9.5 Hz, 1H), 5.58 (s, 2H), 4.44-4.28 (m, 1H), 3.90 (br t, J = 8.5 Hz, 1H), 2.62 (br s, 1H), 2.45-2.31 (m, 3H), 2.27-2.14 (m, 2H), 2.09-1.97 (m, 1H), 1.22 (br d, J = 5.8 Hz, 2H), 1.03 (br s, 2H) |
| 141 | (benzyloxy trifluoromethyl pyridine structure) | 6-(benzyloxy)-N-((αR)-6-(4-oxo-3,4-dihydrophthalazin-1-yl)spiro[3.3]heptan-2-yl)-7-(trifluoromethyl)pyrazolo[1,5-α]pyridine-3-carboxamide | 574.3 | E: 2.07  F: 2.04 | 1H NMR: (500 MHz, DMSO-d6) δ ppm 12.50 (s, 1H), 8.57 (s, 1H), 8.51 (br d, J = 7.4 Hz, 1H), 8.41 (br d, J = 9.8 Hz, 1H), 8.24 (br d, J = 7.7 Hz, 1H), 7.95-7.88 (m, 1H), 7.86 (br d, J = 8.7 Hz, 1H), 7.84-7.75 (m, 1H), 7.47-7.36 (m, 4H), 7.34 (br d, J = 7.1 Hz, 1H), 5.34 (s, 2H), 4.41-4.30 (m, 1H), 3.94-3.84 (m, 1H), 2.62 (br s, 1H), 2.59-2.54 (m, 1H), 2.42-2.29 (m, 4H), 2.28-2.15 (m, 2H), 2.03 (br t, J = 9.9 Hz, 1H) |

Example 142: 6-cyclopropyl-1-(2-hydroxy-2-methylpropyl)-N-((aR)-6-(4-oxo-3,4-dihydrophthalazin-1-yl)spiro[3.3]heptan-2-yl)-1H-indazole-3-carboxamide

Example 143: 1-(2-hydroxy-2-methylpropyl)-N-((aR)-6-(4-oxo-3,4-dihydrophthalazin-1-yl)spiro[3.3]heptan-2-yl)-6-phenyl-1H-indazole-3-carboxamide

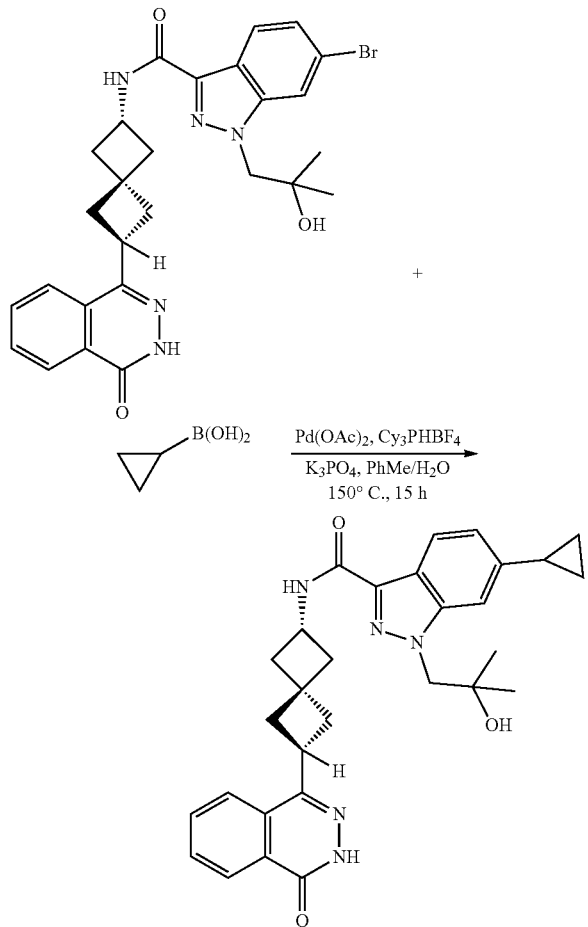

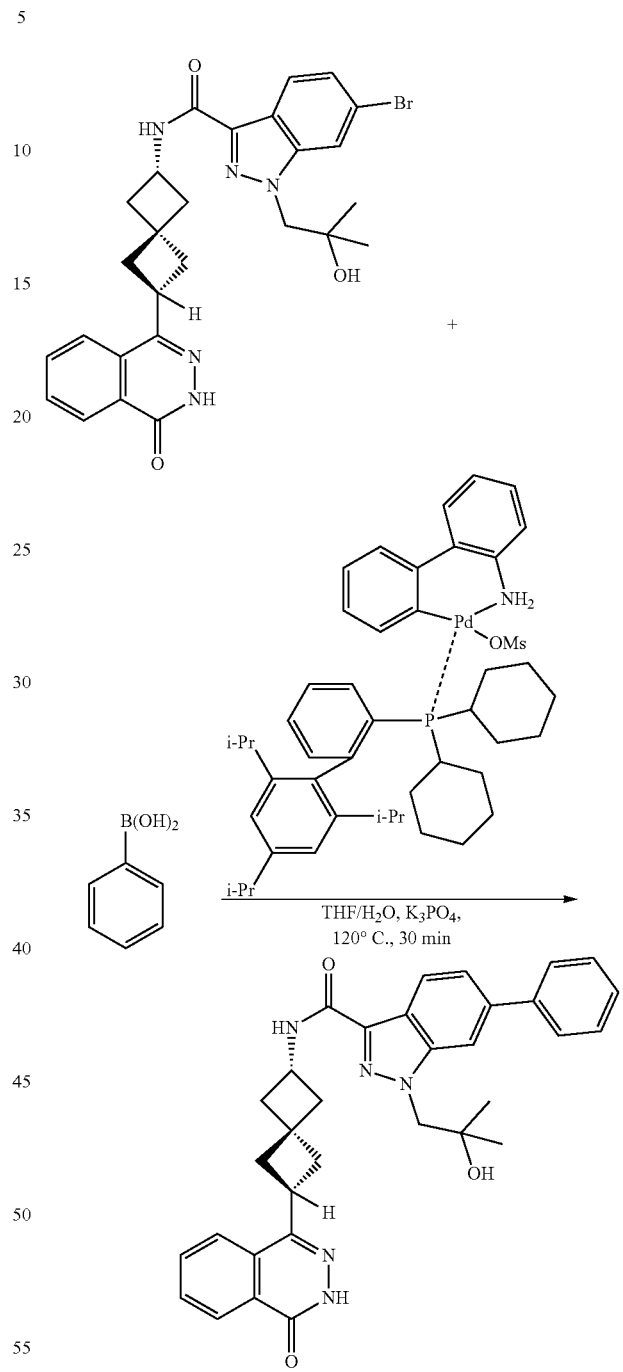

Intermediate 68 (15 mg, 0.027 mmol), cyclopropylboronic acid (9.36 mg, 0.109 mmol), palladium(II) acetate (0.6 mg, 3 μmol), tricyclohexylphosphonium tetrafluoroborate (2.0 mg, 5.5 μmol) and phosphoric acid, potassium salt (17 mg, 0.082 mmol) were placed in a pressure vial, and the mixture was degassed (3× Ar/vacuum). Then, PhMe (2.0 mL) and water (0.2 mL) were added, and the reaction mixture was degassed again. Afterwards, the vial was capped, the reaction mixture was heated to 150° C. under microwave irradiation for 15 min. Solvent was removed under reduced pressure, the residue was diluted with DMF, filtered and purified by preparative HPLC to afford Example 142 (3.1 mg, 22% yield) was obtained. MS(ESI) m/z: 512.3 (M+H)$^+$; $^1$H NMR (500 MHz, DMSO-d$_6$) δ ppm 12.49 (s, 1H), 8.38 (br d, J=8.0 Hz, 1H), 8.25 (d, J=7.8 Hz, 1H), 8.11-8.02 (m, 1H), 7.99-7.78 (m, 5H), 7.43 (s, 1H), 6.95 (d, J=8.5 Hz, 1H), 4.47-4.34 (m, 2H), 4.32 (s, 2H), 3.95-3.84 (m, 1H), 2.44-2.27 (m, 4H), 2.26-2.10 (m, 3H), 2.07-1.97 (m, 1H), 1.12 (s, 6H), 1.04-0.94 (m, 2H), 0.75 (br d, J=4.9 Hz, 2H). HPLC RT=E: 1.84; F: 1.72.

Intermediate 68 (15 mg, 0.027 mmol), phenylboronic acid (10 mg, 0.082 mmol) and Pd-XPhos G3 (1.7 mg, 2.0 μmol) were placed in a pressure vial. Then THF (1.25 mL) and phosphoric acid, potassium salt (0.5 M aq.) (0.109 mL, 0.055 mmol) were added, and the reaction mixture was degassed (3×, vacuum/Ar). The pressure vial was capped, and the reaction mixture was stirred at 120° C. for 30 min. Most of the solvent was removed under reduced pressure. Most of the solvent was removed under reduced pressure, the obtained residue was diluted with DMF (2 mL), filtered and purified by preparative HPLC to give Example 143 (6.0 mg, 39% yield) was obtained. MS(ESI) m/z: 548.40 (M+H)$^+$; $^1$H NMR (500 MHz, DMSO-d$_6$) δ ppm 12.47 (s, 1H), 8.42 (br d, J=7.9 Hz, 1H), 8.26 (d, J=7.9 Hz, 1H), 8.19 (d, J=8.5 Hz, 1H), 8.05 (s, 1H), 7.96-7.87 (m, 2H), 7.86-7.82 (m, 1H), 7.86-7.82 (m, 1H), 7.77 (d, J=7.3 Hz, 2H), 7.58-7.54 (m, 1H), 7.56 (dd, J=8.4, 0.8 Hz, 1H), 7.51 (t, J=7.8 Hz, 2H), 7.43-7.37 (m, 1H), 4.78-4.72 (m, 1H), 4.74 (s, 1H), 4.45 (s, 2H), 4.45-4.39 (m, 1H), 2.67-2.56 (m, 2H), 2.45-2.33 (m, 4H), 2.28-2.14 (m, 2H), 1.17 (s, 6H). HPLC RT=E: 1.98; F: 1.97.

The following Examples in Table 8 were prepared by using a similar procedure as shown in Example 143 by reacting Intermediate 68 with the appropriate boronic acids/boronate esters/potassium trifluoroborates.

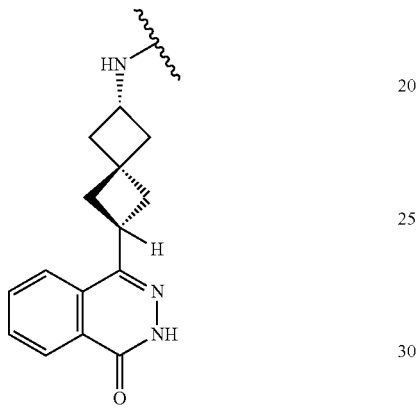

TABLE 8

| Ex. | R | Name | LCMS (M + H)+ | HPLC Method, RT (min.) | 1H NMR |
|---|---|---|---|---|---|
| 144 | 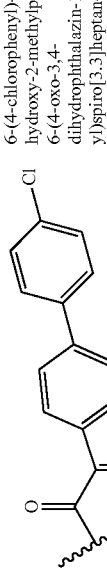 | 6-(4-chlorophenyl)-1-(2-hydroxy-2-methylpropyl)-N-((αR)-6-(4-oxo-3,4-dihydrophthalazin-1-yl)spiro[3.3]heptan-2-yl)-1H-indazole-3-carboxamide | 582.4 | E: 2.13 F: 2.12 | 1H NMR: (500 MHz, DMSO-d6) δ ppm 12.48 (s, 1H), 8.44 (br d, J = 7.9 Hz, 1H), 8.27 (d, J = 7.9 Hz, 1H), 8.20 (d, J = 8.5 Hz, 1H), 8.08 (s, 1H), 7.96-7.91 (m, 1H), 7.96-7.91 (m, 1H), 7.91-7.87 (m, 1H), 7.87-7.83 (m, 1H), 7.81 (d, J = 8.5 Hz, 2H), 7.62-7.50 (m, 2H), 4.76 (s, 1H), 4.50-4.41 (m, 3H), 3.96-3.91 (m, 1H), 2.67-2.56 (m, 2H), 2.47-2.33 (m, 4H), 2.28-2.16 (m, 2H), 1.18 (s, 6H) |
| 145 | 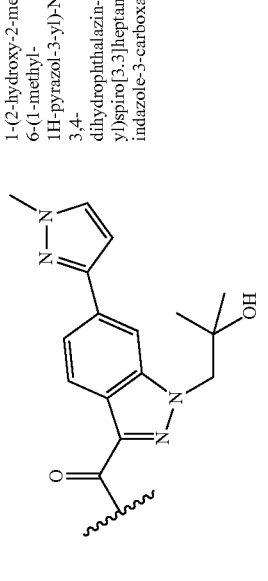 | 1-(2-hydroxy-2-methylpropyl)-6-(1-methyl-1H-pyrazol-3-yl)-N-((αR)-6-(4-oxo-3,4-dihydrophthalazin-1-yl)spiro[3.3]heptan-2-yl)-1H-indazole-3-carboxamide | 552.5 | E: 1.55 F: 1.58 | 1H NMR: (500 MHz, DMSO-d6) δ ppm 12.47 (s, 1H), 8.46 (br d, J = 7.9 Hz, 1H), 8.26 (d, J = 7.6 Hz, 1H), 8.20 (d, J = 8.5 Hz, 1H), 7.94 (s, 1H), 7.93-7.90 (m, 1H), 7.90-7.87 (m, 1H), 7.86-7.80 (m, 1H), 7.51 (d, J = 1.8 Hz, 1H), 7.42-7.30 (m, 1H), 6.47 (d, J = 1.8 Hz, 1H), 4.73 (s, 1H), 4.51-4.36 (m, 3H), 3.98-3.90 (m, 1H), 3.90 (s, 3H), 2.70-2.56 (m, 2H), 2.46-2.31 (m, 4H), 2.29-2.14 (m, 2H), 1.16 (s, 6H) |
| 146 | 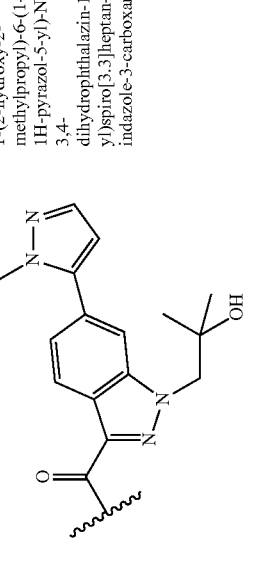 | 1-(2-hydroxy-2-methylpropyl)-6-(1-methyl-1H-pyrazol-5-yl)-N-((αR)-6-(4-oxo-3,4-dihydrophthalazin-1-yl)spiro[3.3]heptan-2-yl)-1H-indazole-3-carboxamide | 552.4 | E: 1.56 F: 1.59 | 1H NMR: (500 MHz, DMSO-d6) δ ppm 12.47 (s, 1H), 8.46 (br d, J = 7.9 Hz, 1H), 8.26 (d, J = 7.9 Hz, 1H), 8.20 (d, J = 8.2 Hz, 1H), 7.97-7.87 (m, 3H), 7.86-7.81 (m, 1H), 7.51 (d, J = 1.8 Hz, 1H), 7.40-7.34 (m, 3H), 6.47 (d, J = 1.5 Hz, 1H), 4.48-4.40 (m, 3H), 3.96-3.91 (m, 1H), 3.90 (s, 3H), 2.66-2.56 (m, 2H), 2.45-2.32 (m, 4H), 2.28-2.14 (m, 2H), 1.16 (s, 6H) |

TABLE 8-continued

| Ex. | R | Name | LCMS (M + H)+ | HPLC Method, *RT (min.) | 1H NMR |
|---|---|---|---|---|---|
| 147 | 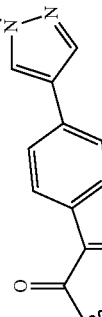 | 1-(2-hydroyx-2-methylpropyl)-6-(1-methyl-1H-pyrazol-4-yl)-N-((αR)-6-(4-oxo-3,4-dihydrophthalazin-1-yl)spiro[3.3]heptan-2-yl)-1H-indazole-3-carboxamide | 552.5 | E: 1.53 F: 1.53 | 1H NMR: (500 MHz, DMSO-d6) δ ppm 12.47 (s, 1H), 8.37 (br d, J = 7.9 Hz, 1H), 8.26 (d, J = 7.9 Hz, 1H), 8.21 (s, 1H), 8.07 (d, J = 8.5 Hz, 1H), 7.96 (s, 1H), 7.94-7.86 (m, 3H), 7.86-7.81 (m, 1H), 7.46 (d, J = 9.2 Hz, 1H), 4.47-4.39 (m, 1H), 4.38 (s, 2H), 3.94-3.90 (m, 1H), 3.89 (s, 3H), 2.67-2.54 (m, 2H), 2.46-2.31 (m, 4H), 2.27-2.13 (m, 2H), 1.17 (s, 6H) |
| 148 | 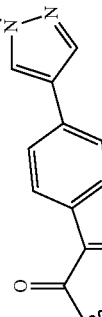 | 1-(2-hydroxy-2-methylpropyl)-N-((αR)-6-(4-oxo-3,4-dihydrophthalazin-1-yl)spiro[3.3]heptan-2-yl)-6-((E)-styryl)-1H-indazole-3-carboxamide | 574.3 | E: 2.09 F: 2.10 | 1H NMR: (500 MHz, DMSO-d6) δ ppm 8.42 (br d, J = 7.6 Hz, 1H), 8.25 (d, J = 7.6 Hz, 1H), 8.09 (d, J = 8.5 Hz, 1H), 7.96-7.90 (m, 2H), 7.89-7.81 (m, 2H), 7.63 (d, J = 7.6 Hz, 2H), 7.57 (d, J = 8.5 Hz, 1H), 7.44-7.35 (m, 4H), 7.32-7.25 (m, 1H), 4.81 (s, 1H), 4.47-4.40 (m, 1H), 4.39 (s, 2H), 2.67-2.55 (m, 2H), 2.44-2.29 (m, 4H), 2.27-2.20 (m, 1H), 2.19-2.11 (m, 1H), 1.17 (s, 6H) |
| 149 | 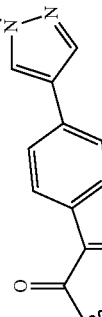 | 6-((E)-2-cyclopropylvinyl)-1-(2-hydroxy-2-methylpropyl)-N-((αR)-6-(4-oxo-3,4-dihydrophthalazin-1-yl)spiro[3.3]heptan-2-yl)-1H-indazole-3-carboxamide | 538.3 | E: 1.98 F: 1.99 | 1H NMR: (500 MHz, DMSO-d6) δ ppm 8.37 (br s, 1H), 8.25 (br s, 1H), 7.98 (br d, J = 7.3 Hz, 1H), 7.91 (br s, 1H), 7.89-7.76 (m, 2H), 7.61 (br s, 1H), 7.29 (br d, J = 6.7 Hz, 1H), 6.57 (br d, J = 15.3 Hz, 1H), 6.02-5.91 (m, 1H), 4.76 (br s, 1H), 4.40 (br s, 1H), 4.33 (br s, 2H), 3.88 (br s, 1H), 2.58 (br d, J = 9.8 Hz, 2H), 2.44-2.27 (m, 4H), 2.26-2.08 (m, 2H), 1.61 (br s, 1H), 1.13 (br s, 6H), 0.82 (br s, 2H), 0.53 (br s, 2H) |
| 150 | 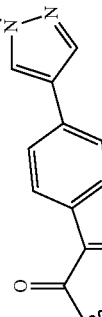 | 1-(2-hydroxy-2-methylpropyl)-6-(6-methoxypyridin-2-yl)-N-((αR)-6-(4-oxo-3,4-dihydrophthalazin-1-yl)spiro[3.3]heptan-2-yl)-1H-indazole-3-carboxamide | 579.3 | E: 1.89 F: 1.94 | 1H NMR: (500 MHz, DMSO-d6) δ ppm 12.47 (s, 1H), 8.47 (br d, J = 7.9 Hz, 1H), 8.25 (s, 1H), 8.42 (s, 1H), 8.18 (d, J = 3.7 Hz, 2H), 8.18 (d, J = 8.5 Hz, 1H), 8.03-7.97 (m, 1H), 7.95-7.90 (m, 1H), 7.89-7.77 (m, 3H), 7.67 (d, J = 7.6 Hz, 1H), 6.81 (d, J = 7.9 Hz, 1H), 4.51-4.36 (m, 3H), 3.98 (s, 3H), 3.95-3.85 (m, 1H), 2.70-2.55 (m, 2H), 2.47-2.29 (m, 4H), 2.29-2.20 (m, 1H), 2.20-2.11 (m, 1H), 1.17 (s, 6H) |

TABLE 8-continued

| Ex. | R | Name | LCMS (M + H)+ | HPLC Method, RT (min.) | 1H NMR |
|---|---|---|---|---|---|
| 151 | (structure: 6-((Z)-2-cyclopropylvinyl) indazole with 2-hydroxy-2-methylpropyl N-substituent) | 6-((Z)-2-cyclopropylvinyl)-1-(2-hydroxy-2-methylpropyl)-N-(((αR)-6-(4-oxo-3,4-dihydrophthalazin-1-yl)spiro[3.3]heptan-2-yl)-1H-indazole-3-carboxamide | 538.3 | E: 2.04 F: 2.05 | 1H NMR: (500 MHz, DMSO-d6) δ ppm 12.47 (s, 1H), 8.42 (br d, J = 8.2 Hz, 1H), 8.25 (d, J = 7.9 Hz, 2H), 8.07 (d, J = 8.5 Hz, 1H), 7.95-7.89 (m, 2H), 7.88-7.79 (m, 3H), 7.15 (d, J = 8.5 Hz, 1H), 6.38 (br d, J = 15.9 Hz, 1H), 5.70-5.60 (m, 1H), 4.46-4.38 (m, 2H), 3.95-3.89 (m, 1H), 2.66-2.58 (m, 2H), 2.44-2.28 (m, 4H), 2.27-2.18 (m, 1H), 2.17-2.09 (m, 1H), 1.76 (d, J = 6.1 Hz, 2H), 1.13 (s, 8H) |
| 152 | (structure: 6-bromo indazole with 2-hydroxy-2-methylpropyl N-substituent) | 6-bromo-1-(2-hydroxy-2-methylpropyl)-N-((αR)-6-(4-oxo-3,4-dihydrophthalazin-1-yl)spiro[3.3]heptan-2-yl)-1H-indazole-3-carboxamide | 550.3 | E: 1.83 F: 1.80 | 1H NMR: (500 MHz, DMSO-d6) δ ppm 12.46 (s, 1H), 8.46 (d, J = 8.0 Hz, 1H), 8.26 (dd, J = 8.0, 0.8 Hz, 1H), 8.10 (d, J = 1.1 Hz, 1H), 8.06 (d, J = 8.8 Hz, 1H), 7.98-7.85 (m, 2H), 7.86-7.80 (m, 1H), 7.36 (dd, J = 8.7, 1.5 Hz, 1H), 4.70 (s, 1H), 4.37 (s, 2H), 4.03 (q, J = 7.2 Hz, 1H), 3.90 (quin, J = 8.5 Hz, 1H), 2.65-2.54 (m, 2H), 2.45-2.31 (m, 4H), 2.26-2.12 (m, 2H), 1.15 (s, 6H) |
| 153 | (structure: 6-(4-methoxyphenyl) indazole with 2-hydroxy-2-methylpropyl N-substituent) | 1-(2-hydroxy-2-methylpropyl)-6-(4-methoxyphenyl)-N-((αR)-6-(4-oxo-3,4-dihydrophthalazin-1-yl)spiro[3.3]heptan-2-yl)-1H-indazole-3-carboxamide | 578.4 | E: 1.95 F: 1.96 | 1H NMR: (500 MHz, DMSO-d6) δ ppm 12.48 (s, 1H), 8.44 (br d, J = 7.9 Hz, 1H), 8.25 (d, J = 7.6 Hz, 1H), 8.13 (d, J = 8.5 Hz, 1H), 7.96 (s, 1H), 7.91 (br d, J = 7.0 Hz, 1H), 7.89-7.80 (m, 2H), 7.70 (br d, J = 8.5 Hz, 2H), 7.51 (br d, J = 8.2 Hz, 1H), 7.05 (br d, J = 8.5 Hz, 2H), 4.43 (s, 2H), 4.41-4.37 (m, 1H), 3.90 (br t, J = 8.5 Hz, 1H), 3.80 (s, 3H), 2.59 (br d, J = 10.1 Hz, 2H), 2.44-2.29 (m, 5H), 2.23 (br d, J = 4.6 Hz, 1H), 2.19-2.11 (m, 1H), 1.16 (s, 6H) |
| 154 | (structure: 6-(1-methyl-1H-1,2,3-triazol-4-yl) indazole with 2-hydroxy-2-methylpropyl N-substituent) | 1-(2-hydroxy-2-methylpropyl)-6-(1-methyl-1H-1,2,3-triazol-4-yl)-N-((αR)-6-(4-oxo-3,4-dihydrophthalazin-1-yl)spiro[3.3]heptan-2-yl)-1H-indazole-3-carboxamide | 553.3 | E: 1.43 F: 1.43 | 1H NMR: (500 MHz, DMSO-d6) δ ppm 12.48 (s, 1H), 8.56 (s, 1H), 8.44 (d, J = 7.9 Hz, 1H), 8.29-8.22 (m, 2H), 8.16 (d, J = 8.2 Hz, 1H), 7.96-7.78 (m, 3H), 7.70 (d, J = 8.2 Hz, 1H), 4.80 (s, 1H), 4.41 (s, 2H), 4.11 (s, 3H), 3.90 (quin, J = 8.5 Hz, 1H), 2.68-2.55 (m, 3H), 2.45-2.29 (m, 4H), 2.27-2.11 (m, 2H), 1.17 (s, 6H) |

TABLE 8-continued

| Ex. | R | Name | LCMS (M + H)+ | HPLC Method, RT (min.) | 1H NMR |
|---|---|---|---|---|---|
| 155 | (3,5-dimethylisoxazol-4-yl on indazole scaffold with 2-hydroxy-2-methylpropyl N-substituent) | 6-(3,5-dimethylisoxazol-4-yl)-1-(2-hydroxy-2-methylpropyl)-N-((αR)-6-(4-oxo-3,4-dihydrophthalazin-1-yl)spiro[3.3]heptan-2-yl)-1H-indazole-3-carboxamide | 567.3 | E: 1.72 F: 1.77 | 1H NMR: (500 MHz, DMSO-d6) δ ppm 12.44 (s, 1H), 8.45 (d, J = 7.9 Hz, 1H), 8.21 (d, J = 7.6 Hz, 1H), 8.13 (d, J = 8.2 Hz, 1H), 7.92-7.85 (m, 1H), 7.84-7.76 (m, 2H), 7.70 (s, 1H), 7.19 (d, J = 8.5 Hz, 1H), 4.82 (s, 1H), 3.86 (quin, J = 8.4 Hz, 1H), 2.64-2.53 (m, 2H), 2.38 (s, 3H), 2.36-2.24 (m, 4H), 2.21 (s, 4H), 2.15-2.05 (m, 1H), 1.10 (s, 6H) |
| 156 | (3-chlorophenyl) | 6-(3-chlorophenyl)-1-(2-hydroxy-2-methylpropyl)-N-((αR)-6-(4-oxo-3,4-dihydrophthalazin-1-yl)spiro[3.3]heptan-2-yl)-1H-indazole-3-carboxamide | 582.3 | E: 2.10 F: 2.09 | 1H NMR: (500 MHz, DMSO-d6) δ ppm 12.48 (s, 1H), 8.46 (br d, J = 7.9 Hz, 1H), 8.25 (br d, J = 7.9 Hz, 1H), 8.19 (d, J = 8.5 Hz, 1H), 8.10 (s, 1H), 7.98-7.79 (m, 4H), 7.74 (br d, J = 7.6 Hz, 1H), 7.60-7.50 (m, 2H), 7.46 (br d, J = 7.3 Hz, 1H), 4.80 (s, 1H), 4.46 (s, 2H), 4.45-4.37 (m, 1H), 3.90 (quin, J = 8.5 Hz, 1H), 2.69-2.55 (m, 2H), 2.46-2.30 (m, 4H), 2.29-2.11 (m, 2H), 1.16 (s, 6H) |
| 157 | (2-methoxyphenyl) | 1-(2-hydroxy-2-methylpropyl)-6-(2-methoxyphenyl)-N-((αR)-6-(4-oxo-3,4-dihydrophthalazin-1-yl)spiro[3.3]heptan-2-yl)-1H-indazole-3-carboxamide | 578.3 | E: 1.92 F: 1.92 | 1H NMR: (500 MHz, DMSO-d6) δ ppm 12.48 (s, 1H), 8.42 (br d, J = 8.2 Hz, 1H), 8.25 (br d, J = 7.6 Hz, 1H), 8.10 (br d, J = 8.5 Hz, 1H), 7.98-7.79 (m, 4H), 7.41-7.31 (m, 3H), 7.13 (br d, J = 8.2 Hz, 1H), 7.06 (t, J = 7.3 Hz, 1H), 4.49-4.41 (m, 1H), 4.39 (s, 2H), 3.90 (quin, J = 8.4 Hz, 1H), 3.76 (s, 3H), 2.68-2.55 (m, 2H), 2.46-2.28 (m, 4H), 2.20-2.12 (m, 1H), 1.15 (s, 6H) |
| 158 | (3-methoxyphenyl) | 1-(2-hydroxy-2-methylpropyl)-6-(3-methoxyphenyl)-N-((αR)-6-(4-oxo-3,4-dihydrophthalazin-1-yl)spiro[3.3]heptan-2-yl)-1H-indazole-3-carboxamide | 578.3 | E: 1.93 F: 1.93 | 1H NMR: (500 MHz, DMSO-d6) δ ppm 8.45 (d, J = 7.9 Hz, 1H), 8.25 (d, J = 7.6 Hz, 1H), 8.17 (d, J = 8.5 Hz, 1H), 8.03 (s, 1H), 7.96-7.90 (m, 2H), 7.90-7.80 (m, 2H), 7.55 (d, J = 8.5 Hz, 1H), 7.47 (d, J = 8.2 Hz, 1H), 7.44-7.35 (m, 1H), 7.33 (br d, J = 7.9 Hz, 1H), 7.28 (s, 1H), 7.00-6.93 (m, 1H), 4.45 (s, 2H), 4.44-4.36 (m, 1H), 3.90 (quin, J = 8.4 Hz, 1H), 3.84 (s, 3H), 2.67-2.56 (m, 2H), 2.45-2.30 (m, 4H), 2.28-2.20 (m, 1H), 1.16 (s, 6H), 2.20-2.13 (m, 1H) |

TABLE 8-continued

| Ex. | R | Name | LCMS (M + H)+ | HPLC Method, RT (min.) | 1H NMR |
|---|---|---|---|---|---|
| 159 | 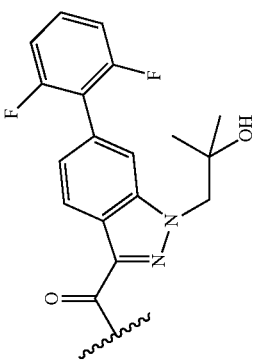 | 6-(2,6-difluorophenyl)-1-(2-hydroxy-2-methylpropyl)-N-(((αR)-6-(4-oxo-3,4-dihydrophthalazin-1-yl)spiro[3.3]heptan-2-yl)-1H-indazole-3-carboxamide | 584.2 | E: 1.96<br>F: 2.06 | 1H NMR: (500 MHz, DMSO-d6) δ ppm 12.44 (s, 1H), 8.49 (br d, J = 7.9 Hz, 1H), 8.21 (br d, J = 7.6 Hz, 1H), 8.16 (d, J = 8.5 Hz, 1H), 7.92-7.86 (m, 1H), 7.85-7.75 (m, 3H), 7.50-7.39 (m, 1H), 7.27-7.15 (m, 3H), 4.42-4.37 (m, 1H), 4.36 (s, 2H), 3.91-3.80 (m, 1H), 2.66-2.55 (m, 1H), 2.41-2.25 (m, 4H), 2.19 (br d, J = 4.9 Hz, 1H), 2.15-2.07 (m, 1H), 1.09 (s, 6H) |
| 160 | 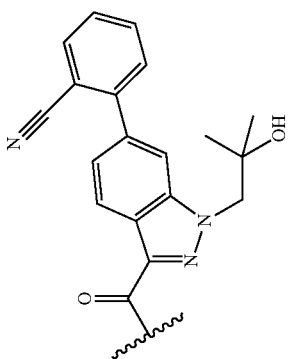 | 6-(2-cyanophenyl)-1-(2-hydroxy-2-methylpropyl)-N-(((αR)-6-(4-oxo-3,4-dihydrophthalazin-1-yl)spiro[3.3]heptan-2-yl)-1H-indazole-3-carboxamide | 573.3 | E: 1.78<br>F: 1.78 | 1H NMR: (500 MHz, DMSO-d6) δ ppm 12.48 (s, 1H), 8.52 (br d, J = 7.9 Hz, 1H), 8.29-8.21 (m, 2H), 8.02-7.96 (m, 2H), 7.95-7.90 (m, 1H), 7.90-7.86 (m, 1H), 7.86-7.79 (m, 2H), 7.69 (d, J = 7.6 Hz, 1H), 7.62 (t, J = 7.5 Hz, 1H), 7.43 (d, J = 8.2 Hz, 1H), 4.77 (s, 1H), 4.49-4.39 (m, 3H), 3.91 (quin, J = 8.3 Hz, 1H), 2.68-2.56 (m, 2H), 2.38 (td, J = 20.1, 9.9 Hz, 4H), 2.29-2.21 (m, 1H), 2.21-2.13 (m, 1H), 1.16 (s, 6H) |
| 161 | 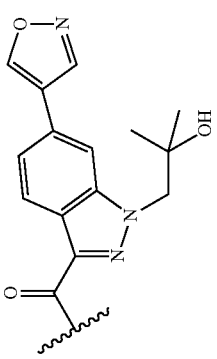 | 1-(2-hydroxy-2-methylpropyl)-6-(isoxazol-4-yl)-N-(((αR)-6-(4-oxo-3,4-dihydrophthalazin-1-yl)spiro[3.3]heptan-2-yl)-1H-indazole-3-carboxamide | 539.4 | E: 1.48<br>F: 1.25 | 1H NMR: (500 MHz, DMSO-d6) δ ppm 12.47 (s, 1H), 8.40 (br dd, J = 28.5, 8.1 Hz, 1H), 8.25 (d, J = 7.9 Hz, 1H), 8.09-7.97 (m, 2H), 7.94-7.80 (m, 3H), 7.55-7.25 (m, 1H), 4.46-4.23 (m, 3H), 3.90 (quin, J = 8.5 Hz, 1H), 2.66-2.55 (m, 2H), 2.45-2.27 (m, 5H), 2.24-2.08 (m, 2H), 1.13 (br s, 6H) |

The following Examples in Table 9 were made by using the same procedure as shown in Example 1. Intermediate 69 was coupled with the appropriate acid. Various coupling reagents could be used other than the one described in Example 1 such as BOP, PyBop, EDC/HOBt or HATU.

Example 165: N-((aR)-6-(4-oxo-3,4-dihydrophthalazin-1-yl)spiro[3.3]heptan-2-yl)-6-(2-oxopyrrolidin-1-yl)pyrazolo[1,5-a]pyridine-3-carboxamide

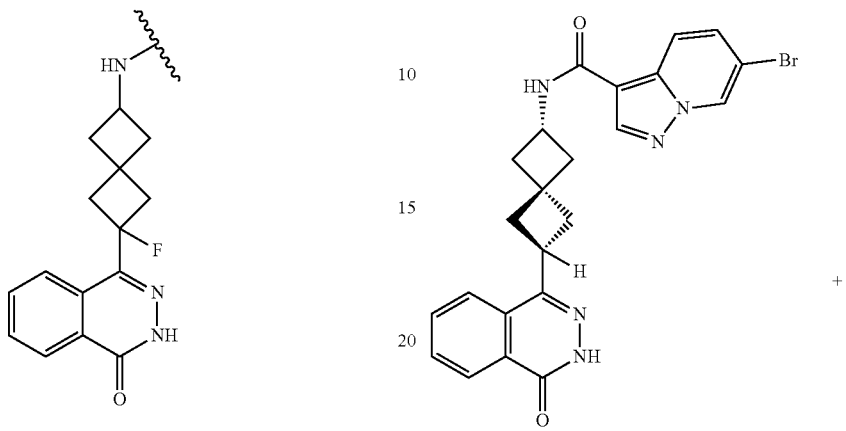

TABLE 9

| Ex. | R | Name | LCMS (M + H)+ | HPLC Method, RT (min.) | $^1$H NMR |
|---|---|---|---|---|---|
| 162 | | N-(6-fluoro-6-(4-oxo-3,4-dihydrophthalazin-1-yl)spiro[3.3]heptan-2-yl)-1-(2-hydroxy-2-methylpropyl)-1H-indazole-3-carboxamide | 490.1 | E: 1.55 F: 1.55 | $^1$H NMR: (500 MHz, DMSO-d$_6$) δ ppm 12.82 (br s, 1H), 8.43 (br d, J = 7.8 Hz, 1H), 8.31 (br d, J = 7.7 Hz, 1H), 8.11 (br d, J = 8.1 Hz, 1H), 8.02-7.84 (m, 3H), 7.76 (br d, J = 8.4 Hz, 1H), 7.40 (br t, J = 7.5 Hz, 1H), 7.22 (br t, J = 7.4 Hz, 1H), 4.48-4.38 (m, 1H), 4.36 (s, 2H), 3.11 (br t, J = 13.4 Hz, 1H), 3.03-2.91 (m, 1H), 2.86-2.74 (m, 1H), 2.45-2.35 (m, 1H), 2.26-2.09 (m, 2H), 1.13 (s, 6H) |
| 163 | | 6-fluoro-N-(6-fluoro-6-(4-oxo-3,4-dihydrophthalazin-1-yl)spiro[3.3]heptan-2-yl)-1-(2-hydroxy-2-methylpropyl)-1H-indazole-3-carboxamide | 508.1 | E: 1.62 F: 1.63 | $^1$H NMR: (500 MHz, DMSO-d$_6$) δ ppm 12.82 (s, 1H), 8.49 (br d, J = 7.8 Hz, 1H), 8.31 (br d, J = 7.7 Hz, 1H), 8.10 (br dd, J = 8.6, 5.4 Hz, 1H), 8.00-7.93 (m, 1H), 7.93-7.84 (m, 2H), 7.61 (br d, J = 9.6 Hz, 1H), 7.11 (br t, J = 8.3 Hz, 1H), 4.44-4.35 (m, 1H), 4.32 (s, 2H), 3.10 (br t, J = 12.4 Hz, 1H), 2.95 (br t, J = 12.1 Hz, 1H), 2.81 (br dd, J = 21.7, 12.6 Hz, 1H), 2.69 (br d, J = 13.7 Hz, 1H), 2.44-2.34 (m, 1H), 2.25-2.09 (m, 2H), 1.13 (s, 6H) |
| 164 | | N-(6-fluoro-6-(4-oxo-3,4-dihydrophthalazin-1-yl)spiro[3.3]heptan-2-yl)pyrazolo[1,5-a]pyridine-3-carboxamide | 418.1 | E: 1.32 F: 1.31 | $^1$H NMR: (500 MHz, DMSO-d$_6$) δ ppm 12.82 (s, 1H), 8.74 (br d, J = 6.7 Hz, 1H), 8.53 (s, 1H), 8.36-8.25 (m, 2H), 8.16 (br d, J = 8.8 Hz, 1H), 8.00-7.94 (m, 1H), 7.94-7.84 (m, 2H), 7.43 (br t, J = 7.8 Hz, 1H), 7.04 (br t, J = 6.6 Hz, 1H), 4.42-4.28 (m, 1H), 3.14-3.05 (m, 1H), 2.97 (br t, J = 12.4 Hz, 1H), 2.87-2.68 (m, 2H), 2.33-2.16 (m, 2H), 2.03 (br t, J = 9.9 Hz, 1H) |

-continued

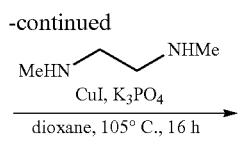
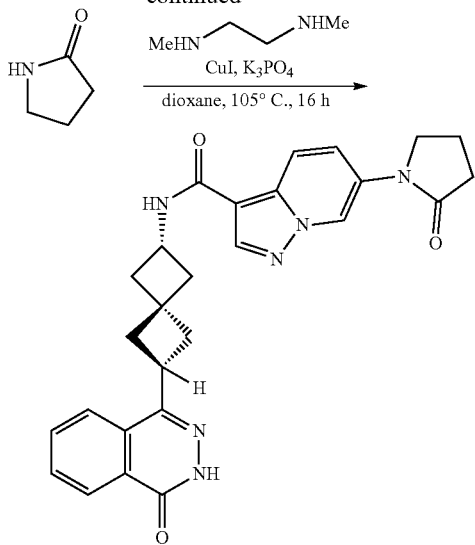

Pyrrolidin-2-one (0.012 mL, 0.16 mmol), copper(I) iodide (3.0 mg, 0.016 mmol) and N1,N2-dimethylethane-1,2-diamine (1.7 μl, 0.016 mmol) were placed in a pressure vial, and dioxane (0.75 mL) was added, followed by Intermediate 70 (15 mg, 0.031 mmol) and Phosphoric acid, potassium salt (17 mg, 0.078 mmol). The reaction mixture was degassed (3×, vacuum/Ar), the pressure vial was capped, and the reaction mixture was stirred at 105° C. for 16 h. Most of the solvent was removed under reduced pressure, the residue was diluted with DMF (2 mL), acidified with TFA, filtered and purified by preparative HPLC to afford Example 165 (1.3 mg, 9% yield). MS(ESI) m/z: 483.35 (M+H)$^+$; $^1$H NMR (500 MHz, DMSO-d$_6$) δ ppm 12.47 (s, 1H), 9.07 (s, 1H), 8.53 (s, 1H), 8.32 (br d, J=7.6 Hz, 1H), 8.25 (br d, J=7.6 Hz, 1H), 8.16 (br d, J=9.5 Hz, 1H), 7.95-7.90 (m, 1H), 7.88-7.80 (m, 3H), 4.42-4.30 (m, 1H), 3.94-3.83 (m, 3H), 2.63 (br s, 2H), 2.45-2.31 (m, 4H), 2.28-2.17 (m, 3H), 2.12-2.00 (m, 3H). HPLC RT=E: 1.31; F: 1.32.

The following Examples in Table 10 were prepared by using similar procedures as outlined in Example 142, Example 143, Intermediate 54A and Example 165 by reacting Intermediate 70 with the appropriate boronic acids/boronate esters/potassium trifluoroborates, inorganic cyanides, amides, alcohols and heterocycles.

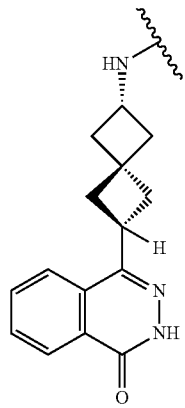

TABLE 10

| Ex. | R | Name | LCMS (M + H)+ | HPLC Method, RT (min.) | 1H NMR |
|---|---|---|---|---|---|
| 166 | 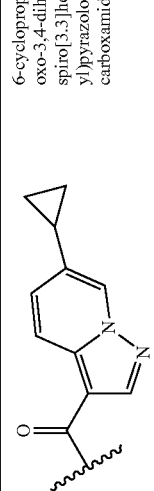 | 6-cyclopropyl-N-((αR)-6-(4-oxo-3,4-dihydrophthalazin-1-yl)spiro[3.3]heptan-2-yl)pyrazolo[1,5-a]pyridine-3-carboxamide | 440.2 | E: 1.52 F: 1.52 | 1H NMR: (500 MHz, DMSO-d6) δ ppm 12.49 (s, 1H), 8.56 (s, 1H), 8.47 (s, 1H), 8.26 (br dd, J = 13.0, 7.8 Hz, 2H), 8.06 (br d, J = 8.9 Hz, 1H), 7.96-7.89 (m, 1H), 7.89-7.78 (m, 2H), 7.17 (br d, J = 9.2 Hz, 1H), 4.42-4.30 (m, 1H), 3.90 (br t, J = 8.4 Hz, 1H), 2.62 (br s, 1H), 2.44-2.30 (m, 3H), 2.27-2.15 (m, 2H), 2.08-1.95 (m, 2H), 0.95 (br d, J = 7.3 Hz, 2H), 0.76 (br d, J = 4.1 Hz, 2H) |
| 167 | 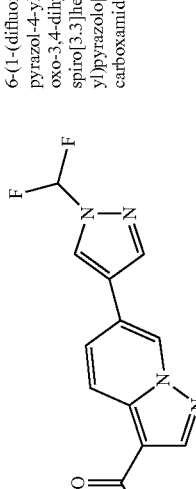 | 6-(1-(difluoromethyl)-1H-pyrazol-4-yl)-N-((αR)-6-(4-oxo-3,4-dihydrophthalazin-1-yl)spiro[3.3]heptan-2-yl)pyrazolo[1,5-a]pyridine-3-carboxamide | 516.1 | E: 1.45 F: 1.46 | 1H NMR: (500 MHz, DMSO-d6) δ ppm 12.49 (s, 1H), 9.22 (s, 1H), 8.86 (s, 1H), 8.56 (s, 1H), 8.43 (s, 1H), 8.37 (br d, J = 7.6 Hz, 1H), 8.25 (br d, J = 7.8 Hz, 1H), 8.20 (d, J = 9.2 Hz, 1H), 7.95-7.76 (m, 5H), 4.45-4.31 (m, 1H), 3.96-3.85 (m, 1H), 2.64 (br s, 1H), 2.57 (br t, J = 8.0 Hz, 1H), 2.44-2.31 (m, 3H), 2.29-2.17 (m, 2H), 2.05 (br t, J = 10.0 Hz, 1H) |
| 168 | 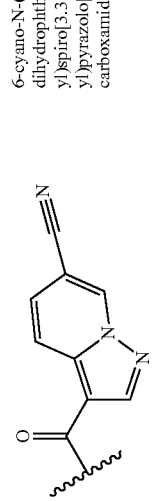 | 6-cyano-N-((αR)-6-(4-oxo-3,4-dihydrophthalazin-1-yl)spiro[3.3]heptan-2-yl)pyrazolo[1,5-a]pyridine-3-carboxamide | 426.2 | E: 1.39 F: 1.40 | 1H NMR: (500 MHz, DMSO-d6) δ ppm 12.47 (s, 1H), 9.61 (s, 1H), 8.75 (s, 1H), 8.52 (br d, J = 7.3 Hz, 1H), 8.25 (br d, J = 8.9 Hz, 2H), 7.96-7.88 (m, 1H), 7.88-7.79 (m, 2H), 7.65 (d, J = 9.5 Hz, 1H), 4.41-4.28 (m, 1H), 3.90 (quin, J = 8.5 Hz, 1H), 2.68-2.59 (m, 1H), 2.45-2.30 (m, 3H), 2.27-2.16 (m, 2H), 2.04 (br t, J = 10.1 Hz, 1H) |
| 169 | 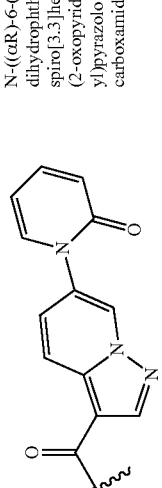 | N-((αR)-6-(4-oxo-3,4-dihydrophthalazin-1-yl)spiro[3.3]heptan-2-yl)-6-(2-oxopyridin-1(2H)-yl)pyrazolo[1,5-a]pyridine-3-carboxamide | 493.4 | E: 1.25 F: 1.26 | 1H NMR: (500 MHz, DMSO-d6) δ ppm 12.47 (s, 1H), 9.09 (s, 1H), 8.65 (s, 1H), 8.41 (br d, J = 7.3 Hz, 1H), 8.24 (br t, J = 9.0 Hz, 2H), 7.95-7.90 (m, 1H), 7.90-7.86 (m, 1H), 7.86-7.80 (m, 1H), 7.78 (br d, J = 6.1 Hz, 1H), 7.56 (br t, J = 7.3 Hz, 1H), 7.51 (br d, J = 9.5 Hz, 1H), 6.53 (br d, J = 9.2 Hz, 1H), 6.37 (br t, J = 6.6 Hz, 1H), 4.44-4.34 (m, 1H), 3.91 (br d, J = 8.4 Hz, 1H), 2.65 (br s, 1H), 2.45-2.45 (m, 4H), 2.30-2.19 (m, 2H), 2.10-2.01 (m, 1H) |
| 170 | 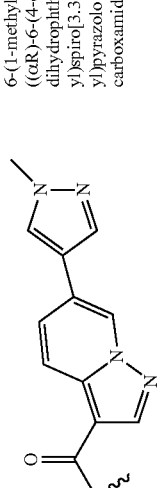 | 6-(1-methyl-1H-pyrazol-4-yl)-N-(((αR)-6-(4-oxo-3,4-dihydrophthalazin-1-yl)spiro[3.3]heptan-2-yl)pyrazolo[1,5-a]pyridine-3-carboxamide | 480.2 | E: 1.27 F: 1.27 | 1H NMR: (500 MHz, DMSO-d6) δ ppm 12.50 (s, 1H), 9.00 (s, 1H), 8.51 (s, 1H), 8.36 (br d, J = 7.3 Hz, 1H), 8.28-8.21 (m, 2H), 8.15 (br d, J = 9.2 Hz, 1H), 7.99 (s, 1H), 7.95-7.89 (m, 1H), 7.89-7.79 (m, 2H), 7.70 (br d, J = 9.3 Hz, 1H), 4.41-4.29 (m, 1H), 3.95-3.88 (m, 1H), 3.86 (s, 3H), 2.68-2.55 (m, 2H), 2.44-2.30 (m, 3H), 2.27-2.15 (m, 2H), 2.04 (br t, J = 10.0 Hz, 1H) |

TABLE 10-continued

| Ex. | R | Name | LCMS (M + H)+ | HPLC Method, RT (min.) | 1H NMR |
|---|---|---|---|---|---|
| 171 | | N-((αR)-6-(4-oxo-3,4-dihydrophthalazin-2-yl)spiro[3.3]heptan-2-yl)-6-(1-((S)-3,3,3-trifluoro-2-hydroxypropyl)-1H-pyrazol-4-yl)pyrazolo[1,5-a]pyridine-3-carboxamide | 578.2 | E: 1.40 F: 1.41 | 1H NMR: (500 MHz, DMSO-d6) δ ppm 9.05 (s, 1H), 8.52 (s, 1H), 8.39-9.31 (m, 2H), 8.25 (br d, J = 7.8 Hz, 1H), 8.17 (br d, J = 9.2 Hz, 1H), 8.11 (s, 1H), 7.96-7.89 (m, 1H), 7.89-7.79 (m, 2H), 7.72 (br d, J = 9.1 Hz, 1H), 4.40-4.31 (m, 1H), 4.29-4.19 (m, 1H), 3.96-3.84 (m, 1H), 3.54 (br s, 2H), 2.63 (br s, 1H), 2.44-2.30 (m, 3H), 2.29-2.17 (m, 2H), 2.04 (br t, J = 10.0 Hz, 1H) |
| 172 | | N-((αR)-6-(4-oxo-3,4-dihydrophthalazin-2-yl)spiro[3.3]heptan-2-yl)-6-(3-(trifluoromethyl)-1H-pyrazol-4-yl)pyrazolo[1,5-a]pyridine-3-carboxamide | 534.2 | E: 1.44 F: 1.44 | 1H NMR: (500 MHz, DMSO-d6) δ ppm 12.50 (s, 1H), 8.76 (s, 1H), 8.58 (s, 1H), 8.41 (br d, J = 7.5 Hz, 1H), 8.32 (s, 1H), 8.25 (br d, J = 7.8 Hz, 1H), 8.21 (br d, J = 9.2 Hz, 1H), 7.95-7.89 (m, 1H), 7.89-7.79 (m, 2H), 7.49 (br d, J = 9.1 Hz, 1H), 4.43-4.31 (m, 1H), 3.96-3.84 (m, 1H), 2.63 (br s, 1H), 2.60-2.55 (m, 1H), 2.43-2.30 (m, 3H), 2.29-2.16 (m, 2H), 2.04 (br t, J = 10.0 Hz, 1H) |
| 173 | | N-((αR)-6-(4-oxo-3,4-dihydrophthalazin-2-yl)spiro[3.3]heptan-2-yl)-6-(thiazol-2-yl)pyrazolo[1,5-a]pyridine-3-carboxamide | 483.1 | E: 1.44 F: 1.44 | 1H NMR: (500 MHz, DMSO-d6) δ ppm 9.30 (s, 1H), 8.65 (s, 1H), 8.46 (br d, J = 7.4 Hz, 1H), 8.26 (br dd, J = 11.9, 8.9 Hz, 2H), 8.03-7.95 (m, 2H), 7.95-7.89 (m, 1H), 7.88-7.77 (m, 3H), 4.43-4.32 (m, 1H), 3.96-3.85 (m, 1H), 2.64 (br s, 1H), 2.60-2.54 (m, 1H), 2.45-2.30 (m, 3H), 2.30-2.17 (m, 2H), 2.05 (br t, J = 10.1 Hz, 1H) |
| 174 | | N-((αR)-6-(4-oxo-3,4-dihydrophthalazin-1-yl)spiro[3.3]heptan-2-yl)-6-(1H-pyrazol-4-yl)pyrazolo[1,5-a]pyridine-3-carboxamide | 466.2 | E: 1.16 F: 1.17 | 1H NMR: (500 MHz, DMSO-d6) δ ppm 12.50 (s, 1H), 9.04 (s, 1H), 8.50 (s, 1H), 8.37 (br d, J = 7.5 Hz, 1H), 8.24 (br d, J = 7.8 Hz, 1H), 8.15 (br d, J = 9.2 Hz, 1H), 7.96-7.89 (m, 1H), 7.89-7.81 (m, 2H), 7.76 (br d, J = 9.3 Hz, 1H), 4.41-4.29 (m, 1H), 3.90 (br t, J = 8.4 Hz, 1H), 3.69 (br s, 1H), 2.62 (br s, 1H), 2.42-2.29 (m, 3H), 2.27-2.14 (m, 2H), 2.04 (br t, J = 9.9 Hz, 1H) |
| 175 | | 6-(1,4-dimethyl-1H-1,2,3-triazol-5-yl)-N-((αR)-6-(4-oxo-3,4-dihydrophthalazin-1-yl)spiro[3.3]heptan-2-yl)pyrazolo[1,5-a]pyridine-3-carboxamide | 495.2 | E: 1.21 F: 1.22 | 1H NMR: (500 MHz, DMSO-d6) δ ppm 12.50 (s, 1H), 9.09 (s, 1H), 8.68 (s, 1H), 8.43 (br d, J = 7.7 Hz, 1H), 8.30 (br d, J = 9.1 Hz, 1H), 8.27 (br d, J = 7.9 Hz, 1H), 7.99-7.88 (m, 3H), 7.86 (br d, J = 7.8 Hz, 1H), 7.56 (br d, J = 9.2 Hz, 1H), 4.41 (br d, J = 8.4 Hz, 1H), 3.99 (s, 3H), 3.93 (br t, J = 8.5 Hz, 1H), 2.67 (br d, J = 18.9 Hz, 1H), 2.41 (br dd, J = 13.9, 9.2 Hz, 3H), 2.32-2.18 (m, 5H), 2.11-2.03 (m, 1H) |

TABLE 10-continued

| Ex. | R | Name | LCMS (M + H)+ | HPLC Method, RT (min.) | 1H NMR |
|---|---|---|---|---|---|
| 176 | (structure: imidazole-substituted indolizine with carbonyl) | 6-(1H-imidazol-1-yl)-N-((αR)-6-(4-oxo-3,4-dihydrophthalazin-1-yl)spiro[3.3]heptan-2-yl)pyrazolo[1,5-α]pyridine-3-carboxamide | 466.1 | E: 1.09 F: 1.26 | 1H NMR: (500 MHz, DMSO-d6) δ ppm 12.49 (s, 1H), 9.44 (s, 1H), 9.00 (br s, 1H), 8.71 (s, 1H), 8.47 (br d, J = 7.3 Hz, 1H), 8.35 (d, J = 9.5 Hz, 1H), 8.28 (br d, J = 7.9 Hz, 1H), 7.97-7.92 (m, 1H), 7.91-7.83 (m, 3H), 4.46-4.36 (m ,1H), 3.94 (br t, J = 8.5 Hz, 1H), 2.66 (br s, 2H), 2.47-2.36 (m, 4H), 2.32-2.21 (m, 2H), 2.09 (br t, J = 10.1 Hz, 1H) |
| 177 | (structure: pyrazole-substituted indolizine with carbonyl) | N-((αR)-6-(4-oxo-3,4-dihydrophthalazin-1-yl)spiro[3.3]heptan-2-yl)-6-(1H-pyrazol-1-yl)pyrazolo[1,5-α]pyridine-3-carboxamide | 466.1 | E: 1.39 F: 1.31 | 1H NMR: (500 MHz, DMSO-d6) δ ppm 12.49 (s, 1H), 9.30 (s, 1H), 8.61 (br d, J = 6.1 Hz, 2H), 8.40 (br d, J = 7.4 Hz, 1H), 8.29 (br d, J = 9.5 Hz, 1H), 8.25 (br d, J = 8.0 Hz, 1H), 8.06 (br d, J = 9.5 Hz, 1H), 7.97-7.76 (m, 4H), 6.61 (br s, 1H), 4.46-4.33 (m, 1H), 3.97-3.83 (m, 1H), 2.64 (br s, 1H), 2.58 (br s, 1H), 2.45-2.31 (m, 3H), 2.30-2.17 (m, 2H), 2.06 (br t, J = 9.9 Hz, 1H) |
| 178 | (structure: triazole-substituted indolizine with carbonyl) | N-((αR)-6-(4-oxo-3,4-dihydrophthalazin-1-yl)spiro[3.3]heptan-2-yl)-6-(1H-1,2,4-triazol-1-yl)pyrazolo[1,5-α]pyridine-3-carboxamide | 467.1 | E: 1.20 F: 1.12 | 1H NMR: (500 MHz, DMSO-d6) δ ppm 12.49 (s, 1H), 9.41 (s, 1H), 9.33 (s, 1H), 8.66 (s, 1H), 8.45 (br d, J = 7.5 Hz, 1H), 8.39-8.30 (m, 2H), 8.25 (br d, J = 7.7 Hz, 1H), 7.97 (br d, J = 9.6 Hz, 1H), 7.95-7.90 (m, 1H), 7.90-7.86 (m, 1H), 7.85-7.81 (m, 1H), 4.43-4.35 (m, 1H), 3.96-3.87 (m, 1H), 2.64 (br s, 1H), 2.61-2.55 (m, 1H), 2.45-2.31 (m, 3H), 2.29-2.19 (m, 2H), 2.06 (br s, J = 10.0 Hz, 1H) |
| 179 | (structure: 2-methoxyethoxy pyrazolopyridine with carbonyl) | 6-(2-methoxyethoxy)-N-((αR)-6-(4-oxo-3,4-dihydrophthalazin-1-yl)spiro[3.3]heptan-2-yl)pyrazolo[1,5-α]pyridine-3-carboxamide | 474.1 | E: 1.29 F: 1.26 | 1H NMR: (500 MHz, DMSO-d6) δ ppm 12.49 (s, 1H), 8.45 (br d, J = 6.1 Hz, 2H), 8.26 (t, J = 7.3 Hz, 2H), 8.07 (d, J = 9.6 Hz, 1H), 7.94-7.82 (m, 3H), 7.26 (br d, J = 9.6 Hz, 1H), 4.40-4.32 (m, 1H), 4.15 (br d, J = 4.1 Hz, 2H), 3.90 (br t, J = 8.5 Hz, 1H), 3.68 (br s, 2H), 2.62 (br s, 1H), 2.54 (s, 3H), 2.44-2.31 (m, 3H), 2.26-2.17 (m, 2H), 2.04 (br t, J = 10.0 Hz, 1H) |
| 180 | (structure: 4-oxopyridinyl pyrazolopyridine with carbonyl) | N-((αR)-6-(4-oxo-3,4-dihydrophthalazin-1-yl)spiro[3.3]heptan-2-yl)-6-(4-oxopyridin-1(4H)-yl)pyrazolo[1,5-α]pyridine-3-carboxamide | 493.2 | E: 1.14 F: 1.20 | 1H NMR: (500 MHz, DMSO-d6) δ ppm 12.49 (s, 1H), 9.30 (s, 1H), 8.70 (s, 1H), 8.44 (br d, J = 7.3 Hz, 1H), 8.30 (br d, J = 9.5 Hz, 1H), 8.28 (br d, J = 7.6 Hz, 1H), 8.09 (br d, J = 7.0 Hz, 2H), 7.93 (br d, J = 7.3 Hz, 1H), 7.92-7.88 (m, 1H), 7.88-7.82 (m, 1H), 7.73 (br d, J = 9.8 Hz, 1H), 6.33 (br d, J = 7.3 Hz, 2H), 4.46-4.36 (m, 1H), 3.98-3.88 (m, 1H), 2.65 (br s, 1H), 2.59 (br d, J = 10.4 Hz, 1H), 2.48-2.35 (m, 3H), 2.32-2.20 (m, 2H), 2.12-2.03 (m, 1H) |

Example 181: 6-(2-hydroxyethoxy)pyrazolo[1,5-a]pyridine-3-carboxylic acid

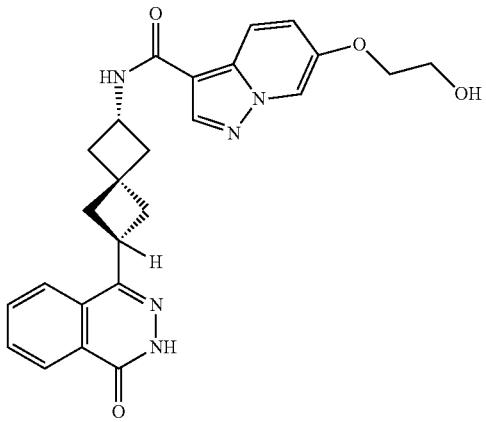

Intermediate 71 was purified by preparative HPLC to give rise to Example 181. MS(ESI) m/z: 460.1 (M+H)+; 1H NMR (500 MHz, DMSO-d6) δ ppm 12.50 (s, 1H), 8.43 (br d, J=10.4 Hz, 2H), 8.33 (br d, J=7.3 Hz, 1H), 8.27 (br d, J=7.9 Hz, 1H), 8.08 (d, J=9.5 Hz, 1H), 7.99-7.91 (m, 1H), 7.90-7.81 (m, 2H), 7.32-7.24 (m, 1H), 4.42-4.30 (m, 1H), 4.10-4.03 (m, 2H), 3.90 (br dd, J=16.8, 8.2 Hz, 1H), 2.62 (br d, J=11.6 Hz, 2H), 2.44-2.31 (m, 4H), 2.27-2.16 (m, 2H), 2.09-2.00 (m, 1H). HPLC RT=E: 1.23; F: 1.28.

Example 182: 6-(2-(3-fluoroazetidin-1-yl)ethoxy)-N-((aR)-6-(4-oxo-3,4-dihydrophthalazin-1-yl)spiro[3.3]heptan-2-yl)pyrazolo[1,5-a]pyridine-3-carboxamide

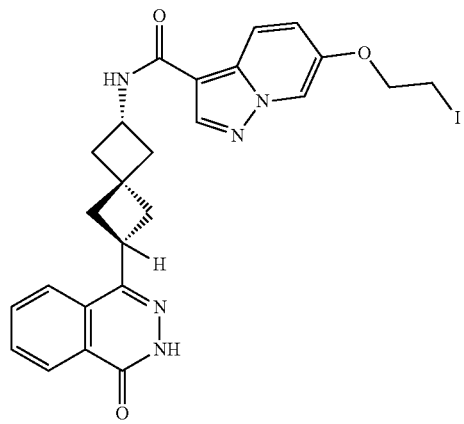

+

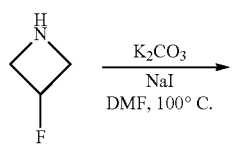

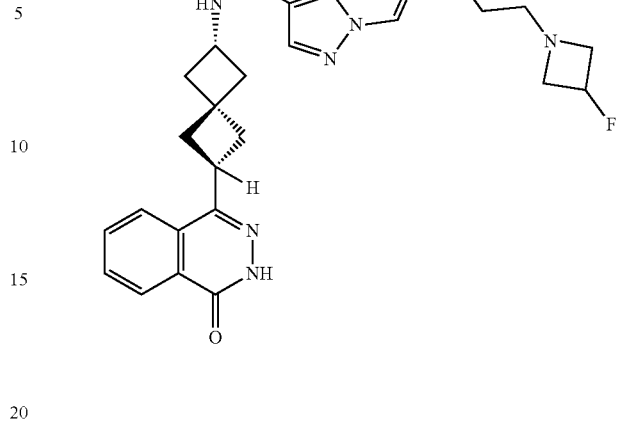

To a solution of Intermediate 72 (10 mg, 0.018 mmol) in DMF (1 mL) was sequentially added 3-fluoroazetidine, HCl (9.8 mg, 0.088 mmol), sodium iodide (13.2 mg, 0.088 mmol) and K2CO3 (18.2 mg, 0.132 mmol). The reaction vial was capped, and was stirred at 100° C. for 2 h. The reaction mixture was cooled to rt, acidified with TFA, filtered, and purified by preparative HPLC to give rise to Example 182 (0.8 mg, 6% yield) was obtained. MS(ESI) m/z: 517.1 (M+H)+; 1H NMR (500 MHz, DMSO-d6) δ ppm 12.50 (s, 1H), 8.44 (br d, J=7.7 Hz, 2H), 8.29 (br d, J=7.4 Hz, 1H), 8.26 (br d, J=7.9 Hz, 1H), 8.07 (br d, J=9.6 Hz, 1H), 7.96-7.91 (m, 1H), 7.90-7.87 (m, 1H), 7.87-7.82 (m, 1H), 7.24 (br d, J=9.6 Hz, 1H), 5.15 (br d, J=58.1 Hz, 1H), 4.43-4.28 (m, 2H), 4.02 (br t, J=5.0 Hz, 2H), 3.98-3.84 (m, 1H), 3.71-3.58 (m, 1H), 2.92-2.79 (m, 2H), 2.61 (br d, J=18.8 Hz, 2H), 2.44-2.31 (m, 3H), 2.27-2.15 (m, 3H), 2.04 (br t, J=9.9 Hz, 1H). HPLC RT=E: 1.02; F: 1.33.

The following Examples in Table 11 were prepared by using a similar procedure as shown in Example 182 by reacting Intermediate 72 with the appropriate amine or alcohol.

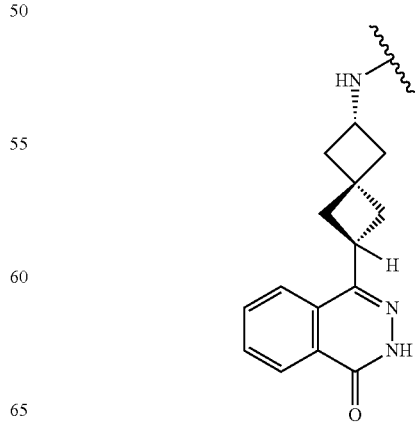

TABLE 11

| Ex. | R | Name |
|---|---|---|
| 183 | | 6-(2-(dimethylamino)ethoxy)-N-((aR)-6-(4-oxo-3,4-dihydrophthalazin-1-yl)spiro[3.3]heptan-2-yl)pyrazolo[1,5-a]pyridine-3-carboxamide |
| 184 | | 6-(2-(4-hydroxy-3,3-dimethylpiperidin-1-yl)ethoxy)-N-((aR)-6-(4-oxo-3,4-dihydrophthalazin-1-yl)spiro[3.3]heptan-2-yl)pyrazolo[1,5-a]pyridine-3-carboxamide |
| 185 | | 6-(2-(3,3-difluoropyrrolidin-1-yl)ethoxy)-N-((aR)-6-(4-oxo-3,4-dihydrophthalazin-1-yl)spiro[3.3]heptan-2-yl)pyrazolo[1,5-a]pyridine-3-carboxamide |
| 186 | | 6-(2-(azetidin-1-yl)ethoxy)-N-((aR)-6-(4-oxo-3,4-dihydrophthalazin-1-yl)spiro[3.3]heptan-2-yl)pyrazolo[1,5-a]pyridine-3-carboxamide |
| 187 | | 6-(2-(2,2-dimethylmorpholino)ethoxy)-N-((aR)-6-(4-oxo-3,4-dihydrophthalazin-1-yl)spiro[3.3]heptan-2-yl)pyrazolo[1,5-a]pyridine-3-carboxamide |
| 188 | | 6-(2-(4-methylpiperazin-1-yl)ethoxy)-N-((aR)-6-(4-oxo-3,4-dihydrophthalazin-1-yl)spiro[3.3]heptan-2-yl)pyrazolo[1,5-a]pyridine-3-carboxamide |
| 189 | | 6-(2-((R)-3-fluoropyrrolidin-1-yl)ethoxy)-N-((aR)-6-(4-oxo-3,4-dihydrophthalazin-1-yl)spiro[3.3]heptan-2-yl)pyrazolo[1,5-a]pyridine-3-carboxamide |

TABLE 11-continued

| 190 | 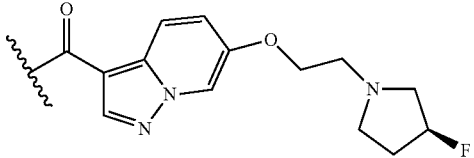 [SMILES: *C(=O)c1cnn2cc(OCCN3CC[C@H](F)C3)ccc12] | 6-(2-((S)-3-fluoropyrrolidin-1-yl)ethoxy)-N-((aR)-6-(4-oxo-3,4-dihydrophthalazin-1-yl)spiro[3.3]heptan-2-yl)pyrazolo[1,5-a]pyridine-3-carboxamide |
|---|---|---|

| Ex. | LCMS (M + H)+ | HPLC Method, RT (min.) | $^1$H NMR |
|---|---|---|---|
| 183 | 487.4 | E: 0.99<br>F: 1.06 | $^1$H NMR: (500 MHz, DMSO-d$_6$) δ ppm 12.49 (s, 1H), 8.46 (br d, J = 10.5 Hz, 2H), 8.28 (br d, J = 7.7 Hz, 1H), 8.25 (br d, J = 7.8 Hz, 1H), 8.07 (d, J = 9.6 Hz, 1H), 7.96-7.90 (m, 1H), 7.89-7.86 (m, 1H), 7.86-7.80 (m, 1H), 7.24 (br d, J = 9.7 Hz, 1H), 4.41-4.31 (m, 1H), 4.11 (br t, J = 5.4 Hz, 2H), 3.90 (quin, J = 8.5 Hz, 1H), 2.69 (br t, J = 5.3 Hz, 2H), 2.65-2.57 (m, 2H), 2.44-2.32 (m, 3H), 2.25 (s, 7H), 2.03 (br t, J = 10.0 Hz, 1H) |
| 184 | 571.1 | E: 1.07<br>F: 1.30 | $^1$H NMR: (500 MHz, DMSO-d$_6$) δ ppm 12.49 (s, 1H), 8.47 (s, 1H), 8.44 (s, 1H), 8.28 (br d, J = 7.6 Hz, 1H), 8.25 (br d, J = 7.8 Hz, 1H), 8.06 (br d, J = 9.5 Hz, 1H), 7.96-7.90 (m, 1H), 7.89-7.86 (m, 1H), 7.86-7.80 (m, 1H), 7.24 (br d, J = 9.2 Hz, 1H), 4.40-4.31 (m, 1H), 4.10 (br s, 2H), 3.90 (br t, J = 8.4 Hz, 1H), 3.05 (br s, 1H), 2.78 (br s, 1H), 2.63 (br s, 3H), 2.46-2.31 (m, 4H), 2.27-2.16 (m, 2H), 2.10-1.99 (m, 2H), 1.81 (br d, J = 10.8 Hz, 1H), 1.54 (br s, 1H), 1.47 (br d, J = 9.3 Hz, 1H), 0.84 (br d, J = 3.8 Hz, 6H) |
| 185 | 547.2 | E: 1.28<br>F: 1.70 | $^1$H NMR: (500 MHz, DMSO-d$_6$) δ ppm 12.50 (s, 1H), 8.53 (s, 1H), 8.47 (s, 1H), 8.32 (br d, J = 7.6 Hz, 1H), 8.25 (br d, J = 7.8 Hz, 1H), 8.10 (br d, J = 9.5 Hz, 1H), 7.91 (br d, J = 7.4 Hz, 1H), 7.87 (br d, J = 7.8 Hz, 1H), 7.86-7.80 (m, 1H), 7.31 (br d, J = 9.6 Hz, 1H), 4.40-4.32 (m, 1H), 4.28 (br s, 2H), 3.95-3.84 (m, 1H), 3.46 (br s, 2H), 2.62 (br s, 1H), 2.59-2.55 (m, 1H), 2.43-2.29 (m, 4H), 2.27-2.15 (m, 2H), 2.03 (br t, J = 10.1 Hz, 1H) |
| 186 | 499.2 | E: 1.02<br>F: 1.04 | $^1$H NMR: (500 MHz, DMSO-d$_6$) δ ppm 12.49 (s, 1H), 8.56 (s, 1H), 8.49 (s, 1H), 8.30 (br d, J = 7.7 Hz, 1H), 8.25 (br d, J = 8.0 Hz, 1H), 8.12 (br d, J = 9.6 Hz, 1H), 7.95-7.90 (m, 1H), 7.89-7.86 (m, 1H), 7.86-7.82 (m, 1H), 7.28 (br d, J = 9.7 Hz, 1H), 4.43-4.32 (m, 1H), 4.26 (br s, 2H), 4.15 (br d, J = 6.5 Hz, 4H), 3.91 (br t, J = 8.4 Hz, 1H), 3.62 (br s, 1H), 2.99 (br s, 1H), 2.62 (br s, 1H), 2.45-2.32 (m, 4H), 2.31-2.15 (m, 3H), 2.08-2.00 (m, 1H) |
| 187 | 557.2 | E: 1.10<br>F: 1.55 | $^1$H NMR: (500 MHz, DMSO-d$_6$) δ ppm 12.45 (s, 1H), 8.44 (s, 1H), 8.40 (s, 1H), 8.24 (br d, J = 7.3 Hz, 1H), 8.21 (br d, J = 7.8 Hz, 1H), 8.02 (br d, J = 9.6 Hz, 1H), 7.92-7.86 (m, 1H), 7.85-7.82 (m, 1H), 7.82-7.75 (m, 1H), 7.21 (br d, J = 9.5 Hz, 1H), 4.38-4.27 (m, 1H), 4.14-4.05 (m, 2H), 3.92-3.80 (m, 1H), 3.54 (br s, 1H), 2.62 (br t, J = 5.3 Hz, 2H), 2.58 (br s, 1H), 2.40-2.26 (m, 5H), 2.24-2.10 (m, 4H), 1.99 (br t, J = 10.0 Hz, 1H), 1.09 (s, 6H) |
| 188 | 542.2 | E: 0.94<br>F: 0.95 | $^1$H NMR: (500 MHz, DMSO-d$_6$) δ ppm 12.51 (s, 1H), 8.44 (br s, 2H), 8.32 (br d, J = 7.5 Hz, 1H), 8.26 (br d, J = 7.6 Hz, 1H), 8.06 (br d, J = 9.6 Hz, 1H), 7.92 (br d, J = 7.4 Hz, 1H), 7.90-7.80 (m, 2H), 7.25 (br d, J = 8.1 Hz, 1H), 4.41-4.28 (m, 1H), 4.12 (br s, 2H), 3.96-3.84 (m, 1H), 2.70 (br s, 2H), 2.62 (br s, 1H), 2.44-2.32 (m, 6H), 2.28-2.17 (m, 3H), 2.14 (s, 3H), 2.03 (br t, J = 9.9 Hz, 1H) |
| 189 | 531.2 | E: 1.24<br>F: 1.24 | $^1$H NMR: (500 MHz, DMSO-d$_6$) δ ppm 12.49 (s, 1H), 8.44 (br d, J = 6.7 Hz, 2H), 8.30 (br d, J = 7.5 Hz, 1H), 8.25 (br d, J = 7.8 Hz, 1H), 8.06 (br d, J = 9.6 Hz, 1H), 7.95-7.90 (m, 1H), 7.89-7.80 (m, 2H), 7.26 (br d, J = 10.0 Hz, 1H), 5.19 (br d, J = 55.8 Hz, 1H), 4.41-4.29 (m, 1H), 4.12 (br s, 2H), 3.93-3.84 (m, 1H), 2.87 (br d, J = 15.0 Hz, 3H), 2.72 (br s, 1H), 2.59 (br d, J = 27.4 Hz, 2H), 2.44-2.30 (m, 4H), 2.25-2.17 (m, 2H), 2.16-2.06 (m, 1H), 2.03 (br t, J = 10.0 Hz, 1H), 1.84 (br s, 1H) |
| 190 | 531.2 | E: 1.36<br>F: 1.36 | $^1$H NMR: (500 MHz, DMSO-d$_6$) δ ppm 12.50 (s, 1H), 8.45 (br d, J = 9.3 Hz, 2H), 8.31 (br d, J = 7.3 Hz, 1H), 8.25 (br d, J = 7.7 Hz, 1H), 8.07 (br d, J = 9.7 Hz, 1H), 7.95-7.90 (m, 1H), 7.89-7.86 (m, 1H), 7.85-7.80 (m, 1H), 7.26 (br d, J = 9.6 Hz, 1H), 5.21 (br d, J = 56.3 Hz, 1H), 4.41-4.31 (m, 1H), 4.14 (br s, 2H), 3.95-3.84 (m, 1H), 3.56 (br s, 1H), 2.91 (br s, 2H), 2.59 (br d, J = 27.3 Hz, 2H), 2.43-2.30 (m, 3H), 2.26-2.17 (m, 2H), 2.09 (br s, 1H), 2.03 (br t, J = 10.1 Hz, 1H), 1.96-1.80 (m, 1H |

Example 191: 6-(3-morpholinopropyl)-N-((aR)-6-(4-oxo-3,4-dihydrophthalazin-1-yl)spiro[3.3]heptan-2-yl)pyrazolo[1,5-a]pyridine-3-carboxamide

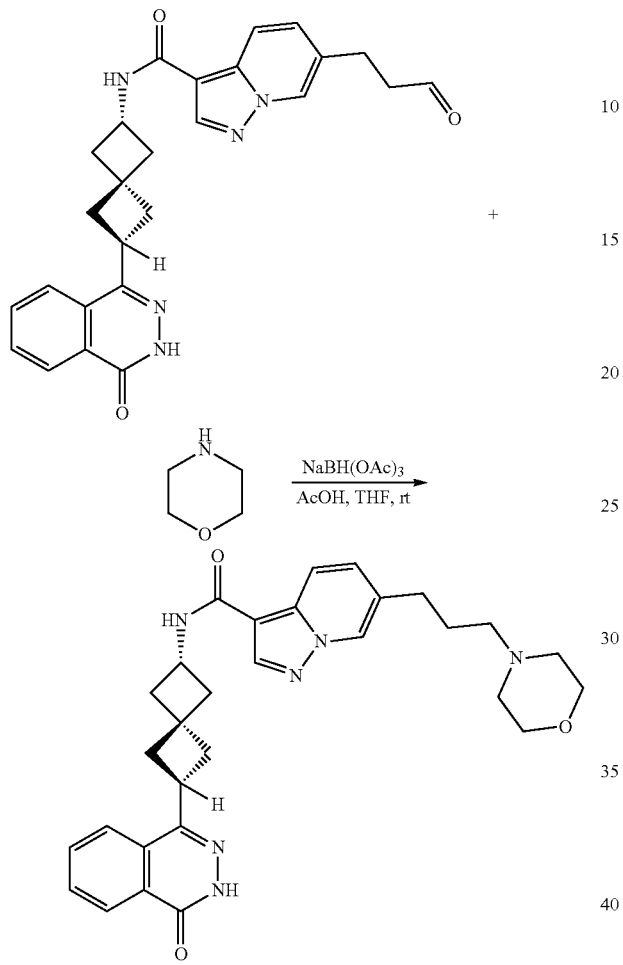

To a solution of Intermediate 73 (10 mg, 0.022 mmol), morpholine (3.8 μl, 0.044 mmol) and acetic acid (1.3 μl, 0.022 mmol) in anhydrous THF (1 mL) was added sodium triacetoxyborohydride (14 mg, 0.066 mmol), and the reaction mixture was stirred at rt for 4 h. The reaction mixture was quenched with TFA (CAUTION), solvent was removed under reduced pressure, the residue was suspended in DMF (2 mL), filtered, and purified by preparative HPLC to afford Example 191 (9.3 mg, 80% yield). MS(ESI) m/z: 527.0 (M+H)$^+$; $^1$H NMR (500 MHz, DMSO-d$_6$) δ ppm 12.43 (s, 1H), 8.61 (s, 1H), 8.48 (s, 1H), 8.25 (br d, J=7.3 Hz, 1H), 8.22 (br d, J=7.9 Hz, 1H), 8.10 (d, J=9.2 Hz, 1H), 7.91-7.85 (m, 1H), 7.85-7.76 (m, 2H), 7.34 (br d, J=9.5 Hz, 1H), 4.38-4.28 (m, 1H), 3.90 (br s, 2H), 3.89-3.81 (m, 2H), 3.75-3.70 (m, 1H), 3.63 (br s, 2H), 3.06 (br s, 2H), 2.66 (br t, J=7.3 Hz, 2H), 2.62-2.55 (m, 1H), 2.40-2.28 (m, 3H), 2.24-2.13 (m, 2H), 2.04-1.92 (m, 3H). HPLC RT=E: 1.21; F: 1.42.

The following Examples in Table 12 were prepared by using a similar procedure as shown in Example 191 by reacting Intermediate 73 with the appropriate amine.

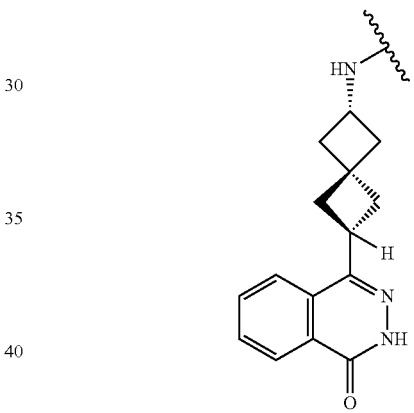

TABLE 12

| Ex. | R | Name |
|---|---|---|
| 192 | | N-((aR)-6-(4-oxo-3,4-dihydrophthalazin-1-yl)spiro[3.3]heptan-2-yl)-6-(3-(pyrrolidin-1-yl)propyl)pyrazolo[1,5-a]pyridine-3-carboxamide |
| 193 | | 6-(3-(dimethylamino)propyl)-N-((aR)-6-(4-oxo-3,4-dihydrophthalazin-1-yl)spiro[3.3]heptan-2-yl)pyrazolo[1,5-a]pyridine-3-carboxamide |
| 194 | | 6-(3-cyclopropylamino)propyl)-N-((aR)-6-(4-oxo-3,4-dihydrophthalazin-1-yl)spiro[3.3]heptan-2-yl)pyrazolo[1,5-a]pyridine-3-carboxamide |

TABLE 12-continued

| Ex. | Structure | Name |
|---|---|---|
| 195 | [structure] | 6-(3-hydroxypropyl)-N-((aR)-6-(4-oxo-3,4-dihydrophthalazin-1-yl)spiro[3.3]heptan-2-yl)pyrazolo[1,5-a]pyridine-3-carboxamide |
| 196 | [structure] | 6-(3-(4,4-difluoropiperidin-1-yl)propyl)-N-((aR)-6-(4-oxo-3,4-dihydrophthalazin-1-yl)spiro[3.3]heptan-2-yl)pyrazolo[1,5-a]pyridine-3-carboxamide |
| 197 | [structure] | 6-(3-(3,3-difluoropyrrolidin-1-yl)propyl)-N-((aR)-6-(4-oxo-3,4-dihydrophthalazin-1-yl)spiro[3.3]heptan-2-yl)pyrazolo[1,5-a]pyridine-3-carboxamide |

| Ex. | LCMS (M + H)⁺ | HPLC Method, RT (min.) | $^1$H NMR |
|---|---|---|---|
| 192 | 511 | E: 1.24<br>F: 1.25 | $^1$H NMR: (500 MHz, DMSO-d$_6$) δ ppm 12.47 (s, 1H), 8.57 (s, 1H), 8.49 (s, 1H), 8.25 (br d, J = 7.6 Hz, 2H), 8.10 (d, J = 9.2 Hz, 1H), 7.95-7.89 (m, 1H), 7.89-7.86 (m, 1H), 7.86-7.79 (m, 1H), 7.37 (br d, J = 9.5 Hz, 1H), 4.43-4.31 (m, 1H), 3.91 (br t, J = 8.4 Hz, 1H), 2.71-2.60 (m, 3H), 2.43 (br d, J = 7.3 Hz, 4H), 2.41-2.33 (m, 3H), 2.27-2.16 (m, 2H), 2.09-1.99 (m, 1H), 1.90 (s, 3H), 1.78 (br dd, J = 14.5, 7.5 Hz, 2H), 1.68 (br s, 4H) |
| 193 | 485.3 | E: 1.09<br>F: 1.01 | $^1$H NMR: (500 MHz, DMSO-d$_6$) δ ppm 12.49 (s, 1H), 8.61 (s, 1H), 8.50 (s, 1H), 8.28 (br d, J = 7.4 Hz, 1H), 8.25 (br d, J = 7.9 Hz, 1H), 8.12 (br d, J = 8.9 Hz, 1H), 7.94-7.90 (m, 1H), 7.90-7.86 (m, 1H), 7.86-7.81 (m, 1H), 7.38 (br d, J = 8.9 Hz, 1H), 4.42-4.32 (m, 1H), 3.91 (br t, J = 8.3 Hz, 1H), 3.38 (br s, 2H), 2.68-2.60 (m, 3H), 2.44-2.32 (m, 8H), 2.28-2.18 (m, 2H), 2.04 (br t, J = 10.0 Hz, 1H), 1.88-1.79 (m, 2H) |
| 194 | 497 | E: 1.08<br>F: 1.09 | $^1$H NMR: (500 MHz, DMSO-d$_6$) δ ppm 12.51 (s, 1H), 8.62 (s, 1H), 8.52 (s, 1H), 8.32 (br s, 1H), 8.26 (br d, J = 7.7 Hz, 1H), 8.13 (br d, J = 8.9 Hz, 1H), 7.97-7.91 (m, 1H), 7.90-7.87 (m, 1H), 7.87-7.80 (m, 1H), 7.38 (br d, J = 9.2 Hz, 1H), 4.43-4.33 (m, 1H), 3.96-3.87 (m, 1H), 2.82 (br t, J = 7.1 Hz, 2H), 2.69 (br t, J = 7.0 Hz, 2H), 2.64 (br s, 1H), 2.40 (br dd, J = 22.0, 9.3 Hz, 4H), 2.28-2.18 (m, 2H), 2.05 (br t, J = 10.0 Hz, 1H), 1.90-1.80 (m, 2H), 0.57 (br d, J = 5.9 Hz, 2H), 0.53 (br s, 2H) |
| 195 | 458.2 | E: 1.19<br>F: 1.19 | $^1$H NMR: (500 MHz, DMSO-d$_6$) δ ppm 8.57 (br s, 1H), 8.50 (s, 1H), 8.28 (br dd, J = 13.0, 7.4 Hz, 2H), 8.11 (br d, J = 8.9 Hz, 1H), 7.97-7.91 (m, 1H), 7.91-7.87 (m, 2H), 7.87-7.82 (m, 1H), 7.37 (br d, J = 9.3 Hz, 1H), 4.38 (br d, J = 7.7 Hz, 2H), 3.97-3.87 (m, 2H), 2.73-2.62 (m, 3H), 2.44-2.33 (m, 4H), 2.29-2.16 (m, 3H), 2.08-2.00 (m, 1H), 1.80-1.70 (m, 2H) |
| 196 | 561.4 | E: 1.12<br>F: 1.58 | $^1$H NMR: (500 MHz, DMSO-d$_6$) δ ppm 12.50 (s, 1H), 8.58 (s, 1H), 8.48 (s, 1H), 8.31 (br d, J = 6.7 Hz, 1H), 8.25 (br d, J = 7.9 Hz, 1H), 8.09 (br d, J = 8.9 Hz, 1H), 7.95-7.90 (m, 1H), 7.89-7.86 (m, 1H), 7.86-7.81 (m, 1H), 7.38 (br d, J = 9.2 Hz, 1H), 4.41-4.31 (m, 1H), 3.95-3.85 (m, 1H), 2.68-2.59 (m, 4H), 2.43-2.32 (m, 4H), 2.27-2.15 (m, 3H), 2.07-1.93 (m, 5H), 1.81 (br s, 2H) |
| 197 | 547.2 | E: 1.61<br>F: 1.63 | $^1$H NMR: (500 MHz, DMSO-d$_6$) δ ppm 12.49 (s, 1H), 8.64 (s, 1H), 8.52 (s, 1H), 8.30 (br d, J = 7.5 Hz, 1H), 8.25 (br d, J = 7.8 Hz, 1H), 8.13 (d, J = 9.1 Hz, 1H), 7.96-7.90 (m, 1H), 7.96-7.90 (m, 1H), 7.89-7.86 (m, 1H), 7.86-7.80 (m, 1H), 7.38 (br d, J = 9.3 Hz, 1H), 4.43-4.32 (m, 1H), 3.91 (br t, J = 8.5 Hz, 1H), 2.69 (br t, J = 7.3 Hz, 2H), 2.62 (br d, J = 16.0 Hz, 1H), 2.59-2.52 (m, 3H), 2.44-2.32 (m, 3H), 2.28-2.17 (m, 2H), 2.04 (br t, J = 10.0 Hz, 1H), 1.95 (br s, 2H) |

Example 198: 6-(3-hydroxy-3-methylbutyl)-N-((aR)-6-(4-oxo-3,4-dihydrophthalazin-1-yl)spiro[3.3]heptan-2-yl)pyrazolo[1,5-a]pyridine-3-carboxamide

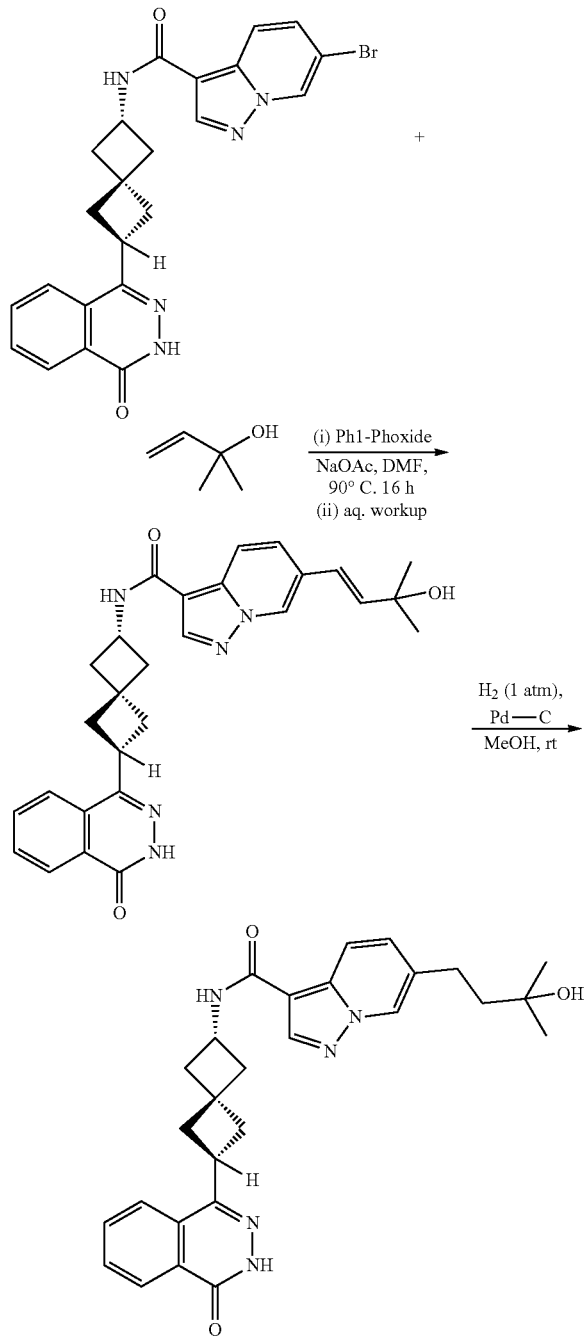

A solution of Intermediate 70 (20 mg, 0.042 mmol), 2-methylbut-3-en-2-ol (10.49 μl, 0.100 mmol), dihydrogen di-mu-chlorotetrakis(diphenylphosphinito-kp)dipalladate (2-) (2.3 mg, 2.091 μmol) and sodium acetate (8.9 mg, 0.109 mmol) in anhydrous DMF (1 mL) was degassed (3× vacuum/Ar) at rt, and then was stirred at 90° C. for 16 h under Ar atmosphere. The reaction mixture was diluted with EtOAc (50 mL), washed with water (2×15 mL), brine (1×20 mL), and dried ($Na_2SO_4$). EtOAc was removed under reduced pressure and the residue was dissolved in MeOH (5 mL). The reaction mixture was degassed (3× vacuum/Ar), then Pd—C (5% wt.) (4.5 mg, 4.2 μmol) was added. The reaction mixture was degassed again, and was stirred under dihydrogen gas (1 atm.) for 1 h at rt. The reaction mixture was degassed, additional amount of Pd—C (5% wt.) (4.5 mg, 4.2 μmol) was added, the reaction mixture was degassed again, and was stirred under dihydrogen gas (1 atm.) for 14 h at rt. Pd—C was filtered off, and MeOH was removed under reduced pressure. The residue was dissolved in DMF (2 mL), and purified by preparative HPLC to afford Example 198 (7.1 mg, 35% yield). MS(ESI) m/z: 486.0 $(M+H)^+$; $^1H$ NMR (500 MHz, DMSO-$d_6$) δ ppm 12.49 (s, 1H), 8.56 (s, 1H), 8.49 (s, 1H), 8.31-8.21 (m, 2H), 8.10 (br d, J=9.0 Hz, 1H), 7.96-7.89 (m, 1H), 7.89-7.86 (m, 1H), 7.86-7.81 (m, 1H), 7.35 (br d, J=9.3 Hz, 1H), 4.42-4.32 (m, 1H), 3.90 (quin, J=8.2 Hz, 1H), 2.70-2.61 (m, 3H), 2.43-2.31 (m, 3H), 2.28-2.16 (m, 2H), 2.04 (br t, J=10.0 Hz, 1H), 1.73-1.62 (m, 2H), 1.15 (s, 6H). HPLC RT=E: 1.35; F: 1.35.

Example 199: N-((aR)-6-(4-oxo-3,4-dihydrophthalazin-1-yl)spiro[3.3]heptan-2-yl)-6-(4,4,4-trifluoro-3-hydroxy-3-(trifluoromethyl)butyl)pyrazolo[1,5-a]pyridine-3-carboxamide

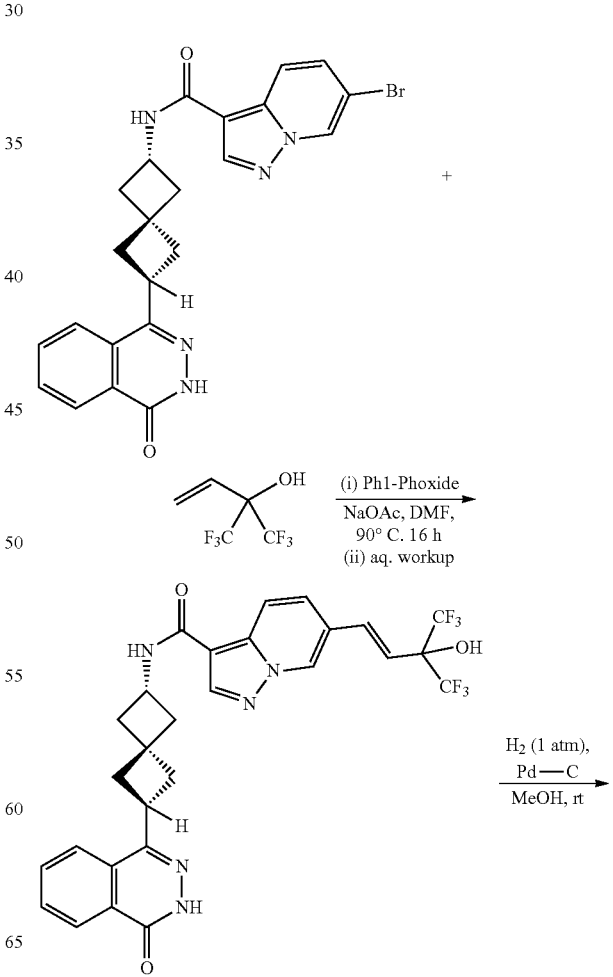

347
-continued

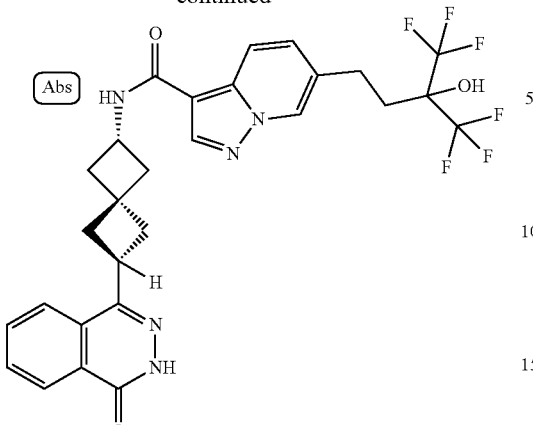

A solution of Intermediate 70 (20 mg, 0.042 mmol), 1,1,1-trifluoro-2-(trifluoromethyl)but-3-en-2-ol (0.014 mL, 0.10 mmol), dihydrogen di-mu-chlorotetrakis(diphenylphosphinito-kp)dipalladate(2-) (2.3 mg, 2.1 µmol) and sodium acetate (8.9 mg, 0.11 mmol) in anhydrous DMF (1 mL) was degassed (3× vacuum/Ar) at rt, and then was stirred at 90° C. for 16 h under Ar atmosphere. The reaction mixture was diluted with EtOAc (50 mL), washed with water (2×15 mL), brine (1×20 mL), and dried ($Na_2SO_4$). EtOAc was removed under reduced pressure and the residue was dissolved in MeOH (5 mL). The reaction mixture was degassed (3× vacuum/Ar), then Pd—C (5% wt.) (4.5 mg, 4.2 µmol) was added. The reaction mixture was degassed again, and stirred under dihydrogen gas (1 atm.) for 1 h at rt. The reaction mixture was degassed, additional amount of Pd—C (5% wt.) (4.5 mg, 4.2 µmol) was added, the reaction mixture was degassed again, and was stirred under dihydrogen gas (1 atm.) for 14 h at rt. The reaction mixture was filtered through a membrane filter, degassed, Pd—C (5% wt.) (4.5 mg, 4.2 µmol) was added. The reaction mixture was degassed again, and stirred under dihydrogen gas (1 atm.) for 20 h at rt. Pd—C was filtered off, and MeOH was removed under reduced pressure. The residue was dissolved in DMF (2 mL), and purified by preparative HPLC to afford Example 199 (0.9 mg, 4% yield). MS(ESI) m/z: 594.3 (M+H)$^+$; $^1$H NMR (500 MHz, DMSO-$d_6$) δ ppm 8.69 (br s, 1H), 8.51 (s, 1H), 8.31 (br d, J=6.6 Hz, 1H), 8.25 (br d, J=7.8 Hz, 1H), 8.13 (br d, J=8.9 Hz, 1H), 7.95-7.90 (m, 1H), 7.89-7.86 (m, 1H), 7.86-7.81 (m, 1H), 7.43 (br d, J=8.8 Hz, 1H), 4.37 (br d, J=7.9 Hz, 2H), 3.96-3.86 (m, 2H), 2.83 (br s, 2H), 2.62 (br s, 1H), 2.44-2.32 (m, 3H), 2.22 (br d, J=9.0 Hz, 4H), 2.07-1.99 (m, 1H). HPLC RT=E: 1.72; F: 1.72.

Example 200: 6-(morpholinomethyl)-N-((aR)-6-(4-oxo-3,4-dihydrophthalazin-1-yl)spiro[3.3]heptan-2-yl)pyrazolo[1,5-a]pyridine-3-carboxamide

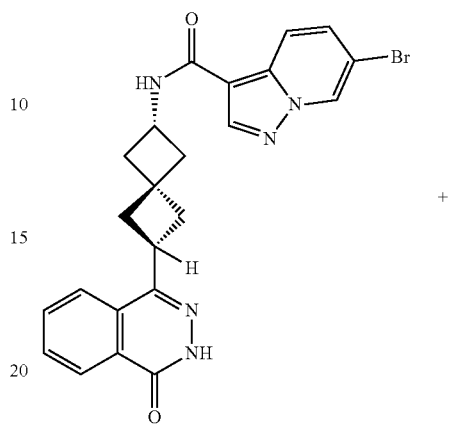

+

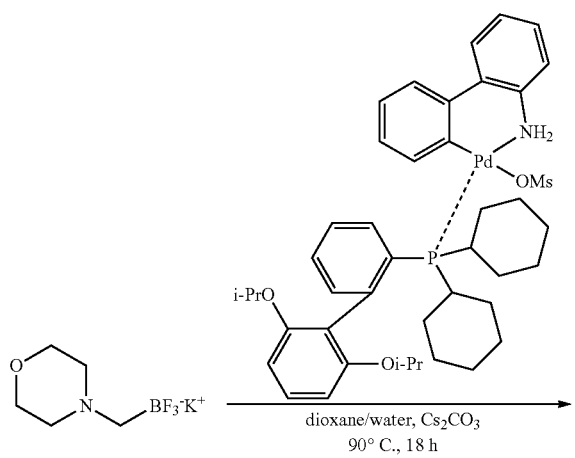

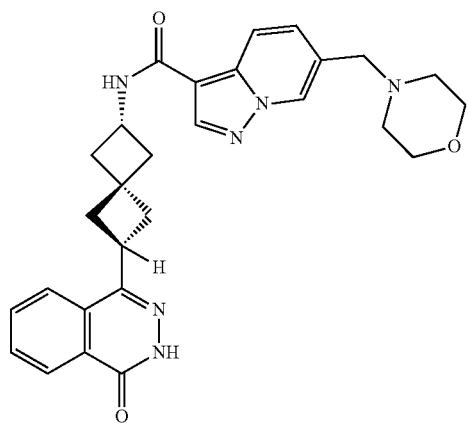

A pressure vial was charged with Intermediate 70, potassium (morpholinomethyl)trifluoroborate (13 mg, 0.063 mmol), RuPhos-Pd G3 (2.6 mg, 3.1 µmol) and cesium carbonate (30.7 mg, 0.094 mmol). The mixture was degassed (3×, vacuum/Ar). Then Dioxane (1 mL) and water (0.100 mL) were added, and the reaction mixture was degassed again. The pressure vial was capped, and the reaction mixture was stirred at 90° C. for 18 h. The reaction mixture was acidified with TFA, solvent was removed under reduced pressure, the residue was suspended in DMF, filtered, and purified by preparative HPLC to give Example 200 (8.1 mg, 52% yield). MS(ESI) m/z: 498.9 (M+H)$^+$; $^1$H NMR (500 MHz, DMSO-d$_6$) δ ppm 12.43 (s, 1H), 8.90 (s, 1H), 8.60 (s, 1H), 8.35 (br d, J=7.3 Hz, 1H), 8.21 (br t, J=8.5 Hz, 2H), 7.92-7.86 (m, 1H), 7.86-7.82 (m, 1H), 7.82-7.73 (m, 1H), 7.50 (br d, J=9.2 Hz, 1H), 4.39-4.29 (m, 3H), 3.87 (quin, J=8.3 Hz, 1H), 2.60 (br s, 1H), 2.46 (br s, 6H), 2.41-2.28 (m, 3H), 2.25-2.14 (m, 2H), 2.01 (br t, J=9.9 Hz, 1H). HPLC RT=E: 1.14; F: 1.44.

The following Examples in Table 13 were prepared by using a similar procedure as shown in Example 200 by reacting Intermediate 70 with the appropriate potassium trifluoroborates/boronic acids/boronate esters.

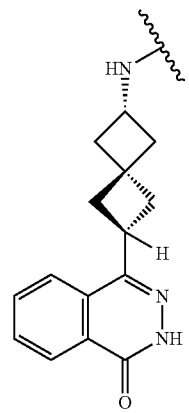

TABLE 13

| Ex. | R | Name |
|---|---|---|
| 201 | | 6-((4-methylpiperazin-1-yl)methyl)-N-((aR)-6-(4-oxo-3,4-dihydrophthalazin-1-yl)spiro[3.3]heptan-2-yl)pyrazolo[1,5-a]pyridine-3-carboxamide |
| 202 | | N-((aR)-6-(4-oxo-3,4-dihydrophthalazin-1-yl)spiro[3.3]heptan-2-yl)-6-(piperidin-1-ylmethyl)pyrazolo[1,5-a]pyridine-3-carboxamide |
| 203 | | 6-((dimethylamino)methyl)-N-((aR)-6-(4-oxo-3,4-dihydrophthalazin-1-yl)spiro[3.3]heptan-2-yl)pyrazolo[1,5-a]pyridine-3-carboxamide |
| 204 | | 6-benzyl-N-((aR)-6-(4-oxo-3,4-dihydrophthalazin-1-yl)spiro[3.3]heptan-2-yl)pyrazolo[1,5-a]pyridine-3-carboxamide |
| 205 | | 6-(3-morpholino-3-oxopropyl)-N-((aR)-6-(4-oxo-3,4-dihydrophthalazin-1-yl)spiro[3.3]heptan-2-yl)pyrazolo[1,5-a]pyridine-3-carboxamide |
| 206 | | N-((aR)-6-(4-oxo-3,4-dihydrophthalazin-1-yl)spiro[3.3]heptan-2-yl)-6-(3,3,3-trifluoropropyl)pyrazolo[1,5-a]pyridine-3-carboxamide |

TABLE 13-continued

| | | |
|---|---|---|
| 207 | | 6-(2-cyanoethyl)-N-((aR)-6-(4-oxo-3,4-dihydrophthalazin-1-yl)spiro[3.3]heptan-2-yl)pyrazolo[1,5-a]pyridine-3-carboxamide |
| 208 | | 6-((2-morpholinoethoxy)methyl)-N-((aR)-6-(4-oxo-3,4-dihydrophthalazin-1-yl)spiro[3.3]heptan-2-yl)pyrazolo[1,5-a]pyridine-3-carboxamide |
| 209 | | 6-(methoxymethyl)-N-((aR)-6-(4-oxo-3,4-dihydrophthalazin-1-yl)spiro[3.3]heptan-2-yl)pyrazolo[1,5-a]pyridine-3-carboxamide |
| 210 | | 6-(2-methoxypyrimidin-5-yl)-N-((aR)-6-(4-oxo-3,4-dihydrophthalazin-1-yl)spiro[3.3]heptan-2-yl)pyrazolo[1,5-a]pyridine-3-carboxamide |
| 211 | | N-((aR)-6-(4-oxo-3,4-dihydrophthalazin-1-yl)spiro[3.3]heptan-2-yl)-6-(((tetrahydro-2H-pyran-4-yl)methoxy)methyl)pyrazolo[1,5-a]pyridine-3-carboxamide |

| Ex. | LCMS (M + H)+ | HPLC Method, RT (min.) | 1H NMR |
|---|---|---|---|
| 201 | 512.1 | E: 1.10<br>F: 1.25 | 1H NMR: (500 MHz, DMSO-d6) δ ppm 12.43 (s, 1H), 8.58 (s, 1H), 8.48 (s, 1H), 8.24 (br d, J = 7.3 Hz, 1H), 8.21 (br d, J = 7.9 Hz, 1H), 8.09 (d, J = 8.9 Hz, 1H), 7.91-7.86 (m, 1H), 7.83 (d, J = 8.2 Hz, 1H), 7.81-7.74 (m, 1H), 7.36 (br d, J = 8.9 Hz, 1H), 4.38-4.28 (m, 1H), 3.86 (br t, J = 8.4 Hz, 1H), 3.47 (s, 1H), 2.59 (br s, 1H), 2.35 (br dd, J = 22.6, 9.2 Hz, 9H), 2.18 (br d, J = 9.5 Hz, 2H), 2.14 (s, 3H), 2.04-1.94 (m, 1H), 1.86 (s, 2H) |
| 202 | 497.1 | E: 1.29<br>F: 1.44 | 1H NMR: (500 MHz, DMSO-d6) δ ppm 12.44 (s, 1H), 8.91 (s, 1H), 8.60 (s, 1H), 8.35 (br d, J = 7.6 Hz, 1H), 8.21 (br t, J = 9.5 Hz, 2H), 7.92-7.86 (m, 1H), 7.83 (d, J = 8.4 Hz, 1H), 7.82-7.76 (m, 1H), 7.50 (br d, J = 8.9 Hz, 1H), 4.39-4.33 (m, 1H), 4.32 (br s, 2H), 3.87 (quin, J = 8.3 Hz, 1H), 2.60 (br s, 1H), 2.56-2.51 (m, 1H), 2.46 (br s, 6H), 2.41-2.28 (m, 3H), 2.25-2.14 (m, 2H), 2.01 (br t, J = 9.9 Hz, 1H), 1.77 (br s, 2H), 1.61 (br s, 2H) |
| 203 | 457.1 | E: 1.22<br>F: 1.31 | 1H NMR: (500 MHz, DMSO-d6) δ ppm 12.43 (s, 1H), 8.92 (s, 1H), 8.60 (s, 1H), 8.36 (br d, J = 7.6 Hz, 1H), 8.21 (t, J = 8.1 Hz, 2H), 7.92-7.86 (m, 1H), 7.85-7.82 (m, 1H), 7.82-7.76 (m, 1H), 7.50 (br d, J = 9.2 Hz, 1H), 4.38-4.33 (m, 1H), 4.32 (br s, 2H), 3.87 (br t, J = 8.2 Hz, 1H), 2.74 (s, 6H), 2.60 (br s, 1H), 2.41-2.30 (m, 3H), 2.24-2.14 (m, 2H), 2.01 (br t, J = 10.1 Hz, 1H) |
| 204 | 490.1 | E: 1.84<br>F: 2.02 | 1H NMR: (500 MHz, DMSO-d6) δ ppm 12.47 (s, 1H), 8.67 (s, 1H), 8.50 (s, 1H), 8.31-8.21 (m, 2H), 8.09 (br d, J = 9.2 Hz, 1H), 7.96-7.89 (m, 1H), 7.89-7.85 (m, 1H), 7.85-7.78 (m, 1H), 7.30 (br d, J = 4.3 Hz, 5H), 7.22 (br d, J = 4.3 Hz, 1H), 4.42-4.30 (m, 1H), 3.99 (s, 2H), 3.90 (br t, J = 8.4 Hz, 1H), 2.62 (br s, 1H), 2.44-2.30 (m, 3H), 2.27-2.14 (m, 2H), 2.04 (br t, J = 9.9 Hz, 1H) |
| 205 | 541.1 | E: 1.41<br>F: 1.38 | 1H NMR: (500 MHz, DMSO-d6) δ ppm 12.43 (s, 1H), 8.57 (s, 1H), 8.45 (s, 1H), 8.22 (br d, J = 7.6 Hz, 2H), 8.05 (br d, J = 9.2 Hz, 1H), 7.92-7.86 (m, 1H), 7.86-7.82 (m, 1H), 7.82-7.75 (m, 1H), 7.36 (br d, J = 9.2 Hz, 1H), 4.42-4.27 (m, 1H), 3.86 (br t, J = 7.9 Hz, 1H), 3.47 (br s, 3H), 3.40 (br s, 1H), 2.87-2.77 (m, 2H), 2.71-2.63 (m, 2H), 2.59 (br s, 1H), 2.46 (br s, 4H), 2.41-2.27 (m, 3H), 2.25-2.12 (m, 2H), 2.05-1.96 (m, 1H) |
| 206 | 496.1 | E: 1.81<br>F: 1.81 | 1H NMR: (500 MHz, DMSO-d6) δ ppm 12.43 (s, 1H), 8.68 (s, 1H), 8.48 (s, 1H), 8.24 (br d, J = 7.6 Hz, 1H), 8.21 (br d, J = 7.9 Hz, 1H), 8.08 (br d, J = 9.2 Hz, 1H), 7.91-7.85 (m, 1H), 7.85-7.82 (m, 1H), 7.82-7.76 (m, 1H), 7.41 (br d, J = 9.5 Hz, 1H), 4.39- |

TABLE 13-continued

| | | | |
|---|---|---|---|
| | | | 4.27 (m, 1H), 3.87 (br t, J = 8.4 Hz, 1H), 2.89-2.81 (m, 2H), 2.70-2.56 (m, 3H), 2.56-2.51 (m, 1H), 2.40-2.28 (m, 3H), 2.24-2.13 (m, 2H), 2.05-1.96 (m, 1H) |
| 207 | 453.3 | E: 1.37 F: 1.43 | $^1$H NMR: (500 MHz, DMSO-$d_6$) δ ppm 12.43 (s, 1H), 8.68 (s, 1H), 8.49 (s, 1H), 8.26 (br d, J = 7.3 Hz, 1H), 8.21 (br d, J = 7.9 Hz, 1H), 8.10 (d, J = 9.2 Hz, 1H), 7.91-7.85 (m, 1H), 7.85-7.82 (m, 1H), 7.82-7.73 (m, 1H), 7.40 (br d, J = 9.2 Hz, 1H), 4.38-4.28 (m, 1H), 3.87 (br t, J = 8.4 Hz, 1H), 2.91 (br d, J = 6.4 Hz, 2H), 2.87 (br d, J = 6.4 Hz, 2H), 2.64-2.56 (m, 1H), 2.56-2.51 (m, 1H), 2.44-2.28 (m, 3H), 2.24-2.12 (m, 2H), 2.07-1.97 (m, 1H) |
| 208 | 543 | E: 1.05 F: 1.22 | $^1$H NMR: (500 MHz, DMSO-$d_6$) δ ppm 12.50 (s, 1H), 8.80 (s, 1H), 8.57 (s, 1H), 8.34 (br d, J = 7.2 Hz, 1H), 8.25 (d, J = 7.7 Hz, 1H), 8.19 (br d, J = 9.1 Hz, 1H), 7.97-7.90 (m, 1H), 7.90-7.86 (m, 1H), 7.86-7.79 (m, 1H), 7.45 (br d, J = 9.3 Hz, 1H), 4.59 (s, 2H), 4.43-4.31 (m, 1H), 3.96-3.85 (m, 2H), 2.69-2.60 (m, 1H), 2.54 (s, 8H), 2.44-2.32 (m, 3H), 2.29-2.17 (m, 2H), 2.04 (br t, J = 10.1 Hz, 1H) |
| 209 | 444.3 | E: 1.38 F: 1.28 | $^1$H NMR: (500 MHz, DMSO-$d_6$) δ ppm 12.49 (s, 1H), 8.72 (s, 1H), 8.55 (s, 1H), 8.33 (br d, J = 7.4 Hz, 1H), 8.25 (br d, J = 7.9 Hz, 1H), 8.16 (br d, J = 9.1 Hz, 1H), 7.41 (br d, J = 9.1 Hz, 1H), 4.46 (s, 2H), 4.42-4.30 (m, 1H), 3.90 (br t, J = 8.4 Hz, 1H), 3.48 (br s, 3H), 2.68-2.56 (m, 2H), 2.44-2.30 (m, 3H), 2.28-2.15 (m, 2H), 2.04 (br t, J = 10.0 Hz, 1H) |
| 210 | 508.1 | E: 1.46 F: 1.52 | $^1$H NMR: (500 MHz, DMSO-$d_6$) δ ppm 12.47 (s, 1H), 9.25 (s, 1H), 9.05 (s, 2H), 8.62 (s, 1H), 8.36 (br d, J = 7.3 Hz, 1H), 8.30-8.21 (m, 2H), 7.97-7.81 (m, 4H), 4.44-4.35 (m, 1H), 3.98 (s, 3H), 3.95-3.85 (m, 1H), 2.69-2.55 (m, 2H), 2.45-2.33 (m, 3H), 2.30-2.17 (m, 2H), 2.07 (br t, J = 10.1 Hz, 1H) |
| 211 | 528.2 | E: 1.57 F: 1.63 | $^1$H NMR: (500 MHz, DMSO-$d_6$) δ ppm 12.43 (s, 1H), 8.66 (s, 1H), 8.51 (s, 1H), 8.26 (br d, J = 7.6 Hz, 1H), 8.22 (br d, J = 7.6 Hz, 1H), 8.13 (br d, J = 9.2 Hz, 1H), 7.93-7.86 (m, 1H), 7.86-7.82 (m, 1H), 7.82-7.75 (m, 1H), 7.37 (br d, J = 9.2 Hz, 1H), 4.47 (s, 2H), 4.39-4.25 (m, 1H), 3.87 (br t, J = 8.2 Hz, 1H), 3.32-3.17 (m, 2H), 2.59 (br s, 1H), 2.41-2.28 (m, 3H), 2.25-2.12 (m, 2H), 2.06-1.97 (m, 1H), 1.78 (br s, 1H), 1.54 (br d, J = 12.8 Hz, 2H), 1.23-1.05 (m, 2H) |

Example 212: 6-((allyloxy)methyl)-N-((aR)-6-(4-oxo-3,4-dihydrophthalazin-1-yl)spiro[3.3]heptan-2-yl)pyrazolo[1,5-a]pyridine-3-carboxamide

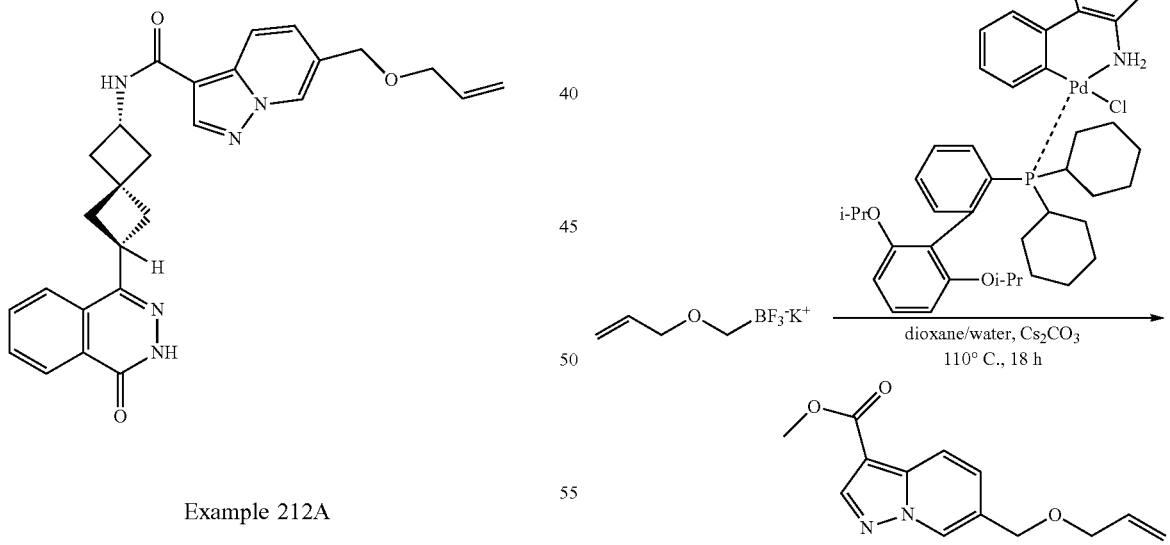

Example 212A methyl 6-((allyloxy)methyl)pyrazolo[1,5-a]pyridine-3-carboxylate

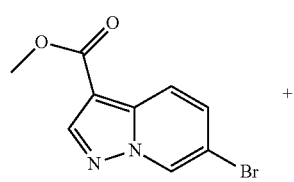

A pressure vial was charged with methyl 6-bromopyrazolo[1,5-a]pyridine-3-carboxylate (200 mg, 0.784 mmol), potassium (allyloxy)methyltrifluoroborate (181 mg, 1.02 mmol), RuPhos-Pd G2 (30.5 mg, 0.039 mmol) and cesium carbonate (766 mg, 2.35 mmol). The mixture was degassed (3×, vacuum/Ar). Then dioxane (4 mL) and water (0.4 mL) were added, and the reaction mixture was degassed again. The pressure vial was capped, and the reaction mixture was stirred at 110° C. for 18 h. The reaction mixture was diluted with EtOAc (100 mL), and CELITE® was added. Solvent was removed under reduced pressure and the residue was purified by flash chromatography (solid loading on CELITE®) to give Example 212A (112 mg, 58% yield) as a colorless oil. MS(ESI) m/z: 247.0 (M+H)⁺; ¹H NMR (500 MHz, DMSO-d₆) δ ppm 8.84 (d, J=0.8 Hz, 1H), 8.45 (s, 1H), 8.07 (dd, J=9.1, 0.8 Hz, 1H), 7.60 (dd, J=9.1, 1.4 Hz, 1H), 5.95 (ddt, J=17.3, 10.6, 5.3 Hz, 1H), 5.31 (dq, J=17.2, 1.8 Hz, 1H), 5.19 (dq, J=10.5, 1.6 Hz, 1H), 4.57 (s, 2H), 4.05 (dt, J=5.4, 1.4 Hz, 2H), 3.83 (s, 3H).

Example 212B 6-((allyloxy)methyl)pyrazolo[1,5-a]pyridine-3-carboxylic acid

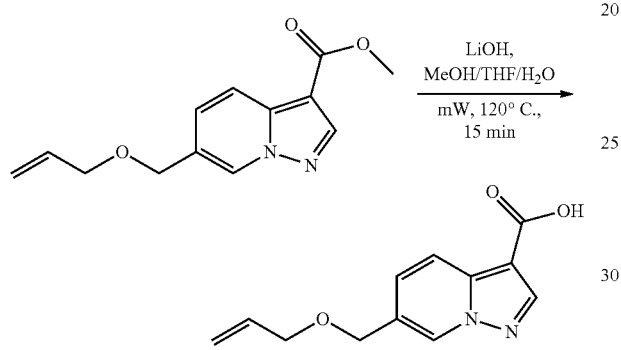

Example 212A (112 mg, 0.455 mmol) was dissolved in MeOH (1.5 mL)/THF (1.5 mL), and LiOH (1 M aq.) (1.364 mL, 1.364 mmol) was added. The reaction mixture was stirred under microwave irradiation at 120° C. for 15 min. The reaction mixture was acidified with TFA, diluted with MeOH, and was purified by preparative HPLC to afford Example 212B (53 mg, 50% yield) as a white solid. MS(ESI) m/z: 233.1 (M+H)⁺; ¹H NMR (500 MHz, DMSO-d₆) δ ppm 12.45 (br s, 1H), 8.81 (s, 1H), 8.38 (s, 1H), 8.06 (d, J=9.1 Hz, 1H), 7.55 (dd, J=9.1, 1.1 Hz, 1H), 5.94 (ddt, J=17.2, 10.5, 5.4 Hz, 1H), 5.31 (dq, J=17.3, 1.7 Hz, 1H), 5.18 (dq, J=10.5, 1.6 Hz, 1H), 4.56 (s, 2H), 4.04 (dt, J=5.4, 1.4 Hz, 2H).

Example 212

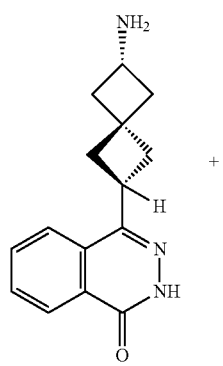

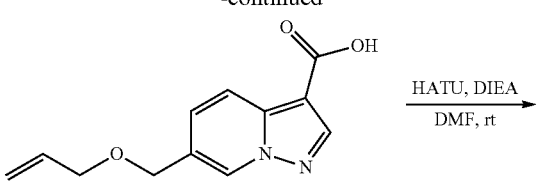

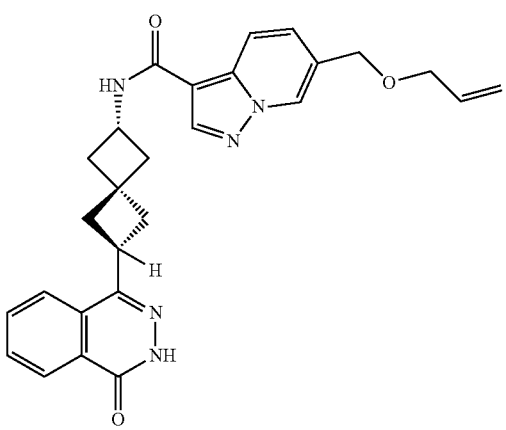

Example 212 was prepared according to the procedure described in Example 14 to afford Example 212 (73 mg, 68% yield) as a colorless glass, which solidified upon standing. MS(ESI) m/z: 470.1 (M+H)⁺; ¹H NMR (500 MHz, DMSO-d₆) δ ppm 12.46 (s, 1H), 8.74-8.68 (m, 1H), 8.55 (s, 1H), 8.32-8.23 (m, 2H), 8.17 (dd, J=9.1, 0.8 Hz, 1H), 7.95-7.90 (m, 1H), 7.90-7.86 (m, 1H), 7.86-7.80 (m, 1H), 7.43 (dd, J=9.2, 1.5 Hz, 1H), 5.94 (ddt, J=17.2, 10.5, 5.4 Hz, 1H), 5.30 (dq, J=17.3, 1.7 Hz, 1H), 5.18 (dq, J=10.5, 1.6 Hz, 1H), 4.53 (s, 2H), 4.44-4.31 (m, 1H), 4.06-4.00 (m, 3H), 3.91 (quin, J=8.5 Hz, 1H), 2.68-2.55 (m, 2H), 2.46-2.33 (m, 3H), 2.29-2.17 (m, 2H).

Example 213: 6-(hydroxymethyl)-N-((aR)-6-(4-oxo-3,4-dihydrophthalazin-1-yl)spiro[3.3]heptan-2-yl)pyrazolo[1,5-a]pyridine-3-carboxamide

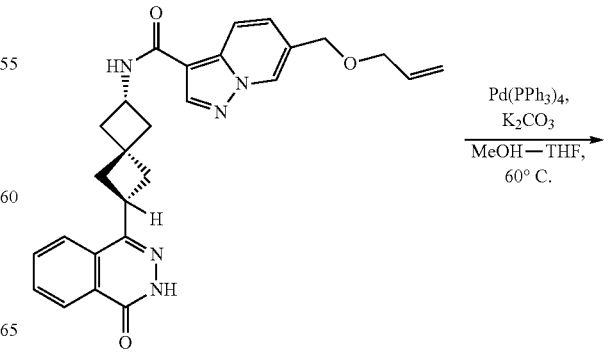

357

-continued

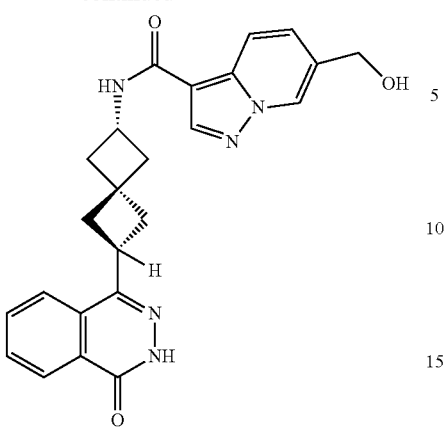

Example 212 (15 mg, 0.032 mmol) was dissolved in THF (0.5 mL) and MeOH (1.5 mL), then Pd(PPh₃)₄ (9.2 mg, 8.0 µmol) was added. The slightly yellow solution was stirred at rt for 5 min, then potassium carbonate (13 mg, 0.096 mmol) was added. The reaction mixture was stirred at 60° C. for 3 h. The reaction mixture was acidified with TFA. Solvent was removed under reduced pressure, the residue was diluted with DMF, filtered, and purified by preparative HPLC to afford Example 213 (12.3 mg, 90% yield). MS(ESI) m/z: 429.9 (M+H)⁺; ¹H NMR (500 MHz, DMSO-d₆) δ ppm 12.43 (s, 1H), 8.56 (s, 1H), 8.49 (s, 1H), 8.22 (br t, J=7.6 Hz, 2H), 8.11 (br d, J=9.2 Hz, 1H), 7.92-7.86 (m, 1H), 7.86-7.82 (m, 1H), 7.82-7.75 (m, 1H), 7.37 (br d, J=8.9 Hz, 1H), 4.51 (br d, J=5.5 Hz, 2H), 4.39-4.28 (m, 1H), 3.87 (br t, J=8.4 Hz, 1H), 2.60 (br s, 1H), 2.41-2.28 (m, 3H), 2.26-2.13 (m, 2H), 2.06-1.96 (m, 1H). HPLC RT=E: 1.28; F: 1.26. HPLC RT=E: 1.66; F: 1.64.

Example 214: 6-acetyl-N-((aR)-6-(4-oxo-3,4-dihydrophthalazin-1-yl)spiro[3.3]heptan-2-yl)pyrazolo[1,5-a]pyridine-3-carboxamide

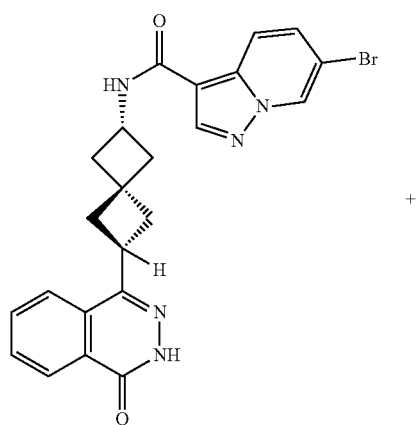

358

-continued

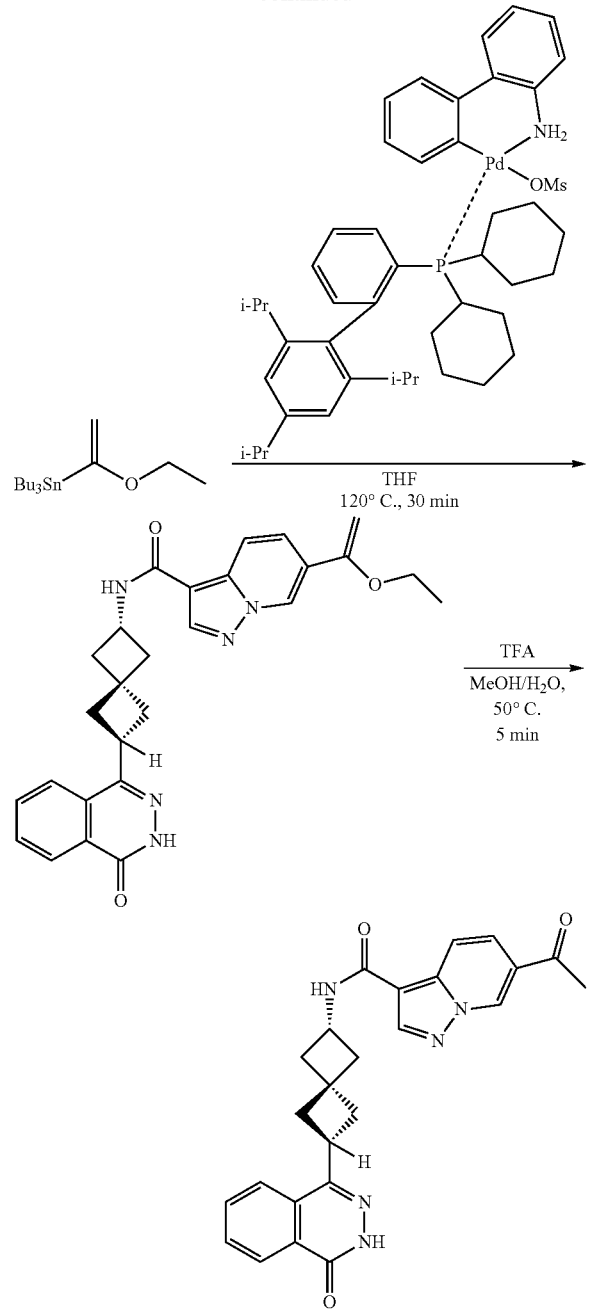

Intermediate 70 (50 mg, 0.105 mmol) and Pd-XPhos G3 (6.6 mg, 7.8 µmol) were placed in a pressure vial. Then THF (2 mL) and tributyl(1-ethoxyvinyl)stannane (0.106 mL, 0.314 mmol) were added, and the reaction mixture was degassed (3×, vacuum/Ar). The pressure vial was capped, and the reaction mixture was stirred at 120° C. for 30 min. Most of the solvent was removed under reduced pressure, the obtained residue was dissolved with wet MeOH (2 mL), and TFA (0.040 mL, 0.52 mmol) was added. The reaction mixture was heated at 50° C. for 5 min. Solvent was removed under reduced pressure, the residue was purified by preparative HPLC to afford Example 214 (23 mg, 49% yield). MS(ESI) m/z: 442.1 (M+H)⁺; ¹H NMR (500 MHz, DMSO-d₆) δ ppm 12.46 (s, 1H), 9.51 (s, 1H), 8.74 (s, 1H), 8.41 (d, J=7.4 Hz, 1H), 8.26 (d, J=8.0 Hz, 1H), 8.22 (d, J=9.4

Hz, 1H), 7.95-7.90 (m, 1H), 7.89-7.86 (m, 1H), 7.86-7.79 (m, 2H), 4.39 (dq, J=16.0, 8.0 Hz, 1H), 3.91 (quin, J=8.5 Hz, 1H), 2.65 (s, 3H), 2.61-2.54 (m, 1H), 2.46-2.36 (m, 3H), 2.29-2.20 (m, 2H), 2.10-2.02 (m, 1H). HPLC RT=E: 1.46; F: 1.47. HPLC RT=A: 6.89; B: 7.14.

Example 215: 6-(2-hydroxypropan-2-yl)-N-((aR)-6-(4-oxo-3,4-dihydrophthalazin-1-yl)spiro[3.3]heptan-2-yl)pyrazolo[1,5-a]pyridine-3-carboxamide

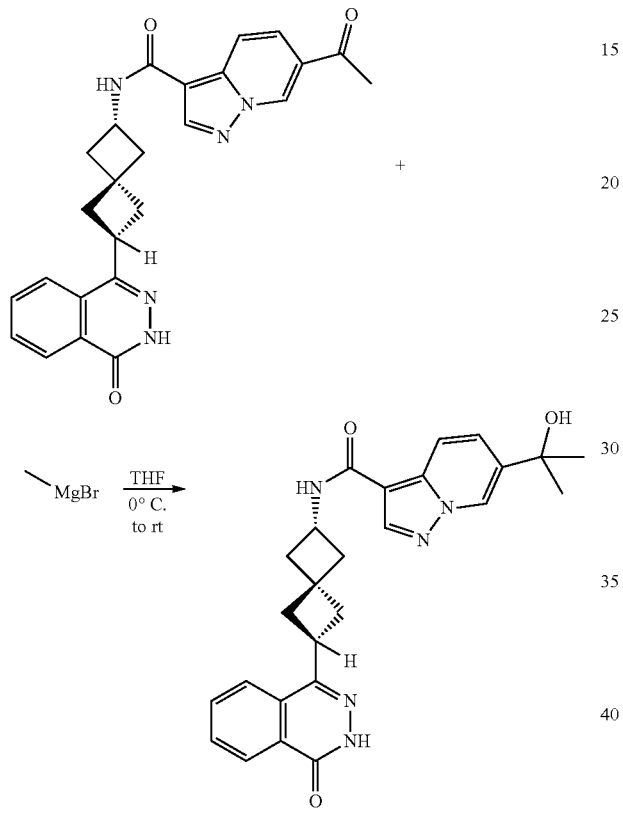

Methylmagnesium bromide (3 M in Et₂O) (0.076 mL, 0.23 mmol) was added to anhydrous THF (1 mL), and the reaction mixture was cooled to 0° C. To this mixture, a solution/suspension of Example 214 (10 mg, 0.023 mmol) in anhydrous THF (1 mL), was added in one portion. The reaction mixture was stirred at 0° C. for 15 min, and then was allowed to reach rt within 1 h. Additional amount of methylmagnesium bromide (3 M in Et₂O) (0.076 mL, 0.227 mmol) was added, and the reaction mixture was stirred at rt for additional 16 h. The reaction mixture was cooled to rt, and quenched with MeOH (1 mL). Solvent was removed under reduced pressure, the residue was triturated with DMF (2 mL), filtered, and purified by preparative HPLC to afford Example 215 (3.5 mg, 34% yield) was obtained. MS(ESI) m/z: 458.1 (M+H)⁺; ¹H NMR (500 MHz, DMSO-d₆) δ ppm 12.47 (s, 1H), 8.59 (s, 1H), 8.52 (s, 1H), 8.26 (br t, J=8.7 Hz, 2H), 8.11 (d, J=9.2 Hz, 1H), 7.95-7.90 (m, 1H), 7.89-7.85 (m, 1H), 7.85-7.79 (m, 1H), 7.56 (br d, J=9.5 Hz, 1H), 4.43-4.31 (m, 1H), 3.95-3.85 (m, 1H), 2.63 (br s, 1H), 2.44-2.31 (m, 4H), 2.28-2.17 (m, 3H), 2.09-2.01 (m, 1H), 1.48 (s, 6H). HPLC RT=E: 1.46; F: 1.47.

Example 216: 6-(1,5-dimethyl-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide

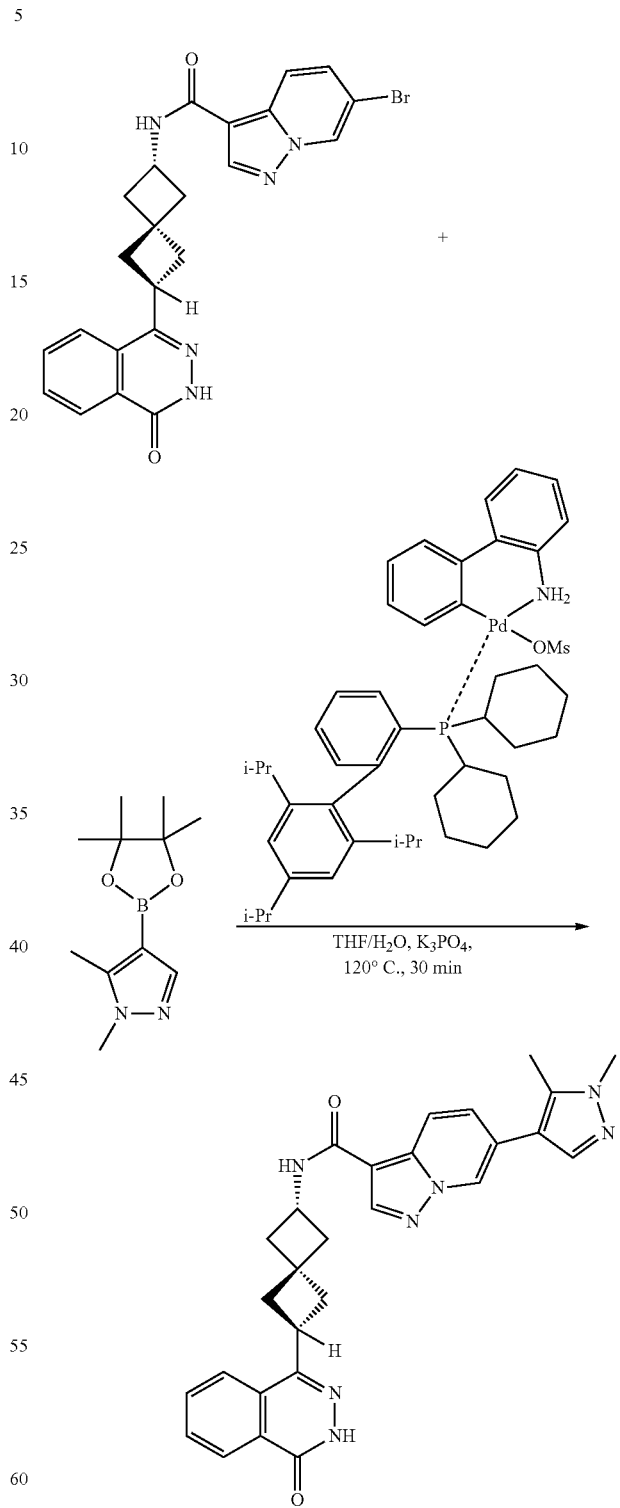

Intermediate 70 (15 mg, 0.031 mmol), 1,5-dimethyl-4-(4,4,5,5-tetramethyl-1,3,2-dioxaborolan-2-yl)-1H-pyrazole (20.9 mg, 0.094 mmol) and Pd-XPhos G3 (2.0 mg, 2.4 μmol) were placed in a pressure vial. Then THF (1.25 mL) and Phosphoric acid, potassium salt (0.5 M aq.) (0.125 mL, 0.063 mmol) were added, and the reaction mixture was degassed (3×, vacuum/Ar). The pressure vial was capped, and the reaction mixture was stirred at 120° C. for 30 min. Most of the solvent was removed under reduced pressure, the obtained residue was diluted with DMF (2 mL), filtered and purified by preparative HPLC to provide Example 216 (14.6 mg, 87% yield) was obtained. MS(ESI) m/z: 494.0 (M+H)$^+$; $^1$H NMR (500 MHz, DMSO-d$_6$) δ ppm 12.47 (s, 1H), 8.71 (s, 1H), 8.54 (s, 1H), 8.30 (br d, J=7.6 Hz, 1H), 8.26 (d, J=7.6 Hz, 1H), 8.18 (d, J=9.2 Hz, 1H), 8.03 (s, 1H), 7.97-7.90 (m, 1H), 7.90-7.86 (m, 1H), 7.86-7.80 (m, 1H), 7.56 (d, J=9.2 Hz, 1H), 4.45-4.32 (m, 1H), 3.91 (quin, J=8.4 Hz, 1H), 3.80 (s, 3H), 2.68-2.61 (m, 1H), 2.60-2.55 (m, 1H), 2.45-2.35 (m, 3H), 2.33 (s, 3H), 2.29-2.14 (m, 2H), 2.06 (br t, J=10.1 Hz, 1H). HPLC RT=E: 1.50; F: 1.53.

The following Examples in Table 14 were prepared by using a similar procedure as shown in Example 216 by reacting Intermediate 70 with the appropriate boronic acids/boronate esters/potassium trifluoroborates.

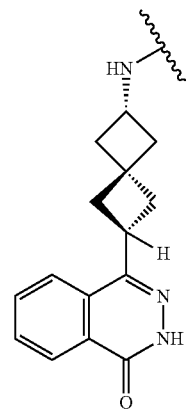

TABLE 14

| Ex. | R | Name |
|---|---|---|
| 217 |  | 6-(1-cyclopropyl-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide |
| 218 |  | 6-(1-(cyclopropylmethyl)-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide |
| 219 |  | 6-(1-(($^2$H$_3$)methyl-1H-pyrazol-4-yl)-N-((aR)-6-(4-oxo-3,4-dihydrophthalazin-1-yl)spiro[3.3]heptan-2-yl)pyrazolo[1,5-c]pyridine-3-carboxamide |
| 220 |  | 6-(1-isopropyl-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide |
| 221 |  | N-((aR)-6-(4-oxo-3,4-dihydrophthalazin-1-yl)spiro[3.3]heptan-2-yl)-6-(1,3,5-trimethyl-1H-pyrazol-4-yl)pyrazolo[1,5-a]pyridine-3-carboxamide |

TABLE 14-continued

| | | | |
|---|---|---|---|
| 222 | 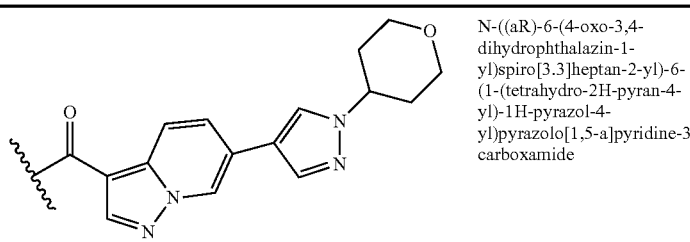 | | N-((aR)-6-(4-oxo-3,4-dihydrophthalazin-1-yl)spiro[3.3]heptan-2-yl)-6-(1-(tetrahydro-2H-pyran-4-yl)-1H-pyrazol-4-yl)pyrazolo[1,5-a]pyridine-3-carboxamide |
| 223 | 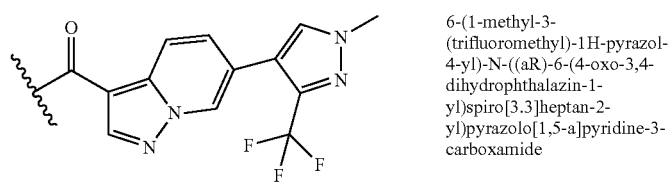 | | 6-(1-methyl-3-(trifluoromethyl)-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide |
| 224 | 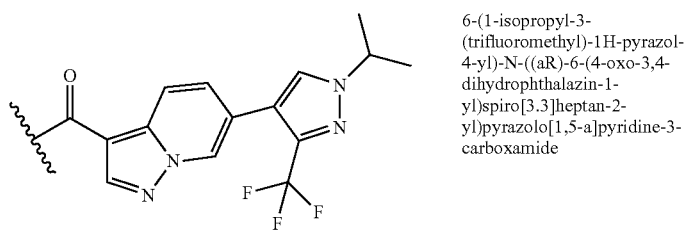 | | 6-(1-isopropyl-3-(trifluoromethyl)-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide |
| 225 | 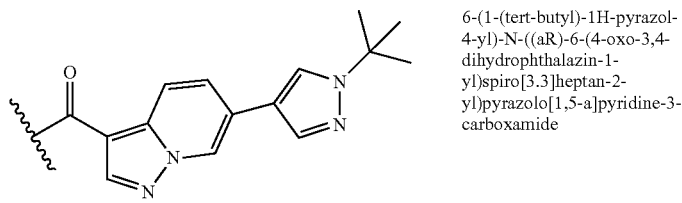 | | 6-(1-(tert-butyl)-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide |
| 226 | 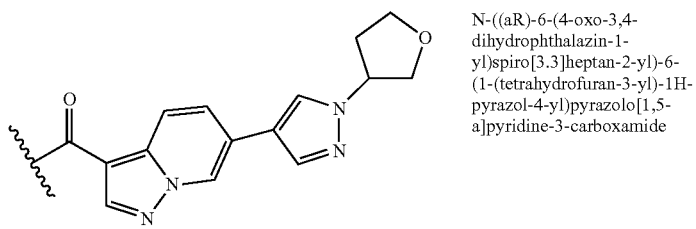 | | N-((aR)-6-(4-oxo-3,4-dihydrophthalazin-1-yl)spiro[3.3]heptan-2-yl)-6-(1-(tetrahydrofuran-3-yl)-1H-pyrazol-4-yl)pyrazolo[1,5-a]pyridine-3-carboxamide |

| Ex. | LCMS (M + H)+ | HPLC Method, RT (min.) | 1H NMR |
|---|---|---|---|
| 217 | 506 | E: 1.62<br>F: 1.63 | 1H NMR: (500 MHz, DMSO-d6) δ ppm 12.47 (s, 1H), 9.05 (s, 1H), 8.52 (s, 1H), 8.38 (s, 1H), 8.29 (br d, J = 7.3 Hz, 1H), 8.26 (d, J = 7.9 Hz, 1H), 8.16 (d, J = 9.2 Hz, 1H), 8.01 (s, 1H), 7.96-7.90 (m, 1H), 7.89-7.86 (m, 1H), 7.86-7.80 (m, 1H), 7.73 (d, J = 9.2 Hz, 1H), 4.43-4.32 (m, 1H), 3.96-3.86 (m, 1H), 3.75 (tt, J = 7.3, 3.7 Hz, 1H), 2.69-2.61 (m, 1H), 2.58 (br t, J = 7.9 Hz, |

TABLE 14-continued

| | | | |
|---|---|---|---|
| | | | 1H), 2.47-2.33 (m, 3H), 2.29-2.18 (m, 2H), 2.05 (br t, J = 10.1 Hz, 1H), 1.11-1.04 (m, 2H), 1.02-0.94 (m, 2H) |
| 218 | 520.1 | E: 1.70<br>F: 1.71 | ¹H NMR: (500 MHz, DMSO-d₆) δ ppm 9.06 (s, 1H), 8.53 (s, 1H), 8.36 (s, 1H), 8.29 (br d, J = 7.6 Hz, 1H), 8.26 (br d, J = 7.6 Hz, 1H), 8.17 (d, J = 9.2 Hz, 1H), 8.03 (s, 1H), 7.96-7.90 (m, 1H), 7.90-7.86 (m, 1H), 7.86-7.80 (m, 1H), 7.73 (d, J = 9.5 Hz, 1H), 4.44-4.33 (m, 1H), 4.00 (d, J = 7.0 Hz, 2H), 3.91 (quin, J = 8.5 Hz, 1H), 2.68-2.61 (m, 1H), 2.58 (br t, J = 8.1 Hz, 1H), 2.45-2.33 (m, 3H), 2.28-2.18 (m, 2H), 2.06 (br t, J = 10.1 Hz, 1H), 1.31-1.24 (m, 1H), 0.56 (br d, J = 7.9 Hz, 2H), 0.40 (br d, J = 4.9 Hz, 2H) |
| 219 | 483 | E: 1.49<br>F: 1.49 | ¹H NMR: (500 MHz, DMSO-d₆) δ ppm 12.47 (s, 1H), 9.03 (s, 1H), 8.52 (s, 1H), 8.29 (br d, J = 7.6 Hz, 1H), 8.27-8.22 (m, 2H), 8.17 (d, J = 9.2 Hz, 1H), 8.01 (s, 1H), 7.95-7.90 (m, 1H), 7.90-7.86 (m, 1H), 7.86-7.80 (m, 1H), 7.70 (d, J = 9.5 Hz, 1H), 4.44-4.33 (m, 1H), 3.91 (quin, J = 8.4 Hz, 1H), 2.68-2.62 (m, 1H), 2.61-2.55 (m, 1H), 2.45-2.32 (m, 3H), 2.30-2.17 (m, 2H), 2.06 (br t, J = 9.9 Hz, 1H) |
| 220 | 508.3 | E: 1.58<br>F: 1.53 | ¹H NMR: (500 MHz, DMSO-d₆) δ ppm 12.49 (s, 1H), 9.05 (s, 1H), 8.38 (s, 1H), 8.32 (br d, J = 7.6 Hz, 1H), 8.25 (d, J = 7.7 Hz, 1H), 8.16 (d, J = 9.1 Hz, 1H), 8.02 (s, 1H), 7.95-7.90 (m, 1H), 7.89-7.86 (m, 1H), 7.86-7.81 (m, 1H), 7.74 (br d, J = 9.3 Hz, 1H), 4.51 (dt, J = 13.3, 6.6 Hz, 1H), 4.43-4.32 (m, 1H), 3.91 (quin, J = 8.4 Hz, 1H), 2.67-2.60 (m, 1H), 2.60-2.55 (m, 1H), 2.45-2.32 (m, 3H), 2.28-2.17 (m, 2H), 2.05 (br t, J = 10.1 Hz, 1H), 1.45 (d, J = 6.6 Hz, 6H) |
| 221 | 508.3 | E: 1.35<br>F: 1.41 | ¹H NMR: (500 MHz, DMSO-d₆) δ ppm 12.49 (s, 1H), 8.61 (s, 1H), 8.56 (s, 1H), 8.33 (d, J = 7.6 Hz, 1H), 8.25 (d, J = 7.8 Hz, 1H), 8.20 (d, J = 9.1 Hz, 1H), 7.96-7.90 (m, 1H), 7.90-7.86 (m, 1H), 7.86-7.81 (m, 1H), 7.39 (d, J = 9.9 Hz, 1H), 4.44-4.33 (m, 1H), 3.95-3.85 (m, 1H), 3.71 (s, 3H), 2.64 (br t, J = 11.5 Hz, 1H), 2.61-2.55 (m, 1H), 2.45-2.32 (m, 3H), 2.24 (s, 4H), 2.15 (s, 3H), 2.05 (br t, J = 10.0 Hz, 1H) |
| 222 | 550.2 | E: 1.54<br>F: 1.59 | ¹H NMR: (500 MHz, DMSO-d₆) δ ppm 12.47 (s, 1H), 9.05 (s, 1H), 8.52 (s, 1H), 8.42 (s, 1H), 8.30 (br d, J = 7.6 Hz, 1H), 8.25 (d, J = 7.9 Hz, 1H), 8.16 (d, J = 9.2 Hz, 1H), 8.05 (s, 1H), 7.95-7.89 (m, 1H), 7.89-7.86 (m, 1H), 7.86-7.80 (m, 1H), 7.74 (d, J = 9.5 Hz, 1H), 4.46-4.32 (m, 2H), 3.97 (br d, J = 9.2 Hz, 2H), 3.91 (quin, J = 8.5 Hz, 1H), 3.53-3.45 (m, 1H), 2.68-2.60 (m, 1H), 2.60-2.55 (m, 1H), 2.45-2.32 (m, 3H), 2.28-2.18 (m, 2H), 2.09-2.00 (m, 3H), 1.99-1.88 (m, 2H) |
| 223 | 548.1 | E: 1.75<br>F: 1.80 | ¹H NMR: (500 MHz, DMSO-d₆) δ ppm 12.47 (s, 1H), 8.74 (s, 1H), 8.60 (s, 1H), 8.37 (br d, J = 7.6 Hz, 1H), 8.27 (s, 1H), 8.26-8.24 (m, 1H), 8.22 (d, J = 9.2 Hz, 1H), 7.95-7.90 (m, 1H), 7.89-7.86 (m, 1H), 7.85-7.80 (m, 1H), 7.45 (br d, J = 8.9 Hz, 1H), 4.44-4.33 (m, 1H), 3.98 (s, 3H), 3.91 (br t, J = 8.4 Hz, 1H), 2.68-2.62 (m, 1H), 2.60-2.55 (m, 1H), 2.45-2.32 (m, 3H), 2.30-2.18 (m, 2H), 2.05 (br t, J = 9.9 Hz, 1H) |
| 224 | 576.1 | E: 1.97<br>F: 2.03 | ¹H NMR: (500 MHz, DMSO-d₆) δ ppm 12.47 (s, 1H), 8.78 (s, 1H), 8.60 (s, 1H), 8.42 (s, 1H), 8.36 (br d, J = 7.6 Hz, 1H), 8.26 (d, J = 7.9 Hz, 1H), 8.23 (d, J = 9.2 Hz, 1H), 7.91 (br d, J = 7.0 Hz, 1H), 7.89-7.86 (m, 1H), 7.85-7.79 (m, 1H), 7.49 (br d, J = 9.2 Hz, 1H), 4.64 (dt, J = 13.2, 6.7 Hz, 1H), 4.44-4.33 (m, 1H), 3.91 (quin, J = 8.5 Hz, 1H), 2.68-2.61 (m, 1H), 2.61-2.55 (m, 1H), 2.46-2.32 (m, 3H), 2.29-2.18 (m, 2H), 2.06 (br t, J = 10.1 Hz, 1H), 1.50 (d, J = 6.4 Hz, 6H) |
| 225 | 522.2 | E: 1.76<br>F: 1.83 | ¹H NMR: (500 MHz, DMSO-d₆) δ ppm 12.47 (s, 1H), 9.07 (s, 1H), 8.52 (s, 1H), 8.46 (s, 1H), 8.29 (br d, J = 7.3 Hz, 1H), 8.26 (d, J = 7.6 Hz, 1H), 8.16 (d, J = 9.2 Hz, 1H), 8.04 (s, 1H), 7.96-7.89 (m, 1H), 7.90-7.86 (m, 1H), 7.85-7.80 (m, 1H), 7.77 (d, J = 9.2 Hz, 1H), 4.43-4.32 (m, 1H), 3.91 (quin, J = 8.5 Hz, 1H), 2.64 (br t, J = 11.4 Hz, 1H), 2.60-2.55 (m, 1H), 2.45-2.32 (m, 3H), 2.30-2.17 (m, 2H), 2.06 (br t, J = 10.1 Hz, 1H), 1.56 (s, 9H) |
| 226 | 536.1 | E: 1.50<br>F: 1.57 | ¹H NMR: (500 MHz, DMSO-d₆) δ ppm 12.47 (s, 1H), 9.07 (s, 1H), 8.52 (s, 1H), 8.40 (s, 1H), 8.30 (br d, J = 7.3 Hz, 1H), 8.25 (br d, J = 7.6 Hz, 1H), 8.16 (d, J = 9.2 Hz, 1H), 8.07 (s, 1H), 7.95-7.89 (m, 1H), 7.90-7.86 (m, 1H), 7.86-7.80 (m, 1H), 7.74 (br d, J = 9.2 Hz, 1H), 5.03 (br s, 1H), 4.43-4.33 (m, 1H), 4.04-3.97 (m, 2H), 3.96-3.88 (m, 2H), 3.86-3.79 (m, 1H), 2.64 (br t, J = 11.3 Hz, 1H), 2.60-2.56 (m, 1H), 2.46-2.36 (m, 4H), 2.35-2.28 (m, 1H), 2.28-2.18 (m, 2H), 2.05 (br t, J = 10.1 Hz, 1H) |

Example 227: 1-(4-bromophenyl)-3-((aR)-6-(4-oxo-3,4-dihydrophthalazin-1-yl)spiro[3.3]heptan-2-yl)urea

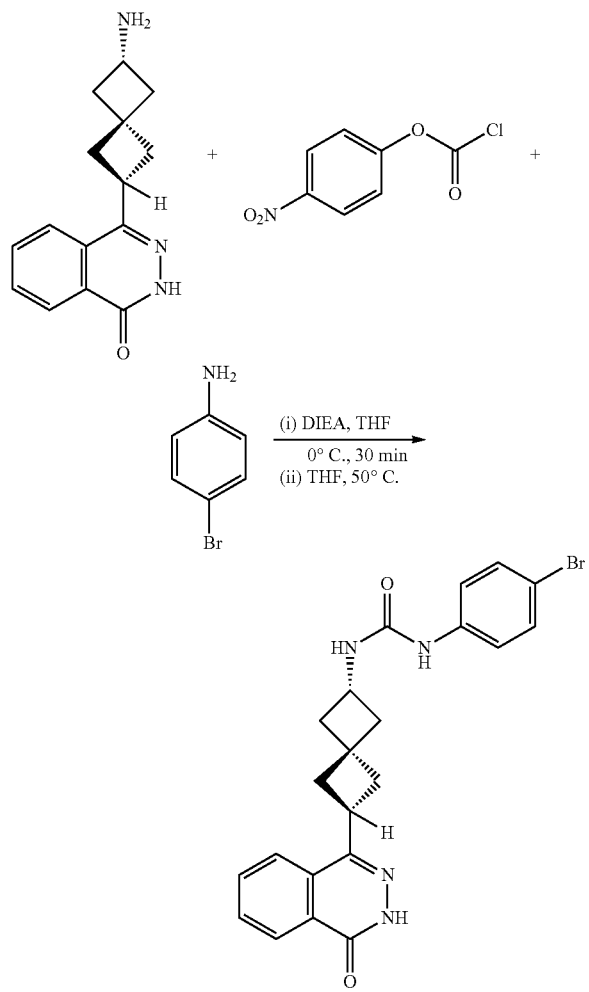

To a suspension of Intermediate 2, HCl (200 mg, 0.685 mmol) in THF (15 mL), was added DIEA (0.299 mL, 1.71 mmol). The reaction mixture was cooled to 0° C., and 4-nitrophenyl carbonochloridate (166 mg, 0.823 mmol) was added in one portion. The reaction mixture was stirred at 0° C. for 30 min. Then, 4-bromoaniline (236 mg, 1.37 mmol) and DIEA (0.299 mL, 1.714 mmol) were added, cooling bath was removed, and the reaction mixture was stirred at 50° C. for 16 h. The reaction mixture was concentrated under reduced pressure, and the residue was purified by flash chromatography (40-100% EtOAc/DCM gradient) to afford Example 227 (244 mg, 79% yield) as a white solid. MS(ESI) m/z: 453.0 (M+H)$^+$; $^1$H NMR: (500 MHz, DMSO-d$_6$) δ ppm 12.47 (s, 1H), 8.48 (s, 1H), 8.24 (br d, J=7.6 Hz, 1H), 7.93-7.87 (m, 1H), 7.86-7.79 (m, 2H), 7.39-7.28 (m, 4H), 6.43 (br d, J=7.6 Hz, 1H), 4.08-3.97 (m, 1H), 3.86 (quin, J=8.4 Hz, 1H), 2.58 (br s, 1H), 2.41-2.27 (m, 3H), 2.23-2.14 (m, 1H), 1.99 (br t, J=9.6 Hz, 1H), 1.82 (br t, J=9.9 Hz, 1H); HPLC RT=1.79 min (E), 1.86 min (F).

The following Examples in Table 15 were prepared by using a similar procedure as shown in Example 216 by reacting Example 227 with the appropriate boronic acids/boronate esters/potassium trifluoroborates.

TABLE 15

| Ex. | R | Name | LCMS (M + H)$^+$ | HPLC Method, RT (min.) | $^1$H NMR |
|---|---|---|---|---|---|
| 228 | (pyrazol-N-methyl) | 1-(4-(1-methyl-1H-pyrazol-4-yl)phenyl)-3-((aR)-6-(4-oxo-3,4-dihydrophthalazin-1-yl)spiro[3.3]heptan-2-yl)urea | 455.4 | E: 1.37 F: 1.35 | $^1$H NMR: (500 MHz, DMSO-d$_6$) δ ppm 12.48 (s, 1H), 8.31 (s, 1H), 8.25 (d, J = 7.8 Hz, 1H), 7.99 (s, 1H), 7.93-7.89 (m, 1H), 7.86 (br d, J = 9.3 Hz, 1H), 7.84-7.80 (m, 1H), 7.74 (s, 1H), 7.42-7.37 (m, 2H), 7.36-7.30 (m, 2H), 6.37 (d, J = 7.8 Hz, 1H), 4.05 (sxt, J = 8.0 Hz, 1H), 3.93-3.85 (m, 1H), 3.83 (s, 3H), 2.66-2.57 (m, 1H), 2.41-2.28 (m, 3H), 2.26-2.17 (m, 1H), 2.00 (br t, J = 9.6 Hz, 1H), 1.86-1.78 (m, 1H) |
| 229 | (pyrazol-N-CD$_3$) | 1-(4-(1-($^2$H$_3$)methyl-1H-pyrazol-4-yl)phenyl)-3-((aR)-6-(4-oxo-3,4-dihydrophthalazin-1-yl)spiro[3.3]heptan-2-yl)urea | 458.2 | E: 1.32 F: 1.33 | $^1$H NMR: (500 MHz, DMSO-d$_6$) δ ppm 12.48 (s, 1H), 8.32 (s, 1H), 8.25 (d, J = 7.7 Hz, 1H), 7.99 (s, 1H), 7.94-7.89 (m, 1H), 7.88-7.80 (m, 2H), 7.74 (s, 1H), 7.42-7.37 (m, 2H), 7.36-7.31 (m, 2H), 6.37 (br d, J = 7.7 Hz, 1H), 4.10-4.00 (m, 1H), 3.93-3.83 (m, 1H), 2.60 (br t, J = 11.4 Hz, 1H), 2.41-2.29 (m, 3H), 2.25-2.17 (m, 1H), 2.00 (br t, J = 9.6 Hz, 1H), 1.82 (br t, J = 9.8 Hz, 1H) |

TABLE 15-continued

| Ex. | R | Name | LCMS (M + H)+ | HPLC Method, RT (min.) | 1H NMR |
|---|---|---|---|---|---|
| 230 | | 1-(4-(1-cyclopropyl-1H-pyrazol-4-yl)phenyl)-3-((aR)-6-(4-oxo-3,4-dihydrophthalazin-1-yl)spiro[3.3]heptan-2-yl)urea | 481.1 | E: 1.47<br>F: 1.49 | 1H NMR: (500 MHz, DMSO-$d_6$) δ ppm 12.48 (s, 1H), 8.32 (s, 1H), 8.25 (d, J = 7.7 Hz, 1H), 8.09 (s, 1H), 7.96-7.89 (m, 1H), 7.88-7.80 (m, 2H), 7.74 (s, 1H), 7.43-7.38 (m, 2H), 7.33 (d, J = 8.5 Hz, 2H), 6.37 (br d, J = 7.8 Hz, 1H), 4.11-3.99 (m, 1H), 3.88 (quin, J = 8.5 Hz, 1H), 3.73-3.66 (m, 1H), 2.64-2.56 (m, 1H), 2.41-2.28 (m, 3H), 2.25-2.16 (m, 1H), 2.00 (br t, J = 9.8 Hz, 1H), 1.82 (br t, J = 9.8 Hz, 1H), 1.08-1.01 (m, 2H), 0.98-0.91 (m, 2H) |
| 231 | | 1-((aR)-6-(4-oxo-3,4-dihydrophthalazin-1-yl)spiro[3.3]heptan-2-yl)-3-(4-(1-(tetrahydro-2H-pyran-4-yl)-1H-pyrazol-4-yl)phenyl)urea | 525.3 | E: 1.41<br>F: 1.42 | 1H NMR: (500 MHz, DMSO-$d_6$) δ ppm 12.48 (s, 1H), 8.32 (s, 1H), 8.25 (d, J = 7.7 Hz, 1H), 8.13 (s, 1H), 7.94-7.89 (m, 1H), 7.88-7.81 (m, 2H), 7.78 (s, 1H), 7.45-7.40 (m, 2H), 7.34 (d, J = 8.6 Hz, 2H), 6.37 (br d, J = 7.8 Hz, 1H), 4.37 (tt, J = 10.4, 5.1 Hz, 1H), 4.11-4.00 (m, 1H), 3.96 (br d, J = 11.1 Hz, 2H), 3.88 (quin, J = 8.5 Hz, 1H), 2.64-2.56 (m, 1H), 2.41-2.28 (m, 3H), 2.26-2.16 (m, 1H), 2.05-1.91 (m, 5H), 1.87-1.77 (m, 1H) |
| 232 | | 1-(4-(1-methyl-3-(trifluoromethyl)-1H-pyrazol-4-yl)phenyl)-3-((aR)-6-(4-oxo-3,4-dihydrophthalazin-1-yl)spiro[3.3]heptan-2-yl)urea | 523.2 | E: 1.65<br>F: 1.65 | 1H NMR: (500 MHz, DMSO-$d_6$) δ ppm 12.48 (s, 1H), 8.44 (s, 1H), 8.25 (d, J = 7.8 Hz, 1H), 8.05 (s, 1H), 7.94-7.89 (m, 1H), 7.88-7.80 (m, 2H), 7.41 (d, J = 8.6 Hz, 2H), 7.23 (d, J = 8.4 Hz, 2H), 6.43 (br d, J = 7.7 Hz, 1H), 4.11-4.01 (m, 1H), 3.93 (s, 3H), 3.90-3.83 (m, 1H), 2.64-2.57 (m, 1H), 2.42-2.29 (m, 3H), 2.25-2.17 (m, 1H), 2.01 (br t, J = 9.6 Hz, 1H), 1.88-1.79 (m, 1H) |
| 233 | | 1-((aR)-6-(4-oxo-3,4-dihydrophthalazin-1-yl)spiro[3.3]heptan-2-yl)-3-(4-(1,3,5-trimethyl-1H-pyrazol-4-yl)phenyl)urea | 483.3 | E: 1.65<br>F: 1.65 | 1H NMR: (500 MHz, DMSO-$d_6$) δ ppm 12.48 (s, 1H), 8.35 (s, 1H), 8.25 (d, J = 7.8 Hz, 1H), 7.95-7.89 (m, 1H), 7.88-7.80 (m, 2H), 7.39 (d, J = 8.5 Hz, 2H), 7.08 (d, J = 8.4 Hz, 2H), 6.39 (d, J = 7.9 Hz, 1H), 4.06 (sxt, J = 8.0 Hz, 1H), 3.93-3.83 (m, 1H), 3.67 (s, 3H), 2.65-2.56 (m, 1H), 2.41-2.28 (m, 3H), 2.25-2.18 (m, 1H), 2.17 (s, 3H), 2.08 (s, 3H), 2.00 (br t, J = 9.6 Hz, 1H), 1.86-1.78 (m, 1H) |

Example 234: 5-Bromo-N-((aR)-6-(4-oxo-3,4-dihydrophthalazin-1-yl)spiro[3.3]heptan-2-yl)indoline-1-carboxamide

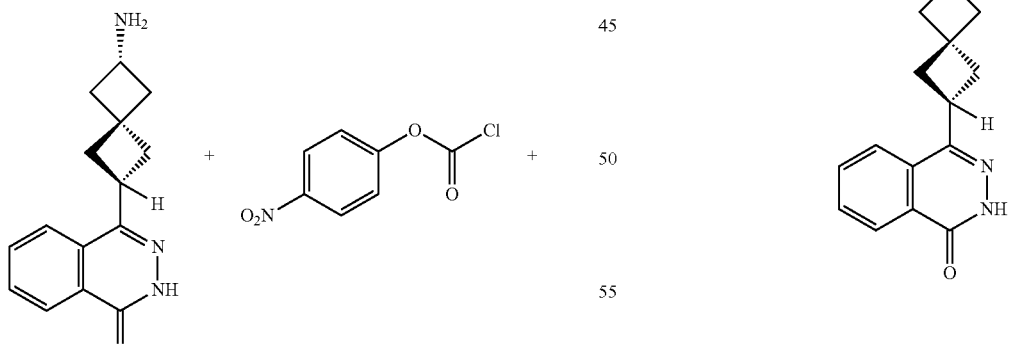

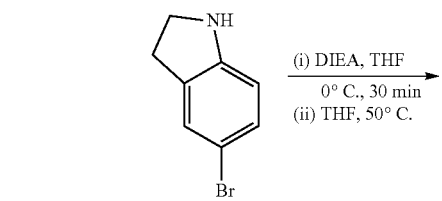

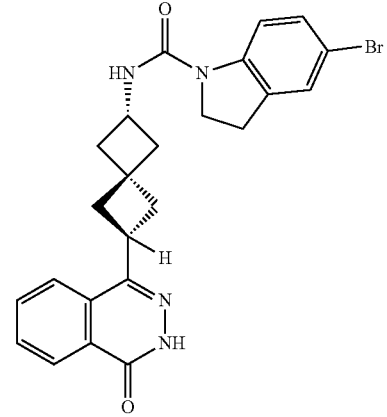

To a suspension of Intermediate 2, HCl (200 mg, 0.685 mmol) in THF (15 mL), was added DIEA (0.299 mL, 1.71 mmol). The reaction mixture was cooled to 0° C., and 4-nitrophenyl carbonochloridate (166 mg, 0.823 mmol) was added in one portion. The reaction mixture was stirred at 0° C. for 30 min. Then, 5-bromoindoline (272 mg, 1.37 mmol) and DIEA (0.299 mL, 1.71 mmol) were added, cooling bath was removed, and the reaction mixture was stirred at 50° C. for 16 h. The reaction mixture was concentrated, and the residue was purified by flash chromatography (30-100% EtOAc/DCM gradient) to afford Example 234 (229 mg, 70% yield) as a white solid. MS(ESI) m/z: 479.0 (M+H)+; 1H NMR: (500 MHz, DMSO-d6) δ ppm 12.48 (s, 1H), 8.27 (d, J=7.9 Hz, 1H), 7.98-7.91 (m, 1H), 7.90-7.81 (m, 2H), 7.74 (d, J=8.5 Hz, 1H), 7.31 (s, 1H), 7.23 (br d, J=8.2 Hz, 1H), 6.78 (br d, J=7.3 Hz, 1H), 4.19-4.05 (m, 1H), 3.90 (br t, J=8.7 Hz, 3H), 3.11 (br t, J=8.7 Hz, 2H), 2.60 (br s, 1H), 2.43-2.29 (m, 3H), 2.19 (q, J=9.8 Hz, 2H), 2.03 (br t, J=10.1 Hz, 1H); HPLC RT=1.97 min (Method E), 2.04 min (Method F).

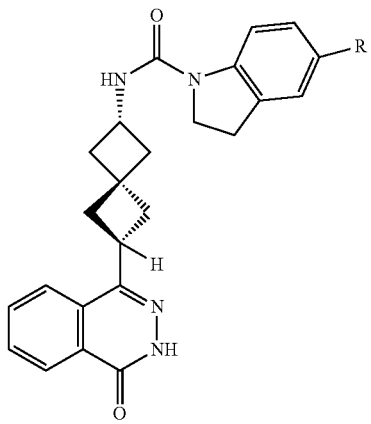

The following Examples in Table 16 were prepared by using a similar procedure as shown in Example 216 by reacting Example 234 with the appropriate boronic acids/boronate esters/potassium trifluoroborates.

TABLE 16

| Ex. | R | Name | LCMS (M + H)+ | HPLC Method, RT (min.) | 1H NMR |
|---|---|---|---|---|---|
| 235 | | 5-(1-methyl-1H-pyrazol-4-yl)-N-((aR)-6-(4-oxo-3,4-dihydrophthalazin-1-yl)spiro[3.3]heptan-2-yl)indoline-1-carboxamide | 481.3 | E: 1.51 F: 1.55 | 1H NMR: (500 MHz, DMSO-d6) δ ppm 12.49 (s, 1H), 8.25 (d, J = 7.8 Hz, 1H), 7.97 (s, 1H), 7.95-7.89 (m, 1H), 7.89-7.80 (m, 2H), 7.77-7.70 (m, 2H), 7.32 (s, 1H), 7.25 (br d, J = 8.3 Hz, 1H), 6.70 (br d, J = 7.4 Hz, 1H), 4.18-4.06 (m, 1H), 3.93-3.83 (m, 3H), 3.82 (s, 3H), 3.09 (br t, J = 8.5 Hz, 2H), 2.58 (br s, 1H), 2.40-2.30 (m, 3H), 2.23-2.12 (m, 2H), 2.06-1.97 (m, 1H) |
| 236 | | 5-(1-cyclopropyl-1H-pyrazol-4-yl)-N-((aR)-6-(4-oxo-3,4-dihydrophthalazin-1-yl)spiro[3.3]heptan-2-yl)indoline-1-carboxamide | 507.3 | E: 1.66 F: 1.70 | 1H NMR: (500 MHz, DMSO-d6) δ ppm 12.49 (s, 1H), 8.25 (d, J = 7.8 Hz, 1H), 8.08 (s, 1H), 7.95-7.90 (m, 1H), 7.88-7.80 (m, 2H), 7.77-7.71 (m, 2H), 7.35 (s, 1H), 7.27 (br d, J = 8.2 Hz, 1H), 6.70 (br d, J = 7.5 Hz, 1H), 4.18-4.08 (m, 1H), 3.93-3.83 (m, 4H), 3.68 (dt, J = 7.3, 3.6 Hz, 1H), 3.09 (br t, J = 8.6 Hz, 2H), 2.59 (br s, 1H), 2.41-2.30 (m, 3H), 2.23-2.11 (m, 2H), 2.02 (br t, J = 10.0 Hz, 1H), 1.06-1.01 (m, 2H), 0.98-0.91 (m, 2H) |
| 237 | | N-((aR)-6-(4-oxo-3,4-dihydrophthalazin-1-yl)spiro[3.3]heptan-2-yl)-5-(1,3,5-trimethyl-1H-pyrazol-4-yl)indoline-1-carboxamide | 509.4 | E: 1.37 F: 1.65 | 1H NMR: (500 MHz, DMSO-d6) δ ppm 12.49 (s, 1H), 8.25 (d, J = 7.8 Hz, 1H), 7.94-7.90 (m, 1H), 7.89-7.77 (m, 3H), 6.99 (s, 1H), 6.91 (br d, J = 8.2 Hz, 1H), 6.71 (br d, J = 7.5 Hz, 1H), 4.19-4.08 (m, 1H), 3.94-3.84 (m, 3H), 3.11 (br t, J = 8.6 Hz, 2H), 2.61-2.55 (m, 1H), 2.41-2.30 (m, 3H), 2.22-2.17 (m, 1H), 2.16 (s, 3H), 2.07 (s, 3H), 2.05-1.97 (m, 1H) |
| 238 | | 5-(1-methyl-3-(trifluoromethyl)-1H-pyrazol-4-yl)-N-((aR)-6-(4-oxo-3,4-dihydrophthalazin-1-yl)spiro[3.3]heptan-2-yl)indoline-1-carboxamide | 549.4 | E: 1.81 F: 1.83 | 1H NMR: (500 MHz, DMSO-d6) δ ppm 12.48 (s, 1H), 8.25 (d, J = 7.7 Hz, 1H), 8.04 (s, 1H), 7.94-7.90 (m, 1H), 7.89-7.78 (m, 3H), 7.14 (s, 1H), 7.09 (br d, J = 8.2 Hz, 1H), 6.76 (d, J = 7.4 Hz, 1H), 4.15 (sxt, J = 8.1 Hz, 1H), 3.92 (s, 3H), 3.92-3.85 (m, 3H), 3.12 (br t, J = 8.6 Hz, 2H), 2.60-2.55 (m, 1H), 2.42-2.32 (m, 3H), 2.24-2.14 (m, 2H) |

TABLE 16-continued

| Ex. | R | Name | LCMS (M + H)+ | HPLC Method, RT (min.) | 1H NMR |
|---|---|---|---|---|---|
| 239 | (pyrazole with N-CD3) | 5-(1-(²H₃)methyl-1H-pyrazol-4-yl)-N-((aR)-6-(4-oxo-3,4-dihydrophthalazin-1-yl)spiro[3.3]heptan-2-yl)indoline-1-carboxamide | 484.2 | E: 1.46 F: 1.47 | 1H NMR: (500 MHz, DMSO-d₆) δ ppm 12.48 (s, 1H), 8.25 (d, J = 7.8 Hz, 1H), 7.98 (s, 1H), 7.94-7.90 (m, 1H), 7.89-7.80 (m, 2H), 7.76 (d, J = 8.3 Hz, 1H), 7.74 (s, 1H), 7.33 (s, 1H), 7.26 (br d, J = 8.2 Hz, 1H), 6.69 (br d, J = 7.4 Hz, 1H), 4.20-4.10 (m, 1H), 3.93-3.84 (m, 3H), 3.10 (br t, J = 8.6 Hz, 2H), 2.59 (br s, 1H), 2.41-2.31 (m, 3H), 2.23-2.12 (m, 2H), 2.06-1.99 (m, 1H) |
| 240 | (pyrazole-tetrahydropyran) | N-((aR)-6-(4-oxo-3,4-dihydrophthalazin-1-yl)spiro[3.3]heptan-2-yl)-5-(1-(tetrahydro-2H-pyran-4-yl)-1H-pyrazol-4-yl)indoline-1-carboxamide | 551.2 | E: 1.59 F: 1.55 | 1H NMR: (500 MHz, DMSO-d₆) δ ppm 12.49 (s, 1H), 8.25 (d, J = 7.7 Hz, 1H), 8.11 (s, 1H), 7.95-7.89 (m, 1H), 7.89-7.80 (m, 2H), 7.79-7.72 (m, 2H), 7.36 (s, 1H), 7.28 (br d, J = 8.3 Hz, 1H), 6.70 (br d, J = 7.4 Hz, 1H), 4.41-4.31 (m, 1H), 4.18-4.08 (m, 1H), 3.95 (br d, J = 10.8 Hz, 2H), 3.88 (td, J = 8.4, 4.2 Hz, 3H), 3.13-3.05 (m, 2H), 2.59 (br s, 1H), 2.41-2.29 (m, 3H), 2.22-2.13 (m, 2H), 2.06-1.88 (m, 5H) |
| 241 | (pyrazole-CH2-cyclopropyl) | 5-(1-(cyclopropylmethyl)-1H-pyrazol-4-yl)-N-((aR)-6-(4-oxo-3,4-dihydrophthalazin-1-yl)spiro[3.3]heptan-2-yl)indoline-1-carboxamide | 521.2 | E: 1.75 F: 1.74 | 1H NMR: (500 MHz, DMSO-d₆) δ ppm 12.49 (s, 1H), 8.25 (d, J = 7.7 Hz, 1H), 8.06 (s, 1H), 7.95-7.90 (m, 1H), 7.89-7.80 (m, 2H), 7.78-7.72 (m, 2H), 7.35 (s, 1H), 7.27 (br d, J = 8.3 Hz, 1H), 6.70 (br d, J = 7.4 Hz, 1H), 4.13 (sxt, J = 7.9 Hz, 1H), 3.93 (d, J = 7.1 Hz, 2H), 3.91-3.83 (m, 3H), 3.14-3.06 (m, 2H), 2.60-2.54 (m, 1H), 2.41-2.29 (m, 3H), 2.23-2.13 (m, 2H), 2.05-1.98 (m, 1H), 1.28-1.19 (m, 1H), 0.56-0.49 (m, 2H), 0.36 (br d, J = 5.0 Hz, 2H) |
| 242 | (pyrazole-tBu) | 5-(1-(tert-butyl)-1H-pyrazol-4-yl)-N-((aR)-6-(4-oxo-3,4-dihydrophthalazin-1-yl)spiro[3.3]heptan-2-yl)indoline-1-carboxamide | 523.2 | E: 1.85 F: 1.84 | 1H NMR: (500 MHz, DMSO-d₆) δ ppm 12.49 (s, 1H), 8.25 (d, J = 7.8 Hz, 1H), 8.14 (s, 1H), 7.96-7.90 (m, 1H), 7.89-7.85 (m, 1H), 7.85-7.81 (m, 1H), 7.76 (t, J = 4.1 Hz, 2H), 7.38 (s, 1H), 7.30 (br d, J = 8.3 Hz, 1H), 6.69 (br d, J = 7.4 Hz, 1H), 4.13 (sxt, J = 8.1 Hz, 1H), 3.94-3.83 (m, 3H), 3.10 (br t, J = 8.6 Hz, 2H), 2.61-2.54 (m, 1H), 2.41-2.29 (m, 3H), 2.23-2.12 (m, 2H), 2.05-1.97 (m, 1H), 1.52 (s, 9H) |
| 243 | (pyrazole-tetrahydrofuran-3-yl) | N-((aR)-6-(4-oxo-3,4-dihydrophthalazin-1-yl)spiro[3.3]heptan-2-yl)-5-(1-(tetrahydrofuran-3-yl)-1H-pyrazol-4-yl)indoline-1-carboxamide | 537.4 | E: 1.57 F: 1.54 | 1H NMR: (500 MHz, DMSO-d₆) δ ppm 12.49 (s, 1H), 8.25 (d, J = 7.7 Hz, 1H), 8.09 (s, 1H), 7.95-7.90 (m, 1H), 7.89-7.85 (m, 1H), 7.85-7.81 (m, 1H), 7.79 (s, 1H), 7.76 (d, J = 8.3 Hz, 1H), 7.36 (s, 1H), 7.29 (br d, J = 8.4 Hz, 1H), 6.70 (br d, J = 7.3 Hz, 1H), 5.02-4.94 (m, 1H), 4.19-4.08 (m, 1H), 4.02-3.94 (m, 2H), 3.93-3.84 (m, 4H), 3.84-3.77 (m, 1H), 3.10 (br t, J = 8.5 Hz, 2H), 2.61-2.54 (m, 1H), 2.43-2.32 (m, 4H), 2.32-2.24 (m, 1H), 2.20-2.11 (m, 2H), 2.02 (br t, J = 10.1 Hz, 1H) |
| 244 | (pyrazole-iPr-CF3) | 5-(1-isopropyl-3-(trifluoromethyl)-1H-pyrazol-4-yl)-N-((aR)-6-(4-oxo-3,4-dihydrophthalazin-1-yl)spiro[3.3]heptan-2-yl)indoline-1-carboxamide | 577.3 | E: 2.00 F: 2.05 | 1H NMR: (500 MHz, DMSO-d₆) δ ppm 12.49 (s, 1H), 8.25 (d, J = 7.8 Hz, 1H), 8.13 (s, 1H), 7.95-7.89 (m, 1H), 7.87 (s, 1H), 7.85-7.81 (m, 1H), 7.80 (d, J = 8.3 Hz, 1H), 7.17 (s, 1H), 7.11 (br d, J = 8.2 Hz, 1H), 6.77 (br d, J = 7.3 Hz, 1H), 4.57 (dt, J = 13.3, 6.6 Hz, 1H), 4.18-4.07 (m, 1H), 3.95-3.83 (m, 3H), 3.12 (br t, J = 8.6 Hz, 2H), 2.61-2.55 (m, 1H), 2.40-2.28 (m, 3H), 2.18 (q, J = 9.5 Hz, 2H), 2.05-1.98 (m, 1H), 1.45 (d, J = 6.6 Hz, 6H) |

TABLE 16-continued

| Ex. | R | Name | LCMS (M + H)+ | HPLC Method, RT (min.) | 1H NMR |
|---|---|---|---|---|---|
| 245 | ~~~CF3 | N-((aR)-6-(4-oxo-3,4-dihydrophthalazin-1-yl)spiro[3.3]heptan-2-yl)-5-(3,3,3-trifluoropropyl) indoline-1-carboxamide | 497.3 | E: 2.00 F: 2.00 | 1H NMR: (500 MHz, DMSO-$d_6$) δ ppm 12.49 (s, 1H), 8.24 (br d, J = 7.7 Hz, 1H), 7.95-7.89 (m, 1H), 7.87-7.79 (m, 2H), 7.65 (d, J = 8.2 Hz, 1H), 7.03 (s, 1H), 6.94 (br d, J = 8.0 Hz, 1H), 6.68 (br d, J = 7.2 Hz, 1H), 4.15-4.03 (m, 1H), 3.04 (br t, J = 8.5 Hz, 2H), 2.94-2.79 (m, 1H), 2.73-2.65 (m, 2H), 2.49-2.41 (m, 3H), 2.38-2.24 (m, 3H), 2.14 (br t, J = 9.6 Hz, 2H), 1.97 (br t, J = 10.0 Hz, 1H) |

The following Examples in Table 17 were prepared by using a similar procedure as shown in Example 216 by reacting Intermediate 74 with the appropriate boronic acids/boronate esters/potassium trifluoroborates.

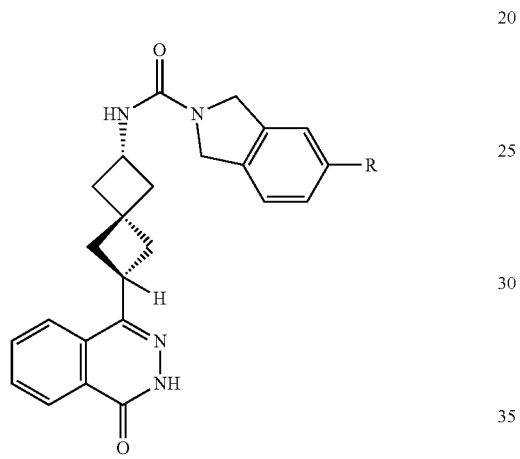

TABLE 17

| Ex. | R | Name | LCMS (M + H)+ | HPLC Method, RT (min.) | 1H NMR |
|---|---|---|---|---|---|
| 246 | (1,3,5-trimethyl-1H-pyrazol-4-yl) | N-((aR)-6-(4-oxo-3,4-dihydrophthalazin-1-yl)spiro[3.3]heptan-2-yl)-5-(1,3,5-trimethyl-1H-pyrazol-4-yl) isoindoline-2-carboxamide | 509.4 | E: 1.33 F: 1.52 | 1H NMR: (500 MHz, DMSO-$d_6$) δ ppm 12.48 (s, 1H), 8.25 (d, J = 7.8 Hz, 1H), 7.96-7.89 (m, 1H), 7.89-7.78 (m, 2H), 7.34 (d, J = 7.7 Hz, 1H), 7.19-7.09 (m, 2H), 6.48 (br d, J = 7.7 Hz, 1H), 4.59 (br s, 2H), 4.59 (br s, 2H), 4.16-4.05 (m, 1H), 3.88 (quin, J = 8.5 Hz, 1H), 3.68 (s, 3H), 2.58-2.55 (m, 1H), 2.39-2.31 (m, 3H), 2.19 (s, 3H), 2.18-2.12 (m, 2H), 2.10 (s, 3H), 1.97 (br t, J = 10.0 Hz, 1H) |
| 247 | 1-cyclopropyl-1H-pyrazol-4-yl | 5-(1-cyclopropyl-1H-pyrazol-4-yl)-N-((aR)-6-(4-oxo-3,4-dihydrophthalazin-1-yl)spiro[3.3]heptan-2-yl)isoindoline-2-carboxamide | 507.4 | E: 1.58 F: 1.59 | 1H NMR: (500 MHz, DMSO-$d_6$) δ ppm 12.48 (s, 1H), 8.25 (d, J = 7.9 Hz, 1H), 8.21 (s, 1H), 7.96-7.90 (m, 1H), 7.88-7.80 (m, 3H), 7.52-7.45 (m, 2H), 7.27 (d, J = 7.8 Hz, 1H), 6.49 (br d, J = 7.7 Hz, 1H), 4.56 (br s, 2H), 4.54 (br s, 2H), 4.10 (sxt, J = 8.1 Hz, 1H), 3.88 (quin, J = 8.5 Hz, 1H), 3.72 (tt, J = 7.3, 3.8 Hz, 1H), 2.57 (br s, 1H), 2.39-2.28 (m, 3H), 2.15 (br t, J = 9.7 Hz, 2H), 1.98 (br t, J = 10.0 Hz, 1H), 1.09-1.03 (m, 2H), 0.99-0.93 (m, 2H) |

TABLE 17-continued

| Ex. | R | Name | LCMS (M + H)+ | HPLC Method, RT (min.) | 1H NMR |
|---|---|---|---|---|---|
| 248 | 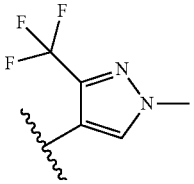 [SMILES: *c1cn(C)nc1C(F)(F)F] | 5-(1-methyl-3-(trifluoromethyl)-1H-pyrazol-4-yl)-N-((aR)-6-(4-oxo-3,4-dihydrophthalazin-1-yl)spiro[3.3]heptan-2-yl)isoindoline-2-carboxamide | 543.9 | E: 1.69<br>F: 1.69 | 1H NMR: (500 MHz, DMSO-d6) δ ppm 8.25 (d, J = 7.8 Hz, 1H), 8.12 (s, 1H), 7.96-7.89 (m, 1H), 7.88-7.85 (m, 1H), 7.85-7.80 (m, 1H), 7.37 (d, J = 7.8 Hz, 1H), 7.31 (s, 1H), 7.30-7.27 (m, 1H), 6.50 (br d, J = 7.7 Hz, 1H), 4.59 (s, 4H), 4.15-4.05 (m, 1H), 3.94 (s, 3H), 3.88 (quin, J = 8.4 Hz, 1H), 2.57 (br s, 1H), 2.39-2.31 (m, 3H), 2.18-2.12 (m, 2H), 2.01-1.94 (m, 1H) |
| 249 | 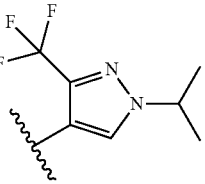 | 5-(1-isopropyl-3-(trifluoromethyl)-1H-pyrazol-4-yl)-N-((aR)-6-(4-oxo-3,4-dihydrophthalazin-1-yl)spiro[3.3]heptan-2-yl)isoindoline-2-carboxamide | 578.1 | E: 1.92<br>F: 1.97 | 1H NMR: (500 MHz, DMSO-d6) δ ppm 12.48 (s, 1H), 8.27-8.20 (m, 2H), 7.95-7.89 (m, 1H), 7.88-7.85 (m, 1H), 7.85-7.79 (m, 1H), 7.40-7.36 (m, 1H), 7.34 (s, 1H), 7.33-7.28 (m, 1H), 6.51 (d, J = 7.7 Hz, 1H), 4.64-4.55 (m, 4H), 4.15-4.05 (m, 1H), 3.88 (quin, J = 8.5 Hz, 1H), 2.57 (br s, 1H), 2.40-2.30 (m, 3H), 2.20-2.11 (m, 2H), 1.97 (t, J = 10.0 Hz, 1H), 1.47 (d, J = 6.6 Hz, 6H) |
| 250 | 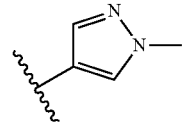 [SMILES: *c1cnn(C)c1] | 5-(1-methyl-1H-pyrazol-4-yl)-N-((aR)-6-(4-oxo-3,4-dihydrophthalazin-1-yl)spiro[3.3]heptan-2-yl)isoindoline-2-carboxamide | 481.1 | E: 1.39<br>F: 1.40 | 1H NMR: (500 MHz, DMSO-d6) δ ppm 12.48 (s, 1H), 8.25 (d, J = 7.9 Hz, 1H), 8.12 (s, 1H), 7.97-7.88 (m, 1H), 7.88-7.78 (m, 3H), 7.51-7.41 (m, 2H), 7.28 (d, J = 7.8 Hz, 1H), 6.48 (br d, J = 7.7 Hz, 1H), 4.57 (br s, 2H), 4.54 (br s, 2H), 4.10 (sxt, J = 8.2 Hz, 1H), 3.92-3.86 (m, 1H), 3.85 (s, 3H), 2.60-2.55 (m, 1H), 2.39-2.28 (m, 3H), 2.15 (br t, J = 9.8 Hz, 2H), 1.98 (br t, J = 10.0 Hz, 1H) |
| 251 | 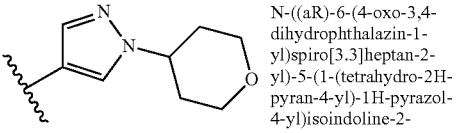 | N-((aR)-6-(4-oxo-3,4-dihydrophthalazin-1-yl)spiro[3.3]heptan-2-yl)-5-(1-(tetrahydro-2H-pyran-4-yl)-1H-pyrazol-4-yl)isoindoline-2-carboxamide | 551.5 | E: 1.51<br>F: 1.51 | 1H NMR: (500 MHz, DMSO-d6) δ ppm 12.49 (s, 1H), 8.28-8.22 (m, 2H), 7.95-7.90 (m, 1H), 7.89-7.78 (m, 3H), 7.55-7.45 (m, 2H), 7.28 (br d, J = 7.8 Hz, 1H), 6.50 (br d, J = 7.6 Hz, 1H), 4.57 (br s, 2H), 4.54 (br s, 2H), 4.38 (td, J = 10.5, 5.4 Hz, 1H), 4.17-4.03 (m, 1H), 3.88 (br t, J = 8.5 Hz, 1H), 3.53-3.39 (m, 1H), 2.60-2.55 (m, 1H), 2.41-2.26 (m, 3H), 2.15 (br t, J = 9.5 Hz, 2H), 2.03-1.81 (m, 6H) |
| 252 | 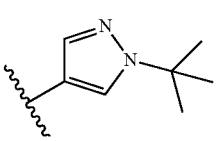 [SMILES: *c1cnn(C(C)(C)C)c1] | 5-(1-(tert-butyl)-1H-pyrazol-4-yl)-N-((aR)-6-(4-oxo-3,4-dihydrophthalazin-1-yl)spiro[3.3]heptan-2-yl)isoindoline-2-carboxamide | 523.2 | E: 1.73<br>F: 1.76 | 1H NMR: (500 MHz, DMSO-d6) δ ppm 12.48 (s, 1H), 8.28-8.23 (m, 2H), 7.95-7.89 (m, 1H), 7.88-7.79 (m, 3H), 7.56-7.48 (m, 2H), 7.27 (d, J = 7.9 Hz, 1H), 6.49 (br d, J = 7.7 Hz, 1H), 4.57 (br s, 2H), 4.55 (br s, 2H), 4.15-4.04 (m, 1H), 3.93-3.83 (m, 1H), 2.57 (br s, 1H), 2.39-2.28 (m, 3H), 2.15 (br t, J = 9.8 Hz, 2H), 1.98 (br t, J = 10.0 Hz, 1H), 1.54 (s, 9H) |

TABLE 17-continued

| Ex. | R | Name | LCMS (M + H)+ | HPLC Method, RT (min.) | 1H NMR |
|---|---|---|---|---|---|
| 253 | (pyrazole with N-CD₃ group) | 5-(1-($^2$H$_3$)methyl-1H-pyrazol-4-yl)-N-((aR)-6-(4-oxo-3,4-dihydrophthalazin-1-yl)spiro[3.3]heptan-2-yl)isoindoline-2-carboxamide | 484.3 | E: 1.39 F: 1.40 | $^1$H NMR: (500 MHz, DMSO-d$_6$) δ ppm 12.53-12.45 (m, 1H), 12.48 (s, 1H), 8.25 (d, J = 7.8 Hz, 1H), 8.11 (s, 1H), 7.95-7.81 (m, 4H), 7.51-7.41 (m, 2H), 7.28 (d, J = 7.8 Hz, 1H), 6.49 (br d, J = 7.7 Hz, 1H), 4.56 (br s, 2H), 4.54 (br s, 2H), 4.14-4.06 (m, 1H), 3.92-3.82 (m, 1H), 2.39-2.29 (m, 3H), 2.15 (br t, J = 9.6 Hz, 2H), 1.98 (br t, J = 9.9 Hz, 1H) |

The following Examples in Table 18 were prepared by using a similar procedure as shown in Example 50 by reacting Example 50A with the appropriate amine.

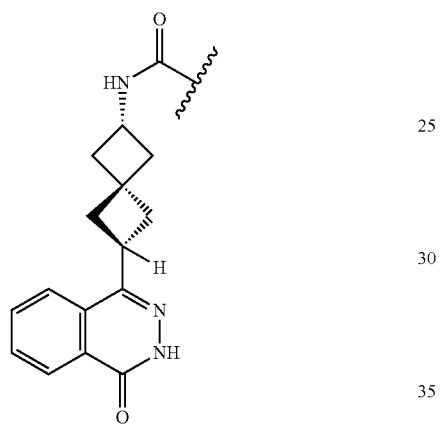

TABLE 18

| Ex. | R | Name | LCMS (M + H)+ | HPLC Method, RT (min.) | 1H NMR |
|---|---|---|---|---|---|
| 255 | (3,3-dimethylindoline) | 3,3-dimethyl-N-(aR)-6-(4-oxo-3,4-dihydrophthalazin-1-yl)spiro[3.3]heptan-2-yl)indoline-1-carboxamide | 429.0 | E: 1.84 F: 1.84 | $^1$H NMR: (500 MHz, DMSO-d$_6$) δ ppm 12.50 (s, 1H), 8.25 (d, J = 7.8 Hz, 1H), 7.95-7.90 (m, 1H), 7.89-7.81 (m, 2H), 7.77 (d, J = 8.0 Hz, 1H), 7.15 (d, J = 7.3 Hz, 1H), 7.07 (t, J = 7.7 Hz, 1H), 6.87 (t, J = 7.4 Hz, 1H), 6.74 (br d, J = 7.4 Hz, 1H), 4.17-4.06 (m, 1H), 3.89 (quin, J = 8.4 Hz, 1H), 2.91 (br d, J = 5.2 Hz, 1H), 2.61-2.56 (m, 1H), 2.41-2.28 (m, 3H), 2.21-2.11 (m, 2H), 2.00 (br t, J = 10.0 Hz, 1H), 1.26 (d, J = 2.5 Hz, 6H), 1.16 (t, J = 7.3 Hz, 1H) |
| 256 | (2,3-dihydropyrrolo[2,3-b]pyridine) | N-((aR)-6-(4-oxo-3,4-dihydrophthalazin-1-yl)spiro[3.3]heptan-2-yl)-2,3-dihydro-1H-pyrrolo[2,3-b]pyridine-1-carboxamide | 402.1 | E: 1.18 F: 1.63 | $^1$H NMR: (500 MHz, DMSO-d$_6$) δ ppm 12.49 (s, 1H), 9.20 (d, J = 7.5 Hz, 1H), 8.24 (d, J = 7.8 Hz, 1H), 8.00 (d, J = 5.0 Hz, 1H), 7.94-7.89 (m, 1H), 7.87-7.79 (m, 2H), 7.56 (br d, J = 7.1 Hz, 1H), 6.86 (dd, J = 7.1, 5.5 Hz, 1H), 4.22-4.10 (m, 1H), 3.94-3.82 (m, 3H), 3.01 (br t, J = 8.6 Hz, 2H), 2.70-2.60 (m, 1H), 2.36 (br t, J = 8.8 Hz, 3H), 2.30-2.21 (m, 1H), 2.10-2.01 (m, 1H), 1.92-1.82 (m, 1H) |

TABLE 18-continued

| Ex. | R | Name | LCMS (M + H)+ | HPLC Method, RT (min.) | 1H NMR |
|---|---|---|---|---|---|
| 257 | (pyrrolo[3,4-b]pyridine structure) | N-((aR(-6-(4-oxo-3,4-dihydrophthalazin-l-yl)spiro[3.3]heptan-2-yl)-5H-pyrrolo(3,4-b)pyridine-6(7H)-carboxamide | 402.3 | E: 098 F: 1.15 | 1H NMR: (500 MHz, DMSO-d6) δ ppm 12.48 (s, 1H), 8.43 (d, J = 4.6 Hz, 1H), 8.24 (d, J = 7.7 Hz, 1H), 7.95-7.88 (m, 1H), 7.88-7.80 (m, 2H), 7.75 (d, J = 7.7 Hz, 1H), 7.29 (dd, J = 7.6, 5.0 Hz, 1H), 6.57 (d, J = 7.7 Hz, 1H), 4.57 (br d, J = 24.2 Hz, 4H), 4.14-4.05 (m, 1H), 3.88 (quin, J = 8.5 Hz, IH), 2.40-2.29 (m, 3H), 2.15 (br t, J = 9.6 Hz, 2H), 1.98 (br t, J = 10.0 Hz, IH) |
| 258 | (5-methoxyindoline) | 5-methoxy-N-((aR)-6-(4-oxo-3,4-dihydrophthalazin-1-yl)spiro[3.3]heptan-2-yl)indoline-1-carboxamide | 431.1 | E: 1.56 F: 1.56 | 1H NMR: (500 MHz, DMSO-d6) δ ppm 12.49 (s, 1H), 8.24 (d, J = 7.7 Hz, 1H), 7.96-7.88 (m, 1H), 7.87-7.79 (m, 2H), 7.66 (d, J = 8.7 Hz, 1H), 6.75 (s, 1H), 6.64-6.55 (m, 1H), 4.17-4.04 (m, 1H), 3.93-3.78 (m, 2H), 3.64 (s, 2H), 3.04 (br t, J = 8.5 Hz, 2H), 2.57 (br s, 1H), 2.54 (s, 3H), 2.38-2.26 (m, 3H), 2.15 (br t, J = 9.8 Hz, 2H), 1.98 (br t, J = 9.9 Hz, 1H) |
| 259 | (6-CF3 indoline) | N-((aR)-6-(4-oxo-3,4-dihydrophthalazin-1-yl)spiro[3.3]heptan-2-yl)-6-(trifluoromethyl)indoline-1-carboxamide | 469.2 | E: 1.90 F: 1.90 | 1H NMR: (500 MHz, DMSO-d6) δ ppm 12.49 (s, 1H), 8.24 (d, J = 7.9 Hz, 1H), 8.08 (s, 1H), 7.94-7.89 (m, 1H), 7.88-7.80 (m, 2H), 7.32 (d, J = 7.7 Hz, 1H), 7.15 (br d, J = 7.7 Hz, 1H), 6.89 (d, J = 7.3 Hz, 1H), 4.17-4.06 (m, 1H), 3.93 (br t, J = 8.8 Hz, 2H), 3.88 (t, J = 8.5 Hz, 1H), 3.16 (br t, J = 8.5 Hz, 2H), 2.58 (br s, 1H), 2.40-2.28 (m, 3H), 2.22-2.11 (m, 2H), 2.06-1.94 (m, 1H) |
| 260 | (5-N,N-dimethylsulfamoyl indoline) | 5-(N,N-dimethylsulfamoyl)-N-((aR)-6-(4-oxo-3,4-dihydrophthalazin-1-yl)spiro[3.3]heptan-2-yl)indoline-1-carboxamide | 508.1 | E: 1.54 F: 1.53 | 1H NMR: (500 MHz, DMSO-d6) δ ppm 12.49 (s, 1H), 8.24 (d, J = 7.8 Hz, 1H), 7.94 (d, J = 8.5 Hz, 1H), 7.90 (br d, J = 7.3 Hz, 1H), 7.87-7.80 (m, 2H), 7.49-7.42 (m, 2H), 6.97 (br d, J = 7.2 Hz, 1H), 4.17-4.07 (m, 1H), 3.95 (br t, J = 8.9 Hz, 2H), 3.88 (quin, J = 8.5 Hz, 1H), 3.17 (br t, J = 8.7 Hz, 2H), 2.55 (br s, 1H), 2.54 (s, 7H), 2.40-2.27 (m, 3H), 2.22-2.11 (m, 2H), 2.05-1.96 (m, 1H) |
| 261 | (3-(morpholinomethyl)indoline) | 3-(morpholinomethyl)-N-((aR)-6-(4-oxo-3,4-dihydrophthalazin-1-yl)spiro[3.3]heptan-2-yl)indoline-1-carboxamide | 500.1 | E: 1.16 F: 1.61 | 1H NMR: (500 MHz, DMSO-d6) δ ppm 12.49 (s, 1H), 8.24 (d, J = 7.8 Hz, 1H), 7.97-7.90 (m, 1H), 7.88-7.80 (m, 2H), 7.78 (d, J = 8.1 Hz, 1H), 7.18 (d, J = 7.4 Hz, 1H), 7.07 (t, J = 7.7 Hz, 1H), 6.83 (t, J = 7.4 Hz, 1H), 6.79 (br d, J = 7.5 Hz, 1H), 4.17-4.07 (m, 1H), 4.00-3.92 (m, 1H), 3.87 (quin, J = 8.4 Hz, 1H), 3.69-3.63 (m, 2H), 3.60 (br s, 1H), 2.60-2.52 (m, 3H), 2.44-2.26 (m, 5H), 2.22-2.10 (m, 2H), 2.06-1.96 (m, 1H) |
| 262 | (2-(p-tolyl)-5H-pyrrolo[3,4-d]pyrimidine) | N-((aR)-6-(4-oxo-3,4-dihydrophthalazin-1-yl)spiro[3.3]heptan-2-yl)-2-(p-tolyl)-5H-pyrrolo[3,4-d]pyrimidine-6(7H)-carboxamide | 493.2 | E: 1.71 F: 1.72 | 1H NMR: (500 MHz, DMSO-d6) δ ppm 12.48 (s, 1H), 8.82 (s, 1H), 8.30-8.21 (m, 3H), 7.95-7.89 (m, 1H), 7.88-7.86 (m, 1H), 7.85-7.79 (m, 1H), 7.32 (d, J = 8.1 Hz, 2H), 6.63 (d, J = 7.7 Hz, 1H), 4.64 (br s, 2H), 4.62 (br s, 2H), 4.17-4.05 (m, 1H), 3.89 (quin, J = 8.4 Hz, 1H), 2.59 (br s, 1H), 2.37 (s, 3H), 2.35 (br d, J = 8.6 Hz, 3H), 2.17 (br t, J = 9.8 Hz, 2H), 2.00 (br t, J = 10.0 Hz, 1H) |

TABLE 18-continued

| Ex. | R | Name | LCMS (M + H)+ | HPLC Method, RT (min.) | 1H NMR |
|---|---|---|---|---|---|
| 263 | (isoindoline with OMe) | 5-methoxy-N-((aR)-6-(4-oxo-3,4-dihydrophthalazin-1-yl)spiro[3.3]heptan-2-yl)isoindoline-2-carboxamide | 431.2 | E: 1.50 F: 1.50 | 1H NMR: (500 MHz, DMSO-d6) δ ppm 12.48 (s, 1H), 8.24 (d, J = 7.8 Hz, 1H), 7.96-7.88 (m, 1H), 7.88-7.78 (m, 2H), 7.20 (d, J = 8.3 Hz, 1H), 6.87 (s, 1H), 6.84 (br d, J = 8.3 Hz, 1H), 6.45 (d, J = 7.7 Hz, 1H), 4.52 (br s, 2H), 4.48 (br s, 2H), 4.14-4.03 (m, 1H), 3.87 (quin, J = 8.4 Hz, 1H), 3.73 (s, 3H), 2.40-2.25 (m, 3H), 2.13 (br t, J = 9.5 Hz, 2H), 1.96 (t, J = 10.0 Hz, 1H) |
| 264 | (pyrrolopyridine) | N-((aR)-6-(4-oxo-3,4-dihydrophthalazin-1-yl)spiro[3.3]heptan-2-yl)-1H-pyrrolo[3,4-c]pyridine-2(3H)-carboxamide | 402.3 | E: 0.87 F: 1.13 | 1H NMR: (500 MHz, DMSO-d6) δ ppm 12.48 (s, 1H), 8.54 (s, 1H), 8.45 (d, J = 5.0 Hz, 1H), 8.24 (d, J = 7.8 Hz, 1H), 7.95-7.88 (m, 1H), 7.88-7.79 (m, 2H), 7.38 (d, J = 4.9 Hz, 1H), 6.60-6.53 (m, 1H), 6.57 (br d, J = 7.6 Hz, 1H), 4.60 (br d, J = 8.2 Hz, 4H), 4.14-4.03 (m, 1H), 3.87 (quin, J = 8.5 Hz, 1H), 2.39-2.28 (m, 3H), 2.19-2.11 (m, 2H), 1.97 (br t, J = 10.0 Hz, 1H) |

Example 265: N-((aR)-6-(4-oxo-3,4-dihydrophthalazin-1-yl)spiro[3.3]heptan-2-yl)spiro[indoline-3,4'-piperidine]-1-carboxamide

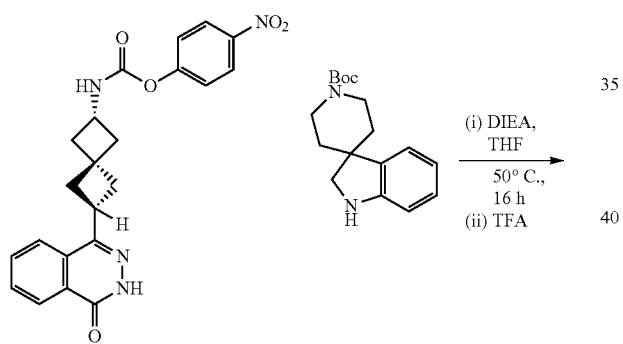

tert-Butyl spiro[indoline-3,4'-piperidine]-1'-carboxylate (37 mg, 0.128 mmol) was placed in a pressure vial, and a solution of Example 50A (21.6 mg, 0.051 mmol) in THF (2 mL) was added, followed by DIEA (0.027 mL, 0.15 mmol). The reaction mixture was stirred at rt for 5 min, and then at 50° C. for 16 h. The mixture was concentrated, then the residue was treated with TFA (2 mL) at rt for 15 min. The mixture was concentrated and the residue was purified by preparative HPLC to afford Example 265 (11.6 mg, 48% yield). MS(ESI) m/z: 470.3 (M+H)+; 1H NMR: (500 MHz, DMSO-d6) δ ppm 12.49 (s, 1H), 8.25 (d, J=7.8 Hz, 1H), 7.96-7.90 (m, 1H), 7.84 (dd, J=17.1, 8.2 Hz, 3H), 7.18-7.06 (m, 2H), 6.91 (t, J=7.4 Hz, 1H), 6.72 (br d, J=7.4 Hz, 1H), 4.19-4.09 (m, 1H), 3.94-3.83 (m, 3H), 3.36 (br d, J=11.7 Hz, 1H), 2.92 (br t, J=13.1 Hz, 2H), 2.63-2.56 (m, 1H), 2.42-2.31 (m, 3H), 2.24-2.11 (m, 2H), 2.04-1.92 (m, 3H), 1.77 (br d, J=12.9 Hz, 2H); HPLC RT=1.18 min (Method E), 1.13 min (Method F).

Example 266: N,1-dimethyl-N-((aR)-6-(4-oxo-3,4-dihydrophthalazin-1-yl)spiro[3.3]heptan-2-yl)-1H-indazole-3-carboxamide

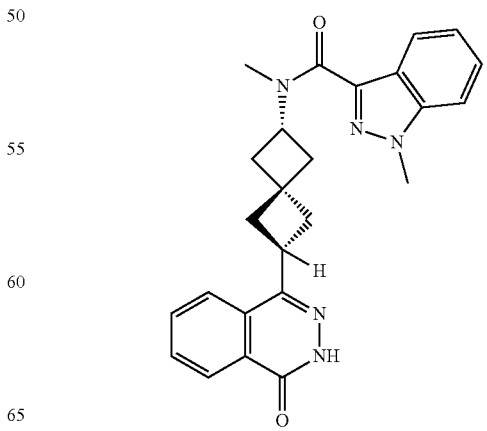

Example 266A

N-((aR)-6-(3-(dicyclopropylmethyl)-4-oxo-3,4-dihydrophthalazin-1-yl)spiro[3.3]heptan-2-yl)-1-methyl-1H-indazole-3-carboxamide

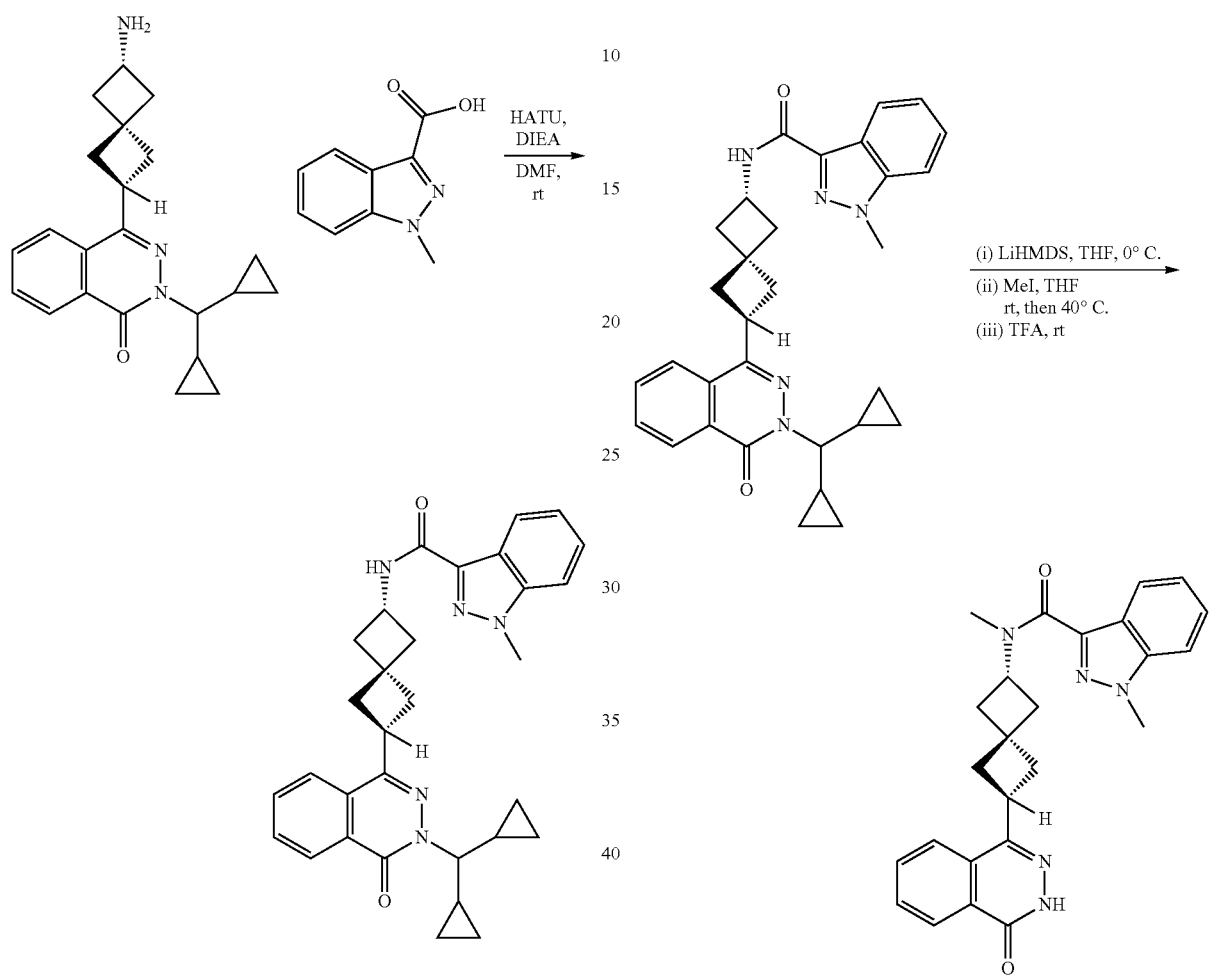

Example 266

To a solution of 1-methyl-1H-indazole-3-carboxylic acid (108 mg, 0.611 mmol) was dissolved in anhydrous DMF (2.5 mL), then DIEA (0.291 mL, 1.66 mmol) and HATU (243 mg, 0.638 mmol) were added. After stirring for 30 min at rt, the obtained solution was added to a solution of Intermediate 76 (194 mg, 0.555 mmol) and DIEA (0.291 mL, 1.66 mmol) in anhydrous DMF (2.5 mL), and the reaction mixture was stirred at rt for 1 h. The reaction mixture was quenched with MeOH (0.5 mL), diluted with EtOAc (100 mL), washed with water (2×) and brine, dried ($Na_2SO_4$) and concentrated. The residue was purified by flash chromatography (0-30% EtOAc/DCM gradient) to afford Example 266a (107 mg, 38% yield) as a colorless foam. MS(ESI) m/z: 508.4 (M+H)$^+$; $^1$H NMR: (500 MHz, $CDCl_3$) δ ppm 8.47 (dd, J=7.8, 1.0 Hz, 1H), 8.38 (d, J=8.3 Hz, 1H), 7.81-7.76 (m, 1H), 7.76-7.71 (m, 1H), 7.70-7.66 (m, 1H), 7.47-7.38 (m, 2H), 7.29 (ddd, J=8.0, 6.5, 1.1 Hz, 1H), 7.09 (br d, J=8.0 Hz, 1H), 4.61 (sxt, J=8.2 Hz, 1H), 4.10 (s, 3H), 3.89 (quin, J=8.0 Hz, 1H), 3.82 (br t, J=9.2 Hz, 1H), 2.83-2.76 (m, 1H), 2.66 (d, J=8.0 Hz, 2H), 2.61-2.55 (m, 1H), 2.55-2.45 (m, 2H), 2.21 (dd, J=11.0, 8.8 Hz, 1H), 2.10-2.06 (m, 1H), 1.62-1.57 (m, 1H), 0.74-0.67 (m, 2H), 0.56-0.49 (m, 2H), 0.40-0.32 (m, 4H).

Example 266

To a solution of Example 266A (15 mg, 0.030 mmol) in THF (1 mL) at 0° C., was added LiHMDS (1 M in THF) (0.044 mL, 0.044 mmol). The reaction mixture was stirred at 0° C. for 5 min, then methyl iodide (5.5 µl, 0.089 mmol) was added. The reaction mixture was stirred at rt for 30 min. Additional LiHMDS (1 M in THF) (0.044 mL, 0.044 mmol) was added, and the reaction mixture was stirred at 40° C. for 4 h. The solvent was evaporated, and the residue was treated with TFA (2 mL) for 15 min at rt. The solvent was evaporated and the residue was purified by preparative HPLC to afford Example 266 (5.2 mg, 39% yield). MS(ESI) m/z: 428.3 (M+H)$^+$; $^1$H NMR: (500 MHz, DMSO-$d_6$) δ ppm 12.48 (br s, 1H), 8.24 (br d, J=7.4 Hz, 1H), 7.97-7.78 (m, 4H), 7.70 (d, J=8.5 Hz, 1H), 7.45 (t, J=7.6 Hz, 1H), 7.23 (t, J=7.5 Hz, 1H), 4.98 (br s, 1H), 4.11 (s, 3H), 3.89 (s, 1H), 2.54 (s, 3H), 2.46-2.31 (m, 4H), 2.24 (br t, J=10.1 Hz, 1H); HPLC RT=1.64 min (Method E), 1.63 min (Method F).

Example 267: N-ethyl-1-methyl-N-((aR)-6-(4-oxo-3,4-dihydrophthalazin-1-yl)spiro[3.3]heptan-2-yl)-1H-indazole-3-carboxamide Example 268: 2-methyl-1-((3-(((aR)-6-(4-oxo-3,4-dihydrophthalazin-1-yl)spiro[3.3]heptan-2-yl)carbamoyl)pyrazolo[1,5-a]pyridin-6-yl)oxy)propan-2-yl2-aminoacetate, TFA

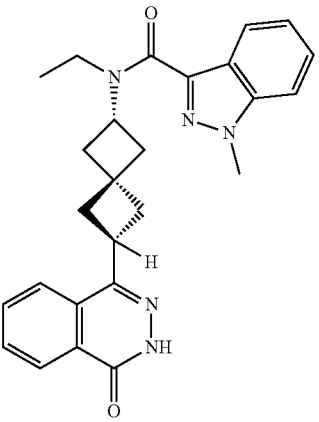

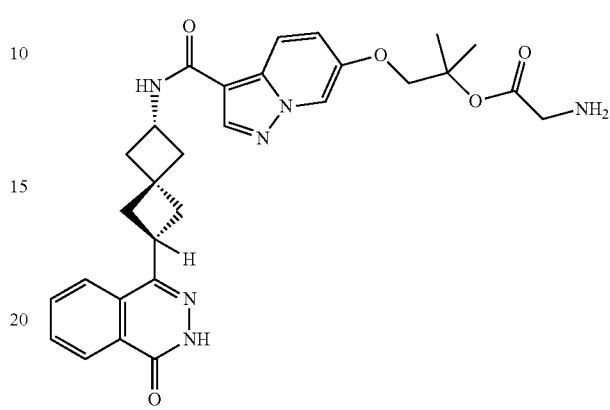

According to the procedure for the preparation of Example 266, substituting EtI for MeI afforded Example 267. MS(ESI) m/z: 442.1 (M+H)$^+$; $^1$H NMR: (500 MHz, DMSO-d$_6$) δ ppm 12.46 (br s, 1H), 8.24 (br d, J=7.6 Hz, 1H), 7.98-7.78 (m, 4H), 7.69 (d, J=8.5 Hz, 1H), 7.45 (br t, J=7.6 Hz, 1H), 7.23 (t, J=7.5 Hz, 1H), 4.10 (s, 3H), 3.89 (br s, 1H), 3.38 (br s, 2H), 2.54 (s, 3H), 2.43-2.27 (m, 4H), 2.21-2.10 (m, 2H), 1.13 (br s, 3H); HPLC RT=1.96 min (Method E), 2.00 min (Method F).

Example 268A

N-((aR)-6-(3-(dicyclopropylmethyl)-4-oxo-3,4-dihydrophthalazin-1-yl)spiro[3.3]heptan-2-yl)-6-(2-hydroxy-2-methylpropoxy)pyrazolo[1,5-a]pyridine-3-carboxamide

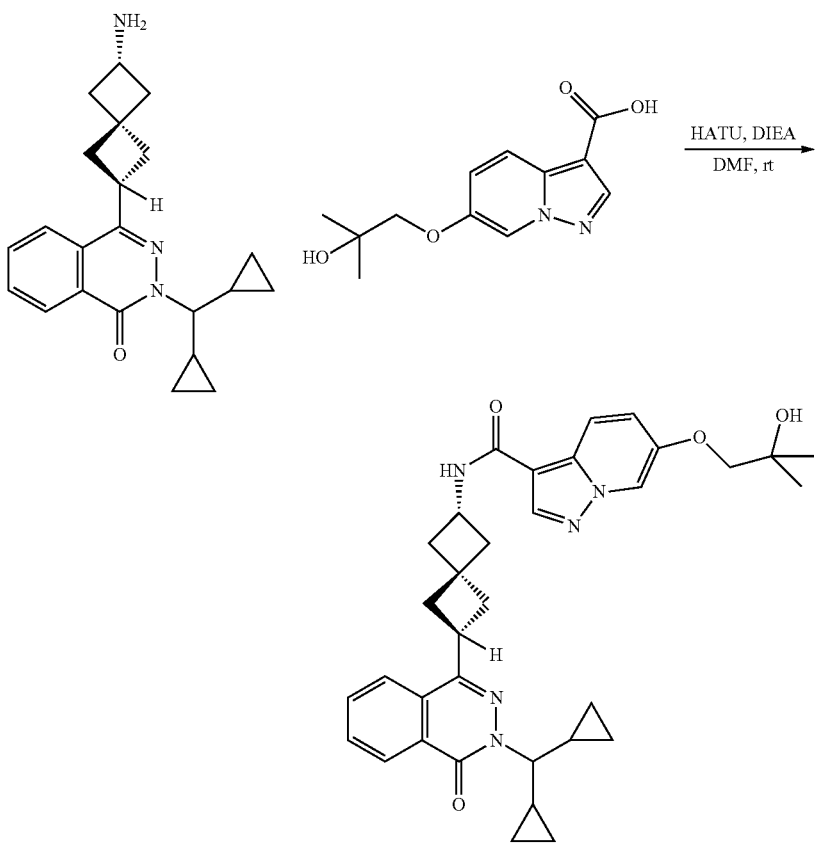

Intermediate 29 (113 mg, 0.451 mmol) was dissolved in DMF (4.0 mL), then DIEA (0.225 mL, 1.29 mmol) and HATU (171 mg, 0.451 mmol) were added. After stirring for 30 min at rt, the obtained solution was added to a solution of Intermediate 76 (150 mg, 0.429 mmol) and DIEA (0.225 mL, 1.29 mmol) in DMF (4.0 mL), and the reaction mixture was stirred at rt for 1 h. The reaction mixture was quenched with MeOH (0.5 mL), diluted with EtOAc (200 mL), washed with water (3×), brine (1×50 mL), dried ($Na_2SO_4$) and concentrated. The residue was purified by flash chromatography (30-100% EtOAc/DCM gradient) to give Example 268A (215 mg, 86% yield) as a white solid. MS(ESI) m/z: 582.6 $(M+H)^+$; $^1$H NMR: (500 MHz, DMSO-$d_6$) δ ppm 8.45-8.41 (m, 2H), 8.28 (dd, J=8.0, 0.8 Hz, 1H), 8.21 (d, J=7.7 Hz, 1H), 8.07 (d, J=9.1 Hz, 1H), 7.95-7.91 (m, 1H), 7.89-7.81 (m, 2H), 7.27 (dd, J=9.6, 2.2 Hz, 1H), 4.67 (s, 1H), 4.36 (sxt, J=8.1 Hz, 1H), 3.97 (quin, J=8.0 Hz, 1H), 3.79 (s, 2H), 3.68 (br t, J=9.1 Hz, 1H), 2.66-2.56 (m, 2H), 2.48-2.45 (m, 2H), 2.45-2.38 (m, 1H), 2.31-2.24 (m, 1H), 2.22-2.16 (m, 1H), 2.07 (dd, J=10.9, 9.2 Hz, 1H), 1.52 (dt, J=7.6, 4.8 Hz, 2H), 1.22 (s, 6H), 0.66 (tt, J=8.6, 4.5 Hz, 2H), 0.55 (dq, J=9.5, 4.9 Hz, 2H), 0.32 (qd, J=8.4, 4.1 Hz, 2H), 0.17 (dq, J=9.7, 4.7 Hz, 2H).

Example 268B 1-((3-(((aR)-6-(3-(dicyclopropylmethyl)-4-oxo-3,4-dihydrophthalazin-1-yl)spiro[3.3]heptan-2-yl)carbamoyl)pyrazolo[1,5-a]pyridin-6-yl)oxy)-2-methyl-propan-2-yl2-(((tert-butoxycarbonyl)amino)acetate

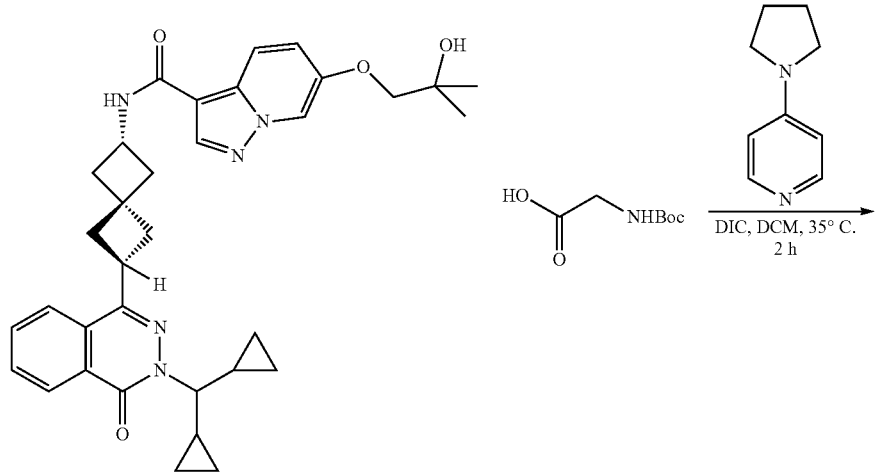

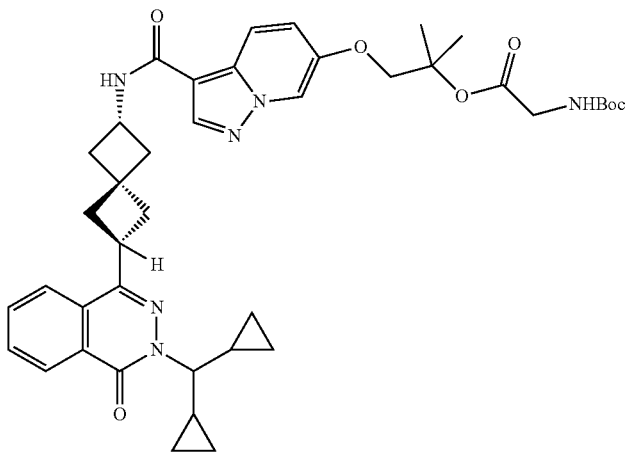

Example 268A (70 mg, 0.120 mmol) was dissolved in anhydrous DCM (5.0 mL), then 2-((tert-butoxycarbonyl)amino)acetic acid (63 mg, 0.36 mmol) and 4-(pyrrolidin-1-yl)pyridine (17.8 mg, 0.120 mmol) were added. The reaction mixture was heated to 35° C., and DIC (0.056 mL, 0.36 mmol) was added dropwise over 15 min. The reaction mixture was stirred for additional 1 h at 35° C., then at rt for additional 16 h. Additional 2-((tert-butoxy carbonyl)amino)acetic acid (63 mg, 0.36 mmol) was added, followed by dropwise addition of DIC (0.056 mL, 0.36 mmol) over 15 min at 35° C. The reaction mixture was stirred at 35° C. for 1 h. The reaction mixture was cooled to rt, quenched with MeOH (1 mL), and concentrated. The residue was purified by preparative HPLC to afford Example 268B (50 mg, 56% yield) as a white solid. MS(ESI) m/z: 739.7 (M+H)+; 1H NMR: (500 MHz, DMSO-$d_6$) δ ppm 8.55-8.49 (m, 1H), 8.45 (s, 1H), 8.28 (d, J=8.0 Hz, 1H), 8.26-8.20 (m, 1H), 8.16-8.06 (m, 2H), 7.96-7.90 (m, 1H), 7.89-7.80 (m, 2H), 7.32-7.26 (m, 1H), 7.12 (t, J=6.2 Hz, 1H), 4.37 (sxt, J=8.1 Hz, 1H), 4.26-4.16 (m, 2H), 3.97 (quin, J=8.0 Hz, 1H), 3.83-3.64 (m, 1H), 3.59 (d, J=6.1 Hz, 1H), 2.66-2.61 (m, 1H), 2.61-2.54 (m, 1H), 2.45-2.38 (m, 1H), 2.31-2.24 (m, 1H), 2.22-2.15 (m, 1H), 2.07 (t, J=10.0 Hz, 1H), 1.60-1.46 (m, 9H), 1.36 (s, 6H), 0.66 (tt, J=8.6, 4.6 Hz, 2H), 0.55 (dq, J=9.3, 4.8 Hz, 2H), 0.36-0.27 (m, 2H), 0.17 (dq, J=9.4, 4.8 Hz, 2H).

Example 268

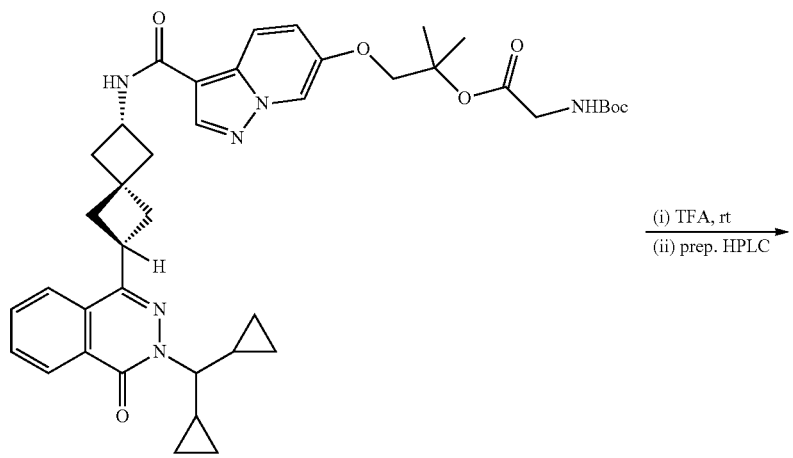

(i) TFA, rt
(ii) prep. HPLC

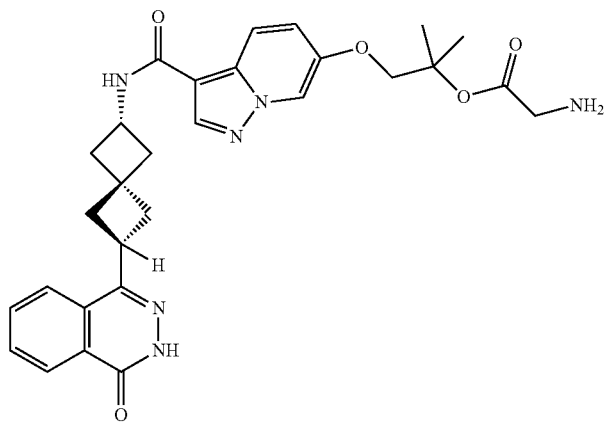

Example 268B (50 mg, 0.068 mmol) was dissolved in TFA (3 mL), and the reaction mixture was stirred for 30 min at rt. TFA was removed under reduced pressure, the residue was purified by preparative HPLC to afford Example 268 (20.9 mg, 47% yield) as a white solid. MS(ESI) m/z: 545.4 (M+H)$^+$; $^1$H NMR: (500 MHz, DMSO-d$_6$) δ ppm 12.47 (s, 1H), 8.53 (d, J=1.7 Hz, 1H), 8.47 (s, 1H), 8.26 (d, J=8.0 Hz, 2H), 8.14 (br s, 3H), 8.11 (d, J=9.9 Hz, 1H), 7.95-7.90 (m, 1H), 7.89-7.86 (m, 1H), 7.86-7.79 (m, 1H), 7.28 (dd, J=9.6, 2.2 Hz, 1H), 4.37 (sxt, J=8.1 Hz, 1H), 4.24 (s, 2H), 3.91 (t, J=8.5 Hz, 1H), 3.78 (br d, J=5.2 Hz, 2H), 2.67-2.60 (m, 1H), 2.57 (ddd, J=10.9, 8.0, 3.0 Hz, 1H), 2.44-2.33 (m, 3H), 2.28-2.17 (m, 2H), 2.04 (dd, J=11.0, 9.1 Hz, 1H), 1.58 (s, 6H); HPLC RT=5.18 min (Method A), 5.86 min (Method B).

Example 269: (S)-2-methyl-1-((3-(((aR)-6-(4-oxo-3,4-dihydrophthalazin-1-yl)spiro[3.3]heptan-2-yl)carbamoyl)pyrazolo[1,5-a]pyridin-6-yl)oxy)propan-2-yl 2-amino-3-methylbutanoate, TFA

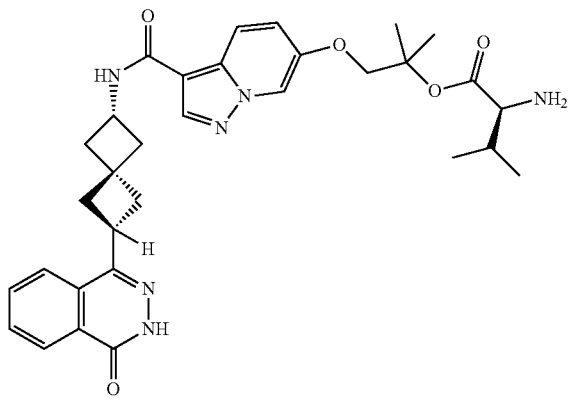

According to the procedure for the preparation of Example 268, substituting (S)-2-((tert-butoxycarbonyl)amino)-3-methylbutanoic acid for 2-((tert-butoxycarbonyl)amino)acetic acid afforded Example 269. MS(ESI) m/z: 587.6 (M+H)$^+$; $^1$H NMR: (500 MHz, DMSO-d$_6$) δ ppm 12.46 (s, 1H), 8.52 (d, J=1.7 Hz, 1H), 8.47 (s, 1H), 8.30-8.20 (m, 5H), 8.11 (d, J=9.6 Hz, 1H), 7.95-7.90 (m, 1H), 7.89-7.86 (m, 1H), 7.85-7.80 (m, 1H), 7.23 (dd, J=9.6, 2.2 Hz, 1H), 4.42-4.34 (m, 1H), 4.33 (d, J=10.5 Hz, 1H), 4.21 (d, J=10.5 Hz, 1H), 3.95-3.88 (m, 1H), 3.88-3.83 (m, 1H), 2.66-2.60 (m, 1H), 2.57 (ddd, J=10.9, 8.1, 3.0 Hz, 1H), 2.45-2.35 (m, 3H), 2.28-2.17 (m, 2H), 2.17-2.09 (m, 1H), 2.04 (dd, J=11.0, 9.1 Hz, 1H), 1.60 (s, 3H), 1.58 (s, 3H), 0.99 (d, J=6.9 Hz, 3H), 0.94 (d, J=7.2 Hz, 3H); HPLC RT=5.67 min (Method A), 6.43 min (Method B).

Example 270: (S)-2-methyl-1-((3-(((aR)-6-(4-oxo-3,4-dihydrophthalazin-1-yl)spiro[3.3]heptan-2-yl)carbamoyl)pyrazolo[1,5-a]pyridin-6-yl)oxy)propan-2-yl 2-aminopropanoate, TFA

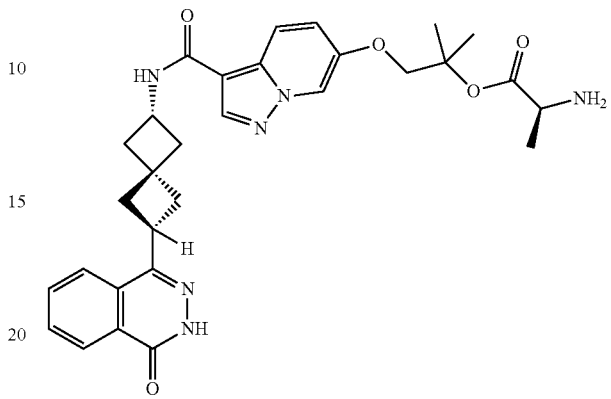

According to the procedure for the preparation of Example 268, substituting (S)-2-((tert-butoxycarbonyl)amino)propanoic acid for 2-((tert-butoxycarbonyl)amino)acetic acid afforded Example 270. MS(ESI) m/z: 559.5 (M+H)$^+$; $^1$H NMR: (500 MHz, DMSO-d$_6$) δ ppm 12.47 (s, 1H), 8.52 (d, J=2.2 Hz, 1H), 8.48 (s, 1H), 8.32-8.21 (m, 5H), 8.11 (d, J=9.6 Hz, 1H), 7.95-7.90 (m, 1H), 7.89-7.86 (m, 1H), 7.85-7.80 (m, 1H), 7.31-7.21 (m, 1H), 4.37 (dq, J=16.1, 8.2 Hz, 2H), 4.32-4.27 (m, 1H), 4.25-4.19 (m, 1H), 3.90 (quin, J=8.5 Hz, 1H), 2.67-2.60 (m, 1H), 2.57 (ddd, J=11.0, 8.1, 3.2 Hz, 1H), 2.45-2.33 (m, 3H), 2.28-2.17 (m, 2H), 2.08-2.00 (m, 1H), 1.58 (s, 3H), 1.57 (s, 3H), 1.37 (d, J=7.2 Hz, 3H); HPLC RT=5.31 min (Method A), 6.03 min (Method B).

Example 271: 6-(2-hydroxy-2-methylpropoxy)-N-(6-(1-oxo-1,2-dihydroisoquinolin-4-yl)spiro[3.3]heptan-2-yl)pyrazolo[1,5-a]pyridine-3-carboxamide

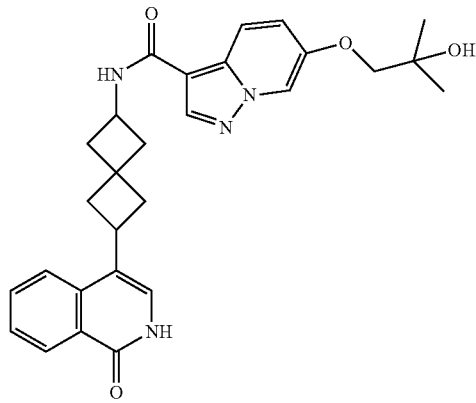 [SMILES: CC(C)(O)COc1ccc2c(C(=O)NC3CC4(C3)CC(c3c[nH]c(=O)c5ccccc35)C4)cnn2c1]

Example 271A 4-bromo-2-(dicyclopropylmethyl)isoquinolin-1(2H)-one

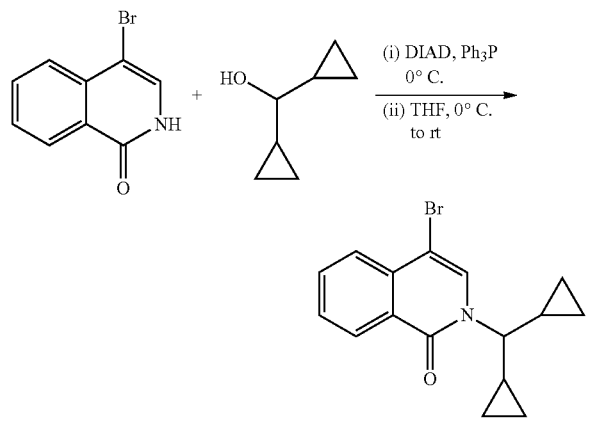

To a solution of Ph₃P (0.937 g, 3.57 mmol) in THF (8 mL) at 0° C., was added DIAD (0.694 mL, 3.57 mmol) dropwise. The reaction mixture was stirred at 0° C. for 15 min (thick suspension formed). Then, a suspension of 4-bromoisoquinolin-1(2H)-one (0.400 g, 1.79 mmol) and dicyclopropylmethanol (0.263 mL, 2.23 mmol) in dry THF (8 mL) was added, and the reaction mixture was allowed to reach rt, and stirred at rt for 16 h. An additional amount of Ph₃P (0.937 g, 3.57 mmol) was added, the reaction mixture was cooled to 0° C., and DIAD (0.694 mL, 3.57 mmol) was added dropwise. The reaction mixture was stirred for additional 2 h at 0° C., and for 2 h at rt. The reaction mixture was quenched with MeOH (1 mL), diluted with EtOAc (100 mL). Then CELITE® was added, the solvent was removed under reduced pressure and the residue was purified by flash chromatography (solid loading on CELITE®): (0-80% EtOAc/DCM gradient) to give Example 271A (0.191 g, 34% yield) as an off-white solid. MS(ESI) m/z: 317.9 (M+H)$^+$; $^1$H NMR: (400 MHz, CDCl₃) δ ppm 8.43 (dd, J=8.1, 0.7 Hz, 1H), 7.85-7.81 (m, 1H), 7.74 (td, J=7.6, 1.3 Hz, 1H), 7.63 (s, 1H), 7.58-7.52 (m, 1H), 3.99 (t, J=7.4 Hz, 1H), 1.21-1.15 (m, 2H), 0.79-0.69 (m, 2H), 0.57 (dq, J=9.8, 4.9 Hz, 2H), 0.49-0.32 (m, 4H).

Example 271B 2-(dicyclopropylmethyl)-4-(4,4,5,5-tetramethyl-1,3,2-dioxaborolan-2-yl)isoquinolin-1(2H)-one

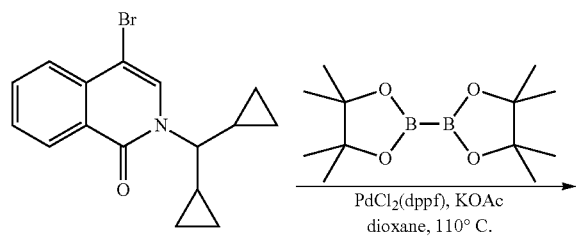

-continued

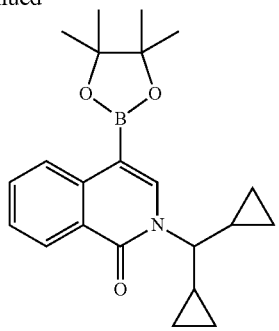

A mixture of Example 271A (191 mg, 0.600 mmol), 4,4,4',4',5,5,5',5'-octamethyl-2,2'-bi(1,3,2-dioxaborolane) (229 mg, 0.900 mmol), and potassium acetate (177 mg, 1.80 mmol) in dioxane (4 mL) was degassed (3× vacuum/Ar). Then, PdCl₂(dppf) CH₂Cl₂ $_{adduct}$ (13 mg, 0.018 mmol) was added, the reaction mixture was degassed again (3× vacuum/Ar), sealed in a vial and heated at 110° C. for 2 h. The reaction mixture was cooled to rt, diluted with EtOAc, CELITE® was added and the solvent was removed under reduced pressure. The residue was purified by flash chromatography (solid loading on CELITE®, 0-50% EtOAc/hex gradient) to give Example 271B (196 mg, 89% yield) as a white solid. MS(ESI) m/z: 366.1 (M+H)$^+$; $^1$H NMR: (500 MHz, DMSO-d₆) δ ppm 8.33 (d, J=7.7 Hz, 1H), 8.23 (dd, J=8.1, 1.0 Hz, 1H), 7.90 (br s, 1H), 7.74 (ddd, J=8.3, 7.0, 1.5 Hz, 1H), 7.50 (ddd, J=8.0, 7.1, 1.1 Hz, 1H), 1.52-1.39 (m, 2H), 1.34 (s, 12H), 0.72-0.63 (m, 2H), 0.56 (dq, J=9.6, 4.7 Hz, 2H), 0.40-0.31 (m, 2H), 0.14 (dq, J=9.8, 4.9 Hz, 2H).

Example 271C (2-(dicyclopropylmethyl)-1-oxo-1,2-dihydroisoquinolin-4-yl)boronic acid

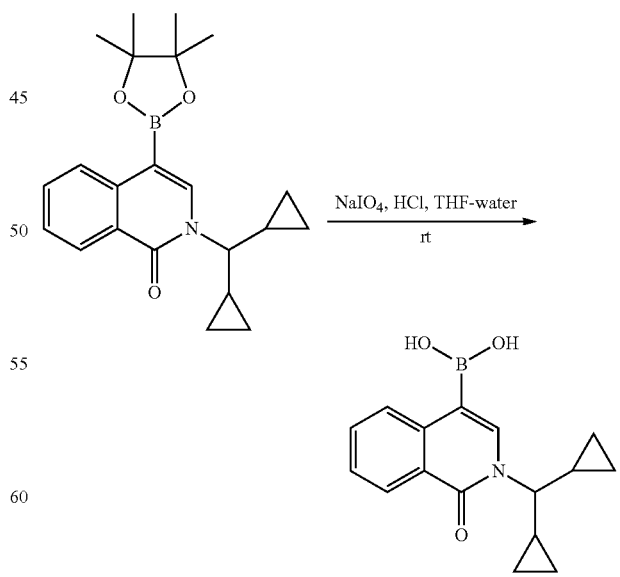

A mixture of Example 271B (196 mg, 0.537 mmol) and sodium periodate (344 mg, 1.61 mmol), was stirred in THF (4 mL) and water (1 mL) for 30 min. Then, HCl (1M aq.)

(0.376 mL, 0.376 mmol) was added, and the reaction mixture was stirred at rt for 6 h. The reaction mixture was filtered and was purified by preparative HPLC to afford Example 271C (42 mg, 28% yield) as a white solid. MS(ESI) m/z: 284.0 (M+H)$^+$; $^1$H NMR: (500 MHz, DMSO-d$_6$) δ ppm 8.47 (d, J=8.3 Hz, 1H), 8.22 (dd, J=8.0, 1.1 Hz, 1H), 8.15 (s, 2H), 7.66 (ddd, J=8.3, 7.0, 1.5 Hz, 1H), 7.48-7.40 (m, 1H), 1.45 (br s, 2H), 0.72-0.62 (m, 2H), 0.56 (dq, J=9.3, 4.8 Hz, 2H), 0.39-0.29 (m, 2H), 0.15 (dq, J=9.9, 4.8 Hz, 2H).

Example 271D tert-butyl (6-(2-(dicyclopropylmethyl)-1-oxo-1,2-dihydroisoquinolin-4-yl)spiro[3.3]heptan-2-yl)carbamate tert-Butyl (6-oxospiro[3.3]heptan-2-yl)carbamate (100 mg, 0.44 mmol) and 4-methoxybenzenesulfonohydrazide (90 mg, 0.44 mmol) were dissolved in dioxane (2. mL), and MS 4A (100 mg) were added. The reaction mixture degassed (3× vacuum/Ar), and then was stirred at 90° C. for 3 h under Ar. The reaction mixture was cooled to rt, and Example 271C (42 mg, 0.148 mmol), cesium carbonate (72.5 mg, 0.223 mmol) and MS 4A (100 mg) were added. The vial was degassed again (3× vacuum/Ar), and the reaction mixture was stirred at 110° C. under Ar for 18 h. Additional cesium carbonate (72.5 mg, 0.223 mmol) was added, along with water (0.1 mL), and the reaction mixture was stirred at 110° C. for 3 h. The reaction mixture was cooled to rt, degassed, capped, and stirred at 110° C. for 14 h. The material was purified by preparative HPLC to afford Example 271D (19 mg, 29% yield) as an off-white solid. MS(ESI) m/z: 449.4 (M+H)$^+$.

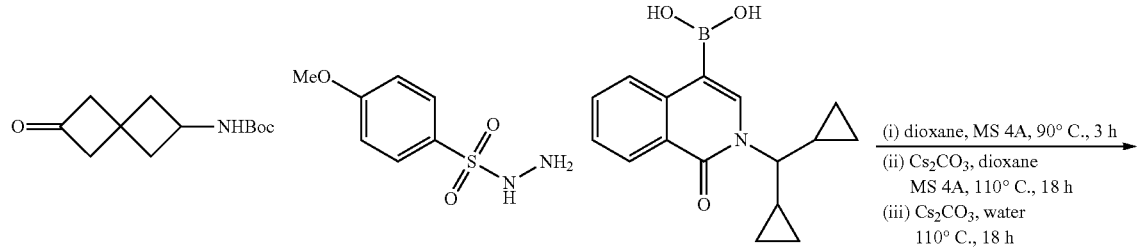

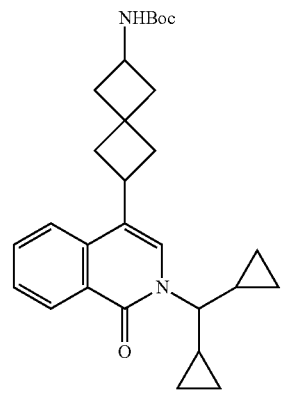

Example 271E

N-(6-(2-(dicyclopropylmethyl)-1-oxo-1,2-dihydroisoquinolin-4-yl)spiro[3.3]heptan-2-yl)-6-(2-hydroxy-2-methylpropoxy)pyrazolo[1,5-a]pyridine-3-carboxamide

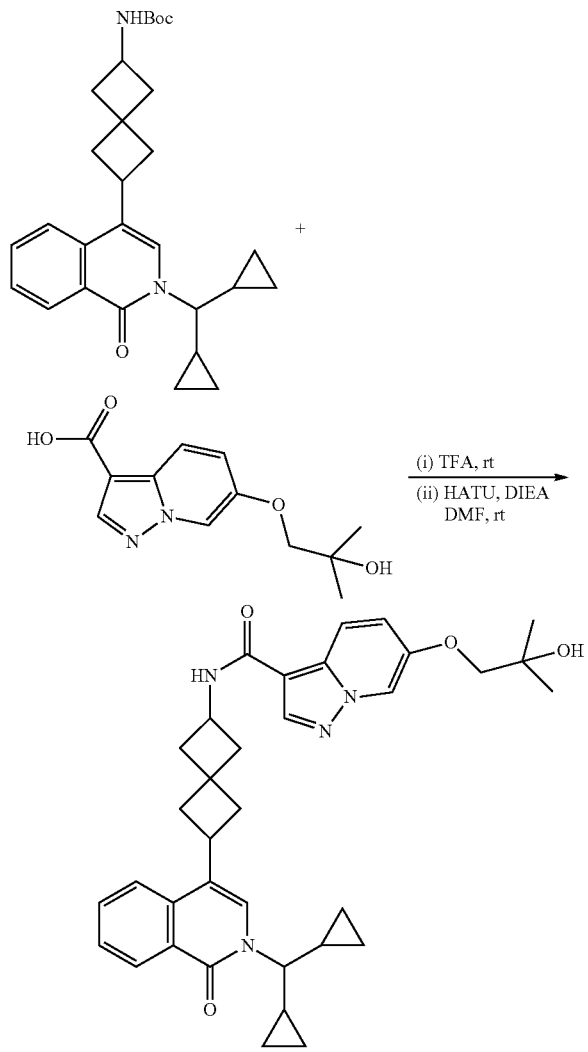

Example 271D (19 mg, 0.042 mmol) was dissolved in TFA (1.0 mL), and the reaction mixture was stirred for 30 min. The solvent was evaporated to afford the amine salt. In a separate vial, Intermediate 29 (13.8 mg, 0.055 mmol) was suspended in anhydrous DMF (1 mL), then DIEA (0.022 mL, 0.13 mmol) and HATU (18.5 mg, 0.049 mmol) were added. After stirring for 30 min at rt, the obtained solution was added to a solution of the amine salt and DIEA (0.022 mL, 0.13 mmol) in anhydrous DMF (0.5 mL).

The reaction mixture was stirred at rt for 1 h, then was quenched with MeOH (0.1 mL), diluted with DMF and purified by preparative HPLC to afford Example 271E (10 mg, 41% yield). MS(ESI) m/z: 581.5 (M+H)$^+$; $^1$H NMR: (500 MHz, THF-d$_8$) δ ppm 8.38-8.34 (m, 1H), 8.27 (d, J=2.2 Hz, 1H), 8.21 (d, J=9.6 Hz, 1H), 8.13 (s, 1H), 7.64-7.57 (m, 2H), 7.41 (ddd, J=8.1, 6.5, 1.7 Hz, 1H), 7.29 (br d, J=7.7 Hz, 1H), 7.23 (s, 1H), 7.15 (dd, J=9.6, 2.2 Hz, 1H), 4.60-4.51 (m, 1H), 3.80 (s, 2H), 3.69-3.63 (m, 1H), 2.71-2.65 (m, 4H), 2.52-2.44 (m, 1H), 2.39-2.31 (m, 1H), 2.26 (t, J=9.9 Hz, 1H), 2.18 (dt, J=18.9, 9.7 Hz, 2H), 2.03 (t, J=10.0 Hz, 1H), 1.28 (s, 6H), 0.71-0.64 (m, 2H), 0.57 (dq, J=9.3, 4.5 Hz, 2H), 0.40-0.28 (m, 4H).

Example 271

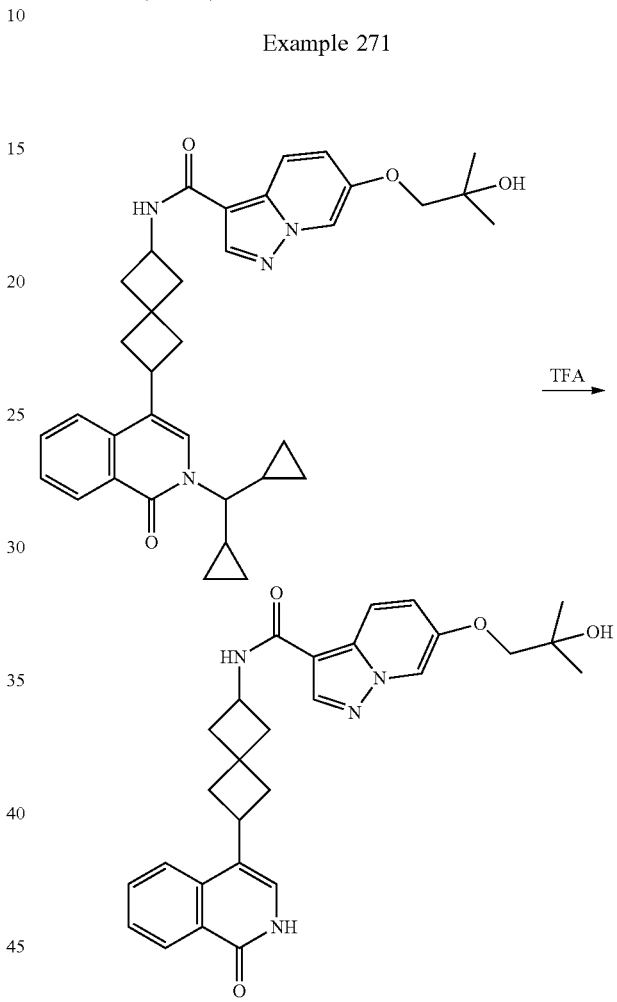

Example 271E (10 mg, 0.017 mmol) was dissolved in TFA (2 mL) and was stirred at rt for 30 min. The reaction mixture was transferred into microwave vial, capped and was irradiated at 80° C. for 15 min. TFA was removed under reduced pressure, and the residue was purified by preparative HPLC to afford Example 271 (1.2 mg, 11% yield). MS(ESI) m/z: 487.4 (M+H)$^+$; $^1$H NMR: (500 MHz, DMSO-d$_6$) δ ppm 10.19 (br s, 1H), 8.34-8.30 (m, 1H), 8.27 (d, J=1.7 Hz, 1H), 8.21 (d, J=9.6 Hz, 1H), 8.12 (s, 1H), 7.64-7.60 (m, 1H), 7.60-7.56 (m, 1H), 7.40 (ddd, J=8.0, 6.7, 1.5 Hz, 1H), 7.27 (br d, J=7.7 Hz, 1H), 7.15 (dd, J=9.6, 1.9 Hz, 1H), 4.59-4.49 (m, 1H), 3.80 (s, 2H), 2.76-2.69 (m, 1H), 2.67-2.60 (m, 1H), 2.45-2.38 (m, 1H), 2.35-2.28 (m, 1H), 2.18 (t, J=9.9 Hz, 2H), 2.11 (t, J=10.2 Hz, 1H), 2.01 (dd, J=11.0, 9.1 Hz, 1H), 1.28 (s, 6H); HPLC RT=6.81 min (Method A), 6.92 min (Method B).

401

Example 272: tert-butyl 3-(((aR)-6-(4-oxo-3,4-dihydrophthalazin-1-yl)spiro[3.3]heptan-2-yl)carbamoyl)-4,5-dihydrothieno[2,3-c]pyridine-6(7H)-carboxylate

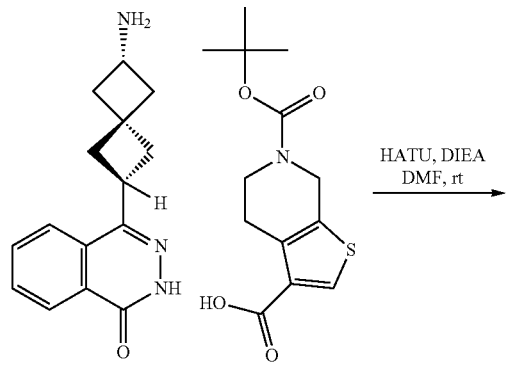

To a suspension of 6-Boc-4,5,6,7-tetrahydro-thieno[2,3-c]pyridine-3-carboxylic acid (53.4 mg, 0.189 mmol) and Intermediate 2, HCl (50 mg, 0.171 mmol) in DMF (1 mL), were added HATU (71.7 mg, 0.189 mmol) and DIEA (0.090 mL, 0.51 mmol). The resultant yellow solution was stirred at rt for 15 h. The mixture was partitioned between EtOAc and water. The aqueous phase was extracted with EtOAc. The combined organic phase was washed with 1N HCl and brine, dried ($Na_2SO_4$) and concentrated. The crude product was purified by preparative HPLC to afford Example 272 (88 mg, 98% yield). MS(ESI) m/z: 521.1 (M+H)$^+$; $^1$H NMR (500 MHz, DMSO-$d_6$) δ 12.48 (s, 1H), 8.33 (d, J=7.5 Hz, 1H), 8.25 (d, J=7.8 Hz, 1H), 7.96-7.89 (m, 1H), 7.89-7.80 (m, 3H), 4.53 (br. s., 2H), 4.33-4.19 (m, 1H), 3.88 (quin, J=8.4 Hz, 1H), 3.53 (br. s., 1H), 2.78 (br. s., 2H), 2.63-2.56 (m, 1H), 2.41-2.30 (m, 3H), 2.24-2.13 (m, 2H), 2.00 (t, J=10.0 Hz, 1H), 1.41 (s, 9H); HPLC RT=1.88 min (Method E), 1.88 min (Method F).

402

Example 273: N-((aR)-6-(4-oxo-3,4-dihydrophthalazin-1-yl)spiro[3.3]heptan-2-yl)-4,5,6,7-tetrahydrothieno[2,3-c]pyridine-3-carboxamide, TFA

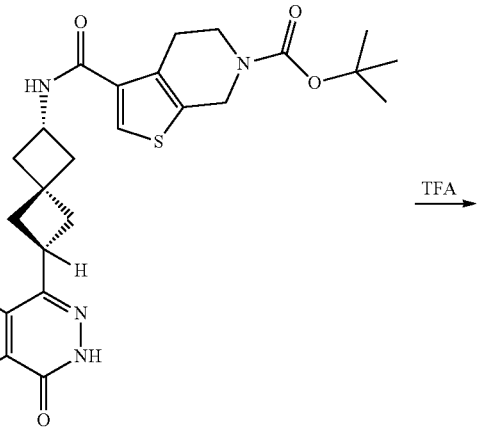

Example 272 (79 mg, 0.151 mmol) was dissolved in TFA (1 mL). The mixture was stirred at rt for 20 min, then was concentrated to afford the title compound (70 mg) as a white solid. MS(ESI) m/z: 421.2 (M+H)$^+$; $^1$H NMR (500 MHz, DMSO-$d_6$) δ 12.48 (s, 1H), 8.27 (dd, J=19.2, 7.6 Hz, 2H), 8.02-7.70 (m, 4H), 4.32-4.18 (m, 1H), 3.94-3.81 (m, 2H), 2.89 (d, J=5.4 Hz, 2H), 2.72 (d, J=7.3 Hz, 2H), 2.61-2.55 (m, 1H), 2.43-2.27 (m, 3H), 2.25-2.11 (m, 2H), 2.05-1.95 (m, 1H), 1.90 (br. s., 3H); HPLC RT=1.11 min (Method E), 0.94 min (Method F).

403

Example 274: 6-acetyl-N-((aR)-6-(4-oxo-3,4-dihydrophthalazin-1-yl)spiro[3.3]heptan-2-yl)-4,5,6,7-tetrahydrothieno[2,3-c]pyridine-3-carboxamide

404

Example 275: methyl 3-(((aR)-6-(4-oxo-3,4-dihydrophthalazin-1-yl)spiro[3.3]heptan-2-yl)carbamoyl)-4,5-dihydrothieno[2,3-c]pyridine-6(7H)-carboxylate

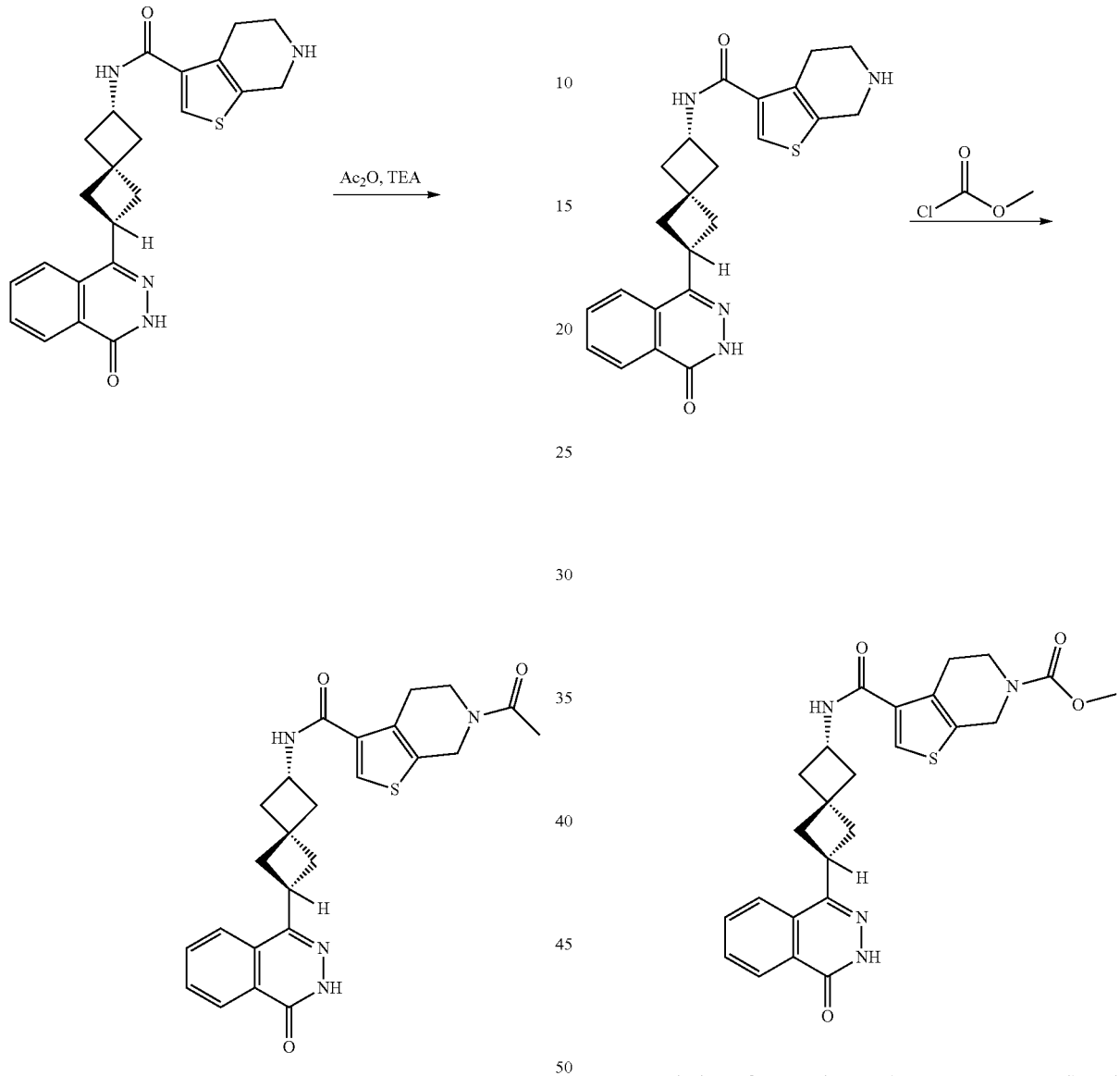

To a solution of Example 273 (15 mg, 0.028 mmol) and TEA (20 μL, 0.14 mmol) in THF (1 mL) at rt, was added Ac$_2$O (4 μL, 0.042 mmol). The mixture was stirred at rt 25 min, then was quenched with a drop of MeOH. The mixture was concentrated, then was purified by preparative HPLC to afford Example 274 (12.1 mg, 93% yield). MS(ESI) m/z: 463.0 (M+H)$^+$; $^1$H NMR (500 MHz, DMSO-d$_6$) δ 12.46 (s, 1H), 8.32 (d, J=7.3 Hz, 1H), 8.25 (d, J=7.9 Hz, 1H), 7.95-7.79 (m, 4H), 4.31-4.20 (m, 1H), 3.88 (quin, J=8.3 Hz, 1H), 3.68-3.59 (m, 2H), 3.39 (br. s., 2H), 2.91-2.84 (m, 2H), 2.75 (br. s., 1H), 2.57 (d, J=11.3 Hz, 1H), 2.41-2.30 (m, 3H), 2.24-2.14 (m, 2H), 2.11-2.03 (m, 3H), 2.03-1.96 (m, 1H); HPLC RT=1.42 min (Method E), 1.46 min (Method F).

To a solution of Example 273 (15 mg, 0.028 mmol) and TEA (20 μL, 0.143 mmol) in THF (1 mL) at rt, was added methyl chloroformate (3.26 μL, 0.042 mmol). The heterogeneous mixture was stirred at rt for 25 min, then was quenched with a drop of MeOH. The mixture was concentrated, then was purified by preparative HPLC to afford Example 275 (13.0 mg, 97% yield). MS(ESI) m/z: 479.1 (M+H)$^+$; $^1$H NMR (500 MHz, DMSO-d$_6$) δ 12.46 (s, 1H), 8.31 (d, J=7.3 Hz, 1H), 8.25 (d, J=7.9 Hz, 1H), 7.97-7.80 (m, 4H), 4.59 (br. s., 2H), 4.31-4.20 (m, 1H), 3.88 (quin, J=8.5 Hz, 1H), 3.63 (s, 3H), 3.58 (t, J=5.8 Hz, 2H), 2.80 (br. s., 2H), 2.62-2.55 (m, 1H), 2.41-2.29 (m, 3H), 2.24-2.13 (m, 2H), 2.04-1.96 (m, 1H); HPLC RT=1.61 min (Method E), 1.67 min (Method F).

405

Example 276: 6-(methylsulfonyl)-N-((aR)-6-(4-oxo-3,4-dihydrophthalazin-1-yl)spiro[3.3]heptan-2-yl)-4,5,6,7-tetrahydrothieno[2,3-c]pyridine-3-carboxamide

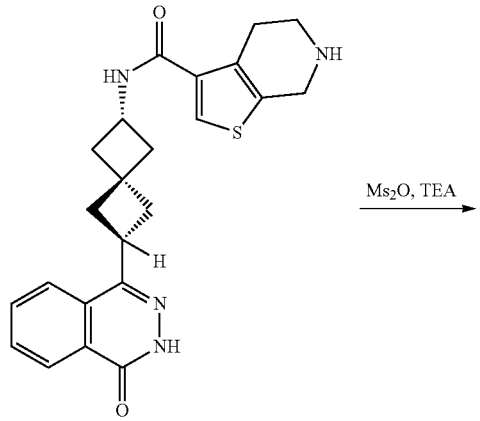

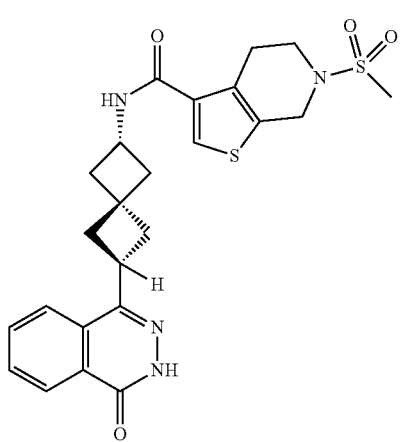

To a solution of Example 273 (15 mg, 0.028 mmol) and TEA (20 µL, 0.14 mmol) in THF (1 mL) at rt, was added methanesulfonic anhydride (7.3 mg, 0.42 mmol). The mixture was stirred at rt for 25 min, then was quenched with a drop of MeOH. The mixture was concentrated. The residue was dissolved in 1:1 MeOH/DMSO, filtered and submitted for purification, then was purified by preparative HPLC to afford Example 276. (3.2 mg, 23% yield). MS(ESI) m/z: 499.1 (M+H)+; $^1$H NMR (500 MHz, DMSO-$d_6$) δ 12.48 (s, 1H), 8.36 (d, J=7.3 Hz, 1H), 8.27 (d, J=7.6 Hz, 1H), 7.97-7.90 (m, 2H), 7.90-7.82 (m, 2H), 4.44 (s, 2H), 4.28 (q, J=8.1 Hz, 1H), 3.91 (quin, J=8.4 Hz, 1H), 2.96 (s, 3H), 2.94 (br. s., 2H), 2.65-2.58 (m, 1H), 2.44-2.30 (m, 3H), 2.26-2.15 (m, 2H), 2.03 (t, J=10.1 Hz, 1H); HPLC RT=1.50 min (Method E), 1.49 min (Method F).

406

Example 277: 6-(1-methyl-1H-pyrazol-4-yl)-N-((aR)-6-(4-oxo-3,4-dihydrophthalazin-1-yl)spiro[3.3]heptan-2-yl)benzo[c]isoxazole-3-carboxamide

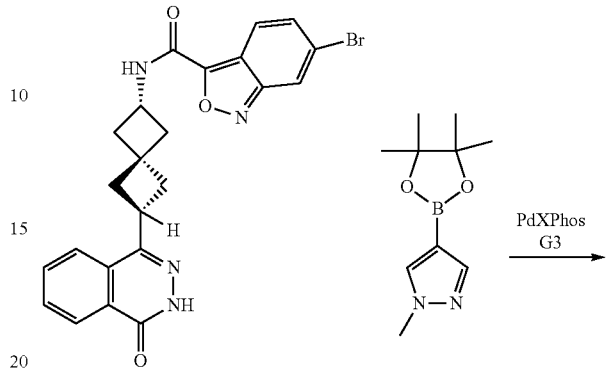

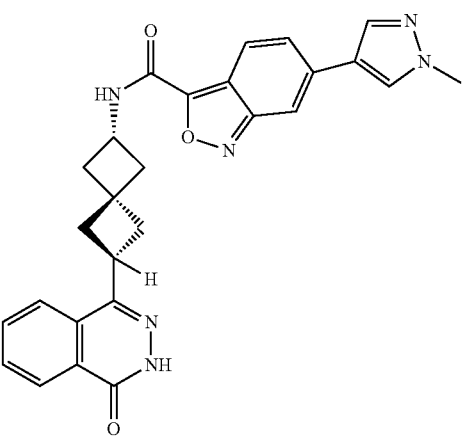

A solution of Example 284 (10 mg, 0.021 mmol), 1-methyl-4-(4,4,5,5-tetramethyl-1,3,2-dioxaborolan-2-yl)-1H-pyrazole (13 mg, 0.063 mmol) in THF (2.0 mL) and Phosphoric acid, potassium salt (0.5 M aq.) (0.083 mL, 0.042 mmol) was purged with argon. Pd-XPhos G3 (1.7 mg, 2.0 µmol) was added. The pressure vial was capped, and the reaction mixture was stirred at 120° C. for 30 min. The mixture was concentrated, then was purified by preparative HPLC to afford Example 277 (2.0 mg, 20% yield). MS(ESI) m/z: 481.1 (M+H)+; $^1$H NMR (500 MHz, DMSO-$d_6$) δ 12.50 (s, 1H), 9.44 (d, J=7.6 Hz, 1H), 8.37 (s, 1H), 8.27 (d, J=7.9 Hz, 1H), 8.10 (s, 1H), 7.99-7.77 (m, 5H), 7.57 (d, J=9.2 Hz, 1H), 4.46-4.36 (m, 1H), 3.95-3.86 (m, 4H), 2.70-2.57 (m, 2H), 2.46-2.32 (m, 4H), 2.30-2.23 (m, 1H), 2.22-2.15 (m, 1H); HPLC RT=1.72 min (Method E), 1.76 min (Method F).

Example 278: 1-(2-hydroxy-2-methylpropyl)-N-(6-(4-oxo-3,4-dihydropyrrolo[1,2-d][1,2,4]triazin-1-yl)spiro[3.3]heptan-2-yl)-1H-indazole-3-carboxamide, TFA

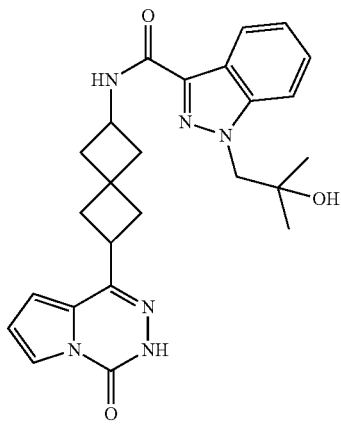 [SMILES: CC(C)(O)Cn1nc(C(=O)NC2CC3(C2)CC(c2n[nH]c(=O)n4cccc24)C3)c2ccccc21]

Example 278a

S-pyridin-2-yl6-((tert-butoxycarbonyl)amino)spiro[3.3]heptane-2-carbothioate

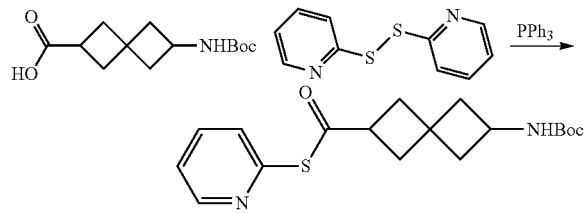

6-(Boc-amino)spiro[3.3]heptane-2-carboxylic acid (197 mg, 0.733 mmol), triphenylphosphine (250 mg, 0.953 mmol), 2,2'-dipyridyl disulfide (210 mg, 0.953 mmol) in degassed Toluene (5 mL) was stirred at RT for 3 days. The mixture was concentrated, and the residue purified by flash chromatography (0-70% EtOAc/hexanes gradient) to afford Example 278a (238 mg, 93% yield), as a pale yellow solid. MS(ESI) m/z: 349.2 (M+H)+; 1H NMR (400 MHz, chloroform-d) δ 8.65-8.59 (m, 1H), 7.77-7.70 (m, 1H), 7.61 (dt, J=7.9, 0.9 Hz, 1H), 7.31-7.25 (m, 1H), 4.60 (br. s., 1H), 3.99 (br. s., 1H), 3.39 (quin, J=8.4 Hz, 1H), 2.58-2.31 (m, 5H), 2.21 (ddd, J=11.8, 8.5, 3.5 Hz, 1H), 1.94-1.75 (m, 2H), 1.43 (s, 9H).

Example 278b tert-butyl (6-(1H-pyrrole-2-carbonyl)spiro[3.3]heptan-2-yl)carbamate

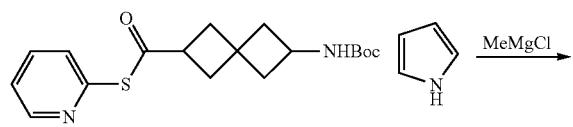

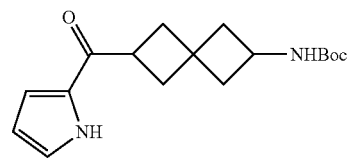

To a solution of 1H-pyrrole (0.093 mL, 1.34 mmol) in THF (1 mL) at 0° C., was added dropwise methylmagnesium chloride (3M in THF) (0.35 mL, 1.05 mmol). The mixture was stirred 15 mins, then was cooled to −78° C. To this mixture was added a solution of Example 278a (112 mg, 0.321 mmol) in THF. The mixture was stirred at −78° C. for 10 mins, then gradually warmed up to 0° C. and stirred at that temperature for 1 hr. The mixture was quenched with conc. NH4Cl, then was extracted with EtOAc. The organic phase washed with brine, dried (MgSO4), and concentrated. The residue purified by flash chromatography (0-75% EtOAc/hexanes gradient) to afford Example 278b (92 mg, 94% yield). MS(ESI) m/z: 305.1 (M+H)+; 1H NMR (400 MHz, chloroform-d) δ 9.44 (br s, 1H), 7.02 (td, J=2.6, 1.3 Hz, 1H), 6.81 (ddd, J=3.7, 2.4, 1.3 Hz, 1H), 6.26 (dt, J=3.7, 2.5 Hz, 1H), 4.62 (br. s., 1H), 4.02 (br. s., 1H), 3.69 (quin, J=8.5 Hz, 1H), 2.66-2.52 (m, 1H), 2.49-2.24 (m, 4H), 2.21-2.09 (m, 1H), 1.91 (dd, J=10.9, 8.7 Hz, 1H), 1.79 (dd, J=11.3, 8.7 Hz, 1H), 1.44 (s, 9H).

Example 278c (E)-tert-butyl (6-(hydrazono(1H-pyrrol-2-yl)methyl)spiro[3.3]heptan-2-yl)carbamate Example 278b (75 mg, 0.25 mmol), hydrazine hydrate (0.5 mL, 10 mmol) in a sealed vial was heated at 90° C. for 4 hr, then was stirred at RT for 3 days. The reaction mixture was diluted with DCM, then was washed with water and brine, dried (MgSO4) and concentrated to afford Example 278c (78 mg, 100% yield) as a light brown gum. The material was used in the following step without further purification. MS(ESI) m/z: 319.3 (M+H)+.

Example 278d (E)-methyl-2-((6-((tert-butoxycarbonyl)amino)spiro[3.3]heptan-2-yl)(2-(methoxycarbonyl)hydrazono)methyl)-1H-pyrrole-1-carboxylate

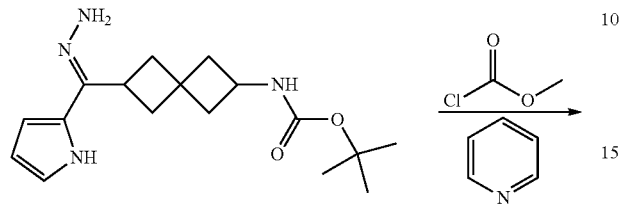

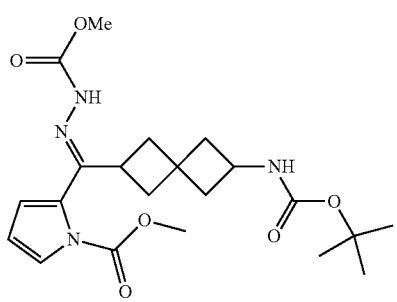

To a mixture of Example 278c (76 mg, 0.24 mmol) and pyridine (0.048 mL, 0.60 mmol) in CH$_2$Cl$_2$ (2 mL) at 0° C., was added methyl carbonochloridate (0.037 mL, 0.48 mmol) dropwise. The mixture was stirred at 0° C. for 20 min, then was partitioned between water and DCM. The organic phase was washed with brine, dried (MgSO$_4$) and concentrated. The crude product was purified by flash chromatography (0-90% EtOAc/hexanes gradient) to afford Example 278d (64 mg, 61% yield). MS(ESI) m/z: 435.3 (M+H)$^+$.

Example 278e tert-butyl (6-(4-oxo-3,4-dihydropyrrolo[1,2-d][1,2,4]triazin-1-yl)spiro[3.3]heptan-2-yl)carbamate

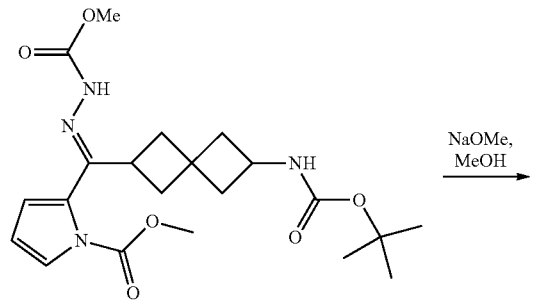

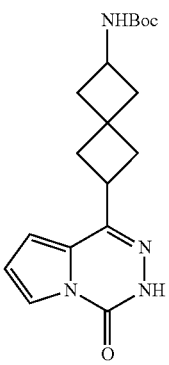

To Example 278d (64 mg, 0.147 mmol) in MeOH (2 mL), was added sodium methoxide (25 wt % in MeOH) (159 mg, 0.737 mmol). The mixture was sealed and heated at 100° C. for 30 min. To the reaction mixture was added HCl (1.25N in MeOH) (0.589 mL, 0.737 mmol), then was purified by preparative HPLC to afford Example 278e (32 mg, 63% yield), MS(ESI) m/z: 345.2 (M+H)$^+$; $^1$H NMR (400 MHz, methanol-d$_4$) δ 7.72 (dd, J=3.1, 1.3 Hz, 1H), 6.79 (dd, J=3.6, 3.0 Hz, 1H), 6.75 (dd, J=3.7, 1.5 Hz, 1H), 4.01-3.87 (m, 1H), 3.65 (quin, J=8.5 Hz, 1H), 2.64-2.55 (m, 1H), 2.55-2.23 (m, 5H), 2.05 (dd, J=10.7, 8.9 Hz, 1H), 1.91 (dd, J=11.2, 8.8 Hz, 1H), 1.46 (s, 9H).

Example 278f 1-(6-aminospiro[3.3]heptan-2-yl)pyrrolo[1,2-d][1,2,4]triazin-4(3H)-one, HCl

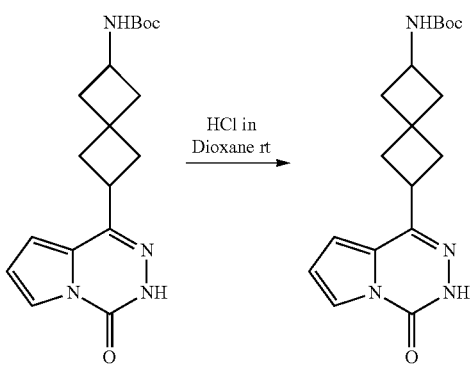 [SMILES: CC(C)(C)OC(=O)NC1CC2(C1)CC(c1n[nH]c(=O)n3cccc13)C2 ; CC(C)(C)OC(=O)NC1CC2(C1)CC(c1n[nH]c(=O)n3cccc13)C2]

Example 278e (32 mg, 0.093 mmol) in 4M HCl in Dioxane (1 mL) was stirred at rt for 2 h. The mixture was concentrated to afford Example 278f (25 mg, 96% yield) as a grey solid. MS(ESI) m/z: 245.1 (M+H)$^+$.

Example 278

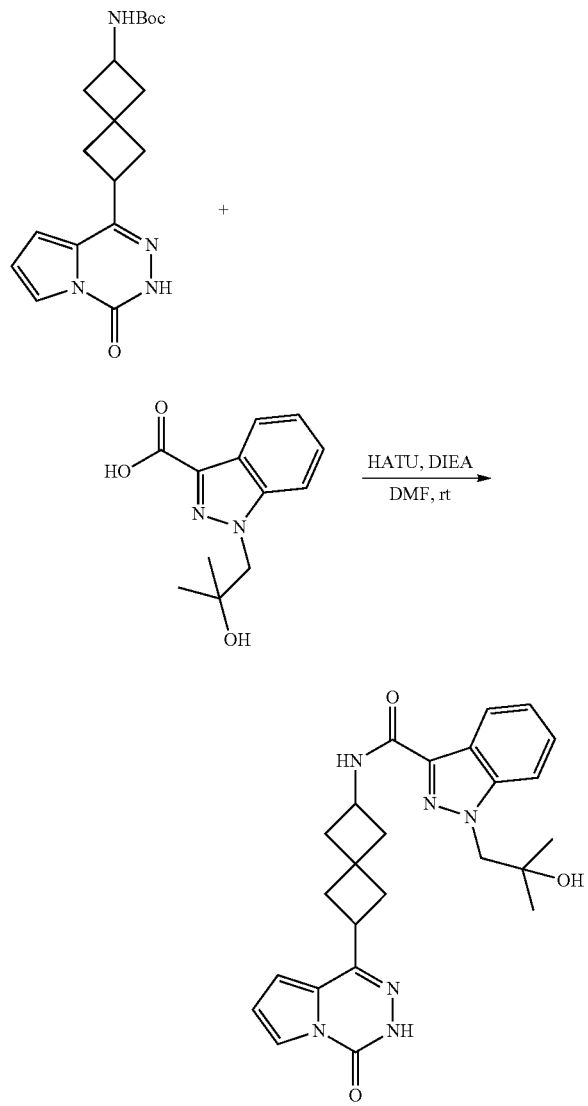 [SMILES: CC(C)(C)OC(=O)NC1CC2(C1)CC(c1n[nH]c(=O)n3cccc13)C2 ; CC(C)(O)Cn1nc(C(=O)O)c2ccccc21 ; CC(C)(O)Cn1nc(C(=O)NC2CC3(C2)CC(c2n[nH]c(=O)n4cccc24)C3)c2ccccc21]

To Example 278f (6 mg, 0.025 mmol), 1-(2-hydroxy-2-methylpropyl)-1H-indazole-3-carboxylic acid (5.8 mg, 0.025 mmol), HATU (14 mg, 0.037 mmol) in DMF (0.5 mL), was added DIEA (0.013 mL, 0.074 mmol). The mixture was sonicated to make a homogeneous solution then was stirred at rt for 1 h. The product was purified by preparative HPLC to afford Example 278 (8.5 mg, 58% yield). MS(ESI) m/z: 461.2 (M+H)$^+$; $^1$H NMR (400 MHz, methanol-$d_4$) δ 8.23 (d, J=8.4 Hz, 1H), 7.73 (dd, J=2.9, 1.3 Hz, 1H), 7.70 (d, J=8.6 Hz, 1H), 7.46 (ddd, J=8.4, 7.2, 1.0 Hz, 1H), 7.28 (t, J=7.6 Hz, 1H), 6.82-6.79 (m, 1H), 6.79-6.76 (m, 1H), 4.56-4.48 (m, 1H), 4.47 (s, 2H), 3.70 (quin, J=8.5 Hz, 1H), 2.80-2.71 (m, 1H), 2.65-2.38 (m, 5H), 2.32 (dd, J=10.7, 8.9 Hz, 1H), 2.18 (dd, J=11.2, 9.0 Hz, 1H), 1.27 (s, 6H); HPLC RT=8.25 min (Method A), 7.26 min (Method B).

Example 279: 6-(2-hydroxy-2-methylpropoxy)-N-(6-(4-oxo-3,4-dihydropyrrolo[1,2-d][1,2,4]triazin-1-yl)spiro[3.3]heptan-2-yl)pyrazolo[1,5-a]pyridine-3-carboxamide, TFA

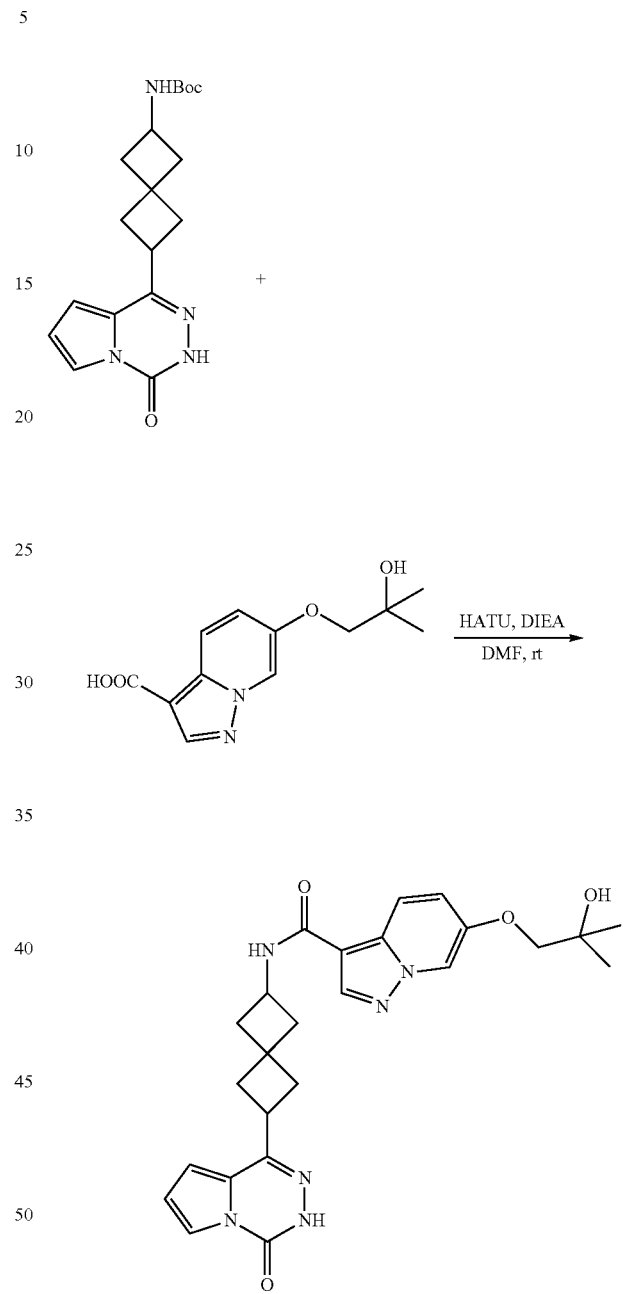

According to the procedure for the preparation of Example 278, substituting Intermediate 29 for 1-(2-hydroxy-2-methylpropyl)-1H-indazole-3-carboxylic acid afforded Example 279. MS(ESI) m/z: 477.3 (M+H)$^+$; $^1$H NMR (400 MHz, methanol-$d_4$) δ 8.36 (s, 1H), 8.29 (s, 1H), 8.13 (d, J=9.9 Hz, 1H), 7.71 (br. s., 1H), 7.33 (d, J=8.8 Hz, 1H), 6.78 (d, J=8.4 Hz, 2H), 4.52-4.35 (m, 1H), 3.86 (s, 2H), 3.75-3.60 (m, 1H), 2.71 (br. s., 1H), 2.63-2.33 (m, 5H), 2.25 (t, J=9.6 Hz, 1H), 2.11 (t, J=10.0 Hz, 1H), 2.03 (br. s., 1H), 1.35 (s, 6H); HPLC RT=6.92 min (Method A), 6.16 min (Method B).

Example 280: 1-methyl-N-(6-(4-oxo-3,4-dihydropyrrolo[1,2-d][1,2,4]triazin-1-yl)spiro[3.3]heptan-2-yl)-1H-indazole-3-carboxamide, TFA

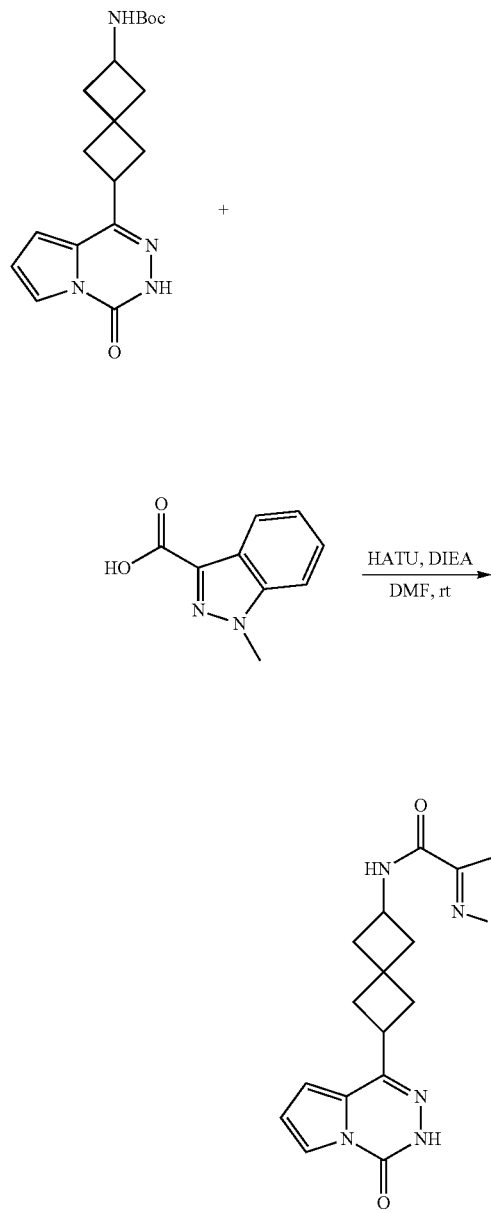

According to the procedure for the preparation of Example 278, substituting 1-methyl-1H-indazole-3-carboxylic acid for 1-(2-hydroxy-2-methylpropyl)-1H-indazole-3-carboxylic acid afforded Example 280. MS(ESI) m/z: 403.2 (M+H)$^+$; $^1$H NMR (400 MHz, methanol-d$_4$) δ 8.36 (s, 1H), 8.29 (s, 1H), 8.13 (d, J=9.9 Hz, 1H), 7.71 (br. s., 1H), 7.33 (d, J=8.8 Hz, 1H), 6.78 (d, J=8.4 Hz, 2H), 4.52-4.35 (m, 1H), 3.86 (s, 2H), 3.75-3.60 (m, 1H), 2.71 (br. s., 1H), 2.63-2.33 (m, 5H), 2.25 (t, J=9.6 Hz, 1H), 2.11 (t, J=10.0 Hz, 1H), 2.03 (br. s., 1H), 1.35 (s, 6H); HPLC RT=8.84 min (Method A), 7.76 min (Method B).

Example 281: 6-(2-hydroxy-2-methylpropoxy)-N-(6-(8-methyl-4-oxo-3,4-dihydropyrrolo[1,2-d][1,2,4]triazin-1-yl)spiro[3.3]heptan-2-yl)pyrazolo[1,5-a]pyridine-3-carboxamide, TFA

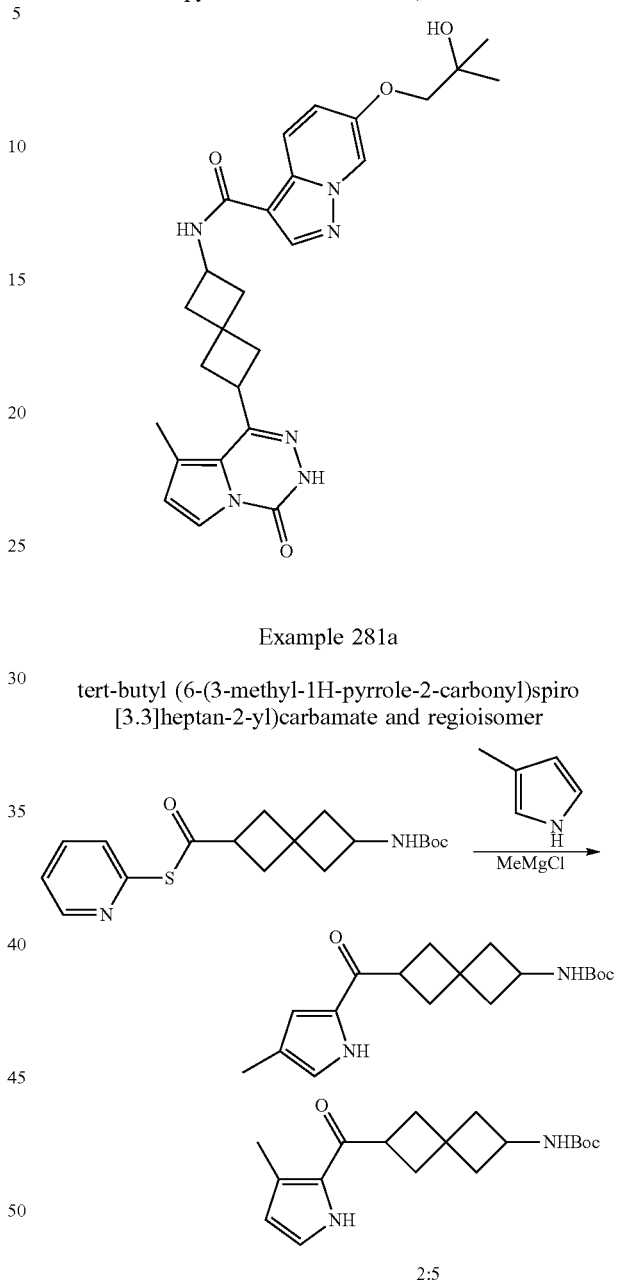

Example 281a tert-butyl (6-(3-methyl-1H-pyrrole-2-carbonyl)spiro[3.3]heptan-2-yl)carbamate and regioisomer To a solution of 3-methyl-1H-pyrrole (52 mg, 0.45 mmol) in THF (0.5 mL) at 0° C., methylmagnesium chloride (3M in THF) (0.143 mL, 0.430 mmol) was added dropwise. After 15 min, the solution was cooled to −78° C. and Example 278a (50 mg, 0.14 mmol) in 0.5 mL THF was added. The mixture was stirred at −78° C. for 10 min, gradually warmed to 0° C. and stirred for 1 hr. The reaction was quenched with sat. NH$_4$Cl aq and extracted with EtOAc. The organic phase was washed with brine, dried (MgSO$_4$) and concentrated. The residue was purified by flash chromatography (0-60% EtOAc/hexanes gradient) to afford Example 281a (33 mg, 72% yield) as an off-white solid. The product is a 2:5 mixture of regioisomers. MS(ESI) m/z: 319.3 (M+H)$^+$.

Example 281b (E)-tert-butyl (6-(hydrazono(3-methyl-1H-pyrrol-2-yl)methyl)spiro[3.3]heptan-2-yl)carbamate and regioisomer

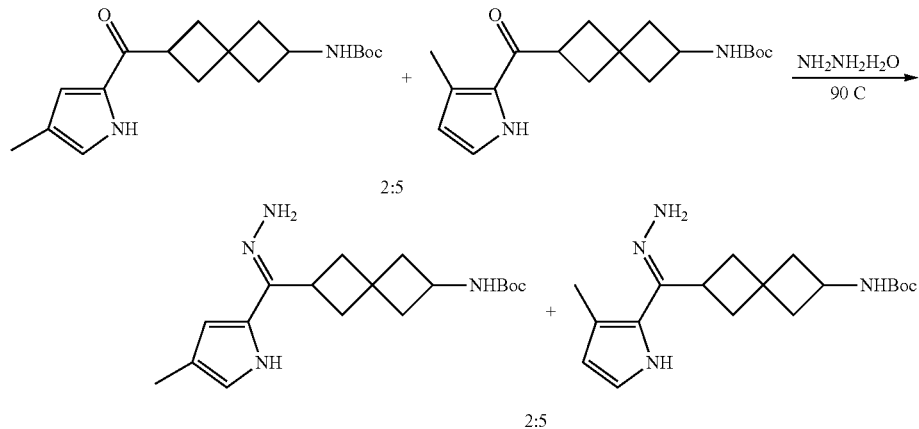

A mixture of Example 281a (32 mg, 0.10 mol) in hydrazine hydrate (0.3 mL, 6.18 mmol) was sealed and heated at 90° C. for 6 h. The reaction mixture was partitioned between DCM and water. The DCM phase was washed with brine, dried (MgSO$_4$) and concentrated to afford Example 281b (33 mg). The product is a 2:5 mixture of regioisomers. MS(ESI) m/z: 333.2 (M+H)$^+$.

Example 281c methyl (E)-2-((6-((tert-butoxycarbonyl)amino)spiro[3.3]heptan-2-yl)(2-(methoxycarbonyl)hydrazono)methyl)-3-methyl-1H-pyrrole-1-carboxylate

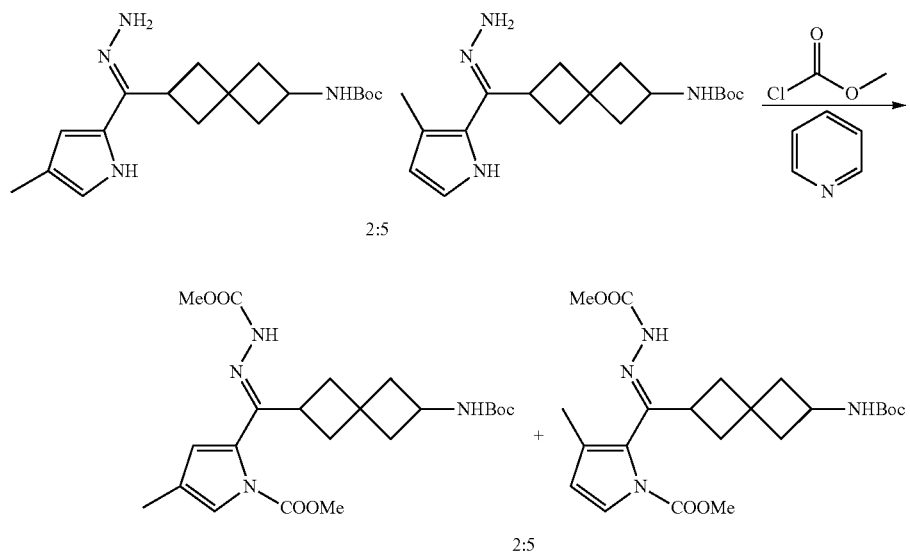

To a solution of Example 281b, pyridine (50 µl, 0.62 mmol) in CH$_2$Cl$_2$ (1 mL) at 0° C., methyl carbonochloridate (30 µl, 0.388 mmol) was added dropwise. The mixture was stirred for 15 min, then was diluted with DCM, washed with water and brine, dried (MgSO$_4$) and concentrated. The residue was purified by flash chromatography (0-80% EtOAc/hexanes gradient) to afford Example 281c (40 mg, 90% yield) as a white solid. The product is a 2:5 mixture of regioisomers. MS(ESI) m/z: 449.3 (M+H)$^+$.

Example 281d tert-butyl (6-(8-methyl-4-oxo-3,4-dihydropyrrolo[1,2-d][1,2,4]triazin-1-yl)spiro[3.3]heptan-2-yl)carbamate

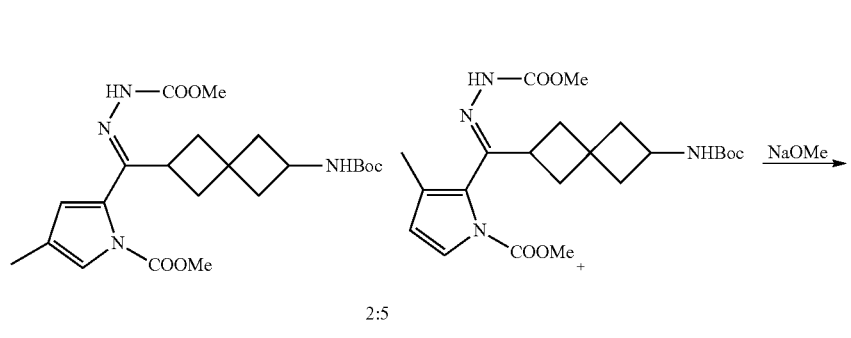

Example 281c (30 mg, 0.067 mmol) and sodium methanolate (25% wt in MeOH) (72.3 mg, 0.334 mmol) in MeOH (0.5 mL) was sealed and heated at 100° C. for 30 mins. The mixture was treated with 0.4 mL 1.25N HCl in MeOH, then was purified by preparative HPLC to afford Example 281d (6 mg, 25% yield). MS(ESI) m/z: 359.2 (M+H)$^+$; $^1$H NMR (400 MHz, methanol-$d_4$) δ 7.59 (d, J=3.1 Hz, 1H), 6.58 (d, J=3.1 Hz, 1H), 3.99-3.85 (m, 1H), 3.74 (quin, J=8.1 Hz, 1H), 2.58-2.37 (m, 7H), 2.32-2.22 (m, 2H), 2.06-1.95 (m, 1H), 1.88 (dd, J=11.2, 8.8 Hz, 1H), 1.42 (s, 9H).

Example 281e 1-(6-aminospiro[3.3]heptan-2-yl)-8-methylpyrrolo[1,2-d][1,2,4]triazin-4(3H)-one, HCl

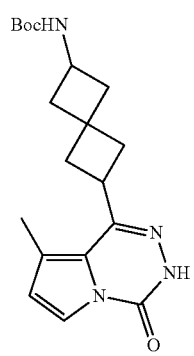 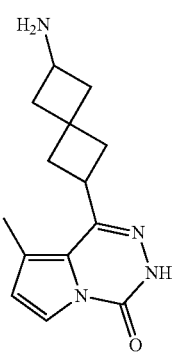

Example 281d (6 mg, 0.017 mmol) in 4N HCl in Dioxane (0.2 mL, 0.800 mmol) was stirred at rt for 30 min. The reaction mixture was concentrated to afford Example 281e (4.9 mg, 100% yield), which was used as is in the following step. MS(ESI) m/z: 259.1 (M+H)$^+$.

Example 281

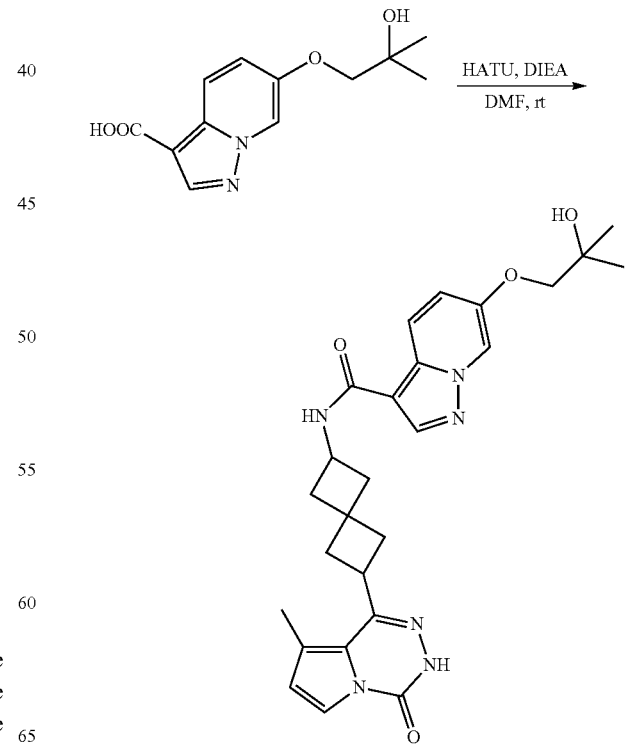

Example 281e (5.0 mg, 0.017 mmol), Intermediate 29 (4.3 mg, 0.017 mmol), HATU (9.7 mg, 0.026 mmol), DIEA (8.9 μl, 0.051 mmol) in DMF was stirred at rt for 1 hr. The product was purified by preparative HPLC to afford Example 281 (2.5 mg, 24% yield). MS(ESI) m/z: 333.2 (M+H)$^+$; $^1$H NMR (400 MHz, methanol-d$_4$) δ 8.35 (s, 1H), 8.28 (d, J=1.5 Hz, 1H), 8.12 (d, J=9.7 Hz, 1H), 7.61 (d, J=2.9 Hz, 1H), 7.32 (dd, J=9.7, 2.2 Hz, 1H), 6.60 (d, J=3.1 Hz, 1H), 4.49-4.35 (m, 1H), 3.86 (s, 2H), 3.83-3.74 (m, 1H), 2.74-2.05 (m, 11H), 1.35 (s, 6H); HPLC RT=6.50 min (Method A), 7.60 min (Method B).

The following Examples in Table 19 were made by using the same procedure as shown in Example 1. Intermediate 2 was coupled with the appropriate acids. Various coupling reagents could be used other than the one described in Example 1 such as HBTU, HATU, BOP, PyBop, EDC/HOBt.

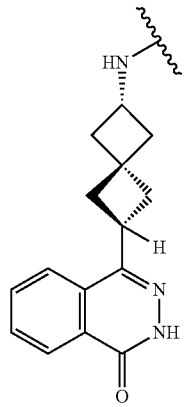

TABLE 19

| Ex. | R | Name | LCMS (M + H)$^+$ | HPLC Method, RT (min.) | $^1$H NMR |
|---|---|---|---|---|---|
| 282 | (pyrazolo[1,5-a]pyrimidine-3-carbonyl) | N-((aR)-6-(4-oxo-3,4-dihydrophthalazin-1-yl)spiro[3.3]heptan-2-yl)pyrazolo[1,5-a]pyrimidine-3-carboxamide | 401.2 | E: 1.28 F: 1.34 | $^1$H NMR (500 MHz, DMSO-d$_6$) δ 12.47 (s, 1H), 9.29 (d, J = 7.0 Hz, 1H), 8.83 (d, J = 4.0 Hz, 1H), 8.56 (s, 1H), 8.25 (d, J = 7.9 Hz, 1H), 8.06 (d, J = 7.9 Hz, 1H), 7.96-7.77 (m, 3H), 7.27 (dd, J = 6.3, 4.4 Hz, 1H), 4.47-4.34 (m, 1H), 3.97-3.82 (m, 1H), 2.75-2.66 (m, 1H), 2.62-2.57 (m, 1H), 2.44-2.35 (m, 3H), 2.32 (d, J = 5.5 Hz, 1H), 2.18 (t, J = 9.6 Hz, 1H), 2.00 (t, J = 9.9 Hz, 1H) |
| 283 | (6-((3,5-dimethylphenyl)amino)imidazo[1,2-b]pyridazine-3-carbonyl) | 6-((3,5-dimethylphenyl)amino)-N-((aR)-6-(4-oxo-3,4-dihydrophthalazin-1-yl)spiro[3.3]heptan-2-yl)imidazo[1,2-b]pyridazine-3-carboxamide | 520.1 | E: 1.47 F: 1.70 | $^1$H NMR (500 MHz, DMSO-d$_6$) δ 12.47 (s, 1H), 9.36 (s, 1H), 8.55 (d, J = 7.3 Hz, 1H), 8.26 (d, J = 7.6 Hz, 1H), 8.00 (d, J = 9.8 Hz, 1H), 7.97-7.89 (m, 2H), 7.88-7.79 (m, 2H), 7.11 (s, 2H), 7.01 (d, J = 9.5 Hz, 1H), 6.76 (s, 1H), 4.32-4.20 (m, 1H), 3.93-3.80 (m, 1H), 2.36 (t, J = 9.8 Hz, 1H), 2.28 (s, 8H), 2.20-2.13 (m, 1H), 1.81 (t, J = 9.6 Hz, 1H), 1.64 (t, J = 9.8 Hz, 1H) |
| 284 | (6-bromobenzo[c]isoxazole-3-carbonyl) | 6-bromo-N-((aR)-6-(4-oxo-3,4-dihydrophthalazin-1-yl)spiro[3.3]heptan-2-yl)benzo[c]isoxazole-3-carboxamide | 479.0 | E: 1.86 F: 1.87 | $^1$H NMR (400 MHz, DMSO-d$_6$) δ 12.49 (s, 1H), 8.34-8.20 (m, 1H), 8.09 (br s, 2H), 7.97-7.88 (m, 1H), 7.89-7.79 (m, 2H), 3.89 (t, J = 8.4 Hz, 1H), 3.63-3.52 (m, 1H), 2.62-2.53 (m, 2H), 2.43-2.34 (m, 3H), 2.28 (dd, J = 11.2, 8.6 Hz, 1H), 2.24-2.16 (m, 1H), 2.14-2.04 (m, 1H) |
| 285 | (1-ethyl-1H-pyrazole-5-carbonyl) | 1-ethyl-N-((aR)-6-(4-oxo-3,4-dihydrophthalazin-1-yl)spiro[3.3]heptan-2-yl)-1H-pyrazole-5-carboxamide | 378.0 | E: 1.43 F: 1.42 | $^1$H NMR (500 MHz, DMSO-d$_6$) δ 12.46 (s, 1H), 8.25 (d, J = 7.6 Hz, 1H), 8.16 (d, J = 8.2 Hz, 1H), 7.94-7.89 (m, 1H), 7.89-7.80 (m, 2H), 7.79 (d, J = 1.2 Hz, 1H), 6.59 (d, J = 1.2 Hz, 1H), 4.37-4.25 (m, 1H), 4.17 (q, J = 7.2 Hz, 2H), 3.88 (quin, J = 8.4 Hz, 1H), 2.59-2.55 (m, 1H), 2.42-2.30 (m, 3H), 2.27 (t, J = 9.9 Hz, 1H), 2.21-2.12 (m, 1H), 2.12-2.05 (m, 1H), 1.39 (t, J = 7.3 Hz, 3H) |

TABLE 19-continued

| Ex. | R | Name | LCMS (M + H)+ | HPLC Method, RT (min.) | 1H NMR |
|---|---|---|---|---|---|
| 286 | | 1-(difluoromethyl)-N-((aR)-6-(4-oxo-3,4-dihydrophthalazin-1-yl)spiro[3.3]heptan-2-yl)-1H-pyrazole-5-carboxamide | 400.0 | E: 1.59 F: 1.61 | $^1$H NMR (500 MHz, DMSO-$d_6$) δ 12.46 (s, 1H), 8.59 (d, J = 7.6 Hz, 1H), 8.30 (d, J = 2.1 Hz, 1H), 8.25 (d, J = 7.9 Hz, 1H), 7.98-7.69 (m, 4H), 6.85 (d, J = 2.1 Hz, 1H), 4.38-4.26 (m, 1H), 3.88 (quin, J = 8.3 Hz, 1H), 2.60-2.56 (m, 1H), 2.43-2.26 (m, 4H), 2.22-2.04 (m, 2H) |
| 287 | | 6-(2-hydroxy-2-methylpropoxy)-N-((aR)-6-(4-oxo-3,4-dihydrophthalazin-1-yl)spiro[3.3]heptan-2-yl)benzo[c]isoxazole-3-carboxamide, TFA | 489.2 | A: 7.00 B: 8.05 | $^1$H NMR (400 MHz, methanol-$d_4$) δ 8.45-8.29 (m, 1H), 8.00-7.78 (m, 4H), 6.97 (dd, J = 9.5, 2.0 Hz, 1H), 6.81 (d, J = 1.3 Hz, 1H), 4.55-4.41 (m, 1H), 3.96 (t, J = 8.4 Hz, 1H), 3.91-3.83 (m, 2H), 2.79-2.70 (m, 1H), 2.70-2.61 (m, 1H), 2.60-2.53 (m, 1H), 2.51-2.44 (m, 2H), 2.42-2.29 (m, 2H), 2.19 (dd, J = 11.1, 9.1 Hz, 1H), 1.40-1.31 (m, 6H) |

The following Examples in Table 20 were prepared by using a similar procedure as shown in Example 123 by reacting Intermediate 2 with the appropriate esters.

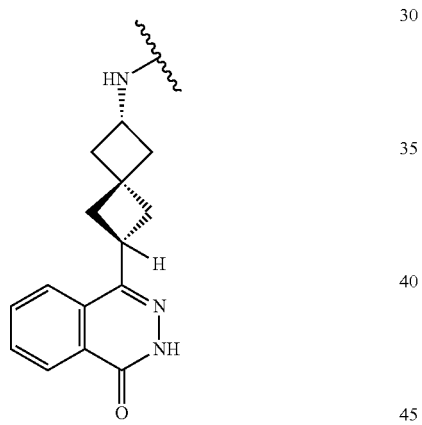

TABLE 20

| Ex. | R | Name | LCMS (M + H)+ | HPLC Method, RT (min.) | 1H NMR |
|---|---|---|---|---|---|
| 288 | | 1-(3-chlorophenyl)-7-oxo-N-((aR)-6-(4-oxo-3,4-dihydrophthalazin-1-yl)spiro[3.3]heptan-2-yl)-4,5,6,7-tetrahydro-1H-pyrazolo[3,4-c]pyridine-3-carboxamide | 529.0 | E: 1.78 F: 1.79 | $^1$H NMR (500 MHz, DMSO-$d_6$) δ 12.46 (s, 1H), 8.53 (d, J = 8.2 Hz, 1H), 8.25 (d, J = 7.9 Hz, 1H), 7.96 (br s, 1H), 7.93-7.88 (m, 1H), 7.88-7.80 (m, 2H), 7.78 (s, 1H), 7.64 (d, J = 3.4 Hz, 1H), 7.55-7.50 (m, 2H), 4.40-4.30 (m, 1H), 3.88 (quin, J = 8.4 Hz, 1H), 3.47-3.40 (m, 1H), 2.98 (t, J = 6.7 Hz, 2H), 2.60-2.55 (m, 2H), 2.42-2.27 (m, 4H), 2.22- 2.08 (m, 2H) |

TABLE 20-continued

| Ex. | R | Name | LCMS (M + H)+ | HPLC Method, RT (min.) | 1H NMR |
|---|---|---|---|---|---|
| 289 | (structure with pyrazolopyridine-methoxyphenyl) | 1-(4-methoxyphenyl)-7-oxo-N-((aR)-6-(4-oxo-3,4-dihydrophthalazin-1-yl)spiro[3.3]heptan-2-yl)-4,5,6,7-tetrahydro-1H-pyrazolo[3,4-c]pyridine-3-carboxamide | 525.1 | E: 1.64  F: 1.64 | 1H NMR (500 MHz, DMSO-d6) δ 12.46 (s, 1H), 8.45 (d, J = 8.2 Hz, 1H), 8.25 (d, J = 7.6 Hz, 1H), 7.94-7.88 (m, 1H), 7.88-7.79 (m, 3H), 7.50 (d, J = 8.9 Hz, 2H), 7.01 (d, J = 9.2 Hz, 2H), 4.40-4.29 (m, 1H), 3.92-3.83 (m, 1H), 3.82 (s, 3H), 3.42 (br s, 1H), 2.98 (t, J = 6.7 Hz, 2H), 2.54 (br. s., 2H), 2.42-2.27 (m, 4H), 2.21-2.08 (m, 2H) |
| 290 | (5-chlorobenzo[d]isoxazole structure) | 5-chloro-N-((aR)-6-(4-oxo-3,4-dihydrophthalazin-1-yl)spiro[3.3]heptan-2-yl)benzo[d]isoxazole-3-carboxamide | 435.3 | E: 2.09  F: 2.11 | 1H NMR (500 MHz, DMSO-d6) δ 12.49 (s, 1H), 9.36 (d, J = 7.6 Hz, 1H), 8.27 (d, J = 7.6 Hz, 1H), 8.07 (s, 1H), 7.98-7.81 (m, 4H), 7.78 (d, J = 8.9 Hz, 1H), 4.47-4.31 (m, 1H), 3.91 (t, J = 8.4 Hz, 1H), 2.72-2.57 (m, 2H), 2.47-2.32 (m, 4H), 2.26 (d, J = 5.2 Hz, 1H), 2.21-2.12 (m, 1H) |
| 291 | (6-acetamidobenzo[d]isoxazole structure) | 6-acetamido-N-((aR)-6-(4-oxo-3,4-dihydrophthalazin-1-yl)spiro[3.3]heptan-2-yl)benzo[d]isoxazole-3-carboxamide | 458.1 | E: 1.64  F: 1.67 | 1H NMR (500 MHz, DMSO-d6) δ 12.49 (s, 1H), 10.52 (s, 1H), 9.22 (d, J = 7.6 Hz, 1H), 8.30-8.24 (m, 2H), 7.96-7.90 (m, 2H), 7.89-7.81 (m, 2H), 7.43 (d, J = 8.8 Hz, 1H), 4.43-4.33 (m, 1H), 3.90 (t, J = 8.4 Hz, 1H), 2.67-2.59 (m, 1H), 2.44-2.29 (m, 4H), 2.28-2.21 (m, 1H), 2.16 (d, J = 9.5 Hz, 1H), 2.12 (s, 3H) |
| 467 | (pyrazolo[1,5-a]pyrazine structure) | N-((aR)-6-(4-oxo-3,4-dihydrophthalazin-1-yl)spiro[3.3]heptan-2-yl)pyrazolo[1,5-a]pyrazine-3-carboxamide | 401.2 | E: 1.21  F: 1.07 | 1H NMR (500 MHz, DMSO-d6) δ 12.50 (s, 1H), 9.55(s, 1H), 8.86 (d, J = 4.3 Hz, 1H), 8.67 (s, 1H), 8.62 (d, J = 6.9 Hz, 1H), 8.25 (d, J = 7.7 Hz, 1H), 8.06 (d, J = 4.6 Hz, 1H), 7.98-7.77 (m, 3H), 4.46-4.31 (m, 1H), 3.91 (quin, J = 8.5 Hz, 1H), 2.70-2.62 (m, J = 11.6 Hz, 1H), 2.61-2.56 (m, 1H), 2.45-2.32 (m, 3H), 2.30-2.19 (m, 2H),2.07 (t, J = 10.0 Hz, 1H) |
| 468 | (5-bromoindoline structure) | 5-bromo-N-((aR)-6-(4-oxo-3,4-dihydrophthalazin-1-yl)spiro[3.3]heptan-2-yl)indoline-2-carboxamide,TFA | 479.0 | E: 1.91  F: 1.97 | 1H NMR (500 MHz, DMSO-d6) δ 12.47 (s, 1H), 8.26 (d, J = 7.6 Hz, 1H), 8.07 (d, J = 7.6 Hz, 1H), 7.95-7.89 (m, 1H), 7.88-7.79 (m, 2H), 7.14 (s, 1H), 7.08 (d, J = 8.5 Hz, 1H), 6.50 (d, J = 8.2 Hz, 1H), 6.06 (br s, 1H), 4.17 (td, J = 16.5, 7.9 Hz, 2H), 3.93-3.77 (m, 1H), 3.27 (dd, J = 16.3, 10.5 Hz, 1H), 2.98-2.91 (m, 1H), 2.42-2.29 (m, 3H), 2.21-2.06 (m, 2H), 1.99-1.89 (m, 2H) |
| 470 | (7-morpholino-imidazo[1,2-a]pyridine structure) | 7-morpholino-N-((aR)-6-(4-oxo-3,4-dihydrophthalazin-1-yl)spiro[3.3]heptan-2-yl)imidazo[1,2-a]pyridine-3-carboxamide, TFA | 485.1 | A: 4.34  B: 6.61 | 1H NMR (400 MHz, DMSO-d6) δ 12.47 (s, 1H), 9.27 (d, J = 7.9 Hz, 1H), 8.85 (d, J = 7.3 Hz, 1H), 8.43 (s, 1H), 8.26 (d, J = 8.1 Hz, 1H), 7.97-7.78 (m, 3H), 7.38 (dd, J = 8.0, 2.5 Hz, 1H), 6.94 (d, J = 2.4 Hz, 1H), 4.35 (sxt, J = 7.9 Hz, 1H), 3.91 (quin, J = 8.4 Hz, 1H), 3.80-3.66 (m, 4H), 3.55- 3.42 (m, 4H), 2.72-2.54 (m, 2H), 2.44-2.36 (m, 3H), 2.33-2.18 (m, 2H), 2.11- 2.00 (m, 1H) |

The following Examples in Table 21 were made by using the same procedure as shown in Example 1. Intermediate 2 was coupled with the appropriate acids. Various coupling reagents could be used other than the one described in Example 1, such as HBTU, HATU, BOP, PyBop, EDC/HOBt.

TABLE 21

| Ex. | Structure | Name | LCMS [M + H]+ | HPLC Method, RT (min.) | 1H NMR (δ NMR) |
|---|---|---|---|---|---|
| 292 | 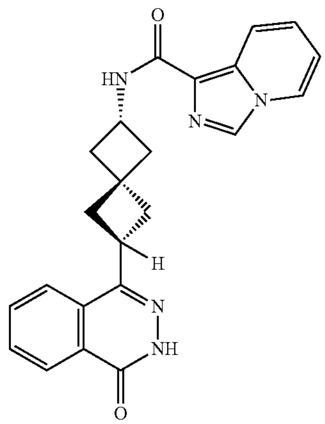 | N-((aR)-6-(4-oxo-3,4-dihydrophthalazin-1-yl)spiro[3.3]heptan-2-yl)imidazo[1,5-a]pyridine-1-carboxamide | 400.2 | E: 1.32 F: 1.36 | (500 MHz, DMSO-$d_6$) δ 12.47 (s, 1H), 8.47-8.37 (m, 2H), 8.25 (d, J = 7.6 Hz, 1H), 8.14 (d, J = 7.9 Hz, 1H), 8.04 (d, J = 9.2 Hz, 1H), 7.96-7.78 (m, 3H), 7.12-7.06 (m, 1H), 6.84 (t, J = 6.7 Hz, 1H), 4.47-4.29 (m, 1H), 3.88 (quin, J = 8.4 Hz, 1H), 2.57 (br. s., 2H), 2.43-2.25 (m, 4H), 2.24-2.15 (m, 1H), 2.14-2.06 (m, 1H) |
| 293 | 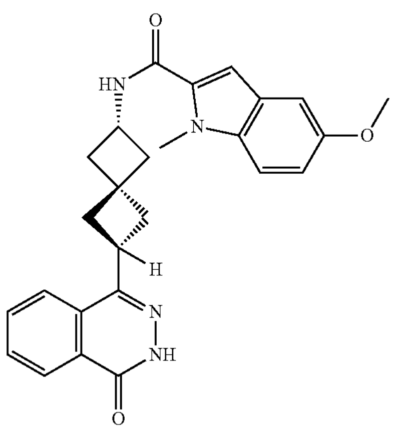 | 5-methoxy-1-methyl-N-((aR)-6-(4-oxo-3,4-dihydrophthalazin-1-yl)spiro[3.3]heptan-2-yl)-1H-indole-2-carboxamide | 443.4 | E: 1.73 F: 1.75 | (500 MHz, DMSO-$d_6$) δ 12.47 (s, 1H), 8.57 (d, J = 7.3 Hz, 1H), 8.25 (d, J = 7.9 Hz, 1H), 7.97-7.79 (m, 3H), 7.40 (d, J = 8.9 Hz, 1H), 7.08 (d, J = 1.8 Hz, 1H), 7.00 (s, 1H), 6.90 (dd, J = 9.0, 2.3 Hz, 1H), 4.45-4.25 (m, 1H), 3.92 (s, 3H), 3.90-3.85 (m, 1H), 3.76 (s, 3H), 2.66-2.55 (m, 2H), 2.44-2.32 (m, 3H), 2.30-2.16 (m, 2H), 2.13-2.01 (m, 1H) |
| 294 | 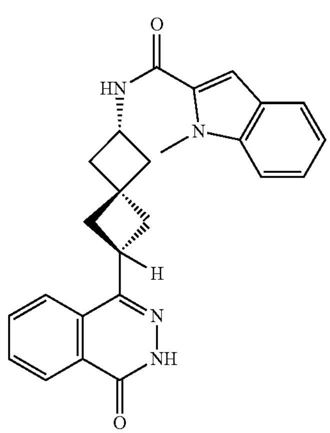 | 1-methyl-N-((aR)-6-(4-oxo-3,4-dihydrophthalazin-1-yl)spiro[3.3]heptan-2-yl)-1H-indole-2-carboxamide | 413.2 | E: 1.83 F: 1.81 | (500 MHz, DMSO-$d_6$) δ 12.47 (s, 1H), 8.63 (d, J = 7.6 Hz, 1H), 8.25 (d, J = 7.6 Hz, 1H), 7.98-7.79 (m, 3H), 7.62 (d, J = 7.6 Hz, 1H), 7.50 (d, J = 8.5 Hz, 1H), 7.26 (t, J = 7.6 Hz, 1H), 7.13-7.08 (m, 2H), 4.41-4.27 (m, 1H), 3.96 (s, 3H), 3.90 (quin, J = 8.5 Hz, 1H), 2.66-2.56 (m, 2H), 2.45-2.32 (m, 3H), 2.30-2.19 (m, 2H), 2.14-2.02 (m, 1H) |

TABLE 21-continued

| Ex. | Structure | Name | LCMS [M + H]+ | HPLC Method, RT (min.) | 1H NMR (δ NMR) |
|---|---|---|---|---|---|
| 295 | 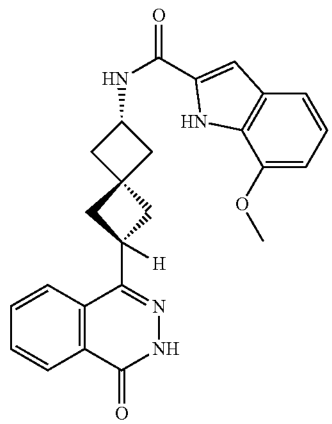 | 7-methoxy-N-((aR)-6-(4-oxo-3,4-dihydrophthalazin-1-yl)spiro[3.3]heptan-2-yl)-1H-indole-2-carboxamide | 429.4 | E: 1.65 F: 1.66 | (500 MHz, DMSO-d₆) δ 12.44 (s, 1H), 11.22 (br s, 1H), 8.49 (d, J = 7.3 Hz, 1H), 8.22 (d, J = 7.6 Hz, 1H), 7.95-7.71 (m, 3H), 7.14 (d, J = 7.9 Hz, 1H), 7.00 (d, J = 1.5 Hz, 1H), 6.93 (t, J = 7.9 Hz, 1H), 6.70 (d, J = 7.6 Hz, 1H), 4.40-4.23 (m, 1H), 3.88 (s, 3H), 3.87-3.81 (m, 1H), 2.68-2.58 (m, 1H), 2.57-2.51 (m, 1H), 2.42-2.29 (m, 3H), 2.24 (br. s., 1H), 2.16 (t, J = 9.8 Hz, 1H), 2.03-1.94 (m, 1H) |
| 296 | 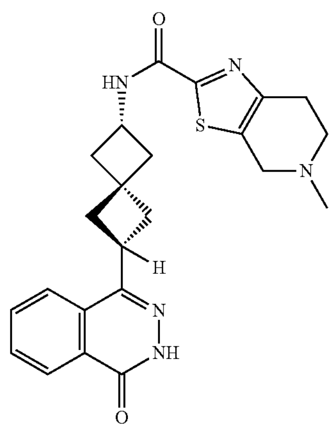 | 5-methyl-N-((aR)-6-(4-oxo-3,4-dihydrophthalazin-1-yl)spiro[3.3]heptan-2-yl)-4,5,6,7-tetrahydrothiazolo[5,4-c]pyridine-2-carboxamide | 436.1 | E: 1.07 F: 1.36 | (500 MHz, DMSO-d₆) δ 12.48 (s, 1H), 8.99 (d, J = 7.9 Hz, 1H), 8.27 (d, J = 7.9 Hz, 1H), 7.96-7.90 (m, 1H), 7.90-7.80 (m, 2H), 4.38-4.25 (m, 1H), 4.05-3.73 (m, 3H), 3.04-2.84 (m, 3H), 2.61-2.54 (m, 6H), 2.45-2.27 (m, 4H), 2.19 (d, J = 8.2 Hz, 2H) |
| 297 | 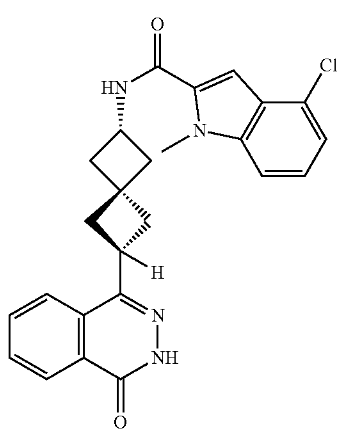 | 4-chloro-1-methyl-N-((aR)-6-(4-oxo-3,4-dihydrophthalazin-1-yl)spiro[3.3]heptan-2-yl)-1H-indole-2-carboxamide | 447.1 | E: 1.98 F: 1.99 | (500 MHz, DMSO-d₆) δ 12.49 (s, 1H), 8.81 (d, J = 7.6 Hz, 1H), 8.27 (d, J = 7.6 Hz, 1H), 8.00-7.81 (m, 3H), 7.54 (d, J = 8.2 Hz, 1H), 7.30-7.26 (m, 1H), 7.23 (s, 1H), 7.19 (d, J = 7.6 Hz, 1H), 4.37 (sxt, J = 8.0 Hz, 1H), 4.01 (s, 3H), 3.92 (quin, J = 8.5 Hz, 1H), 2.69-2.57 (m, 2H), 2.48-2.34 (m, 3H), 2.33-2.21 (m, 2H), 2.12 (t, J = 9.9 Hz, 1H) |

TABLE 21-continued

| Ex. | Structure | Name | LCMS [M + H]+ | HPLC Method, RT (min.) | 1H NMR (δ NMR) |
|---|---|---|---|---|---|
| 298 | 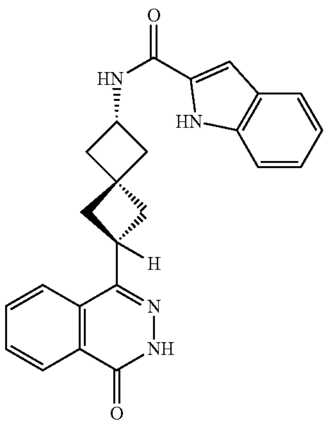 | N-((aR)-6-(4-oxo-3,4-dihydrophthalazin-1-yl)spiro[3.3]heptan-2-yl)-1H-indole-2-carboxamide | 399.1 | E: 1.62 F: 1.61 | (500 MHz, DMSO-d6) δ 12.48 (s, 1H), 11.47 (br s, 1H), 8.59 (d, J = 7.6 Hz, 1H), 8.25 (d, J = 7.6 Hz, 1H), 7.95-7.80 (m, 3H), 7.59 (d, J = 7.9 Hz, 1H), 7.42 (d, J = 8.2 Hz, 1H), 7.16 (t, J = 7.6 Hz, 1H), 7.13 (s, 1H), 7.02 (t, J = 7.3 Hz, 1H), 4.45-4.30 (m, 1H), 4.00-3.83 (m, 1H), 2.64 (br. s., 1H), 2.60-2.56 (m, 1H), 2.45-2.33 (m, 3H), 2.25 (t, J = 9.6 Hz, 2H), 2.11-2.02 (m, 1H) |
| 299 | 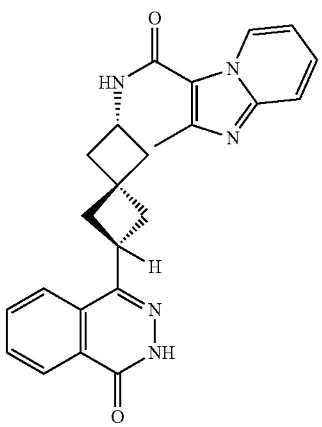 | 2-methyl-N-((aR)-6-(4-oxo-3,4-dihydrophthalazin-1-yl)spiro[3.3]heptan-2-yl)imidazo[1,2-a]pyridine-3-carboxamide | 414.3 | E: 1.12 F: 1.37 | (500 MHz, DMSO-d6) δ 12.44 (s, 1H), 8.88 (d, J = 7.0 Hz, 1H), 8.21 (d, J = 7.9 Hz, 1H), 8.01 (d, J = 7.3 Hz, 1H), 7.92-7.76 (m, 3H), 7.51 (d, J = 8.9 Hz, 1H), 7.34 (t, J = 7.9 Hz, 1H), 6.96 (t, J = 6.9 Hz, 1H), 4.41-4.27 (m, 1H), 3.86 (quin, J = 8.4 Hz, 1H), 2.61 (t, J = 11.3 Hz, 1H), 2.57-2.52 (m, 1H), 2.46 (br. s., 3H), 2.41-2.29 (m, 3H), 2.27-2.17 (m, 2H), 2.05 (t, J = 10.1 Hz, 1H) |
| 300 | 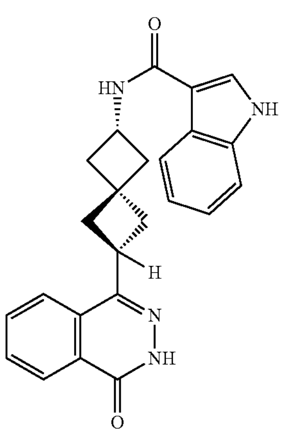 | N-((aR)-6-(4-oxo-3,4-dihydrophthalazin-1-yl)spiro[3.3]heptan-2-yl)-1H-indole-3-carboxamide | 399.0 | E: 1.48 F: 1.50 | (500 MHz, DMSO-d6) δ 12.47 (s, 1H), 11.51 (br s, 1H), 8.26 (d, J = 7.9 Hz, 1H), 8.12 (d, J = 7.6 Hz, 1H), 8.02 (br. s., 1H), 7.99 (d, J = 7.6 Hz, 1H), 7.95-7.80 (m, 3H), 7.40 (d, J = 8.2 Hz, 1H), 7.16-7.10 (m, 1H), 7.10-7.04 (m, 1H), 4.47-4.31 (m, 1H), 3.90 (quin, J = 8.3 Hz, 1H), 2.66-2.56 (m, 2H), 2.45-2.32 (m, 3H), 2.27-2.16 (m, 2H), 2.04 (t, J = 10.1 Hz, 1H) |

TABLE 21-continued

| Ex. | Structure | Name | LCMS [M + H]+ | HPLC Method, RT (min.) | 1H NMR (δ NMR) |
|---|---|---|---|---|---|
| 301 | 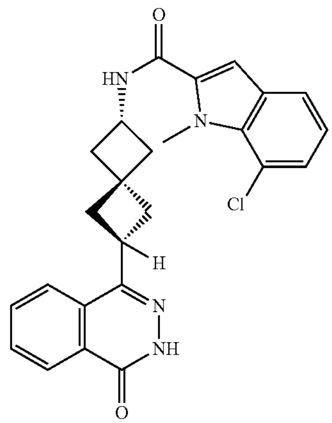 | 7-chloro-1-methyl-N-((aR)-6-(4-oxo-3,4-dihydrophthalazin-1-yl)spiro[3.3]heptan-2-yl)-1H-indole-2-carboxamide | 446.9 | E: 2.04 F: 2.06 | (500 MHz, DMSO-d6) δ 12.47 (s, 1H), 8.76 (d, J = 7.6 Hz, 1H), 8.25 (d, J = 7.9 Hz, 1H), 7.98-7.77 (m, 3H), 7.60 (d, J = 7.9 Hz, 1H), 7.26 (d, J = 7.3 Hz, 1H), 7.09-7.03 (m, 2H), 4.42-4.29 (m, 1H), 4.24 (s, 3H), 3.90 (quin, J = 8.3 Hz, 1H), 2.63 (t, J = 11.6 Hz, 1H), 2.59-2.55 (m, 1H), 2.44-2.32 (m, 3H), 2.30-2.19 (m, 2H), 2.08 (t, J = 9.9 Hz, 1H) |
| 302 | 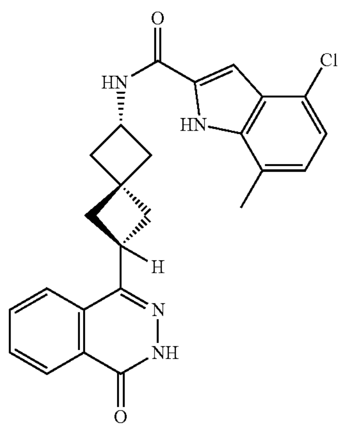 | 4-chloro-7-methyl-N-((aR)-6-(4-oxo-3,4-dihydrophthalazin-1-yl)spiro[3.3]heptan-2-yl)-1H-indole-2-carboxamide | 447.1 | E: 1.97 F: 1.97 | (500 MHz, DMSO-d6) δ 12.49 (s, 1H), 11.72 (br s, 1H), 8.74 (d, J = 7.3 Hz, 1H), 8.28 (d, J = 7.6 Hz, 1H), 8.01-7.77 (m, 3H), 7.26 (s, 1H), 7.07-7.01 (m, 1H), 6.98 (d, J = 7.6 Hz, 1H), 4.52-4.32 (m, 1H), 3.93 (t, J = 8.4 Hz, 1H), 2.68 (br. s., 1H), 2.64-2.58 (m, 1H), 2.56 (s, 3H), 2.47-2.36 (m, 3H), 2.29 (t, J = 9.5 Hz, 2H), 2.11 (t, J = 10.1 Hz, 1H) |
| 303 | 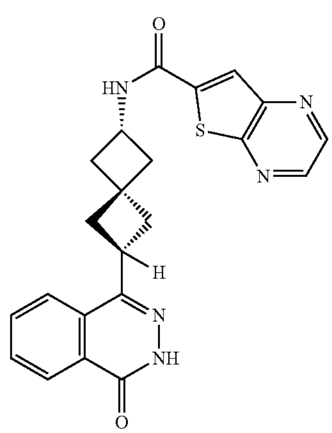 | N-((aR)-6-(4-oxo-3,4-dihydrophthalazin-1-yl)spiro[3.3]heptan-2-yl)thieno[2,3-b]pyrazine-6-carboxamide | 418.2 | E: 1.45 F: 1.45 | (500 MHz, DMSO-d6) δ 12.47 (s, 1H), 9.14 (d, J = 7.0 Hz, 1H), 8.82 (s, 1H), 8.70 (s, 1H), 8.31 (s, 1H), 8.26 (d, J = 7.9 Hz, 1H), 7.95-7.80 (m, 3H), 4.43-4.29 (m, 1H), 3.91 (quin, J = 8.4 Hz, 1H), 2.68 (br. s., 1H), 2.59 (t, J = 7.9 Hz, 1H), 2.46-2.34 (m, 3H), 2.32-2.23 (m, 2H), 2.12 (t, J = 10.1 Hz, 1H) |

TABLE 21-continued

| Ex. | Structure | Name | LCMS [M + H]+ | HPLC Method, RT (min.) | 1H NMR (δ NMR) |
|---|---|---|---|---|---|
| 304 | 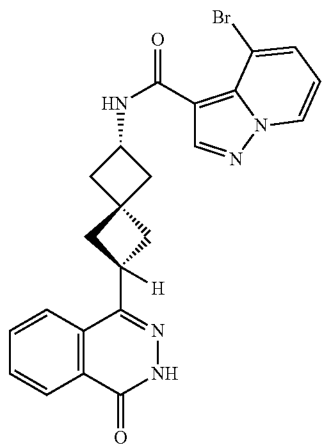 | 4-bromo-N-((aR)-6-(4-oxo-3,4-dihydrophthalazin-1-yl)spiro[3.3]heptan-2-yl)pyrazolo[1,5-a]pyridine-3-carboxamide | 477.9/ 479.9 | A: 5.77 B: 7.27 | (400 MHz, DMSO-d6) δ 12.46 (s, 1H), 8.80 (dd, J = 6.8, 0.7 Hz, 1H), 8.48 (d, J = 7.5 Hz, 1H), 8.29-8.23 (m, 1H), 8.21 (s, 1H), 7.96-7.80 (m, 3H), 7.66 (dd, J = 7.5 , 0.7 Hz, 1H), 6.91 (t, J = 7.2 Hz, 1H), 4.32 (sxt, J = 8.1 Hz, 1H), 3.89 (quin, J = 8.4 Hz, 1H), 2.68-2.53 (m, 2H), 2.43-2.31 (m, 3H), 2.29-2.15 (m, 2H), 2.02 (dd, J = 11.0, 8.8 Hz, 1H) |
| 305 | 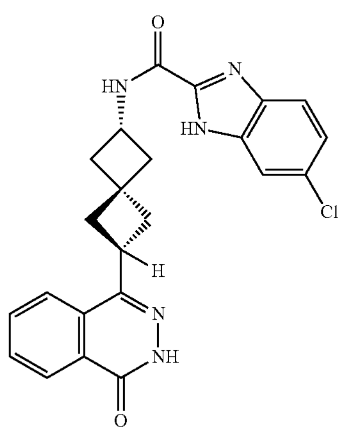 | 6-chloro-N-((aR)-6-(4-oxo-3,4-dihydrophthalazin-1-yl)spiro[3.3]heptan-2-yl)-1H-benzo[d]imidazole-2-carboxamide | 434.2 | E: 1.70 F: 1.73 | (500 MHz, DMSO-d6) δ 12.46 (s, 1H), 9.20 (d, J = 8.0 Hz, 1H), 8.26 (d, J = 7.2 Hz, 1H), 7.95-7.81 (m, 3H), 7.80-7.42 (m, 2H), 7.32 (d, J = 8.0 Hz, 1H), 4.45-4.32 (m, 1H), 3.95-3.85 (m, 1H), 2.66-2.55 (m, 2H), 2.43-2.33 (m, 4H), 2.21 (d, J = 8.5 Hz, 2H) |
| 306 | 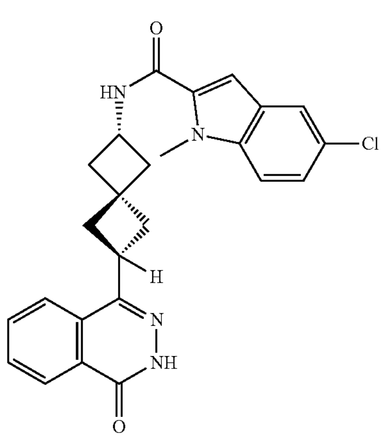 | 5-chloro-1-methyl-N-((aR)-6-(4-oxo-3,4-dihydrophthalazin-1-yl)spiro[3.3]heptan-2-yl)-1H-indole-2-carboxamide | 447.0 | E: 2.00 F: 2.00 | (500 MHz, DMSO-d6) δ 12.47 (s, 1H), 8.71 (d, J = 7.6 Hz, 1H), 8.25 (d, J = 7.9 Hz, 1H), 7.95-7.81 (m, 3H), 7.71 (s, 1H), 7.56 (d, J = 8.5 Hz, 1H), 7.25 (d, J = 8.5 Hz, 1H), 7.08 (s, 1H), 4.42-4.29 (m, 1H), 3.96 (s, 3H), 3.90 (t, J = 8.4 Hz, 1H), 2.62 (br. s, 1H), 2.56 (br. s., 1H), 2.44-2.32 (m, 3H), 2.29-2.19 (m, 2H), 2.12-2.04 (m, 1H) |

TABLE 21-continued

| Ex. | Structure | Name | LCMS [M + H]+ | HPLC Method, RT (min.) | 1H NMR (δ NMR) |
|---|---|---|---|---|---|
| 307 | 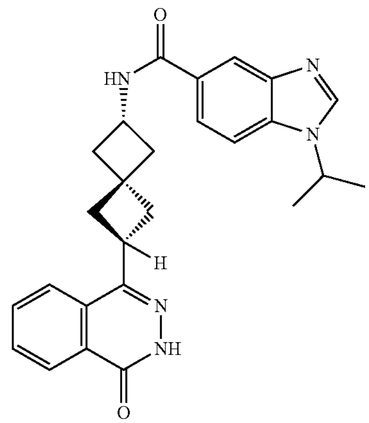 | 1-isopropyl-N-((aR)-6-(4-oxo-3,4-dihydrophthalazin-1-yl)spiro[3.3]heptan-2-yl)-1H-benzo[d]imidazole-5-carboxamide | 442.2 | E: 1.21 F: 1.44 | (500 MHz, DMSO-d6) δ 12.47 (s, 1H), 9.09 (br s, 1H), 8.73 (d, J = 7.0 Hz, 1H), 8.34-8.20 (m, 2H), 7.98-7.81 (m, 5H), 4.99-4.82 (m, 1H), 4.46-4.28 (m, 1H), 3.91 (t, J = 8.2 Hz, 1H), 2.70-2.56 (m, 2H), 2.45-2.33 (m, 3H), 2.32-2.20 (m, 2H), 2.14-2.04 (m, 1H), 1.59 (d, J = 6.7 Hz, 6H) |
| 308 | 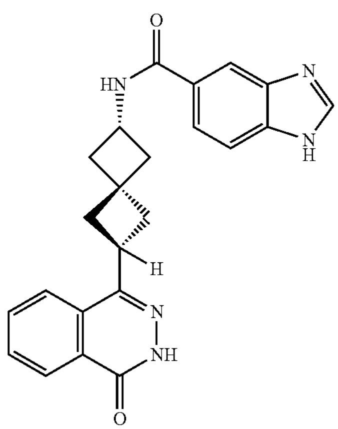 | N-((aR)-6-(4-oxo-3,4-dihydrophthalazin-1-yl)spiro[3.3]heptan-2-yl)-1H-benzo[d]imidazole-5-carboxamide | 400.2 | E: 1.09 F: 1.19 | (500 MHz, DMSO-d6) δ 12.47 (s, 1H), 8.57 (d, J = 7.3 Hz, 1H), 8.37 (s, 1H), 8.26 (d, J = 7.9 Hz, 1H), 8.16 (s, 1H), 7.95-7.80 (m, 3H), 7.75 (d, J = 8.5 Hz, 1H), 7.61 (d, J = 8.5 Hz, 1H), 4.47-4.29 (m, 1H), 3.90 (quin, J = 8.5 Hz, 1H), 2.69-2.56 (m, 2H), 2.44-2.32 (m, 3H), 2.30-2.17 (m, 2H), 2.09 (t, J = 9.9 Hz, 1H) |
| 309 | 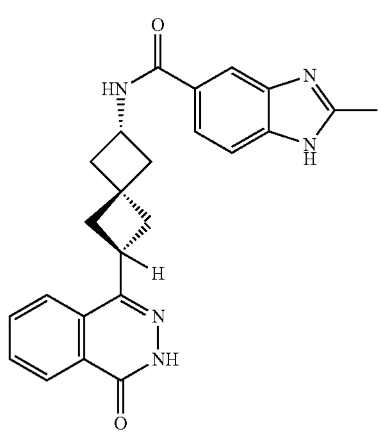 | 2-methyl-N-((aR)-6-(4-oxo-3,4-dihydrophthalazin-1-yl)spiro[3.3]heptan-2-yl)-1H-benzo[d]imidazole-5-carboxamide | 414.2 | E: 1.11 F: 1.22 | (500 MHz, DMSO-d6) δ 12.47 (s, 1H), 8.52 (d, J = 7.3 Hz, 1H), 8.25 (d, J = 7.6 Hz, 1H), 8.00 (s, 1H), 7.95-7.80 (m, 3H), 7.68 (d, J = 8.5 Hz, 1H), 7.47 (d, J = 8.5 Hz, 1H), 4.44-4.29 (m, 1H), 3.90 (quin, J = 8.4 Hz, 1H), 2.65-2.56 (m, 2H), 2.52 (s, 3H), 2.44-2.33 (m, 3H), 2.30-2.19 (m, 2H), 2.15-2.03 (m, 1H) |

TABLE 21-continued

| Ex. | Structure | Name | LCMS [M + H]+ | HPLC Method, RT (min.) | 1H NMR (δ NMR) |
|---|---|---|---|---|---|
| 310 | 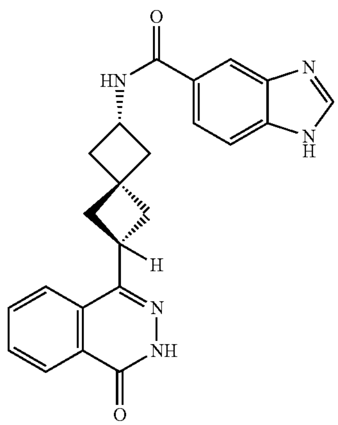 | N-((aR)-6-(4-oxo-3,4-dihydrophthalazin-1-yl)spiro[3.3]heptan-2-yl)-3H-imidazo[4,5-b]pyridine-6-carboxamide | 400.9 | E: 1.07 F: 1.11 | (500 MHz, DMSO-d$_6$) δ 12.47 (s, 1H), 8.86 (s, 1H), 8.75 (d, J = 7.0 Hz, 1H), 8.59 (s, 1H), 8.47 (s, 1H), 8.25 (d, J = 7.6 Hz, 1H), 7.96-7.79 (m, 3H), 4.44-4.33 (m, 1H), 3.91 (t, J = 8.5 Hz, 1H), 2.70-2.56 (m, 2H), 2.45-2.32 (m, 3H), 2.31-2.20 (m, 2H), 2.15-2.03 (m, 1H) |
| 311 | 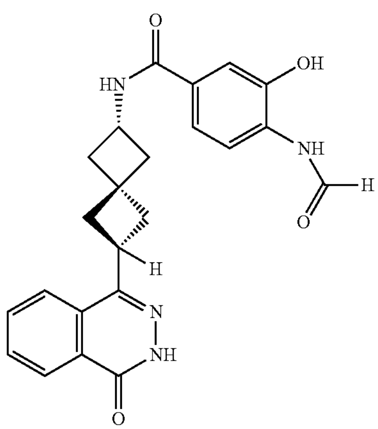 | 4-formamido-3-hydroxy-N-((aR)-6-(4-oxo-3,4-dihydrophthalazin-1-yl)spiro[3.3]heptan-2-yl)benzamide | 418.9 | E: 1.23 F: 1.21 | (500 MHz, DMSO-d$_6$) δ 12.46 (s, 1H), 9.72 (s, 1H), 8.42 (d, J = 7.6 Hz, 1H), 8.31 (s, 1H), 8.25 (d, J = 7.9 Hz, 1H), 8.12 (d, J = 8.2 Hz, 1H), 7.94-7.80 (m, 3H), 7.35 (s, 1H), 7.29 (d, J = 8.2 Hz, 1H), 4.41-4.22 (m, 1H), 3.89 (t, J = 8.5 Hz, 1H), 2.57 (br. s., 2H), 2.42-2.33 (m, 3H), 2.25-2.17 (m, 2H), 2.10-2.00 (m, 1H) |
| 312 | 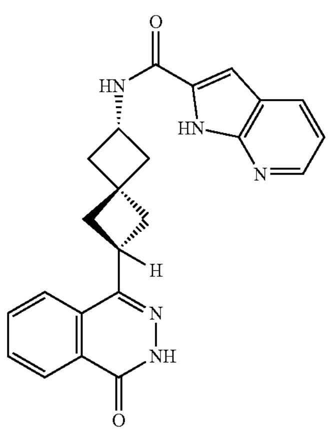 | N-((aR)-6-(4-oxo-3,4-dihydrophthalazin-1-yl)spiro[3.3]heptan-2-yl)-1H-pyrrolo[2,3-b]pyridine-2-carboxamide | 399.9 | E: 1.18 F: 1.40 | (500 MHz, DMSO-d$_6$) δ 12.47 (s, 1H), 11.99 (br. s., 1H), 8.62 (d, J = 7.3 Hz, 1H), 8.31 (d, J = 4.6 Hz, 1H), 8.26 (d, J = 7.6 Hz, 1H), 8.06 (d, J = 7.9 Hz, 1H), 7.96-7.80 (m, 3H), 7.16-7.05 (m, 2H), 4.44-4.29 (m, 1H), 3.91 (quin, J = 8.4 Hz, 1H), 2.66 (br. s., 1H), 2.57 (d, J = 11.0 Hz, 1H), 2.45-2.33 (m, 3H), 2.30-2.20 (m, 2H), 2.11-2.04 (m, 1H) |

TABLE 21-continued

| Ex. | Structure | Name | LCMS [M + H]+ | HPLC Method, RT (min.) | 1H NMR (δ NMR) |
|---|---|---|---|---|---|
| 313 | 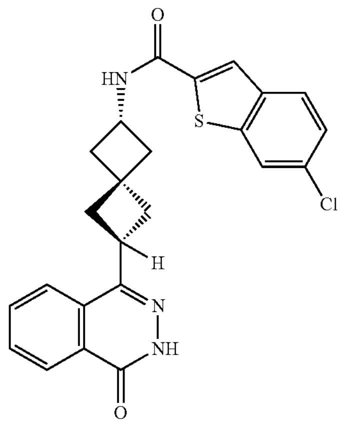 | 6-chloro-N-((aR)-6-(4-oxo-3,4-dihydrophthalazin-1-yl)spiro[3.3]heptan-2-yl)benzo[b]thiophene-2-carboxamide | 450.1 | E: 1.99 F: 1.99 | (500 MHz, DMSO-$d_6$) δ 12.47 (s, 1H), 8.93 (d, J = 7.3 Hz, 1H), 8.25 (d, J = 7.6 Hz, 1H), 8.17 (s, 1H), 8.09 (s, 1H), 7.97-7.79 (m, 4H), 7.46 (d, J = 8.5 Hz, 1H), 4.38-4.25 (m, 1H), 3.90 (quin, J = 8.4 Hz, 1H), 2.70-2.60 (m, 1H), 2.57 (br. s., 1H), 2.44-2.33 (m, 3H), 2.26 (t, J = 9.6 Hz, 2H), 2.14-2.04 (m, 1H) |
| 314 | 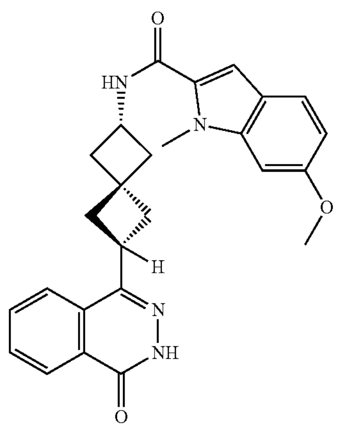 | 6-methoxy-1-methyl-N-((aR)-6-(4-oxo-3,4-dihydrophthalazin-1-yl)spiro[3.3]heptan-2-yl)-1H-indole-2-carboxamide | 443.0 | E: 1.79 F: 1.79 | (500 MHz, DMSO-$d_6$) δ 12.47 (s, 1H), 8.48 (d, J = 7.6 Hz, 1H), 8.25 (d, J = 7.6 Hz, 1H), 7.97-7.79 (m, 3H), 7.49 (d, J = 8.9 Hz, 1H), 7.05 (s, 1H), 6.99 (s, 1H), 6.73 (d, J = 8.5 Hz, 1H), 4.40-4.26 (m, 1H), 3.93 (s, 3H), 3.89 (d, J = 8.5 Hz, 1H), 3.82 (s, 3H), 2.65-2.55 (m, 2H), 2.44-2.34 (m, 3H), 2.29-2.20 (m, 2H), 2.07 (t, J = 9.9 Hz, 1H) |
| 315 | 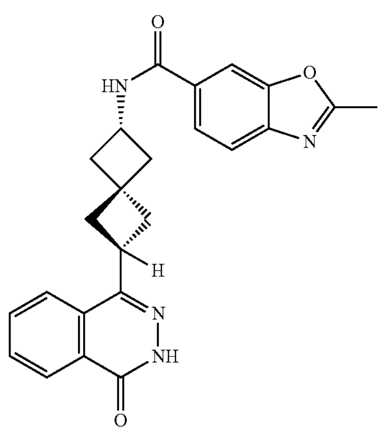 | 2-methyl-N-((aR)-6-(4-oxo-3,4-dihydrophthalazin-1-yl)spiro[3.3]heptan-2-yl)benzo[d]oxazole-6-carboxamide | 415.2 | E: 1.43 F: 1.43 | (500 MHz, DMSO-$d_6$) δ 12.47 (s, 1H), 8.66 (d, J = 7.3 Hz, 1H), 8.25 (d, J = 7.9 Hz, 1H), 8.11 (s, 1H), 7.96-7.79 (m, 4H), 7.70 (d, J = 8.2 Hz, 1H), 4.46-4.30 (m, 1H), 3.90 (quin, J = 8.4 Hz, 1H), 2.64 (s, 4H), 2.57 (br. s., 1H), 2.43-2.34 (m, 3H), 2.30-2.21 (m, 2H), 2.13-2.05 (m, 1H) |

TABLE 21-continued

| Ex. | Structure | Name | LCMS [M + H]+ | HPLC Method, RT (min.) | 1H NMR (δ NMR) |
|---|---|---|---|---|---|
| 316 | 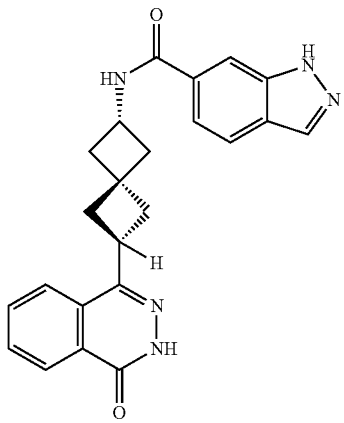 | N-((aR)-6-(4-oxo-3,4-dihydrophthalazin-1-yl)spiro[3.3]heptan-2-yl)-1H-indazole-6-carboxamide | 399.9 | E: 1.33 F: 1.33 | (500 MHz, DMSO-d6) δ 12.47 (s, 1H), 8.70 (d, J = 7.3 Hz, 1H), 8.25 (d, J = 7.9 Hz, 1H), 8.13 (s, 1H), 8.04 (s, 1H), 7.95-7.77 (m, 4H), 7.58 (d, J = 8.5 Hz, 1H), 4.50-4.27 (m, 1H), 3.91 (t, J = 8.4 Hz, 1H), 2.70-2.56 (m, 2H), 2.44-2.33 (m, 3H), 2.31-2.20 (m, 2H), 2.15-2.04 (m, 1H) |
| 317 | 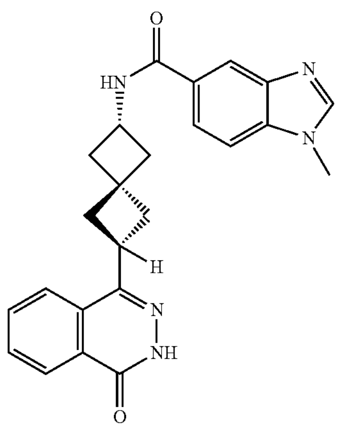 | 1-methyl-N-((aR)-6-(4-oxo-3,4-dihydrophthalazin-1-yl)spiro[3.3]heptan-2-yl)-1H-benzo[d]imidazole-5-carboxamide | 414.0 | E: 1.11 F: 1.28 | (500 MHz, DMSO-d6) δ 12.47 (s, 1H), 8.57 (d, J = 7.3 Hz, 1H), 8.30-8.17 (m, 3H), 7.95-7.76 (m, 4H), 7.61 (d, J = 8.5 Hz, 1H), 4.47-4.32 (m, 1H), 3.95-3.87 (m, 1H), 3.86 (s, 3H), 2.67-2.55 (m, 2H), 2.45-2.33 (m, 3H), 2.31-2.19 (m, 2H), 2.13-2.05 (m, 1H) |
| 318 | 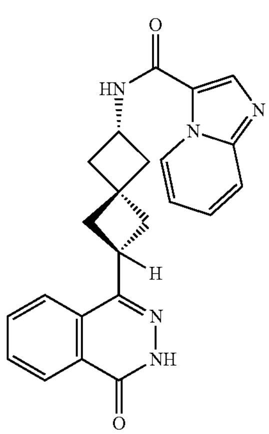 | N-((aR)-6-(4-oxo-3,4-dihydrophthalazin-1-yl)spiro[3.3]heptan-2-yl)imidazo[1,2-a]pyridine-3-carboxamide | 400.0 | E: 1.12 F: 1.38 | (500 MHz, DMSO-d6) δ 12.48 (s, 1H), 9.54 (d, J = 7.0 Hz, 1H), 8.85 (d, J = 7.0 Hz, 1H), 8.53 (s, 1H), 8.25 (d, J = 7.9 Hz, 1H), 7.96-7.89 (m, 1H), 7.89-7.79 (m, 3H), 7.74 (t, J = 7.9 Hz, 1H), 7.18-7.11 (m, 1H), 4.45-4.31 (m, 1H), 3.90 (t, J = 8.4 Hz, 1H), 2.66 (br. s., 1H), 2.58 (br. s., 1H), 2.45-2.32 (m, 3H), 2.31-2.19 (m, 2H), 2.07 (t, J = 10.1 Hz, 1H) |

TABLE 21-continued

| Ex. | Structure | Name | LCMS [M + H]+ | HPLC Method, RT (min.) | 1H NMR (δ NMR) |
|---|---|---|---|---|---|
| 319 | 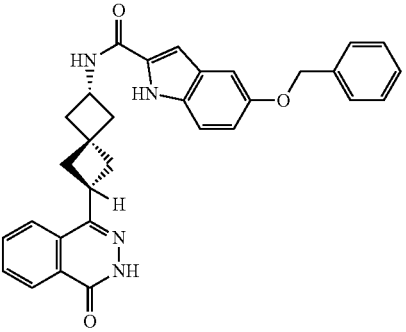 | 5-(benzyloxy)-N-((aR)-6-(4-oxo-3,4-dihydrophthalazin-1-yl)spiro[3.3]heptan-2-yl)-1H-indole-2-carboxamide | 505.0 | E: 1.99 F: 1.99 | (500 MHz, DMSO-d6) δ 12.48 (s, 1H), 11.31 (s, 1H), 8.54 (d, J = 7.6 Hz, 1H), 8.25 (d, J = 7.9 Hz, 1H), 7.96-7.79 (m, 3H), 7.45 (d, J = 7.6 Hz, 2H), 7.38 (t, J = 7.5 Hz, 2H), 7.34-7.27 (m, 2H), 7.15 (s, 1H), 7.03 (s, 1H), 6.90 (d, J = 8.5 Hz, 1H), 5.07 (s, 2H), 4.43-4.27 (m, 1H), 3.99-3.81 (m, 1H), 2.63 (br. s., 1H), 2.56 (br. s., 1H), 2.43-2.33 (m, 3H), 2.29-2.19 (m, 2H), 2.06 (t, J = 9.8 Hz, 1H) |
| 320 | 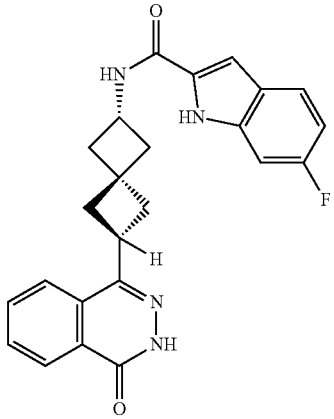 | 6-fluoro-N-((aR)-6-(4-oxo-3,4-dihydrophthalazin-1-yl)spiro[3.3]heptan-2-yl)-1H-indole-2-carboxamide | 416.9 | E: 1.70 F: 1.77 | (500 MHz, DMSO-d6) δ 12.48 (s, 1H), 11.54 (br s, 1H), 8.61 (d, J = 7.6 Hz, 1H), 8.25 (d, J = 7.6 Hz, 1H), 7.95-7.89 (m, 1H), 7.88-7.79 (m, 2H), 7.66-7.57 (m, 1H), 7.15 (br. s., 2H), 6.90 (t, J = 9.0 Hz, 1H), 4.42-4.26 (m, 1H), 3.89 (quin, J = 8.5 Hz, 1H), 2.63 (br. s., 1H), 2.56 (br. s., 1H), 2.43-2.33 (m, 3H), 2.23 (t, J = 9.3 Hz, 2H), 2.06 (t, J = 9.6 Hz, 1H) |
| 321 | 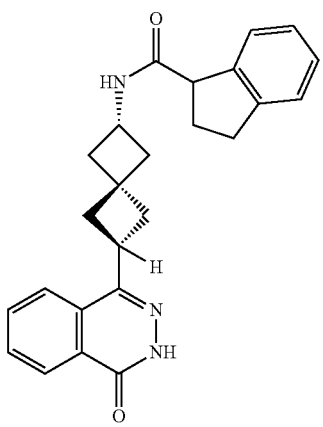 | N-((aR)-6-(4-oxo-3,4-dihydrophthalazin-1-yl)spiro[3.3]heptan-2-yl)-2,3-dihydro-1H-indene-1-carboxamide | 400.2 | E: 1.62 F: 1.68 | (500 MHz, DMSO-d6) δ 12.47 (s, 1H), 8.39 (d, J = 7.0 Hz, 1H), 8.24 (d, J = 7.6 Hz, 1H), 7.95-7.88 (m, 1H), 7.87-7.79 (m, 2H), 7.24- 7.06 (m, 4H), 4.20-4.04 (m, 1H), 3.86 (quin, J = 8.3 Hz, 1H), 3.79 (t, J = 7.5 Hz, 1H), 3.02-2.91 (m, 1H), 2.80 (dt, J = 15.7, 8.0 Hz, 1H), 2.61-2.51 (m, 2H), 2.41-2.28 (m, 3H), 2.25-2.03 (m, 4H), 1.91 (q, J = 10.1 Hz, 1H) |

TABLE 21-continued

| Ex. | Structure | Name | LCMS [M + H]+ | HPLC Method, RT (min.) | 1H NMR (δ NMR) |
|---|---|---|---|---|---|
| 322 | 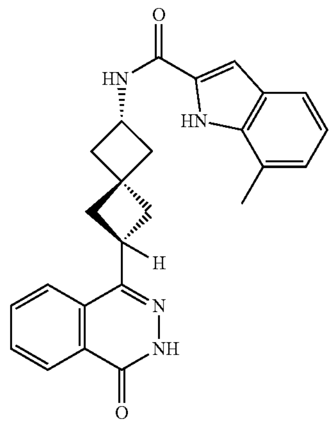 | 7-methyl-N-((aR)-6-(4-oxo-3,4-dihydrophthalazin-1-yl)spiro[3.3]heptan-2-yl)-1H-indole-2-carboxamide | 413.4 | E: 1.74 F: 1.78 | (500 MHz, DMSO-d6) δ 12.49 (s, 1H), 11.26 (br s, 1H), 8.57 (d, J = 7.6 Hz, 1H), 8.28 (d, J = 7.6 Hz, 1H), 7.99-7.81 (m, 3H), 7.44 (d, J = 7.6 Hz, 1H), 7.14 (s, 1H), 7.02-6.91 (m, 2H), 4.47-4.33 (m, 1H), 3.93 (quin, J = 8.5 Hz, 1H), 2.67 (d, J = 11.9 Hz, 1H), 2.63-2.58 (m, 1H), 2.56 (s, 3H), 2.47-2.36 (m, 3H), 2.33-2.23 (m, 2H), 2.10 (t, J = 9.8 Hz, 1H) |
| 323 | 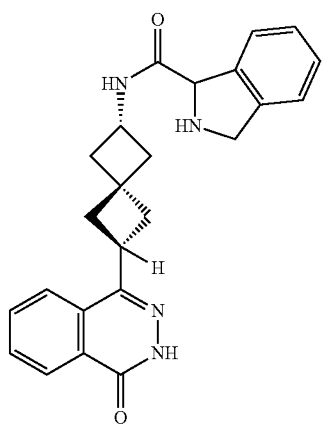 | N-((aR)-6-(4-oxo-3,4-dihydrophthalazin-1-yl)spiro[3.3]heptan-2-yl)isoindoline-1-carboxamide | 401.0 | E: 1.24 F: 1.45 | (500 MHz, DMSO-d6) δ 12.47 (s, 1H), 9.20 (d, J = 7.0 Hz, 1H), 8.25 (d, J = 7.9 Hz, 1H), 7.95-7.88 (m, 1H), 7.87-7.79 (m, 2H), 7.52 (br. s., 1H), 7.44 (s, 3H), 5.35 (s, 1H), 4.70-4.51 (m, 2H), 4.21-4.06 (m, 1H), 3.93-3.81 (m, 1H), 2.58 (d, J = 11.6 Hz, 2H), 2.43-2.34 (m, 3H), 2.28 (br. s., 1H), 2.11 (t, J = 9.6 Hz, 1H), 2.06-1.98 (m, 1H) |
| 325 | 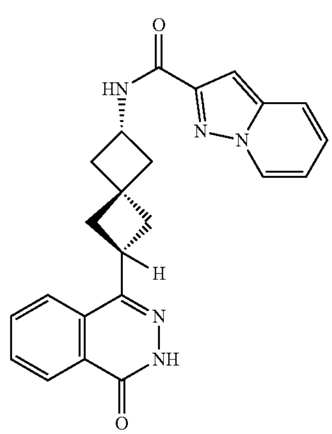 | N-((aR)-6-(4-oxo-3,4-dihydrophthalazin-1-yl)spiro[3.3]heptan-2-yl)pyrazolo[1,5-a]pyridine-2-carboxamide | 399.4 | E: 1.53 F: 1.54 | (500 MHz, DMSO-d6) δ 12.46 (s, 1H), 8.66 (d, J = 7.0 Hz, 1H), 8.58 (d, J = 7.9 Hz, 1H), 8.25 (d, J = 7.6 Hz, 1H), 7.95-7.81 (m, 3H), 7.76 (d, J = 8.9 Hz, 1H), 7.33-7.23 (m, 1H), 7.02 (t, J = 6.3 Hz, 1H), 6.97 (s, 1H), 4.45-4.30 (m, 1H), 3.89 (quin, J = 8.4 Hz, 1H), 2.64-2.55 (m, 2H), 2.45-2.27 (m, 4H), 2.24-2.17 (m, 1H), 2.16-2.10 (m, 1H) |

TABLE 21-continued

| Ex. | Structure | Name | LCMS [M + H]+ | HPLC Method, RT (min.) | ¹H NMR (δ NMR) |
|---|---|---|---|---|---|
| 326 | 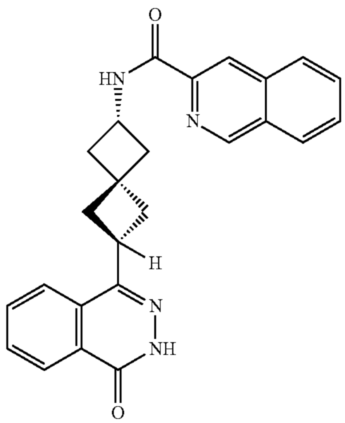 | N-((aR)-6-(4-oxo-3,4-dihydrophthalazin-1-yl)spiro[3.3]heptan-2-yl)isoquinoline-3-carboxamide | 411.4 | E: 1.59 F: 1.78 | (500 MHz, DMSO-d$_6$) δ 12.47 (s, 1H), 9.37 (s, 1H), 9.00 (d, J = 8.2 Hz, 1H), 8.52 (s, 1H), 8.25 (t, J = 6.9 Hz, 2H), 8.17 (d, J = 8.2 Hz, 1H), 7.96-7.75 (m, 5H), 4.45 (sxt, J = 8.2 Hz, 1H), 3.89 (quin, J = 8.4 Hz, 1H), 2.67-2.55 (m, 2H), 2.45-2.30 (m, 4H), 2.28-2.12 (m, 2H) |
| 327 | 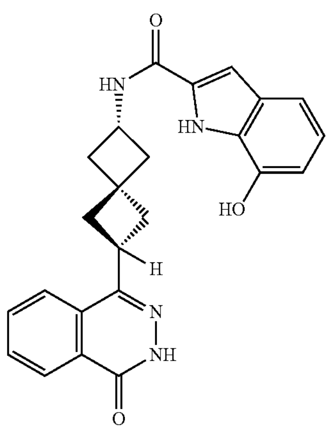 | 7-hydroxy-N-((aR)-6-(4-oxo-3,4-dihydrophthalazin-1-yl)spiro[3.3]heptan-2-yl)-1H-indole-2-carboxamide | 415.1 | E: 1.38 F: 1.40 | (500 MHz, DMSO-d$_6$) δ 12.49 (s, 1H), 11.04 (br s, 1H), 8.59 (d, J = 7.5 Hz, 1H), 8.25 (d, J = 7.8 Hz, 1H), 8.01-7.74 (m, 3H), 7.11-6.97 (m, 2H), 6.85 (t, J = 7.7 Hz, 1H), 6.57 (d, J = 7.4 Hz, 1H), 4.46-4.25 (m, 1H), 3.91 (t, J = 8.4 Hz, 1H), 2.71-2.56 (m, 2H), 2.45-2.33 (m, 3H), 2.30-2.19 (m, 2H), 2.05 (t, J = 9.9 Hz, 1H) |
| 328 | 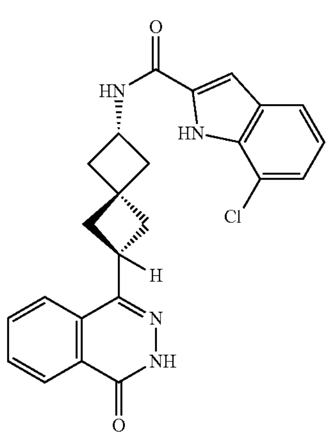 | 7-chloro-N-((aR)-6-(4-oxo-3,4-dihydrophthalazin-1-yl)spiro[3.3]heptan-2-yl)-1H-indole-2-carboxamide | 433.0 | E: 1.73 F: 1.74 | (500 MHz, DMSO-d$_6$) δ 12.49 (s, 1H), 11.58 (br. s., 1H), 8.69 (d, J = 7.2 Hz, 1H), 8.26 (d, J = 7.8 Hz, 1H), 7.98-7.79 (m, 3H), 7.61 (d, J = 7.9 Hz, 1H), 7.29 (d, J = 7.5 Hz, 1H), 7.19 (s, 1H), 7.06 (t, J = 7.7 Hz, 1H), 4.43-4.31 (m, 1H), 3.98-3.84 (m, 1H), 2.73-2.56 (m, 2H), 2.44-2.33 (m, 3H), 2.31-2.17 (m, 2H), 2.07 (t, J = 10.1 Hz, 1H) |

TABLE 21-continued

| Ex. | Structure | Name | LCMS [M + H]+ | HPLC Method, RT (min.) | 1H NMR (δ NMR) |
|---|---|---|---|---|---|
| 329 | 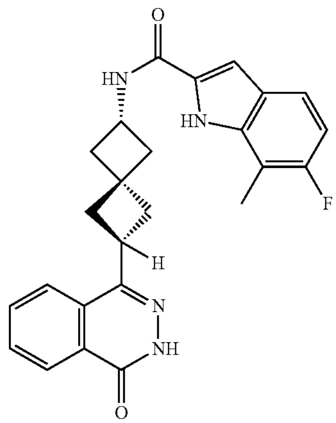 | 6-fluoro-7-methyl-N-((aR)-6-(4-oxo-3,4-dihydrophthalazin-1-yl)spiro[3.3]heptan-2-yl)-1H-indole-2-carboxamide | 431.1 | E: 1.72 F: 1.75 | (500 MHz, DMSO-$d_6$) δ 12.50 (s, 1H), 11.48 (br s, 1H), 8.57 (d, J = 7.5 Hz, 1H), 8.27 (d, J = 7.7 Hz, 1H), 7.98-7.77 (m, 3H), 7.45 (dd, J = 8.3, 5.2 Hz, 1H), 7.15 (s, 1H), 6.89 (t, J = 9.5 Hz, 1H), 4.46-4.29 (m, 1H), 3.98-3.82 (m, 1H), 2.66 (br. s., 1H), 2.62-2.56 (m, 1H), 2.42 (s, 3H), 2.46-2.33 (m, 3H), 2.31-2.20 (m, 2H), 2.08 (t, J = 9.9 Hz, 1H) |
| 330 | 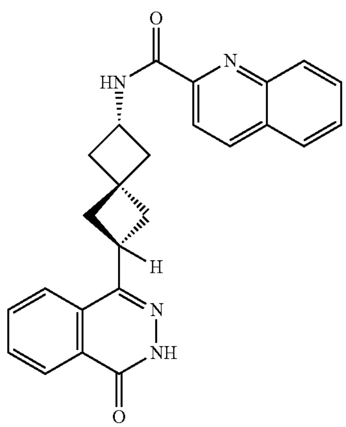 | N-((aR)-6-(4-oxo-3,4-dihydrophthalazin-1-yl)spiro[3.3]heptan-2-yl)quinoline-2-carboxamide | 411.1 | E: 1.78 F: 1.86 | (500 MHz, DMSO-$d_6$) δ 12.47 (s, 1H), 9.02 (d, J = 8.2 Hz, 1H), 8.55 (d, J = 8.2 Hz, 1H), 8.26 (d, J = 7.9 Hz, 1H), 8.17 (d, J = 8.2 Hz, 1H), 8.12 (d, J = 8.2 Hz, 1H), 8.08 (d, J = 8.2 Hz, 1H), 7.96-7.80 (m, 4H), 7.72 (t, J = 7.2 Hz, 1H), 4.44 (sxt, J = 8.1 Hz, 1H), 3.91 (quin, J = 8.5 Hz, 1H), 2.70-2.56 (m, 2H), 2.46-2.34 (m, 4H), 2.30-2.20 (m, 2H) |
| 331 | 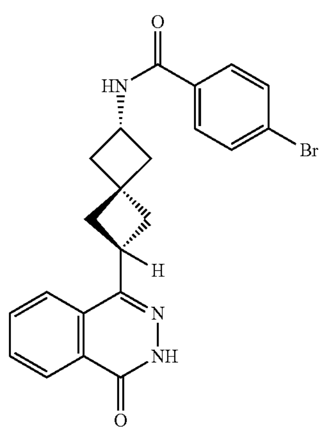 | 4-bromo-N-((aR)-6-(4-oxo-3,4-dihydrophthalazin-1-yl)spiro[3.3]heptan-2-yl)benzamide | 438.0/ 440.0 | E: 1.70 F: 1.77 | (500 MHz, DMSO-$d_6$) δ 12.46 (s, 1H), 8.67 (d, J = 7.3 Hz, 1H), 8.25 (d, J = 7.9 Hz, 1H), 7.94-7.88 (m, 1H), 7.88-7.81 (m, 2H), 7.79 (d, J = 8.2 Hz, 2H), 7.66 (d, J = 8.5 Hz, 2H), 4.32 (sxt, J = 7.9 Hz, 1H), 3.89 (quin, J = 8.4 Hz, 1H), 2.65-2.55 (m, 2H), 2.44-2.29 (m, 3H), 2.28-2.15 (m, 2H), 2.05 (t, J = 10.1 Hz, 1H) |

TABLE 21-continued

| Ex. | Structure | Name | LCMS [M + H]+ | HPLC Method, RT (min.) | 1H NMR (δ NMR) |
|---|---|---|---|---|---|
| 332 | 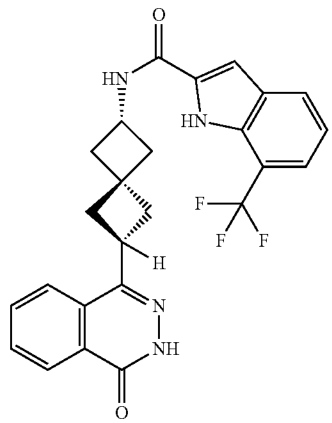 | N-((aR)-6-(4-oxo-3,4-dihydrophthalazin-1-yl)spiro[3.3]heptan-2-yl)-7-(trifluoromethyl)-1H-indole-2-carboxamide | 467.0 | E: 1.84 F: 1.84 | (500 MHz, DMSO-d$_6$) δ 12.50 (s, 1H), 11.34 (br s, 1H), 8.83 (d, J = 7.1 Hz, 1H), 8.25 (d, J = 7.9 Hz, 1H), 8.03-7.79 (m, 4H), 7.58 (d, J = 7.3 Hz, 1H), 7.33-7.16 (m, 2H), 4.44-4.27 (m, 1H), 3.91 (t, J = 8.2 Hz, 1H), 2.68 (br. s., 1H), 2.58 (d, J = 7.6 Hz, 1H), 2.45-2.33 (m, 3H), 2.32-2.20 (m, 2H), 2.07 (t, J = 10.0 Hz, 1H) |
| 333 | 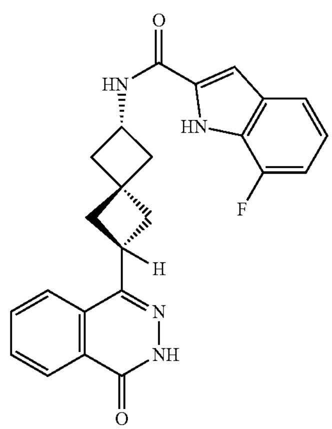 | 7-fluoro-N-((aR)-6-(4-oxo-3,4-dihydrophthalazin-1-yl)spiro[3.3]heptan-2-yl)-1H-indole-2-carboxamide | 417.1 | E: 1.61 F: 1.62 | (500 MHz, DMSO-d$_6$) δ 12.49 (s, 1H), 11.95 (br. s., 1H), 8.64 (d, J = 7.4 Hz, 1H), 8.25 (d, J = 7.7 Hz, 1H), 8.00-7.75 (m, 3H), 7.43 (br. s., 1H), 7.19 (br. s., 1H), 7.04-6.91 (m, 2H), 4.44-4.28 (m, 1H), 3.97-3.83 (m, 1H), 2.70-2.55 (m, 2H), 2.44-2.32 (m, 3H), 2.31-2.16 (m, 2H), 2.06 (t, J = 9.9 Hz, 1H) |
| 334 | 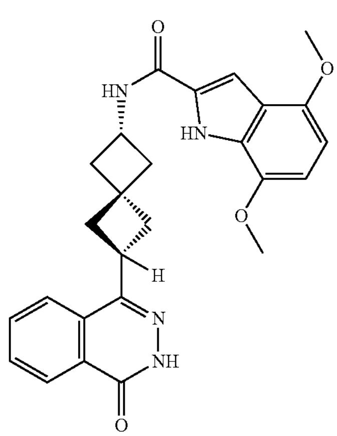 | 4,7-dimethoxy-N-((aR)-6-(4-oxo-3,4-dihydrophthalazin-1-yl)spiro[3.3]heptan-2-yl)-1H-indole-2-carboxamide | 459.4 | E: 1.66 F: 1.72 | (500 MHz, DMSO-d$_6$) δ 12.47 (s, 1H), 11.29 (s, 1H), 8.49 (d, J = 7.3 Hz, 1H), 8.25 (d, J = 7.6 Hz, 1H), 7.96-7.80 (m, 3H), 7.09 (d, J = 2.1 Hz, 1H), 6.61 (d, J = 8.2 Hz, 1H), 6.37 (d, J = 8.2 Hz, 1H), 4.40-4.27 (m, 1H), 3.90 (t, J = 8.4 Hz, 1H), 3.86 (s, 3H), 3.82 (s, 3H), 2.70-2.61 (m, 1H), 2.60-2.55 (m, 1H), 2.45-2.33 (m, 3H), 2.31-2.23 (m, 1H), 2.20 (t, J = 9.8 Hz, 1H), 2.05-1.98 (m, 1H) |

TABLE 21-continued

| Ex. | Structure | Name | LCMS [M + H]+ | HPLC Method, RT (min.) | 1H NMR (δ NMR) |
|---|---|---|---|---|---|
| 335 | 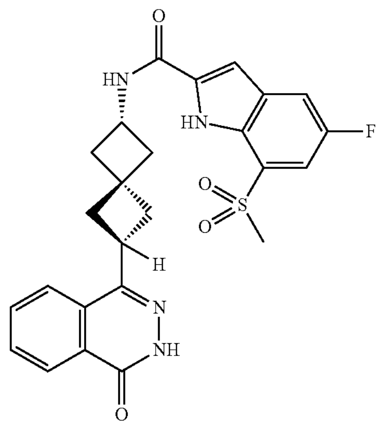 | 5-fluoro-7-(methylsulfonyl)-N-((aR)-6-(4-oxo-3,4-dihydrophthalazin-1-yl)spiro[3.3]heptan-2-yl)-1H-indole-2-carboxamide | 495.0 | E: 1.58 F: 1.65 | (500 MHz, DMSO-$d_6$) δ 12.47 (s, 1H), 10.76 (s, 1H), 9.00 (d, J = 7.3 Hz, 1H), 8.25 (d, J = 7.6 Hz, 1H), 7.97-7.80 (m, 4H), 7.62 (dd, J = 8.7, 2.3 Hz, 1H), 7.34 (s, 1H), 4.45-4.29 (m, 1H), 3.91 (quin, J = 8.5 Hz, 1H), 2.71-2.63 (m, 1H), 2.62-2.56 (m, 1H), 2.54 (s, 3H), 2.45-2.34 (m, 3H), 2.31-2.21 (m, 2H), 2.13-2.04 (m, 1H) |
| 336 | 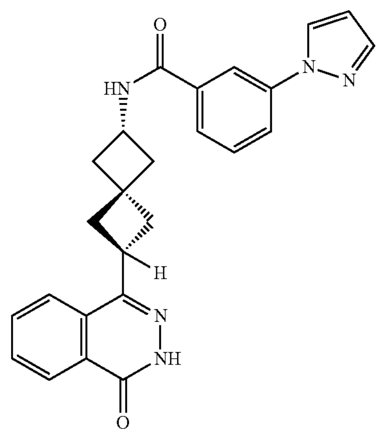 | N-((aR)-6-(4-oxo-3,4-dihydrophthalazin-1-yl)spiro[3.3]heptan-2-yl)-3-(1H-pyrazol-1-yl)benzamide | 426.1 | E: 1.49 F: 1.54 | (500 MHz, DMSO-$d_6$) δ 12.47 (s, 1H), 8.64 (d, J = 7.3 Hz, 1H), 8.58 (d, J = 2.4 Hz, 1H), 8.25 (d, J = 7.6 Hz, 1H), 8.00-7.95 (m, 2H), 7.94-7.80 (m, 5H), 7.79 (s, 1H), 6.58 (s, 1H), 4.41-4.30 (m, 1H), 3.95-3.84 (m, 1H), 2.66-2.55 (m, 2H), 2.44-2.31 (m, 3H), 2.29-2.19 (m, 2H), 2.12-2.03 (m, 1H) |
| 337 | 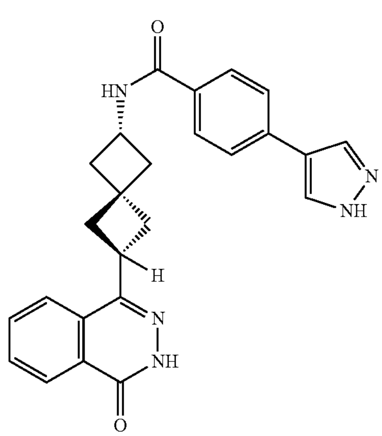 | N-((aR)-6-(4-oxo-3,4-dihydrophthalazin-1-yl)spiro[3.3]heptan-2-yl)-4-(1H-pyrazol-4-yl)benzamide | 426.1 | E: 1.29 F: 1.34 | (500 MHz, DMSO-$d_6$) δ 12.47 (s, 1H), 8.53 (d, J = 7.3 Hz, 1H), 8.25 (d, J = 7.9 Hz, 1H), 8.03 (br. s., 2H), 7.94-7.78 (m, 5H), 7.68 (d, J = 8.2 Hz, 2H), 4.41-4.29 (m, 1H), 3.99-3.79 (m, 1H), 2.66-2.56 (m, 2H), 2.44-2.31 (m, 3H), 2.28-2.18 (m, 2H), 2.07 (t, J = 9.9 Hz, 1H) |

TABLE 21-continued

| Ex. | Structure | Name | LCMS [M + H]+ | HPLC Method, RT (min.) | 1H NMR (δ NMR) |
|---|---|---|---|---|---|
| 338 | 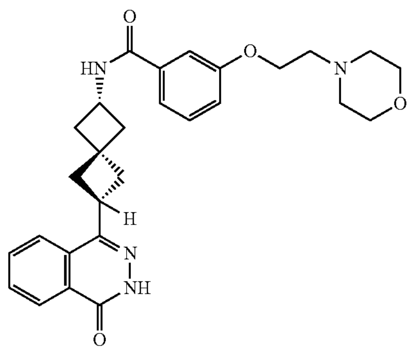 | 3-(2-morpholino-ethoxy)-N-((aR)-6-(4-oxo-3,4-dihydrophthalazin-1-yl)spiro[3.3]heptan-2-yl)benzamide | 489.2 | E: 1.17 F: 1.46 | (500 MHz, DMSO-$d_6$) δ 12.46 (s, 1H), 8.54 (d, J = 7.3 Hz, 1H), 8.25 (d, J = 7.6 Hz, 1H), 7.97-7.80 (m, 3H), 7.46-7.38 (m, 2H), 7.35 (t, J = 7.8 Hz, 1H), 7.08 (d, J = 7.9 Hz, 1H), 4.41-4.27 (m, 1H), 4.15 (br. s., 2H), 3.90 (quin, J = 8.4 Hz, 1H), 3.59 (br. s., 2H), 3.41-2.66 (m, 8H), 2.64-2.56 (m, 2H), 2.43-2.31 (m, 3H), 2.29-2.17 (m, 2H), 2.11-2.02 (m, 1H) |
| 339 | 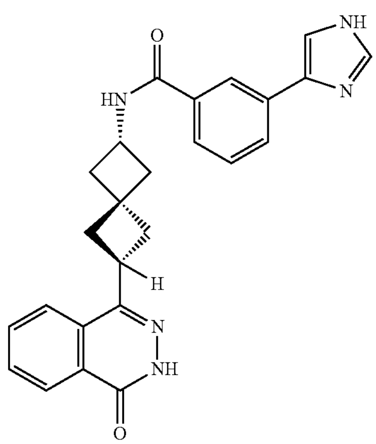 | N-((aR)-6-(4-oxo-3,4-dihydrophthalazin-1-yl)spiro[3.3]heptan-2-yl)-3-(1H-pyrazol-4-yl)benzamide | 426.1 | E: 1.32 F: 1.37 | (500 MHz, DMSO-$d_6$) δ 12.47 (s, 1H), 8.57 (d, J = 7.3 Hz, 1H), 8.25 (d, J = 7.9 Hz, 1H), 8.11 (s, 2H), 8.03 (s, 1H), 7.96-7.79 (m, 3H), 7.74 (d, J = 7.6 Hz, 1H), 7.64 (d, J = 7.6 Hz, 1H), 7.42 (t, J = 7.8 Hz, 1H), 4.43-4.30 (m, 1H), 3.91 (quin, J = 8.3 Hz, 1H), 2.69-2.55 (m, 2H), 2.44-2.33 (m, 3H), 2.29-2.20 (m, 2H), 2.13-2.03 (m, 1H) |
| 340 | 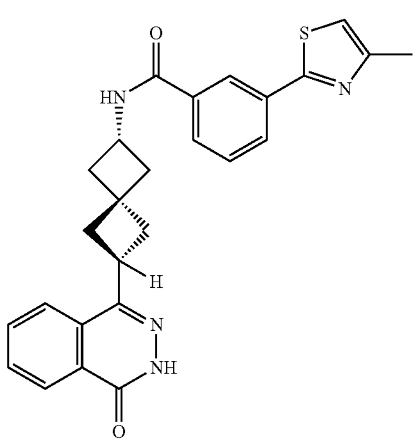 | 3-(4-methylthiazol-2-yl)-N-((aR)-6-(4-oxo-3,4-dihydrophthalazin-1-yl)spiro[3.3]heptan-2-yl)benzamide | 457.1 | E: 1.64 F: 1.76 | (500 MHz, DMSO-$d_6$) δ 12.47 (s, 1H), 8.80 (d, J = 7.3 Hz, 1H), 8.34 (s, 1H), 8.25 (d, J = 7.9 Hz, 1H), 8.04 (d, J = 7.9 Hz, 1H), 7.96-7.79 (m, 4H), 7.57 (t, J = 7.8 Hz, 1H), 7.37 (s, 1H), 4.44-4.31 (m, 1H), 3.90 (quin, J = 8.4 Hz, 1H), 2.68-2.56 (m, 2H), 2.45 (s, 3H), 2.43- 2.33 (m, 3H), 2.31-2.20 (m, 2H), 2.11 (t, J = 10.1 Hz, 1H) |

TABLE 21-continued

| Ex. | Structure | Name | LCMS [M + H]+ | HPLC Method, RT (min.) | 1H NMR (δ NMR) |
|---|---|---|---|---|---|
| 341 | 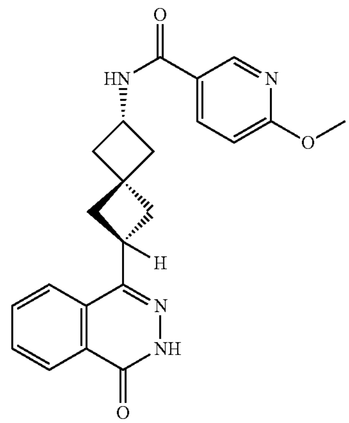 | 6-methoxy-N-((aR)-6-(4-oxo-3,4-dihydrophthalazin-1-yl)spiro[3.3]heptan-2-yl)nicotinamide | 391.2 | E: 1.35 F: 1.43 | (500 MHz, DMSO-d$_6$) δ 12.46 (s, 1H), 8.64 (d, J = 2.1 Hz, 1H), 8.58 (d, J = 7.3 Hz, 1H), 8.25 (d, J = 7.9 Hz, 1H), 8.11 (dd, J = 8.7, 2.3 Hz, 1H), 7.95-7.79 (m, 3H), 6.87 (d, J = 8.5 Hz, 1H), 4.39-4.27 (m, 1H), 3.96-3.82 (m, 4H), 2.66-2.55 (m, 2H), 2.44-2.30 (m, 3H), 2.22 (t, J = 9.6 Hz, 2H), 2.09-1.99 (m, 1H) |
| 342 | 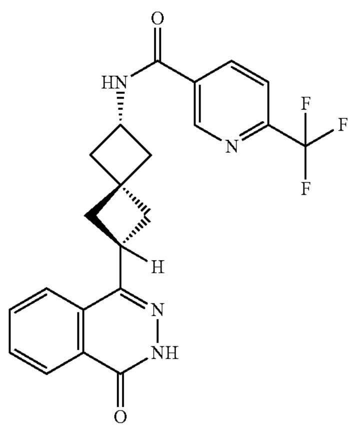 | N-((aR)-6-(4-oxo-3,4-dihydrophthalazin-1-yl)spiro[3.3]heptan-2-yl)-6-(trifluoromethyl)nicotinamide | 429.1 | E: 1.56 F: 1.62 | (500 MHz, DMSO-d$_6$) δ 12.47 (s, 1H), 9.13 (s, 1H), 9.01 (d, J = 7.0 Hz, 1H), 8.45 (d, J = 7.9 Hz, 1H), 8.25 (d, J = 7.9 Hz, 1H), 8.03 (d, J = 8.2 Hz, 1H), 7.95-7.80 (m, 3H), 4.36 (sxt, J = 8.0 Hz, 1H), 3.90 (quin, J = 8.5 Hz, 1H), 2.71-2.61 (m, 1H), 2.60-2.55 (m, 1H), 2.45-2.32 (m, 3H), 2.31-2.21 (m, 2H), 2.08 (t, J = 9.9 Hz, 1H) |
| 343 | 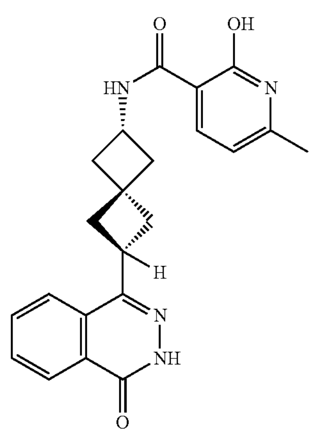 | 2-hydroxy-6-methyl-N-((aR)-6-(4-oxo-3,4-dihydrophthalazin-1-yl)spiro[3.3]heptan-2-yl)nicotinamide | 391.2 | E: 1.18 F: 1.23 | (500 MHz, DMSO-d$_6$) δ 12.46 (s, 1H), 9.89 (d, J = 7.6 Hz, 1H), 8.25 (d, J = 7.9 Hz, 1H), 8.18 (d, J = 7.6 Hz, 1H), 7.95-7.78 (m, 3H), 6.29 (d, J = 7.3 Hz, 1H), 4.38-4.17 (m, 1H), 3.89 (quin, J = 8.4 Hz, 1H), 2.71-2.61 (m, 1H), 2.57 (br. s., 1H), 2.43-2.32 (m, 3H), 2.28 (s, 3H), 2.31-2.26 (m, 1H), 2.12-2.04 (m, 1H), 1.93-1.84 (m, 1H) |

TABLE 21-continued

| Ex. | Structure | Name | LCMS [M + H]+ | HPLC Method, RT (min.) | 1H NMR (δ NMR) |
|---|---|---|---|---|---|
| 344 | 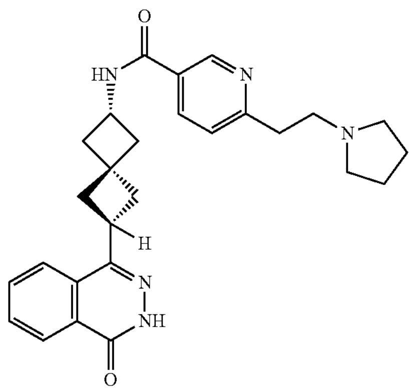 | N-((aR)-6-(4-oxo-3,4-dihydrophthalazin-1-yl)spiro[3.3]heptan-2-yl)-6-(2-(pyrrolidin-1-yl)ethyl)nicotinamide | 458.2 | E: 1.08 F: 1.12 | (500 MHz, DMSO-d$_6$) δ 12.47 (s, 1H), 8.95 (s, 1H), 8.78 (d, J = 7.0 Hz, 1H), 8.25 (d, J = 7.9 Hz, 1H), 8.18 (d, J = 8.2 Hz, 1H), 7.95-7.75 (m, 3H), 7.46 (d, J = 7.9 Hz, 1H), 4.44-4.26 (m, 1H), 3.90 (t, J = 8.4 Hz, 1H), 3.57 (br. s., 2H), 3.23 (t, J = 7.3 Hz, 2H), 2.68-2.55 (m, 2H), 2.44-2.32 (m, 3H), 2.24 (t, J = 9.5 Hz, 2H), 2.07 (t, J = 9.9 Hz, 1H), 2.03-1.77 (m, 4H). |
| 345 | 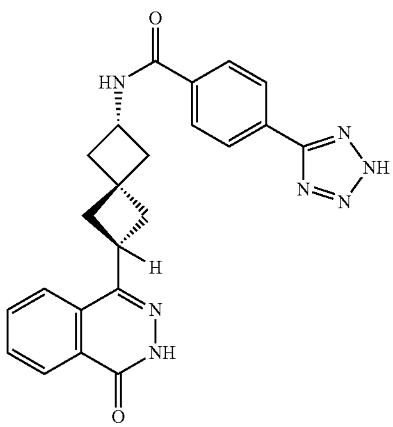 | N-((aR)-6-(4-oxo-3,4-dihydrophthalazin-1-yl)spiro[3.3]heptan-2-yl)-4-(2H-tetrazol-5-yl)benzamide | 427.9 | E: 1.29 F: 1.09 | (500 MHz, DMSO-d$_6$) δ 12.47 (s, 1H), 8.76 (d, J = 7.3 Hz, 1H), 8.25 (d, J = 7.9 Hz, 1H), 8.14-8.06 (m, 2H), 8.03 (d, J = 8.2 Hz, 2H), 7.95-7.89 (m, 1H), 7.88-7.80 (m, 2H), 4.43-4.25 (m, 1H), 3.90 (quin, J = 8.5 Hz, 1H), 2.68-2.61 (m, 1H), 2.60-2.55 (m, 1H), 2.44-2.33 (m, 3H), 2.29-2.20 (m, 2H), 2.12-2.04 (m, 1H) |
| 346 | 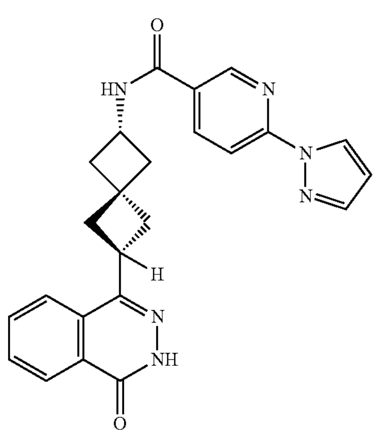 | N-((aR)-6-(4-oxo-3,4-dihydrophthalazin-1-yl)spiro[3.3]heptan-2-yl)-6-(1H-pyrazol-1-yl)nicotinamide | 427.2 | E: 1.53 F: 1.53 | (500 MHz, DMSO-d$_6$) δ 12.47 (s, 1H), 8.88 (d, J = 1.8 Hz, 1H), 8.82 (d, J = 7.3 Hz, 1H), 8.66 (d, J = 2.4 Hz, 1H), 8.37 (dd, J = 8.5, 2.1 Hz, 1H), 8.25 (d, J = 7.9 Hz, 1H), 7.98 (d, J = 8.5 Hz, 1H), 7.94-7.89 (m, 1H), 7.89-7.80 (m, 3H), 6.61 (s, 1H), 4.42-4.30 (m, 1H), 3.90 (quin, J = 8.5 Hz, 1H), 2.64 (t, J = 11.6 Hz, 1H), 2.57 (br. s., 1H), 2.45-2.32 (m, 3H), 2.30-2.19 (m, 2H), 2.13-2.03 (m, 1H) |

TABLE 21-continued

| Ex. | Structure | Name | LCMS [M + H]+ | HPLC Method, RT (min.) | 1H NMR (δ NMR) |
|---|---|---|---|---|---|
| 347 | 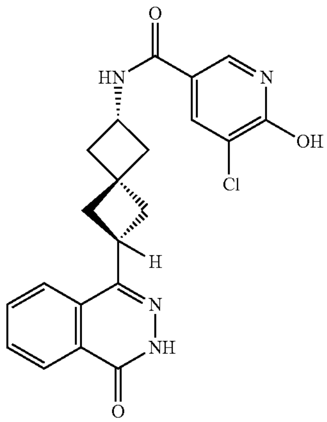 | 5-chloro-6-hydroxy-N-((aR)-6-(4-oxo-3,4-dihydrophthalazin-1-yl)spiro[3.3]heptan-2-yl)nicotinamide | 411.1 | E: 1.22 F: 1.23 | (500 MHz, DMSO-$d_6$) δ 12.46 (s, 1H), 8.43 (d, J = 7.3 Hz, 1H), 8.25 (d, J = 7.6 Hz, 1H), 8.15 (d, J = 2.4 Hz, 1H), 8.00 (d, J = 2.1 Hz, 1H), 7.94-7.88 (m, 1H), 7.88-7.79 (m, 2H), 4.37-4.15 (m, 1H), 3.88 (quin, J = 8.5 Hz, 1H), 2.64-2.54 (m, 2H), 2.42-2.29 (m, 3H), 2.25-2.13 (m, 2H), 2.03-1.93 (m, 1H) |
| 348 | 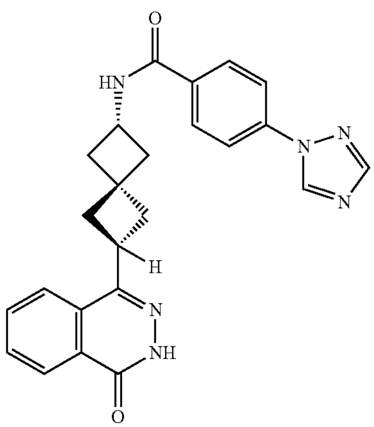 | N-((aR)-6-(4-oxo-3,4-dihydrophthalazin-1-yl)spiro[3.3]heptan-2-yl)-4-(1H-1,2,4-triazol-1-yl)benzamide | 426.9 | E: 1.32 F: 1.34 | (500 MHz, DMSO-$d_6$) δ 12.47 (s, 1H), 9.37 (s, 1H), 8.71 (d, J = 7.3 Hz, 1H), 8.27 (s, 1H), 8.25 (d, J = 7.9 Hz, 1H), 8.06-7.99 (m, 2H), 7.98-7.94 (m, 2H), 7.93-7.81 (m, 3H), 4.42-4.28 (m, 1H), 3.90 (quin, J = 8.5 Hz, 1H), 2.67-2.60 (m, 1H), 2.57 (br. s., 1H), 2.44-2.32 (m, 3H), 2.30-2.20 (m, 2H), 2.12-2.03 (m, 1H) |
| 349 | 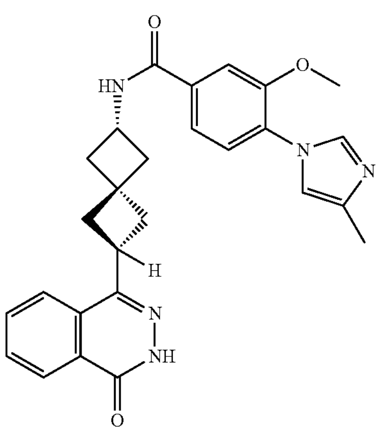 | 3-methoxy-4-(4-methyl-1H-imidazol-1-yl)-N-((aR)-6-(4-oxo-3,4-dihydrophthalazin-1-yl)spiro[3.3]heptan-2-yl)benzamide | 470.2 | E: 1.20 F: 1.48 | (500 MHz, DMSO-$d_6$) δ 12.48 (s, 1H), 8.71 (d, J = 7.6 Hz, 1H), 8.25 (d, J = 7.6 Hz, 1H), 7.99-7.79 (m, 4H), 7.61 (s, 1H), 7.56-7.50 (m, 1H), 7.46 (d, J = 8.2 Hz, 1H), 7.22 (s, 1H), 4.41-4.28 (m, 1H), 3.95-3.89 (m, 1H), 3.88 (s, 3H), 2.70-2.55 (m, 2H), 2.43-2.32 (m, 3H), 2.24 (t, J = 9.6 Hz, 2H), 2.16 (s, 3H), 2.11-2.02 (m, 1H) |

TABLE 21-continued

| Ex. | Structure | Name | LCMS [M + H]+ | HPLC Method, RT (min.) | 1H NMR (δ NMR) |
|---|---|---|---|---|---|
| 350 | 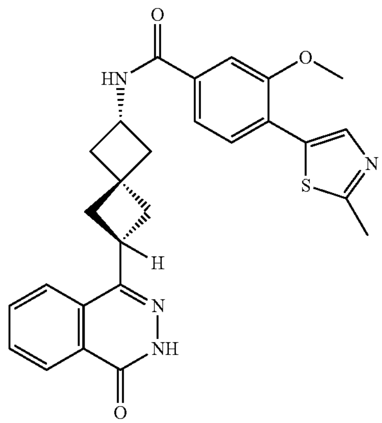 | 3-methoxy-4-(2-methylthiazol-5-yl)-N-((aR)-6-(4-oxo-3,4-dihydrophthalazin-1-yl)spiro[3.3]heptan-2-yl)benzamide | 487.1 | E: 1.40 F: 1.68 | (500 MHz, DMSO-d6) δ 12.47 (s, 1H), 8.67 (d, J = 7.3 Hz, 1H), 8.25 (d, J = 7.6 Hz, 1H), 8.18 (s, 1H), 7.96-7.88 (m, 1H), 7.88-7.81 (m, 2H), 7.79 (d, J = 7.9 Hz, 1H), 7.54 (s, 1H), 7.50 (d, J = 8.9 Hz, 1H), 4.35 (sxt, J = 8.1 Hz, 1H), 3.95 (s, 3H), 3.89 (quin, J = 8.5 Hz, 1H), 2.65 (s, 3H), 2.69-2.56 (m, 2H), 2.43-2.29 (m, 3H), 2.28-2.18 (m, 2H), 2.08 (t, J = 10.1 Hz, 1H) |
| 351 | 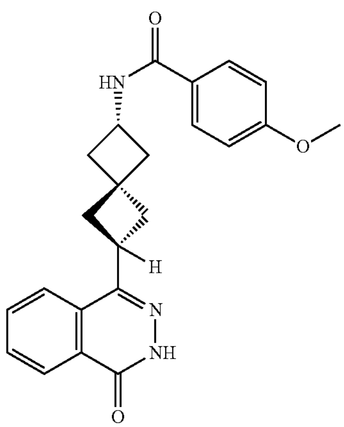 | 5-methoxy-N-((aR)-6-(4-oxo-3,4-dihydrophthalazin-1-yl)spiro[3.3]heptan-2-yl)picolinamide | 390.9 | E: 1.53 F: 1.56 | (500 MHz, DMSO-d6) δ 12.47 (s, 1H), 8.67 (d, J = 8.2 Hz, 1H), 8.28 (d, J = 2.7 Hz, 1H), 8.24 (d, J = 7.6 Hz, 1H), 7.96 (d, J = 8.5 Hz, 1H), 7.93-7.88 (m, 1H), 7.87-7.80 (m, 2H), 7.51 (dd, J = 8.5, 2.7 Hz, 1H), 4.42-4.23 (m, 1H), 3.87 (s, 3H), 3.94-3.81 (m, 1H), 2.62-2.52 (m, 2H), 2.42-2.25 (m, 4H), 2.24-2.14 (m, 1H), 2.14-2.06 (m, 1H) |
| 352 | 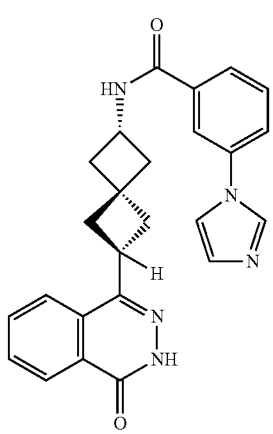 | 3-(1H-imidazol-1-yl)-N-((aR)-6-(4-oxo-3,4-dihydrophthalazin-1-yl)spiro[3.3]heptan-2-yl)benzamide | 426.2 | E: 1.13 F: 1.38 | (500 MHz, DMSO-d6) δ 12.48 (s, 1H), 8.72 (d, J = 7.0 Hz, 1H), 8.33 (s, 1H), 8.25 (d, J = 7.9 Hz, 1H), 8.02 (s, 1H), 7.95-7.89 (m, 1H), 7.88-7.74 (m, 5H), 7.64-7.57 (m, 1H), 7.16 (s, 1H), 4.42-4.29 (m, 1H), 3.90 (quin, J = 8.4 Hz, 1H), 2.69-2.60 (m, 1H), 2.60-2.55 (m, 1H), 2.44-2.30 (m, 3H), 2.29-2.19 (m, 2H), 2.11-2.02 (m, 1H) |

TABLE 21-continued

| Ex. | Structure | Name | LCMS [M + H]+ | HPLC Method, RT (min.) | 1H NMR (δ NMR) |
|---|---|---|---|---|---|
| 353 | 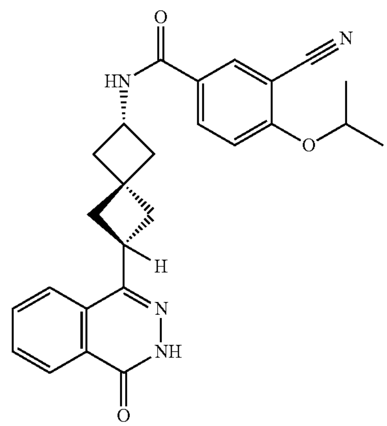 | 3-cyano-4-isopropoxy-N-((aR)-6-(4-oxo-3,4-dihydrophthalazin-1-yl)spiro[3.3]heptan-2-yl)benzamide | 443.1 | F: 1.60 | (500 MHz, DMSO-d6) δ 12.49 (s, 1H), 8.63 (d, J = 7.2 Hz, 1H), 8.25(d, J = 7.7 Hz, 1H), 8.20 (s, 1H), 8.10 (d, J = 8.8 Hz, 1H), 7.95-7.79 (m, 3H), 7.34 (d, J = 9.0 Hz, 1H), 4.94-4.78 (m, 1H), 4.39-4.22 (m, 1H), 3.89 (t, J = 8.3 Hz, 1H), 2.61 (br. s., 2H), 2.43-2.28 (m, 3H), 2.22 (d, J = 9.3 Hz, 2H), 2.03 (t, J = 9.9 Hz, 1H), 1.32 (d, J = 5.9 Hz, 6H) |
| 354 | 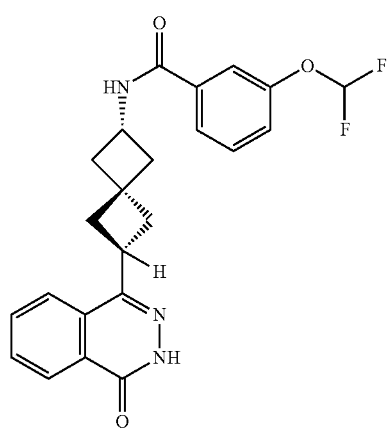 | 3-(difluoromethoxy)-N-((aR)-6-(4-oxo-3,4-dihydrophthalazin-1-yl)spiro[3.3]heptan-2-yl)benzamide | 426.0 | F: 1.52 | (500 MHz, DMSO-d6) δ 12.49 (s, 1H), 8.70 (d, J = 7.2 Hz, 1H), 8.25 (d, J = 7.7 Hz, 1H), 7.98-7.79 (m, 3H), 7.73 (d, J = 7.7 Hz, 1H), 7.63 (br. s., 1H), 7.52 (t, J = 7.9 Hz, 1H), 7.33 (d, J = 8.0 Hz, 1H), 7.29 (t, J = 74.2 Hz, 1H), 4.41-4.26 (m, 1H), 3.97-3.81 (m, 1H), 2.67-2.55 (m, 2H), 2.44-2.31 (m, 3H), 2.28-2.18 (m, 2H), 2.07 (t, J = 10.0 Hz, 1H) |
| 355 | 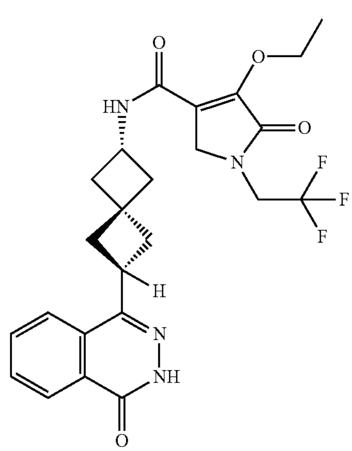 | 4-ethoxy-5-oxo-N-((aR)-6-(4-oxo-3,4-dihydrophthalazin-1-yl)spiro[3.3]heptan-2-yl)-1-(2,2,2-trifluoroethyl)-2,5-dihydro-1H-pyrrole-3-carboxamide | 490.8 | F: 1.56 | (500 MHz, DMSO-d6) δ 12.48 (s, 1H), 8.25 (d, J = 7.7 Hz, 1H), 7.97-7.77 (m, 4H), 4.49 (q, J = 6.9 Hz, 2H), 4.30-4.16 (m, 3H), 4.11 (s, 2H), 3.88 (quin, J = 8.3 Hz, 1H), 2.60 (br. s., 1H), 2.42-2.29 (m, 3H), 2.22 (br. s., 1H), 2.15 (t, J = 9.6 Hz, 1H), 1.97 (t, J = 9.8 Hz, 1H), 1.28 (t, J = 6.9 Hz, 3H) |

TABLE 21-continued

| Ex. | Structure | Name | LCMS [M + H]+ | HPLC Method, RT (min.) | 1H NMR (δ NMR) |
|---|---|---|---|---|---|
| 356 | 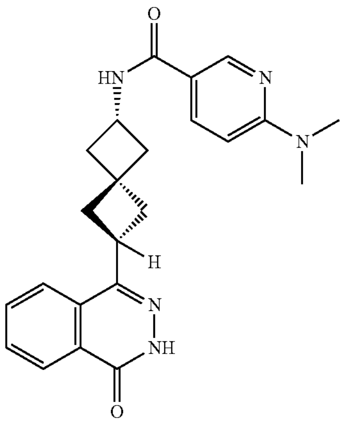 | 6-(dimethylamino)-N-((aR)-6-(4-oxo-3,4-dihydrophthalazin-1-yl)spiro[3.3]heptan-2-yl)nicotinamide | 404.1 | E: 1.25 | (500 MHz, DMSO-d$_6$) δ 12.48 (s, 1H), 8.56 (br s, 1H), 8.33 (d, J = 7.1 Hz, 1H), 8.25 (d, J = 7.8 Hz, 1H), 7.99-7.78 (m, 4H), 6.65 (d, J = 9.1 Hz, 1H), 4.40-4.25 (m, 1H), 3.89 (t, J = 8.3 Hz, 1H), 3.07 (s, 6H), 2.64-2.54 (m, 2H), 2.42-2.29 (m, 3H), 2.25-2.12 (m, 2H), 2.03 (t, J = 9.9 Hz, 1H) |
| 357 | 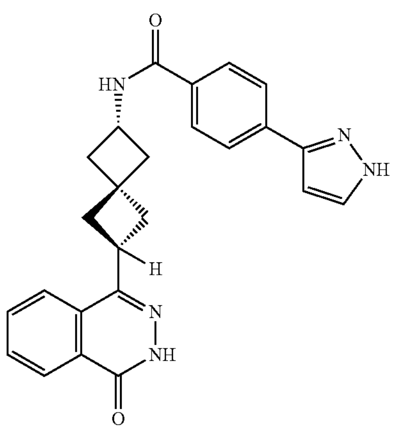 | N-((aR)-6-(4-oxo-3,4-dihydrophthalazin-1-yl)spiro[3.3]heptan-2-yl)-4-(1H-pyrazol-3-yl)benzamide | 426.4 | E: 1.31 F: 1.40 | (500 MHz, DMSO-d$_6$) δ 12.47 (s, 1H), 8.58 (d, J = 7.3 Hz, 1H), 8.25 (d, J = 7.9 Hz, 1H), 8.01-7.68 (m, 8H), 6.80 (s, 1H), 4.44-4.24 (m, 1H), 4.01-3.78 (m, 1H), 2.67-2.56 (m, 2H), 2.45-2.32 (m, 3H), 2.29-2.18 (m, 2H), 2.08 (t, J = 9.9 Hz, 1H) |
| 358 | 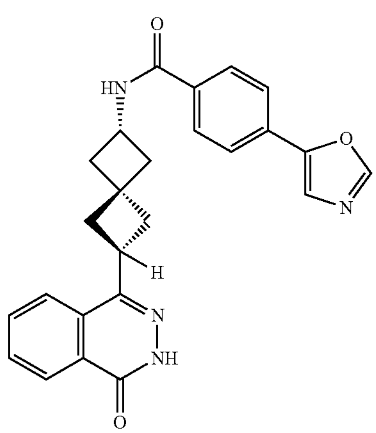 | 4-(oxazol-5-yl)-N-((aR)-6-(4-oxo-3,4-dihydrophthalazin-1-yl)spiro[3.3]heptan-2-yl)benzamide | 427.1 | E: 1.40 F: 1.47 | (500 MHz, DMSO-d$_6$) δ 12.47 (s, 1H), 8.66 (d, J = 7.3 Hz, 1H), 8.49 (s, 1H), 8.25 (d, J = 7.9 Hz, 1H), 7.98-7.76 (m, 8H), 4.43-4.29 (m, 1H), 3.99-3.82 (m, 1H), 2.67-2.55 (m, 2H), 2.44-2.32 (m, 3H), 2.29-2.19 (m, 2H), 2.08 (t, J = 10.1 Hz, 1H) |

TABLE 21-continued

| Ex. | Structure | Name | LCMS [M + H]+ | HPLC Method, RT (min.) | 1H NMR (δ NMR) |
|---|---|---|---|---|---|
| 359 | 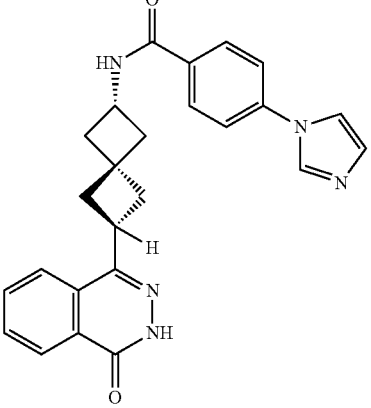 | 4-(1H-imidazol-1-yl)-N-((aR)-6-(4-oxo-3,4-dihydrophthalazin-1-yl)spiro[3.3]heptan-2-yl)benzamide | 426.1 | E: 1.08 F: 1.35 | (500 MHz, DMSO-$d_6$) δ 12.47 (s, 1H), 8.66 (d, J = 7.3 Hz, 1H), 8.41 (s, 1H), 8.25 (d, J = 7.9 Hz, 1H), 7.99 (d, J = 8.5 Hz, 2H), 7.95-7.81 (m, 4H), 7.77 (d, J = 8.5 Hz, 2H), 7.16 (s, 1H), 4.43-4.30 (m, 1H), 3.90 (t, J = 8.4 Hz, 1H), 2.69-2.56 (m, 2H), 2.45-2.33 (m, 3H), 2.30-2.19 (m, 2H), 2.09 (t, J = 9.8 Hz, 1H) |
| 360 | 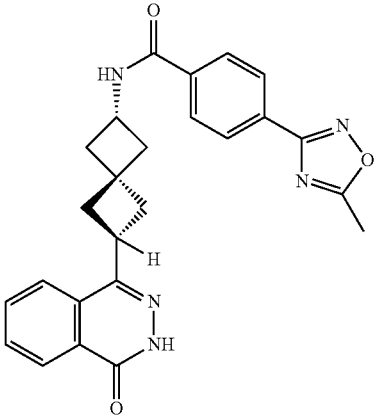 | 4-(5-methyl-1,2,4-oxadiazol-3-yl)-N-((aR)-6-(4-oxo-3,4-dihydrophthalazin-1-yl)spiro[3.3]heptan-2-yl)benzamide | 442.2 | E: 1.52 F: 1.58 | (500 MHz, DMSO-$d_6$) δ 12.47 (s, 1H), 8.76 (d, J = 7.3 Hz, 1H), 8.25 (d, J = 7.9 Hz, 1H), 8.09-8.04 (m, 2H), 8.03-7.97 (m, 2H), 7.95-7.80 (m, 3H), 4.43-4.30 (m, 1H), 3.90 (t, J = 8.4 Hz, 1H), 2.68 (s, 3H), 2.65-2.55 (m, 2H), 2.44-2.32 (m, 3H), 2.30-2.19 (m, 2H), 2.13-2.02 (m, 1H) |
| 361 | 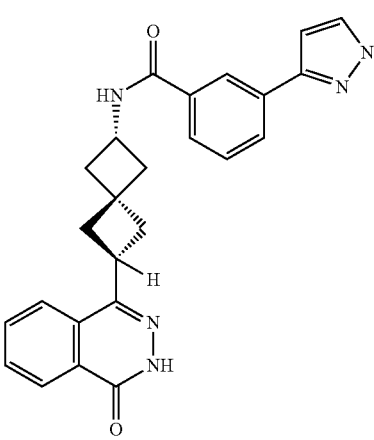 | N-((aR)-6-(4-oxo-3,4-dihydrophthalazin-1-yl)spiro[3.3]heptan-2-yl)-3-(1H-pyrazol-3-yl)benzamide | 426.1 | E: 1.34 F: 1.43 | (500 MHz, DMSO-$d_6$) δ 12.47 (s, 1H), 8.66 (d, J = 7.0 Hz, 1H), 8.26 (d, J = 7.6 Hz, 2H), 8.00-7.69 (m, 6H), 7.48 (br. s., 1H), 6.77 (s, 1H), 4.38 (sxt, J = 8.1 Hz, 1H), 3.91 (quin, J = 8.4 Hz, 1H), 2.69-2.56 (m, 2H), 2.45-2.32 (m, 3H), 2.30-2.19 (m, 2H), 2.10 (t, J = 9.9 Hz, 1H) |

TABLE 21-continued

| Ex. | Structure | Name | LCMS [M + H]+ | HPLC Method, RT (min.) | 1H NMR (δ NMR) |
|---|---|---|---|---|---|
| 362 | 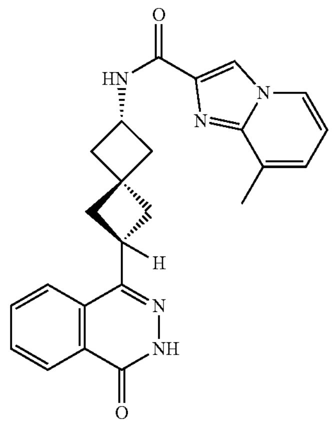 | 8-methyl-N-((aR)-6-(4-oxo-3,4-dihydrophthalazin-1-yl)spiro[3.3]heptan-2-yl)imidazo[1,2-a]pyridine-2-carboxamide | 414.2 | E: 1.11 F: 1.53 | (500 MHz, DMSO-$d_6$) δ 12.47 (s, 1H), 8.41 (d, J = 6.7 Hz, 1H), 8.32 (s, 1H), 8.31-8.28 (m, 1H), 8.25 (d, J = 7.6 Hz, 1H), 7.96-7.79 (m, 3H), 7.13 (d, J = 6.7 Hz, 1H), 6.87 (t, J = 6.9 Hz, 1H), 4.46-4.32 (m, 1H), 3.89 (quin, J = 8.5 Hz, 1H), 2.65-2.56 (m, 2H), 2.53 (s, 3H), 2.44-2.30 (m, 4H), 2.26-2.13 (m, 2H) |
| 363 | 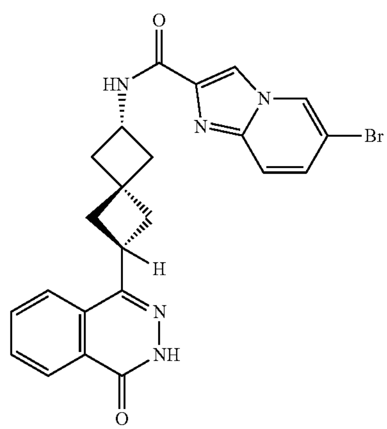 | 6-bromo-N-((aR)-6-(4-oxo-3,4-dihydrophthalazin-1-yl)spiro[3.3]heptan-2-yl)imidazo[1,2-a]pyridine-2-carboxamide | 477.9 | E: 1.32 F: 1.60 | (500 MHz, DMSO-$d_6$) δ 12.46 (s, 1H), 8.93 (s, 1H), 8.55 (d, J = 8.2 Hz, 1H), 8.29 (s, 1H), 8.25 (d, J = 7.9 Hz, 1H), 7.96-7.79 (m, 3H), 7.57 (d, J = 9.8 Hz, 1H), 7.46 (d, J = 9.5 Hz, 1H), 4.36 (sxt, J = 8.2 Hz, 1H), 3.88 (quin, J = 8.5 Hz, 1H), 2.61-2.54 (m, 2H), 2.44-2.27 (m, 4H), 2.24-2.09 (m, 2H) |
| 364 | 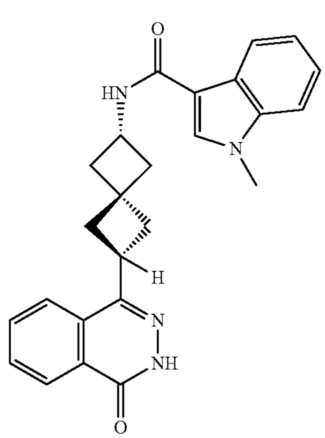 | 1-methyl-N-((aR)-6-(4-oxo-3,4-dihydrophthalazin-1-yl)spiro[3.3]heptan-2-yl)-1H-indole-3-carboxamide | 413.2 | E: 1.62 F: 1.63 | (500 MHz, DMSO-$d_6$) δ 12.47 (s, 1H), 8.26 (d, J = 7.6 Hz, 1H), 8.12 (d, J = 7.9 Hz, 1H), 8.03-7.95 (m, 2H), 7.94-7.78 (m, 3H), 7.47 (d, J = 7.9 Hz, 1H), 7.25-7.16 (m, 1H), 7.13 (t, J = 7.5 Hz, 1H), 4.44-4.30 (m, 1H), 3.97-3.85 (m, 1H), 3.82 (s, 3H), 2.67-2.54 (m, 2H), 2.45-2.31 (m, 3H), 2.28-2.15 (m, 2H), 2.03 (t, J = 10.1 Hz, 1H) |

TABLE 21-continued

| Ex. | Structure | Name | LCMS [M + H]+ | HPLC Method, RT (min.) | 1H NMR (δ NMR) |
|---|---|---|---|---|---|
| 365 | 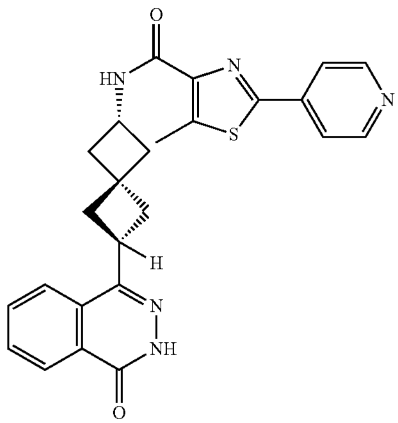 | 5-methyl-N-((aR)-6-(4-oxo-3,4-dihydrophthalazin-1-yl)spiro[3.3]heptan-2-yl)-2-(pyridin-4-yl)thiazole-4-carboxamide | 458.2 | E: 1.22 F: 1.69 | (500 MHz, DMSO-d$_6$) δ 12.47 (s, 1H), 8.73 (br s, 2H), 8.60 (d, J = 7.9 Hz, 1H), 8.26 (d, J = 7.9 Hz, 1H), 7.98 (d, J = 4.9 Hz, 2H), 7.94-7.79 (m, 3H), 4.37 (sxt, J = 8.3 Hz, 1H), 3.91 (quin, J = 8.4 Hz, 1H), 2.80 (s, 3H), 2.66-2.55 (m, 2H), 2.45-2.30 (m, 4H), 2.26-2.13 (m, 2H) |
| 366 | 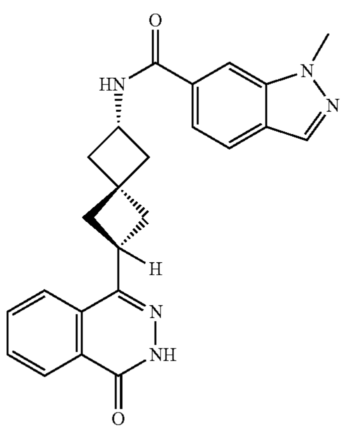 | 1-methyl-N-((aR)-6-(4-oxo-3,4-dihydrophthalazin-1-yl)spiro[3.3]heptan-2-yl)-1H-indazole-6-carboxamide | 414.3 | E: 1.40 | (500 MHz, DMSO-d$_6$) δ 12.50 (s, 1H), 8.69 (d, J = 7.3 Hz, 1H), 8.25 (d, J = 7.8 Hz, 1H), 8.14 (s, 1H), 8.10 (s, 1H), 7.97-7.75 (m, 4H), 7.60 (d, J = 8.4 Hz, 1H), 4.40 (sxt, J = 8.1 Hz, 1H), 4.10 (s, 3H), 3.91 (quin, J = 8.4 Hz, 1H), 2.65 (t, J = 10.7 Hz, 1H), 2.57 (d, J = 10.9 Hz, 1H), 2.46-2.33 (m, 3H), 2.31-2.21 (m, 2H), 2.10 (t, J = 10.0 Hz, 1H) |
| 367 | 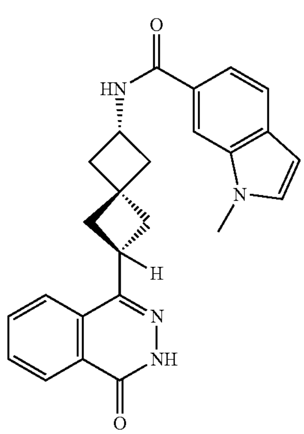 | 1-methyl-N-((aR)-6-(4-oxo-3,4-dihydrophthalazin-1-yl)spiro[3.3]heptan-2-yl)-1H-indole-6-carboxamide | 413.3 | E: 1.60 | (500 MHz, DMSO-d$_6$) δ 12.50 (s, 1H), 8.51 (d, J = 7.6 Hz, 1H), 8.25 (d, J = 7.7 Hz, 1H), 7.98 (s, 1H), 7.95-7.80 (m, 3H), 7.56 (s, 2H), 7.46 (d, J = 2.8 Hz, 1H), 6.46 (br. s., 1H), 4.39 (d, J = 7.9 Hz, 1H), 3.94-3.88 (m, 1H), 3.83 (s, 3H), 2.64 (br. s., 1H), 2.60-2.55 (m, 1H), 2.43-2.33 (m, 3H), 2.29-2.19 (m, 2H), 2.11-2.05 (m, 1H) |

| Ex. | Structure | Name | LCMS [M + H]+ | HPLC Method, RT (min.) | ¹H NMR (δ NMR) |
|---|---|---|---|---|---|
| 368 | 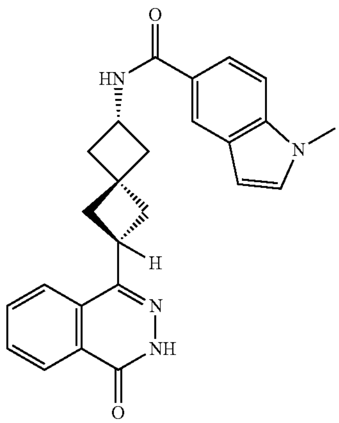 | 1-methyl-N-((aR)-6-(4-oxo-3,4-dihydrophthalazin-1-yl)spiro[3.3]heptan-2-yl)-1H-indole-5-carboxamide | 413.3 | E: 1.55 | (500 MHz, DMSO-d$_6$) δ 12.49 (s, 1H), 8.46 (d, J = 7.4 Hz, 1H), 8.25 (d, J = 7.8 Hz, 1H), 8.13 (s, 1H), 7.97-7.79 (m, 3H), 7.69 (d, J = 8.6 Hz, 1H), 7.46 (d, J = 8.6 Hz, 1H), 7.40 (d, J = 2.6 Hz, 1H), 6.52 (d, J = 2.6 Hz, 1H), 4.46-4.32 (m, 1H), 3.90 (quin, J = 8.4 Hz, 1H), 3.81 (s, 3H), 2.60 (d, J = 13.0 Hz, 2H), 2.45-2.32 (m, 3H), 2.30-2.17 (m, 2H), 2.13-2.02 (m, 1H) |
| 369 | 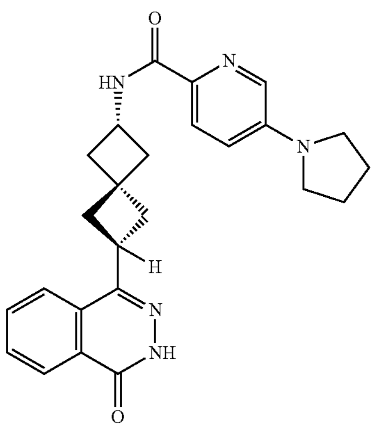 | N-((aR)-6-(4-oxo-3,4-dihydrophthalazin-1-yl)spiro[3.3]heptan-2-yl)-5-(pyrrolidin-1-yl)picolinamide | 430.1 | E: 1.44 F: 1.89 | (500 MHz, DMSO-d$_6$) δ 12.46 (s, 1H), 8.39 (d, J = 8.2 Hz, 1H), 8.25 (d, J = 7.6 Hz, 1H), 7.98-7.64 (m, 5H), 6.95 (d, J = 6.4 Hz, 1H), 4.41-4.23 (m, 1H), 3.99-3.76 (m, 1H), 3.39-3.26 (m, 4H), 2.57 (br. s., 2H), 2.44-2.31 (m, 3H), 2.31-2.24 (m, 1H), 2.19 (br. s., 1H), 2.13-2.04 (m, 1H), 1.97 (br. s., 4H) |
| 370 | 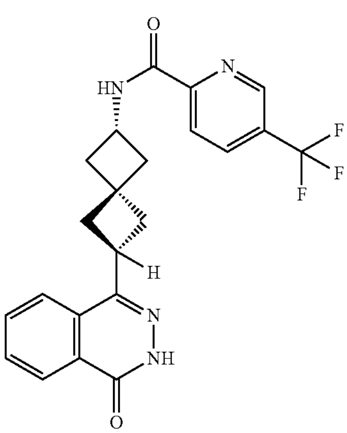 | N-((aR)-6-(4-oxo-3,4-dihydrophthalazin-1-yl)spiro[3.3]heptan-2-yl)-5-(trifluoromethyl)picolinamide | 429.0 | E: 1.88 F: 1.89 | (500 MHz, DMSO-d$_6$) δ 12.46 (s, 1H), 9.10 (d, J = 7.9 Hz, 1H), 9.02 (s, 1H), 8.41 (d, J = 8.2 Hz, 1H), 8.25 (d, J = 7.6 Hz, 1H), 8.20 (d, J = 8.2 Hz, 1H), 7.96-7.79 (m, 3H), 4.45-4.32 (m, 1H), 3.89 (quin, J = 8.5 Hz, 1H), 2.58 (d, J = 8.9 Hz, 2H), 2.45-2.29 (m, 4H), 2.26-2.13 (m, 2H) |

TABLE 21-continued

| Ex. | Structure | Name | LCMS [M + H]+ | HPLC Method, RT (min.) | 1H NMR (δ NMR) |
|---|---|---|---|---|---|
| 371 | 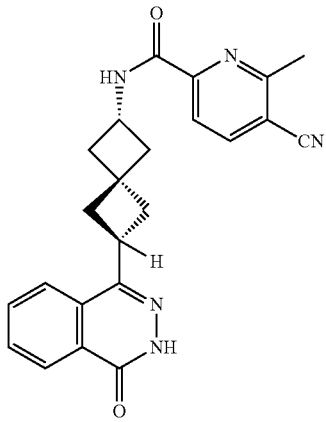 | 5-cyano-6-methyl-N-((aR)-6-(4-oxo-3,4-dihydrophthalazin-1-yl)spiro[3.3]heptan-2-yl)picolinamide | 400.3 | E: 1.67 F: 1.69 | (500 MHz, DMSO-d6) δ 12.48 (s, 1H), 8.97 (d, J = 8.2 Hz, 1H), 8.41 (d, J = 7.9 Hz, 1H), 8.27 (d, J = 7.9 Hz, 1H), 7.96 (d, J = 8.2 Hz, 1H), 7.93 (d, J = 7.3 Hz, 1H), 7.90-7.82 (m, 2H), 4.46-4.31 (m, 1H), 3.91 (quin, J = 8.3 Hz, 1H), 2.78 (s, 3H), 2.60 (d, J = 7.9 Hz, 2H), 2.47-2.31 (m, 4H), 2.27-2.13 (m, 2H) |
| 372 | 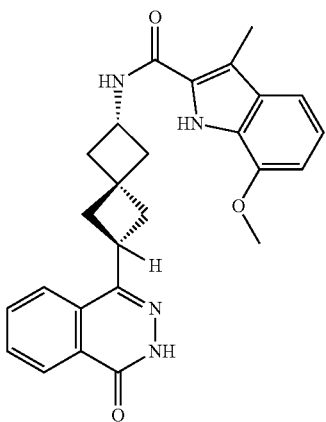 | 7-methoxy-3-methyl-N-((aR)-6-(4-oxo-3,4-dihydrophthalazin-1-yl)spiro[3.3]heptan-2-yl)-1H-indole-2-carboxamide | 443.1 | E: 1.81 F: 1.84 | (500 MHz, DMSO-d6) δ 12.47 (s, 1H), 11.02 (s, 1H), 8.31 (d, J = 6.7 Hz, 1H), 8.26 (d, J = 7.9 Hz, 1H), 7.97-7.80 (m, 3H), 7.16 (d, J = 7.9 Hz, 1H), 6.99-6.92 (m, 1H), 6.77 (d, J = 7.9 Hz, 1H), 4.40-4.26 (m, 1H), 3.94 (s, 3H), 3.92-3.88 (m, 1H), 2.67 (br. s., 1H), 2.57 (br. s., 1H), 2.49 (br. s., 3H), 2.45-2.34 (m, 3H), 2.29 (d, J = 5.8 Hz, 1H), 2.17 (t, J = 9.8 Hz, 1H), 2.00 (t, J = 9.9 Hz, 1H) |
| 373 | 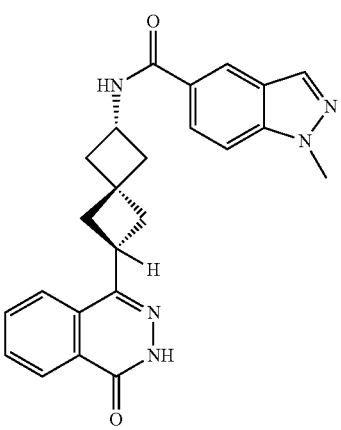 | 1-methyl-N-((aR)-6-(4-oxo-3,4-dihydrophthalazin-1-yl)spiro[3.3]heptan-2-yl)-1H-indazole-5-carboxamide | 414.1 | E: 1.46 F: 1.42 | (500 MHz, DMSO-d6) δ 12.47 (s, 1H), 8.59 (d, J = 7.3 Hz, 1H), 8.32 (s, 1H), 8.26 (d, J = 7.9 Hz, 1H), 8.17 (s, 1H), 7.98-7.79 (m, 4H), 7.67 (d, J = 8.9 Hz, 1H), 4.38 (sxt, J = 7.9 Hz, 1H), 4.06 (s, 3H), 3.90 (quin, J = 8.5 Hz, 1H), 2.68-2.54 (m, 2H), 2.46-2.32 (m, 3H), 2.30-2.18 (m, 2H), 2.09 (t, J = 9.8 Hz, 1H) |

TABLE 21-continued

| Ex. | Structure | Name | LCMS [M + H]+ | HPLC Method, RT (min.) | 1H NMR (δ NMR) |
|---|---|---|---|---|---|
| 374 | 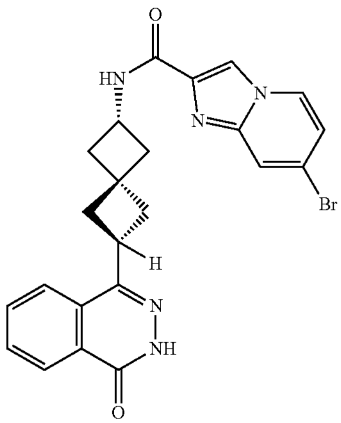 | 7-bromo-N-((aR)-6-(4-oxo-3,4-dihydrophthalazin-1-yl)spiro[3.3]heptan-2-yl)imidazo[1,2-a]pyridine-2-carboxamide | 478.1 | E: 1.38 F: 1.59 | (500 MHz, DMSO-d$_6$) δ 12.47 (s, 1H), 8.92 (s, 1H), 8.54 (d, J = 8.2 Hz, 1H), 8.29 (s, 1H), 8.25 (d, J = 7.9 Hz, 1H), 7.95-7.88 (m, 1H), 7.88-7.79 (m, 2H), 7.57 (d, J = 9.5 Hz, 1H), 7.45 (d, J = 9.5 Hz, 1H), 4.42-4.28 (m, 1H), 3.88 (quin, J = 8.4 Hz, 1H), 2.57 (br. s., 2H), 2.43-2.27 (m, 4H), 2.24-2.10 (m, 2H) |
| 375 | 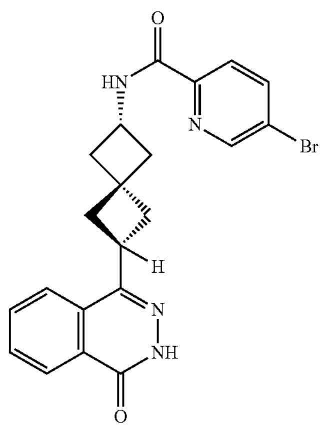 | 5-bromo-N-((aR)-6-(4-oxo-3,4-dihydrophthalazin-1-yl)spiro[3.3]heptan-2-yl)picolinamide | 438.9 | E: 1.78 F: 1.82 | (500 MHz, DMSO-d$_6$) δ 12.46 (s, 1H), 8.93 (d, J = 7.9 Hz, 1H), 8.76 (s, 1H), 8.24 (t, J = 6.9 Hz, 2H), 7.99-7.78 (m, 4H), 4.44-4.29 (m, 1H), 3.92-3.84 (m, 1H), 2.62-2.54 (m, 2H), 2.44-2.29 (m, 4H), 2.24-2.11 (m, 2H) |

Example 376: 7-morpholino-N-((aR)-6-(4-oxo-3,4-dihydrophthalazin-1-yl)spiro[3.3]heptan-2-yl)imidazo[1,2-a]pyridine-3-carboxamide, TFA salt

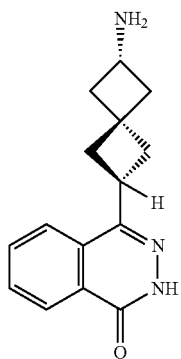

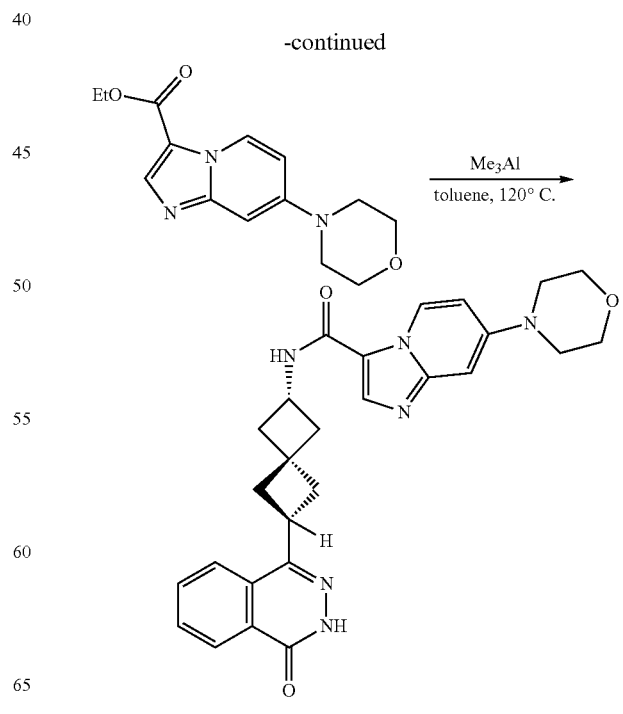

To a solution of Intermediate 2 (21 mg, 0.082 mmol) in toluene (2 mL) was Me₃Al (2 M solution in toluene, 0.12 mL, 0.25 mmol) dropwise at rt. After stirring at rt for 5 min, Intermediate 114 (23 mg, 0.082 mmol) was added. The reaction was stirred under N₂ at reflux for 1 h. After cooled to rt, TFA and MeOH were carefully added to quench the reaction. The solvent was removed. The crude product was purified by reverse phase HPLC to provide Example 376 (24 mg, 47%) as a white solid. ¹H NMR (400 MHz, DMSO-d₆) δ 12.47 (s, 1H), 9.27 (d, J=7.9 Hz, 1H), 8.85 (d, J=7.3 Hz, 1H), 8.43 (s, 1H), 8.26 (d, J=8.1 Hz, 1H), 7.97-7.78 (m, 3H), 7.38 (dd, J=8.0, 2.5 Hz, 1H), 6.94 (d, J=2.4 Hz, 1H), 4.35 (sxt, J=7.9 Hz, 1H), 3.91 (quin, J=8.4 Hz, 1H), 3.80-3.66 (m, 4H), 3.55-3.42 (m, 4H), 2.72-2.54 (m, 2H), 2.44-2.36 (m, 3H), 2.33-2.18 (m, 2H), 2.11-2.00 (m, 1H). LC-MS(ESI) m/z: 485.1 [M+H]⁺. Analytical HPLC RT=4.34 min (Method A), 6.61 min (Method B).

Examples in Table 22 were prepared by following a similar procedure to that described in Example 376 by reacting Intermediate 2 with the appropriate esters.

TABLE 22

| Ex. | Structure | Name | LCMS [M + H]⁺ | HPLC Method, RT (min.) | ¹H NMR (δ NMR) |
|---|---|---|---|---|---|
| 377 | 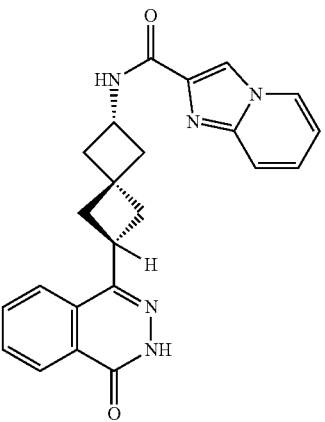 | N-((aR)-6-(4-oxo-3,4-dihydrophthalazin-1-yl)spiro[3.3]heptan-2-yl)imidazo[1,2-a]pyridine-2-carboxamide | 400.1 | E: 1.06 F: 1.38 | (500 MHz, DMSO-d₆) δ 12.46 (s, 1H), 8.57 (d, J = 7.0 Hz, 1H), 8.48 (d, J = 8.2 Hz, 1H), 8.34 (s, 1H), 8.25 (d, J = 7.9 Hz, 1H), 7.96-7.80 (m, 3H), 7.58 (d, J = 9.2 Hz, 1H), 7.39-7.29 (m, 1H), 6.97 (t, J = 6.7 Hz, 1H), 4.43-4.28 (m, 1H), 3.89 (quin, J = 8.5 Hz, 1H), 2.56 (d, J = 7.3 Hz, 2H), 2.44-2.28 (m, 4H), 2.23-2.08 (m, 2H) |
| 378 | 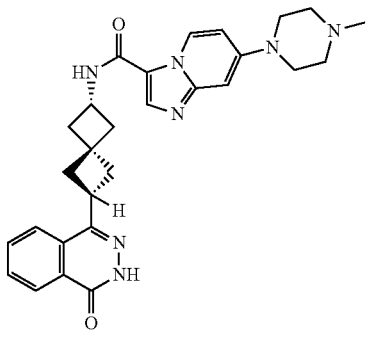 | 7-(4-methylpiperazin-1-yl)-N-((aR)-6-(4-oxo-3,4-dihydrophthalazin-1-yl)spiro[3.3]heptan-2-yl)imidazo[1,2-a]pyridine-3-carboxamide) | 498.1 | E: 1.06 F: 1.35 | (500 MHz, DMSO-d₆) δ 12.47 (s, 1H), 9.17 (d, J = 7.6 Hz, 1H), 8.35 (d, J = 7.3 Hz, 1H), 8.25 (d, J = 7.9 Hz, 1H), 8.14 (s, 1H), 7.96-7.77 (m, 3H), 7.02 (d, J = 8.2 Hz, 1H), 6.81 (br. s., 1H), 4.43-4.28 (m, 1H), 3.90 (quin, J = 8.6 Hz, 1H), 3.50-3.00 (m, 4H), 2.75-2.55 (m, 6H), 2.45-2.31 (m, 6H), 2.29-2.17 (m, 2H), 2.05 (t, J = 9.9 Hz, 1H) |
| 379 | 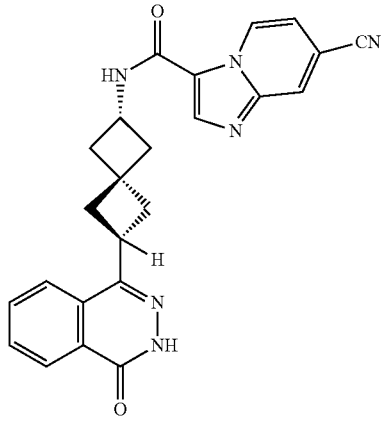 | 7-cyano-N-((aR)-6-(4-oxo-3,4-dihydrophthalazin-1-yl)spiro[3.3]heptan-2-yl)imidazo[1,2-a]pyridine-3-carboxamide | 425.1 | E: 1.41 F: 1.55 | (500 MHz, DMSO-d₆) δ 12.47 (s, 1H), 9.53 (d, J = 7.0 Hz, 1H), 8.82 (d, J = 7.3 Hz, 1H), 8.54 (s, 1H), 8.46 (s, 1H), 8.25 (d, J = 7.9 Hz, 1H), 7.96-7.81 (m, 3H), 7.40 (d, J = 7.0 Hz, 1H), 4.46-4.32 (m, 1H), 3.91 (quin, J = 8.5 Hz, 1H), 2.70-2.62 (m, 1H), 2.62-2.55 (m, 1H), 2.45-2.34 (m, 3H), 2.31-2.21 (m, 2H), 2.13-2.03 (m, 1H) |

TABLE 22-continued

| Ex. | Structure | Name | LCMS [M + H]+ | HPLC Method, RT (min.) | 1H NMR (δ NMR) |
|---|---|---|---|---|---|
| 380 | 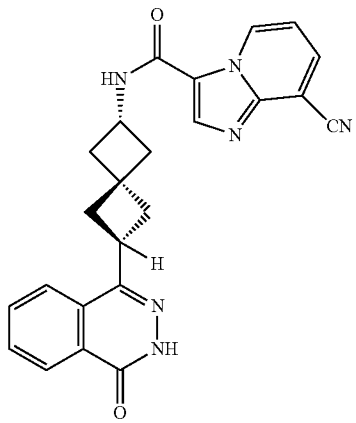 | 8-cyano-N-((aR)-6-(4-oxo-3,4-dihydrophthalazin-1-yl)spiro[3.3]heptan-2-yl)imidazo[1,2-a]pyridine-3-carboxamide | 425.0 | E: 1.45<br>F: 1.53 | (500 MHz, DMSO-$d_6$) δ 12.47 (s, 1H), 9.68 (d, J = 6.7 Hz, 1H), 8.79 (d, J = 7.3 Hz, 1H), 8.48 (s, 1H), 8.25 (d, J = 7.9 Hz, 1H), 8.15 (d, J = 7.0 Hz, 1H), 7.96-7.80 (m, 3H), 7.26 (t, J = 7.2 Hz, 1H), 4.47-4.32 (m, 1H), 3.91 (quin, J = 8.5 Hz, 1H), 2.71-2.62 (m, 1H), 2.58 (t, J = 7.8 Hz, 1H), 2.46-2.34 (m, 3H), 2.31-2.21 (m, 2H), 2.14-2.05 (m, 1H) |
| 381 | 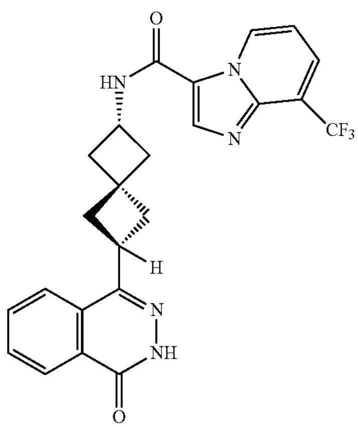 | N-((aR)-6-(4-oxo-3,4-dihydrophthalazin-1-yl)spiro[3.3]heptan-2-yl)-8-(trifluoromethyl)imidazo[1,2-a]pyridine-3-carboxamide | 468.0 | E: 1.58<br>F: 1.73 | (500 MHz, DMSO-$d_6$) δ 12.48 (s, 1H), 9.67 (d, J = 6.7 Hz, 1H), 8.77 (d, J = 7.3 Hz, 1H), 8.45 (s, 1H), 8.25 (d, J = 7.9 Hz, 1H), 7.96-7.80 (m, 4H), 7.25 (t, J = 7.0 Hz, 1H), 4.40 (sxt, J = 7.9 Hz, 1H), 3.91 (quin, J = 8.5 Hz, 1H), 2.70-2.62 (m, 1H), 2.62-2.54 (m, 1H), 2.45-2.33 (m, 3H), 2.31-2.22 (m, 2H), 2.14-2.05 (m, 1H) |
| 382 | 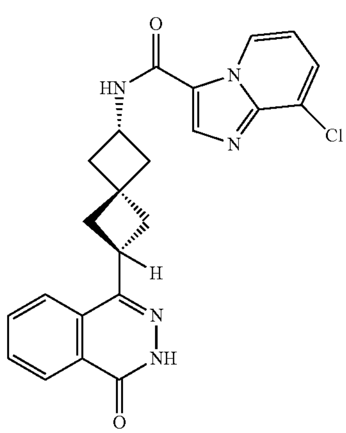 | 8-chloro-N-((aR)-6-(4-oxo-3,4-dihydrophthalazin-1-yl)spiro[3.3]heptan-2-yl)imidazo[1,2-a]pyridine-3-carboxamide | 434.0 | E: 1.36<br>F: 1.61 | (500 MHz, DMSO-$d_6$) δ 12.47 (s, 1H), 9.43 (d, J = 7.0 Hz, 1H), 8.71 (d, J = 7.3 Hz, 1H), 8.40 (s, 1H), 8.25 (d, J = 7.9 Hz, 1H), 7.98-7.77 (m, 3H), 7.65 (d, J = 7.3 Hz, 1H), 7.10 (t, J = 7.2 Hz, 1H), 4.48-4.27 (m, 1H), 3.91 (quin, J = 8.4 Hz, 1H), 2.66 (t, J = 11.4 Hz, 1H), 2.58 (t, J = 8.1 Hz, 1H), 2.46-2.33 (m, 3H), 2.31-2.21 (m, 2H), 2.08 (t, J = 9.9 Hz, 1H) |

TABLE 22-continued

| Ex. | Structure | Name | LCMS [M + H]+ | HPLC Method, RT (min.) | 1H NMR (δ NMR) |
|---|---|---|---|---|---|
| 383 | 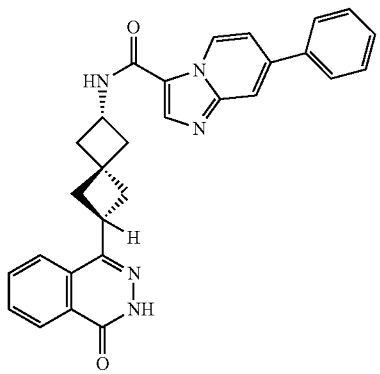 | N-((aR)-6-(4-oxo-3,4-dihydrophthalazin-1-yl)spiro[3.3]heptan-2-yl)-7-phenylimidazo[1,2-a]pyridine-3-carboxamide | 476.0 | E: 1.54<br>F: 1.91 | (500 MHz, DMSO-d6) δ 12.48 (s, 1H), 9.52 (d, J = 7.3 Hz, 1H), 8.71 (d, J = 7.3 Hz, 1H), 8.46 (s, 1H), 8.26 (d, J = 7.6 Hz, 1H), 8.06 (s, 1H), 7.97-7.79 (m, 5H), 7.61 (d, J = 7.0 Hz, 1H), 7.57-7.50 (m, 2H), 7.50-7.44 (m, 1H), 4.41 (sxt, J = 8.0 Hz, 1H), 3.91 (quin, J = 8.4 Hz, 1H), 2.71-2.63 (m, 1H), 2.59 (t, J = 7.9 Hz, 1H), 2.46-2.34 (m, 3H), 2.33-2.21 (m, 2H), 2.09 (t, J = 9.9 Hz, 1H) |
| 384 | 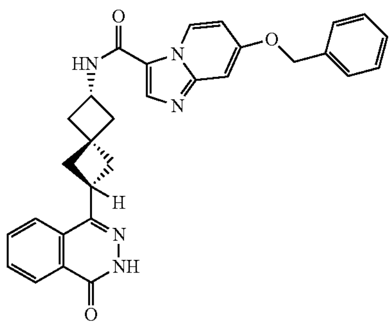 | 7-(benzyloxy)-N-((aR)-6-(4-oxo-3,4-dihydrophthalazin-1-yl)spiro[3.3]heptan-2-yl)imidazo[1,2-a]pyridine-3-carboxamide | 506.1 | E: 1.62<br>F: 1.94 | (500 MHz, DMSO-d6) δ 12.48 (s, 1H), 9.26 (d, J = 7.6 Hz, 1H), 8.48 (d, J = 7.3 Hz, 1H), 8.25 (d, J = 7.6 Hz, 1H), 8.19 (s, 1H), 7.95-7.80 (m, 3H), 7.52-7.45 (m, 2H), 7.41 (t, J = 7.5 Hz, 2H), 7.37-7.32 (m, 1H), 7.14 (d, J = 1.8 Hz, 1H), 6.87 (dd, J = 7.6, 2.1 Hz, 1H), 5.20 (s, 2H), 4.35 (sxt, J = 7.9 Hz, 1H), 3.89 (quin, J = 8.5 Hz, 1H), 2.63 (t, J = 11.4 Hz, 1H), 2.57 (br. s., 1H), 2.43-2.32 (m, 3H), 2.28-2.18 (m, 2H), 2.09-2.01 (m, 1H) |
| 385 | 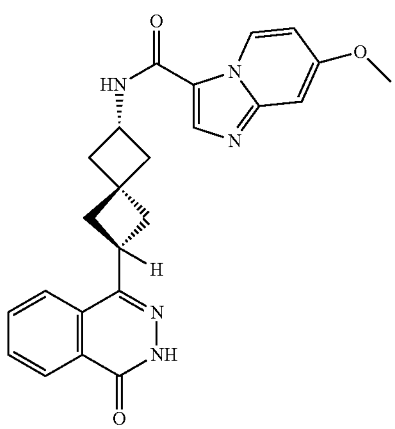 | 7-methoxy-N-((aR)-6-(4-oxo-3,4-dihydrophthalazin-1-yl)spiro[3.3]heptan-2-yl)imidazo[1,2-a]pyridine-3-carboxamide | 430.0 | E: 1.32<br>F: 1.58 | (500 MHz, DMSO-d6) δ 12.48 (s, 1H), 9.39 (d, J = 7.9 Hz, 1H), 8.80 (d, J = 7.3 Hz, 1H), 8.44 (s, 1H), 8.25 (d, J = 7.6 Hz, 1H), 7.97-7.79 (m, 3H), 7.25 (d, J = 2.1 Hz, 1H), 7.09 (dd, J = 7.8, 2.3 Hz, 1H), 4.44-4.30 (m, 1H), 3.95 (s, 3H), 3.93-3.85 (m, 1H), 2.65 (d, J = 11.6 Hz, 1H), 2.61-2.55 (m, 1H), 2.45-2.34 (m, 3H), 2.31-2.19 (m, 2H), 2.06 (t, J = 9.9 Hz, 1H) |
| 386 | 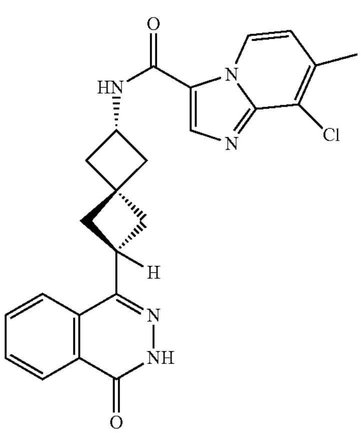 | 8-chloro-7-methyl-N-((aR)-6-(4-oxo-3,4-dihydrophthalazin-1-yl)spiro[3.3]heptan-2-yl)imidazo[1,2-a]pyridine-3-carboxamide | 448.2 | E: 1.44<br>F: 1.77 | (500 MHz, DMSO-d6) δ 12.47 (s, 1H), 9.56 (s, 1H), 8.71 (d, J = 7.3 Hz, 1H), 8.40 (s, 1H), 8.25 (d, J = 7.6 Hz, 1H), 7.96-7.89 (m, 1H), 7.89-7.80 (m, 2H), 7.77 (s, 1H), 4.37 (sxt, J = 8.0 Hz, 1H), 3.90 (quin, J = 8.4 Hz, 1H), 2.70-2.62 (m, 1H), 2.57 (d, J = 11.0 Hz, 1H), 2.44 (s, 3H), 2.42-2.34 (m, 3H), 2.30-2.21 (m, 2H), 2.07 (t, J = 10.1 Hz, 1H) |

TABLE 22-continued

| Ex. | Structure | Name | LCMS [M + H]+ | HPLC Method, RT (min.) | ¹H NMR (δ NMR) |
|---|---|---|---|---|---|
| 387 | 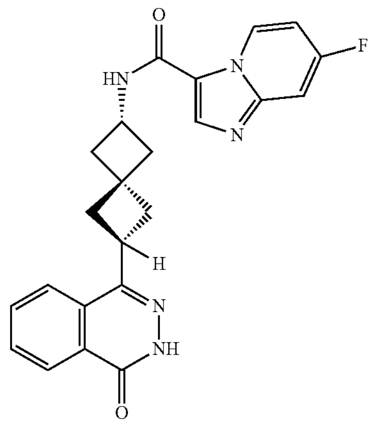 | 7-fluoro-N-((aR)-6-(4-oxo-3,4-dihydrophthalazin-1-yl)spiro[3.3]heptan-2-yl)imidazo[1,2-a]pyridine-3-carboxamide | 418.0 | E: 1.20<br>F: 1.83 | (500 MHz, DMSO-$d_6$) δ 12.47 (s, 1H), 9.47 (t, J = 6.9 Hz, 1H), 8.61 (d, J = 7.6 Hz, 1H), 8.33 (s, 1H), 8.25 (d, J = 7.6 Hz, 1H), 7.96-7.80 (m, 3H), 7.56 (dd, J = 9.6, 2.3 Hz, 1H), 7.20-7.10 (m, 1H), 4.37 (sxt, J = 8.0 Hz, 1H), 3.90 (quin, J = 8.4 Hz, 1H), 2.68-2.61 (m, 1H), 2.57 (d, J = 10.7 Hz, 1H), 2.44-2.33 (m, 3H), 2.29-2.20 (m, 2H), 2.11-2.02 (m, 1H) |
| 388 | 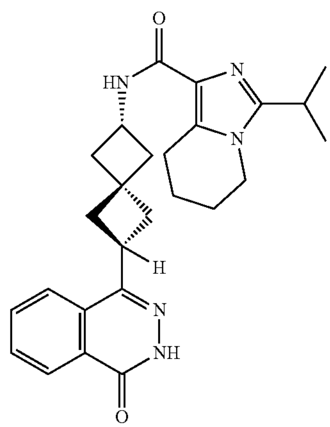 | 3-isopropyl-N-((aR)-6-(4-oxo-3,4-dihydrophthalazin-1-yl)spiro[3.3]heptan-2-yl)-5,6,7,8-tetrahydro-imidazo[1,5-a]pyridine-1-carboxamide | 446.0 | E: 1.27<br>F: 1.71 | (500 MHz, DMSO-$d_6$) δ 12.46 (s, 1H), 8.25 (d, J = 7.6 Hz, 1H), 7.94-7.88 (m, 1H), 7.88-7.79 (m, 2H), 7.54 (br. s., 1H), 4.36-4.20 (m, 1H), 3.94-3.81 (m, 3H), 3.07-2.96 (m, 1H), 2.92 (t, J = 6.3 Hz, 2H), 2.60-2.54 (m, 2H), 2.43-2.29 (m, 3H), 2.26-2.12 (m, 2H), 2.08-1.99 (m, 1H), 1.85 (d, J = 4.3 Hz, 2H), 1.70 (br. s., 2H), 1.22 (d, J = 6.7 Hz, 6H) |
| 389 | 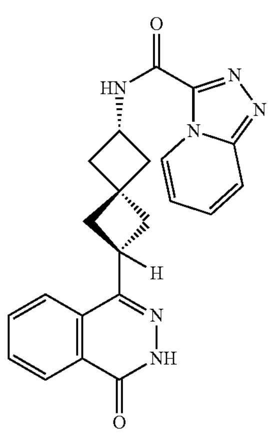 | N-((aR)-6-(4-oxo-3,4-dihydrophthalazin-1-yl)spiro[3.3]heptan-2-yl)-[1,2,4]triazolo[4,3-a]pyridine-3-carboxamide | 401.2 | E: 1.33<br>F: 1.37 | (500 MHz, DMSO-$d_6$) δ 12.47 (s, 1H), 9.37 (d, J = 7.6 Hz, 1H), 9.19 (d, J = 6.7 Hz, 1H), 8.25 (d, J = 7.9 Hz, 1H), 7.97-7.80 (m, 4H), 7.59-7.52 (m, 1H), 7.19 (t, J = 6.9 Hz, 1H), 4.49-4.35 (m, 1H), 3.90 (quin, J = 8.4 Hz, 1H), 2.66-2.56 (m, 2H), 2.45-2.32 (m, 4H), 2.22 (d, J = 8.2 Hz, 2H) |

TABLE 22-continued

| Ex. | Structure | Name | LCMS [M + H]+ | HPLC Method, RT (min.) | 1H NMR (δ NMR) |
|---|---|---|---|---|---|
| 390 | 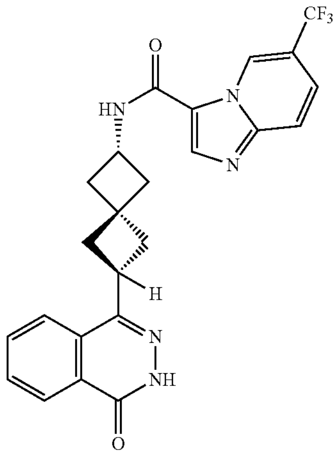 | N-((aR)-6-(4-oxo-3,4-dihydrophthalazin-1-yl)spiro[3.3]heptan-2-yl)-6-(trifluoromethyl)imidazo[1,2-a]pyridine-3-carboxamide | 468.0 | E: 1.54 F: 1.78 | (500 MHz, DMSO-d$_6$) δ 12.47 (s, 1H), 9.92 (br s, 1H), 8.81 (d, J = 7.3 Hz, 1H), 8.50 (s, 1H), 8.25 (d, J = 7.6 Hz, 1H), 7.97-7.79 (m, 4H), 7.71 (d, J = 9.5 Hz, 1H), 4.39 (sxt, J = 7.8 Hz, 1H), 3.91 (quin, J = 8.3 Hz, 1H), 2.66 (br. s., 1H), 2.58 (br. s., 1H), 2.45-2.33 (m, 3H), 2.32-2.21 (m, 2H), 2.09 (t, J = 10.1 Hz, 1H) |

The Examples in Table 23 were prepared by using the similar procedure to that described in Example 1. Intermediate 2 was coupled with the appropriate acid intermediates. Various coupling reagents could be used other than the one described in Example 1 such as BOP, PyBop, EDC/HOBt or HATU.

TABLE 23

| Ex. | Structure | Name | LCMS [M + H]+ | HPLC Method, RT (min.) | 1H NMR (δ NMR) |
|---|---|---|---|---|---|
| 391 | 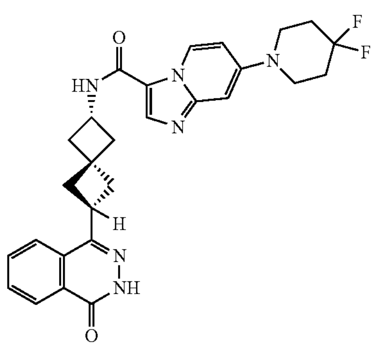 | 7-(4,4-difluoropiperidin-1-yl)-N-((aR)-6-(4-oxo-3,4-dihydrophthalazin-1-yl)spiro[3.3]heptan-2-yl)imidazo[1,2-a]pyridine-3 carboxamide | 519.2 | A: 5.23 B: 7.75 | (400 MHz, CD$_3$OD) δ 9.33 (d, J = 8.1 Hz, 1H), 8.37 (d, J = 7.9 Hz, 1H), 8.26 (s, 1H), 7.99-7.80 (m, 3H), 7.34 (dd, J = 8.0, 2.5 Hz, 1H), 6.98 (d, J = 2.6 Hz, 1H), 4.45 (quin, J = 8.2 Hz, 1H), 3.96 (quin, J = 8.4 Hz, 1H), 3.83-3.71 (m, 4H), 2.81-2.71 (m, 1H), 2.70-2.61 (m, 1H), 2.61-2.52 (m, 1H), 2.52-2.35 (m, 3H), 2.32-2.23 (m, 1H), 2.21-2.06 (m, 5H) |
| 392 | 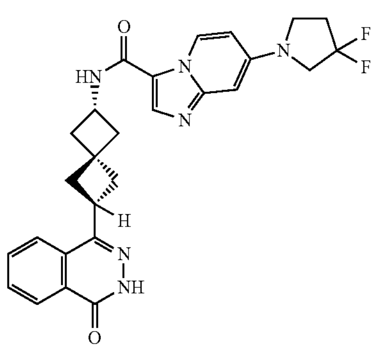 | 7-(3,3-difluoropyrrolidin-1-yl)-N-((aR)-6-(4-oxo-3,4-dihydrophthalazin-1-yl)spiro[3.3]heptan-2-yl)imidazo[1,2-a]pyridine-3 carboxamide | 505.1 | E: 1.38 F: 1.62 | (500 MHz, DMSO-d$_6$) δ 12.47 (s, 1H), 9.29 (d, J = 8.0 Hz, 1H), 8.87 (d, J = 7.4 Hz, 1H), 8.44 (s, 1H), 8.25 (d, J = 8.0 Hz, 1H), 7.95-7.89 (m, 1H), 7.88-7.80 (m, 2H), 7.08-7.03 (m, 1H), 6.66 (s, 1H), 4.43-4.27 (m, 1H), 3.97 (t, J = 12.9 Hz, 2H), 3.90 (t, J = 8.3 Hz, 1H), 3.71 (t, J = 7.2 Hz, 2H), 2.71-2.57 (m, 4H), 2.45-2.35 (m, 3H), 2.31-2.18 (m, 2H), 2.06 (t, J = 10.2 Hz, 1H) |

TABLE 23-continued

| Ex. | Structure | Name | LCMS [M + H]+ | HPLC Method, RT (min.) | ¹H NMR (δ NMR) |
|---|---|---|---|---|---|
| 393 | 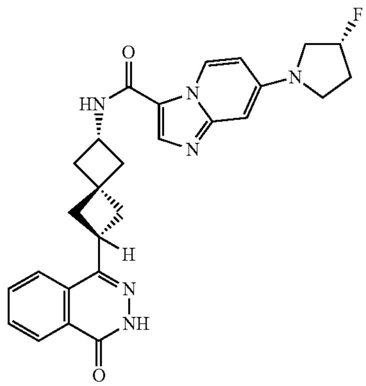 | 7-((R)-3-fluoropyrrolidin-1-yl)-N-((aR)-6-(4-oxo-3,4-dihydrophthalazin-1-yl)spiro[3.3]heptan-2-yl)imidazo[1,2-a]pyridine-3-carboxamide | 487.1 | E: 1.33 F: 1.50 | (500 MHz, DMSO-$d_6$) δ 12.47 (s, 1H), 9.19 (d, J = 7.4 Hz, 1H), 8.34 (d, J = 7.4 Hz, 1H), 8.25 (d, J = 7.7 Hz, 1H), 8.13 (s, 1H), 7.95-7.90 (m, 1H), 7.89-7.81 (m, 2H), 6.75 (d, J = 8.3 Hz, 1H), 6.44 (s, 1H), 5.58-5.38 (m, 1H), 4.41-4.28 (m, 1H), 3.93-3.86 (m, 1H), 3.65 (br. s., 1H), 3.61-3.51 (m, 2H), 3.44 (d, J = 8.5 Hz, 1H), 2.69-2.56 (m, 2H), 2.44-2.35 (m, 3H), 2.31-2.17 (m, 4H), 2.08-1.98 (m, 1H) |
| 394 | 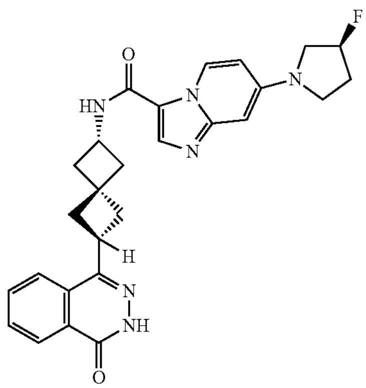 | 7-((S)-3-fluoropyrrolidin-1-yl)-N-((aR)-6-(4-oxo-3,4-dihydrophthalazin-1-yl)spiro[3.3]heptan-2-yl)imidazo[1,2-a]pyridine-3-carboxamide | 487.1 | E: 1.33 F: 1.51 | (500 MHz, DMSO-$d_6$) δ 12.47 (s, 1H), 9.18 (d, J = 7.4 Hz, 1H), 8.26 (t, J = 8.9 Hz, 2H), 8.10 (s, 1H), 7.96-7.89 (m, 1H), 7.89-7.81 (m, 2H), 6.71 (d, J = 8.0 Hz, 1H), 6.42 (s, 1H), 5.60-5.37 (m, 1H), 4.36 (q, J = 8.0 Hz, 1H), 3.90 (t, J = 7.7 Hz, 1H), 3.69-3.60 (m, 1H), 3.58-3.50 (m, 2H), 3.48-3.40 (m, 1H), 2.68-2.56 (m, 2H), 2.46-2.34 (m, 3H), 2.31-2.14 (m, 4H), 2.08-1.99 (m, 1H) |
| 395 | 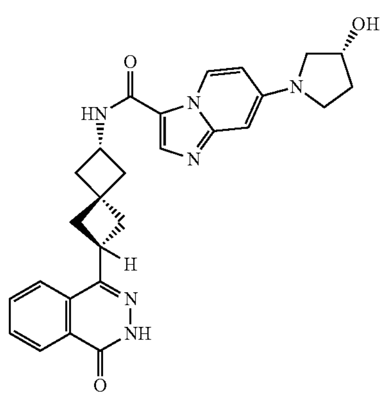 | 7-((R)-3-hydroxypyrrolidin-1-yl)-N-((aR)-6-(4-oxo-3,4-dihydrophthalazin-1-yl)spiro[3.3]heptan-2-yl)imidazo[1,2-a]pyridine-3-carboxamide | 485.1 | E: 1.20 F: 1.34 | (500 MHz, DMSO-$d_6$) δ 12.47 (s, 1H), 9.15 (d, J = 7.6 Hz, 1H), 8.30 (d, J = 7.3 Hz, 1H), 8.25 (d, J = 7.9 Hz, 1H), 8.10 (s, 1H), 7.96-7.89 (m, 1H), 7.89-7.80 (m, 2H), 6.69 (d, J = 7.3 Hz, 1H), 6.34 (s, 1H), 4.42 (br. s., 1H), 4.39-4.28 (m, 1H), 3.90 (quin, J = 8.4 Hz, 1H), 3.55-3.32 (m, 3H), 3.20 (d, J = 10.4 Hz, 1H), 2.69-2.56 (m, 2H), 2.44-2.30 (m, 3H), 2.28-2.15 (m, 2H), 2.11-1.98 (m, 2H), 1.92 (d, J = 11.6 Hz, 1H) |
| 396 | 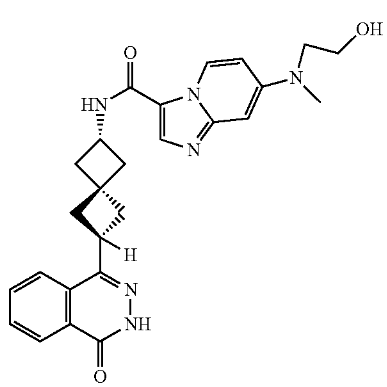 | 7-((2-hydroxy-ethyl)(methyl)amino)-N-((aR)-6-(4-oxo-3,4-dihydrophthalazin-1-yl)spiro[3.3]heptan-2-yl)imidazo[1,2-a]pyridine-3-carboxamide | 473.1 | E: 1.19 F: 1.32 | (500 MHz, DMSO-$d_6$) δ 12.47 (s, 1H), 9.15 (d, J = 7.9 Hz, 1H), 8.60 (d, J = 7.0 Hz, 1H), 8.33-8.19 (m, 2H), 7.99-7.73 (m, 3H), 7.05 (d, J = 7.6 Hz, 1H), 6.60 (br. s., 1H), 4.45-4.24 (m, 1H), 3.99-3.82 (m, 1H), 3.60 (br. s., 2H), 3.56 (d, J = 4.9 Hz, 2H), 3.07 (s, 3H), 2.64 (br. s., 1H), 2.57 (br. s., 1H), 2.45-2.32 (m, 3H), 2.30-2.18 (m, 2H), 2.09-1.99 (m, 1H) |

TABLE 23-continued

| Ex. | Structure | Name | LCMS [M + H]+ | HPLC Method, RT (min.) | ¹H NMR (δ NMR) |
|---|---|---|---|---|---|
| 397 | 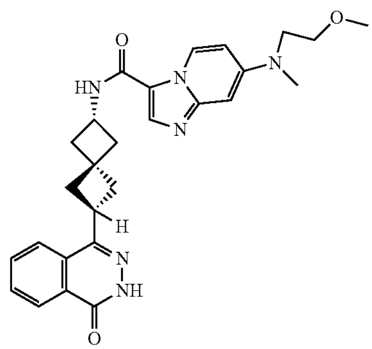 | 7-((2-methoxy-ethyl)(methyl)amino)-N-((aR)-6-(4-oxo-3,4-dihydrophthalazin-1-yl)spiro[3.3]heptan-2-yl)imidazo[1,2-a]pyridine-3-carboxamide | 487.1 | E: 1.32 F: 1.47 | (500 MHz, DMSO-$d_6$) δ 12.47 (s, 1H), 9.20 (d, J = 8.2 Hz, 1H), 8.86 (d, J = 7.0 Hz, 1H), 8.40 (s, 1H), 8.26 (d, J = 7.9 Hz, 1H), 7.97-7.77 (m, 3H), 7.21 (d, J = 7.6 Hz, 1H), 6.71 (br. s., 1H), 4.43-4.26 (m, 1H), 3.91 (t, J = 8.2 Hz, 1H), 3.72 (br. s., 2H), 3.55 (br. s., 2H), 3.25 (s, 3H), 3.11 (s, 3H), 2.66 (br. s., 1H), 2.58 (br. s., 1H), 2.45-2.33 (m, 3H), 2.31-2.18 (m, 2H), 2.05 (t, J = 9.9 Hz, 1H) |
| 398 | 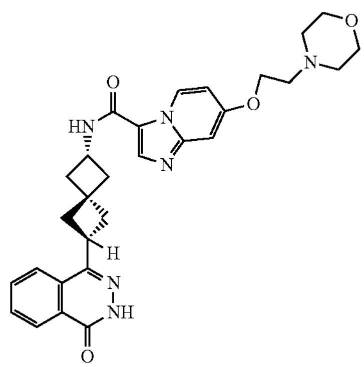 | 7-(2-morpholinoethoxy)-N-((aR)-6-(4-oxo-3,4-dihydrophthalazin-1-yl)spiro[3.3]heptan-2-yl)imidazo[1,2-a]pyridine-3-carboxamide | 529.0 | E: 1.09 F: 1.42 | (500 MHz, DMSO-$d_6$) δ 12.47 (s, 1H), 9.27 (d, J = 7.7 Hz, 1H), 8.45 (d, J = 7.4 Hz, 1H), 8.26 (d, J = 7.7 Hz, 1H), 8.21 (s, 1H), 7.95-7.79 (m, 3H), 7.10 (br. s., 1H), 6.81 (d, J = 8.3 Hz, 1H), 4.41-4.32 (m, 1H), 4.24 (br. s., 2H), 3.90 (t, J = 8.4 Hz, 1H), 3.62 (br. s., 4H), 3.01-2.54 (m, 8H), 2.43-2.35 (m, 3H), 2.29-2.18 (m, 2H), 2.06 (t, J = 10.0 Hz, 1H) |
| 399 | 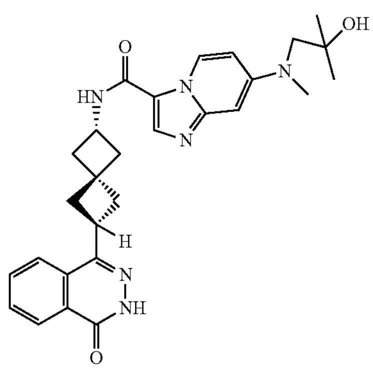 | 7-((2-hydroxy-2-methyl-propyl)(methyl)amino)-N-((aR)-6-(4-oxo-3,4-dihydrophthalazin-1-yl)spiro[3.3]heptan-2-yl)imidazo[1,2-a]pyridine-3-carboxamide | 501.1 | A: 4.44 B: 6.46 | (400 MHz, CD$_3$OD) δ 9.22 (d, J = 7.9 Hz, 1H), 8.44-8.31 (m, 1H), 8.20 (s, 1H), 7.97-7.76 (m, 3H), 7.26 (dd, J = 7.8, 2.3 Hz, 1H), 6.75 (br. s., 1H), 4.44 (quin, J = 8.2 Hz, 1H), 3.95 (quin, J = 8.4 Hz, 1H), 3.60 (s, 2H), 3.25 (s, 3H), 2.80-2.69 (m, 1H), 2.69-2.61 (m, 1H), 2.60-2.51 (m, 1H), 2.51-2.34 (m, 3H), 2.27 (dd, J = 10.8, 9.0 Hz, 1H), 2.10 (dd, J = 11.2, 9.0 Hz, 1H), 1.27 (s, 6H) |
| 400 | 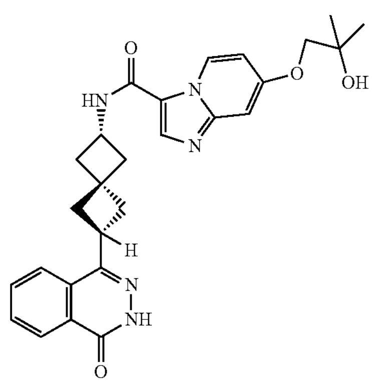 | 7-(2-hydroxy-2-methylpropoxy)-N-((aR)-6-(4-oxo-3,4-dihydrophthalazin-1-yl)spiro[3.3]heptan-2-yl)imidazo[1,2-a]pyridine-3-carboxamide | 488.1 | A: 4.29 B: 6.22 | (400 MHz, CD$_3$OD) δ 9.54 (d, J = 7.7 Hz, 1H), 8.41 (s, 1H), 8.37 (d, J = 7.7 Hz, 1H), 7.97-7.80 (m, 3H), 7.30 (d, J = 2.2 Hz, 1H), 7.27 (dd, J = 7.7, 2.6 Hz, 1H), 4.47 (quin, J = 8.2 Hz, 1H), 4.05 (s, 2H), 3.96 (quin, J = 8.4 Hz, 1H), 2.82-2.71 (m, 1H), 2.70-2.61 (m, 1H), 2.61-2.52 (m, 1H), 2.52-2.37 (m, 3H), 2.29 (dd, J = 10.8, 9.0 Hz, 1H), 2.12 (dd, J = 11.2, 9.0 Hz, 1H), 1.36 (s, 6H) |

TABLE 23-continued

| Ex. | Structure | Name | LCMS [M + H]⁺ | HPLC Method, RT (min.) | ¹H NMR (δ NMR) |
|---|---|---|---|---|---|
| 401 | 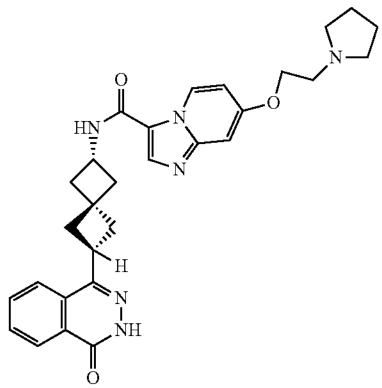 | N-((aR)-6-(4-oxo-3,4-dihydrophthalazin-1-yl)spiro[3.3]heptan-2-yl)-7-(2-(pyrrolidin-1-yl)ethoxy)imidazo[1,2-a]pyridine-3-carboxamide | 513.1 | E: 1.11 F: 1.26 | (500 MHz, DMSO-d₆) δ 12.47 (s, 1H), 9.26 (d, J = 7.6 Hz, 1H), 8.44 (d, J = 7.6 Hz, 1H), 8.25 (d, J = 7.9 Hz, 1H), 8.21 (s, 1H), 7.96-7.79 (m, 3H), 7.08 (br. s., 1H), 6.81 (d, J = 7.6 Hz, 1H), 4.43-4.31 (m, 1H), 4.20 (br. s., 2H), 3.91 (t, J = 8.2 Hz, 1H), 3.34 (br. s., 4H), 2.91 (br. s., 2H), 2.70-2.54 (m, 2H), 2.45-2.32 (m, 3H), 2.29-2.18 (m, 2H), 2.06 (t, J = 9.8 Hz, 1H), 1.71 (br. s., 4H) |
| 402 | 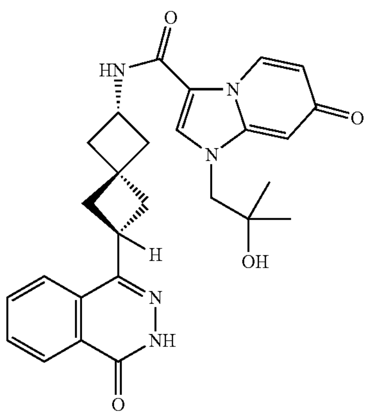 | 1-(2-hydroxy-2-methylpropyl)-7-oxo-N-((aR)-6-(4-oxo-3,4-dihydrophthalazin-1-yl)spiro[3.3]heptan-2-yl)-1,7-dihydroimidazo[1,2-a]pyridine-3-carboxamide | 488.1 | A: 4.39 B: 6.30 | (400 MHz, DMSO-d₆) δ 12.47 (s, 1H), 9.51 (d, J = 7.7 Hz, 1H), 9.06 (d, J = 7.3 Hz, 1H), 8.58 (s, 1H), 8.26 (dd, J = 7.8, 0.8 Hz, 1H), 7.97-7.79 (m, 3H), 7.43 (d, J = 2.2 Hz, 1H), 7.18 (dd, J = 7.6, 2.3 Hz, 1H), 4.44-4.31 (m, 1H), 4.22 (s, 2H), 3.91 (quin, J = 8.5 Hz, 1H), 2.72-2.63 (m, 1H), 2.59 (ddd, J = 10.9, 8.1, 2.8 Hz, 1H), 2.45-2.37 (m, 3H), 2.33-2.20 (m, 2H), 2.11-2.03 (m, 1H), 1.21-1.14 (m, 6H) |
| 403 | 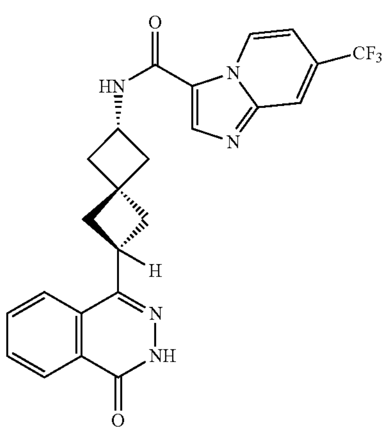 | N-((aR)-6-(4-oxo-3,4-dihydrophthalazin-1-yl)spiro[3.3]heptan-2-yl)-7-(trifluoromethyl)imidazo[1,2-a]pyridine-3-carboxamide | 468.0 | E: 1.53 F: 1.77 | (500 MHz, DMSO-d₆) δ 12.48 (s, 1H), 9.61 (d, J = 7.3 Hz, 1H), 8.78 (d, J = 7.3 Hz, 1H), 8.51 (s, 1H), 8.25 (d, J = 7.9 Hz, 1H), 8.19 (s, 1H), 7.95-7.79 (m, 3H), 7.38 (d, J = 5.8 Hz, 1H), 4.46-4.34 (m, 1H), 3.91 (quin, J = 8.4 Hz, 1H), 2.71-2.62 (m, 1H), 2.62-2.55 (m, 1H), 2.45-2.33 (m, 3H), 2.31-2.21 (m, 2H), 2.13-2.04 (m, 1H) |

TABLE 23-continued

| Ex. | Structure | Name | LCMS [M + H]+ | HPLC Method, RT (min.) | ¹H NMR (δ NMR) |
|---|---|---|---|---|---|
| 404 | 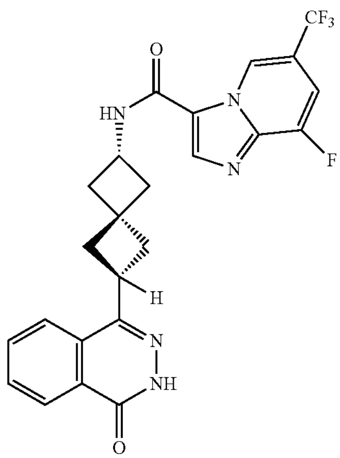 | 8-fluoro-N-((aR)-6-(4-oxo-3,4-dihydrophthalazin-1-yl)spiro[3.3]heptan-2-yl)-6-(trifluoromethyl)imidazo[1,2-a]pyridine-3-carboxamide | 486.0 | E: 1.80<br>F: 1.87 | (500 MHz, DMSO-$d_6$) δ 12.47 (s, 1H), 9.75 (s, 1H), 8.90 (d, J = 7.0 Hz, 1H), 8.50 (s, 1H), 8.25 (d, J = 7.6 Hz, 1H), 7.95-7.79 (m, 4H), 4.39 (sxt, J = 8.0 Hz, 1H), 3.91 (quin, J = 8.5 Hz, 1H), 2.71-2.62 (m, 1H), 2.62-2.56 (m, 1H), 2.46-2.34 (m, 3H), 2.32-2.21 (m, 2H), 2.13-2.06 (m, 1H) |
| 405 | 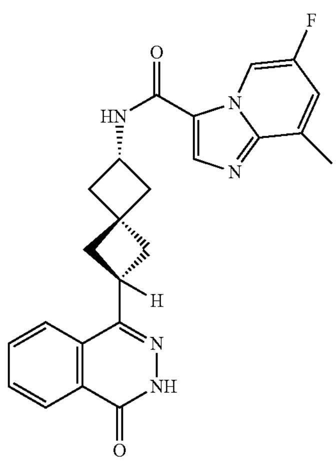 | 6-fluoro-8-methyl-N-((aR)-6-(4-oxo-3,4-dihydrophthalazin-1-yl)spiro[3.3]heptan-2-yl)imidazo[1,2-a]pyridine-3-carboxamide | 432.0 | E: 1.32<br>F: 1.67 | (500 MHz, DMSO-$d_6$) δ 12.47 (s, 1H), 9.33 (br s, 1H), 8.65 (d, J = 7.3 Hz, 1H), 8.38 (s, 1H), 8.25 (d, J = 7.6 Hz, 1H), 7.97-7.77 (m, 3H), 7.42 (d, J = 8.5 Hz, 1H), 4.46-4.30 (m, 1H), 3.98-3.83 (m, 1H), 2.65 (br. s., 1H), 2.61-2.57 (m, 1H), 2.55 (s, 3H), 2.45-2.34 (m, 3H), 2.30-2.20 (m, 2H), 2.12-2.04 (m, 1H) |
| 406 | 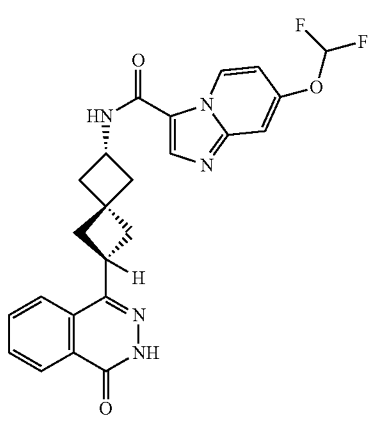 | 7-(difluoromethoxy)-N-((aR)-6-(4-oxo-3,4-dihydrophthalazin-1-yl)spiro[3.3]heptan-2-yl)imidazo[1,2-a]pyridine-3-carboxamide | 466.0 | E: 1.33<br>F: 1.63 | (500 MHz, DMSO-$d_6$) δ 12.47 (s, 1H), 9.44 (d, J = 7.6 Hz, 1H), 8.59 (d, J = 7.3 Hz, 1H), 8.33 (s, 1H), 8.25 (d, J = 7.6 Hz, 1H), 7.96-7.79 (m, 3H), 7.43 (s, 1H), 7.47 (t, J = 73.5 Hz, 1H), 7.03 (dd, J = 7.6, 2.4 Hz, 1H), 4.38 (sxt, J = 8.1 Hz, 1H), 3.91 (quin, J = 8.4 Hz, 1H), 2.69-2.61 (m, 1H), 2.61-2.55 (m, 1H), 2.45-2.33 (m, 3H), 2.30-2.19 (m, 2H), 2.12-2.02 (m, 1H) |

TABLE 23-continued

| Ex. | Structure | Name | LCMS [M + H]+ | HPLC Method, RT (min.) | 1H NMR (δ NMR) |
|---|---|---|---|---|---|
| 407 | 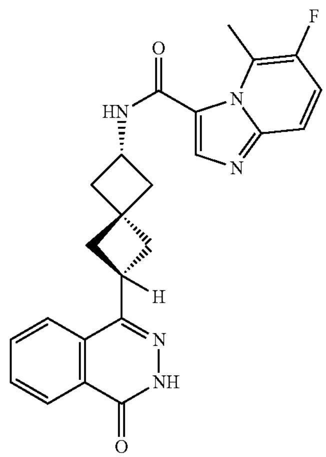 | 6-fluoro-5-methyl-N-((aR)-6-(4-oxo-3,4-dihydrophthalazin-1-yl)spiro[3.3]heptan-2-yl)imidazo[1,2-a]pyridine-3-carboxamide | 432.0 | E: 1.23 F: 1.50 | (500 MHz, DMSO-d6) δ 12.47 (s, 1H), 8.93 (d, J = 7.3 Hz, 1H), 8.25 (d, J = 7.6 Hz, 1H), 7.93 (s, 1H), 7.91 (d, J = 7.6 Hz, 1H), 7.89-7.79 (m, 2H), 7.63 (dd, J = 9.6, 5.0 Hz, 1H), 7.51 (t, J = 9.2 Hz, 1H), 4.38-4.22 (m, 1H), 3.90 (quin, J = 8.4 Hz, 1H), 2.70-2.61 (m, 1H), 2.60-2.55 (m, 1H), 2.54 (s, 3H), 2.44-2.33 (m, 3H), 2.31-2.20 (m, 2H), 2.09-2.01 (m, 1H) |
| 408 | 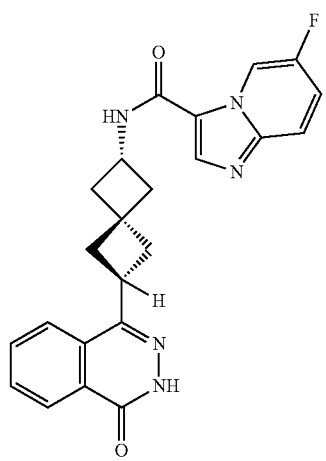 | 6-fluoro-N-((aR)-6-(4-oxo-3,4-dihydrophthalazin-1-yl)spiro[3.3]heptan-2-yl)imidazo[1,2-a]pyridine-3-carboxamide | 418.0 | E: 1.27 F: 1.54 | (500 MHz, DMSO-d6) δ 12.47 (s, 1H), 9.47 (dd, J = 4.9, 2.4 Hz, 1H), 8.66 (d, J = 7.3 Hz, 1H), 8.40 (s, 1H), 8.25 (d, J = 7.6 Hz, 1H), 7.96-7.81 (m, 3H), 7.78 (dd, J = 9.9, 5.3 Hz, 1H), 7.60-7.51 (m, 1H), 4.39 (sxt, J = 8.1 Hz, 1H), 3.91 (quin, J = 8.5 Hz, 1H), 2.69-2.62 (m, 1H), 2.61-2.55 (m, 1H), 2.46-2.33 (m, 3H), 2.31-2.20 (m, 2H), 2.13-2.03 (m, 1H) |
| 409 | 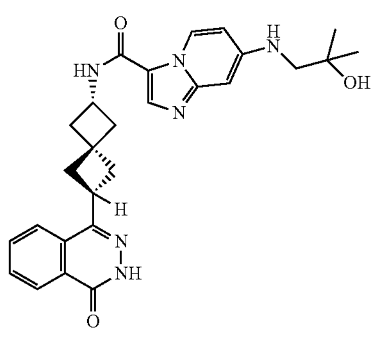 | 7-((2-hydroxy-2-methylpropyl)amino)-N-((aR)-6-(4-oxo-3,4-dihydrophthalazin-1-yl)spiro[3.3]heptan-2-yl)imidazo[1,2-a]pyridine-3-carboxamide, | 487.1 | E: 1.26 F: 1.37 | (500 MHz, DMSO-d6) δ 12.47 (s, 1H), 9.10 (d, J = 7.9 Hz, 1H), 8.83 (d, J = 7.3 Hz, 1H), 8.34 (s, 1H), 8.25 (d, J = 7.6 Hz, 1H), 7.97-7.89 (m, 1H), 7.88-7.79 (m, 2H), 7.65 (t, J = 5.5 Hz, 1H), 7.10-7.03 (m, 1H), 6.66 (br. s., 1H), 4.33 (sxt, J = 8.0 Hz, 1H), 3.97-3.82 (m, 1H), 3.11 (d, J = 5.2 Hz, 2H), 2.69-2.62 (m, 1H), 2.60-2.55 (m, 1H), 2.44-2.33 (m, 3H), 2.30-2.18 (m, 2H), 2.08-2.00 (m, 1H), 1.18 (s, 6H) |

TABLE 23-continued

| Ex. | Structure | Name | LCMS [M + H]+ | HPLC Method, RT (min.) | 1H NMR (δ NMR) |
|---|---|---|---|---|---|
| 410 | 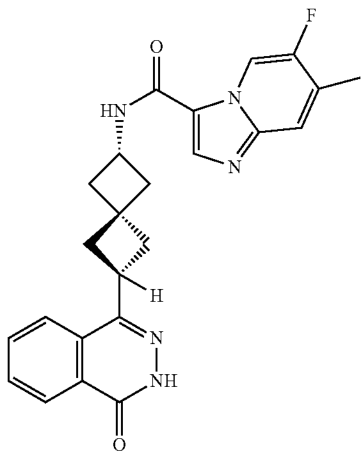 | 6-fluoro-7-methyl-N-((aR)-6-(4-oxo-3,4-dihydrophthalazin-1-yl)spiro[3.3]heptan-2-yl)imidazo[1,2-a]pyridine-3-carboxamide | 432.0 | E: 1.38 F: 1.67 | (500 MHz, DMSO-$d_6$) δ 12.47 (s, 1H), 9.40 (d, J = 5.8 Hz, 1H), 8.59 (d, J = 7.3 Hz, 1H), 8.33 (s, 1H), 8.25 (d, J = 7.9 Hz, 1H), 7.95-7.89 (m, 1H), 7.89-7.79 (m, 2H), 7.65 (d, J = 7.0 Hz, 1H), 4.38 (sxt, J = 8.1 Hz, 1H), 3.90 (quin, J = 8.5 Hz, 1H), 2.68-2.61 (m, 1H), 2.61-2.54 (m, 1H), 2.36 (s, 3H), 2.45-2.32 (m, 3H), 2.30-2.20 (m, 2H), 2.07 (t, J = 10.1 Hz, 1H) |
| 411 | 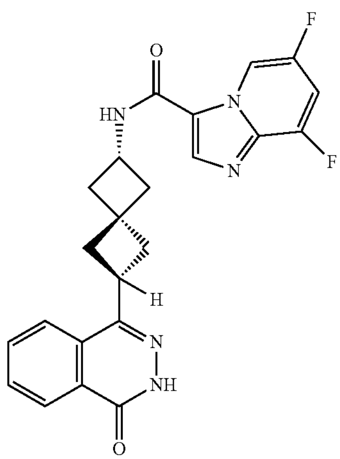 | 6,8-difluoro-N-((aR)-6-(4-oxo-3,4-dihydrophthalazin-1-yl)spiro[3.3]heptan-2-yl)imidazo[1,2-a]pyridine-3-carboxamide | 436.0 | E: 1.58 F: 1.64 | (500 MHz, DMSO-$d_6$) δ 12.47 (s, 1H), 9.36 (d, J = 3.1 Hz, 1H), 8.77 (d, J = 7.3 Hz, 1H), 8.42 (s, 1H), 8.25 (d, J = 7.9 Hz, 1H), 7.96-7.89 (m, 1H), 7.89-7.80 (m, 2H), 7.79-7.71 (m, J = 9.0, 9.0 Hz, 1H), 4.38 (sxt, J = 7.9 Hz, 1H), 3.91 (quin, J = 8.5 Hz, 1H), 2.70-2.62 (m, 1H), 2.62-2.56 (m, 1H), 2.45-2.33 (m, 3H), 2.31-2.21 (m, 2H), 2.12-2.03 (m, 1H) |
| 412 | 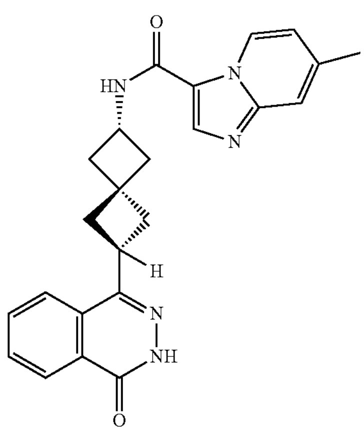 | 7-methyl-N-((aR)-6-(4-oxo-3,4-dihydrophthalazin-1-yl)spiro[3.3]heptan-2-yl)imidazo[1,2-a]pyridine-3-carboxamide | 414.0 | E: 1.32 F: 1.58 | (500 MHz, DMSO-$d_6$) δ 12.47 (s, 1H), 9.31 (d, J = 7.0 Hz, 1H), 8.50 (d, J = 7.3 Hz, 1H), 8.27 (s, 1H), 8.25 (d, J = 7.6 Hz, 1H), 7.96-7.80 (m, 3H), 7.47 (s, 1H), 6.95 (d, J = 6.4 Hz, 1H), 4.38 (sxt, J = 8.1 Hz, 1H), 3.96-3.84 (m, 1H), 2.69-2.61 (m, 1H), 2.61-2.55 (m, 1H), 2.39 (s, 3H), 2.45-2.33 (m, 3H), 2.29-2.20 (m, 2H), 2.07 (t, J = 10.1 Hz, 1H) |

TABLE 23-continued

| Ex. | Structure | Name | LCMS [M + H]+ | HPLC Method, RT (min.) | 1H NMR (δ NMR) |
|---|---|---|---|---|---|
| 413 | 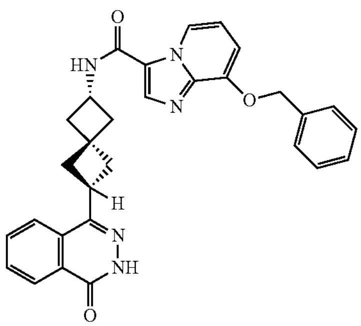 | 8-(benzyloxy)-N-((aR)-6-(4-oxo-3,4-dihydrophthalazin-1-yl)spiro[3.3]heptan-2-yl)imidazo[1,2-a]pyridine-3-carboxamide | 506.3 | E: 1.40 F: 1.78 | (500 MHz, DMSO-d6) δ 12.49 (s, 1H), 9.06 (d, J = 5.2 Hz, 1H), 8.60 (d, J = 7.5 Hz, 1H), 8.32-8.20 (m, 2H), 7.97-7.79 (m, 3H), 7.51 (d, J = 7.3 Hz, 2H), 7.46-7.39 (m, 2H), 7.39-7.32 (m, 1H), 7.06-6.92 (m, 2H), 5.30 (s, 2H), 4.45-4.30 (m, 1H), 3.97-3.84 (m, 1H), 2.64 (t, J = 11.4 Hz, 1H), 2.60-2.54 (m, 1H), 2.44-2.33 (m, 3H), 2.29-2.20 (m, 2H), 2.07 (t, J = 10.0 Hz, 1H) |
| 414 | 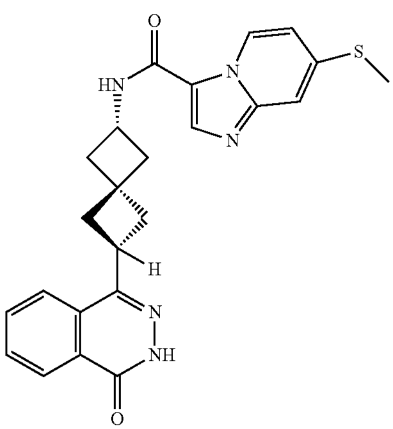 | 7-(methylthio)-N-((aR)-6-(4-oxo-3,4-dihydrophthalazin-1-yl)spiro[3.3]heptan-2-yl)imidazo[1,2-a]pyridine-3-carboxamide | 446.3 | E: 1.23 F: 1.49 | (500 MHz, DMSO-d6) δ 12.50 (s, 1H), 9.25 (d, J = 7.3 Hz, 1H), 8.57 (d, J = 7.1 Hz, 1H), 8.25 (br. s., 2H), 7.96-7.89 (m, 1H), 7.88-7.80 (m, 2H), 7.36 (s, 1H), 6.99 (d, J = 6.9 Hz, 1H), 4.42-4.31 (m, 1H), 3.96-3.81 (m, 1H), 2.63 (br. s., 1H), 2.60-2.57 (m, 1H), 2.56 (br. s., 3H), 2.43-2.34 (m, 3H), 2.24 (d, J = 7.9 Hz, 2H), 2.05 (t, J = 10.0 Hz, 1H) |
| 415 | 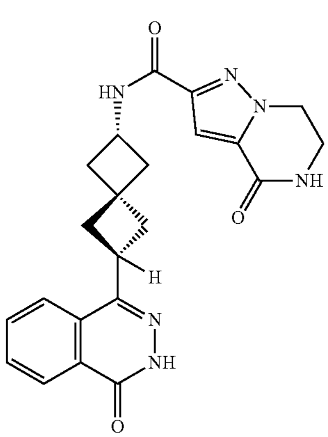 | 4-oxo-N-((aR)-6-(4-oxo-3,4-dihydrophthalazin-1-yl)spiro[3,3]heptan-2-yl)-4,5,6,7-tetrahydropyrazolo[1,5-a]pyrazine-2-carboxamide | 419.4 | E: 1.10 F: 1.11 | (500 MHz, DMSO-d6) δ 12.46 (s, 1H), 8.46 (d, J = 7.9 Hz, 1H), 8.33 (br. s., 1H), 8.25 (d, J = 7.9 Hz, 1H), 7.96-7.79 (m, 3H), 7.02 (s, 1H), 4.42-4.23 (m, 3H), 3.88 (quin, J = 8.5 Hz, 1H), 3.63 (br. s., 2H), 2.58-2.54 (m, 2H), 2.42-2.22 (m, 4H), 2.21-2.13 (m, 1H), 2.11-2.03 (m, 1H) |

TABLE 23-continued

| Ex. | Structure | Name | LCMS [M + H]+ | HPLC Method, RT (min.) | 1H NMR (δ NMR) |
|---|---|---|---|---|---|
| 416 | 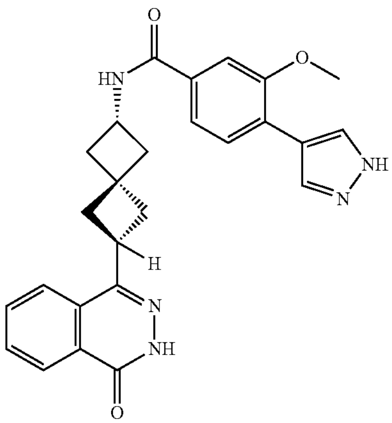 | 3-methoxy-N-((aR)-6-(4-oxo-3,4-dihydrophthalazin-1-yl)spiro[3.3]heptan-2-yl)-4-(1H-pyrazol-4-yl)benzamide | 455.9 | E: 1.37 F: 1.40 | (500 MHz, DMSO-d$_6$) δ 12.47 (s, 1H), 8.54 (d, J = 7.3 Hz, 1H), 8.25 (d, J = 7.9 Hz, 1H), 8.12 (s, 2H), 7.96-7.80 (m, 3H), 7.70 (d, J = 7.6 Hz, 1H), 7.54-7.43 (m, 2H), 4.43-4.31 (m, 1H), 3.93 (s, 3H), 3.92-3.86 (m, 1H), 2.67-2.55 (m, 2H), 2.45-2.35 (m, 3H), 2.30-2.20 (m, 2H), 2.09 (t, J = 10.1 Hz, 1H) |
| 417 | 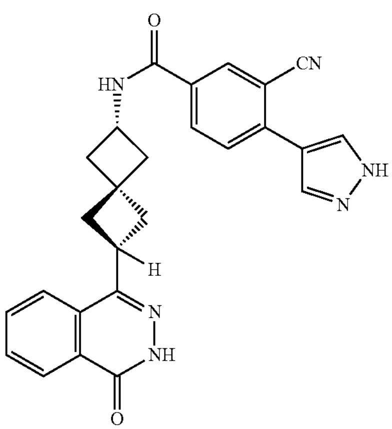 | 3-cyano-N-((aR)-6-(4-oxo-3,4-dihydrophthalazin-1-yl)spiro[3.3]heptan-2-yl)-4-(1H-pyrazol-4-yl)benzamide | 451.1 | E: 1.28 F: 1.31 | (500 MHz, DMSO-d$_6$) δ 12.49 (s, 1H), 8.79 (d, J = 7.2 Hz, 1H), 8.31 (s, 1H), 8.25 (d, J = 7.8 Hz, 1H), 8.12 (d, J = 7.7 Hz, 1H), 8.44-8.04 (br. s, 2H), 7.97-7.78 (m, 4H), 4.43-4.26 (m, 1H), 3.98-3.81 (m, 1H), 2.68-2.55 (m, 2H), 2.44-2.31 (m, 3H), 2.25 (t, J = 9.6 Hz, 2H), 2.07 (t, J = 10.0 Hz, 1H) |
| 418 | 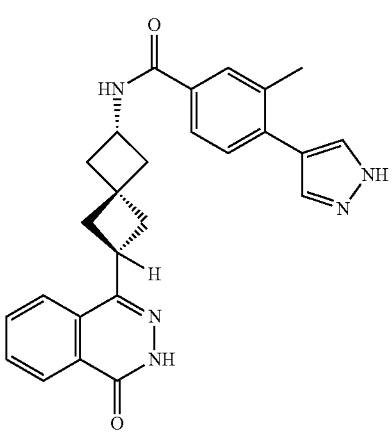 | 3-methyl-N-((aR)-6-(4-oxo-3,4-dihydrophthalazin-1-yl)spiro[3.3]heptan-2-yl)-4-(1H-pyrazol-4-yl)benzamide | 440.1 | E: 1.27 F: 1.31 | (500 MHz, DMSO-d$_6$) δ 12.49 (s, 1H), 8.54 (d, J = 7.2 Hz, 1H), 8.25 (d, J = 7.8 Hz, 1H), 8.05 (br. s., 1H), 7.94-7.76 (m, 4H), 7.74 (s, 1H), 7.66 (d, J = 7.8 Hz, 1H), 7.48 (d, J = 7.9 Hz, 1H), 4.45-4.24 (m, 1H), 3.90 (t, J = 8.3 Hz, 1H), 2.66-2.55 (m, 2H), 2.42 (s, 3H), 2.40-2.31 (m, 3H), 2.28-2.17 (m, 2H), 2.07 (t, J = 9.9 Hz, 1H) |

TABLE 23-continued

| Ex. | Structure | Name | LCMS [M + H]+ | HPLC Method, RT (min.) | ¹H NMR (δ NMR) |
|---|---|---|---|---|---|
| 419 | 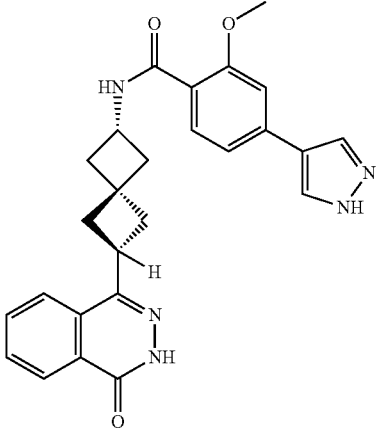 | 2-methoxy-N-((aR)-6-(4-oxo-3,4-dihydrophthalazin-1-yl)spiro[3.3]heptan-2-yl)-4-(1H-pyrazol-4-yl)benzamide | 456.0 | F: 1.25 | (500 MHz, DMSO-$d_6$) δ 12.49 (s, 1H), 8.25 (d, J = 7.9 Hz, 1H), 8.20 (d, J = 7.3 Hz, 1H), 8.08 (br. s., 2H), 7.96-7.81 (m, 3H), 7.70 (d, J = 7.9 Hz, 1H), 7.32 (s, 1H), 7.27 (d, J = 7.9 Hz, 1H), 4.40-4.25 (m, 1H), 3.96 (s, 3H), 3.90 (t, J = 8.5 Hz, 1H), 2.67-2.54 (m, 2H), 2.43-2.31 (m, 3H), 2.25 (br. s., 1H), 2.18 (t, J = 9.6 Hz, 1H), 2.01 (t, J = 9.7 Hz, 1H) |
| 420 | 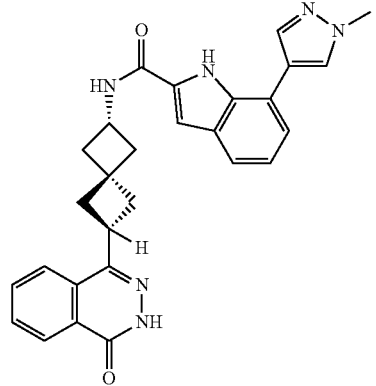 | 7-(1-methyl-1H-pyrazol-4-yl)-N-((aR)-6-(4-oxo-3,4-dihydrophthalazin-1-yl)spiro[3.3]heptan-2-yl)-1H-indole-2-carboxamide | 479.2 | E: 1.52 F: 1.51 | (500 MHz, DMSO-$d_6$) δ 12.49 (s, 1H), 10.52 (br s, 1H), 8.71 (d, J = 6.9 Hz, 1H), 8.35-8.16 (m, 2H), 7.98-7.79 (m, 4H), 7.53 (d, J = 7.8 Hz, 1H), 7.28 (d, J = 7.0 Hz, 1H), 7.17 (s, 1H), 7.09 (t, J = 7.4 Hz, 1H), 4.45-4.29 (m, 1H), 3.94 (s, 3H), 3.92-3.85 (m, 1H), 2.72-2.62 (m, 1H), 2.58 (br. s., 1H), 2.45-2.33 (m, 3H), 2.31-2.19 (m, 2H), 2.07 (t, J = 9.9 Hz, 1H) |
| 421 | 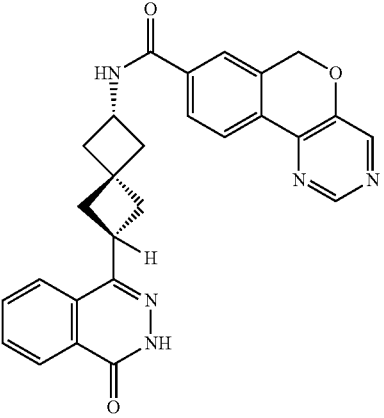 | N-((aR)-6-(4-oxo-3,4-dihydrophthalazin-1-yl)spiro[3.3]heptan-2-yl)-6H-isochromeno[4,3-d]pyrimidine-8-carboxamide | 466.2 | E: 1.41 F: 1.50 | (500 MHz, DMSO-$d_6$) δ 12.47 (s, 1H), 8.88 (s, 1H), 8.76 (d, J = 7.3 Hz, 1H), 8.53 (s, 1H), 8.25 (d, J = 7.9 Hz, 1H), 8.19 (d, J = 8.2 Hz, 1H), 7.96 (d, J = 7.9 Hz, 1H), 7.91 (d, J = 7.3 Hz, 1H), 7.89-7.81 (m, 2H), 7.80 (s, 1H), 5.45 (s, 2H), 4.48-4.25 (m, 1H), 3.90 (t, J = 8.4 Hz, 1H), 2.69-2.56 (m, 2H), 2.45-2.32 (m, 3H), 2.30-2.20 (m, 2H), 2.08 (t, J = 9.9 Hz, 1H) |

TABLE 23-continued

| Ex. | Structure | Name | LCMS [M + H]+ | HPLC Method, RT (min.) | ¹H NMR (δ NMR) |
|---|---|---|---|---|---|
| 422 | 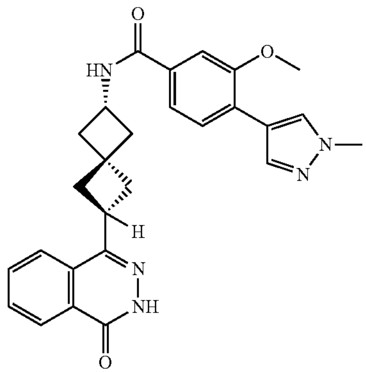 | 3-methoxy-4-(1-methyl-1H-pyrazol-4-yl)-N-((aR)-6-(4-oxo-3,4-dihydrophthalazin-1-yl)spiro[3.3]heptan-2-yl)benzamide | 470.2 | E: 1.44 F: 1.52 | (500 MHz, DMSO-d$_6$) δ 12.47 (s, 1H), 8.53 (d, J = 7.3 Hz, 1H), 8.26 (d, J = 7.6 Hz, 1H), 8.18 (s, 1H), 7.96 (s, 1H), 7.94-7.79 (m, 3H), 7.67 (d, J = 7.9 Hz, 1H), 7.53-7.42 (m, 2H), 4.43-4.29 (m, 1H), 3.93 (s, 3H), 3.87 (s, 3H), 4.01-3.81 (m, 1H), 2.68-2.55 (m, 2H), 2.45-2.33 (m, 3H), 2.30-2.19 (m, 2H), 2.09 (t, J = 9.9 Hz, 1H) |
| 423 | 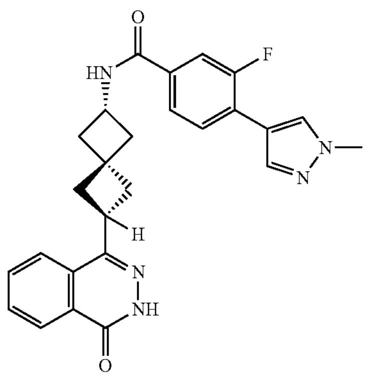 | 3-fluoro-4-(1-methyl-1H-pyrazol-4-yl)-N-((aR)-6-(4-oxo-3,4-dihydrophthalazin-1-yl)spiro[3.3]heptan-2-yl)benzamide | 458.0 | E: 1.55 F: 1.55 | (500 MHz, DMSO-d$_6$) δ 12.47 (s, 1H), 8.63 (d, J = 7.0 Hz, 1H), 8.25 (d, J = 7.9 Hz, 1H), 8.21 (s, 1H), 8.00-7.94 (m, 1H), 7.94-7.89 (m, 1H), 7.88-7.77 (m, 3H), 7.75-7.67 (m, 2H), 4.34 (sxt, J = 7.8 Hz, 1H), 3.90 (s, 3H), 4.01-3.79 (m, 1H), 2.66-2.54 (m, 2H), 2.44-2.31 (m, 3H), 2.28-2.18 (m, 2H), 2.07 (t, J = 10.1 Hz, 1H) |
| 425 | 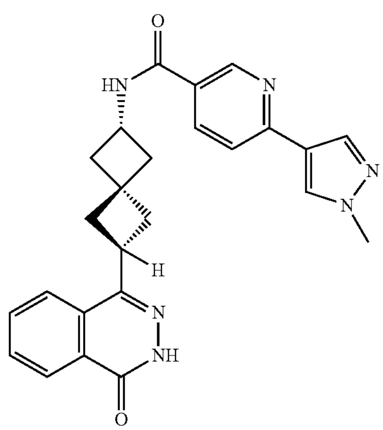 | 6-(1-methyl-1H-pyrazol-4-yl)-N-((aR)-6-(4-oxo-3,4-dihydrophthalazin-1-yl)spiro[3.3]heptan-2-yl)nicotinamide | 441.0 | E: 1.20 F: 1.37 | (500 MHz, DMSO-d$_6$) δ 12.47 (s, 1H), 8.92 (s, 1H), 8.68 (d, J = 7.3 Hz, 1H), 8.36 (s, 1H), 8.25 (d, J = 7.6 Hz, 1H), 8.15 (d, J = 7.9 Hz, 1H), 8.05 (s, 1H), 7.96-7.80 (m, 3H), 7.72 (d, J = 8.2 Hz, 1H), 4.41-4.30 (m, 1H), 3.89 (s, 3H), 3.92 (br. s., 1H), 2.68-2.55 (m, 2H), 2.45-2.33 (m, 3H), 2.25 (t, J = 9.3 Hz, 2H), 2.08 (t, J = 9.9 Hz, 1H) |
| 426 | 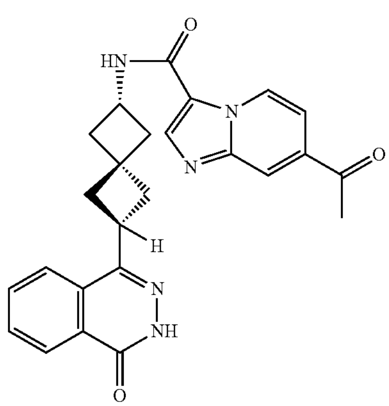 | 7-acetyl-N-((aR)-6-(4-oxo-3,4-dihydrophthalazin-1-yl)spiro[3.3]heptan-2-yl)imidazo[1,2-a]pyridine-3-carboxamide | 442.0 | E: 1.27 F: 1.48 | (500 MHz, DMSO-d$_6$) δ 12.47 (s, 1H), 9.48 (d, J = 7.0 Hz, 1H), 8.75 (d, J = 7.3 Hz, 1H), 8.52 (s, 1H), 8.40 (br. s., 1H), 8.26 (d, J = 7.6 Hz, 1H), 7.96-7.78 (m, 3H), 7.50 (d, J = 7.0 Hz, 1H), 4.40 (d, J = 8.2 Hz, 1H), 3.98-3.85 (m, 1H), 2.67 (s, 3H), 2.73-2.63 (m, 1H), 2.59 (br. s., 1H), 2.45-2.33 (m, 3H), 2.27 (t, J = 9.0 Hz, 2H), 2.10 (t, J = 9.8 Hz, 1H) |

TABLE 23-continued

| Ex. | Structure | Name | LCMS [M + H]+ | HPLC Method, RT (min.) | 1H NMR (δ NMR) |
|---|---|---|---|---|---|
| 427 | 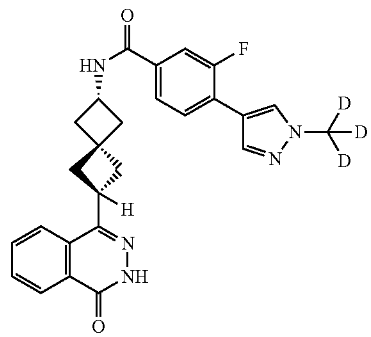 | 3-fluoro-4-(1-d3-methyl-1H-pyrazol-4-yl)-N-((aR)-6-(4-oxo-3,4-dihydrophthalazin-1-yl)spiro[3.3]heptan-2-yl)benzamide | 461.1 | E: 1.55 F: 1.53 | (500 MHz, DMSO-d6) δ 12.47 (s, 1H), 8.62 (d, J = 7.3 Hz, 1H), 8.25 (d, J = 7.6 Hz, 1H), 8.22 (d, J = 1.8 Hz, 1H), 7.97 (s, 1H), 7.94-7.89 (m, 1H), 7.89-7.78 (m, 3H), 7.75-7.68 (m, 2H), 4.34 (sxt, J = 8.1 Hz, 1H), 3.90 (quin, J = 8.5 Hz, 1H), 2.67-2.53 (m, 2H), 2.45-2.32 (m, 3H), 2.29-2.19 (m, 2H), 2.12-2.03 (m, 1H) |
| 428 | 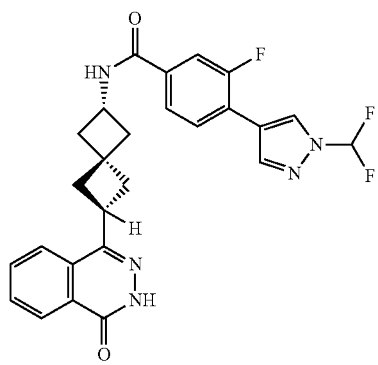 | 4-(1-(difluoromethyl)-1H-pyrazol-4-yl)-3-fluoro-N-((aR)-6-(4-oxo-3,4-dihydrophthalazin-1-yl)spiro[3.3]heptan-2-yl)benzamide | 494.3 | E: 1.79 F: 1.79 | (500 MHz, DMSO-d6) δ 12.47 (s, 1H), 8.74 (s, 1H), 8.69 (d, J = 7.0 Hz, 1H), 8.35 (s, 1H), 8.25 (d, J = 7.9 Hz, 1H), 8.04-7.72 (m, 7H), 4.42-4.27 (m, 1H), 3.90 (quin, J = 8.4 Hz, 1H), 2.68-2.53 (m, 2H), 2.44-2.32 (m, 3H), 2.29-2.19 (m, 2H), 2.12-2.03 (m, 1H) |
| 429 | 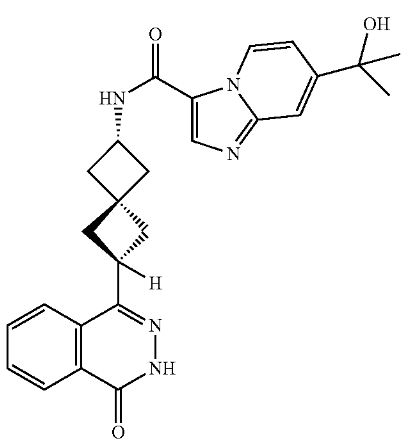 | 7-(2-hydroxypropan-2-yl)-N-((aR)-6-(4-oxo-3,4-dihydrophthalazin-1-yl)spiro[3.3]heptan-2-yl)imidazo[1,2-a]pyridine-3-carboxamide | 458.1 | E: 1.27 F: 1.45 | (500 MHz, DMSO-d6) δ 12.47 (s, 1H), 9.38 (d, J = 7.3 Hz, 1H), 8.61 (d, J = 7.6 Hz, 1H), 8.38 (s, 1H), 8.26 (d, J = 7.6 Hz, 1H), 7.97-7.80 (m, 3H), 7.70 (s, 1H), 7.29 (d, J = 7.0 Hz, 1H), 4.47-4.31 (m, 1H), 3.97-3.86 (m, 1H), 2.64 (br. s., 1H), 2.57 (d, J = 11.0 Hz, 1H), 2.45-2.34 (m, 3H), 2.30-2.21 (m, 2H), 2.08 (t, J = 9.9 Hz, 1H), 1.47 (s, 6H) |

TABLE 23-continued

| Ex. | Structure | Name | LCMS [M + H]+ | HPLC Method, RT (min.) | 1H NMR (δ NMR) |
|---|---|---|---|---|---|
| 430 | 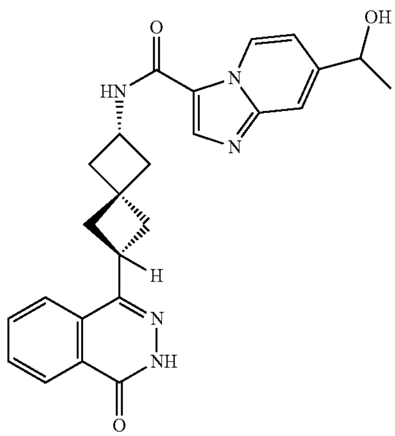 | 7-(1-hydroxyethyl)-N-((aR)-6-(4-oxo-3,4-dihydrophthalazin-1-yl)spiro[3.3]heptan-2-yl)imidazo[1,2-a]pyridine-3-carboxamide | 444.0 | E: 1.18 F: 1.70 | (500 MHz, DMSO-d6) δ 9.36 (d, J = 7.3 Hz, 1H), 8.53 (d, J = 7.3 Hz, 1H), 8.30 (s, 1H), 8.25 (d, J = 7.9 Hz, 1H), 7.97-7.80 (m, 3H), 7.56 (s, 1H), 7.10 (d, J = 7.0 Hz, 1H), 4.80 (d, J = 6.4 Hz, 1H), 4.45-4.32 (m, 1H), 3.97-3.85 (m, 1H), 2.68-2.61 (m, 1H), 2.61-2.55 (m, 1H), 2.45-2.35 (m, 3H), 2.29-2.21 (m, 2H), 1.36 (d, J = 6.4 Hz, 3H) |
| 431 | 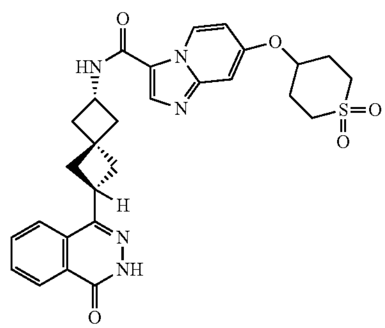 | 7-((1,1-dioxidotetrahydro-2H-thiopyran-4-yl)oxy)-N-((aR)-6-(4-oxo-3,4-dihydrophthalazin-1-yl)spiro[3.3]heptan-2-yl)imidazo[1,2-a]pyridine-3-carboxamide | 548.1 | E: 1.43 F: 1.60 | (500 MHz, DMSO-d6) δ 12.47 (s, 1H), 9.29 (d, J = 7.3 Hz, 1H), 8.46 (d, J = 7.3 Hz, 1H), 8.25 (d, J = 7.6 Hz, 1H), 8.21 (s, 1H), 7.96-7.79 (m, 3H), 7.24 (br. s., 1H), 6.88 (d, J = 7.6 Hz, 1H), 4.89 (br. s., 1H), 4.43-4.31 (m, 1H), 3.90 (quin, J = 8.4 Hz, 1H), 3.22 (br. s., 4H), 2.67-2.56 (m, 2H), 2.45-2.33 (m, 3H), 2.24 (d, J = 8.2 Hz, 6H), 2.06 (t, J = 10.1 Hz, 1H) |
| 432 | 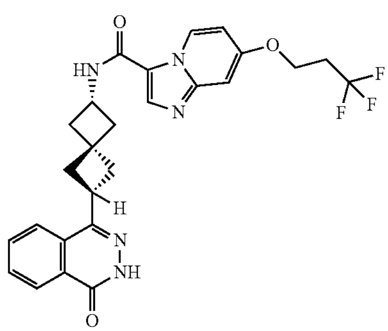 | N-((aR)-6-(4-oxo-3,4-dihydrophthalazin-1-yl)spiro[3.3]heptan-2-yl)-7-(3,3,3-trifluoropropoxy)imidazo[1,2-a]pyridine-3-carboxamide | 512.4 | A: 5.53 B: 8.11 | (400 MHz, DMSO-d6) δ 12.47 (s, 1H), 9.43 (d, J = 7.7 Hz, 1H), 8.82 (d, J = 7.3 Hz, 1H), 8.49 (s, 1H), 8.26 (d, J = 7.9 Hz, 1H), 7.96-7.81 (m, 3H), 7.38 (d, J = 2.4 Hz, 1H), 7.13 (dd, J = 7.7, 2.4 Hz, 1H), 4.44 (t, J = 5.7 Hz, 2H), 4.41-4.31 (m, 1H), 3.91 (quin, J = 8.5 Hz, 1H), 2.90 (qt, J = 11.3, 5.7 Hz, 2H), 2.72-2.63 (m, 1H), 2.62-2.54 (m, 1H), 2.44-2.36 (m, 3H), 2.32-2.21 (m, 2H), 2.11-2.03 (m, 1H) |
| 433 | 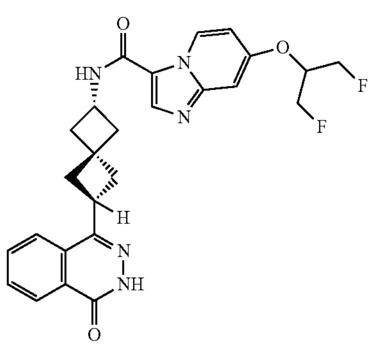 | 7-((1,3-difluoropropan-2-yl)oxy)-N-((aR)-6-(4-oxo-3,4-dihydrophthalazin-1-yl)spiro[3.3]heptan-2-yl)imidazo[1,2-a]pyridine-3-carboxamide | 494.0 | E: 1.54 F: 1.74 | (500 MHz, DMSO-d6) δ 12.47 (s, 1H), 9.30 (d, J = 7.6 Hz, 1H), 8.48 (d, J = 7.3 Hz, 1H), 8.25 (d, J = 7.6 Hz, 1H), 8.22 (s, 1H), 7.97-7.80 (m, 3H), 7.28 (s, 1H), 6.88 (dd, J = 7.6, 2.1 Hz, 1H), 5.26-5.10 (m, 1H), 4.90-4.82 (m, 1H), 4.79-4.71 (m, 2H), 4.66 (dd, J = 10.4, 4.9 Hz, 1H), 4.43-4.29 (m, 1H), 3.90 (quin, J = 8.3 Hz, 1H), 2.69-2.55 (m, 2H), 2.45-2.33 (m, 3H), 2.29-2.19 (m, 2H), 2.10-2.02 (m, 1H) |

TABLE 23-continued

| Ex. | Structure | Name | LCMS [M + H]+ | HPLC Method, RT (min.) | ¹H NMR (δ NMR) |
|---|---|---|---|---|---|
| 434 | 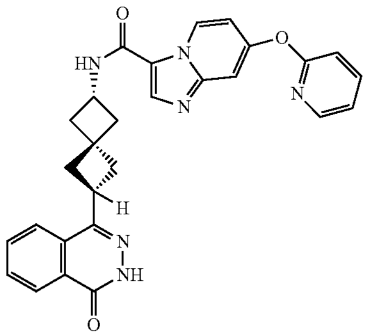 | N-((aR)-6-(4-oxo-3,4-dihydrophthalazin-1-yl)spiro[3.3]heptan-2-yl)-7-(pyridin-2-yloxy)imidazo[1,2-a]pyridine-3-carboxamide | 493.0 | E: 1.22 F: 1.49 | (500 MHz, DMSO-$d_6$) δ 12.50 (s, 1H), 9.51 (d, J = 7.4 Hz, 1H), 8.77 (d, J = 7.4 Hz, 1H), 8.45 (br. s., 1H), 8.25 (d, J = 6.9 Hz, 2H), 7.97 (t, J = 7.7 Hz, 1H), 7.94-7.89 (m, 1H), 7.89-7.80 (m, 2H), 7.52 (br. s., 1H), 7.32-7.26 (m, 1H), 7.23 (d, J = 8.3 Hz, 1H), 7.17 (d, J = 7.3 Hz, 1H), 4.38 (sxt, J = 8.1 Hz, 1H), 3.91 (quin, J = 8.4 Hz, 1H), 2.70-2.62 (m, 1H), 2.61-2.55 (m, 1H), 2.45-2.33 (m, 3H), 2.31-2.20 (m, 2H), 2.07 (t, J = 10.0 Hz, 1H) |
| 435 | 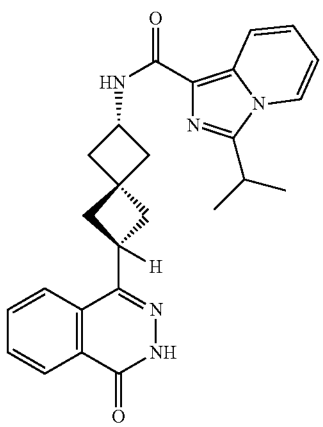 | 3-isopropyl-N-((aR)-6-(4-oxo-3,4-dihydrophthalazin-1-yl)spiro[3.3]heptan-2-yl)imidazo[1,5-a]pyridine-1-carboxamide | 442.0 | E: 1.84 F: 1.97 | (500 MHz, DMSO-$d_6$) δ 8.33 (d, J = 7.0 Hz, 1H), 8.25 (d, J = 7.9 Hz, 1H), 8.05 (d, J = 9.2 Hz, 1H), 7.97-7.80 (m, 4H), 7.05 (t, J = 7.8 Hz, 1H), 6.82 (t, J = 6.9 Hz, 1H), 4.45-4.33 (m, 1H), 3.90 (t, J = 8.4 Hz, 1H), 3.53-3.47 (m, 1H), 2.58 (br. s., 2H), 2.43-2.28 (m, 4H), 2.20 (br. s., 1H), 2.17-2.10 (m, 1H), 1.35 (d, J = 6.7 Hz, 6H) |
| 436 | 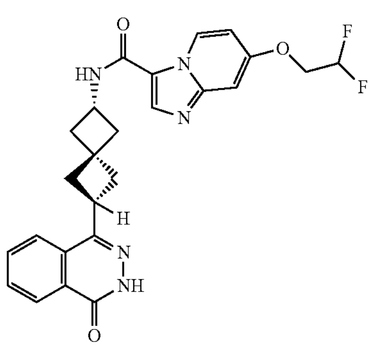 | 7-(2,2-difluoroethoxy)-N-((aR)-6-(4-oxo-3,4-dihydrophthalazin-1-yl)spiro[3.3]heptan-2-yl)imidazo[1,2-a]pyridine-3-carboxamide | 480.1 | E: 1.56 F: 1.79 | (500 MHz, DMSO-$d_6$) δ 12.48 (s, 1H), 9.30 (d, J = 7.6 Hz, 1H), 8.55 (d, J = 7.0 Hz, 1H), 8.25 (br. s., 2H), 7.98-7.77 (m, 3H), 7.20 (br. s., 1H), 6.92 (d, J = 7.6 Hz, 1H), 6.43 (t, J = 54.0 Hz, 1H), 4.46 (t, J = 13.9 Hz, 2H), 4.40-4.30 (m, 1H), 3.90 (t, J = 8.4 Hz, 1H), 2.64 (br. s., 1H), 2.57 (br. s., 1H), 2.45-2.32 (m, 3H), 2.29-2.18 (m, 2H), 2.11-2.00 (m, 1H) |

TABLE 23-continued

| Ex. | Structure | Name | LCMS [M + H]+ | HPLC Method, RT (min.) | 1H NMR (δ NMR) |
|---|---|---|---|---|---|
| 437 | 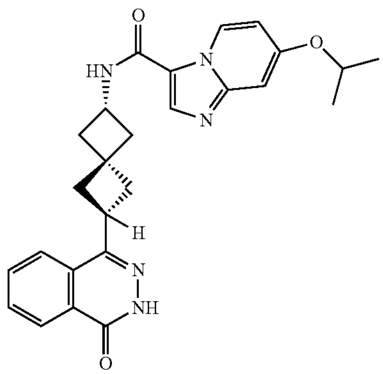 | 7-isopropoxy-N-((aR)-6-(4-oxo-3,4-dihydrophthalazin-1-yl)spiro[3.3]heptan-2-yl)imidazo[1,2-a]pyridine-3-carboxamide | 458.3 | E: 1.36 F: 1.57 | (500 MHz, DMSO-$d_6$) δ 12.49 (s, 1H), 9.23 (d, J = 7.6 Hz, 1H), 8.47 (d, J = 7.5 Hz, 1H), 8.25 (d, J = 7.8 Hz, 1H), 8.18 (s, 1H), 7.96-7.90 (m, 1H), 7.89-7.80 (m, 2H), 7.03 (d, J = 2.1 Hz, 1H), 6.75 (dd, J = 7.6, 2.4 Hz, 1H), 4.75 (dt, J = 12.1, 6.1 Hz, 1H), 4.35 (sxt, J = 8.1 Hz, 1H), 3.90 (quin, J = 8.4 Hz, 1H), 2.66-2.60 (m, 1H), 2.59-2.55 (m, 1H), 2.42-2.32 (m, 3H), 2.27-2.17 (m, 2H), 2.04 (t, J = 10.1 Hz, 1H), 1.30 (d, J = 6.0 Hz, 6H) |
| 438 | 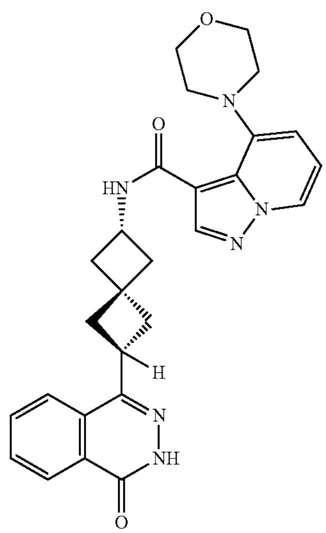 | 4-morpholino-N-((aR)-6-(4-oxo-3,4-dihydrophthalazin-1-yl)spiro[3.3]heptan-2-yl)pyrazolo[1,5-a]pyridine-3-carboxamide | 485.2 | E: 1.23 F: 1.41 | (500 MHz, DMSO-$d_6$) δ 12.47 (s, 1H), 8.70 (d, J = 6.4 Hz, 1H), 8.49 (d, J = 6.7 Hz, 1H), 8.25 (d, J = 7.6 Hz, 1H), 8.23 (s, 1H), 7.95-7.79 (m, 3H), 7.08-7.01 (m, 1H), 7.00-6.92 (m, 1H), 4.36-4.24 (m, 1H), 3.91 (quin, J = 8.5 Hz, 1H), 3.78 (d, J = 4.0 Hz, 4H), 2.96 (br. s., 4H), 2.71 (t, J = 11.3 Hz, 1H), 2.59 (t, J = 8.1 Hz, 1H), 2.45-2.38 (m, 1H), 2.37-2.21 (m, 4H), 2.06 (t, J = 9.9 Hz, 1H). |
| 471 | 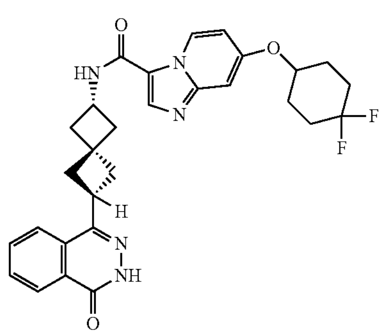 | 7-((4,4-difluoro-cyclohexyl)oxy)-N-((aR)-6-(4-oxo-3,4-dihydro-phthalazin-1-yl)spiro[3.3]heptan-2-yl)imidazo[1,2-a]pyridine-3-carboxamide, TFA | 534.4 | A: 5.67 B: 8.51 | (400 MHz, DMSO-$d_6$) δ 12.47 (s, 1H), 9.45 (d, J = 7.7 Hz, 1H), 8.86 (d, J = 7.5 Hz, 1H), 8.52 (s, 1H), 8.26 (d, J = 7.9 Hz, 1H), 7.97-7.75 (m, 3H), 7.43 (d, J = 2.4 Hz, 1H), 7.22 (dd, J = 7.8, 2.3 Hz, 1H), 4.92 (br. s., 1H), 4.46-4.30 (m, 1H), 3.91 (quin, J = 8.5 Hz, 1H), 2.71-2.63 (m, 1H), 2.62-2.54 (m, 1H), 2.44-2.36 (m, 4H), 2.32-2.22 (m, 2H), 2.11-1.97 (m, 6H), 1.95-1.84 (m, 2H) |

Example 439: 7-(1-ethyl-1H-pyrazol-4-yl)-N-((aR)-6-(4-oxo-3,4-dihydrophthalazin-1-yl)spiro[3.3]heptan-2-yl)imidazo[1,2-a]pyridine-3-carboxamide, TFA salt

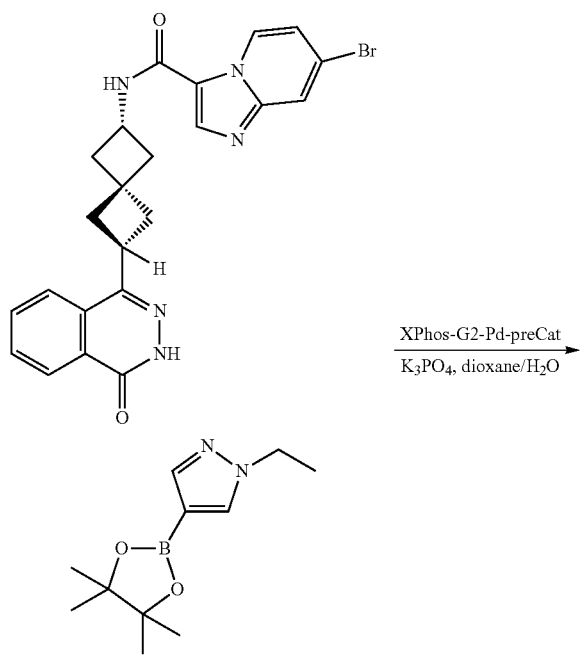
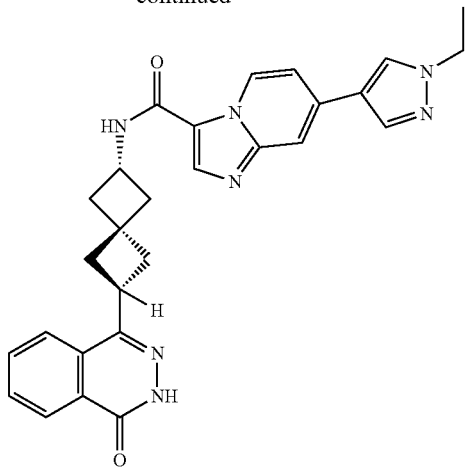

To a solution of Example 363 (10 mg, 0.021 mmol) in dioxane (1 mL) were added 1-ethyl-4-(4,4,5,5-tetramethyl-1,3,2-dioxaborolan-2-yl)-1H-pyrazole (9.3 mg, 0.042 mmol), $K_3PO_4$ (13.3 mg, 0.063 mmol), water (0.2 mL), and XPhos-Pd-G2 (1.6 mg, 2.1 μmol) at rt. The reaction was stirred under $N_2$ at 100° C. for 2 h. The reaction was cooled to rt, and the solvent was removed. Purification by reverse phase chromatography provided Example 439 (7.9 mg, 62%). $^1$H NMR (500 MHz, DMSO-$d_6$) δ 12.48 (s, 1H), 9.43 (d, J=7.3 Hz, 1H), 8.70 (d, J=7.3 Hz, 1H), 8.49 (s, 1H), 8.43 (s, 1H), 8.26 (d, J=7.9 Hz, 1H), 8.14 (s, 1H), 7.97-7.80 (m, 4H), 7.53 (d, J=7.0 Hz, 1H), 4.38 (sxt, J=8.1 Hz, 1H), 4.18 (q, J=7.1 Hz, 2H), 3.91 (quin, J=8.5 Hz, 1H), 2.70-2.62 (m, 1H), 2.58 (t, J=7.9 Hz, 1H), 2.45-2.35 (m, 3H), 2.32-2.22 (m, 2H), 2.08 (t, J=10.1 Hz, 1H), 1.42 (t, J=7.3 Hz, 3H). LC-MS(ESI) m/z: 494.1 [M+H]$^+$. Analytical HPLC RT=1.42 min (Method E), 1.63 min (Method F).

Examples in Table 24 were prepared by following a similar Suzuki-Miyara coupling reaction procedure to that described in Example 439 using the appropriate halides and boronic acids or esters. Other appropriate palladium catalysts and ligands could also be used.

TABLE 24

| Ex. | Structure | Name | LCMS [M + H]$^+$ | HPLC Method, RT (min.) | $^1$H NMR (δ NMR) |
|---|---|---|---|---|---|
| 440 | 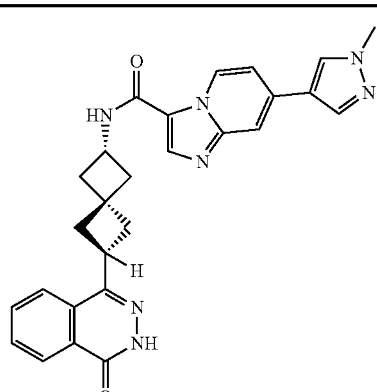 | 7-(1-methyl-1H-pyrazol-4-yl)-N-((aR)-6-(4-oxo-3,4-dihydrophthalazin-1-yl)spiro[3.3]heptan-2-yl)imidazo[1,2-a]pyridine-3-carboxamide | 480.3 | E: 1.10 F: 1.12 | (500 MHz, DMSO-$d_6$) δ 12.49 (s, 1H), 9.38 (d, J = 7.2 Hz, 1H), 8.58 (d, J = 7.3 Hz, 1H), 8.37 (s, 1H), 8.32 (s, 1H), 8.25 (d, J = 7.9 Hz, 1H), 8.09 (s, 1H), 7.96-7.79 (m, 4H), 7.39 (d, J = 7.2 Hz, 1H), 4.45-4.31 (m, 1H), 3.95-3.89 (m, 1H), 3.88 (s, 3H), 2.65 (br. s., 1H), 2.58 (t, J = 8.0 Hz, 1H), 2.44-2.33 (m, 3H), 2.30-2.20 (m, 2H), 2.07 (t, J = 10.0 Hz, 1H) |

TABLE 24-continued

| Ex. | Structure | Name | LCMS [M + H]+ | HPLC Method, RT (min.) | ¹H NMR (δ NMR) |
|---|---|---|---|---|---|
| 441 | 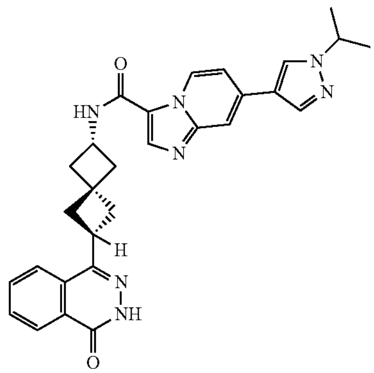 | 7-(1-isopropyl-1H-pyrazol-4-yl)-N-((aR)-6-(4-oxo-3,4-dihydrophthalazin-1-yl)spiro[3.3]heptan-2-yl)imidazo[1,2-a]pyridine-3-carboxamide | 508.1 | E: 1.51 F: 1.72 | (500 MHz, DMSO-d$_6$) δ 9.38 (d, J = 7.0 Hz, 1H), 8.56 (d, J = 7.3 Hz, 1H), 8.48 (s, 1H), 8.31 (s, 1H), 8.27 (d, J = 7.9 Hz, 1H), 8.10 (s, 1H), 7.98-7.82 (m, 4H), 7.41 (d, J = 7.0 Hz, 1H), 4.54 (dt, J = 13.2, 6.4 Hz, 1H), 4.44-4.34 (m, 1H), 3.99-3.86 (m, 1H), 2.67 (br. s., 1H), 2.63-2.57 (m, 1H), 2.47-2.35 (m, 3H), 2.33-2.22 (m, 2H), 2.09 (t, J = 9.8 Hz, 1H), 1.48 (d, J = 6.7 Hz, 6H) |
| 442 | 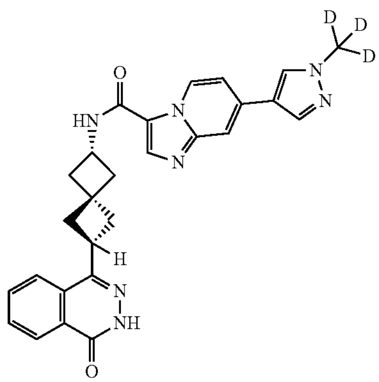 | 7-(1-(methyl-d3)-1H-pyrazol-4-yl)-N-((aR)-6-(4-oxo-3,4-dihydrophthalazin-1-yl)spiro[3.3]heptan-2-yl)imidazo[1,2-a]pyridine-3-carboxamide | 483.1 | E: 1.38 F: 1.55 | (500 MHz, DMSO-d$_6$) δ 12.48 (s, 1H), 9.43 (d, J = 7.0 Hz, 1H), 8.73 (d, J = 7.3 Hz, 1H), 8.49-8.37 (m, 2H), 8.25 (d, J = 7.9 Hz, 1H), 8.13 (s, 1H), 7.97-7.80 (m, 4H), 7.53 (d, J = 7.0 Hz, 1H), 4.38 (sxt, J = 8.0 Hz, 1H), 3.91 (quin, J = 8.4 Hz, 1H), 2.65 (d, J = 10.7 Hz, 1H), 2.61-2.55 (m, 1H), 2.45-2.33 (m, 3H), 2.31-2.20 (m, 2H), 2.07 (t, J = 9.9 Hz, 1H) |
| 443 | 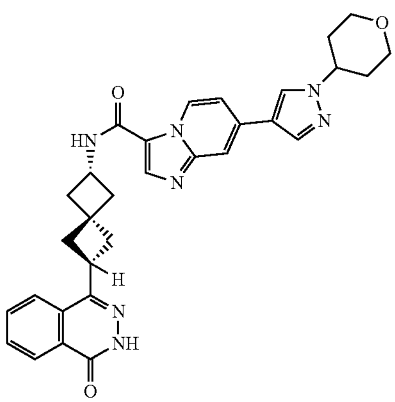 | N-(aR)-6-(4-oxo-3,4-dihydrophthalazin-1-yl)spiro[3.3]heptan-2-yl)-7-(1-(tetrahydro-2H-pyran-4-yl)-1H-pyrazol-4-yl)imidazo[1,2-a]pyridine-3-carboxamide | 550.1 | E: 1.43 F: 1.63 | (500 MHz, DMSO-d$_6$) δ 12.48 (s, 1H), 9.36 (d, J = 7.3 Hz, 1H), 8.55 (d, J = 7.3 Hz, 1H), 8.50 (s, 1H), 8.30 (s, 1H), 8.25 (d, J = 7.6 Hz, 1H), 8.11 (s, 1H), 7.96-7.80 (m, 4H), 7.40 (d, J = 7.3 Hz, 1H), 4.47-4.32 (m, 2H), 3.97 (d, J = 9.2 Hz, 2H), 3.93-3.86 (m, 1H), 3.53-3.42 (m, 2H), 2.65 (br. s., 1H), 2.58 (t, J = 8.4 Hz, 1H), 2.46-2.33 (m, 3H), 2.30-2.20 (m, 2H), 2.11-1.92 (m, 5H) |
| 444 | 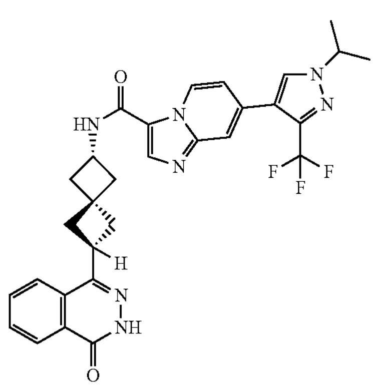 | 7-(1-isopropyl-3-(trifluoromethyl)-1H-pyrazol-4-yl)-N-((aR)-6-(4-oxo-3,4-dihydrophthalazin-1-yl)spiro[3.3]heptan-2-yl)imidazo[1,2-a]pyridine-3-carboxamide | 576.1 | E: 1.76 F: 2.03 | (500 MHz, DMSO-d$_6$) δ 12.48 (s, 1H), 9.45 (d, J = 7.3 Hz, 1H), 8.62 (d, J = 7.3 Hz, 1H), 8.52 (s, 1H), 8.38 (s, 1H), 8.26 (d, J = 7.6 Hz, 1H), 7.96-7.80 (m, 3H), 7.70 (s, 1H), 7.20 (d, J = 7.3 Hz, 1H), 4.64 (dt, J = 13.4, 6.6 Hz, 1H), 4.40 (sxt, J = 8.2 Hz, 1H), 3.91 (quin, J = 8.5 Hz, 1H), 2.70-2.62 (m, 1H), 2.62-2.55 (m, J = 7.9, 7.9 Hz, 1H), 2.46-2.35 (m, 3H), 2.32-2.22 (m, 2H), 2.09 (t, J = 9.8 Hz, 1H), 1.50 (d, J = 6.7 Hz, 6H) |

TABLE 24-continued

| Ex. | Structure | Name | LCMS [M + H]+ | HPLC Method, RT (min.) | 1H NMR (δ NMR) |
|---|---|---|---|---|---|
| 445 | 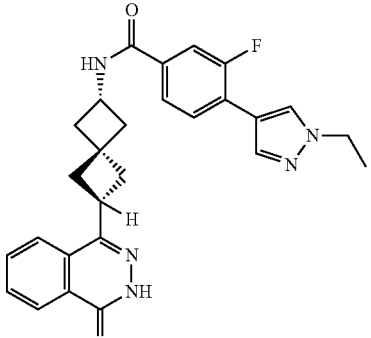 | 4-(1-ethyl-1H-pyrazol-4-yl)-3-fluoro-N-((aR)-6-(4-oxo-3,4-dihydrophthalazin-1-yl)spiro[3.3]heptan-2-yl)benzamide | 472.1 | E: 1.72 F: 1.77 | (500 MHz, DMSO-$d_6$) δ 12.47 (s, 1H), 8.64 (d, J = 7.3 Hz, 1H), 8.32-8.18 (m, 2H), 7.97 (s, 1H), 7.94-7.89 (m, 1H), 7.89-7.77 (m, 3H), 7.75-7.67 (m, 2H), 4.42-4.29 (m, 1H), 4.19 (q, J = 7.3 Hz, 2H), 3.90 (quin, J = 8.4 Hz, 1H), 2.66-2.53 (m, 2H), 2.44-2.31 (m, 3H), 2.28-2.18 (m, 2H), 2.07 (t, J = 9.9 Hz, 1H), 1.40 (t, J = 7.2 Hz, 3H) |
| 446 | 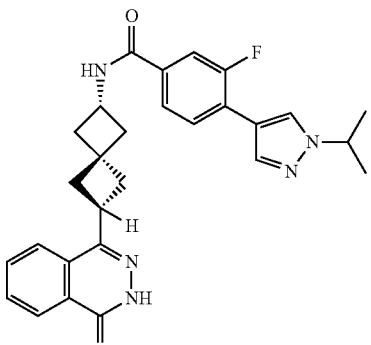 | 3-fluoro-4-(1-isopropyl-1H-pyrazol-4-yl)-N-((aR)-6-(4-oxo-3,4-dihydrophthalazin-1-yl)spiro[3.3]heptan-2-yl)benzamide | 486.1 | E: 1.62 F: 1.87 | (500 MHz, DMSO-$d_6$) δ 12.47 (s, 1H), 8.64 (d, J = 7.3 Hz, 1H), 8.31-8.20 (m, 2H), 7.96 (s, 1H), 7.94-7.78 (m, 4H), 7.75-7.66 (m, 2H), 4.56 (dt, J = 13.2, 6.7 Hz, 1H), 4.40-4.28 (m, 1H), 3.95-3.83 (m, 1H), 2.67-2.55 (m, 2H), 2.45-2.32 (m, 3H), 2.28-2.17 (m, 2H), 2.07 (t, J = 10.1 Hz, 1H), 1.45 (d, J = 6.7 Hz, 6H) |
| 447 | 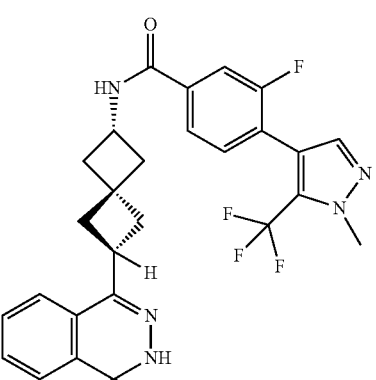 | 3-fluoro-4-(1-methyl-5-(trifluoromethyl)-1H-pyrazol-4-yl)-N-((aR)-6-(4-oxo-3,4-dihydrophthalazin-1-yl)spiro[3.3]heptan-2-yl)benzamide | 526.1 | E: 1.84 F: 2.15 | (500 MHz, DMSO-$d_6$) δ 12.49 (s, 1H), 8.74 (d, J = 7.3 Hz, 1H), 8.27 (d, J = 7.9 Hz, 1H), 8.19 (s, 1H), 7.98-7.82 (m, 3H), 7.79-7.71 (m, 2H), 7.48 (t, J = 7.6 Hz, 1H), 4.42-4.30 (m, 1H), 4.00 (s, 3H), 3.92 (quin, J = 8.5 Hz, 1H), 2.68-2.57 (m, 2H), 2.46-2.33 (m, 3H), 2.26 (t, J = 9.8 Hz, 2H), 2.09 (t, J = 9.9 Hz, 1H) |
| 448 | 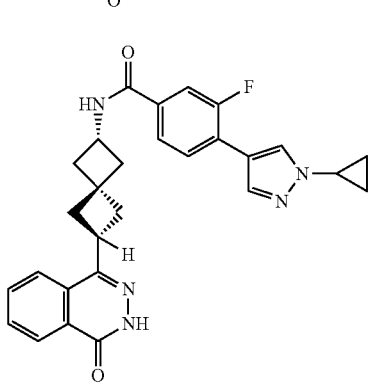 | 4-(1-cyclopropyl-1H-pyrazol-4-yl)-3-fluoro-N-((aR)-6-(4-oxo-3,4-dihydrophthalazin-1-yl)spiro[3.3]heptan-2-yl)benzamide | 484.1 | E: 1.76 F: 1.82 | (500 MHz, DMSO-$d_6$) δ 12.47 (s, 1H), 8.64 (d, J = 7.3 Hz, 1H), 8.28 (s, 1H), 8.25 (d, J = 7.9 Hz, 1H), 7.93 (s, 1H), 7.91 (d, J = 7.3 Hz, 1H), 7.89-7.77 (m, 3H), 7.73-7.65 (m, 2H), 4.34 (sxt, J = 7.9 Hz, 1H), 3.97-3.83 (m, J = 8.5, 8.5 Hz, 1H), 3.79 (br. s., 1H), 2.66-2.55 (m, 2H), 2.44-2.33 (m, 3H), 2.28-2.19 (m, 2H), 2.11-2.02 (m, 1H), 1.12-1.06 (m, 2H), 1.02-0.96 (m, J = 5.5 Hz, 2H) |

TABLE 24-continued

| Ex. | Structure | Name | LCMS [M + H]+ | HPLC Method, RT (min.) | 1H NMR (δ NMR) |
|---|---|---|---|---|---|
| 449 | 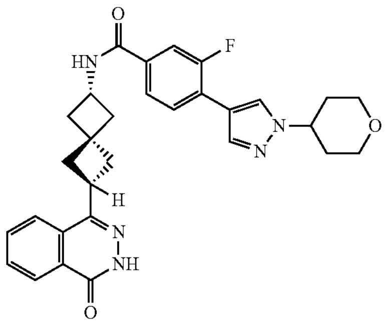 | 3-fluoro-N-((aR)-6-(4-oxo-3,4-dihydrophthalazin-1-yl)spiro[3.3]heptan-2-yl)-4-(1-(tetrahydro-2H-pyran-4-yl)-1H-pyrazol-4-yl)benzamide | 528.0 | E: 1.64 F: 1.98 | (500 MHz, DMSO-d<sub>6</sub>) δ 12.47 (br s, 1H), 8.64 (d, J = 7.0 Hz, 1H), 8.32 (br. s., 1H), 8.25 (d, J = 7.3 Hz, 1H), 7.99 (br. s., 1H), 7.93-7.79 (m, 4H), 7.76-7.69 (m, 2H), 4.48 (br. s., 1H), 4.35 (d, J = 7.0 Hz, 1H), 3.98 (d, J = 10.7 Hz, 2H), 3.90 (br. s., 2H), 3.49 (d, J = 13.4 Hz, 1H), 2.62 (br. s., 2H), 2.39 (d, J = 13.7 Hz, 3H), 2.24 (d, J = 8.2 Hz, 2H), 2.09 (d, J = 9.8 Hz, 1H), 2.00 (br. s., 4H) |
| 450 | 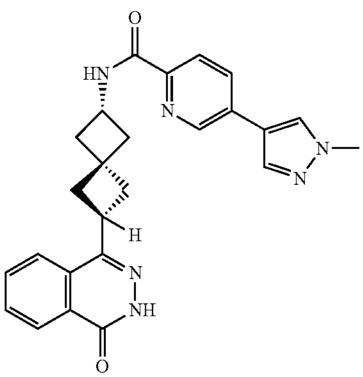 | 5-(1-methyl-1H-pyrazol-4-yl)-N-((aR)-6-(4-oxo-3,4-dihydrophthalazin-1-yl)spiro[3.3]heptan-2-yl)picolinamide | 441.0 | E: 1.45 F: 1.52 | (500 MHz, DMSO-d<sub>6</sub>) δ 12.46 (s, 1H), 8.85 (s, 1H), 8.80 (d, J = 7.9 Hz, 1H), 8.37 (s, 1H), 8.25 (d, J = 7.9 Hz, 1H), 8.12 (d, J = 7.9 Hz, 1H), 8.06 (s, 1H), 7.97 (d, J = 8.2 Hz, 1H), 7.94-7.80 (m, 3H), 4.46-4.28 (m, 1H), 3.90 (s, 3H), 3.95-3.84 (m, 1H), 2.58 (d, J = 9.2 Hz, 2H), 2.45-2.30 (m, 4H), 2.26-2.12 (m, 2H) |
| 451 | 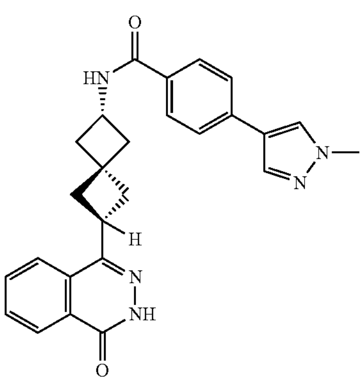 | 4-(1-methyl-1H-pyrazol-4-yl)-N-((aR)-6-(4-oxo-3,4-dihydrophthalazin-1-yl)spiro[3.3]heptan-2-yl)benzamide | 440.3 | E: 1.38 F: 1.33 | (500 MHz, DMSO-d<sub>6</sub>) δ 12.49 (s, 1H), 8.54 (d, J = 7.3 Hz, 1H), 8.25 (d, J = 7.8 Hz, 1H), 8.23 (s, 1H), 7.94 (s, 1H), 7.91 (d, J = 7.2 Hz, 1H), 7.88 (s, 1H), 7.83 (d, J = 7.7 Hz, 3H), 7.64 (d, J = 8.2 Hz, 2H), 4.44-4.27 (m, 1H), 3.95-3.88 (m, 1H), 3.86 (s, 3H), 2.68-2.55 (m, 2H), 2.44-2.31 (m, 3H), 2.28-2.17 (m, 2H), 2.07 (t, J = 10.0 Hz, 1H) |
| 452 | 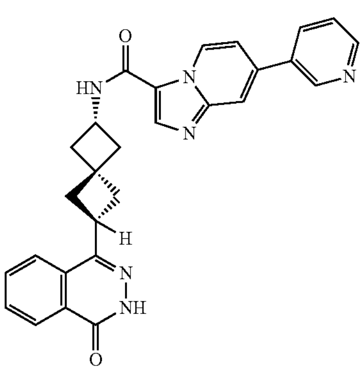 | N-((aR)-6-(4-oxo-3,4-dihydrophthalazin-1-yl)spiro[3.3]heptan-2-yl)-7-(pyridin-3-yl)imidazo[1,2-a]pyridine-3-carboxamide | 477.1 | E: 1.39 F: 1.71 | (500 MHz, DMSO-d<sub>6</sub>) δ 12.48 (s, 1H), 9.51 (d, J = 7.3 Hz, 1H), 9.09 (s, 1H), 8.69-8.59 (m, 2H), 8.41 (s, 1H), 8.31-8.22 (m, 2H), 8.14 (s, 1H), 7.97-7.80 (m, 3H), 7.61-7.50 (m, 2H), 4.48-4.34 (m, 1H), 3.98-3.85 (m, 1H), 2.67 (br. s., 1H), 2.63-2.55 (m, 1H), 2.45-2.34 (m, 3H), 2.32-2.23 (m, 2H), 2.09 (t, J = 10.1 Hz, 1H) |

TABLE 24-continued

| Ex. | Structure | Name | LCMS [M + H]+ | HPLC Method, RT (min.) | 1H NMR (δ NMR) |
|---|---|---|---|---|---|
| 453 | 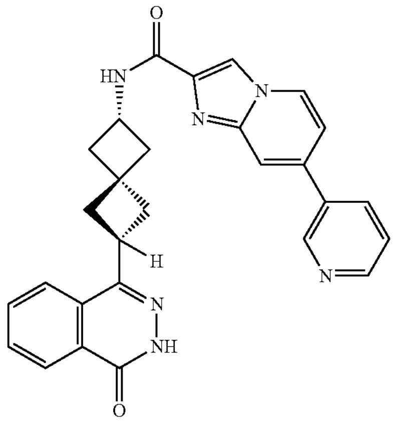 | N-((aR)-6-(4-oxo-3,4-dihydrophthalazin-1-yl)spiro[3.3]heptan-2-yl)-7-(pyridin-3-yl)imidazo[1,2-a]pyridine-2-carboxamide | 477.0 | E: 1.40 F: 1.68 | (500 MHz, DMSO-$d_6$) δ 12.47 (s, 1H), 9.05 (s, 1H), 8.95 (s, 1H), 8.63 (d, J = 4.3 Hz, 1H), 8.57 (d, J = 8.2 Hz, 1H), 8.35 (s, 1H), 8.25 (d, J = 7.6 Hz, 1H), 8.15 (d, J = 7.9 Hz, 1H), 7.95-7.81 (m, 3H), 7.79-7.69 (m, 2H), 7.59-7.52 (m, 1H), 4.46-4.32 (m, 1H), 3.97-3.81 (m, J = 8.4, 8.4 Hz, 1H), 2.65-2.53 (m, 2H), 2.44-2.30 (m, 4H), 2.25-2.13 (m, 2H) |
| 454 | 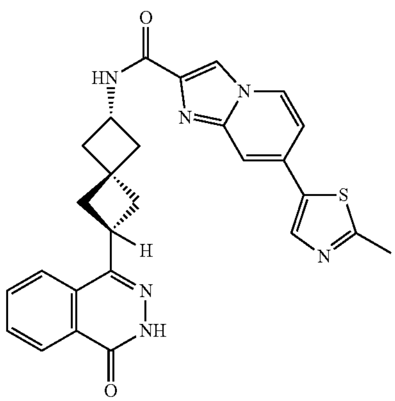 | 7-(2-methylthiazol-5-yl)-N-((aR)-6-(4-oxo-3,4-dihydrophthalazin-1-yl)spiro[3.3]heptan-2-yl)imidazo[1,2-a]pyridine-2-carboxamide | 497.2 | E: 1.22 F: 1.45 | (400 MHz, DMSO-$d_6$) δ 12.46 (s, 1H), 8.90 (s, 1H), 8.52 (d, J = 8.1 Hz, 1H), 8.32 (s, 1H), 8.25 (d, J = 7.0 Hz, 1H), 8.08 (s, 1H), 7.95-7.81 (m, 3H), 7.70-7.62 (m, 2H), 4.38 (sxt, J = 8.0 Hz, 1H), 3.89 (quin, J = 8.4 Hz, 1H), 2.71 (s, 3H), 2.62-2.55 (m, 2H), 2.42-2.32 (m, 5H), 2.21-2.16 (m, 1H) |
| 455 | 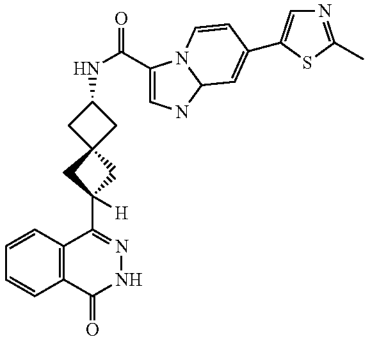 | 7-(2-methylthiazol-5-yl)-N-((aR)-6-(4-oxo-3,4-dihydrophthalazin-1-yl)spiro[3.3]heptan-2-yl)imidazo[1,2-a]pyridine-3-carboxamide | 497.3 | A: 4.78 B. 6.80 | (400 MHz, DMSO-$d_6$) δ 12.47 (s, 1H), 9.49 (d, J = 7.3 Hz, 1H), 8.77 (d, J = 7.5 Hz, 1H), 8.50 (s, 1H), 8.37 (s, 1H), 8.26 (d, J = 7.9 Hz, 1H), 7.98 (s, 1H), 7.95-7.80 (m, 3H), 7.61 (dd, J = 7.4, 1.9 Hz, 1H), 4.40 (sxt, J = 8.1 Hz, 1H), 3.92 (quin, J = 8.5 Hz, 1H), 2.75-2.70 (m, 3H), 2.69-2.63 (m, 3H), 2.62-2.55 (m, 1H), 2.44-2.36 (m, 3H), 2.31-2.22 (m, 2H), 2.14-2.04 (m, 1H) |

Example 457: 4-((aR)-6-(1-oxoisoindolin-2-yl)spiro[3.3]heptan-2-yl)phthalazin-1(2H)-one

Example 458: 4-((aR)-6-((S)-4-benzyl-2-oxoimidazolidin-1-yl)spiro[3.3]heptan-2-yl)phthalazin-1(2H)-one

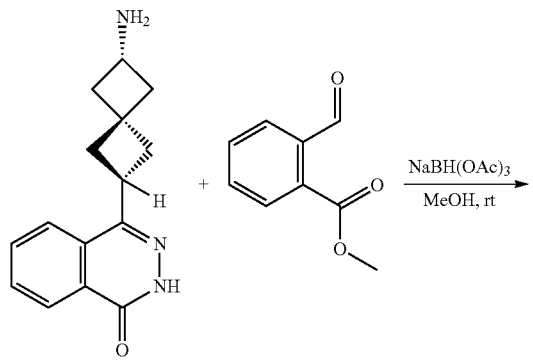

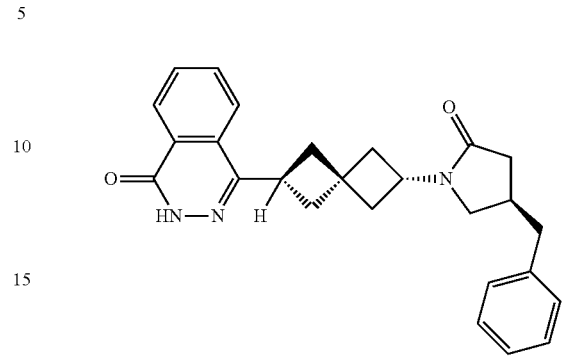

Example 458A tert-butyl ((S)-1-(((aR)-6-(4-oxo-3,4-dihydrophthalazin-1-yl)spiro[3.3]heptan-2-yl)amino)-3-phenylpropan-2-yl)carbamate

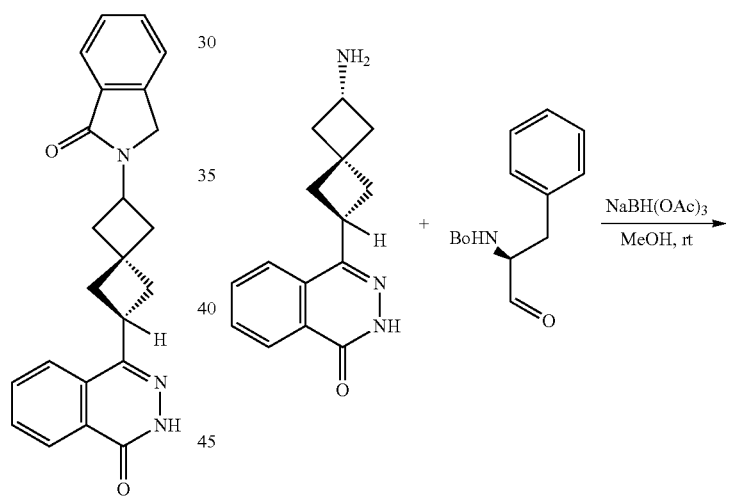

To a solution of Intermediate 2 (15 mg, 0.051 mmol) in MeOH (1 mL) were added methyl-2-formylbenzoate (25 mg, 0.15 mmol) and NaBH(OAc)$_3$ (33 mg, 0.15 mmol) at rt. The reaction was stirred under N$_2$ at rt for 1 h. It was heated then at 50° C. for another 1 h. The reaction was quenched by adding one drop of TFA, and then was diluted with DMF. Purification by reverse phase chromatography provided Example 457 (4.0 mg, 21%). LC-MS(ESI) m/z: 372.0 [M+H]$^+$. $^1$H NMR (500 MHz, DMSO-d$_6$) δ 12.50 (s, 1H), 8.26 (d, J=7.8 Hz, 1H), 7.98-7.78 (m, 3H), 7.66 (d, J=7.5 Hz, 1H), 7.59 (d, J=3.7 Hz, 2H), 7.48 (d, J=3.5 Hz, 1H), 4.69 (t, J=8.4 Hz, 1H), 4.61-4.46 (m, 2H), 4.02-3.82 (m, 1H), 2.68-2.53 (m, 2H), 2.48-2.35 (m, 4H), 2.34-2.26 (m, 1H), 2.18 (d, J=4.7 Hz, 1H). Analytical HPLC RT=1.45 min (Method E), 1.46 min (Method F).

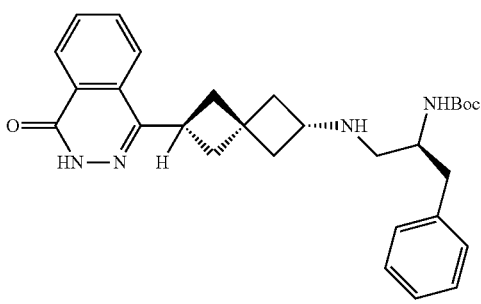

To a solution of Intermediate 2 (20 mg, 0.069 mmol) in MeOH (1 mL) were added (S)-tert-butyl (1-oxo-3-phenylpropan-2-yl)carbamate (18.8 mg, 0.075 mmol) and NaBH(OAc)$_3$ (44 mg, 0.21 mmol) at rt. The reaction was stirred under N$_2$ at rt for 3 h. The solvent was removed to give a white solid of crude product, which was used in the next step. LC-MS(ESI) m/z: 489.1 [M+H]$^+$.

Example 458

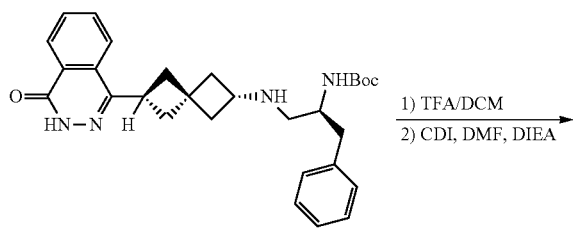

To a solution of Example 458A (33.7 mg, 0.069 mmol) in DCM (2 mL) was added TFA (1.0 mL) at rt. The reaction was stirred at rt for 30 min and the solvent was removed. To the residue were added DMF (1 mL), DIEA (0.1 mL) and then CDI (11 mg, 0.069 mmol) at rt. The reaction was stirred under $N_2$ at 60° C. for 1 h. Purification by reverse phase chromatography provided Example 458 (2.2 mg, 8%). LC-MS(ESI) m/z: 415.3 [M+H]$^+$. $^1$H NMR (500 MHz, DMSO-$d_6$) δ 12.47 (s, 1H), 8.24 (d, J=7.7 Hz, 1H), 7.90 (d, J=7.6 Hz, 1H), 7.84 (d, J=8.1 Hz, 2H), 7.36-7.26 (m, 2H), 7.23 (d, J=7.4 Hz, 3H), 6.51 (s, 1H), 4.10 (t, J=8.5 Hz, 1H), 3.93-3.71 (m, 2H), 3.30 (t, J=8.5 Hz, 1H), 3.04 (t, J=7.4 Hz, 1H), 2.81 (d, J=9.0 Hz, 1H), 2.69-2.61 (m, 1H), 2.39-2.19 (m, 4H), 2.18-2.08 (m, 1H), 2.01 (t, J=9.8 Hz, 1H), 1.90 (s, 2H). Analytical HPLC RT=1.68 min (Method E).

Example 459: 4-((aR)-6-((R)-4-benzyl-2-oxoimidazolidin-1-yl)spiro[3.3]heptan-2-yl)phthalazin-1(2H)-one

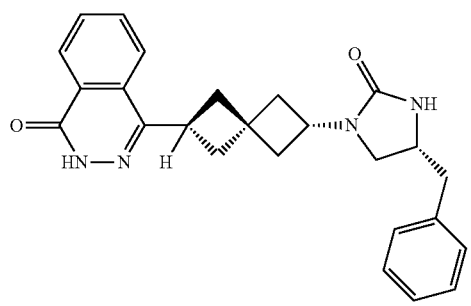

Example 459 was prepared by following the same procedure as described in the Example 458 by replacing (S)-tert-butyl (1-oxo-3-phenylpropan-2-yl)carbamate with (R)-tert-butyl (1-oxo-3-phenylpropan-2-yl)carbamate. LC-MS (ESI) m/z: 415.1 [M+H]$^+$. $^1$H NMR (500 MHz, DMSO-$d_6$) δ 12.45 (s, 1H), 8.24 (d, J=7.9 Hz, 1H), 7.93-7.87 (m, 1H), 7.86-7.78 (m, 2H), 7.33-7.26 (m, 2H), 7.22 (d, J=7.3 Hz, 4H), 4.17-4.06 (m, J=8.1, 8.1 Hz, 1H), 3.93-3.73 (m, 2H), 3.39-3.27 (m, 2H), 3.08-2.98 (m, 1H), 2.81 (dd, J=13.4, 4.9 Hz, 1H), 2.64 (dd, J=13.6, 7.8 Hz, 1H), 2.38-2.24 (m, 4H), 2.21-2.15 (m, 1H), 1.99 (t, J=10.4 Hz, 1H), 1.86 (br. s., 1H). Analytical HPLC RT=1.69 min (Method E), 1.74 min (Method F).

Example 460: 4-((aR)-6-((2-nitrophenyl)amino)spiro[3.3]heptan-2-yl)phthalazin-1(2H)-one

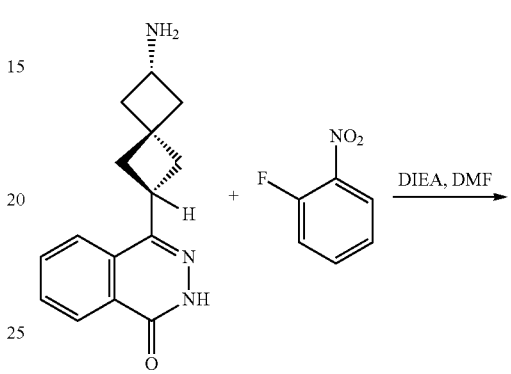

To a solution of Intermediate 2 (20 mg, 0.069 mmol) in DMF (1 mL) were added 1-fluoro-2-nitrobenzene (11 mg, 0.075 mmol) and DIEA (0.060 mL, 0.34 mmol) at rt. The reaction was stirred under $N_2$ at 50° C. for 3 h. The solvent was removed. Purification by normal phase chromatography provided Example 460 (24 mg, 91%) as a yellow solid. $^1$H NMR (400 MHz, DMSO-$d_6$) δ 12.46 (s, 1H), 8.28-8.19 (m, 1H), 8.07 (dd, J=8.6, 1.5 Hz, 1H), 7.99 (d, J=5.7 Hz, 1H), 7.95-7.89 (m, 1H), 7.88-7.79 (m, 2H), 7.54 (td, J=7.8, 1.5 Hz, 1H), 6.92 (d, J=8.8 Hz, 1H), 6.72 (ddd, J=8.4, 7.0, 1.1 Hz, 1H), 4.13-4.00 (m, 1H), 3.92 (quin, J=8.4 Hz, 1H), 2.84 (ddd, J=11.1, 6.7, 4.8 Hz, 1H), 2.64-2.56 (m, 1H), 2.47-2.36 (m, 4H), 2.19 (dd, J=10.8, 7.9 Hz, 1H), 1.98 (dd, J=11.1, 7.8 Hz, 1H). LC-MS(ESI) m/z: 377.1 [M+H]$^+$. Analytical HPLC RT=9.71 min (Method A), 10.64 min (Method B).

Example 461: 4-((aR)-6-(2-oxo-2,3-dihydro-1H-benzo[d]imidazol-1-yl)spiro[3.3]heptan-2-yl)phthalazin-1(2H)one

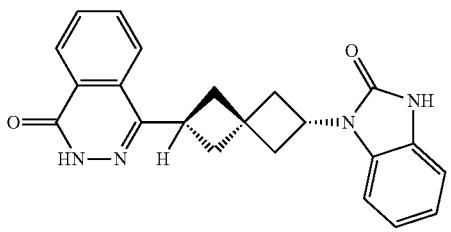

Example 461A 4-((aR)-6-((2-aminophenyl)amino)spiro[3.3]heptan-2-yl)phthalazin-1(2H)-one

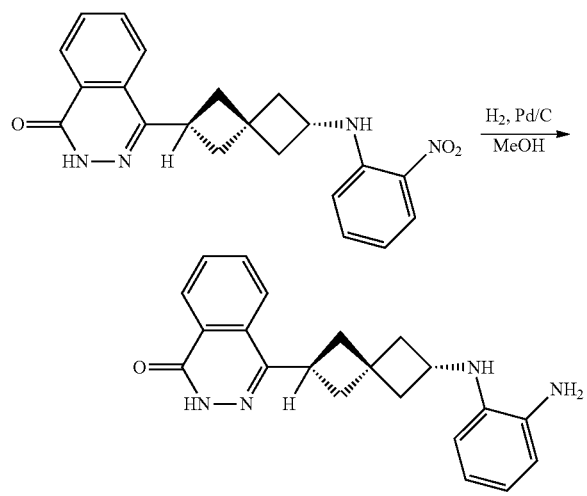

To a flask containing Example 460 (22 mg, 0.058 mmol) were added catalytic amount of 10% Pd/C and MeOH (5 mL). The reaction was stirred under a hydrogen balloon at rt for 2 h. The catalyst was filtered, and the solvent was removed from filtrate to give a white solid (19.5 mg, 96%). LC-MS(ESI) m/z: 347.1 [M+H]+.

Example 461

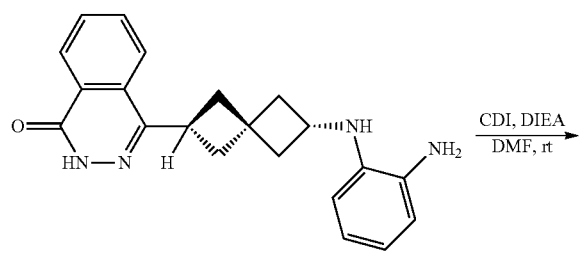

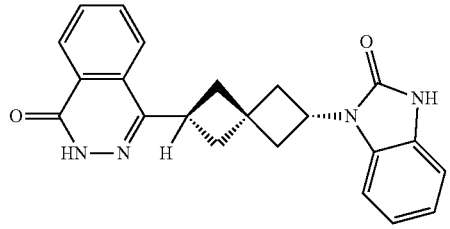

To a solution of Example 461A (19 mg, 0.055 mmol) in DMF (1 mL) were added CDI (8.9 mg, 0.055 mmol) and DIEA (0.03 mL, 0.17 mmol) at rt. The reaction was stirred under $N_2$ at rt for 1 h. Purification by reverse phase chromatography provided Example 461 (7.4 mg, 36%). $^1$H NMR (500 MHz, DMSO-$d_6$) δ 12.48 (s, 1H), 10.82 (s, 1H), 8.26 (d, J=7.9 Hz, 1H), 7.96-7.87 (m, 2H), 7.87-7.80 (m, 1H), 7.23 (d, J=7.0 Hz, 1H), 7.06-6.92 (m, 3H), 4.73 (quin, J=8.9 Hz, 1H), 4.01-3.85 (m, 1H), 2.98 (t, J=10.2 Hz, 1H), 2.81 (t, J=10.5 Hz, 1H), 2.72-2.61 (m, 2H), 2.53-2.41 (m, 3H), 2.32-2.22 (m, 1H). LC-MS(ESI) m/z: 373.2 [M+H]+. Analytical HPLC RT=1.55 min (Method E), 1.52 min (Method F).

Example 462: 4-cyclopropyl-N-((aR)-6-(4-oxo-3,4-dihydrophthalazin-1-yl)spiro[3.3]heptan-2-yl)pyrazolo[1,5-a]pyridine-3-carboxamide

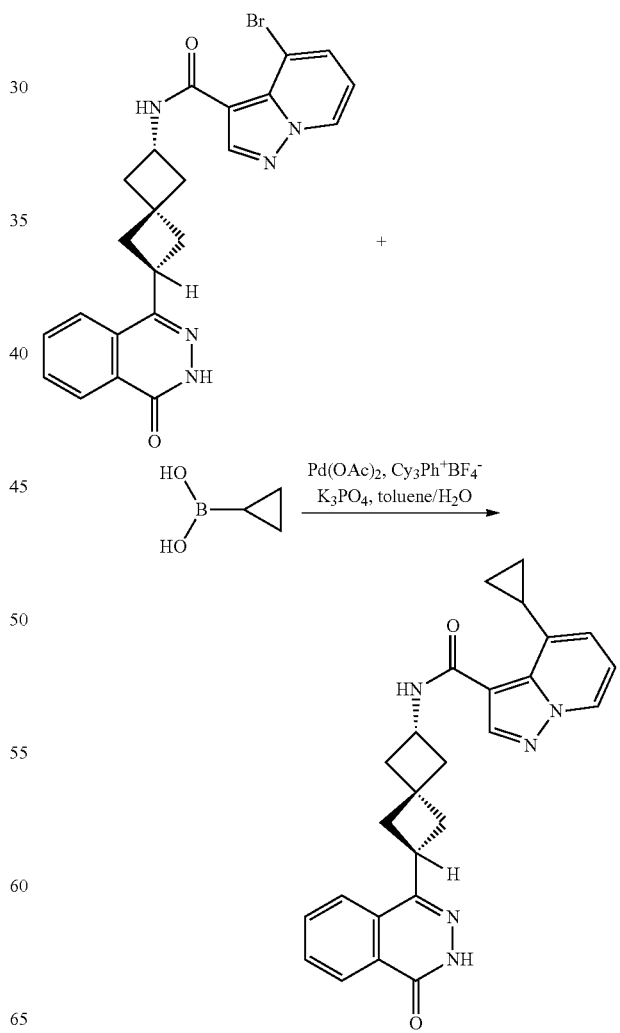

A vial charged with Example 304 (15 mg, 0.031 mmol), cyclopropylboronic acid (10.8 mg, 0.13 mmol), Pd(OAc)$_2$ (0.70 mg, 3.1 µmol) and K$_3$PO$_4$ (20 mg, 0.094 mmol) was degassed and purged with argon, and then toluene (2.0 mL) and H$_2$O (0.2 mL) were added. The mixture was degassed again and then tricyclohexylphosphonium tetrafluoroborate (2.3 mg, 6.3 µmol) was added at rt. The reaction was heated in a sealed vial at 100° C. for 3 h. The solvent was removed. Purification by reverse phase chromatography provided Example 462 (2.2 mg, 15%). $^1$H NMR (500 MHz, DMSO-d$_6$) δ 12.49 (s, 1H), 8.55 (d, J=6.5 Hz, 1H), 8.48 (d, J=7.3 Hz, 1H), 8.25 (d, J=7.7 Hz, 1H), 8.22 (s, 1H), 7.98-7.75 (m, 3H), 6.97-6.85 (m, 2H), 4.32 (sxt, J=8.0 Hz, 1H), 3.89 (quin, J=8.4 Hz, 1H), 2.89 (d, J=7.8 Hz, 1H), 2.67-2.58 (m, 1H), 2.58-2.54 (m, 1H), 2.44-2.29 (m, 3H), 2.27-2.13 (m, 2H), 2.01 (t, J=10.0 Hz, 1H), 0.88 (d, J=8.4 Hz, 2H), 0.67 (d, J=4.5 Hz, 2H). LC-MS(ESI) m/z: 440.2 [M+H]$^+$. Analytical HPLC RT=1.42 min (Method F).

Example 463: 3-fluoro-5-(1-methyl-1H-pyrazol-4-yl)-N-((aR)-6-(4-oxo-3,4-dihydrophthalazin-1-yl)spiro[3.3]heptan-2-yl)picolinamide

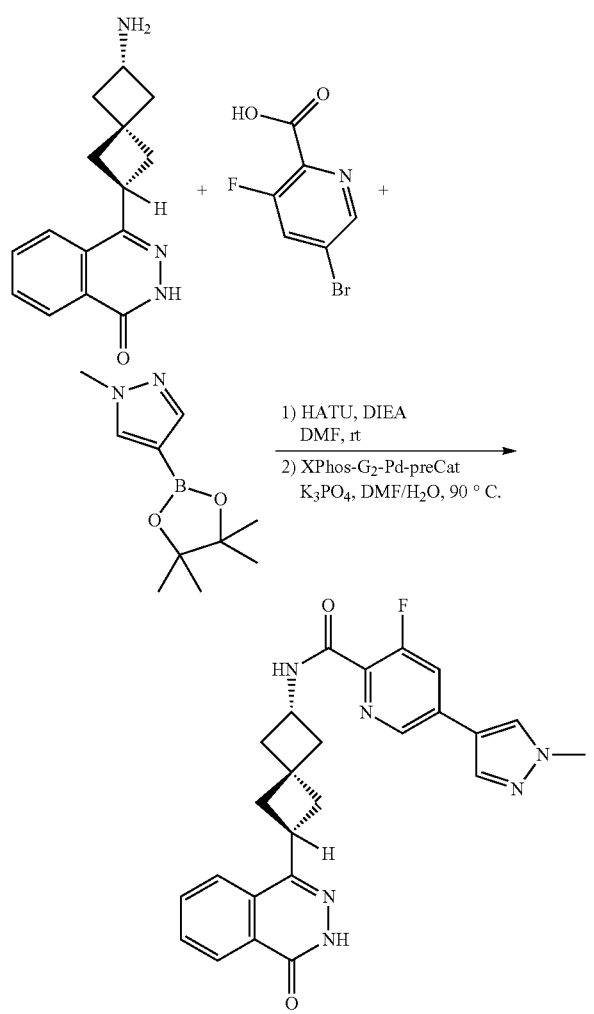

To a solution of Intermediate 2 (20 mg, 0.078 mmol) in DMF (1 mL) were added 5-bromo-3-fluoropicolinic acid (17.2 mg, 0.078 mmol), HATU (32.8 mg, 0.086 mmol) and DIEA (0.068 mL, 0.39 mmol) at rt. The reaction was stirred under N$_2$ at rt for 1 h. To the reaction were added 1-methyl-4-(4,4,5,5-tetramethyl-1,3,2-dioxaborolan-2-yl)-1H-pyrazole (24.5 mg, 0.12 mmol), K$_3$PO$_4$ (50 mg, 0.24 mmol), water (0.2 mL), and XPhos-G2-Pd-preCat (6.2 mg, 7.8 µmol). The reaction was heated at 90° C. for 2 h, and then it was cooled to rt. It was filtered. Purification by reverse phase chromatography provided Example 463 (7.4 mg, 21%). $^1$H NMR (500 MHz, DMSO-d$_6$) δ 12.46 (s, 1H), 8.73 (d, J=7.9 Hz, 1H), 8.71 (br. s., 1H), 8.42 (s, 1H), 8.25 (d, J=7.6 Hz, 1H), 8.11 (s, 1H), 8.04 (d, J=12.2 Hz, 1H), 7.95-7.80 (m, 3H), 4.40-4.26 (m, 1H), 3.89 (s, 3H), 3.95-3.82 (m, 1H), 2.57 (d, J=9.5 Hz, 2H), 2.45-2.33 (m, 3H), 2.32-2.25 (m, 1H), 2.22 (br. s., 1H), 2.15-2.04 (m, 1H). LC-MS(ESI) m/z: 459.1 [M+H]$^+$. Analytical HPLC RT=1.44 min (Method E), 1.48 min (Method F).

Example 464: 6-(4-oxo-3,4-dihydrophthalazin-1-yl)spiro[3.3]heptan-2-yl isoindoline-2-carboxylate

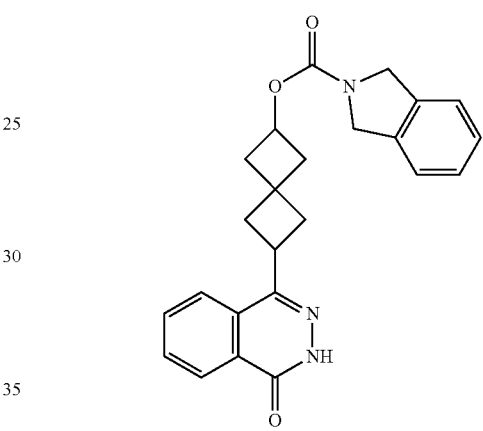

Example 464A 4-(6-hydroxyspiro[3.3]heptan-2-yl)phthalazin-1(2H)-one

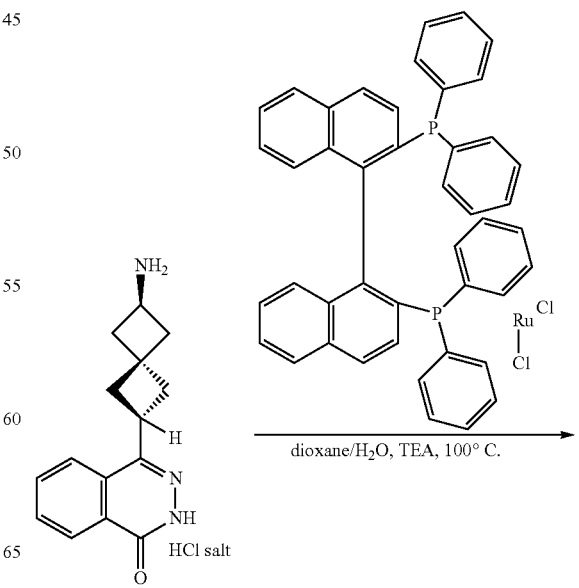

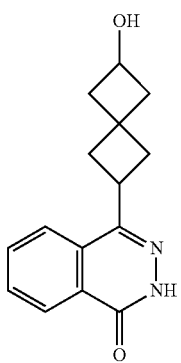

To a solution of Intermediate 2 (50 mg, 0.17 mmol) in dioxane (1 mL) and H₂O (1 mL) were added dichloro[(R)-(+)-2,2'-bis(diphenylphosphino)-1,1'-binaphthyl]ruthenium (II) (6.8 mg, 8.6 µmol) and TEA (1 drop) at rt. The reaction was heated in a sealed vial at 120° C. for 12 h. The solvent was removed. The crude product was purified by reverse phase chromatography to give Example 464A (10 mg, 23%) as a white solid. ¹H NMR (400 MHz, CD₃OD) δ 8.35 (dd, J=7.8, 1.0 Hz, 1H), 7.83-7.78 (m, 1H), 7.77-7.71 (m, 1H), 7.69 (d, J=8.1 Hz, 1H), 4.13 (quin, J=7.4 Hz, 1H), 3.80 (quin, J=8.5 Hz, 1H), 2.62-2.54 (m, 1H), 2.47-2.31 (m, 4H), 2.25 (dt, J=11.7, 6.1 Hz, 1H), 2.02 (dd, J=11.0, 7.7 Hz, 1H), 1.86 (dd, J=11.4, 7.7 Hz, 1H). LC-MS(ESI) m/z: 257.0 [M+H]⁺.

Example 464

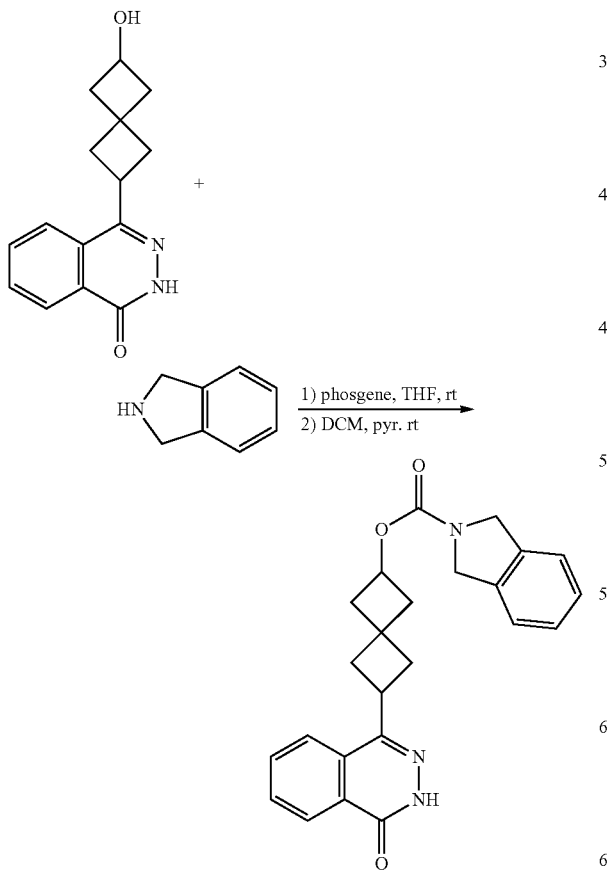

To a solution of Example 464A (10 mg, 0.039 mmol) in THF (2 mL) was added phosgene (129 mg, 0.20 mmol) at rt. The reaction was stirred at rt overnight. The solvent was removed. To the residue were added DCM (2 mL), isoindoline (14 mg, 0.12 mmol) and TEA at 0° C. The reaction was stirred under N₂ at rt for 2 h. The solvent was removed. The crude product was purified by reverse phase chromatography to provide Example 464 (2.5 mg, 16%) as a light tan solid. ¹H NMR (400 MHz, CD₃OD) δ 8.36 (d, J=7.9 Hz, 1H), 7.96-7.87 (m, 2H), 7.87-7.80 (m, 1H), 7.35-7.25 (m, 4H), 4.96 (quin, J=7.1 Hz, 1H), 4.72 (s, 2H), 4.68 (s, 2H), 3.96 (quin, J=8.3 Hz, 1H), 2.82-2.72 (m, 1H), 2.62-2.48 (m, 4H), 2.42 (dt, J=11.9, 5.9 Hz, 1H), 2.31 (dd, J=11.4, 7.3 Hz, 1H), 2.13 (dd, J=11.8, 7.4 Hz, 1H). LC-MS(ESI) m/z: 402.2 [M+H]⁺. Analytical HPLC RT=8.75 min (Method A), 9.65 min (Method B).

Example 465: 7-(methylsulfonyl)-N-((aR)-6-(4-oxo-3,4-dihydrophthalazin-1-yl)spiro[3.3]heptan-2-yl)imidazo[1,2-a]pyridine-3-carboxamide

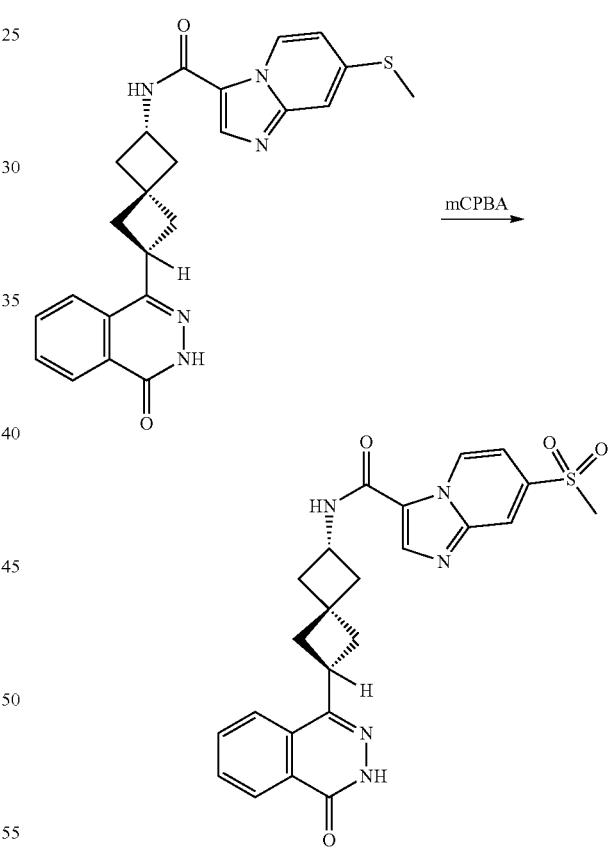

To a solution of Example 414 (15 mg, 0.027 mmol) in DCM (3 mL) were added mCPBA (23 mg, 0.13 mmol) at rt. The reaction was stirred under N₂ at rt for 2 h. The solvent was removed. Purification by reverse phase chromatography provided Example 465 (3.1 mg, 18%). ¹H NMR (500 MHz, DMSO-d₆) δ 12.50 (s, 1H), 9.61 (d, J=7.3 Hz, 1H), 8.87 (d, J=7.3 Hz, 1H), 8.54 (br. s., 1H), 8.30-8.16 (m, 2H), 7.95-7.89 (m, 1H), 7.89-7.81 (m, 2H), 7.54 (d, J=7.1 Hz, 1H), 4.39 (sxt, J=8.1 Hz, 1H), 3.95-3.84 (m, 1H), 3.32 (s, 3H), 2.65 (br. s., 1H), 2.58 (br. s., 1H), 2.43-2.33 (m, 3H), 2.29-2.21 (m, 2H), 2.12-2.02 (m, 1H). LC-MS(ESI) m/z: 478.1 [M+H]+. Analytical HPLC RT=1.18 min (Method E), 1.23 min (Method F).

Example 469: 2-methyl-2-((3-(((aR)-6-(4-oxo-3,4-dihydrophthalazin-1-yl)spiro[3.3]heptan-2-yl)carbamoyl)pyrazolo[1,5-a]pyridin-6-yl)oxy)propanoic acid

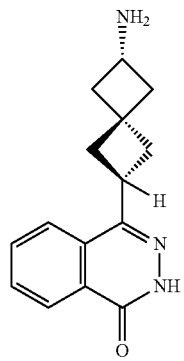

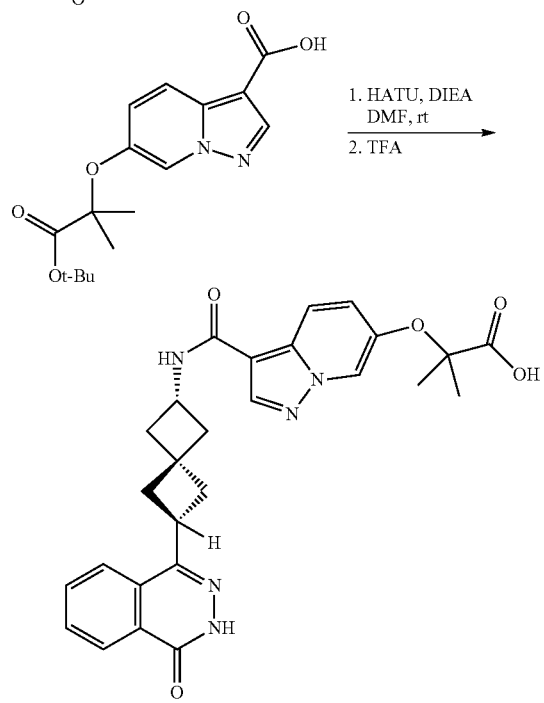

To a suspension of Intermediate 77 (17.3 mg, 0.054 mmol) and Intermediate 2, HCl (13.7 mg, 0.047 mmol) in DMF (5 mL), were added HATU (19.6 mg, 0.052 mmol) and DIEA (0.025 mL, 0.141 mmol). The mixture was stirred at rt for 1 h, then was diluted with EtOAc. The organic phase was washed with H₂O (2×) and brine, dried (Na₂SO₄) and concentrated. The residue was dissolved in TFA (1 mL) with a drop of water. The mixture was stirred at rt for 45 min, then was concentrated. The product was purified by preparative HPLC to afford Example 469 (24 mg, 100% yield). ¹H NMR (500 MHz, DMSO-d₆) δ 12.43 (s, 1H), 8.45 (s, 1H), 8.27 (s, 1H), 8.23 (dd, J=14.2, 7.8 Hz, 2H), 8.05 (d, J=9.8 Hz, 1H), 7.91-7.85 (m, 1H), 7.85-7.76 (m, 2H), 7.23 (d, J=9.5 Hz, 1H), 4.38-4.26 (m, 1H), 3.86 (quin, J=8.4 Hz, 1H), 2.64-2.52 (m, 2H), 2.41-2.29 (m, 3H), 2.24-2.11 (m, 2H), 2.00 (t, J=10.1 Hz, 1H), 1.48 (s, 6H); LC-MS(ESI) m/z: 424.4 [M+H]+. Analytical HPLC RT=1.48 min (Method E), 1.163 min (Method F).

What is claimed is:
1. A compound of Formula (I):

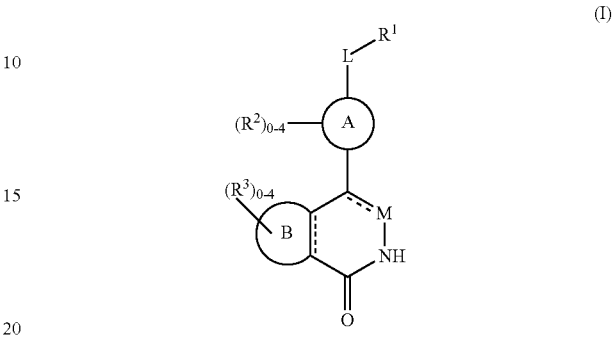

or a stereoisomer, a tautomer, a pharmaceutically-acceptable salt thereof, wherein:
Ring A is a 5- to 9-membered bicyclic spiro carbocycle;

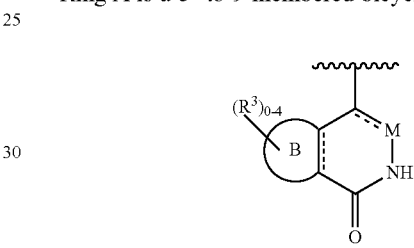

is selected from

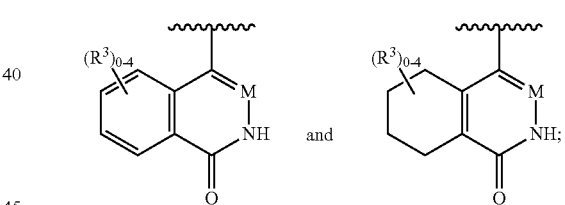

M is absent or selected from N and CR¹⁰;
L is selected from —(CR⁴R⁴)₀₋₁—, —(CR⁴R⁴)₀₋₁C(O)—, —OC(O)—, —NR⁶C(O)—, and —NR⁶—;
R¹ is selected from NR⁵R⁵, OR⁵, —(CR⁴R⁴)ₙC₃₋₁₀ carbocycle and —(CR⁴R⁴)ₙ-4- to 15-membered heterocycle comprising carbon atoms and 1-4 heteroatoms selected from N, NR⁸, O, and S(O)ₚ; wherein said carbocycle, and heterocycle are substituted with 1-4 R⁷;
R², at each occurrence, is independently selected from halogen, C₁₋₆ alkyl, C₁₋₄ alkoxy, C₁₋₄ alkylthio, C₁₋₄ haloalkyl, —OH, —CH₂OH, —OCH₂F, —OCHF₂, —OCF₃, CN, —NH₂, —NH(C₁₋₄ alkyl), —N(C₁₋₄ alkyl)₂, —CO₂H, —CH₂CO₂H, —CO₂(C₁₋₄ alkyl), —CO(C₁₋₄ alkyl), —CH₂NH₂, —CONH₂, —CONH (C₁₋₄ alkyl), —CON(C₁₋₄ alkyl)₂, —OCH₂CO₂H, —NHCO(C₁₋₄ alkyl), —NHCO₂(C₁₋₄ alkyl), —NHSO₂(C₁₋₄ alkyl), —SO₂NH₂, —C(=NH)NH₂, a carbocycle, and a heterocycle, wherein said alkyl, alkoxy, alkylthio, haloalkyl, carbocycle, and heterocycle are substituted with 0-4 R⁹;

R³, at each occurrence, is independently selected from halogen, $C_{1-6}$ alkyl, $C_{1-4}$ alkoxy, $C_{1-4}$ alkylthio, $C_{1-4}$ haloalkyl, —$CH_2OH$, —$OCH_2F$, —$OCHF_2$, —$OCF_3$, CN, —$NH_2$, —NH($C_{1-4}$ alkyl), —N($C_{1-4}$ alkyl)$_2$, —$CO_2H$, —$CH_2CO_2H$, —$CO_2(C_{1-4}$ alkyl), —$CO(C_{1-4}$ alkyl), —$CH_2NH_2$, —$CONH_2$, —CONH($C_{1-4}$ alkyl), —CON($C_{1-4}$ alkyl)$_2$, —$OCH_2CO_2H$, —NHCO($C_{1-4}$ alkyl), —$NHCO_2(C_{1-4}$ alkyl), —$NHSO_2(C_{1-4}$ alkyl), —$SO_2NH_2$, —C(=NH)$NH_2$, a carbocycle, and a heterocycle, wherein said alkyl, alkoxy, alkylthio, haloalkyl, carbocycle, and heterocycle are substituted with 0-4 $R^9$;

R⁴, at each occurrence, is independently selected from H, OH, $NH_2$, $CH_2NH_2$, $C_{1-4}$ haloalkyl, $OCH_2F$, $OCHF_2$, $OCF_3$, —NH($C_{1-4}$ alkyl), —N($C_{1-4}$ alkyl)$_2$, $C_{1-4}$ alkoxy, $CH_2OH$, $CH_2O(C_{1-4}$ alkyl), $CH_2CO_2H$, $CH_2CO_2(C_{1-4}$ alkyl), $C_{1-4}$ alkyl, a carbocycle, and a heterocycle, wherein said alkyl, alkoxy, haloalkyl, carbocycle, and heterocycle are substituted with 0-4 $R^9$;

R⁵, at each occurrence, is independently selected from H, $C_{1-4}$ alkyl, —(CR⁶R⁶)$_n$—$C_{3-10}$ carbocycle and —(CR⁶R⁶)$_n$-4- to 10-membered heterocycle comprising carbon atoms and 1-4 heteroatoms selected from N, NR⁸, O, and S(O)$_p$, wherein said alkyl, carbocycle and heterocycle are substituted with 1-4 $R^7$;

alternatively, R⁵ and R⁵ are taken together with the nitrogen atom to which they are attached to form a 4- to 15-membered substituted with 1-4 $R^7$;

R⁶, at each occurrence, is independently selected from H, $C_{1-4}$ alkyl, $CH_2NH_2$, $C_{1-4}$ haloalkyl, $C_{1-4}$ alkoxy, $CH_2OH$, $CH_2O(C_{1-4}$ alkyl), $CH_2CO_2H$, $CH_2CO_2(C_{1-4}$ alkyl), a carbocycle, and a heterocycle, wherein said alkyl, alkoxy, haloalkyl, carbocycle, and heterocycle are substituted with 0-4 $R^9$;

alternatively, R¹ and R⁶ are taken together with the nitrogen atom to which they are attached to form a heterocycle comprising carbon atoms and 1-4 heteroatoms selected from N, NR⁸, O, and S(O)$_p$ and substituted with 1-4 R;

R⁷, at each occurrence, is independently selected from H, =O, $NO_2$, halogen, $C_{1-7}$ alkyl, $C_{2-4}$ alkenyl, $C_{2-4}$ alkynyl, $C_{1-4}$ alkoxy, CN, OH, $CHF_2$, $CF_3$, —(CH$_2$)$_n$—$CO_2H$, —(CH$_2$)$_n$—$CO_2(C_{1-4}$ alkyl), —(CH$_2$)$_n$—NR⁸R⁸, —NHCOH, —NHCO($C_{1-4}$ alkyl), —$NHCOCF_3$, —$NHCO_2(C_{1-4}$ alkyl), —$NHCO_2$(CH$_2$)$_2$ O($C_{1-4}$ alkyl), —$NHCO_2$(CH$_2$)$_3$O($C_{1-4}$ alkyl), —$NHCO_2$(CH$_2$)$_2$OH, —$NHCO_2$(CH$_2$)$_2$NH$_2$, —$NHCO_2$(CH$_2$)$_2$N($C_{1-4}$ alkyl)$_2$, —$NHCO_2CH_2CO_2H$, —$CH_2NHCO_2(C_{1-4}$ alkyl), —NHC(O)NR⁸R⁸, —$NHSO_2(C_{1-4}$ alkyl), —S(O)$_p$($C_{1-4}$ alkyl), —$SO_2NH_2$, —$SO_2NH(C_{1-4}$ alkyl), —$SO_2N(C_{1-4}$ alkyl)$_2$, —$SO_2NH$(CH$_2$)$_2$OH, —$SO_2NH$(CH$_2$)$_2$O($C_{1-4}$ alkyl), —(CH$_2$)$_n$—CONR⁸R⁸, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR⁸, O, and S(O)$_p$, wherein said alkyl, alkenyl, alkynyl, alkoxyl, carbocycle, and heterocycle are substituted with 0-4 $R^9$;

R⁸, at each occurrence, is independently selected from H, $C_{1-6}$ alkyl, $C_{2-4}$ alkenyl, $C_{2-4}$ alkynyl, —(CH$_2$)$_n$—C(O)$C_{1-4}$alkyl, —(CH$_2$)$_n$—C(O)carbocycle, —(CH$_2$)$_n$—C(O)heterocycle, —(CH$_2$)$_n$—C(O)NR$^a$R$^a$, —(CH$_2$)$_n$—NR$^a$C(O) $C_{1-4}$alkyl, —(CH$_2$)$_n$—C(O)OC$_{1-4}$alkyl, —(CH$_2$)$_n$—C(O)$C_{1-4}$alkyl, —(CH$_2$)$_n$—C(O)O-carbocycle, —(CH$_2$)$_n$—C(O)O-heterocycle, —(CH$_2$)$_n$—SO$_2$alkyl, —(CH$_2$)$_n$—SO$_2$carbocycle, —(CH$_2$)$_n$—SO$_2$heterocycle, —(CH$_2$)$_n$—SO$_2$NR$^a$R$^a$, —(CH$_2$)$_n$-carbocycle, and —(CH$_2$)$_n$-heterocycle, wherein said alkyl, carbocycle, and heterocycle are substituted with 0-4 $R^9$;

alternatively, R⁸ and R⁸ are taken together with the nitrogen atom to which they are attached to form a 4- to 10-membered heterocycle substituted with 0-4 $R^9$;

R⁹, at each occurrence, is independently selected from halogen, OH, =O, CN, $NO_2$, $CHF_2$, $CF_3$, $C_{1-4}$ alkyl, $C_{1-4}$ alkoxy, $CH_2OH$, $CO(C_{1-4}$ alkyl), $CO_2H$, $CO_2(C_{1-4}$ alkyl), —(CHR¹⁰)$_n$NR$^a$R$^a$, —(CHR¹⁰)$_n$CONR$^a$R$^a$, —(CHR¹⁰)$_n$NR$^a$CO($C_{1-4}$ alkyl), —O(CHR¹⁰)$_n$carbocycle, —O(CHR¹⁰)$_n$heterocycle, —O(CHR¹⁰)$_n$NR$^a$R$^a$, and —(CR¹⁰R¹⁰)$_n$-4- to 10-membered heterocycle, wherein said alkyl, alkoxy, carbocycle, and heterocycle are substituted with 0-4 $R^b$;

R¹⁰ is selected from H and $C_{1-4}$ alkyl;

R$^a$, at each occurrence, is independently selected from H, $C_{1-4}$ alkyl, —(CH$_2$)$_n$OH, CO($C_{1-4}$ alkyl), COCF$_3$, $CO_2$($C_{1-4}$ alkyl), —$CONH_2$, —CONH—$C_{1-4}$ alkylene-$CO_2$($C_{1-4}$ alkyl), $C_{1-4}$ alkylene-$CO_2$($C_{1-4}$ alkyl), R$^c$, $CO_2$R$^c$, and CONHR$^c$; alternatively, R$^a$ and R$^a$ are taken together with the nitrogen atom to which they are attached to form a 4- to 10-membered heterocycle, wherein said alkyl, alkylene, and heterocycle are substituted with 0-4 $R^b$;

R$^b$, at each occurrence, is independently selected from =O, OH, halogen, $C_{1-4}$ alkyl, $C_{1-4}$ alkoxy, OCF$_3$, OC(O)$C_{1-4}$ alkyl, NH$_2$, NO$_2$, N($C_{1-4}$ alkyl)$_2$, CO($C_{1-4}$ alkyl), CO($C_{1-4}$ haloalkyl), CO$_2$($C_{1-4}$ alkyl), CONH$_2$, —CONH($C_{1-4}$ alkyl), —CON($C_{1-4}$ alkyl)$_2$, —CONH—$C_{1-4}$ alkylene-O($C_{1-4}$ alkyl), —CONH—$C_{1-4}$ alkylene-N($C_{1-4}$ alkyl)$_2$, —$C_{1-4}$ alkylene-O—P(O)(OH)$_2$, —NHCO$_2$($C_{1-4}$ alkyl), —R$^c$, COR$^c$, CO$_2$R$^c$, and CONHR$^c$, wherein said alkyl and alkoxy are substituted with $R^d$;

R$^c$, at each occurrence, is independently selected from —(CH$_2$)$_n$—$C_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N($C_{1-4}$ alkyl), O, and S(O)$_p$; wherein each ring moiety is substituted with 0-2 $R^d$;

R$^d$, at each occurrence, is independently selected from =O, halogen, —OH, $C_{1-4}$ alkyl, NH$_2$, NH($C_{1-4}$ alkyl), N($C_{1-4}$ alkyl)$_2$, $C_{1-4}$ alkoxy, and —NHCO($C_{1-4}$ alkyl), and a heterocycle containing carbon atoms and 1-4 heteroatoms selected from the group consisting of: N, NH, N($C_{1-4}$ alkyl), O, and S(O)$_p$;

n, at each occurrence, is independently selected from 0, 1, 2, 3, and 4; and p, at each occurrence, is independently selected from 0, 1, and 2.

2. The compound of claim 1, having Formula (II):

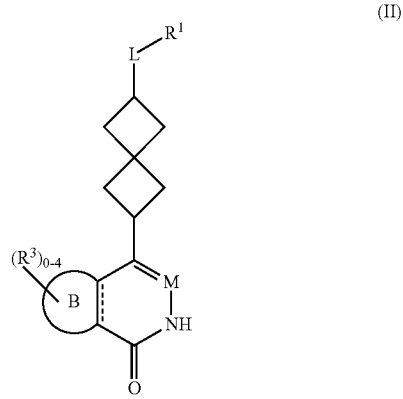

(II)

or a stereoisomer, a tautomer, a pharmaceutically-acceptable salt thereof, wherein:

is selected from

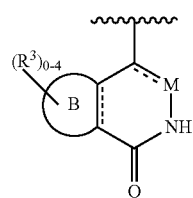

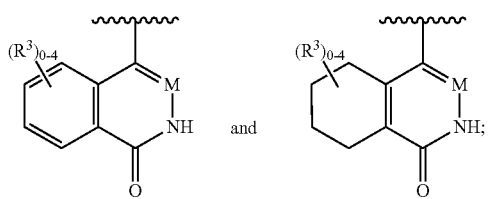

M is selected from N and $CR^{10}$;

L is selected from $-(CR^4R^4)_{0-1}-$, $-(CR^4R^4)_{0-1}C(O)-$, $-OC(O)-$, $-NR^6C(O)-$, and $-NR^6-$;

$R^1$ is selected from $NR^5R^5$, $OR^5$, $-(CR^4R^4)_nC_{3-10}$ carbocycle and $-(CR^4R^4)_n$-4- to 15-membered heterocycle comprising carbon atoms and 1-4 heteroatoms selected from N, $NR^8$, O, and $S(O)_p$; wherein said carbocycle, and heterocycle are substituted with 1-4 $R^7$;

$R^3$, at each occurrence, is independently selected from halogen, $C_{1-6}$ alkyl, $C_{1-4}$ alkoxy, $C_{1-4}$ alkylthio, $C_{1-4}$ haloalkyl, $-CH_2OH$, $-OCH_2F$, $-OCHF_2$, $-OCF_3$, CN, $-NH_2$, $-NH(C_{1-4}$ alkyl), $-N(C_{1-4}$ alkyl)$_2$, $-CO_2H$, $-CH_2CO_2H$, $-CO_2(C_{1-4}$ alkyl), $-CO(C_{1-4}$ alkyl), $-CH_2NH_2$, $-CONH_2$, $-CONH(C_{1-4}$ alkyl), $-CON(C_{1-4}$ alkyl)$_2$, $-OCH_2CO_2H$, $-NHCO(C_{1-4}$ alkyl), $-NHCO_2(C_{1-4}$ alkyl), $-NHSO_2(C_{1-4}$ alkyl), $-SO_2NH_2$, $-C(=NH)NH_2$, a carbocycle, and a heterocycle, wherein said alkyl, alkoxy, alkylthio, haloalkyl, carbocycle, and heterocycle are substituted with 0-4 $R^9$;

$R^4$, at each occurrence, is independently selected from H, OH, $NH_2$, $CH_2NH_2$, $C_{1-4}$ haloalkyl, $OCH_2F$, $OCHF_2$, $OCF_3$, $-NH(C_{1-4}$ alkyl), $-N(C_{1-4}$ alkyl)$_2$, $C_{1-4}$ alkoxy, $CH_2OH$, $CH_2O(C_{1-4}$ alkyl), $CH_2CO_2H$, $CH_2CO_2(C_{1-4}$ alkyl), $C_{1-4}$ alkyl, a carbocycle, and a heterocycle, wherein said alkyl, alkoxy, haloalkyl, carbocycle, and heterocycle are substituted with 0-4 $R^9$;

$R^5$, at each occurrence, is independently selected from H, $C_{1-4}$ alkyl, $-(CR^6R^6)_n-C_{3-10}$ carbocycle and $-(CR^6R^6)_n$-4- to 10-membered heterocycle comprising carbon atoms and 1-4 heteroatoms selected from N, $NR^8$, O, and $S(O)_p$, wherein said alkyl, carbocycle and heterocycle are substituted with 1-4 $R^7$;

alternatively, $R^5$ and $R^5$ are taken together with the nitrogen atom to which they are attached to form a 4- to 15-membered heterocycle substituted with 1-4 $R^7$;

$R^6$, at each occurrence, is independently selected from H, $C_{1-4}$ alkyl, $CH_2NH_2$, $C_{1-4}$ haloalkyl, $C_{1-4}$ alkoxy, $CH_2OH$, $CH_2O(C_{1-4}$ alkyl), $CH_2CO_2H$, $CH_2CO_2(C_{1-4}$ alkyl), a carbocycle, and a heterocycle, wherein said alkyl, alkoxy, haloalkyl, carbocycle, and heterocycle are substituted with 0-4 $R^9$;

alternatively, $R^1$ and $R^6$ are taken together with the nitrogen atom to which they are attached to form a heterocycle comprising carbon atoms and 1-4 heteroatoms selected from N, $NR^8$, O, and $S(O)_p$ and substituted with 1-4 $R^7$;

$R^7$, at each occurrence, is independently selected from H, =O, $NO_2$, halogen, $C_{1-6}$ alkyl, $C_{2-4}$ alkenyl, $C_{1-4}$ alkoxy, CN, OH, $CF_3$, $-(CH_2)_n-CO_2H$, $-(CH_2)_n-CO_2(C_{1-4}$ alkyl), $-(CH_2)_n-NR^8R^8$, $-NHCOH$, $-NHCO(C_{1-4}$ alkyl), $-NHCOCF_3$, $-NHCO_2(C_{1-4}$ alkyl), $-NHCO_2(CH_2)_2O(C_{1-4}$ alkyl), $-NHCO_2(CH_2)_3O(C_{1-4}$ alkyl), $-NHCO_2(CH_2)_2OH$, $-NHCO_2(CH_2)_2NH_2$, $-NHCO_2(CH_2)_2N(C_{1-4}$ alkyl)$_2$, $-NHCO_2CH_2CO_2H$, $-CH_2NHCO_2(C_{1-4}$ alkyl), $-NHC(O)NR^8R^8$, $-NHSO_2(C_{1-4}$ alkyl), $-S(O)_p(C_{1-4}$ alkyl), $-SO_2NH_2$, $-SO_2NH(C_{1-4}$ alkyl), $-SO_2N(C_{1-4}$ alkyl)$_2$, $-SO_2NH(CH_2)_2OH$, $-SO_2NH(CH_2)_2O(C_{1-4}$ alkyl), $-(CH_2)_n-CONR^8R^8$, $-O(CH_2)_n$-carbocycle, $-O(CH_2)_n$-heterocycle, $-NHCO$-carbocycle, $-NHCO$-heterocycle, $-(CH_2)_n$-carbocycle, and $-(CH_2)_n$-heterocycle comprising carbon atoms and 1-4 heteroatoms selected from N, $NR^8$, O, and $S(O)_p$, wherein said alkyl, alkenyl, alkoxyl, a carbocycle, and a heterocycle are substituted with 0-4 $R^9$;

$R^8$, at each occurrence, is independently selected from H, $C_{1-4}$ alkyl, $C_{2-4}$ alkenyl, $C_{2-4}$ alkynyl, $-(CH_2)_n-C(O)C_{1-4}$alkyl, $-(CH_2)_n-C(O)$carbocycle, $-(CH_2)_n-C(O)$heterocycle, $-(CH_2)_n-C(O)NR^aR^a$, $-(CH_2)_n-NR^aC(O)C_{1-4}$alkyl, $-(CH_2)_n-C(O)OC_{1-4}$alkyl, $-(CH_2)_n-C(O)C_{1-4}$alkyl, $-(CH_2)_n-C(O)O$-carbocycle, $-(CH_2)_n-C(O)O$-heterocycle, $-(CH_2)_n-SO_2$alkyl, $-(CH_2)_n$ $SO_2$carbocycle, $-(CH_2)_n-SO_2$heterocycle, $-(CH_2)_n-SO_2NR^aR^a$, $-(CH_2)_n$-carbocycle, and $-(CH_2)_n$-heterocycle, wherein said alkyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, =O, CN, $NO_2$, $CHF_2$, $CF_3$, $C_{1-4}$ alkyl, $C_{1-4}$ alkoxy, $CH_2OH$, $CO(C_{1-4}$ alkyl), $CO_2H$, $CO_2(C_{1-4}$ alkyl), $-(CHR^{10})_nNR^aR^a$, $-(CHR^{10})_nCONR^aR^a$, $-(CHR^{10})_nNR^aCO(C_{1-4}$ alkyl), $-O(CHR^{10})_n$carbocycle, $-O(CHR^{10})_n$heterocycle, $-O(CHR^{10})_nNR^aR^a$, and $-(CR^{10}R^{10})_n$-4- to 10-membered heterocycle, wherein said alkyl, alkoxy, carbocycle, and heterocycle are substituted with 0-4 $R^b$;

$R^{10}$ is selected from H and $C_{1-4}$ alkyl;

$R^a$, at each occurrence, is independently selected from H, $C_{1-4}$ alkyl, —$(CH_2)_n$OH, CO($C_{1-4}$ alkyl), COCF$_3$, CO$_2$ ($C_{1-4}$ alkyl), —CONH$_2$, —CONH—$C_{1-4}$ alkylene-CO$_2$ ($C_{1-4}$ alkyl), $C_{1-4}$ alkylene-CO$_2$($C_{1-4}$ alkyl), $R^c$, CO$_2R^c$, and CONHR$^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, OH, halogen, $C_{1-4}$ alkyl, $C_{1-4}$ alkoxy, OCF$_3$, OC(O)$C_{1-4}$ alkyl, NH$_2$, NO$_2$, N($C_{1-4}$ alkyl)$_2$, CO($C_{1-4}$ alkyl), CO($C_{1-4}$ haloalkyl), CO$_2$($C_{1-4}$ alkyl), CONH$_2$, —CONH($C_{1-4}$ alkyl), —CON($C_{1-4}$ alkyl)$_2$, —CONH—$C_{1-4}$ alkylene-O($C_{1-4}$ alkyl), —CONH—$C_{1-4}$ alkylene-N($C_{1-4}$ alkyl)$_2$, —$C_{1-4}$ alkylene-O—P(O)(OH)$_2$, —NHCO$_2$($C_{1-4}$ alkyl), —$R^c$, COR$^c$, CO$_2R^c$, and CONHR$^c$, wherein said alkyl and alkoxy are substituted with $R^d$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, N($C_{1-4}$ alkyl), O, and S(O)$_p$; wherein each ring moiety is substituted with 0-2 $R^d$;

$R^d$, at each occurrence, is independently selected from =O, halogen, —OH, $C_{1-4}$ alkyl, NH$_2$, NH($C_{1-4}$ alkyl), N($C_{1-4}$ alkyl)$_2$, $C_{1-4}$ alkoxy, and —NHCO($C_{1-4}$ alkyl), and a heterocycle containing carbon atoms and 1-4 heteroatoms selected from the group consisting of: N, NH, N($C_{1-4}$ alkyl), O, and S(O)$_p$;

n, at each occurrence, is independently selected from 0, 1, 2, 3, and 4; and p, at each occurrence, is independently selected from 0, 1, and 2.

3. The compound of claim 2, having Formula (III):

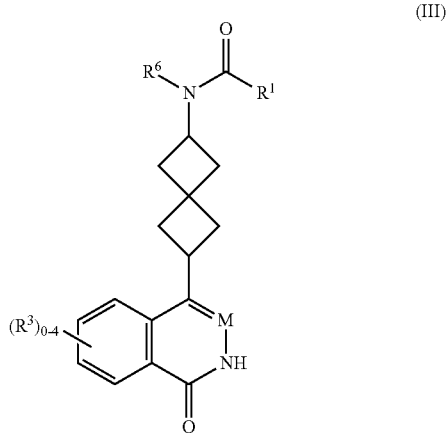

(III)

or a stereoisomer, a tautomer, a pharmaceutically-acceptable salt thereof, wherein:

M is selected from N and CR$^{10}$;

$R^1$ is selected from NR$^5$R$^5$, OR$^5$, —$(CH_2)_n$—C3-10 carbocycle, and —$(CH_2)_n$-5- to 15-membered heterocycle, wherein said carbocycle and heterocycle are substituted with 1-4 $R^7$;

$R^3$, at each occurrence, is independently selected from halogen, $C_{1-6}$ alkyl, $C_{1-4}$ alkoxy, $C_{1-4}$ alkylthio, $C_{1-4}$ haloalkyl, —CH$_2$OH, —OCH$_2$F, —OCHF$_2$, —OCF$_3$, CN, and —NH$_2$;

$R^5$, at each occurrence, is independently selected from H, $C_{1-4}$ alkyl, —(CR$^6$R$^6$)$_n$—C$_{3-10}$ carbocycle, and —(CR$^6$R$^6$)$_n$-4- to 10-membered heterocycle comprising carbon atoms and 1-4 heteroatoms selected from N, NR$^8$, O, and S(O)$_p$, wherein said alkyl, carbocycle, and heterocycle are substituted with 1-4 R;

alternatively, $R^5$ and $R^5$ are taken together with the nitrogen atom to which they are attached to form a 4- to 10-membered heterocycle substituted with 1-4 R;

$R^6$, at each occurrence, is independently selected from H and C1-4 alkyl;

$R^7$, at each occurrence, is independently selected from H, =O, NO$_2$, halogen, $C_{1-6}$ alkyl, $C_{1-4}$ alkoxy, CN, OH, CF$_3$, —$(CH_2)_n$—CO$_2$H, —$(CH_2)_n$—CO$_2$($C_{1-4}$ alkyl), —$(CH_2)_n$—NR$^8$R$^8$, —NHCOH, —NHCO($C_{1-4}$ alkyl), —NHCOCF$_3$, —NHCO$_2$($C_{1-4}$ alkyl), —NHCO$_2$ (CH$_2$)$_2$O($C_{1-4}$ alkyl), —NHCO$_2$(CH$_2$)$_3$O($C_{1-4}$ alkyl), —NHCO$_2$(CH$_2$)$_2$OH, —NHCO$_2$(CH$_2$)$_2$NH$_2$, —NHCO$_2$(CH$_2$)$_2$N($C_{1-4}$ alkyl)$_2$, —NHCO$_2$CH$_2$CO$_2$H, —CH$_2$NHCO$_2$($C_{1-4}$ alkyl), —NHC(O)NR$^8$R$^8$, —NHSO$_2$($C_{1-4}$ alkyl), —S(O)$_p$($C_{1-4}$ alkyl), —SO$_2$NH$_2$, —SO$_2$NH($C_{1-4}$ alkyl), —SO$_2$N($C_{1-4}$ alkyl)$_2$, —SO$_2$NH(CH$_2$)$_2$OH, —SO$_2$NH(CH$_2$)$_2$O($C_{1-4}$ alkyl), —$(CH_2)_n$—CONR$^8$R$^8$, —O(CH$_2$)$_n$-carbocycle, —O(CH$_2$)$_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, NR$^8$, O, and S(O)$_p$, wherein said alkyl, alkenyl, alkynyl, alkoxyl, carbocycle, and heterocycle are substituted with 0-4 $R^9$;

$R^8$, at each occurrence, is independently selected from H, $C_{1-4}$ alkyl, $C_{2-4}$ alkenyl, C(O)$C_{1-4}$alkyl, C(O)carbocycle, C(O)heterocycle, —$(CH_2)_n$—C(O)NR$^a$R$^a$, —$(CH_2)_n$—NR$^a$C(O)$C_{1-4}$alkyl, C(O)O$C_{1-4}$alkyl, C(O)O-carbocycle, C(O)O-heterocycle, SO$_2$alkyl, SO$_2$carbocycle, SO$_2$heterocycle, SO$_2$NR$^a$R$^a$, —$(CH_2)_n$-carbocycle, and —$(CH_2)_n$-heterocycle, wherein said alkyl, alkenyl, carbocycle, and heterocycle are substituted with 0-4 $R^9$;

alternatively, $R^8$ and $R^8$ are taken together with the nitrogen atom to which they are attached to form a 4- to 10-membered heterocycle substituted with 0-4 $R^9$;

$R^9$, at each occurrence, is independently selected from halogen, OH, CN, NO$_2$, CHF$_2$, CF$_3$, $C_{1-4}$ alkyl, $C_{1-4}$ alkoxy, CH$_2$OH, CO($C_{1-4}$ alkyl), CO$_2$H, CO$_2$($C_{1-4}$ alkyl), —(CHR$^{10}$)$_n$NR$^a$R$^a$, —(CHR$^{10}$)$_n$CONR$^a$R$^a$, —(CHR$^{10}$)$_n$NR$^a$CO($C_{1-4}$ alkyl), —O(CHR$^{10}$)$_n$carbocycle, —O(CHR$^{10}$)$_n$heterocycle, —O(CHR$^{10}$)$_n$NR$^a$R$^a$, and —(CR$^{10}$R$^{10}$)$_n$-4- to 10-membered heterocycle, wherein said alkyl, alkoxy, carbocycle, and heterocycle are substituted with 0-4 $R^b$;

$R^{10}$ is selected from H and C1-4 alkyl;

$R^a$, at each occurrence, is independently selected from H, $C_{1-4}$ alkyl, —$(CH_2)_n$OH, CO($C_{1-4}$ alkyl), COCF$_3$, CO$_2$ ($C_{1-4}$ alkyl), —CONH$_2$, —CONH—$C_{1-4}$ alkylene-CO$_2$ ($C_{1-4}$ alkyl), $C_{1-4}$ alkylene-CO$_2$($C_{1-4}$ alkyl), $R^c$, CO$_2R^c$, and CONHR$^c$; alternatively, $R^a$ and $R^a$ are taken together with the nitrogen atom to which they are attached to form a 4- to 10-membered heterocycle, wherein said alkyl, alkylene, and heterocycle are substituted with 0-4 $R^b$;

$R^b$, at each occurrence, is independently selected from =O, halogen, $C_{1-4}$ alkyl, $C_{1-4}$ alkoxy, OCF$_3$, OC(O)

C$_{1-4}$ alkyl, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —C$_{1-4}$ alkylene-O—P(O)(OH)$_2$, —NHCO$_2$(C$_{1-4}$ alkyl), —R$^c$, COR$^c$, CO$_2$R$^c$, and CONHR$^c$, wherein said alkyl and alkoxy are substituted with R$^d$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and a heterocycle containing carbon atoms and 1-4 heteroatoms selected from the group consisting of: N, NH, N(C$_{1-4}$ alkyl), O, and S(O)$_p$;

n, at each occurrence, is independently selected from 0, 1, 2, 3, and 4; and p, at each occurrence, is independently selected from 0, 1, and 2.

4. The compound of claim 3 or a stereoisomer, a tautomer, a pharmaceutically-acceptable salt thereof, wherein:

R$^1$ is NR$^5$R$^5$;

R$^5$ and R$^5$ are taken together with the nitrogen atom to which they are attached to form a 4- to 10-membered heterocycle substituted with 1-4 R$^7$;

R$^7$, at each occurrence, is independently selected from H, halogen, C$_{1-4}$ alkyl, C$_{1-4}$ alkoxy, CN, OH, CF$_3$, and —NR$^8$R$^8$; and R$^8$, at each occurrence, is independently selected from H and C$_{1-4}$ alkyl.

5. The compound of claim 1, having Formula (V):

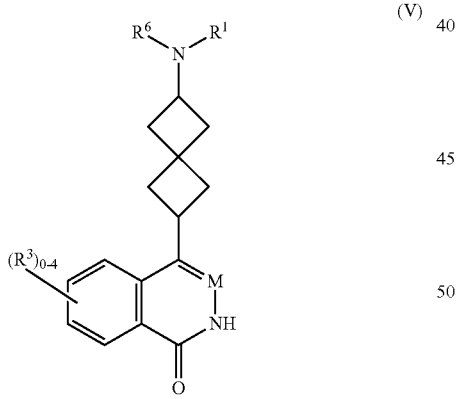

(V)

or a stereoisomer, a tautomer, a pharmaceutically-acceptable salt thereof, wherein:

M is selected from N and CR$^{10}$;

R$^1$ is a 5- to 10-membered heterocycle substituted with 1-4 R$^7$;

R$^6$, at each occurrence, is independently selected from H and C1-4 alkyl;

alternatively, R$^1$ and R$^6$ are taken together with the nitrogen atom to which they are attached to form a heterocycle comprising carbon atoms and 1-4 heteroatoms selected from N, NR$^8$, O, and S(O)$_p$ and substituted with 1-4 R$^7$;

R$^7$, at each occurrence, is independently selected from H, =O, NO$_2$, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NR$^8$R$^8$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —(CH$_2$)$_n$—CONR$^8$R$^8$, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxyl, carbocycle, and heterocycle are substituted with 0-4 R$^9$;

R$^8$, at each occurrence, is independently selected from H, C$_{1-4}$ alkyl, —(CH$_2$)$_n$-carbocycle, and —(CH$_2$)$_n$-heterocycle, wherein said alkyl, carbocycle, and heterocycle are substituted with 0-4 R$^9$;

R$^9$, at each occurrence, is independently selected from halogen, OH, CN, NO$_2$, CHF$_2$, CF$_3$, C$_{1-4}$ alkyl, C$_{1-4}$ alkoxy, CH$_2$OH, CO(C$_{1-4}$ alkyl), CO$_2$H, CO$_2$(C$_{1-4}$ alkyl), —(CHR$^{10}$)$_n$NR$^a$R$^a$, —(CHR$^{10}$)$_n$CONR$^a$R$^a$, —(CHR$^{10}$)$_n$NR$^a$CO(C$_{1-4}$ alkyl), —O(CHR$^{10}$)$_n$carbocycle, —O(CHR$^{10}$)$_n$heterocycle, —O(CHR$^{10}$)$_n$NR$^a$R$^a$, and —(CR$^{10}$R$^{10}$)$_n$-4- to 10-membered heterocycle, wherein said alkyl, alkoxy, carbocycle, and heterocycle are substituted with 0-4 R$^b$;

R$^{10}$ is selected from H and C$_{1-4}$ alkyl;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form a 4- to 10-membered heterocycle, wherein said alkyl, alkylene, and heterocycle are substituted with 0-4 R$^b$;

R$^b$, at each occurrence, is independently selected from =O, halogen, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —C$_{1-4}$ alkylene-O—P(O)(OH)$_2$, —NHCO$_2$(C$_{1-4}$ alkyl), —R$^c$, COR$^c$, CO$_2$R$^c$, and CONHR$^c$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and a heterocycle containing carbon atoms and 1-4 heteroatoms selected from the group consisting of: N, NH, N(C$_{1-4}$ alkyl), O, and S(O)$_p$;

n, at each occurrence, is independently selected from 0, 1, 2, 3, and 4; and p, at each occurrence, is independently selected from 0, 1, and 2.

6. The compound of claim 5, having Formula (VI):

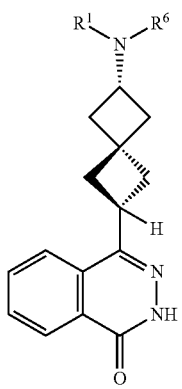

(VI)

or a stereoisomer, a tautomer, a pharmaceutically-acceptable salt thereof, wherein:
R$^1$ is selected from

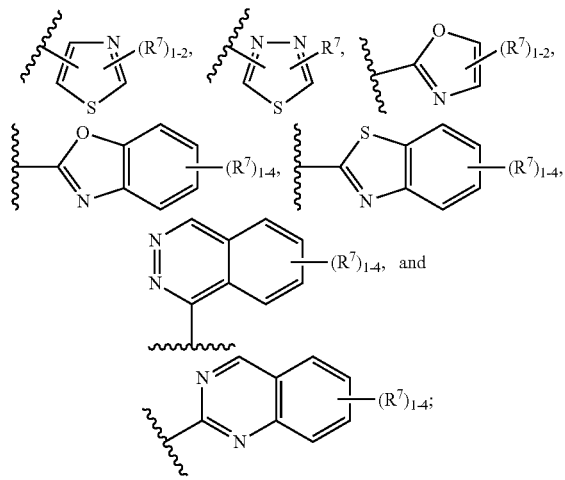

R$^6$ is H; and
R$^7$, at each occurrence, is independently selected from H, halogen, C$_{1-4}$ alkyl, C$_{1-4}$ alkoxy, CN, OH, —(CH$_2$)$_n$-carbocycle, and —(CH$_2$)$_n$-heterocycle, wherein said alkyl, alkoxyl, carbocycle, and heterocycle are substituted with 0-4 R$^9$.

7. The compound of claim 1, having Formula (VII):

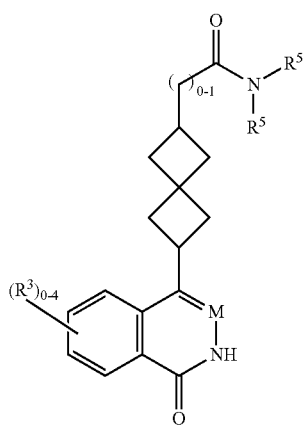

(VII)

or a stereoisomer, a tautomer, a pharmaceutically-acceptable salt thereof, wherein:
M is selected from N and CR$^{10}$;
R$^5$, at each occurrence, is independently selected from H, C$_{1-4}$ alkyl, —(CR$^6$R$^6$)$_n$—C$_{3-10}$ carbocycle, and —(CR$^6$R$^6$)$_n$-4 to 10-membered heterocycle comprising carbon atoms and 1-4 heteroatoms selected from N, NR$^8$, O, and S(O)$_p$, wherein said alkyl, carbocycle, and heterocycle are substituted with 1-4 R$^7$;
alternatively, R$^5$ and R$^5$ are taken together with the nitrogen atom to which they are attached to form a 4- to 10-membered heterocycle substituted with 1-4 R$^7$;
R$^7$, at each occurrence, is independently selected from H, =O, NO$_2$, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NR$^8$R$^8$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_{20}$H, —SO$_2$NH(CH$_2$)$_2$O(C$_{1-4}$ alkyl), —(CH$_2$)$_n$—CONR$^8$R$^8$, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxyl, carbocycle, and heterocycle are substituted with 0-4 R$^9$;
R$^8$, at each occurrence, is independently selected from H, C$_{1-4}$ alkyl, C(O)C$_{1-4}$alkyl, C(O)carbocycle, C(O)heterocycle, —(CH$_2$)$_n$ C(O)NR$^a$R$^a$, C(O)OC$_{1-4}$alkyl, C(O)O-carbocycle, C(O)O-heterocycle, SO$_2$alkyl, SO$_2$carbocycle, SO$_2$heterocycle, SO$_2$NR$^a$R$^a$, —(CH$_2$)$_n$-carbocycle, and —(CH$_2$)$_n$-heterocycle, wherein said alkyl, carbocycle, and heterocycle are substituted with 0-4 R$^9$;
R$^9$, at each occurrence, is independently selected from halogen, OH, CN, NO$_2$, CHF$_2$, CF$_3$, C$_{1-4}$ alkyl, C$_{1-4}$ alkoxy, CH$_2$OH, CO(C$_{1-4}$ alkyl), CO$_2$H, CO$_2$(C$_{1-4}$ alkyl), —(CHR$^{10}$)$_n$NR$^a$R$^a$, —(CHR$^{10}$)$_n$CONR$^a$R$^a$, —(CHR$^{10}$)$_n$NR$^a$CO(C$_{1-4}$ alkyl), —O(CHR$^{10}$)$_n$carbocycle, —O(CHR$^{10}$)$_n$heterocycle, —O(CHR$^{10}$)$_n$NR$^a$R$^a$, and —(CR$^{10}$R$^{10}$)$_n$-4- to 10-membered heterocycle, wherein said alkyl, alkoxy, carbocycle, and heterocycle are substituted with 0-4 R$^b$;
R$^{10}$ is selected from H and C$_{1-4}$ alkyl;
R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form a 4- to 10-membered heterocycle, wherein said alkyl, alkylene, and heterocycle are substituted with 0-4 R$^b$;
R$^b$, at each occurrence, is independently selected from =O, halogen, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —C$_{1-4}$ alkylene-O—P(O)(OH)$_2$, —NHCO$_2$(C$_{1-4}$ alkyl), —R$^c$, COR$^c$, CO$_2$R$^c$, and CONHR$^c$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and a heterocycle containing carbon atoms and 1-4 heteroatoms selected from the group consisting of: N, NH, N(C$_{1-4}$ alkyl), O, and S(O)$_p$;

n, at each occurrence, is independently selected from 0, 1, 2, 3, and 4; and p, at each occurrence, is independently selected from 0, 1, and 2.

8. The compound of claim 7 or a stereoisomer, a tautomer, a pharmaceutically-acceptable salt thereof, wherein:

M is N;

R$^5$ is selected from H, C$_{1-4}$ alkyl, —(CH$_2$)$_n$—C$_{3-10}$ carbocycle, —(CH$_2$)$_n$-aryl, —(CH$_2$)$_n$-4- to 10-membered heterocycle selected from

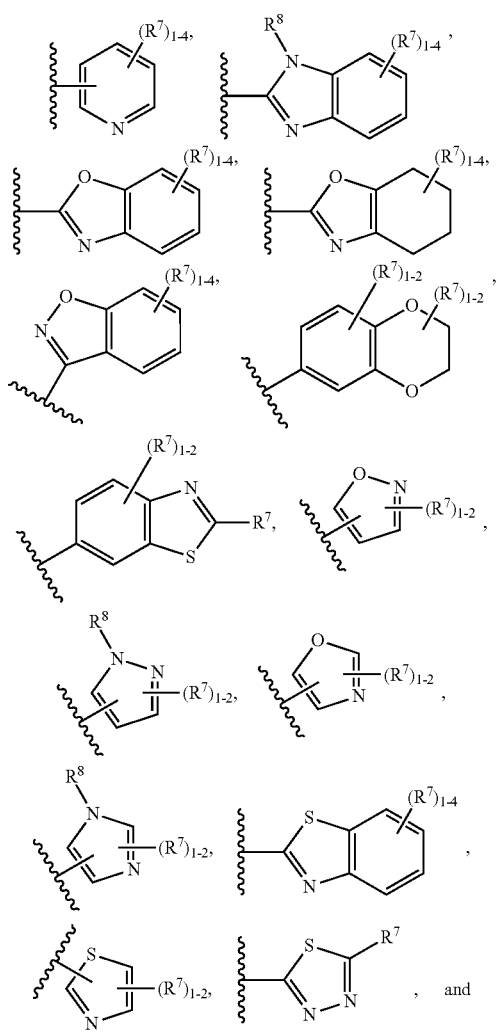

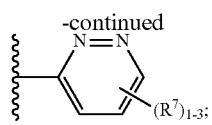

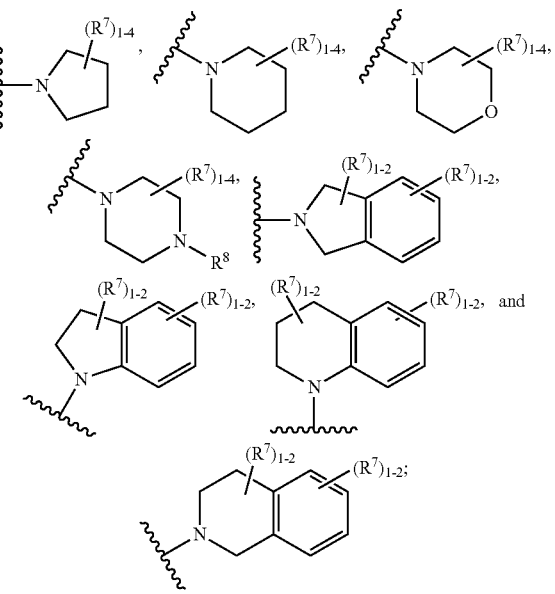

wherein said alkyl, cycloalkyl, aryl are substituted with 1-4 R$^7$;

alternatively, R$^5$ and R$^5$ are taken together with the nitrogen atom to which they are attached to form a heterocycle selected from R$^7$, at each occurrence, is independently selected from H, halogen, C$_{1-4}$ alkyl, C$_{1-4}$ alkoxy, CN, OH, —(CH$_2$)$_n$-carbocycle, and —(CH$_2$)$_n$-heterocycle, wherein said alkyl, alkoxyl, carbocycle, an heterocycle are substituted with 0-4 R$^9$;

R$^9$, at each occurrence, is independently selected from halogen, OH, NO$_2$, CHF$_2$, CF$_3$, C$_{1-4}$ alkyl, C$_{1-4}$ alkoxy, CH$_2$OH, CO$_2$H, CO$_2$(C$_{1-4}$ alkyl), CONH$_2$, —NH$_2$, and a 4- to 10-membered heterocycle.

9. The compound of claim 1 having Formula (VIII):

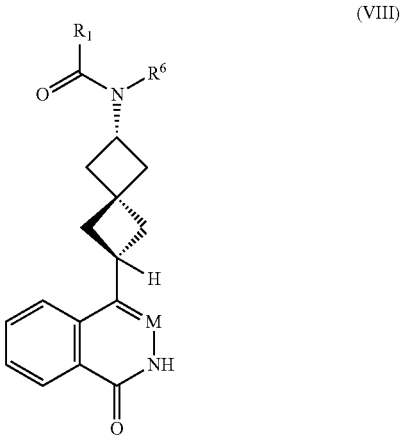

or a stereoisomer, a tautomer, a pharmaceutically-acceptable salt thereof, wherein:

M is selected from N and CH;

R$^1$ is NR$^5$R$^5$;

R$^5$ and R$^5$ are taken together with the nitrogen atom to which they are attached to form a heterocycle selected from

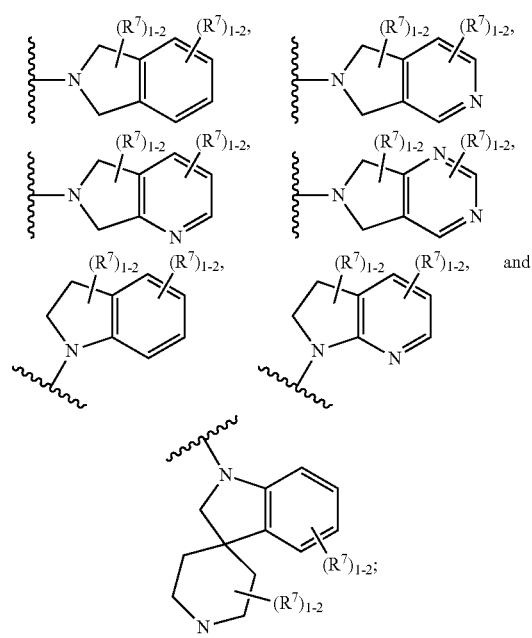

R$^7$, at each occurrence, is independently selected from H, =O, F, Cl, Br, C$_{1-4}$ alkyl, C$_{1-4}$ alkoxy, CN, OH, CF$_3$, —(CH$_2$)$_n$—NR$^8$R$^8$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —(CH$_2$)$_n$—CONR$^8$R$^8$, —(CH$_2$)$_n$-phenyl, and —(CH$_2$)$_n$-heterocycle selected from

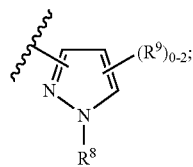

R$^8$, at each occurrence, is independently selected from H, CF$_3$, CD$_3$, CH$_3$, C(CH$_3$)$_3$,

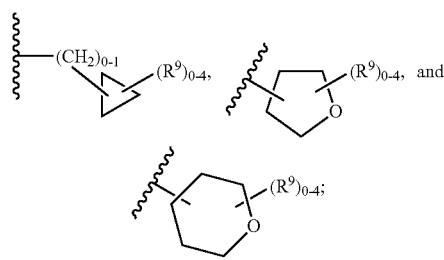

alternatively, R$^8$ and R$^8$ are taken together to form

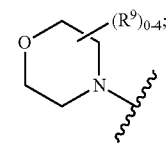

and

R$^9$, at each occurrence, is independently selected from F, Cl, OH, NO$_2$, CHF$_2$, (CH$_2$)$_{0-2}$CF$_3$, CD$_3$, CH$_3$, OC$_{1-4}$ alkyl, SO$_2$NH$_2$, and phenyl substituted with C$_{1-4}$ alkyl.

10. The compound of claim 3, having Formula (IV):

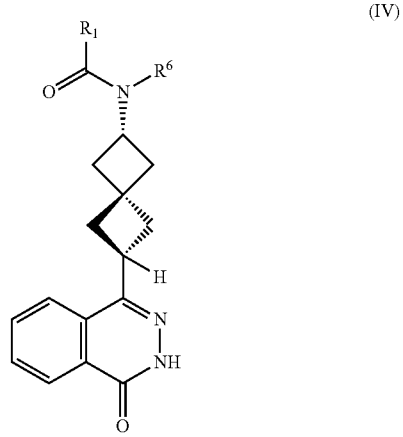

or a stereoisomer, a tautomer, a pharmaceutically-acceptable salt thereof, wherein:

R$^1$ is selected from

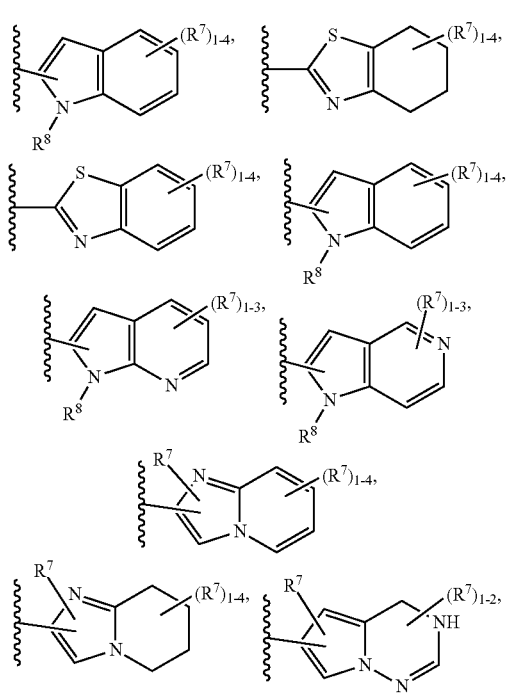

-continued

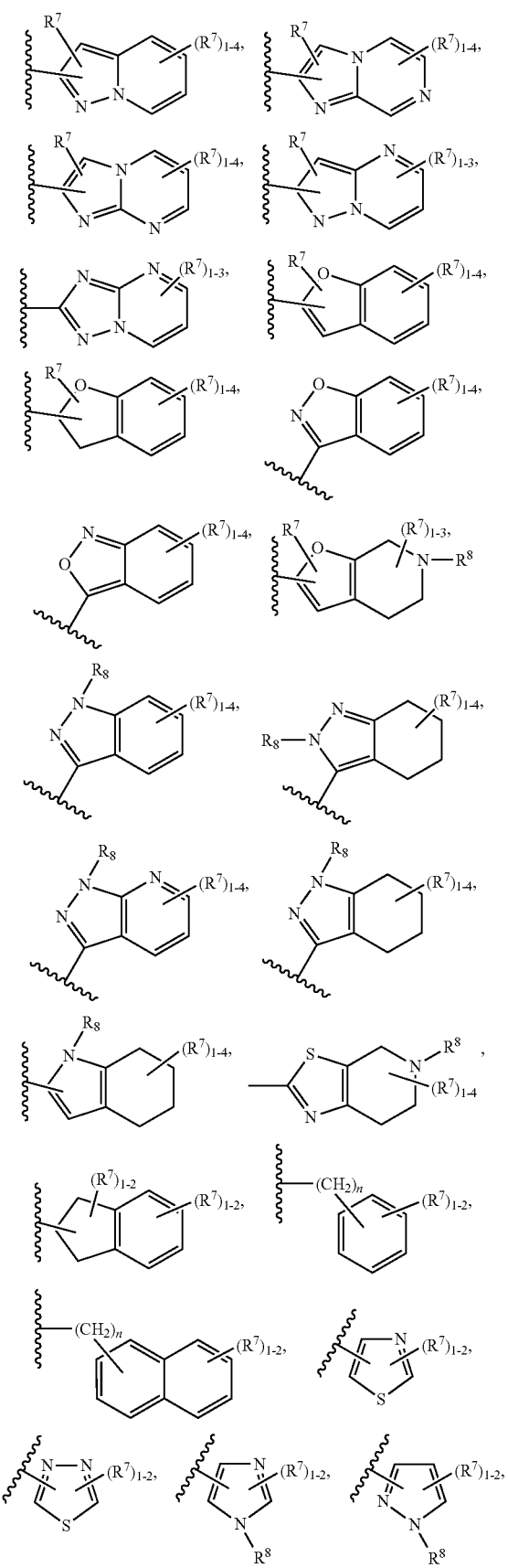

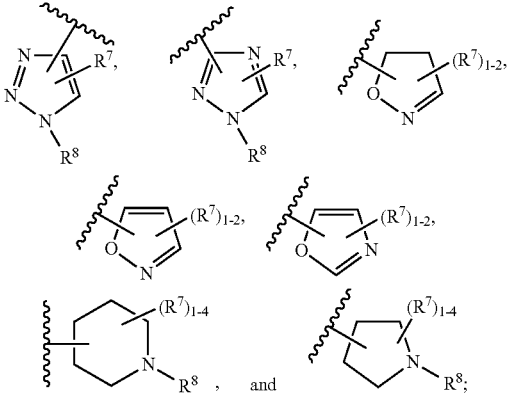

R⁷, at each occurrence, is independently selected from H, =O, NO₂, halogen, $C_{1-4}$ alkyl, $C_{1-4}$ alkoxy, CN, OH, CF₃, —(CH₂)ₙ—CO₂H, —(CH₂)ₙ—CO₂($C_{1-4}$ alkyl), —(CH₂)ₙ—NR⁸R⁸, —NHCO($C_{1-4}$ alkyl), NHCOCF₃, —NHCO₂($C_{1-4}$ alkyl), —NHCO₂(CH₂)₂O($C_{1-4}$ alkyl), —NHCO₂(CH₂)₃O($C_{1-4}$ alkyl), —NHCO₂(CH₂)₂OH, —NHCO₂(CH₂)₂NH₂, —NHCO₂(CH₂)₂N($C_{1-4}$ alkyl)₂, —NHCO₂CH₂CO₂H, —CH₂NHCO₂($C_{1-4}$ alkyl), —NHC(O)NR⁸R⁸, —NHSO₂($C_{1-4}$ alkyl), —SO₂NH($C_{1-4}$ alkyl), —SO₂N($C_{1-4}$ alkyl)₂, —SO₂NH(CH₂)₂OH, —SO₂NH(CH₂)₂O($C_{1-4}$ alkyl), —(CH₂)ₙ—CONR⁸R⁸, —O(CH₂)ₙ-carbocycle, —O(CH₂)ₙ-heterocycle, —NHCO-carbocycle, —NHCO-heterocycle, —(CH₂)ₙ-carbocycle, and —(CH₂)ₙ-heterocycle comprising carbon atoms and 1-4 heteroatoms selected from N, NR⁸, O, and S(O)ₚ, wherein said alkyl, alkenyl, alkynyl, alkoxylm carbocycle, and heterocycle are substituted with 0-4 R⁹;

R⁸, at each occurrence, is independently selected from H, $C_{1-4}$ alkyl, C(O)$C_{1-4}$alkyl, C(O)carbocycle, C(O)heterocycle, —(CH₂)ₙ-C(O)NRᵃRᵃ, C(O)O$C_{1-4}$alkyl, C(O)O-carbocycle, C(O)O-heterocycle, SO₂alkyl, SO₂carbocycle, SO₂heterocycle, SO₂NRᵃRᵃ, —(CH₂)ₙ-carbocycle, and —(CH₂)ₙ-heterocycle, wherein said alkyl, cabocycle, and heterocycle are substituted with 0-4 R⁹;

alternatively, R⁸ and R⁸ are taken together with the nitrogen atom to which they are attached to form a 4- to 10-membered heterocycle substituted with 0-4 R⁹;

R⁹, at each occurrence, is independently selected from halogen, OH, CN, NO₂, CHF₂, CF₃, $C_{1-4}$ alkyl, $C_{1-4}$ alkoxy, CH₂OH, CO₂H, CO₂($C_{1-4}$ alkyl), CONH₂, —(CH₂)ₙNRᵃRᵃ, —(CH₂)ₙCONRᵃRᵃ, —(CH₂)ₙNHCO($C_{1-4}$ alkyl), —O(CH₂)ₙheterocycle, —O(CH₂)₂₋₄NRᵃRᵃ, and —(CR¹⁰R¹⁰)ₙ-4- to 10-membered heterocycle, wherein said alkyl, alkoxy, carbocycle, and heterocycle are substituted with 0-4 Rᵇ;

Rᵃ, at each occurrence, is independently selected from H and $C_{1-4}$ alkyl; alternatively, Rᵃ and Rᵃ are taken together with the nitrogen atom to which they are attached to form a 4- to 10-membered heterocycle, wherein said alkyl, alkylene, and heterocycle are substituted with 0-4 Rᵇ; and Rᵇ, at each occurrence, is independently selected from =O, halogen, $C_{1-4}$ alkyl, $C_{1-4}$ alkoxy, OCF₃, NH₂, NO₂, N($C_{1-4}$ alkyl)₂, CO($C_{1-4}$ alkyl), CO($C_{1-4}$ haloalkyl), CO₂($C_{1-4}$ alkyl), CONH₂, —CONH($C_{1-4}$ alkyl), —CON($C_{1-4}$ alkyl)₂, —CONH—$C_{1-4}$ alkylene—O($C_{1-4}$ alkyl), —CONH—$C_{1-4}$ alkylene—N($C_{1-4}$ alkyl)$_2$, and —NHCO$_2$($C_{1-4}$ alkyl).

11. The compound of claim 10 or stereoisomer, a tautomer, a pharmaceutically-acceptable salt thereof, wherein:
$R^1$ is selected from

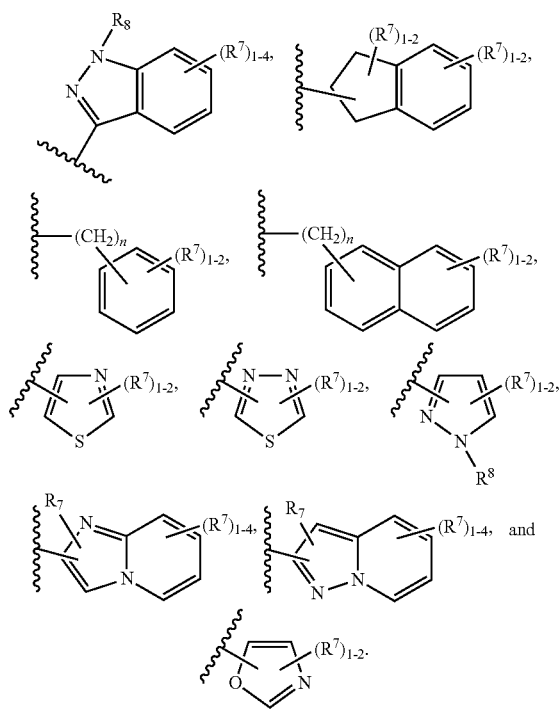

$R^7$, at each occurrence, is independently selected from H, halogen, $C_{1-4}$ alkyl, $C_{1-4}$ alkoxy, —NR$^8$R$^8$, $C_{3-6}$ ctcloaklkyl, phenyl, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxyl, carbocycle, and heterocycle are substituted with 0-4 R$^9$;

$R^8$, at each occurrence, is independently selected from H, $C_{1-4}$ alkyl, —(CH$_2$)$_n$-$C_{3-6}$ cycloalkyl, —(CH$_2$)$_n$-phenyl, and —(CH$_2$)$_n$-heterocycle, wherein said alkyl, cycloalkyl, phenyl, and heterocycle are substituted with 0-4 R$^9$;

alternatively, $R^8$ and $R^8$ are taken together with the nitrogen atom to which they are attached to form a heterocycle selected from

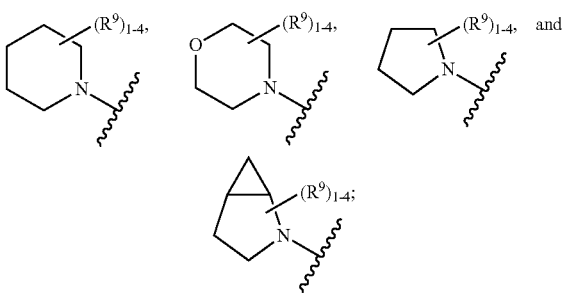

$R^9$, at each occurrence, is independently selected from F, Cl, OH, CN, $C_{1-4}$ alkyl, $C_{1-4}$ alkoxy, —(CH$_2$)$_n$NR$^a$R$^a$, and a 4- to 10-membered heterocycle, wherein said alkyl, alkoxyl, and heterocycle are substituted with 0-4 R$^b$;

$R^a$, at each occurrence, is independently selected from H, $C_{1-4}$ alkyl, —(CH$_2$)$_n$OH, CO($C_{1-4}$ alkyl), COCF$_3$, CO2($C_{1-4}$ alkyl), —CONH$_2$, —CONH—$C_{1-4}$ alkylene—CO$_2$($C_{1-4}$ alkyl), and $C_{1-4}$ alkylene—CO$_2$($C_{1-4}$ alkyl); and $R^b$, at each occurrence, is independently selected from halogen, $C_{1-4}$ alkyl, $C_{1-4}$ alkoxy, OCF$_3$, NH$_2$, NO$_2$, N($C_{1-4}$ alkyl)$_2$, CO($C_{1-4}$ alkyl), CO($C_{1-4}$ haloalkyl), CO$_2$($C_{1-4}$ alkyl), CONH$_2$, —CONH($C_{1-4}$ alkyl), —CON($C_{1-4}$ alkyl)$_2$, —CONH—$C_{1-4}$ alkylene—O($C_{1-4}$ alkyl), —CONH—$C_{1-4}$ alkylene—N($C_{1-4}$ alkyl)$_2$, —$C_{1-4}$ alkylene—O—P(O)(OH)$_2$, and NHCO$_2$($C_{1-4}$ alkyl).

12. The compound of claim 3, having Formula (VIII):

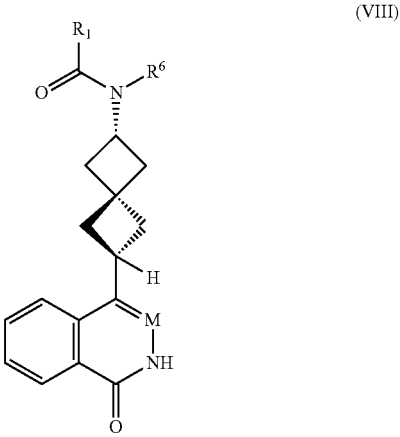

(VIII)

or a stereoisomer, a tautomer, a pharmaceutically-acceptable salt thereof, wherein:

M is selected from N and CH;

$R^1$ is selected from

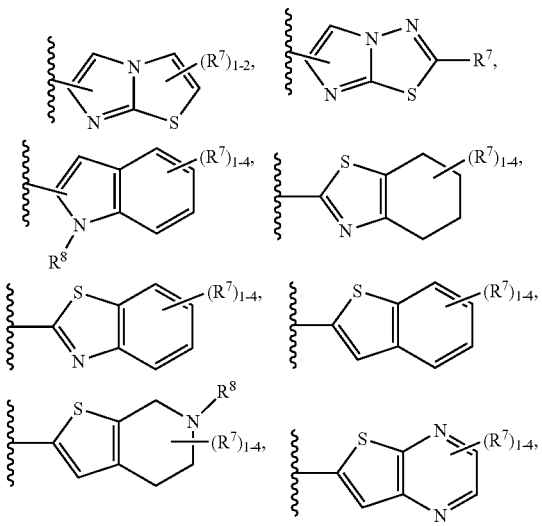

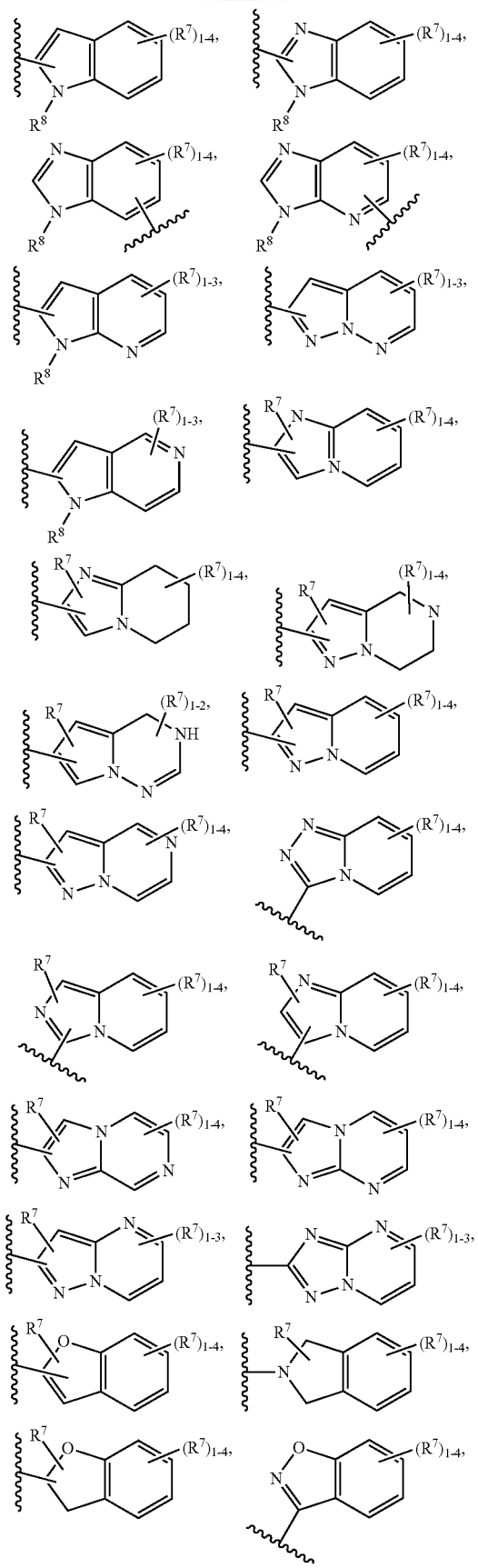
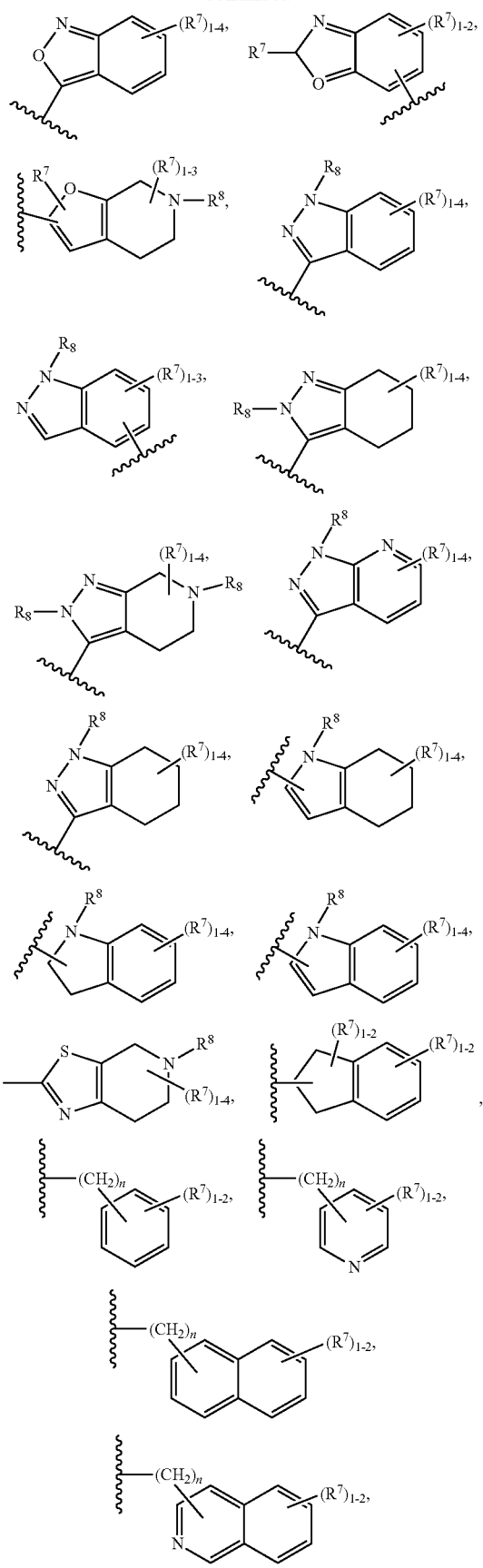

-continued

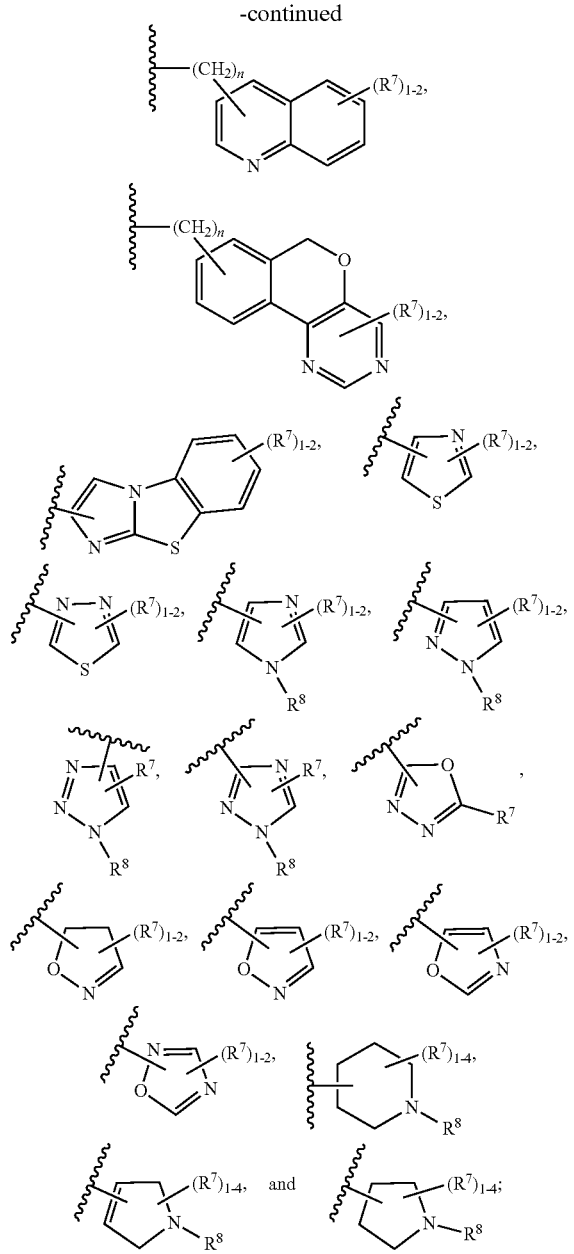

R[7], at each occurrence, is independently selected from H, =O, NO$_2$, F, Cl, Br, C$_{1-6}$ alkyl, C$_{2-4}$ alkenyl, C$_{2-4}$ alkynyl, C$_{1-4}$ alkoxy, CN, OH, CF$_3$, —(CH$_2$)$_n$-CO$_2$H, —(CH$_2$)$_n$-CO$_2$(C$_{1-4}$ alkyl), —(CH$_2$)$_n$-NR[8]R[8], —NHCOH, —NHCOH, —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —(CH$_2$)1-2NHCO$_2$(C$_{1-4}$ alkyl), —NHC(O)NR[8]R[8], —NHSO$_2$(C$_{1-4}$ alkyl), S(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —(CH$_2$)$_n$—CONR[8]R[8], —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR[8], O, and S(O)$_p$;

wherein said alkyl, alkenyl, alkynyl, alkoxyl, carbocycle, and heterocycle are substituted with 0-4 R[9] and wherein said carbocycle is selected from

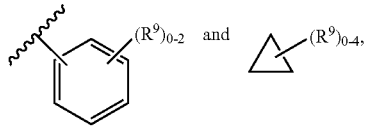

and wherein said heterocycle is selected from

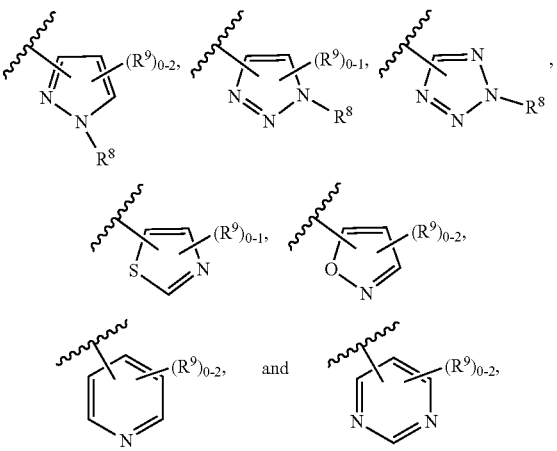

R[8], at each occurrence, is independently selected from H, C$_{1-4}$ alkyl, C(O)C$_{1-4}$alkyl, C(O)carbocycle, C(O)heterocycle, —(CH$_2$)$_n$—C(O)NR[a]R[a], —(CH$_2$)$_n$—NHC(O)C$_{1-4}$alkyl, C(O)O—C$_{1-4}$alkyl, C(O)O-carbocycle, C(O)O-heterocycle, SO$_2$alkyl, SO$_2$carbocycle, SO$_2$heterocycle, SO$_2$NR[a]R[a], —(CH$_2$)$_n$—C$_{3-6}$cycloalkyl, —(CH$_2$)$_n$-aryl, and —C(CH$_2$)$_n$-heterocycle, wherein said alkyl, cycloalkyl, aryl, and heterocycle are substituted with 0-4 R[9];

alternatively, R[8] and R[8] are taken together with the nitrogen atom to which they are attached to form a heterocycle selected from

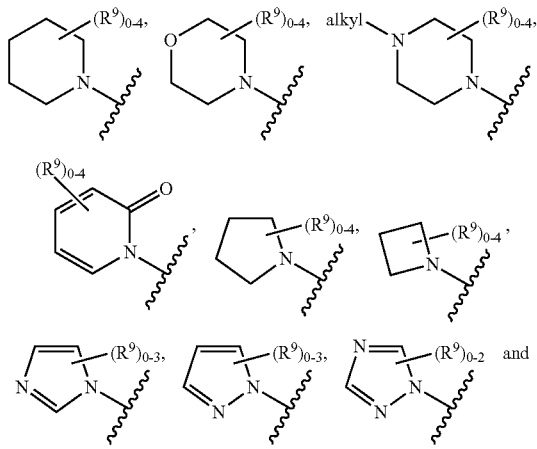

-continued

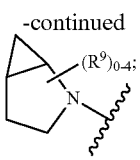

R⁹, at each occurrence, is independently selected from F, Cl, Br, I, OH, =O, CN, NO₂, CHF₂, CF₃, $C_{1-4}$ alkyl, $C_{1-4}$ alkoxy, CH₂OH, CO₂H, CO₂($C_{1-4}$ alkyl), CONH₂, —(CH₂)$_n$NR$^a$R$^a$, —(CH₂)$_n$CONR$^a$R$^a$, —(CH₂)$_n$NHCO($C_{1-4}$ alkyl), —O(CH₂)$_n$heterocycle, —O(CH₂)$_{2-4}$NR$^a$R$^a$, —(CH₂)$_n$-carbocycle, and —(CH₂)$_n$-4- to 10-membered heterocycle, wherein said alkyl, alkoxyl, carbocycle, and heterocycle are substituted with 0-4 R$^b$;

R$^a$, at each occurrence, is independently selected from H and $C_{1-4}$ alkyl; alternatively, R$^a$ abd R$^a$ are taken together with the nitrogen atom to which theu are attached to form a 4- to 10-membered heterocycle, wherein said alkyl, alkylene, and heterocycle are substituted with 0-4 R$^b$;

R$^b$, at each occurrence, is independently selected from =O, halogen, $C_{1-4}$ alkyl, $C_{1-4}$ alkoxy, OCF₃, OC(O) $C_{1-4}$ alkyl, NH₂, NO₂, N($C_{1-4}$ alkyl)₂, CO($C_{1-4}$ alkyl), CO($C_{1-4}$ haloalkyl), CO₂($C_{1-4}$ alkyl), CONH₂, —CONH($C_{1-4}$ alkyl), —CON($C_{1-4}$ alkyl)₂, —CONH—$C_{1-4}$ alkylene—O($C_{1-4}$ alkyl), —CONH—$C_{1-4}$ alkylene—N($C_{1-4}$ alkyl)₂, and —NHCO₂($C_{1-4}$ alkyl), wherein said alkyl and alkoxy are substituted with R$^d$;

R$^d$, at each occurrence, is independently selected from =O, halogen, —OH, $C_{1-4}$ alkyl, NH₂, NH($C_{1-4}$ alkyl), N($C_{1-4}$ alkyl)₂, $C_{1-4}$ alkoxy, and —NHCO($C_{1-4}$ alkyl), and a heterocycle containing carbon atoms and 1-4 heteroatoms selected deom the group cobsisting of: N, NH, N($C_{1-4}$ alkyl), O, and S(O)$_p$;

n, at each occurrence, is independently selected from 0, 1, 2, 3, and 4; and p, at each occurrence, is independently selected from 0, 1, and 2.

13. The compound of claim 7 or a stereoisomer, a tautomer, a pharmaceutically-acceptable salt thereof, wherein: M is N;

R¹ and R⁶ are taken together with the nitrogen atom to which they are attached to form a heterocycle selected from

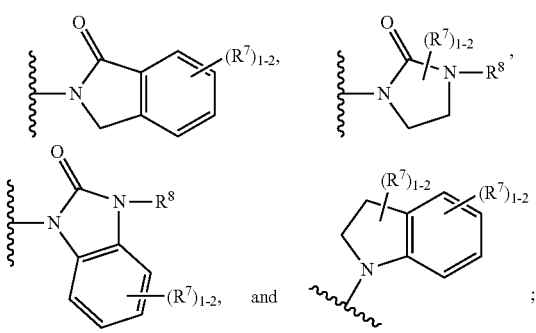

R⁷, at each occurrence, is independently selected from H, halogen, $C_{1-4}$ alkyl, $C_{1-4}$ alkoxy, CN, OH, CF₃, —(CH₂)$_n$—CO₂H, —(CH₂)$_n$—CO₂($C_{1-4}$ alkyl), —(CH₂)$_n$—NR⁸R⁸, —NHCO($C_{1-4}$ alkyl), —NHC(O) NR⁸R⁸, —NHSO₂($C_{1-4}$ alkyl), —SO₂NH₂, —SO₂NH ($C_{1-4}$ alkyl), —SO₂N($C_{1-4}$ alkyl)₂, —SO₂NH (CH₂)₂OH, —SO₂NH(CH₂)₂O($C_{1-4}$ alkyl), —(CH₂)$_n$—CONR⁸R⁸, —(CH₂)$_n$-carbocycle, and —(CH₂)$_n$-heterocycle comprising carbon atoms and 1-4 heteroatoms selected from N, NR⁸, O, and S(O)$_p$, wherein said alkyl, alkenyl, alkynyl, alkoxyl, carbocycle, and heterocycle are substituted with 0-4 R⁹;

R⁸, at each occurrence, is independently selected from H and $C_{1-4}$ alkyl:

R⁹, at each occurrence, is independently selected from halogen, OH, CN, NO₂, CHF₂, CF₃, $C_{1-4}$ alkyl, $C_{1-4}$ alkoxy, CH₂OH, CO($C_{1-4}$ alkyl), CO₂H, and CO₂($C_{1-4}$ alkyl);

n, at each occurrence, is independently selected from 0, 1, 2, 3, and 4; and p, at each occurence, is independently selected from 0, 1, and 2.

14. A compound of claim 1 selected from the group consisting of

N-[6-(4-oxo-3,4-dihydrophthalazin-1-yl)spiro[3.3]heptan-2-yl]-2,3-dihydro-1H-indene-2-carboxamide, 4-(dimethylamino)-N-[6-(4-oxo-3,4-dihydrophthalazin-1-yl)spiro[3.3]heptan-2-yl]benzamide, 2-(naphthalen-1-yl)-N-[6-(4-oxo-3,4-dihydrophthalazin-1-yl)spiro[3.3]heptan-2-yl]acetamide, 2-(naphthalen-2-yl)-N-[6-(4-oxo-3,4-dihydrophthalazin-1-yl)spiro[3.3]heptan-2-yl]acetamide, 1-methyl-N-[6-(4-oxo-3,4-dihydrophthalazin-1-yl)spiro[3.3]heptan-2-yl]-1H-indazole-3-carboxamide, N-[6-(4-oxo-3,4-dihydrophthalazin-1-yl)spiro[3.3]heptan-2-yl]-3-phenylpropanamide, N-[6-(4-oxo-3,4-dihydrophthalazin-1-yl)spiro[3.3]heptan-2-yl]-1-(2,2,2-trifluoroethyl)-1H-pyrazole-3-carboxamide, 3-methyl-N-[6-(4-oxo-3,4-dihydrophthalazin-1-yl)spiro[3.3]heptan-2-yl]-1-phenyl-1H-pyrazole-4-carboxamide, 1-tert-butyl-N-[6-(4-oxo-3,4-dihydrophthalazin-1-yl) spiro[3.3]heptan-2-yl]-1H-pyrazole-4-carboxamide, N-[6-(4-oxo-3,4-dihydrophthalazin-1-yl)spiro[3.3]heptan-2-yl]-1-phenyl-1H-pyrazole-3-carboxamide, 1-(2-hydroxy-2-methylpropyl)-N-[6-(4-oxo-3,4-dihydrophthalazin-1-yl)spiro[3.3]heptan-2-yl]-1H-indazole-3-carboxamide, N-[6-(4-oxo-3,4-dihydrophthalazin-1-yl)spiro[3.3]heptan-2-yl]-1-phenyl-1H-pyrazole-4-carboxamide, 5-methyl-N-[6-(4-oxo-3,4-dihydrophthalazin-1-yl)spiro[3.3]heptan-2-yl]-1-phenyl-1H-pyrazole-4-carboxamide, 1-methyl-N-[(aR)-6-(4-oxo-3,4-dihydrophthalazin-1-yl) spiro[3.3]heptan-2-yl]-1H-indazole-3-carboxamide, N-[(aR)-6-(4-oxo-3,4-dihydrophthalazin-1-yl)spiro[3.3] heptan-2-yl]-1-(2,2,2-trifluoroethyl)-1H-pyrazole-3-carboxamide, 1-(2,2-difluoroethyl)-N-[(aR)-6-(4-oxo-3,4-dihydrophthalazin-1-yl)spiro[3.3]heptan-2-yl]-1H-pyrazole-3-carboxamide, 1-methyl-N-[(aS)-6-(4-oxo-3,4-dihydrophthalazin-1-yl) spiro[3.3]heptan-2-yl]-1H-indazole-3-carboxamide, N-[(aS)-6-(4-oxo-3,4-dihydrophthalazin-1-yl)spiro[3.3] heptan-2-yl]-1-(2,2,2-trifluoroethyl)-1H-pyrazole-3-carboxamide, 1-(2,2-difluoroethyl)-N-[(aS)-6-(4-oxo-3,4-dihydrophthalazin-1-yl)spiro[3.3]heptan-2-yl]-1H-pyrazole-3-carboxamide, 5-methyl-N-[(aR)-6-(4-oxo-3,4-dihydrophthalazin-1-yl)spiro[3.3]heptan-2-yl]-1-phenyl-1H-pyrazole-4-carboxamide, 1-(2-hydroxy-2-methylpropyl)-N-[(aR)-6-(4-oxo-3,4-dihydrophthalazin-1-yl)spiro[3.3]heptan-2-yl]-1H-indazole-3-carboxamide, N-[(aR)-6-(4-oxo-3,4-dihydrophthalazin-1-yl)spiro[3.3]heptan-2-yl]-1-(3,3,3-trifluoropropyl)-1H-pyrazole-3-carboxamide, 1-(cyclopropylmethyl)-N-[(aR)-6-(4-oxo-3,4-dihydrophthalazin-1-yl)spiro[3.3]heptan-2-yl]-1H-pyrazole-3-carboxamide, 3-cyclopropyl-1-methyl-N-[(aR)-6-(4-oxo-3,4-dihydrophthalazin-1-yl)spiro[3.3]heptan-2-yl]-1H-pyrazole-5-carboxamide, 1-methyl-N-[(aR)-6-(4-oxo-3,4-dihydrophthalazin-1-yl)spiro[3.3]heptan-2-yl]-3-(trifluoromethyl)-1H-pyrazole-5-carboxamide, 5-cyclopropyl-1-methyl-N-[(aR)-6-(4-oxo-3,4-dihydrophthalazin-1-yl)spiro[3.3]heptan-2-yl]-1H-pyrazole-3-carboxamide, 1-cyclopropyl-N-[(aR)-6-(4-oxo-3,4-dihydrophthalazin-1-yl)spiro[3.3]heptan-2-yl]-1H-pyrazole-4-carboxamide, 5-(difluoromethoxy)-1-methyl-N-[(aR)-6-(4-oxo-3,4-dihydrophthalazin-1-yl)spiro[3.3]heptan-2-yl]-1H-pyrazole-3-carboxamide, 1-cyclopropyl-N-[(aR)-6-(4-oxo-3,4-dihydrophthalazin-1-yl)spiro[3.3]heptan-2-yl]-1H-pyrazole-3-carboxamide, 1-(2-hydroxy-2-methylpropyl)-N-[(aR)-6-(4-oxo-3,4-dihydrophthalazin-1-yl)spiro[3.3]heptan-2-yl]-1H-pyrazole-3-carboxamide, 6-fluoro-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide, 1-(2,2-difluoroethyl)-3-methyl-N-[(aR)-6-(4-oxo-3,4-dihydrophthalazin-1-yl)spiro[3.3]heptan-2-yl]-1H-pyrazole-4-carb oxamide, 4-methyl-N-[(aR)-6-(4-oxo-3,4-dihydrophthalazin-1-yl)spiro[3.3]heptan-2-yl]-2-(piperidin-1-yl)-1,3-thiazole-5-carboxamide, 4-methyl-2-(morpholin-4-yl)-N-[(aR)-6-(4-oxo-3,4-dihydrophthalazin-1-yl)spiro[3.3]heptan-2-yl]-1,3-thiazole-5-carboxamide, 4-methyl-N-[(aR)-6-(4-oxo-3,4-dihydrophthalazin-1-yl)spiro[3.3]heptan-2-yl]-2-(pyrrolidin-1-yl)-1,3-thiazole-5-carboxamide, 2-[(3 S)-3-fluoropyrrolidin-1-yl]-4-methyl-N-[(aR)-6-(4-oxo-3,4-dihydrophthalazin-1-yl)spiro[3.3]heptan-2-yl]-1,3-thiazole-5-carboxamide, 2-[(3R)-3-fluoropyrrolidin-1-yl]-4-methyl-N-[(aR)-6-(4-oxo-3,4-dihydrophthalazin-1-yl)spiro[3.3]heptan-2-yl]-1,3-thiazole-5-carboxamide, 2-[(3 S)-3-cyanopyrrolidin-1-yl]-4-methyl-N-[(aR)-6-(4-oxo-3,4-dihydrophthalazin-1-yl)spiro[3.3]heptan-2-yl]-1,3-thiazole-5-carboxamide, 2-[(3R)-3-cyanopyrrolidin-1-yl]-4-methyl-N-[(aR)-6-(4-oxo-3,4-dihydrophthalazin-1-yl)spiro[3.3]heptan-2-yl]-1,3-thiazole-5-carboxamide, rel-2-[(1 S,5R)-2-azabicyclo[3.1]hexan-2-yl]-4-methyl-N-[(aR)-6-(4-oxo-3,4-dihydrophthalazin-1-yl)spiro[3.3]heptan-2-yl]-1,3-thiazole-5-carboxamide, 2-(3,3-difluoropyrrolidin-1-yl)-4-methyl-N-[(aR)-6-(4-oxo-3,4-dihydrophthalazin-1-yl)spiro[3.3]heptan-2-yl]-1,3-thiazole-5-carboxamide, 2-(cyclopropylamino)-4-methyl-N-[(aR)-6-(4-oxo-3,4-dihydrophthalazin-1-yl)spiro[3.3]heptan-2-yl]-1,3-thiazole-5-carboxamide, 4-(aR)-{6-[(5-phenyl-1,3,4-thiadiazol-2-yl)amino]spiro[3.3]heptan-2-yl}-1,2-dihydrophthalazin-1-one, 4-(aR)-{6-[(5-phenyl-1,3-oxazol-2-yl)amino]spiro[3.3]heptan-2-yl}-1,2-dihydrophthalazin-1-one, 4-(aR)-{6-[(phthalazin-1-yl)amino]spiro[3.3]heptan-2-yl}-1,2-dihydrophthalazin-1-one, 4-[6-(2,3-dihydro-1H-indole-1-carbonyl)spiro[3.3]heptan-2-yl]-1,2-dihydrophthalazin-1-one, 4-[6-(2,3-dihydro-1H-isoindole-2-carbonyl)spiro[3.3]heptan-2-yl]-1,2-dihydrophthalazin-1-one, N-(5-methyl-1,3,4-thiadiazol-2-yl)-6-(4-oxo-3,4-dihydrophthalazin-1-yl)spiro[3.3]heptane-2-carboxamide, N-(5-methyl-1,2-oxazol-3-yl)-6-(4-oxo-3,4-dihydrophthalazin-1-yl)spiro[3.3]heptane-2-carboxamide, N-[(aR)-6-(4-oxo-3,4-dihydrophthalazin-1-yl)spiro[3.3]heptan-2-yl]-2,3-dihydro-1H-indole-1-carboxamide, N-[(aR)-6-(4-oxo-3,4-dihydrophthalazin-1-yl)spiro[3.3]heptan-2-yl]-2,3-dihydro-1H-isoindole-2-carboxamide, 4-{6-[2-(2,3-dihydro-1H-indol-1-yl)-2-oxoethyl]spiro[3.3]heptan-2-yl}-1,2-dihydrophthalazin-1-one, 2-[(3R)-3-fluoropyrrolidin-1-yl]-5-methyl-N-[(aR)-6-(4-oxo-3,4-dihydrophthalazin-1-yl)spiro[3.3]heptan-2-yl]-1,3-thiazole-4-carboxamide, 2-(3,3-difluoropyrrolidin-1-yl)-5-methyl-N-[(aR)-6-(4-oxo-3,4-dihydrophthalazin-1-yl)spiro[3.3]heptan-2-yl]-1,3-thiazole-4-carboxamide, 2-[(3 S)-3-cyanopyrrolidin-1-yl]-5-methyl-N-[(aR)-6-(4-oxo-3,4-dihydrophthalazin-1-yl)spiro[3.3]heptan-2-yl]-1,3-thiazole-4-carboxamide, 2-[(3R)-3-cyanopyrrolidin-1-yl]-5-methyl-N-[(aR)-6-(4-oxo-3,4-dihydrophthalazin-1-yl)spiro[3.3]heptan-2-yl]-1,3-thiazole-4-carboxamide, 2-[(3,3-difluorocyclobutyl)amino]-5-methyl-N-[(aR)-6-(4-oxo-3,4-dihydrophthalazin-1-yl)spiro[3.3]heptan-2-yl]-1,3-thiazole-4-carboxamide, 2-[(3 S)-3-fluoropyrrolidin-1-yl]-5-methyl-N-[(aR)-6-(4-oxo-3,4-dihydrophthalazin-1-yl)spiro[3.3]heptan-2-yl]-1,3-thiazole-4-carboxamide, 5-methyl-N-[(aR)-6-(4-oxo-3,4-dihydrophthalazin-1-yl)spiro[3.3]heptan-2-yl]-2-[(2 S)-2-(trifluoromethyl)pyrrolidin-1-yl]-1,3-thiazole-4-carboxamide, 5-methyl-N-[(aR)-6-(4-oxo-3,4-dihydrophthalazin-1-yl)spiro[3.3]heptan-2-yl]-2-[(2R)-2-(trifluoromethyl)pyrrolidin-1-yl]-1,3-thiazole-4-carboxamide, 1-(2-hydroxy-2-methylpropyl)-5-methoxy-N-[(aR)-6-(4-oxo-3,4-dihydrophthalazin-1-yl)spiro[3.3]heptan-2-yl]-1H-indazole-3-carboxamide, 1-(2-hydroxy-2-methylpropyl)-6-methoxy-N-[(aR)-6-(4-oxo-3,4-dihydrophthalazin-1-yl)spiro[3.3]heptan-2-yl]-1H-indazole-3-carboxamide, 6-methoxy-N-[(aR)-6-(4-oxo-3,4-dihydrophthalazin-1-yl)spiro[3.3]heptan-2-yl]pyrazolo[1,5-a]pyridine-3-carboxamide, 5-methoxy-N-[(aR)-6-(4-oxo-3,4-dihydrophthalazin-1-yl)spiro[3.3]heptan-2-yl]pyrazolo[1,5-a]pyridine-3-carboxamide, 5-fluoro-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide, 1-(2-hydroxy-2-methylpropyl)-N-[(aR)-6-(4-oxo-3,4-dihydrophthalazin-1-yl)spiro[3.3]heptan-2-yl]-1H-pyrrolo[2,3-b]pyridine-3-carboxamide, 6-(2-hydroxy-2-methylpropoxy)-N-[(aR)-6-(4-oxo-3,4-dihydrophthalazin-1-yl)spiro[3.3]heptan-2-yl]pyrazolo[1,5-a]pyridine-3-carboxamide, 6-[2-(morpholin-4-yl)ethoxy]-N-[(aR)-6-(4-oxo-3,4-dihydrophthalazin-1-yl)spiro[3.3]heptan-2-yl]pyrazolo[1,5-a]pyridine-3-carboxamide, 2-(morpholin-4-yl)-N-[(aR)-6-(4-oxo-3,4-dihydrophthalazin-1-yl)spiro[3.3]heptan-2-yl]-1,3-thiazole-5-carboxamide, N-[(aR)-6-(4-oxo-3,4-dihydrophthalazin-1-yl)spiro[3.3]heptan-2-yl]-2-(pyrrolidin-1-yl)-1,3-thiazole-5-carboxamide, N-[(aR)-6-(4-oxo-3,4-dihydrophthalazin-1-yl)spiro[3.3]heptan-2-yl]-1,2-benzoxazole-3-carboxamide, 1-(2-hydroxy-2-methylpropyl)-N-[(aR)-6-(4-oxo-3,4-dihydrophthalazin-1-yl)spiro[3.3]heptan-2-yl]-1H-indole-3-carboxamide, 5-[2-(morpholin-4-yl)ethoxy]-N-[(aR)-6-(4-oxo-3,4-dihydrophthalazin-1-yl)spiro[3.3]heptan-2-yl]pyrazolo[1,5-a]pyridine-3-carboxamide, N-[(aR)-6-(4-oxo-3,4-dihydrophthalazin-1-yl)spiro[3.3]heptan-2-yl]pyrazolo[1,5-a]pyridine-3-carboxamide, 5-(2-hydroxy-3-methoxypropoxy)-N-[(aR)-6-(4-oxo-3,4-dihydrophthalazin-1-yl)spiro[3.3]heptan-2-yl]pyrazolo[1,5-a]pyridine-3-carboxamide, 6-(morpholin-4-yl)-N-[(aR)-6-(4-oxo-3,4-dihydrophthalazin-1-yl)spiro[3.3]heptan-2-yl]pyrazolo[1,5-a]pyridine-3-carboxamide, 5-(2-hydroxyethoxy)-N-[(aR)-6-(4-oxo-3,4-dihydrophthalazin-1-yl)spiro[3.3]heptan-2-yl]pyrazolo[1,5-a]pyridine-3-carboxamide, N-[(aR)-6-(4-oxo-3,4-dihydrophthalazin-1-yl)spiro[3.3]heptan-2-yl]-2,1-benzoxazole-3-carboxamide, 6-(difluoromethoxy)-N-[(aR)-6-(4-oxo-3,4-dihydrophthalazin-1-yl)spiro[3.3]heptan-2-yl]pyrazolo[1,5-a]pyridine-3-carboxamide, 6-(2,2-difluoroethoxy)-N-[(aR)-6-(4-oxo-3,4-dihydrophthalazin-1-yl)spiro[3.3]heptan-2-yl]pyrazolo[1,5-a]pyridine-3-carboxamide, N-[(aR)-6-(4-oxo-3,4-dihydrophthalazin-1-yl)spiro[3.3]heptan-2-yl]-6-[2-(1H-pyrazol-1-yl)ethoxy]pyrazolo[1,5-a]pyridine-3-carboxamide, 6-(4,4-difluoropiperidin-1-yl)-N-[(aR)-6-(4-oxo-3,4-dihydrophthalazin-1-yl)spiro[3.3]heptan-2-yl]pyrazolo[1,5-a]pyridine-3-carboxamide, N-[(aR)-6-(4-oxo-3,4-dihydrophthalazin-1-yl)spiro[3.3]heptan-2-yl]-6-[2-(pyrrolidin-1-yl)ethoxy]pyrazolo[1,5-a]pyridine-3-carboxamide, 5-(morpholin-4-yl)-N-[(aR)-6-(4-oxo-3,4-dihydrophthalazin-1-yl)spiro[3.3]heptan-2-yl]pyrazolo[1,5-a]pyridine-3-carboxamide, 5-(1-methyl-1H-pyrazol-4-yl)-N-[(aR)-6-(4-oxo-3,4-dihydrophthalazin-1-yl)spiro[3.3]heptan-2-yl]pyrazolo[1,5-a]pyridine-3-carboxamide, 6-(4-methylpiperazin-1-yl)-N-[(aR)-6-(4-oxo-3,4-dihydrophthalazin-1-yl)spiro[3.3]heptan-2-yl]pyrazolo[1,5-a]pyridine-3-carboxamide, N-[(aR)-6-(4-oxo-3,4-dihydrophthalazin-1-yl)spiro[3.3]heptan-2-yl]-6-(pyrrolidin-1-yl)pyrazolo[1,5-a]pyridine-3-carboxamide, 6-[(3R)-3-fluoropyrrolidin-1-yl]-N-[(aR)-6-(4-oxo-3,4-dihydrophthalazin-1-yl)spiro[3.3]heptan-2-yl]pyrazolo[1,5-a]pyridine-3-carboxamide, 6-[(3 S)-3-fluoropyrrolidin-1-yl]-N-[(aR)-6-(4-oxo-3,4-dihydrophthalazin-1-yl)spiro[3.3]heptan-2-yl]pyrazolo[1,5-a]pyridine-3-carboxamide, 6-(3,3-difluoropyrrolidin-1-yl)-N-[(aR)-6-(4-oxo-3,4-dihydrophthalazin-1-yl)spiro[3.3]heptan-2-yl]pyrazolo[1,5-a]pyridine-3-carboxamide, 6-(3-fluoroazetidin-1-yl)-N-[(aR)-6-(4-oxo-3,4-dihydrophthalazin-1-yl)spiro[3.3]heptan-2-yl]pyrazolo[1,5-a]pyridine-3-carboxamide, 6-(3,3-difluoroazetidin-1-yl)-N-[(aR)-6-(4-oxo-3,4-dihydrophthalazin-1-yl)spiro[3.3]heptan-2-yl]pyrazolo[1,5-a]pyridine-3-carboxamide, N-[(aR)-6-(4-oxo-3,4-dihydrophthalazin-1-yl)spiro[3.3]heptan-2-yl]benzo[d]imidazo[2,1-b]thiazole-2-carboxamide, N-[(aR)-6-(4-oxo-3,4-dihydrophthalazin-1-yl)spiro[3.3]heptan-2-yl]imidazo[2,1-b][1,3]thiazole-6-carboxamide, 2-ethyl-N-[(aR)-6-(4-oxo-3,4-dihydrophthalazin-1-yl)spiro[3.3]heptan-2-yl]imidazo[2,1-b][1,3,4]thiadiazole-6-carboxamide, N-[(aR)-6-(4-oxo-3,4-dihydrophthalazin-1-yl)spiro[3.3]heptan-2-yl]pyrazolo[1,5-b]pyridazine-3-carboxamide, 7-cyclopropyl-6-(2-hydroxy-2-methylpropoxy)-N-[(aR)-6-(4-oxo-3,4-dihydrophthalazin-1-yl)spiro[3.3]heptan-2-yl]pyrazolo[1,5-a]pyridine-3-carboxamide, N-[(aR)-6-(4-oxo-3,4-dihydrophthalazin-1-yl)spiro[3.3]heptan-2-yl]-6-[3,3,3-trifluoro-2-hydroxy-2-(trifluoromethyl)propoxy]pyrazolo[1,5-a]pyridine-3-carboxamide, 6-(benzyloxy)-N-[(aR)-6-(4-oxo-3,4-dihydrophthalazin-1-yl)spiro[3.3]heptan-2-yl]pyrazolo[1,5-a]pyridine-3-carboxamide, 1-(2,2-difluoroethyl)-N-[(aR)-6-(4-oxo-3,4-dihydrophthalazin-1-yl)spiro[3.3]heptan-2-yl]-1H-pyrazole-5-carboxamide, N-[(aR)-6-(4-oxo-3,4-dihydrophthalazin-1-yl)spiro[3.3]heptan-2-yl]-1-(3,3,3-trifluoropropyl)-1H-pyrazole-5-carboxamide, 1-[(4-methoxyphenyl)methyl]-N-[(aR)-6-(4-oxo-3,4-dihydrophthalazin-1-yl)spiro[3.3]heptan-2-yl]-1H-pyrazole-4-carb oxamide, 1-(cyclopropylmethyl)-N-[(aR)-6-(4-oxo-3,4-dihydrophthalazin-1-yl)spiro[3.3]heptan-2-yl]-1H-pyrazole-5-carboxamide, 1-(oxan-4-yl)-N-[(aR)-6-(4-oxo-3,4-dihydrophthalazin-1-yl)spiro[3.3]heptan-2-yl]-1H-pyrazole-5-carboxamide, N-[(aR)-6-(4-oxo-3,4-dihydrophthalazin-1-yl)spiro[3.3]heptan-2-yl]-6-(oxolan-3-yloxy)pyrazolo[1,5-a]pyridine-3-carboxamide, tert-butyl N-[2-(4-{[(aR)-6-(4-oxo-3,4-dihydrophthalazin-1-yl)spiro[3.3]heptan-2-yl]carbamoyl}-1H-pyrazol-1-yl)ethyl]carbamate, N-[(aR)-6-(4-oxo-3,4-dihydrophthalazin-1-yl)spiro[3.3]heptan-2-yl]-6-(3,3,3-trifluoro-2-hydroxypropoxy)pyrazolo[1,5-a]pyridine-3-carboxamide, 1-(3-methoxyphenyl)-N-[(aR)-6-(4-oxo-3,4-dihydrophthalazin-1-yl)spiro[3.3]heptan-2-yl]-1H-pyrazole-4-carboxamide, 1-benzyl-N-[(aR)-6-(4-oxo-3,4-dihydrophthalazin-1-yl)spiro[3.3]heptan-2-yl]-1H-pyrazole-4-carboxamide, 6-(2-hydroxy-2-methylpropoxy)-3-N-[(aR)-6-(4-oxo-3,4-dihydrophthalazin-1-yl)spiro[3.3]heptan-2-yl]pyrazolo[1,5-a]pyridine-3,7-dicarboxamide, 7-cyano-6-hydroxy-N-[(aR)-6-(4-oxo-3,4-dihydrophthalazin-1-yl)spiro[3.3]heptan-2-yl]pyrazolo[1,5-a]pyridine-3-carboxamide, 6-(2-hydroxy-2-methylpropoxy)-7-methyl-N-[(aR)-6-(4-oxo-3,4-dihydrophthalazin-1-yl)spiro[3.3]heptan-2-yl]pyrazolo[1,5-a]pyridine-3-carboxamide, 6-(2-hydroxy-2-methylpropoxy)-7-(methoxymethyl)-N-[(aR)-6-(4-oxo-3,4-dihydrophthalazin-1-yl)spiro[3.3]heptan-2-yl]pyrazolo[1,5-a]pyridine-3-carboxamide, 5-methyl-N-[(aR)-6-(4-oxo-3,4-dihydrophthalazin-1-yl)spiro[3.3]heptan-2-yl]-1-phenyl-1H-1,2,3-triazole-4-carboxamide, 1-(4-methoxyphenyl)-5-methyl-N-[(aR)-6-(4-oxo-3,4-dihydrophthalazin-1-yl)spiro[3.3]heptan-2-yl]-1H-1,2,3-triazole-4-carboxamide, 1-(3-methoxyphenyl)-N-[(aR)-6-(4-oxo-3,4-dihydrophthalazin-1-yl)spiro[3.3]heptan-2-yl]-1H-1,2,3-triazole-4-carboxamide, 1-(2-methoxyphenyl)-5-methyl-N-[(aR)-6-(4-oxo-3,4-dihydrophthalazin-1-yl)spiro[3.3]heptan-2-yl]-1H-1,2,3-triazole-4-carboxamide, 5-(4-fluorophenyl)-N-[(aR)-6-(4-oxo-3,4-dihydrophthalazin-1-yl)spiro[3.3]heptan-2-yl]-1,2,4-oxadiazole-3-carboxamide, N-[(aR)-6-(4-oxo-3,4-dihydrophthalazin-1-yl)spiro[3.3]heptan-2-yl]-6-(3,3,3-trifluoro-2-hydroxypropoxy)pyrazolo[1,5-a]pyridine-3-carboxamide, N-[(aR)-6-(4-oxo-3,4-dihydrophthalazin-1-yl)spiro[3.3]heptan-2-yl]-6-(3,3,3-trifluoro-2-hydroxypropoxy)pyrazolo[1,5-a]pyridine-3-carboxamide, N-[(aR)-6-(4-oxo-3,4-dihydrophthalazin-1-yl)spiro[3.3]heptan-2-yl]-6-(oxolan-3-yloxy)pyrazolo[1,5-a]pyridine-3-carboxamide, N-[(aR)-6-(4-oxo-3,4-dihydrophthalazin-1-yl)spiro[3.3]heptan-2-yl]-6-(oxolan-3-yloxy)pyrazolo[1,5-a]pyridine-3-carboxamide, 7-methyl-N-[(aR)-6-(4-oxo-3,4-dihydrophthalazin-1-yl)spiro[3.3]heptan-2-yl]pyrazolo[1,5-a]pyridine-3-carboxamide, 3-methoxy-N-[(aR)-6-(4-oxo-3,4-dihydrophthalazin-1-yl)spiro[3.3]heptan-2-yl]imidazo[1,2-a]pyridine-2-carboxamide, 6-(benzyloxy)-7-cyclopropyl-N-[(aR)-6-(4-oxo-3,4-dihydrophthalazin-1-yl)spiro[3.3]heptan-2-yl]pyrazolo[1,5-a]pyridine-3-carboxamide, 6-(benzyloxy)-7-methyl-N-[(aR)-6-(4-oxo-3,4-dihydrophthalazin-1-yl)spiro[3.3]heptan-2-yl]pyrazolo[1,5-a]pyridine-3-carboxamide, 6-(benzyloxy)-7-cyano-N-[(aR)-6-(4-oxo-3,4-dihydrophthalazin-1-yl)spiro[3.3]heptan-2-yl]pyrazolo[1,5-a]pyridine-3-carboxamide, 7-cyclopropyl-6-hydroxy-N-[(aR)-6-(4-oxo-3,4-dihydrophthalazin-1-yl)spiro[3.3]heptan-2-yl]pyrazolo[1,5-a]pyridine-3-carboxamide, 1-(2-methoxyphenyl)-N-[(aR)-6-(4-oxo-3,4-dihydrophthalazin-1-yl)spiro[3.3]heptan-2-yl]-1H-1,2,3-triazole-4-carboxamide, 6-(benzyloxy)-7-[(dimethylamino)methyl]-N-[(aR)-6-(4-oxo-3,4-dihydrophthalazin-1-yl)spiro[3.3]heptan-2-yl]pyrazolo[1,5-a]pyridine-3-carboxamide, 6-[(1,3-difluoropropan-2-yl)oxy]-N-[(aR)-6-(4-oxo-3,4-dihydrophthalazin-1-yl)spiro[3.3]heptan-2-yl]pyrazolo[1,5-a]pyridine-3-carboxamide, 6-[(1,1-dioxo-1$\lambda^6$-thian-4-yl)oxy]-N-[(aR)-6-(4-oxo-3,4-dihydrophthalazin-1-yl)spiro[3.3]heptan-2-yl]pyrazolo[1,5-a]pyridine-3-carboxamide, N-[(aR)-6-(4-oxo-3,4-dihydrophthalazin-1-yl)spiro[3.3]heptan-2-yl]-6-(3,3,3-trifluoropropoxy)pyrazolo[1,5-a]pyridine-3-carboxamide, 6-[(4,4-difluorocyclohexyl)oxy]-N-[(aR)-6-(4-oxo-3,4-dihydrophthalazin-1-yl)spiro[3.3]heptan-2-yl]pyrazolo[1,5-a]pyridine-3-carboxamide, 6-(oxan-4-yloxy)-N-[(aR)-6-(4-oxo-3,4-dihydrophthalazin-1-yl)spiro[3.3]heptan-2-yl]pyrazolo[1,5-a]pyridine-3-carboxamide, methyl 3-[(3-{[(aR)-6-(4-oxo-3,4-dihydrophthalazin-1-yl)spiro[3.3]heptan-2-yl]carbamoyl}pyrazolo[1,5-a]pyridin-6-yl)oxy]azetidine-1-carboxylate, 6-hydroxy-N-[(aR)-6-(4-oxo-3,4-dihydrophthalazin-1-yl)spiro[3.3]heptan-2-yl]pyrazolo[1,5-a]pyridine-3-carboxamide, 6-(3,3-difluorocyclobutoxy)-N-[(aR)-6-(4-oxo-3,4-dihydrophthalazin-1-yl)spiro[3.3]heptan-2-yl]pyrazolo[1,5-a]pyridine-3-carboxamide, N-[(aR)-6-(4-oxo-3,4-dihydrophthalazin-1-yl)spiro[3.3]heptan-2-yl]-6-[2-(2,2,2-trifluoroethoxy)ethoxy]pyrazolo[1,5-a]pyridine-3-carboxamide, 6-[(5-cyclopropyl-1,3,4-thiadiazol-2-yl)methoxy]-N-[(aR)-6-(4-oxo-3,4-dihydrophthalazin-1-yl)spiro[3.3]heptan-2-yl]pyrazolo[1,5-a]pyridine-3-carboxamide, 6-(benzyloxy)-N-[(aR)-6-(4-oxo-3,4-dihydrophthalazin-1-yl)spiro[3.3]heptan-2-yl]-7-(trifluoromethyl)pyrazolo[1,5-a]pyridine-3-carboxamide, 6-cyclopropyl-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide, 1-(2-hydroxy-2-methylpropyl)-N-[(aR)-6-(4-oxo-3,4-dihydrophthalazin-1-yl)spiro[3.3]heptan-2-yl]-6-phenyl-1H-indazole-3-carboxamide, 6-(4-chlorophenyl)-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide, 1-(2-hydroxy-2-methylpropyl)-6-(1-methyl-1H-pyrazol-3-yl)-N-[(aR)-6-(4-oxo-3,4-dihydrophthalazin-1-yl)spiro[3.3]heptan-2-yl]-1H-indazole-3-carboxamide, 1-(2-hydroxy-2-methylpropyl)-6-(1-methyl-1H-pyrazol-5-yl)-N-[(aR)-6-(4-oxo-3,4-dihydrophthalazin-1-yl)spiro[3.3]heptan-2-yl]-1H-indazole-3-carboxamide, 1-(2-hydroxy-2-methylpropyl)-6-(1-methyl-1H-pyrazol-4-yl)-N-[(aR)-6-(4-oxo-3,4-dihydrophthalazin-1-yl)spiro[3.3]heptan-2-yl]-1H-indazole-3-carboxamide, 1-(2-hydroxy-2-methylpropyl)-N-[(aR)-6-(4-oxo-3,4-dihydrophthalazin-1-yl)spiro[3.3]heptan-2-yl]-6-[(E)-2-phenylethenyl]-1H-indazole-3-carboxamide, 6-[(E)-2-cyclopropylethenyl]-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide, 1-(2-hydroxy-2-methylpropyl)-6-(6-methoxypyridin-2-yl)-N-[(aR)-6-(4-oxo-3,4-dihydrophthalazin-1-yl)spiro[3.3]heptan-2-yl]-1H-indazole-3-carboxamide, 6-[(Z)-2-cyclopropylethenyl]-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide, 6-bromo-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide, 1-(2-hydroxy-2-methylpropyl)-6-(4-methoxyphenyl)-N-[(aR)-6-(4-oxo-3,4-dihydrophthalazin-1-yl)spiro[3.3]heptan-2-yl]-1H-indazole-3-carboxamide, 1-(2-hydroxy-2-methylpropyl)-6-(1-methyl-1H-1,2,3-triazol-4-yl)-N-[(aR)-6-(4-oxo-3,4-dihydrophthalazin-1-yl)spiro[3.3]heptan-2-yl]-1H-indazole-3-carboxamide, 6-(dimethyl-1,2-oxazol-4-yl)-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide, 6-(3-chlorophenyl)-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide, 1-(2-hydroxy-2-methylpropyl)-6-(2-methoxyphenyl)-N-[(aR)-6-(4-oxo-3,4-dihydrophthalazin-1-yl)spiro[3.3]heptan-2-yl]-1H-indazole-3-carboxamide, 1-(2-hydroxy-2-methylpropyl)-6-(3-methoxyphenyl)-N-[(aR)-6-(4-oxo-3,4-dihydrophthalazin-1-yl)spiro[3.3]heptan-2-yl]-1H-indazole-3-carboxamide, 6-(2, 6-difluorophenyl)-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide, 6-(2-cyanophenyl)-1-(2-hydroxy-2-methylpropyl)-N-[(aR)-6-(4-oxo-3,4-dihydrophthalazin-1-yl)spiro[3.3]heptan-2-yl]-1H-indazole-3-carboxamide, 1-(2-hydroxy-2-methylpropyl)-6-(1,2-oxazol-4-yl)-N-[(aR)-6-(4-oxo-3,4-dihydrophthalazin-1-yl)spiro[3.3]heptan-2-yl]-1H-indazole-3-carboxamide, N-[6-fluoro-6-(4-oxo-3,4-dihydrophthalazin-1-yl)spiro[3.3]heptan-2-yl]-1-(2-hydroxy-2-methylpropyl)-1H-indazole-3-carboxamide, 6-fluoro-N-[6-fluoro-6-(4-oxo-3,4-dihydrophthalazin-1-yl)spiro[3.3]heptan-2-yl]-1-(2-hydroxy-2-methylpropyl)-1H-indazole-3-carboxamide, N-[6-fluoro-6-(4-oxo-3,4-dihydrophthalazin-1-yl)spiro[3.3]heptan-2-yl]pyrazolo[1,5-a]pyridine-3-carboxamide, N-[(aR)-6-(4-oxo-3,4-dihydrophthalazin-1-yl)spiro[3.3]heptan-2-yl]-6-(2-oxopyrrolidin-1-yl)pyrazolo[1,5-a]pyridine-3-carboxamide, 6-cyclopropyl-N-[(aR)-6-(4-oxo-3,4-dihydrophthalazin-1-yl)spiro[3.3]heptan-2-yl]pyrazolo[1,5-a]pyridine-3-carboxamide, 6-[1-(difluoromethyl)-1H-pyrazol-4-yl]-N-[(aR)-6-(4-oxo-3,4-dihydrophthalazin-1-yl)spiro[3.3]heptan-2-yl]pyrazolo[1,5-a]pyridine-3-carboxamide, 6-cyano-N-[(aR)-6-(4-oxo-3,4-dihydrophthalazin-1-yl)spiro[3.3]heptan-2-yl]pyrazolo[1, 5-a]pyridine-3-carboxamide, 6-(2-oxo-1,2-dihydropyridin-1-yl)-N-[(aR)-6-(4-oxo-3,4-dihydrophthalazin-1-yl)spiro[3.3]heptan-2-yl]pyrazolo[1,5-a]pyridine-3-carboxamide, 6-(1-methyl-1H-pyrazol-4-yl)-N-[(aR)-6-(4-oxo-3,4-dihydrophthalazin-1-yl)spiro[3.3]heptan-2-yl]pyrazolo[1,5-a]pyridine-3-carboxamide, N-[(aR)-6-(4-oxo-3,4-dihydrophthalazin-1-yl)spiro[3.3]heptan-2-yl]-6-{1-[(2S)-3,3,3-trifluoro-2-hydroxypropyl]-1H-pyrazol-4-yl}pyrazolo[1,5-a]pyridine-3-carboxamide, N-[(aR)-6-(4-oxo-3,4-dihydrophthalazin-1-yl)spiro[3.3]heptan-2-yl]-6-[3-(trifluoromethyl)-1H-pyrazol-4-yl]pyrazolo[1,5-a]pyridine-3-carboxamide, N-[(aR)-6-(4-oxo-3,4-dihydrophthalazin-1-yl)spiro[3.3]heptan-2-yl]-6-(1,3-thiazol-2-yl)pyrazolo[1,5-a]pyridine-3-carboxamide, N-[(aR)-6-(4-oxo-3,4-dihydrophthalazin-1-yl)spiro[3.3]heptan-2-yl]-6-(1H-pyrazol-4-yl)pyrazolo[1,5-a]pyridine-3-carboxamide, 6-(dimethyl-1H-1,2,3-triazol-5-yl)-N-[(aR)-6-(4-oxo-3,4-dihydrophthalazin-1-yl)spiro[3.3]heptan-2-yl]pyrazolo[1,5-a]pyridine-3-carboxamide, 6-(1H-imidazol-1-yl)-N-[(aR)-6-(4-oxo-3,4-dihydrophthalazin-1-yl)spiro[3.3]heptan-2-yl]pyrazolo[1,5-a]pyridine-3-carboxamide, N-[(aR)-6-(4-oxo-3,4-dihydrophthalazin-1-yl)spiro[3.3]heptan-2-yl]-6-(1H-pyrazol-1-yl)pyrazolo[1,5-a]pyridine-3-carboxamide, N-[(aR)-6-(4-oxo-3,4-dihydrophthalazin-1-yl)spiro[3.3]heptan-2-yl]-6-(1H-1,2,4-triazol-1-yl)pyrazolo[1,5-a]pyridine-3-carboxamide, 6-(2-methoxyethoxy)-N-[(aR)-6-(4-oxo-3,4-dihydrophthalazin-1-yl)spiro[3.3]heptan-2-yl]pyrazolo[1,5-a]pyridine-3-carboxamide, 6-(4-oxo-1,4-dihydropyridin-1-yl)-N-[(aR)-6-(4-oxo-3,4-dihydrophthalazin-1-yl)spiro[3.3]heptan-2-yl]pyrazolo[1,5-a]pyridine-3-carboxamide, 6-(2-hydroxyethoxy)-N-[(aR)-6-(4-oxo-3,4-dihydrophthalazin-1-yl)spiro[3.3]heptan-2-yl]pyrazolo[1,5-a]pyridine-3-carboxamide, 6-[2-(3-fluoroazetidin-1-yl)ethoxy]-N-[(aR)-6-(4-oxo-3,4-dihydrophthalazin-1-yl)spiro[3.3]heptan-2-yl]pyrazolo[1,5-a]pyridine-3-carboxamide, 6-[2-(dimethylamino)ethoxy]-N-[(aR)-6-(4-oxo-3,4-dihydrophthalazin-1-yl)spiro[3.3]heptan-2-yl]pyrazolo[1,5-a]pyridine-3-carboxamide, 6-[2-(4-hydroxy-3,3-dimethylpiperidin-1-yl)ethoxy]-N-[(aR)-6-(4-oxo-3,4-dihydrophthalazin-1-yl)spiro[3.3]heptan-2-yl]pyrazolo[1,5-a]pyridine-3-carboxamide, 6-[2-(3,3-difluoropyrrolidin-1-yl)ethoxy]-N-[(aR)-6-(4-oxo-3,4-dihydrophthalazin-1-yl)spiro[3.3]heptan-2-yl]pyrazolo[1,5-a]pyridine-3-carboxamide, 6-[2-(azetidin-1-yl)ethoxy]-N-[(aR)-6-(4-oxo-3,4-dihydrophthalazin-1-yl)spiro[3.3]heptan-2-yl]pyrazolo[1,5-a]pyridine-3-carboxamide, 6-[2-(2,2-dimethylmorpholin-4-yl)ethoxy]-N-[(aR)-6-(4-oxo-3,4-dihydrophthalazin-1-yl)spiro[3.3]heptan-2-yl]pyrazolo[1,5-a]pyridine-3-carboxamide, 6-[2-(4-methylpiperazin-1-yl)ethoxy]-N-[(aR)-6-(4-oxo-3,4-dihydrophthalazin-1-yl)spiro[3.3]heptan-2-yl]pyrazolo[1,5-a]pyridine-3-carboxamide, 6-{2-[(3R)-3-fluoropyrrolidin-1-yl]ethoxy}-N-[(aR)-6-(4-oxo-3,4-dihydrophthalazin-1-yl)spiro[3.3]heptan-2-yl]pyrazolo[1,5-a]pyridine-3-carboxamide, 6-{2-[(3 S)-3-fluoropyrrolidin-1-yl]ethoxy}-N-[(aR)-6-(4-oxo-3,4-dihydrophthalazin-1-yl)spiro[3.3]heptan-2-yl]pyrazolo[1,5-a]pyridine-3-carboxamide, 6-[3-(morpholin-4-yl)propyl]-N-[(aR)-6-(4-oxo-3,4-dihydrophthalazin-1-yl)spiro[3.3]heptan-2-yl]pyrazolo[1,5-a]pyridine-3-carboxamide, N-[(aR)-6-(4-oxo-3,4-dihydrophthalazin-1-yl)spiro[3.3]heptan-2-yl]-6-[3-(pyrrolidin-1-yl)propyl]pyrazolo[1,5-a]pyridine-3-carboxamide, 6-[3-(dimethylamino)propyl]-N-[(aR)-6-(4-oxo-3,4-dihydrophthalazin-1-yl)spiro[3.3]heptan-2-yl]pyrazolo[1,5-a]pyridine-3-carboxamide, 6-[3-(cyclopropylamino)propyl]-N-[(aR)-6-(4-oxo-3,4-dihydrophthalazin-1-yl)spiro[3.3]heptan-2-yl]pyrazolo[1,5-a]pyridine-3-carboxamide, 6-(3-hydroxypropyl)-N-[(aR)-6-(4-oxo-3,4-dihydrophthalazin-1-yl)spiro[3.3]heptan-2-yl]pyrazolo[1,5-a]pyridine-3-carboxamide, 6-[3-(4,4-difluoropiperidin-1-yl)propyl]-N-[(aR)-6-(4-oxo-3,4-dihydrophthalazin-1-yl)spiro[3.3]heptan-2-yl]pyrazolo[1,5-a]pyridine-3-carboxamide, 6-[3-(3,3-difluoropyrrolidin-1-yl)propyl]-N-[(aR)-6-(4-oxo-3,4-dihydrophthalazin-1-yl)spiro[3.3]heptan-2-yl]pyrazolo[1,5-a]pyridine-3-carboxamide, 6-(3-hydroxy-3-methylbutyl)-N-[(aR)-6-(4-oxo-3,4-dihydrophthalazin-1-yl)spiro[3.3]heptan-2-yl]pyrazolo[1,5-a]pyridine-3-carboxamide, N-[(aR)-6-(4-oxo-3,4-dihydrophthalazin-1-yl)spiro[3.3]heptan-2-yl]-6-[4,4,4-trifluoro-3-hydroxy-3-(trifluoromethyl)butyl]pyrazolo[1,5-a]pyridine-3-carboxamide, 6-(morpholin-4-ylmethyl)-N-[(aR)-6-(4-oxo-3,4-dihydrophthalazin-1-yl)spiro[3.3]heptan-2-yl]pyrazolo[1,5-a]pyridine-3-carboxamide, 6-[(4-methylpiperazin-1-yl)methyl]-N-[(aR)-6-(4-oxo-3,4-dihydrophthalazin-1-yl)spiro[3.3]heptan-2-yl]pyrazolo[1,5-a]pyridine-3-carboxamide, N-[(aR)-6-(4-oxo-3,4-dihydrophthalazin-1-yl)spiro[3.3]heptan-2-yl]-6-(piperidin-1-ylmethyl)pyrazolo[1,5-a]pyridine-3-carboxamide, 6-[(dimethylamino)methyl]-N-[(aR)-6-(4-oxo-3,4-dihydrophthalazin-1-yl)spiro[3.3]heptan-2-yl]pyrazolo[1,5-a]pyridine-3-carboxamide, 6-benzyl-N-[(aR)-6-(4-oxo-3,4-dihydrophthalazin-1-yl)spiro[3.3]heptan-2-yl]pyrazolo[1, 5-a]pyridine-3-carboxamide, 6-[3-(morpholin-4-yl)-3-oxopropyl]-N-[(aR)-6-(4-oxo-3,4-dihydrophthalazin-1-yl)spiro[3.3]heptan-2-yl]pyrazolo[1,5-a]pyridine-3-carboxamide, N-[(aR)-6-(4-oxo-3,4-dihydrophthalazin-1-yl)spiro[3.3]heptan-2-yl]-6-(3,3,3-trifluoropropyl)pyrazolo[1,5-a]pyridine-3-carboxamide, 6-(2-cyanoethyl)-N-[(aR)-6-(4-oxo-3,4-dihydrophthalazin-1-yl)spiro[3.3]heptan-2-yl]pyrazolo[1,5-a]pyridine-3-carboxamide, 6-{[2-(morpholin-4-yl)ethoxy]methyl}-N-[(aR)-6-(4-oxo-3,4-dihydrophthalazin-1-yl)spiro[3.3]heptan-2-yl]pyrazolo[1,5-a]pyridine-3-carboxamide, 6-(methoxymethyl)-N-[(aR)-6-(4-oxo-3,4-dihydrophthalazin-1-yl)spiro[3.3]heptan-2-yl]pyrazolo[1,5-a]pyridine-3-carboxamide, 6-(2-methoxypyrimidin-5-yl)-N-[(aR)-6-(4-oxo-3,4-dihydrophthalazin-1-yl)spiro[3.3]heptan-2-yl]pyrazolo[1,5-a]pyridine-3-carboxamide, 6-[(oxan-4-ylmethoxy)methyl]-N-[(aR)-6-(4-oxo-3,4-dihydrophthalazin-1-yl)spiro[3.3]heptan-2-yl]pyrazolo[1,5-a]pyridine-3-carboxamide, N-[(aR)-6-(4-oxo-3,4-dihydrophthalazin-1-yl)spiro[3.3]heptan-2-yl]-6-[(prop-2-en-1-yloxy)methyl]pyrazolo[1,5-a]pyridine-3-carboxamide, 6-(hydroxymethyl)-N-[(aR)-6-(4-oxo-3,4-dihydrophthalazin-1-yl)spiro[3.3]heptan-2-yl]pyrazolo[1,5-a]pyridine-3-carboxamide, 6-acetyl-N-[(aR)-6-(4-oxo-3,4-dihydrophthalazin-1-yl)spiro[3.3]heptan-2-yl]pyrazolo[1, 5-a]pyridine-3-carboxamide, 6-(2-hydroxypropan-2-yl)-N-[(aR)-6-(4-oxo-3,4-dihydrophthalazin-1-yl)spiro[3.3]heptan-2-yl]pyrazolo[1,5-a]pyridine-3-carboxamide, 6-(1,5-dimethyl-1H-pyrazol-4-yl)-N-[(aR)-6-(4-oxo-3,4-dihydrophthalazin-1-yl)spiro[3.3]heptan-2-yl]pyrazolo[1,5-a]pyridine-3-carboxamide, 6-(1-cyclopropyl-1H-pyrazol-4-yl)-N-[(aR)-6-(4-oxo-3,4-dihydrophthalazin-1-yl)spiro[3.3]heptan-2-yl]pyrazolo[1,5-a]pyridine-3-carboxamide, 6-[1-(cyclopropylmethyl)-1H-pyrazol-4-yl]-N-[(aR)-6-(4-oxo-3,4-dihydrophthalazin-1-yl)spiro[3.3]heptan-2-yl]pyrazolo[1,5-a]pyridine-3-carboxamide, 6-[1-($^2$H3)methyl-1H-pyrazol-4-yl]-N-[(aR)-6-(4-oxo-3,4-dihydrophthalazin-1-yl)spiro[3.3]heptan-2-yl]pyrazolo[1,5-a]pyridine-3-carboxamide, N-[(aR)-6-(4-oxo-3,4-dihydrophthalazin-1-yl)spiro[3.3]heptan-2-yl]-6-[1-(propan-2-yl)-1H-pyrazol-4-yl]pyrazolo[1,5-a]pyridine-3-carboxamide, N-[(aR)-6-(4-oxo-3,4-dihydrophthalazin-1-yl)spiro[3.3]heptan-2-yl]-6-(trimethyl-1H-pyrazol-4-yl)pyrazolo[1,5-a]pyridine-3-carboxamide, 6-[1-(oxan-4-yl)-1H-pyrazol-4-yl]-N-[(aR)-6-(4-oxo-3,4-dihydrophthalazin-1-yl)spiro[3.3]heptan-2-yl]pyrazolo[1,5-a]pyridine-3-carboxamide, 6-[1-methyl-3-(trifluoromethyl)-1H-pyrazol-4-yl]-N-[(aR)-6-(4-oxo-3,4-dihydrophthalazin-1-yl)spiro[3.3]heptan-2-yl]pyrazolo[1,5-a]pyridine-3-carboxamide, N-[(aR)-6-(4-oxo-3,4-dihydrophthalazin-1-yl)spiro[3.3]heptan-2-yl]-6-[1 1-(propan-2-yl)-3-(trifluoromethyl)-1H-pyrazol-4-yl]pyrazolo[1,5-a]pyridine-3-carboxamide, 6-(1-tert-butyl-1H-pyrazol-4-yl)-N-[(aR)-6-(4-oxo-3,4-dihydrophthalazin-1-yl)spiro[3.3]heptan-2-yl]pyrazolo[1,5-a]pyridine-3-carboxamide, N-[(aR)-6-(4-oxo-3,4-dihydrophthalazin-1-yl)spiro[3.3]heptan-2-yl]-6-[1-(oxolan-3-yl)-1H-pyrazol-4-yl]pyrazolo[1,5-a]pyridine-3-carboxamide, 1-(4-bromophenyl)-3-[(aR)-6-(4-oxo-3,4-dihydrophthalazin-1-yl)spiro[3.3]heptan-2-yl]urea, 1-[4-(1-methyl-1H-pyrazol-4-yl)phenyl]-3-[(aR)-6-(4-oxo-3,4-dihydrophthalazin-1-yl)spiro[3.3]heptan-2-yl]urea, 1-{4-[1-($^2$H3)methyl-1H-pyrazol-4-yl]phenyl}-3-[(aR)-6-(4-oxo-3,4-dihydrophthalazin-1-yl)spiro[3.3]heptan-2-yl]urea, 1-[4-(1-cyclopropyl-1H-pyrazol-4-yl)phenyl]-3-[(aR)-6-(4-oxo-3,4-dihydrophthalazin-1-yl)spiro[3.3]heptan-2-yl]urea, 1-{4-[1-(oxan-4-yl)-1H-pyrazol-4-yl]phenyl}-3-[(aR)-6-(4-oxo-3,4-dihydrophthalazin-1-yl)spiro[3.3]heptan-2-yl]urea, 1-{4-[1-methyl-3-(trifluoromethyl)-1H-pyrazol-4-yl]phenyl}-3-[(aR)-6-(4-oxo-3,4-dihydrophthalazin-1-yl)spiro[3.3]heptan-2-yl]urea, 3-[(aR)-6-(4-oxo-3,4-dihydrophthalazin-1-yl)spiro[3.3]heptan-2-yl]-1-[4-(trimethyl-1H-pyrazol-4-yl)phenyl]urea, 5-bromo-N-[(aR)-6-(4-oxo-3,4-dihydrophthalazin-1-yl)spiro[3.3]heptan-2-yl]-2,3-dihydro-1H-indole-1-carboxamide, 5-(1-methyl-1H-pyrazol-4-yl)-N-[(aR)-6-(4-oxo-3,4-dihydrophthalazin-1-yl)spiro[3.3]heptan-2-yl]-2,3-dihydro-1H-indole-1-carboxamide, 5-(1-cyclopropyl-1H-pyrazol-4-yl)-N-[(aR)-6-(4-oxo-3,4-dihydrophthalazin-1-yl)spiro[3.3]heptan-2-yl]-2,3-dihydro-1H-indole-1-carboxamide, N-[(aR)-6-(4-oxo-3,4-dihydrophthalazin-1-yl)spiro[3.3]heptan-2-yl]-5-(trimethyl-1H-pyrazol-4-yl)-2,3-dihydro-1H-indole-1-carboxamide, 5-[1-methyl-3-(trifluoromethyl)-1H-pyrazol-4-yl]-N-[(aR)-6-(4-oxo-3,4-dihydrophthalazin-1-yl)spiro[3.3]heptan-2-yl]-2,3-dihydro-1H-indole-1-carboxamide, 5-[1-($^2$H3)methyl-1H-pyrazol-4-yl]-N-[(aR)-6-(4-oxo-3,4-dihydrophthalazin-1-yl)spiro[3.3]heptan-2-yl]-2,3-dihydro-1H-indole-1-carboxamide, 5-[1 1-(oxan-4-yl)-1H-pyrazol-4-yl]-N-[(aR)-6-(4-oxo-3,4-dihydrophthalazin-1-yl)spiro[3.3]heptan-2-yl]-2,3-dihydro-1H-indole-1-carboxamide, 5-[1-(cyclopropylmethyl)-1H-pyrazol-4-yl]-N-[(aR)-6-(4-oxo-3,4-dihydrophthalazin-1-yl)spiro[3.3]heptan-2-yl]-2,3-dihydro-1H-indole-1-carboxamide, 5-(1-tert-butyl-1H-pyrazol-4-yl)-N-[(aR)-6-(4-oxo-3,4-dihydrophthalazin-1-yl)spiro[3.3]heptan-2-yl]-2,3-dihydro-1H-indole-1-carboxamide, N-[(aR)-6-(4-oxo-3,4-dihydrophthalazin-1-yl)spiro[3.3]heptan-2-yl]-5-[1-(oxolan-3-yl)-1H-pyrazol-4-yl]-2,3-dihydro-1H-indole-1-carboxamide, N-[(aR)-6-(4-oxo-3,4-dihydrophthalazin-1-yl)spiro[3.3]
heptan-2-yl]-5-[(propan-2-yl)-3-(trifluoromethyl)-1H-
pyrazol-4-yl]-2,3-dihydro-1H-indole-1-carboxamide, N-[(aR)-6-(4-oxo-3,4-dihydrophthalazin-1-yl)spiro[3.3]
heptan-2-yl]-5-(3,3,3-trifluoropropyl)-2,3-dihydro-1H-
indole-1-carboxamide, N-[(aR)-6-(4-oxo-3,4-dihydrophthalazin-1-yl)spiro[3.3]
heptan-2-yl]-5-(trimethyl-1H-pyrazol-4-yl)-2,3-di-
hydro-1H-isoindole-2-carboxamide, 5-(1-cyclopropyl-1H-pyrazol-4-yl)-N-[(aR)-6-(4-oxo-3,
4-dihydrophthalazin-1-yl)spiro[3.3]heptan-2-yl]-2,3-
dihydro-1H-isoindole-2-carboxamide, 5-[1-methyl-3-(trifluoromethyl)-1H-pyrazol-4-yl]-N-
[(aR)-6-(4-oxo-3,4-dihydrophthalazin-1-yl)spiro[3.3]
heptan-2-yl]-2,3-dihydro-1H-isoindole-2-carboxam-
ide, N-[(aR)-6-(4-oxo-3,4-dihydrophthalazin-1-yl)spiro[3.3]
heptan-2-yl]-5-[-(propan-2-yl)-3-(trifluoromethyl)-1H-
pyrazol-4-yl]-2,3-dihydro-1H-isoindole-2-carboxam-
ide, 5-(1-methyl-1H-pyrazol-4-yl)-N-[(aR)-6-(4-oxo-3,4-di-
hydrophthalazin-1-yl)spiro[3.3]heptan-2-yl]-2,3-di-
hydro-1H-isoindole-2-carboxamide, 5-[1 1-(oxan-4-yl)-1H-pyrazol-4-yl]-N-[(aR)-6-(4-oxo-3,
4-dihydrophthalazin-1-yl)spiro[3.3]heptan-2-yl]-2,3-
dihydro-1H-isoindole-2-carboxamide, 5-(1-tert-butyl-1H-pyrazol-4-yl)-N-[(aR)-6-(4-oxo-3,4-
dihydrophthalazin-1-yl)spiro[3.3]heptan-2-yl]-2,3-di-
hydro-1H-isoindole-2-carboxamide, 5-[1-($^2$H3)methyl-1H-pyrazol-4-yl]-N-[(aR)-6-(4-oxo-3,
4-dihydrophthalazin-1-yl)spiro[3.3]heptan-2-yl]-2,3-
dihydro-1H-isoindole-2-carboxamide, 3,3-dimethyl-N-[(aR)-6-(4-oxo-3,4-dihydrophthalazin-1-
yl)spiro[3.3]heptan-2-yl]-2,3-dihydro-1H-indole-1-
carboxamide, N-[(aR)-6-(4-oxo-3,4-dihydrophthalazin-1-yl)spiro[3.3]
heptan-2-yl]-1H,2H,3H-pyrrolo[2,3-b]pyridine-1-car-
boxamide, N-[(aR)-6-(4-oxo-3,4-dihydrophthalazin-1-yl)spiro[3.3]
heptan-2-yl]-5H,6H,7H-pyrrolo[3,4-b]pyridine-6-car-
boxamide, 5-methoxy-N-[(aR)-6-(4-oxo-3,4-dihydrophthalazin-1-
yl)spiro[3.3]heptan-2-yl]-2,3-dihydro-1H-indole-1-
carboxamide, N-[(aR)-6-(4-oxo-3,4-dihydrophthalazin-1-yl)spiro[3.3]
heptan-2-yl]-6-(trifluoromethyl)-2,3-dihydro-1H-in-
dole-1-carboxamide, 5-(dimethylsulfamoyl)-N-[(aR)-6-(4-oxo-3,4-dihy-
drophthalazin-1-yl)spiro[3.3]heptan-2-yl]-2,3-dihydro-
1H-indole-1-carboxamide, 3-(morpholin-4-ylmethyl)-N-[(aR)-6-(4-oxo-3,4-dihy-
drophthalazin-1-yl)spiro[3.3]heptan-2-yl]-2,3-dihydro-
1H-indole-1-carboxamide, 2-(4-methylphenyl)-N-[(aR)-6-(4-oxo-3,4-dihy-
drophthalazin-1-yl)spiro[3.3]heptan-2-yl]-5H, 6H,7H-
pyrrolo[3,4-d]pyrimidine-6-carboxamide, 5-methoxy-N-[(aR)-6-(4-oxo-3,4-dihydrophthalazin-1-
yl)spiro[3.3]heptan-2-yl]-2,3-dihydro-1H-isoindole-2-
carboxamide, N-[(aR)-6-(4-oxo-3,4-dihydrophthalazin-1-yl)spiro[3.3]
heptan-2-yl]-1H,2H,3H-pyrrolo[3,4-c]pyridine-2-car-
boxamide, N-[(aR)-6-(4-oxo-3,4-dihydrophthalazin-1-yl)spiro[3.3]
heptan-2-yl]-1,2-dihydrospiro[indole-3,4'-piperidine]-
1-carboxamide, N, 1-dimethyl-N-[(aR)-6-(4-oxo-3,4-dihydrophthalazin-
1-yl)spiro[3.3]heptan-2-yl]-1H-indazole-3-carboxam-
ide, N-ethyl-1-methyl-N-[(aR)-6-(4-oxo-3,4-dihy-
drophthalazin-1-yl)spiro[3.3]heptan-2-yl]-1H-inda-
zole-3-carboxamide, 2-methyl-1-[(3-{[(aR)-6-(4-oxo-3,4-dihydrophthalazin-
1-yl)spiro[3.3]heptan-2-yl]carbamoyl}pyrazolo[1,5-a]
pyridin-6-yl)oxy]propan-2-yl2-aminoacetate, 2-methyl-1-[(3-{[(aR)-6-(4-oxo-3,4-dihydrophthalazin-
1-yl)spiro[3.3]heptan-2-yl]carbamoyl}pyrazolo[1,5-a]
pyridin-6-yl)oxy]propan-2-yl (2S)-2-amino-3-meth-
ylbutanoate, 2-methyl-1-[(3-{[(aR)-6-(4-oxo-3,4-dihydrophthalazin-
1-yl)spiro[3.3]heptan-2-yl]carbamoyl}pyrazolo[1,5-a]
pyridin-6-yl)oxy]propan-2-yl (2S)-2-aminopropanoate, 6-(2-hydroxy-2-methylpropoxy)-N-[6-(1-oxo-1,2-dihy-
droisoquinolin-4-yl)spiro[3.3]heptan-2-yl]pyrazolo[1,
5-a]pyridine-3-carboxamide, tert-butyl 3-{[(aR)-6-(4-oxo-3,4-dihydrophthalazin-1-yl)
spiro[3.3]heptan-2-yl]carbamoyl})-4H, 5H,6H,7H-
thieno[2,3-c]pyridine-6-carboxylate, N-[(aR)-6-(4-oxo-3,4-dihydrophthalazin-1-yl)spiro[3.3]
heptan-2-yl]-4H, 5H, 6H,7H-thieno[2,3-c]pyridine-3-
carboxamide, 6-acetyl-N-[(aR)-6-(4-oxo-3,4-dihydrophthalazin-1-yl)
spiro[3.3]heptan-2-yl]-4H, 5H, 6H,7H-thieno[2,3-c]
pyridine-3-carboxamide, methyl 3-{[(aR)-6-(4-oxo-3,4-dihydrophthalazin-1-yl)
spiro[3.3]heptan-2-yl]carbamoyl})-4H, 5H,6H,7H-
thieno[2,3-c]pyridine-6-carboxylate, 6-methanesulfonyl-N-[(aR)-6-(4-oxo-3,4-dihy-
drophthalazin-1-yl)spiro[3.3]heptan-2-yl]-4H, 5H,6H,
7H-thieno[2,3-c]pyridine-3-carboxamide, 6-(1-methyl-1H-pyrazol-4-yl)-N-[(aR)-6-(4-oxo-3,4-di-
hydrophthalazin-1-yl)spiro[3.3]heptan-2-yl]-2,1-ben-
zoxazole-3-carboxamide, 1-(2-hydroxy-2-methylpropyl)-N-(6-{4-oxo-3H,4H-pyr-
rolo[1,2-d][1,2,4]triazin-1-yl})spiro[3.3]heptan-2-yl)-
1H-indazole-3-carboxamide, 6-(2-hydroxy-2-methylpropoxy)-N-(6-{4-oxo-3H,4H-
pyrrolo[1,2-d][1,2,4]triazin-1-yl}spiro[3.3]heptan-2-
yl)pyrazolo[1,5-a]pyridine-3-carboxamide, 1-methyl-N-(6-{4-oxo-3H,4H-pyrrolo[1,2-d][1,2,4]tri-
azin-1-yl})spiro[3.3]heptan-2-yl)-1H-indazole-3-car-
boxamide, 6-(2-hydroxy-2-methylpropoxy)-N-(6-{8-methyl-4-oxo-
3H,4H-pyrrolo[1,2-d][1,2,4]triazin-1-yl}spiro[3.3]
heptan-2-yl)pyrazolo[1,5-a]pyridine-3-carboxamide, N-[(aR)-6-(4-oxo-3,4-dihydrophthalazin-1-yl)spiro[3.3]
heptan-2-yl]pyrazolo[1,5-a]pyrimidine-3-carboxam-
ide, 6-[(3,5-dimethylphenyl)amino]-N-[(aR)-6-(4-oxo-3,4-di-
hydrophthalazin-1-yl)spiro[3.3]heptan-2-yl]imidazo[1,
2-b]pyridazine-3-carboxamide, 6-bromo-N-[(aR)-6-(4-oxo-3,4-dihydrophthalazin-1-yl)
spiro[3.3]heptan-2-yl]-2,1-benzoxazole-3-carboxam-
ide, 1-ethyl-N-[(aR)-6-(4-oxo-3,4-dihydrophthalazin-1-yl)
spiro[3.3]heptan-2-yl]-1H-pyrazole-5-carboxamide, 1-(difluoromethyl)-N-[(aR)-6-(4-oxo-3,4-dihy-
drophthalazin-1-yl)spiro[3.3]heptan-2-yl]-1H-pyra-
zole-5-carboxamide, 6-(2-hydroxy-2-methylpropoxy)-N-[(aR)-6-(4-oxo-3,4-
dihydrophthalazin-1-yl)spiro[3.3]heptan-2-yl]-2,1-
benzoxazole-3-carboxamide, 1-(3-chlorophenyl)-7-oxo-N-[(aR)-6-(4-oxo-3,4-dihydrophthalazin-1-yl)spiro[3.3]heptan-2-yl]-1H,4H,5H,6H,7H-pyrazolo[3,4-c]pyridine-3-carboxamide, 1-(4-methoxyphenyl)-7-oxo-N-[(aR)-6-(4-oxo-3,4-dihydrophthalazin-1-yl)spiro[3.3]heptan-2-yl]-1H,4H,5H,6H,7H-pyrazolo[3,4-c]pyridine-3-carboxamide, 5-chloro-N-[(aR)-6-(4-oxo-3,4-dihydrophthalazin-1-yl)spiro[3.3]heptan-2-yl]-1,2-benzoxazole-3-carboxamide, 6-acetamido-N-[(aR)-6-(4-oxo-3,4-dihydrophthalazin-1-yl)spiro[3.3]heptan-2-yl]-1,2-benzoxazole-3-carboxamide, N-[(aR)-6-(4-oxo-3,4-dihydrophthalazin-1-yl)spiro[3.3]heptan-2-yl]imidazo[1,5-a]pyridine-1-carboxamide, 5-methoxy-1-methyl-N-[(aR)-6-(4-oxo-3,4-dihydrophthalazin-1-yl)spiro[3.3]heptan-2-yl]-1H-indole-2-carboxamide, 1-methyl-N-[(aR)-6-(4-oxo-3,4-dihydrophthalazin-1-yl)spiro[3.3]heptan-2-yl]-1H-indole-2-carboxamide, 7-methoxy-N-[(aR)-6-(4-oxo-3,4-dihydrophthalazin-1-yl)spiro[3.3]heptan-2-yl]-1H-indole-2-carboxamide, 5-methyl-N-[(aR)-6-(4-oxo-3,4-dihydrophthalazin-1-yl)spiro[3.3]heptan-2-yl]-4H,5H,6H,7H-[1,3]thiazolo[5,4-c]pyridine-2-carboxamide, 4-chloro-1-methyl-N-[(aR)-6-(4-oxo-3,4-dihydrophthalazin-1-yl)spiro[3.3]heptan-2-yl]-1H-indole-2-carboxamide, N-[(aR)-6-(4-oxo-3,4-dihydrophthalazin-1-yl)spiro[3.3]heptan-2-yl]-1H-indole-2-carboxamide, 2-methyl-N-[(aR)-6-(4-oxo-3,4-dihydrophthalazin-1-yl)spiro[3.3]heptan-2-yl]imidazo[1,2-a]pyridine-3-carboxamide, N-[(aR)-6-(4-oxo-3,4-dihydrophthalazin-1-yl)spiro[3.3]heptan-2-yl]-1H-indole-3-carboxamide, 7-chloro-1-methyl-N-[(aR)-6-(4-oxo-3,4-dihydrophthalazin-1-yl)spiro[3.3]heptan-2-yl]-1H-indole-2-carboxamide, 4-chloro-7-methyl-N-[(aR)-6-(4-oxo-3,4-dihydrophthalazin-1-yl)spiro[3.3]heptan-2-yl]-1H-indole-2-carboxamide, N-[(aR)-6-(4-oxo-3,4-dihydrophthalazin-1-yl)spiro[3.3]heptan-2-yl]thieno[2,3-b]pyrazine-6-carboxamide, 4-bromo-N-[(aR)-6-(4-oxo-3,4-dihydrophthalazin-1-yl)spiro[3.3]heptan-2-yl]pyrazolo[1,5-a]pyridine-3-carboxamide, 6-chloro-N-[(aR)-6-(4-oxo-3,4-dihydrophthalazin-1-yl)spiro[3.3]heptan-2-yl]-1H-1,3-benzodiazole-2-carboxamide, 5-chloro-1-methyl-N-[(aR)-6-(4-oxo-3,4-dihydrophthalazin-1-yl)spiro[3.3]heptan-2-yl]-1H-indole-2-carboxamide, N-[(aR)-6-(4-oxo-3,4-dihydrophthalazin-1-yl)spiro[3.3]heptan-2-yl]-1-(propan-2-yl)-1H-1,3-benzodiazole-5-carboxamide, N-[(aR)-6-(4-oxo-3,4-dihydrophthalazin-1-yl)spiro[3.3]heptan-2-yl]-1H-1,3-benzodiazole-5-carboxamide, 2-methyl-N-[(aR)-6-(4-oxo-3,4-dihydrophthalazin-1-yl)spiro[3.3]heptan-2-yl]-1H-1,3-benzodiazole-5-carboxamide, N-[(aR)-6-(4-oxo-3,4-dihydrophthalazin-1-yl)spiro[3.3]heptan-2-yl]-3H-imidazo[4,5-b]pyridine-6-carboxamide, 4-formamido-3-hydroxy-N-[(aR)-6-(4-oxo-3,4-dihydrophthalazin-1-yl)spiro[3.3]heptan-2-yl]benzamide, N-[(aR)-6-(4-oxo-3,4-dihydrophthalazin-1-yl)spiro[3.3]heptan-2-yl]-1H-pyrrolo[2,3-b]pyridine-2-carboxamide, 6-chloro-N-[(aR)-6-(4-oxo-3,4-dihydrophthalazin-1-yl)spiro[3.3]heptan-2-yl]-1-benzothiophene-2-carboxamide, 6-methoxy-1-methyl-N-[(aR)-6-(4-oxo-3,4-dihydrophthalazin-1-yl)spiro[3.3]heptan-2-yl]-1H-indole-2-carboxamide, 2-methyl-N-[(aR)-6-(4-oxo-3,4-dihydrophthalazin-1-yl)spiro[3.3]heptan-2-yl]-1,3-benzoxazole-6-carboxamide, N-[(aR)-6-(4-oxo-3,4-dihydrophthalazin-1-yl)spiro[3.3]heptan-2-yl]-1H-indazole-6-carboxamide, 1-methyl-N-[(aR)-6-(4-oxo-3,4-dihydrophthalazin-1-yl)spiro[3.3]heptan-2-yl]-1H-1,3-benzodiazole-5-carboxamide, N-[(aR)-6-(4-oxo-3,4-dihydrophthalazin-1-yl)spiro[3.3]heptan-2-yl]imidazo[1,2-a]pyridine-3-carboxamide, 5-(benzyloxy)-N-[(aR)-6-(4-oxo-3,4-dihydrophthalazin-1-yl)spiro[3.3]heptan-2-yl]-1H-indole-2-carboxamide, 6-fluoro-N-[(aR)-6-(4-oxo-3,4-dihydrophthalazin-1-yl)spiro[3.3]heptan-2-yl]-1H-indole-2-carboxamide, N-[(aR)-6-(4-oxo-3,4-dihydrophthalazin-1-yl)spiro[3.3]heptan-2-yl]-2,3-dihydro-1H-indene-1-carboxamide, 7-methyl-N-[(aR)-6-(4-oxo-3,4-dihydrophthalazin-1-yl)spiro[3.3]heptan-2-yl]-1H-indole-2-carboxamide, N-[(aR)-6-(4-oxo-3,4-dihydrophthalazin-1-yl)spiro[3.3]heptan-2-yl]-2,3-dihydro-1H-isoindole-1-carboxamide, N-[(aR)-6-(4-oxo-3,4-dihydrophthalazin-1-yl)spiro[3.3]heptan-2-yl]pyrazolo[1,5-a]pyridine-2-carboxamide, N-[(aR)-6-(4-oxo-3,4-dihydrophthalazin-1-yl)spiro[3.3]heptan-2-yl]isoquinoline-3-carboxamide, 7-hydroxy-N-[(aR)-6-(4-oxo-3,4-dihydrophthalazin-1-yl)spiro[3.3]heptan-2-yl]-1H-indole-2-carboxamide, 7-chloro-N-[(aR)-6-(4-oxo-3,4-dihydrophthalazin-1-yl)spiro[3.3]heptan-2-yl]-1H-indole-2-carboxamide, 6-fluoro-7-methyl-N-[(aR)-6-(4-oxo-3,4-dihydrophthalazin-1-yl)spiro[3.3]heptan-2-yl]-1H-indole-2-carboxamide, N-[(aR)-6-(4-oxo-3,4-dihydrophthalazin-1-yl)spiro[3.3]heptan-2-yl]quinoline-2-carboxamide, 4-bromo-N-[(aR)-6-(4-oxo-3,4-dihydrophthalazin-1-yl)spiro[3.3]heptan-2-yl]benzamide, N-[(aR)-6-(4-oxo-3,4-dihydrophthalazin-1-yl)spiro[3.3]heptan-2-yl]-7-(trifluoromethyl)-1H-indole-2-carboxamide, 7-fluoro-N-[(aR)-6-(4-oxo-3,4-dihydrophthalazin-1-yl)spiro[3.3]heptan-2-yl]-1H-indole-2-carboxamide, 4,7-dimethoxy-N-[(aR)-6-(4-oxo-3,4-dihydrophthalazin-1-yl)spiro[3.3]heptan-2-yl]-1H-indole-2-carboxamide, 5-fluoro-7-methanesulfonyl-N-[(aR)-6-(4-oxo-3,4-dihydrophthalazin-1-yl)spiro[3.3]heptan-2-yl]-1H-indole-2-carboxamide, N-[(aR)-6-(4-oxo-3,4-dihydrophthalazin-1-yl)spiro[3.3]heptan-2-yl]-3-(1H-pyrazol-1-yl)benzamide, N-[(aR)-6-(4-oxo-3,4-dihydrophthalazin-1-yl)spiro[3.3]heptan-2-yl]-4-(1H-pyrazol-4-yl)benzamide, 3-[2-(morpholin-4-yl)ethoxy]-N-[(aR)-6-(4-oxo-3,4-dihydrophthalazin-1-yl)spiro[3.3]heptan-2-yl]benzamide, N-[(aR)-6-(4-oxo-3,4-dihydrophthalazin-1-yl)spiro[3.3]heptan-2-yl]-3-(1H-pyrazol-4-yl)benzamide, 3-(4-methyl-1,3-thiazol-2-yl)-N-[(aR)-6-(4-oxo-3,4-dihydrophthalazin-1-yl)spiro[3.3]heptan-2-yl]benzamide, 6-methoxy-N-[(aR)-6-(4-oxo-3,4-dihydrophthalazin-1-yl)spiro[3.3]heptan-2-yl]pyridine-3-carboxamide, N-[(aR)-6-(4-oxo-3,4-dihydrophthalazin-1-yl)spiro[3.3]
heptan-2-yl]-6-(trifluoromethyl)pyridine-3-carboxamide,
2-hydroxy-6-methyl-N-[(aR)-6-(4-oxo-3,4-dihydrophthalazin-1-yl)spiro[3.3]heptan-2-yl]pyridine-3-carboxamide,
N-[(aR)-6-(4-oxo-3,4-dihydrophthalazin-1-yl)spiro[3.3]
heptan-2-yl]-6-[2-(pyrrolidin-1-yl)ethyl]pyridine-3-carboxamide,
N-[(aR)-6-(4-oxo-3,4-dihydrophthalazin-1-yl)spiro[3.3]
heptan-2-yl]-4-(2H-1,2,3,4-tetrazol-5-yl)benzamide,
N-[(aR)-6-(4-oxo-3,4-dihydrophthalazin-1-yl)spiro[3.3]
heptan-2-yl]-6-(1H-pyrazol-1-yl)pyridine-3-carboxamide,
5-chloro-6-hydroxy-N-[(aR)-6-(4-oxo-3,4-dihydrophthalazin-1-yl)spiro[3.3]heptan-2-yl]pyridine-3-carboxamide,
N-[(aR)-6-(4-oxo-3,4-dihydrophthalazin-1-yl)spiro[3.3]
heptan-2-yl]-4-(1H-1,2,4-triazol-1-yl)benzamide,
3-methoxy-4-(4-methyl-1H-imidazol-1-yl)-N-[(aR)-6-(4-oxo-3,4-dihydrophthalazin-1-yl)spiro[3.3]heptan-2-yl]
benzamide,
3-methoxy-4-(2-methyl-1,3-thiazol-5-yl)-N-[(aR)-6-(4-oxo-3,4-dihydrophthalazin-1-yl)spiro[3.3]heptan-2-yl]
benzamide,
5-methoxy-N-[(aR)-6-(4-oxo-3,4-dihydrophthalazin-1-yl)spiro[3.3]heptan-2-yl]pyridine-2-carboxamide,
3-(1H-imidazol-1-yl)-N-[(aR)-6-(4-oxo-3,4-dihydrophthalazin-1-yl)spiro[3.3]heptan-2-yl]benzamide,
3-cyano-N-[(aR)-6-(4-oxo-3,4-dihydrophthalazin-1-yl)
spiro[3.3]heptan-2-yl]-4-(propan-2-yloxy)benzamide,
3-(difluoromethoxy)-N-[(aR)-6-(4-oxo-3,4-dihydrophthalazin-1-yl)spiro[3.3]heptan-2-yl]benzamide,
4-ethoxy-5-oxo-N-[(aR)-6-(4-oxo-3,4-dihydrophthalazin-1-yl)spiro[3.3]heptan-2-yl]-1-(2,2,2-trifluoroethyl)-2,5-dihydro-1H-pyrrole-3-carboxamide,
6-(dimethylamino)-N-[(aR)-6-(4-oxo-3,4-dihydrophthalazin-1-yl)spiro[3.3]heptan-2-yl]pyridine-3-carboxamide,
N-[(aR)-6-(4-oxo-3,4-dihydrophthalazin-1-yl)spiro[3.3]
heptan-2-yl]-4-(1H-pyrazol-3-yl)benzamide,
4-(1,3-oxazol-5-yl)-N-[(aR)-6-(4-oxo-3,4-dihydrophthalazin-1-yl)spiro[3.3]heptan-2-yl]benzamide,
4-(1H-imidazol-1-yl)-N-[(aR)-6-(4-oxo-3,4-dihydrophthalazin-1-yl)spiro[3.3]heptan-2-yl]benzamide,
4-(5-methyl-1,2,4-oxadiazol-3-yl)-N-[(aR)-6-(4-oxo-3,4-dihydrophthalazin-1-yl)spiro[3.3]heptan-2-yl]benzamide,
N-[(aR)-6-(4-oxo-3,4-dihydrophthalazin-1-yl)spiro[3.3]
heptan-2-yl]-3-(1H-pyrazol-3-yl)benzamide,
8-methyl-N-[(aR)-6-(4-oxo-3,4-dihydrophthalazin-1-yl)
spiro[3.3]heptan-2-yl]imidazo[1,2-a]pyridine-2-carboxamide,
6-bromo-N-[(aR)-6-(4-oxo-3,4-dihydrophthalazin-1-yl)
spiro[3.3]heptan-2-yl]imidazo[1,2-a]pyridine-2-carboxamide,
1-methyl-N-[(aR)-6-(4-oxo-3,4-dihydrophthalazin-1-yl)
spiro[3.3]heptan-2-yl]-1H-indole-3-carboxamide,
5-methyl-N-[(aR)-6-(4-oxo-3,4-dihydrophthalazin-1-yl)
spiro[3.3]heptan-2-yl]-2-(pyridin-4-yl)-1,3-thiazole-4-carboxamide,
1-methyl-N-[(aR)-6-(4-oxo-3,4-dihydrophthalazin-1-yl)
spiro[3.3]heptan-2-yl]-1H-indazole-6-carboxamide,
1-methyl-N-[(aR)-6-(4-oxo-3,4-dihydrophthalazin-1-yl)
spiro[3.3]heptan-2-yl]-1H-indole-6-carboxamide,
1-methyl-N-[(aR)-6-(4-oxo-3,4-dihydrophthalazin-1-yl)
spiro[3.3]heptan-2-yl]-1H-indole-5-carboxamide,
N-[(aR)-6-(4-oxo-3,4-dihydrophthalazin-1-yl)spiro[3.3]
heptan-2-yl]-5-(pyrrolidin-1-yl)pyridine-2-carboxamide,
N-[(aR)-6-(4-oxo-3,4-dihydrophthalazin-1-yl)spiro[3.3]
heptan-2-yl]-5-(trifluoromethyl)pyridine-2-carboxamide,
5-cyano-6-methyl-N-[(aR)-6-(4-oxo-3,4-dihydrophthalazin-1-yl)spiro[3.3]heptan-2-yl]pyridine-2-carboxamide,
7-methoxy-3-methyl-N-[(aR)-6-(4-oxo-3,4-dihydrophthalazin-1-yl)spiro[3.3]heptan-2-yl]-1H-indole-2-carboxamide,
1-methyl-N-[(aR)-6-(4-oxo-3,4-dihydrophthalazin-1-yl)
spiro[3.3]heptan-2-yl]-1H-indazole-5-carboxamide,
7-bromo-N-[(aR)-6-(4-oxo-3,4-dihydrophthalazin-1-yl)
spiro[3.3]heptan-2-yl]imidazo[1,2-a]pyridine-2-carboxamide,
5-bromo-N-[(aR)-6-(4-oxo-3,4-dihydrophthalazin-1-yl)
spiro[3.3]heptan-2-yl]pyridine-2-carboxamide,
N-[(aR)-6-(4-oxo-3,4-dihydrophthalazin-1-yl)spiro[3.3]
heptan-2-yl]imidazo[1,2-a]pyridine-2-carboxamide,
7-(4-methylpiperazin-1-yl)-N-[(aR)-6-(4-oxo-3,4-dihydrophthalazin-1-yl)spiro[3.3]heptan-2-yl]imidazo[1,2-a]pyridine-3-carboxamide,
7-cyano-N-[(aR)-6-(4-oxo-3,4-dihydrophthalazin-1-yl)
spiro[3.3]heptan-2-yl]imidazo[1,2-a]pyridine-3-carboxamide,
8-cyano-N-[(aR)-6-(4-oxo-3,4-dihydrophthalazin-1-yl)
spiro[3.3]heptan-2-yl]imidazo[1,2-a]pyridine-3-carboxamide,
N-[(aR)-6-(4-oxo-3,4-dihydrophthalazin-1-yl)spiro[3.3]
heptan-2-yl]-8-(trifluoromethyl)imidazo[1,2-a]pyridine-3-carboxamide,
8-chloro-N-[(aR)-6-(4-oxo-3,4-dihydrophthalazin-1-yl)
spiro[3.3]heptan-2-yl]imidazo[1,2-a]pyridine-3-carboxamide,
N-[(aR)-6-(4-oxo-3,4-dihydrophthalazin-1-yl)spiro[3.3]
heptan-2-yl]-7-phenylimidazo[1,2-a]pyridine-3-carboxamide,
7-(benzyloxy)-N-[(aR)-6-(4-oxo-3,4-dihydrophthalazin-1-yl)spiro[3.3]heptan-2-yl]imidazo[1,2-a]pyridine-3-carboxamide,
7-methoxy-N-[(aR)-6-(4-oxo-3,4-dihydrophthalazin-1-yl)spiro[3.3]heptan-2-yl]imidazo[1,2-a]pyridine-3-carboxamide,
8-chloro-7-methyl-N-[(aR)-6-(4-oxo-3,4-dihydrophthalazin-1-yl)spiro[3.3]heptan-2-yl]imidazo[1,2-a]pyridine-3-carboxamide,
7-fluoro-N-[(aR)-6-(4-oxo-3,4-dihydrophthalazin-1-yl)
spiro[3.3]heptan-2-yl]imidazo[1,2-a]pyridine-3-carboxamide,
N-[(aR)-6-(4-oxo-3,4-dihydrophthalazin-1-yl)spiro[3.3]
heptan-2-yl]-3-(propan-2-yl)-5H,6H,7H,8H-imidazo
[1,5-a]pyridine-1-carboxamide,
N-[(aR)-6-(4-oxo-3,4-dihydrophthalazin-1-yl)spiro[3.3]
heptan-2-yl]-[1,2,4]triazolo[4,3-a]pyridine-3-carboxamide,
N-[(aR)-6-(4-oxo-3,4-dihydrophthalazin-1-yl)spiro[3.3]
heptan-2-yl]-6-(trifluoromethyl)imidazo[1,2-a]pyridine-3-carboxamide,
7-(4,4-difluoropiperidin-1-yl)-N-[(aR)-6-(4-oxo-3,4-dihydrophthalazin-1-yl)spiro[3.3]heptan-2-yl]imidazo[1,2-a]pyridine-3-carboxamide,
7-(3,3-difluoropyrrolidin-1-yl)-N-[(aR)-6-(4-oxo-3,4-dihydrophthalazin-1-yl)spiro[3.3]heptan-2-yl]imidazo[1,2-a]pyridine-3-carboxamide, 7-[(3R)-3-fluoropyrrolidin-1-yl]-N-[(aR)-6-(4-oxo-3,4-dihydrophthalazin-1-yl)spiro[3.3]heptan-2-yl]imidazo[1,2-a]pyridine-3-carboxamide, 7-[(3 S)-3-fluoropyrrolidin-1-yl]-N-[(aR)-6-(4-oxo-3,4-dihydrophthalazin-1-yl)spiro[3.3]heptan-2-yl]imidazo[1,2-a]pyridine-3-carboxamide, 7-[(3R)-3-hydroxypyrrolidin-1-yl]-N-[(aR)-6-(4-oxo-3,4-dihydrophthalazin-1-yl)spiro[3.3]heptan-2-yl]imidazo[1,2-a]pyridine-3-carboxamide, 7-[(2-hydroxyethyl)(methyl)amino]-N-[(aR)-6-(4-oxo-3,4-dihydrophthalazin-1-yl)spiro[3.3]heptan-2-yl]imidazo[1,2-a]pyridine-3-carboxamide, 7-[(2-methoxyethyl)(methyl)amino]-N-[(aR)-6-(4-oxo-3,4-dihydrophthalazin-1-yl)spiro[3.3]heptan-2-yl]imidazo[1,2-a]pyridine-3-carboxamide, 7-[2-(morpholin-4-yl)ethoxy]-N-[(aR)-6-(4-oxo-3,4-dihydrophthalazin-1-yl)spiro[3.3]heptan-2-yl]imidazo[1,2-a]pyridine-3-carboxamide, 7-[(2-hydroxy-2-methylpropyl)(methyl)amino]-N-[(aR)-6-(4-oxo-3,4-dihydrophthalazin-1-yl)spiro[3.3]heptan-2-yl]imidazo[1,2-a]pyridine-3-carboxamide, 7-(2-hydroxy-2-methylpropoxy)-N-[(aR)-6-(4-oxo-3,4-dihydrophthalazin-1-yl)spiro[3.3]heptan-2-yl]imidazo[1,2-a]pyridine-3-carboxamide, N-[(aR)-6-(4-oxo-3,4-dihydrophthalazin-1-yl)spiro[3.3]heptan-2-yl]-7-[2-(pyrrolidin-1-yl)ethoxy]imidazo[1,2-a]pyridine-3-carboxamide, 1-(2-hydroxy-2-methylpropyl)-7-oxo-N-[(aR)-6-(4-oxo-3,4-dihydrophthalazin-1-yl)spiro[3.3]heptan-2-yl]-1H,7H-imidazo[1,2-a]pyridine-3-carboxamide, N-[(aR)-6-(4-oxo-3,4-dihydrophthalazin-1-yl)spiro[3.3]heptan-2-yl]-7-(trifluoromethyl)imidazo[1,2-a]pyridine-3-carboxamide, 8-fluoro-N-[(aR)-6-(4-oxo-3,4-dihydrophthalazin-1-yl)spiro[3.3]heptan-2-yl]-6-(trifluoromethyl)imidazo[1,2-a]pyridine-3-carboxamide, 6-fluoro-8-methyl-N-[(aR)-6-(4-oxo-3,4-dihydrophthalazin-1-yl)spiro[3.3]heptan-2-yl]imidazo[1,2-a]pyridine-3-carboxamide, 7-(difluoromethoxy)-N-[(aR)-6-(4-oxo-3,4-dihydrophthalazin-1-yl)spiro[3.3]heptan-2-yl]imidazo[1,2-a]pyridine-3-carboxamide, 6-fluoro-5-methyl-N-[(aR)-6-(4-oxo-3,4-dihydrophthalazin-1-yl)spiro[3.3]heptan-2-yl]imidazo[1,2-a]pyridine-3-carboxamide, 6-fluoro-N-[(aR)-6-(4-oxo-3,4-dihydrophthalazin-1-yl)spiro[3.3]heptan-2-yl]imidazo[1,2-a]pyridine-3-carboxamide, 7-[(2-hydroxy-2-methylpropyl)amino]-N-[(aR)-6-(4-oxo-3,4-dihydrophthalazin-1-yl)spiro[3.3]heptan-2-yl]imidazo[1,2-a]pyridine-3-carboxamide, 6-fluoro-7-methyl-N-[(aR)-6-(4-oxo-3,4-dihydrophthalazin-1-yl)spiro[3.3]heptan-2-yl]imidazo[1,2-a]pyridine-3-carboxamide, 6, 8-difluoro-N-[(aR)-6-(4-oxo-3,4-dihydrophthalazin-1-yl)spiro[3.3]heptan-2-yl]imidazo[1,2-a]pyridine-3-carboxamide, 7-methyl-N-[(aR)-6-(4-oxo-3,4-dihydrophthalazin-1-yl)spiro[3.3]heptan-2-yl]imidazo[1,2-a]pyridine-3-carboxamide, 8-(benzyloxy)-N-[(aR)-6-(4-oxo-3,4-dihydrophthalazin-1-yl)spiro[3.3]heptan-2-yl]imidazo[1,2-a]pyridine-3-carboxamide, 7-(methyl sulfanyl)-N-[(aR)-6-(4-oxo-3,4-dihydrophthalazin-1-yl)spiro[3.3]heptan-2-yl]imidazo[1,2-a]pyridine-3-carboxamide, 4-oxo-N-[(aR)-6-(4-oxo-3,4-dihydrophthalazin-1-yl)spiro[3.3]heptan-2-yl]-4H, 5H, 6H,7H-pyrazolo[1,5-a]pyrazine-2-carboxamide, 3-methoxy-N-[(aR)-6-(4-oxo-3,4-dihydrophthalazin-1-yl)spiro[3.3]heptan-2-yl]-4-(1H-pyrazol-4-yl)benzamide, 3-cyano-N-[(aR)-6-(4-oxo-3,4-dihydrophthalazin-1-yl)spiro[3.3]heptan-2-yl]-4-(1H-pyrazol-4-yl)benzamide, 3-methyl-N-[(aR)-6-(4-oxo-3,4-dihydrophthalazin-1-yl)spiro[3.3]heptan-2-yl]-4-(1H-pyrazol-4-yl)benzamide, 2-methoxy-N-[(aR)-6-(4-oxo-3,4-dihydrophthalazin-1-yl)spiro[3.3]heptan-2-yl]-4-(1H-pyrazol-4-yl)benzamide, 7-(1-methyl-1H-pyrazol-4-yl)-N-[(aR)-6-(4-oxo-3,4-dihydrophthalazin-1-yl)spiro[3.3]heptan-2-yl]-1H-indole-2-carboxamide, N-[(aR)-6-(4-oxo-3,4-dihydrophthalazin-1-yl)spiro[3.3]heptan-2-yl]-6H-isochromeno[4,3-d]pyrimidine-8-carboxamide, 3-methoxy-4-(1-methyl-1H-pyrazol-4-yl)-N-[(aR)-6-(4-oxo-3,4-dihydrophthalazin-1-yl)spiro[3.3]heptan-2-yl]benzamide, 3-fluoro-4-(1-methyl-1H-pyrazol-4-yl)-N-[(aR)-6-(4-oxo-3,4-dihydrophthalazin-1-yl)spiro[3.3]heptan-2-yl]benzamide, 6-(1-methyl-1H-pyrazol-4-yl)-N-[(aR)-6-(4-oxo-3,4-dihydrophthalazin-1-yl)spiro[3.3]heptan-2-yl]pyridine-3-carboxamide, 7-acetyl-N-[(aR)-6-(4-oxo-3,4-dihydrophthalazin-1-yl)spiro[3.3]heptan-2-yl]imidazo[1,2-a]pyridine-3-carboxamide, 3-fluoro-4-[1-($^{2}$H3)methyl-1H-pyrazol-4-yl]-N-[(aR)-6-(4-oxo-3,4-dihydrophthalazin-1-yl)spiro[3.3]heptan-2-yl]benzamide, 4-[1-(difluoromethyl)-1H-pyrazol-4-yl]-3-fluoro-N-[(aR)-6-(4-oxo-3,4-dihydrophthalazin-1-yl)spiro[3.3]heptan-2-yl]benzamide, 7-(2-hydroxypropan-2-yl)-N-[(aR)-6-(4-oxo-3,4-dihydrophthalazin-1-yl)spiro[3.3]heptan-2-yl]imidazo[1,2-a]pyridine-3-carboxamide, 7-(1-hydroxyethyl)-N-[(aR)-6-(4-oxo-3,4-dihydrophthalazin-1-yl)spiro[3.3]heptan-2-yl]imidazo[1,2-a]pyridine-3-carboxamide, 7-[(1,1-dioxo-1$\lambda^{6}$-thian-4-yl)oxy]-N-[(aR)-6-(4-oxo-3,4-dihydrophthalazin-1-yl)spiro[3.3]heptan-2-yl]imidazo[1,2-a]pyridine-3-carboxamide, N-[(aR)-6-(4-oxo-3,4-dihydrophthalazin-1-yl)spiro[3.3]heptan-2-yl]-7-(3,3,3-trifluoropropoxy)imidazo[1,2-a]pyridine-3-carboxamide, 7-[(1,3-difluoropropan-2-yl)oxy]-N-[(aR)-6-(4-oxo-3,4-dihydrophthalazin-1-yl)spiro[3.3]heptan-2-yl]imidazo[1,2-a]pyridine-3-carboxamide, N-[(aR)-6-(4-oxo-3,4-dihydrophthalazin-1-yl)spiro[3.3]heptan-2-yl]-7-(pyridin-2-yloxy)imidazo[1,2-a]pyridine-3-carboxamide, N-[(aR)-6-(4-oxo-3,4-dihydrophthalazin-1-yl)spiro[3.3]heptan-2-yl]-3-(propan-2-yl)imidazo[1,5-a]pyridine-1-carboxamide, 7-(2,2-difluoroethoxy)-N-[(aR)-6-(4-oxo-3,4-dihydrophthalazin-1-yl)spiro[3.3]heptan-2-yl]imidazo[1,2-a]pyridine-3-carboxamide, N-[(aR)-6-(4-oxo-3,4-dihydrophthalazin-1-yl)spiro[3.3]heptan-2-yl]-7-(propan-2-yloxy)imidazo[1,2-a]pyridine-3-carboxamide, 4-(morpholin-4-yl)-N-[(aR)-6-(4-oxo-3,4-dihydrophthalazin-1-yl)spiro[3.3]heptan-2-yl]pyrazolo[1,5-a]pyridine-3-carboxamide, 7-(1-ethyl-1H-pyrazol-4-yl)-N-[(aR)-6-(4-oxo-3,4-dihydrophthalazin-1-yl)spiro[3.3]heptan-2-yl]imidazo[1,2-a]pyridine-3-carboxamide, 7-(1-methyl-1H-pyrazol-4-yl)-N-[(aR)-6-(4-oxo-3,4-dihydrophthalazin-1-yl)spiro[3.3]heptan-2-yl]imidazo[1,2-a]pyridine-3-carboxamide, N-[(aR)-6-(4-oxo-3,4-dihydrophthalazin-1-yl)spiro[3.3]heptan-2-yl]-7-[1-(propan-2-yl)-1H-pyrazol-4-yl]imidazo[1,2-a]pyridine-3-carboxamide, 7-[1-($^2$H$_3$)methyl-1H-pyrazol-4-yl]-N-[(aR)-6-(4-oxo-3,4-dihydrophthalazin-1-yl)spiro[3.3]heptan-2-yl]imidazo[1,2-a]pyridine-3-carboxamide, 7-[1-(oxan-4-yl)-1H-pyrazol-4-yl]-N-[(aR)-6-(4-oxo-3,4-dihydrophthalazin-1-yl)spiro[3.3]heptan-2-yl]imidazo[1,2-a]pyridine-3-carboxamide, N-[(aR)-6-(4-oxo-3,4-dihydrophthalazin-1-yl)spiro[3.3]heptan-2-yl]-7-[1-(propan-2-yl)-3-(trifluoromethyl)-1H-pyrazol-4-yl]imidazo[1,2-a]pyridine-3-carboxamide, 4-(1-ethyl-1H-pyrazol-4-yl)-3-fluoro-N-[(aR)-6-(4-oxo-3,4-dihydrophthalazin-1-yl)spiro[3.3]heptan-2-yl]benzamide, 3-fluoro-N-[(aR)-6-(4-oxo-3,4-dihydrophthalazin-1-yl)spiro[3.3]heptan-2-yl]-4-[1-(propan-2-yl)-1H-pyrazol-4-yl]benzamide, 3-fluoro-4-[1-methyl-5-(trifluoromethyl)-1H-pyrazol-4-yl]-N-[(aR)-6-(4-oxo-3,4-dihydrophthalazin-1-yl)spiro[3.3]heptan-2-yl]benzamide, 4-(1-cyclopropyl-1H-pyrazol-4-yl)-3-fluoro-N-[(aR)-6-(4-oxo-3,4-dihydrophthalazin-1-yl)spiro[3.3]heptan-2-yl]benzamide, 3-fluoro-4-[1-(oxan-4-yl)-1H-pyrazol-4-yl]-N-[(aR)-6-(4-oxo-3,4-dihydrophthalazin-1-yl)spiro[3.3]heptan-2-yl]benzamide, 5-(1-methyl-1H-pyrazol-4-yl)-N-[(aR)-6-(4-oxo-3,4-dihydrophthalazin-1-yl)spiro[3.3]heptan-2-yl]pyridine-2-carboxamide, 4-(1-methyl-1H-pyrazol-4-yl)-N-[(aR)-6-(4-oxo-3,4-dihydrophthalazin-1-yl)spiro[3.3]heptan-2-yl]benzamide, N-[(aR)-6-(4-oxo-3,4-dihydrophthalazin-1-yl)spiro[3.3]heptan-2-yl]-7-(pyridin-3-yl)imidazo[1,2-a]pyridine-3-carboxamide, N-[(aR)-6-(4-oxo-3,4-dihydrophthalazin-1-yl)spiro[3.3]heptan-2-yl]-7-(pyridin-3-yl)imidazo[1,2-a]pyridine-2-carboxamide, 7-(2-methyl-1,3-thiazol-5-yl)-N-[(aR)-6-(4-oxo-3,4-dihydrophthalazin-1-yl)spiro[3.3]heptan-2-yl]imidazo[1,2-a]pyridine-2-carboxamide, 7-(2-methyl-1,3-thiazol-5-yl)-N-[(aR)-6-(4-oxo-3,4-dihydrophthalazin-1-yl)spiro[3.3]heptan-2-yl]imidazo[1,2-a]pyridine-3-carboxamide, 4-[6-(1-oxo-2,3-dihydro-1H-isoindol-2-yl)spiro[3.3]heptan-2-yl]-1,2-dihydrophthalazin-1-one, 4-{6-[(4S)-4-benzyl-2-oxoimidazolidin-1-yl]spiro[3.3]heptan-2-yl}-1,2-dihydrophthalazin-1-one, 4-{6-[(4R)-4-benzyl-2-oxoimidazolidin-1-yl]spiro[3.3]heptan-2-yl}-1,2-dihydrophthalazin-1-one, 4-{6-[(2-nitrophenyl)amino]spiro[3.3]heptan-2-yl}-1,2-dihydrophthalazin-1-one, 4-[6-(2-oxo-2,3-dihydro-1H-1,3-benzodiazol-1-yl)spiro[3.3]heptan-2-yl]-1,2-dihydrophthalazin-1-one, 4-cyclopropyl-N-[(aR)-6-(4-oxo-3,4-dihydrophthalazin-1-yl)spiro[3.3]heptan-2-yl]pyrazolo[1,5-a]pyridine-3-carboxamide, 3-fluoro-5-(1-methyl-1H-pyrazol-4-yl)-N-[(aR)-6-(4-oxo-3,4-dihydrophthalazin-1-yl)spiro[3.3]heptan-2-yl]pyridine-2-carboxamide, 6-(4-oxo-3,4-dihydrophthalazin-1-yl)spiro[3.3]heptan-2-yl-2,3-dihydro-1H-isoindole-2-carboxylate, 7-methanesulfonyl-N-[(aR)-6-(4-oxo-3,4-dihydrophthalazin-1-yl)spiro[3.3]heptan-2-yl]imidazo[1,2-a]pyridine-3-carboxamide, N-[(aR)-6-(4-oxo-3,4-dihydrophthalazin-1-yl)spiro[3.3]heptan-2-yl]pyrazolo[1,5-a]pyrazine-3-carboxamide, 5-bromo-N-[(aR)-6-(4-oxo-3,4-dihydrophthalazin-1-yl)spiro[3.3]heptan-2-yl]-2,3-dihydro-1H-indole-2-carboxamide, 2-methyl-2-[(3-{[(aR)-6-(4-oxo-3,4-dihydrophthalazin-1-yl)spiro[3.3]heptan-2-yl]carbamoyl}pyrazolo[1,5-a]pyridin-6-yl)oxy]propanoic acid, 7-(morpholin-4-yl)-N-[(aR)-6-(4-oxo-3,4-dihydrophthalazin-1-yl)spiro[3.3]heptan-2-yl]imidazo[1,2-a]pyridine-3-carboxamide, 7-[(4,4-difluorocyclohexyl)oxy]-N-[(aR)-6-(4-oxo-3,4-dihydrophthalazin-1-yl)spiro[3.3]heptan-2-yl]imidazo[1,2-a]pyridine-3-carboxamide, 4-Methyl-N-((aR)-6-(4-oxo-3,4-dihydrophthalazin-1-yl)spiro[3.3]heptan-2-yl)-2-(piperidin-1-yl)thiazole-5-carboxamide, 2-(3,3-difluoropyrrolidin-1-yl)-5-methyl-N-((aR)-6-(4-oxo-3,4-dihydrophthalazin-1-yl)spiro[3.3]heptan-2-yl)thiazole-4-carboxamide, 1-(2-hydroxy-2-methylpropyl)-6-methoxy-N-((aR)-6-(4-oxo-3,4-dihydrophthalazin-1-yl)spiro[3.3]heptan-2-yl)-1H-indazole-3-carboxamide, 6-methoxy-N-((aR)-6-(4-oxo-3,4-dihydrophthalazin-1-yl)spiro[3.3]heptan-2-yl)pyrazolo[1,5-a]pyridine-3-carboxamide, 1-(2-hydroxy-2-methylpropyl)-N-((aR)-6-(4-oxo-3,4-dihydrophthalazin-1-yl)spiro[3.3]heptan-2-yl)-1H-indole-3-carboxamide, 6-(2,2-difluoroethoxy)-N-((aR)-6-(4-oxo-3,4-dihydrophthalazin-1-yl)spiro[3.3]heptan-2-yl)pyrazolo[1,5-a]pyridine-3-carboxamide, 6-(2-(1H-pyrazol-1-yl)ethoxy)-N-((aR)-6-(4-oxo-3,4-dihydrophthalazin-1-yl)spiro[3.3]heptan-2-yl)pyrazolo[1,5-a]pyridine-3-carboxamide, 6-(4-methylpiperazin-1-yl)-N-((aR)-6-(4-oxo-3,4-dihydrophthalazin-1-yl)spiro[3.3]heptan-2-yl)pyrazolo[1,5-a]pyridine-3-carboxamide, N-((aR)-6-(4-oxo-3,4-dihydrophthalazin-1-yl)spiro[3.3]heptan-2-yl)-6-(pyrrolidin-1-yl)pyrazolo[1,5-a]pyridine-3-carboxamide, 6-((R)-3-fluoropyrrolidin-1-yl)-N-((aR)-6-(4-oxo-3,4-dihydrophthalazin-1-yl)spiro[3.3]heptan-2-yl)pyrazolo[1,5-a]pyridine-3-carboxamide, 6-((S)-3-fluoropyrrolidin-1-yl)-N-((aR)-6-(4-oxo-3,4-dihydrophthalazin-1-yl)spiro[3.3]heptan-2-yl)pyrazolo[1,5-a]pyridine-3-carboxamide, 6-(3,3-difluoropyrrolidin-1-yl)-N-((aR)-6-(4-oxo-3,4-dihydrophthalazin-1-yl)spiro[3.3]heptan-2-yl)pyrazolo[1,5-a]pyridine-3-carboxamide, 6-(3-fluoroazetidin-1-yl)-N-((aR)-6-(4-oxo-3,4-dihydrophthalazin-1-yl)spiro[3.3]heptan-2-yl)pyrazolo[1,5-a]pyridine-3-carboxamide, 6-(3,3-difluoroazetidin-1-yl)-N-((aR)-6-(4-oxo-3,4-dihydrophthalazin-1-yl)spiro[3.3]heptan-2-yl)pyrazolo[1,5-a]pyridine-3-carboxamide, 7-cyclopropyl-6-(2-hydroxy-2-methylpropoxy)-N-((aR)-6-(4-oxo-3,4-dihydrophthalazin-1-yl)spiro[3.3]heptan-2-yl)pyrazolo[1,5-a]pyridine-3-carboxamide, 6-(benzyloxy)-N-((aR)-6-(4-oxo-3,4-dihydrophthalazin-1-yl)spiro[3.3]heptan-2-yl)pyrazolo[1,5-a]pyridine-3-carboxamide, N-((aR)-6-(4-oxo-3,4-dihydrophthalazin-1-yl)spiro[3.3]heptan-2-yl)-6-((tetrahydrofuran-3-yl)oxy)pyrazolo[1,5-a]pyridine-3-carboxamide, N-((aR)-6-(4-oxo-3,4-dihydrophthalazin-1-yl)spiro[3.3]heptan-2-yl)-6-(3,3,3-trifluoro-2-hydroxypropoxy)pyrazolo[1,5-a]pyridine-3-carboxamide, 6-(benzyloxy)-7-methyl-N-((aR)-6-(4-oxo-3,4-dihydrophthalazin-1-yl)spiro[3.3]heptan-2-yl)pyrazolo[1,5-a]pyridine-3-carboxamide, 6-(benzyloxy)-7-cyano-N-((aR)-6-(4-oxo-3,4-dihydrophthalazin-1-yl)spiro[3.3]heptan-2-yl)pyrazolo[1,5-a]pyridine-3-carboxamide, 6-((1,3-difluoropropan-2-yl)oxy)-N-((aR)-6-(4-oxo-3,4-dihydrophthalazin-1-yl)spiro[3.3]heptan-2-yl)pyrazolo[1,5-a]pyridine-3-carboxamide, 6-((1,1-dioxidotetrahydro-2H-thiopyran-4-yl)oxy)-N-((aR)-6-(4-oxo-3,4-dihydrophthalazin-1-yl)spiro[3.3]heptan-2-yl)pyrazolo[1,5-a]pyridine-3-carboxamide, N-((aR)-6-(4-oxo-3,4-dihydrophthalazin-1-yl)spiro[3.3]heptan-2-yl)-6-(3,3,3-trifluoropropoxy)pyrazolo[1,5-a]pyridine-3-carboxamide, 6-((4,4-difluorocyclohexyl)oxy)-N-((aR)-6-(4-oxo-3,4-dihydrophthalazin-1-yl)spiro[3.3]heptan-2-yl)pyrazolo[1,5-a]pyridine-3-carboxamide, N-((aR)-6-(4-oxo-3,4-dihydrophthalazin-1-yl)spiro[3.3]heptan-2-yl)-6-((tetrahydro-2H-pyran-4-yl)oxy)pyrazolo[1,5-a]pyridine-3-carboxamide, 6-(3,3-difluorocyclobutoxy)-N-((aR)-6-(4-oxo-3,4-dihydrophthalazin-1-yl)spiro[3.3]heptan-2-yl)pyrazolo[1,5-a]pyridine-3-carboxamide, N-((aR)-6-(4-oxo-3,4-dihydrophthalazin-1-yl)spiro[3.3]heptan-2-yl)-6-(2-(2,2,2-trifluoroethoxy)ethoxy)pyrazolo[1,5-a]pyridine-3-carboxamide, 6-((5-cyclopropyl-1,3,4-thiadiazol-2-yl)methoxy)-N-((aR)-6-(4-oxo-3,4-dihydrophthalazin-1-yl)spiro[3.3]heptan-2-yl)pyrazolo[1,5-a]pyridine-3-carboxamide, 1-(2-hydroxy-2-methylpropyl)-6-(2-methoxyphenyl)-N-((aR)-6-(4-oxo-3,4-dihydrophthalazin-1-yl)spiro[3.3]heptan-2-yl)-1H-indazole-3-carboxamide, 6-(2-cyanophenyl)-1-(2-hydroxy-2-methylpropyl)-N-((aR)-6-(4-oxo-3,4-dihydrophthalazin-1-yl)spiro[3.3]heptan-2-yl)-1H-indazole-3-carboxamide, 6-cyclopropyl-N-((aR)-6-(4-oxo-3,4-dihydrophthalazin-1-yl)spiro[3.3]heptan-2-yl)pyrazolo[1,5-a]pyridine-3-carboxamide, 6-(1-(difluoromethyl)-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide, 6-(1-methyl-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide, N-((aR)-6-(4-oxo-3,4-dihydrophthalazin-1-yl)spiro[3.3]heptan-2-yl)-6-(thiazol-2-yl)pyrazolo[1,5-a]pyridine-3-carboxamide, N-((aR)-6-(4-oxo-3,4-dihydrophthalazin-1-yl)spiro[3.3]heptan-2-yl)-6-(1H-pyrazol-4-yl)pyrazolo[1,5-a]pyridine-3-carboxamide, N-((aR)-6-(4-oxo-3,4-dihydrophthalazin-1-yl)spiro[3.3]heptan-2-yl)-6-(1H-pyrazol-1-yl)pyrazolo[1,5-a]pyridine-3-carboxamide, 6-(2-methoxyethoxy)-N-((aR)-6-(4-oxo-3,4-dihydrophthalazin-1-yl)spiro[3.3]heptan-2-yl)pyrazolo[1,5-a]pyridine-3-carboxamide, 6-(2-(4-hydroxy-3,3-dimethylpiperidin-1-yl)ethoxy)-N-((aR)-6-(4-oxo-3,4-dihydrophthalazin-1-yl)spiro[3.3]heptan-2-yl)pyrazolo[1,5-a]pyridine-3-carboxamide, 6-(2-(3,3-difluoropyrrolidin-1-yl)ethoxy)-N-((aR)-6-(4-oxo-3,4-dihydrophthalazin-1-yl)spiro[3.3]heptan-2-yl)pyrazolo[1,5-a]pyridine-3-carboxamide, 6-(2-(2,2-dimethylmorpholino)ethoxy)-N-((aR)-6-(4-oxo-3,4-dihydrophthalazin-1-yl)spiro[3.3]heptan-2-yl)pyrazolo[1,5-a]pyridine-3-carboxamide, 6-(2-(4-methylpiperazin-1-yl)ethoxy)-N-((aR)-6-(4-oxo-3,4-dihydrophthalazin-1-yl)spiro[3.3]heptan-2-yl)pyrazolo[1,5-a]pyridine-3-carboxamide, 6-(2-((R)-3-fluoropyrrolidin-1-yl)ethoxy)-N-((aR)-6-(4-oxo-3,4-dihydrophthalazin-1-yl)spiro[3.3]heptan-2-yl)pyrazolo[1,5-a]pyridine-3-carboxamide, 6-(2-((S)-3-fluoropyrrolidin-1-yl)ethoxy)-N-((aR)-6-(4-oxo-3,4-dihydrophthalazin-1-yl)spiro[3.3]heptan-2-yl)pyrazolo[1,5-a]pyridine-3-carboxamide, 6-(3-(3,3-difluoropyrrolidin-1-yl)propyl)-N-((aR)-6-(4-oxo-3,4-dihydrophthalazin-1-yl)spiro[3.3]heptan-2-yl)pyrazolo[1,5-a]pyridine-3-carboxamide, 6-(3-hydroxy-3-methylbutyl)-N-((aR)-6-(4-oxo-3,4-dihydrophthalazin-1-yl)spiro[3.3]heptan-2-yl)pyrazolo[1,5-a]pyridine-3-carboxamide, 6-benzyl-N-((aR)-6-(4-oxo-3,4-dihydrophthalazin-1-yl)spiro[3.3]heptan-2-yl)pyrazolo[1,5-a]pyridine-3-carboxamide, N-((aR)-6-(4-oxo-3,4-dihydrophthalazin-1-yl)spiro[3.3]heptan-2-yl)-6-(3,3,3-trifluoropropyl)pyrazolo[1,5-a]pyridine-3-carboxamide, 6-((allyloxy)methyl)-N-((aR)-6-(4-oxo-3,4-dihydrophthalazin-1-yl)spiro[3.3]heptan-2-yl)pyrazolo[1,5-a]pyridine-3-carboxamide, 6-(1,5-dimethyl-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide, 6-(1-cyclopropyl-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide, 6-(1-(cyclopropylmethyl)-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide, 6-(1-(($^{2}$H3)methyl-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide, 6-(1-isopropyl-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide, N-((aR)-6-(4-oxo-3,4-dihydrophthalazin-1-yl)spiro[3.3]heptan-2-yl)-6-(1,3,5-trimethyl-1H-pyrazol-4-yl)pyrazolo[1,5-a]pyridine-3-carboxamide, N-((aR)-6-(4-oxo-3,4-dihydrophthalazin-1-yl)spiro[3.3]heptan-2-yl)-6-(1-(tetrahydro-2H-pyran-4-yl)-1H-pyrazol-4-yl)pyrazolo[1,5-a]pyridine-3-carboxamide, 6-(1-methyl-3-(trifluoromethyl)-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide, 6-(1-isopropyl-3-(trifluoromethyl)-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide, 6-(1-(tert-butyl)-1H-pyrazol-4-yl)-N-((aR)-6-(4-oxo-3,4-dihydrophthalazin-1-yl)spiro[3.3]heptan-2-yl)pyrazolo[1,5-a]pyridine-3-carboxamide, N-((aR)-6-(4-oxo-3,4-dihydrophthalazin-1-yl)spiro[3.3]heptan-2-yl)-6-(1-(tetrahydrofuran-3-yl)-1H-pyrazol-4-yl)pyrazolo[1,5-a]pyridine-3-carboxamide, 5-(1-methyl-1H-pyrazol-4-yl)-N-((aR)-6-(4-oxo-3,4-dihydrophthalazin-1-yl)spiro[3.3]heptan-2-yl)indoline-1-carboxamide,
5-(1-cyclopropyl-1H-pyrazol-4-yl)-N-((aR)-6-(4-oxo-3,4-dihydrophthalazin-1-yl)spiro[3.3]heptan-2-yl)indoline-1-carboxamide,
5-(1-($^2$H3)methyl-1H-pyrazol-4-yl)-N-((aR)-6-(4-oxo-3,4-dihydrophthalazin-1-yl)spiro[3.3]heptan-2-yl)indoline-1-carboxamide,
2-methyl-1-((3-(((aR)-6-(4-oxo-3,4-dihydrophthalazin-1-yl)spiro[3.3]heptan-2-yl)carbamoyl)pyrazolo[1,5-a]pyridin-6-yl)oxy)propan-2-yl-2-aminoacetate,
(S)-2-methyl-1-((3-(((aR)-6-(4-oxo-3,4-dihydrophthalazin-1-yl)spiro[3.3]heptan-2-yl)carbamoyl)pyrazolo[1,5-a]pyridin-6-yl)oxy)propan-2-yl-2-amino-3-methylbutanoate,
(S)-2-methyl-1-((3-(((aR)-6-(4-oxo-3,4-dihydrophthalazin-1-yl)spiro[3.3]heptan-2-yl)carbamoyl)pyrazolo[1,5-a]pyridin-6-yl)oxy)propan-2-yl-2-aminopropanoate,
6-(1-methyl-1H-pyrazol-4-yl)-N-((aR)-6-(4-oxo-3,4-dihydrophthalazin-1-yl)spiro[3.3]heptan-2-yl)benzo[c]isoxazole-3-carboxamide,
6-(2-hydroxy-2-methylpropoxy)-N-((aR)-6-(4-oxo-3,4-dihydrophthalazin-1-yl)spiro[3.3]heptan-2-yl)benzo[c]isoxazole-3-carboxamide,
6-fluoro-7-methyl-N-((aR)-6-(4-oxo-3,4-dihydrophthalazin-1-yl)spiro[3.3]heptan-2-yl)-1H-indole-2-carboxamide,
N-((aR)-6-(4-oxo-3,4-dihydrophthalazin-1-yl)spiro[3.3]heptan-2-yl)-7-(trifluoromethyl)-1H-indole-2-carboxamide,
7-(4-methylpiperazin-1-yl)-N-((aR)-6-(4-oxo-3,4-dihydrophthalazin-1-yl)spiro[3.3]heptan-2-yl)imidazo[1,2-a]pyridine-3-carboxamide),
N-((aR)-6-(4-oxo-3,4-dihydrophthalazin-1-yl)spiro[3.3]heptan-2-yl)-7-phenylimidazo[1,2-a]pyridine-3-carboxamide,
7-(benzyloxy)-N-((aR)-6-(4-oxo-3,4-dihydrophthalazin-1-yl)spiro[3.3]heptan-2-yl)imidazo[1,2-a]pyridine-3-carboxamide,
7-methoxy-N-((aR)-6-(4-oxo-3,4-dihydrophthalazin-1-yl)spiro[3.3]heptan-2-yl)imidazo[1,2-a]pyridine-3-carboxamide,
7-(4,4-difluoropiperidin-1-yl)-N-((aR)-6-(4-oxo-3,4-dihydrophthalazin-1-yl)spiro[3.3]heptan-2-yl)imidazo[1,2-a]pyridine-3-carboxamide,
7-(3,3-difluoropyrrolidin-1-yl)-N-((aR)-6-(4-oxo-3,4-dihydrophthalazin-1-yl)spiro[3.3]heptan-2-yl)imidazo[1,2-a]pyridine-3-carboxamide,
7-((R)-3-fluoropyrrolidin-1-yl)-N-((aR)-6-(4-oxo-3,4-dihydrophthalazin-1-yl)spiro[3.3]heptan-2-yl)imidazo[1,2-a]pyridine-3-carboxamide,
7-((S)-3-fluoropyrrolidin-1-yl)-N-((aR)-6-(4-oxo-3,4-dihydrophthalazin-1-yl)spiro[3.3]heptan-2-yl)imidazo[1,2-a]pyridine-3-carboxamide,
7-((2-methoxyethyl)(methyl)amino)-N-((aR)-6-(4-oxo-3,4-dihydrophthalazin-1-yl)spiro[3.3]heptan-2-yl)imidazo[1,2-a]pyridine-3-carboxamide,
7-(2-morpholinoethoxy)-N-((aR)-6-(4-oxo-3,4-dihydrophthalazin-1-yl)spiro[3.3]heptan-2-yl)imidazo[1,2-a]pyridine-3-carboxamide,
7-(2-hydroxy-2-methylpropoxy)-N-((aR)-6-(4-oxo-3,4-dihydrophthalazin-1-yl)spiro[3.3]heptan-2-yl)imidazo[1,2-a]pyridine-3-carboxamide,
6-fluoro-8-methyl-N-((aR)-6-(4-oxo-3,4-dihydrophthalazin-1-yl)spiro[3.3]heptan-2-yl)imidazo[1,2-a]pyridine-3-carboxamide,
7-(difluoromethoxy)-N-((aR)-6-(4-oxo-3,4-dihydrophthalazin-1-yl)spiro[3.3]heptan-2-yl)imidazo[1,2-a]pyridine-3-carboxamide,
8-(benzyloxy)-N-((aR)-6-(4-oxo-3,4-dihydrophthalazin-1-yl)spiro[3.3]heptan-2-yl)imidazo[1,2-a]pyridine-3-carboxamide,
7-(methylthio)-N-((aR)-6-(4-oxo-3,4-dihydrophthalazin-1-yl)spiro[3.3]heptan-2-yl)imidazo[1,2-a]pyridine-3-carboxamide,
3-methoxy-N-((aR)-6-(4-oxo-3,4-dihydrophthalazin-1-yl)spiro[3.3]heptan-2-yl)-4-(1H-pyrazol-4-yl)benzamide,
3-cyano-N-((aR)-6-(4-oxo-3,4-dihydrophthalazin-1-yl)spiro[3.3]heptan-2-yl)-4-(1H-pyrazol-4-yl)benzamide,
3-methyl-N-((aR)-6-(4-oxo-3,4-dihydrophthalazin-1-yl)spiro[3.3]heptan-2-yl)-4-(1H-pyrazol-4-yl)benzamide,
7-((1,1-dioxidotetrahydro-2H-thiopyran-4-yl)oxy)-N-((aR)-6-(4-oxo-3,4-dihydrophthalazin-1-yl)spiro[3.3]heptan-2-yl)imidazo[1,2-a]pyridine-3-carboxamide,
N-((aR)-6-(4-oxo-3,4-dihydrophthalazin-1-yl)spiro[3.3]heptan-2-yl)-7-(pyridin-2-yloxy)imidazo[1,2-a]pyridine-3-carboxamide,
7-(2,2-difluoroethoxy)-N-((aR)-6-(4-oxo-3,4-dihydrophthalazin-1-yl)spiro[3.3]heptan-2-yl)imidazo[1,2-a]pyridine-3-carboxamide,
7-(1-ethyl-1H-pyrazol-4-yl)-N-((aR)-6-(4-oxo-3,4-dihydrophthalazin-1-yl)spiro[3.3]heptan-2-yl)imidazo[1,2-a]pyridine-3-carboxamide,
7-(1-methyl-1H-pyrazol-4-yl)-N-((aR)-6-(4-oxo-3,4-dihydrophthalazin-1-yl)spiro[3.3]heptan-2-yl)imidazo[1,2-a]pyridine-3-carboxamide,
7-(1-isopropyl-1H-pyrazol-4-yl)-N-((aR)-6-(4-oxo-3,4-dihydrophthalazin-1-yl)spiro[3.3]heptan-2-yl)imidazo[1,2-a]pyridine-3-carboxamide,
7-(1-(methyl-d3)-1H-pyrazol-4-yl)-N-((aR)-6-(4-oxo-3,4-dihydrophthalazin-1-yl)spiro[3.3]heptan-2-yl)imidazo[1,2-a]pyridine-3-carboxamide,
N-((aR)-6-(4-oxo-3,4-dihydrophthalazin-1-yl)spiro[3.3]heptan-2-yl)-7-(1-(tetrahydro-2H-pyran-4-yl)-1H-pyrazol-4-yl)imidazo[1,2-a]pyridine-3-carboxamide,
N-((aR)-6-(4-oxo-3,4-dihydrophthalazin-1-yl)spiro[3.3]heptan-2-yl)-7-(pyridin-3-yl)imidazo[1,2-a]pyridine-3-carboxamide,
N-((aR)-6-(4-oxo-3,4-dihydrophthalazin-1-yl)spiro[3.3]heptan-2-yl)-7-(pyridin-3-yl)imidazo[1,2-a]pyridine-2-carboxamide,
7-(2-methylthiazol-5-yl)-N-((aR)-6-(4-oxo-3,4-dihydrophthalazin-1-yl)spiro[3.3]heptan-2-yl)imidazo[1,2-a]pyridine-2-carboxamide,
7-(2-methylthiazol-5-yl)-N-((aR)-6-(4-oxo-3,4-dihydrophthalazin-1-yl)spiro[3.3]heptan-2-yl)imidazo[1,2-a]pyridine-3-carboxamide,
4-((aR)-6-(1-oxoisoindolin-2-yl)spiro[3.3]heptan-2-yl)phthalazin-1(2H)-one,
4-((aR)-6-((S)-4-benzyl-2-oxoimidazolidin-1-yl)spiro[3.3]heptan-2-yl)phthalazin-1 (2H)-one
4-((aR)-6-((R)-4-benzyl-2-oxoimidazolidin-1-yl)spiro[3.3]heptan-2-yl)phthalazin-1 (2H)-one,
4-((aR)-6-((2-nitrophenyl)amino)spiro[3.3]heptan-2-yl)phthalazin-1 (2H)-one,
4-((aR)-6-(2-oxo-2,3-dihydro-1H-benzo[d]imidazol-1-yl)spiro[3.3]heptan-2-yl)phthalazin-1(2H)-one, 4-cyclopropyl-N-((aR)-6-(4-oxo-3,4-dihydrophthalazin-1-yl)spiro[3.3]heptan-2-yl)pyrazolo[1,5-a]pyridine-3-carboxamide, 3-fluoro-5-(1-methyl-1H-pyrazol-4-yl)-N-((aR)-6-(4-oxo-3,4-dihydrophthalazin-1-yl)spiro[3.3]heptan-2-yl)picolinamide, 6-(4-oxo-3,4-dihydrophthalazin-1-yl)spiro[3.3]heptan-2-yl isoindoline-2-carboxylate, 7-(methylsulfonyl)-N-((aR)-6-(4-oxo-3,4-dihydrophthalazin-1-yl)spiro[3.3]heptan-2-yl)imidazo[1,2-a]pyridine-3-carboxamide, and 2-methyl-2-((3-(((aR)-6-(4-oxo-3,4-dihydrophthalazin-1-yl)spiro[3.3]heptan-2-yl)carbamoyl)pyrazolo[1,5-a]pyridin-6-yl)oxy)propanoic acid.

15. A pharmaceutical composition comprising one or more compounds according to claim 1 and a pharmaceutically acceptable carrier or diluent.

\* \* \* \* \*